US012569565B2

(12) United States Patent
Balkovec et al.

(10) Patent No.: US 12,569,565 B2
(45) Date of Patent: Mar. 10, 2026

(54) COMPOSITIONS AND METHODS FOR THE TREATMENT OF VIRAL INFECTIONS

(71) Applicant: Cidara Therapeutics, Inc., San Diego, CA (US)

(72) Inventors: James M. Balkovec, Martinsville, NJ (US); Daniel C. Bensen, Carlsbad, CA (US); Allen Borchardt, San Diego, CA (US); Thomas P. Brady, San Diego, CA (US); Zhi-Yong Chen, La Jolla, CA (US); Jason Cole, San Diego, CA (US); Quyen-Quyen Thuy Do, San Diego, CA (US); Simon Doehrmann, San Diego, CA (US); Wanlong Jiang, San Diego, CA (US); Thanh Lam, San Diego, CA (US); Alain Noncovich, La Jolla, CA (US); Leslie W. Tari, San Diego, CA (US)

(73) Assignee: Cidara Therapeutics, Inc., San Diego, CA (US)

( * ) Notice: Subject to any disclaimer, the term of this patent is extended or adjusted under 35 U.S.C. 154(b) by 124 days.

(21) Appl. No.: 18/464,421

(22) Filed: Sep. 11, 2023

(65) Prior Publication Data

US 2024/0156975 A1 May 16, 2024

Related U.S. Application Data

(60) Division of application No. 17/236,722, filed on Apr. 21, 2021, now Pat. No. 11,833,213, which is a continuation of application No. 17/193,923, filed on Mar. 5, 2021, now abandoned, which is a continuation of application No. PCT/US2019/050018, filed on Sep. 6, 2019.

(60) Provisional application No. 62/890,475, filed on Aug. 22, 2019, provisional application No. 62/873,678, filed on Jul. 12, 2019, provisional application No. 62/859,983, filed on Jun. 11, 2019, provisional application No. 62/852,075, filed on May 23, 2019, provisional application No. 62/840,899, filed on Apr. 30, 2019, provisional application No. 62/832,992, filed on Apr. 12, 2019, provisional application No. 62/815,235, filed on Mar. 7, 2019, provisional application No. 62/813,463, filed on Mar. 4, 2019, provisional application No. 62/788,386, filed on Jan. 4, 2019, provisional application No. 62/782,119, filed on Dec. 19, 2018, provisional application No. 62/746,865, filed on Oct. 17, 2018, provisional application No. 62/727,821, filed on Sep. 6, 2018.

(51) Int. Cl.
*A61K 47/68* (2017.01)

(52) U.S. Cl.
CPC .................................. *A61K 47/68* (2017.08)

(58) Field of Classification Search
CPC ..................................................... A61K 47/68
See application file for complete search history.

(56) References Cited

U.S. PATENT DOCUMENTS

| | | | | |
|---|---|---|---|---|
| 6,495,580 | B1 | 12/2002 | Nitz et al. | |
| 6,548,476 | B1 | 4/2003 | Wu et al. | |
| 6,680,054 | B1 | 1/2004 | Reece et al. | |
| 7,214,707 | B2 | 5/2007 | Demaine et al. | |
| 8,486,938 | B2 | 7/2013 | Babaoglu et al. | |
| 9,469,676 | B2 * | 10/2016 | Camphausen | C07K 14/78 |
| 9,738,652 | B2 | 8/2017 | Hu et al. | |
| 11,510,992 | B1 | 11/2022 | Borchardt et al. | |
| 11,833,213 | B2 | 12/2023 | Balkovec et al. | |
| 2009/0041791 | A1 | 2/2009 | Feng | |
| 2011/0243966 | A1 | 10/2011 | Farrington et al. | |
| 2012/0009205 | A1 | 1/2012 | Gegg et al. | |
| 2013/0196974 | A1 | 8/2013 | Chen et al. | |
| 2014/0072532 | A1 | 3/2014 | Nitz et al. | |
| 2015/0218258 | A1 | 8/2015 | Francis et al. | |
| 2015/0259367 | A1 | 9/2015 | Tahri et al. | |
| 2016/0158378 | A1 | 6/2016 | Park et al. | |
| 2016/0229853 | A1 | 8/2016 | Gao et al. | |
| 2017/0102387 | A1 | 4/2017 | Wong et al. | |
| 2017/0320926 | A1 | 11/2017 | Scheer et al. | |
| 2017/0362244 | A1 | 12/2017 | Babaoglu et al. | |
| 2019/0233525 | A1 | 8/2019 | Igawa et al. | |
| 2021/0220478 | A1 | 7/2021 | Balkovec et al. | |
| 2021/0228727 | A1 | 7/2021 | Balkovec et al. | |
| 2022/0257787 | A1 | 8/2022 | Balkovec et al. | |
| 2023/0398226 | A1 | 12/2023 | Borchardt et al. | |

(Continued)

FOREIGN PATENT DOCUMENTS

| | | | | |
|---|---|---|---|---|
| EP | 1196408 | B1 | 9/2004 | |
| JP | 2016-527249 | A | 9/2016 | |

(Continued)

OTHER PUBLICATIONS

Shtyrya et al. Influenza virus neuraminidase: structure and function. Acta Naturae, 2009; 1(2):26-32 (Year: 2009).*

(Continued)

*Primary Examiner* — Vanessa L. Ford
*Assistant Examiner* — Sandra Carter
(74) *Attorney, Agent, or Firm* — Clark & Elbing LLP

(57) ABSTRACT

Compositions and methods for the treatment of viral infections include conjugates containing inhibitors of viral neuraminidase (e.g., zanamivir, peramivir, or analogs thereof) linked to an Fc monomer, an Fc domain, and Fc-binding peptide, an albumin protein, or albumin-binding peptide. In particular, conjugates can be used in the treatment of viral infections (e.g., influenza viral infections).

14 Claims, 72 Drawing Sheets

Specification includes a Sequence Listing.

(56) References Cited

U.S. PATENT DOCUMENTS

| | | | |
|---|---|---|---|
| 2024/0174730 | A1 | 5/2024 | Tari |
| 2024/0285786 | A1 | 8/2024 | Tari |

FOREIGN PATENT DOCUMENTS

| | | | | |
|---|---|---|---|---|
| JP | 2021-512856 | A | 5/2021 | |
| WO | WO-00/55149 | A1 | 9/2000 | |
| WO | WO-03/040136 | A1 | 5/2003 | |
| WO | WO-2007/022494 | A2 | 2/2007 | |
| WO | WO-2010/093706 | A2 | 8/2010 | |
| WO | WO-2011143262 | A2 | 11/2011 | |
| WO | WO-2014/060411 | A1 | 4/2014 | |
| WO | WO-2017/046625 | A1 | 3/2017 | |
| WO | WO-2018/006063 | A1 | 1/2018 | |
| WO | WO-2018128826 | A1 * | 7/2018 | ............ A61K 45/06 |
| WO | WO-2020/051498 | A1 | 3/2020 | |
| WO | WO-2020/252393 | A1 | 12/2020 | |
| WO | WO-2020/252396 | A1 | 12/2020 | |
| WO | WO-2021/046549 | A1 | 3/2021 | |

OTHER PUBLICATIONS

U.S. Appl. No. 17/887,776, Borchardt et al.

Ali et al., "A Phase 2a Study to Evaluate the Safety of MEDI8852 in Outpatient Adults with Acute, Uncomplicated Influenza A," Open Forum Infectious Diseases. 4:S519, Abstract 1656 (2017) (1 page).

Almaguer et al., "CD377, a Novel Antiviral Fc-Conjugate, Demonstrates a Lower Resistance Potential than Baloxavir and Oseltamivir against Pandemic Influenza A (H1N1)," Abstract Book—30th ECCMID Apr. 18-21, 2020. p. 2766. Abstract 5707 (2020) (1 page).

Battles et al., "Molecular mechanism of respiratory syncytial virus fusion inhibitors," available in PMC Feb. 1, 2016, published in final edited form as: Nat Chem Biol 12(2):87-93 (2016) (23 pages).

Borchardt et al., "CB-012—A Novel Antiviral-Fc Conjugate for Treatment and Prevention of Influenza Virus," ASM Microbe, Jun. 20-24, San Francisco, California. Poster HMB-385 (Jun. 2019) (1 page).

Borrok et al., "pH-dependent Binding Engineering Reveals an FcRn Affinity Threshold That Governs IgG Recycling," J Biol Chem. 290(7):4282-4290 (2015) (10 pages).

Cheng et al., "From Neuraminidase Inhibitors to Conjugates: a Step Towards Better Anti-Influenza Drugs?" Future Med Chem. 6(7): 757-774 (2014).

Devanaboyina et al., "Engineered clearing agents for the selective depletion of antigen-specific antibodies," Nat Commun. 8:15314 (2017) (6 pages).

Döhrmann et al., "CD377, a Novel Antiviral Fc-Conjugate, Demonstrates Potent Broad-Spectrum Activity in Multiple in vitro Assays Against Influenza A and B," Abstract Book—30th ECCMID Apr. 18-21, 2020. p. 4170. Abstract 8832 (2020) (1 page).

Döhrmann et al., "CD377, A Novel Antiviral Fc-Conjugate, Demonstrates Superior Reduction of Viral Burden and Cytokine Levels Compared to Oseltamivir in a Lethal Mouse Model of Influenza A (H1N1) Infection," Abstract Book—30th ECCMID Apr. 18-21, 2020. p. 4172. Abstract 8839. (2020) (1 page).

Döhrmann et al., "Fc-Mediated Effector Function Contributes to Potency of Novel Antiviral Fc-Conjugate CB-012," Options X for the Control of Influenza, Abstract No. 11094, 507 (Aug. 2019) (1 page).

Döhrmann et al., "Fc-Mediated Effector Function Contributes to Potency of Novel Cloudbreak Antiviral Fc-Conjugate (AVC) CB-012," Options X, Aug. 28-Sep. 1, Singapore (Aug. 2019) (1 page).

Döhrmann et al., "Fc-Mediated Fcgamma Receptor Engagement of CD377, a Novel Antiviral Fc-Conjugate, Translates Into Potent Antibody-Dependent Cellular Phagocytosis and Antibody-Dependent Cellular Cytotoxicity Activity," Abstract Book—30th ECCMID Apr. 18-21, 2020. p. 4169. Abstract 8820 (2020) (1 page).

Döhrmann, "CD377, A Novel Antiviral Fc-Conjugate, Demonstrates Potent Viral Burden Reduction Against Influenza A (H1N1) in Mouse and Ferret Models," IDWeek, Oct. 21-25, Virtual Event. Abstract 162 (2020) (30 pages).

Extended European Search Report for European Application No. 19857366.9, dated Jul. 5, 2022 (12 pages).

Fu et al., "Structure-Based Tetravalent Zanamivir with Potent Inhibitory Activity against Drug-Resistant Influenza Viruses," J Med Chem. 59(13): 6303-6312 (2016).

Greengard et al., "The Anti-Influenza Virus Agent 4-GU-DANA (Zanamivir) Inhibits Cell Fusion Mediated by Human Parainfluenza Virus and Influenza Virus HA," J Virol. 74(23):11108-11114 (2000) (7 pages).

Gubareva et al., "Antivirals Targeting the Neuraminidase," Cold Spring Harb Perspect Med. 12(1):a038455 (2022) (21 pages).

Guillon et al., "Structure-guided discovery of potent and dual-acting human parainfluenza virus haemagglutinin-neuraminidase inhibitors," Nat Commun. 5:5268 (2014) (11 pages).

Hadházi et al., "A Sulfonozanamivir Analogue has Potent Anti-influenza Virus Activity," ChemMedChem. 13:785-789 (Apr. 2018).

Hanessian et al., "Total Synthesis of A-315675: A Potent Inhibitor of Influenza Neuraminidase," J Am Chem Soc. 124(17):4716-4721 (2002).

Hayakawa et al., "A Chemically Programmed Antibody is a Long-Lasting and Potent Inhibitor of Influenza Neuraminidase," Chembiochem. 13(15):2191-5 (2012).

International Search Report and Written Opinion for International Application No. PCT/US2019/050018, mailed Feb. 19, 2020 (11 pages).

International Search Report and Written Opinion for International Application No. PCT/US2020/049772, mailed Feb. 4, 2021 (13 pages).

International Search Report and Written Opinion for International Application No. PCT/US2020/47490, mailed Mar. 18, 2021 (24 pages).

Kallewaard et al., "Structure and Function Analysis of an Antibody Recognizing All Influenza A Subtypes," Cell. 166(3):596-608 (2016) (34 Pages).

Kati et al., "In Vitro Characterization of A-315675, a Highly Potent Inhibitor of A and B Strain Influenza Virus Neuraminidases and Influenza Virus Replication," Antimicrob Agents Chemother. 46(4):1014-1021 (2002).

Laborda et al., "Influenza Neuraminidase Inhibitors: Synthetic Approaches, Derivatives and Biological Activity," Molecules. 21(11):1513 (2016) (40 pages).

Levin et al., "Efficacy of CB-012, A Novel Antiviral Fc-Conjugate, against Influenza A (H1N1) in a Lethal Mouse Model of Severe Combined Immunodeficiency (SCID)," Options X, Aug. 28-Sep. 1, Singapore (Aug. 2019) (1 page).

Levin et al., "Efficacy of CB-012, A Novel Antiviral Fc-Conjugate, in Lethal Mouse Models of Oseltamivir-Sensitive and -Resistant Influenza A H1N1 and H3N2 Isolates," Options X, Aug. 28-Sep. 1, Singapore (2019) (1 page).

Levin et al., "Efficacy of CD377, A Novel Antiviral Fc-Conjugate Against Seasonal Influenza in Lethal Mouse Models," Abstract Book—30th ECCMID Apr. 18-21, 2020. p. 2804. Abstract 5793 (2020) (1 page).

Levin et al., "Efficacy of CD377, a Novel Antiviral Fc-Conjugate, Against Influenza A (H1N1) in a Lethal Mouse Model of Severe Combined Immunodeficiency (SCID)," Abstract Book—30th ECCMID Apr. 18-21, 2020. p. 2871. Abstract 6009 (2020) (1 page).

Levin et al., "Efficacy of CD377, a Novel Antiviral Fc-Conjugate, by Multiple Dosing Routes Against Influenza A (H1N1), and Activity against Oseltamivir-Resistant Isolates in Lethal Mouse Models," ESWI Conference, Virtual Event. Poster 159 (Dec. 2020) (1 page).

Levin et al., "Evaluation of CD377, A Novel Antiviral Fc-Conjugate (AVC) In Vitro Activity and In Vivo Efficacy in Immune-Competent and -Deficient (SCID) Lethal Mouse Models," IDWeek, Oct. 21-25, Virtual Event. Poster 1276 (2020) (1 page).

Levin et al., "In Vitro Potency and In Vivo Efficacy of CD377, a Novel Antiviral Fc-Conjugate, Against Highly Pathogenic Avian Influenza (HPAI)," Cidara Therapeutics Inc., ESWI 2020, Virtual Event (Dec. 2020) (1 page).

Levin et al., "Therapeutic Efficacy of CB-012, a Novel Cloudbreak Antiviral Fc-Conjugate (AVC) in Lethal Mouse Models of Influenza

(56) References Cited

OTHER PUBLICATIONS

A (H1N1) and Influenza B (Victoria)," Open Forum Infectious Diseases 6(Suppl. 2):S313 (Oct. 2019) (1 page). Abstract 689.
Levin, "Efficacy of CD377, A Novel Antiviral Fc-Conjugate, Against Seasonal Influenza in Lethal Mouse Infection Models," IDWeek, Oct. 21-25, Virtual Event. Abstract 159 (2020) (17 pages).
Lin et al., "Synthesis of Acylguanidine Zanamivir Derivatives as Neuraminidase Inhibitors are the Evaluation of their Bio-Activities," Org Biomol Chem. 11(24): 3943-8 (2013).
Locke et al., "Novel Antiviral Fc-Conjugate CB-012 Demonstrates Potent Activity in Cytopathic Effect (CPE) and Viral Growth Inhibition Assays against Influenza A and B Strains," Options X, Aug. 28-Sep. 1, Singapore ( Aug. 2019) (1 page).
Locke, "Characterization of In Vitro Activity and In Vivo Efficacy of CD377, a Novel Antiviral Fc-Conjugate, Against 2020-2021 Northern Hemisphere Influenza Quadrivalent Vaccine Strains," ESWI Conference, Virtual Event. Abstract 269 (Dec. 2020) (22 pages).
Macdonald et al., "Dimeric Zanamivir Conjugates with Various Linking Groups are Potent, Long-Lasting Inhibitors of Influenza Neuraminidase Including H5N1 Avian Influenza," J Med Chem. 48(8): 2964-2971 (Mar. 2005).
Macdonald et al., "Potent and Long-Acting Dimeric Inhibitors of Influenza Virus Neuraminidase are Effective at a Once-Weekly Dosing Regimen," Antimicrob Agents Chemother. 48(12): 4542-9 (Dec. 2004).
Mallory et al., "A phase 1 study to evaluate the safety and pharmacokinetics of MEDI8852, an anti-influenza A monoclonal antibody, in healthy adult volunteers," Biologicals. 50:81-86 (2017) (6 pages).
McKimm-Breschkin et al., "Structural and Functional Analysis of Anti-Influenza Activity of 4-,7-, 8- and 9-Deoxygenated 2,3-Difluoro-N-acetylneuraminic Acid Derivatives," J Med Chem. 61(5):1921-1933 (Mar. 2018) (13 pages).
McKimm-Breschkin et al., "Tethered neuraminidase inhibitors that bind an influenza virus: a first step towards a diagnostic method for influenza," Angew Chem Int Ed Engl. 42(27):3118-21 (2003) (5 pages).
Meng et al., "Multivalent neuraminidase hydrolysis resistant triazole-sialoside protein conjugates as influenza-adsorbents," Chinese Chemical Letters. 29:76-80 (Jan. 2018) (5 pages).
Moscona, "Entry of parainfluenza virus into cells as a target for interrupting childhood respiratory disease," J Clin Invest. 115(7):1688-1698 (2005) (11 pages).
Ong et al., "Next Generation Antiviral Conjugate (AVC): Stable, Safe, and Single," IDWeek, Oct. 21-25, Virtual Event. Poster 1283 (2020) (1 page).
Ong et al., "Preclinical efficacy, pharmacokinetics and safety of CD377, a novel antiviral Fc-conjugate against influenza," Abstract Book—30th ECCMID Apr. 18-21, 2020. p. 2489. Abstract 5126 (2020) (1 page).
Ong et al., "Preclinical Efficacy, Pharmacokinetics, and Safety of CB-012, A Novel Antiviral Fc-Conjugate against Influenza," Options X, Aug. 28-Sep. 1, Singapore (Aug. 2019) (1 page).
Paules et al., "The Hemagglutinin A Stem Antibody MEDI8852 Prevents and Controls Disease and Limits Transmission of Pandemic Influenza Viruses," J Infect Dis. 216(3):356-65 (2017) (10 pages).
Rota et al., "Potent Inhibitors against Newcastle Disease Virus Hemagglutinin-Neuraminidase," ChemMedChem. 13:236-240 (Feb. 2018) (5 pages).
Shtyrya et al., "Influenza Virus Neuraminidase: Structure and Function," Acta Naturae. 1(2):26-32 (2009).
Tarbet et al., "A Zanamivir Dimer with Prophylactic and Enhanced Therapeutic Activity against Influenza viruses," J Antimicrob Chemother. 69(8): 2164-74 (2014).
Tari, "Cloudbreak Influenza," EECMID 2019, Apr. 13-16, Amsterdam, Netherlands (Apr. 2019) (22 pages).
Tari, Transcript of Cidara Therapeutics YouTube video: "Beyond Vaccines and mAbs: Progress Towards Universal Influenza Protection with Cloudbreak® Influenza Antiviral Conjugates (AVCs)," <https://www.youtube.com/watch?v=AqLAwlyl3Jo>, published Dec. 9, 2020. Recorded presentation at European Scientific Working Group on Influenza (ESWI) Conference, virtual event, Dec. 6-9, 2020 (18 pages).
Walker et al., "Spin-labeling of Dexamethasone: Radical Stability vs. Temporal Resolution of EPR-Spectroscopy on Biological Samples," Z Phys Chem. 232(5-6):883-891 (Apr. 2018) (9 pages).
Wang et al., "Peramivir conjugates as orally available agents against influenza H275Y mutant," Eur J Med Chem. 145:224-34 (Feb. 2018) (3 pages) (Abstract Only).
Watson et al., "Highly potent and long-acting trimeric and tetrameric inhibitors of influenza virus neuraminidase," Bioorg Med Chem Lett. 14(6):1589-92 (2004).
Weight et al., "Zanamivir conjugated to poly-L-glutamine is much more active against influenza viruses in mice and ferrets than the drug itself," available in PMC Mar. 25, 2014, published in final edited form as: Pharm Res. 31(2):466-474 (2014) (17 pages).
Wen et al., "Synergistic effect of zanamivir-porphyrin conjugates on inhibition of neuraminidase and inactivation of influenza virus," J Med Chem. 52(15):4903-10 (2009).
Wold et al., "Fc-Small Molecule Antibody Mimetics," Bioconjug Chem. 26(12):2311-4 (2015) (23 pages).
Yu et al., "Guanidinothiosialoside-Human Serum Albumin Conjugate Mimics mucin Barrier to Restrict Influenza Infection," Int J Biol Macromol. 162:84-91 (Jun. 2020) (8 pages).
Zhao et al., "Multivalent zanamivir-bovine serum albumin conjugate as a potent influenza neuraminidase inhibitor," Journal of Carbohydrate Chemistry. 36(4-6):235-246 (2017) (13 pages).
Zhong et al., "Amide-sialoside protein conjugates as neomucin bioshields prevent influenza virus infection," Carbohydr Res. 495:108088 (Jun. 2020) (7 pages).
Zhou et al., "Single chain Fc-dimer-human growth hormone fusion protein for improved drug delivery," Biomaterials. 117:24-31 (Feb. 2017).

* cited by examiner (SEQ ID NO: 1: murine Fc-IgG2a with IL2 signal sequence at the N-terminus)

(SEQ ID NO: 3: human Fc-IgG1 with IL2 signal sequence at the N-terminus)

(SEQ ID NO: 5: murine Fc-IgG2a with IL2 signal sequence at the N-terminus and hexa-histidine peptide at the C-terminus)

(SEQ ID NO: 7: human Fc-IgG1 with IL2 signal sequence at the N-terminus and hexa-histidine peptide at the C-terminus)

(SEQ ID NO: 9: human Fc-IgG1 with IL2 signal sequence at the N-terminus, two additional cysteines in the hinge region, and hexa-histidine peptide at the C-terminus)

(SEQ ID NO: 12: murine Fc-IgG2a with IL2 signal sequence at the N-terminus, Asn to Ala substitution, and hexa-histidine peptide at the C-terminus)

(SEQ ID NO: 14: human Fc-IgG1 with IL2 signal sequence at the N-terminus, Asn to Ala substitution, and hexa-histidine peptide at the C-terminus)

Conjugate 1

Conjugate 2

Conjugate 3

Conjugate 4

Conjugate 5

Conjugate 6

H1N1 Neuraminidase $IC_{50}$ (nM)

H3N2 Neuraminidase $IC_{50}$ (nM)

Conjugate 3

Conjugate 4

Conjugate 6

Mouse Weight

Mouse Survival

Mouse Weight

Mouse Survival

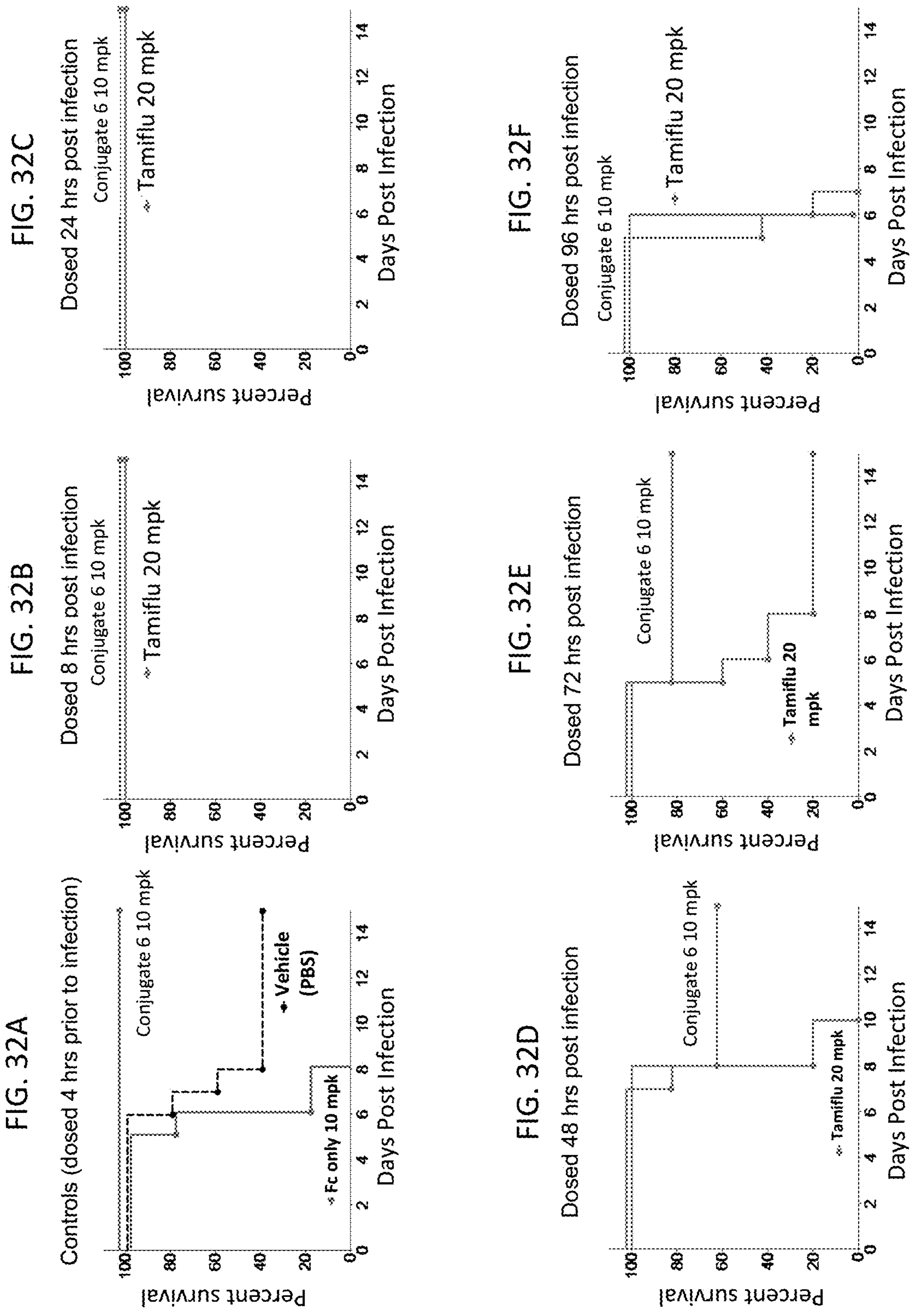
FIG. 32A
Controls (dosed 4 hrs prior to infection)
Conjugate 6 10 mpk
Vehicle (PBS)
Fc only 10 mpk
Percent survival
Days Post Infection
FIG. 32B
Dosed 8 hrs post infection
Conjugate 6 10 mpk
Tamiflu 20 mpk
Percent survival
Days Post Infection
FIG. 32C
Dosed 24 hrs post infection
Conjugate 6 10 mpk
Tamiflu 20 mpk
Percent survival
Days Post Infection
FIG. 32D
Dosed 48 hrs post infection
Conjugate 6 10 mpk
Tamiflu 20 mpk
Percent survival
Days Post Infection
FIG. 32E
Dosed 72 hrs post infection
Conjugate 6 10 mpk
Tamiflu 20 mpk
Percent survival
Days Post Infection
FIG. 32F
Dosed 96 hrs post infection
Conjugate 6 10 mpk
Tamiflu 20 mpk
Percent survival
Days Post Infection Mouse Weight Conjugate 6 plasma and lung levels Conjugate 6 IV, SC, and IM administration Conjugate 8

Conjugate 6

Conjugate 6 in vitro mouse plasma

Conjugate 6 in vitro human plasma

Conjugate 6 mouse liver microsomal stability

Conjugate 6 human liver microsomal stability

Conjugate 6 and Conjugate 12 *in vivo* efficacy

Conjugate 6 and Conjugate 12 *in vivo* efficacy

Conjugate 6 and Conjugate 12 *in vitro* Fcγ receptor IIIA binding

Conjugate 6 and Conjugate 12 *in vitro* Fcγ receptor IIIA binding

Toxicokinetics on days 1 and 8

Mean plasma concentrations following 5 mg/kg IV or SC administration

Conjugate 12

Conjugates 13a-13g

Conjugate 6 *in vivo* efficacy in immune compromised mice

Conjugate 6 *in vivo* efficacy in immune compromised mice

Conjugate 6 dose-dependent viral clearance in lungs

Conjugate 6 dose-dependent reduction in inflammatory cytokines in lungs

Pharmacokinetics of Conjugate 6 in BALB/c SCID mice and CD-1 mice
5 mg/kg IV, single dose Conjugate 33

SEQ ID NO: 64

COMPOSITIONS AND METHODS FOR THE TREATMENT OF VIRAL INFECTIONS

SEQUENCE LISTING

The instant application contains a Sequence Listing which has been submitted electronically in XML format and is hereby incorporated by reference in its entirety. Said XML copy, created on Aug. 10, 2023, is named "50945-0400016_Sequence_Listing_8_10_23" and is 124,415 bytes in size.

BACKGROUND

The need for novel antiviral treatments for influenza is significant and especially critical in the medical field. Influenza virus, the causative agent of influenza, or the flu, is responsible for three to five million cases of severe illness annually, and approximately 500,000 deaths worldwide. While most people recover completely from influenza in about one to two weeks, others develop life-threatening complications, such as pneumonia. Thus, influenza can be deadly, especially for the young, old, or chronically ill. People with weak or compromised immune systems, such as people with advanced HIV infection or transplant patients, whose immune systems are medically suppressed to prevent transplant organ rejection, are at greater risk for complications relating to influenza. Pregnant women and young children are also at a high risk for complications.

The development of antiviral treatments for influenza has been a continuing challenge. Several influenza antiviral agents have been approved for use in the clinic, and these agents play important roles in modulating disease severity and controlling pandemics while vaccines are prepared. However, drug-resistant strains have emerged to the most commonly used inhibitors.

Influenza antiviral agents largely target proteins presented on the surface of the influenza virus particle. The envelope of the influenza virus contains two immunodominant glycoproteins, hemagglutinin and neuraminidase, that play key roles in viral infection and spread. Hemagglutinin effects attachment of the virus to the host cell through its interaction with surface sialic acids, thereby initiating entry.

Neuraminidase is an exo-glycosidase enzyme that cleaves sialic acids (terminal neuraminic acid residues) from glycan structures on the surface of infected host cells, releasing progeny viruses and allowing the spread of the virus from the host cell to uninfected surrounding cells. Inhibition of neuraminidase therefore serves as a pharmacological target for antiviral drugs. Viral neuraminidase inhibitors used to reduce viral spread have been identified, including oseltamivir (Tamiflu™), zanamivir (Relenza™), and peramivir (Rapivab™).

However, influenza in transplant recipients remains characterized by prolonged viral shedding, increasing the likelihood of developing drug resistant strains. New, more effective therapies for treating influenza are needed.

SUMMARY

The disclosure relates to conjugates, compositions, and methods for inhibiting viral growth, and methods for the treatment of viral infections. In particular, such conjugates contain monomers or dimers of a moiety that inhibits influenza virus neuraminidase (e.g., zanamivir, peramivir, or analogs thereof) conjugated to Fc monomers, Fc domains, Fc-binding peptides, albumin proteins, or albumin protein-binding peptides. The neuraminidase inhibitor (e.g., zanamivir, peramivir, or analogs thereof) in the conjugates targets neuraminidase on the surface of the viral particle. The Fc monomers or Fc domains in the conjugates bind to FcγRs (e.g., FcRn, FcγRI, FcγRIIa, FcγRIIc, FcγRIIIa, and FcγRIIIb) on immune cells, e.g., neutrophils, to activate phagocytosis and effector functions, such as antibody-dependent cell-mediated cytotoxicity (ADCC), thus leading to the engulfment and destruction of viral particles by immune cells and further enhancing the antiviral activity of the conjugates. The albumin or albumin-binding peptide may extend the half-life of the conjugate, for example, by binding of albumin to the recycling neonatal Fc receptor. Such compositions are useful in methods for the inhibition of viral growth and in methods for the treatment of viral infections, such as those caused by an influenza virus A, influenza virus B and influenza virus C.

In one aspect, the disclosure features a conjugate described by formula (1):

(1)

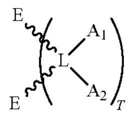

wherein each $A_1$ and each $A_2$ is independently selected from any one of formulas (A-I)-(A-XII):

(A-I)

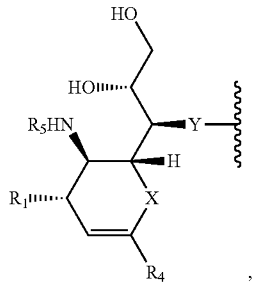

, (A-II)

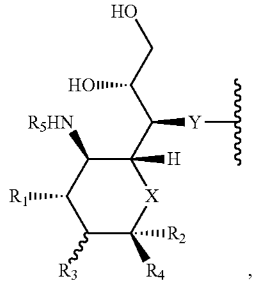

, (A-III)

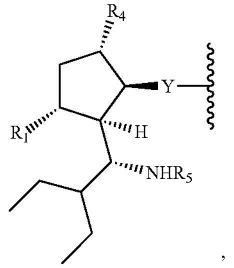

,

-continued
(A-IV)
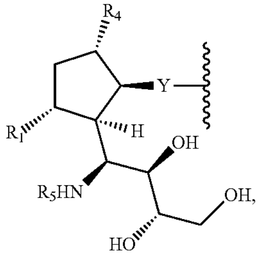
(A-V)
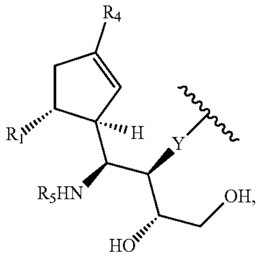
(A-VI)
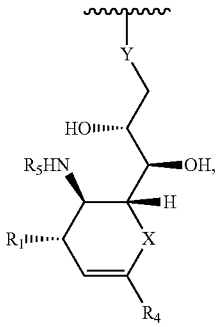
(A-VII)
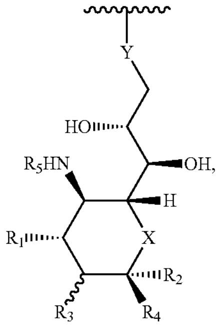
(A-VIII)
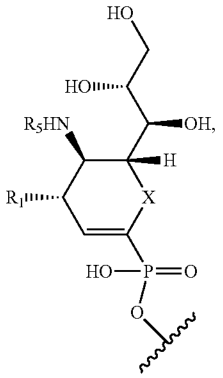
-continued
(A-IX)
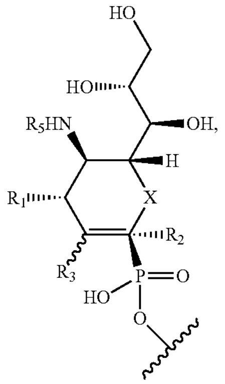
(A-X)
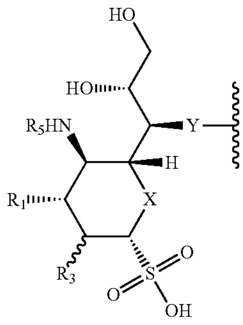
,
(A-XI)
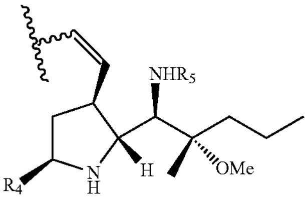
;
(A-XII)
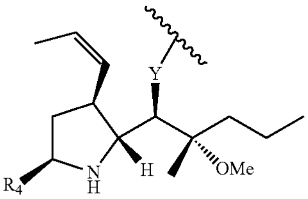
;
wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from
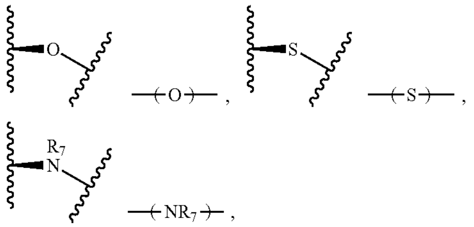

-continued
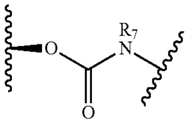
$-(O(C{=}O)NR_7)-$ ,
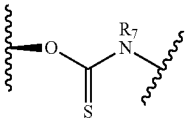
$-(O(C{=}O)NR_7)-$ ,
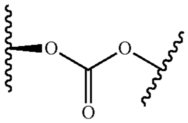
$-(O(C{=}O)O)-$ ,
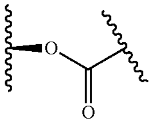
$-(O(C{=}O))-$
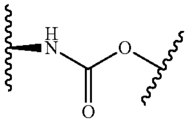
$-(NH(C{=}O)O)-$ ,
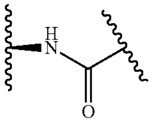
$-(NH(C{=}O))-$ ,
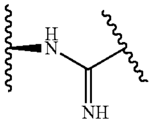
$-(NH(C{=}NH))-$ ,
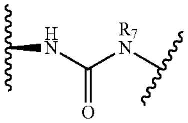
$-(NH(C{=}S)NR_7)-$ ,
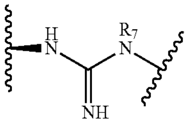
$-(NH(C{=}S)NR_7)-$ ,
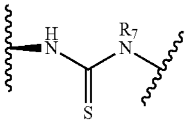
$-(NH(C{=}S)NR_7)-$ ,
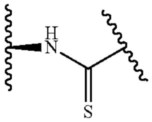
$-(NH(C{=}S))-$ ,
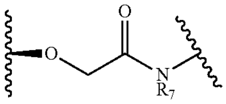
$-(OCH_2(C-O)NR_7)-$ ,
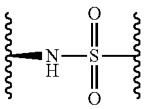
$-(NH(SO_2))-$ ,
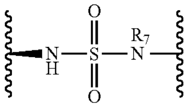
$-(NH(SO_2)NR_7)-$ ,
-continued
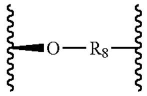
$-(OR_8)-$ ,
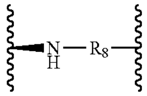
$-(NR_8)-$ , and
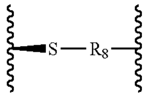
$-(SR_8)-$ ;
$R_6$ is selected from
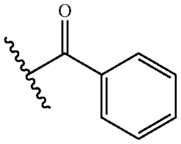 , 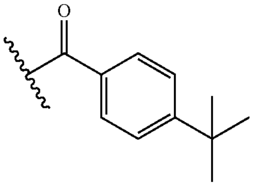 ,
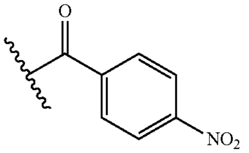 , 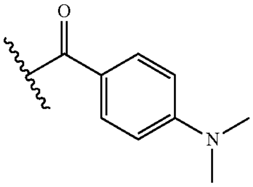 ,
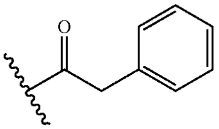 , 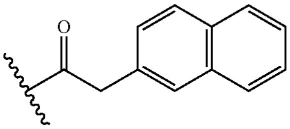 ,
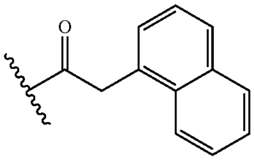 , 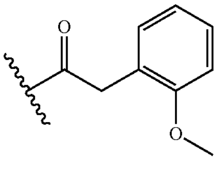 ,
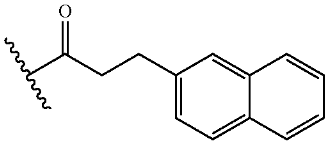 ,
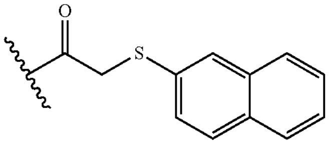 ,
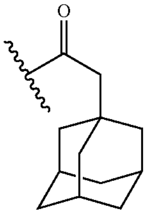 , 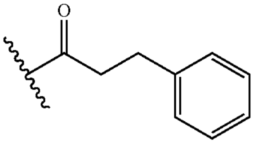 ,
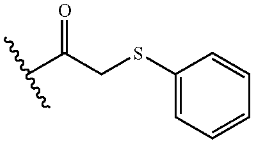 , 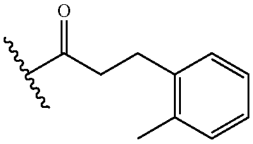 , -continued

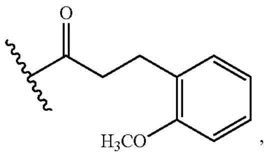,
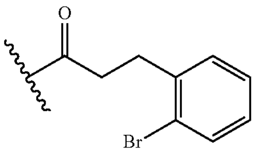,
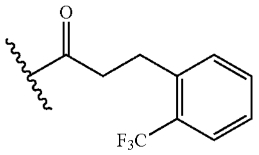,
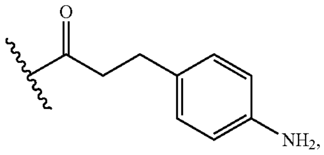
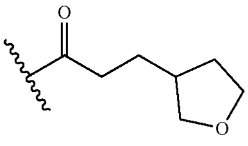,
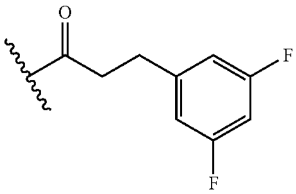,
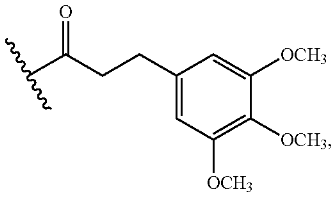
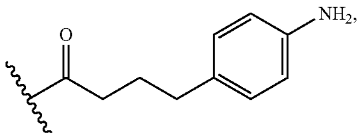
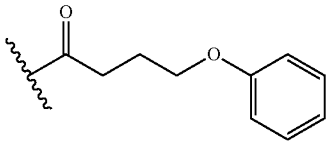,
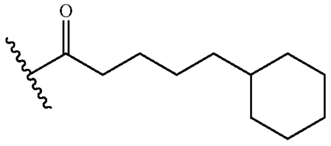,
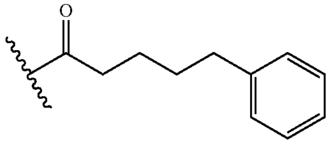,
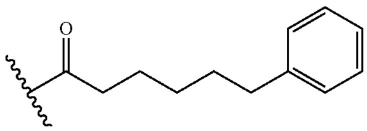, -continued

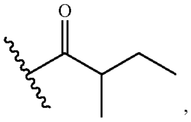,
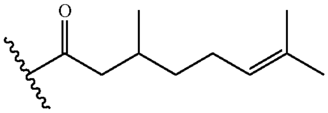,
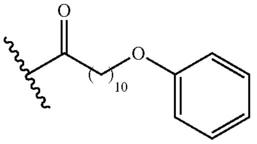,
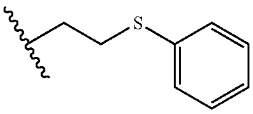,
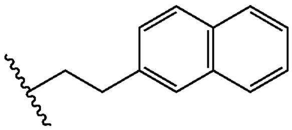, and
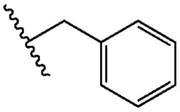;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68); L in each $A_1$-L-$A_2$ is a linker covalently attached to a sulfur atom of a hinge cysteine in each E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two Es indicate that each $A_1$-L-$A_2$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the disclosure features a conjugate described by formula (1):

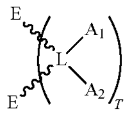
(1)

wherein each $A_1$ and each $A_2$ is independently selected from any one of formulas (A-I)-(A-V):

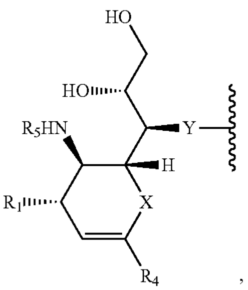
(A-I)
,

-continued (A-II)

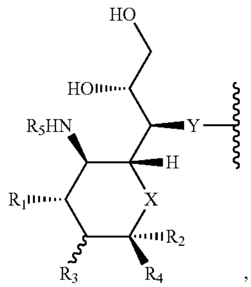

, (A-III)

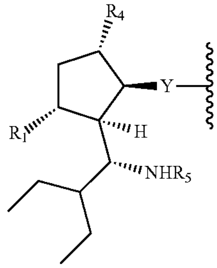

, (A-IV)

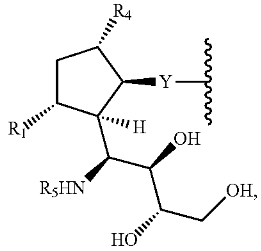

(A-V)

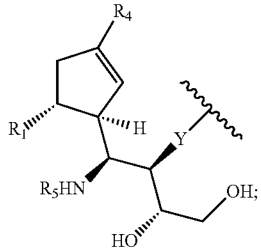

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

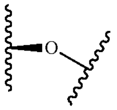 (—O—),

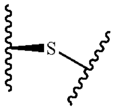 (—S—),

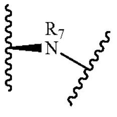 (—$NR_7$—),

-continued

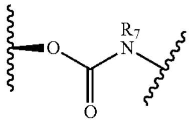 (—O(C═O)$NR_7$—),

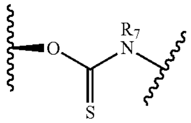 (—O(C═S)$NR_7$—),

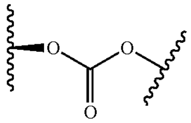 (—O(C═O)O—),

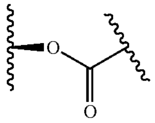 (—O(C═O)—),

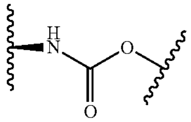 (—NH(C=O)O—),

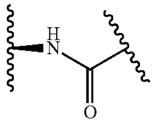 (—NH(C=O)—),

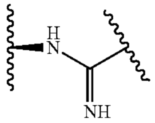 (—NH(C=NH)—),

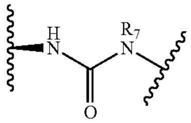 (—NH(C=O)$NR_7$—),

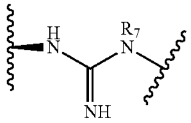 (—NH(C=NH)$NR_7$—),

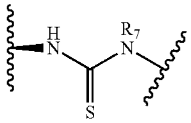 (—NH(C=S)$NR_7$—),

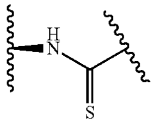 (—NH(C=S)—),

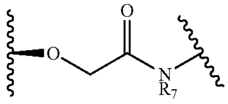 (—$OCH_2$(C═O)$NR_7$—),

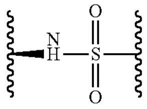 (—NH($SO_2$)—),

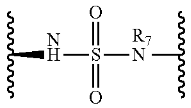 (—NH($SO_2$)$NR_7$—),

-continued
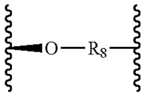 (—$OR_8$—),
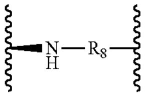 (—$NR_8$—), and
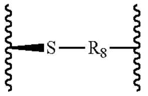 (—$SR_8$—);
$R_6$ is selected from
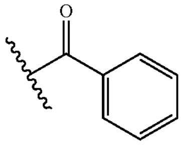, 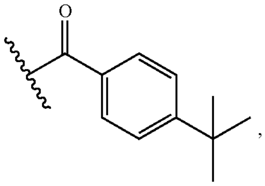,
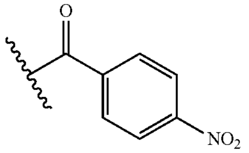, 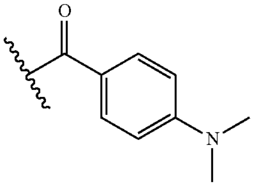,
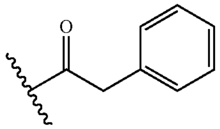, 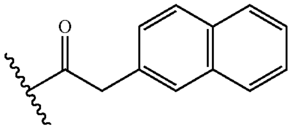,
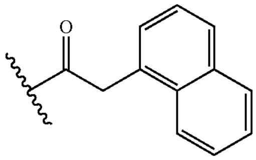, 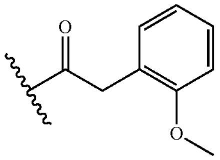,
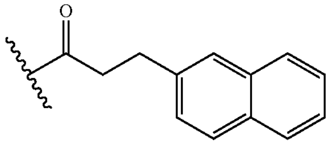,
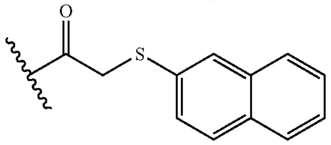,
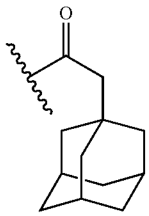, 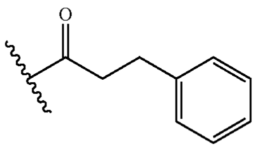,
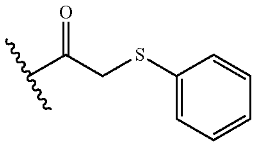, 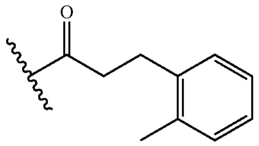,
-continued
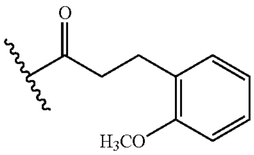, 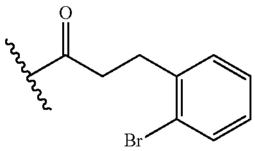,
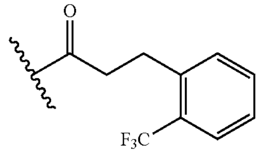,
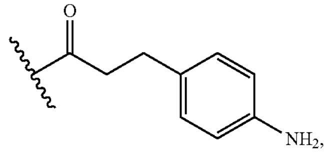
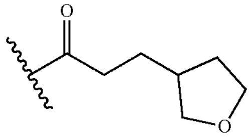, 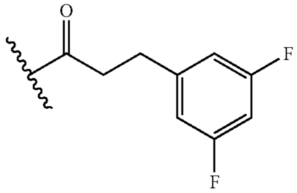,
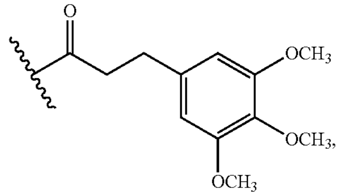
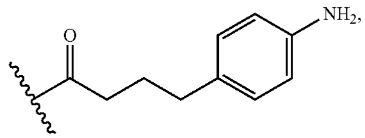
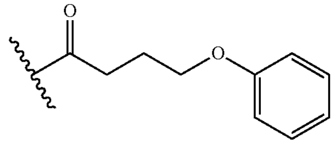,
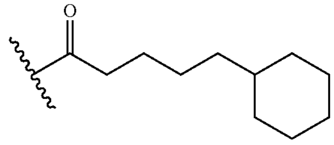,
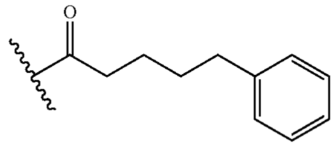,
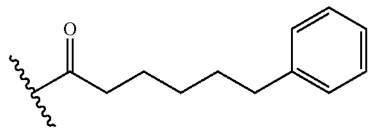,
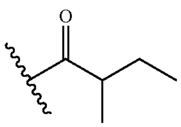, 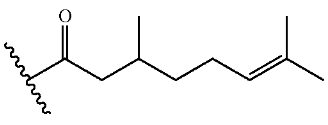, -continued

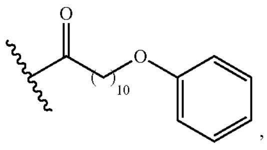,

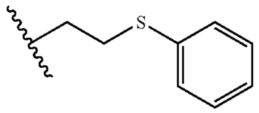,

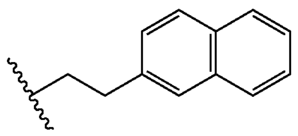, and

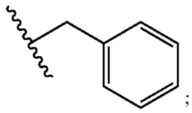;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68); L in each $A_1$-L-$A_2$ is a linker covalently attached to a sulfur atom of a hinge cysteine in each E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two Es indicate that each $A_1$-L-$A_2$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the disclosure features a conjugate described by formula (1):

(1)

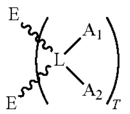

wherein each $A_1$ and each $A_2$ is independently selected from any one of formulas (A-VI)-(A-IX):

(A-VI)

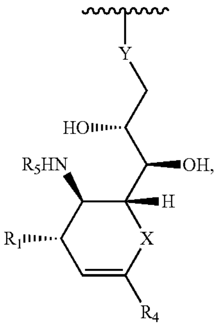

-continued (A-VII)

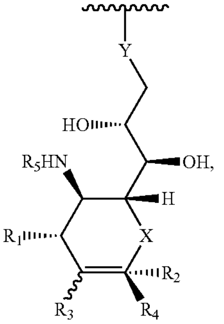

(A-VIII)

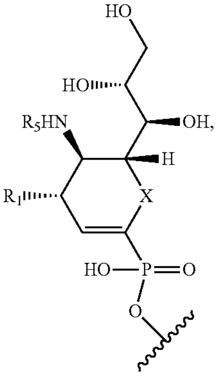

(A-IX)

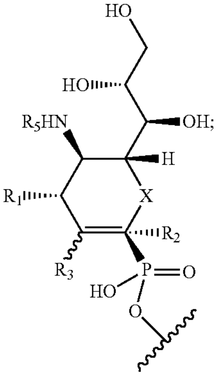

wherein $R_1$ is selected from —OH, —$NH_2$, —NHC(═NH)$NH_2$, and —NHC(═NH)NHR$_6$; $R_2$ and $R_3$ are each independently selected from —H, —OH, —F, —Cl, and —Br; $R_4$ is selected from —$CO_2H$, —P(═O)$(OH)_2$, —$SO_3H$; Rs is selected from —$COCH_3$, —$COCF_3$, —$SO_2CH_3$; X is selected from —O— and —S—; Y is selected from

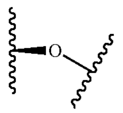 (—O—),

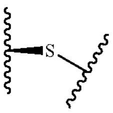 (—S—),

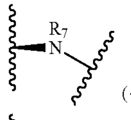 (—NR$_7$—),

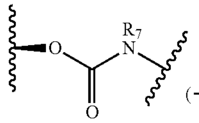 (—O(C═O)NR$_7$—),

-continued
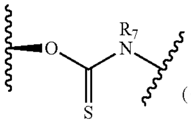 (—O(C=S)$NR_7$—),
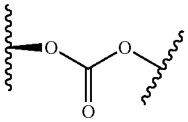 (—O(C=O)O—),
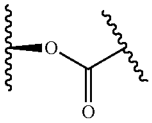 (—O(C=O)—),
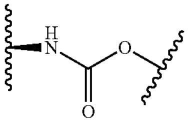 (—NH(C=O)O—),
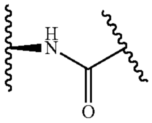 (—NH(C=O)—),
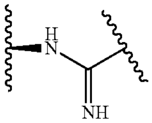 (—NH(C=NH)—),
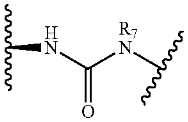 (—NH(C=O)$NR_7$—),
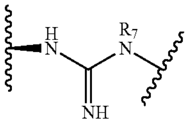 (—NH(C=NH)$NR_7$—),
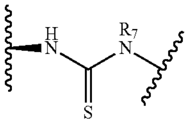 (—NH(C=S)$NR_7$—),
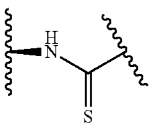 (—NH(C=S)—),
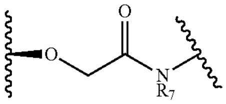 (—$OCH_2$(C=O)$NR_7$—),
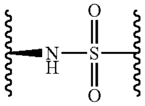 (—NH($SO_2$)—),
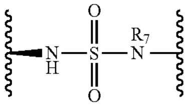 (—NH($SO_2$)$NR_7$—),
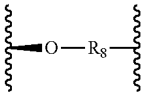 (—$OR_8$—),
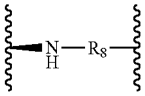 (—$NR_8$—), and
-continued
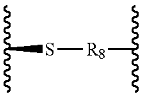 (—$SR_8$—);
$R_6$ is selected from
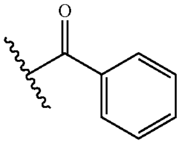, 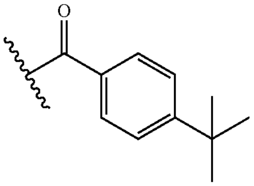,
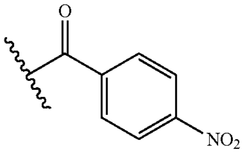, 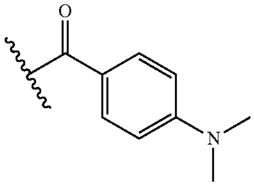,
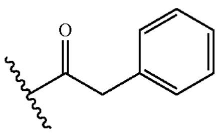, 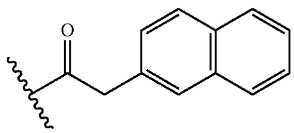,
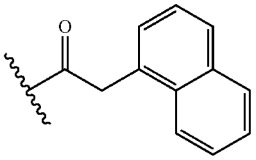, 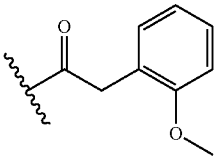,
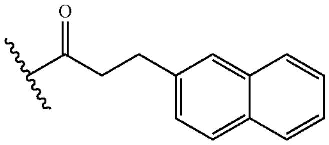,
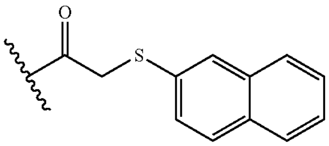,
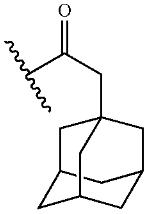, 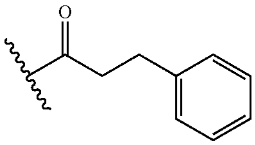,
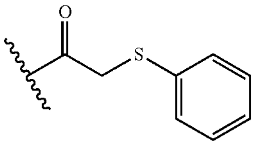, 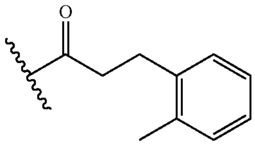,
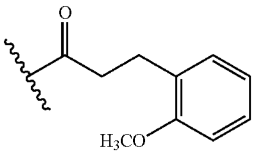, 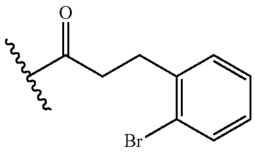, -continued

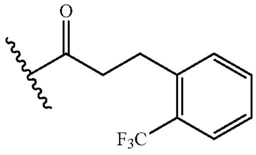,

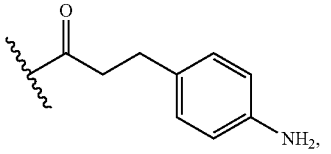

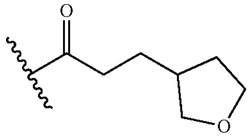, 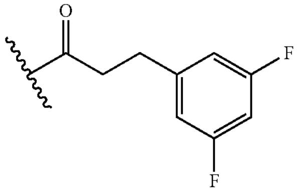

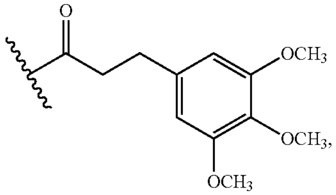

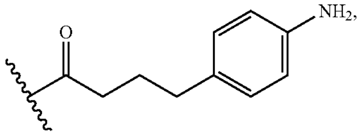

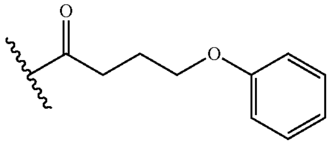,

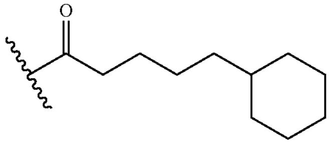,

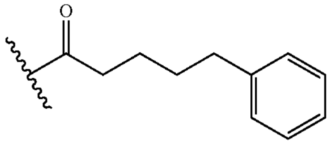,

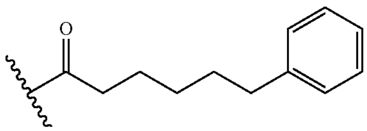,

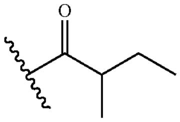, 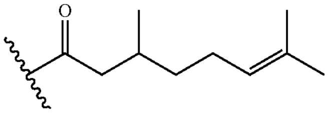,

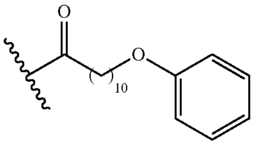, 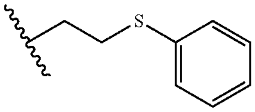,

-continued

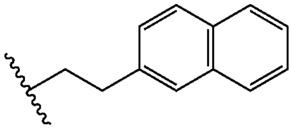, and 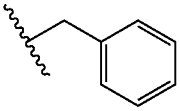;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68); L in each $A_1$-L-$A_2$ is a linker covalently attached to a sulfur atom of a hinge cysteine in each E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two Es indicate that each $A_1$-L-$A_2$ is covalently attached (e.g., by way of a covalent bond or a linker) to a pair of sulfur atoms of two hinge cysteines in the two Es, or a pharmaceutically acceptable salt thereof. When T is greater than 1 (e.g., Tis 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (2):

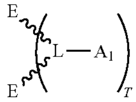

(2)

wherein each $A_1$ is independently selected from any one of formulas (A-I)-(A-XII):

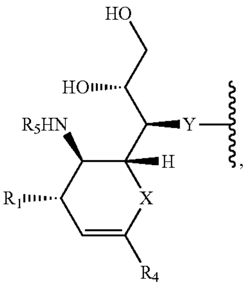

(A-I)

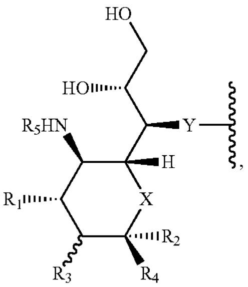

(A-II)

-continued
(A-III)
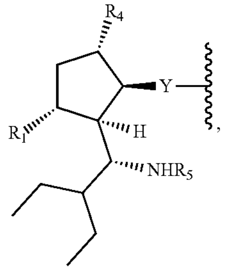
(A-IV)
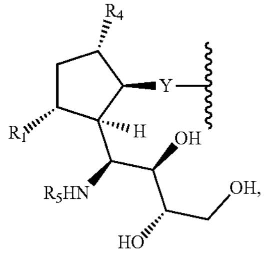
(A-V)
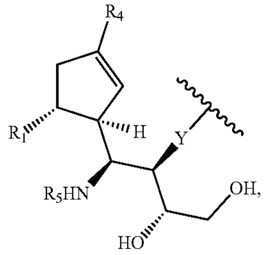
(A-VI)
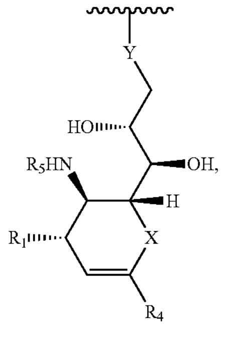
(A-VII)
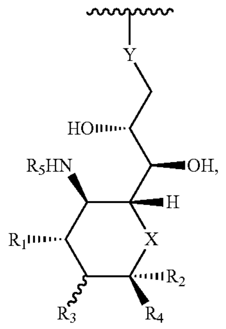
-continued
(A-VIII)
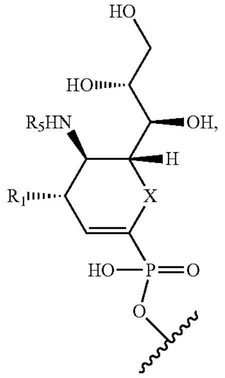
(A-IX)
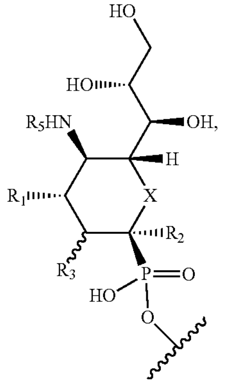
(A-X)
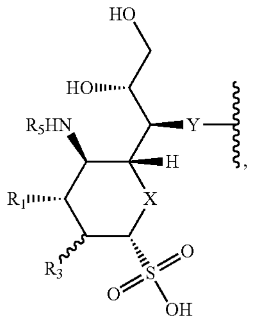
(A-XI)
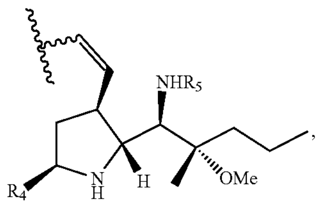
(A-XII)
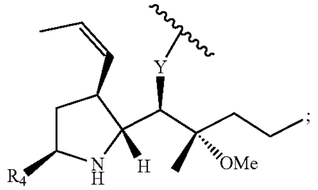
wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; Rs is selected from $—COCH_3$, $—COCF_3$, $—SO_2CH_3$; X is selected from —O— and —S—; Y is selected from
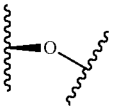 (—O—), 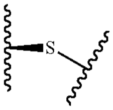 (—S—),
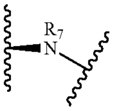 $(—NR_7—)$,
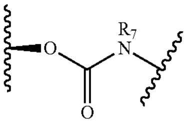 $(—O(C{=}O)NR_7—)$,
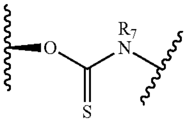 $(—O(C{=}S)NR_7—)$,
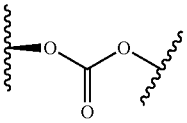 $(—O(C{=}O)O—)$,
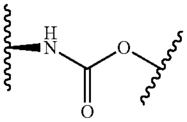 $(—NH(C{=}O)O—)$,
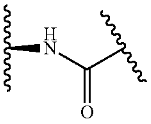 $(—NH(C{=}O)—)$,
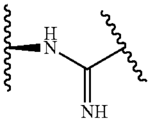 $(—NH(C{=}NH)—)$,
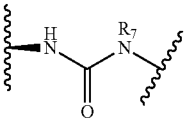 $(—NH(C{=}O)NR_7—)$,
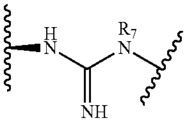 $(—NH(C{=}NH)NR_7—)$,
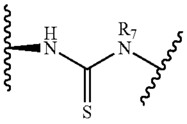 $(—NH(C{=}S)NR_7—)$,
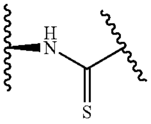 $(—NH(C{=}S)—)$,
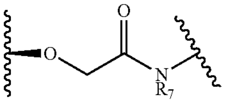 $(—OCH_2(C{=}O)NR_7—)$,
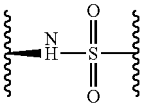 $(—NH(SO_2)—)$,
-continued
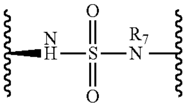 $(—NH(SO_2)NR_7—)$,
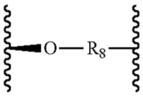 $(—OR_8—)$,
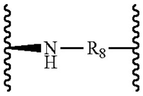 $(—NR_8—)$, and
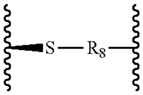 $(—SR_8—)$;
$R_6$ is selected from
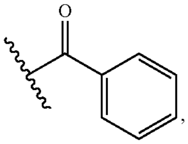, 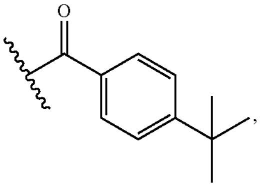,
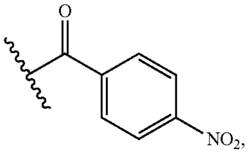 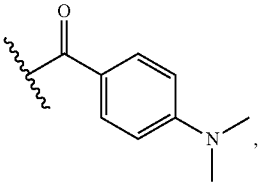,
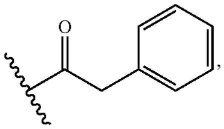, 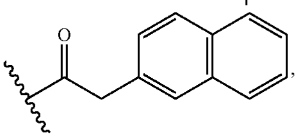,
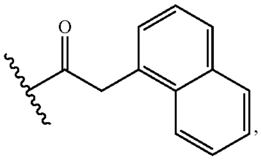, 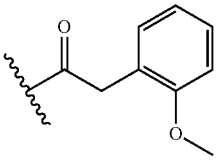,
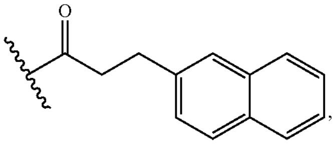,
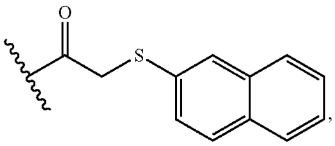,
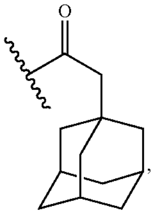, 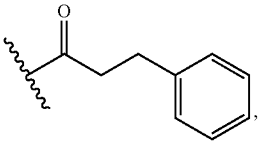, -continued

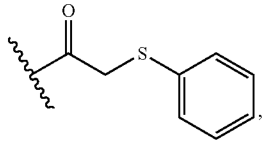,
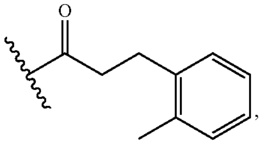,
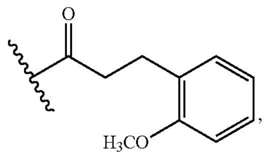,
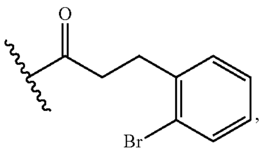,
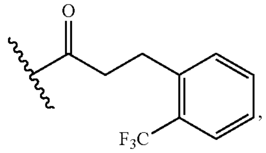,
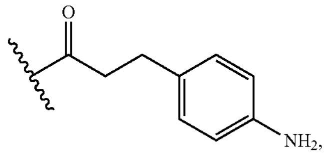,
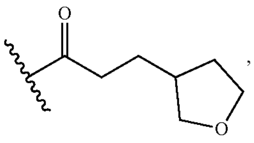,
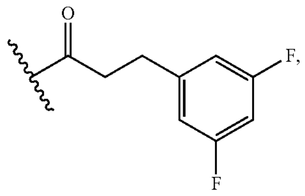,
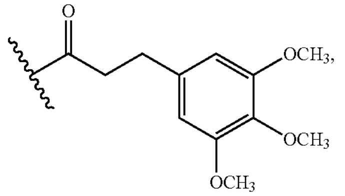,
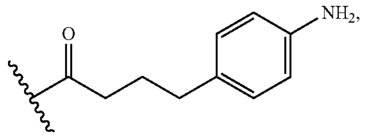,
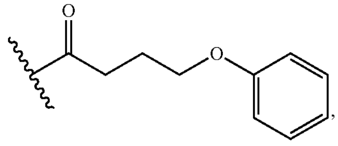,
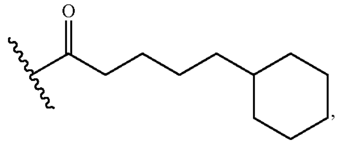,
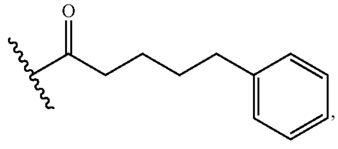,
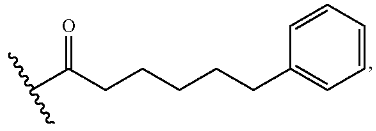, -continued

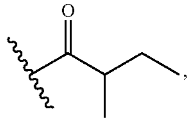,
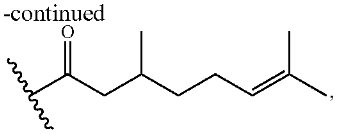,
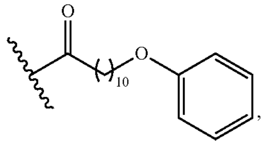,
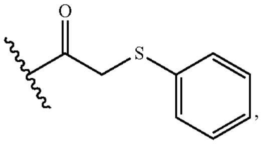,
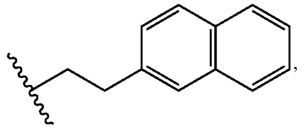, and
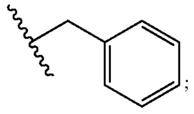;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68); L in each L-$A_1$ is a linker covalently attached to a sulfur atom in a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two sulfur atoms indicate that each L-$A_1$ is covalently (e.g., by way of a covalent bond or a linker) attached to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-XII).

In another aspect, the invention features a conjugate described by formula (2):

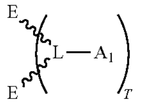

(2)

wherein each $A_1$ is independently selected from any one of formulas (A-I)-(A-V):

(A-I)

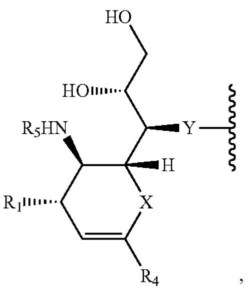,

-continued (A-II)

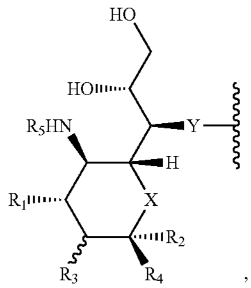

, (A-III)

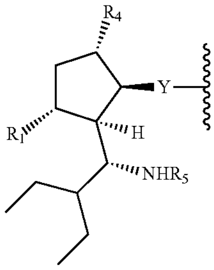

, (A-IV)

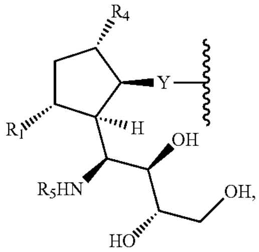

(A-V)

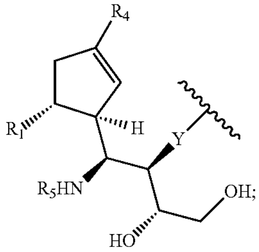

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; Rs is selected from —$COCH_3$, —$COCF_3$, —$SO_2CH_3$; X is selected from —O— and —S—; Y is selected from

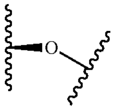

(—O—),

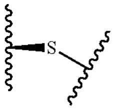

(—S—),

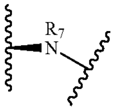

(—$NR_7$—),

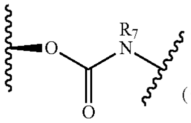

(—O(C═O)$NR_7$—),

-continued

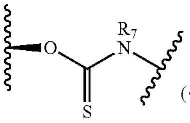

(—O(C═S)$NR_7$—),

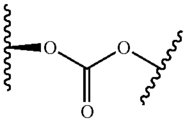

(—O(C═O)O—),

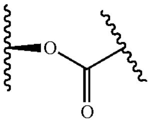

(—O(C═O)—),

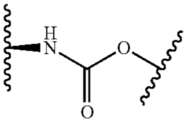

(—NH(C═O)O—),

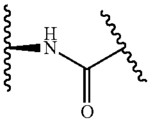

(—NH(C═O)—),

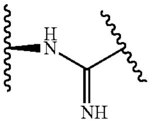

(—NH(C═NH)—),

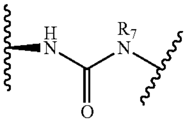

(—NH(C═O)$NR_7$—),

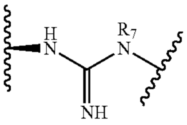

(—NH(C═NH)$NR_7$—),

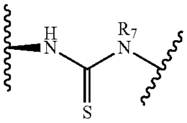

(—NH(C═S)$NR_7$—),

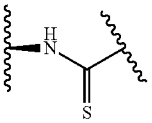

(—NH(C═S)—),

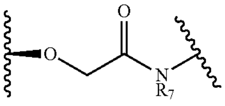

(—$OCH_2$(C═O)$NR_7$—),

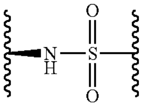

(—NH($SO_2$)—),

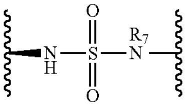

(—NH($SO_2$)$NR_7$—),

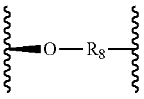

(—$OR_8$—),

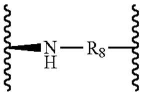

(—$NR_8$—), and

-continued
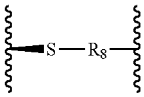 (—$SR_8$—);
$R_6$ is selected from
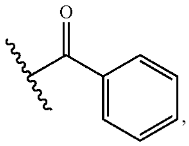, 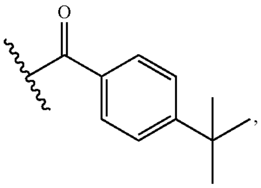,
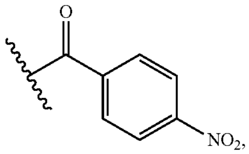 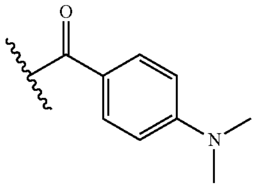,
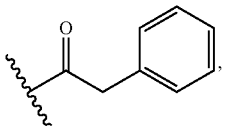, 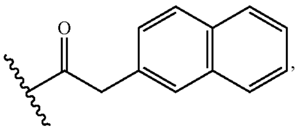,
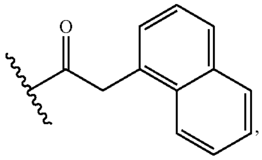, 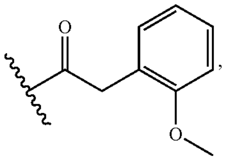,
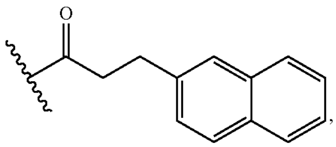,
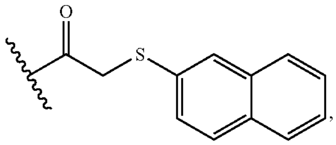,
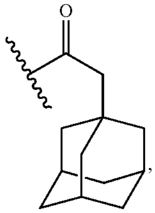, 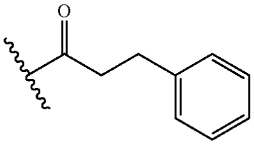,
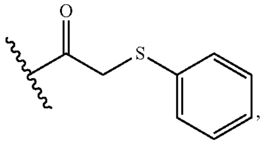, 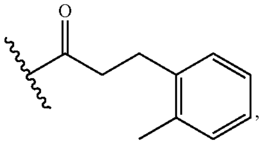,
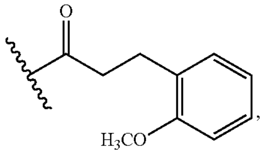, 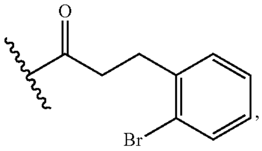,
-continued
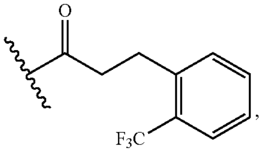,
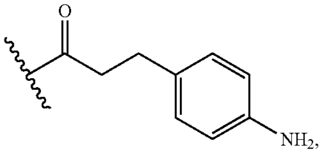
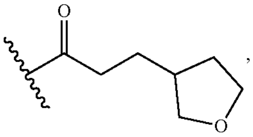, 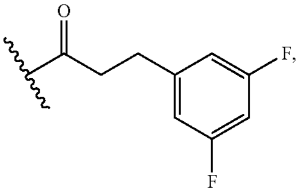
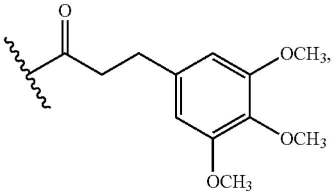
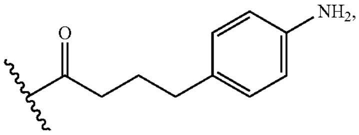
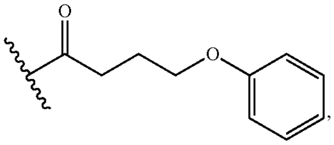,
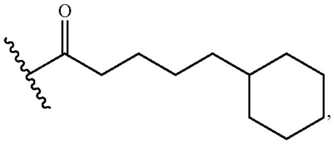,
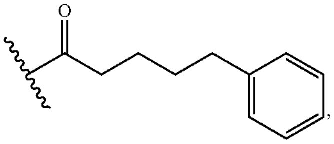,
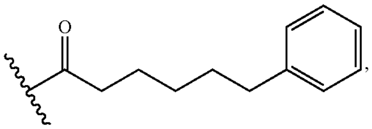,
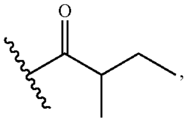, 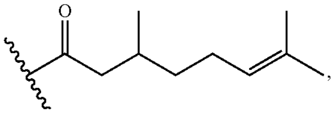,
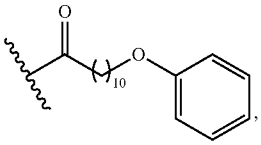, 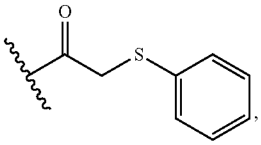, -continued

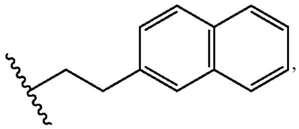
, and
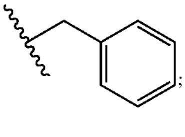
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68); L in each L-$A_1$ is a linker covalently attached to a sulfur atom in a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two sulfur atoms indicate that each L-$A_1$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-1)-(A-V).

In another aspect, the invention features a conjugate described by formula (2):

(2)

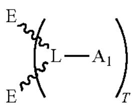

wherein each $A_1$ is independently selected from any one of formulas (A-VI)-(A-IX):

(A-VI)

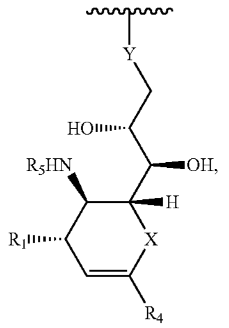

(A-VII)

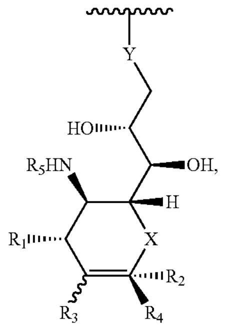

-continued (A-VIII)

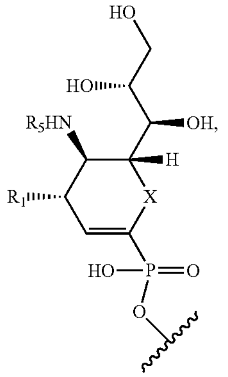

(A-IX)

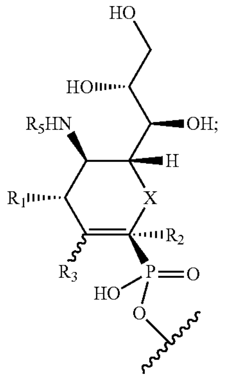

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; Rs is selected from —$COCH_3$, —$COCF_3$, —$SO_2CH_3$; X is selected from —O— and —S—; Y is selected from

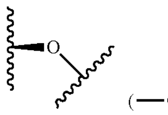
(—O—),
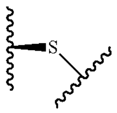
(—S—),

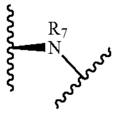
(—$NR_7$—),

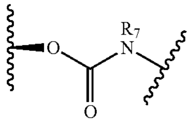
(—O(C=O)$NR_7$—),

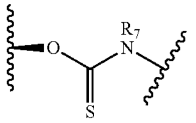
(—O(C=S)$NR_7$—),

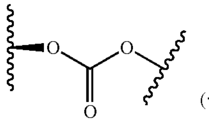
(—O(C=O)O—),

-continued
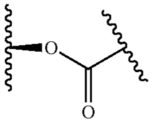
(—O(C=O)—),
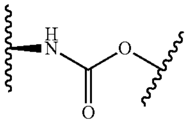
(—NH(C=O)O—),
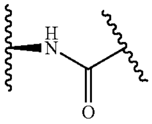
(—NH(C=O)—),
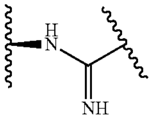
(—NH(C=NH)—),
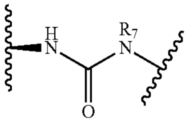
(—NH(C=O)$NR_7$—),
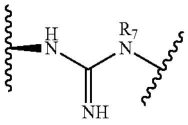
(—NH(C=NH)$NR_7$—),
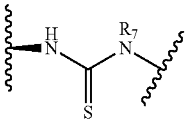
(—NH(C=S)$NR_7$—),
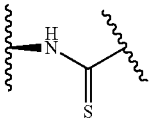
(—NH(C=S)—),
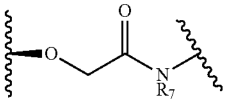
(—$OCH_2$(C=O)$NR_7$—),
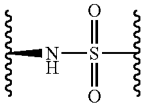
(—NH($SO_2$)—),
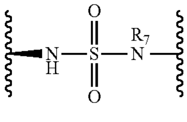
(—NH($SO_2$)$NR_7$—),
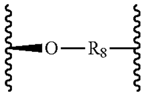
(—$OR_8$—),
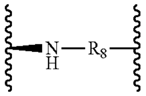
(—$NR_8$—), and
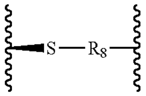
(—$SR_8$—);
$R_6$ is selected from
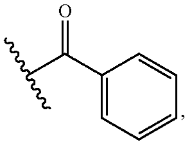
,
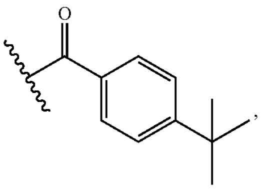
,
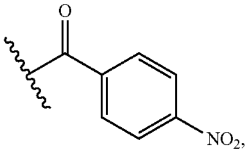
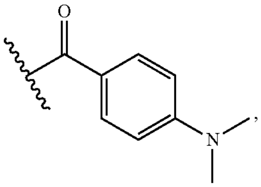
,
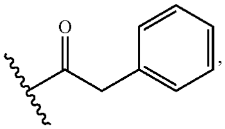
,
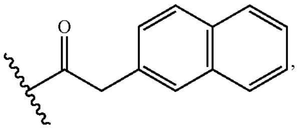
,
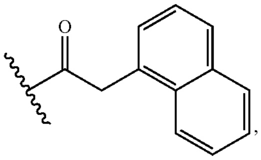
,
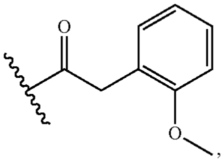
,
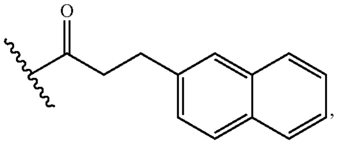
,
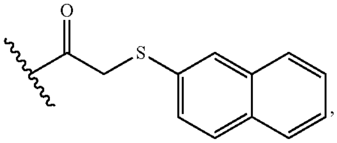
,
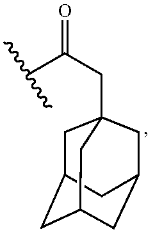
,
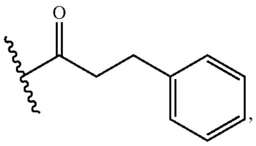
,
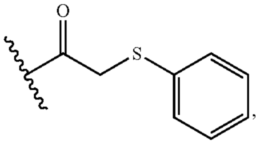
,
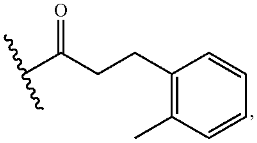
, -continued

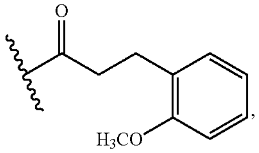,

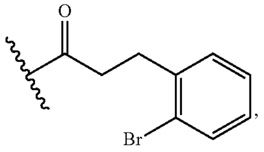,

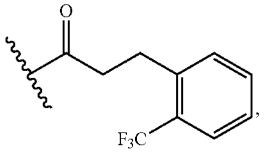,

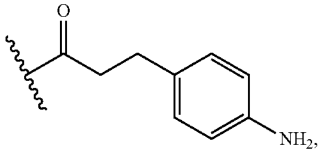,

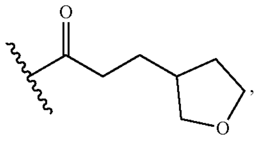,

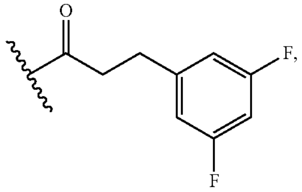,

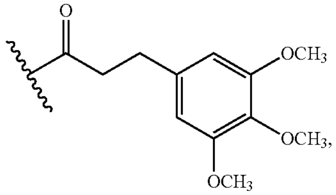,

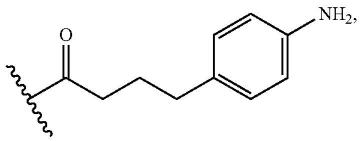,

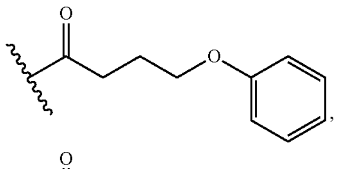,

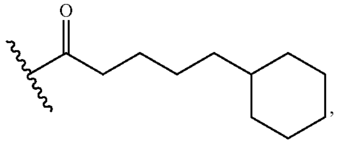,

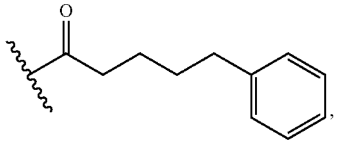,

-continued

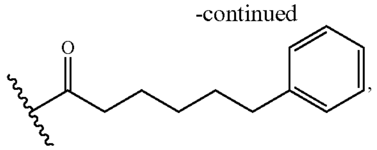,

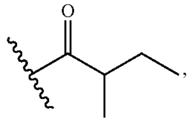, 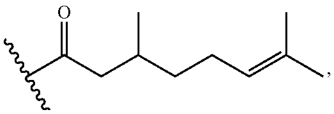,

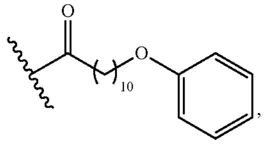,

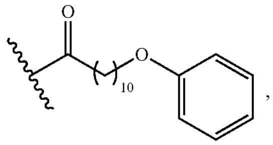,

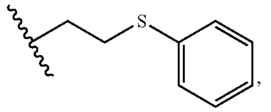,

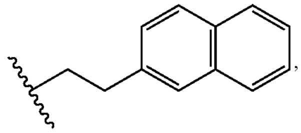, and

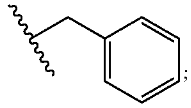;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68); L in each L-$A_1$ is a linker covalently attached to a sulfur atom in a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20), and the two squiggly lines connected to the two sulfur atoms indicate that each L-$A_1$ is covalently attached (e.g., by way of a covalent bond or a linker) to a pair of sulfur atoms of two hinge cysteines in the two Es, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-VI)-(A-IX).

In some embodiments of any of the foregoing embodiments, each E includes an Fc domain monomer having the sequence of any one of SEQ ID NOs: 1-68.

In some embodiments, each E comprises the sequence

```
                                          (SEQ ID NO: 10)
MVRSDKTHTCPPCPPC*KC*PAPELLGGPSVFLFPPKPKDTLMISRTPE

VTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRE
```

-continued

```
EMTKNQVSLTCLVKGFYPSDIAVEWESNGQPENNYKTTPPVLDSDGSFF

LYSKLTVDKSRWQQGNVFSCSVMHEALHNHYTQKSLSLSPGKHHHHHH.
```

In some embodiments, each E comprises the sequence

```
                                      (SEQ ID NO: 11)
MVRSDKTHTCPPCPPC*KC*PAPELLGGPSVFLFPPKPKDTLMISRTPE

VTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFF

LYSKLTVDKSRWQQGNVFSCSVMHEALHNHYTQKSLSLSPGK.
```

In some embodiments, at least one of the pair of sulfur atoms is the sulfur atom corresponding to (e.g., the sulfur atom of) a hinge cysteine of SEQ ID NO: 10 or SEQ ID NO: 11, i.e., Cys10, Cys13, Cys16, or Cys18 of SEQ ID NO: 10 or SEQ ID NO: 11. In some embodiments, the pair of sulfur atoms are the sulfur atoms corresponding to (e.g., the sulfur atoms of) Cys10 and Cys13 in SEQ ID NO: 10 or SEQ ID NO: 11, Cys10 and Cys16 in SEQ ID NO: 10 or SEQ ID NO: 11, Cys 30 and Cys18 in SEQ ID NO: 10 or SEQ ID NO: 11, Cys13 and Cys 36 in SEQ ID NO: 10 or SEQ ID NO: 11, Cys13 and Cys 38 in SEQ ID NO: 10 or SEQ ID NO: 11, and/or Cys 36 and Cys 38 in SEQ ID NO: 10 or SEQ ID NO: 11.

In some embodiments, when T is 2, the pair of sulfur atoms are (e.g., the sulfur atoms corresponding to) Cys10 and Cys13 in SEQ ID NO: 10 or SEQ ID NO: 11 or Cys 36 and Cys 38 in SEQ ID NO: 10 or SEQ ID NO: 11.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 10 or SEQ ID NO: 11). In some embodiments, the pair of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E. In some embodiments, the pair of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E. In some embodiments, the pair of sulfur atoms are the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, the pair of sulfur atoms are the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E. In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 2, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E. In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 3, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E.

In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E; and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, the conjugate has the structure:

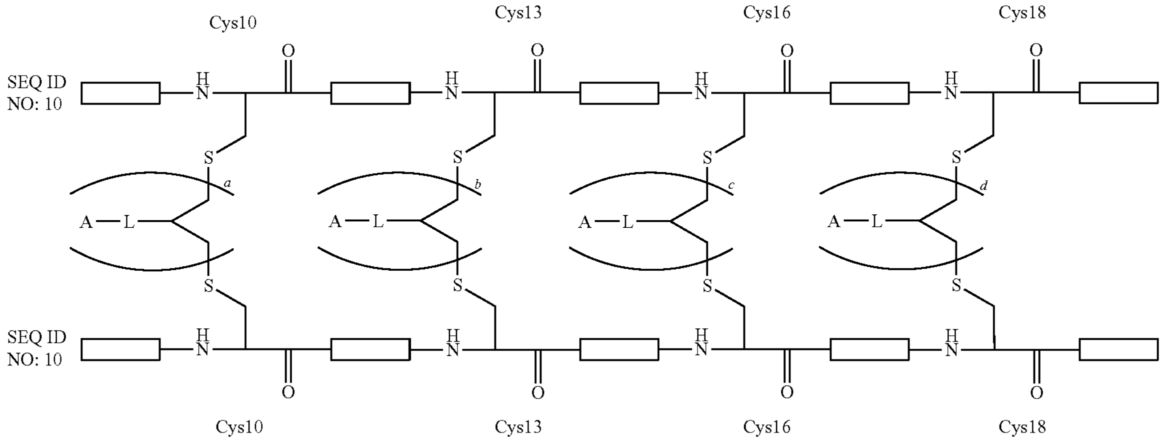

wherein each of a, b, c, and d is, independently, 0 or 1 and wherein when a, b, c, or d is 0, the two sulfur atoms form a disulfide bond.

In some embodiments, a is 1 and b, c, and d are 0. In some embodiments, a and b are 1 and c and d are 0. In some embodiments, a and c are 1 and b and d are 0. In some embodiments, a and d are 1 and b and c are 0. In some embodiments, a, b, and c are 1 and d is 0. In some embodiments, a, b, and d are 1 and c is 0. In some embodiments, a, c, and d are 1 and b is 0. In some embodiments, b and c are 1 and a and d are 0. In some embodiments, b and d are 1 and a and c are 0. In some embodiments, b, c, and d are 1 and a is 0. In some embodiments, c and d are 1 and a and b are 0. In some embodiments, a, b, c, and d are 1.

In some embodiments, each E comprises the sequence

```
                                              (SEQ ID NO: 4)
MVRSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQV

SLTCLVKGFYPSDIAVEWESNGQPENNYKTTPPVLDSDGSFFLYSKLTV

DKSRWQQGNVFSCSVMHEALHNHYTQKSLSLSPGK.
```

In some embodiments, each E comprises the sequence

```
                                             (SEQ ID NO: 33)
MVRSDKTHTCPPCPAPELLGGPSVFLFPPKPKDTLYITREPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQV
```

-continued

SLTCLVKGFYPSDIAVEWESNGQPENNYKTTPPVLDSDGSFFLYSKLTV

DKSRWQQGNVFSCSVMHEALHNHYTQKSLSLSPGK.

In some embodiments, at least one of the pair of sulfur atoms is the sulfur atom corresponding to (e.g., the sulfur atom of) a hinge cysteine of SEQ ID NO: 4 or SEQ ID NO: 33, i.e., Cys10 and/or Cys13. In some embodiments, the pair of sulfur atoms are the sulfur atoms corresponding to (e.g., the sulfur atoms of) Cys10 and Cys13 in SEQ ID NO: 4 or SEQ ID NO: 33.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 4 or SEQ ID NO: 33). In some embodiments, the pair of sulfur atoms are the sulfur atom corresponding to (e.g., the sulfur atom of) Cys10 of SEQ ID NO: 4 or SEQ ID NO: 33 from one E and the sulfur atom corresponding to (e.g., the sulfur atom of) Cys10 of SEQ ID NO: 4 or SEQ ID NO: 33 from another E. In some embodiments, the pair of sulfur atoms are the sulfur atom corresponding to (e.g., the sulfur atom of) Cys13 of SEQ ID NO: 4 or SEQ ID NO: 33 from one E and the sulfur atom corresponding to (e.g., the sulfur atom of) Cys13 of SEQ ID NO: 4 or SEQ ID NO: 33 from another E. In some embodiments, when T is 2, the pairs of sulfur atoms are the sulfur atom corresponding to (e.g., the sulfur atom of) Cys10 of SEQ ID NO: 4 or SEQ ID NO: 33 from one E and the sulfur atom corresponding to (e.g., the sulfur atom of) Cys10 of SEQ ID NO: 4 or SEQ ID NO: 33 from another E and the sulfur atom corresponding to (e.g., the sulfur atom of) Cys13 of SEQ ID NO: 4 or SEQ ID NO: 33 from one E and the sulfur atom corresponding to (e.g., the sulfur atom of) Cys13 of SEQ ID NO: 4 or SEQ ID NO: 33 from another E.

In some embodiments, the conjugate has the structure:

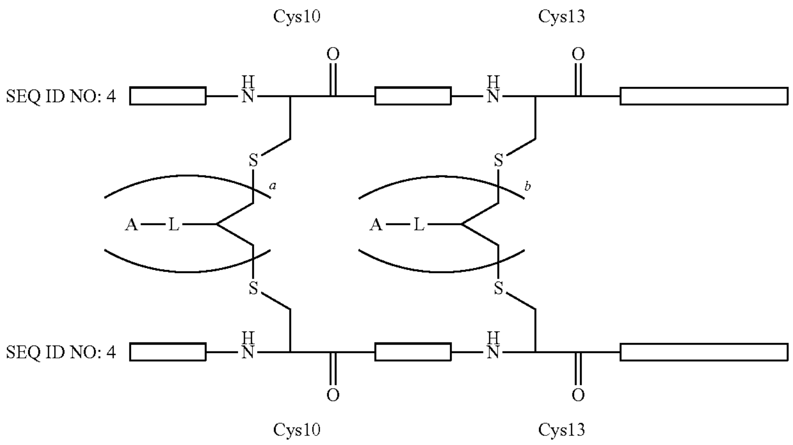

wherein each of a and b is, independently, 0 or 1 and wherein when a or b is 0, the two sulfur atoms form a disulfide bond. In some embodiments, a is 1 and b is 0. In some embodiments, a is 0 and b is 1. In some embodiments, a and b are 1.

In some embodiments, each E comprises the sequence

```
                                              (SEQ ID NO: 8)
MVRSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQV

SLTCLVKGFYPSDIAVEWESNGQPENNYKTTPPVLDSDGSFFLYSKLTV

DKSRWQQGNVFSCSVMHEALHNHYTQKSLSLSPGKHHHHHH.
```

In some embodiments, at least one of the pair of sulfur atoms is the sulfur atom corresponding to (e.g., the sulfur atom of) a hinge cysteine of SEQ ID NO: 8, i.e., Cys10 and/or Cys13. In some embodiments, the pair of sulfur atoms are the sulfur atoms corresponding to (e.g., the sulfur atoms of) Cys10 and Cys13 in SEQ ID NO: 8.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 8). In some embodiments, the pair of sulfur atoms are the sulfur atom corresponding to (e.g., the sulfur atom of) Cys10 of SEQ ID NO: 8 from one E and the sulfur atom corresponding to (e.g., the sulfur atom of) Cys10 of SEQ ID NO: 8 from another E. In some embodiments, the pair of sulfur atoms are the sulfur atom corresponding to (e.g., the sulfur atom of) Cys13 of SEQ ID NO: 8 from one E and the sulfur atom corresponding to (e.g., the sulfur atom of) Cys13 of SEQ ID NO: 8 from another E. In some embodiments, when T is 2, the pairs of sulfur atoms are the sulfur atom corresponding to (e.g., the sulfur atom of) Cys10 of SEQ ID NO: 8 from one E and the sulfur atom corresponding to (e.g., the sulfur atom of) Cys10 of SEQ ID NO: 8 from another E and the sulfur atom corresponding to (e.g., the sulfur atom of) Cys13 of SEQ ID NO: 8 from one E and the sulfur atom corresponding to (e.g., the sulfur atom of) Cys13 of SEQ ID NO: 8 from another E.

In some embodiments, the conjugate has the structure:

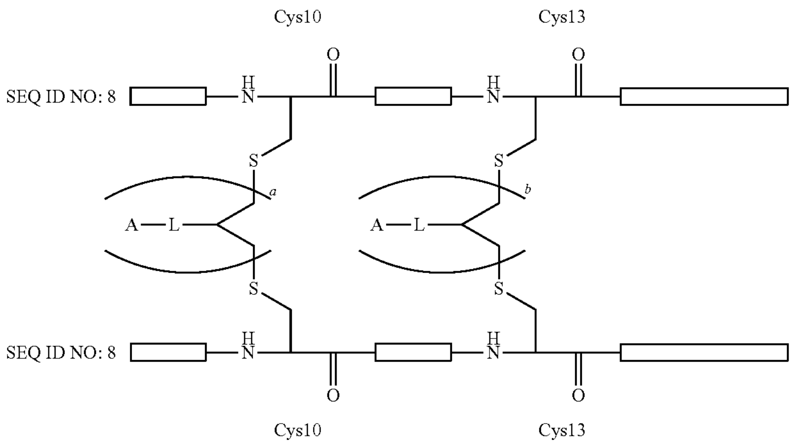

wherein each of a and b is, independently, 0 or 1 and wherein when a or b is 0, the two sulfur atoms form a disulfide bond. In some embodiments, a is 1 and b is 0. In some embodiments, a is 0 and b is 1. In some embodiments, a and b are 1.

In another aspect, the invention also features a population of conjugates described in any of the previous aspects, in which the average value of T is 1 to 20 (e.g., the average value of T is 1 to 2, 1 to 3, 1 to 4, 1 to 5, 5 to 10, 10 to 15, or 15 to 20). In some embodiments, the average value of T is 1, 2, 3, 4, 5, 6, 7, 8, 9, 10, 11, 12, 13, 14, 15, 16, 17, 18, 19, or 20.

In another aspect, the invention features a conjugate described by formula (3):

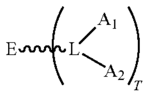

(3)

wherein each $A_1$ and each $A_2$ is independently selected from any one of formulas (A-I)-(A-VII):

(A-I)

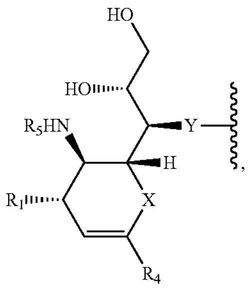

(A-II)

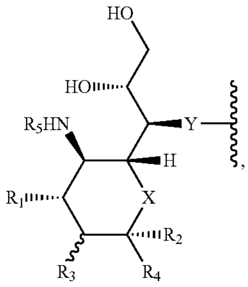

(A-III)

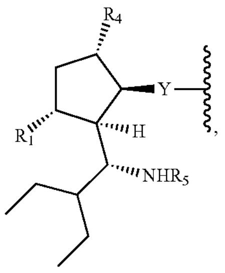

-continued (A-IV)

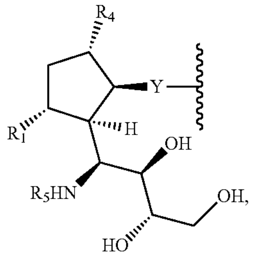

(A-V)

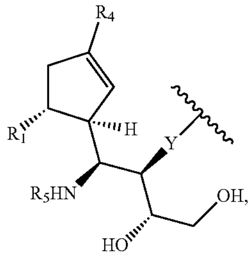

(A-VI)

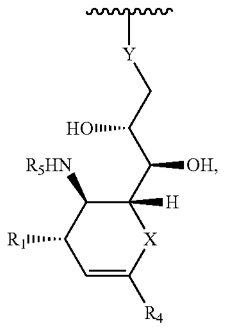

(A-VII)

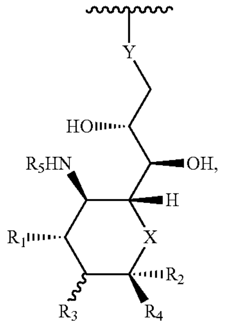

(A-VIII)

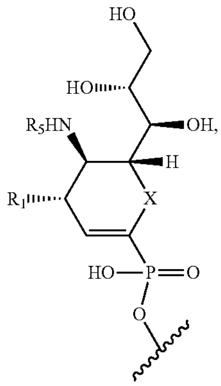

-continued (A-IX)

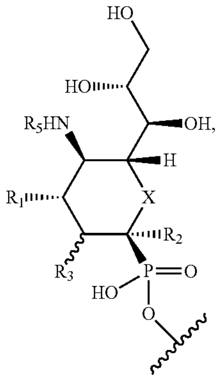

(A-X)

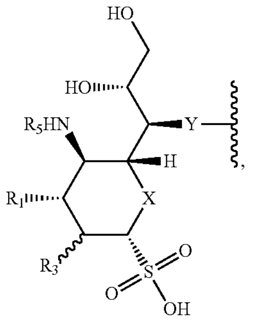

(A-XI)

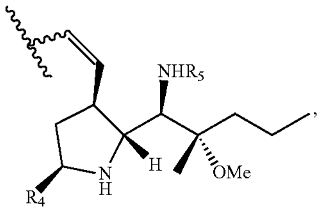

(A-XII)

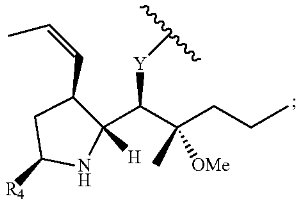

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

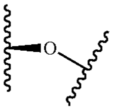

(—O—),

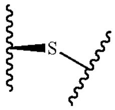

(—S—),

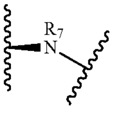

(—$NR_7$—),

-continued

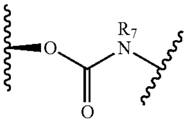

(—O(C=O)$NR_7$—),

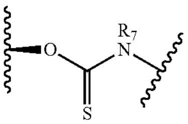

(—O(C=S)$NR_7$—),

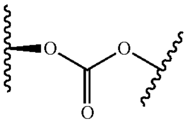

(—O(C=O)O—),

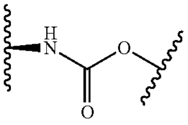

(—NH(C=O)O—),

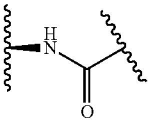

(—NH(C=O)—),

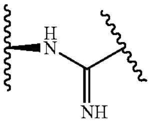

(—NH(C=NH)—),

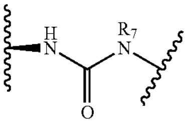

(—NH(C=O)$NR_7$—),

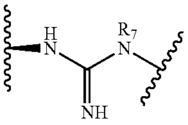

(—NH(C=NH)$NR_7$—),

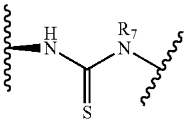

(—NH(C=S)$NR_7$—),

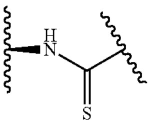

(—NH(C=S)—),

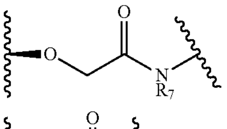

(—$OCH_2$(C=O)$NR_7$—),

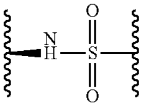

(—NH($SO_2$)—),

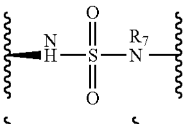

(—NH($SO_2$)$NR_7$—),

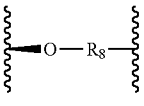

(—$OR_8$—),

-continued
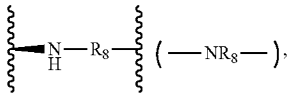 and
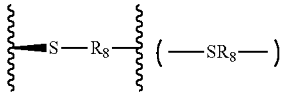;
$R_6$ is selected from
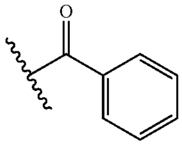, 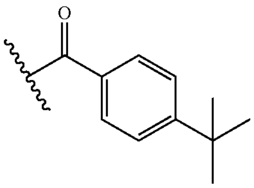,
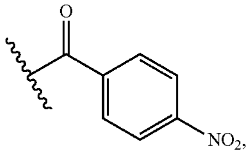 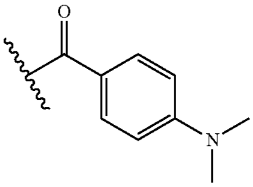,
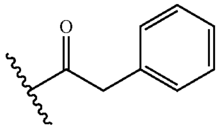, 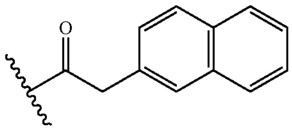,
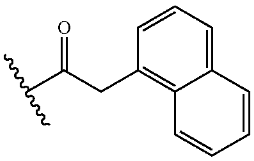,
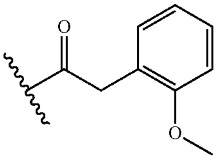,
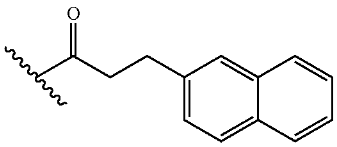,
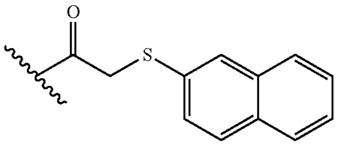,
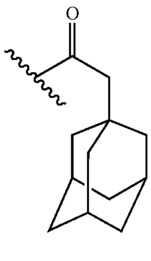,
-continued
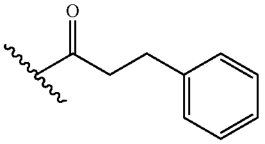,
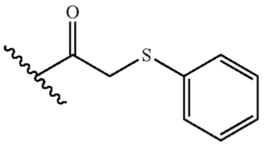,
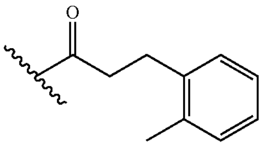,
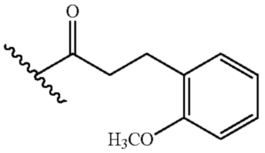,
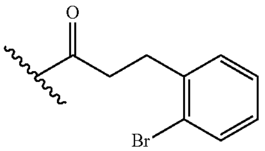,
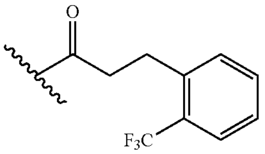,
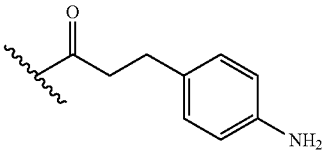,
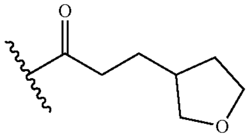,
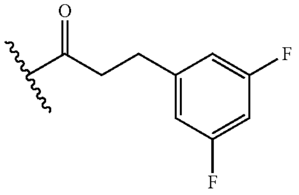,
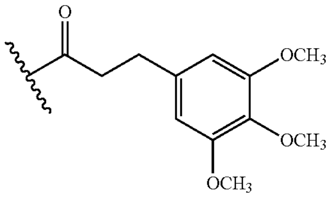,
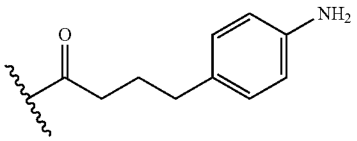, -continued

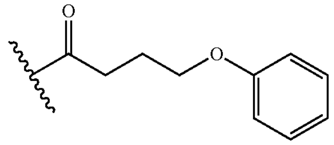
,

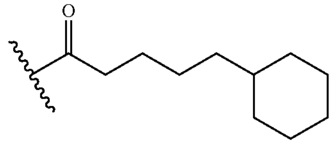
,

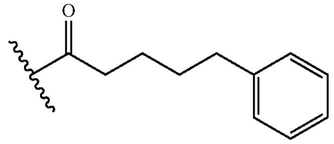
,

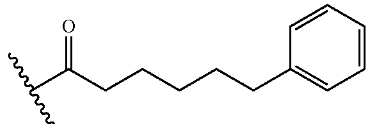
,

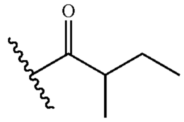
,

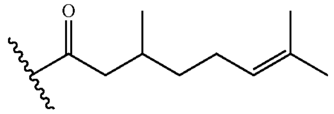
,

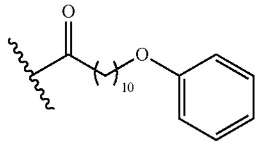
,

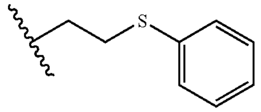
,

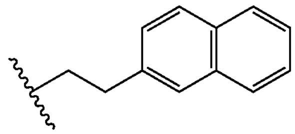
, and

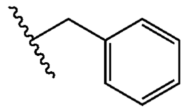
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each $A_1$-L-$A_2$ is a linker covalently attached to a sulfur atom of a hinge cysteine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is covalently (e.g., by way of a covalent bond or a linker) attached to a sulfur atom of a hinge cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (3):

(3)

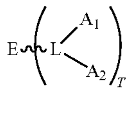

wherein each $A_1$ and each $A_2$ is independently selected from any one of formulas (A-I)-(A-V):

(A-I)

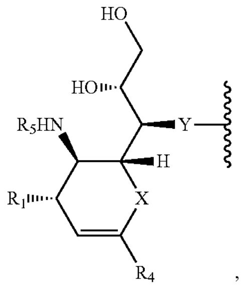
, (A-II)

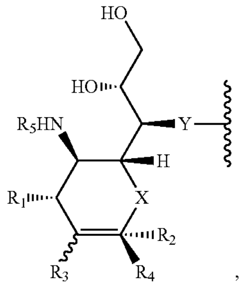
, (A-III)

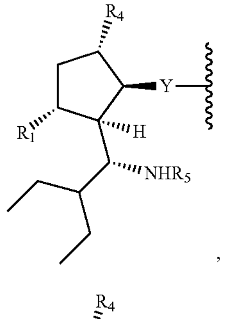
, (A-IV)

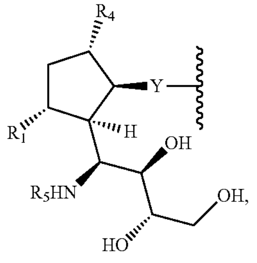

-continued (A-V)

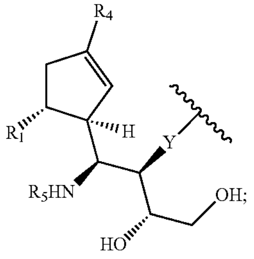

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

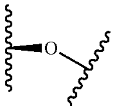 (—O—),

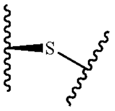 (—S—),

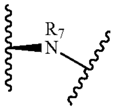 (—$NR_7$—),

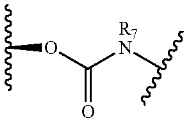 (—O(C═O)$NR_7$—),

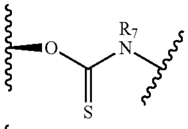 (—O(C═S)$NR_7$—),

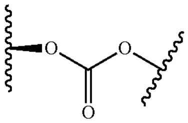 (—O(C═O)O—),

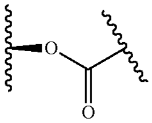 (—O(C═O)—),

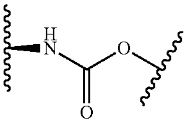 (—NH(C═O)O—),

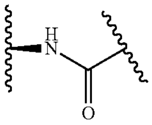 (—NH(C═O)—),

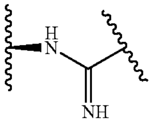 (—NH(C═NH)—),

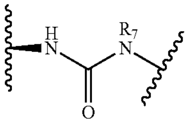 (—NH(C═O)$NR_7$—),

-continued

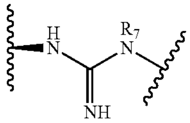 (—NH(C═NH)$NR_7$—),

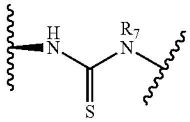 (—NH(C═S)$NR_7$—),

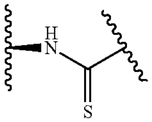 (—NH(C═S)—),

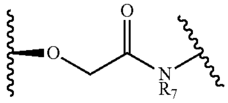 (—$OCH_2$(C═O)$NR_7$—),

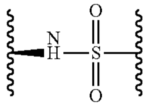 (—NH($SO_2$)—),

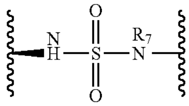 (—NH($SO_2$)$NR_7$—),

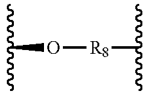 (—$OR_8$—),

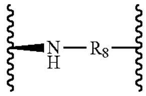 (—$NR_8$—), and

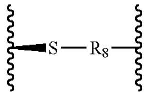 (—$SR_8$—);

$R_6$ is selected from

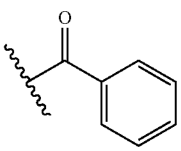,

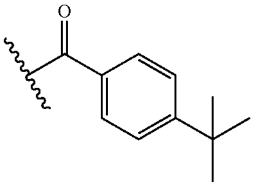,

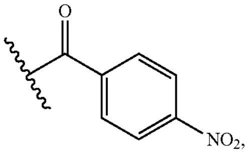

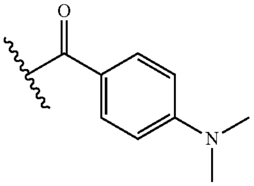,

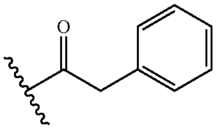,

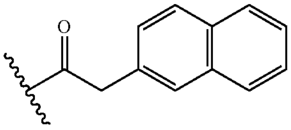,

-continued
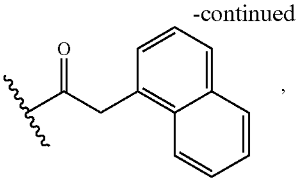
,
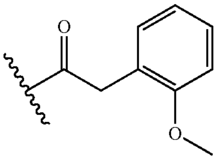
,
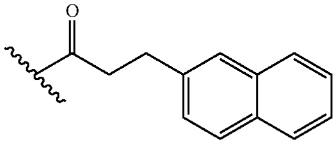
,
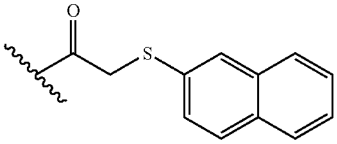
,
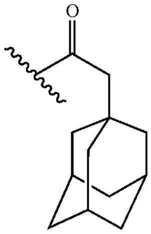
,
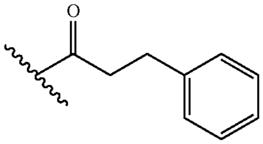
,
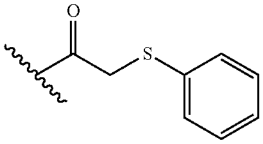
,
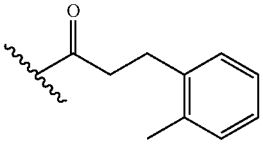
,
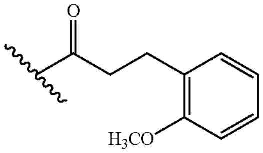
,
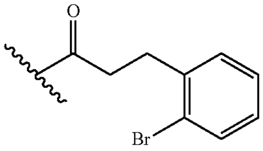
,
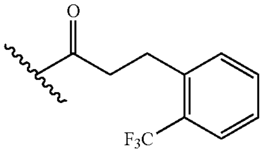
,
-continued
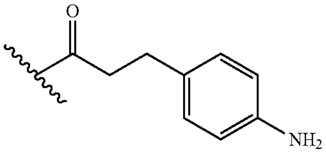
,
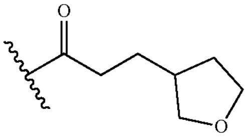
,
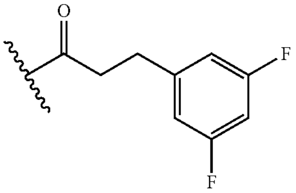
,
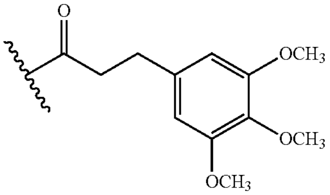
,
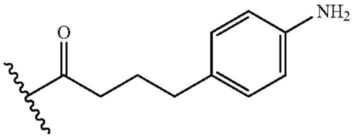
,
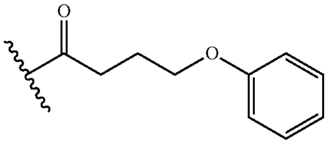
,
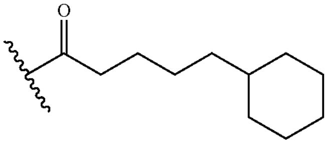
,
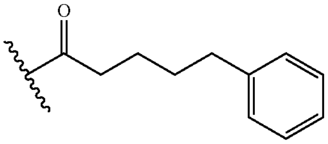
,
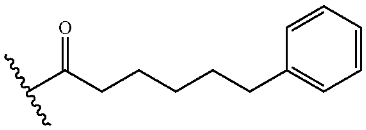
,
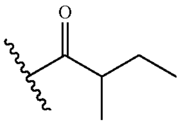
,
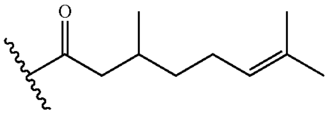
, -continued

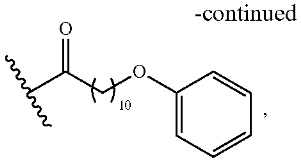

,

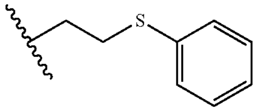

,

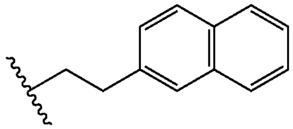

, and

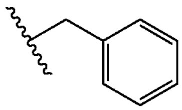

;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each $A_1$-L-$A_2$ is a linker covalently attached to a sulfur atom of a hinge cysteine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is covalently attached (e.g., by way of a covalent bond or a linker) to a sulfur atom of a hinge cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (3):

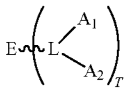

(3)

wherein each $A_1$ and each $A_2$ is independently selected from any one of formulas (A-VI)-(A-IX):

(A-VI)

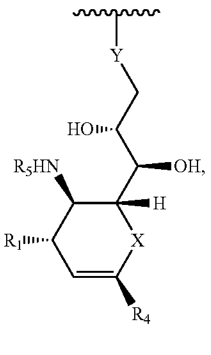

-continued (A-VII)

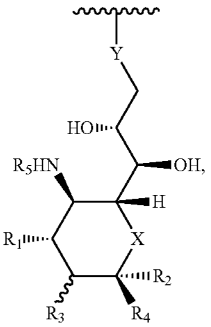

(A-VIII)

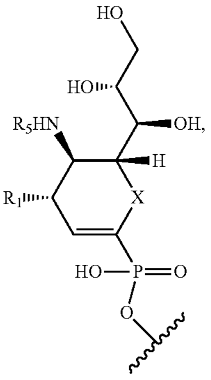

(A-IX)

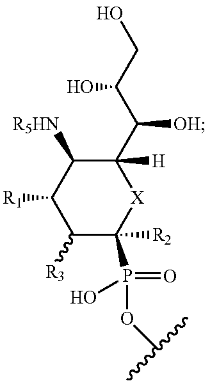

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

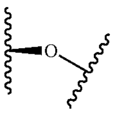

(—O—),

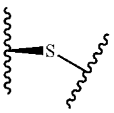

(—S—),

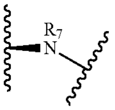

(—$NR_7$—),

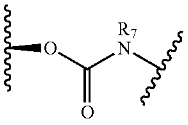

(—O(C=O)$NR_7$—),

-continued
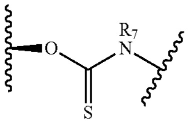
(—O(C=S)$NR_7$—),
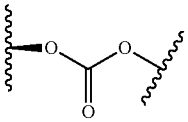
(—O(C=O)O—),
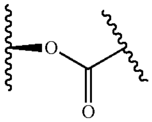
(—O(C=O)—),
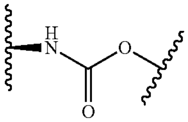
(—NH(C=O)O—),
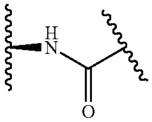
(—NH(C=O)—),
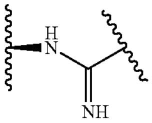
(—NH(C=NH)—),
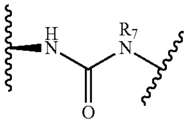
(—NH(C=O)$NR_7$—),
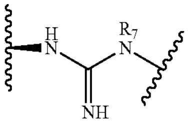
(—NH(C=NH)$NR_7$—),
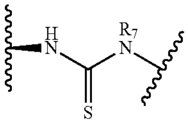
(—NH(C=S)$NR_7$—),
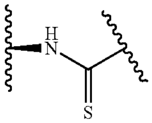
(—NH(C=S)—),
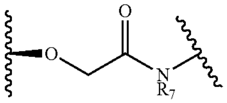
(—$OCH_2$(C=O)$NR_7$—),
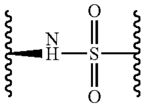
(—$NH(SO_2)$—),
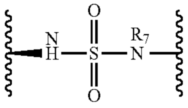
(—$NH(SO_2)NR_7$—),
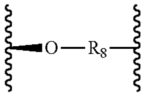
(—$OR_8$—),
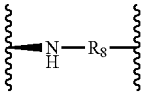
(—$NR_8$—), and
-continued
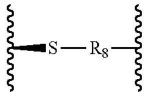
(—$SR_8$—);
$R_6$ is selected from
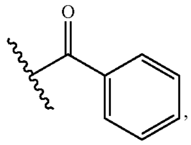,
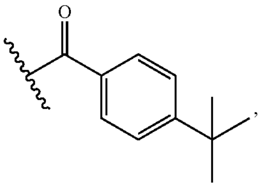,
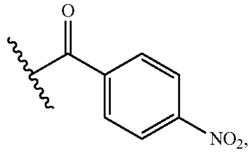
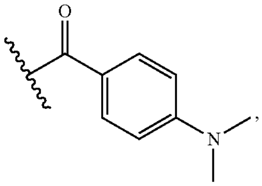,
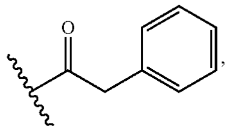,
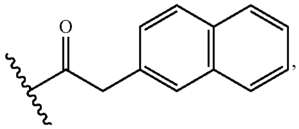,
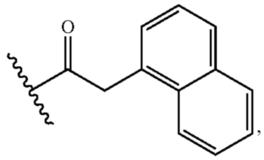,
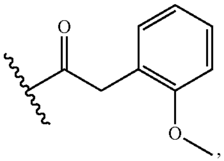,
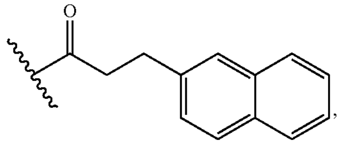,
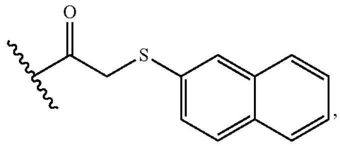,
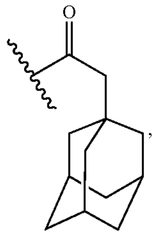,
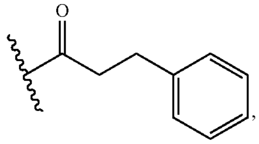,
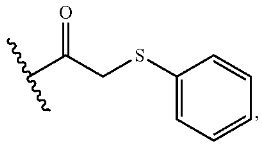, -continued

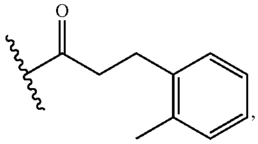,

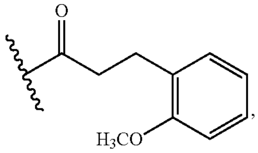,

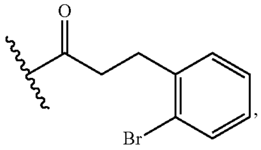,

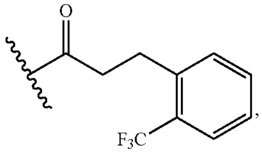,

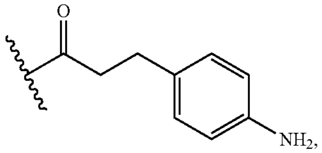

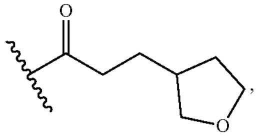,

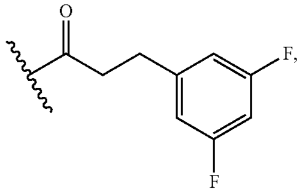

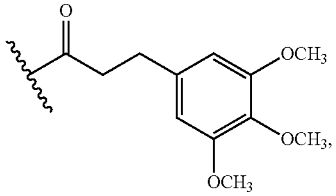

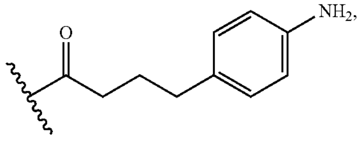

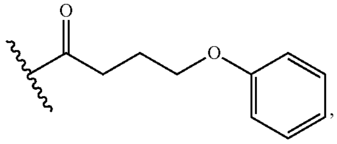,

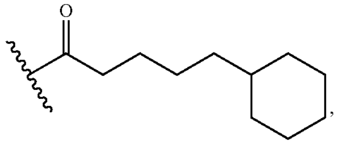,

-continued

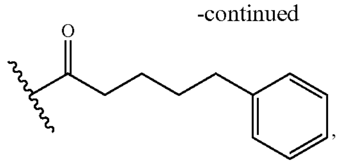,

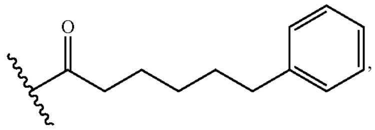,

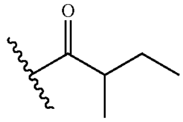, 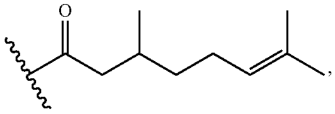,

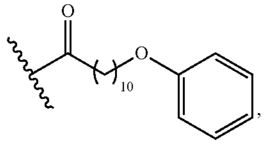,

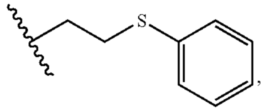,

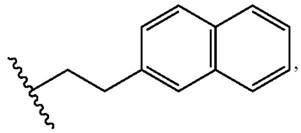, and

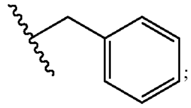;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each $A_1$-L-$A_2$ is a linker covalently attached to a sulfur atom of a hinge cysteine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is covalently attached (e.g., by way of a covalent bond or a linker) to a sulfur atom of a hinge cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In some embodiments, each E includes an Fc domain monomer having the sequence of any one of SEQ ID NOs: 1-68.

In some embodiments, each E comprises the sequence

```
                                    (SEQ ID NO: 10)
MVRSDKTHTCPPCPPC*KC*PAPELLGGPSVFLFPPKPKDTLMISRTPE

VTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRE
```

-continued

```
EMTKNQVSLTCLVKGFYPSDIAVEWESNGQPENNYKTTPPVLDSDGSFF
LYSKLTVDKSRWQQGNVFSCSVMHEALHNHYTQKSLSLSPGKHHHHHH.
```

In some embodiments, each E comprises the sequence

```
                                         (SEQ ID NO: 11)
MVRSDKTHTCPPCPPC*KC*PAPELLGGPSVFLFPPKPKDTLMISRTPE
VTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFF
LYSKLTVDKSRWQQGNVFSCSVMHEALHNHYTQKSLSLSPGK.
```

In some embodiments, at least one of the pair of sulfur atoms is the sulfur atom corresponding to (e.g., the sulfur atom of) a hinge cysteine of SEQ ID NO: 10 or SEQ ID NO: 11, i.e., Cys10, Cys13, Cys16, or Cys18 of SEQ ID NO: 10 or SEQ ID NO: 11. In some embodiments, the pair of sulfur atoms are the sulfur atoms corresponding to (e.g., the sulfur atoms of) Cys10 and Cys13 in SEQ ID NO: 10 or SEQ ID NO: 11, Cys10 and Cys16 in SEQ ID NO: 10 or SEQ ID NO: 11, Cys 30 and Cys18 in SEQ ID NO: 10 or SEQ ID NO: 11, Cys13 and Cys 36 in SEQ ID NO: 10 or SEQ ID NO: 11, Cys13 and Cys 38 in SEQ ID NO: 10 or SEQ ID NO: 11, and/or Cys 36 and Cys 38 in SEQ ID NO: 10 or SEQ ID NO: 11.

In some embodiments, when T is 2, the pair of sulfur atoms are the sulfur atoms corresponding to (e.g., the sulfur atoms of) Cys10 and Cys13 in SEQ ID NO: 10 or SEQ ID NO: 11 and Cys 36 and Cys 38 in SEQ ID NO: 10 or SEQ ID NO: 11.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 10 or SEQ ID NO: 11). In some embodiments, the pair of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E. In some embodiments, the pair of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E. In some embodiments, the pair of sulfur atoms are the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, the pair of sulfur atoms are the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E. In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 2, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 2, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 2, the pairs of sulfur atoms are the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E. In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E. In some embodiments, when T is 3, the pairs of sulfur atoms are the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E; and the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E.

In some embodiments, when T is 3, the pairs of sulfur atoms are the sulfur atom corresponding to (e.g., the sulfur atom of) Cys10 of SEQ ID NO: 10 or SEQ ID NO: 11 from one E and the sulfur atom corresponding to (e.g., the sulfur atom of) Cys10 of SEQ ID NO: 10 or SEQ ID NO: 11 from another E; the sulfur atom corresponding to (e.g., the sulfur atom of) Cys13 of SEQ ID NO: 10 or SEQ ID NO: 11 from one E and the sulfur atom corresponding to (e.g., the sulfur atom of) Cys13 of SEQ ID NO: 10 or SEQ ID NO: 11 from another E; the sulfur atom corresponding to (e.g., the sulfur atom of) Cys16 of SEQ ID NO: 10 or SEQ ID NO: 11 from one E and the sulfur atom corresponding to (e.g., the sulfur atom of) Cys16 of SEQ ID NO: 10 or SEQ ID NO: 11 from another E; and the sulfur atom corresponding to (e.g., the sulfur atom of) Cys18 of SEQ ID NO: 10 or SEQ ID NO: 11 from one E and the sulfur atom corresponding to (e.g., the sulfur atom of) Cys18 of SEQ ID NO: 10 or SEQ ID NO: 11 from another E.

In some embodiments, the conjugate has the structure:

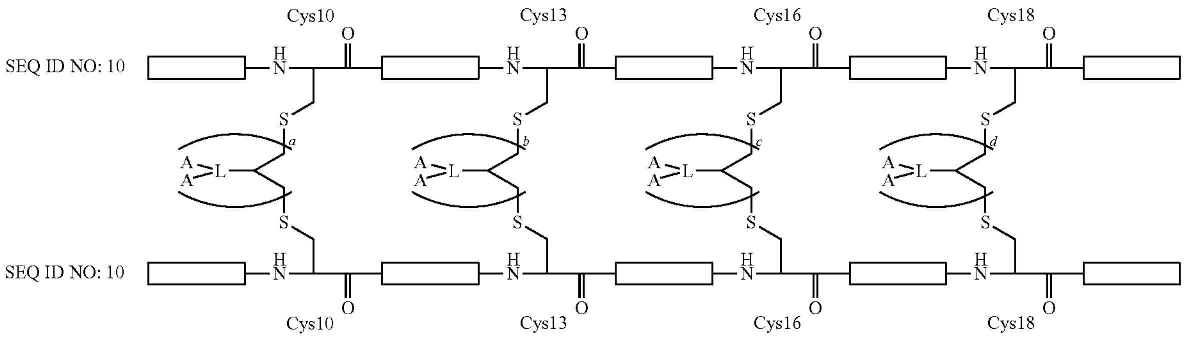

wherein each of a, b, c, and d is, independently, 0 or 1 and wherein when a, b, c, or d is 0, the two sulfur atoms form a disulfide bond.

In some embodiments, a is 1 and b, c, and d are 0. In some embodiments, a and b are 1 and c and d are 0. In some embodiments, a and c are 1 and b and d are 0. In some embodiments, a and d are 1 and b and c are 0. In some embodiments, a, b, and c are 1 and d is 0. In some embodiments, a, b, and d are 1 and c is 0. In some embodiments, a, c, and d are 1 and b is 0. In some embodiments, b and c are 1 and a and d are 0. In some embodiments, b and d are 1 and a and c are 0. In some embodiments, b, c, and d are 1 and a is 0. In some embodiments, c and d are 1 and a and b are 0. In some embodiments, a, b, c, and d are 1.

In some embodiments, each E comprises the sequence (SEQ ID NO: 4)
MVRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTV
DKSRWQQGNVFSCSVMHEALHNHYTQKSLSLSPGK.

In some embodiments, each E comprises the sequence (SEQ ID NO: 33)
MVRSDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQV -continued SLTCLVKGFYPSDIAVEWESNGQPENNYKTTPPVLDSDGSFFLYSKLTV
DKSRWQQGNVFSCSVMHEALHNHYTQKSLSLSPGK.

In some embodiments, at least one of the pair of sulfur atoms is the sulfur atom corresponding to (e.g., the sulfur atom of) a hinge cysteine of SEQ ID NO: 4 or SEQ ID NO: 33, i.e., Cys10 and/or Cys13. In some embodiments, the pair of sulfur atoms are the sulfur atoms corresponding to (e.g., the sulfur atoms of) Cys10 and Cys13 in SEQ ID NO: 4 or SEQ ID NO: 33.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 4 or SEQ ID NO: 33). In some embodiments, the pair of sulfur atoms are the sulfur atom corresponding to (e.g., the sulfur atom of) Cys10 of SEQ ID NO: 4 or SEQ ID NO: 33 from one E and the sulfur atom corresponding to (e.g., the sulfur atom of) Cys10 of SEQ ID NO: 4 or SEQ ID NO: 33 from another E. In some embodiments, the pair of sulfur atoms are the sulfur atom corresponding to (e.g., the sulfur atom of) Cys13 of SEQ ID NO: 4 or SEQ ID NO: 33 from one E and the sulfur atom corresponding to (e.g., the sulfur atom of) Cys13 of SEQ ID NO: 4 or SEQ ID NO: 33 from another E. In some embodiments, when T is 2, the pairs of sulfur atoms are the sulfur atom corresponding to (e.g., the sulfur atom of) Cys10 of SEQ ID NO: 4 or SEQ ID NO: 33 from one E and the sulfur atom corresponding to (e.g., the sulfur atom of) Cys10 of SEQ ID NO: 4 or SEQ ID NO: 33 from another E and the sulfur atom corresponding to (e.g., the sulfur atom of) Cys13 of SEQ ID NO: 4 or SEQ ID NO: 33 from one E and the sulfur atom corresponding to (e.g., the sulfur atom of) Cys13 of SEQ ID NO: 4 or SEQ ID NO: 33 from another E.

In some embodiments, the conjugate has the structure:

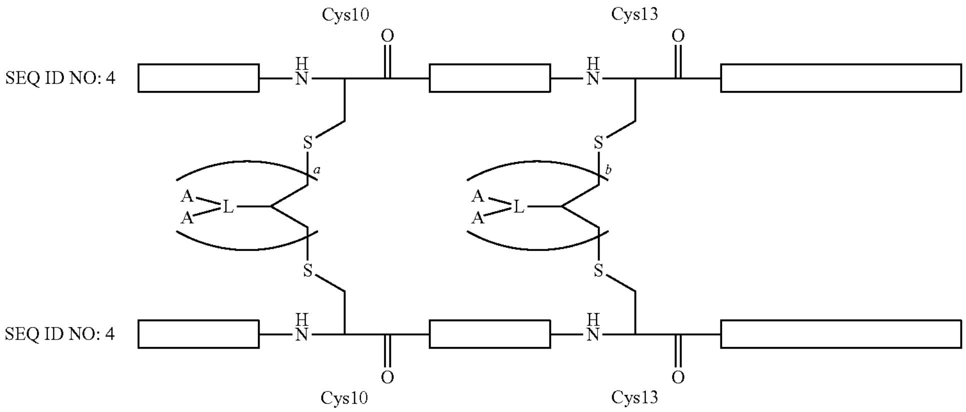

wherein each of a and b is, independently, 0 or 1 and wherein when a or b is 0, the two sulfur atoms form a disulfide bond. In some embodiments, a is 1 and b is 0. In some embodiments, a is 0 and b is 1. In some embodiments, a and b are 1.

In some embodiments, each E comprises the sequence (SEQ ID NO: 8)
MVRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTV
DKSRWQQGNVFSCSVMHEALHNHYTQKSLSLSPGK*HHHHHH*.

In some embodiments, at least one of the pair of sulfur atoms is the sulfur atom corresponding to (e.g., the sulfur atom of) a hinge cysteine of SEQ ID NO: 8, i.e., Cys10 and/or Cys13. In some embodiments, the pair of sulfur atoms are the sulfur atoms corresponding to (e.g., the sulfur atoms of) Cys10 and Cys13 in SEQ ID NO: 8.

In some embodiments, the pair of sulfur atoms include one sulfur atom of a cysteine from each E, i.e., L-A along with the sulfur atoms to which it is attached forms a bridge between two Fc domains (e.g., two Fc domains comprising the sequence of SEQ ID NO: 8). In some embodiments, the pair of sulfur atoms are the sulfur atom corresponding to (e.g., the sulfur atom of) Cys10 of SEQ ID NO: 8 from one E and the sulfur atom corresponding to (e.g., the sulfur atom of) Cys10 of SEQ ID NO: 8 from another E. In some embodiments, the pair of sulfur atoms are the sulfur atom corresponding to (e.g., the sulfur atom of) Cys13 of SEQ ID NO: 8 from one E and the sulfur atom corresponding to (e.g., the sulfur atom of) Cys13 of SEQ ID NO: 8 from another E. In some embodiments, when T is 2, the pairs of sulfur atoms are the sulfur atom corresponding to (e.g., the sulfur atom of) Cys10 of SEQ ID NO: 8 from one E and the sulfur atom corresponding to (e.g., the sulfur atom of) Cys10 of SEQ ID NO: 8 from another E and the sulfur atom corresponding to (e.g., the sulfur atom of) Cys13 of SEQ ID NO: 8 from one E and the sulfur atom corresponding to (e.g., the sulfur atom of) Cys13 of SEQ ID NO: 8 from another E.

In some embodiments, the conjugate has the structure:

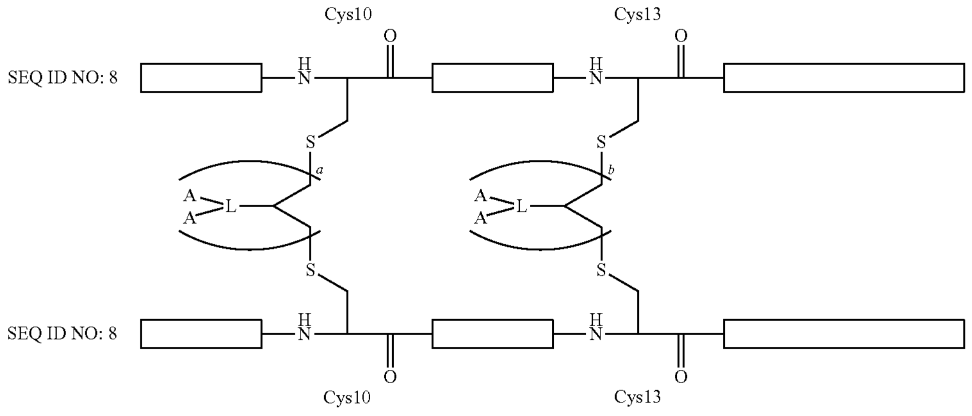

wherein each of a and b is, independently, 0 or 1 and wherein when a or b is 0, the two sulfur atoms form a disulfide bond. In some embodiments, a is 1 and b is 0. In some embodiments, a is 0 and b is 1. In some embodiments, a and b are 1.

In another aspect, the invention features a conjugate described by formula (4):

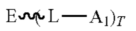
(4)

wherein each $A_1$ is independently selected from any one of formulas (A-I)-(A-XII):

(A-I)
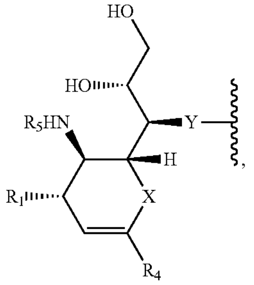

(A-II)
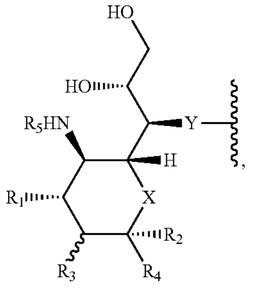

(A-III)
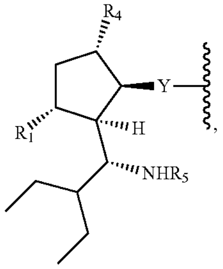

(A-IV)
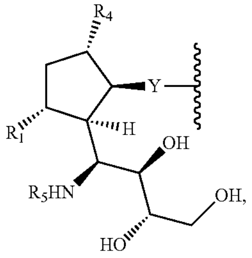

-continued (A-V)
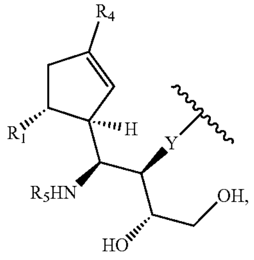

(A-VI)
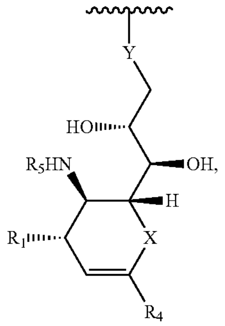

(A-VII)
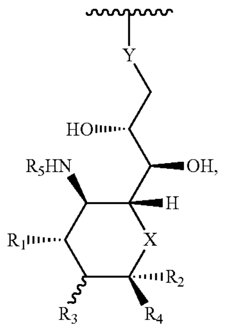

(A-VIII)
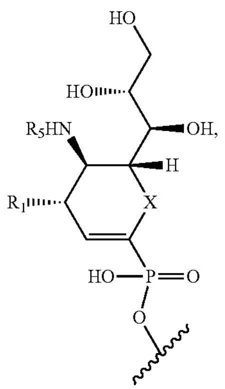

-continued (A-IX)

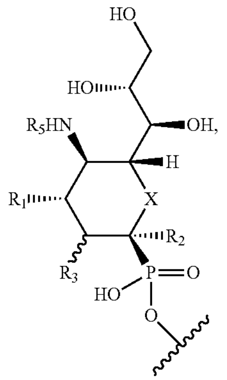

(A-X)

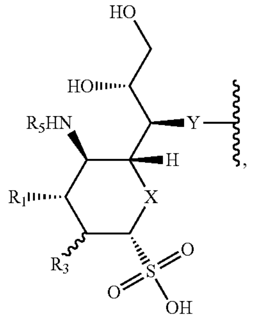

(A-XI)

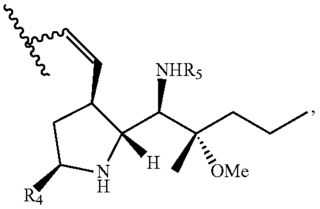

(A-XII)

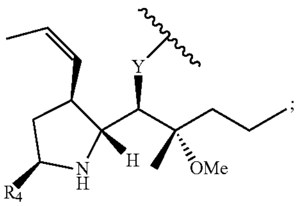

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; Rs is selected from —$COCH_3$, —$COCF_3$, —$SO_2CH_3$; X is selected from —O— and —S—; Y is selected from

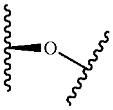

(—O—),

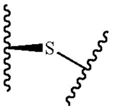

(—S—),

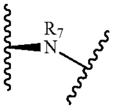

(—$NR_7$—),

-continued

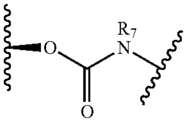

(—O(C=O)$NR_7$—),

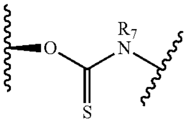

(—O(C=S)$NR_7$—),

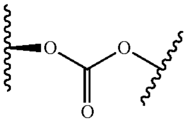

(—O(C=O)O—),

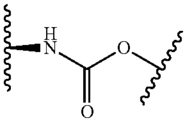

(—NH(C=O)O—),

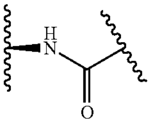

(—NH(C=O)—),

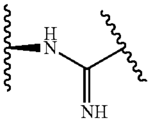

(—NH(C=NH)—),

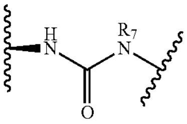

(—NH(C=O)$NR_7$—),

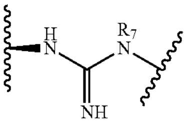

(—NH(C=NH)$NR_7$—),

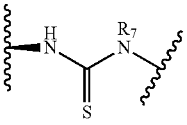

(—NH(C=S)$NR_7$—),

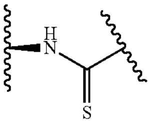

(—NH(C=S)—),

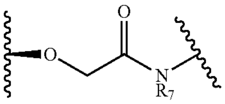

(—$OCH_2$(C=O)$NR_7$—),

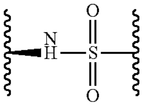

(—NH($SO_2$)—),

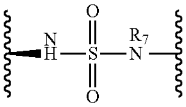

(—NH($SO_2$)$NR_7$—),

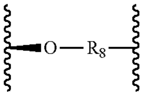

(—$OR_8$—),

-continued
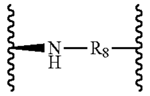 ( $—NR_8—$ ), and
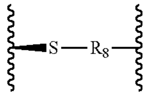 ( $—SR_8—$ );
$R_6$ is selected from
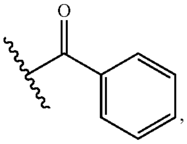, 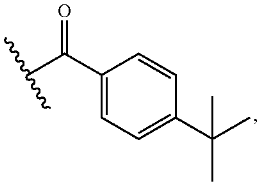,
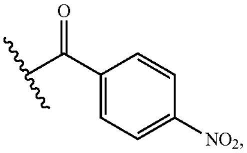 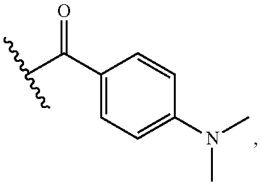,
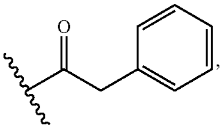, 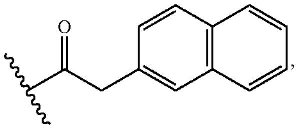,
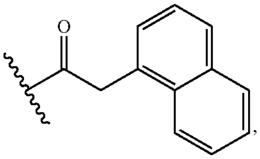, 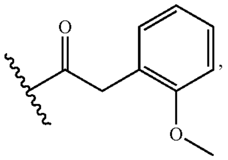,
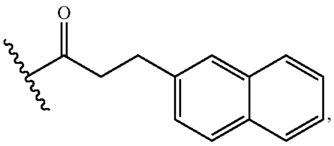,
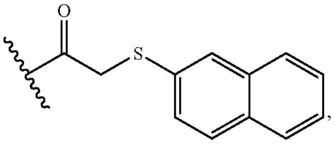,
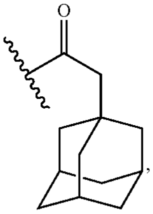, 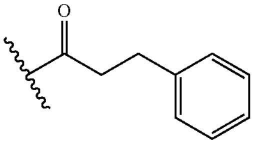,
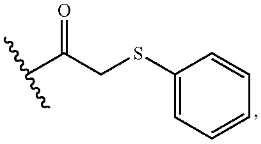, 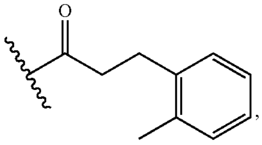,
-continued
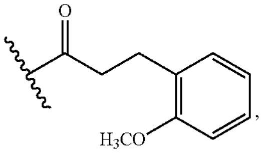, 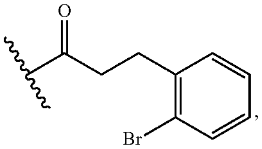,
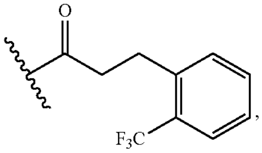,
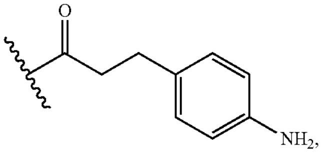
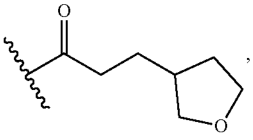, 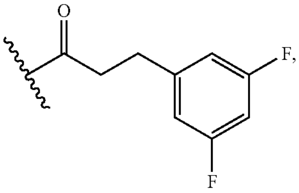
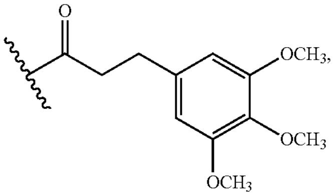
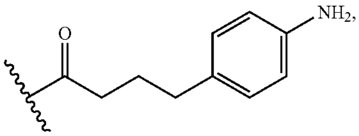
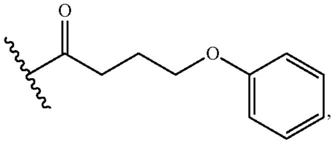,
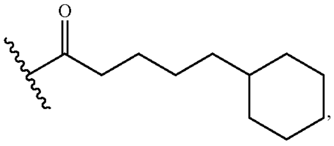,
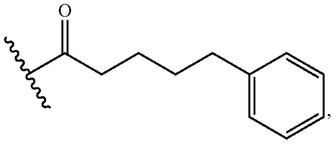,
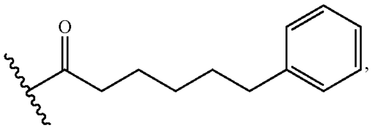,
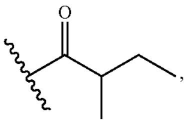, 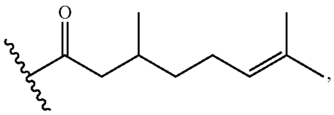, -continued

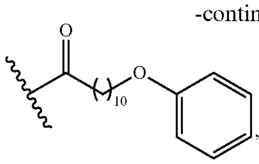
,
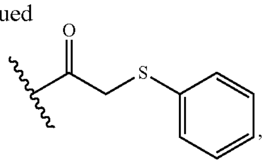
,
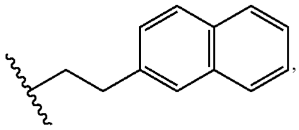
, and
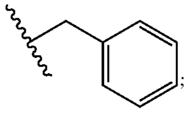
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each L-$A_1$ is a linker covalently attached to a sulfur atom of a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-$A_1$ is covalently attached (e.g., by way of a covalent bond or a linker) to the sulfur atom of the hinge cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-XII).

In another aspect, the invention features a conjugate described by formula (4):

$$E{\sim}(L-A_1)_T \quad (4)$$

wherein each $A_1$ is independently selected from any one of formulas (A-I)-(A-V):

(A-I)

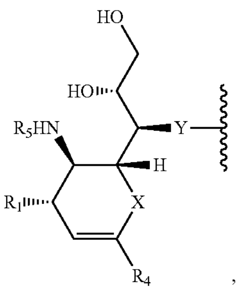
, (A-II)

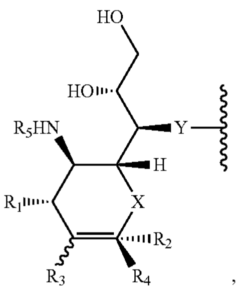
,

-continued (A-III)

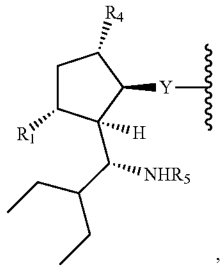
, (A-IV)

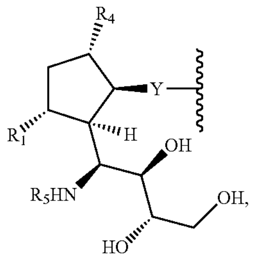

(A-V)

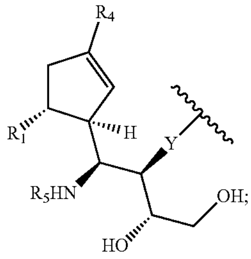

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

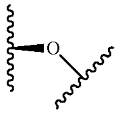
(—O—),
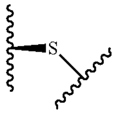
(—S—),
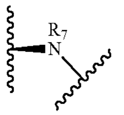
(—$NR_7$—),
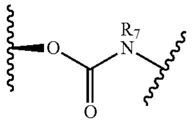
(—O(C═O)$NR_7$—),
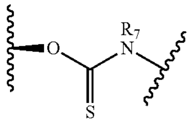
(—O(C═S)$NR_7$—),
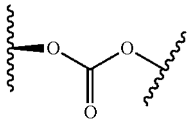
(—O(C═O)O—), -continued
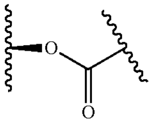
(—O(C═O)—),
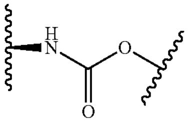
(—NH(C═O)O—),
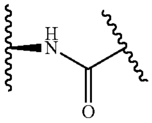
(—NH(C═O)—),
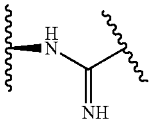
(—NH(C═NH)—),
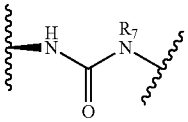
(—NH(C═O)$NR_7$—),
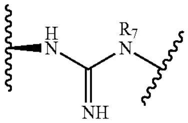
(—NH(C═NH)$NR_7$—),
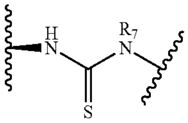
(—NH(C═S)$NR_7$—),
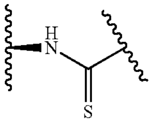
(—NH(C═S—),
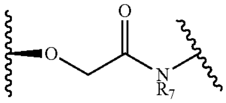
(—$OCH_2$(C═O)$NR_7$—),
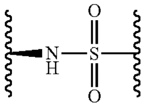
(—NH($SO_2$)—),
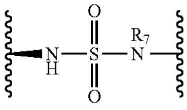
(—NH($SO_2$)$NR_7$—),
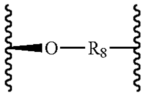
(—$OR_8$—),
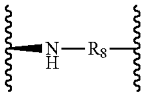
(—$NR_8$—), and
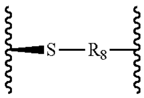
(—$SR_8$—);
$R_6$ is selected from
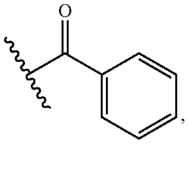
,
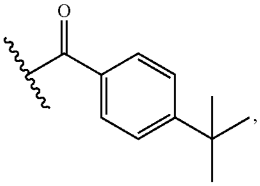
,
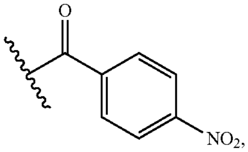
,
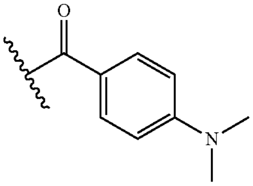
,
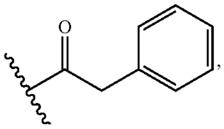
,
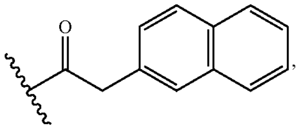
,
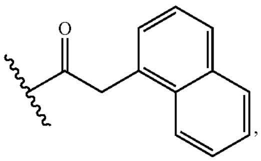
,
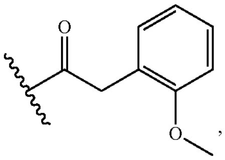
,
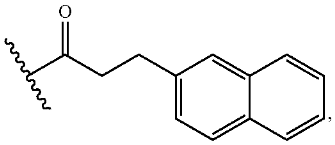
,
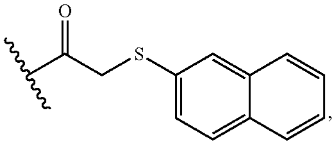
,
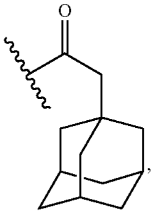
,
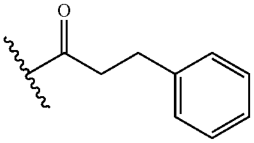
,
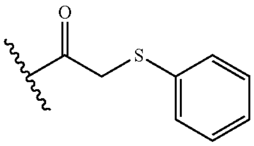
,
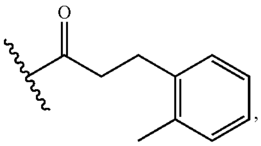
,
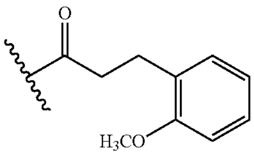
,
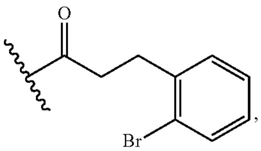
,
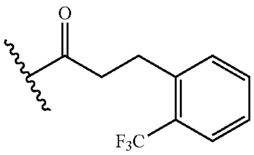
, -continued

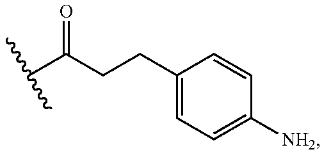

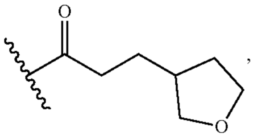, 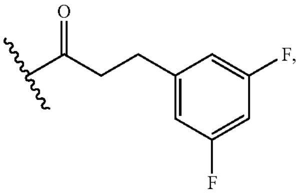

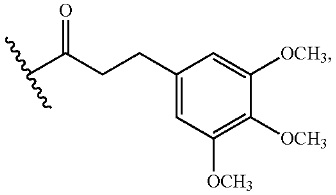

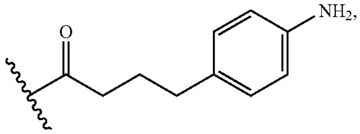

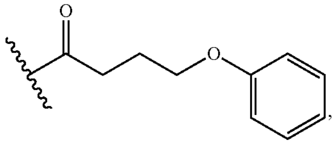,

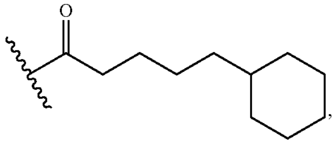,

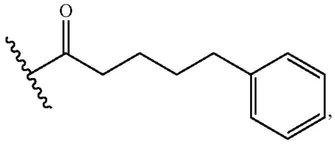,

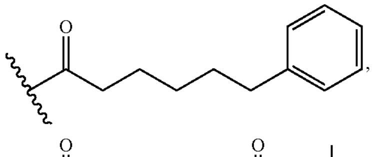,

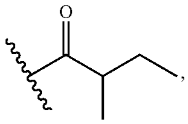, 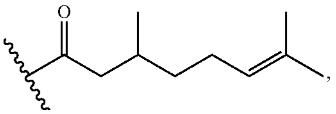,

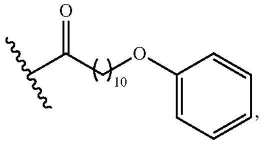, 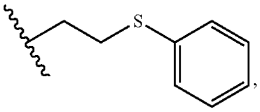,

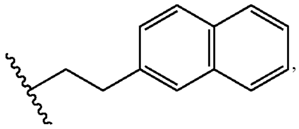, and 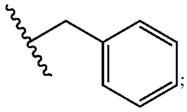;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each L-$A_1$ is a linker covalently attached to a sulfur atom of a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-$A_1$ is covalently attached (e.g., by way of a covalent bond or a linker) to the sulfur atom of the hinge cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-V).

In another aspect, the invention features a conjugate described by formula (4):

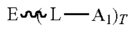

(4)

wherein each $A_1$ is independently selected from any one of formulas (A-VI)-(A-IX):

(A-VI)

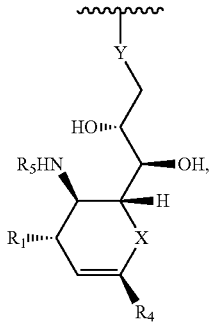

(A-VII)

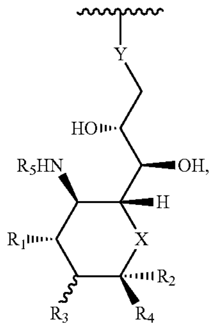

-continued (A-VIII)

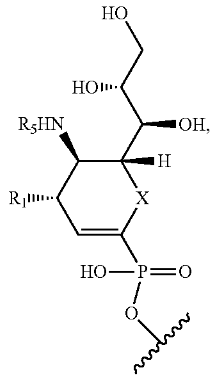

(A-IX)

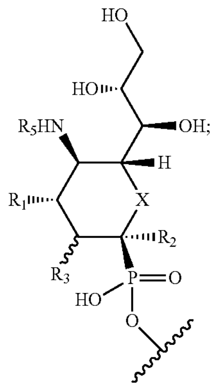

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; Rs is selected from —$COCH_3$, —$COCF_3$, —$SO_2CH_3$; X is selected from —O— and —S—; Y is selected from

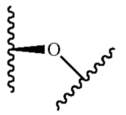

(—O—),

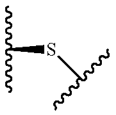

(—S—),

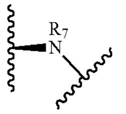

(—$NR_7$—),

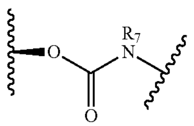

(—O(C=O)$NR_7$—),

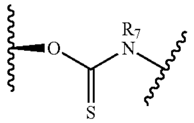

(—O(C=S)$NR_7$—),

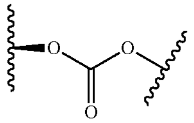

(—O(C=O)O—),

-continued

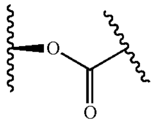

(—O(C=O)—),

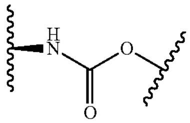

(—NH(C=O)O—),

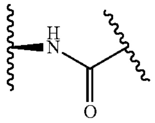

(—NH(C=O—),

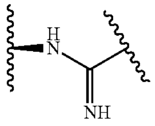

(—NH(C=NH)—),

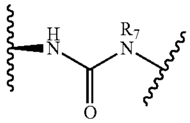

(—NH(C=O)$NR_7$—),

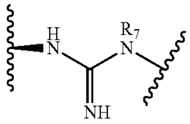

(—NH(C=NH($NR_7$—),

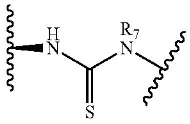

(—NH(C=S)$NR_7$—),

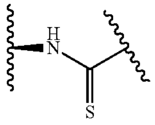

(—NH(C=S)—),

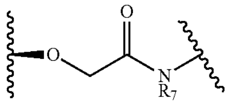

(—$OCH_2$(C=O)$NR_7$—),

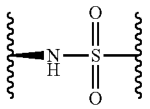

(—NH($SO_2$)—),

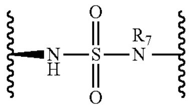

(—NH($SO_2$)$NR_7$—),

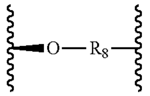

(—$OR_8$—),

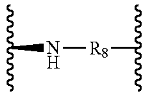

(—$NR_8$—), and

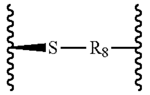

(—$SR_8$—);

$R_6$ is selected from
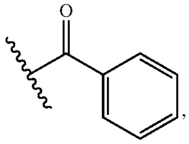, 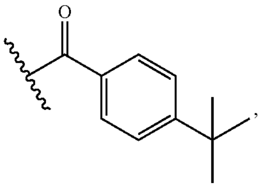,
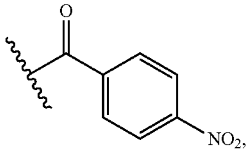 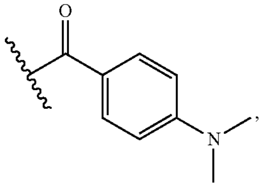,
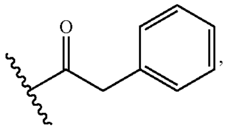, 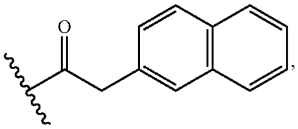,
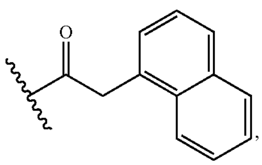, 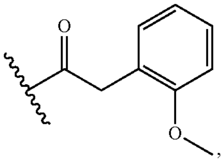,
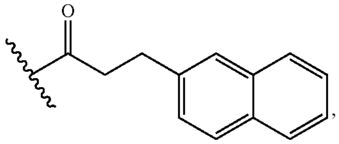,
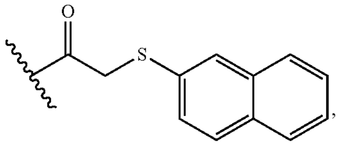,
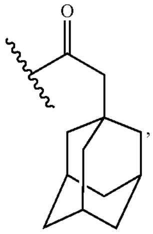,
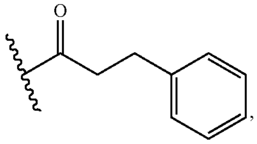,
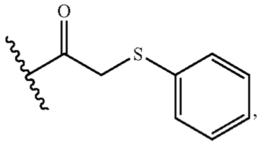,
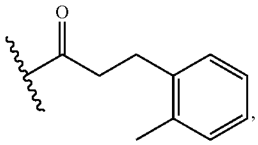,
-continued
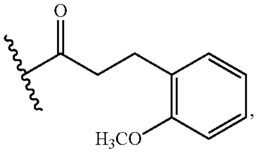,
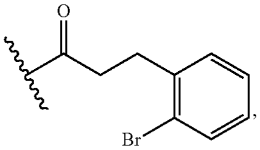,
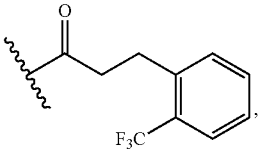,
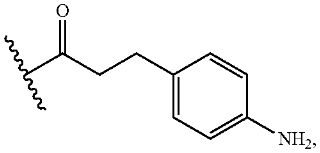
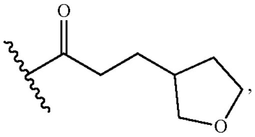,
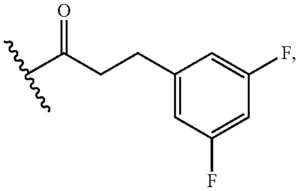
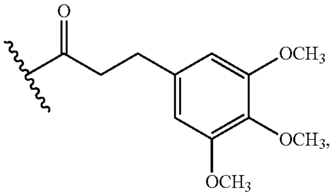
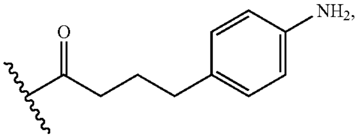
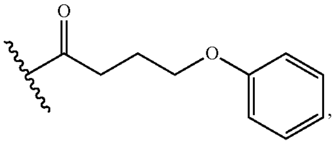,
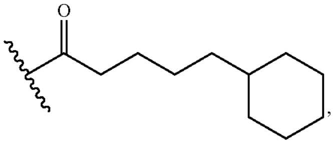,
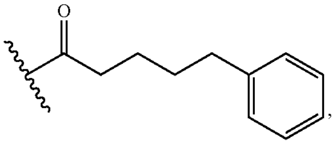, -continued

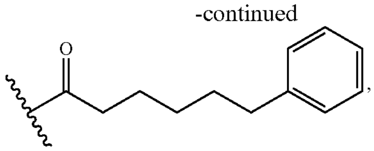,

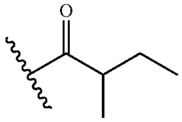, 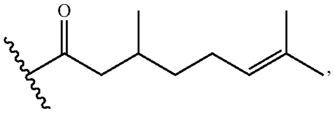,

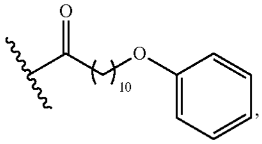,

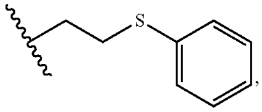,

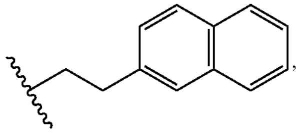, and

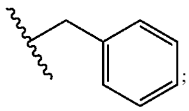;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each L-$A_1$ is a linker covalently attached to a sulfur atom of a hinge cysteine in E and to $A_1$; T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-$A_1$ is covalently attached (e.g., by way of a covalent bond or a linker) to the sulfur atom of the hinge cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-VI)-(A-IX).

In some embodiments, each E includes an Fc domain monomer having the sequence of any one of SEQ ID NOs: 1-68.

In some embodiments, each E comprises the sequence (SEQ ID NO: 4)
MVRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTV
DKSRWQQGNVFSCSVMHEALHNHYTQKSLSLSPGK.

In some embodiments, each E comprises the sequence (SEQ ID NO: 33)
MVRSDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTV
DKSRWQQGNVFSCSVMHEALHNHYTQKSLSLSPGK.

In some embodiments, at least one of the sulfur atoms is the sulfur atom corresponding to (e.g., the sulfur atom of) a hinge cysteine of SEQ ID NO: 4 or SEQ ID NO: 33, i.e., Cys10 and/or Cys13. In some embodiments, the sulfur atoms is the sulfur atom corresponding to (e.g., the sulfur atom of) Cys10 in SEQ ID NO: 4 or SEQ ID NO: 33. In some embodiments, the sulfur atom corresponding to (e.g., the sulfur atom of) Cys10 in SEQ ID NO: 4 or SEQ ID NO: 33.

In some embodiments, the conjugate has the structure:

SEQ ID NO: 4 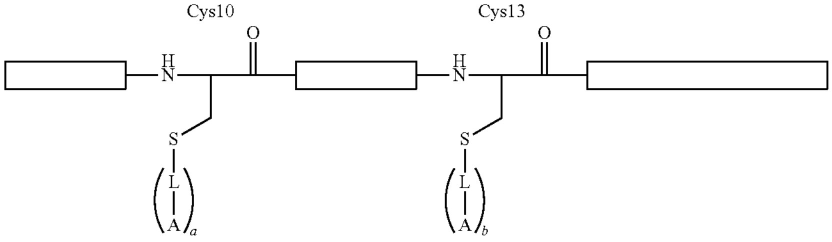

wherein each of a and b is, independently, 0 or 1 and wherein when a or b is 0, the sulfur atoms is a thiol. In some embodiments, a is 1 and b is 0. In some embodiments, a is 0 and b is 1. In some embodiments, a and b are 1.

In another aspect, the invention features a population of conjugates, wherein the average value of T is 1 to 20 (e.g., the average value of T is 1 to 2, 1 to 3, 1 to 4, 1 to 5, 5 to 10, 10 to 15, or 15 to 20). In some embodiments, the average value of T is 1, 2, 3, 4, 5, 6, 7, 8, 9, 10, 11, 12, 13, 14, 15, 16, 17, 18, 19, or 20.

In another aspect, the invention features a conjugate described by formula (3):

(3)

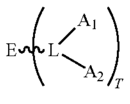

wherein each $A_1$ and each $A_2$ is independently selected from any one of formulas (A-I)-(A-XII):

(A-I)

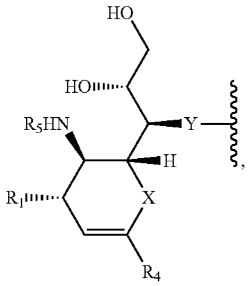

(A-II)

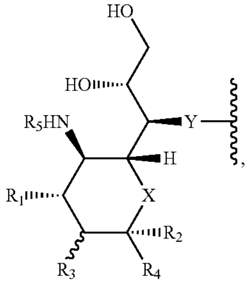

(A-III)

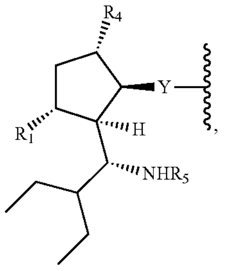

-continued (A-IV)

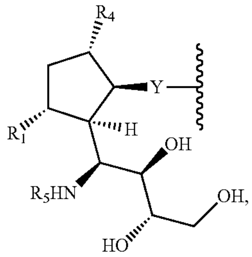

(A-V)

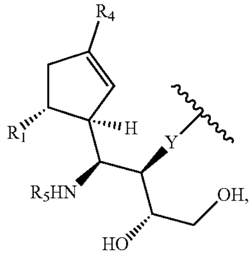

(A-VI)

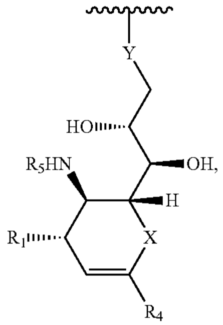

(A-VII)

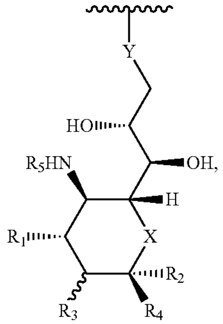

(A-VIII)

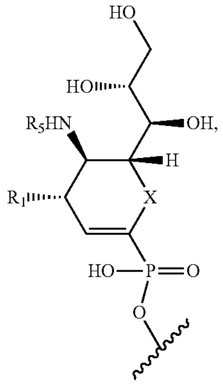

-continued (A-IX)

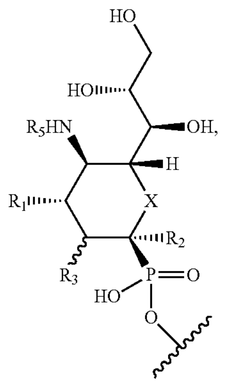

(A-X)

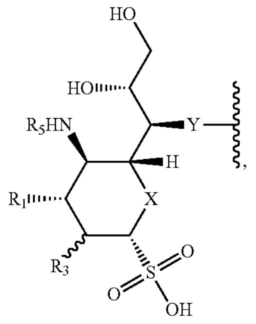

(A-XI)

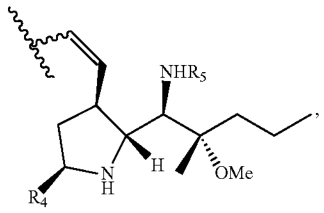

(A-XII)

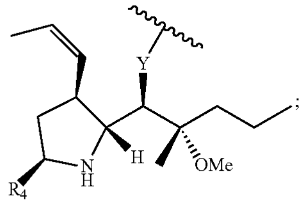

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

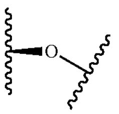

(—O—),

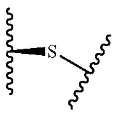

(—S—),

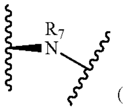

(—$NR_7$—),

-continued

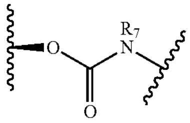

(—O(C=O)$NR_7$—),

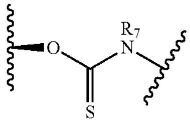

(—O(C=S)$NR_7$—),

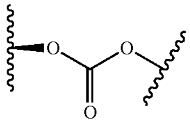

(—O(C=O)O—),

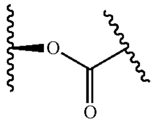

(—O(C=O)—),

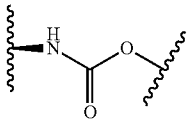

(—NH(C=O)O—),

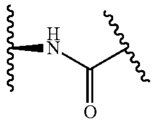

(—NH(C=O)—),

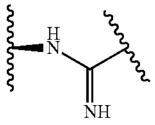

(—NH(C=NH)—),

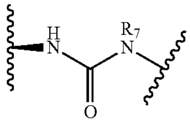

(—NH(C=O)$NR_7$—),

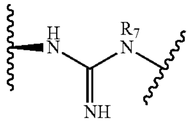

(—NH(C=NH)$NR_7$—),

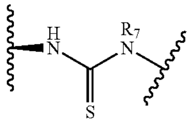

(—NH(C=S)$NR_7$—),

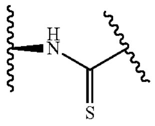

(—NH(C=S)—),

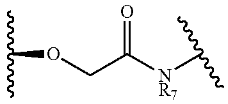

(—$OCH_2$(C=O)$NR_7$—),

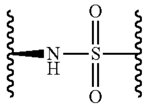

(—NH($SO_2$)—),

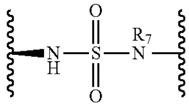

(—NH($SO_2$)$NR_7$—),

-continued
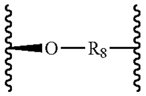
(——$OR_8$——),
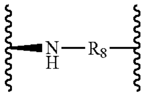
(——$NR_8$——), and
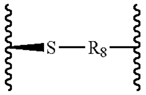
(——$SR_8$——);
$R_6$ is selected from
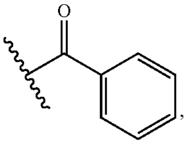
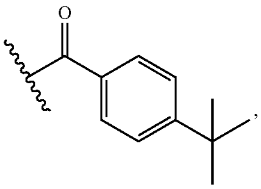
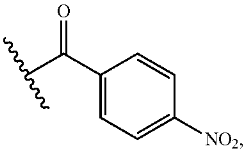
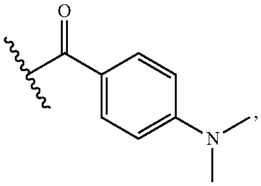
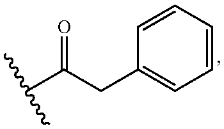
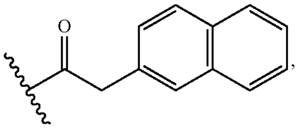
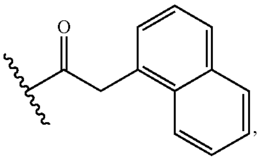
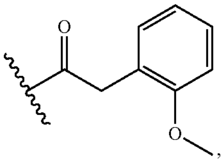
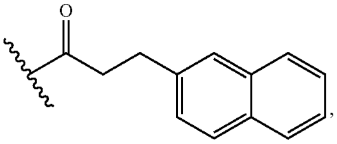
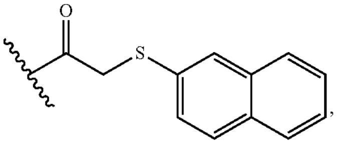
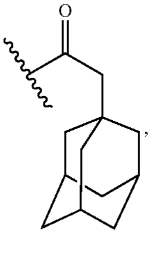
-continued
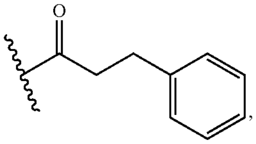
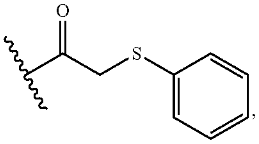
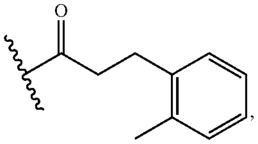
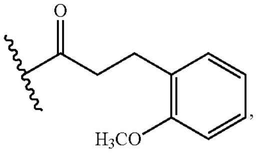
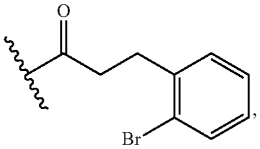
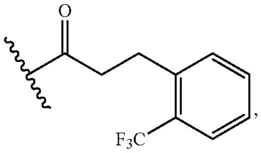
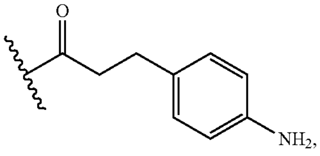
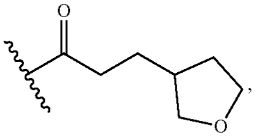
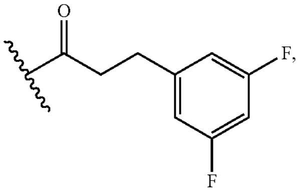
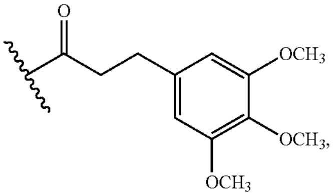
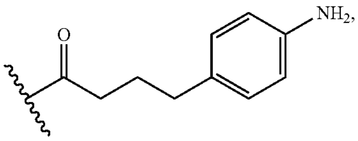

-continued

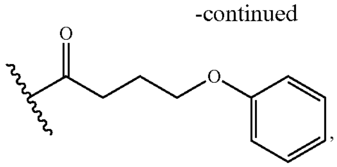,

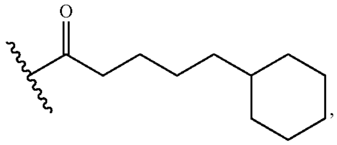,

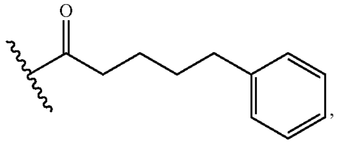,

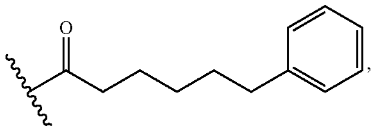,

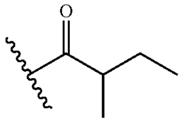, 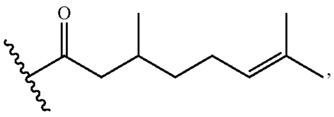,

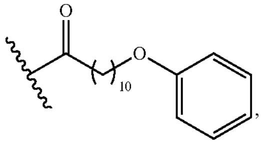,

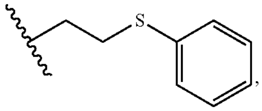,

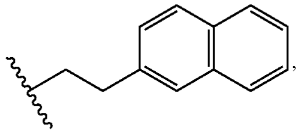, and

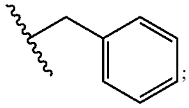;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each $A_1$-L-$A_2$ is a linker covalently attached to a nitrogen atom of a surface exposed lysine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is covalently attached (e.g., by way of a covalent bond or a linker) to the nitrogen atom of a surface exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (3):

(3)

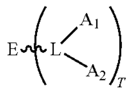

wherein each $A_1$ and each $A_2$ is independently selected from any one of formulas (A-I)-(A-V):

(A-I)

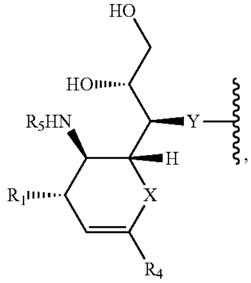, (A-II)

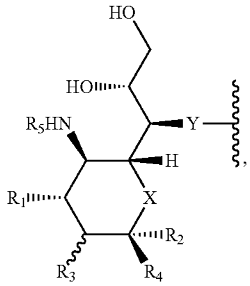, (A-III)

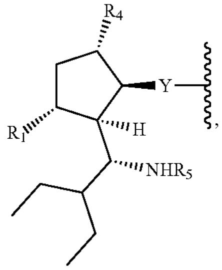, (A-IV)

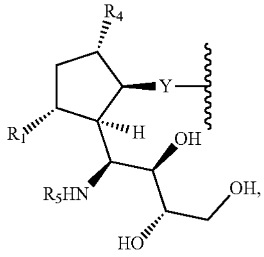

-continued (A-V)

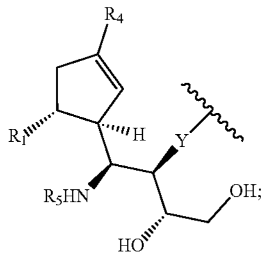

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

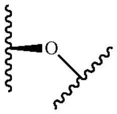 (—O—),

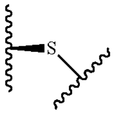 (—S—),

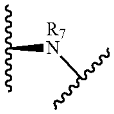 (—$NR_7$—),

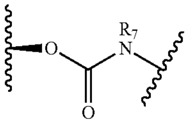 (—O(C═O)$NR_7$—),

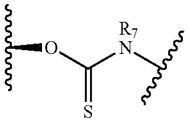 (—O(C═S)$NR_7$—),

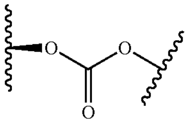 (—O(C═O)O—),

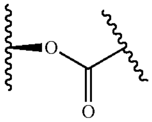 (—O(C═O)—),

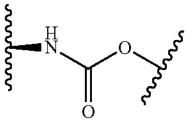 (—NH(C═O)O—),

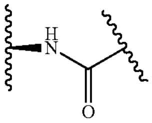 (—NH(C═O)—),

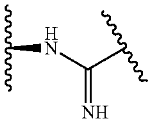 (—NH(C═NH)—),

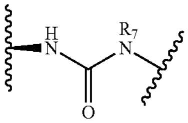 (—NH(C═O)$NR_7$—),

-continued

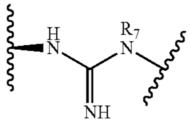 (—NH(C═NH)$NR_7$—),

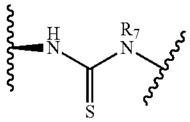 (—NH(C═S)$NR_7$—),

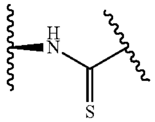 (—NH(C═S)—),

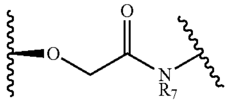 (—$OCH_2$(C═O)$NR_7$—),

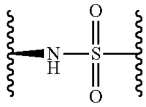 (—NH($SO_2$)—),

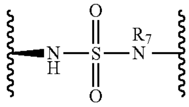 (—NH($SO_2$)$NR_7$—),

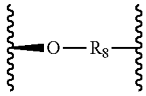 (—$OR_8$—),

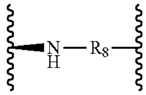 (—$NR_8$—), and

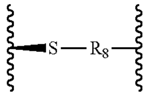 (—$SR_8$—);

$R_6$ is selected from

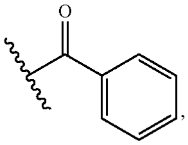,
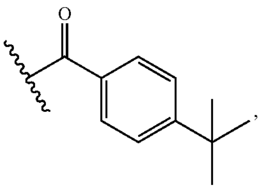,
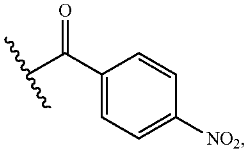,
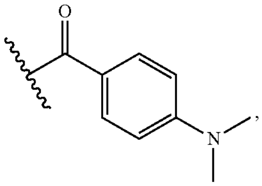,
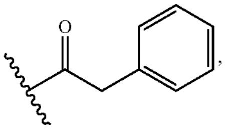,
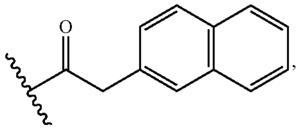,

-continued
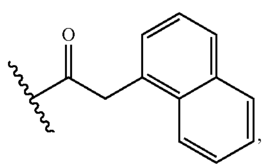
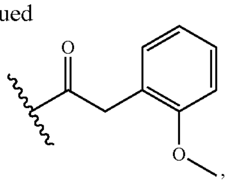
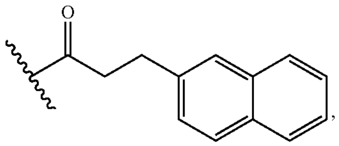
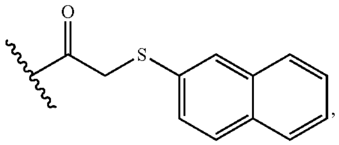
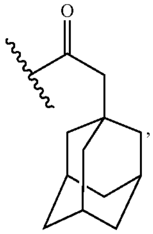
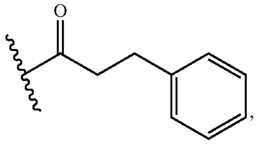
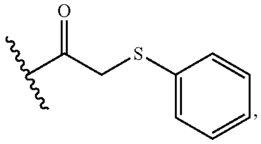
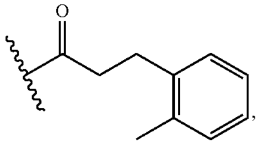
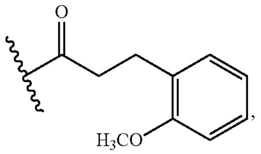
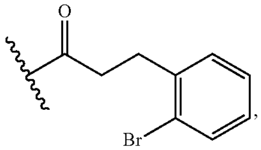
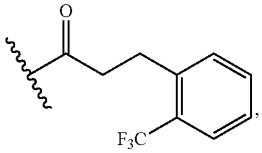
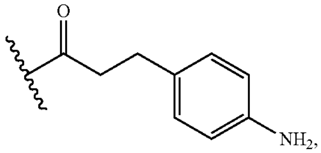
-continued
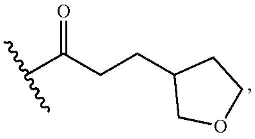
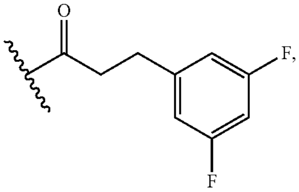
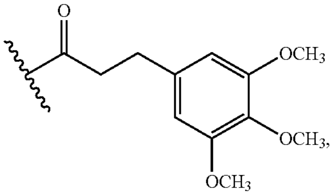
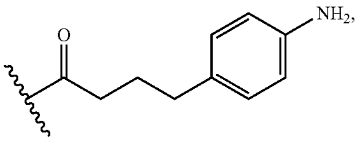
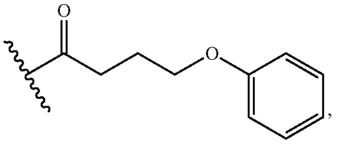
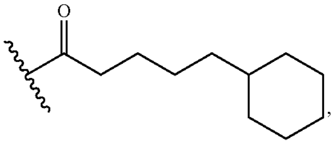
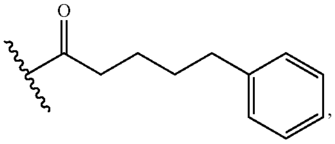
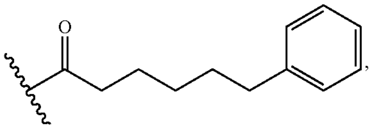
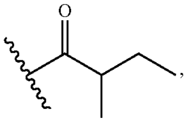
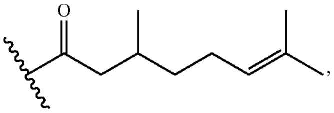
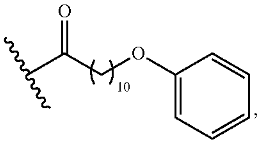
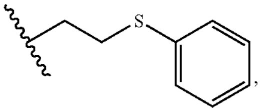

-continued

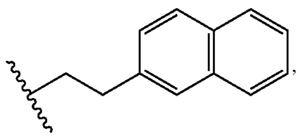, and

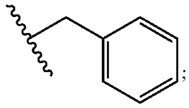;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each $A_1$-L-$A_2$ is a linker covalently attached to a nitrogen atom of a surface exposed lysine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is covalently attached (e.g., by way of a covalent bond or a linker) to the nitrogen atom of a surface exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (3):

(3)

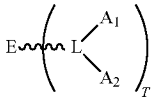

wherein each $A_1$ and each $A_2$ is independently selected from any one of formulas (A-VI)-(A-IX):

(A-VI)

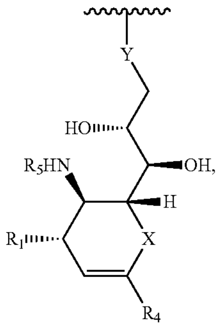

-continued (A-VII)

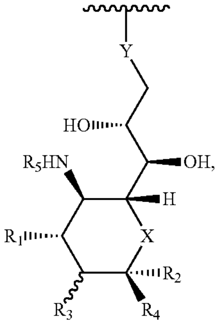

(A-VIII)

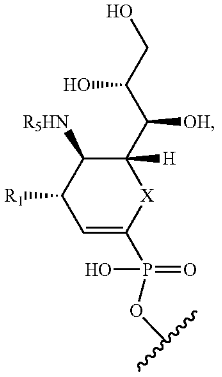

(A-IX)

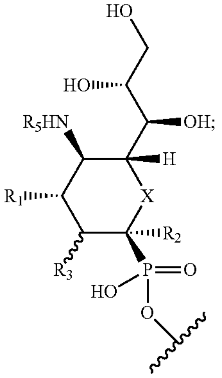

wherein $R_1$ is selected from —OH, —$NH_2$, —NHC(=NH)$NH_2$, and —NHC(=NH)NH$R_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

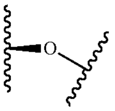 (—O—), 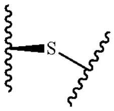 (—S—),

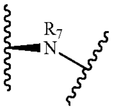 (—$NR_7$—),

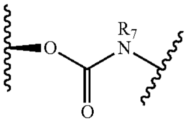 (—O(C=O)$NR_7$—),

-continued
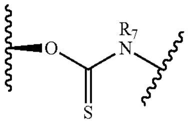
(—O(C=S)N$R_7$—),
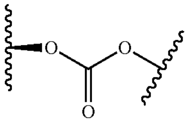
(—O(C=O)O—),
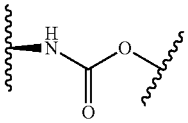
(—NH(C=O)O—),
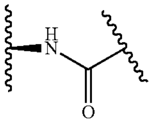
(—NH(C=O)—),
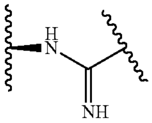
(—NH(C=NH)—),
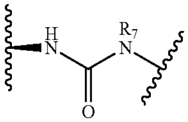
(—NH(C=O)N$R_7$—),
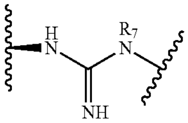
(—NH(C=NH)N$R_7$—),
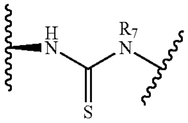
(—NH(C=S)N$R_7$—),
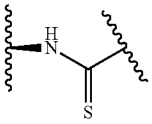
(—NH(C=S)—),
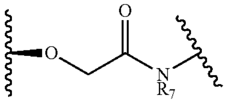
(—O$CH_2$(C=O)N$R_7$—),
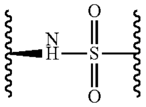
(—NH($SO_2$)—),
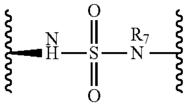
(—NH($SO_2$)N$R_7$—),
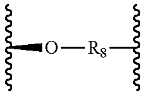
(—O$R_8$—),
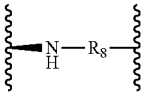
(—N$R_8$—), and
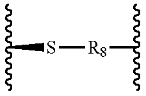
(—S$R_8$—);
$R_6$ is selected from
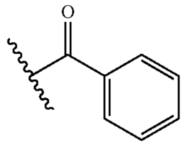
,
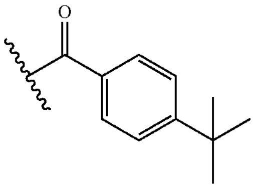
,
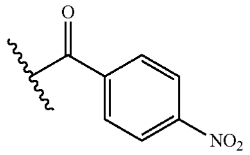
,
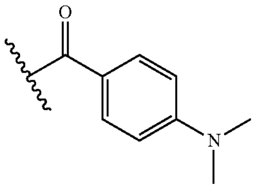
,
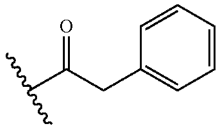
,
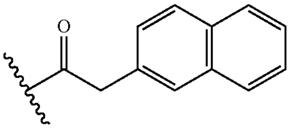
,
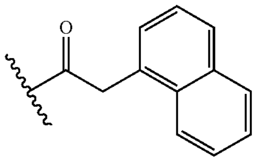
,
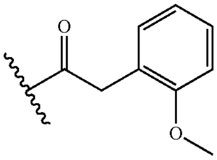
,
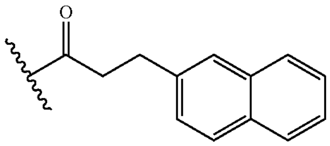
,
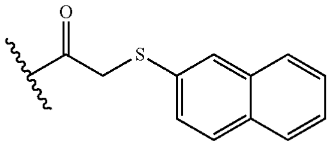
,
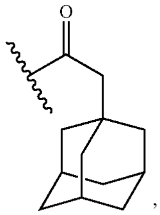
,
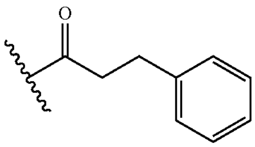
,
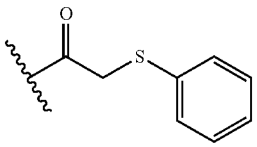
,
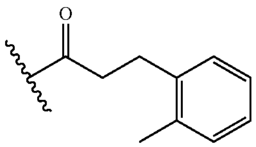
,
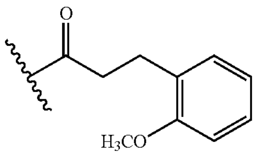
,
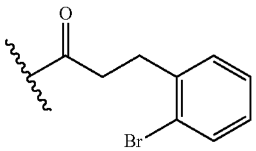
,
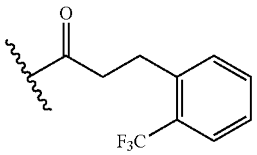
, -continued

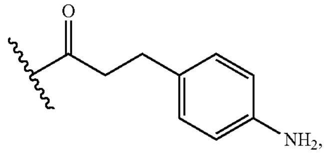

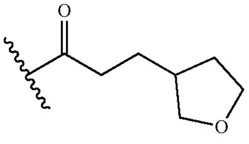
,
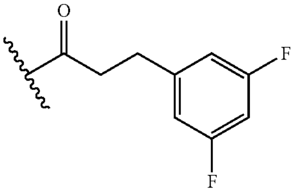
,

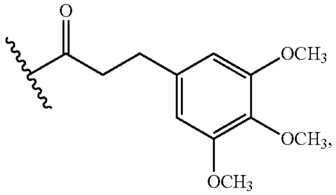

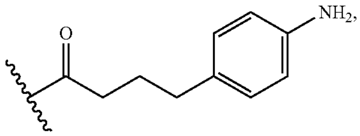

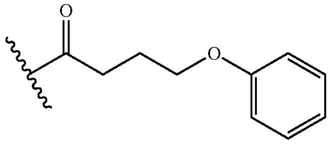
,

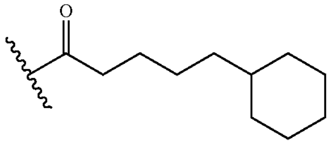
,

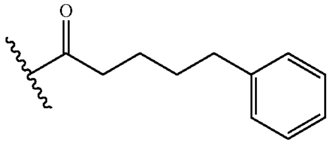
,

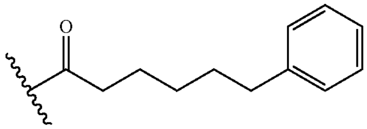
,

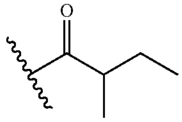
,
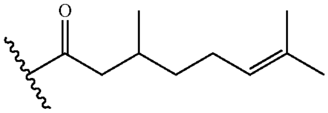
,

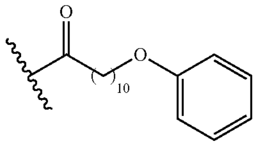
,
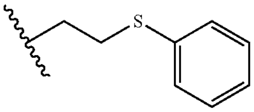
,

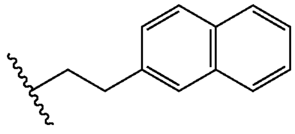
, and
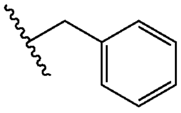
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each $A_1$-L-$A_2$ is a linker covalently attached to a nitrogen atom of a surface exposed lysine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is covalently attached (e.g., by way of a covalent bond or a linker) to the nitrogen atom of a surface exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features, a conjugate described by formula (4):

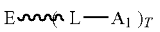
(4)

wherein each $A_1$ is independently selected from any one of formulas (A-I)-(A-XII):

(A-I)
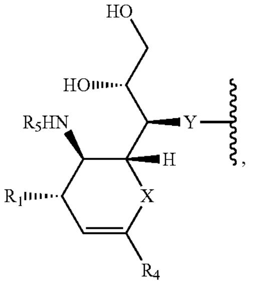

(A-II)
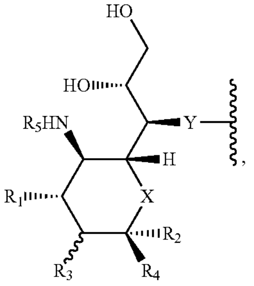

(A-III)
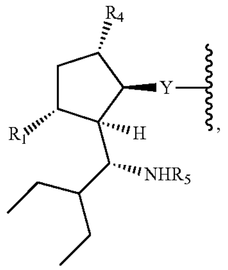

-continued
(A-IV)
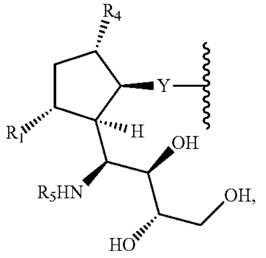
(A-V)
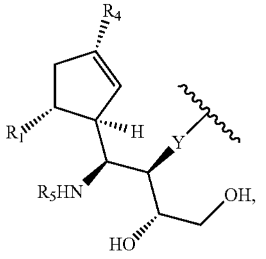
(A-VI)
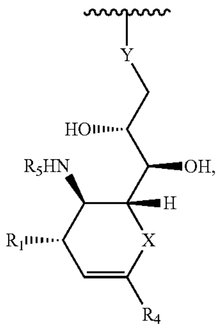
(A-VII)
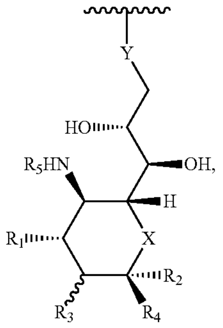
(A-VIII)
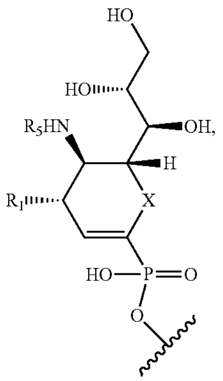
-continued
(A-IX)
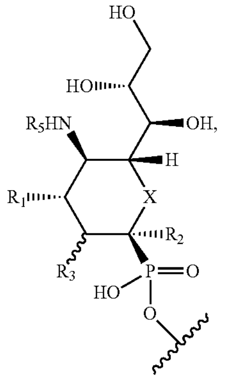
(A-X)
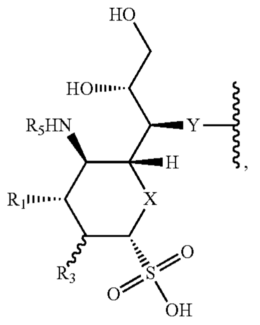
(A-XI)
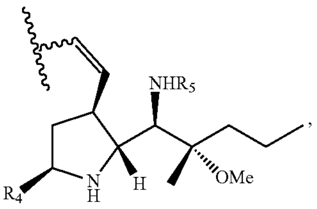
(A-XII)
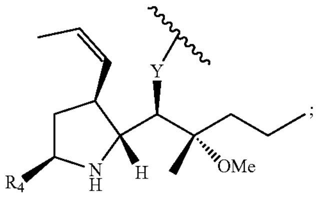
wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from
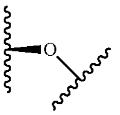
(—O—),
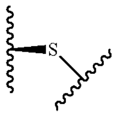
(—S—),
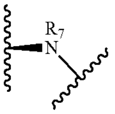
(—$NR_7$—), -continued
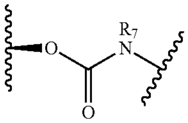
(—O(C=O)$NR_7$—),
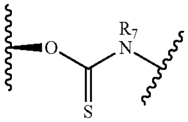
(—O(C=S)$NR_7$—),
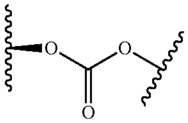
(—O(C=O)O—),
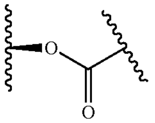
(—O(C=O)—),
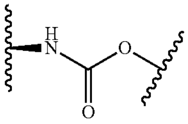
(—NH(C=O)O—),
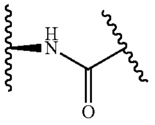
(—NH(C=O)—),
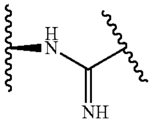
(—NH(C=NH)—),
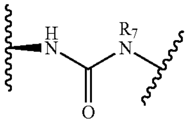
(—NH(C=O)$NR_7$—),
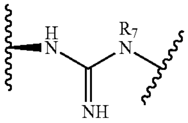
(—NH(C=NH)$NR_7$—),
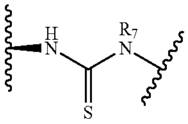
(—NH(C=S)$NR_7$—),
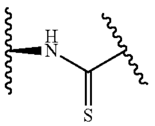
(—NH(C=S)—),
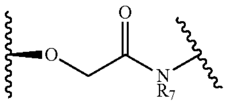
(—$OCH_2$(C=O)$NR_7$—),
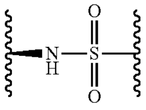
(—NH($SO_2$)—),
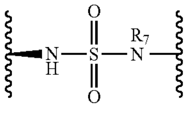
(—NH($SO_2$)$NR_7$—),
-continued
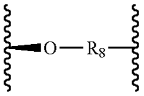
(—$OR_8$—),
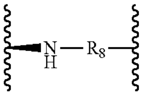
(—$NR_8$—), and
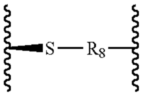
(—$SR_8$—);
$R_6$ is selected from
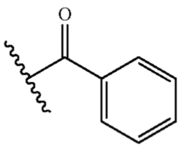
,
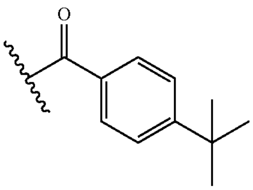
,
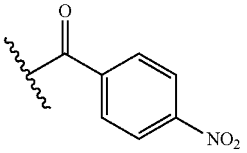
,
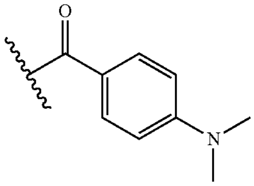
,
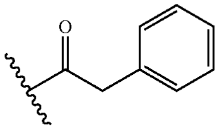
,
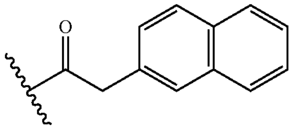
,
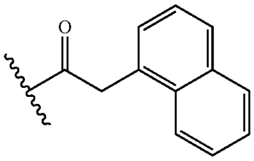
,
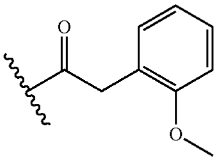
,
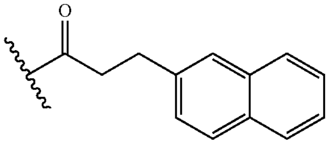
,
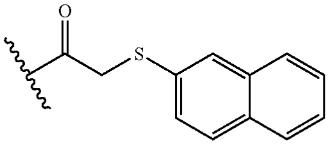
,
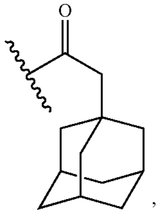
,
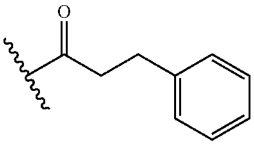
,
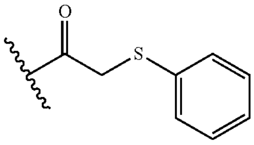
,
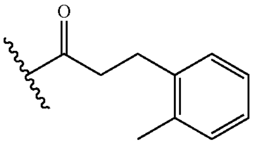
, -continued

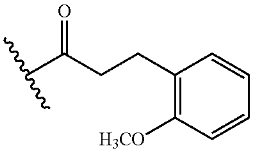,
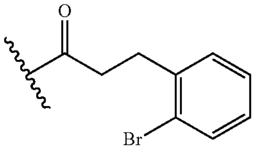,
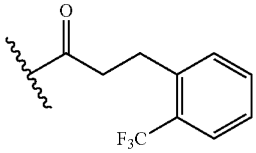,
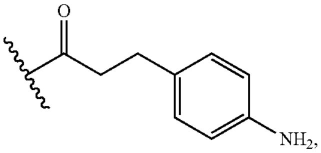
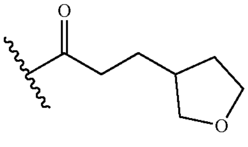,
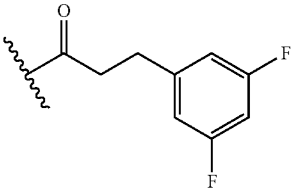,
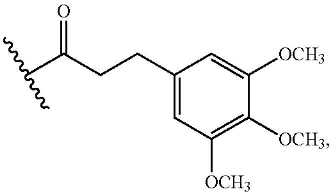
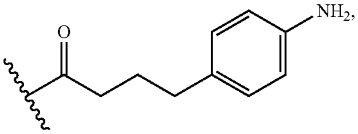
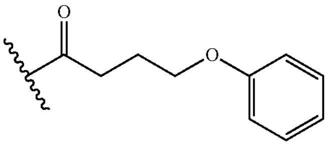,
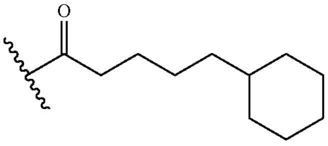,
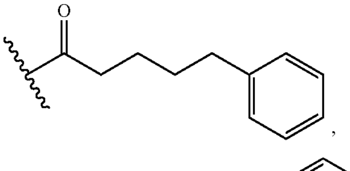,
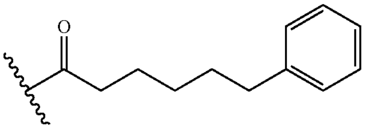,
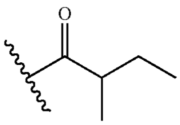,
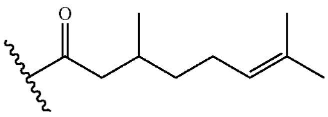, -continued

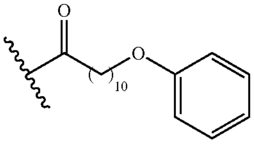,
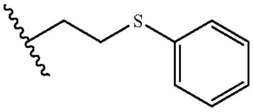,
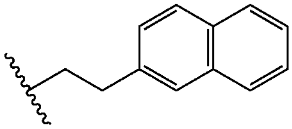, and
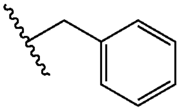;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each L-$A_1$ is a linker covalently attached to a nitrogen atom of a surface exposed lysine in E and to $A_1$; T is an integer from 1 to 20 (e.g., 1, 2, 3, 4, 5, 6, 7, 8, 9, 10, 11, 12, 13, 14, 15, 16, 17, 18, 19, or 20), the squiggly line connected to E indicates that each L-$A_1$ is covalently attached (e.g., by way of a covalent bond or a linker) to the nitrogen atom of a surface exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each A may be independently selected from any one of formulas (A-I)-(A-XII).

In another aspect, the invention features, a conjugate described by formula (4):

(4)

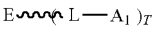

wherein each $A_1$ is independently selected from any one of formulas (A-I)-(A-V):

(A-I)

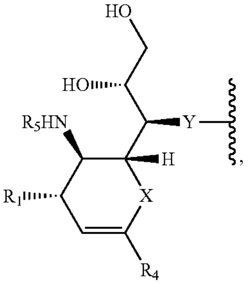, (A-II)

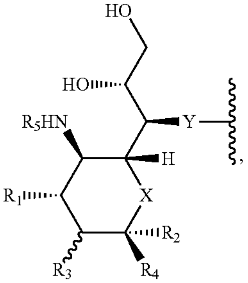,

-continued (A-III)

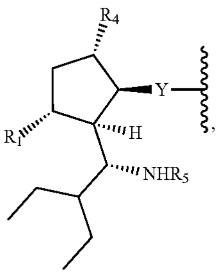

(A-IV)

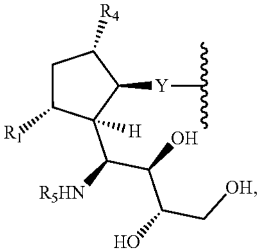

(A-V)

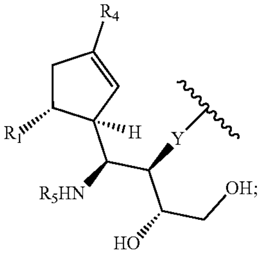

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

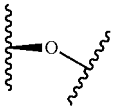

(—O—),

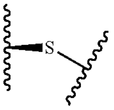

(—S—),

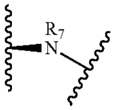

(—$NR_7$—),

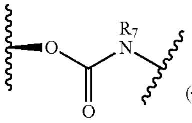

(—O(C=O)$NR_7$—),

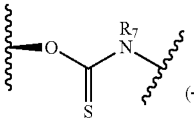

(—O(C=S)$NR_7$—),

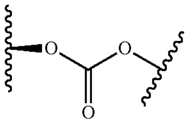

(—O(C=O)O—),

-continued

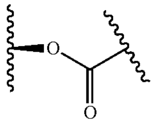

(—O(C=O)—),

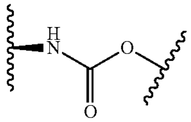

(—NH(C=O)O—),

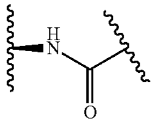

(—NH(C=O)—),

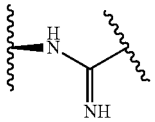

(—NH(C=NH)—),

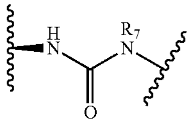

(—NH(C=O)$NR_7$—),

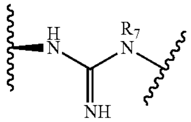

(—NH(C=NH)$NR_7$—),

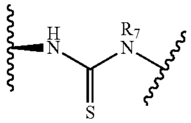

(—NH(C=S)$NR_7$—),

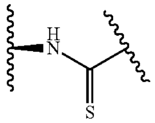

(—NH(C=S)—),

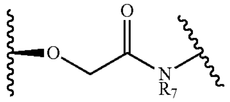

(—$OCH_2$(C=O)$NR_7$—),

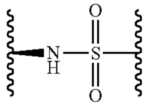

(—NH($SO_2$)—),

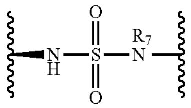

(—NH($SO_2$)$NR_7$—),

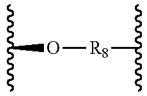

(—$OR_8$—),

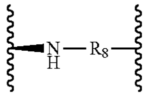

(—$NR_8$—), and

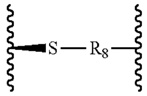

(—$SR_8$—);

$R_6$ is selected from
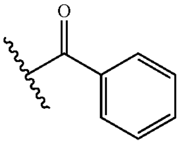, 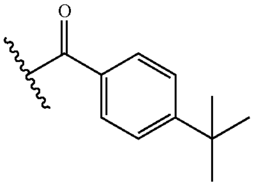,
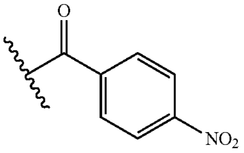, 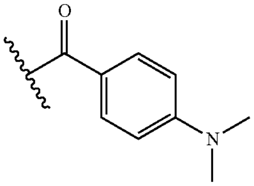,
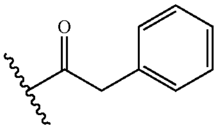, 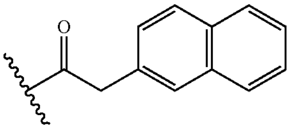,
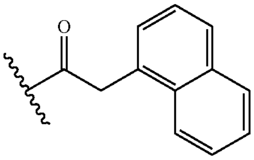, 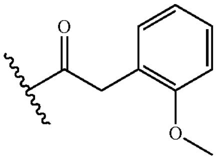,
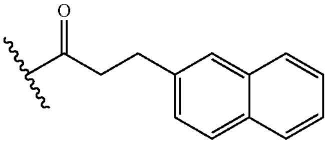,
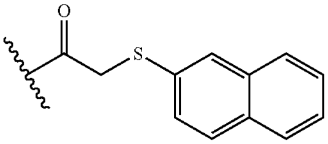,
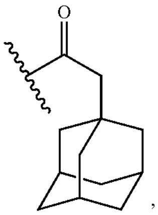, 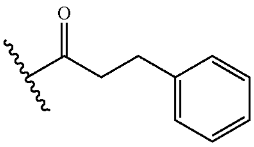,
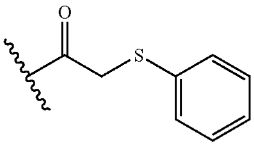, 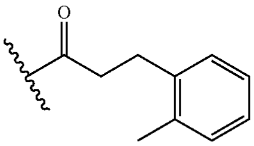,
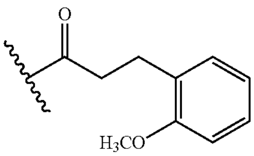, 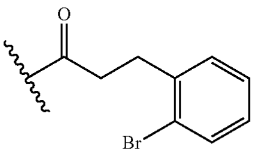,
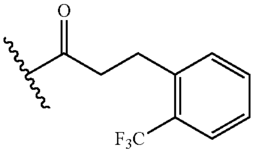,
-continued
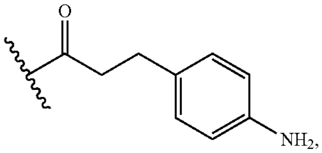
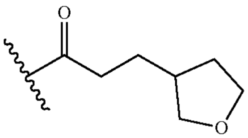, 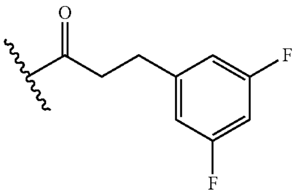,
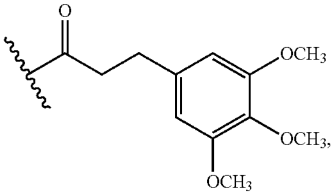
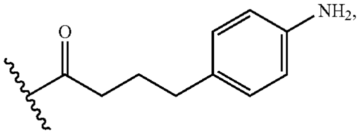
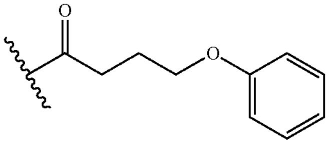,
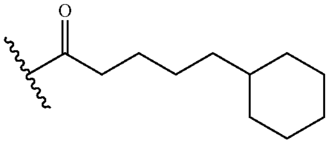,
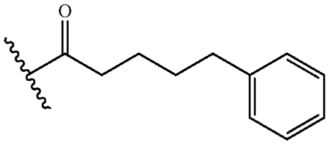,
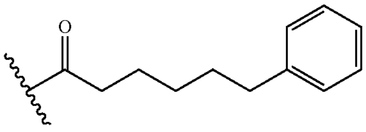,
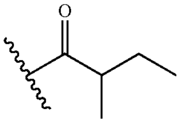, 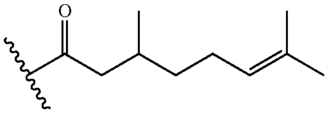,
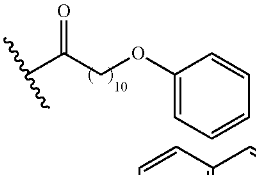, 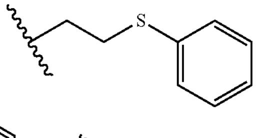,
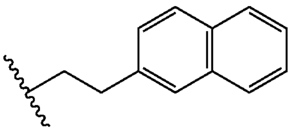, and 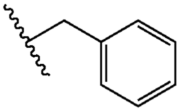;
$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each L-$A_1$ is a linker covalently attached to a nitrogen atom of a surface exposed lysine in E and to $A_1$; T is an integer from 1 to 20 (e.g., 1, 2, 3, 4, 5, 6, 7, 8, 9, 10, 11, 12, 13, 14, 15, 16, 17, 18, 19, or 20), the squiggly line connected to E indicates that each L-$A_1$ is covalently attached (e.g., by way of a covalent bond or a linker) to the nitrogen atom of a surface exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-V).

In another aspect, the invention features, a conjugate described by formula (4):

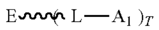

(4)

wherein each $A_1$ is independently selected from any one of formulas (A-VI)-(A-IX):

(A-VI)

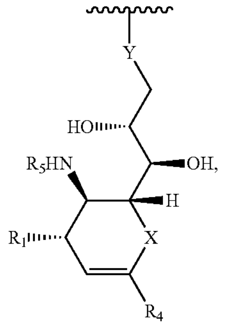

(A-VII)

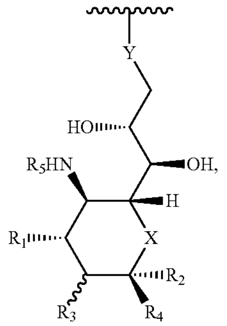

-continued (A-VIII)

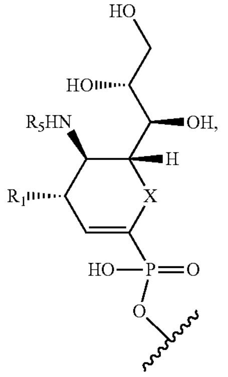

(A-IX)

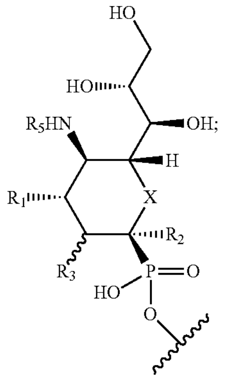

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

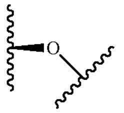

(—O—),

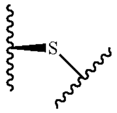

(—S—),

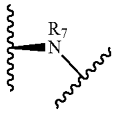

(—$NR_7$—),

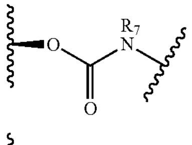

(—O(C=O)$NR_7$—),

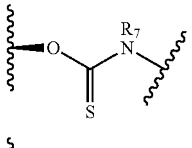

(—O(C=S)$NR_7$—),

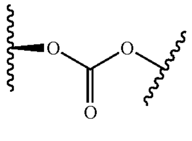

(—O(C=O)O—),

-continued
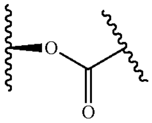
(—O(C=O)—),
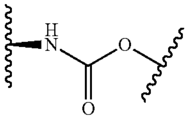
(—NH(C=O)O—),
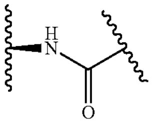
(—NH(C=O)—),
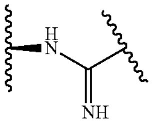
(—NH(C=NH)—),
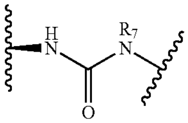
(—NH(C=O)NR$_7$—),
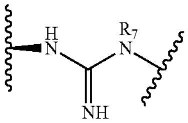
(—NH(C=NH)NR$_7$—),
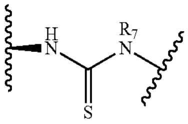
(—NH(C=S)NR$_7$—),
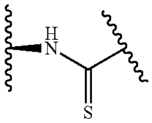
(—NH(C=S)—),
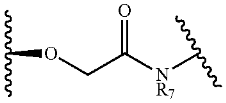
(—OCH$_2$(C=O)NR$_7$—),
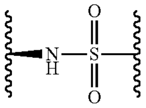
(—NH(SO$_2$)—),
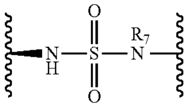
(—NH(SO$_2$)NR$_7$—),
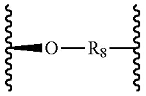
(—OR$_8$—),
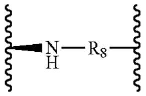
(—NR$_8$—), and
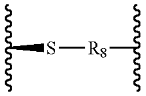
(—SR$_8$—);
$R_6$ is selected from
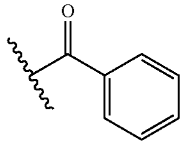,
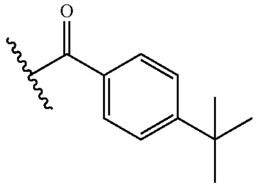,
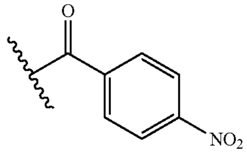,
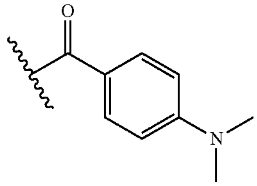,
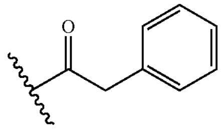,
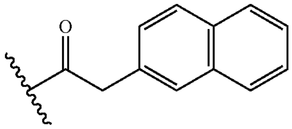,
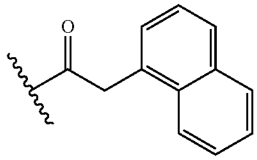,
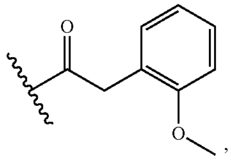,
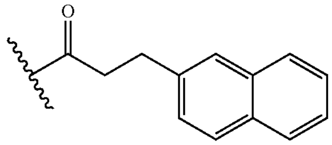,
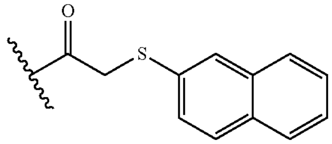,
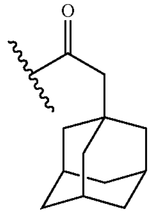,
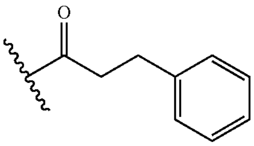,
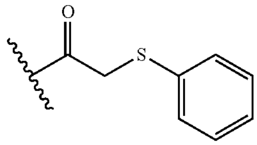,
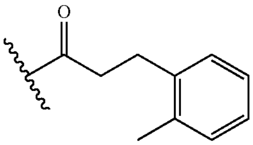,
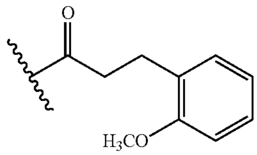,
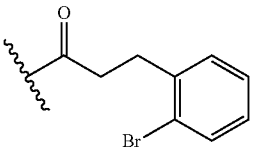,
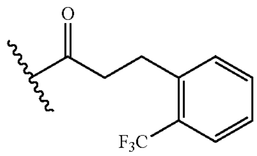, -continued

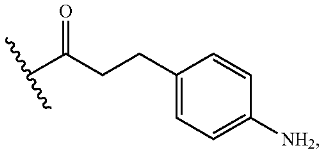

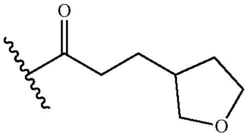
,
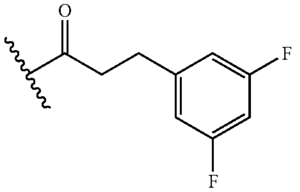
,

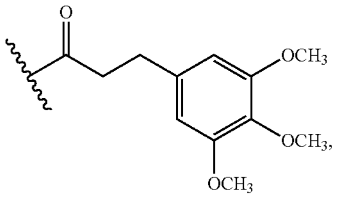

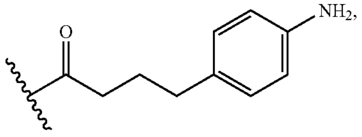

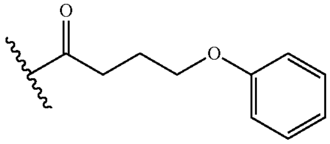
,

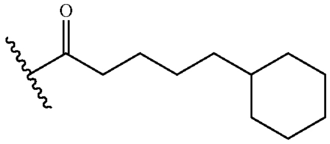
,

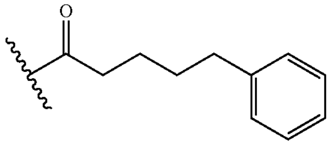
,

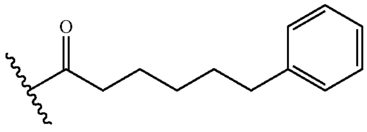
,

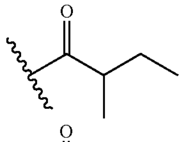
,
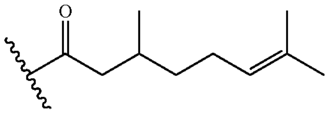
,

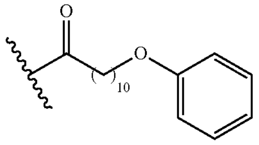
,
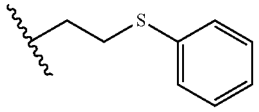
,

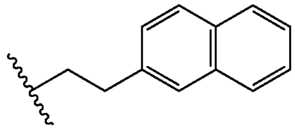
, and
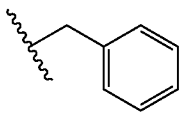
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an Fc domain monomer or an Fc domain (e.g., an Fc domain monomer or an Fc domain, each Fc domain monomer having, independently, the sequence of any one of SEQ ID NOs: 1-68); L in each L-$A_1$ is a linker covalently attached to a nitrogen atom of a surface exposed lysine in E and to A; T is an integer from 1 to 20 (e.g., 1, 2, 3, 4, 5, 6, 7, 8, 9, 10, 11, 12, 13, 14, 15, 16, 17, 18, 19, or 20), the squiggly line connected to E indicates that each L-$A_1$ is covalently attached (e.g., by way of a covalent bond or a linker) to the nitrogen atom of a surface exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-VI)-(A-IX).

In another aspect, the invention features a conjugate described by formula (5):

(5)

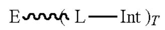

wherein each Int is independently selected from any one of the intermediates of Table 1; E comprises an Fc domain monomer or an Fc domain (e.g., an Fc domain monomer or an Fc domain, each Fc domain monomer having, independently, the sequence of any one of SEQ ID NOs: 1-68); L in each L-Int is a linker covalently attached to a nitrogen atom of a surface exposed lysine in E and to Int; T is an integer from 1 to 20 (e.g., 1, 2, 3, 4, 5, 6, 7, 8, 9, 10, 11, 12, 13, 14, 15, 16, 17, 18, 19, or 20), the squiggly line connected to E indicates that each L-Int is covalently attached (e.g., by way of a covalent bond or a linker) to the nitrogen atom of a surface exposed lysine or the sulfur atom of a surface exposed cysteine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each Int may be independently selected from any one of the intermediates of Table 1.

Intermediates of Table 1 may be conjugated to an Fc domain or Fc domain monomer (e.g., by way of a linker) by any suitable methods known to those of skill in the art, including any of the methods described or exemplified herein. In some embodiments, the conjugate (e.g., a conjugate described by formula (5)) comprises E, wherein E is an Fc domain monomer or an Fc domain (e.g., an Fc domain monomer or an Fc domain, each Fc domain monomer having, independently, the sequence of any one of SEQ ID NOs: 1-68). In preferred embodiments, one or more nitrogen atoms of one or more surface exposed lysine residues of E or one or more sulfur atoms of one or more surface exposed cysteines in E is covalently conjugated to a linker (e.g., a $PEG_2$-$PEG_{20}$ linker). The linker conjugated to E may be functionalized such that it may react to form a covalent bond with any of the Ints described herein (e.g., an Int of Table 1). In preferred embodiments, E is conjugated to a linker functionalized with an azido group and the Int (e.g., an Int of Table 1) is functionalized with an alkyne group. Conjugation (e.g., by click chemistry) of the linker-azido of E and linker-alkyne of the Int forms a conjugate of the invention, for example a conjugate described by formula (5). In yet other embodiments, E is conjugated to a linker functionalized with an alkyne group and the Int (e.g., an Int of Table 1) is functionalized with an azido group. Conjugation (e.g., by click chemistry) of the linker-alkyne of E and linker-azido of the Int forms a conjugate of the invention, for example a conjugate described by formula (5).

TABLE 1
| Intermediates | |
|---|---|
| Intermediate | Structure |
| Int-1 | 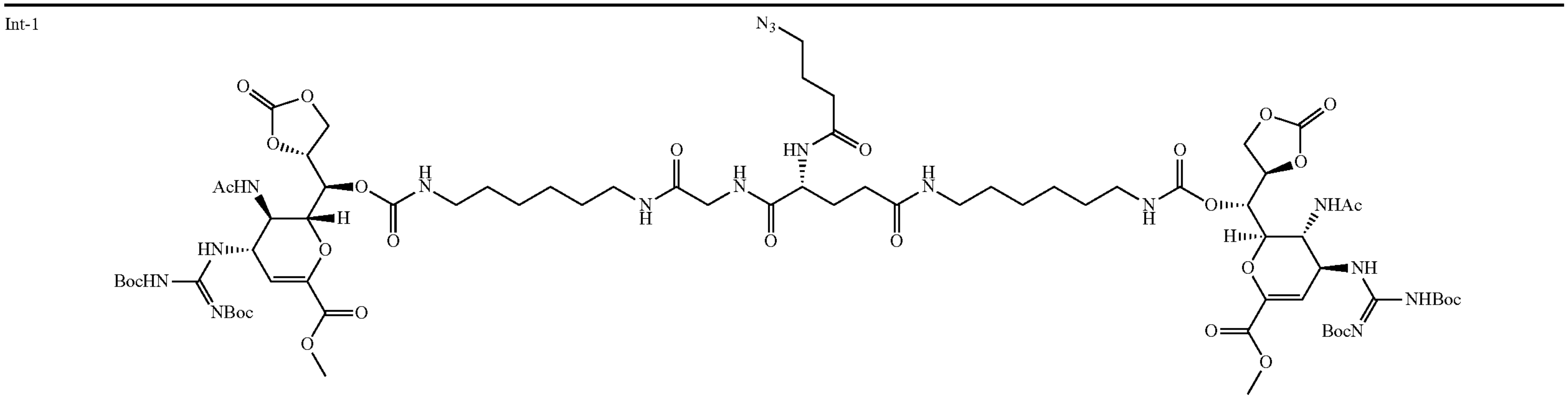 |
| Int-2 | 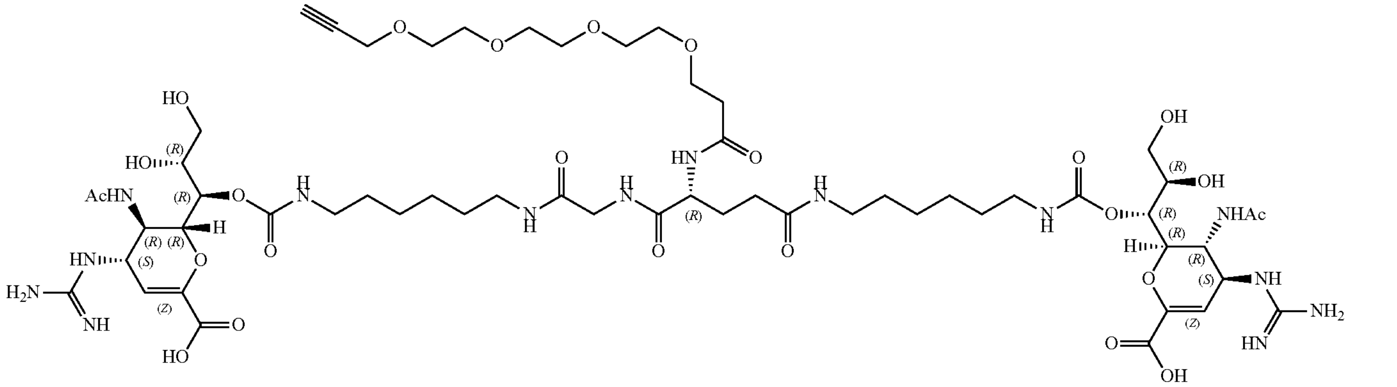 |

TABLE 1-continued
| Intermediates | |
|---|---|
| Intermediate | Structure |
| Int-3 | 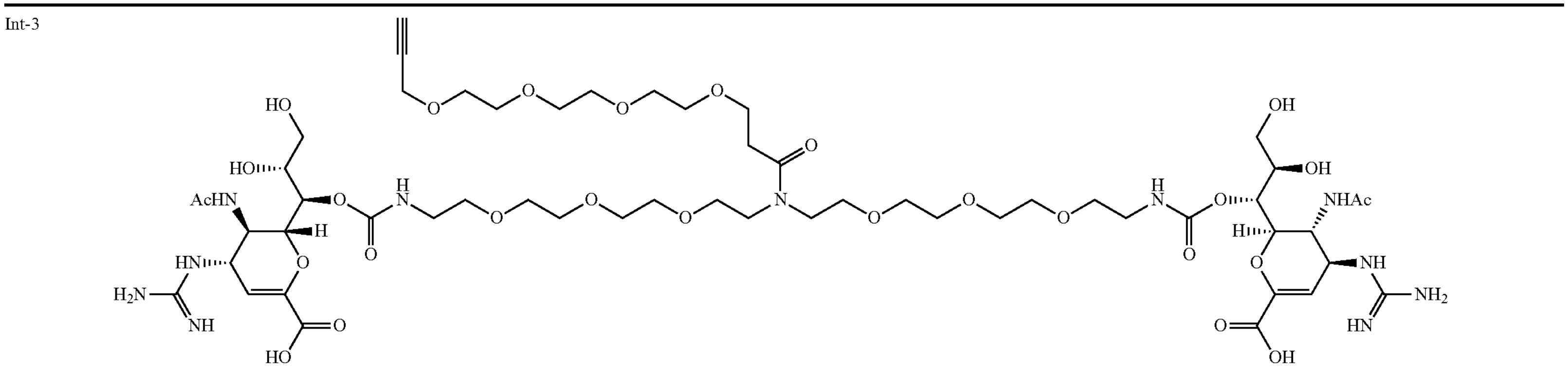 |
| Int-4 | 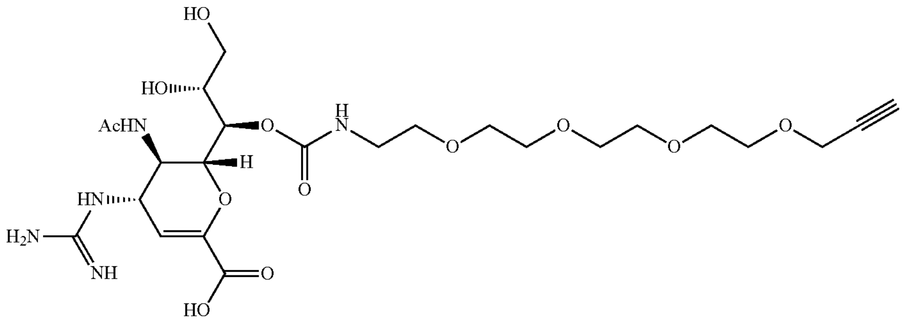 [SMILES: C#CCOCCOCCOCCOCCNC(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-5 | 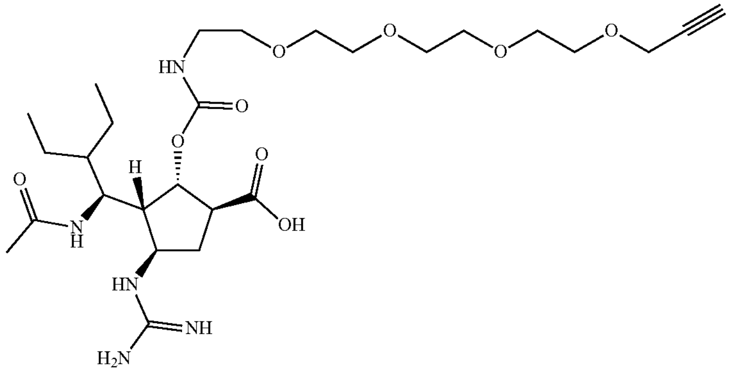 [SMILES: C#CCOCCOCCOCCOCCNC(=O)O[C@H]1[C@@H]([C@@H](NC(C)=O)C(CC)CC)[C@H](NC(=N)N)C[C@@H]1C(=O)O] |
| Int-6 | 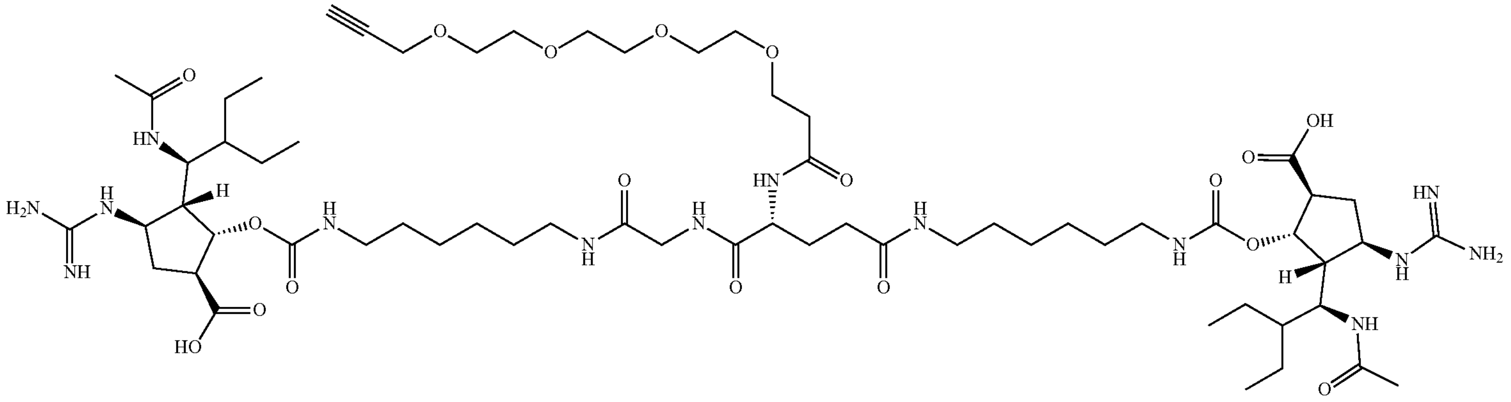 [SMILES: C#CCOCCOCCOCCOCCC(=O)N[C@H](CCC(=O)NCCCCCCNC(=O)O[C@H]1[C@@H]([C@@H](NC(C)=O)C(CC)CC)[C@H](NC(=N)N)C[C@@H]1C(=O)O)C(=O)NCC(=O)NCCCCCCNC(=O)O[C@H]1[C@@H]([C@@H](NC(C)=O)C(CC)CC)[C@H](NC(=N)N)C[C@@H]1C(=O)O] |

TABLE 1-continued
| Intermediates | |
|---|---|
| Intermediate | Structure |
| Int-7 | 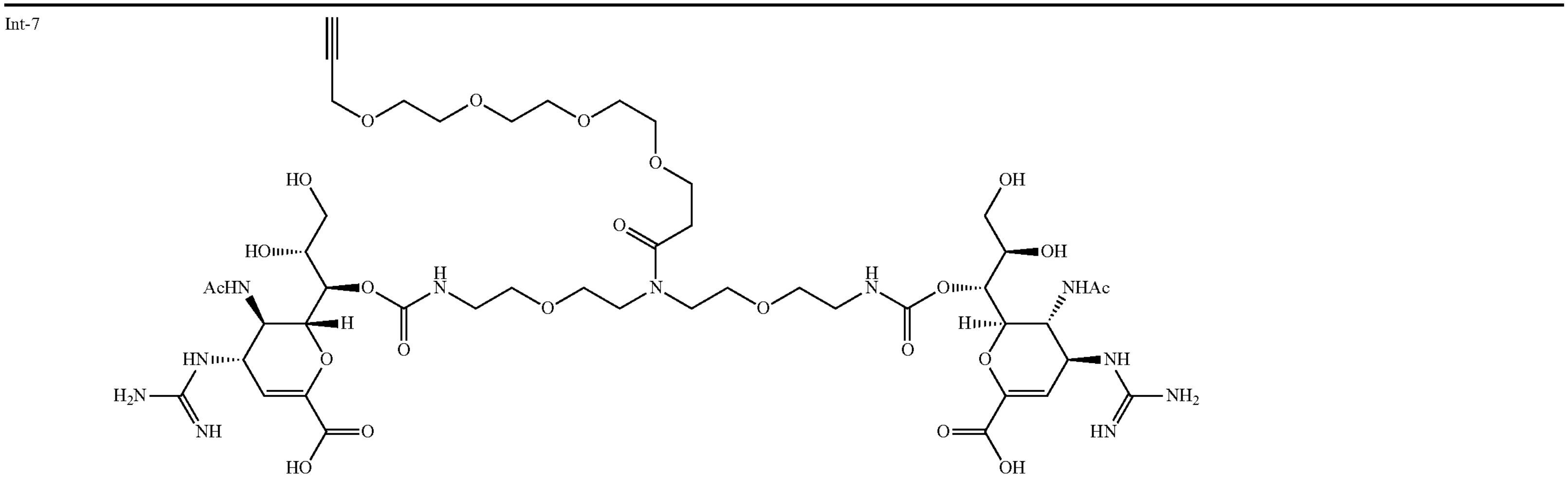 |
| Int-9 | 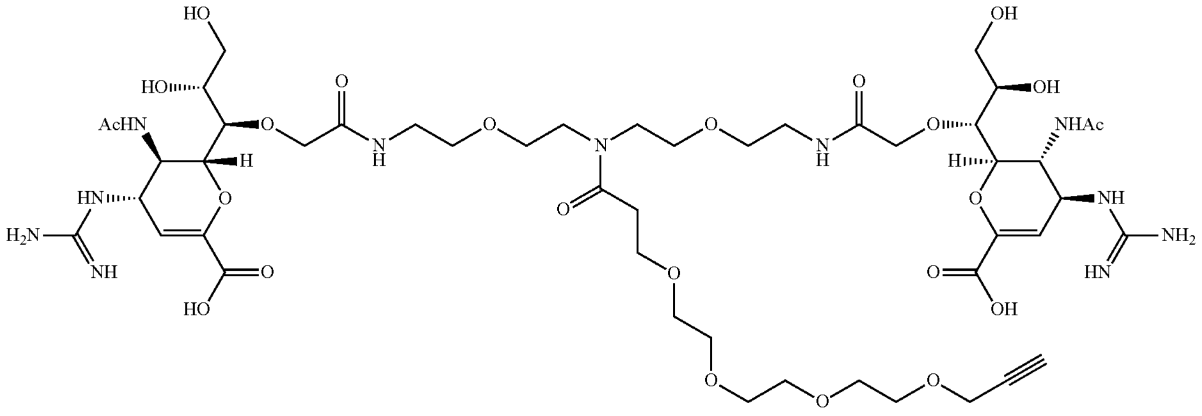 [SMILES: C#CCOCCOCCOCCOCCC(=O)N(CCOCCNC(=O)CO[C@@H]([C@@H]1OC(C(=O)O)=C[C@H](NC(=N)N)[C@H]1NC(C)=O)[C@H](O)CO)CCOCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-12 | 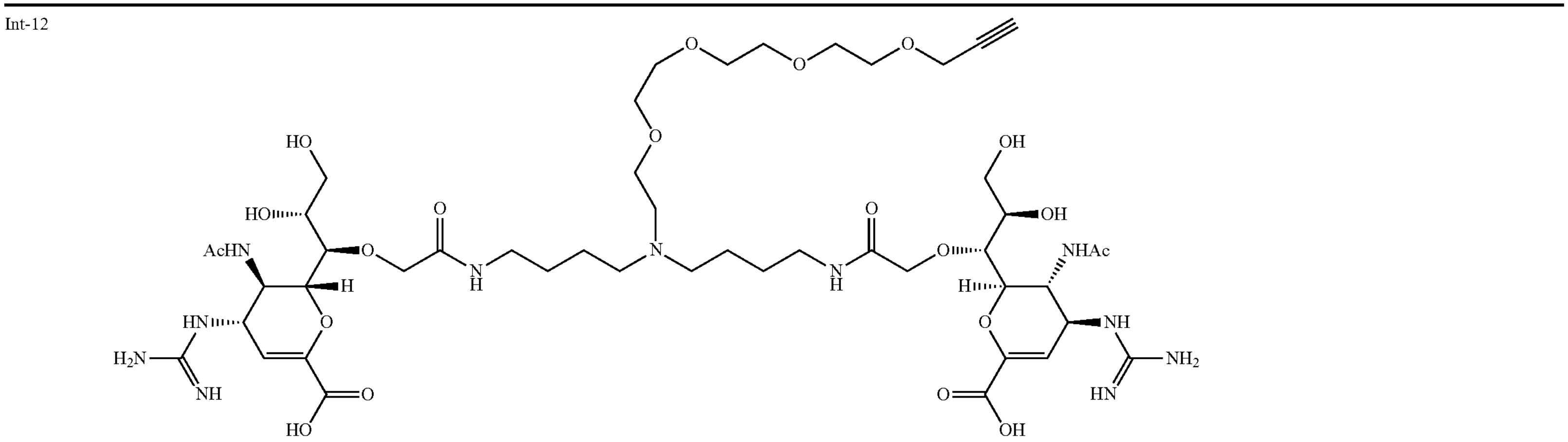 |
| Int-13 | 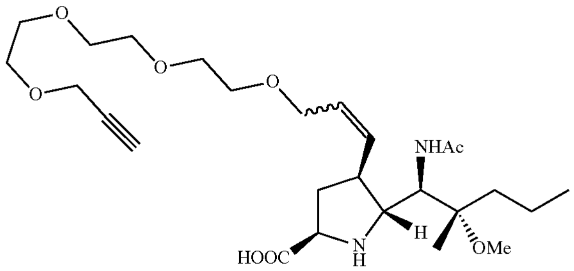 [SMILES: C#CCOCCOCCOCCOCC=C[C@@H]1C[C@H](C(=O)O)N[C@H]1[C@@H](NC(C)=O)[C@](C)(CCC)OC] |

TABLE 1-continued
| Intermediates | |
|---|---|
| Intermediate | Structure |
| Int-14 | 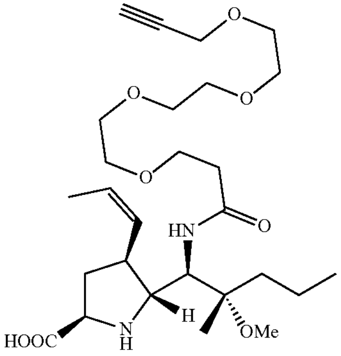 [SMILES: C#CCOCCOCCOCCOCCC(=O)N[C@H]([C@@H]1N[C@@H](C(=O)O)C[C@H]1/C=C\C)[C@](C)(CCC)OC] |
| Int-15 | 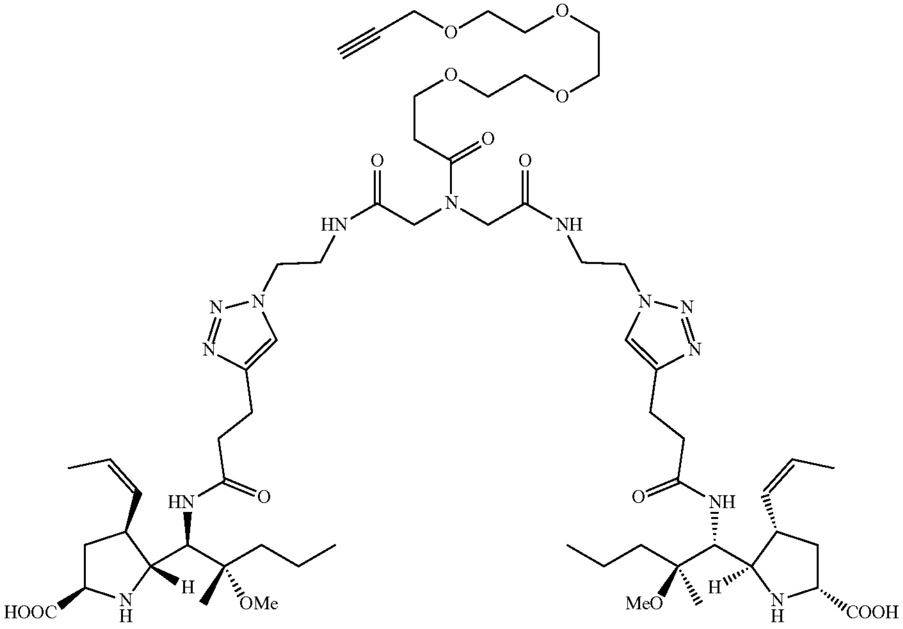 [SMILES: C#CCOCCOCCOCCOCCC(=O)N(CC(=O)NCCn1cc(CCC(=O)N[C@H]([C@@H]2N[C@@H](C(=O)O)C[C@H]2/C=C\C)[C@](C)(CCC)OC)nn1)CC(=O)NCCn1cc(CCC(=O)N[C@H]([C@@H]2N[C@@H](C(=O)O)C[C@H]2/C=C\C)[C@](C)(CCC)OC)nn1] |

TABLE 1-continued
| Intermediates | |
|---|---|
| Intermediate | Structure |
| Int-16 | 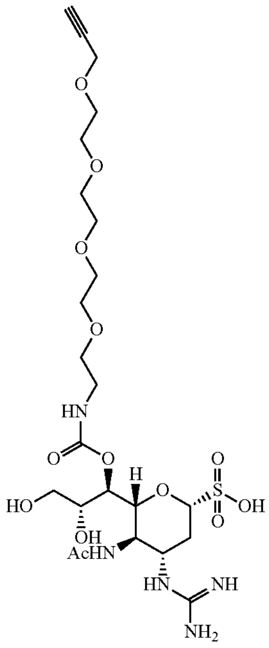 [SMILES: C#CCOCCOCCOCCOCCNC(=O)O[C@@H]([C@@H]1O[C@H](S(=O)(=O)O)C[C@H](NC(=N)N)[C@H]1NC(C)=O)[C@H](O)CO] |

TABLE 1-continued
| Intermediates | |
|---|---|
| Intermediate | Structure |
| Int-17 | 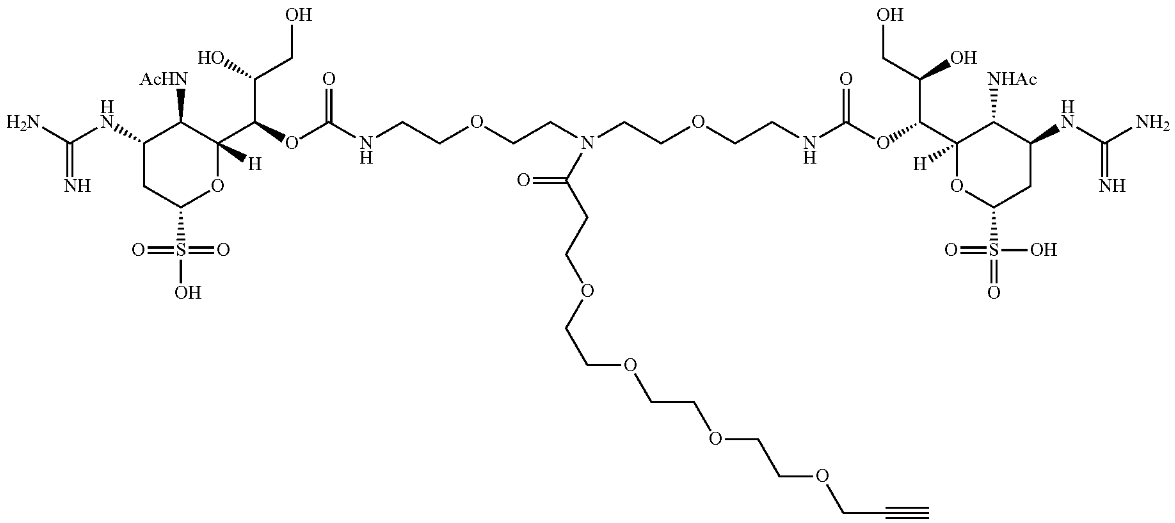 [SMILES: C#CCOCCOCCOCCOCCC(=O)N(CCOCCNC(=O)O[C@@H]([C@@H]1O[C@H](S(=O)(=O)O)C[C@H](NC(=N)N)[C@H]1NC(C)=O)[C@H](O)CO)CCOCCNC(=O)O[C@@H]([C@@H]1O[C@@H](S(=O)(=O)O)C[C@H](NC(=N)N)[C@H]1NC(C)=O)[C@H](O)CO] |

TABLE 1-continued
| Intermediates | |
|---|---|
| Intermediate | Structure |
| Int-18 | 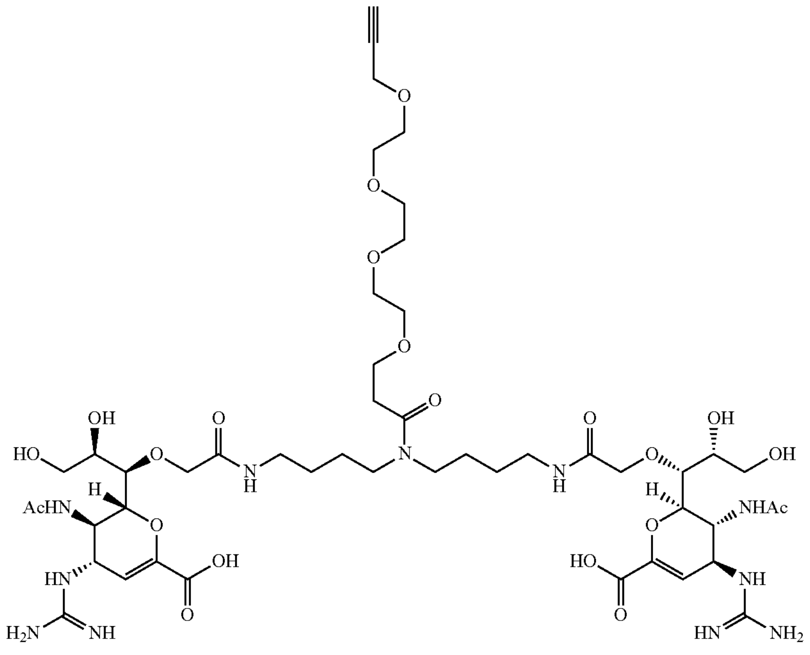 [SMILES: C#CCOCCOCCOCCOCCC(=O)N(CCCCNC(=O)CO[C@@H]([C@@H]1OC(C(=O)O)=C[C@H](NC(=N)N)[C@H]1NC(C)=O)[C@H](O)CO)CCCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-19 | 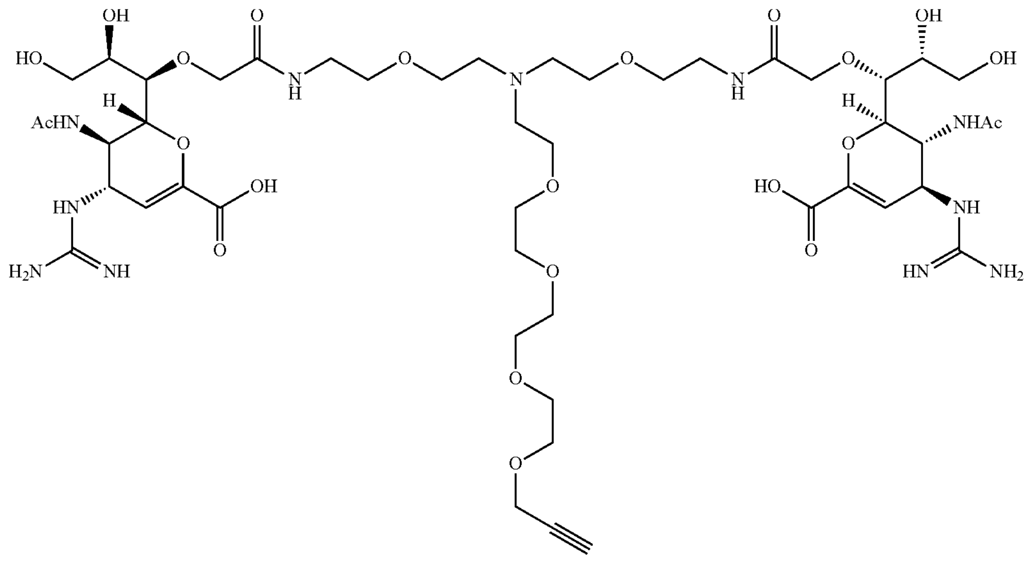 [SMILES: C#CCOCCOCCOCCOCCN(CCOCCNC(=O)CO[C@@H]([C@@H]1OC(C(=O)O)=C[C@H](NC(=N)N)[C@H]1NC(C)=O)[C@H](O)CO)CCOCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-20 | 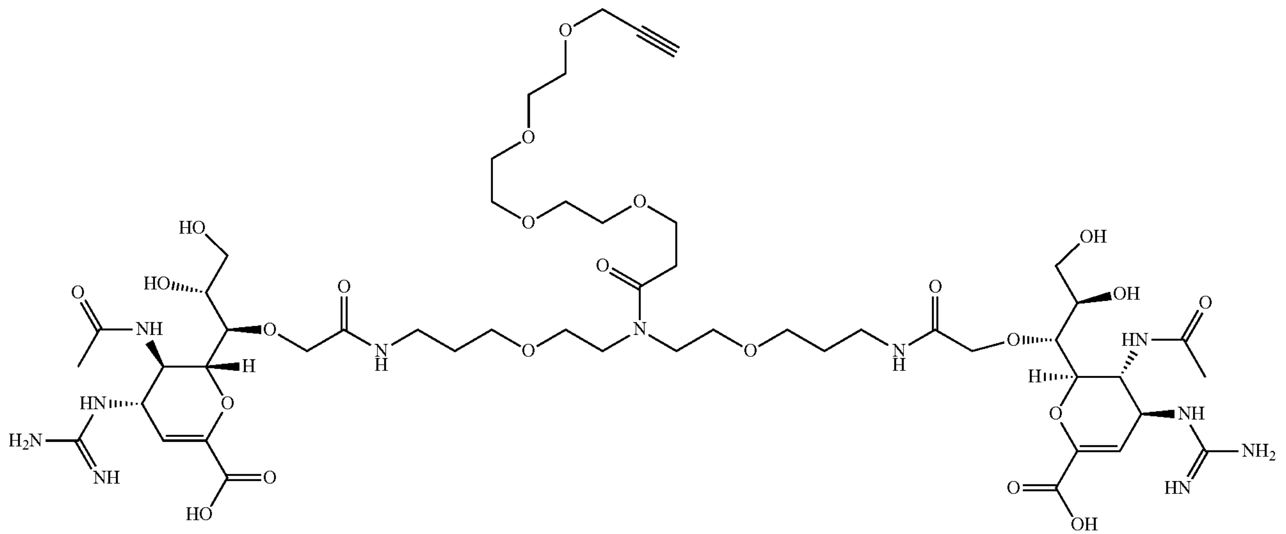 [SMILES: C#CCOCCOCCOCCOCCC(=O)N(CCOCCCNC(=O)CO[C@@H]([C@@H]1OC(C(=O)O)=C[C@H](NC(=N)N)[C@H]1NC(C)=O)[C@H](O)CO)CCOCCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-21 | 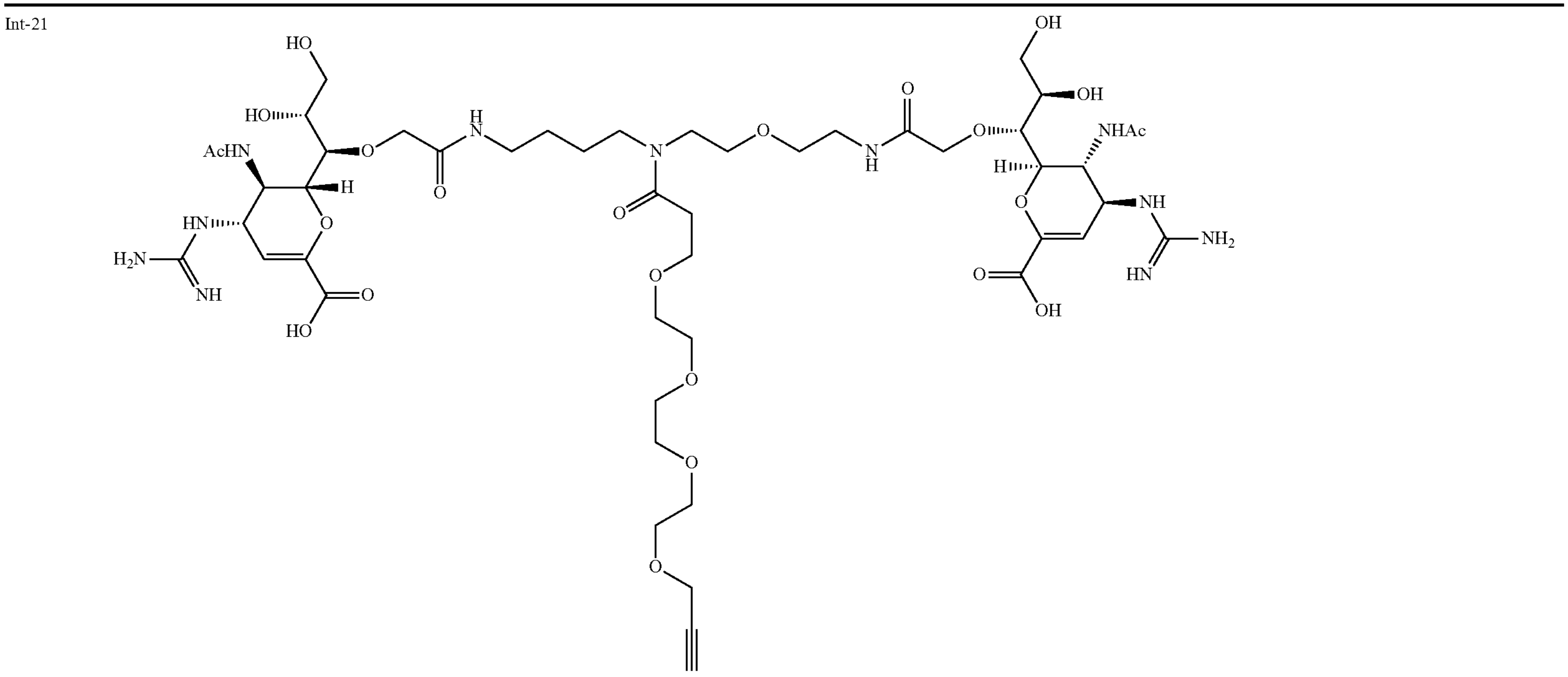 |
| Int-22 | 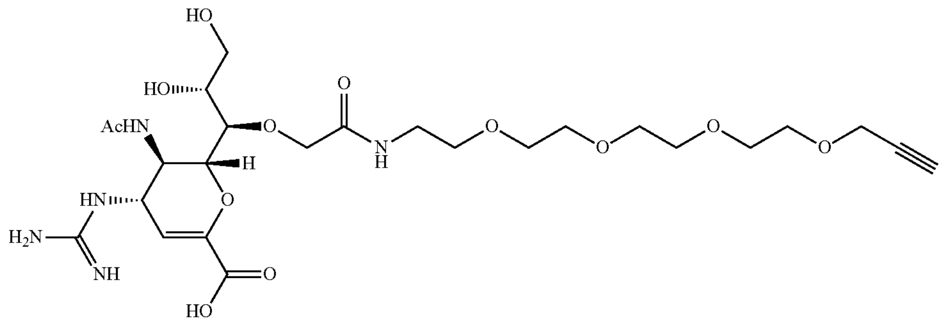 [SMILES: C#CCOCCOCCOCCOCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-23 | 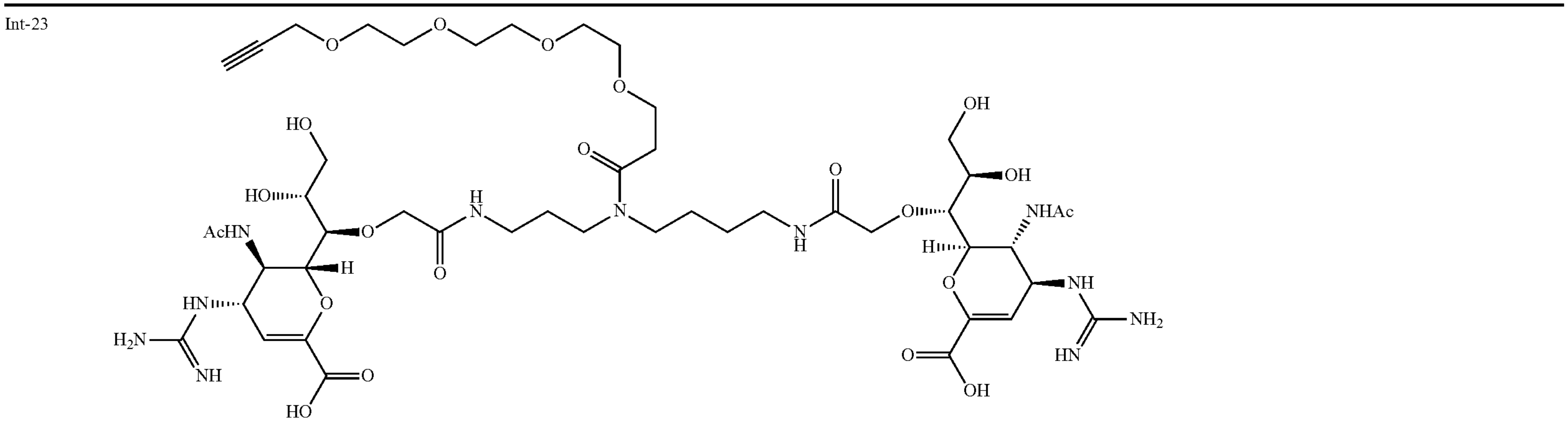 |
| Int-24 | 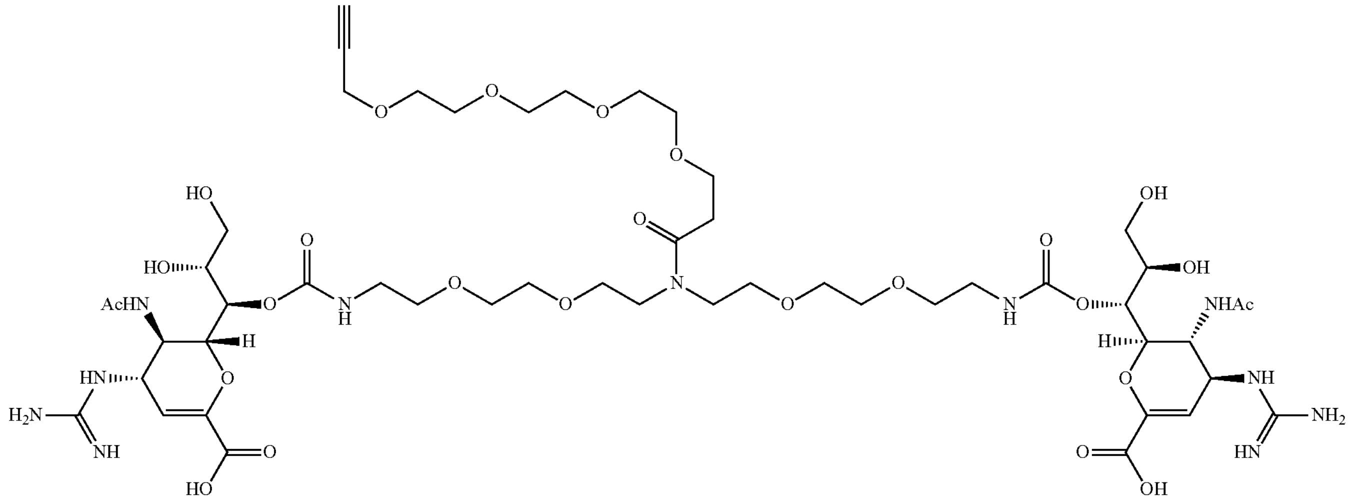 [SMILES: C#CCOCCOCCOCCOCCC(=O)N(CCOCCOCCNC(=O)O[C@@H]([C@@H]1OC(C(=O)O)=C[C@H](NC(=N)N)[C@H]1NC(C)=O)[C@H](O)CO)CCOCCOCCNC(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-25 | 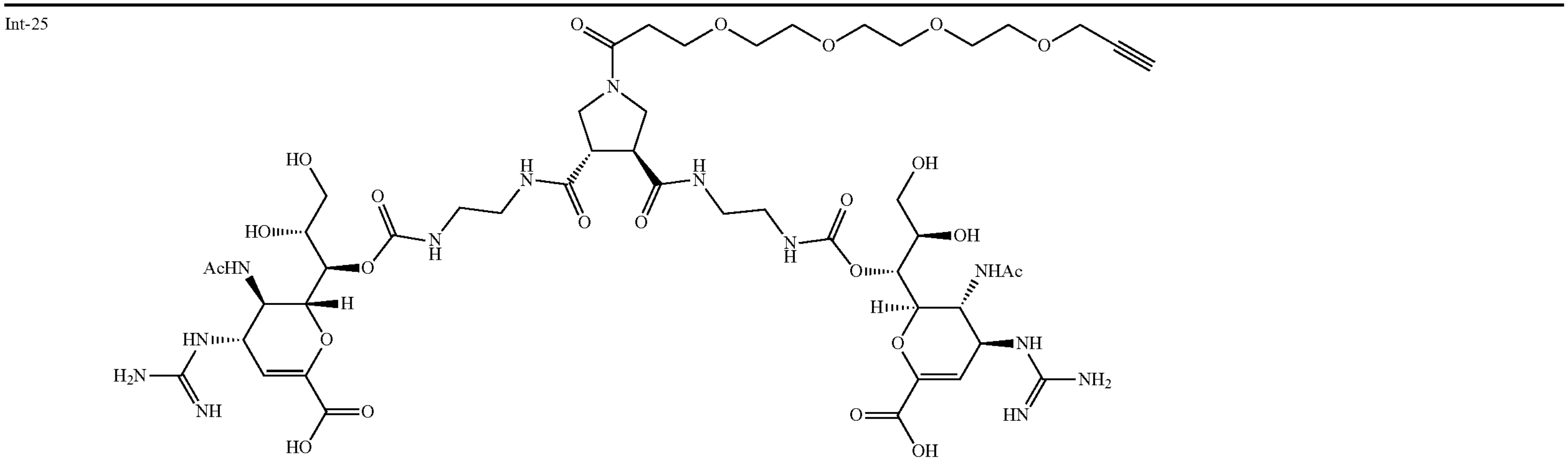 |
| Int-26 | 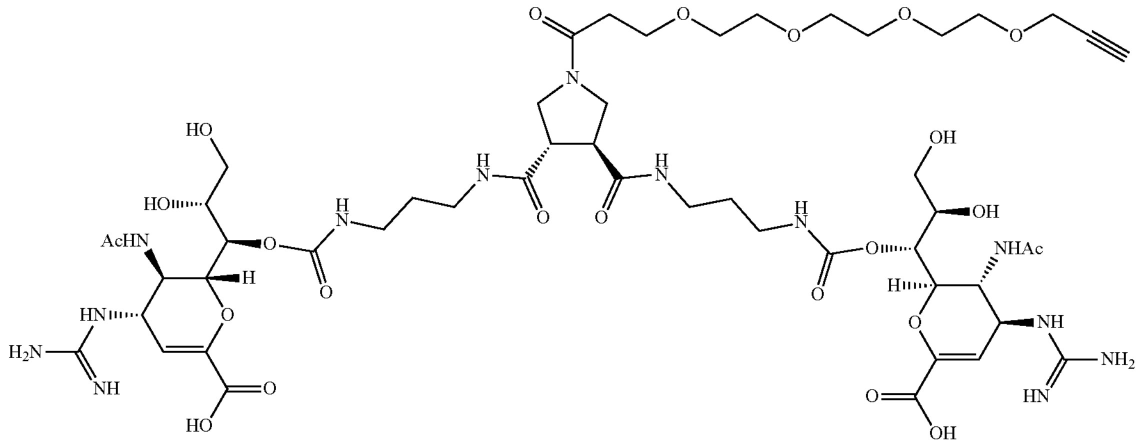 [SMILES: C#CCOCCOCCOCCOCCC(=O)N1C[C@@H](C(=O)NCCCNC(=O)O[C@@H]([C@@H]2OC(C(=O)O)=C[C@H](NC(=N)N)[C@H]2NC(C)=O)[C@H](O)CO)[C@H](C(=O)NCCCNC(=O)O[C@@H]([C@@H]2OC(C(=O)O)=C[C@H](NC(=N)N)[C@H]2NC(C)=O)[C@H](O)CO)C1] |

TABLE 1-continued
| Intermediates | |
|---|---|
| Intermediate | Structure |
| Int-27 | 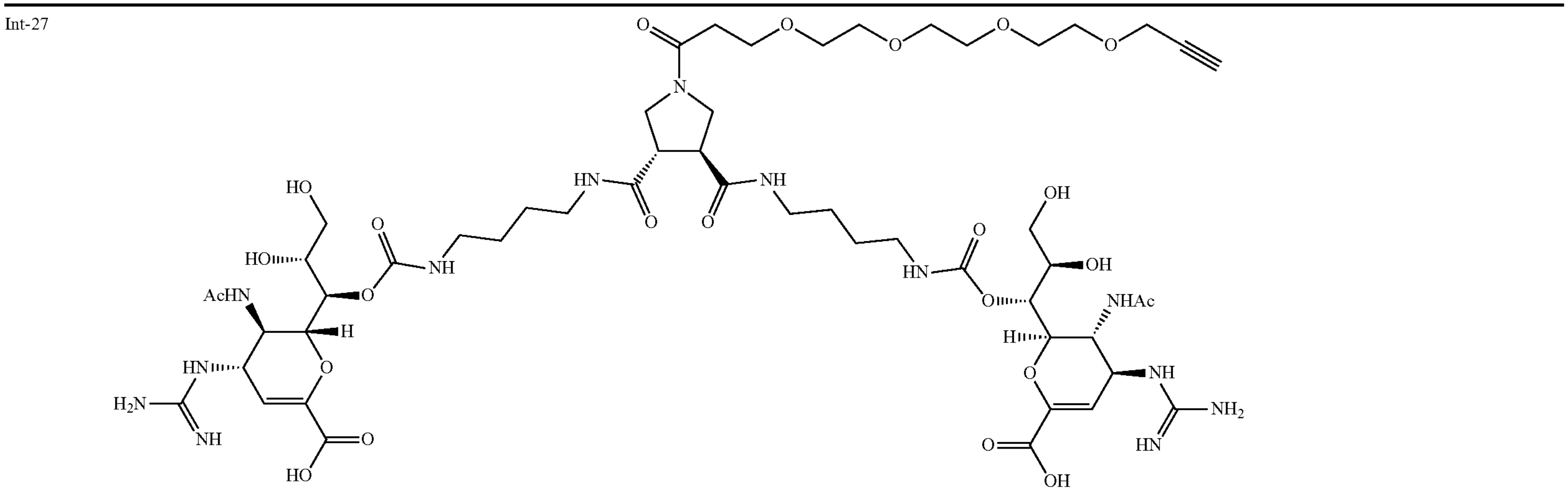 |
| Int-28 | 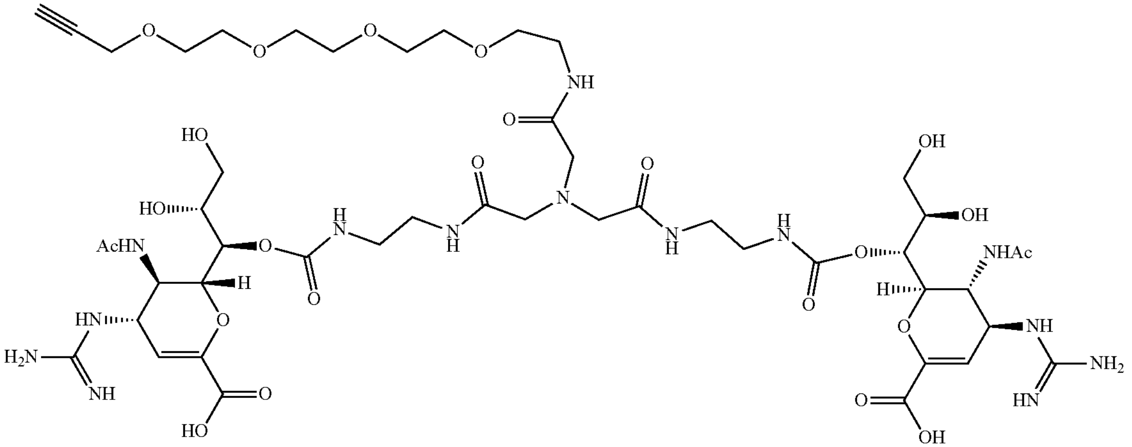 [SMILES: C#CCOCCOCCOCCOCCNC(=O)CN(CC(=O)NCCNC(=O)O[C@@H]([C@@H]1OC(C(=O)O)=C[C@H](NC(=N)N)[C@H]1NC(C)=O)[C@H](O)CO)CC(=O)NCCNC(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-30 | 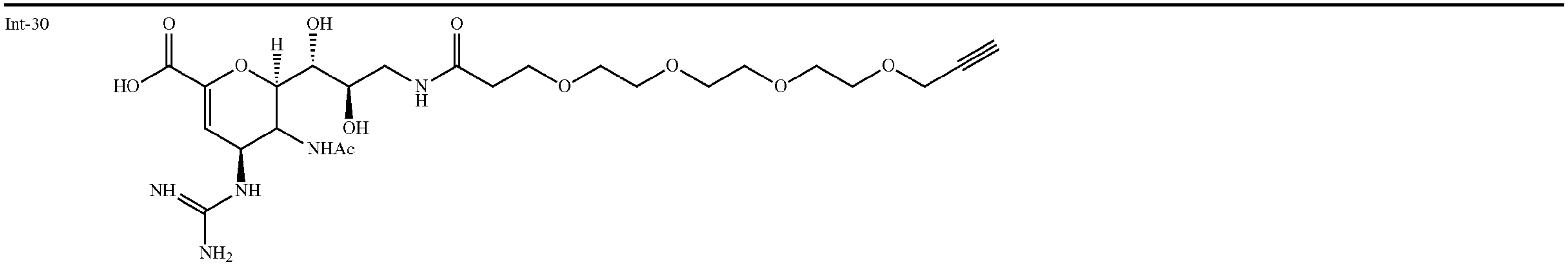 |
| Int-31 | 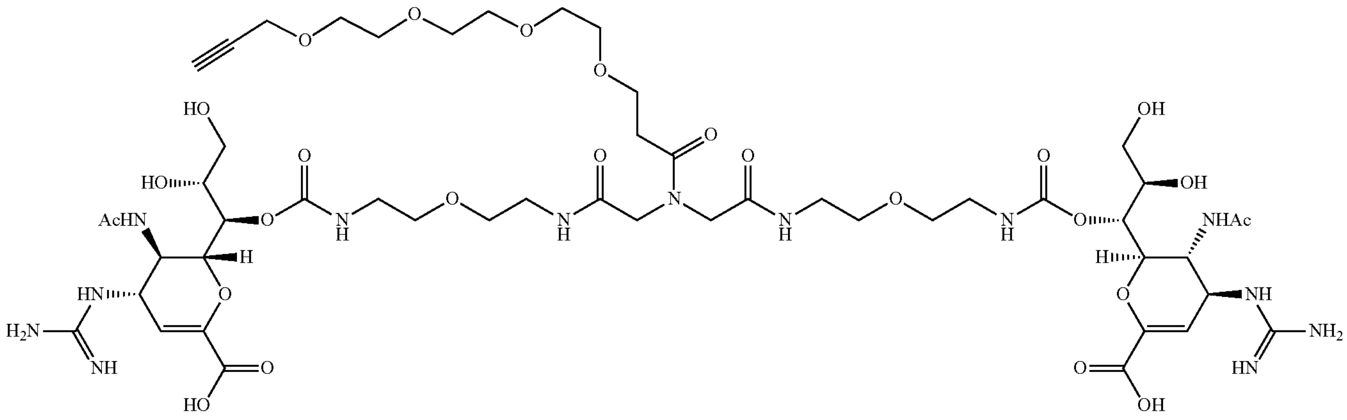 [SMILES: C#CCOCCOCCOCCOCCC(=O)N(CC(=O)NCCOCCNC(=O)O[C@@H]([C@@H]1OC(C(=O)O)=C[C@H](NC(=N)N)[C@H]1NC(C)=O)[C@H](O)CO)CC(=O)NCCOCCNC(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-34 | 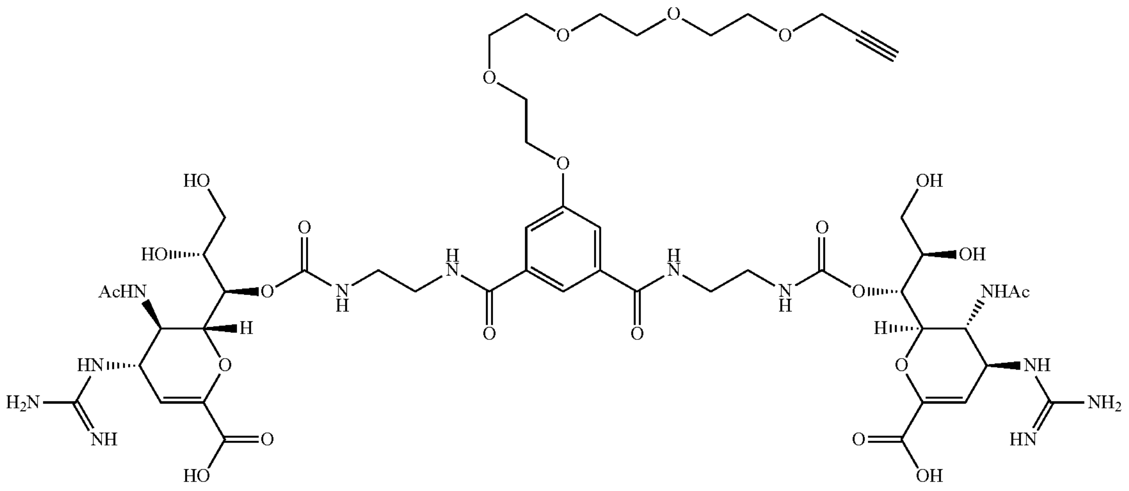 [SMILES: C#CCOCCOCCOCCOCCOc1cc(C(=O)NCCNC(=O)O[C@@H]([C@@H]2OC(C(=O)O)=C[C@H](NC(=N)N)[C@H]2NC(C)=O)[C@H](O)CO)cc(C(=O)NCCNC(=O)O[C@@H]([C@@H]2OC(C(=O)O)=C[C@H](NC(=N)N)[C@H]2NC(C)=O)[C@H](O)CO)c1] |

TABLE 1-continued
| Intermediates | |
|---|---|
| Intermediate | Structure |
| Int-38 | 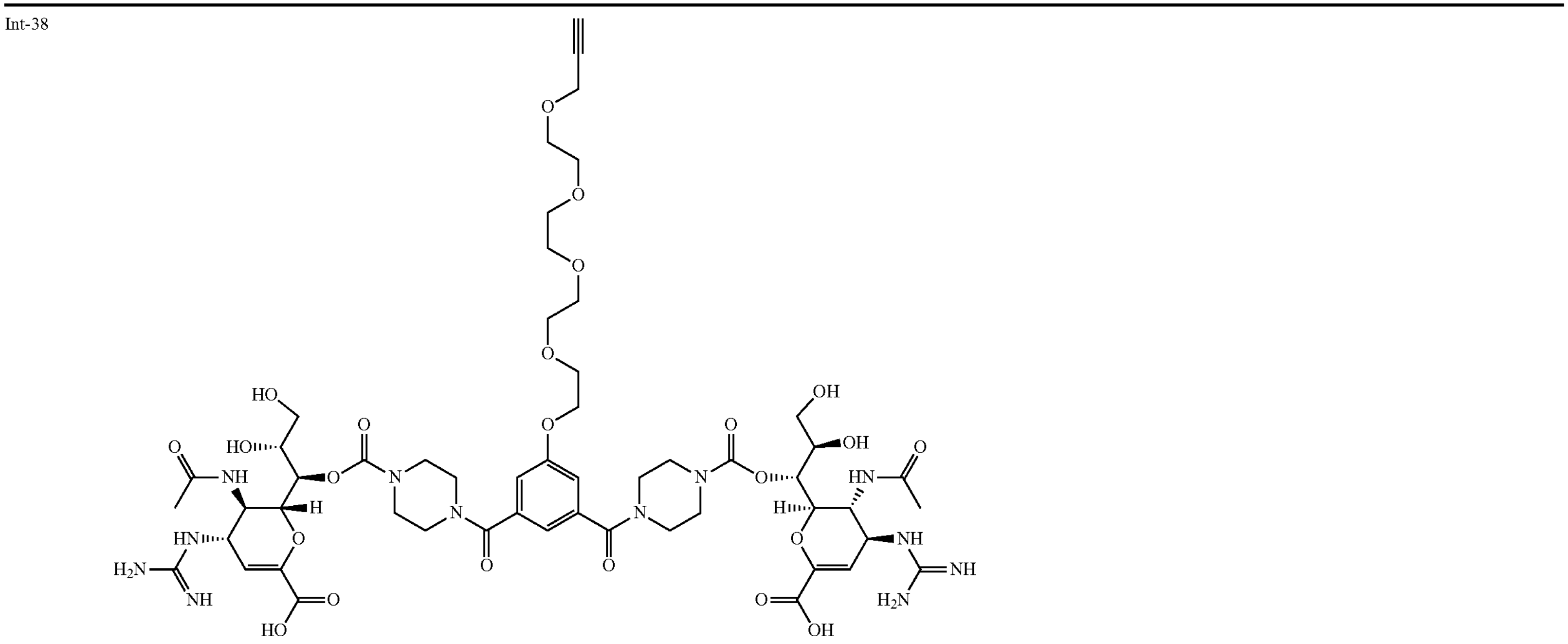 |

TABLE 1-continued
| Intermediates | |
|---|---|
| Intermediate | Structure |
| Int-39 | 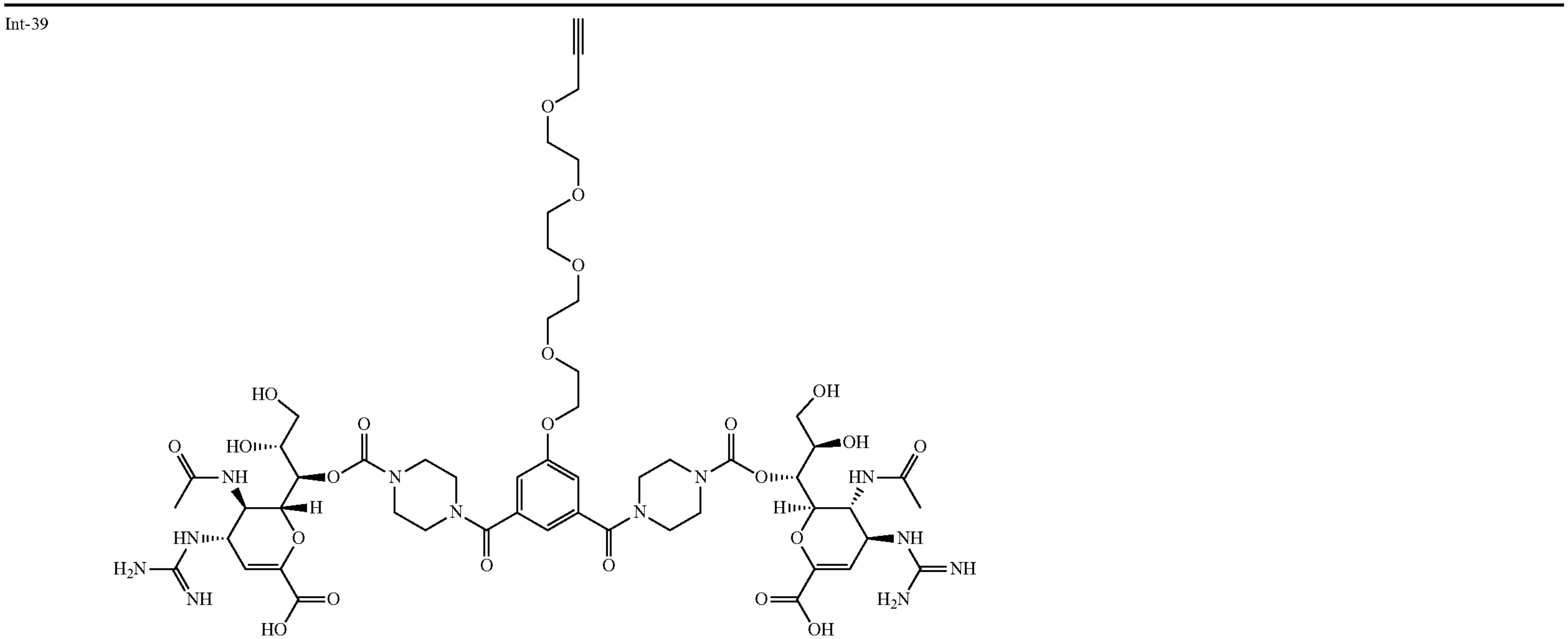 |
| Int-40 | 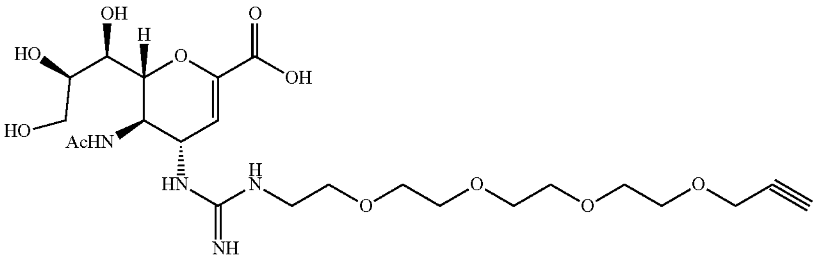 [SMILES: C#CCOCCOCCOCCOCCNC(=N)N[C@H]1C=C(C(=O)O)O[C@@H]([C@H](O)[C@H](O)CO)[C@@H]1NC(C)=O] |

TABLE 1-continued
| Intermediates | |
|---|---|
| Intermediate | Structure |
| Int-42 | 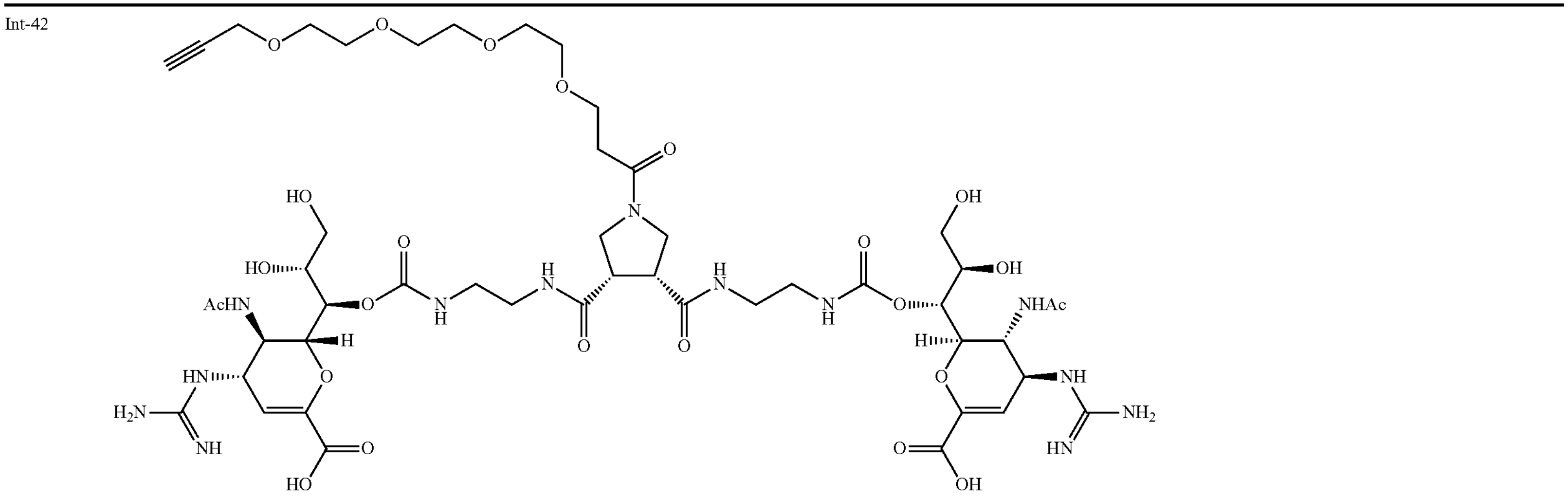 |
| Int-43 | 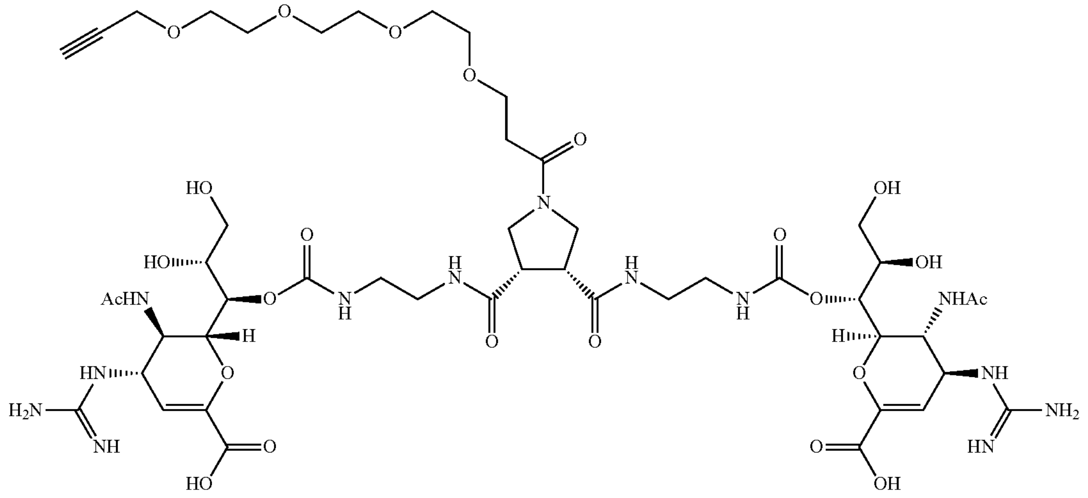 [SMILES: C#CCOCCOCCOCCOCCC(=O)N1C[C@H](C(=O)NCCNC(=O)O[C@@H]([C@@H]2OC(C(=O)O)=C[C@H](NC(=N)N)[C@H]2NC(C)=O)[C@H](O)CO)[C@H](C(=O)NCCNC(=O)O[C@@H]([C@@H]2OC(C(=O)O)=C[C@H](NC(=N)N)[C@H]2NC(C)=O)[C@H](O)CO)C1] |

TABLE 1-continued
| Intermediates | |
| --- | --- |
| Intermediate | Structure |
| Int-44 | 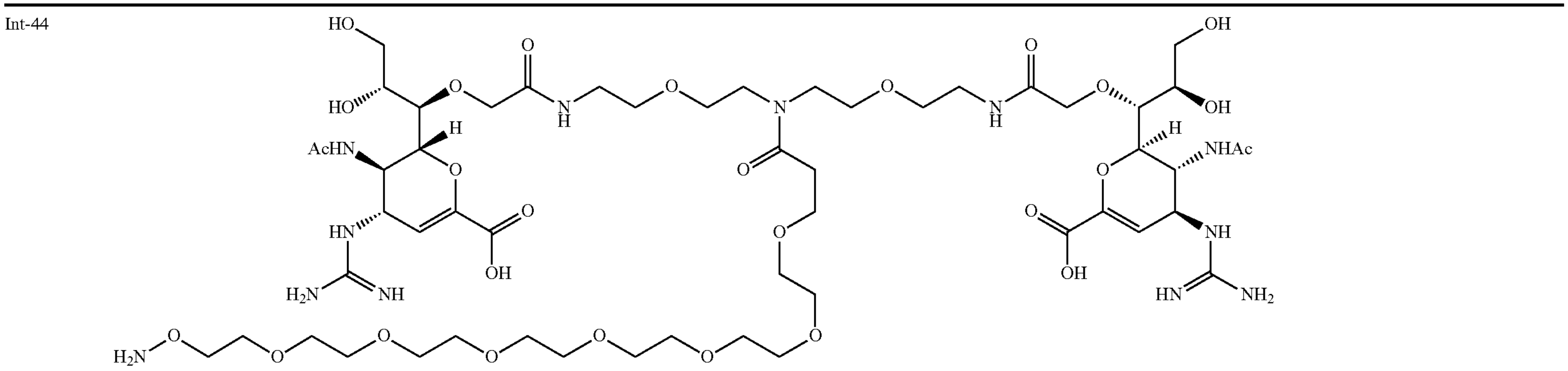 |
| Int-45 | 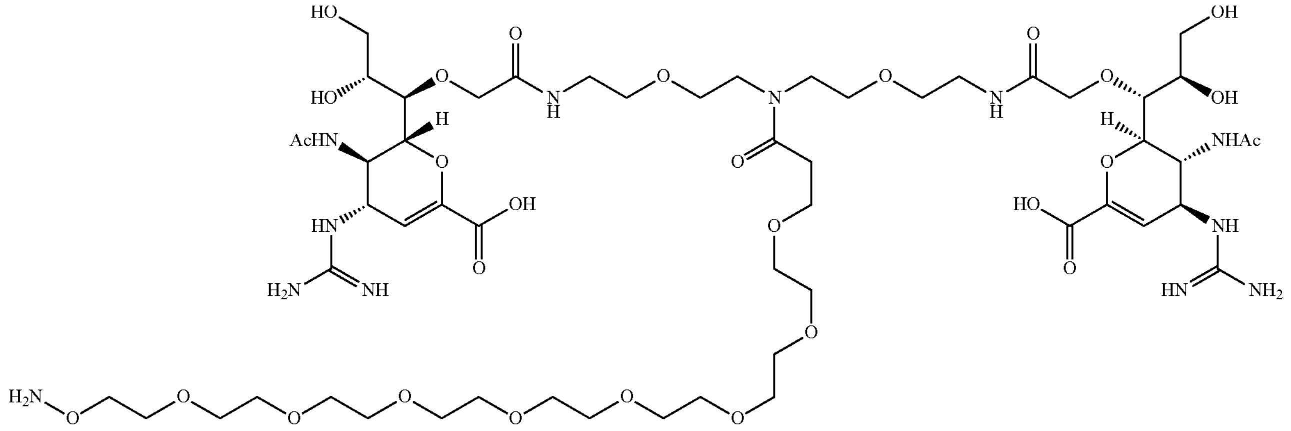 [SMILES: CC(=O)N[C@H]1[C@H]([C@H](OCC(=O)NCCOCCN(CCOCCNC(=O)CO[C@@H]([C@@H]2OC(C(=O)O)=C[C@H](NC(=N)N)[C@H]2NC(C)=O)[C@H](O)CO)C(=O)CCOCCOCCOCCOCCOCCOCCOCCOCCON)[C@H](O)CO)OC(C(=O)O)=C[C@@H]1NC(=N)N] |

TABLE 1-continued
| Intermediates | |
|---|---|
| Intermediate | Structure |
| Int-46 | 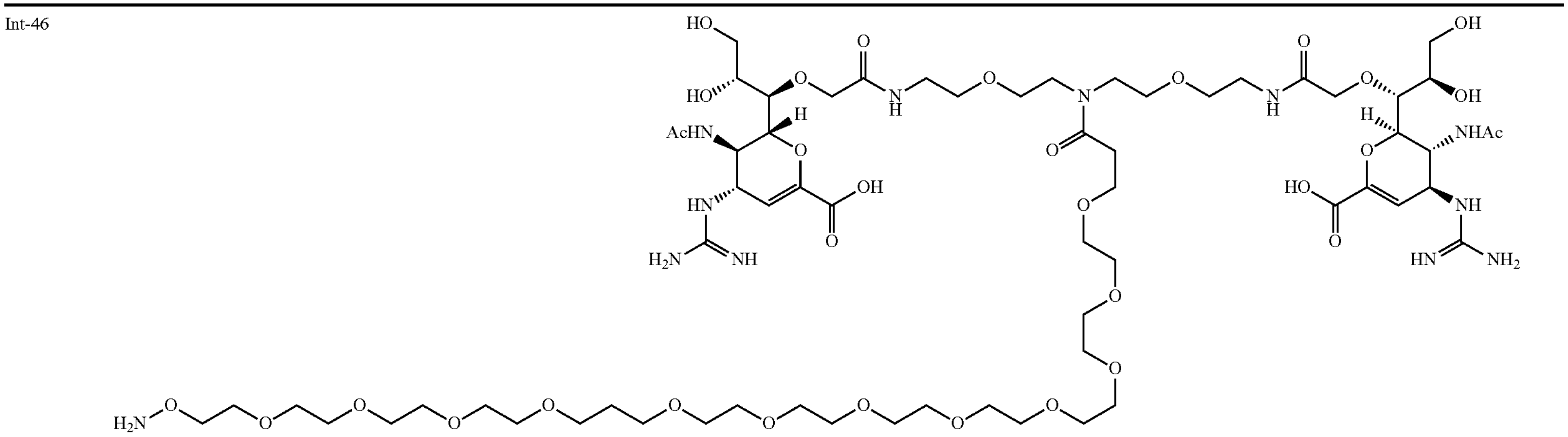 |
| Int-47 | 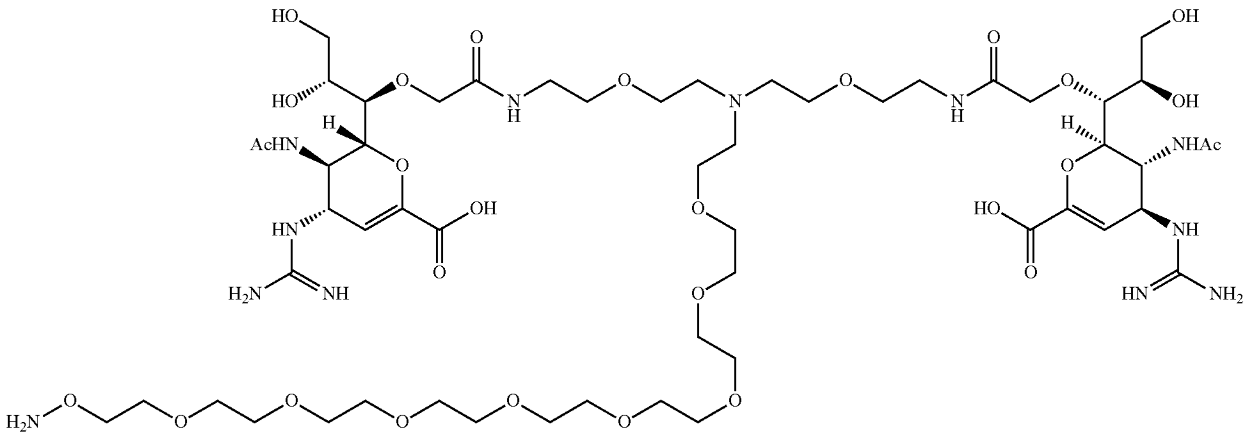 [SMILES: CC(=O)N[C@H]1[C@H]([C@H](OCC(=O)NCCOCCN(CCOCCNC(=O)CO[C@@H]([C@@H]2OC(C(=O)O)=C[C@H](NC(=N)N)[C@H]2NC(C)=O)[C@H](O)CO)CCOCCOCCOCCOCCOCCOCCOCCOCCON)[C@H](O)CO)OC(C(=O)O)=C[C@@H]1NC(=N)N] |

TABLE 1-continued
| Intermediates | |
|---|---|
| Intermediate | Structure |
| Int-48 | 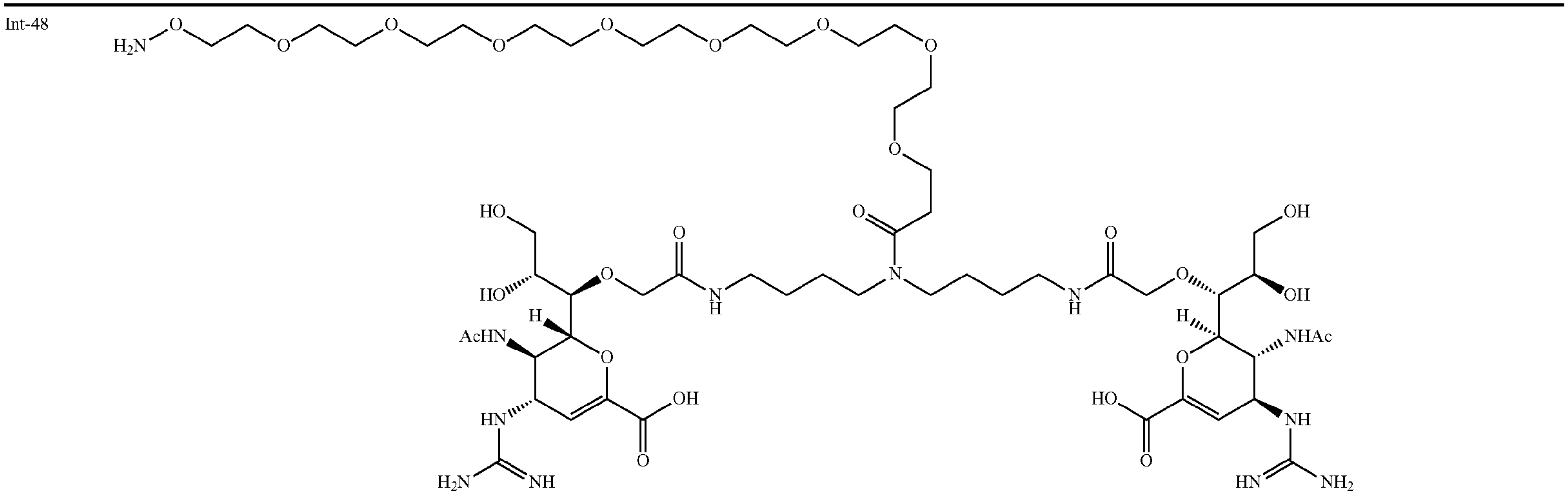 |
| Int-49 | 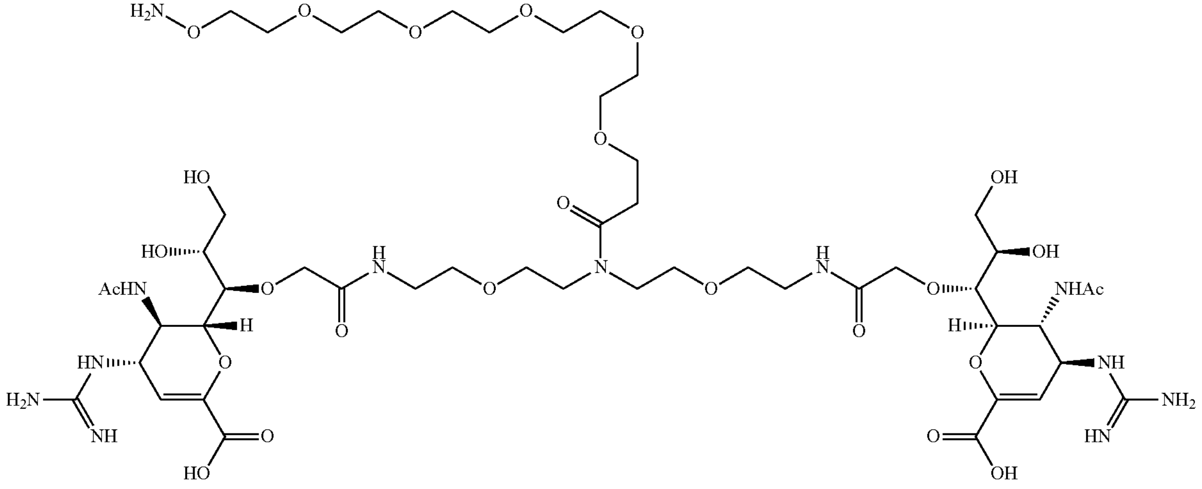 [SMILES: CC(=O)N[C@H]1[C@H]([C@H](OCC(=O)NCCOCCN(CCOCCNC(=O)CO[C@@H]([C@@H]2OC(C(=O)O)=C[C@H](NC(=N)N)[C@H]2NC(C)=O)[C@H](O)CO)C(=O)CCOCCOCCOCCOCCOCCON)[C@H](O)CO)OC(C(=O)O)=C[C@@H]1NC(=N)N] |

TABLE 1-continued
| Intermediates | |
| --- | --- |
| Intermediate | Structure |
| Int-50 | 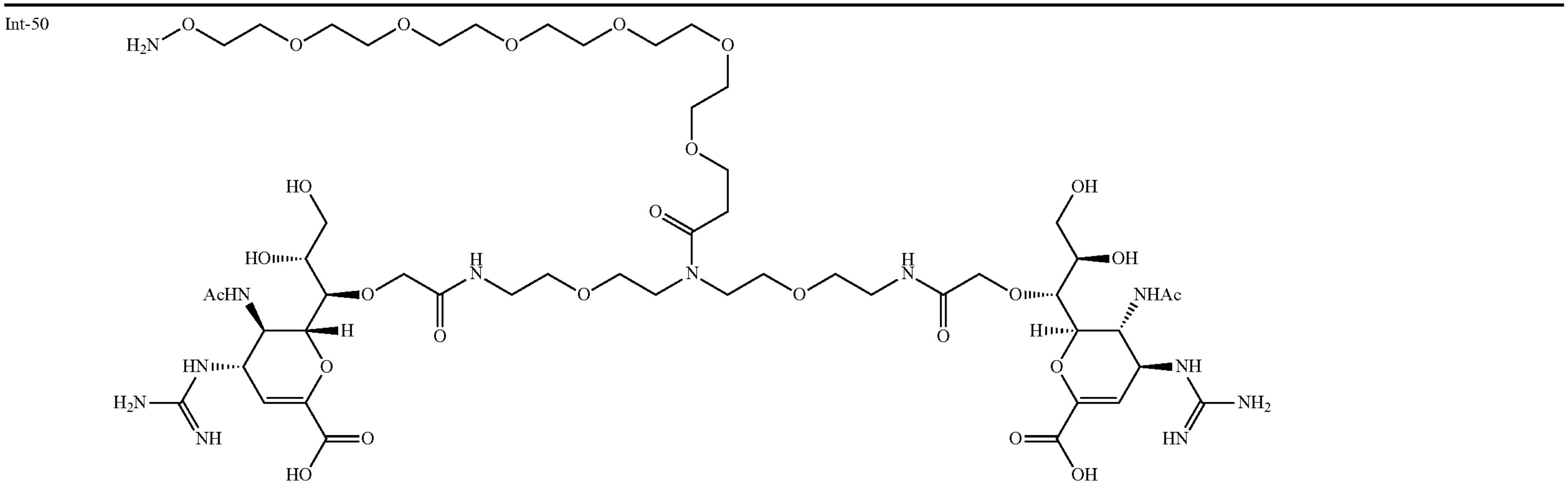 |
| Int-52 | 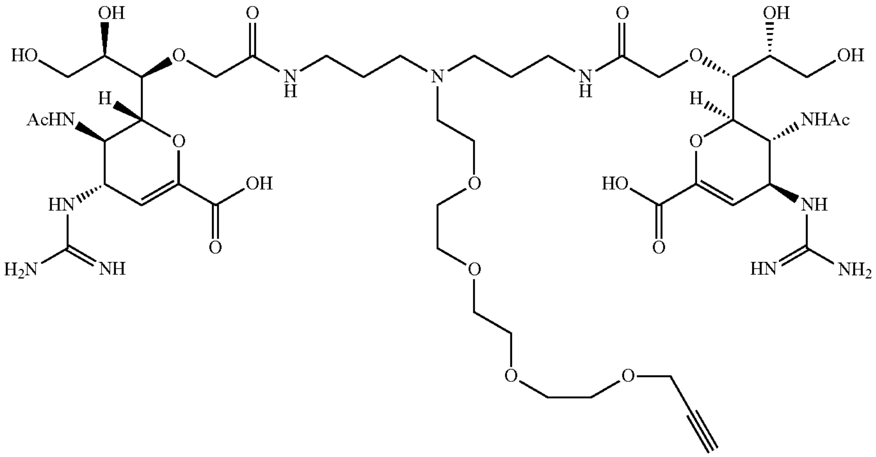 [SMILES: C#CCOCCOCCOCCOCCN(CCCNC(=O)CO[C@@H]([C@@H]1OC(C(=O)O)=C[C@H](NC(=N)N)[C@H]1NC(C)=O)[C@H](O)CO)CCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-53 | 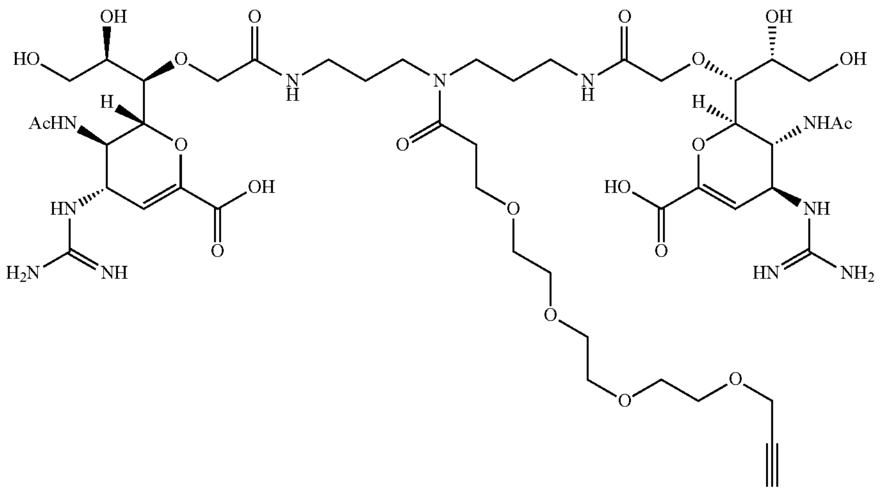 [SMILES: C#CCOCCOCCOCCOCCC(=O)N(CCCNC(=O)CO[C@@H]([C@@H]1OC(C(=O)O)=C[C@H](NC(=N)N)[C@H]1NC(C)=O)[C@H](O)CO)CCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-54 | 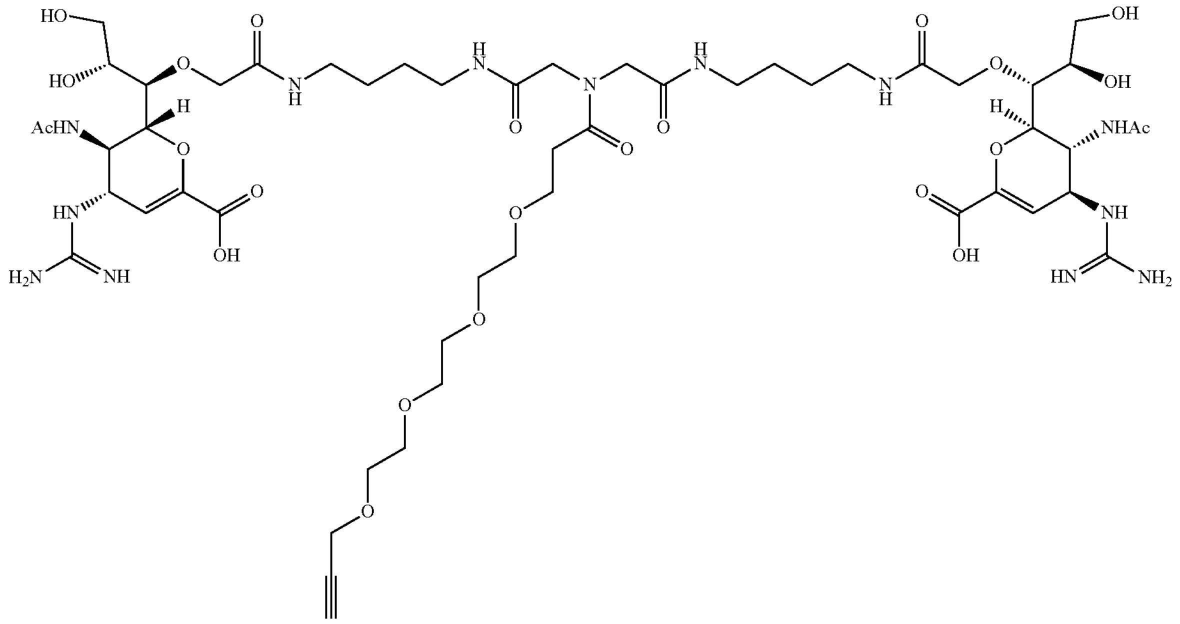 [SMILES: C#CCOCCOCCOCCOCCC(=O)N(CC(=O)NCCCCNC(=O)CO[C@@H]([C@@H]1OC(C(=O)O)=C[C@H](NC(=N)N)[C@H]1NC(C)=O)[C@H](O)CO)CC(=O)NCCCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-55 | 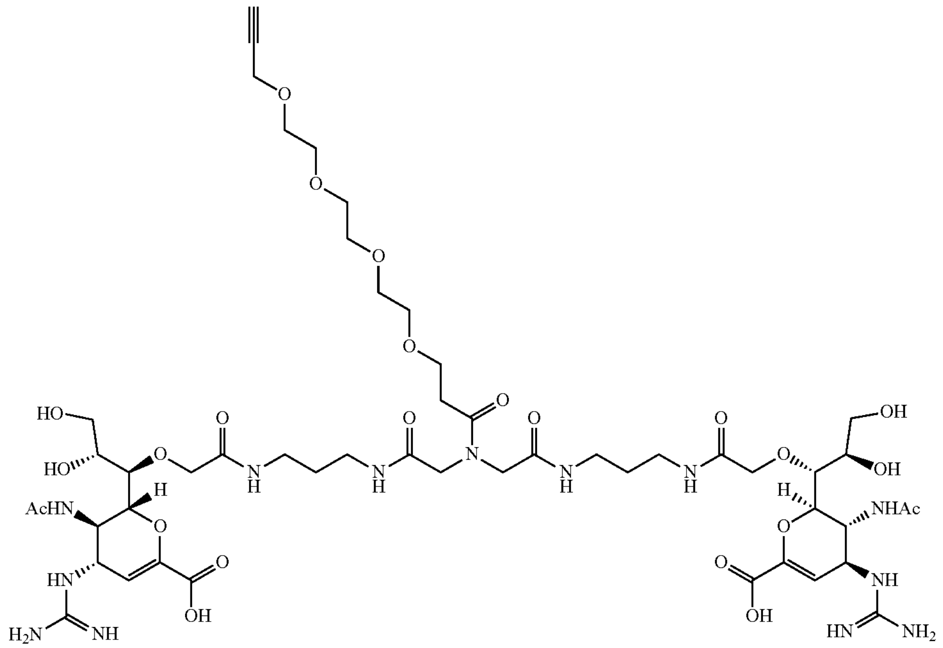 [SMILES: C#CCOCCOCCOCCOCCC(=O)N(CC(=O)NCCCNC(=O)CO[C@@H]([C@@H]1OC(C(=O)O)=C[C@H](NC(=N)N)[C@H]1NC(C)=O)[C@H](O)CO)CC(=O)NCCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-57 | 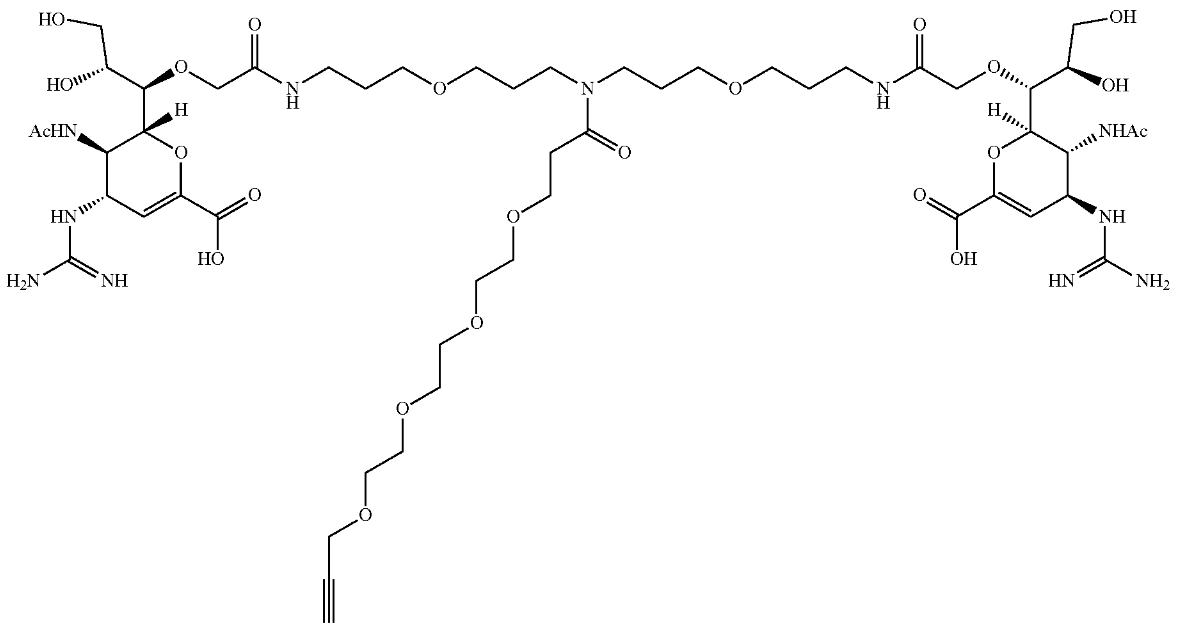 [SMILES: C#CCOCCOCCOCCOCCC(=O)N(CCCOCCCNC(=O)CO[C@@H]([C@@H]1OC(C(=O)O)=C[C@H](NC(=N)N)[C@H]1NC(C)=O)[C@H](O)CO)CCCOCCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
| --- | --- |
| Intermediate | Structure |
| Int-58 | 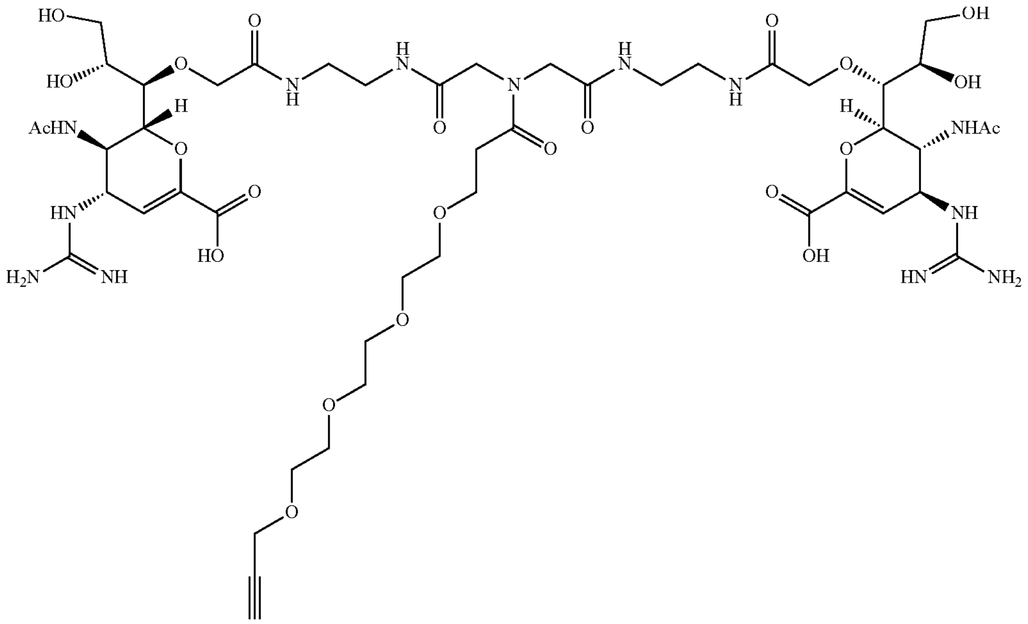 [SMILES: C#CCOCCOCCOCCOCCC(=O)N(CC(=O)NCCNC(=O)CO[C@@H]([C@@H]1OC(C(=O)O)=C[C@H](NC(=N)N)[C@H]1NC(C)=O)[C@H](O)CO)CC(=O)NCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-59 | 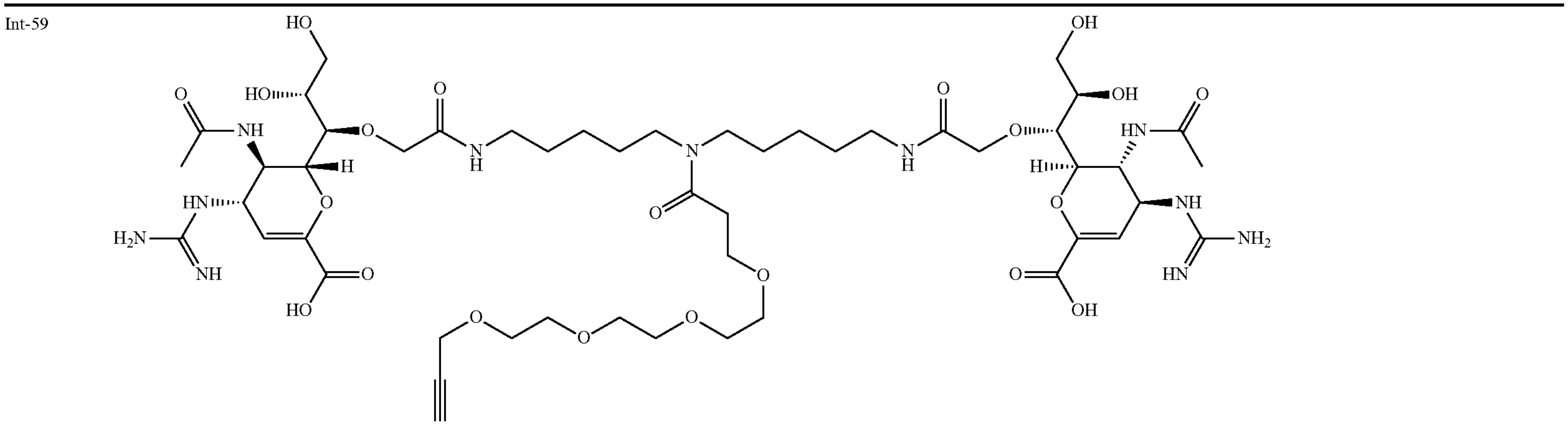 |
| Int-60 | 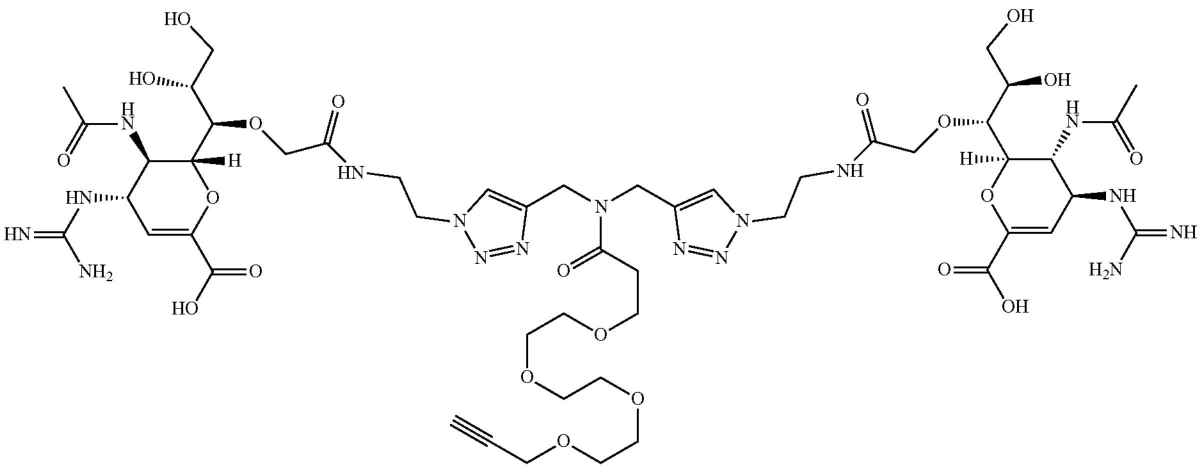 [SMILES: C#CCOCCOCCOCCOCCC(=O)N(Cc1cn(CCNC(=O)CO[C@@H]([C@@H]2OC(C(=O)O)=C[C@H](NC(=N)N)[C@H]2NC(C)=O)[C@H](O)CO)nn1)Cc1cn(CCNC(=O)CO[C@@H]([C@@H]2OC(C(=O)O)=C[C@H](NC(=N)N)[C@H]2NC(C)=O)[C@H](O)CO)nn1] |

TABLE 1-continued
| Intermediates | |
|---|---|
| Intermediate | Structure |
| Int-61 | 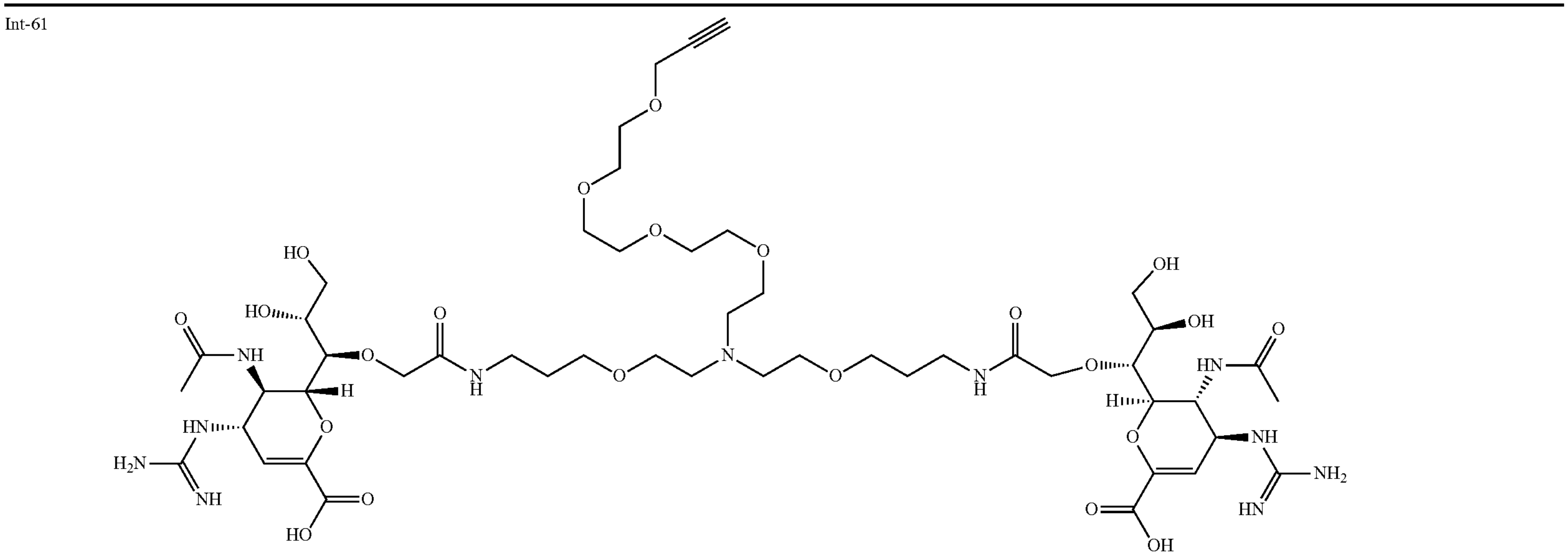 |
| Int-62 | 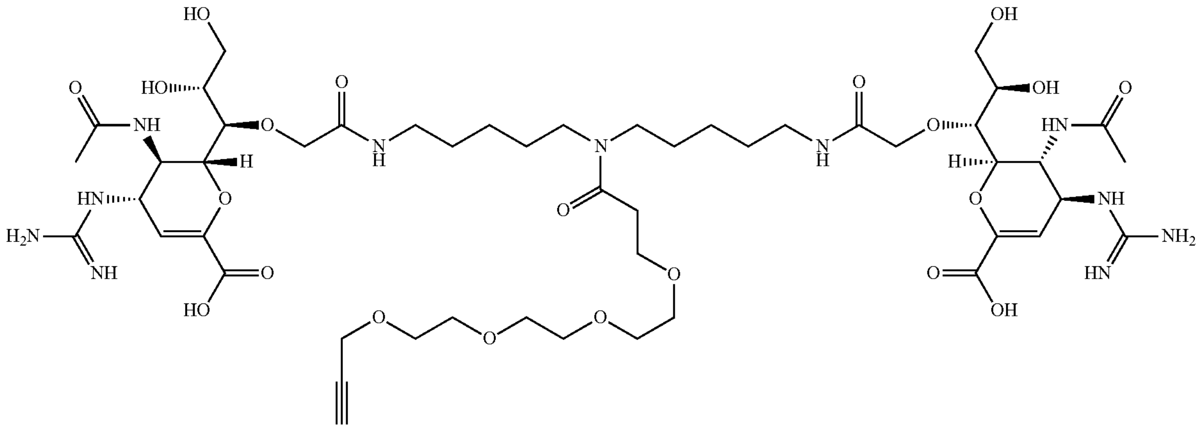 [SMILES: C#CCOCCOCCOCCOCCC(=O)N(CCCCCNC(=O)CO[C@@H]([C@@H]1OC(C(=O)O)=C[C@H](NC(=N)N)[C@H]1NC(C)=O)[C@H](O)CO)CCCCCNC(=O)CO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-63 | 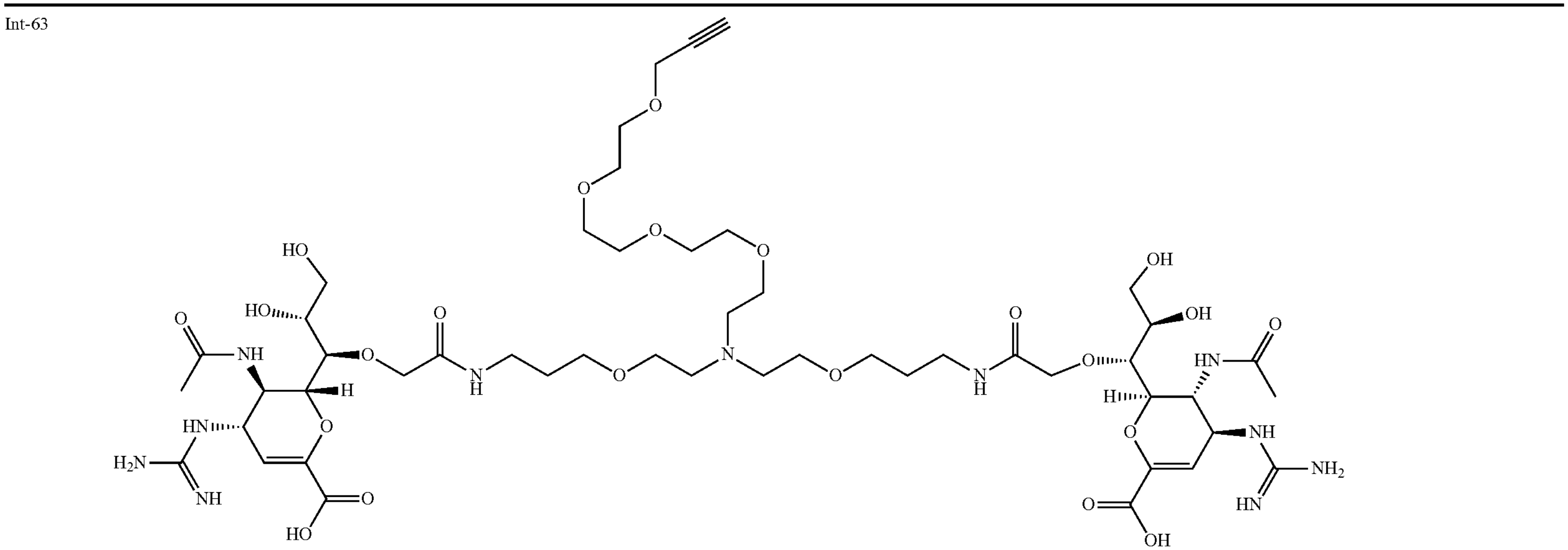 |
| Int-64 | 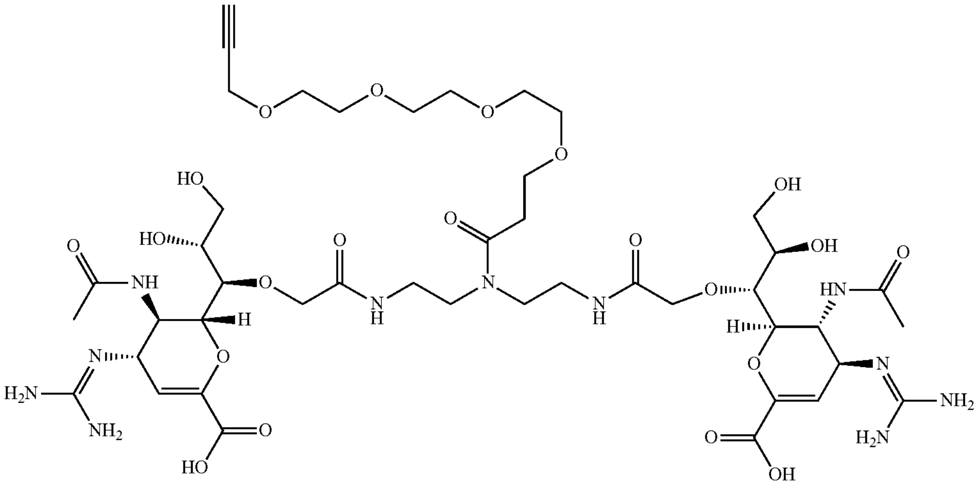 [SMILES: C#CCOCCOCCOCCOCCC(=O)N(CCNC(=O)CO[C@@H]([C@@H]1OC(C(=O)O)=C[C@H](N=C(N)N)[C@H]1NC(C)=O)[C@H](O)CO)CCNC(=O)CO[C@@H]([C@@H]1OC(C(=O)O)=C[C@H](N=C(N)N)[C@H]1NC(C)=O)[C@H](O)CO] |

TABLE 1-continued
| Intermediates | |
|---|---|
| Intermediate | Structure |
| Int-65 | 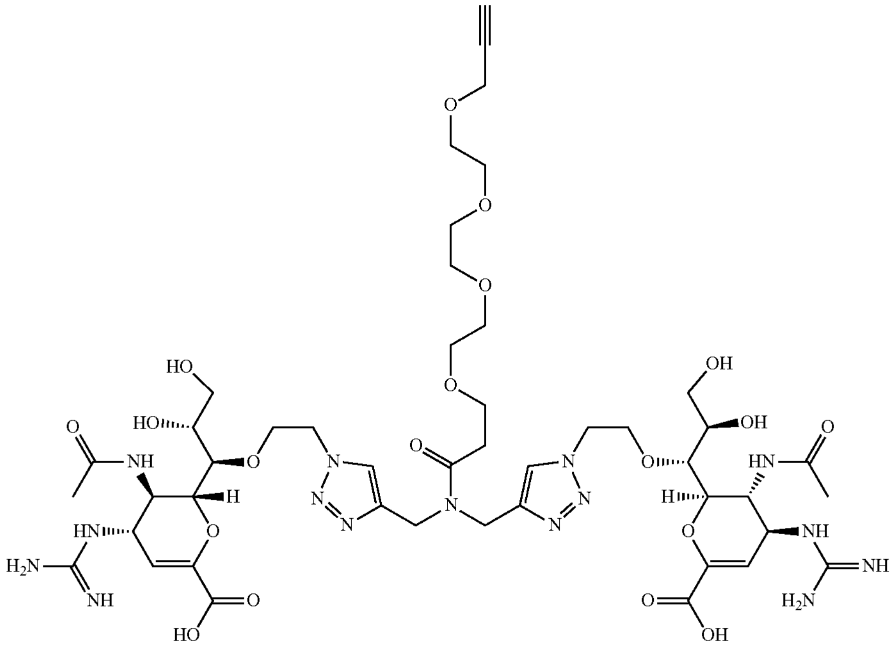 [SMILES: C#CCOCCOCCOCCOCCC(=O)N(Cc1cn(CCO[C@@H]([C@@H]2OC(C(=O)O)=C[C@H](NC(=N)N)[C@H]2NC(C)=O)[C@H](O)CO)nn1)Cc1cn(CCO[C@@H]([C@@H]2OC(C(=O)O)=C[C@H](NC(=N)N)[C@H]2NC(C)=O)[C@H](O)CO)nn1] |
| Int-67 | 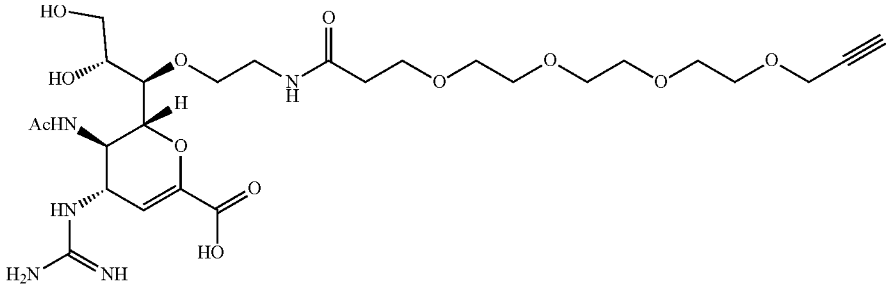 [SMILES: C#CCOCCOCCOCCOCCC(=O)NCCO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-68 | 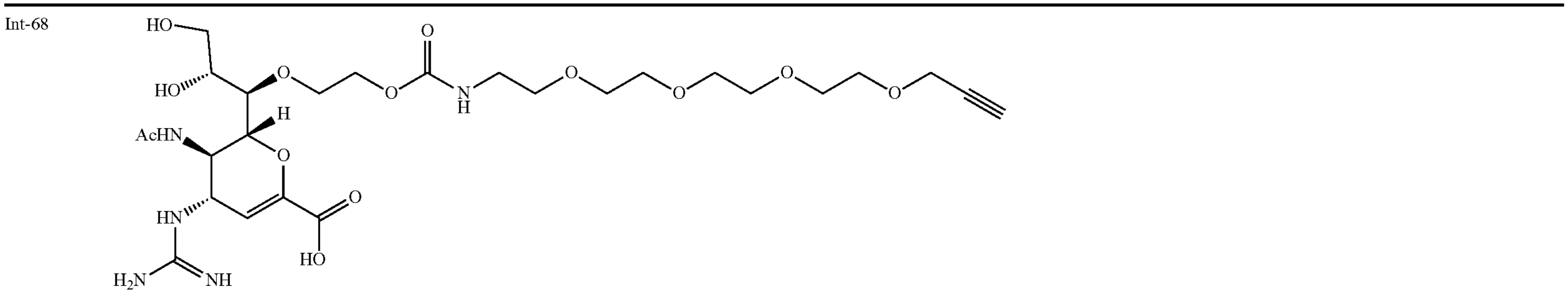 |
| Int-69 | 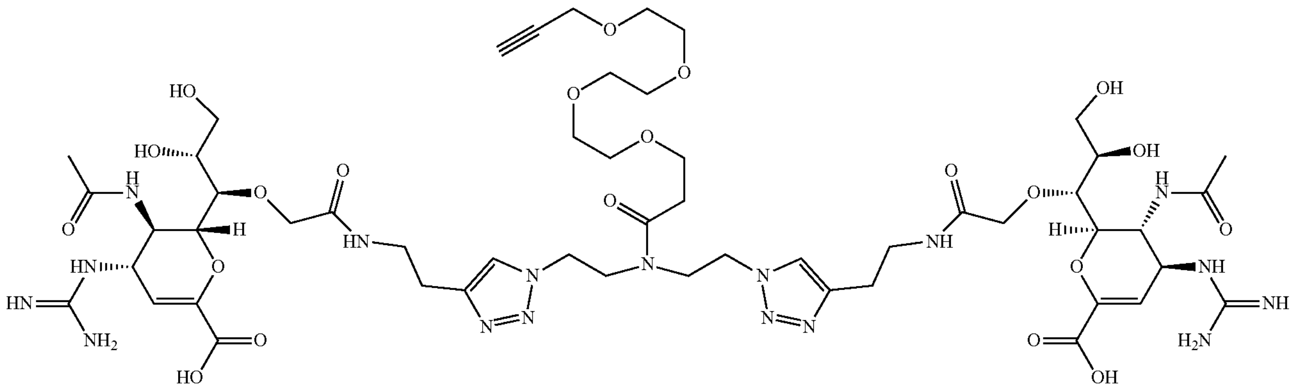 [SMILES: C#CCOCCOCCOCCOCCC(=O)N(CCn1cc(CCNC(=O)CO[C@@H]([C@@H]2OC(C(=O)O)=C[C@H](NC(=N)N)[C@H]2NC(C)=O)[C@H](O)CO)nn1)CCn1cc(CCNC(=O)CO[C@@H]([C@@H]2OC(C(=O)O)=C[C@H](NC(=N)N)[C@H]2NC(C)=O)[C@H](O)CO)nn1] |

TABLE 1-continued
| Intermediates | |
|---|---|
| Intermediate | Structure |
| Int-70 | 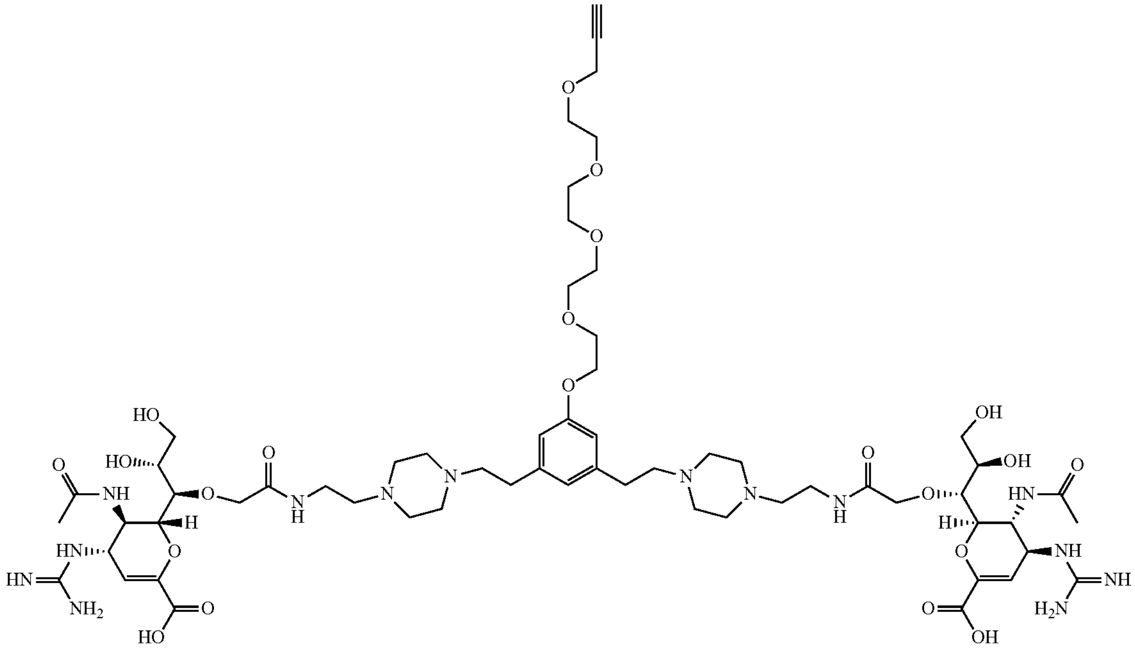 [SMILES: C#CCOCCOCCOCCOCCOc1cc(CCN2CCN(CCNC(=O)CO[C@@H]([C@@H]3OC(C(=O)O)=C[C@H](NC(=N)N)[C@H]3NC(C)=O)[C@H](O)CO)CC2)cc(CCN2CCN(CCNC(=O)CO[C@@H]([C@@H]3OC(C(=O)O)=C[C@H](NC(=N)N)[C@H]3NC(C)=O)[C@H](O)CO)CC2)c1] |

TABLE 1-continued
| Intermediates | |
|---|---|
| Intermediate | Structure |
| Int-71 | 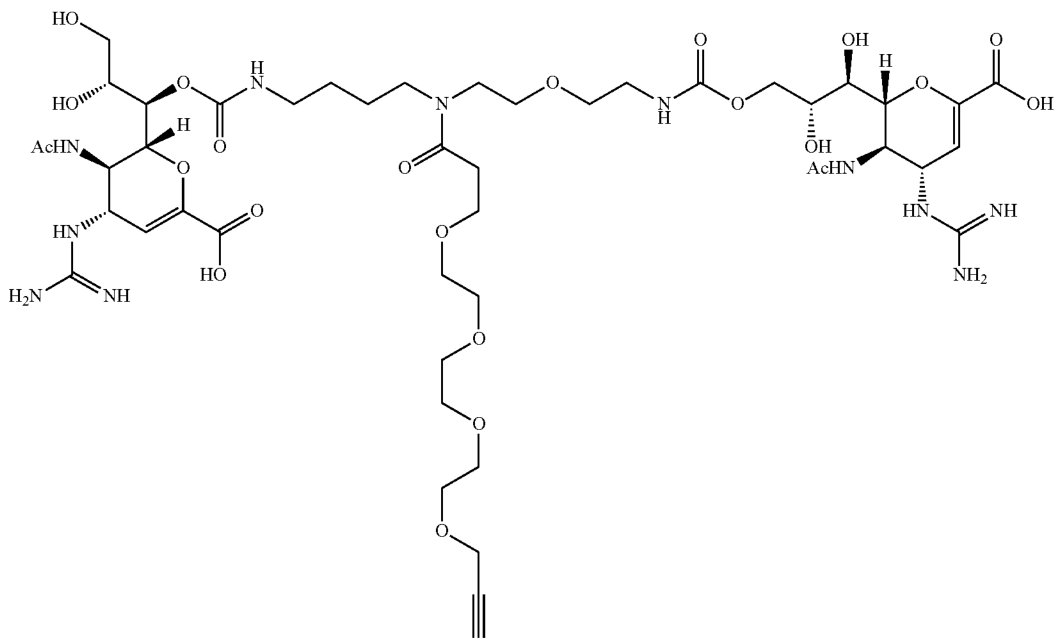 [SMILES: C#CCOCCOCCOCCOCCC(=O)N(CCCCNC(=O)O[C@@H]([C@@H]1OC(C(=O)O)=C[C@H](NC(=N)N)[C@H]1NC(C)=O)[C@H](O)CO)CCOCCNC(=O)OC[C@@H](O)[C@@H](O)[C@@H]1OC(C(=O)O)=C[C@H](NC(=N)N)[C@H]1NC(C)=O] |

TABLE 1-continued
| Intermediates | |
|---|---|
| Intermediate | Structure |
| Int-72 | 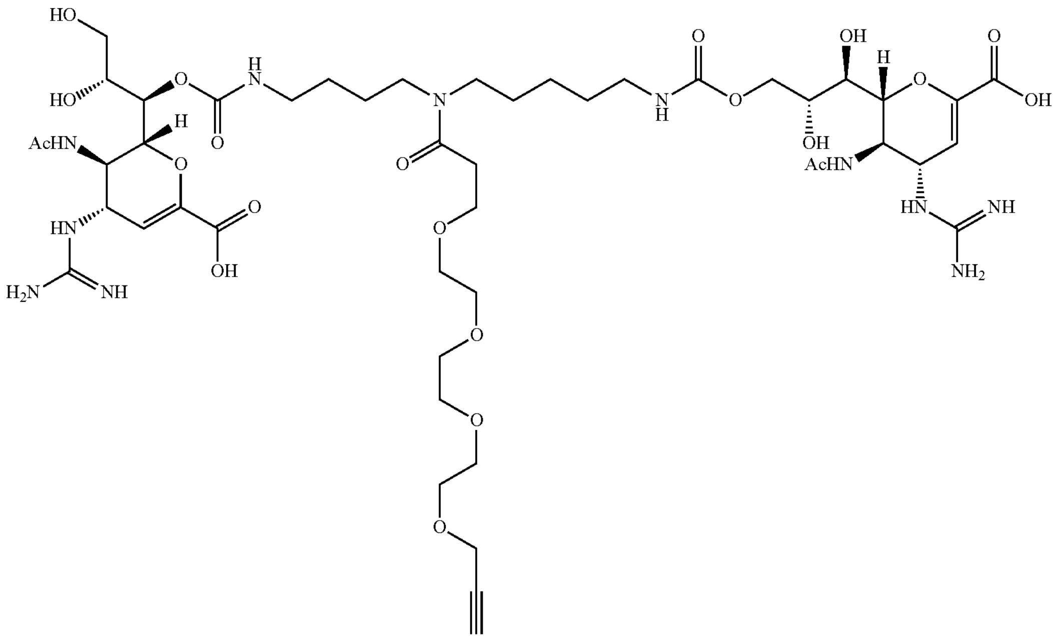 [SMILES: C#CCOCCOCCOCCOCCC(=O)N(CCCCCNC(=O)OC[C@@H](O)[C@@H](O)[C@@H]1OC(C(=O)O)=C[C@H](NC(=N)N)[C@H]1NC(C)=O)CCCCNC(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-73 | 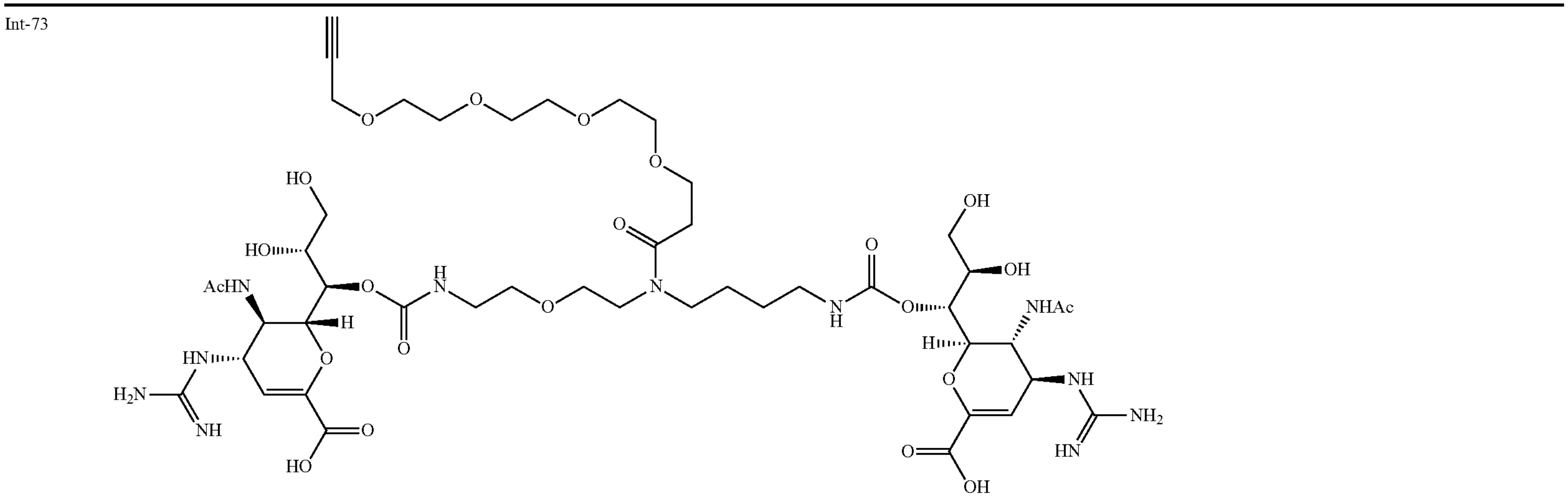 |
| Int-74 | 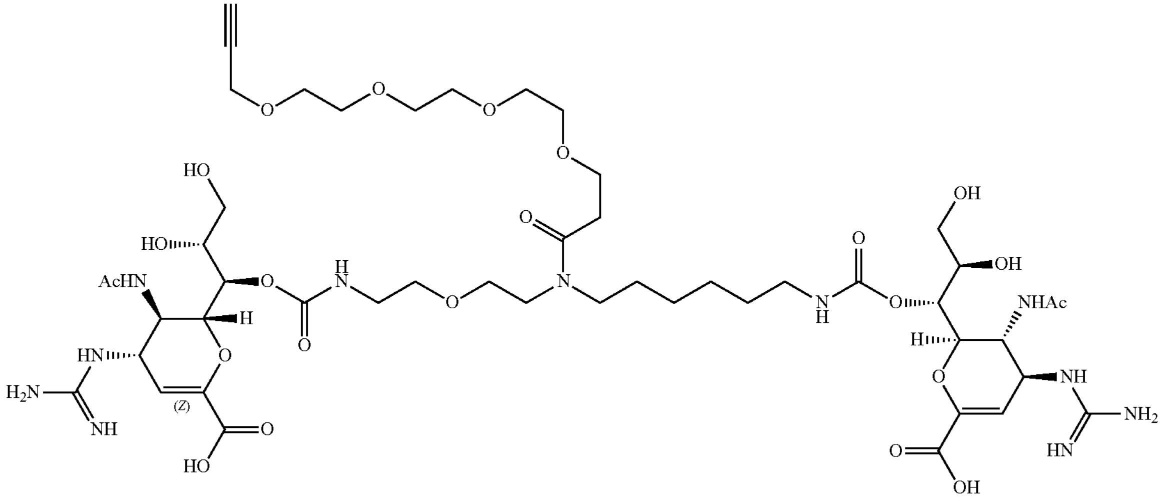 [SMILES: C#CCOCCOCCOCCOCCC(=O)N(CCCCCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-75 | 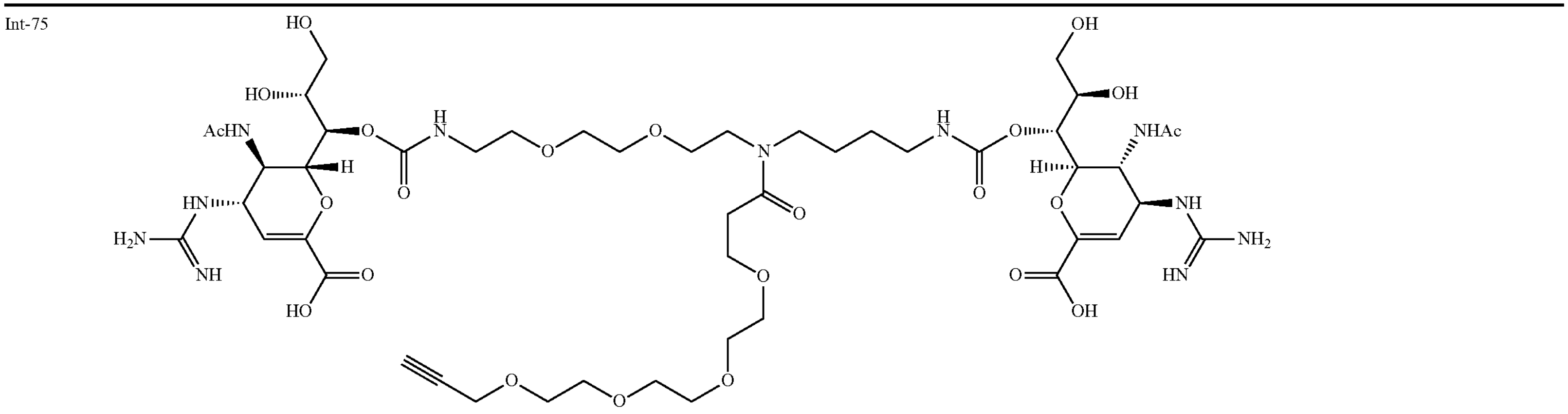 |
| Int-76 | 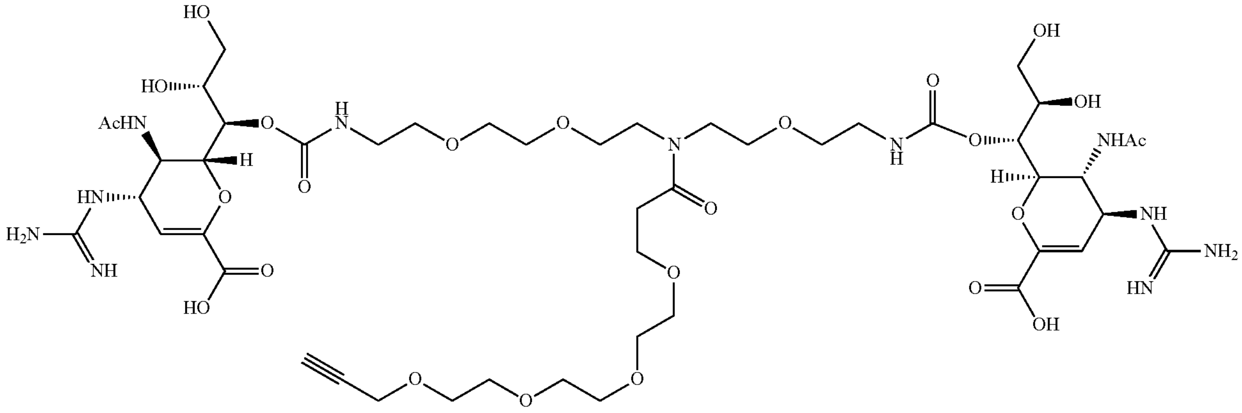 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCOCCNC(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-77 | 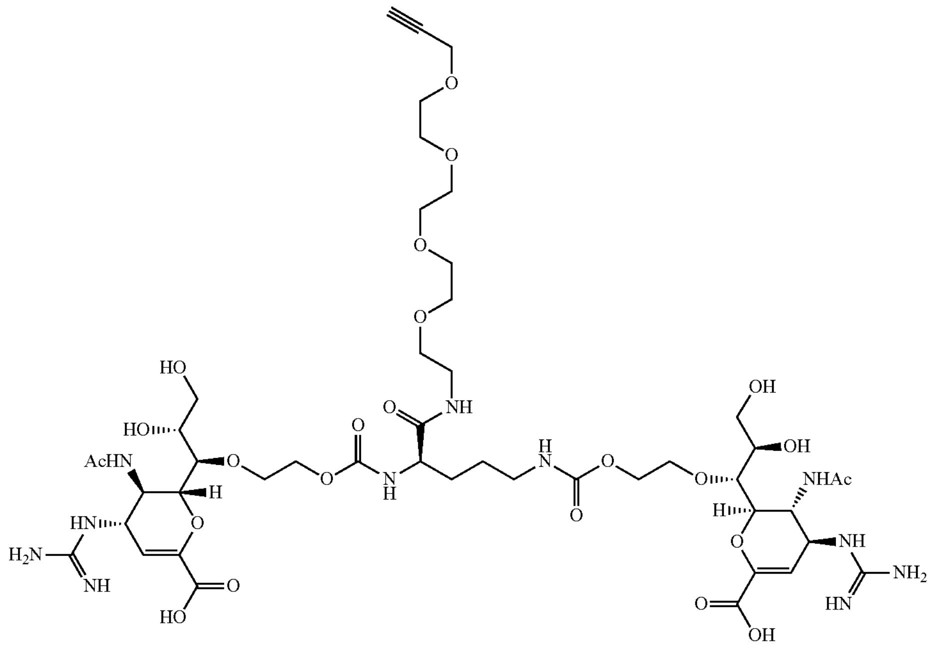 [SMILES: C#CCOCCOCCOCCOCCNC(=O)[C@@H](CCCNC(=O)OCCO[C@@H]([C@@H]1OC(C(=O)O)=C[C@H](NC(=N)N)[C@H]1NC(C)=O)[C@H](O)CO)NC(=O)OCCO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-78 | 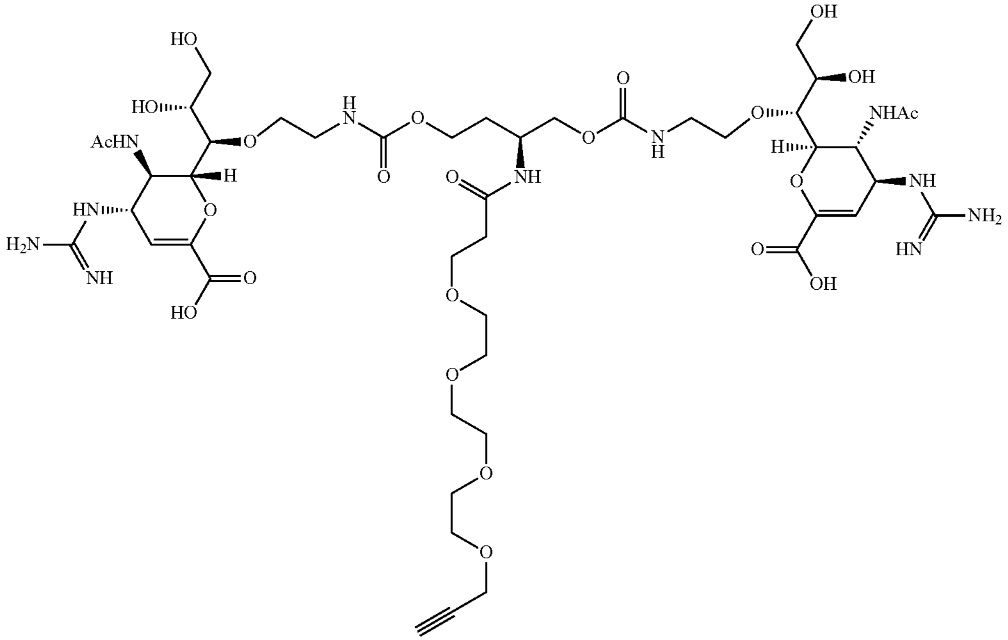 [SMILES: C#CCOCCOCCOCCOCCC(=O)N[C@@H](CCOC(=O)NCCO[C@@H]([C@@H]1OC(C(=O)O)=C[C@H](NC(=N)N)[C@H]1NC(C)=O)[C@H](O)CO)COC(=O)NCCO[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-79 | 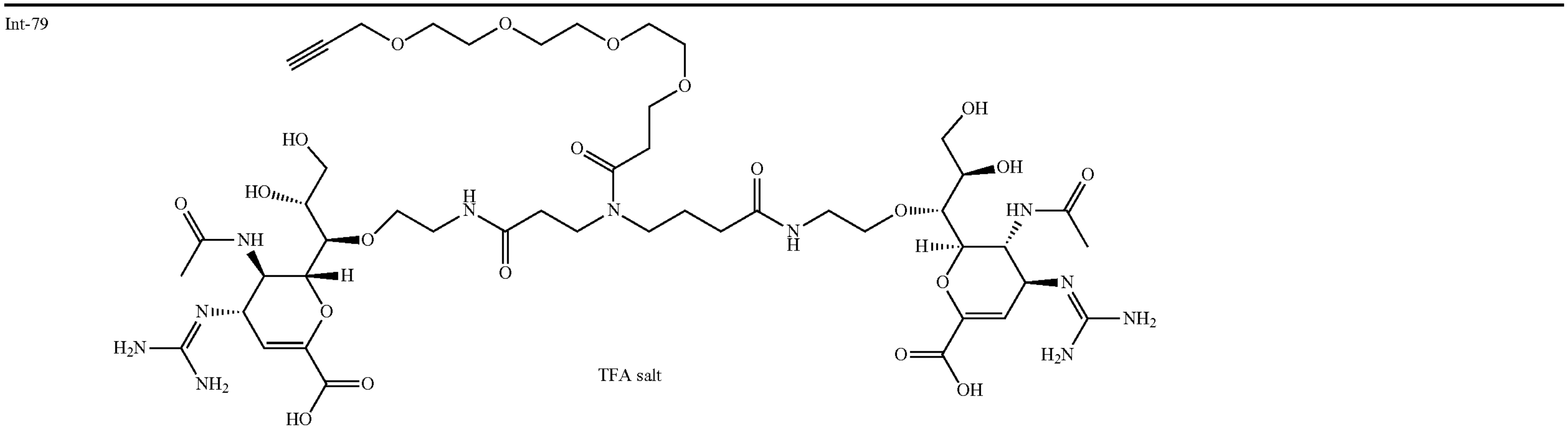 TFA salt |
| Int-80 | 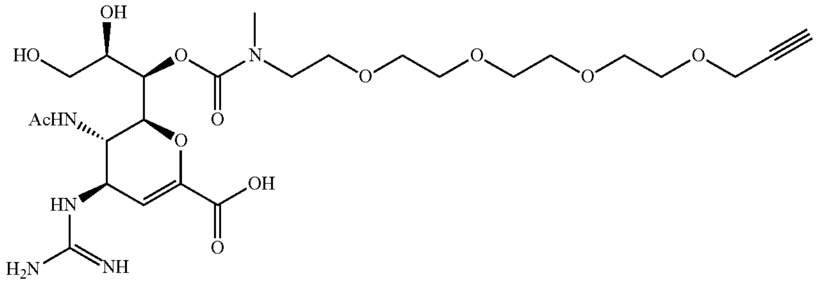 [SMILES: C#CCOCCOCCOCCOCCN(C)C(=O)O[C@@H]([C@H]1OC(C(=O)O)=C[C@@H](NC(=N)N)[C@@H]1NC(C)=O)[C@H](O)CO] |

TABLE 1-continued
| Intermediates | |
|---|---|
| Intermediate | Structure |
| Int-81 | 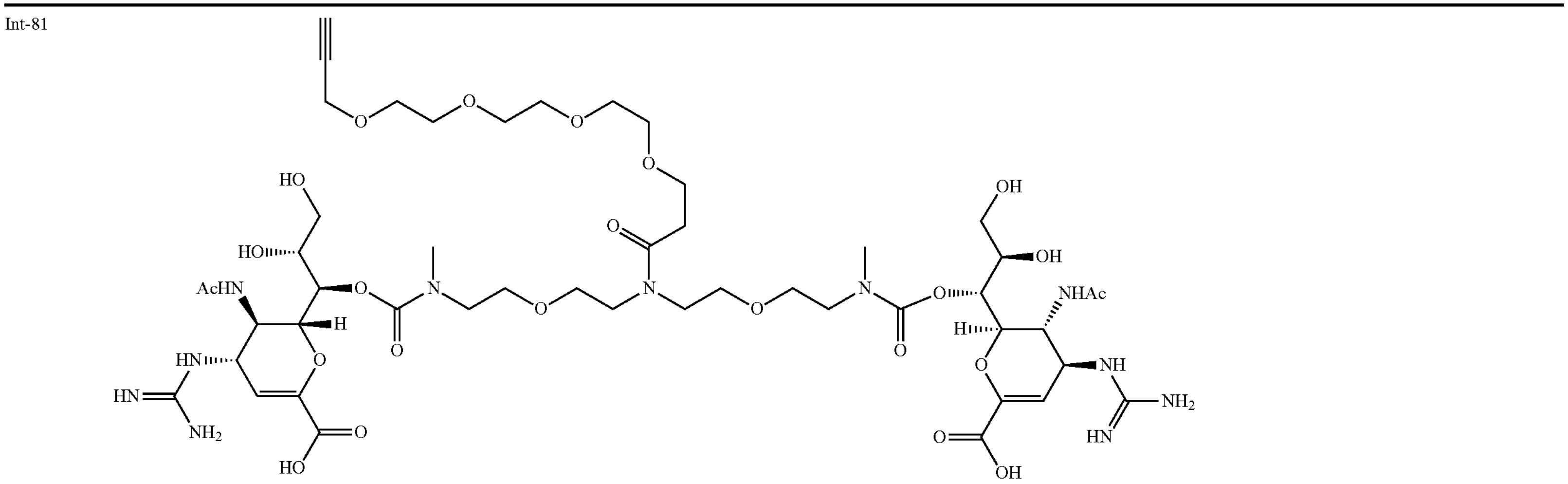 |
| Int-82 | 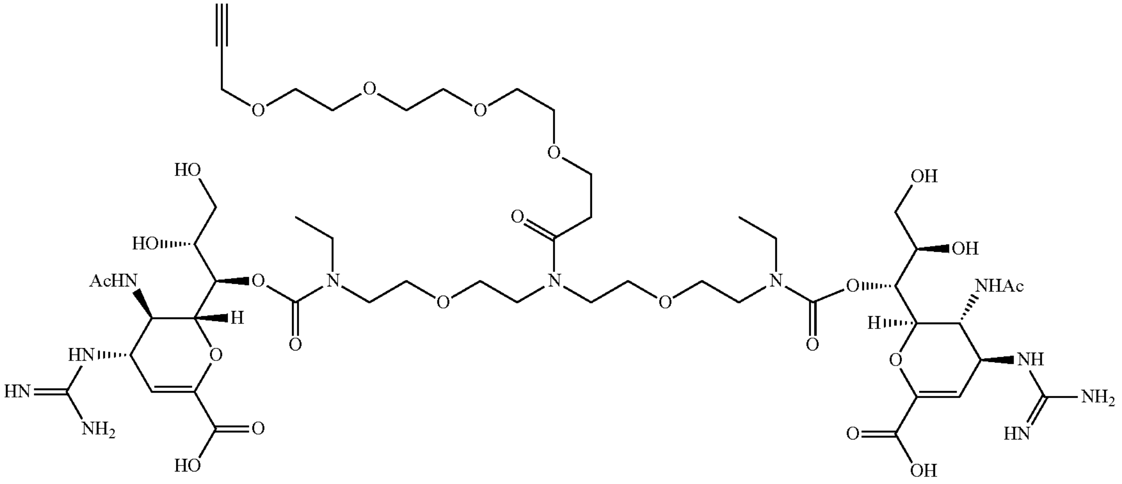 [SMILES: C#CCOCCOCCOCCOCCC(=O)N(CCOCCN(CC)C(=O)O[C@@H]([C@@H]1OC(C(=O)O)=C[C@H](NC(=N)N)[C@H]1NC(C)=O)[C@H](O)CO)CCOCCN(CC)C(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-83 | 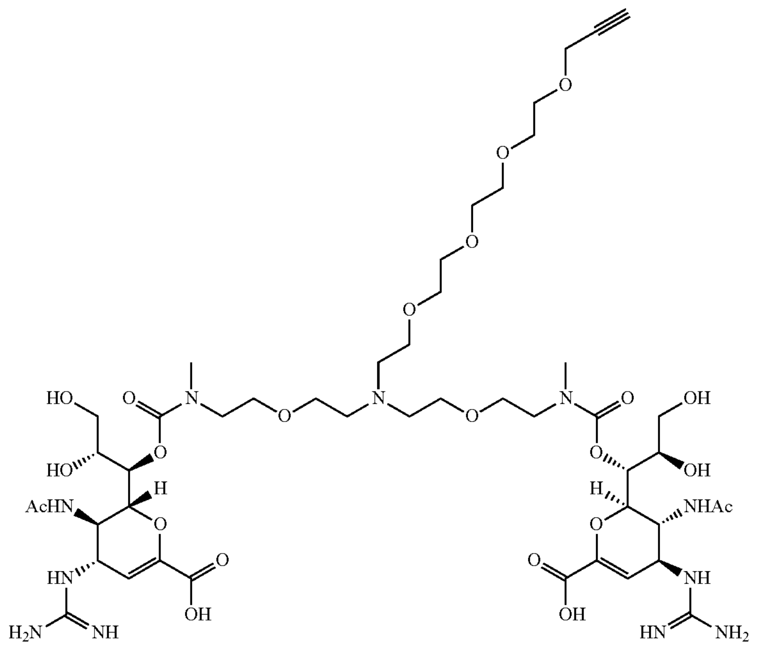 [SMILES: C#CCOCCOCCOCCOCCN(CCOCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO] |

TABLE 1-continued
| Intermediates | |
| --- | --- |
| Intermediate | Structure |
| Int-84 | 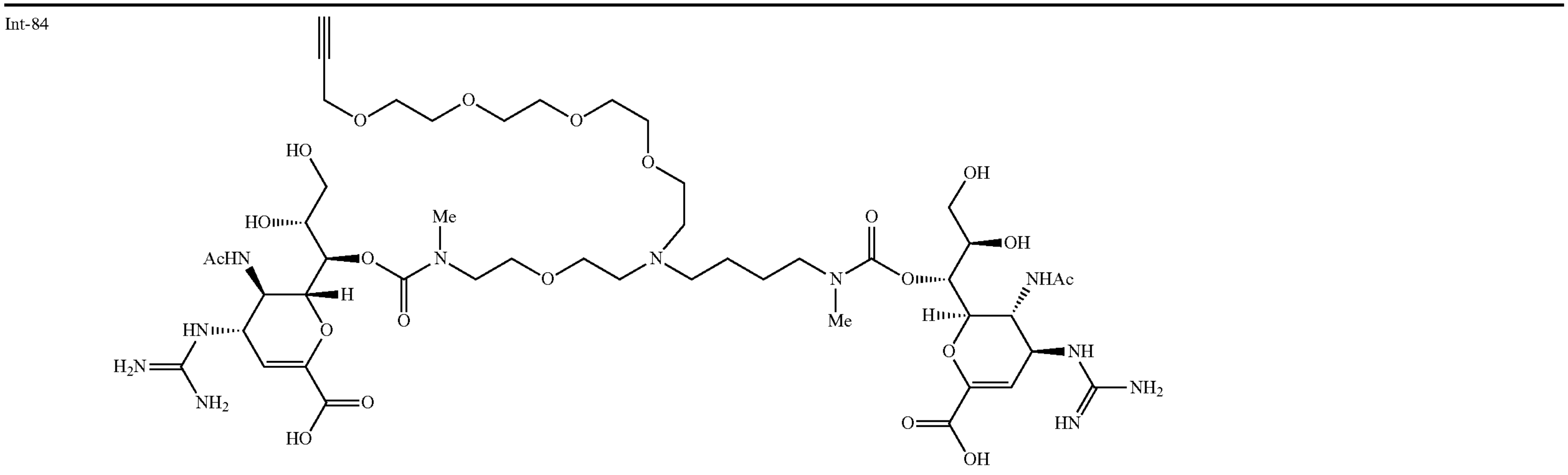 |
| Int-85 | 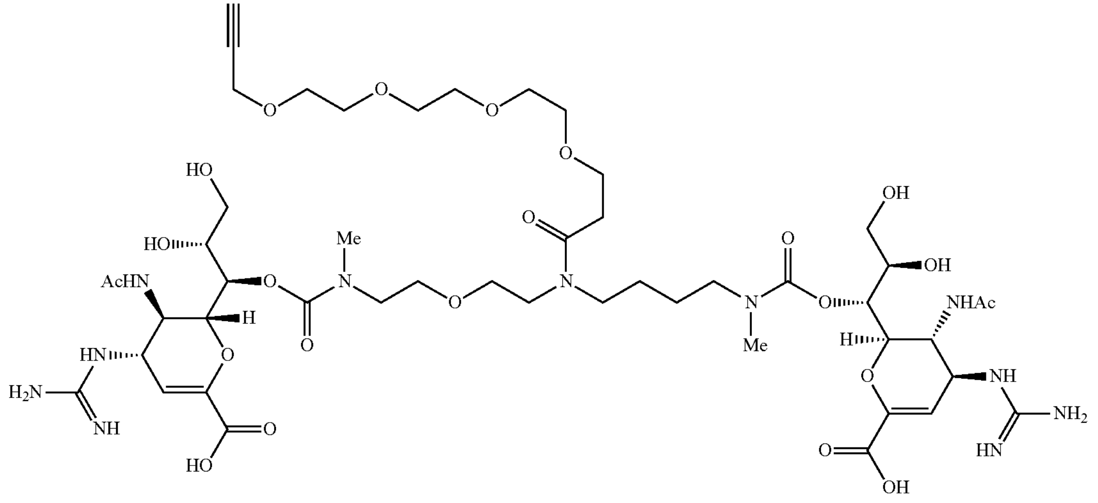 [SMILES: C#CCOCCOCCOCCOCCC(=O)N(CCCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-86 | 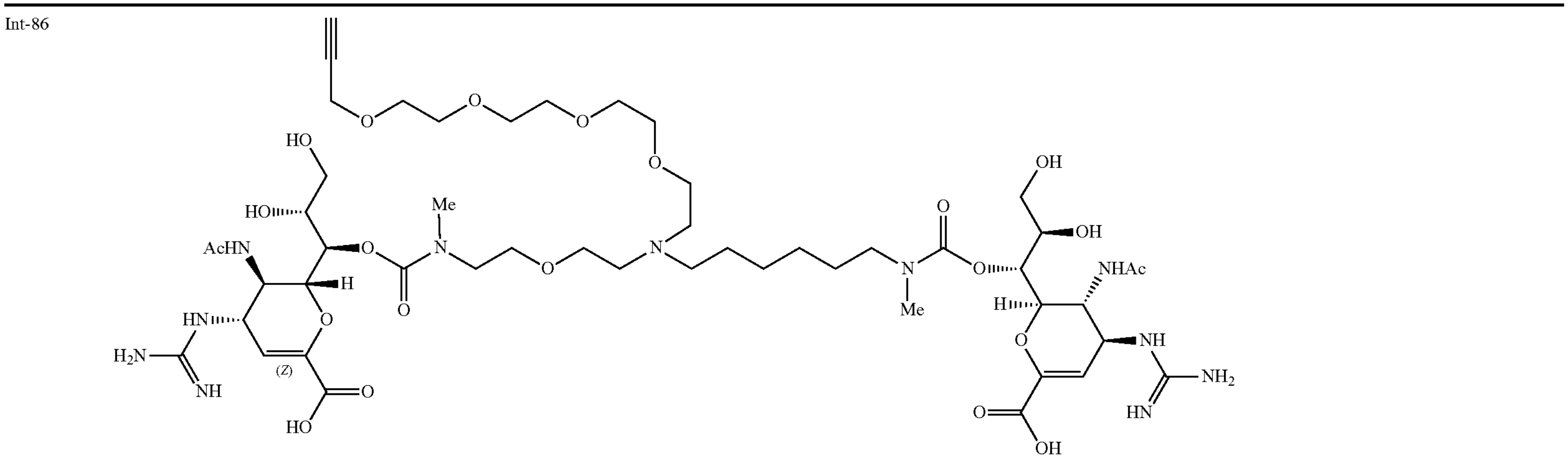 |
| Int-87 | 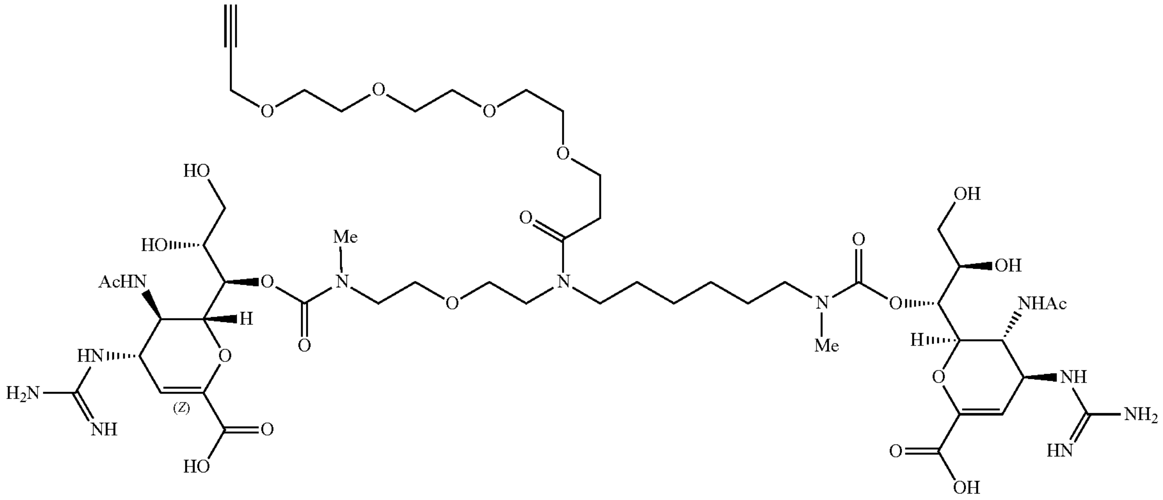 [SMILES: C#CCOCCOCCOCCOCCC(=O)N(CCCCCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-88 | 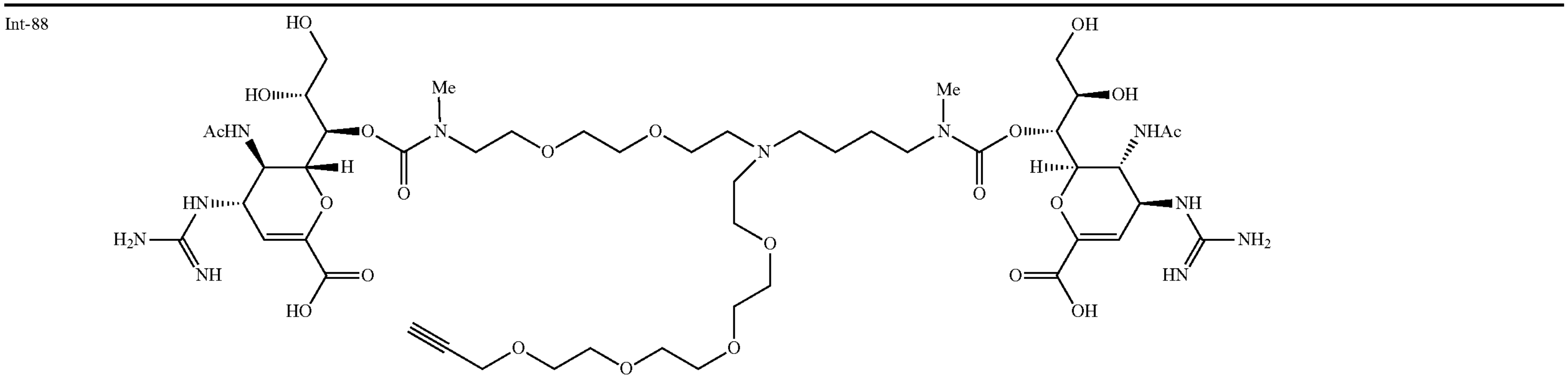 |
| Int-89 | 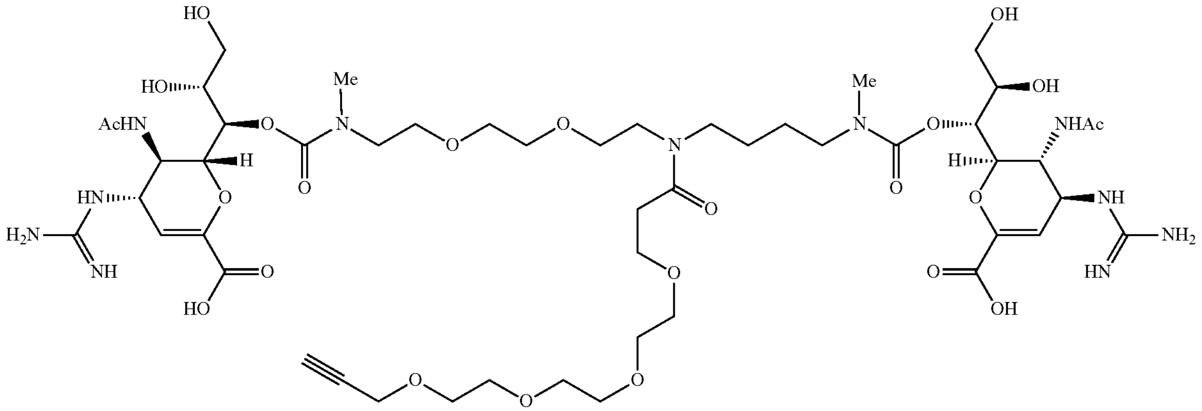 [SMILES: C#CCOCCOCCOCCOCCC(=O)N(CCCCN(C)C(=O)O[C@@H]([C@@H]1OC(C(=O)O)=C[C@H](NC(=N)N)[C@H]1NC(C)=O)[C@H](O)CO)CCOCCOCCN(C)C(=O)O[C@@H]([C@@H]1OC(C(=O)O)=C[C@H](NC(=N)N)[C@H]1NC(C)=O)[C@H](O)CO] |

TABLE 1-continued
| Intermediates | |
|---|---|
| Intermediate | Structure |
| Int-90 | 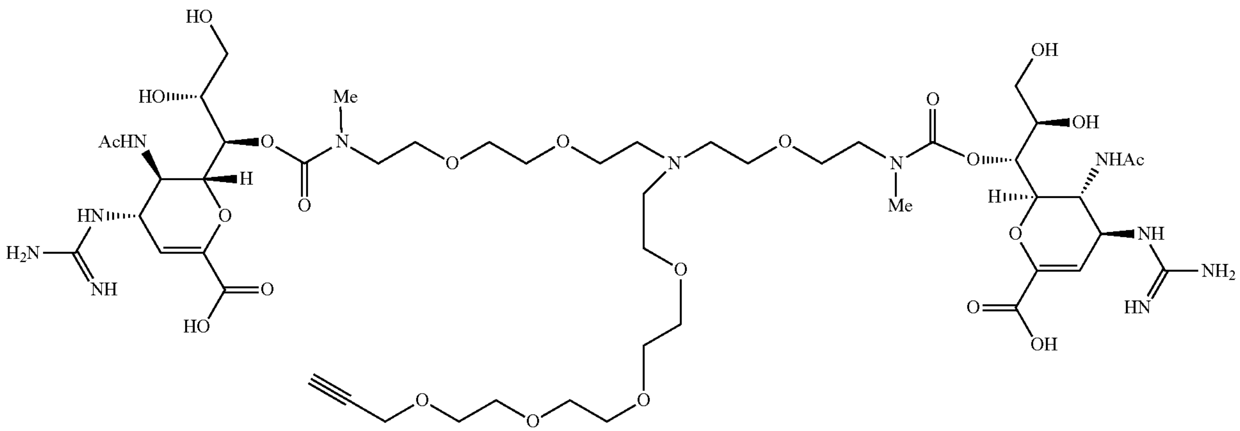 [SMILES: C#CCOCCOCCOCCOCCN(CCOCCOCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO] |

In some embodiments, each E includes an Fc domain monomer having the sequence of any one of SEQ ID NOs: 1-68.

In some embodiments, E includes the sequence (SEQ ID NO: 4)
MVRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTV
DKSRWQQGNVFSCSVMHEALHNHYTQKSLSLSPGK.

In some embodiments, each E includes the sequence (SEQ ID NO: 33)
MVRSDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTV
DKSRWQQGNVFSCSVMHEALHNHYTQKSLSLSPGK.

In some embodiments, E includes the sequence (SEQ ID NO: 10)
MVRSDKTHTCPPCPPC*KC*PAPELLGGPSVFLFPPKPKDTLMISRTPE
VTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFF
LYSKLTVDKSRWQQGNVFSCSVMHEALHNHYTQKSLSLSPGK*HHHHHH*.

In some embodiments, each E comprises the sequence (SEQ ID NO: 11)
MVRSDKTHTCPPCPPC*KC*PAPELLGGPSVFLFPPKPKDTLMISRTPE
VTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFF
LYSKLTVDKSRWQQGNVFSCSVMHEALHNHYTQKSLSLSPGK.

In some embodiments of the previous three aspects, the nitrogen atom is the nitrogen of a surface exposed lysine, e.g., the nitrogen atom corresponding to (e.g., the nitrogen atom of) Lys35, Lys63, Lys77, Lys79, Lys106, Lys123, Lys129, Lys181, Lys203, Lys228, or Lys236 of SEQ ID NO: 10 or SEQ ID NO: 11. In some embodiments, the nitrogen atom is the nitrogen atom corresponding to (e.g., the nitrogen atom of) Lys65, Lys79, Lys108, Lys230, and/or Lys238 of SEQ ID NO: 10 or SEQ ID NO: 11.

In some embodiments, the conjugate has the structure:

SEQ ID NO: 10
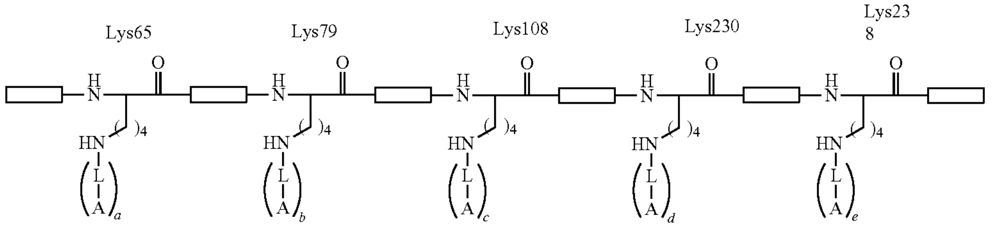

wherein each of a, b, c, d, and e is, independently, 0 or 1 and wherein when a, b, c, d, or e is 0, the two nitrogen atom is $NH_2$. In some embodiments, a is 1 and b, c, d, and e are 0. In some embodiments, b is 1 and a, c, d, and e are 0. In some embodiments, c is 1 and a, b, d, and e are 0. In some embodiments, d is 1 and a, b, c, and e are 0. In some embodiments, e is 1 and a, b, c, and d are 0. In some embodiments, a and b are 1 and c, d, and e are 0. In some embodiments, a and c are 1 and b, d, and e are 0. In some embodiments, a and d are 1 and b, c, and e are 0. In some embodiments, a and e are 1 and b, c, and d are 0. In some embodiments, b and c are 1 and a, d, and e are 0. In some embodiments, b and d are 1 and a, c, and e are 0. In some embodiments, b and e are 1 and a, c, and d are 0. In some embodiments, c and d are 1 and a, b, and e are 0. In some embodiments, c and e are 1 and a, b, and d are 0. In some embodiments, d and e are 1 and a, b, and c are 0. In some embodiments, a, b, and c are 1 and d and e are 0. In some embodiments, a, b, and d are 1 and c and e are 0. In some embodiments, a, b, and e are 1 and c and d are 0. In some embodiments, a, c, and d are 1 and b and e are 0. In some embodiments, a, c, and e are 1 and b and d are 0. In some embodiments, a, d, and e are 1 and b and c are 0. In some embodiments, b, c, and d are 1 and a and e are 0. In some embodiments, b, d, and e are 1 and a and c are 0. In some embodiments, c, d, and e are 1 and a and b are 0.

In another aspect, the invention features a population of conjugates described in any of the previous aspects, wherein the average value of T is 1 to 20 (e.g., the average value of T is 1 to 2, 1 to 3, 1 to 4, 1 to 5, 5 to 10, 10 to 15, or 15 to 20). In some embodiments, the average value of T is 1, 2, 3, 4, 5, 6, 7, 8, 9, 10, 11, 12, 13, 14, 15, 16, 17, 18, 19, or 20.

In some embodiments of the conjugates described herein, the conjugate forms a homodimer including an Fc domain.

In some embodiments of the conjugates described herein, E homodimerizes with another E to form an Fc domain.

In another aspect, the invention features a conjugate described by formula (3):

(3)

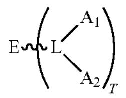

wherein each $A_1$ and each $A_2$ is independently selected from any one of formulas (A-I)-(A-XII):

(A-I)

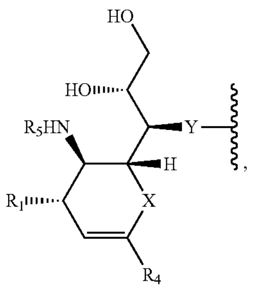

-continued (A-II)

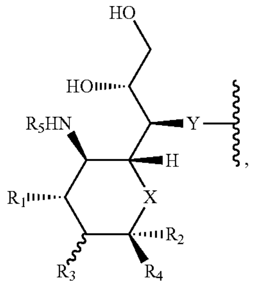

(A-III)

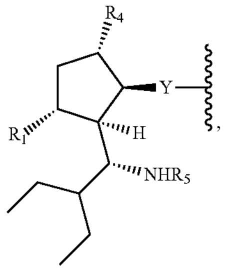

(A-IV)

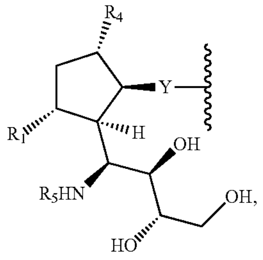

(A-V)

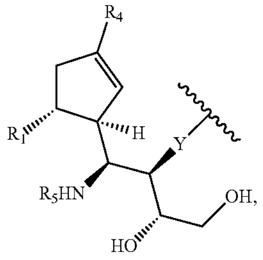

(A-VI)

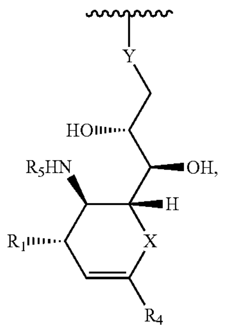

-continued (A-VII)

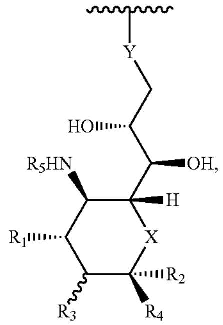

(A-VIII)

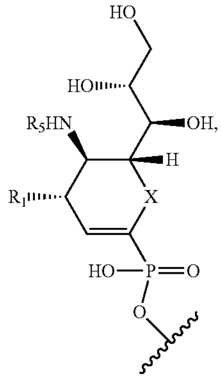

(A-IX)

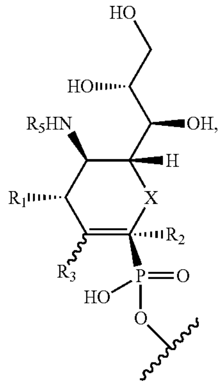

(A-X)

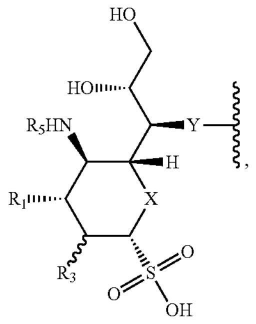

(A-XI)

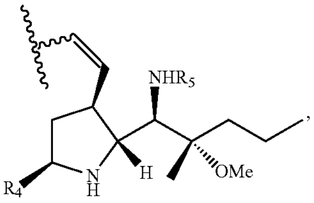

-continued (A-XII)

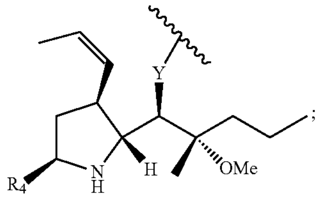

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

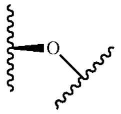

(—O—),

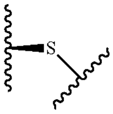

(—S—),

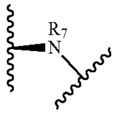

(—$NR_7$—),

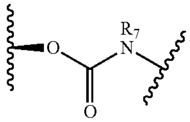

(—O(C=O)$NR_7$—),

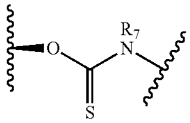

(—O(C=S)$NR_7$—),

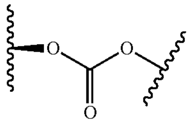

(—O(C=O)O—),

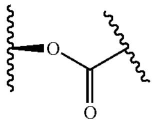

(—O(C=O)—),

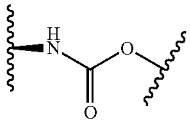

(—NH(C=O)O—),

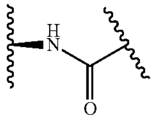

(—NH(C=O)—),

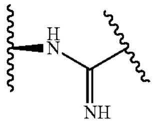

(—NH(C=NH)—),

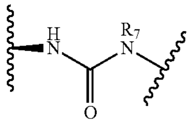

(—NH(C=O)$NR_7$—),

-continued
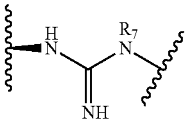
($-NH(C{=}NH)NR_7-$),
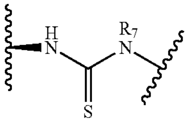
($-NH(C{=}S)NR_7-$),
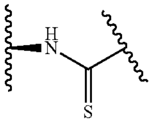
($-NH(C{=}S)-$),
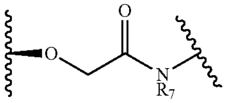
($-OCH_2(C{=}O)NR_7-$),
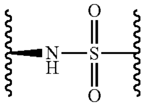
($-NH(SO_2)-$),
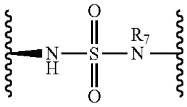
($-NH(SO_2)NR_7-$),
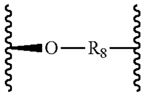
($-OR_8-$),
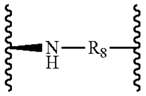
($-NR_8-$), and
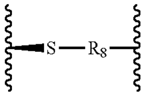
($-SR_8-$);
$R_6$ is selected from
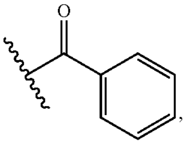,
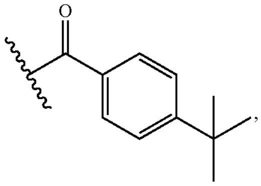,
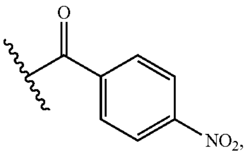,
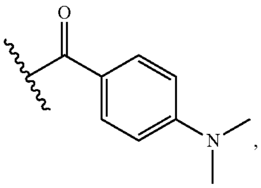,
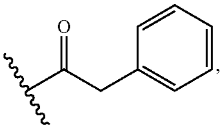,
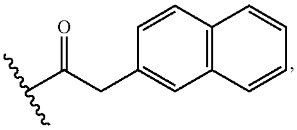,
-continued
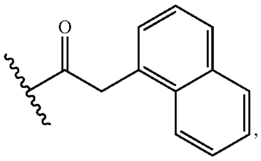,
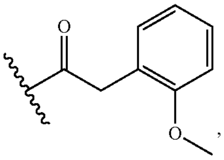,
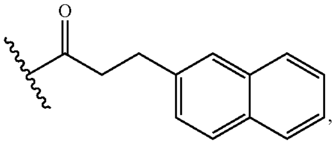,
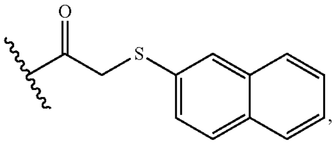,
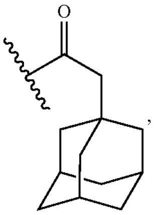,
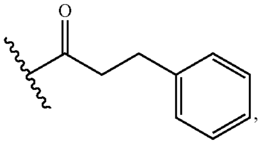,
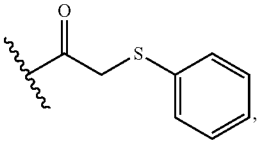,
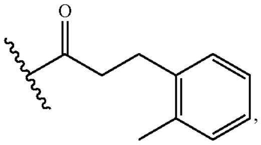,
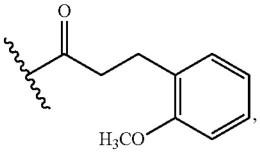,
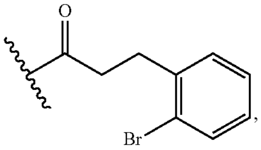,
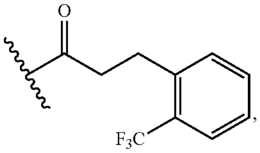,
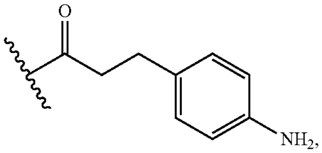,
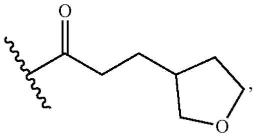,
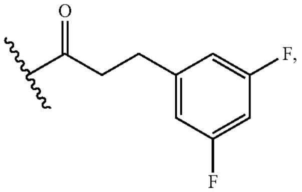,
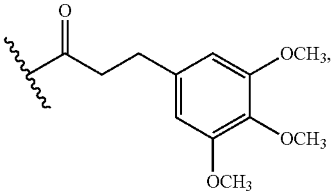

-continued

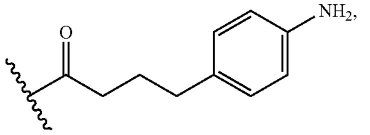

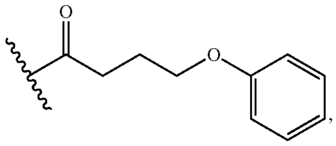,

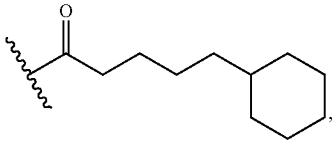,

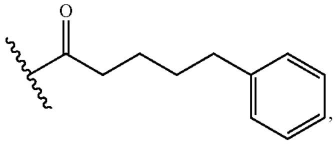,

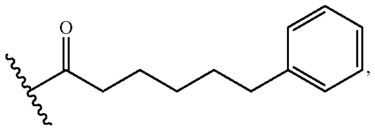,

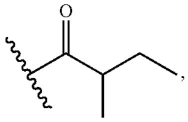, 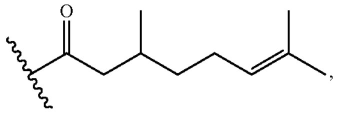,

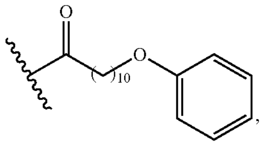, 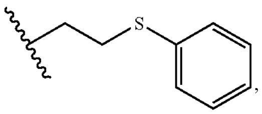,

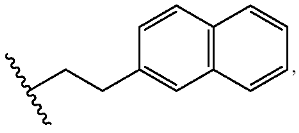, and 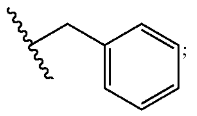;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an albumin protein (e.g., an albumin protein having the sequence of any one of SEQ ID NOs: 69-71), an albumin protein-binding peptide, or an Fc-binding peptide; L in each $A_1$-L-$A_2$ is a linker independently covalently attached to a sulfur atom of a surface exposed cysteine or a nitrogen atom of a surface exposed lysine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is independently covalently attached (e.g., by way of a bond or a linker) to the sulfur atom of a solvent-exposed cysteine or the nitrogen atom of a solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (3):

(3)

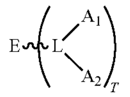

wherein each $A_1$ and each $A_2$ is independently selected from any one of formulas (A-I)-(A-V):

(A-I)

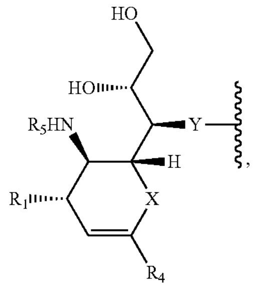, (A-11)

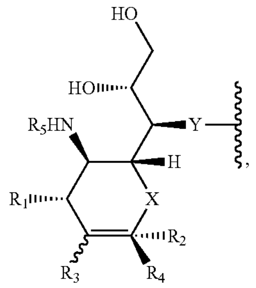, (A-III)

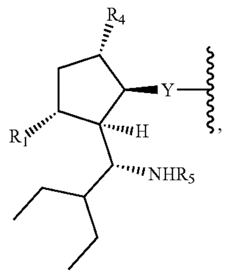, (A-IV)

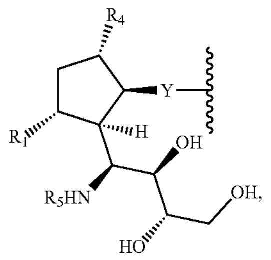

(A-V)

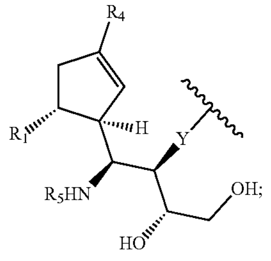

wherein $R_1$ is selected from —OH, —$NH_2$, —NHC(═NH)$NH_2$, and —NHC(═NH)NH$R_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

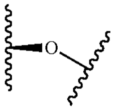 (—O—), 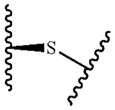 (—S—),

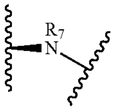 (—$NR_7$—),

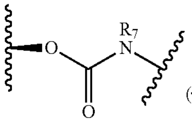 (—O(C═O)$NR_7$—),

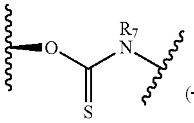 (—O(C═S)$NR_7$—),

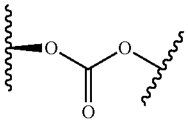 (—O(C═O)O—),

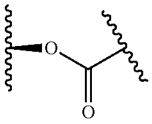 (—O(C═O)—),

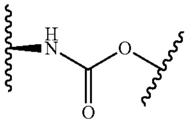 (—NH(C═O)O—),

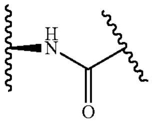 (—NH(C═O)—),

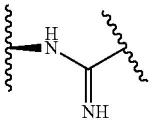 (—NH(C═NH)—),

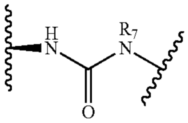 (—NH(C═O)$NR_7$—),

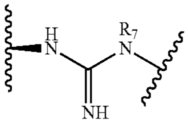 (—NH(C═NH)$NR_7$—),

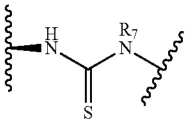 (—NH(C═S)$NR_7$—),

-continued

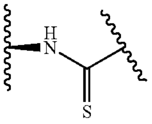 (—NH(C═S)—),

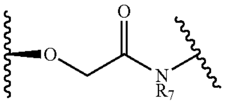 (—$OCH_2$(C═O)$NR_7$—),

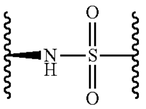 (—NH($SO_2$)—),

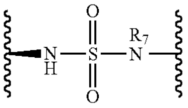 (—NH($SO_2$)$NR_7$—),

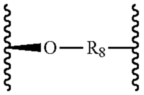 (—$OR_8$—),

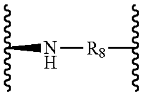 (—$NR_8$—), and

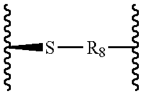 (—$SR_8$—);

$R_6$ is selected from

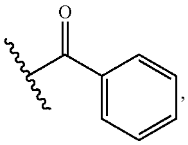, 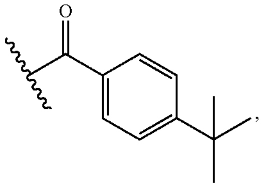,

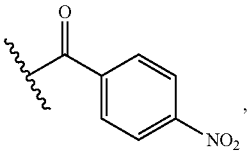, 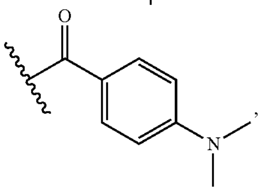,

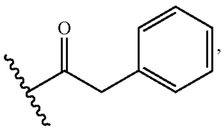, 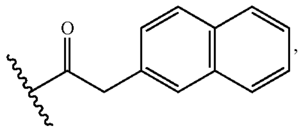,

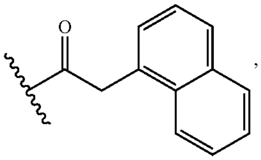, 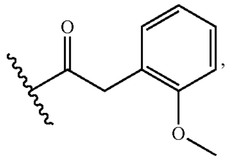,

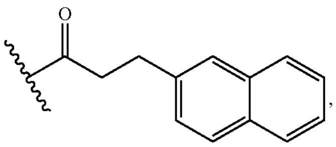,

-continued

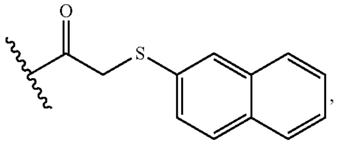,
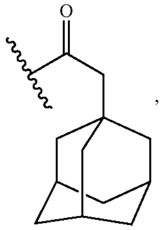,
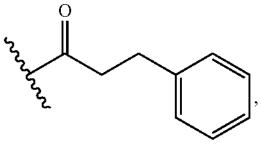,
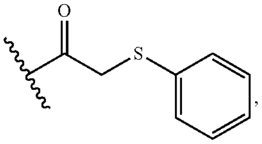,
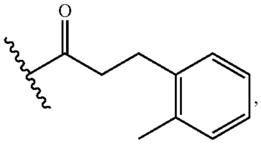,
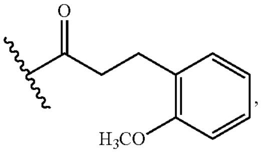,
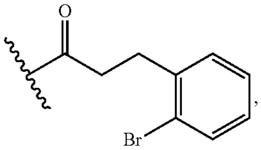,
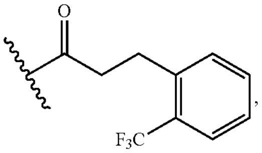,
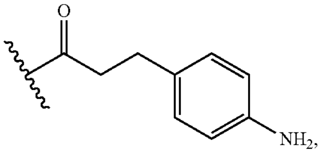,
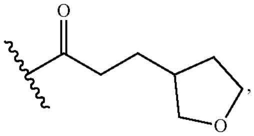,
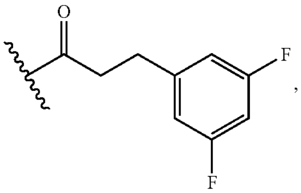,
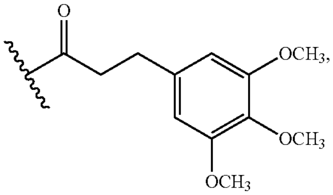,
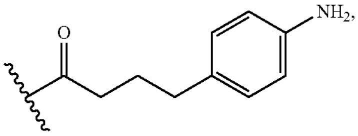,
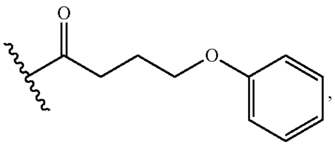,
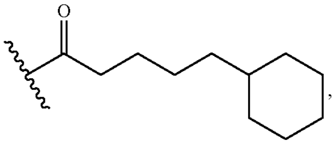, -continued

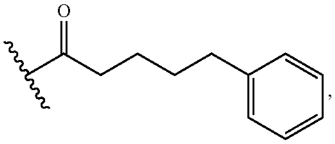,
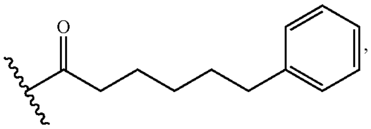,
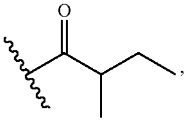,
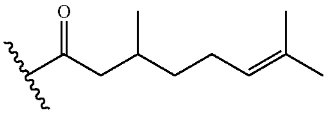,
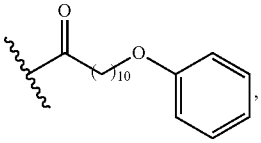,
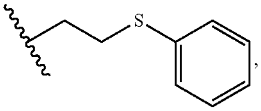,
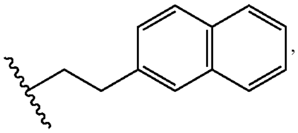, and
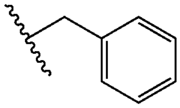;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an albumin protein (e.g., an albumin protein having the sequence of any one of SEQ ID NOs: 69-71), an albumin protein-binding peptide, or an Fc-binding peptide; L in each $A_1$-L-$A_2$ is a linker independently covalently attached to a sulfur atom of a surface exposed cysteine or a nitrogen atom of a surface exposed lysine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is independently covalently attached (e.g., by way of a bond or a linker) to the sulfur atom of a solvent-exposed cysteine or the nitrogen atom of a solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (3):

(3)

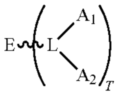

wherein each $A_1$ and each $A_2$ is independently selected from any one of formulas (A-VI)-(A-IX):

(A-VI)

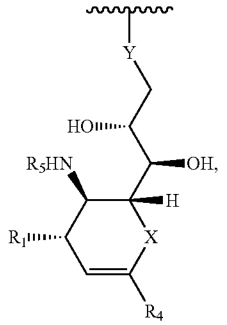

(A-VII)

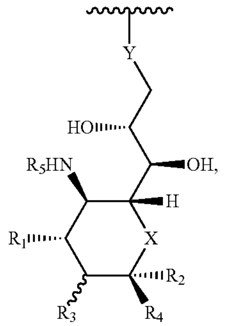

(A-VIII)

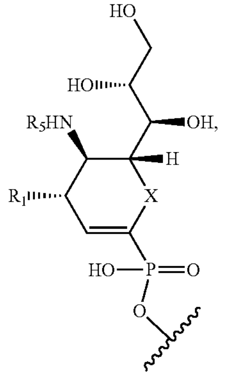

(A-IX)

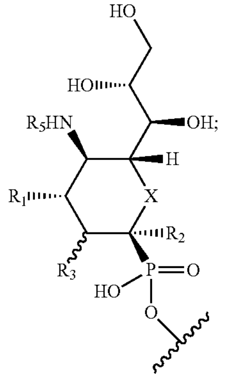

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

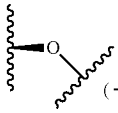
(—O—),

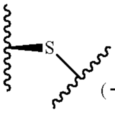
(—S—),

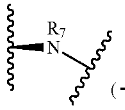
(—$NR_7$—),

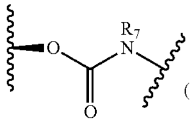
(—O(C=O)$NR_7$—),

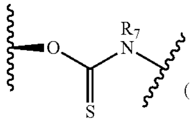
(—O(C=S)$NR_7$—),

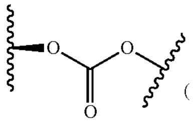
(—O(C=O)O—),

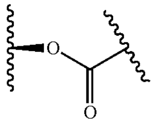
(—O(C=O)—),

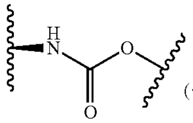
(—NH(C=O)O—),

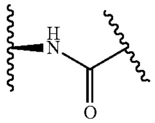
(—NH(C=O)—),

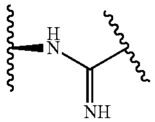
(—NH(C=NH)—),

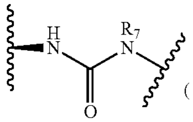
(—NH(C=O)$NR_7$—),

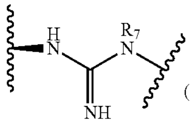
(—NH(C=NH)$NR_7$—),

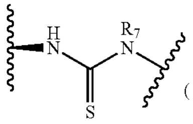
(—NH(C=S)$NR_7$—),

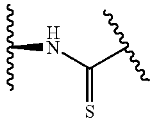
(—NH(C=S)—),

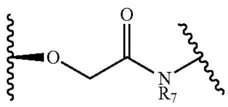
(—$OCH_2$(C=O)$NR_7$—),

-continued
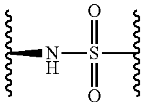
(——NH($SO_2$)——),
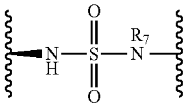
(——NH($SO_2$)$NR_7$——),
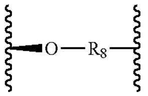
(——$OR_8$——),
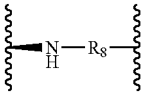
(——$NR_8$——), and
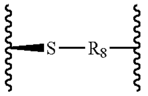
(——$SR_8$——);
$R_6$ is selected from
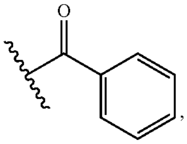,
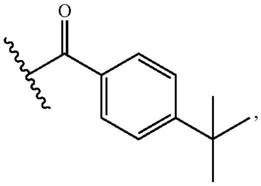,
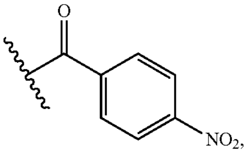,
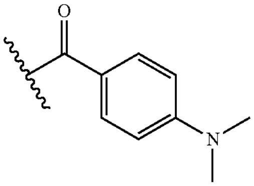,
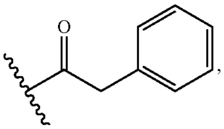,
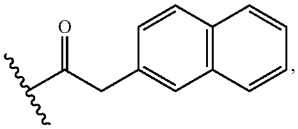,
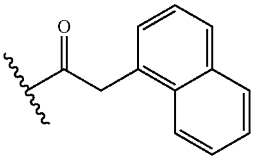,
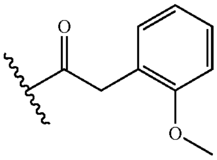,
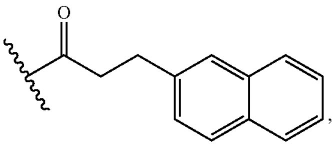,
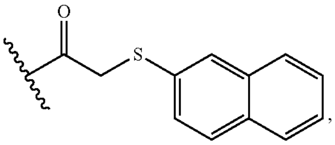,
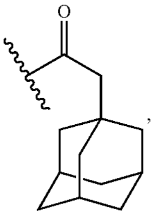,
-continued
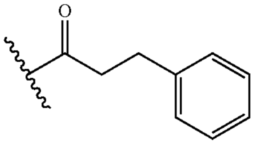,
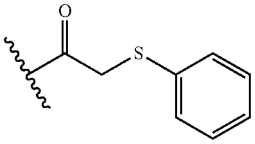,
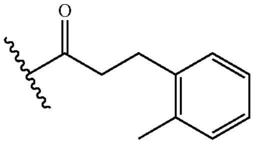,
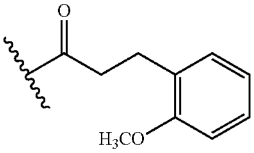,
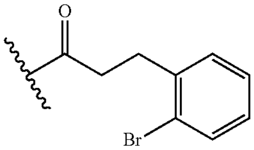,
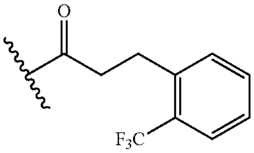,
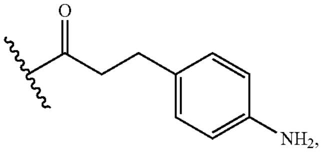
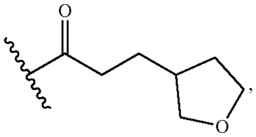,
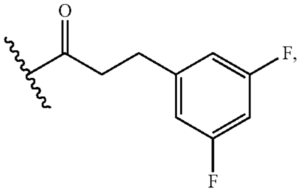
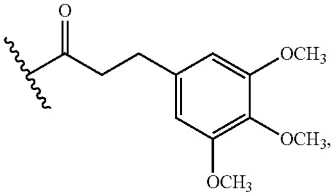
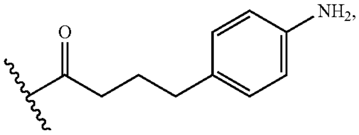
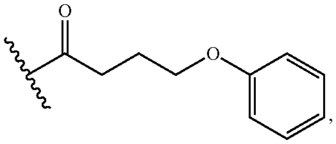,
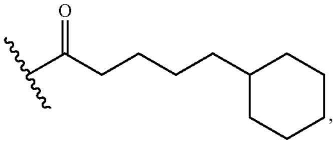,
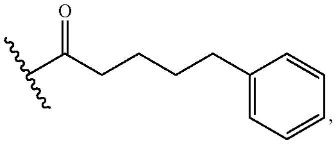, -continued

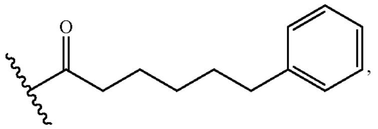

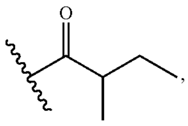

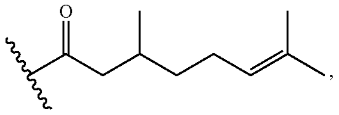

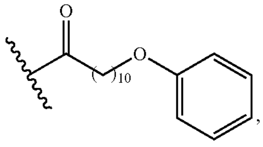

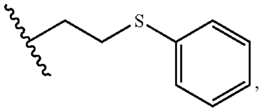

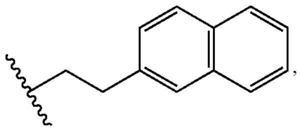

, and

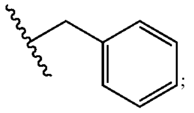

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an albumin protein (e.g., an albumin protein having the sequence of any one of SEQ ID NOs: 69-71), an albumin protein-binding peptide, or an Fc-binding peptide; L in each $A_1$-L-$A_2$ is a linker independently covalently attached to a sulfur atom of a surface exposed cysteine or a nitrogen atom of a surface exposed lysine in E and to each of $A_1$ and $A_2$; T is an integer from 1 to 20 (e.g., 1, 2, 3, 4, 5, 6, 7, 8, 9, 10, 11, 12, 13, 14, 15, 16, 17, 18, 19, or 20), and the squiggly line connected to the E indicates that each $A_1$-L-$A_2$ is independently covalently attached (e.g., by way of a bond or a linker) to the sulfur atom of a solvent-exposed cysteine or the nitrogen atom of a solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (4):

(4)

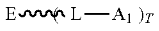

wherein each $A_1$ is independently selected from any one of formulas (A-I)-(A-XII):

(A-I)

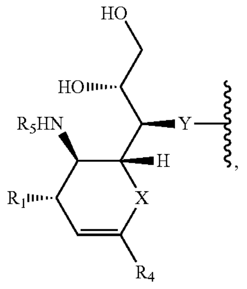

(A-II)

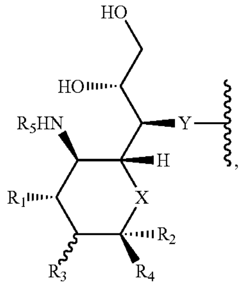

(A-III)

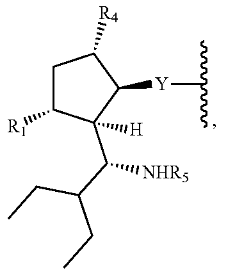

(A-IV)

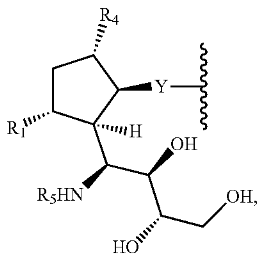

(A-V)

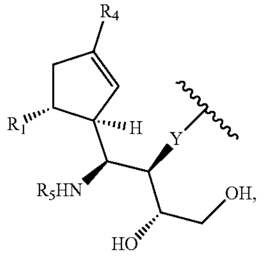

-continued
(A-VI)
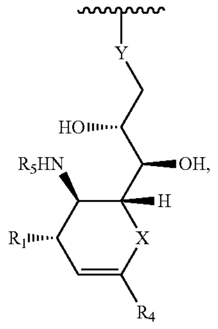
(A-VII)
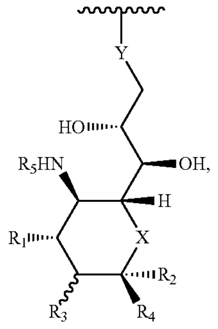
(A-VIII)
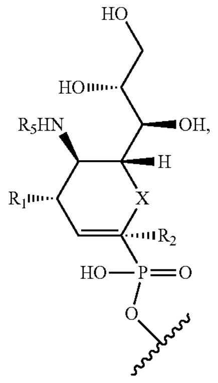
(A-IX)
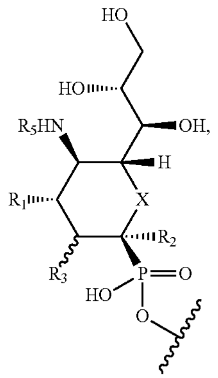
-continued
(A-X)
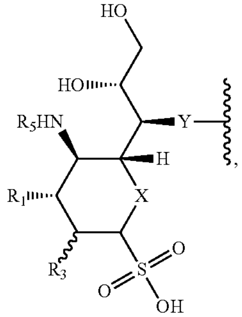
(A-XI)
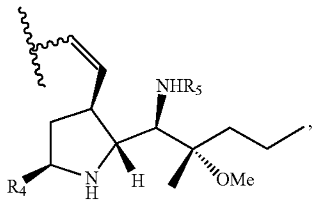
(A-XII)
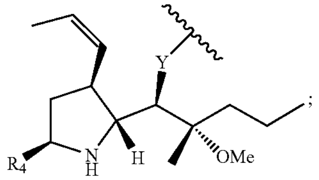
wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from
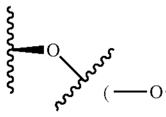
(—O—),
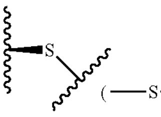
(—S—),
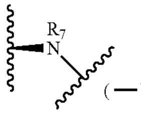
(—$NR_7$—),
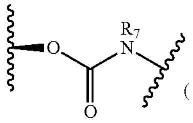
(—O(C═O)$NR_7$—),
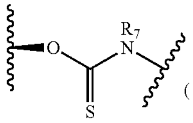
(—O(C═S)$NR_7$—),
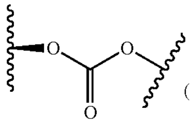
(—O(C═O)O—),
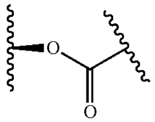
(—O(C═O)—), -continued
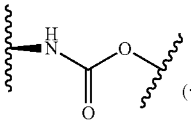
(—NH(C═O)O—),
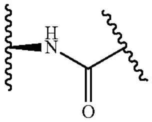
(—NH(C═O)—),
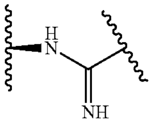
(—NH(C═NH)—),
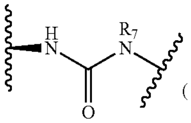
(—NH(C═O)$NR_7$—),
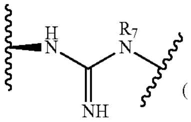
(—NH(C═NH)$NR_7$—),
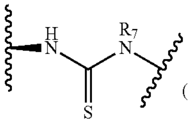
(—NH(C═S)$NR_7$—),
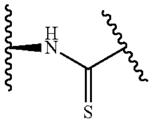
(—NH(C═S)—),
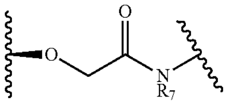
(—$OCH_2$(C═O)$NR_7$—),
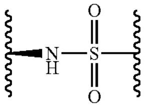
(—NH($SO_2$)—),
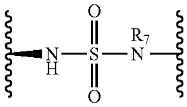
(—NH($SO_2$)$NR_7$—),
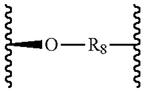
(—$OR_8$—),
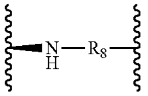
(—$NR_8$—), and
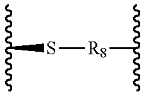
(—$SR_8$—);
$R_6$ is selected from
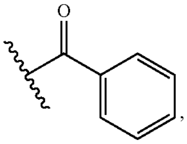
,
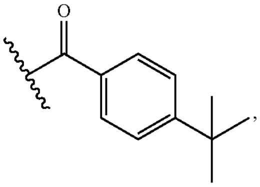
,
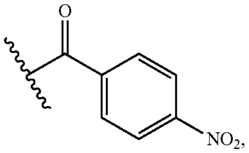
,
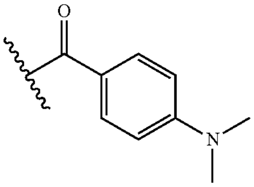
,
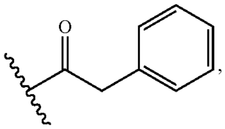
,
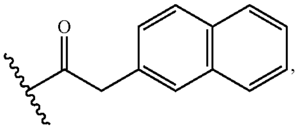
,
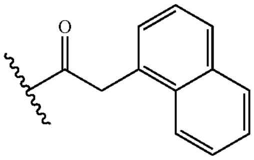
,
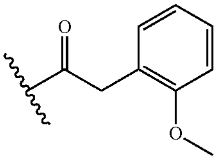
,
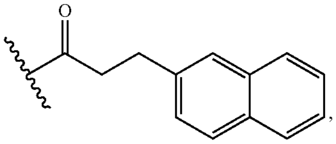
,
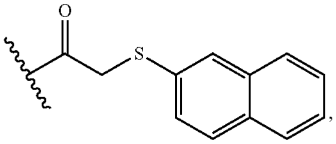
,
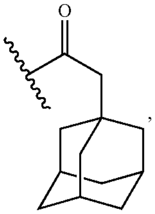
,
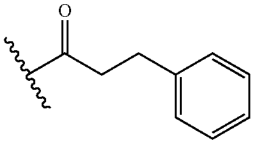
,
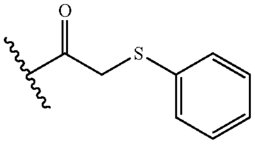
,
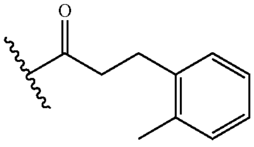
,
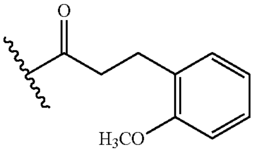
,
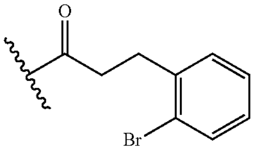
,
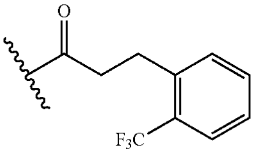
,
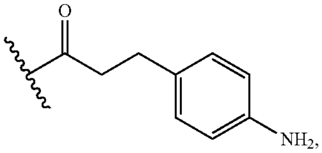
, -continued

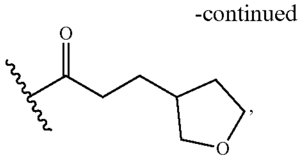

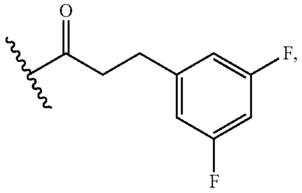

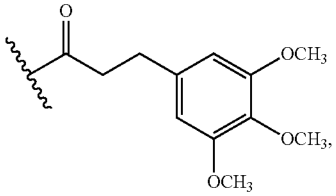

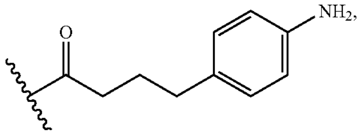

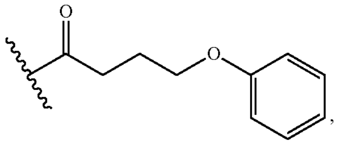

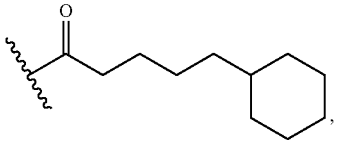

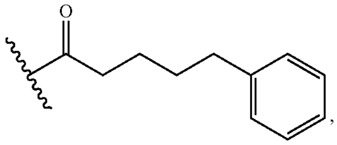

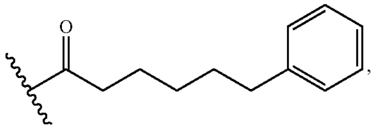

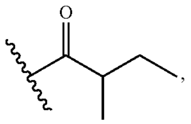

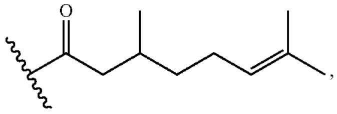

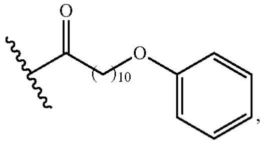

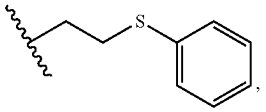

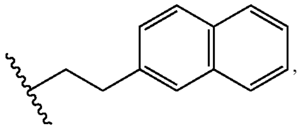

and

-continued

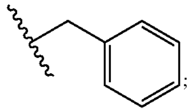

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an albumin protein (e.g., an albumin protein having the sequence of any one of SEQ ID NOs: 69-71), an albumin protein-binding peptide, or an Fc-binding peptide; L in each L-$A_1$ is a linker independently covalently attached to a sulfur atom of a surface exposed cysteine or a nitrogen atom of a surface exposed lysine in E and to $A_1$; T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-$A_1$ is independently covalently attached (e.g., by way of a bond or a linker) to the sulfur atom of the solvent-exposed cysteine or the nitrogen atom of the solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each A may be independently selected from any one of formulas (A-I)-(A-XII).

In another aspect, the invention features a conjugate described by formula (4):

(4)

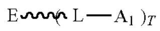

wherein each $A_1$ is independently selected from any one of formulas (A-I)-(A-V):

(A-I)

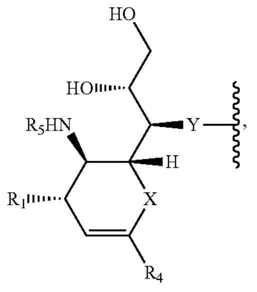

(A-II)

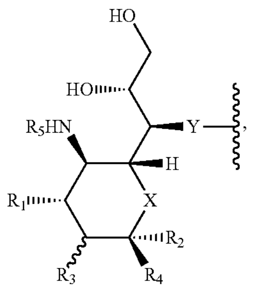

-continued (A-III)

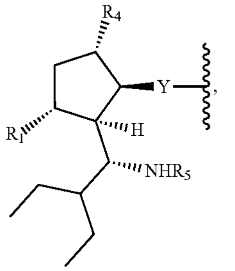

(A-IV)

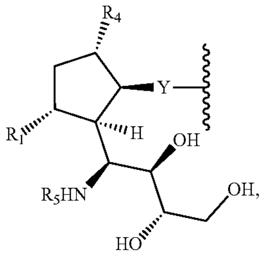

(A-V)

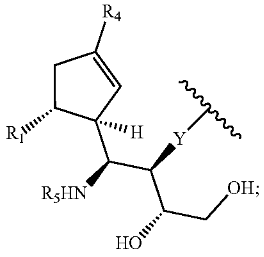

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

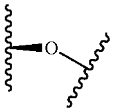
( —O— ),
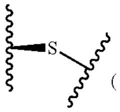
( —S— ),

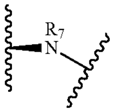
( —$NR_7$— ),

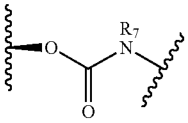
( —O(C=O)$NR_7$— ),

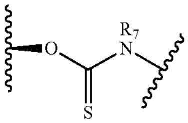
( —O(C=S)$NR_7$— ),

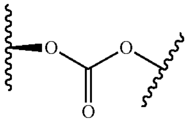
( —O(C=O)O— ),

-continued

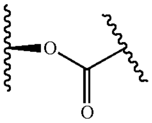
( —O(C=O)— ),

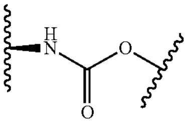
( —NH(C=O)O— ),

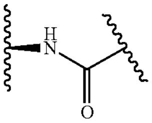
( —NH(C=O)— ),

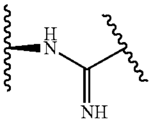
( —NH(C=NH)— ),

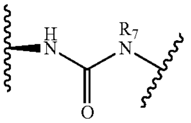
( —NH(C=O)$NR_7$— ),

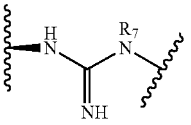
( —NH(C=NH)$NR_7$— ),

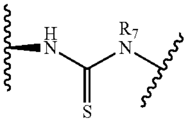
( —NH(C=S)$NR_7$— ),

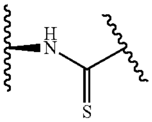
( —NH(C=S)— ),

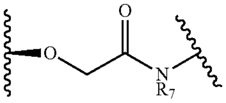
( —$OCH_2$(C=O)$NR_7$— ),

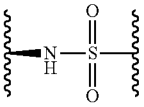
( —NH($SO_2$)— ),

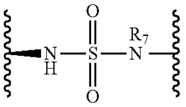
( —NH($SO_2$)$NR_7$)— ),

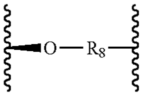
( —$OR_8$— ),

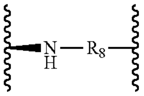
( —$NH_8$— ), and

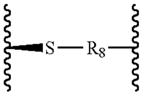
( —$SR_8$— );

$R_6$ is selected from
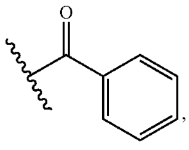
,
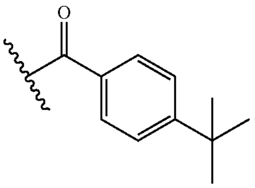
,
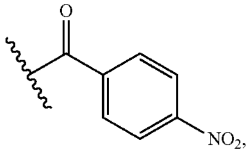
,
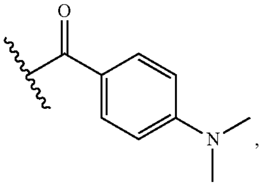
,
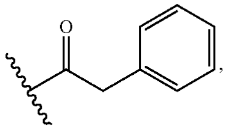
,
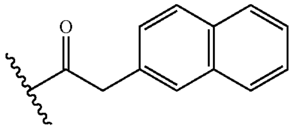
,
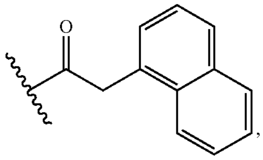
,
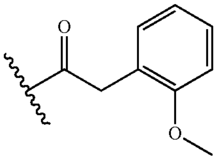
,
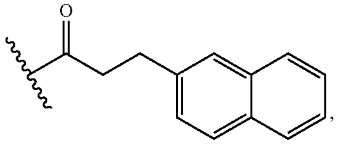
,
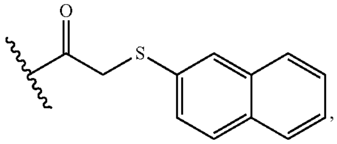
,
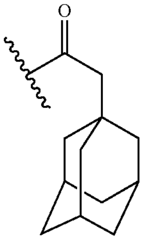
,
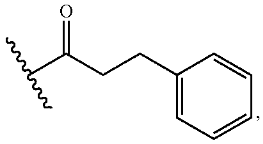
,
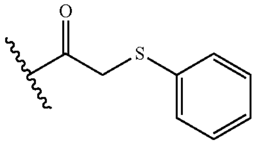
,
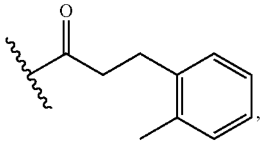
,
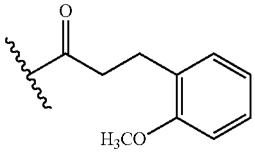
,
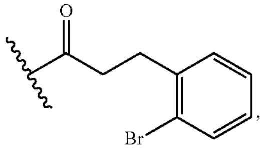
,
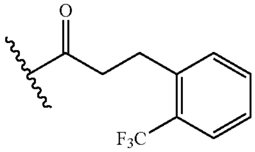
,
-continued
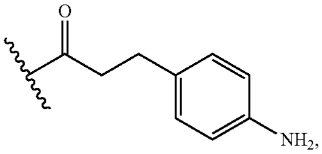
,
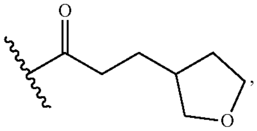
,
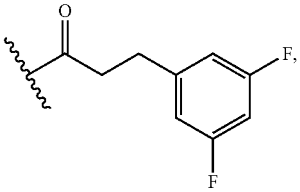
,
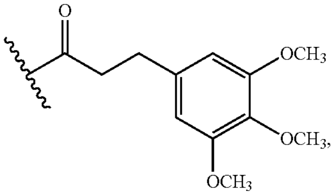
,
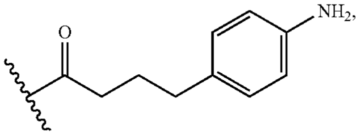
,
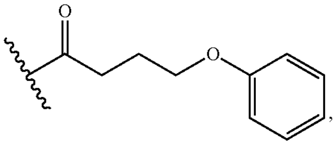
,
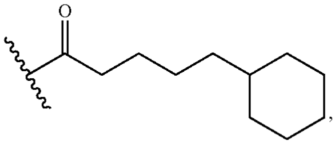
,
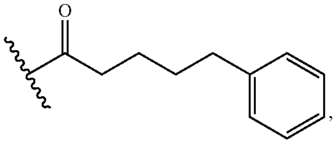
,
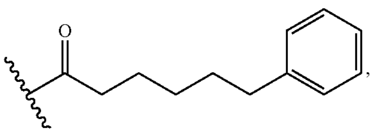
,
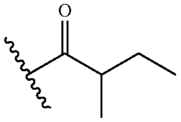
,
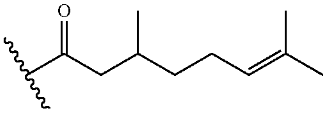
,
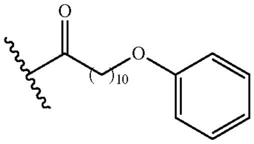
,
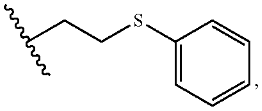
, -continued

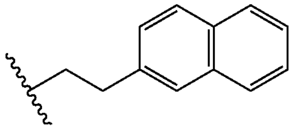

, and

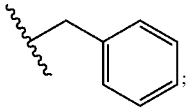

;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an albumin protein (e.g., an albumin protein having the sequence of any one of SEQ ID NOs: 69-71), an albumin protein-binding peptide, or an Fc-binding peptide; L in each L-$A_1$ is a linker independently covalently attached to a sulfur atom of a surface exposed cysteine or a nitrogen atom of a surface exposed lysine in E and to $A_1$; T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-A is independently covalently attached (e.g., by way of a bond or a linker) to the sulfur atom of the solvent-exposed cysteine or the nitrogen atom of the solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-V).

In another aspect, the invention features a conjugate described by formula (4):

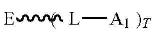

(4)

wherein each $A_1$ is independently selected from any one of formulas (A-VI)-(A-IX):

(A-VI)

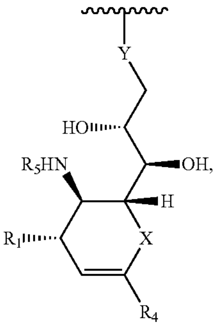

-continued (A-VII)

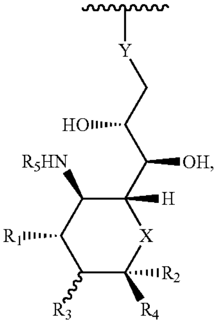

(A-VIII)

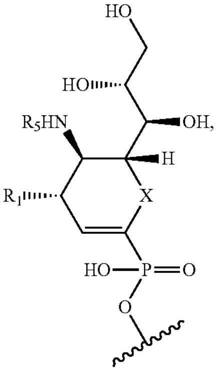

(A-IX)

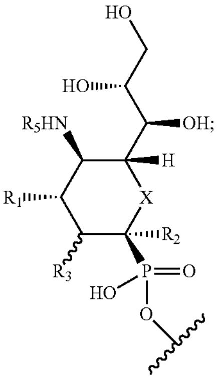

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

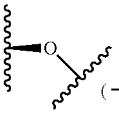

(—O—),

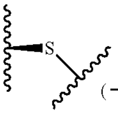

(—S—),

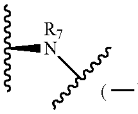

(—$NR_7$—),

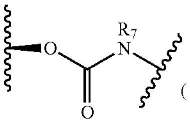

(—O(C═O)$NR_7$—),

-continued
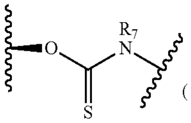
(—O(C═S)$NR_7$—),
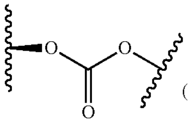
(—O(C═O)O—),
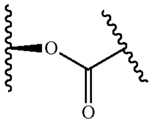
(—O(C═O)—),
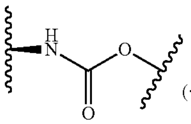
(—NH(C═O)O—),
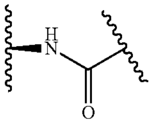
(—NH(C═O)—),
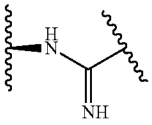
(—NH(C═NH)—),
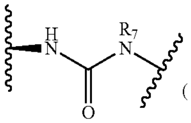
(—NH(C═O)$NR_7$—),
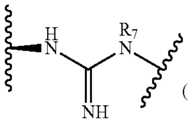
(—NH(C═NH)$NR_7$—),
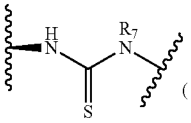
(—NH(C═S)$NR_7$—),
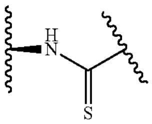
(—NH(C═S)—),
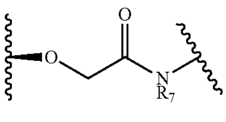
(—$OCH_2$(C═O)$NR_7$—),
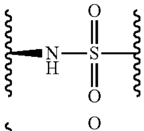
(—NH($SO_2$)—),
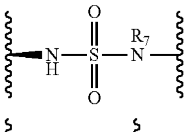
(—NH($SO_2$)$NR_7$—),
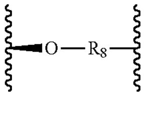
(—$OR_8$—),
-continued
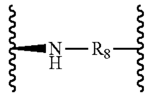
(—$NR_8$—), and
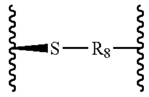
(—$SR_8$—);
$R_6$ is selected from
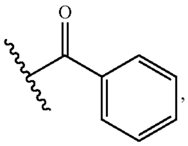
,
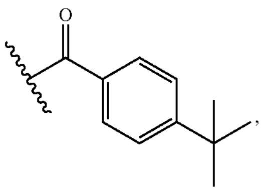
,
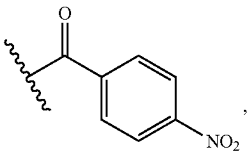
,
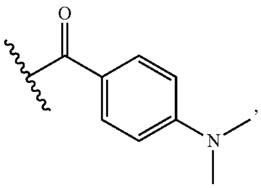
,
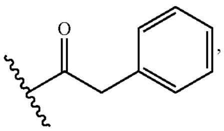
,
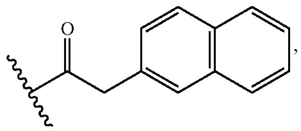
,
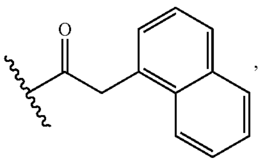
,
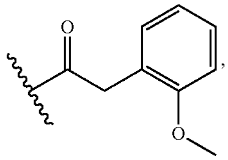
,
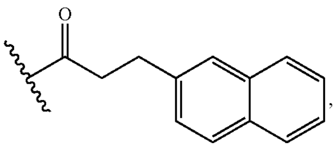
,
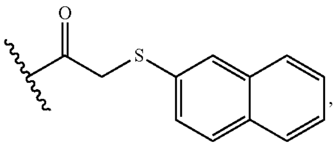
,
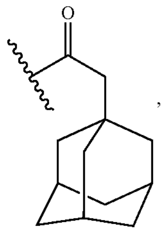
,
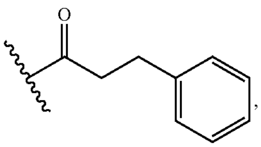
,
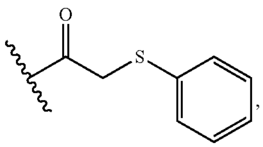
,
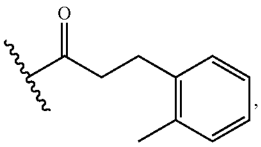
,
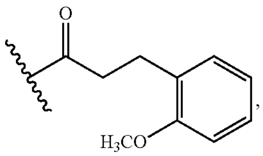
, -continued

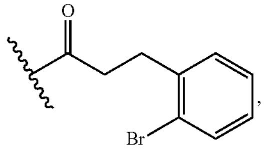,
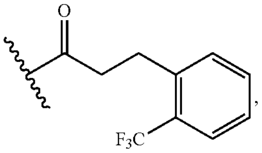,
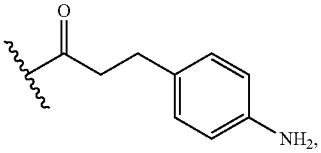
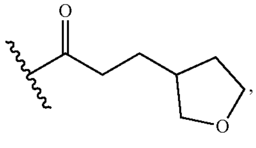,
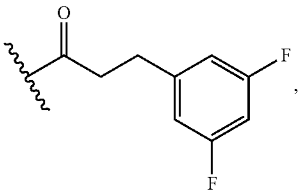,
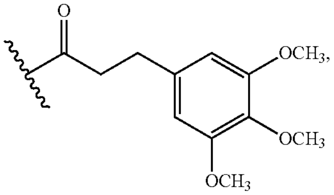
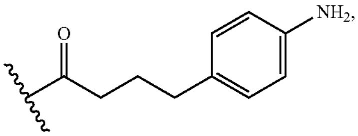
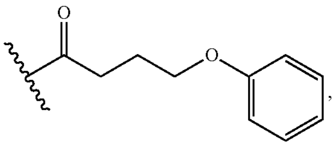,
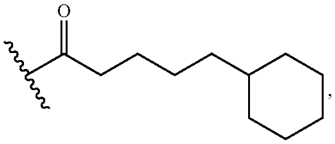,
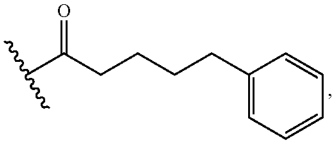,
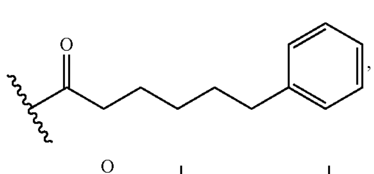,
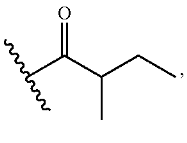,
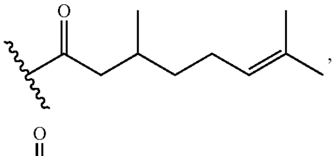,
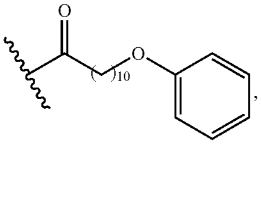,
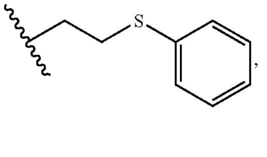, -continued

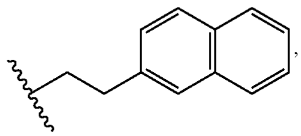, and 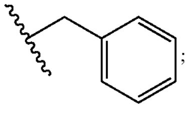;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; E comprises an albumin protein (e.g., an albumin protein having the sequence of any one of SEQ ID NOs: 69-71), an albumin protein-binding peptide, or an Fc-binding peptide; L in each L-$A_1$ is a linker independently covalently attached to a sulfur atom of a surface exposed cysteine or a nitrogen atom of a surface exposed lysine in E and to $A_1$; T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-$A_1$ is independently covalently attached (e.g., by way of a bond or a linker) to the sulfur atom of the solvent-exposed cysteine or the nitrogen atom of the solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each A may be independently selected from any one of formulas (A-VI)-(A-IX).

In another aspect, the invention features a conjugate described by formula (5):

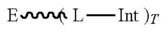
(5)

wherein each Int is independently selected from any one of the intermediates of Table 1; E comprises an albumin protein (e.g., an albumin protein having the sequence of any one of SEQ ID NOs: 69-71), an albumin protein-binding peptide, or an Fc-binding peptide; L in each L-Int is a linker independently covalently attached to a sulfur atom of a surface exposed cysteine or a nitrogen atom of a surface exposed lysine in E and to Int; T is an integer from 1 to 20 (e.g., 1, 2, 3, 4, 5, 6, 7, 8, 9, 10, 11, 12, 13, 14, 15, 16, 17, 18, 19, or 20); and the squiggly line connected to E indicates that each L-Int is independently covalently attached to the sulfur atom of the solvent-exposed cysteine or the nitrogen atom of the solvent-exposed lysine in E, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each Int may be independently selected from any one of the intermediates of Table 1.

Intermediates of Table 1 may be conjugated to an albumin protein, an albumin protein-binding peptide, or an Fc-binding peptide (e.g., by way of a linker) by any suitable methods known to those of skill in the art, including any of the methods described or exemplified herein. In some embodiments, the conjugate (e.g., a conjugate described by formula (5)) comprises E, wherein E is an albumin protein (e.g., an albumin protein having the sequence of any one of SEQ ID NOs: 69-71), an albumin protein-binding peptide, or an Fc-binding peptide. In preferred embodiments, one or more nitrogen atoms of one or more surface exposed lysine residues of E or one or more sulfur atoms of one or more surface exposed cysteines in E is covalently conjugated to a linker (e.g., a $PEG_2$-$PEG_{20}$ linker). The linker conjugated to E may be functionalized such that it may react to form a covalent bond with any of the Ints described herein (e.g., an Int of Table 1). In preferred embodiments, E is conjugated to a linker functionalized with an azido group and the Int (e.g., an Int of Table 1) is functionalized with an alkyne group. Conjugation (e.g., by click chemistry) of the linker-azido of E and linker-alkyne of the Int forms a conjugate of the invention, for example a conjugate described by formula (5). In yet other embodiments, E is conjugated to a linker functionalized with an alkyne group and the Int (e.g., an Int of Table 1) is functionalized with an azido group. Conjugation (e.g., by click chemistry) of the linker-alkyne of E and linker-azido of the Int forms a conjugate of the invention, for example a conjugate described by formula (5).

In some embodiments, each E includes an albumin protein having the sequence of any one of SEQ ID NOs: 69-71.

In some embodiments, T is 1 and L-A is covalently attached to the sulfur atom corresponding to Cys34 of SEQ ID NO: 69.

In another aspect, the invention features a population of conjugates described in any of the previous aspects, wherein the average value of T is 1 to 20 (e.g., the average value of T is 1 to 2, 1 to 3, 1 to 4, 1 to 5, 5 to 10, 10 to 15, or 15 to 20). In some embodiments, the average value of T is 1, 2, 3, 4, 5, 6, 7, 8, 9, 10, 11, 12, 13, 14, 15, 16, 17, 18, 19, or 20.

In another aspect, the invention features a conjugate including (i) a first moiety, $A_1$; (ii) a second moiety, $A_2$; (iii) an Fc domain monomer or an Fc domain; and (iv) a linker covalently attached to $A_1$ and $A_2$, and to the Fc domain monomer or the Fc domain; wherein each $A_1$ and each $A_2$ is independently selected from any one of formulas (A-I)-(A-XII):

(A-I)

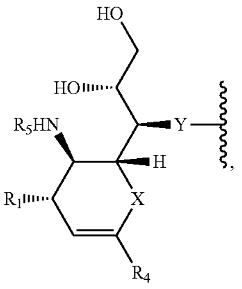

(A-II)

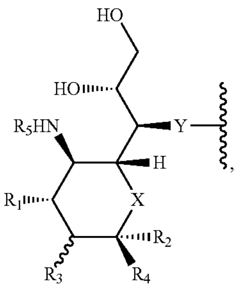

-continued (A-III)

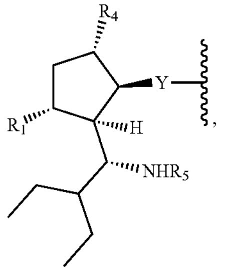

(A-IV)

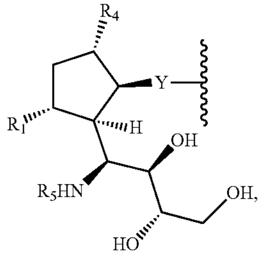

(A-V)

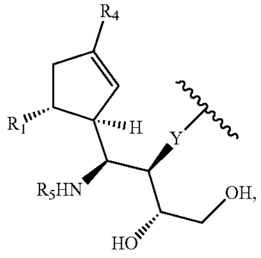

(A-VI)

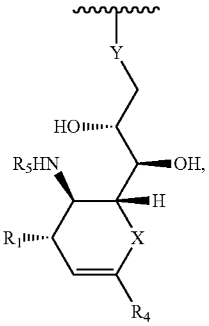

(A-VII)

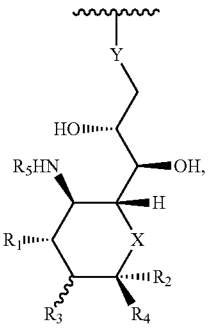

-continued (A-VIII)

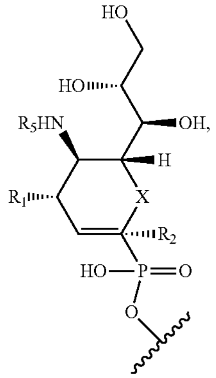

(A-IX)

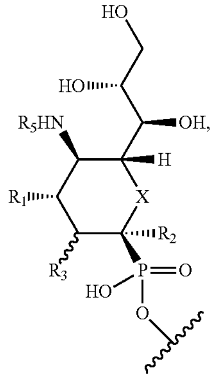

(A-X)

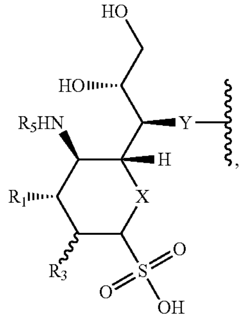

(A-XI)

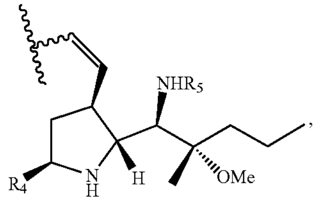

(A-XII)

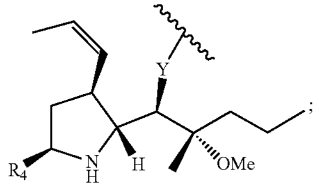

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

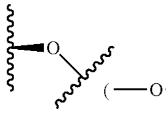

(—O—),

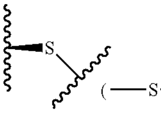

(—S—),

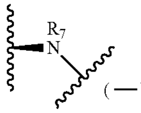

(—$NR_7$—),

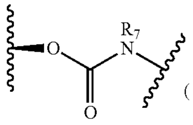

(—O(C═O)$NR_7$—),

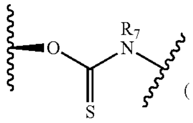

(—O(C═S)$NR_7$—),

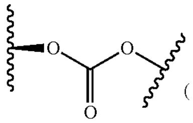

(—O(C═O)O—),

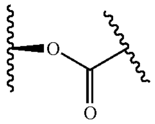

(—O(C═O)—),

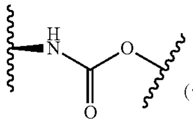

(—NH(C═O)O—),

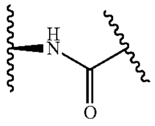

(—NH(C═O)—),

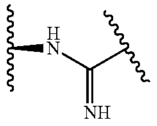

(—NH(C═NH)—),

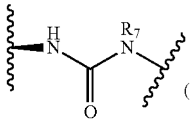

(—NH(C═O)$NR_7$—),

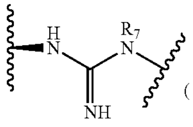

(—NH(C═NH)$NR_7$—),

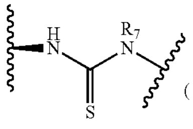

(—NH(C═S)$NR_7$—),

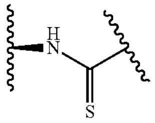

(—NH(C═S)—),

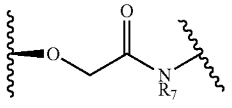

(—$OCH_2$(C═O)$NR_7$—),

-continued
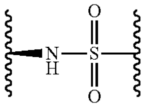
( —NH($SO_2$)— ),
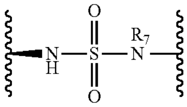
( —NH($SO_2$)$NR_7$— ),
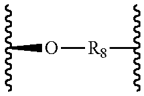
( —$OR_8$— ),
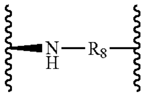
( —$NR_8$— ), and
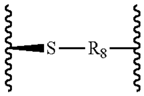
( —$SR_8$— );
$R_6$ is selected from
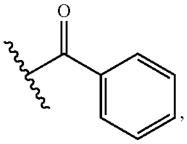
,
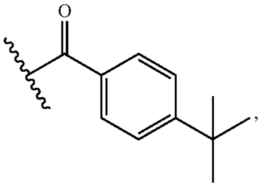
,
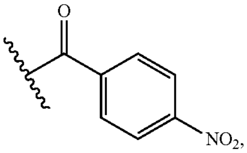
,
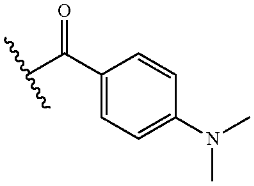
,
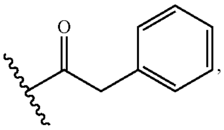
,
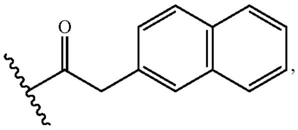
,
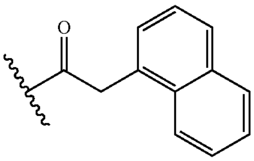
,
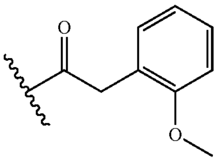
,
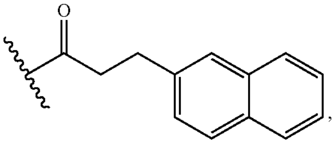
,
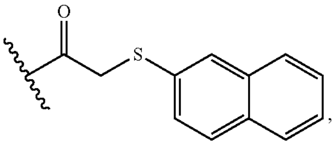
,
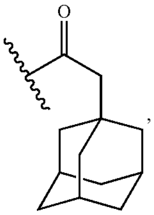
,
-continued
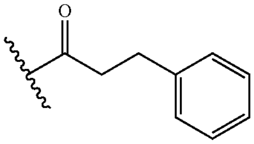
,
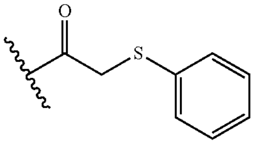
,
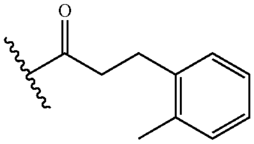
,
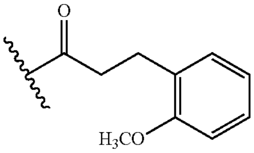
,
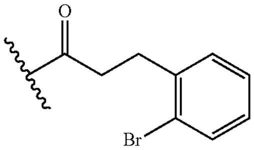
,
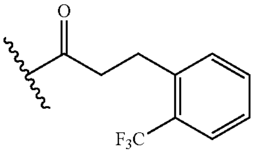
,
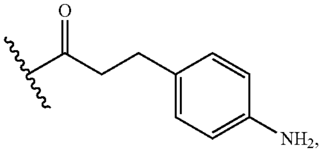
,
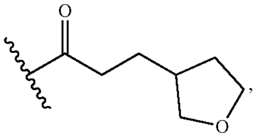
,
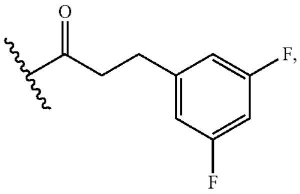
,
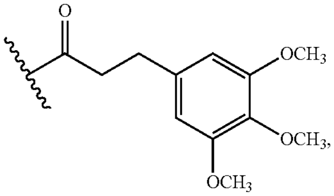
,
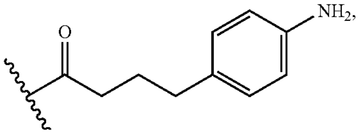
,
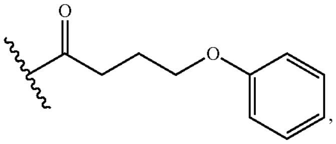
,
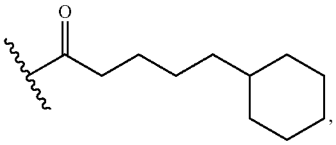
,
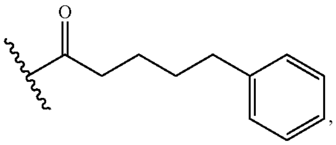
, -continued

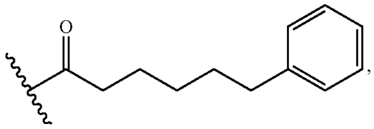

,

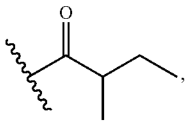

,

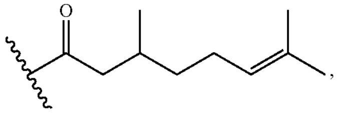

,

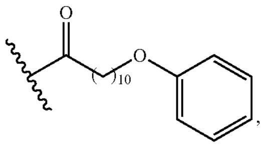

,

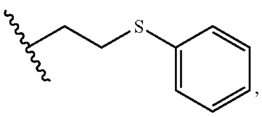

,

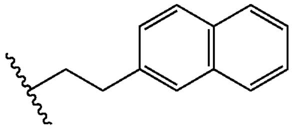

, and

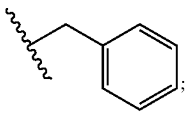

;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl, or a pharmaceutically acceptable salt thereof.

In another aspect, the invention features a conjugate including (i) a first moiety, $A_1$; (ii) a second moiety, $A_2$; (iii) an Fc domain monomer or an Fc domain; and (iv) a linker covalently attached to $A_1$ and $A_2$, and to the Fc domain monomer or the Fc domain; wherein each $A_1$ and each $A_2$ is independently selected from any one of formulas (A-I)-(A-V):

(A-I)

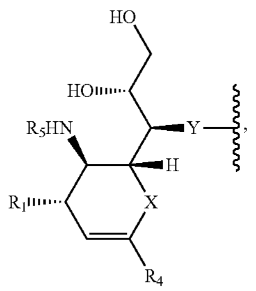

,

-continued (A-II)

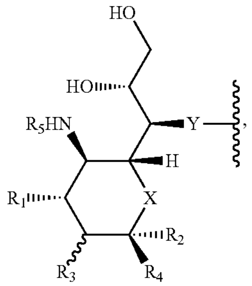

, (A-III)

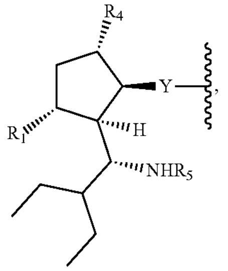

, (A-IV)

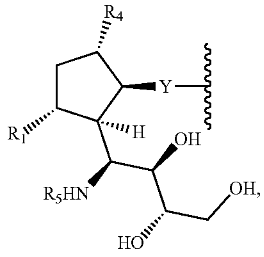

, (A-V)

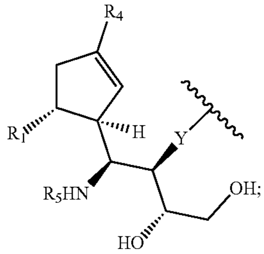

;

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

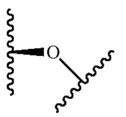

(—O—),

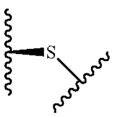

(—S—),

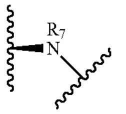

(—$NR_7$—),

-continued
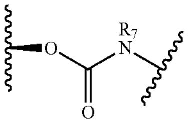 (—O(C=O)NR$_7$—),
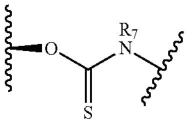 (—O(C=S)NR$_7$—),
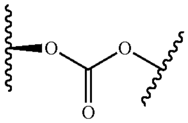 (—O(C=O)O—),
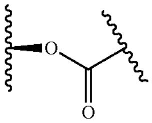 (—O(C=O)—),
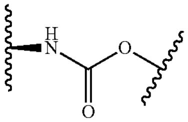 (—NH(C=O)O—),
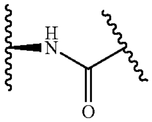 (—NH(C=O)—),
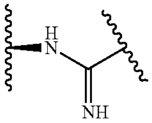 (—NH(C=NH)—),
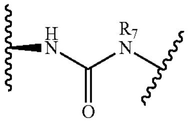 (—NH(C=O)NR$_7$—),
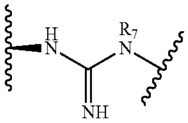 (—NH(C=NH)NR$_7$—),
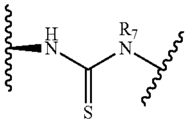 (—NH(C=S)NR$_7$—),
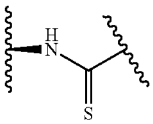 (—NH(C=S)—),
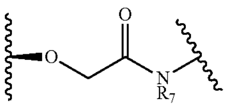 (—OCH$_2$(C=O)NR$_7$—),
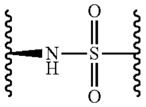 (—NH(SO$_2$)—),
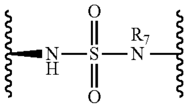 (—NH(SO$_2$)NR$_7$—),
-continued
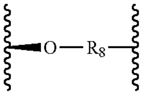 (—OR$_8$—),
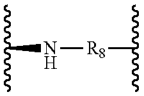 (—NR$_8$—), and
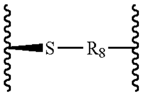 (—SR$_8$—);
$R_6$ is selected from
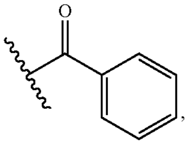, 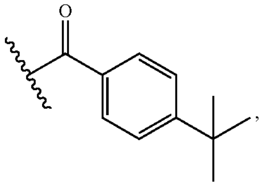,
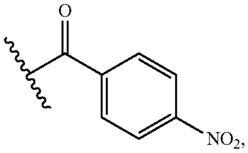 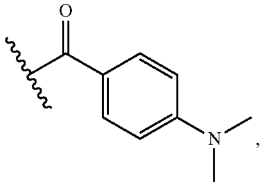,
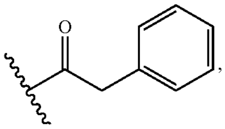,
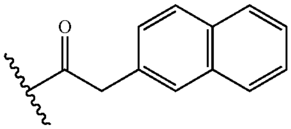,
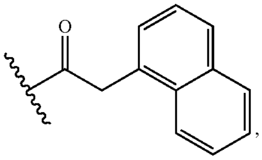, 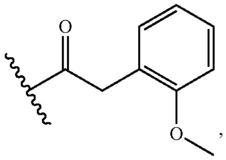,
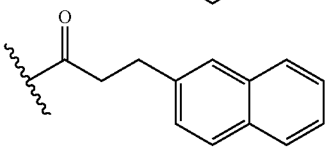,
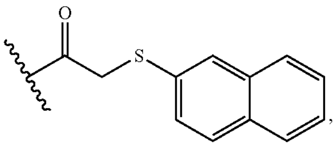, 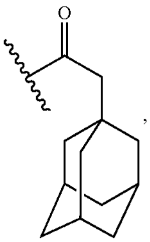,
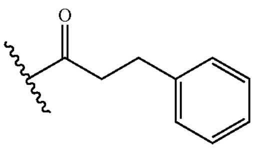, 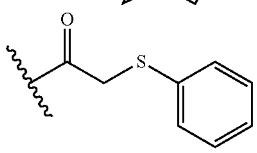, -continued

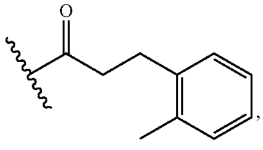
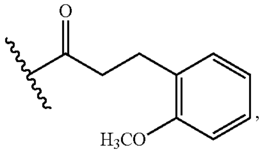
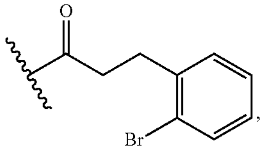
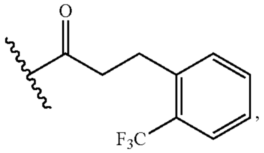
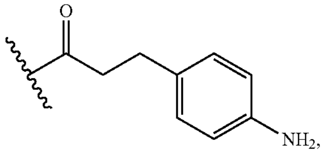
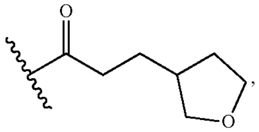
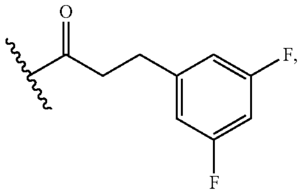
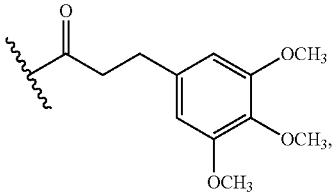
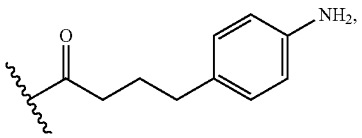
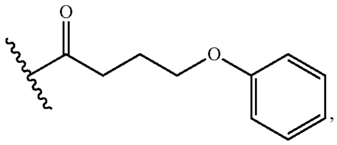
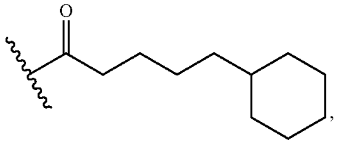
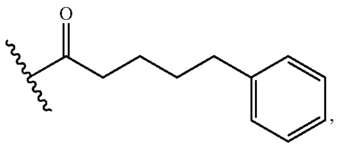
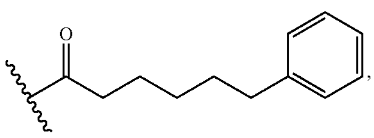

-continued

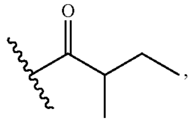
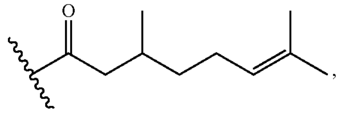
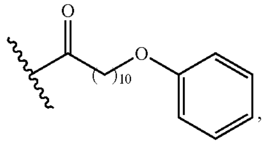
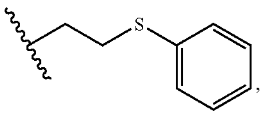
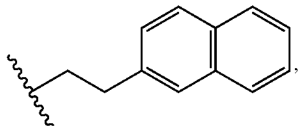
and
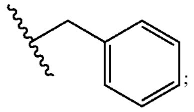

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl, or a pharmaceutically acceptable salt thereof.

In another aspect, the invention features a conjugate including (i) a first moiety, $A_1$; (ii) a second moiety, $A_2$; (iii) an Fc domain monomer or an Fc domain; and (iv) a linker covalently attached to $A_1$ and $A_2$, and to the Fc domain monomer or the Fc domain; wherein each $A_1$ and each $A_2$ is independently selected from any one of formulas (A-VI)-(A-IX):

(A-VI)

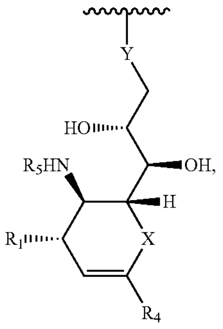

(A-VII)

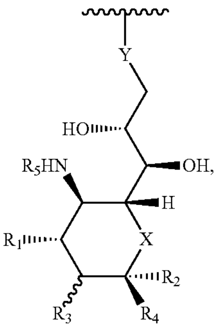

-continued (A-VIII)

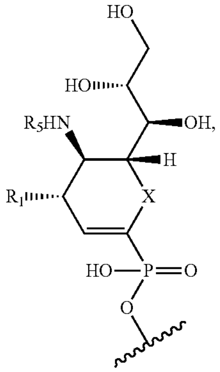

(A-IX)

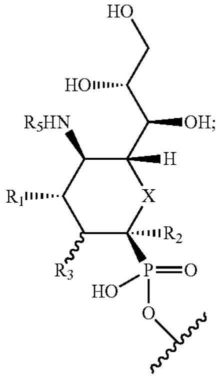

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; Rs is selected from —$COCH_3$, —$COCF_3$, —$SO_2CH_3$; X is selected from —O— and —S—; Y is selected from

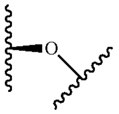

(—O—),

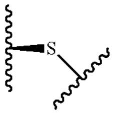

(—S—),

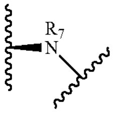

(—$NR_7$—),

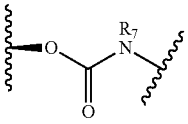

(—O(C=O)$NR_7$—),

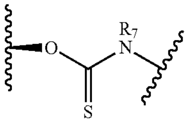

(—O(C=S)$NR_7$—),

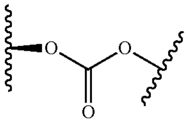

(—O(C=O)O—),

-continued

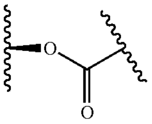

(—O(C=O)—),

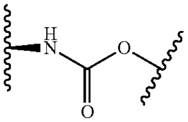

(—NH(C=O)O—),

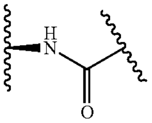

(—NH(C=O)—),

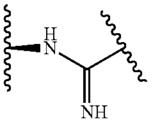

(—NH(C=NH)—),

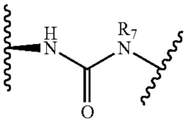

(—NH(C=O)$NR_7$—),

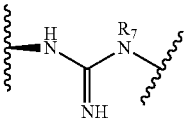

(—NH(C=NH)$NR_7$—),

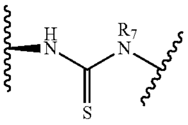

(—NH(C=S)$NR_7$—),

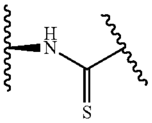

(—NH(C=S)—),

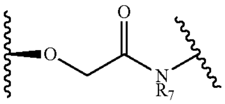

(—$OCH_2$(C=O)$NR_7$—),

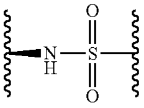

(—NH($SO_2$)—),

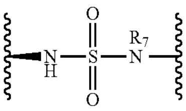

(—NH($SO_2$)$NR_7$—),

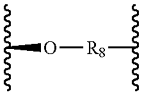

(—$OR_8$—),

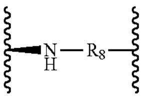

(—$NR_8$—), and

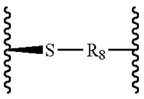

(—$SR_8$—);

$R_6$ is selected from
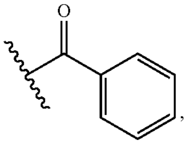,
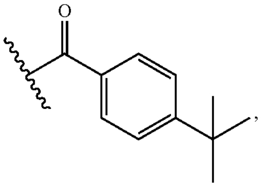,
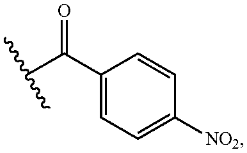,
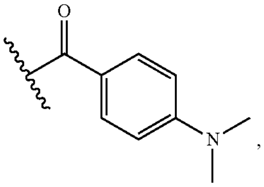,
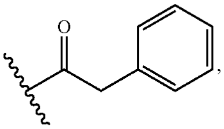,
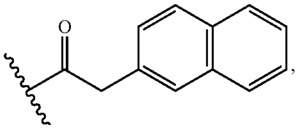,
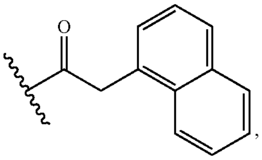,
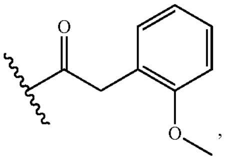,
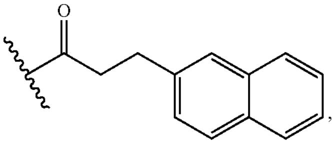,
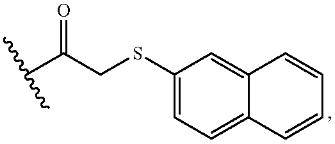,
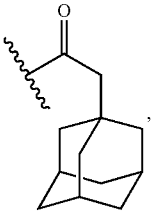,
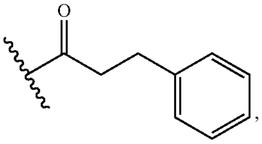,
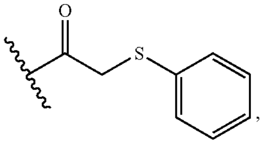,
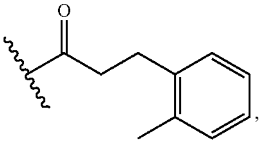,
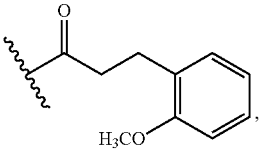,
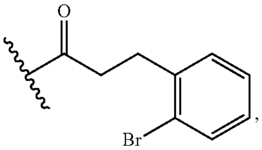,
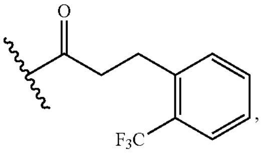,
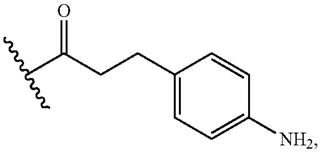
-continued
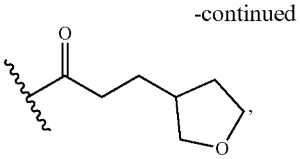,
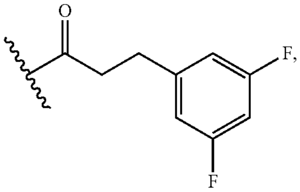
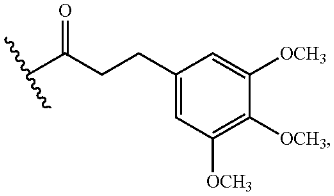
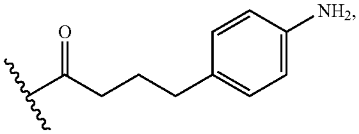
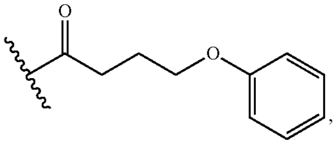,
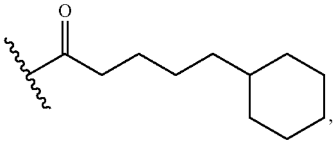,
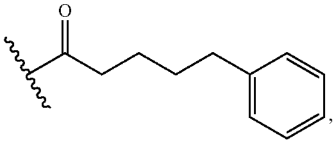,
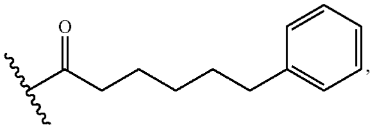,
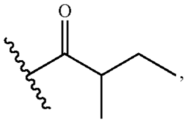,
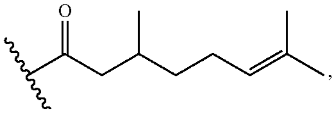,
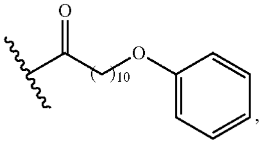,
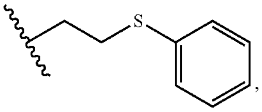,
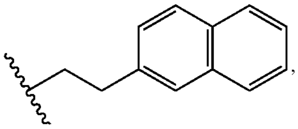, and -continued

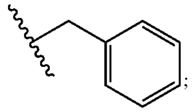

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl, or a pharmaceutically acceptable salt thereof.

In another aspect, the invention features a conjugate including (i) a first moiety, Int; (ii) an Fc domain monomer or an Fc domain; and (iv) a linker covalently attached to Int, and to the Fc domain monomer or the Fc domain; wherein each Int is independently selected from any one of the intermediates of Table 1.

In another aspect, the invention features a conjugate including (i) a first moiety, $A_1$; (ii) a second moiety, $A_2$; (iii) an albumin protein, an albumin protein-binding peptide, or an Fc-binding peptide; and (iv) a linker covalently attached to $A_1$ and $A_2$, and to the albumin protein, the albumin protein-binding peptide, or the Fc-binding peptide; wherein each $A_1$ and each $A_2$ is independently selected from any one of formulas (A-I)-(A-XII):

(A-I)

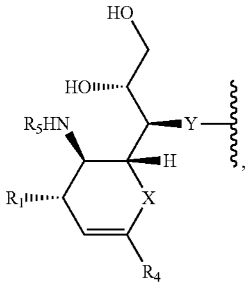

(A-II)

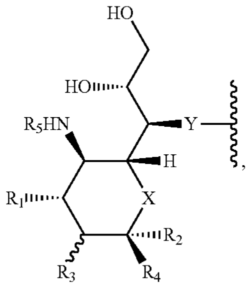

(A-III)

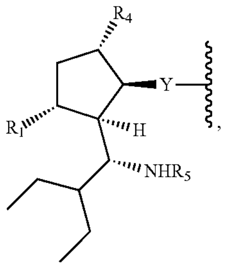

-continued (A-IV)

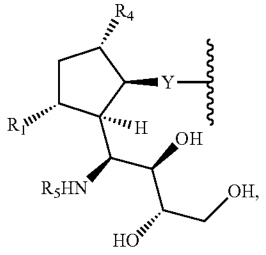

(A-V)

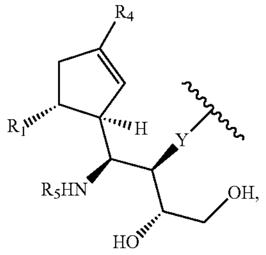

(A-VI)

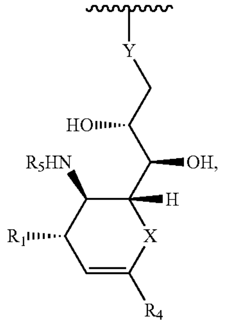

(A-VII)

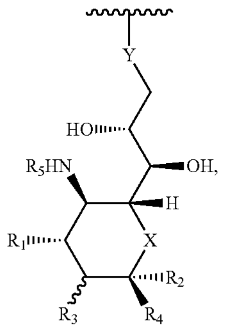

(A-VIII)

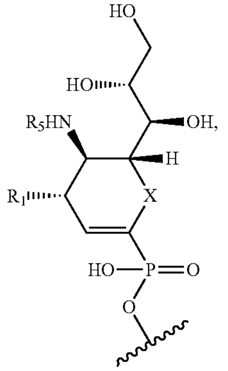

-continued (A-IX)

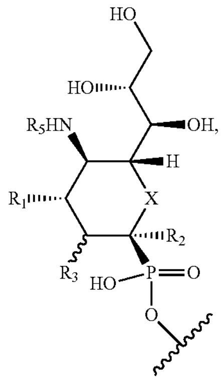

(A-X)

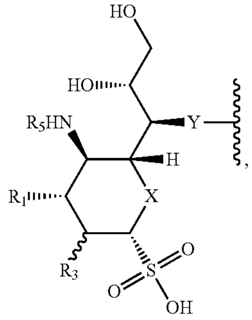

(A-XI)

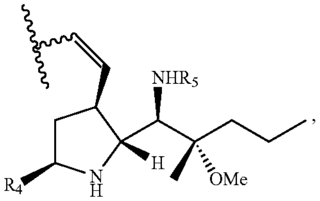

(A-XII)

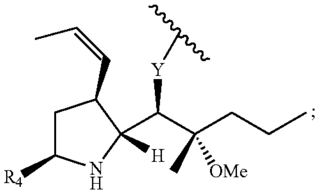

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

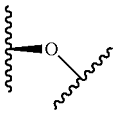

(—O—),

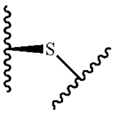

(—S—),

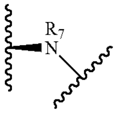

(—$NR_7$—),

-continued

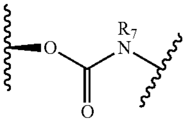

(—O(C=O)$NR_7$—),

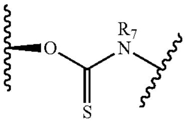

(—O(C=S)$NR_7$—),

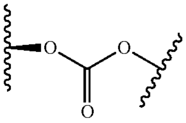

(—O(C=O)O—),

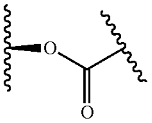

(—O(C=O)—),

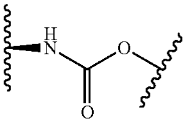

(—NH(C=O)O—),

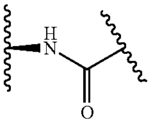

(—NH(C=O)—),

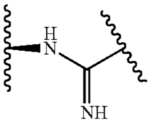

(—NH(C=NH)—),

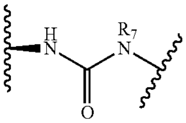

(—NH(C=O)$NR_7$—),

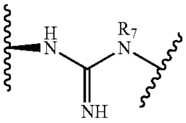

(—NH(C=NH)$NR_7$—),

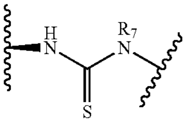

(—NH(C=S)$NR_7$—),

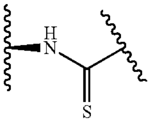

(—NH(C=S)—),

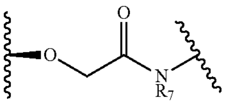

(—$OCH_2$(C=O)$NR_7$—),

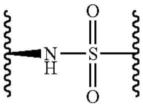

(—NH($SO_2$)—),

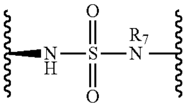

(—NH($SO_2$)$NR_7$—),

-continued
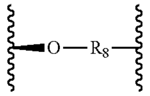
(—$OR_8$—),
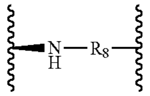
(—$NR_8$—), and
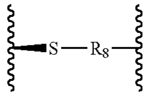
(—$SR_8$—);
$R_6$ is selected from
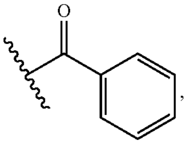
,
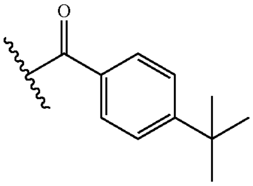
,
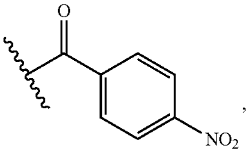
,
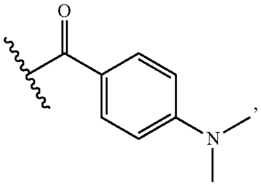
,
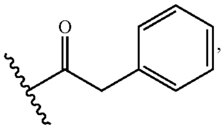
,
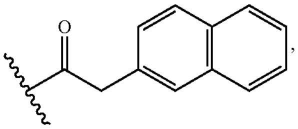
,
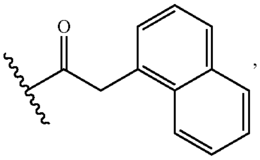
,
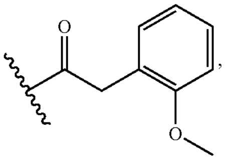
,
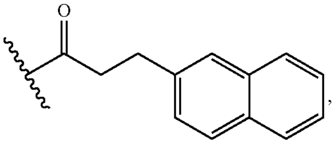
,
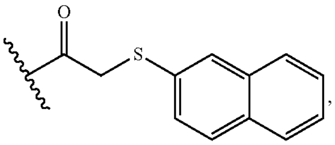
,
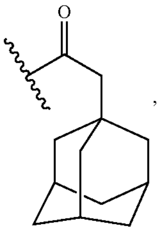
,
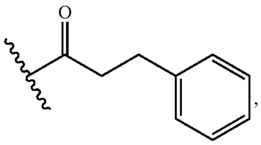
,
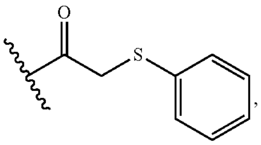
,
-continued
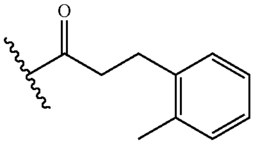
,
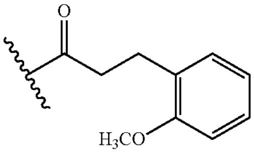
,
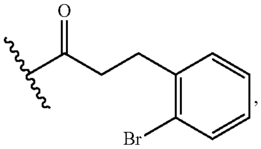
,
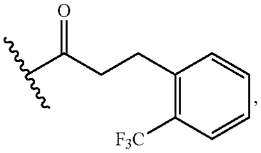
,
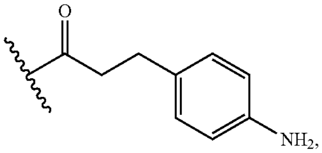
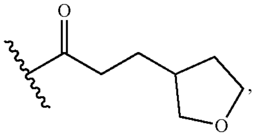
,
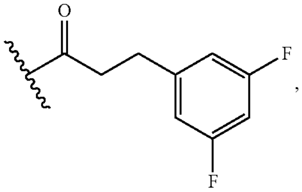
,
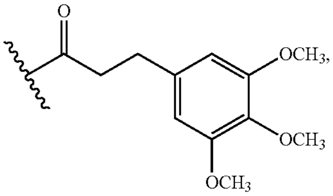
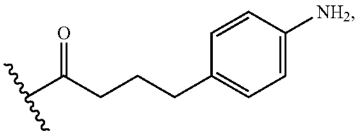
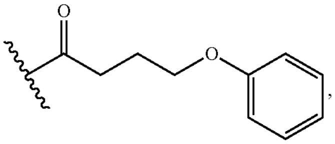
,
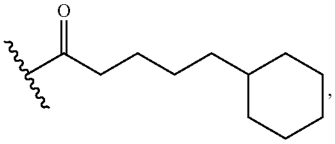
,
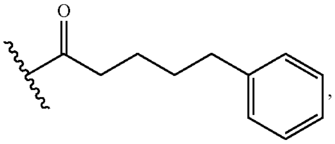
,
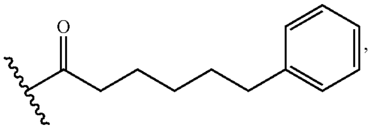
,
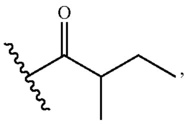
,
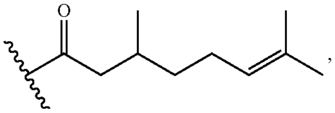
, -continued

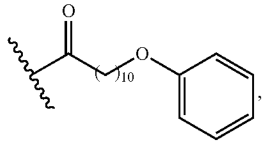,
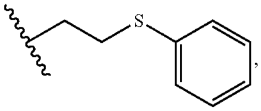,

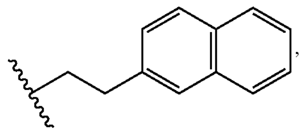, and 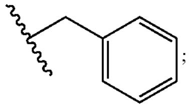;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl, or a pharmaceutically acceptable salt thereof.

In another aspect, the invention features a conjugate including (i) a first moiety, $A_1$; (ii) a second moiety, $A_2$; (iii) an albumin protein, an albumin protein-binding peptide, or an Fc-binding peptide; and (iv) a linker covalently attached to $A_1$ and $A_2$, and to the albumin protein, the albumin protein-binding peptide, or the Fc-binding peptide; wherein each $A_1$ and each $A_2$ is independently selected from any one of formulas (A-I)-(A-V):

(A-I)

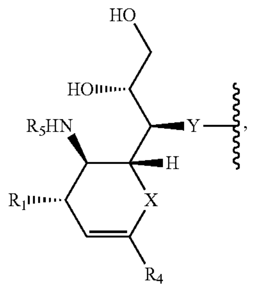, (A-II)

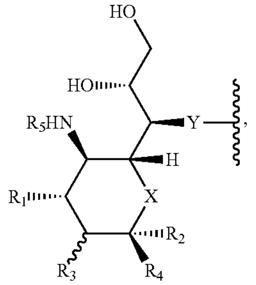, (A-III)

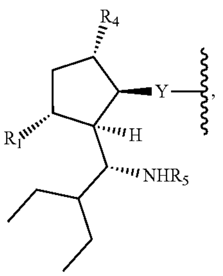,

-continued (A-IV)

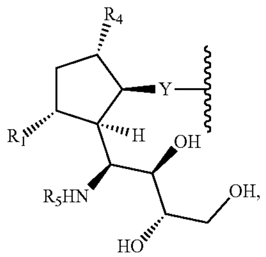, (A-V)

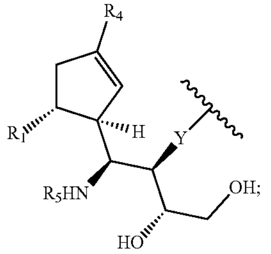;

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

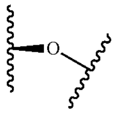 (—O—), 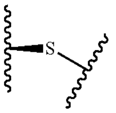 (—S—),

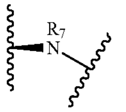 (—$NR_7$—),

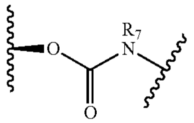 (—O(C═O)$NR_7$—),

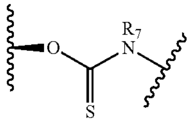 (—O(C═S)$NR_7$—),

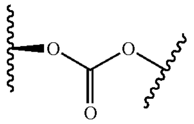 (—O(C═O)O—),

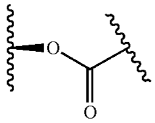 (—O(C═O)—),

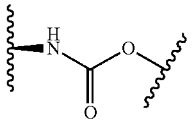 (—NH(C═O)O—),

-continued
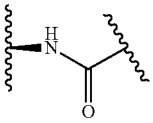
$(-NH(C{=}O)-)$,
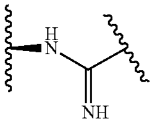
$(-NH(C{=}NH)-)$,
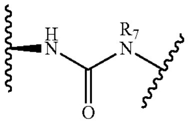
$(-NH(C{=}O)NR_7-)$,
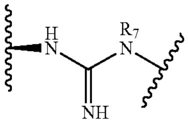
$(-NH(C{=}NH)NR_7-)$,
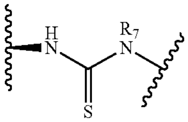
$(-NH(C{=}S)NR_7-)$,
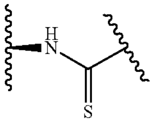
$(-NH(C{=}S)-)$,
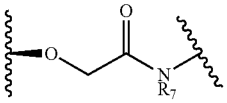
$(-OCH_2(C{=}O)NR_7-)$,
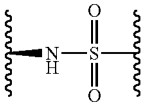
$(-NH(SO_2)-)$,
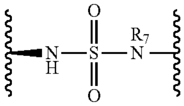
$(-NH(SO_2)NR_7)-)$,
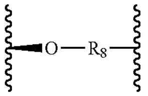
$(-OR_8-)$,
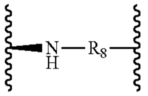
$(-NH_8-)$, and
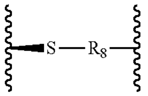
$(-SR_8-)$;
$R_6$ is selected from
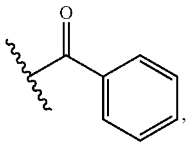,
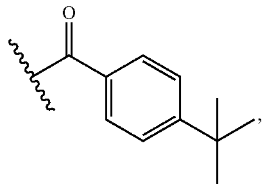,
-continued
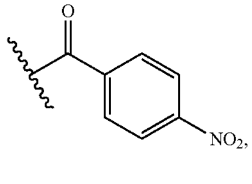
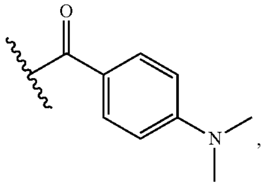,
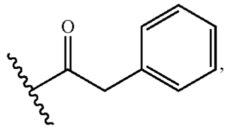,
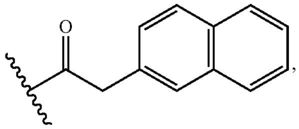,
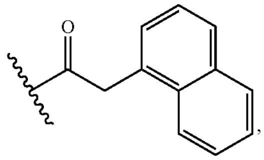,
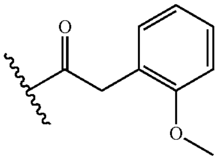,
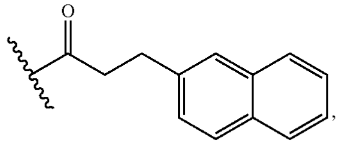,
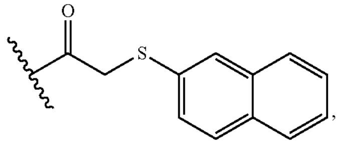,
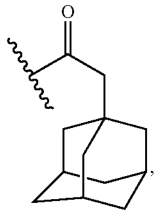,
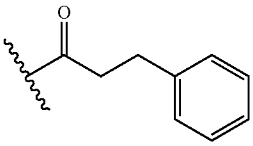,
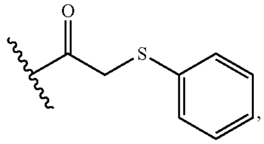,
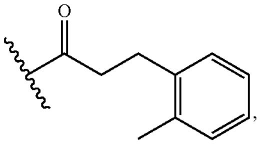,
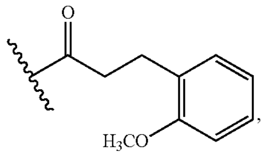,
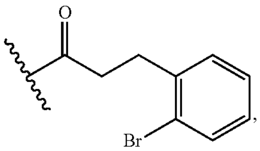,
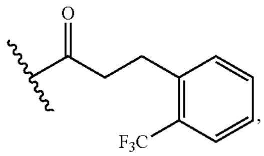,
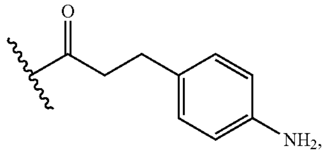

-continued

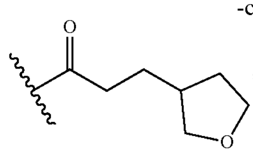
,
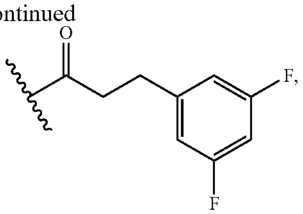

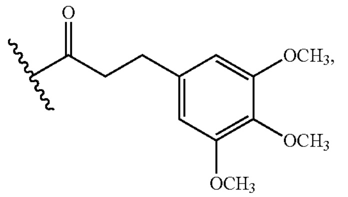

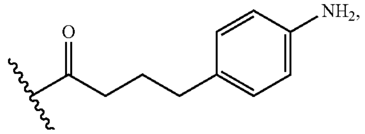

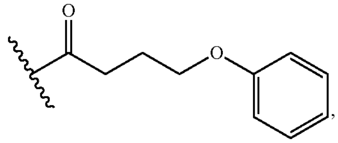
,
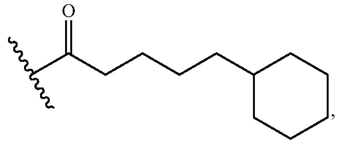
,
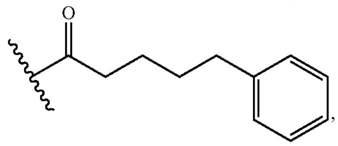
,
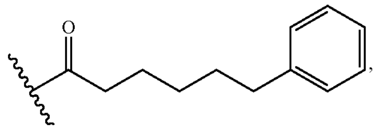
,
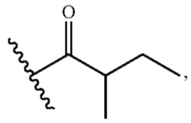
,
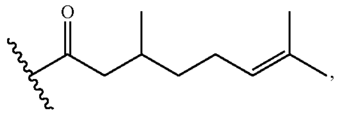
,
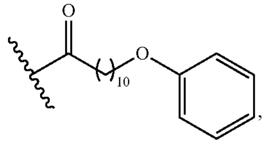
,
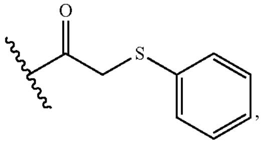
,
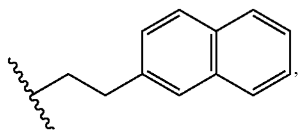
, and
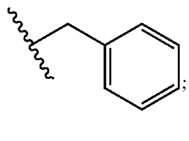
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl, or a pharmaceutically acceptable salt thereof.

In another aspect, the invention features a conjugate including (i) a first moiety, $A_1$; (ii) a second moiety, $A_2$; (iii) an albumin protein, an albumin protein-binding peptide, or an Fc-binding peptide; and (iv) a linker covalently attached to $A_1$ and $A_2$, and to the albumin protein, the albumin protein-binding peptide, or the Fc-binding peptide; wherein each $A_1$ and each $A_2$ is independently selected from any one of formulas (A-VI)-(A-IX):

(A-VI)

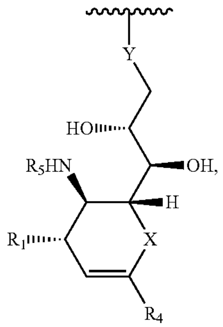

(A-VII)

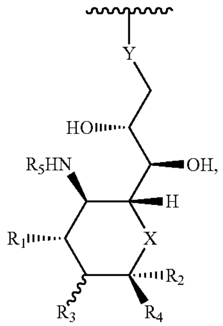

(A-VIII)

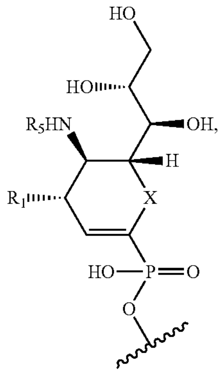

(A-IX)

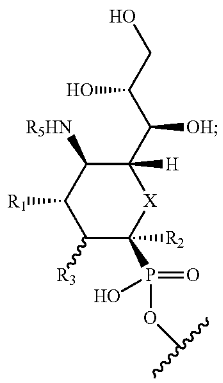

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br;

$R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from
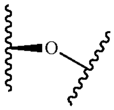 (—O—), 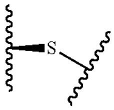 (—S—),
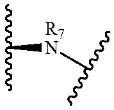 (—$NR_7$—),
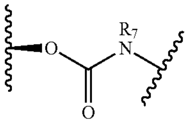 (—O(C=O)$NR_7$—),
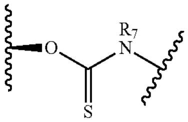 (—O(C=S)$NR_7$—),
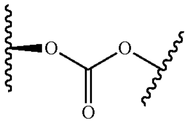 (—O(C=O)O—),
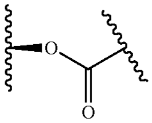 (—O(C=O)—),
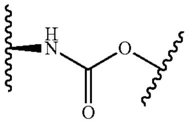 (—NH(C=O)O—),
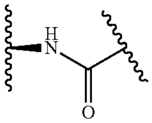 (—NH(C=O)—),
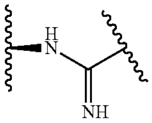 (—NH(C=NH)—),
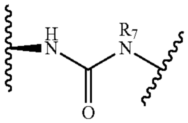 (—NH(C=O)$NR_7$—),
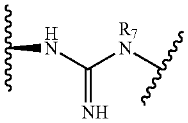 (—NH(C=NH)$NR_7$—),
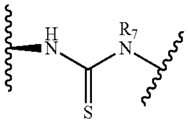 (—NH(C=S)$NR_7$—),
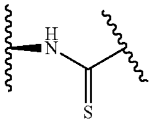 (—NH(C=S)—),
-continued
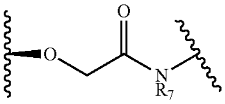 (—$OCH_2$(C=O)$NR_7$—),
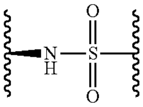 (—NH($SO_2$)—),
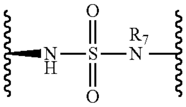 (—NH($SO_2$)$NR_7$—),
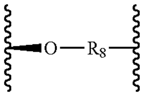 (—$OR_8$—), 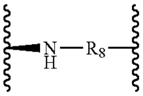 (—$NR_8$—), and
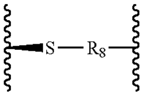 (—$SR_8$—);
$R_6$ is selected from
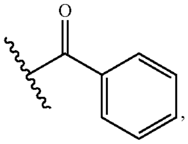, 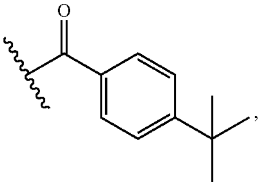,
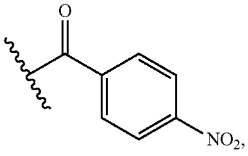 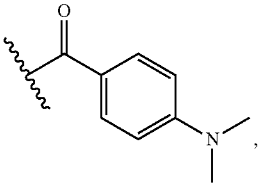,
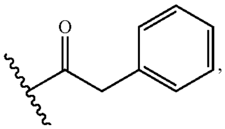,
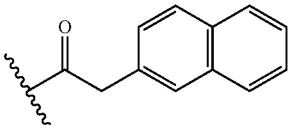,
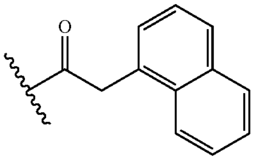, 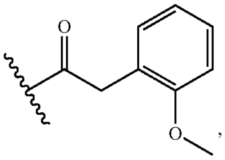,
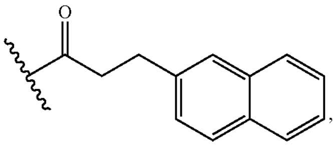, -continued
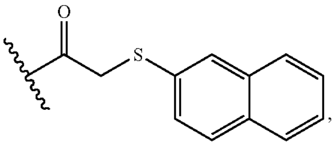,
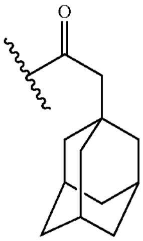,
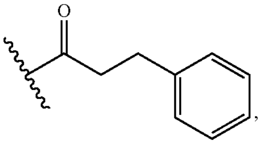,
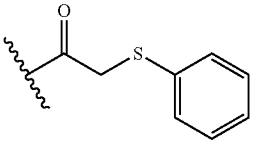,
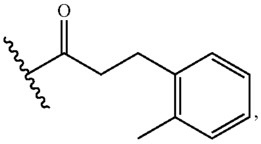,
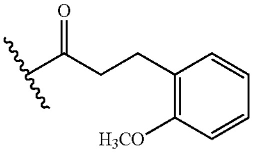,
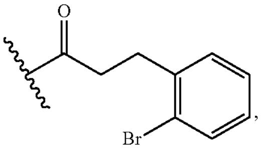,
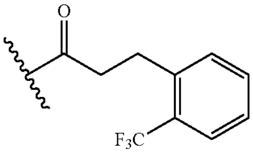,
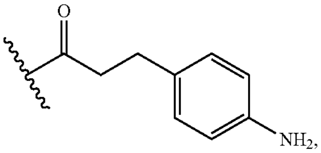
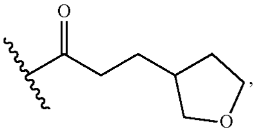,
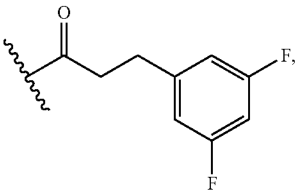
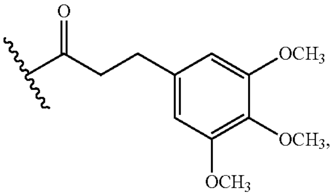
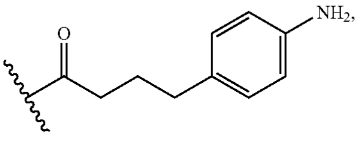
-continued
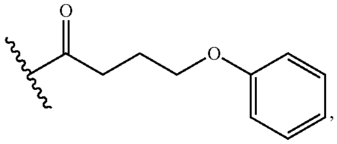,
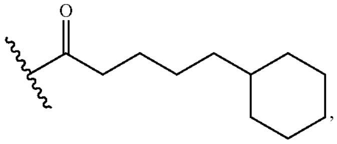,
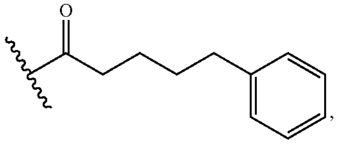,
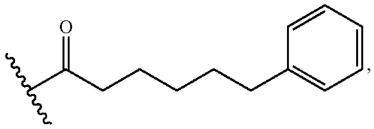,
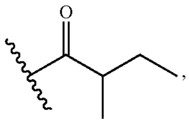,
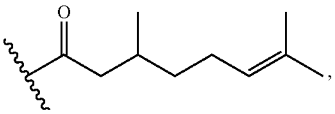,
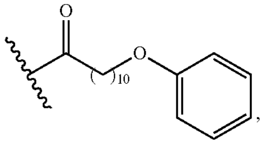,
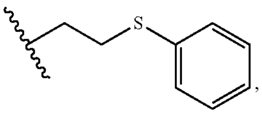,
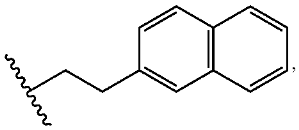, and
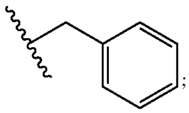;
$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl, or a pharmaceutically acceptable salt thereof.
In another aspect, the invention features a conjugate described by formula (D-1):
(D-I)
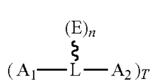

wherein each $A_1$ and each $A_2$ is independently selected from any one of formulas (A-I)-(A-XII):
(A-I)
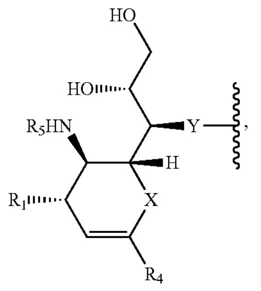
(A-II)
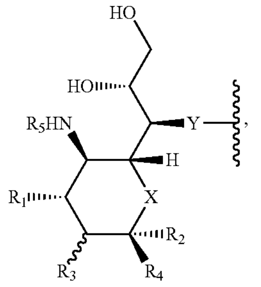
(A-III)
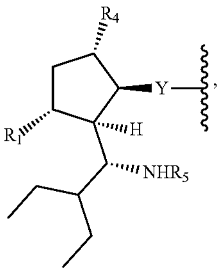
(A-IV)
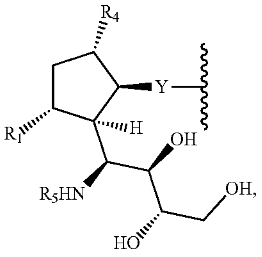
(A-V)
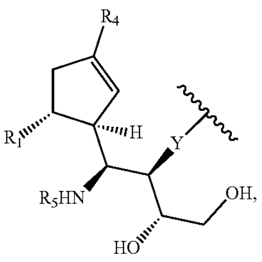
-continued
(A-VI)
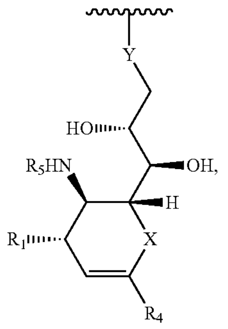
(A-VII)
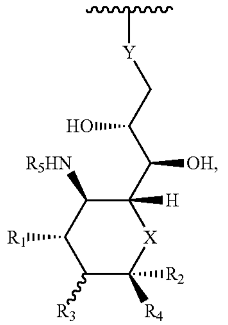
(A-VIII)
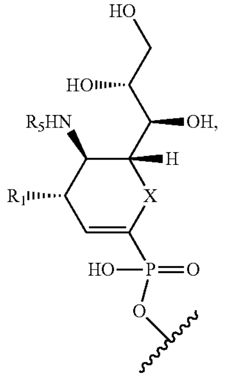
(A-IX)
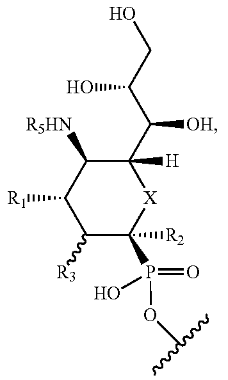

-continued (A-X)

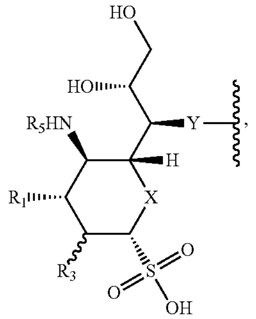

(A-XI)

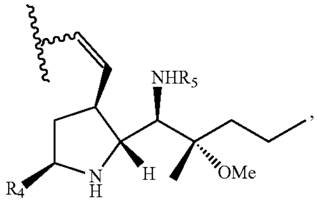

(A-XII)

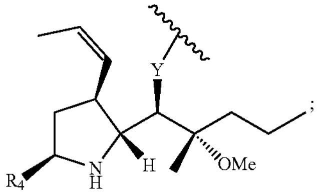

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; Rs is selected from —$COCH_3$, —$COCF_3$, —$SO_2CH_3$; X is selected from —O— and —S—; Y is selected from

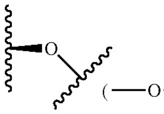

(—O—),

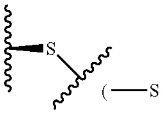

(—S—),

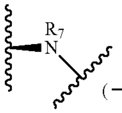

(—$NR_7$—),

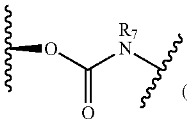

(—O(C=O)$NR_7$—),

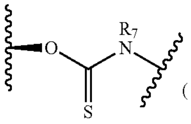

(—O(C=S)$NR_7$—),

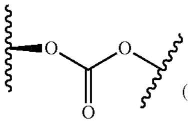

(—O(C=O)O—),

-continued

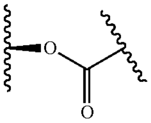

(—O(C=O)—),

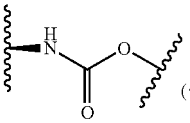

(—NH(C=O)O—),

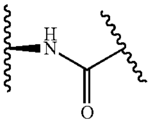

(—NH(C=O)—),

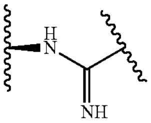

(—NH(C=NH)—),

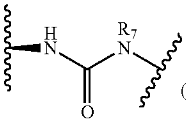

(—NH(C=O)$NR_7$—),

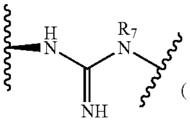

(—NH(C=NH)$NR_7$—),

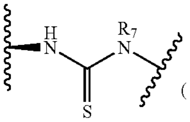

(—NH(C=S)$NR_7$—),

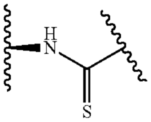

(—NH(C=S)—),

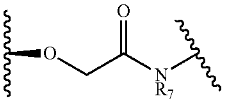

(—$OCH_2$(C=O)$NR_7$—),

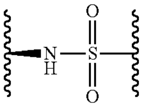

(—NH($SO_2$)—),

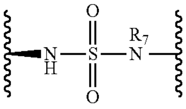

(—NH($SO_2$)$NR_7$—),

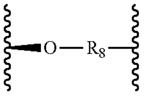

(—$OR_8$—),

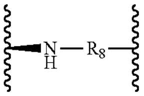

(—$NR_8$—), and

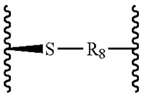

(—$SR_8$—);

$R_6$ is selected from
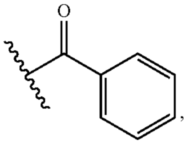,
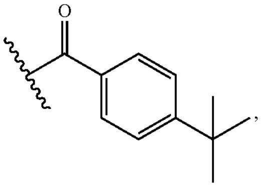,
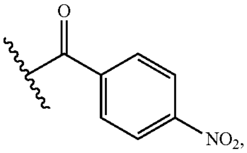,
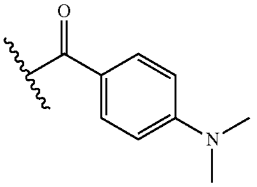,
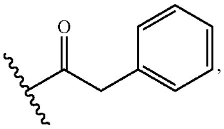,
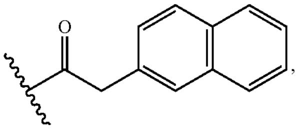,
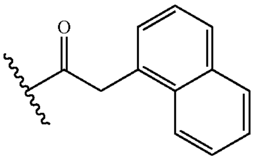,
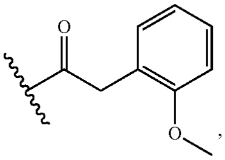,
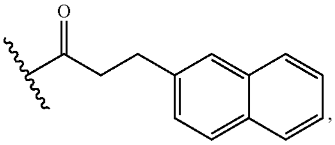,
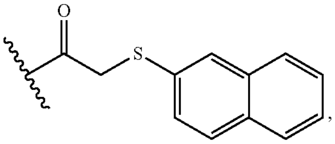,
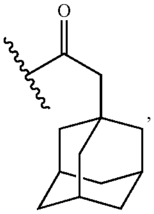,
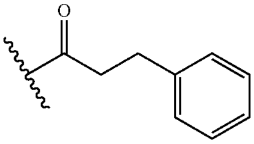,
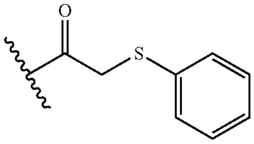,
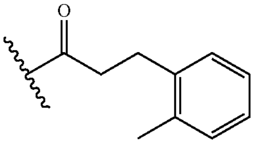,
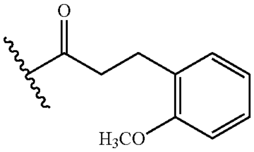,
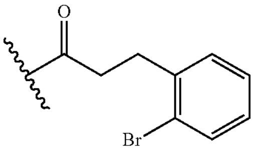,
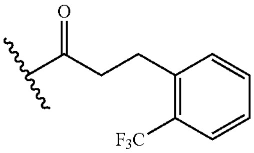,
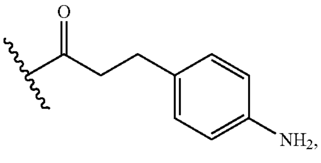,
-continued
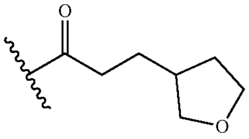,
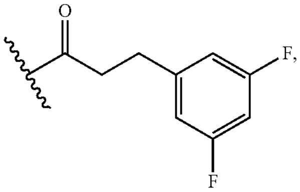,
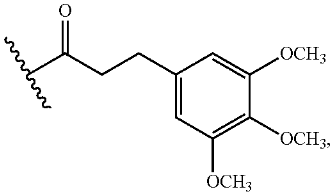,
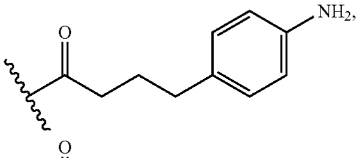,
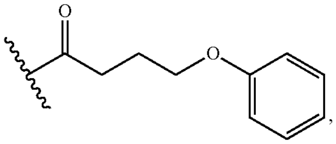,
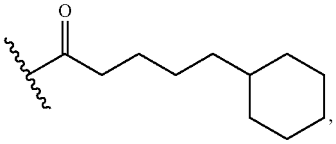,
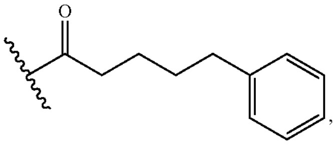,
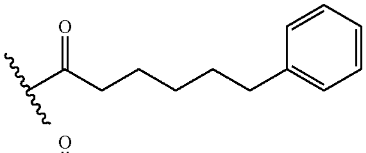,
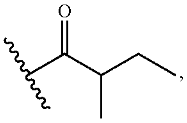,
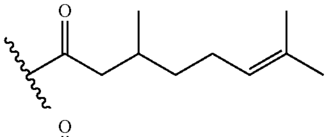,
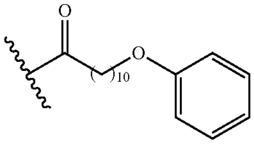,
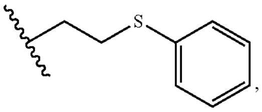,
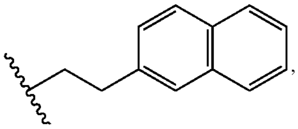, and -continued

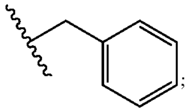

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68), an albumin protein (e.g., an albumin protein having the sequence of any one of SEQ ID NOs: 69-71), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E, $A_1$, and $A_2$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (D-I):

(D-I)

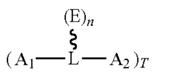

wherein each $A_1$ and each $A_2$ is independently selected from any one of formulas (A-I)-(A-V):

(A-I)

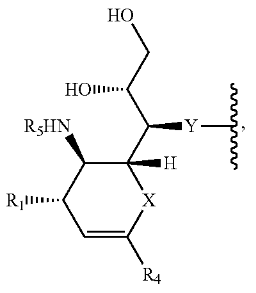

(A-II)

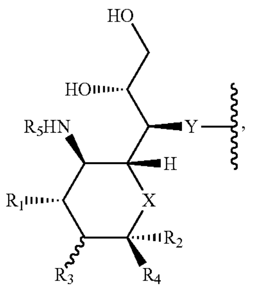

-continued (A-III)

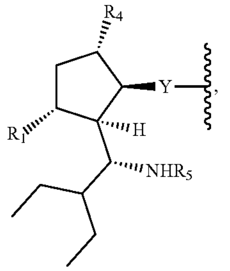

(A-IV)

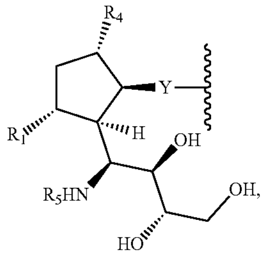

(A-V)

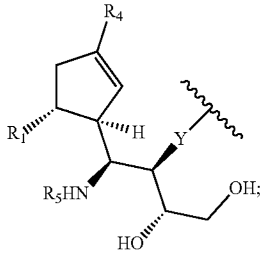

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; Rs is selected from —$COCH_3$, —$COCF_3$, —$SO_2CH_3$; X is selected from —O— and —S—; Y is selected from

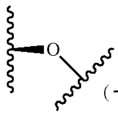 (—O—),

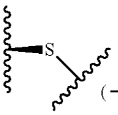 (—S—),

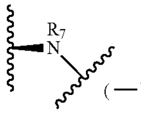 (—$NR_7$—),

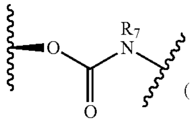 (—O(C=O)$NR_7$—),

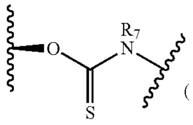 (—O(C=S)$NR_7$—),

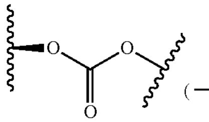 (—O(C=O)O—),

-continued
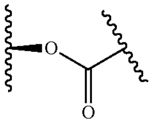
(—O(C═O)—),
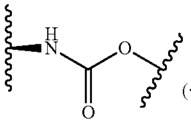
(—NH(C═O)O—),
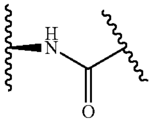
(—NH(C═O)—),
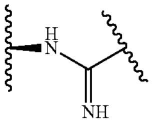
(—NH(C═NH)—),
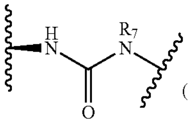
(—NH(C═O)$NR_7$—),
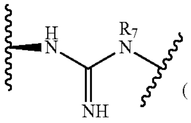
(—NH(C═NH)$NR_7$—),
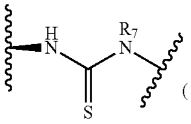
(—NH(C═S)$NR_7$—),
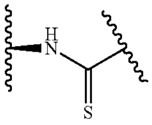
(—NH(C═S)—),
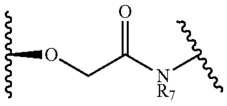
(—$OCH_2$(C═O)$NR_7$—),
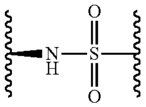
(—NH($SO_2$)—),
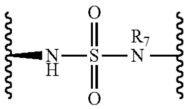
(—NH($SO_2$)$NR_7$—),
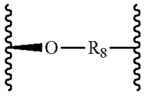
(—$OR_8$—),
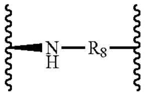
(—$NR_8$—), and
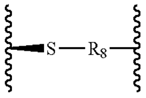
(—$SR_8$—);
$R_6$ is selected from
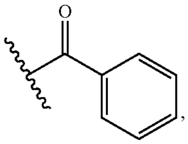
,
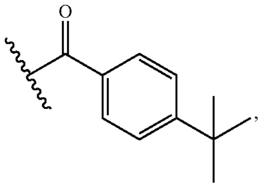
,
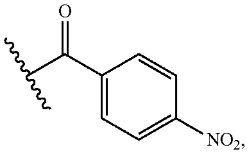
,
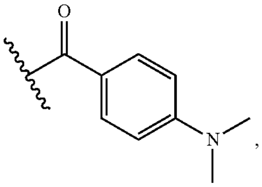
,
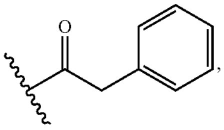
,
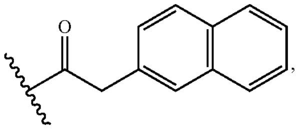
,
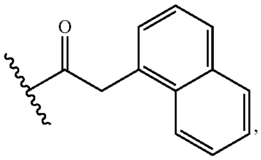
,
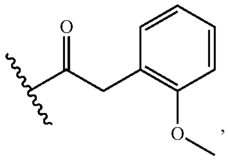
,
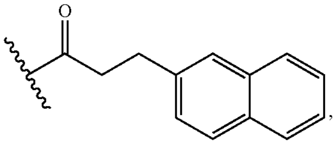
,
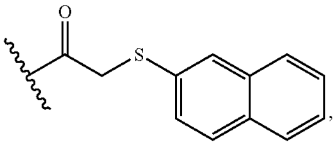
,
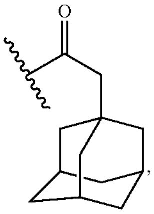
,
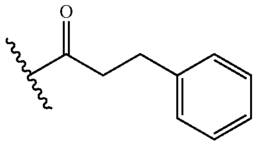
,
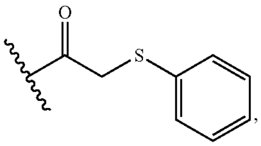
,
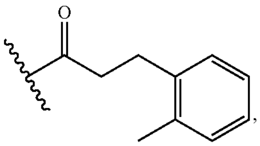
,
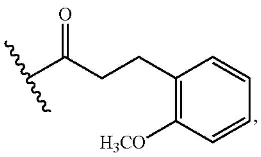
,
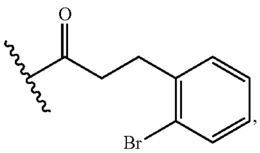
,
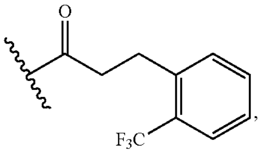
, -continued

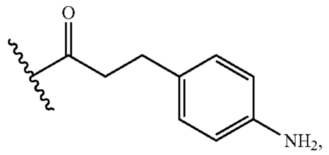

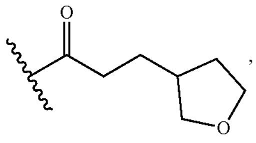
,
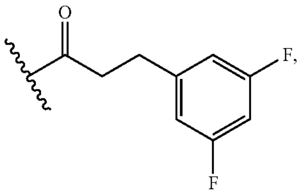

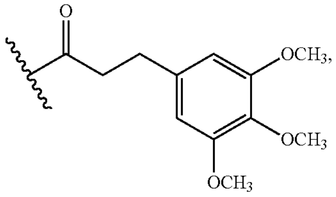

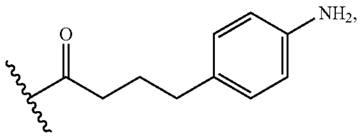

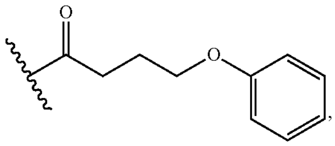
,
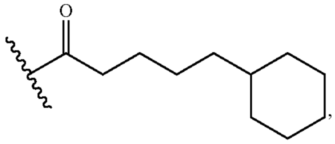
,
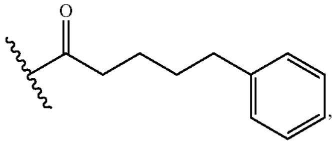
,
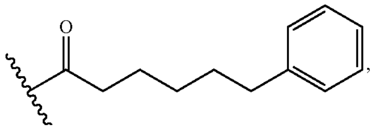
,
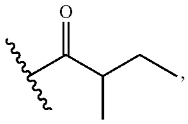
,
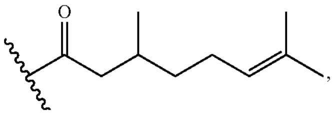
,
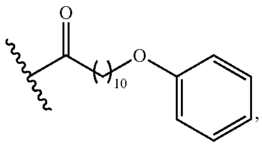
,
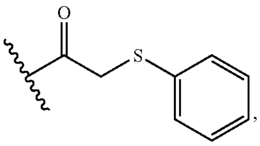
, -continued

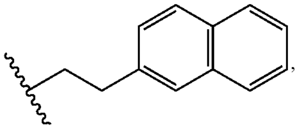
, and
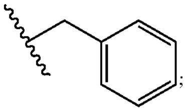
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68), an albumin protein (e.g., an albumin protein having the sequence of any one of SEQ ID NOs: 69-71), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E, $A_1$, and $A_2$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In another aspect, the invention features a conjugate described by formula (D-I):

(D-I)

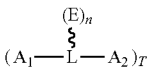

wherein each $A_1$ and each $A_2$ is independently selected from any one of formulas (A-VI)-(A-IX):

(A-VI)

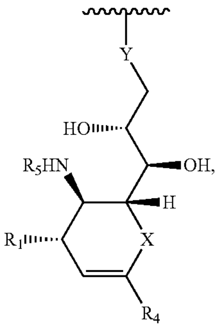

(A-VII)

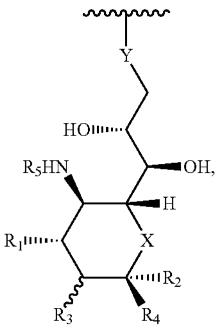

-continued (A-VIII)

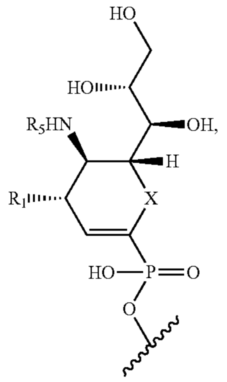

(A-IX)

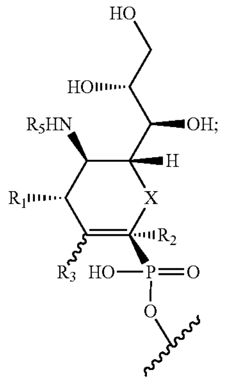

wherein $R_1$ is selected from —OH, —$NH_2$, —NHC(=NH)$NH_2$, and —NHC(=NH)NH$R_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

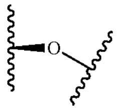 (—O—), 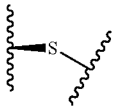 (—S—),

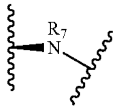 (—$NR_7$—),

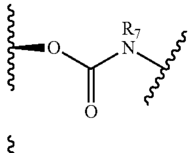 (—O(C=O)$NR_7$—),

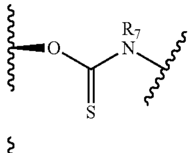 (—O(C=S)$NR_7$—),

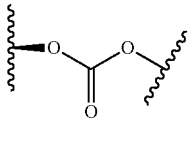 (—O(C=O)O—),

-continued

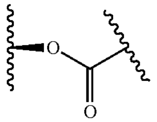 (—O(C=O)—),

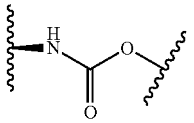 (—NH(C=O)O—),

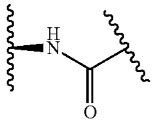 (—NH(C=O)—),

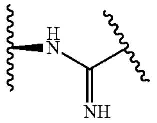 (—NH(C=NH)—),

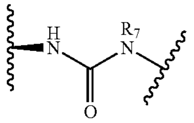 (—NH(C=O)$NR_7$—),

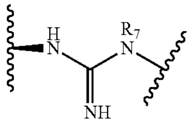 (—NH(C=NH)$NR_7$—),

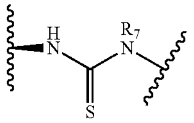 (—NH(C=S)$NR_7$—),

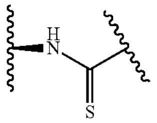 (—NH(C=S)—),

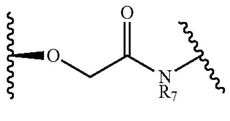 (—$OCH_2$(C=O)$NR_7$—),

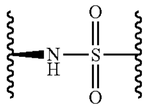 (—NH($SO_2$)—),

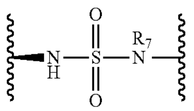 (—NH($SO_2$)$NR_7$—),

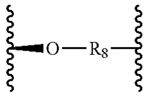 (—$OR_8$—), 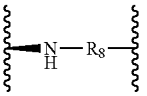 (—$NR_8$—), and

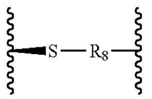 (—$SR_8$—);

$R_6$ is selected from
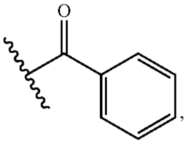,
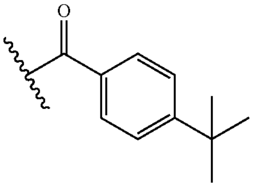,
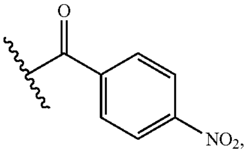,
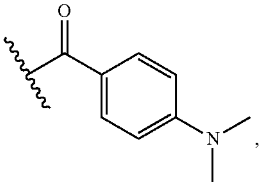,
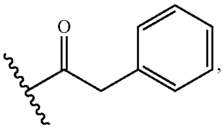,
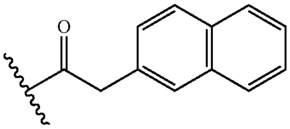,
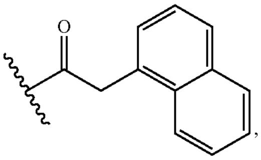,
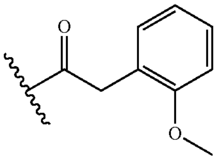,
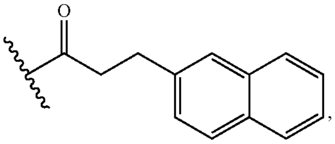,
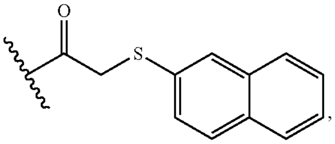,
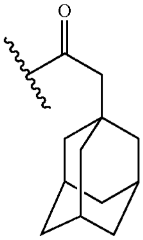,
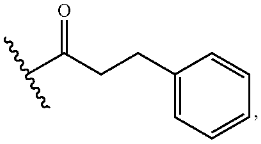,
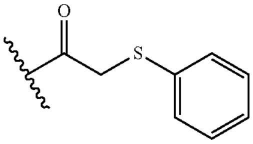,
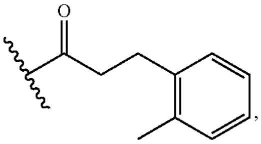,
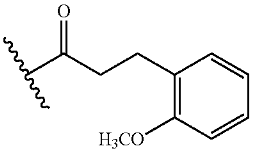,
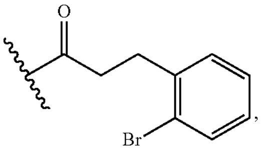,
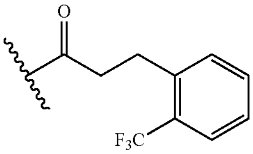,
-continued
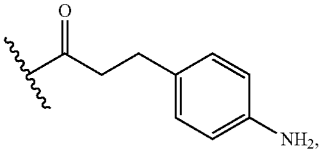,
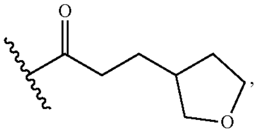,
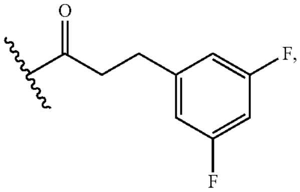,
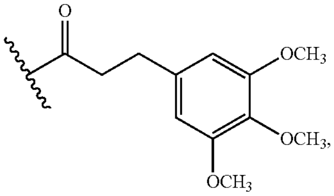,
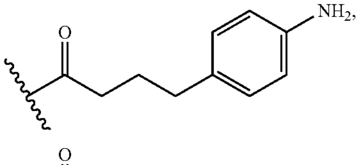,
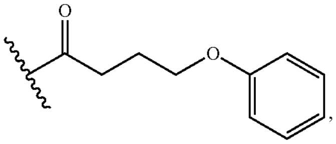,
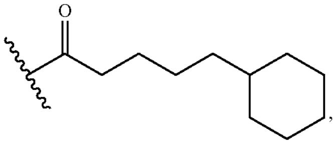,
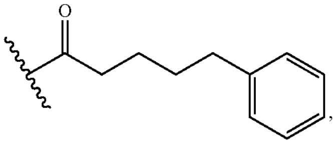,
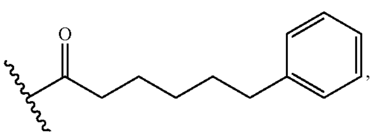,
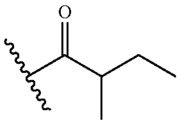,
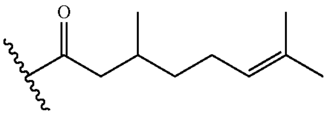,
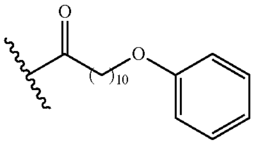,
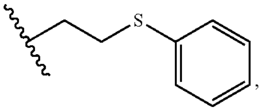, -continued

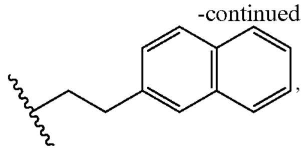

, and

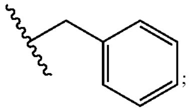

;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68), an albumin protein (e.g., an albumin protein having the sequence of any one of SEQ ID NOs: 69-71), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E, $A_1$, and $A_2$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein).

In some embodiments, the conjugate is described by formula (D-II):

(D-II)

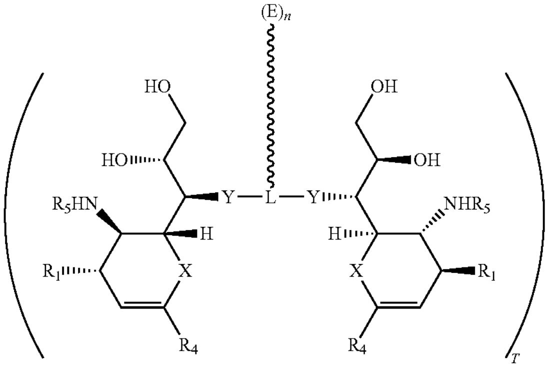

or a pharmaceutically acceptable salt thereof.

In some embodiments, the conjugate is described by formula (D-II-1):

(D-II-1)

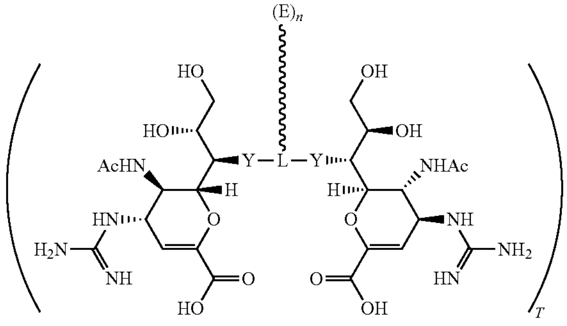

or a pharmaceutically acceptable salt thereof.

In some embodiments, the conjugate is described by formula (D-II-2):

(D-II-2)

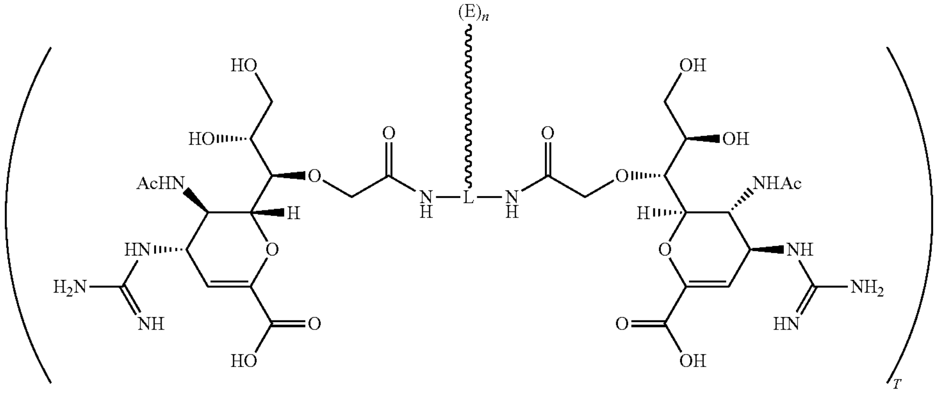

or a pharmaceutically acceptable salt thereof.

In some embodiments, the conjugate is described by formula (D-II-3):

(D-II-3)

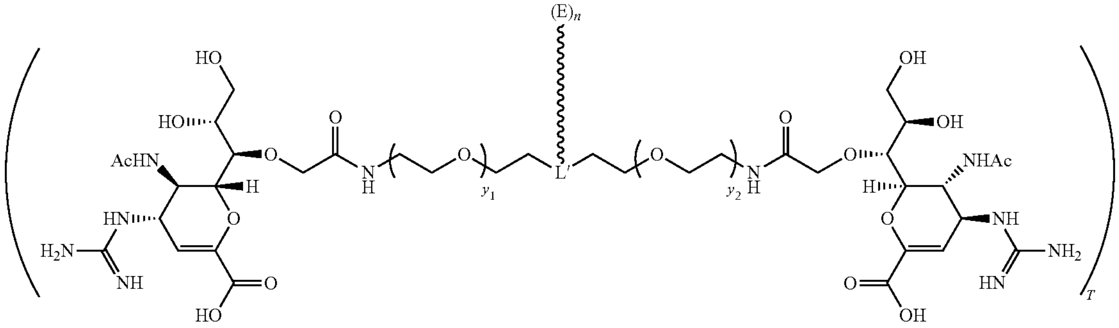

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate has the structure selected from

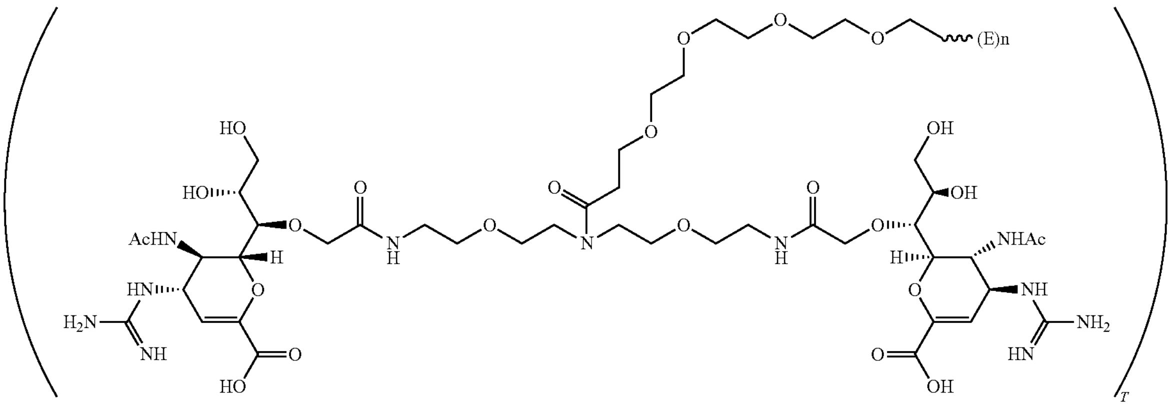

,

-continued
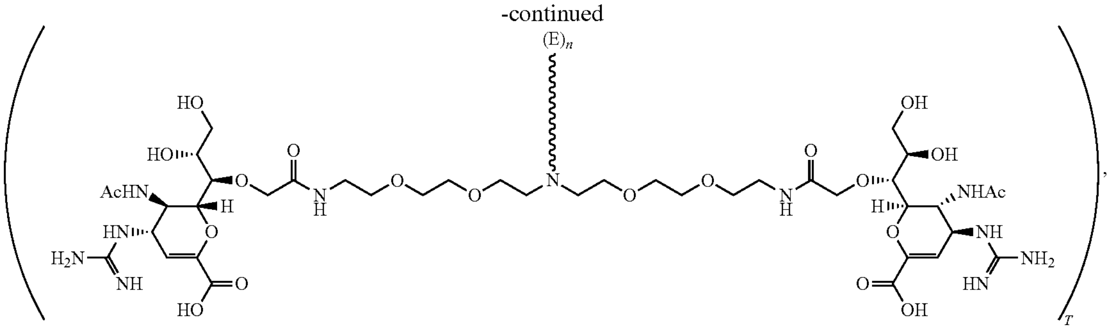
, or
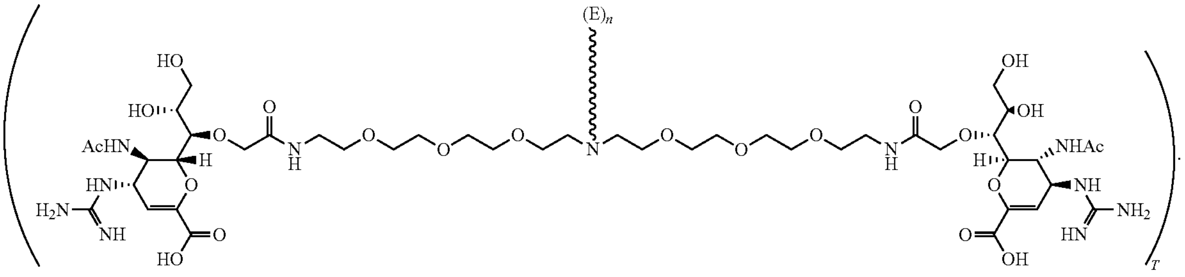
.
In some embodiments, the conjugate is described by formula (D-II-4):
(D-II-4)
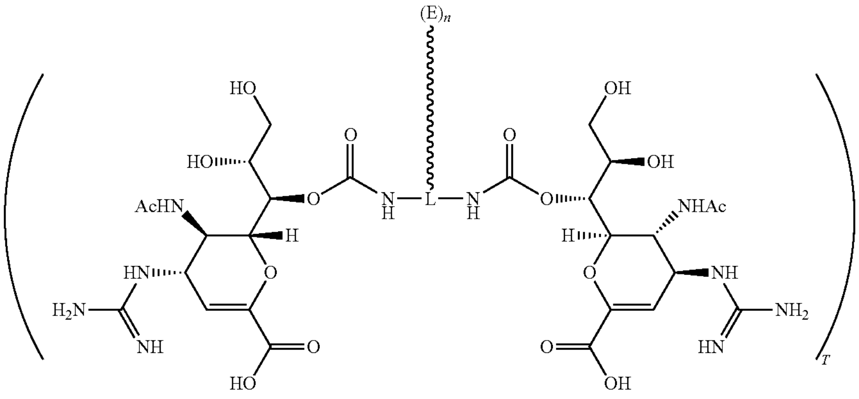
or a pharmaceutically acceptable salt thereof.
In some embodiments, the conjugate is described by formula (D-II-5):
(D-II-5)
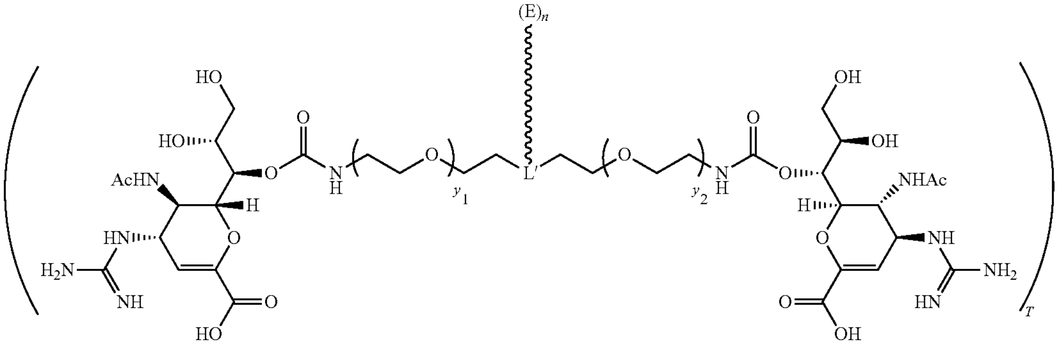

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate has the structure selected from

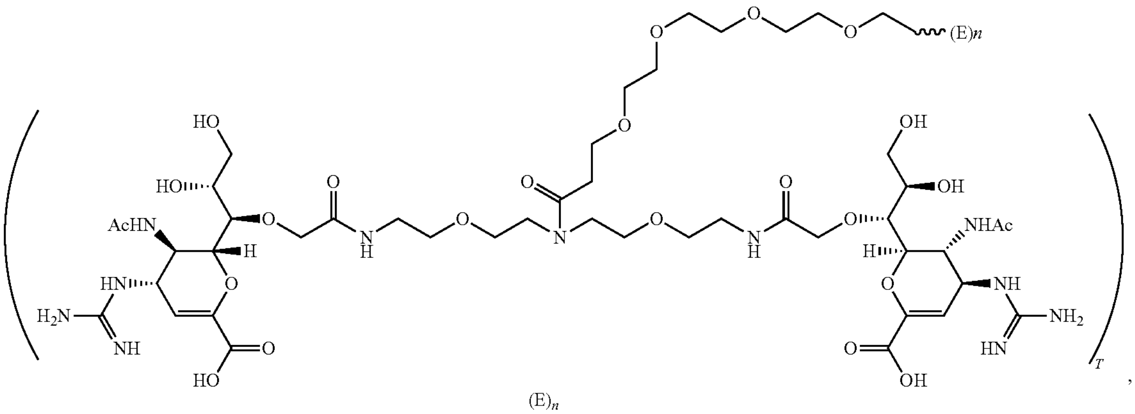

,

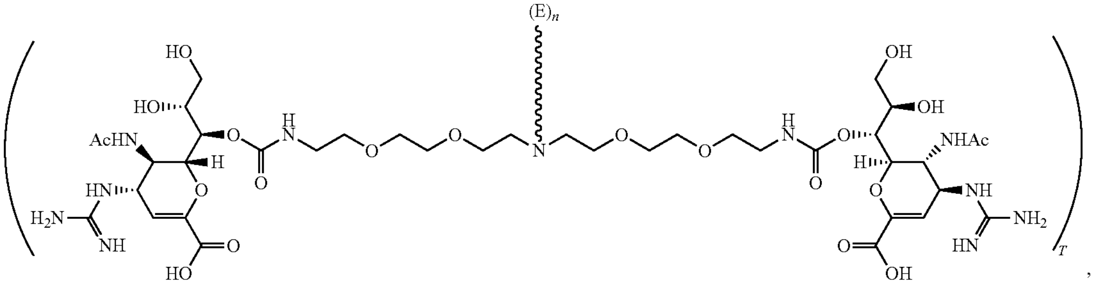

, or

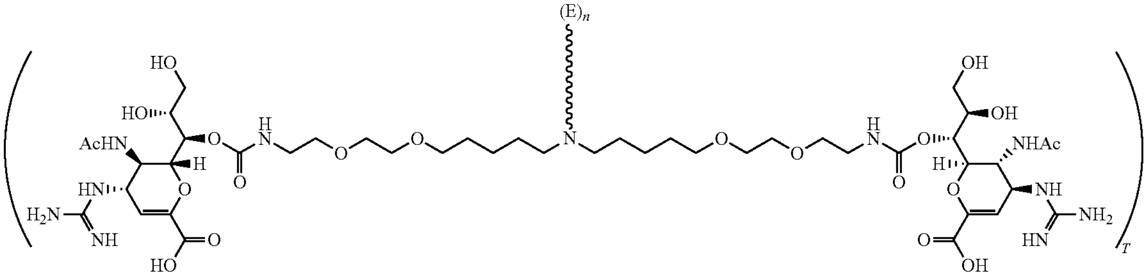

, or a pharmaceutically acceptable salt thereof.

In some embodiments, the conjugate has the structure selected from

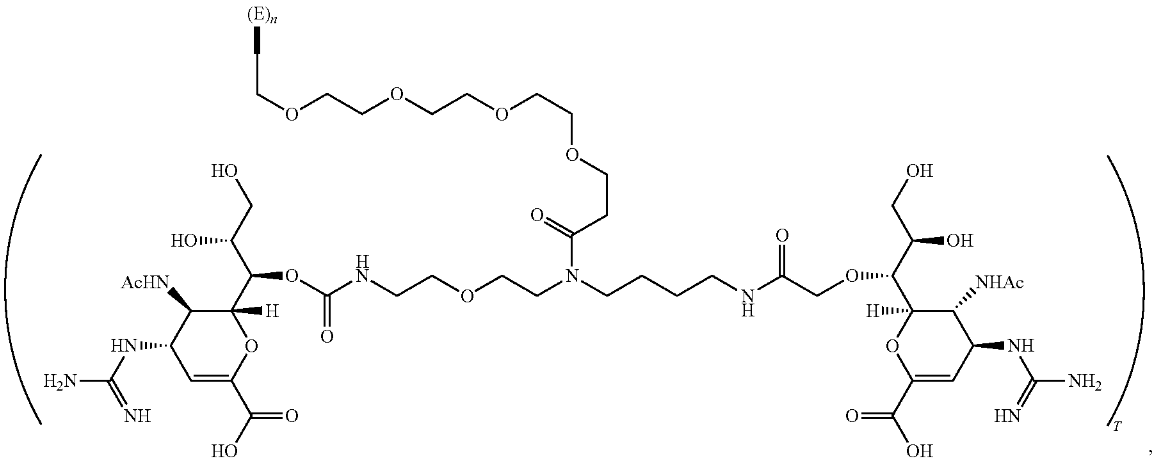
,
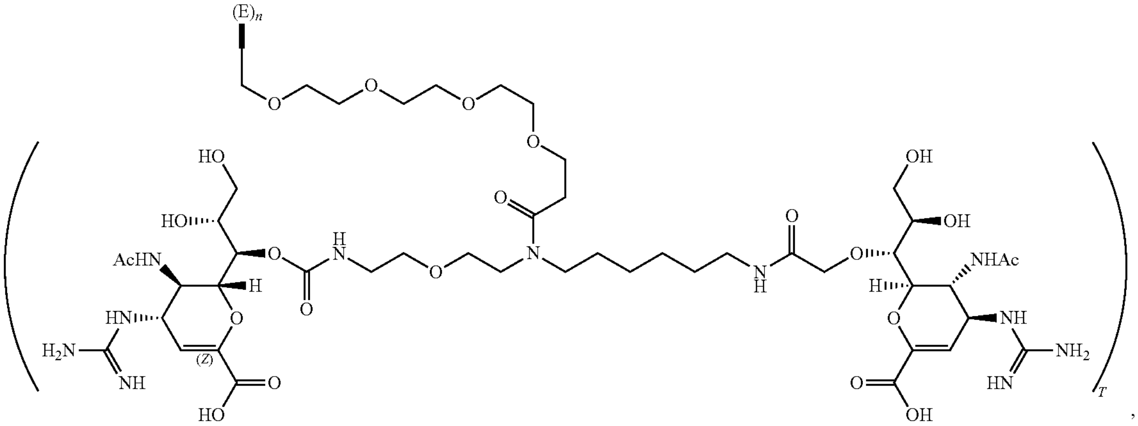
,
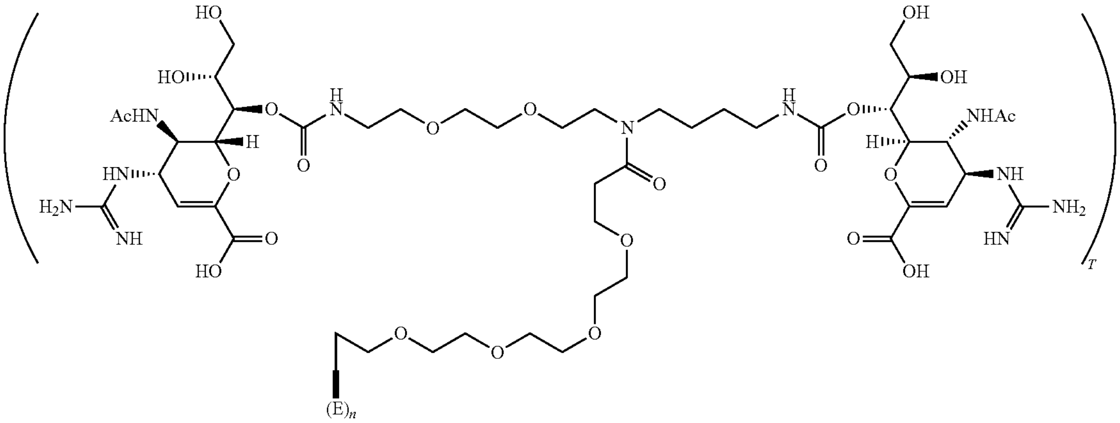
, or

-continued

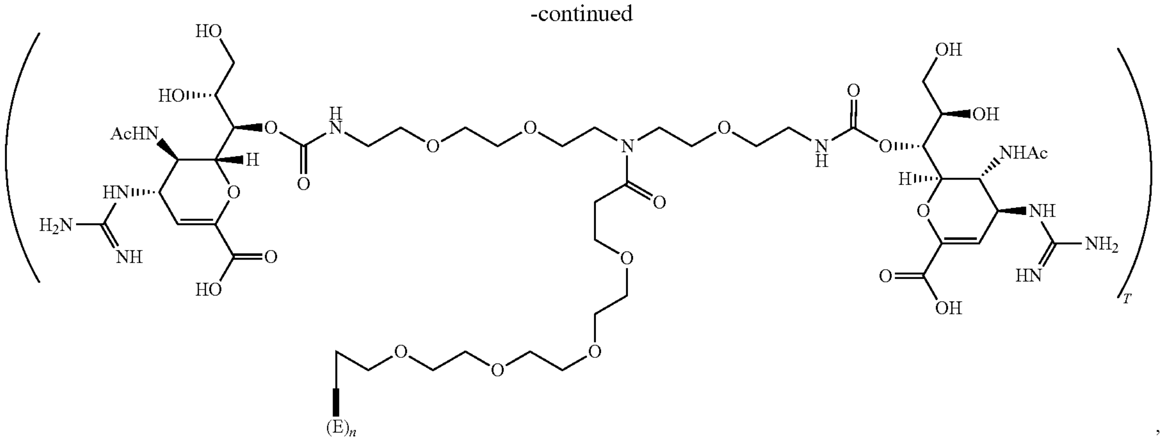

or a pharmaceutically acceptable salt thereof.

In some embodiments, the conjugate is described by formula (D-II-6):

(D-II-6)

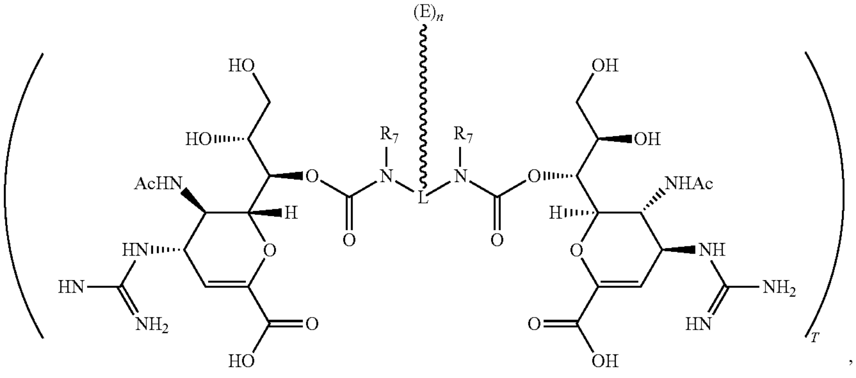

wherein $R_7$ is selected from H, C1-C20 alkyl, C3-C20 cycloalkyl, C3-C20 heterocycloalkyl; C5-C15 aryl, and C2-C15 heteroaryl; or a pharmaceutically acceptable salt thereof.

In some embodiments, the conjugate is described by formula (D-II-7):

(D-II-7)

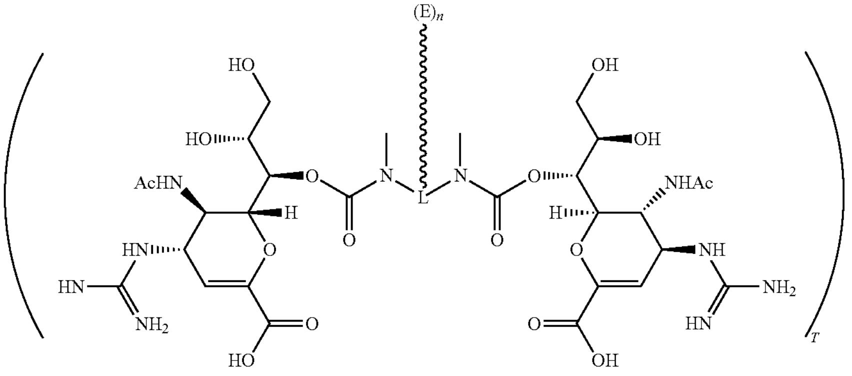

or a pharmaceutically acceptable salt thereof.

In some embodiments, the conjugate is described by formula (D-II-8):

(D-II-8)
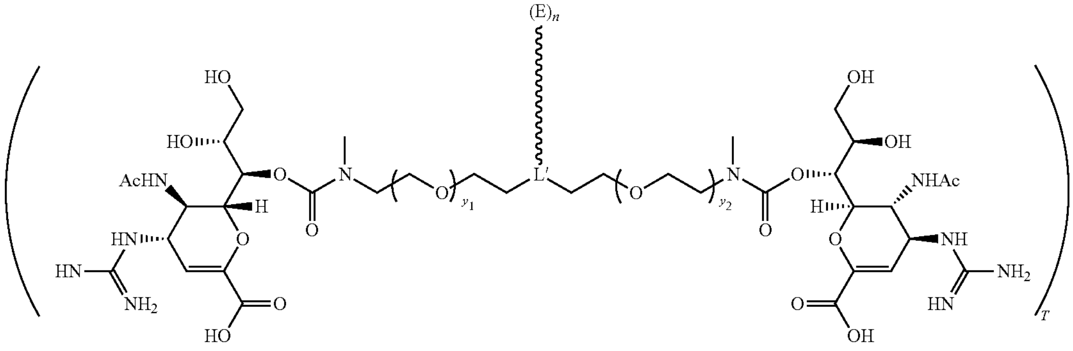
;
wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.
In some embodiments, the conjugate has the structure
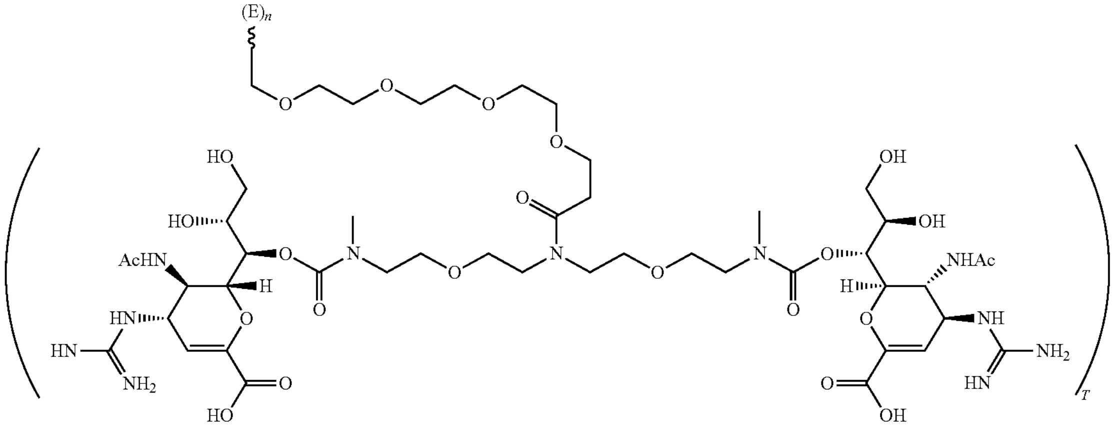
, or -continued
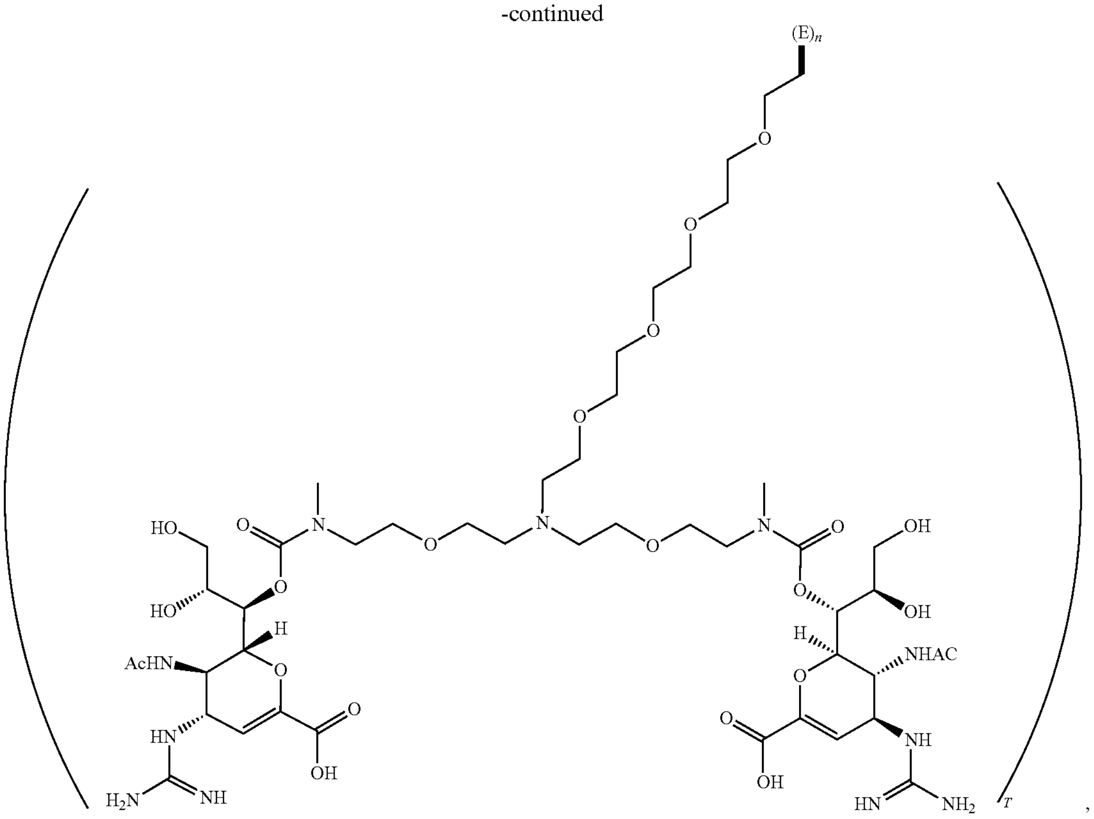
or a pharmaceutically acceptable salt thereof.
In some embodiments, the conjugate has the structure
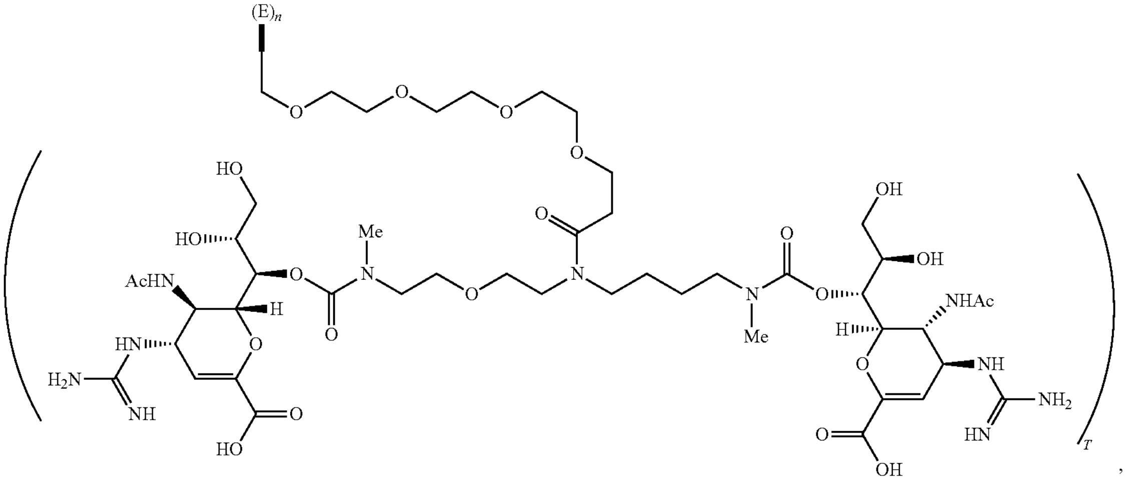
, -continued
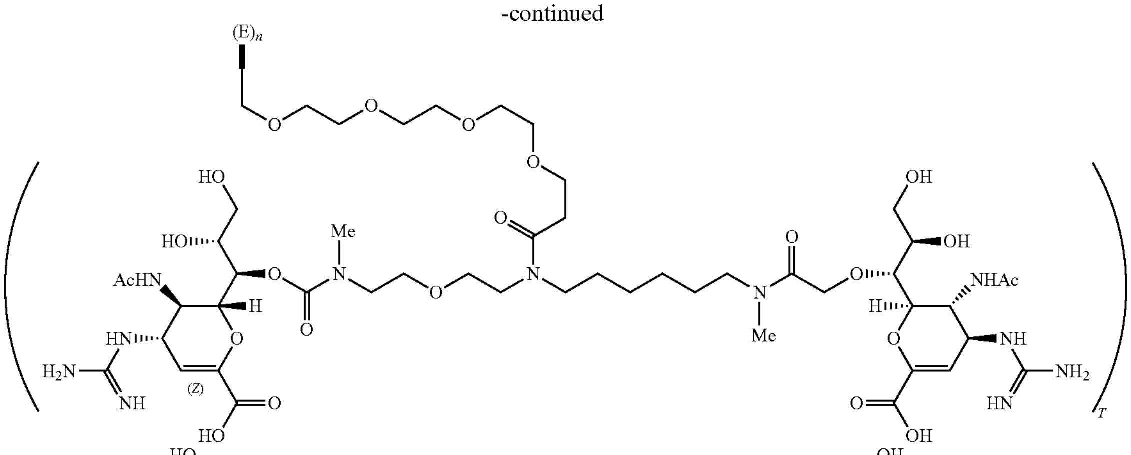
,
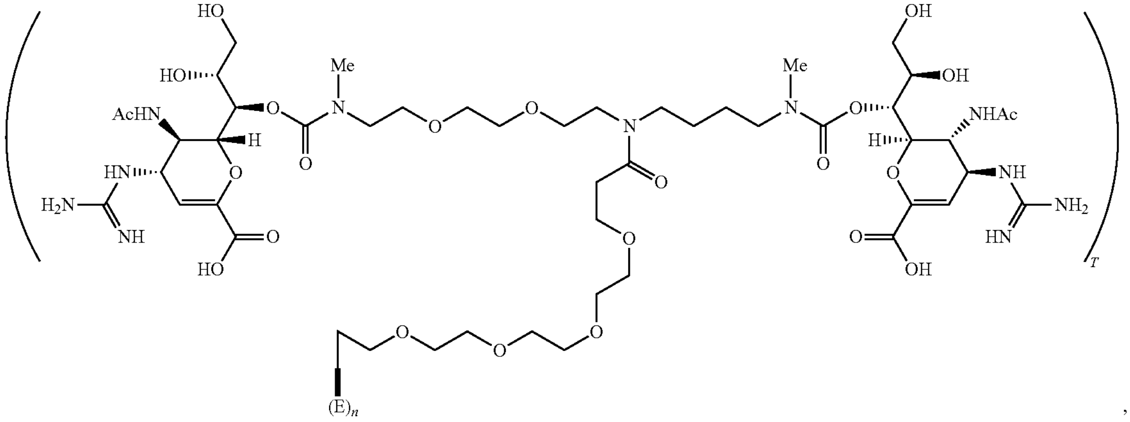
, or
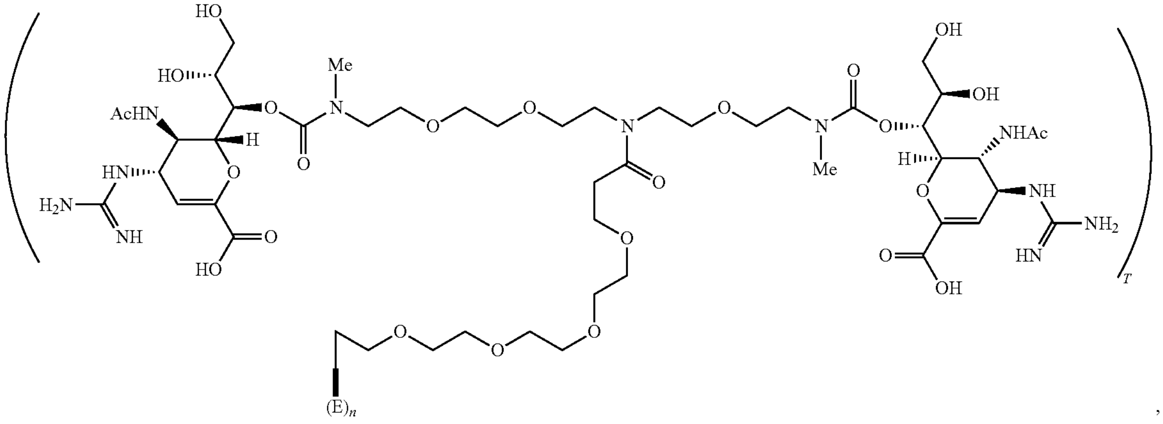
,
or a pharmaceutically acceptable salt thereof.
In some embodiments, the conjugate has the structure

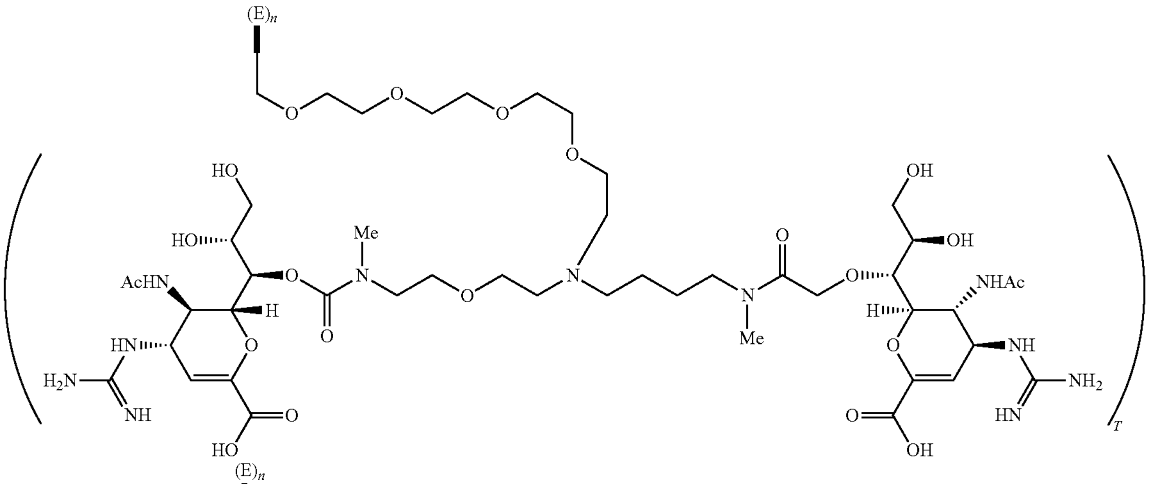
,
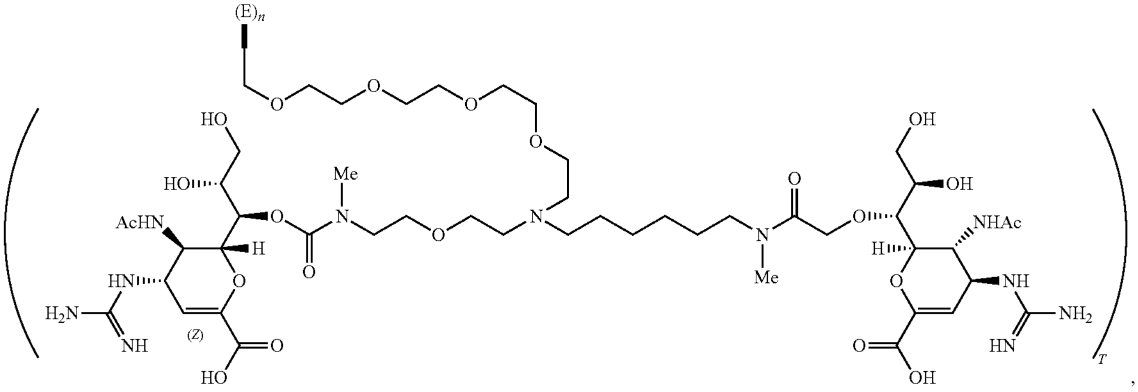
,
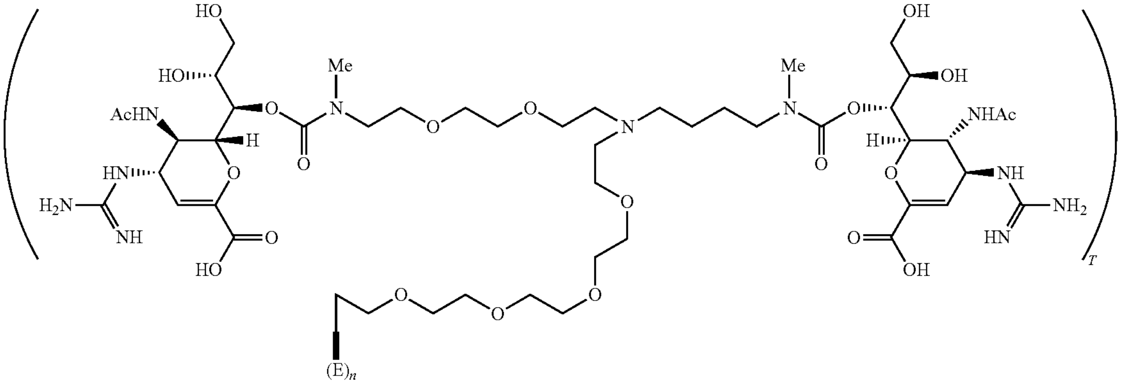
, or
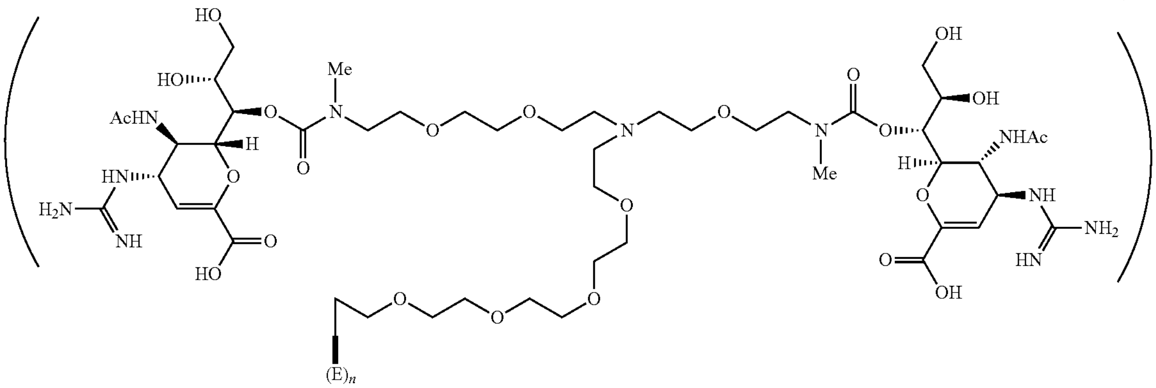
, or a pharmaceutically acceptable salt thereof.

In some embodiments, the conjugate is described by formula (D-II-9):

(D-II-9)

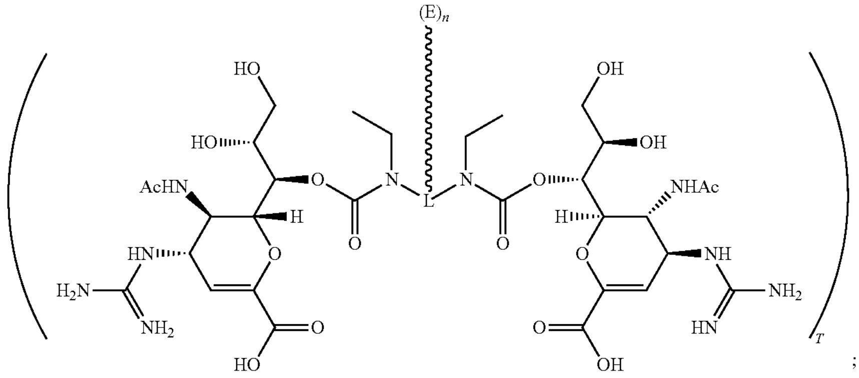

;

or a pharmaceutically acceptable salt thereof.

In some embodiments, the conjugate is described by formula (D-II-10):

(D-II-10)

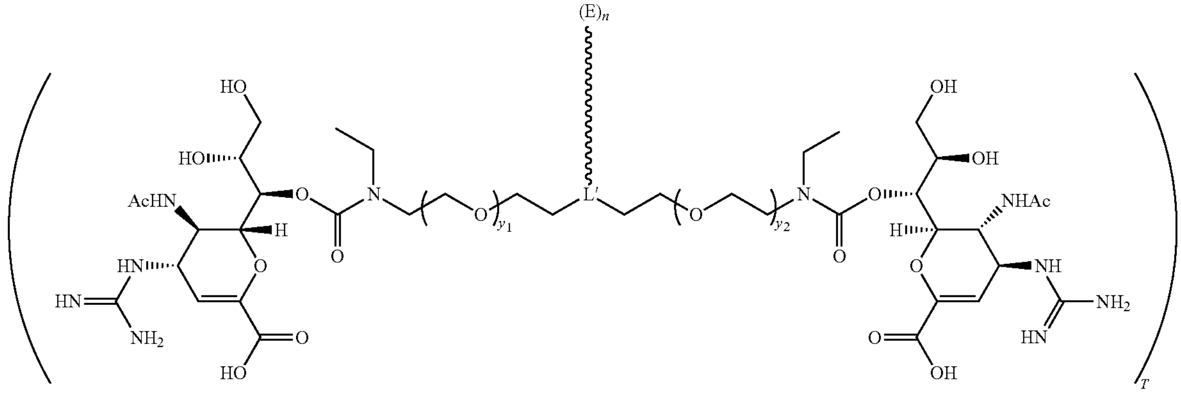

;

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate has the structure

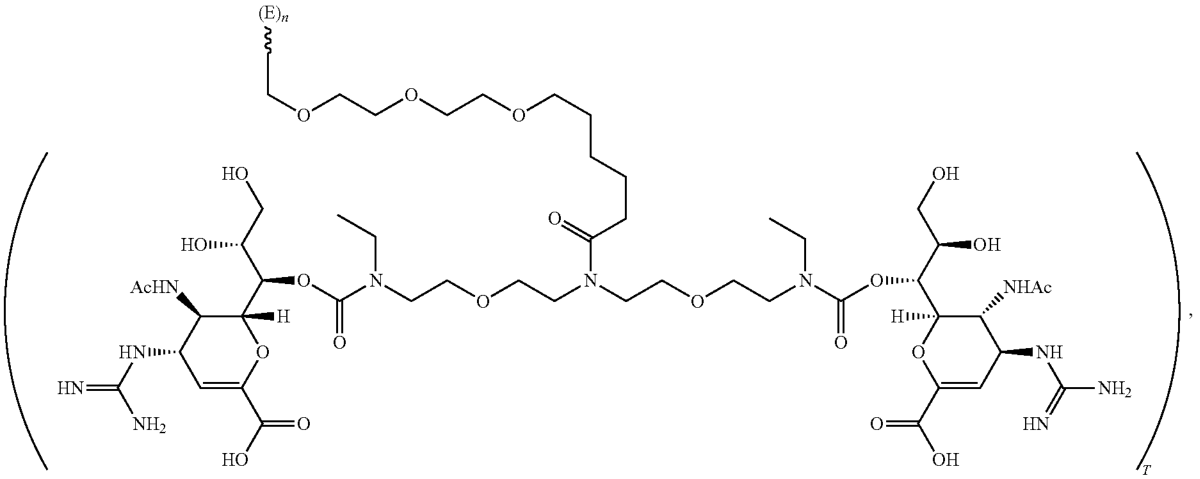, or a pharmaceutically acceptable salt thereof.

In some embodiments, the conjugate has the structure of

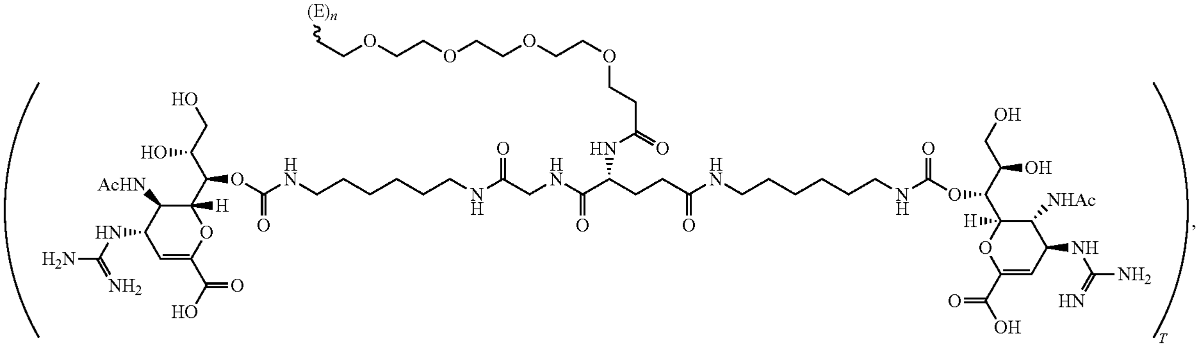, or a pharmaceutically acceptable salt thereof.

In some embodiments, the conjugate is described by formula (D-III):

(D-III)

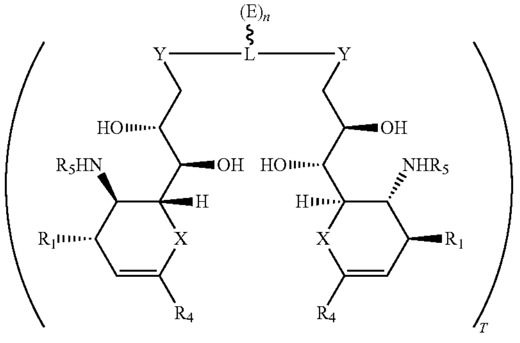

or a pharmaceutically acceptable salt thereof.

In some embodiments, the conjugate is described by formula (D-III-1):

(D-III-1)

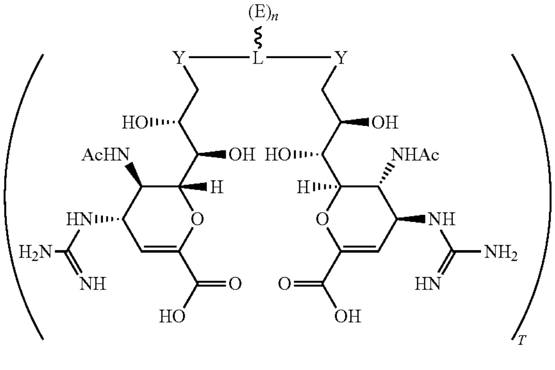

or a pharmaceutically acceptable salt thereof.

In some embodiments, the conjugate is described by formula (D-III-2):

(D-III-2)

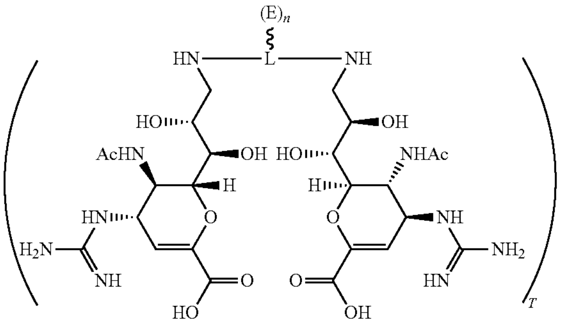

or a pharmaceutically acceptable salt thereof.

In some embodiments, the conjugate is described by formula (D-III-3):

(D-III-3)

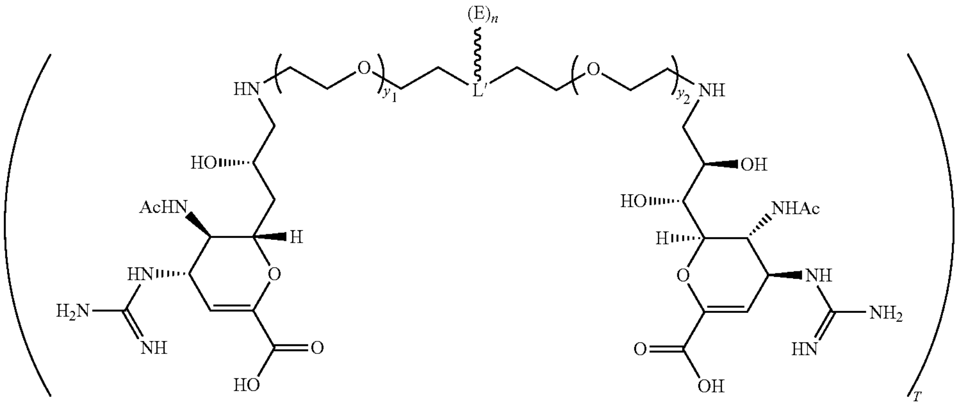

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-III-4):

(D-III-4)

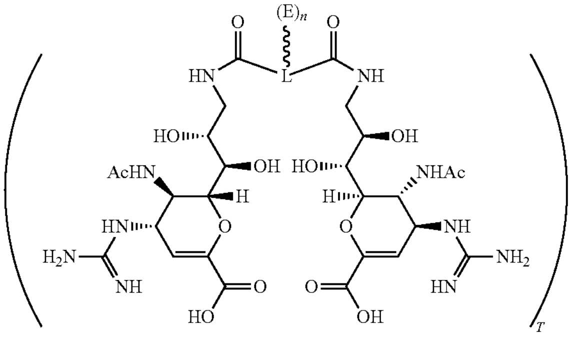

or a pharmaceutically acceptable salt thereof.

In some embodiments, the conjugate is described by formula (D-III-5):

(D-III-5)

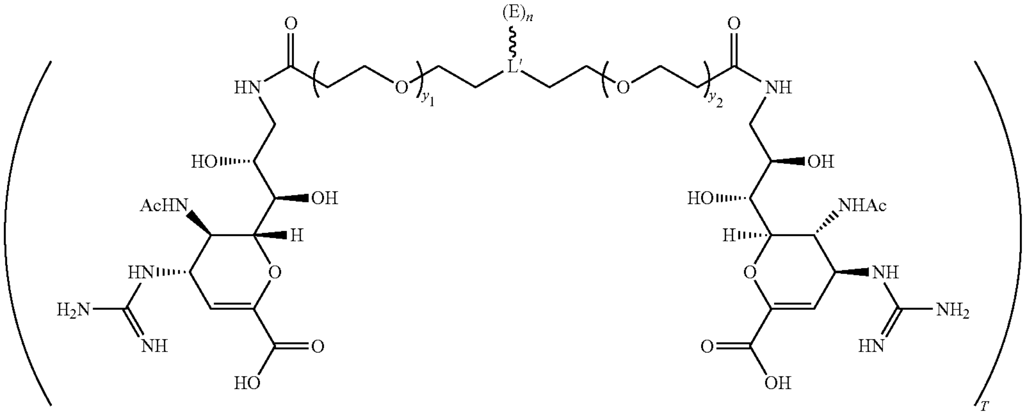

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-III-6):

(D-III-6)

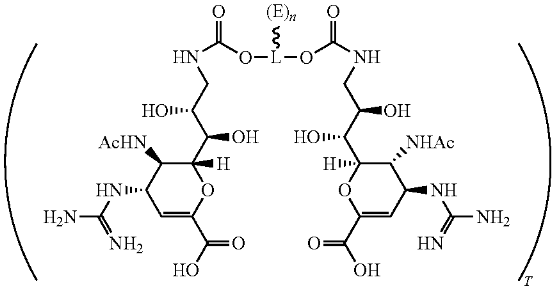

or a pharmaceutically acceptable salt thereof.

In some embodiments, the conjugate is described by formula (D-III-7):

(D-III-7)

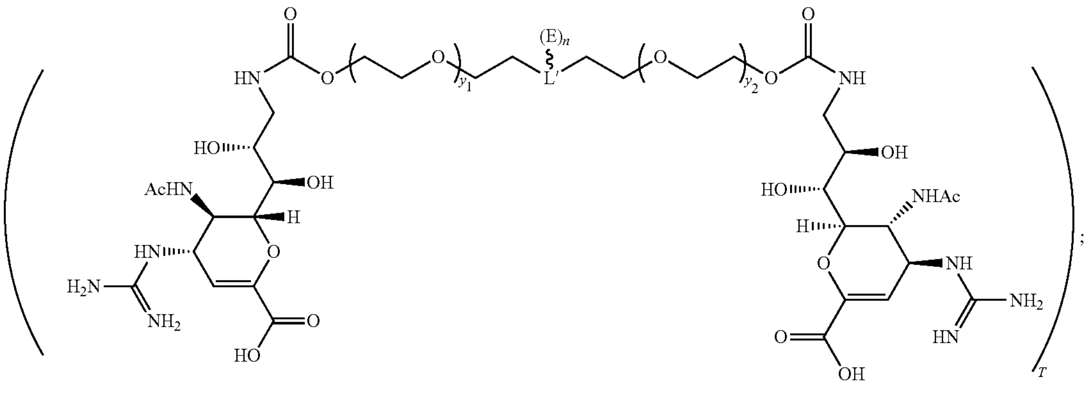

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-III-8):

(D-III-8)

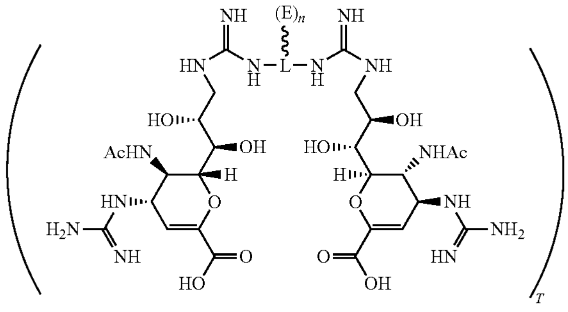

or a pharmaceutically acceptable salt thereof.

In some embodiments, the conjugate is described by formula (D-III-9):

(D-III-9)

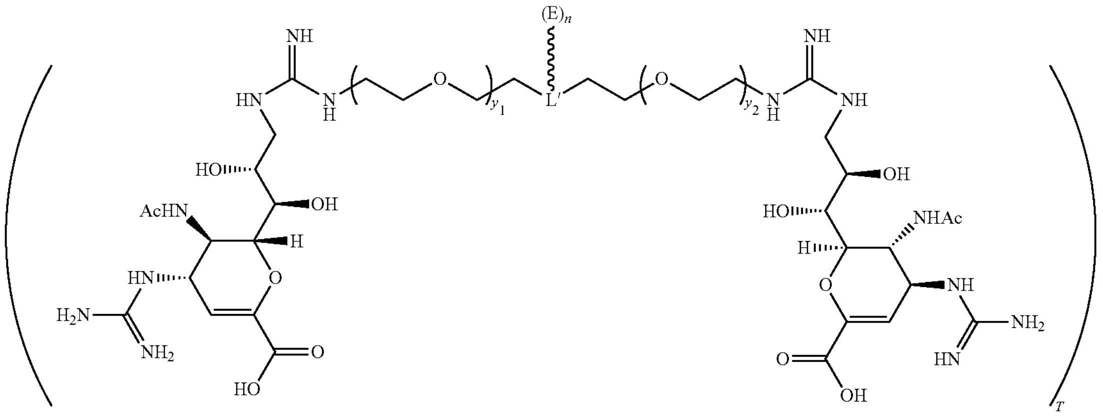

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-IV):

(D-IV)

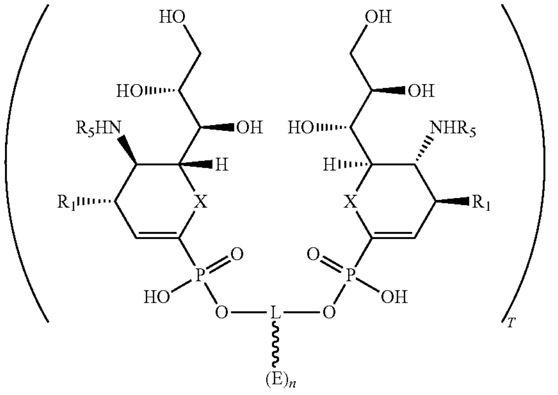

or a pharmaceutically acceptable salt thereof.

In some embodiments, the conjugate is described by formula (D-IV-1):

(D-IV-1)

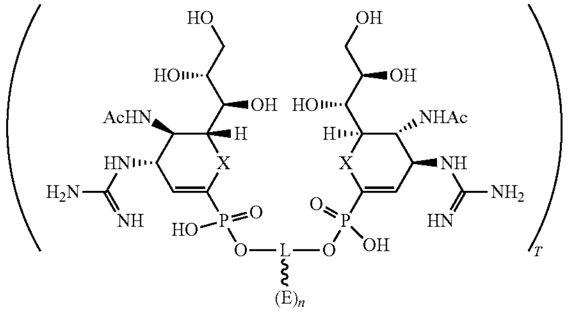

or a pharmaceutically acceptable salt thereof.

(D-IV-2)

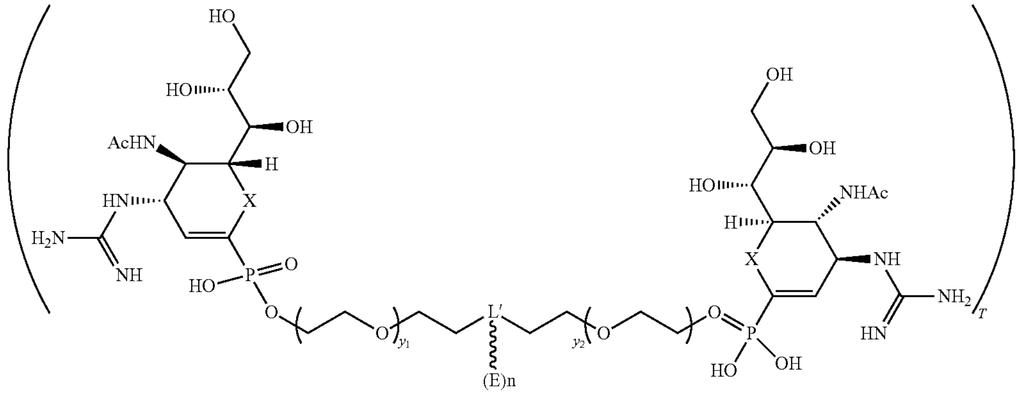

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, the conjugate is described by formula (D-V):

(D-V)

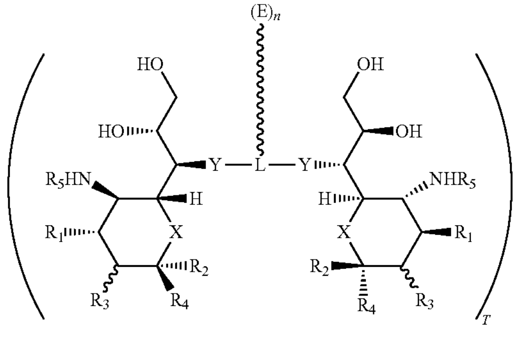

or a pharmaceutically acceptable salt thereof.

In some embodiments, the conjugate is described by formula (D-V-1):

(D-V-1)

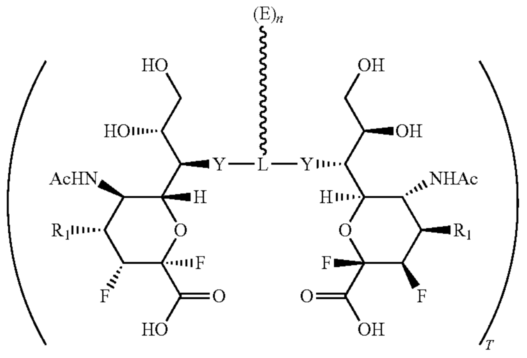

or a pharmaceutically acceptable salt thereof.

In some embodiments, the conjugate is described by formula (D-V-2):

(D-V-2)

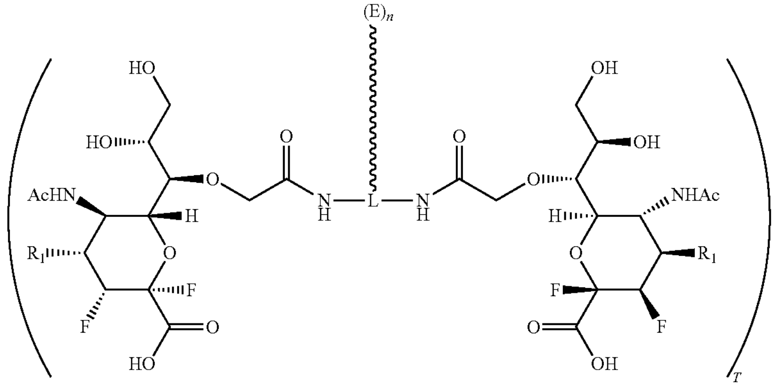

or a pharmaceutically acceptable salt thereof.

In some embodiments, the conjugate is described by formula (D-V-3):

(D-V-3)

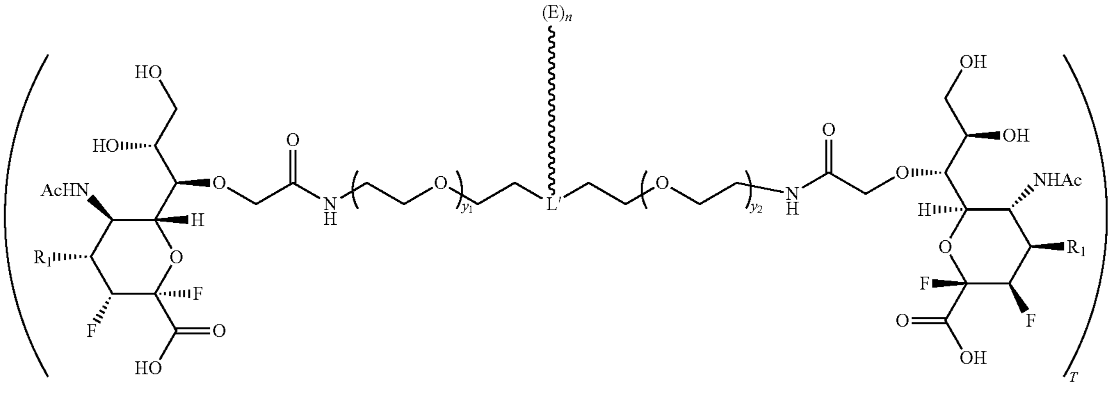

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-V-4):

(D-V-4)

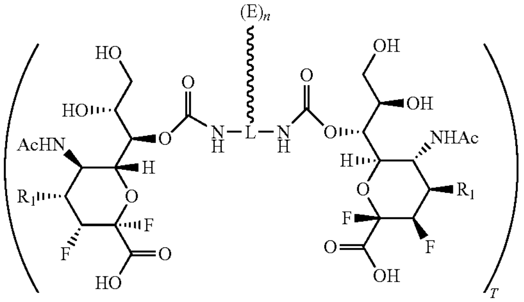

or a pharmaceutically acceptable salt thereof.

In some embodiments, the conjugate is described by formula (D-V-5):

(D-V-5)

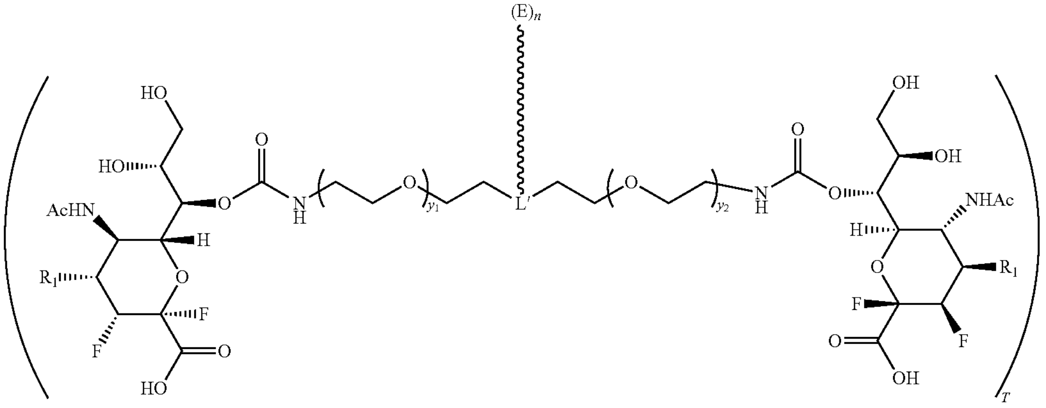

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-V-6):

(D-V-6)

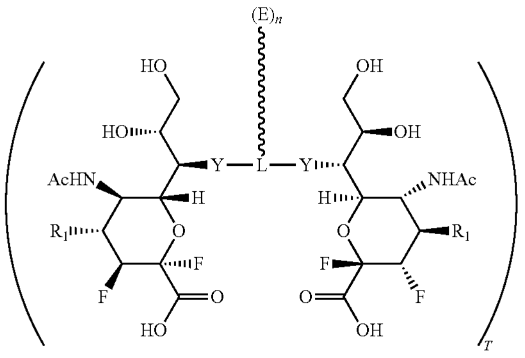

or a pharmaceutically acceptable salt thereof.

In some embodiments, the conjugate is described by formula (D-V-7):

(D-V-7)

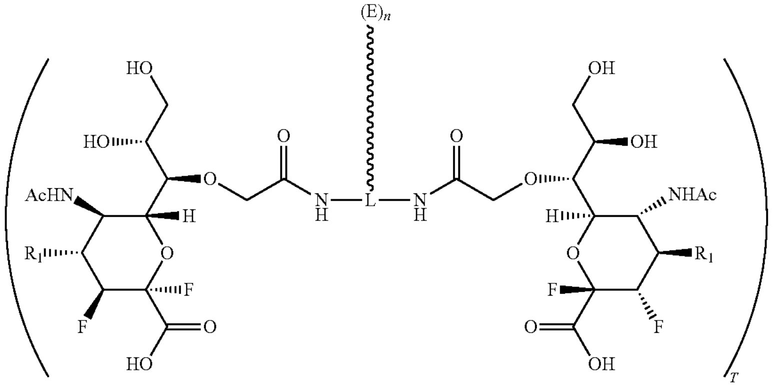

or a pharmaceutically acceptable salt thereof.

In some embodiments, the conjugate is described by formula (D-V-8):

(D-V-8)

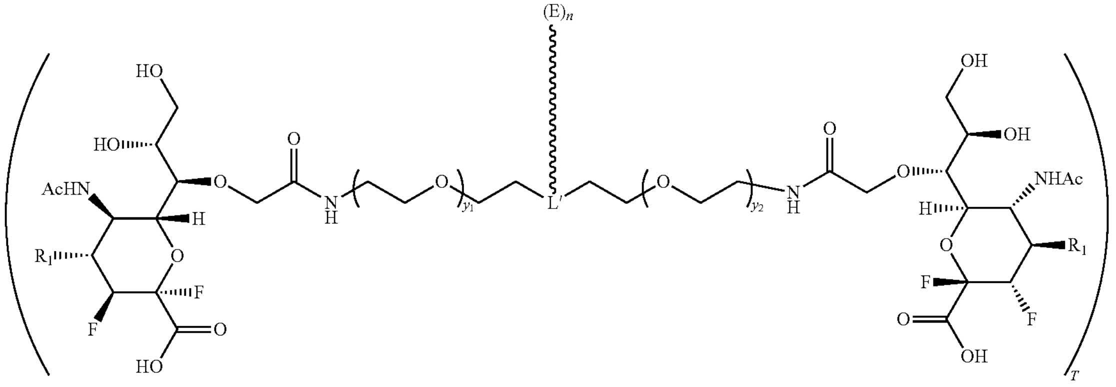

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-V-9):

(D-V-9)

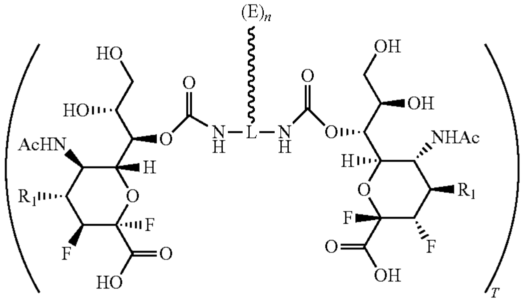

or a pharmaceutically acceptable salt thereof.

In some embodiments, the conjugate is described by formula (D-V-10):

(D-V-10)

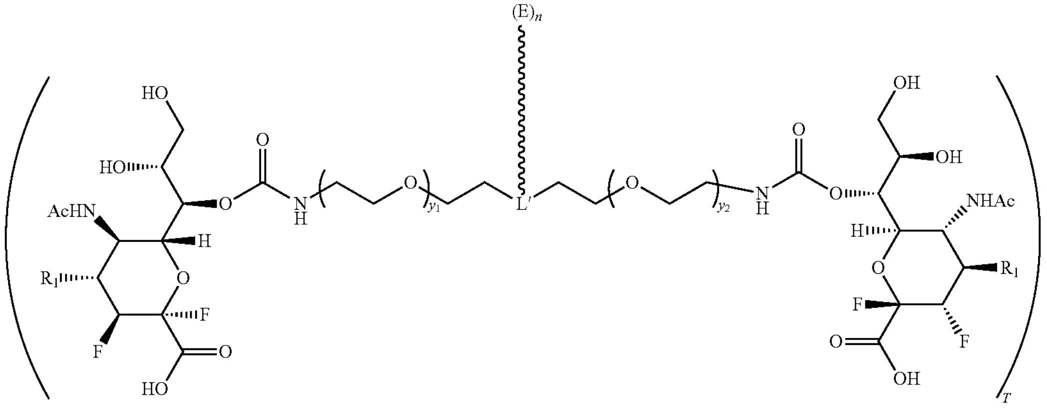

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VI):

(D-VI)

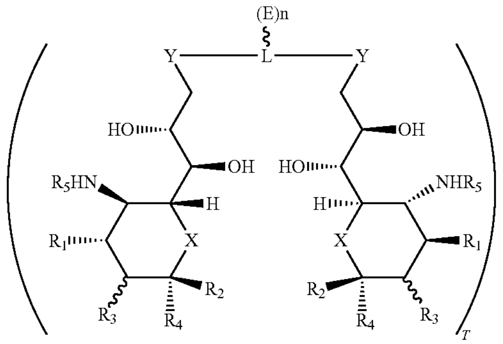

or a pharmaceutically acceptable salt thereof.

In some embodiments, the conjugate is described by formula (D-VI-1):

(D-IV-1)

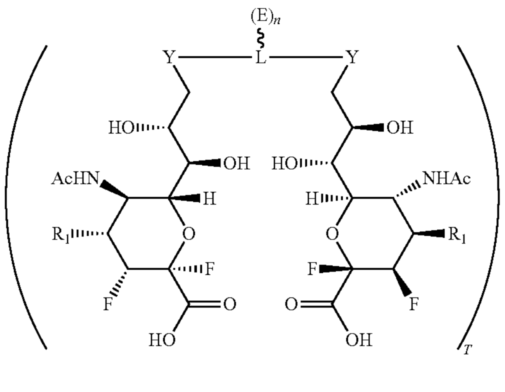

or a pharmaceutically acceptable salt thereof.

In some embodiments, the conjugate is described by formula (D-VI-2):

(D-VI-2)

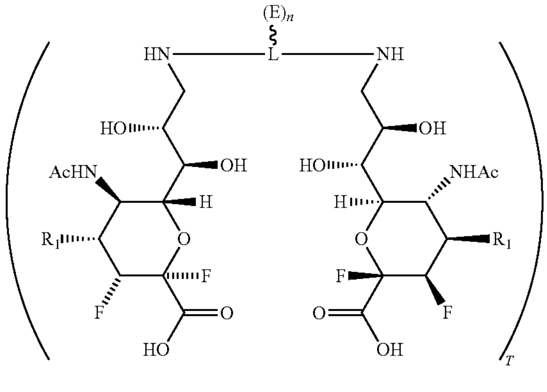

or a pharmaceutically acceptable salt thereof.

In some embodiments, the conjugate is described by formula (D-VI-3):

(D-VI-3)

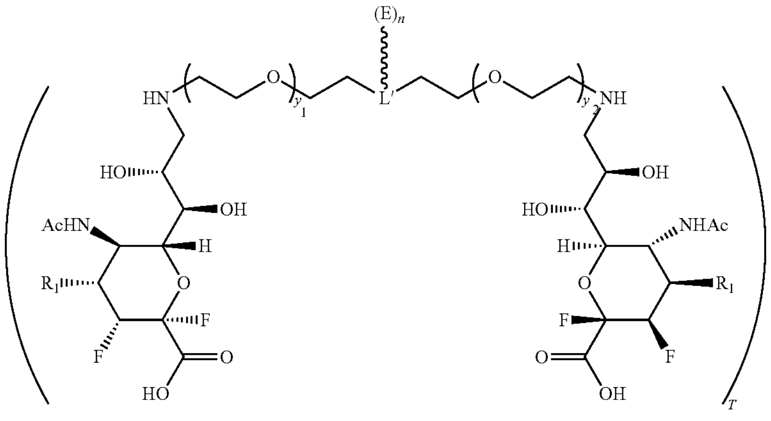

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VI-4):

(D-VI-4)

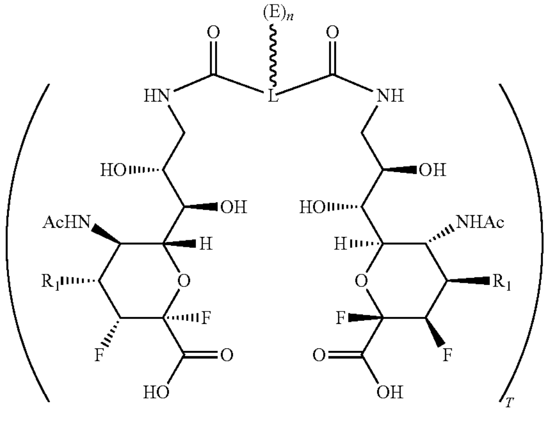

or a pharmaceutically acceptable salt thereof.

In some embodiments, the conjugate is described by formula (D-VI-5):

(D-VI-5)

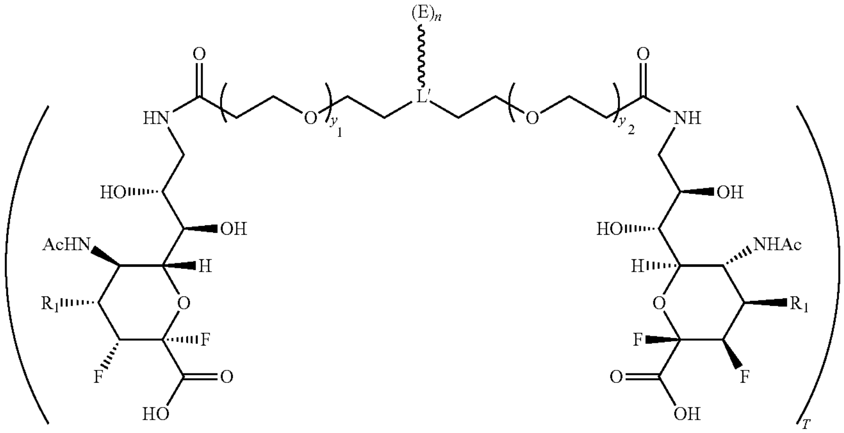

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VI-6):

(D-VI-6)

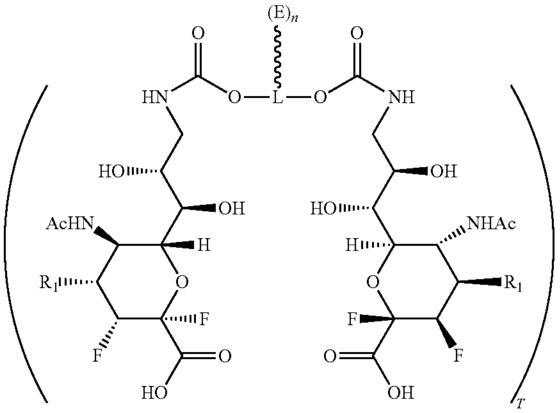

or a pharmaceutically acceptable salt thereof.

In some embodiments, the conjugate is described by formula (D-VI-7):

(D-VI-7)

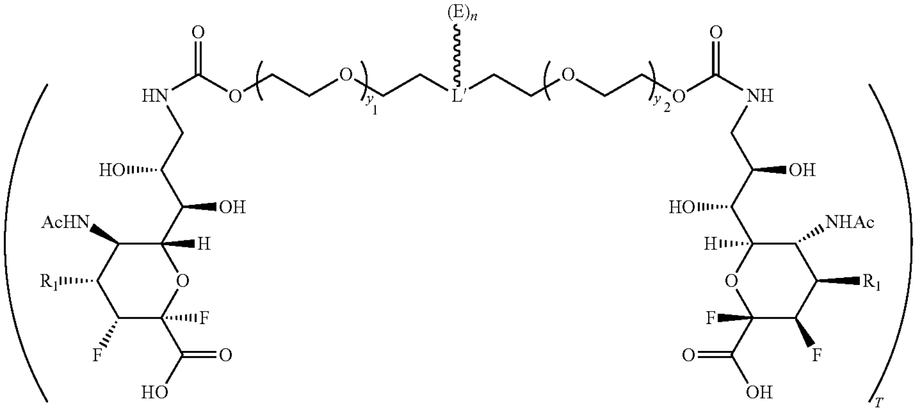

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VI-8):

(D-VI-8)

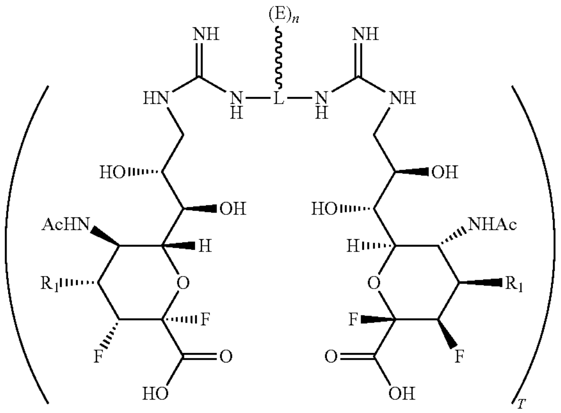

or a pharmaceutically acceptable salt thereof.

In some embodiments, the conjugate is described by formula (D-VI-9):

(D-VI-9)

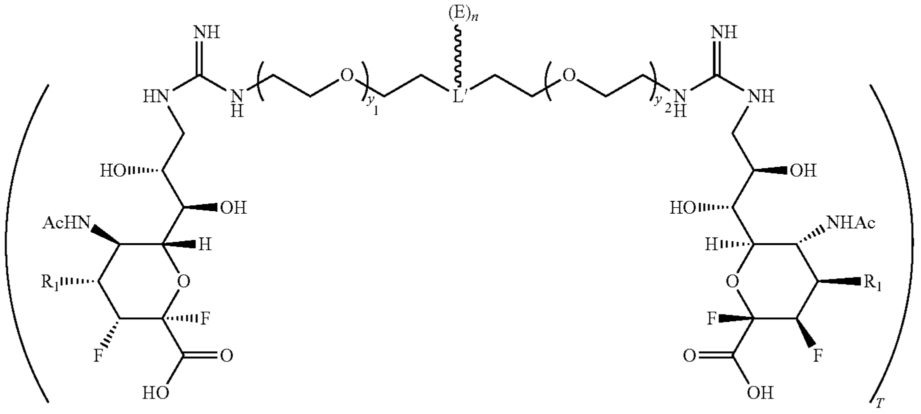

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, $y_1$ and $y_2$ are each 1, $y_1$ and $y_2$ are each 2, or $y_1$ and $y_2$ are each 3.

In some embodiments, the conjugate is described by formula (D-VII):

(D-VIII)

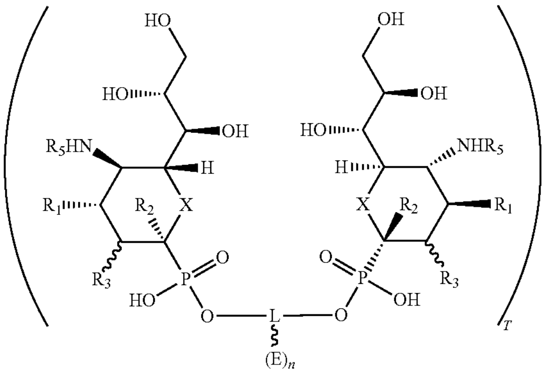

or a pharmaceutically acceptable salt thereof.

In some embodiments of any of the aspects described herein, $R_1$ is OH. In some embodiments of any of the aspects described herein, $R_1$ is $NH_2$. In some embodiments of any of the aspects described herein, $R_1$ is —NHC(=NH)$NH_2$.

In some embodiments, the conjugate is described by formula (D-VIII):

(D-VIII)

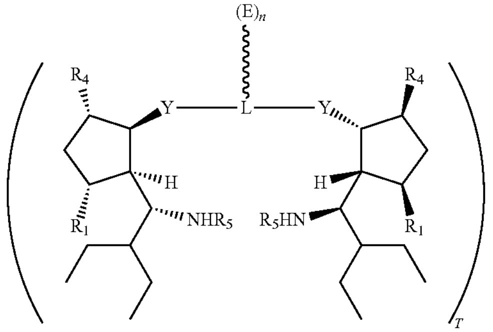

or a pharmaceutically acceptable salt thereof.

In some embodiments, the conjugate is described by formula (D-VIII-1):

(D-VIII-1)

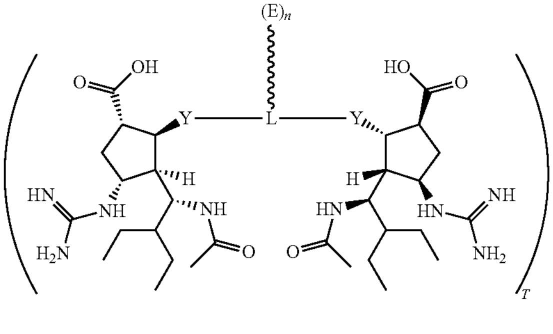

or a pharmaceutically acceptable salt thereof.

In some embodiments, the conjugate is described by formula (D-VIII-2):

(D-VIII-2)

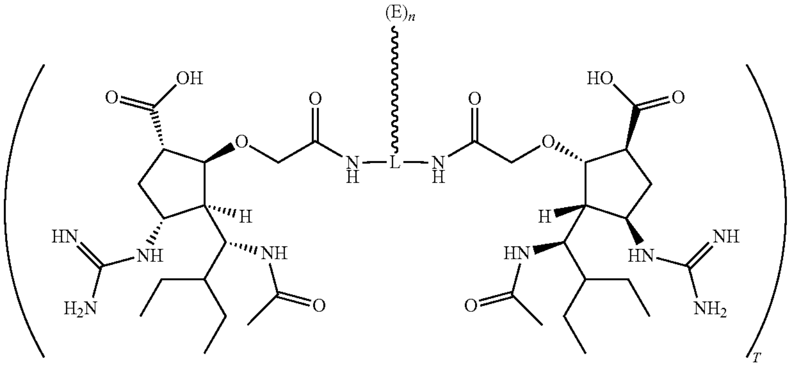

or a pharmaceutically acceptable salt thereof.

In some embodiments, the conjugate is described by formula (D-VIII-3):

(D-VIII-3)

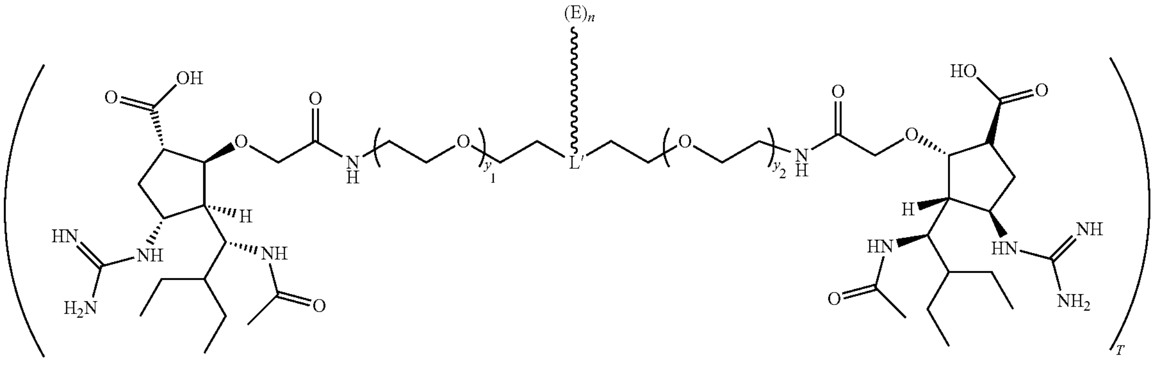

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate has the structure selected from

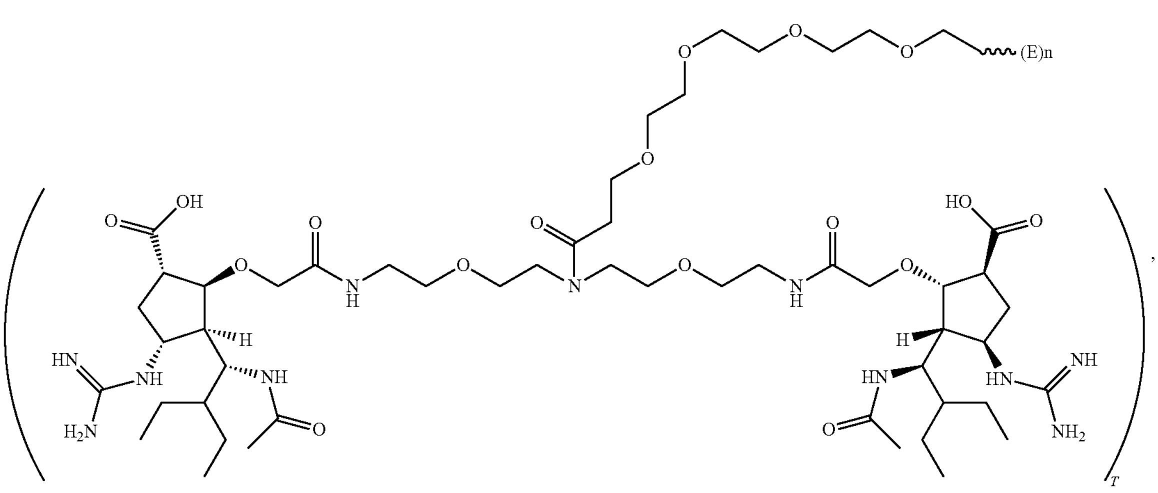

,

-continued
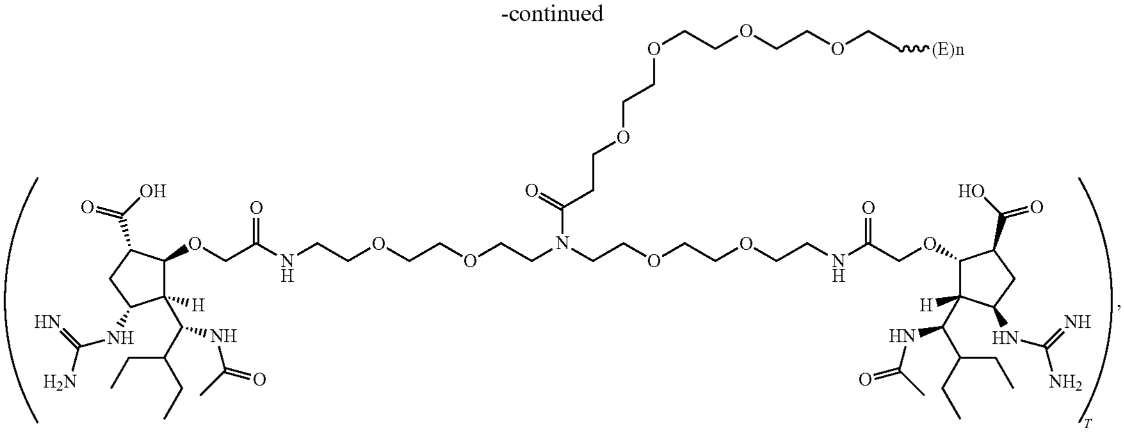
, or
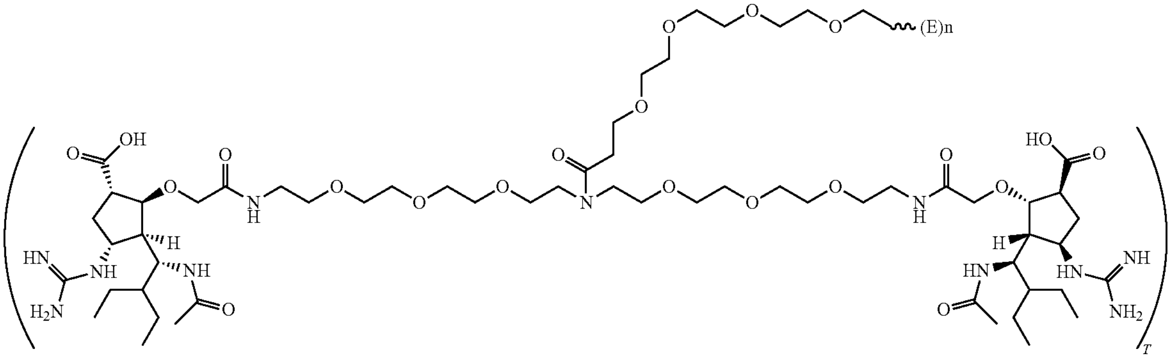
,
or a pharmaceutically acceptable salt thereof.
In some embodiments, the conjugate is described by formula (D-VIII-4):
(D-VIII-4)
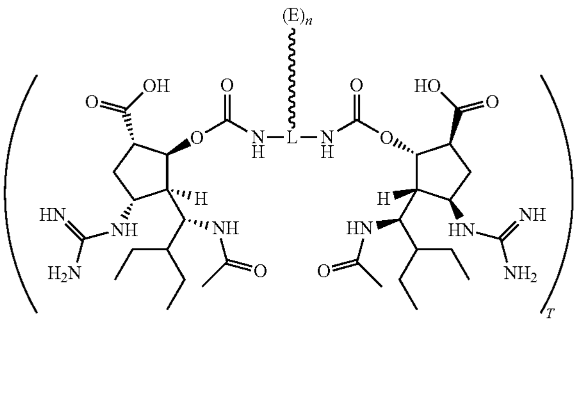
or a pharmaceutically acceptable salt thereof.
In some embodiments, the conjugate is described by formula (D-VIII-5):

(D-VIII-5)
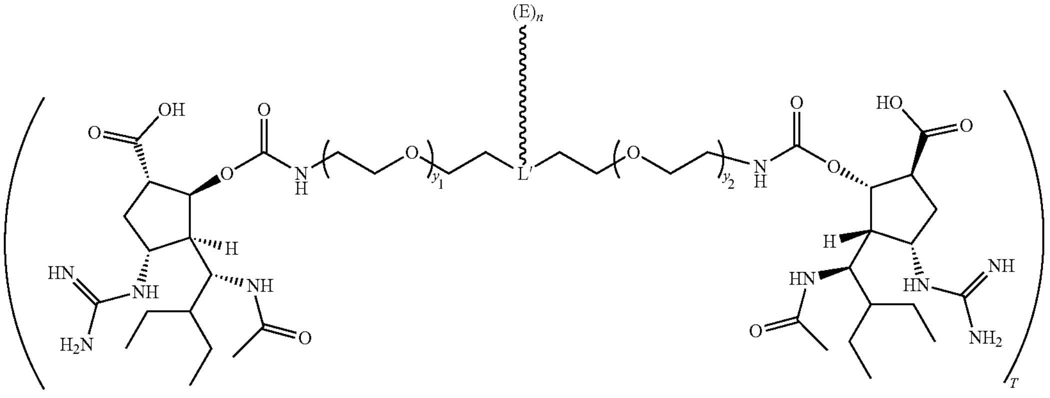
wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.
In some embodiments, the conjugate has the structure selected from
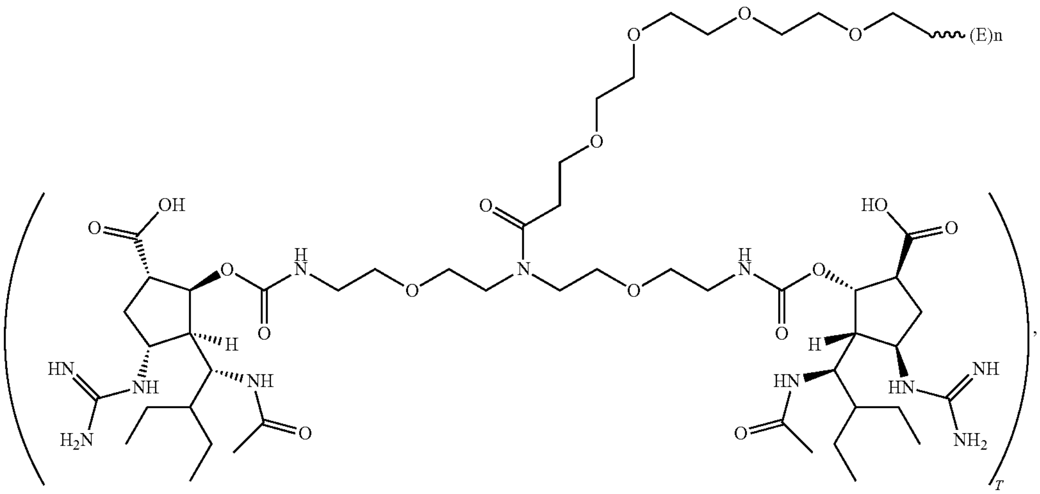
,
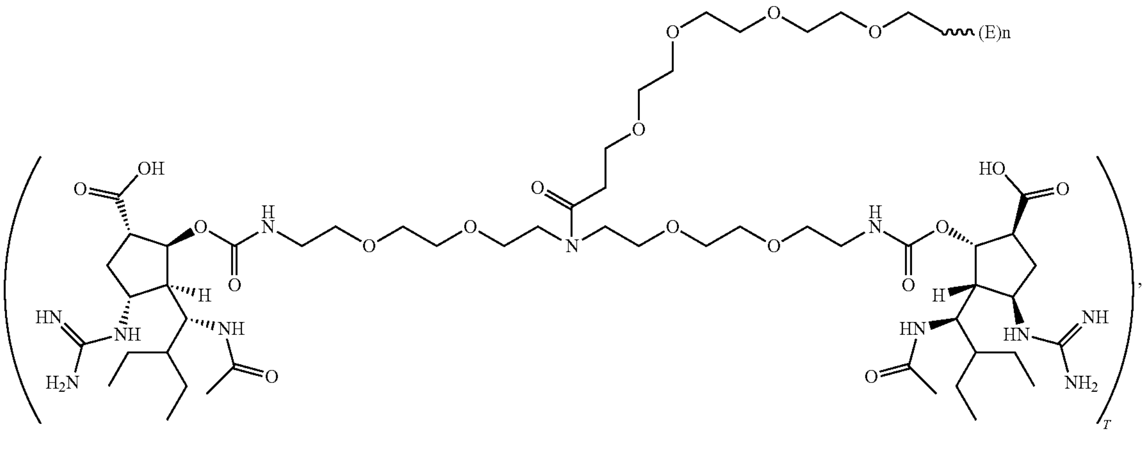
, or -continued
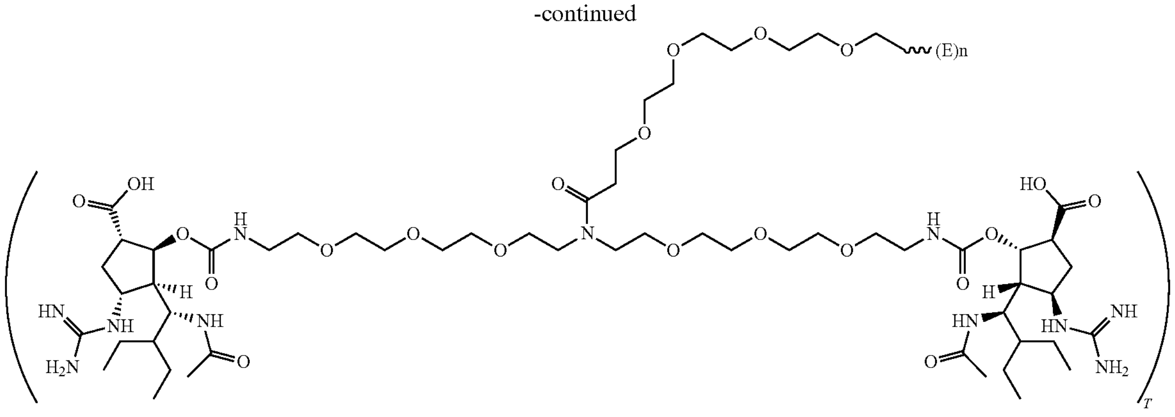
or a pharmaceutically acceptable salt thereof.
In some embodiments, the conjugate is described by the structure
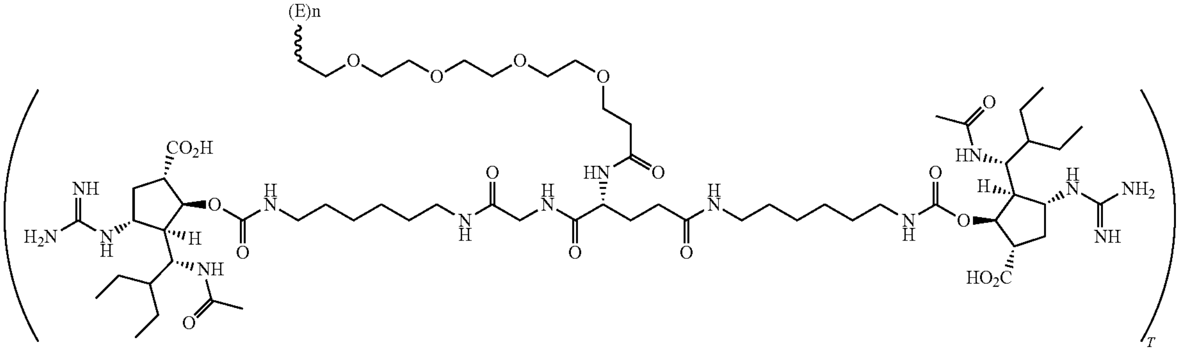
or a pharmaceutically acceptable salt thereof.
In some embodiments, the conjugate is described by formula (D-VIII-6):
(D-VIII-6)
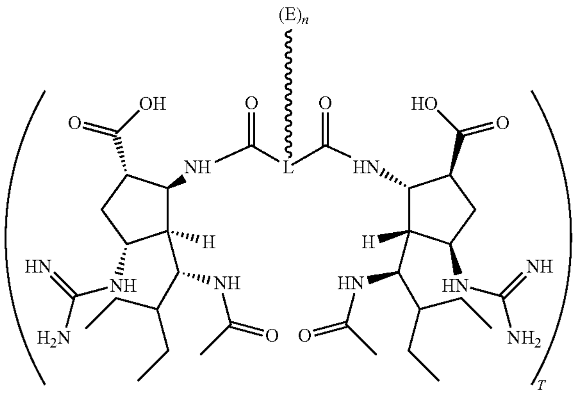
or a pharmaceutically acceptable salt thereof.
In some embodiments, the conjugate is described by formula (D-VIII-7):

(D-VIII-7)

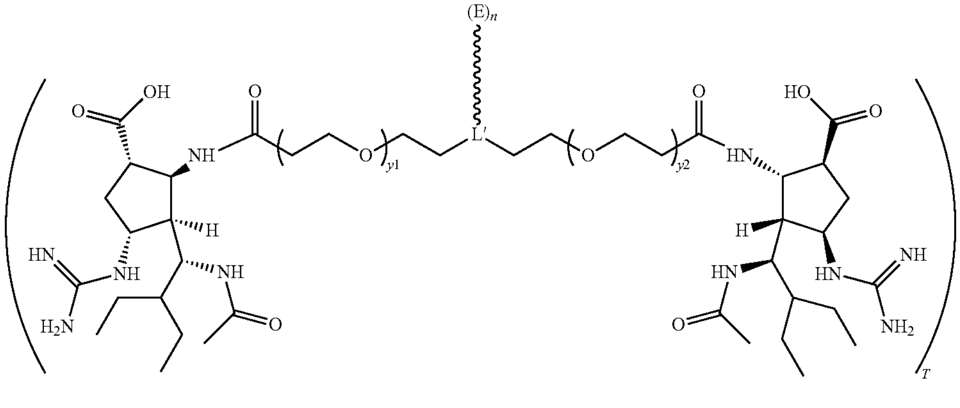

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-VIII-8):

(D-VIII-8)

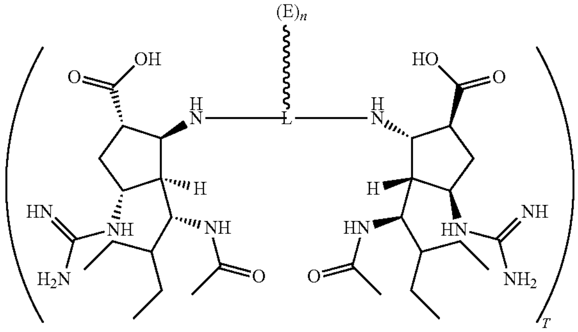

or a pharmaceutically acceptable salt thereof.

In some embodiments, the conjugate is described by formula (D-VIII-9):

(D-VIII-9)

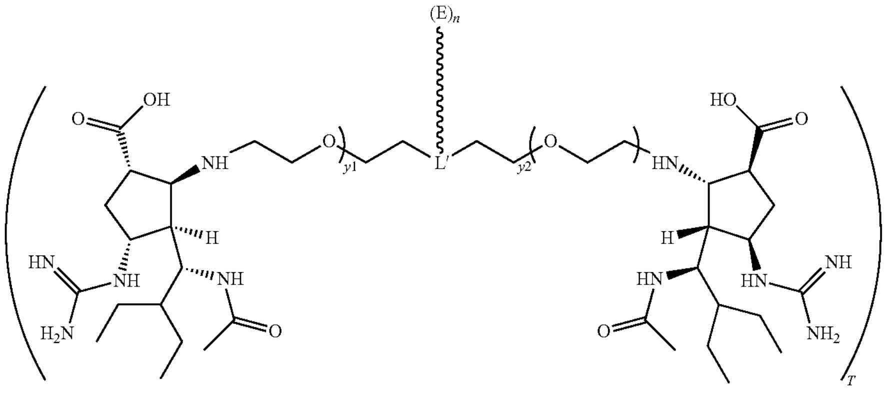

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom.

In some embodiments, the conjugate is described by formula (D-VIII-10):

(D-VIII-10)

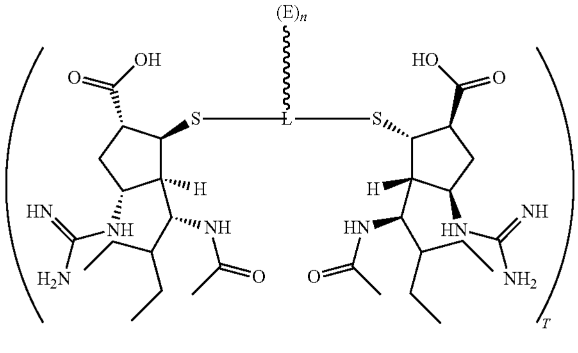

or a pharmaceutically acceptable salt thereof.

In some embodiments, the conjugate is described by formula (D-VIII-11):

(D-VIII-11)

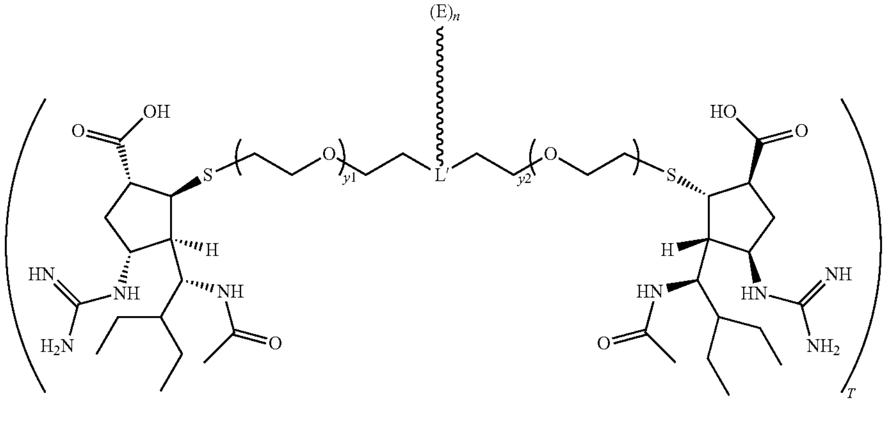

wherein L' is the remainder of L, and $y_1$ and $y_2$ are each independently an integer from 1-20 (e.g., $y_1$ and $y_2$ are each independently 1, 2, 3, 4, 5, 6, 7, 8, 9, 10, 11, 12, 13, 14, 15, 16, 17, 18, 19, or 20), or a pharmaceutically acceptable salt thereof. In some embodiments, L' is a nitrogen atom. In some embodiments, the conjugate is described by formula (D-IX):

(D-IX)

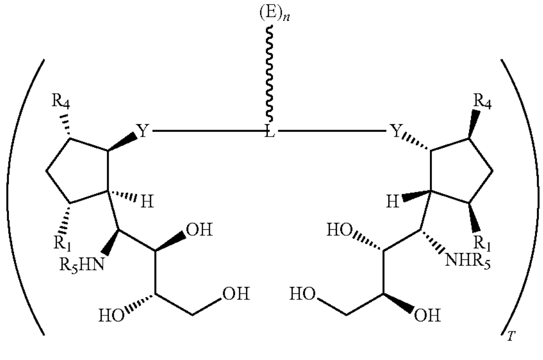

or a pharmaceutically acceptable salt thereof.

In some embodiments, the conjugate is described by formula (D-IX-1):

(D-IX-1)
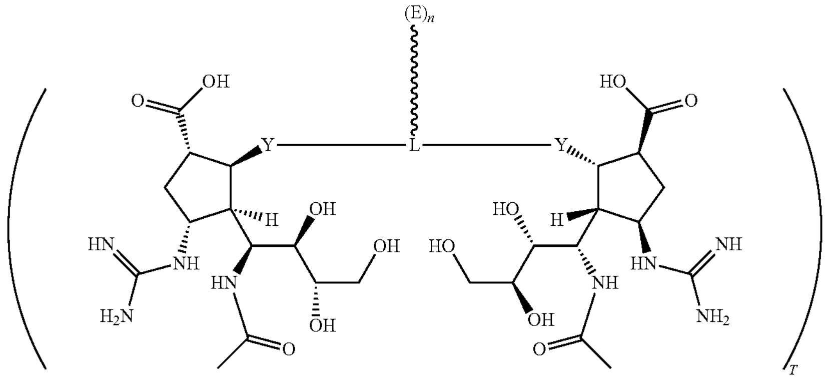
or a pharmaceutically acceptable salt thereof.
In some embodiments, the conjugate is described by formula (D-IX-2):
(D-IX-2)
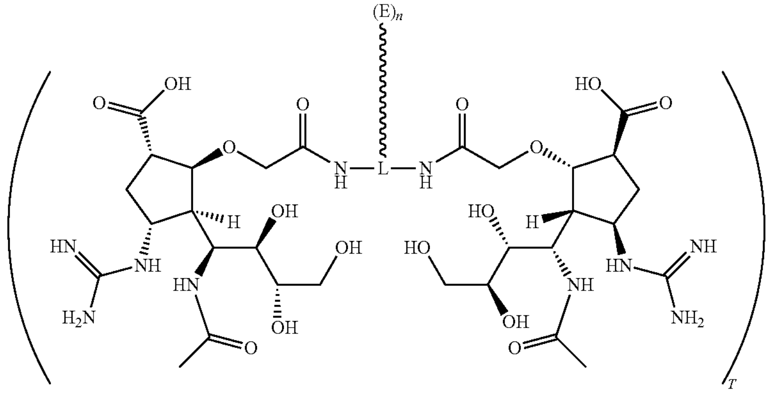
or a pharmaceutically acceptable salt thereof.
In some embodiments, the conjugate is described by formula (D-IX-3):
(D-IX-3)
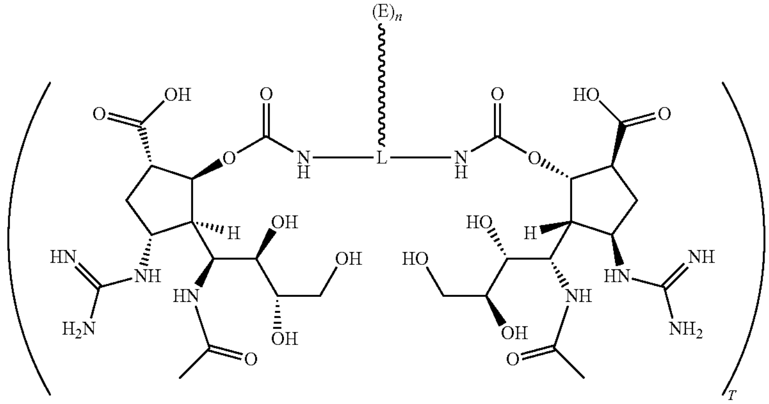
or a pharmaceutically acceptable salt thereof.
In some embodiments, the conjugate is described by formula (D-IX-4):

(D-IX-4)

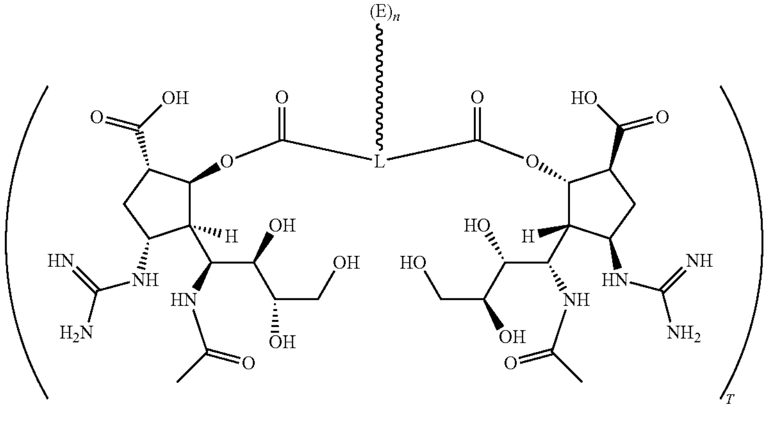

or a pharmaceutically acceptable salt thereof.

In some embodiments, the conjugate is described by formula (D-IX-5):

(D-IX-5)

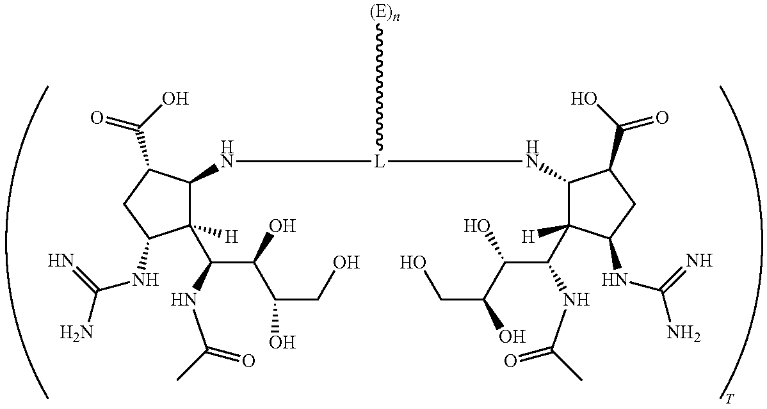

or a pharmaceutically acceptable salt thereof.

In some embodiments, the conjugate is described by formula (D-IX-6):

(D-IX-6)

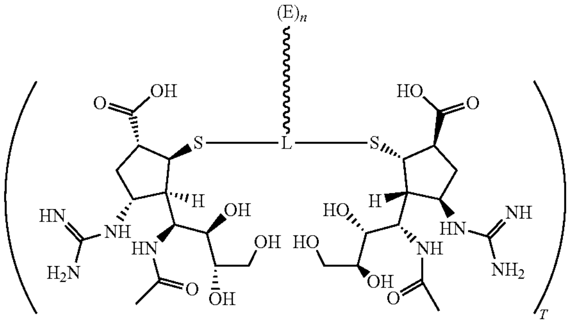

or a pharmaceutically acceptable salt thereof.

In some embodiments, the conjugate is described by formula (D-X):

(D-X)

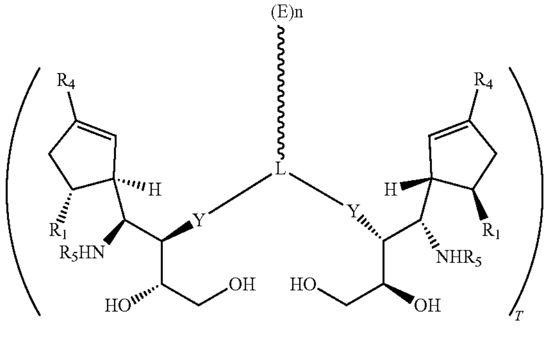

or a pharmaceutically acceptable salt thereof.

In some embodiments, the conjugate is described by formula (D-X-1):

(D-X-1)

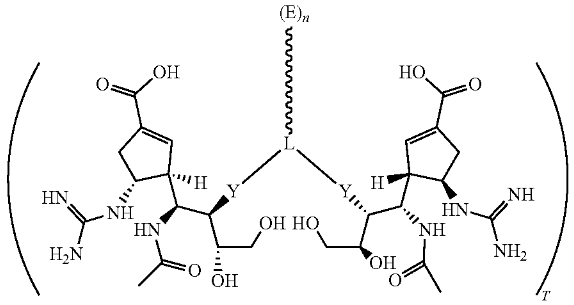

or a pharmaceutically acceptable salt thereof.

In some embodiments, the conjugate is described by formula (D-X-2):

or a pharmaceutically acceptable salt thereof.

(D-X-2)

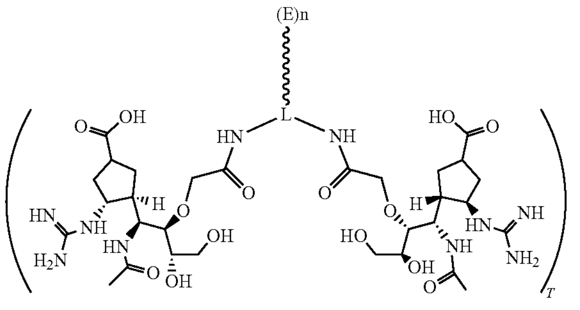

In some embodiments, the conjugate is described by formula (D-X-3):

(D-X-3)

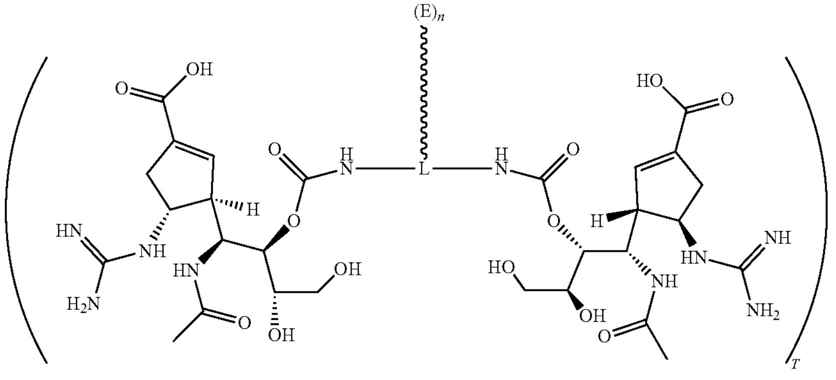

or a pharmaceutically acceptable salt thereof.

In some embodiments of any of the aspects described herein, L or L' includes one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R_i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments of any of the aspects described herein, the backbone of L or L' consists of one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R_i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments of any of the aspects described herein, L or L' is oxo substituted. In some embodiments, the backbone of L or L' comprises no more than 250 atoms. In some embodiments, L or L' is capable of forming an amide, a carbamate, a sulfonyl, or a urea linkage. In some embodiments L or L' is a bond. In some embodiments, L or L' is an atom.

In some embodiments of any of the aspects described herein, each L is described by formula (D-L-1):

(D-L-I)

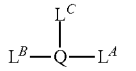

wherein $L^A$ is described by formula $G^{A1}$-$(Z^{A1})_{g1}$—$(Y^{A1})_{h1}$—$(Z^{A2})_{i1}$—$(Y^{A2})_{j1}$—$(Z^{A3})_{k1}$—$(Y^{A3})_{l1}$—$(Z^{A4})_{m1}$—$(Y^{A4})_{n1}$—$(Z^{A5})o_1$-$G^{A2}$; $L^B$ is described by formula $G^{B1}$-$(Z^{B1})_{g2}$—$(Y^{B1})_{h2}$—$(Z^{B2})^{i2}$—$(Y^{B2})_{j2}$—$(Z^{B3})_{k2}$—$(Y^{B3})_{l2}$—$(Z^{B4})_{m2}$—$(Y^{B4})_{n2}$—$(Z^{B5})o_2$-$G^{B2}$; $L^C$ is described by formula $G^{C1}$-$(Z^{C1})_{g3}$—$(Y^{C1})_{h3}$—$(Z^{C2})_{i3}$—$(Y^{C2})_{j3}$—$(Z^{C3})_{k3}$—$(Y^{C3})_{l3}$—$(Z^{C4})_{m3}$—$(Y^{C4})_{n3}$—$(Z^{C5})o_3$-$G^{C2}$; $G^{A1}$ is a bond attached to Q; $G^{A2}$ is a bond attached to A1; $G^{B1}$ is a bond attached to Q); $G^{B2}$ is a bond attached to A2; $G^{C1}$ is a bond attached to Q; $G^{C2}$ is a bond attached to E or a functional group capable of reacting with a functional group conjugated to E (e.g., maleimide and cysteine, amine and activated carboxylic acid, thiol and maleimide, activated sulfonic acid and amine, isocyanate and amine, azide and alkyne, and alkene and tetrazine); each of $Z^{A1}$, $Z^{A2}$, $Z^{A3}$, $Z^{A4}$, $Z^{A5}$, $Z^{B1}$, $Z^{B2}$, $Z^{B3}$, $Z^{B4}$, $Z^{B5}$, $Z^{C1}$, $Z^{C2}$, $Z^{C3}$, $Z^{C4}$ and $Z^{C5}$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene; each of $Y^{A1}$, $Y^{A2}$, $Y^{A3}$, $Y^{A4}$, $Y^{B1}$, $Y^{B2}$, $Y^{B3}$, $Y^{B4}$, $Y^{C1}$, $Y^{C2}$, $Y^{C3}$, and $Y^{C4}$ is, independently, O, S, $NR^i$, P, carbonyl, thiocarbonyl, sulfonyl, phosphate, phosphoryl, or imino; $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; each of g1, h1, i1, j1, k1, l1, m1, n1, o1, g2, h2, i2, j2, k2, l2, m2, n2, o2, g3, h3, i3, j3, k3, l3, m3, n3, and o3 is, independently, 0 or 1; Q is a nitrogen atom, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene.

In some embodiments, $L^C$ may have two points of attachment to the Fc domain, Fc-binding peptide, albumin protein, or albumin protein-binding peptide (e.g., two $G^{C2}$) In some embodiments of any of the aspects described herein, L includes a polyethylene glycol (PEG) linker. A PEG linker includes a linker having the repeating unit structure $(—CH_2CH_2O—)_n$, wherein n is an integer from 2 to 100. A polyethylene glycol linker may covalently join a neuraminidase inhibitor and E (e.g., in a conjugate of any one of formulas (M-I)-(M-X)). A polyethlylene glycol linker may covalently join a first neuraminidase inhibitor and a second neuraminidase inhibitor (e.g., in a conjugate of any one of formulas (D-I)-(D-X)). A polyethylene glycol linker may covalently joining a neuraminidase inhibitor dimer and E (e.g., in a conjugate of any one of formulas (D-I)-(D-X)). A polyethylene glycol linker may selected any one of $PEG_2$ to $PEG_{100}$ (e.g., $PEG_2$, $PEG_3$, $PEG_4$, $PEG_5$, $PEG_5$-$PEG_{10}$, $PEG_{10}$-$PEG_{20}$, $PEG_{20}$-$PEG_{30}$, $PEG_{30}$-$PEG_{40}$, $PEG_{50}$-$PEG_{60}$, $PEG_{60}$-$PEG_{70}$, $PEG_{70}$-$PEG_{80}$, $PEG_{80}$-$PEG_{90}$, $PEG_{90}$-$PEG_{100}$). In some embodiments, $L^C$ includes a PEG linker, where $L^C$ is covalently attached to each of Q and E.

In some embodiments, L is

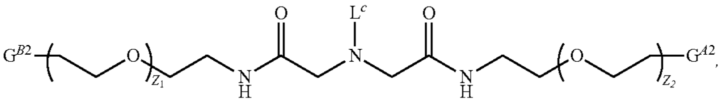

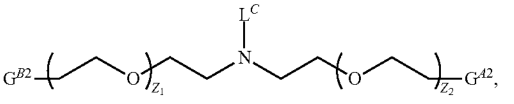

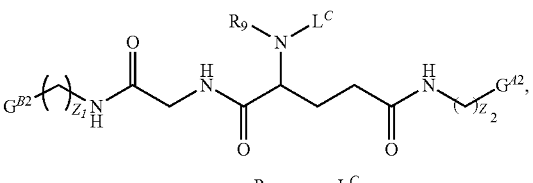

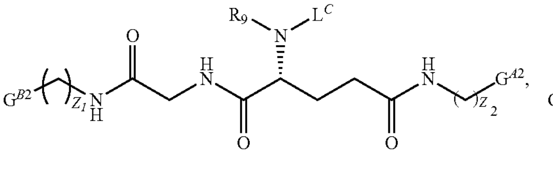

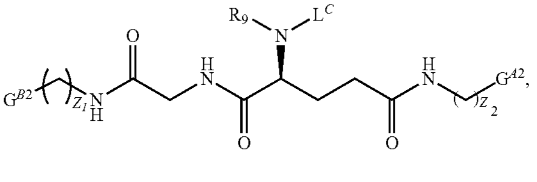

-continued
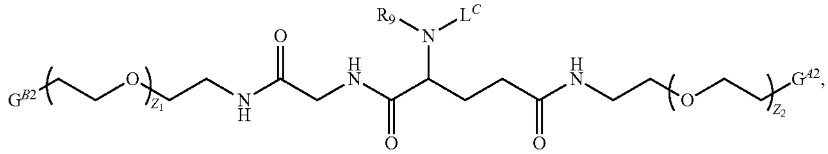,
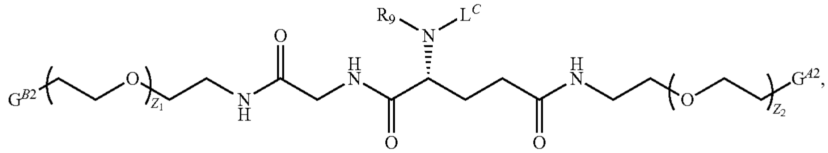,
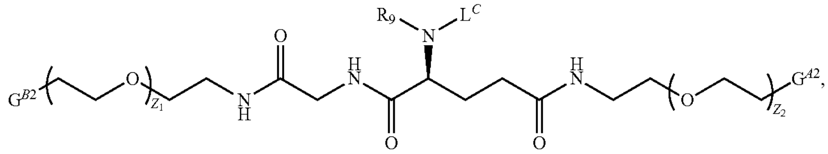,
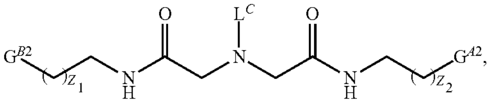, 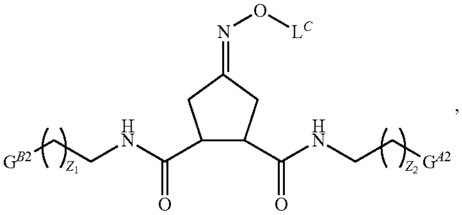,
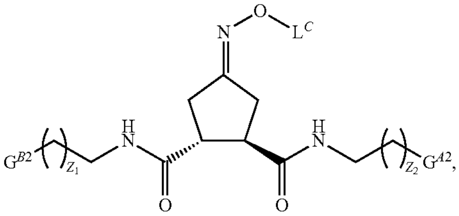, 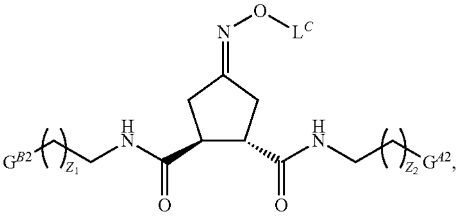,
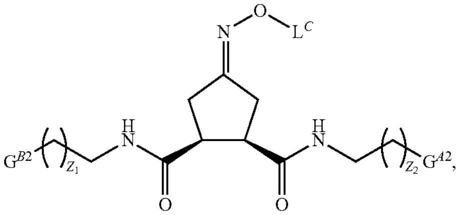, 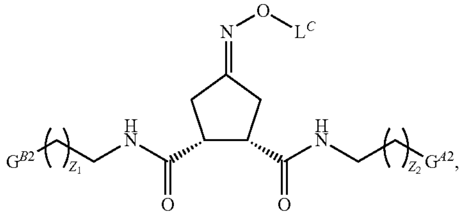,
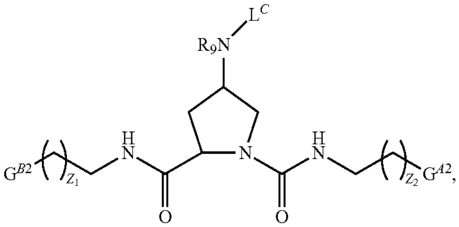, 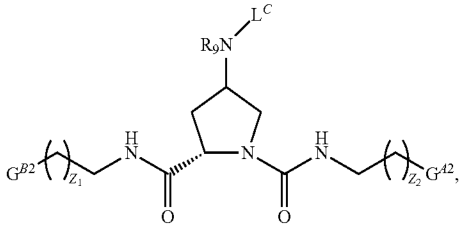,
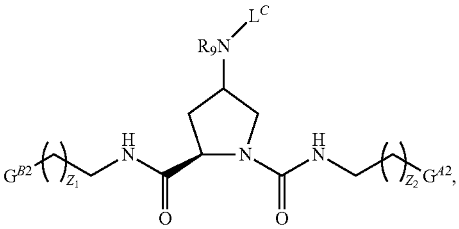, 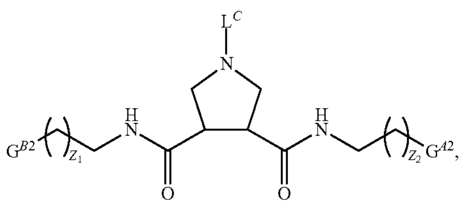, -continued
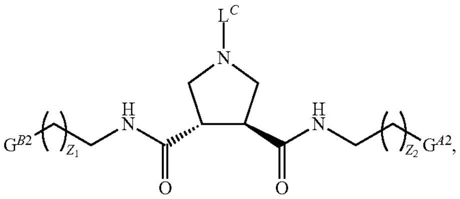,
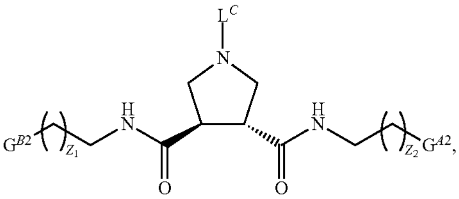,
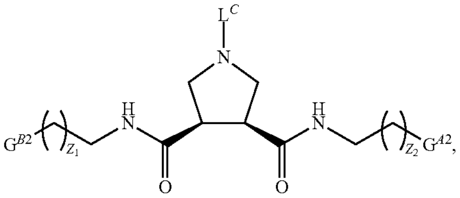,
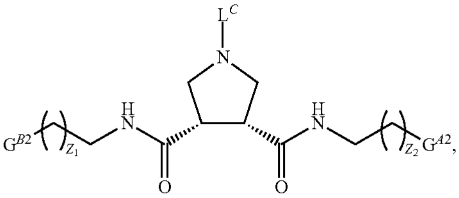,
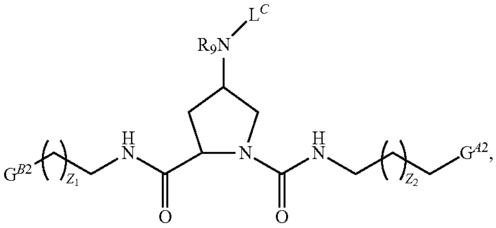,
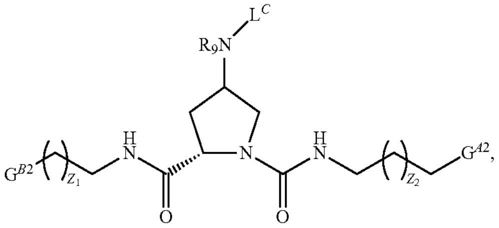,
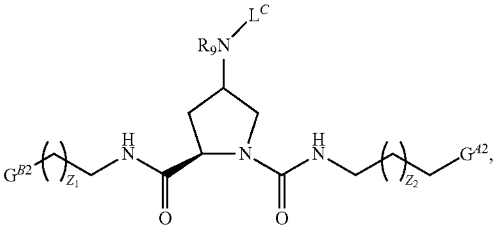,
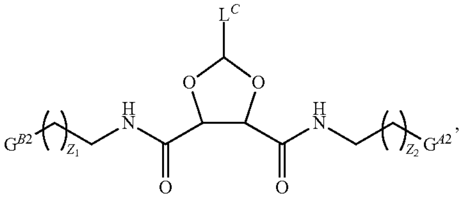,
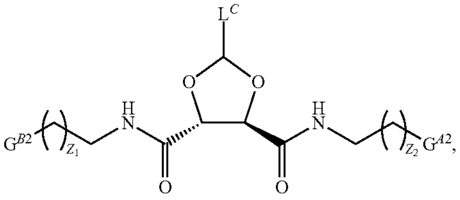,
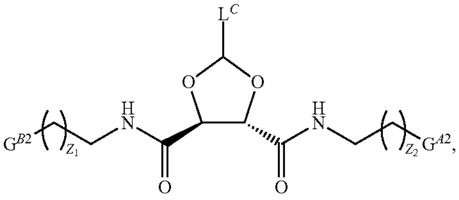,
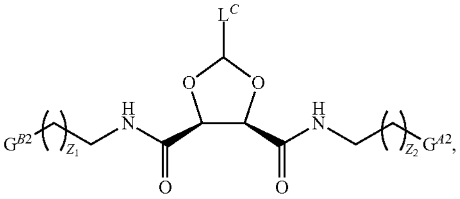,
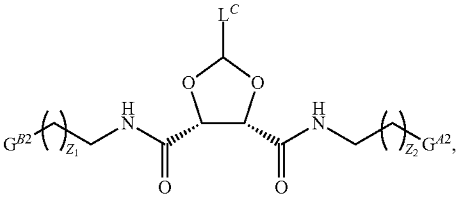,
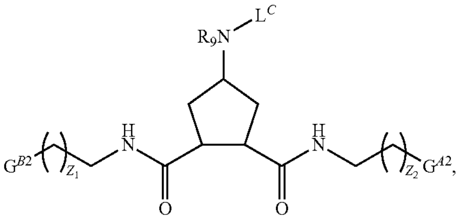,
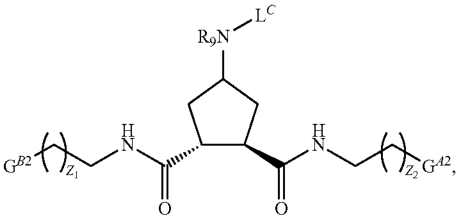,
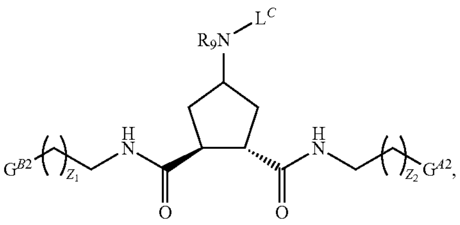,
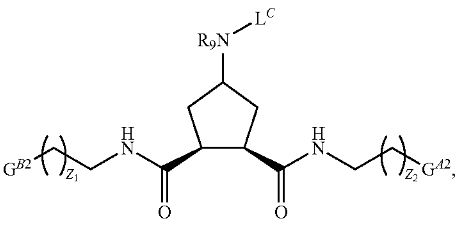, -continued
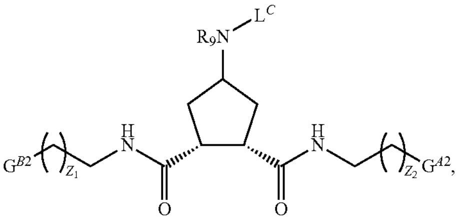,
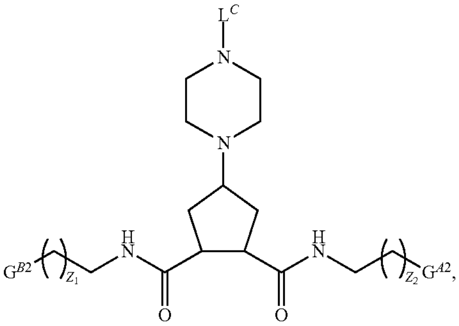,
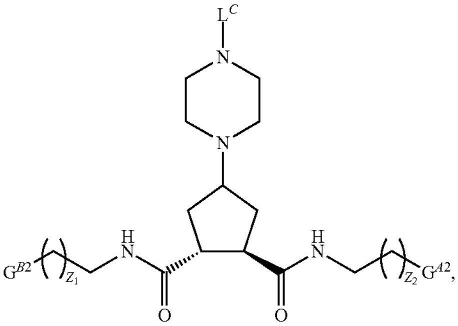,
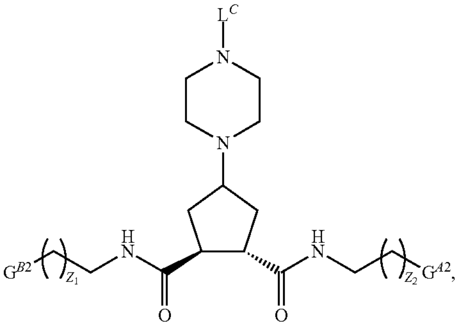,
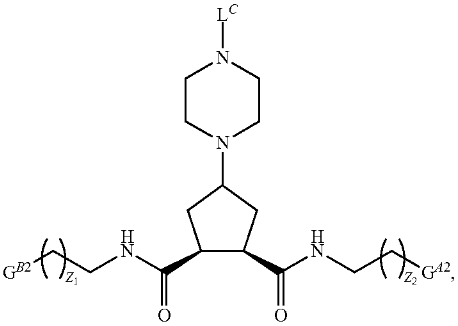,
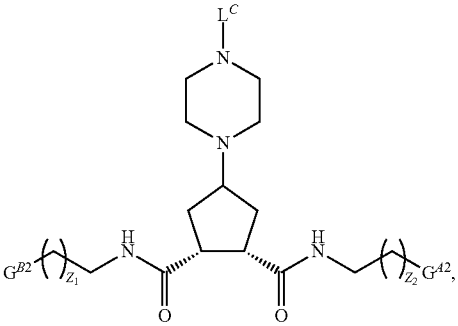,
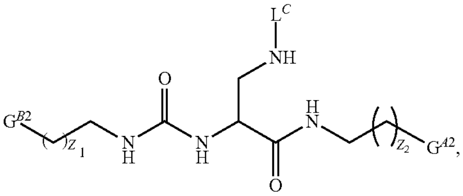,
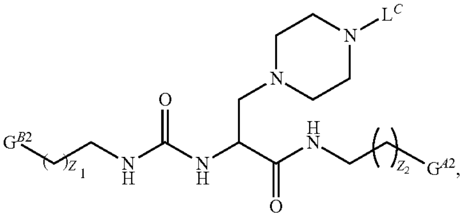,
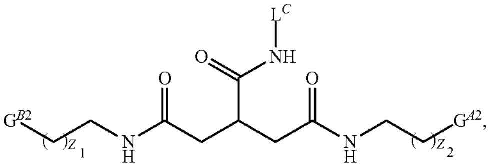,
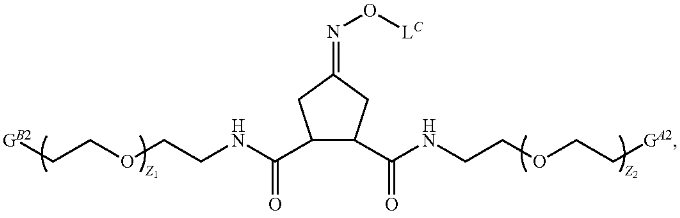, -continued
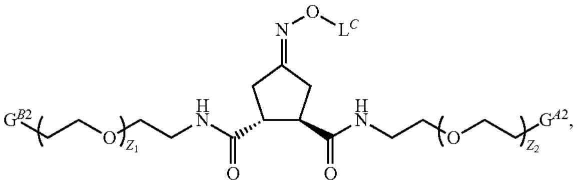
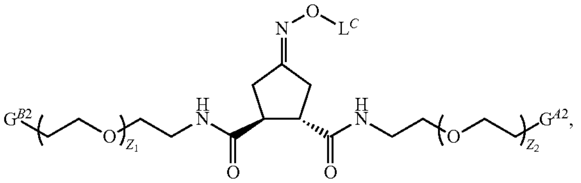
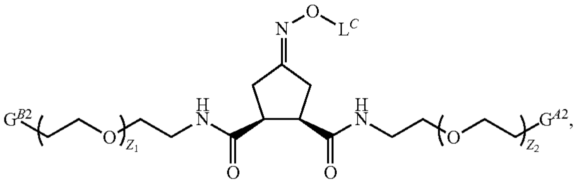
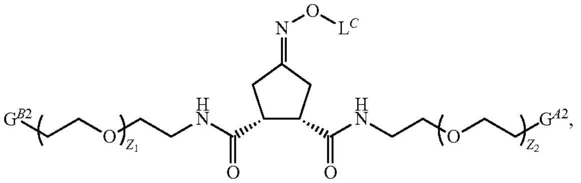
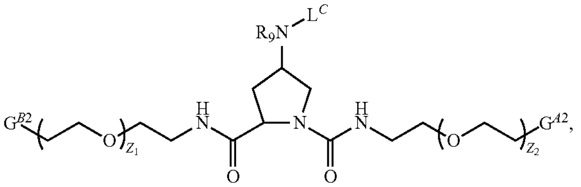
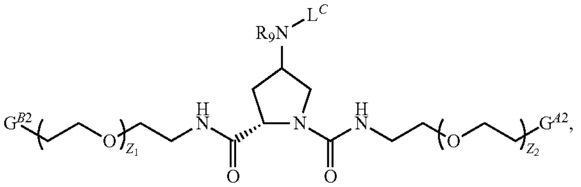
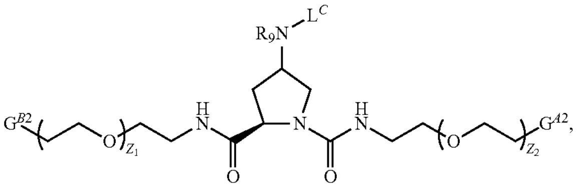
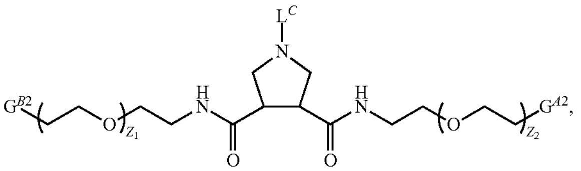
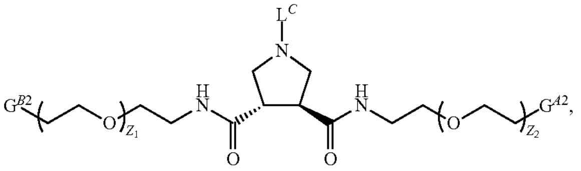

-continued
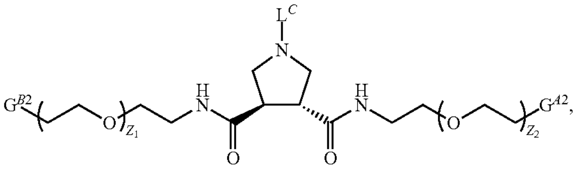
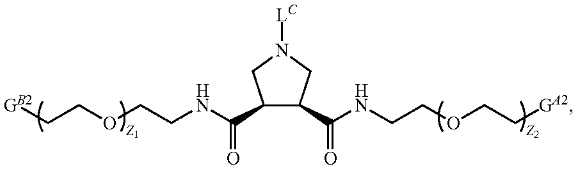
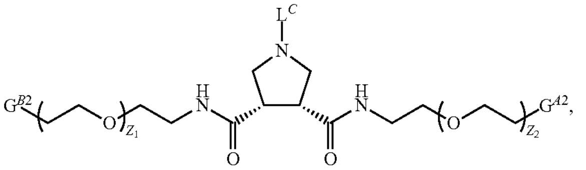
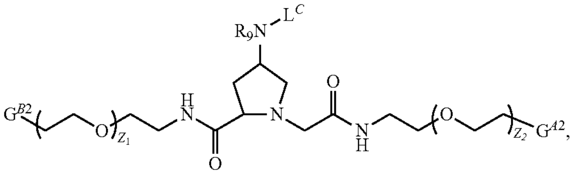
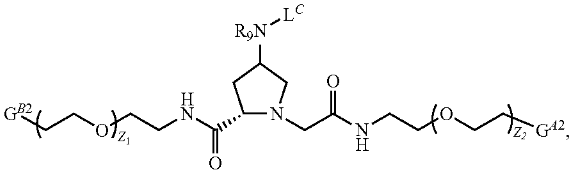
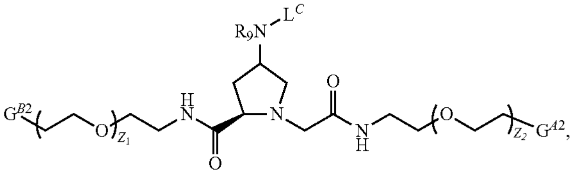
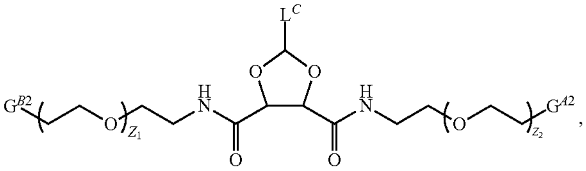
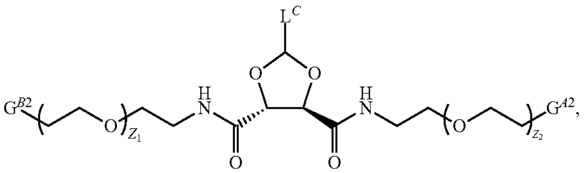
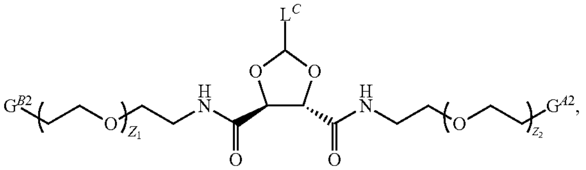
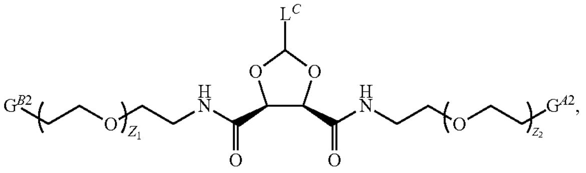

-continued
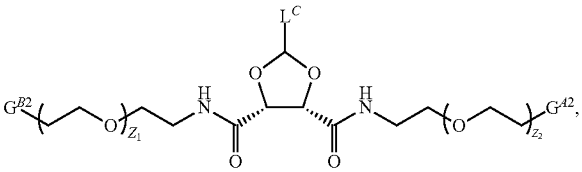,
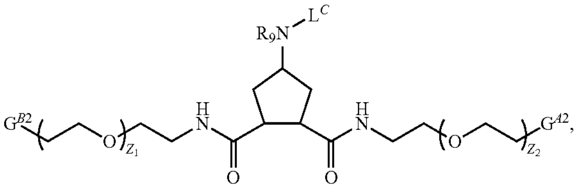,
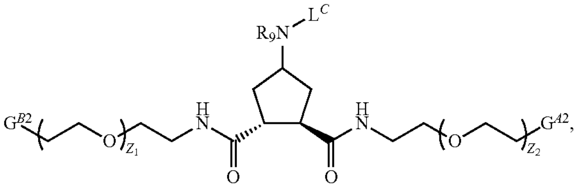,
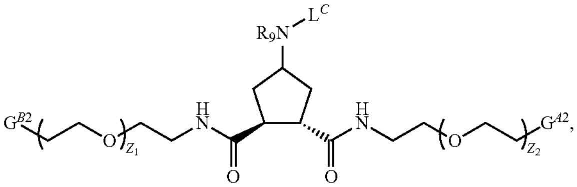,
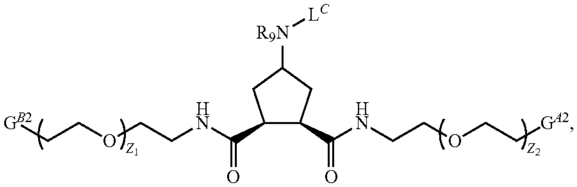,
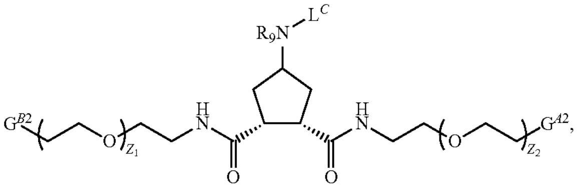,
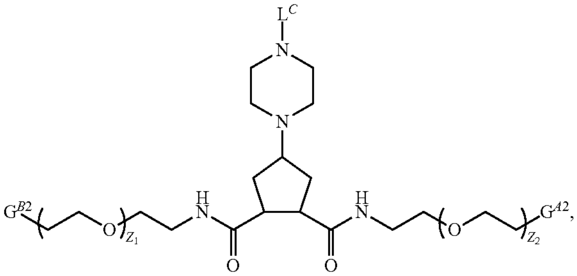,
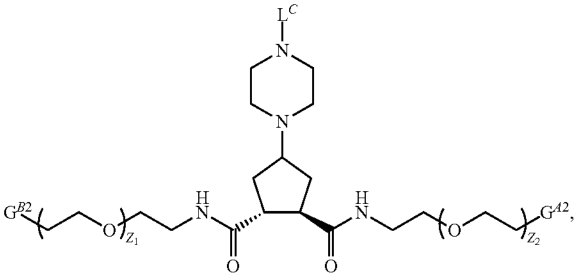, -continued
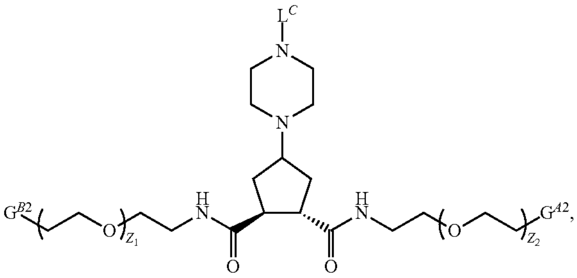,
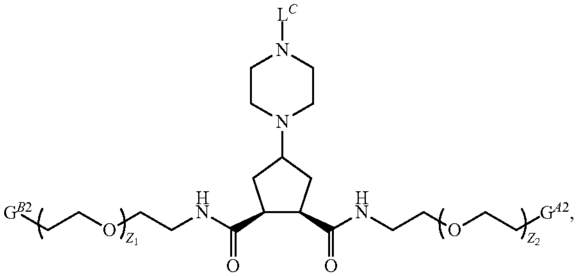,
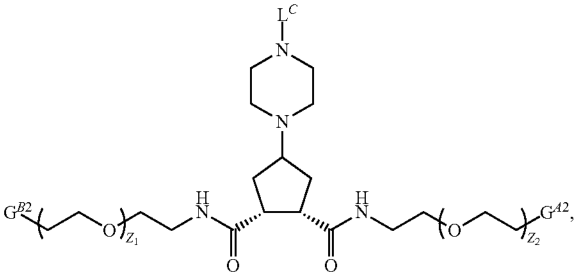,
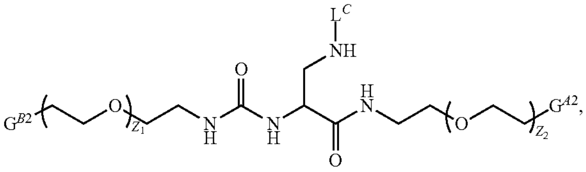,
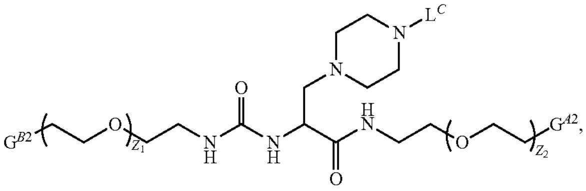,
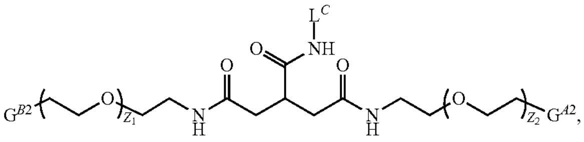,
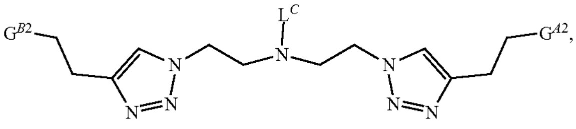,
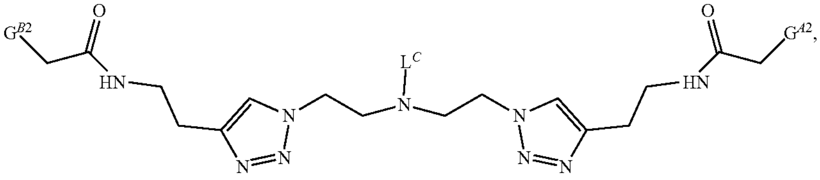, -continued
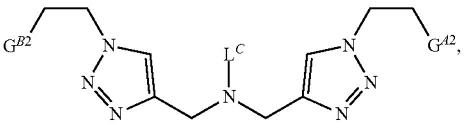
,
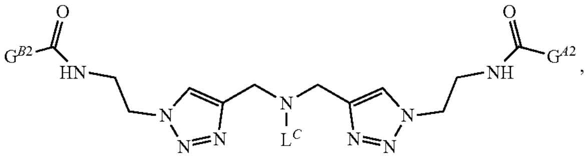
,
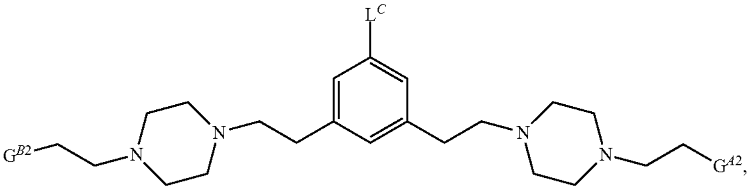
,
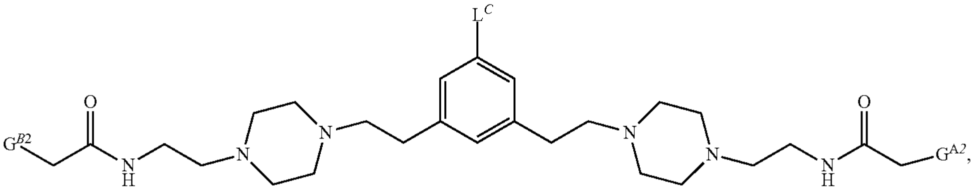
,
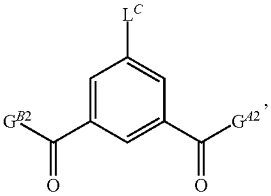
,
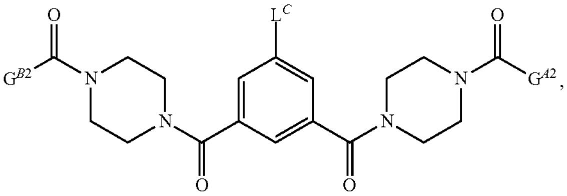
,
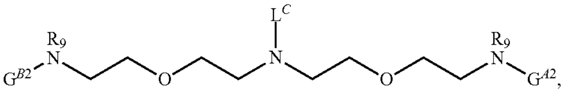
,
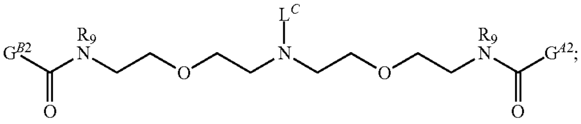
;
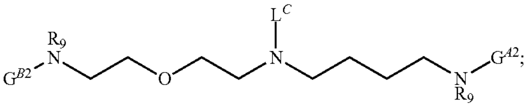
;
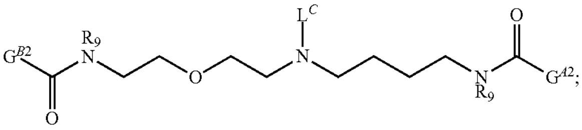
;
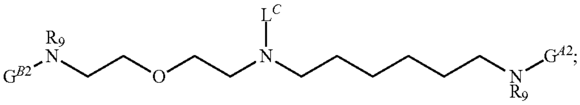
;
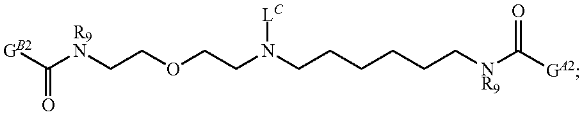
;
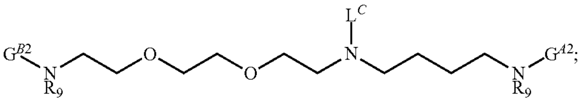
;
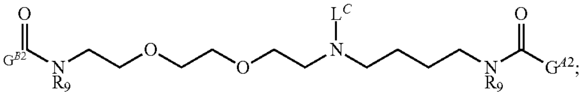
;
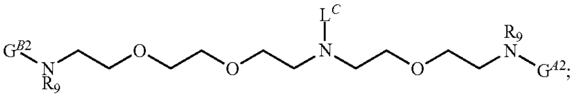
; or -continued
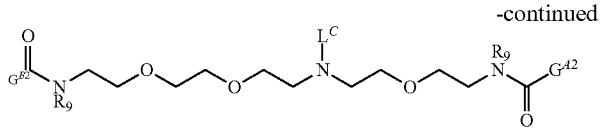
wherein $z_1$ and $z_2$ are each, independently, and integer from 1 to 20; and $R_9$ is selected from H, C1-C20 alkyl, C3-C20 cycloalkyl, C3-C20 heterocycloalkyl; C5-C15 aryl, and C2-C15 heteroaryl.
In some embodiments, L is
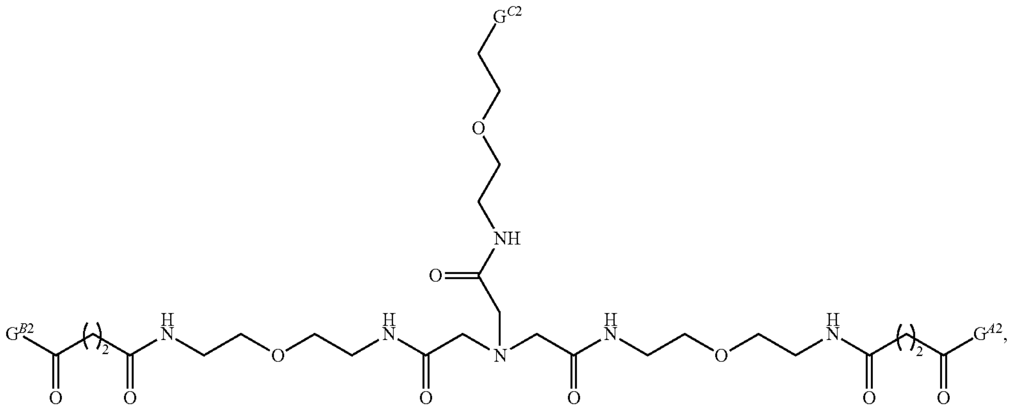
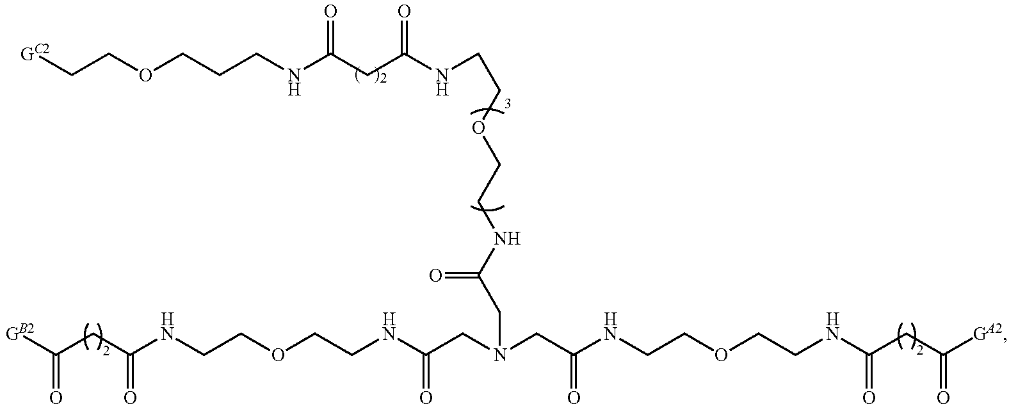
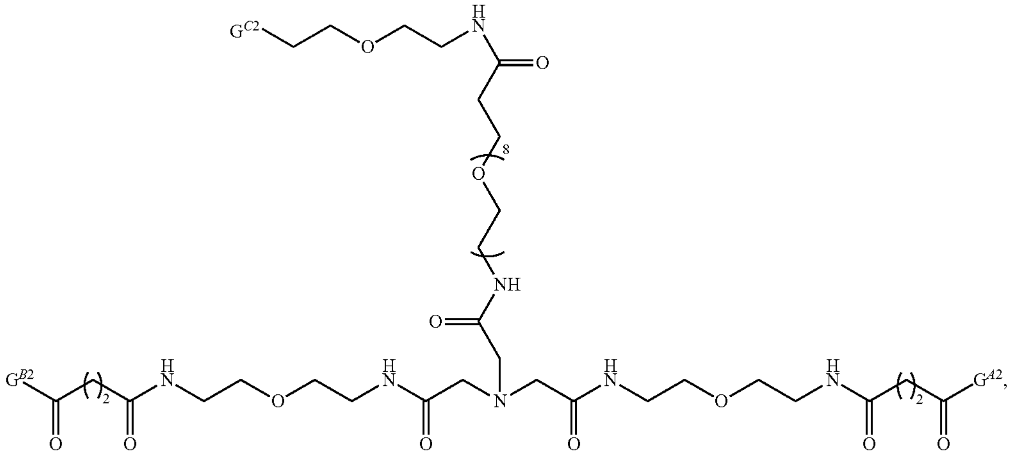

-continued
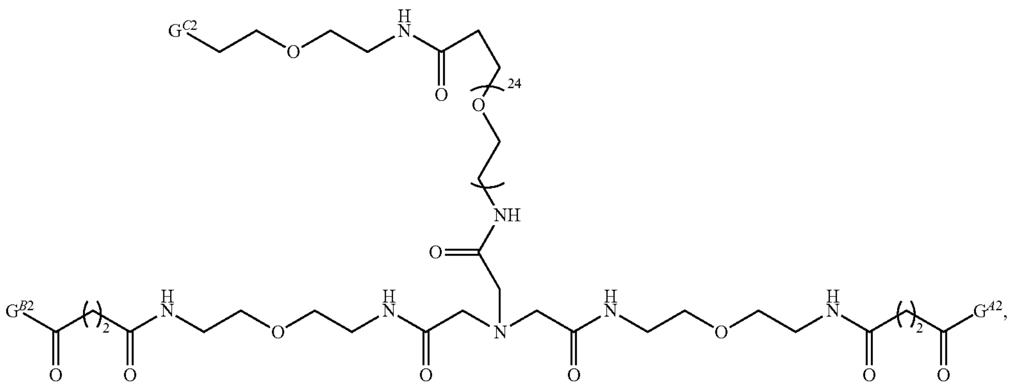
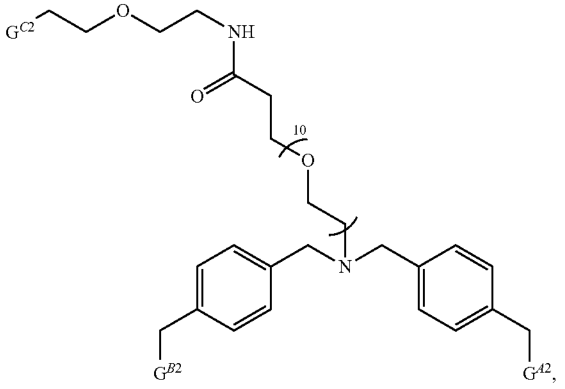
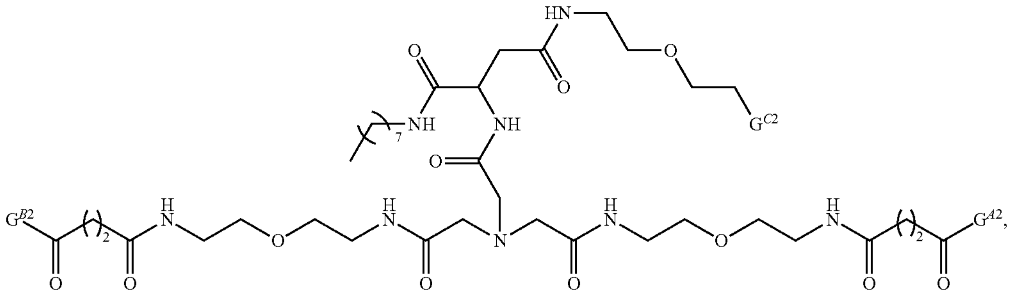
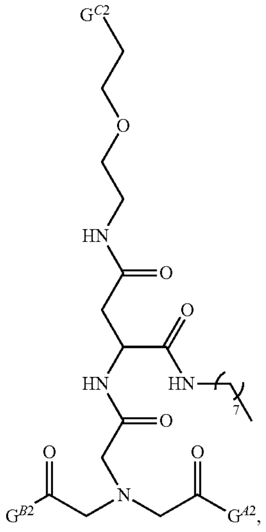
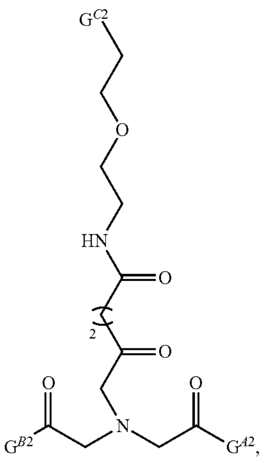
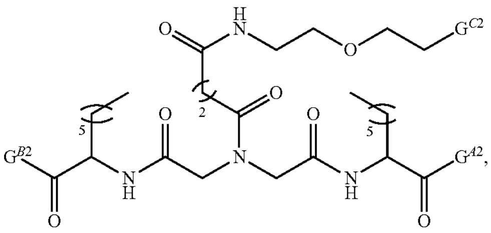

-continued
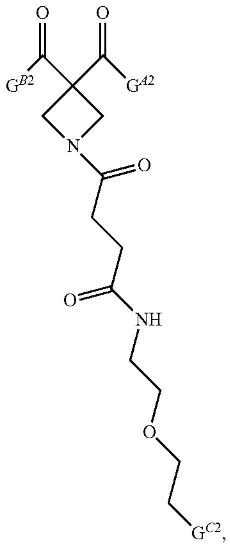
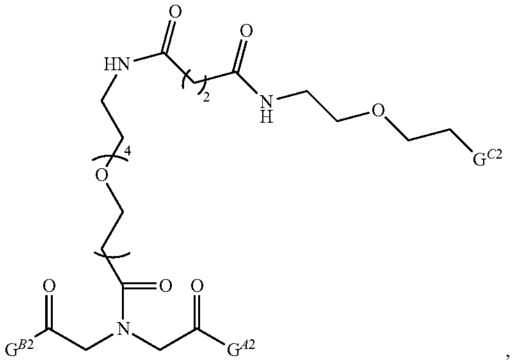
,
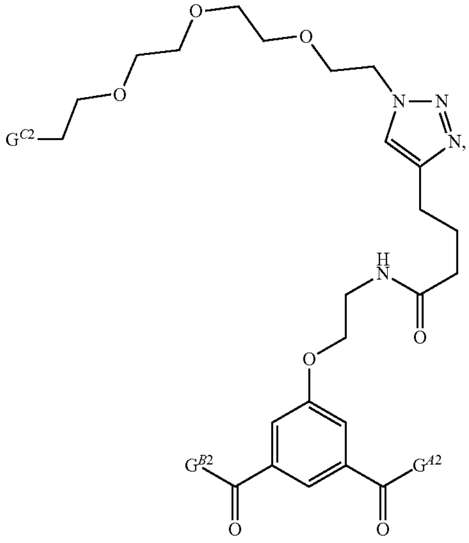
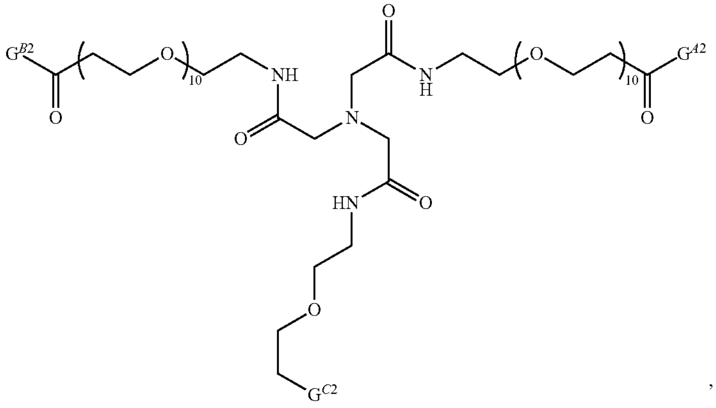
,
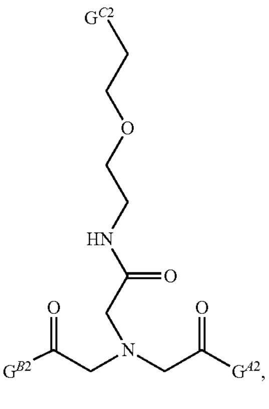

-continued
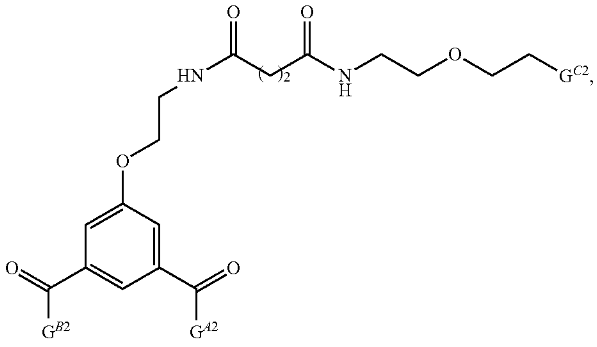
,
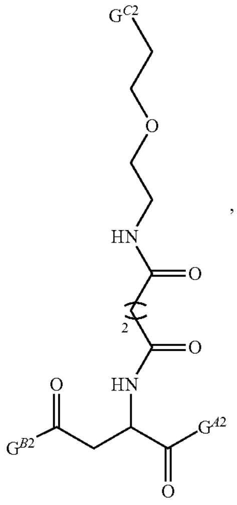
,
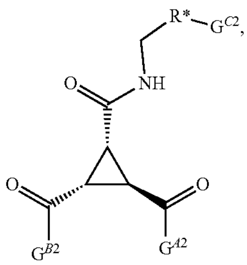
,
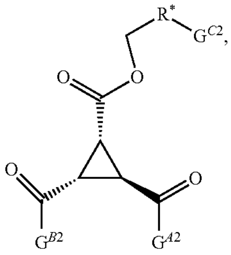
,
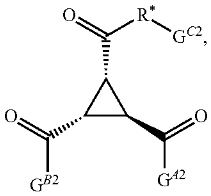
,
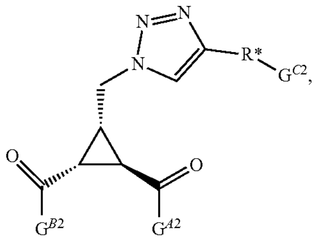
,
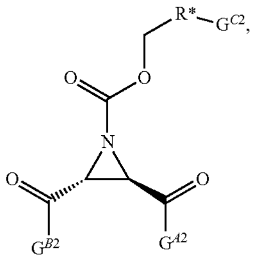
,
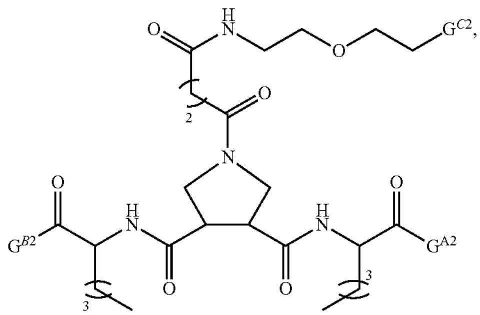
,
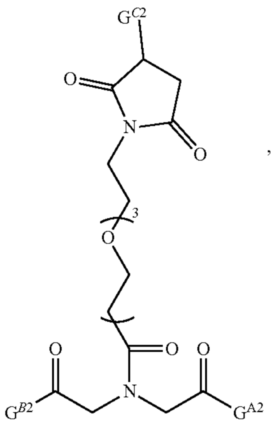
, -continued
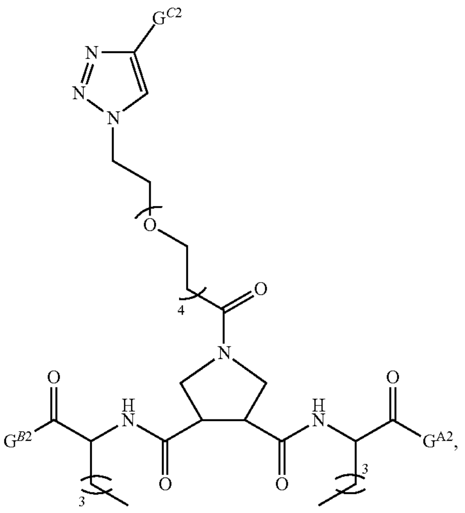
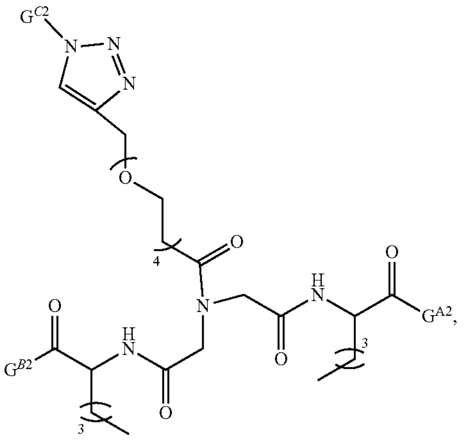
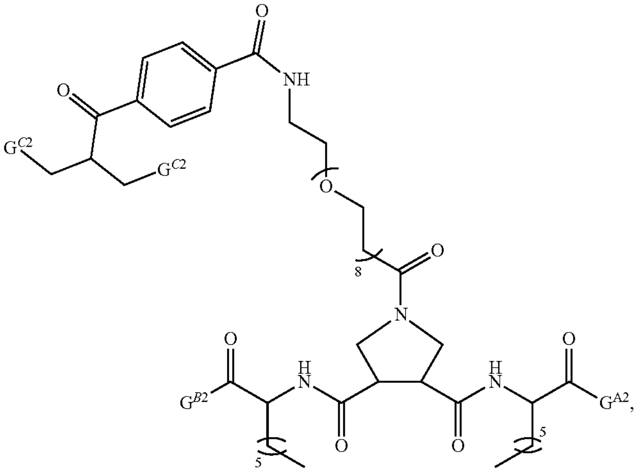
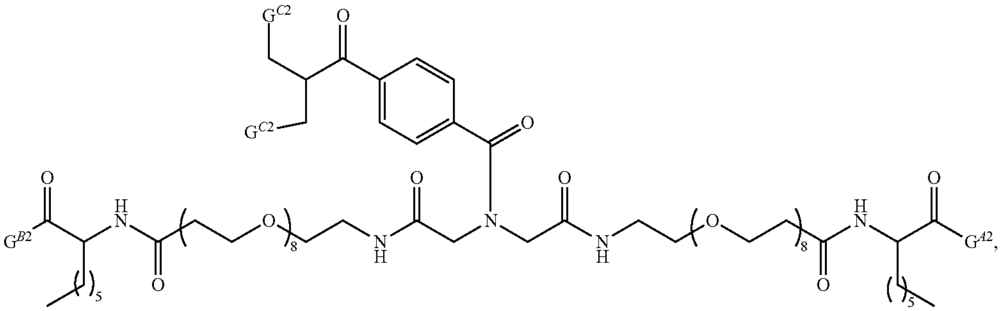
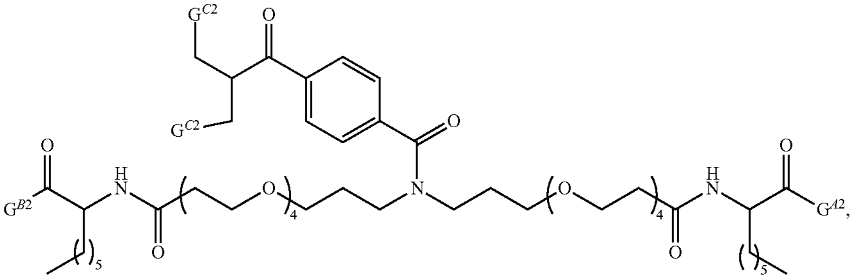

-continued
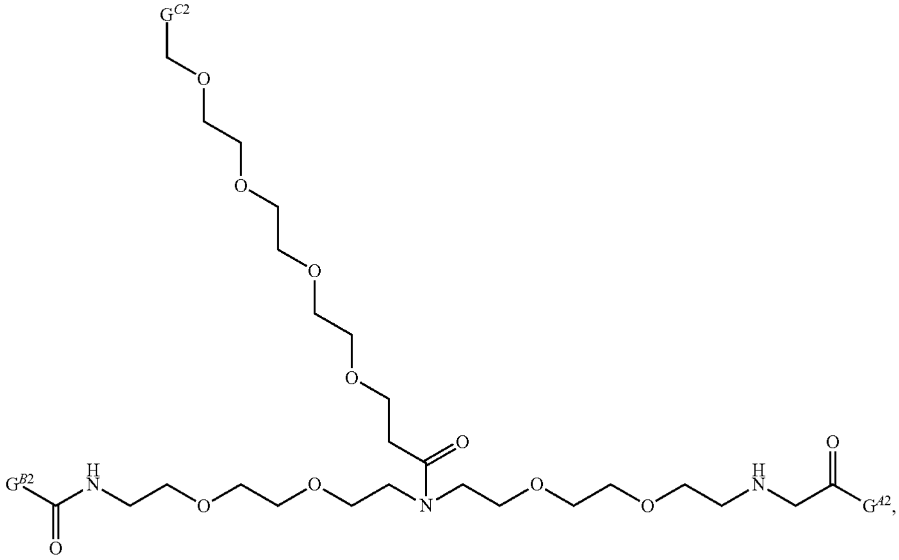
,
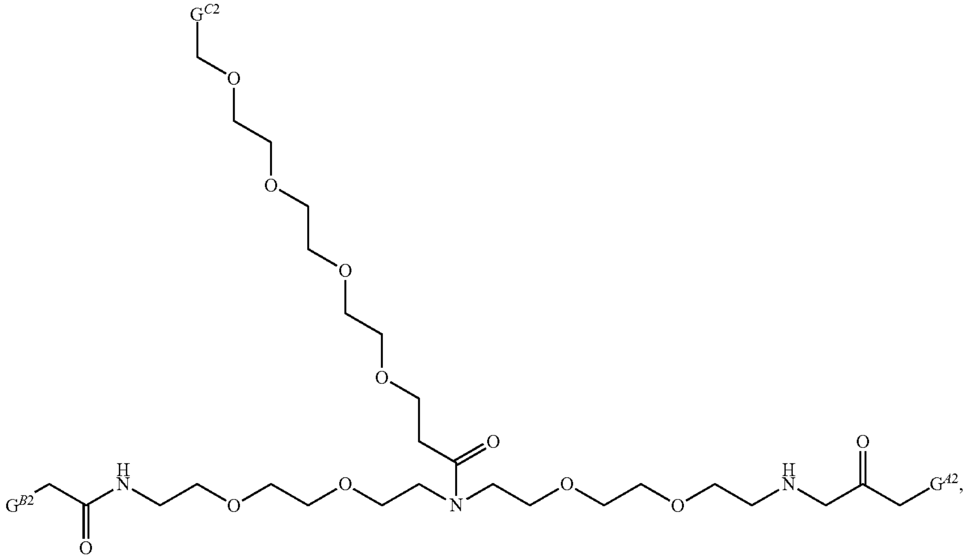
,
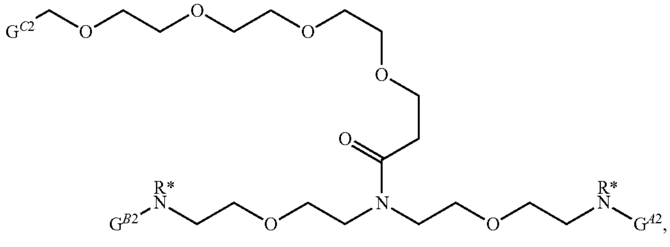
,
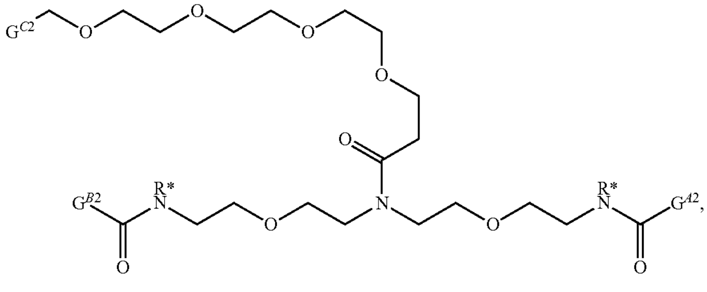
,

-continued
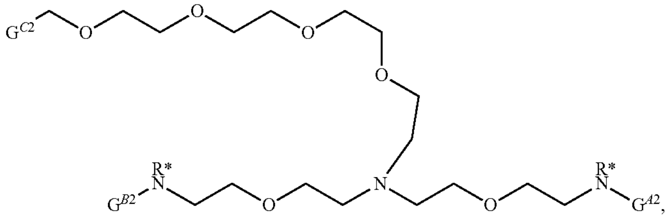
,
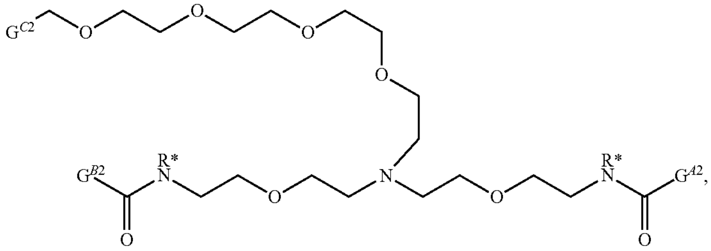
,
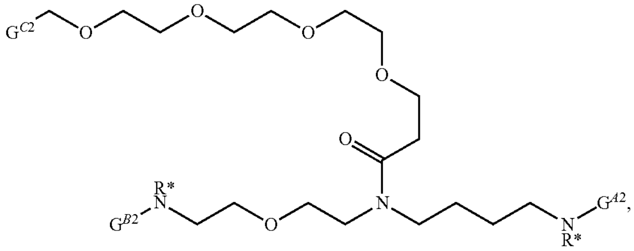
,
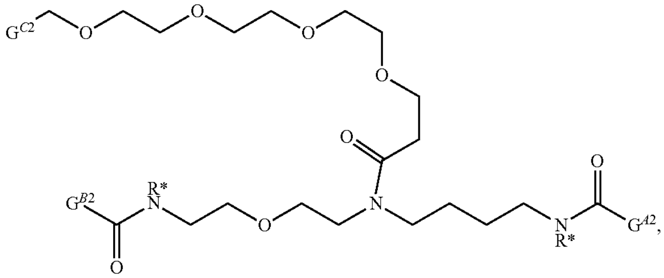
,
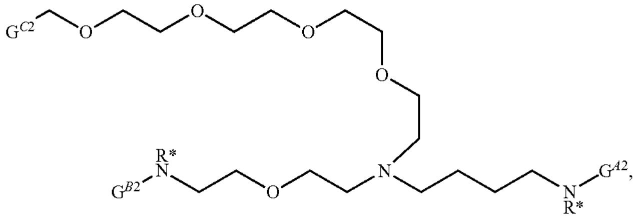
,
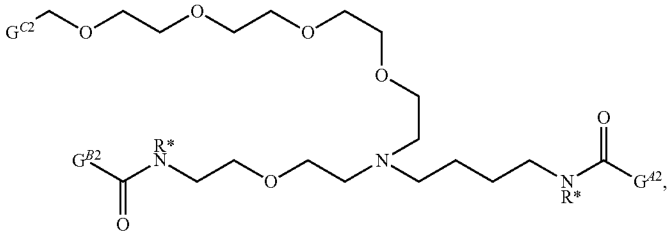
,
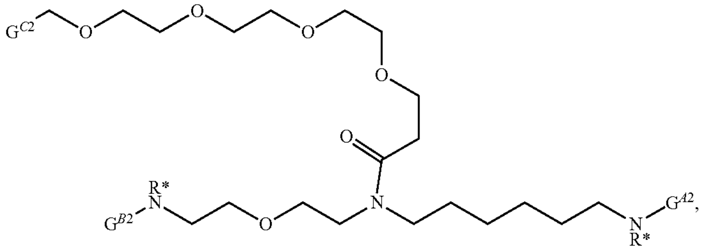
, -continued
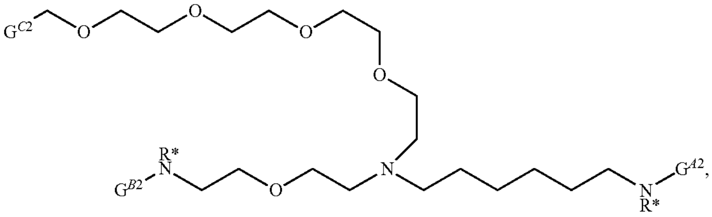
,
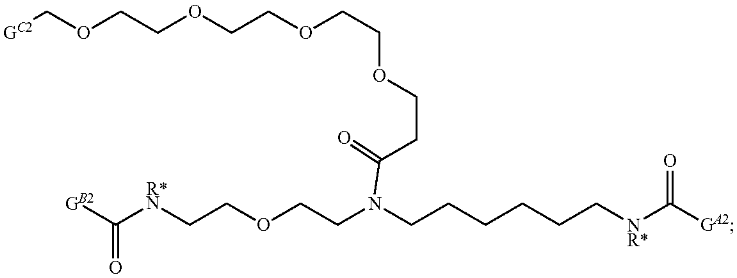
;
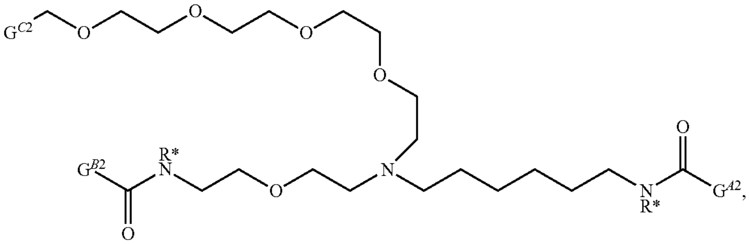
,
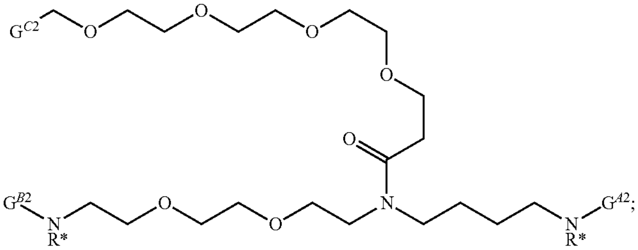
;
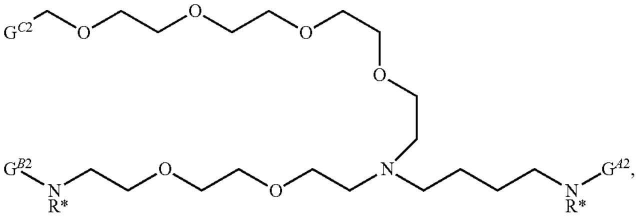
,
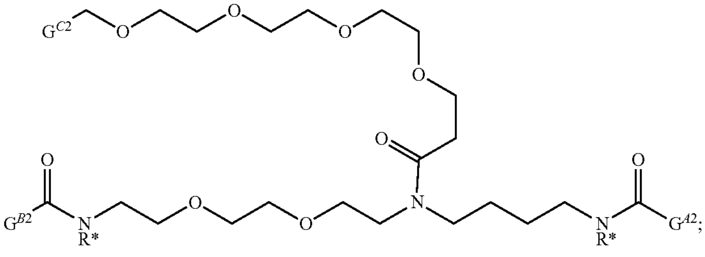
;
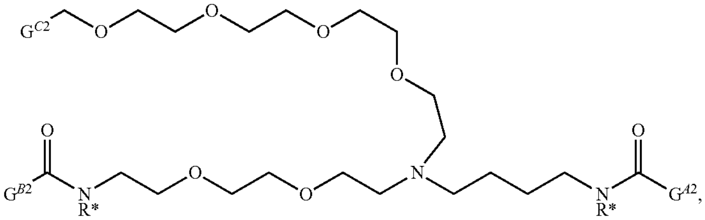
, -continued

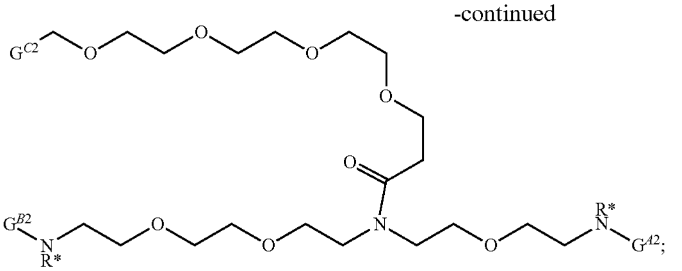

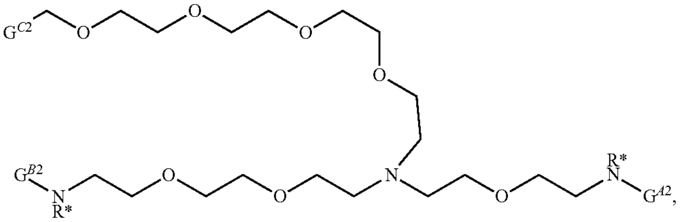

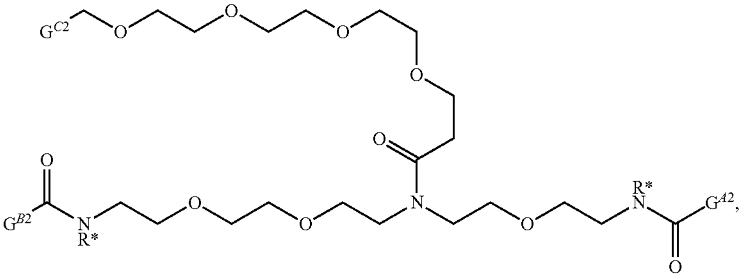

or

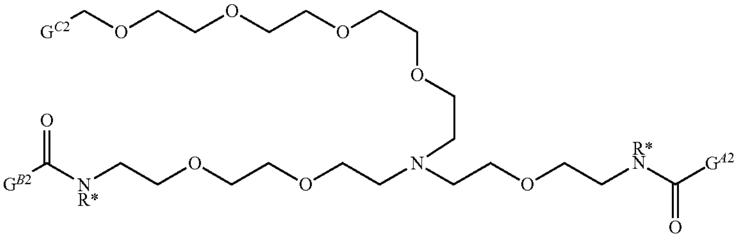

wherein R* is a bond or includes one or more of optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, and imino, and wherein $R_i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments, Y is:

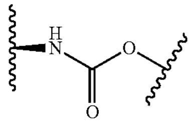

(—NH(C═O)O—) and L is:

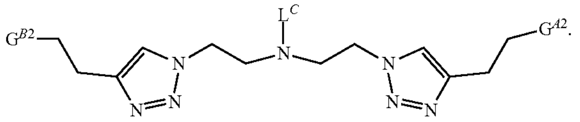

In some embodiments, Y is:

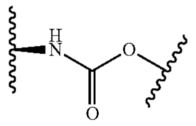

(—NH(C═O)O—) and L is:

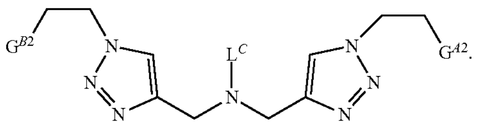
In some embodiments, Y is:
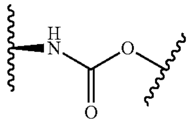
(—NH(C═O)O—) and L is:
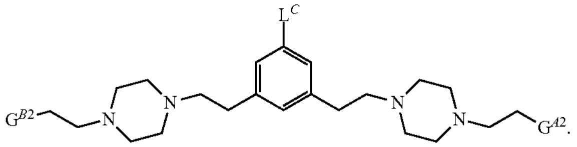
In some embodiment, Y is:
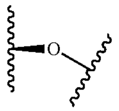
(—O—) and L is:
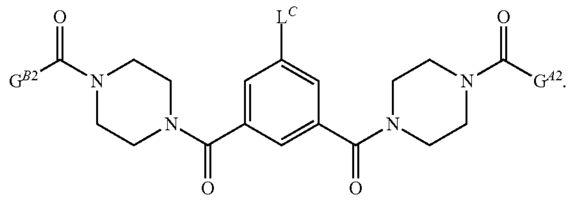
In another aspect, the invention features a conjugate described by formula (M-I):
(M-I)
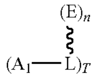
wherein each $A_1$ is independently selected from any one of formulas (A-I)-(A-XII):
(A-I)
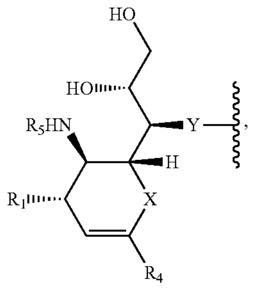
(A-II)
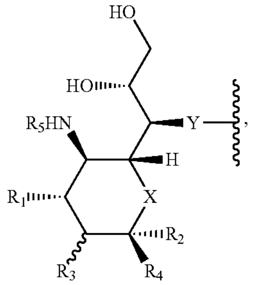
(A-III)
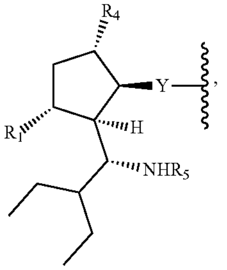
(A-IV)
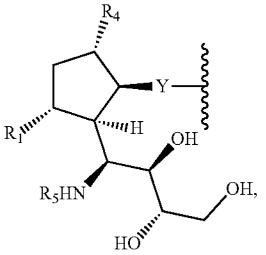
(A-V)
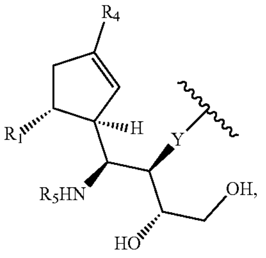

-continued
(A-VI)
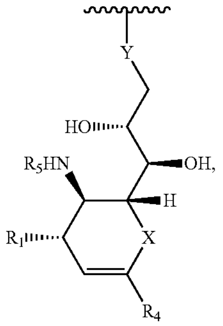
(A-VII)
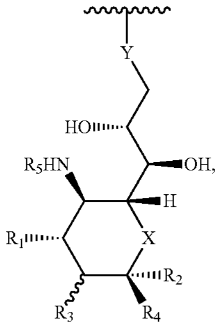
(A-VIII)
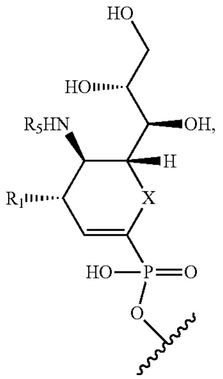
(A-IX)
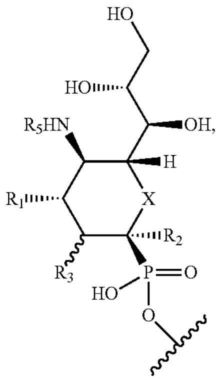
-continued
(A-X)
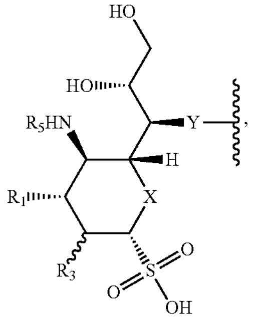
(A-XI)
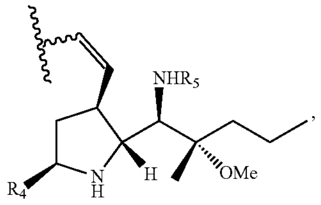
(A-XII)
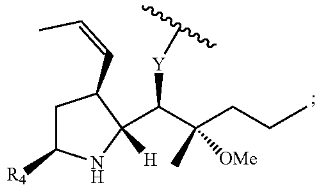
wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from
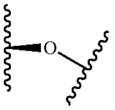
(—O—),
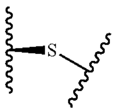
(—S—),
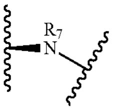
(—$NR_7$—),
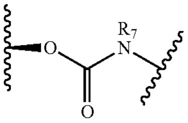
(—O(C=O)$NR_7$—),
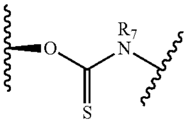
(—O(C=S)$NR_7$—),
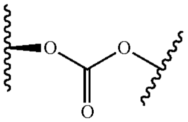
(—O(C=O)O—),
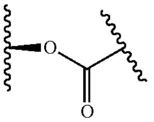
(—O(C=O)—), -continued
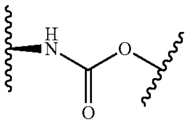
(—NH(C═O)O—),
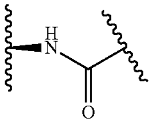
(—NH(C═O)—),
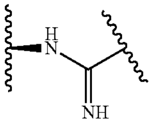
(—NH(C═NH)—),
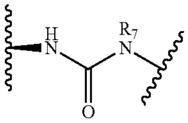
(—NH(C═O)$NR_7$—),
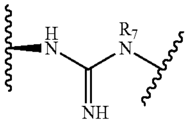
(—NH(C═NH)$NR_7$—),
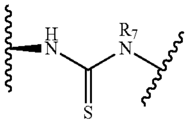
(—NH(C═S)$NR_7$—),
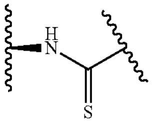
(—NH(C═S)—),
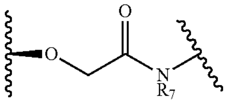
(—$OCH_2$(C═O)$NR_7$—),
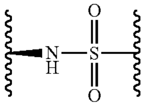
(—NH($SO_2$)—),
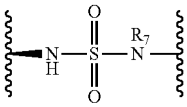
(—NH($SO_2$)$NR_7$—),
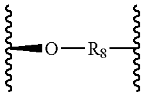
(—$OR_8$—),
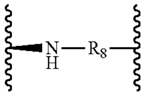
(—$NR_8$—), and
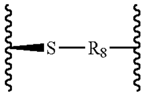
(—$SR_8$—);
$R_6$ is selected from
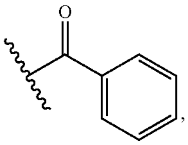
,
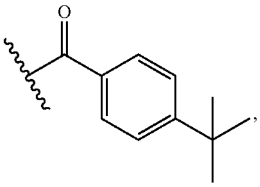
,
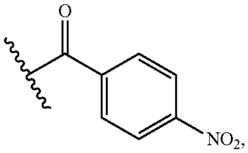
,
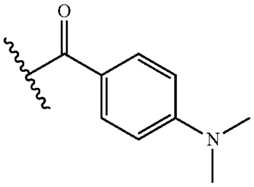
,
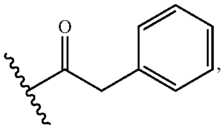
,
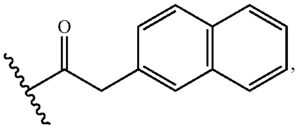
,
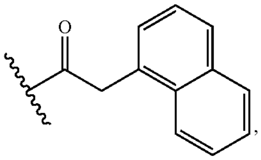
,
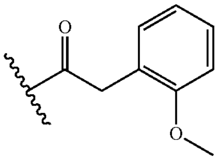
,
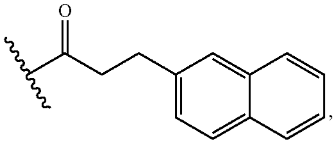
,
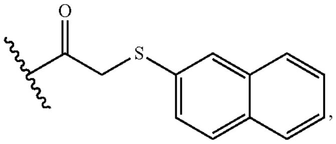
,
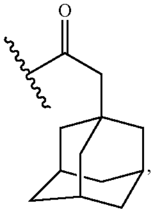
,
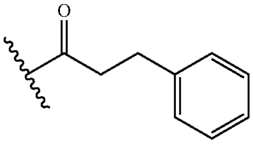
,
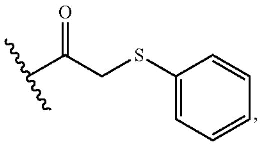
,
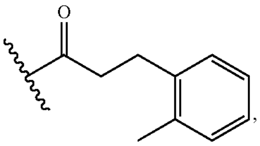
,
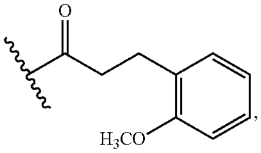
,
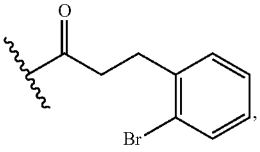
,
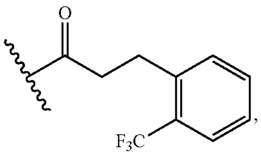
, -continued

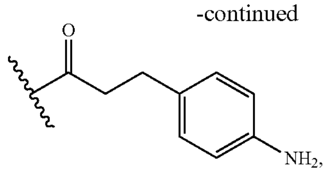

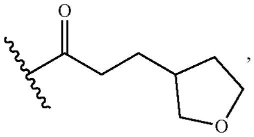,
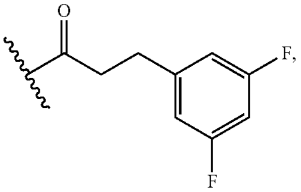

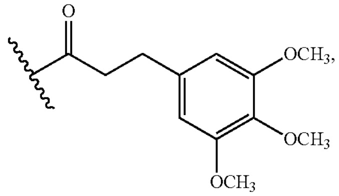

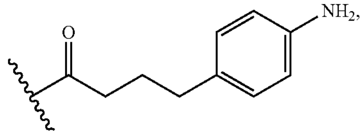

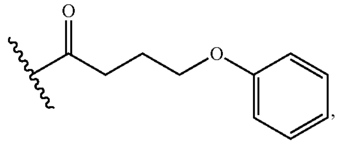

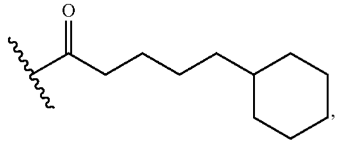

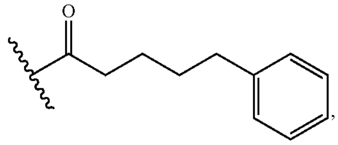

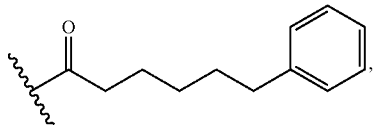

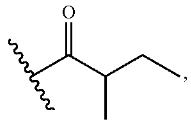,
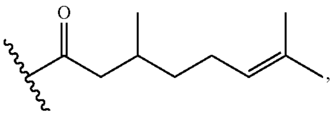

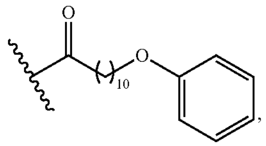
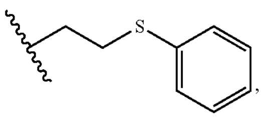

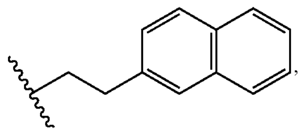, and
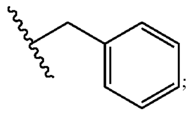;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68), an albumin protein (e.g., an albumin protein having the sequence of any one of SEQ ID NOs: 69-71), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E and $A_1$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-XII).

In another aspect, the invention features a conjugate described by formula (M-I):

(M-I)

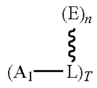

wherein each $A_1$ is independently selected from any one of formulas (A-I)-(A-V):

(A-I)

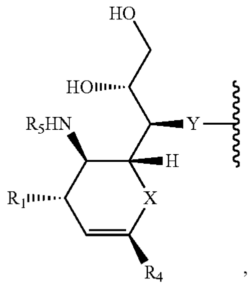, (A-II)

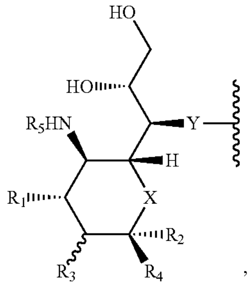, (A-III)

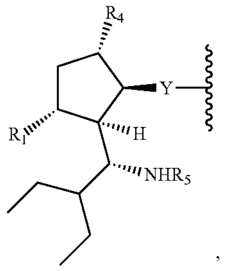,

-continued (A-IV)

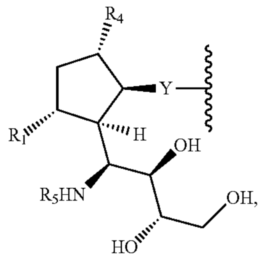

(A-V)

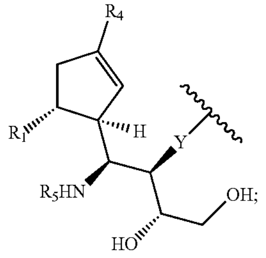

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

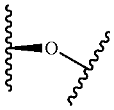
(—O—),

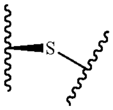
(—S—),

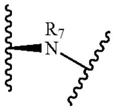
(—$NR_7$—),

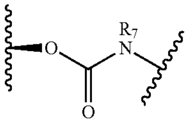
(—O(C=O)$NR_7$—),

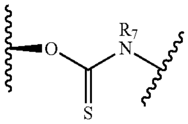
(—O(C=S)$NR_7$—),

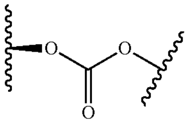
(—O(C=O)O—),

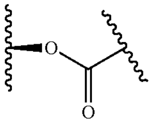
(—O(C=O)—),

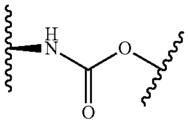
(—NH(C=O)O—),

-continued

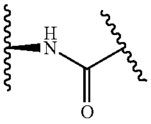
(—NH(C=O)—),

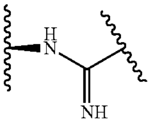
(—NH(C=NH)—),

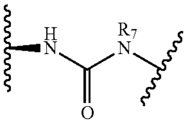
(—NH(C=O)$NR_7$—),

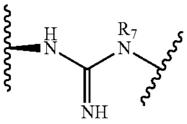
(—NH(C=NH)$NR_7$—),

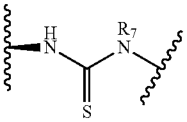
(—NH(C=S)$NR_7$—),

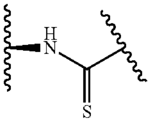
(—NH(C=S)—),

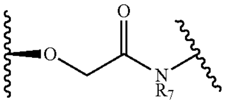
(—$OCH_2$(C=O)$NR_7$—),

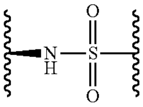
(—NH($SO_2$)—),

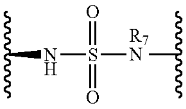
(—NH($SO_2$)$NR_7$—),

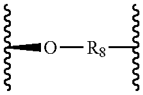
(—$OR_8$—),

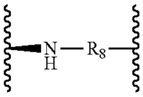
(—$NR_8$—), and

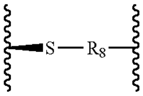
(—$SR_8$—);

$R_6$ is selected from

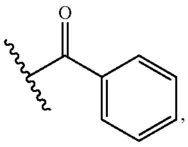
,
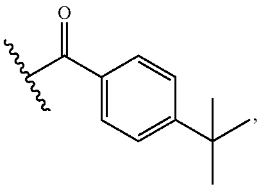
,

-continued

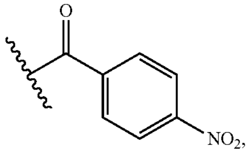
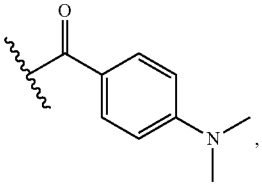
,
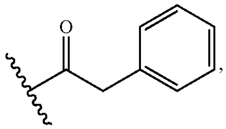
,
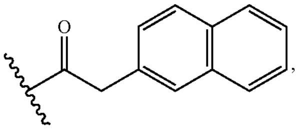
,
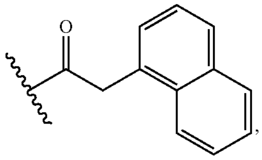
,
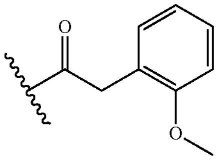
,
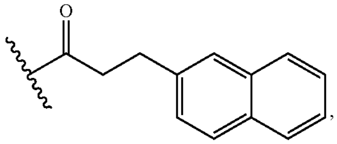
,
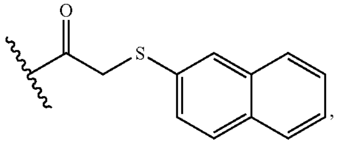
,
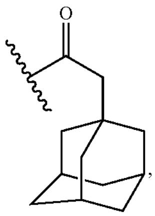
,
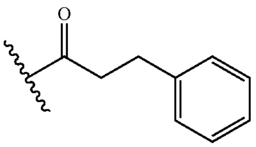
,
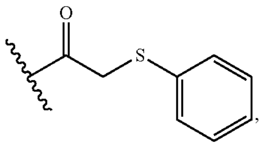
,
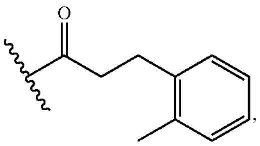
,
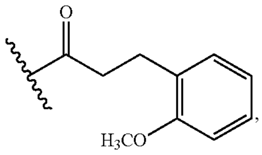
,
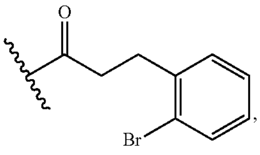
,
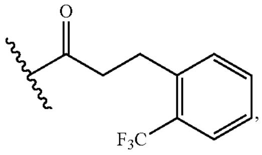
,
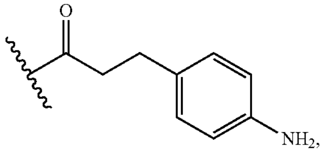

-continued

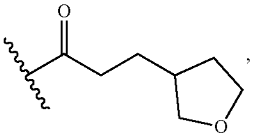
,
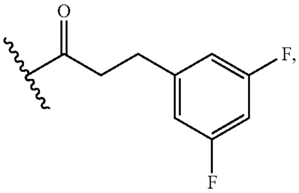
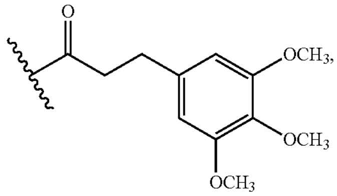
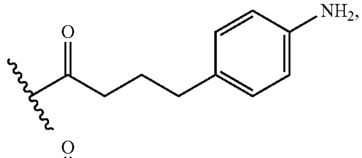
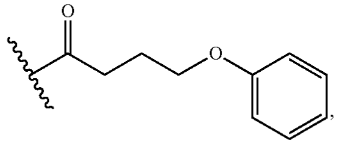
,
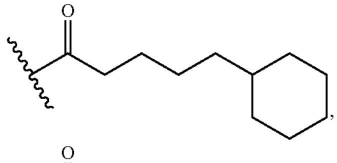
,
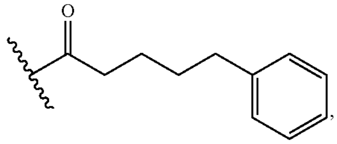
,
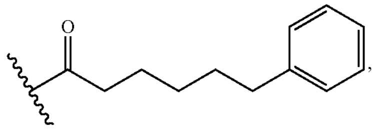
,
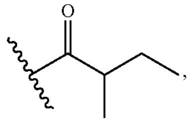
,
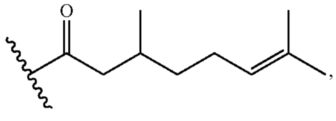
,
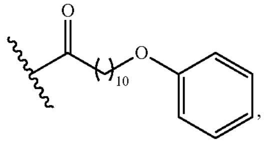
,
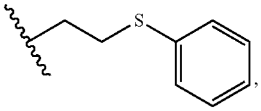
,
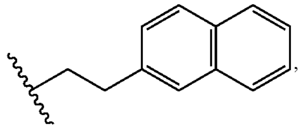
, and
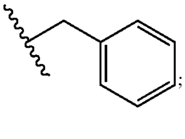
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68), an albumin protein (e.g., an albumin protein having the sequence of any one of SEQ ID NOs: 69-71), an albumin protein-binding peptide, or an Fc-binding peptide; n is 1 or 2; T is an integer from 1 to 20 (e.g., T is 1, 2, 3, 4, 5, 6, 7, 8, 9, 10, 11, 12, 13, 14, 15, 16, 17, 18, 19, or 20); and L is a linker covalently attached to each of E and $A_1$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-I)-(A-V).

In another aspect, the invention features a conjugate described by formula (M-I):

(M-I)

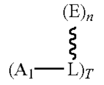

wherein each $A_1$ is independently selected from any one of formulas (A-VI)-(A-IX):

(A-VI)

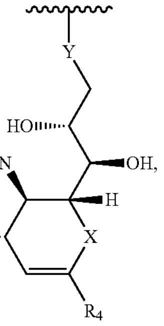

(A-VII)

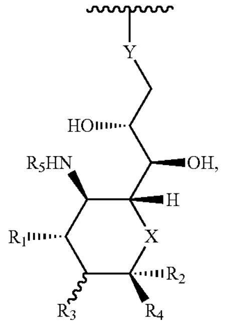

(A-VIII)

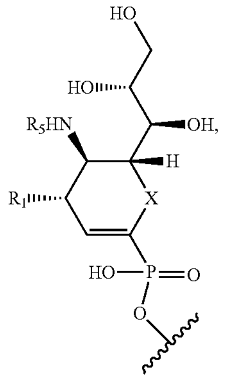

-continued (A-IX)

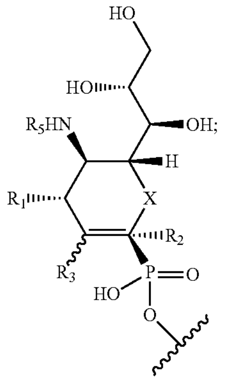

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

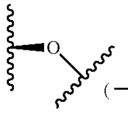 (—O—), 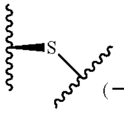 (—S—),

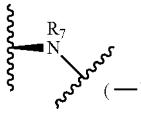 (—$NR_7$—),

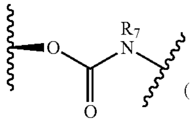 (—O(C=O)$NR_7$—),

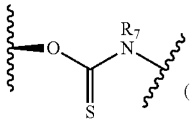 (—O(C=S)$NR_7$—),

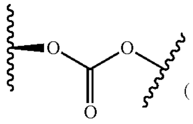 (—O(C=O)O—),

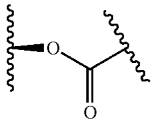 (—O(C=O)—),

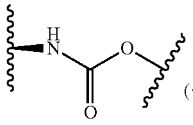 (—NH(C=O)O—),

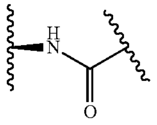 (—NH(C=O)—),

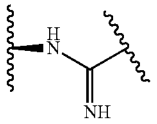 (—NH(C=NH)—),

-continued
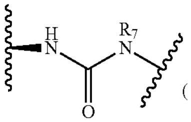
(—NH(C═O)NR7—),
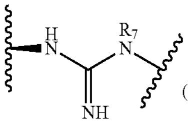
(—NH(C═NH)NR7—),
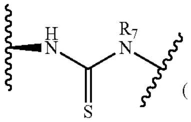
(—NH(C═S)NR7—),
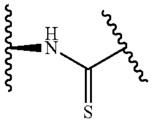
(—NH(C═S)—),
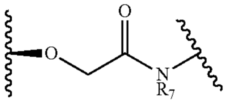
(—OCH2(C═O)NR7—),
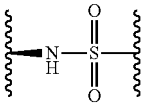
(—NH(SO2)—),
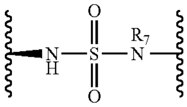
(—NH(SO2)NR7—),
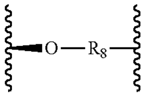
(—OR8—),
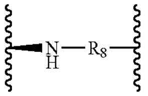
(—NR8—), and
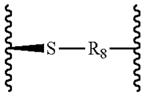
(—SR8—);
$R_6$ is selected from
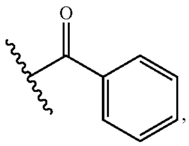
,
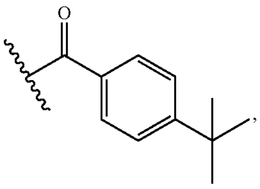
,
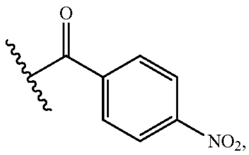
,
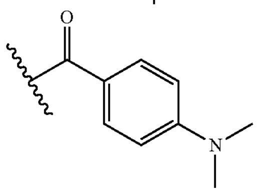
,
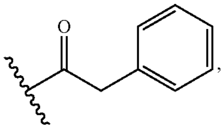
,
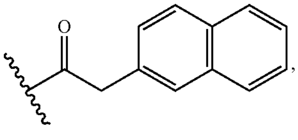
,
-continued
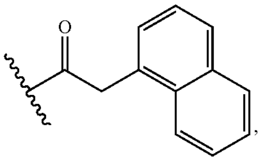
,
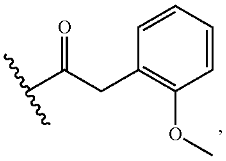
,
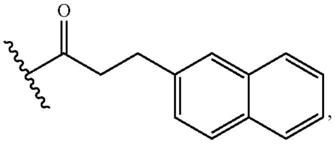
,
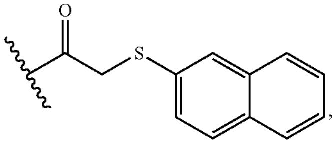
,
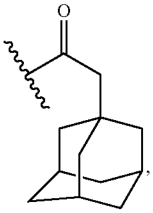
,
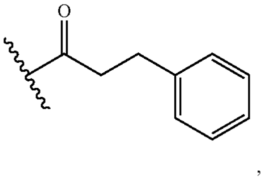
,
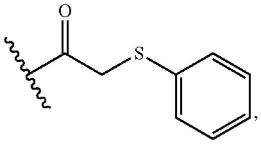
,
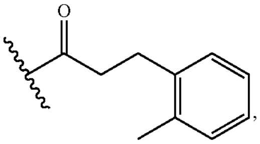
,
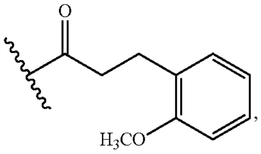
,
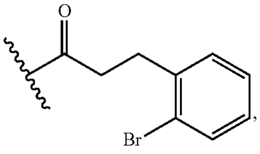
,
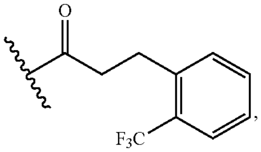
,
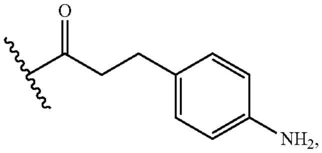
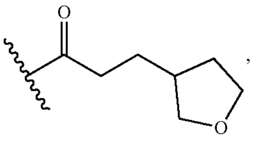
,
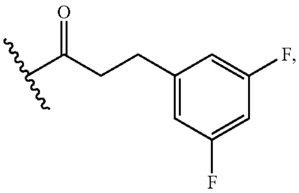
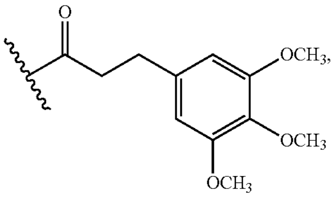

-continued

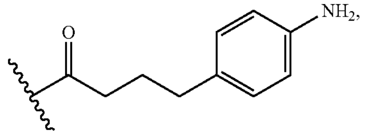

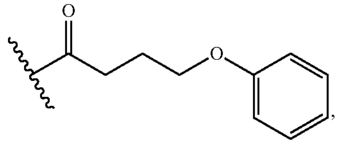,

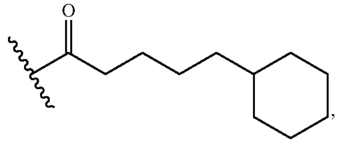,

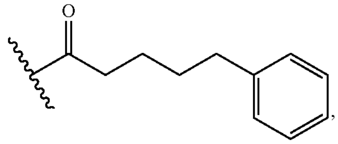,

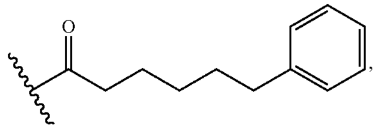,

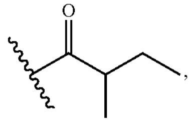, 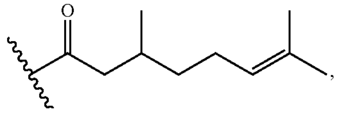,

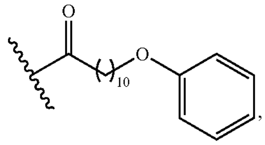, 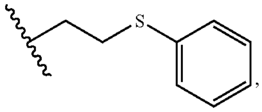,

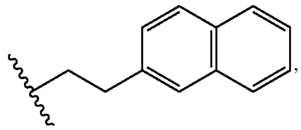, and 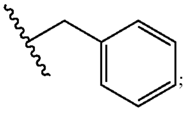;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68), an albumin protein (e.g., an albumin protein having the sequence of any one of SEQ ID NOs: 69-71), an albumin protein-binding peptide, or an Fc-binding peptide; n is 1 or 2; T is an integer from 1 to 20 (e.g., Tis 1, 2, 3, 4, 5, 6, 7, 8, 9, 10, 11, 12, 13, 14, 15, 16, 17, 18, 19, or 20); and L is a linker covalently attached to each of E and $A_1$, or a pharmaceutically acceptable salt thereof. When T is greater than 1 (e.g., T is 2, 3, 4, 5, 6, 7, 8, 9, 10, 11, 12, 13, 14, 15, 16, 17, 18, 19, or 20), each $A_1$ may be independently selected from any one of formulas (A-VI)-(A-IX).

In some embodiments, the conjugate is described by formula (M-II):

(M-II)

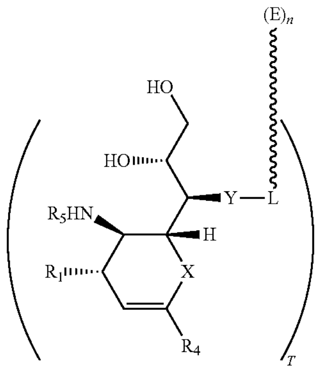

or a pharmaceutically acceptable salt thereof.

In some embodiments, the conjugate is described by formula (M-II-1):

(M-II-1)

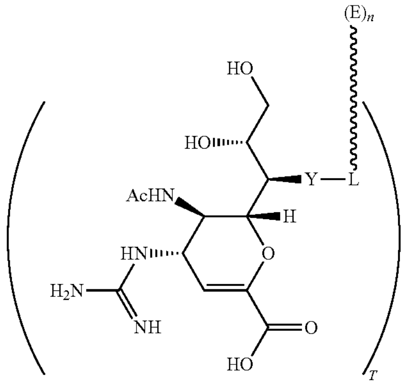

or a pharmaceutically acceptable salt thereof.

In some embodiments, the conjugate is described by formula (M-II-2):

(M-II-2)

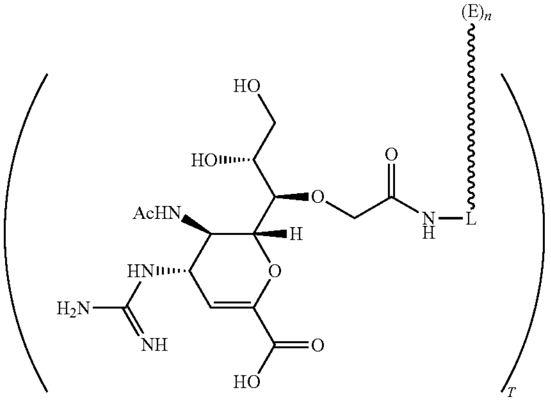

or a pharmaceutically acceptable salt thereof.

In some embodiments, the conjugate is described by formula (M-II-3):

(M-II-3)

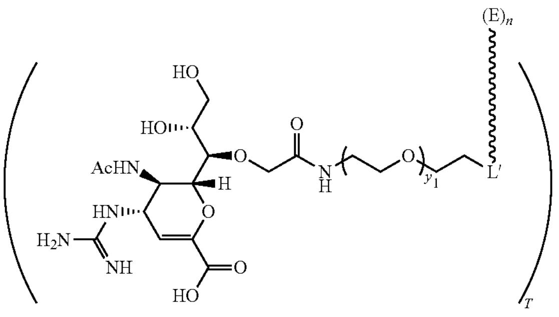

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-II-4):

(M-II-4)

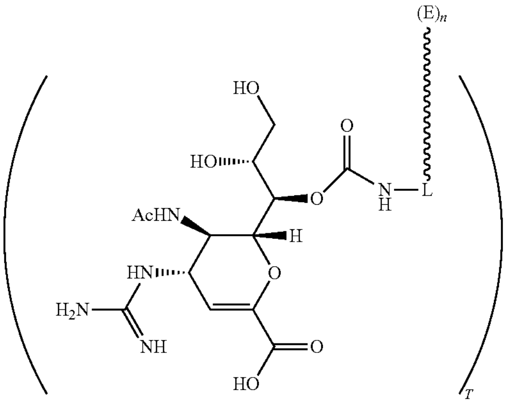

or a pharmaceutically acceptable salt thereof.

In some embodiments, the conjugate is described by formula (M-II-5):

(M-II-5)

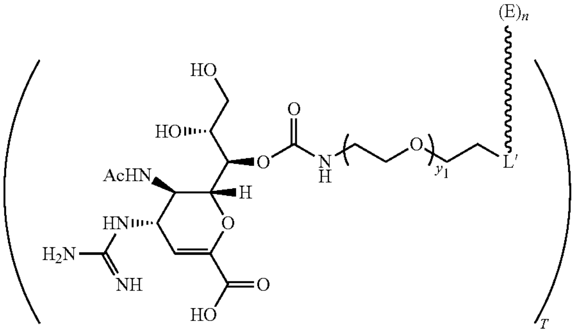

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate has the structure

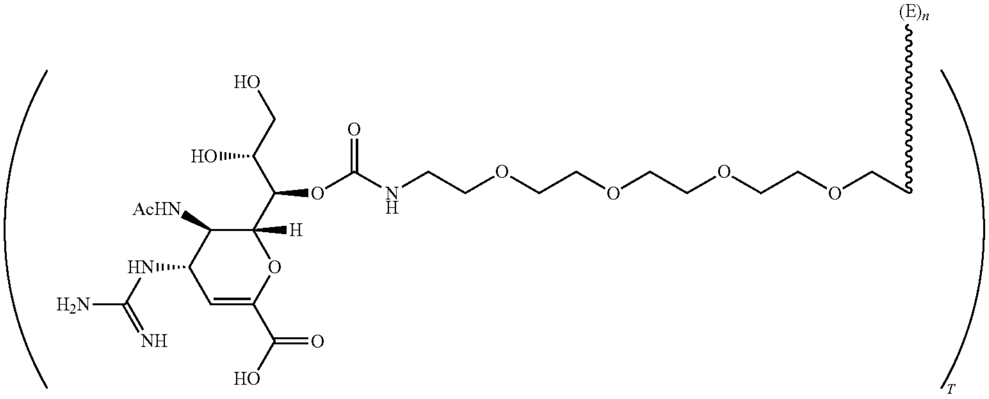

, or a pharmaceutically acceptable salt thereof.

In some embodiments, the conjugate is described by formula (M-II-6):

(M-II-6)

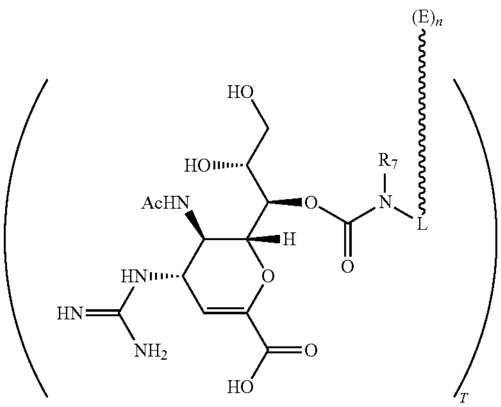

;

wherein $R_7$ is selected from H, C1-C20 alkyl, C3-C20 cycloalkyl, C3-C20 heterocycloalkyl; C5-C15 aryl, and C2-C15 heteroaryl; or a pharmaceutically acceptable salt thereof.

In some embodiments, the conjugate is described by formula (M-II-7):

(M-II-7)

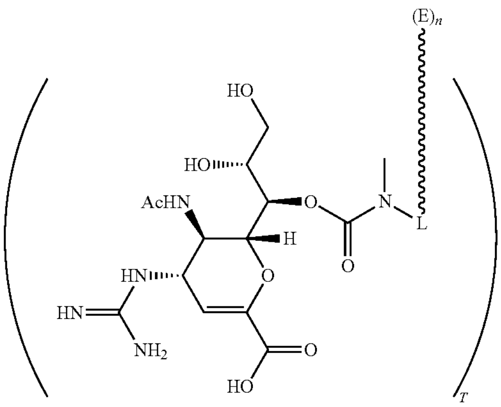

or a pharmaceutically acceptable salt thereof.

In some embodiments, the conjugate is described by formula (M-II-8):

(M-II-8)

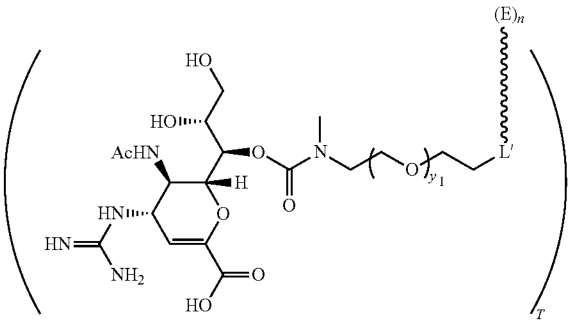

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate has the structure

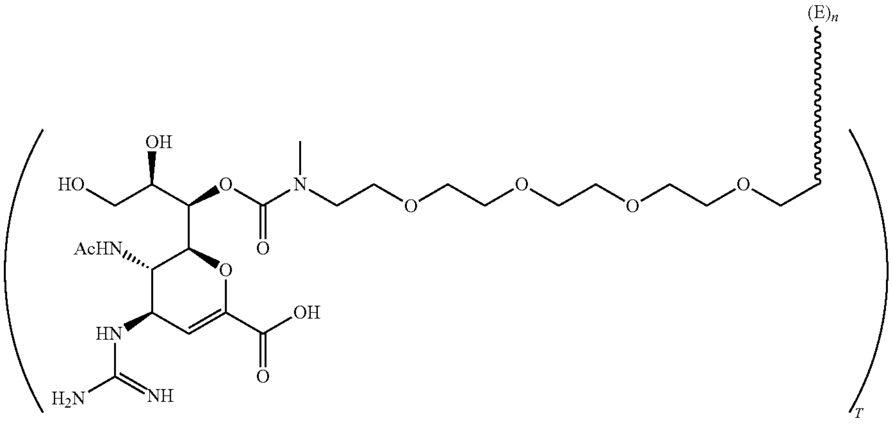

.

In some embodiments, the conjugate is described by formula (M-II-9):

(M-II-9)

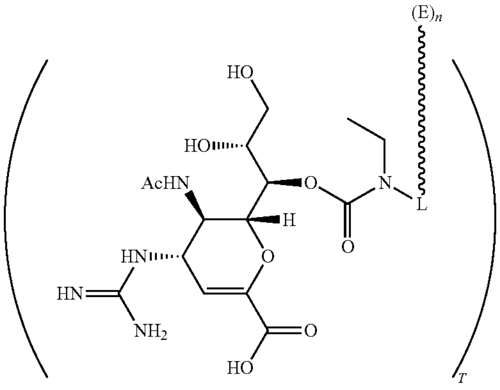

;

or a pharmaceutically acceptable salt thereof.

In some embodiments, the conjugate is described by formula (M-II-10):

(M-II-10)

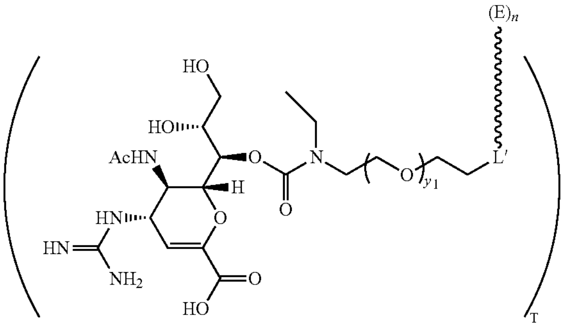

;

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate has the structure

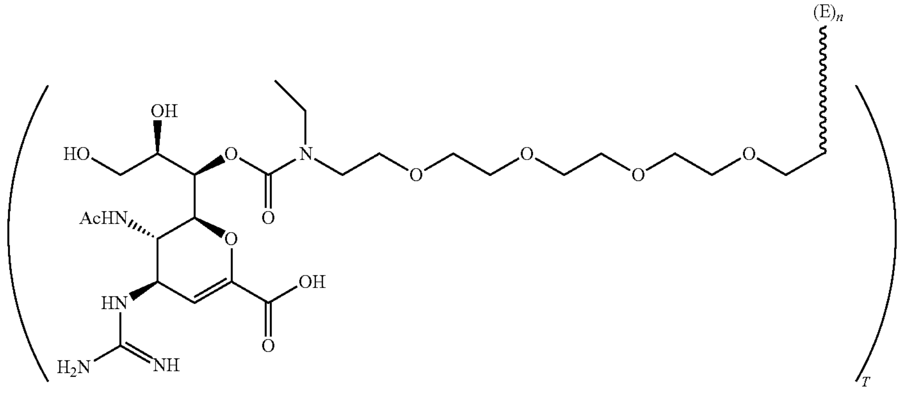

or a pharmaceutically acceptable salt thereof.

In some embodiments, the conjugate is described by formula (M-III):

(M-III)

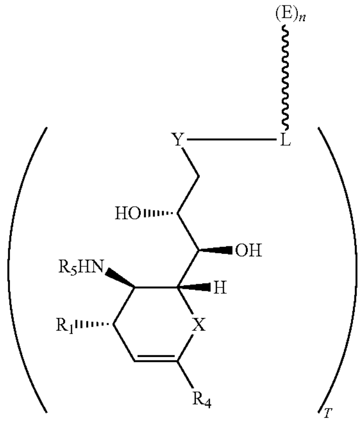

or a pharmaceutically acceptable salt thereof.

In some embodiments, the conjugate is described by formula (M-III-1):

(M-III-1)

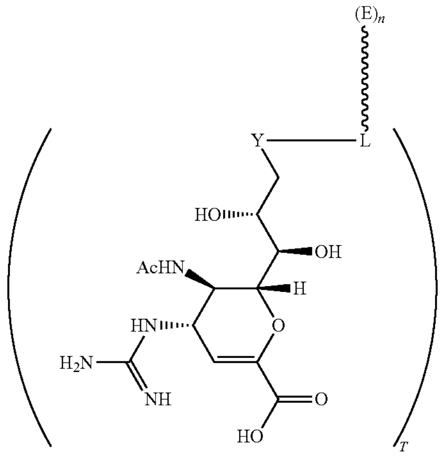

or a pharmaceutically acceptable salt thereof.

In some embodiments, the conjugate is described by formula (M-III-2):

(M-III-2)

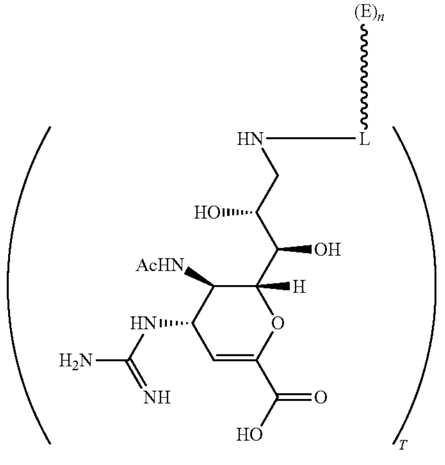

or a pharmaceutically acceptable salt thereof.

In some embodiments, the conjugate is described by formula (M-III-3):

(M-III-3)

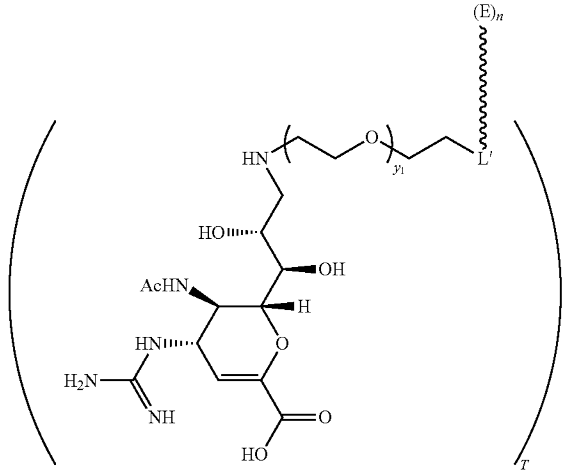

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-III-4):

(M-III-4)

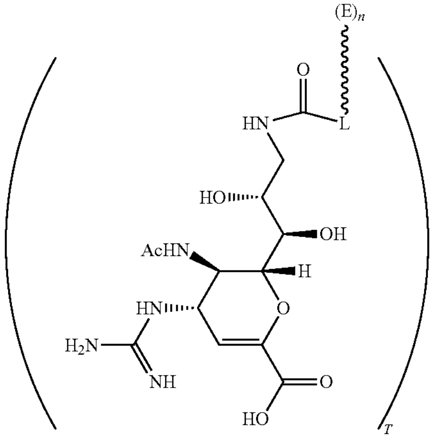

or a pharmaceutically acceptable salt thereof.

In some embodiments, the conjugate is described by formula (M-III-5):

(M-III-5)

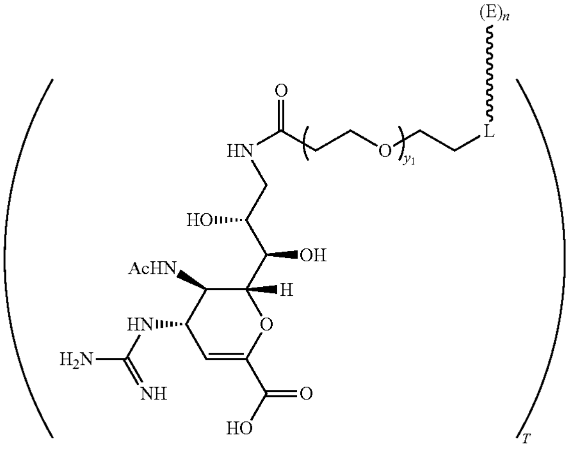

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-III-6):

(M-III-6)

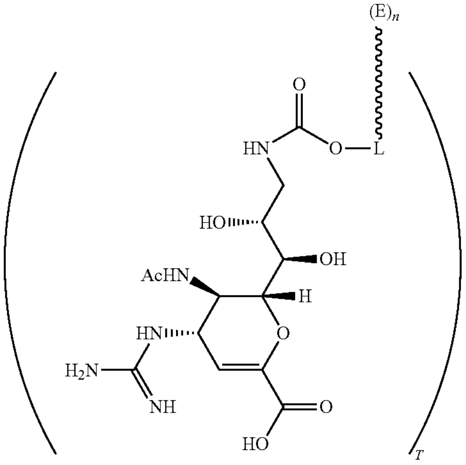

or a pharmaceutically acceptable salt thereof.

In some embodiments, the conjugate is described by formula (M-III-7):

(M-III-7)

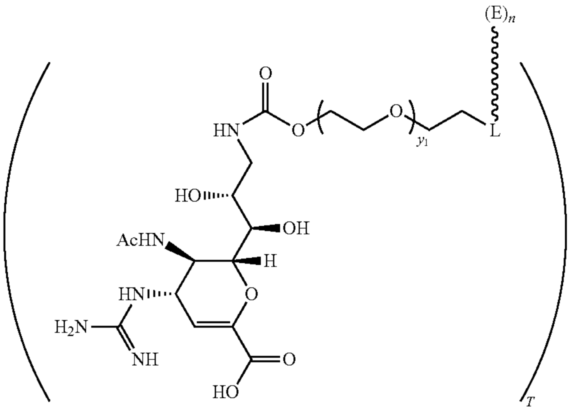

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-III-8):

(M-III-8)

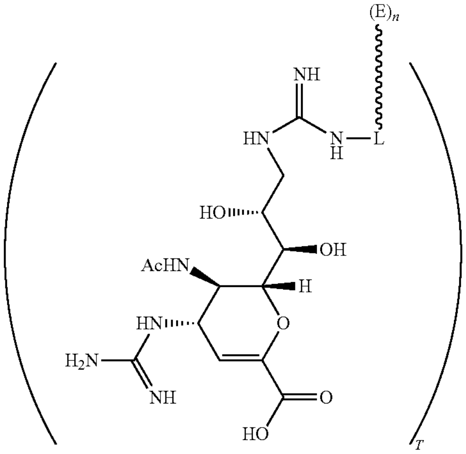

or a pharmaceutically acceptable salt thereof.

In some embodiments, the conjugate is described by formula (M-III-9):

(M-III-9)

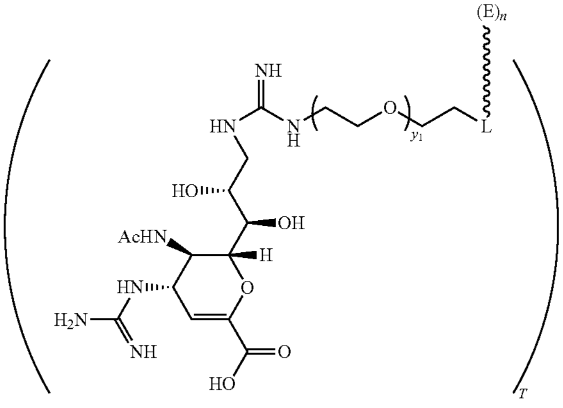

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-IV):

(M-IV)

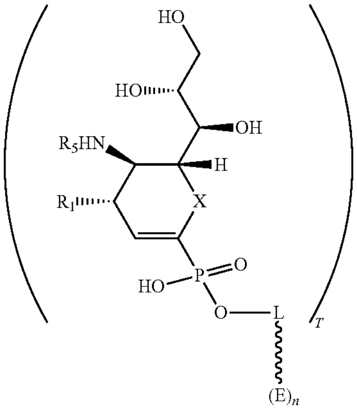

or a pharmaceutically acceptable salt thereof.

In some embodiments, the conjugate is described by formula (M-IV-1):

(M-IV-1)

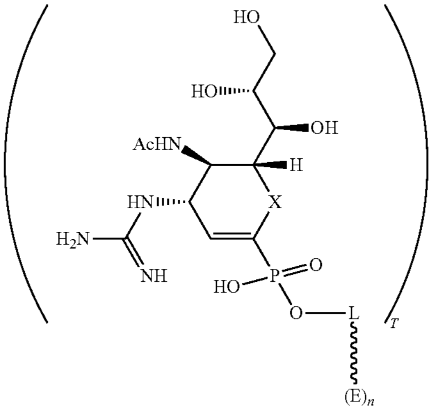

or a pharmaceutically acceptable salt thereof.

In some embodiments, the conjugate is described by formula (M-IV-2):

(M-IV-2)

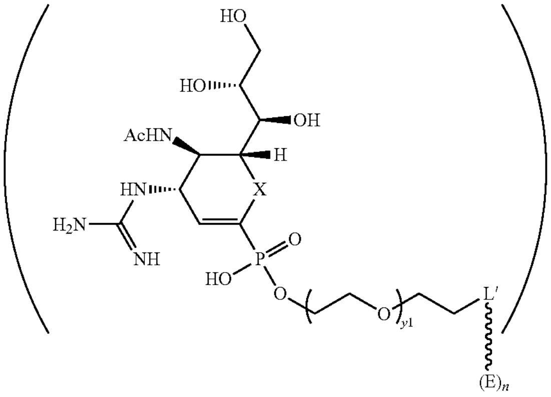

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-V):

(M-V)

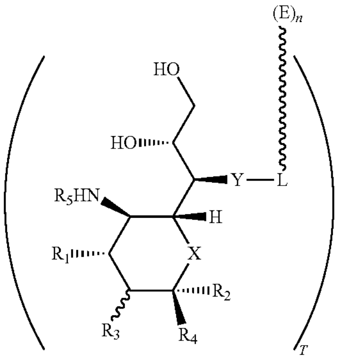

or a pharmaceutically acceptable salt thereof.

In some embodiments, the conjugate is described by formula (M-V-1):

(M-V-1)

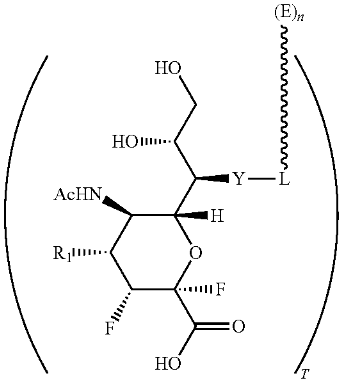

or a pharmaceutically acceptable salt thereof.

In some embodiments, the conjugate is described by formula (M-V-2):

(M-V-2)

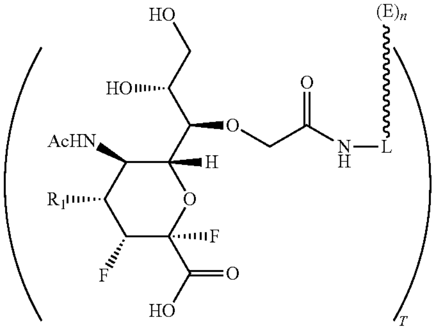

or a pharmaceutically acceptable salt thereof.

In some embodiments, the conjugate is described by formula (M-V-3):

(M-V-3)

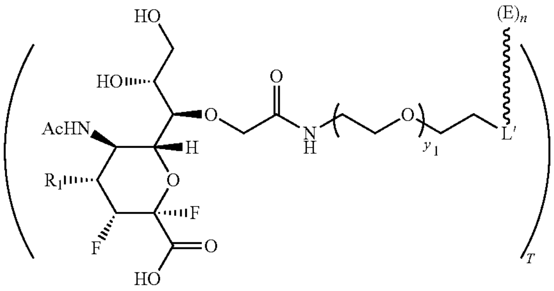

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-V-4):

(M-V-4)

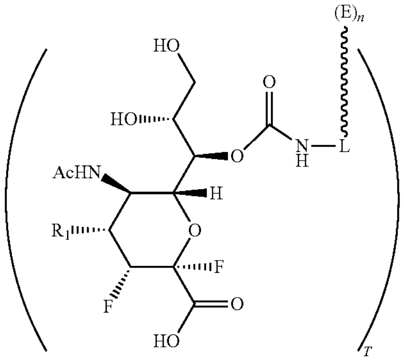

or a pharmaceutically acceptable salt thereof.

In some embodiments, the conjugate is described by formula (M-V-5):

(M-V-5)

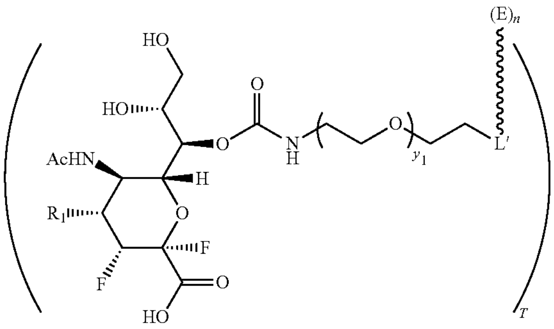

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-V-6):

(M-V-6)

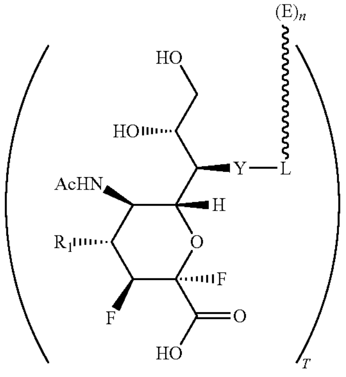

or a pharmaceutically acceptable salt thereof.

In some embodiments, the conjugate is described by formula (M-V-7):

(M-V-7)

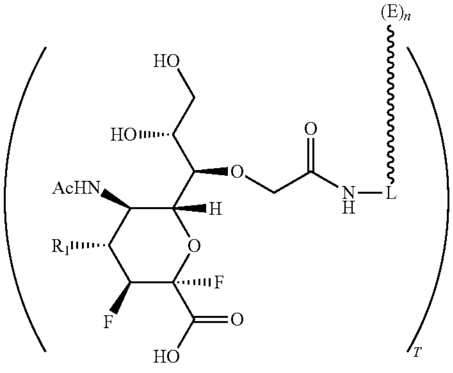

or a pharmaceutically acceptable salt thereof.

In some embodiments, the conjugate is described by formula (M-V-8):

(M-V-8)

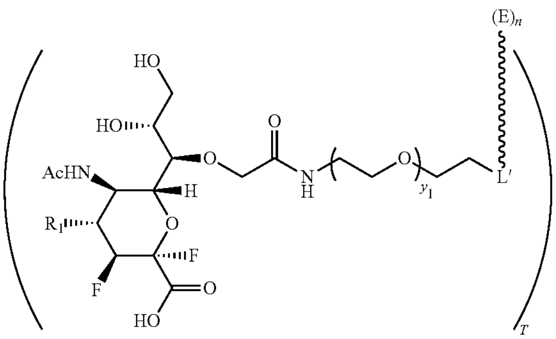

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-V-9):

(M-V-9)

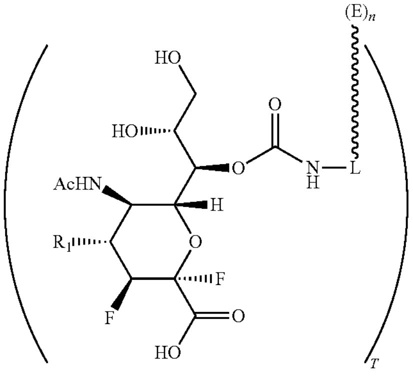

or a pharmaceutically acceptable salt thereof.

In some embodiments, the conjugate is described by formula (M-V-10):

(M-V-10)

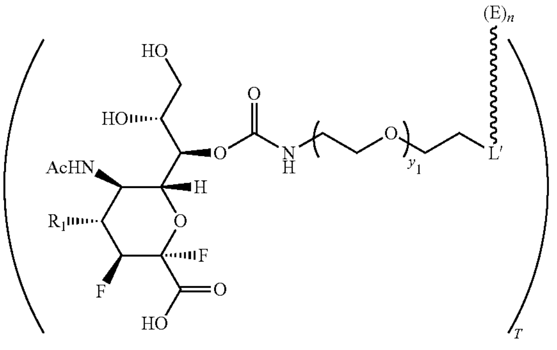

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VI):

(M-VI)

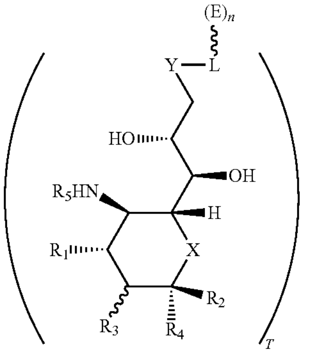

or a pharmaceutically acceptable salt thereof.

In some embodiments, the conjugate is described by formula (M-VI-1):

(M-VI-1)

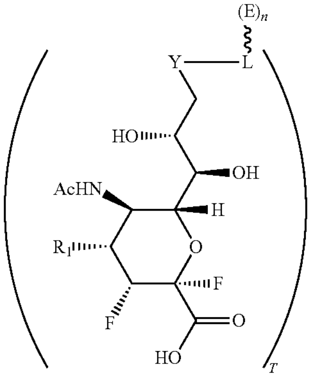

or a pharmaceutically acceptable salt thereof.

In some embodiments, the conjugate is described by formula (M-VI-2):

(M-VI-2)

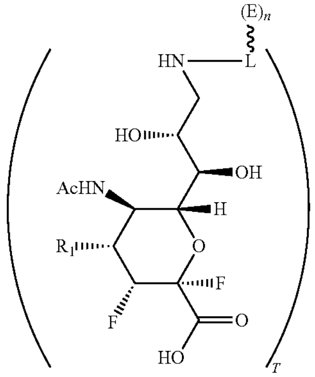

or a pharmaceutically acceptable salt thereof.

In some embodiments, the conjugate is described by formula (M-VI-3):

(M-VI-3)

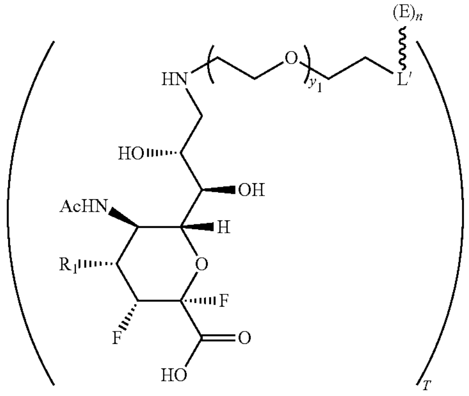

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VI-4):

(M-VI-4)

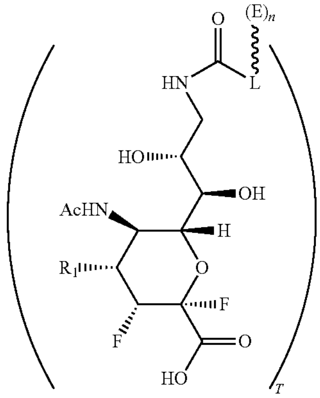

or a pharmaceutically acceptable salt thereof.

In some embodiments, the conjugate is described by formula (M-VI-5):

(M-VI-5)

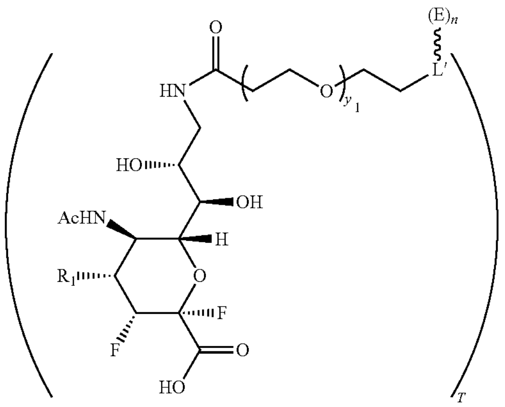

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VI-6):

(M-VI-6)

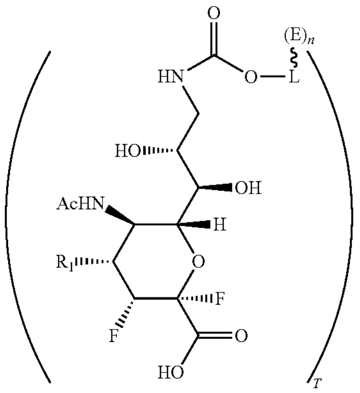

or a pharmaceutically acceptable salt thereof.

In some embodiments, the conjugate is described by formula (M-VI-7):

(M-VI-7)

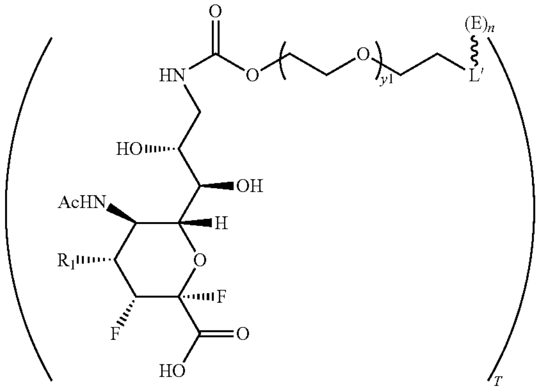

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VI-8):

(M-VI-8)

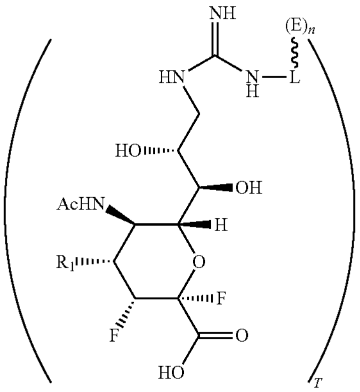

or a pharmaceutically acceptable salt thereof.

In some embodiments, the conjugate is described by formula (M-VI-9):

(M-VI-9)

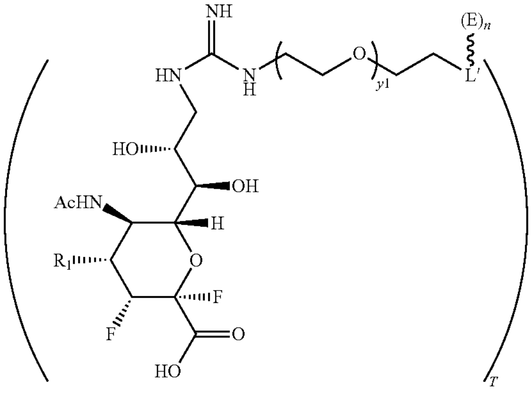

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VII):

(M-VII)

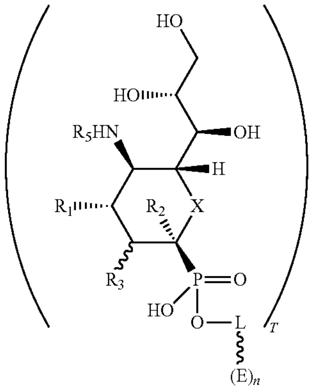

or a pharmaceutically acceptable salt thereof.

In some embodiments of any of the aspects described herein, $R_1$ is OH. In some embodiments of any of the aspects described herein, $R_1$ is $NH_2$. In some embodiments of any of the aspects described herein, $R_1$ is —NHC(═NH)$NH_2$.

In some embodiments, the conjugate is described by formula (M-VIII):

(M-VIII)

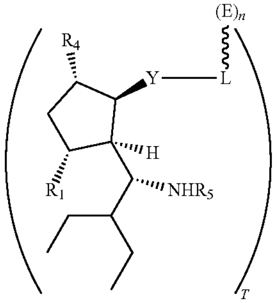

or a pharmaceutically acceptable salt thereof.

In some embodiments, the conjugate is described by formula (M-VIII-1):

(M-VIII-1)

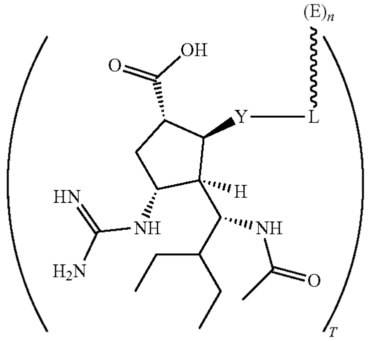

or a pharmaceutically acceptable salt thereof.

In some embodiments, the conjugate is described by (M-VIII-2):

(M-VIII-2)

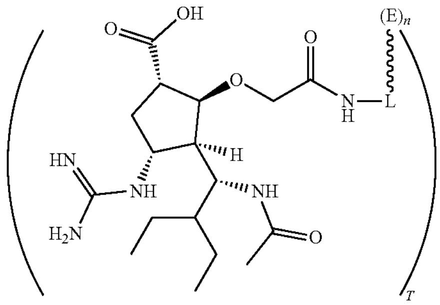

or a pharmaceutically acceptable salt thereof.

In some embodiments, the conjugate is described by formula (M-VIII-3):

(M-VIII-3)

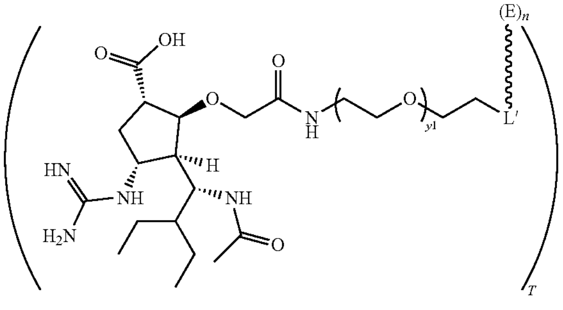

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VIII-4):

(M-VIII-4)

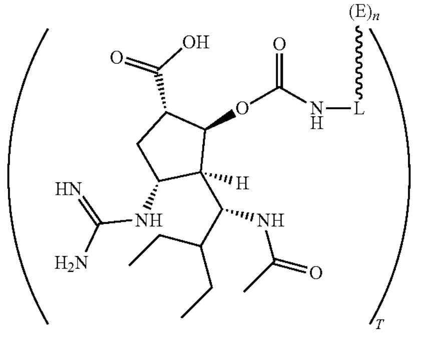

or a pharmaceutically acceptable salt thereof.

In some embodiments, the conjugate is described by formula (M-VIII-5):

(M-VIII-5)

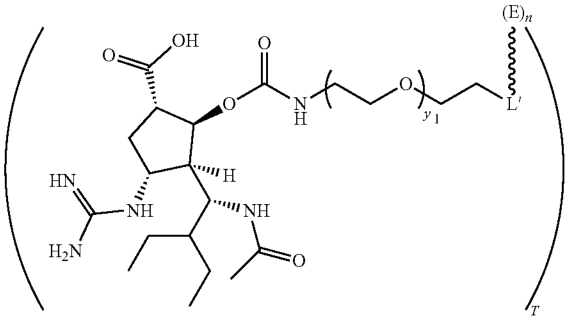

wherein L' is the remainder of L, and $y_1$ is an integer from 1-20, or a pharmaceutically acceptable salt thereof.

In some embodiments, the conjugate has the structure of

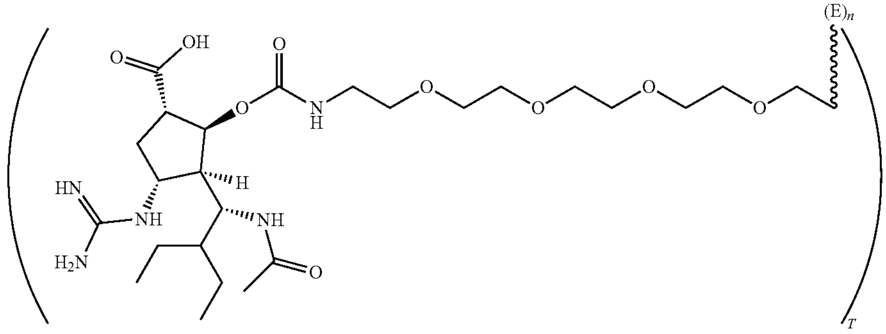

or a pharmaceutically acceptable salt thereof.

In some embodiments, the conjugate is described by formula (M-VIII-6):

(M-VIII-6)

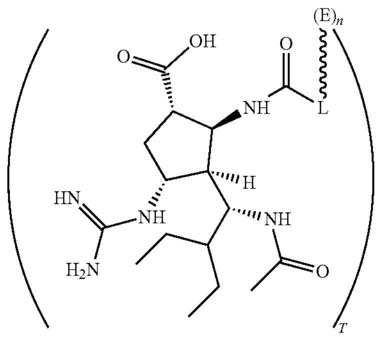

or a pharmaceutically acceptable salt thereof.

In some embodiments, the conjugate is described by formula (M-VIII-7):

(M-VIII-7)

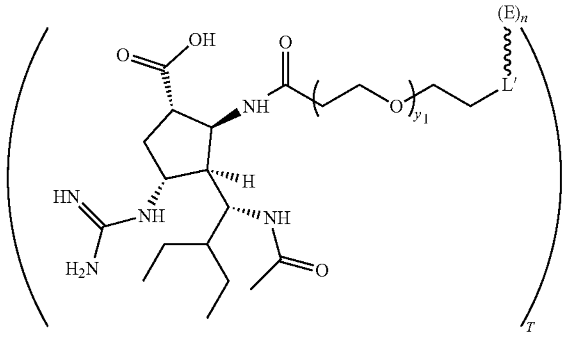

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VIII-8):

(M-VIII-8)

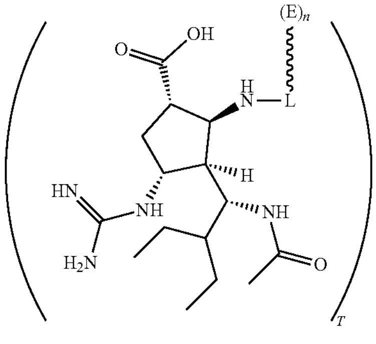

or a pharmaceutically acceptable salt thereof.

In some embodiments, the conjugate is described by formula (M-VIII-9):

(M-VIII-9)

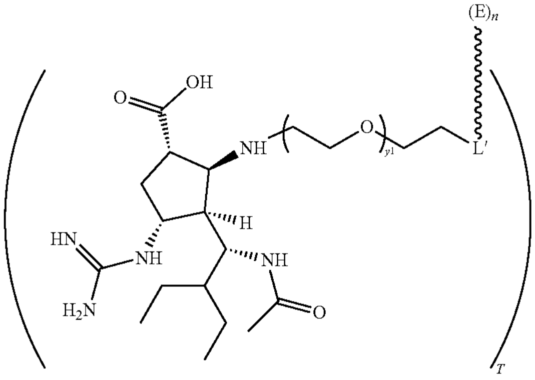

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-VIII-10):

(M-VIII-10)

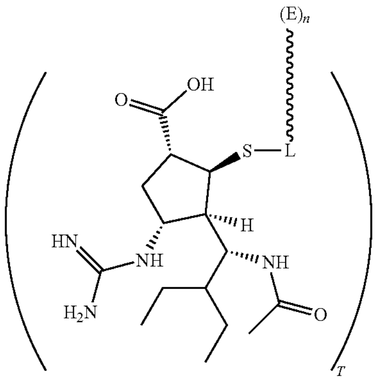

or a pharmaceutically acceptable salt thereof.

In some embodiments, the conjugate is described by formula (M-VIII-11):

(M-VIII-11)

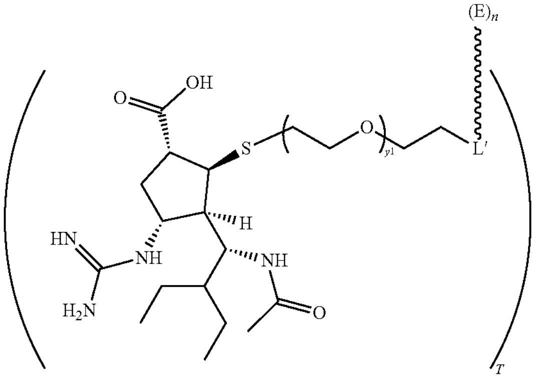

wherein L' is the remainder of L, and $y_1$ is an integer from 1-20 (e.g., $y_1$ is 1, 2, 3, 4, 5, 6, 7, 8, 9, 10, 11, 12, 13, 14, 15, 16, 17, 18, 19, or 20), or a pharmaceutically acceptable salt thereof.

In some embodiments, the conjugate is described by formula (M-IX):

(M-IX)

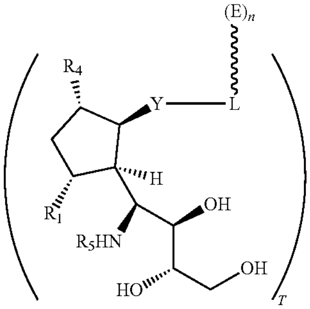

or a pharmaceutically acceptable salt thereof.

In some embodiments, the conjugate is described by formula (M-IX-1):

(M-IX-1)

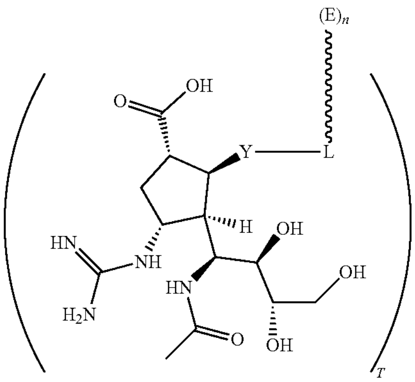

or a pharmaceutically acceptable salt thereof.

In some embodiments, the conjugate is described by formula (M-IX-2):

(M-IX-2)

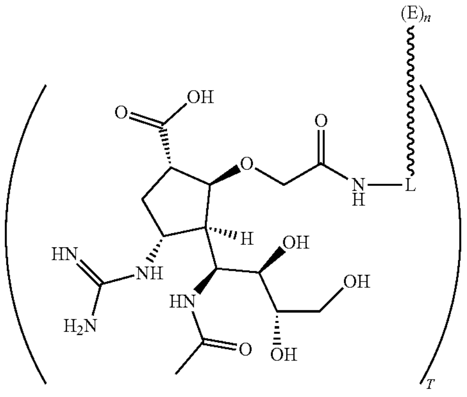

or a pharmaceutically acceptable salt thereof.

In some embodiments, the conjugate is described by formula (M-IX-3):

(M-IX-3)

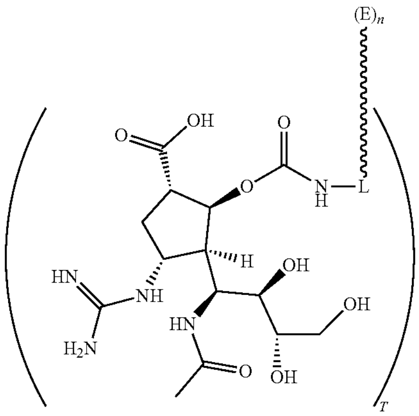

or a pharmaceutically acceptable salt thereof.

In some embodiments, the conjugate is described by formula (M-IX-4):

(M-IX-4)

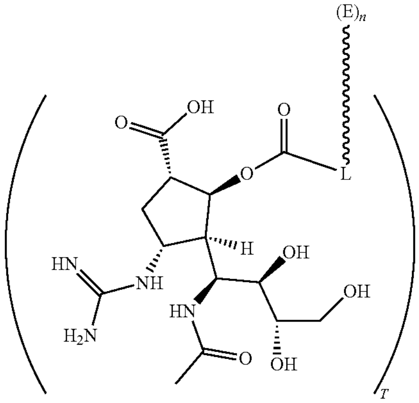

or a pharmaceutically acceptable salt thereof.

In some embodiments, the conjugate is described by formula (M-IX-5):

(M-IX-5)

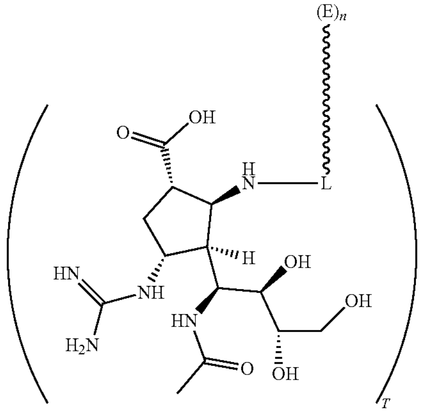

or a pharmaceutically acceptable salt thereof.

In some embodiments, the conjugate is described by formula (M-IX-6):

(M-IX-6)

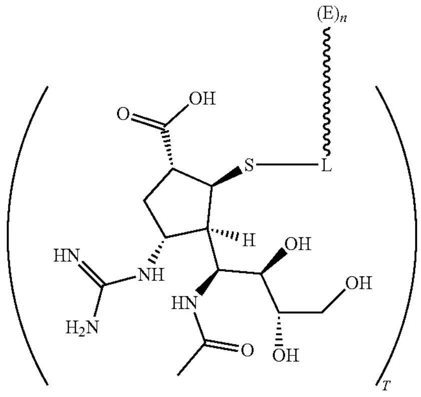

or a pharmaceutically acceptable salt thereof.

In some embodiments, the conjugate is described by formula (M-X):

(M-X)

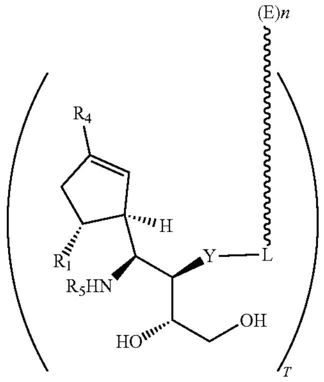

or a pharmaceutically acceptable salt thereof.

In some embodiments, the conjugate is described by formula (M-X-1):

(M-X-1)

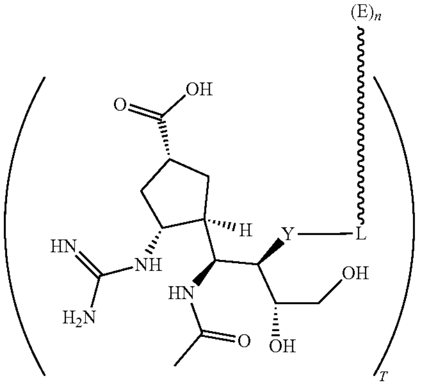

or a pharmaceutically acceptable salt thereof.

In some embodiments, the conjugate is described by formula (M-X-2):

(M-X-2)

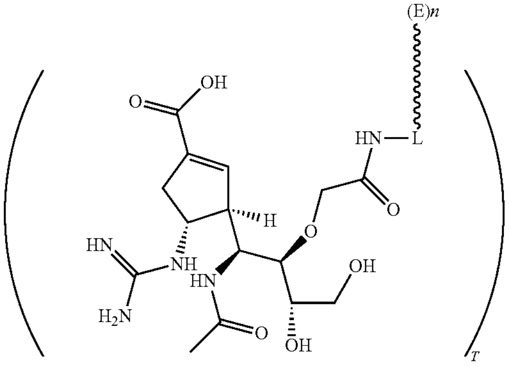

or a pharmaceutically acceptable salt thereof.

In some embodiments, the conjugate is described by formula (M-X-3):

(M-X-3)

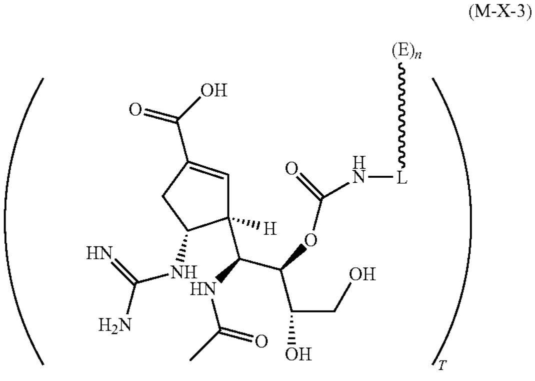

or a pharmaceutically acceptable salt thereof.

In some embodiments of any of the aspects described herein, L or L' comprises one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R_i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments of any of the aspects described herein, the backbone of L or L' consists of one or more optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, optionally substituted C2-C15 heteroarylene, O, S, $NR^i$, P, carbonyl, thiocarbonyl, sulfonyl, phosphate, phosphoryl, or imino, wherein $R_i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl.

In some embodiments of any of the aspects described herein, L or L' is oxo substituted. In some embodiments, the backbone of L or L' comprises no more than 250 atoms. In some embodiments, L or L' is capable of forming an amide, a carbamate, a sulfonyl, or a urea linkage. In some embodiments, L or L' is a bond. In some embodiments, L or L' is an atom. In some embodiments, L' is a nitrogen atom.

In some embodiments, each L is described by formula (M-L-1):

$$J^1\text{-}(Q^1)_g\text{-}(T^1)_h\text{-}(Q^2)_i\text{-}(T^2)_j\text{-}(Q^3)_k\text{-}(T^3)_l\text{-}(Q^4)_m\text{-}(T^4)_n\text{-}(Q^5)_o\text{-}J^2$$

wherein: $J^1$ is a bond attached to A1; $J^2$ is a bond attached to E or a functional group capable of reacting with a functional group conjugated to E (e.g., maleimide and cysteine, amine and activated carboxylic acid, thiol and maleimide, activated sulfonic acid and amine, isocyanate and amine, azide and alkyne, and alkene and tetrazine); each of $Q^1$, $Q^2$, $Q^3$, $Q^4$ and $Q^5$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene; each of $T^1$, $T^2$, $T^3$, $T^4$ is, independently, O, S, $NR^i$, P, carbonyl, thiocarbonyl, sulfonyl, phosphate, phosphoryl, or imino; $R_i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; and each of g, h, i, j, k, l, m, n, and o is, independently, 0 or 1; or a pharmaceutically acceptable salt thereof.

In some embodiments, $J^2$ may have two points of attachment to the Fc domain, Fc-binding peptide, albumin protein, or albumin protein-binding peptide (e.g., two $J^2$).

In some embodiments, L is

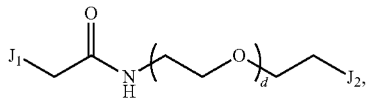

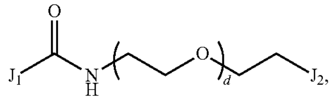

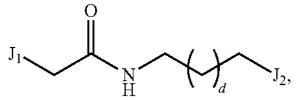

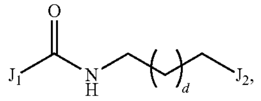

or

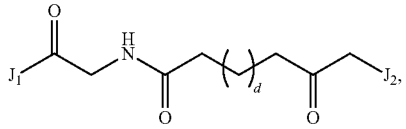

wherein d is an integer from 1 to 20 (e.g., d is 1, 2, 3, 4, 5, 6, 7, 8, 9, 10, 11, 12, 13, 14, 15, 16, 17, 18, 19, or 20).

In some embodiments, L is

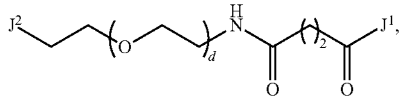

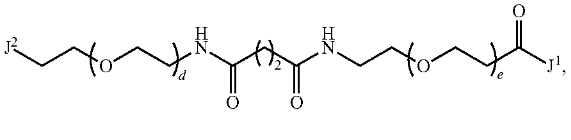

-continued

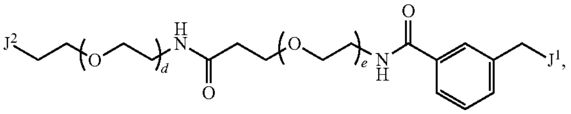

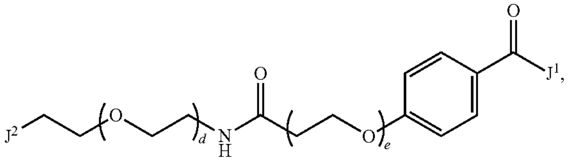

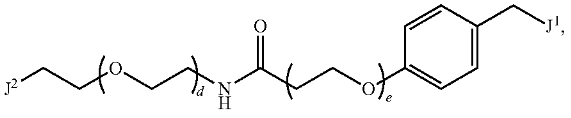

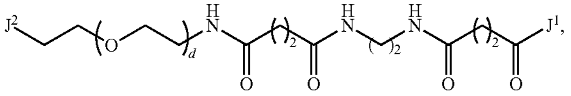

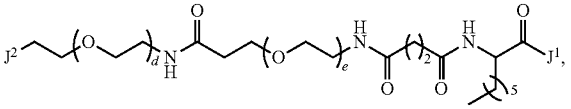

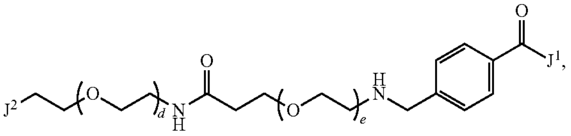

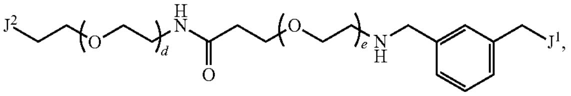

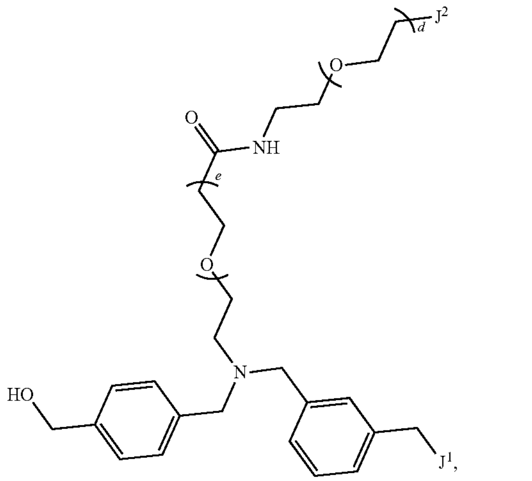

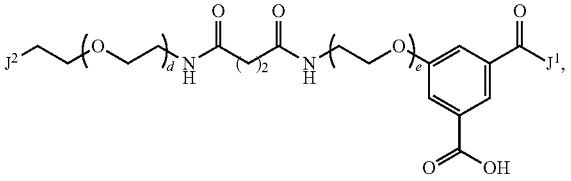

-continued

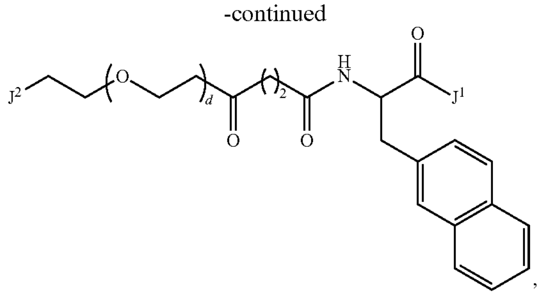

,

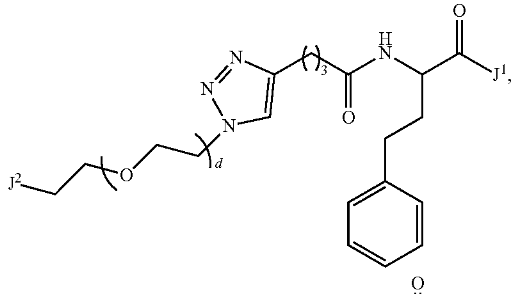

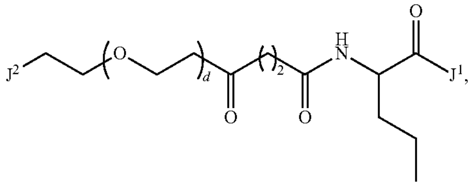

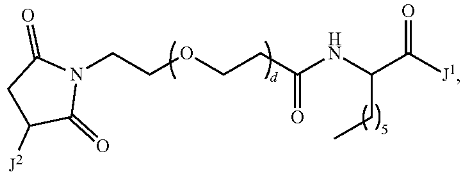

or

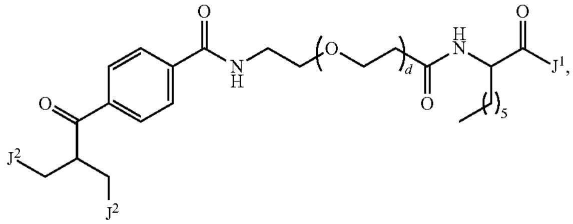

wherein each of d and e is, independently, an integer from 1 to 26; or a pharmaceutically acceptable salt thereof.

In some embodiments of any of the aspects described herein, L includes a polyethylene glycol (PEG) linker. A PEG linker includes a linker having the repeating unit structure $(—CH_2CH_2O—)_n$, wherein n is an integer from 2 to 100. A polyethylene glycol linker may covalently join a neuraminidase inhibitor and E (e.g., in a conjugate of any one of formulas (M-I)-(M-X)). A polyethlylene glycol linker may covalently join a first neuraminidase inhibitor and a second neuraminidase inhibitor (e.g., in a conjugate of any one of formulas (D-I)-(D-X)). A polyethylene glycol linker may covalently join a neuraminidase inhibitor dimer and E (e.g., in a conjugate of any one of formulas (D-I)-(D-X)). A polyethylene glycol linker may selected any one of $PEG_2$ to $PEG_{100}$ (e.g., $PEG_2$, $PEG_3$, $PEG_4$, $PEG_5$, $PEG_5$-$PEG_{10}$, $PEG_{10}$-$PEG_{20}$, $PEG_{20}$-$PEG_{30}$, $PEG_{30}$-$PEG_{40}$, $PEG_{50}$-$PEG_{60}$, $PEG_{60}$-$PEG_{70}$, $PEG_{70}$-$PEG_{80}$, $PEG_{80}$-$PEG_{90}$, $PEG_{90}$-$PEG_{100}$). In some embodiments, $L^C$ includes a PEG linker, where $L^C$ is covalently attached to each of Q and E.

In some embodiments of any of the aspects described herein, $R_1$ is —NHC(═NH)$NH_2$. In some embodiments of any of the aspects described herein, $R_2$ is —F. In some embodiments of any of the aspects described herein, $R_3$ is —F. In some embodiments of any of the aspects described herein, $R_4$ is —$CO_2H$. In some embodiments of any of the aspects described herein, Rs is —$COCH_3$.

In some embodiments of any of the aspects described herein, L is covalently attached to the nitrogen atom of a surface exposed lysine of E or L is covalently attached to the sulfur atom of a surface exposed cysteine of E.

In some embodiments of any of the aspects described herein, E is an Fc domain monomer. In some embodiments, n is 2 and each E dimerizes to form an Fc domain.

In some embodiments, n is 2, each E is an Fc domain monomer, each E dimerizes to form an Fc domain, and the conjugate is described by formula (D-I-1):

(D-I-1)

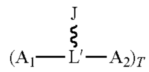

wherein J is an Fc domain; and T is an integer from 1 to 20 (e.g., T is 1, 2, 3, 4, 5, 6, 7, 8, 9, 10, 11, 12, 13, 14, 15, 16, 17, 18, 19, or 20), or a pharmaceutically acceptable salt thereof.

In some embodiments, n is 2, each E is an Fc domain monomer, each E dimerizes to form an Fc domain, and the conjugate is described by formula (M-I-1):

(M-I-1)

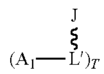

wherein J is an Fc domain; and T is an integer from 1 to 20 (e.g., T is 1, 2, 3, 4, 5, 6, 7, 8, 9, 10, 11, 12, 13, 14, 15, 16, 17, 18, 19, or 20), or a pharmaceutically acceptable salt thereof.

In some embodiments of any of the aspects described herein, E has the sequence of any one of SEQ ID NOs: 1-68.

In some embodiments of any of the aspects described herein, E is an albumin protein, an albumin protein-binding peptide, or an Fc-binding peptide. In some embodiments, where E is an albumin protein, an albumin protein-binding peptide, or an Fc-binding peptide, n is 1.

In some embodiments, n is 1, E is an albumin protein, an albumin protein-binding peptide, or an Fc-binding peptide and the conjugate is described by formula (D-1-2):

(D-I-2)

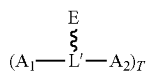

wherein E is an albumin protein, an albumin protein-binding peptide, or Fc-binding peptide; and T is an integer from 1 to 20, or a pharmaceutically acceptable salt thereof.

In some embodiments, n is 1, E is an albumin protein, an albumin protein-binding peptide, or an Fc-binding peptide, and the conjugate is described by formula (M-I-2):

(M-I-2)

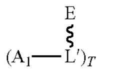

wherein E is an albumin protein, an albumin protein-binding peptide, or an Fc-binding peptide; and T is an integer from 1 to 20, or a pharmaceutically acceptable salt thereof.

In some embodiments of any of the aspects described herein, E is an albumin protein having the sequence of any one of SEQ ID NOs: 69-71.

In some embodiments of any of the aspects described herein, T is 1, 2, 3, 4, or 5.

In another aspect, the invention provides a population of conjugates having the structure of any of the conjugates described herein (e.g., a population of conjugates having the formula of any one of formulas (1)-(5), (D-I)-(D-X), (D'-I), (M-I)-(M-X), or (M'-I)), wherein the average value of T is 1 to 20 (e.g., the average value of T is 1 to 2, 1 to 3, 1 to 4, 1 to 5, 5 to 10, 10 to 15, or 15 to 20). In some embodiments, the average value of T is 1, 2, 3, 4, 5, 6, 7, 8, 9, 10, 11, 12, 13, 14, 15, 16, 17, 18, 19, or 20.

In some embodiments of any of the aspects described herein, when T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein). In some embodiments, E may be conjugated to 2, 3, 4, 5, 6, 7, 8, 9, 10, or more different $A_1$-L-$A_2$ moieties. In some embodiments, E is conjugated to a first $A_1$-L-$A_2$ moiety, and a second $A_1$-L-$A_2$, moiety. In some embodiments, $A_1$ and $A_2$ of the first $A_1$-L-$A_2$ moiety are independently selected from any one of formulas (A-III)-(A-V):

(A-III)

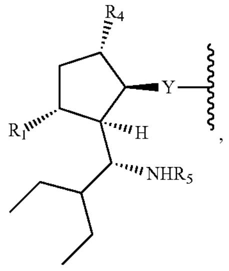

(A-IV)

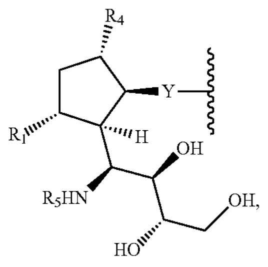

-continued (A-V)

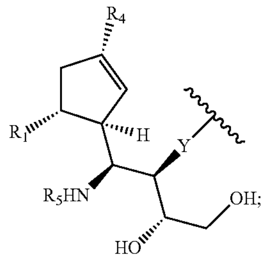

and $A_1$ and $A_2$ of the second $A_1$-L-$A_2$ moiety are independently selected from any one of formulas (A-1), (A-II), (A-VI), (A-VII), (A-VIII), and (A-IX):

(A-I)

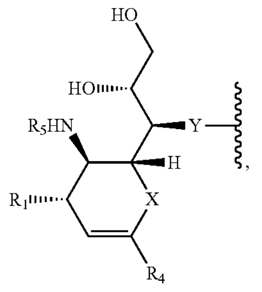

(A-II)

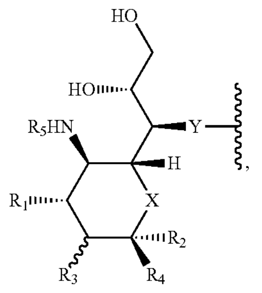

(A-VI)

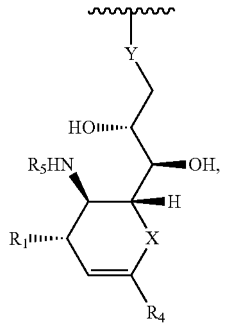

-continued (A-VII)

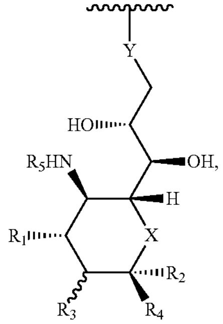

(A-VIII)

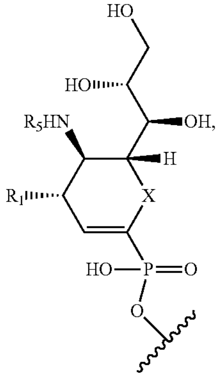

(A-IX)

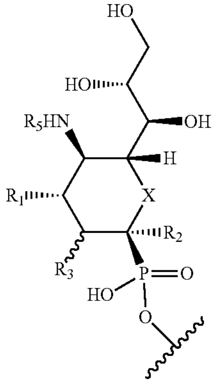

.

In some embodiments, each of the first $A_1$-L-$A_2$ moieties is conjugated specifically to a lysine residue of E (e.g., the nitrogen atom of a surface exposed lysine residue of E), and each of the second $A_1$-L-$A_2$ moieties is conjugated specifically to a cysteine residue of E (e.g., the sulfur atom of a surface exposed cysteine residue of E). In some embodiments, each of the first $A_1$-L-$A_2$ moieties is conjugated specifically to a cysteine residue of E (e.g., the sulfur atom of a surface exposed cysteine residue of E), and each of the second $A_1$-L-$A_2$ moieties is conjugated specifically to a lysine residue of E (e.g., the nitrogen atom of a surface exposed lysine residue of E).

In some embodiments, the number of first $A_1$-L-$A_2$ moieties conjugated to E is an integer from 1 to 10 (e.g., 1, 2, 3, 4, 5, 6, 7, 8, 9, or 10). In some embodiments, the number of second $A_1$-L-$A_2$ moieties conjugated to E is an integer from 1 to 10 (e.g. 1, 2, 3, 4, 5, 6, 7, 8, 9, 10).

In some embodiments of any of the aspects described herein, when T is greater than 1 (e.g., T is 2, 3, 4, 5, 6, 7, 8, 9, 10, 11, 12, 13, 14, 15, 16, 17, 18, 19, or 20), each $A_1$-L may be independently selected (e.g., independently selected from any of the $A_1$-L structures described herein). In some embodiments, E may be conjugated to 2, 3, 4, 5, 6, 7, 8, 9, 10, or more different $A_1$-L moieties. In some embodiments, E is conjugated to a first $A_1$-L moiety, and a second $A_1$-L, moiety. In some embodiments, $A_1$ of the first $A_1$-L moiety is selected from any one of formulas (A-III)-(A-V):

(A-III)

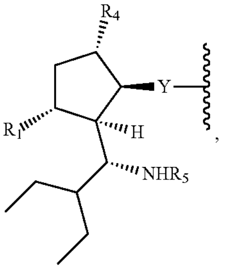

, (A-IV)

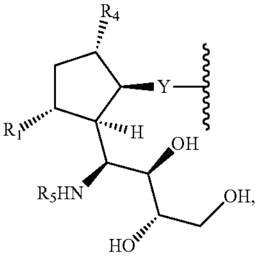

(A-V)

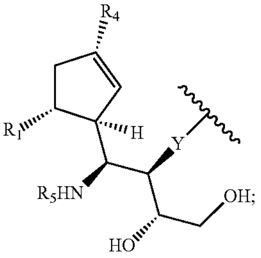

and $A_1$ of the second $A_1$-L moiety is selected from any one of formulas (A-I), (A-II), (A-VI), (A-VII), (A-VIII), or (A-IX):

(A-I)

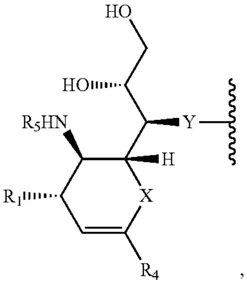

,

-continued (A-II)

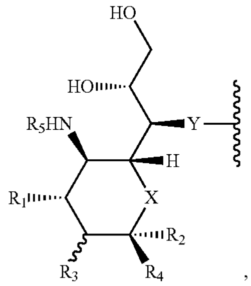

, (A-VI)

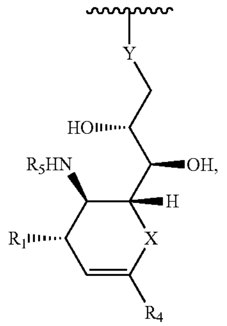

(A-VII)

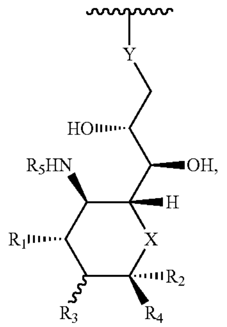

(A-VIII)

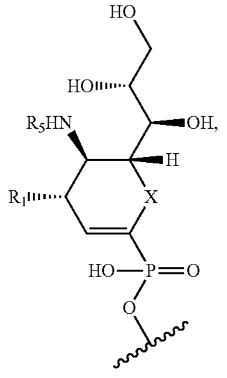

-continued (A-IX)

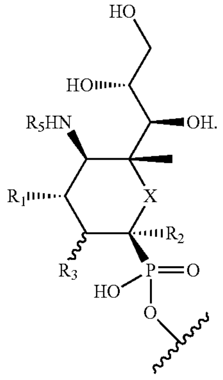

In some embodiments, each of the first $A_1$-L moieties is conjugated specifically to a lysine residue of E (e.g., the nitrogen atom of a surface exposed lysine residue of E), and each of the second $A_1$-L moieties is conjugated specifically to a cysteine residue of E (e.g., the sulfur atom of a surface exposed cysteine residue of E). In some embodiments, each of the first $A_1$-L moieties is conjugated specifically to a cysteine residue of E (e.g., the sulfur atom of a surface exposed cysteine residue of E), and each of the second $A_1$-L moieties is conjugated specifically to a lysine residue of E (e.g., the nitrogen atom of a surface exposed lysine residue of E).

In some embodiments, the number of first $A_1$-L moieties conjugated to E is an integer from 1 to 10 (e.g., 1, 2, 3, 4, 5, 6, 7, 8, 9, or 10). In some embodiments, the number of second $A_1$-L moieties conjugated to E is an integer from 1 to 10 (e.g. 1, 2, 3, 4, 5, 6, 7, 8, 9, 10).

In another aspect, the invention features a conjugate described by formula (D'-I):

(D'-I)

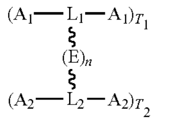

wherein each $A_1$ is independently selected from any one of formulas (A-III)-(A-V):

(A-III)

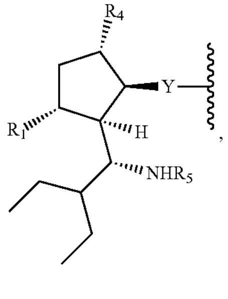

,

-continued (A-IV)

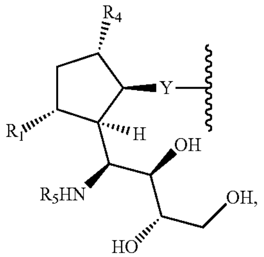

(A-V)

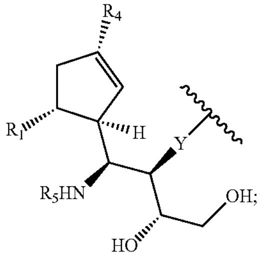

wherein each $A_2$ is independently selected from any one of formulas (A-I), (A-II), (A-VI), (A-VII), (A-VIII), and (A-IX):

(A-I)

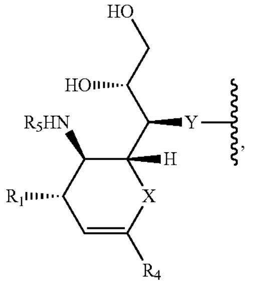

(A-II)

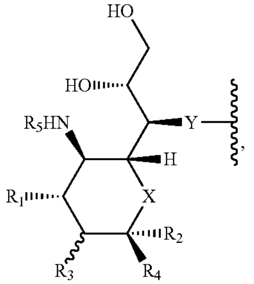

(A-VI)

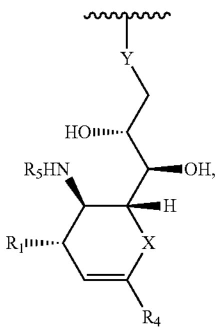

-continued (A-VII)

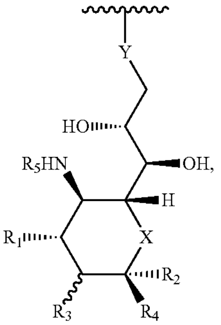

(A-VIII)

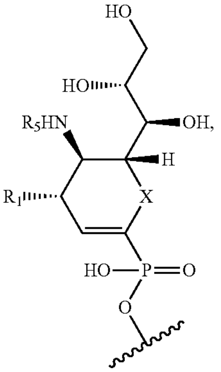

(A-IX)

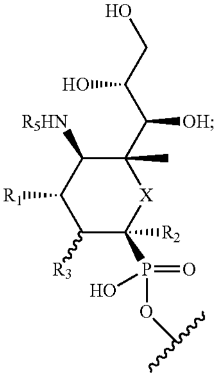

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

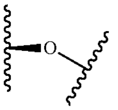

(—O—),

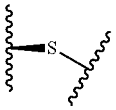

(—S—),

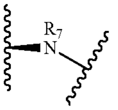

(—$NR_7$—),

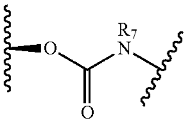

(—O(C═O)$NR_7$—),

-continued
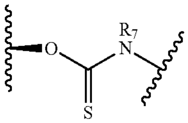
(—O(C=S)NR$_7$—),
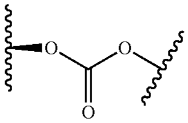
(—O(C=O)O—),
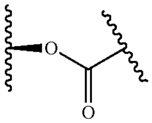
(—O(C=O)—),
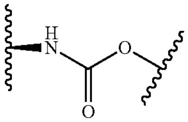
(—NH(C=O)O—),
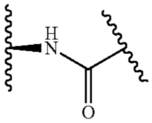
(—NH(C=O)—),
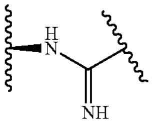
(—NH(C=NH)—),
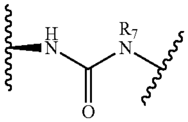
(—NH(C=O)NR$_7$—),
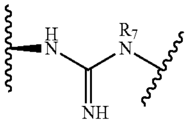
(—NH(C=NH)NR$_7$—),
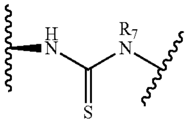
(—NH(C=S)NR$_7$—),
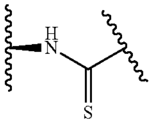
(—NH(C=S)—),
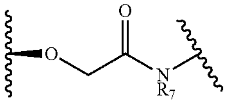
(—OCH$_2$(C=O)NR$_7$—),
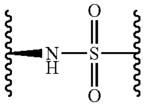
(—NH(SO$_2$)—),
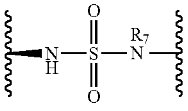
(—NH(SO$_2$)NR$_7$—),
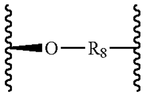
(—OR$_8$—),
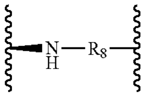
(—NR$_8$—), and
-continued
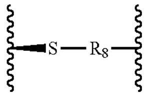
(—SR$_8$—);
$R_6$ is selected from
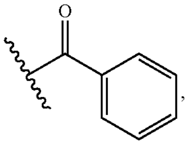,
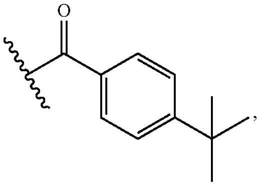,
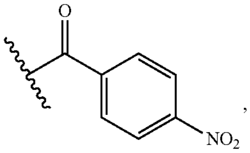,
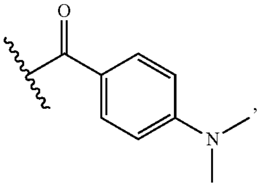,
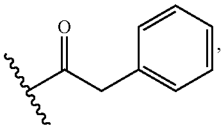,
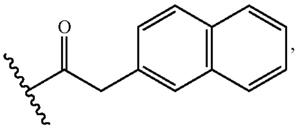,
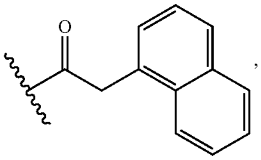,
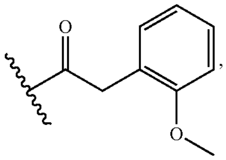,
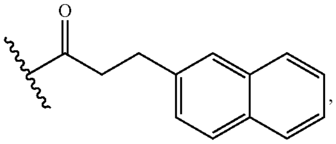,
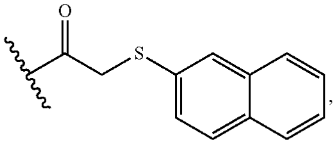,
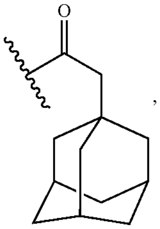,
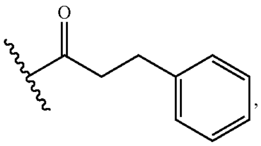,
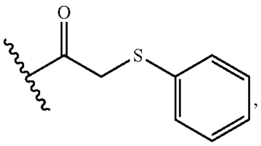,
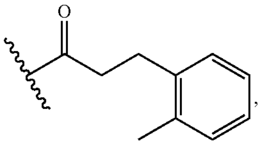,
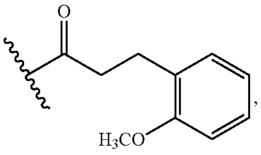,
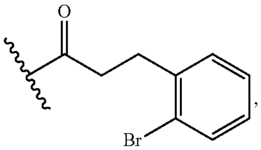,
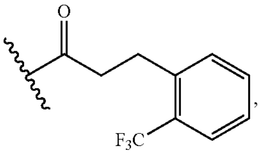, -continued

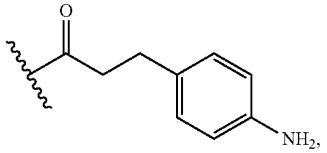

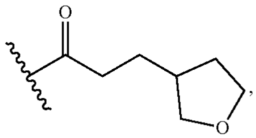, 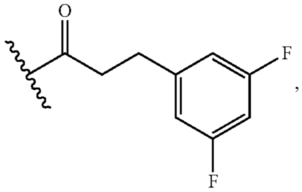,

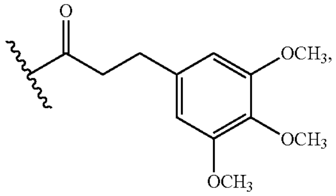

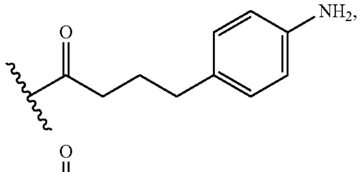

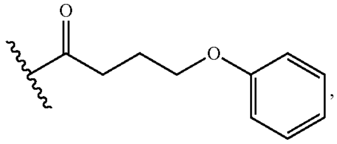,

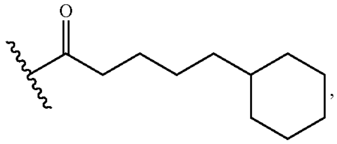,

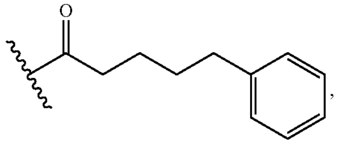,

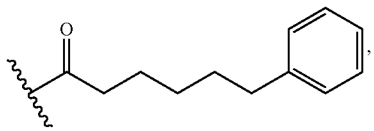, 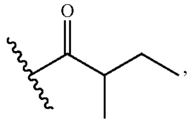,

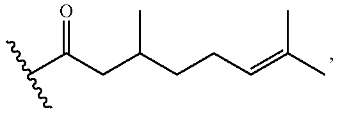,

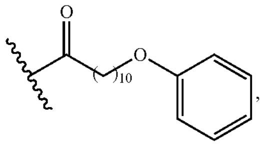, 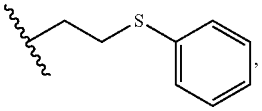,

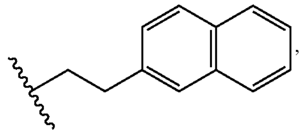, and 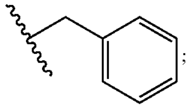;

$R_7$ is selected from H, C1-C20 alkyl, C3-C20 cycloalkyl, C3-C20 heterocycloalkyl; C5-C15 aryl, and 02-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68), an albumin protein (e.g., an albumin protein having the sequence of any one of SEQ ID NOs: 69-71), an albumin protein-binding peptide, or an Fc-binding peptide; n is 1 or 2; Ti is an integer from 1 to 10 (e.g., $T_1$ is 1, 2, 3, 4, 5, 6, 7, 8, 9, 10); $L_1$ is a linker covalently conjugated to E and to each $A_1$; $T_1$ is an integer from 1 to 10 (e.g., $T_1$ is 1, 2, 3, 4, 5, 6, 7, 8, 9, 10); $L_2$ is a linker covalently conjugated to E and each $A_2$; $T_2$ is an integer from 1 to 10 (e.g., $T_2$ is 1, 2, 3, 4, 5, 6, 7, 8, 9, 10), or a pharmaceutically acceptable salt thereof.

In some embodiments, each $A_1$-L-$A_1$ is conjugated specifically to a lysine residue of E (e.g., the nitrogen atom of a surface exposed lysine residue of E), and each the $A_2$-L-$A_2$ is conjugated specifically to a cysteine residue of E (e.g., the sulfur atom of a surface exposed cysteine residue of E). In some embodiments, each $A_1$-L-$A_1$ moiety is conjugated specifically a cysteine residue of E (e.g., the sulfur atom of a surface exposed cysteine residue of E), and each $A_2$-L-$A_2$ moiety is conjugated specifically to a lysine residue of E (e.g., the nitrogen atom of a surface exposed lysine residue of E).

In another aspect, the invention features a conjugate described by formula (M'-I):

(M'-I)

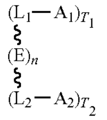

wherein each $A_1$ is independently selected from any one (M-IX) of formulas (A-III)-(A-V):

(A-III)

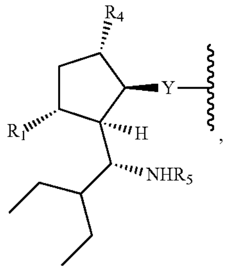, (A-IV)

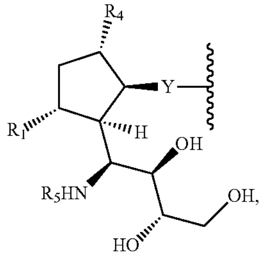

-continued (A-V)

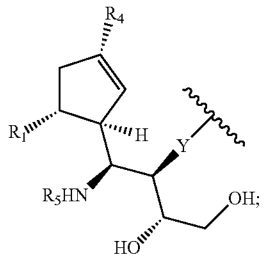

wherein each $A_2$ is independently selected from any one of formulas (A-I), (A-II), (A-VI), (A-VII), (A-VIII), and (A-IX):

(A-I)

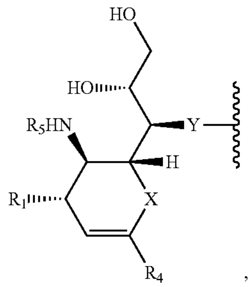

, (A-II)

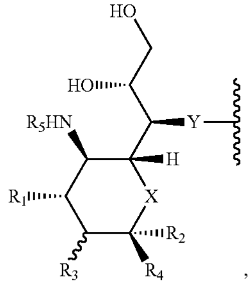

, (A-VI)

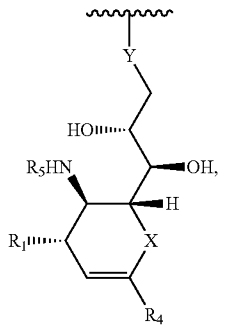

-continued (A-VII)

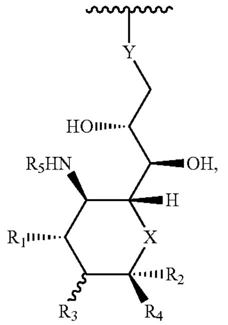

(A-VIII)

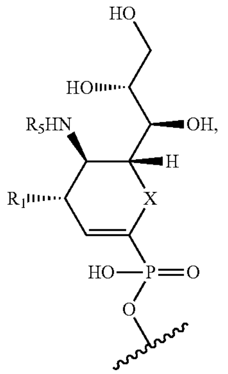

(A-IX)

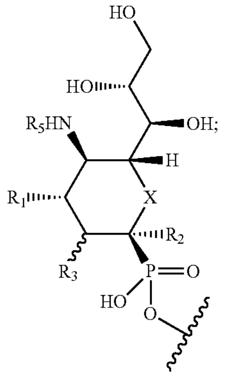

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

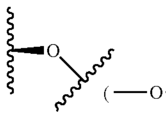

(—O—),

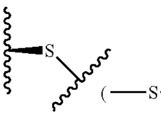

(—S—),

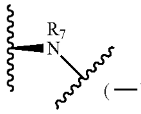

(—$NR_7$—),

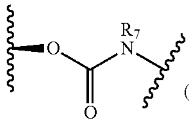

(—O(C═O)$NR_7$—),

-continued
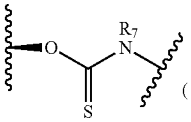
( —O(C=S)$NR_7$— ),
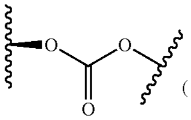
( —O(C=O)O— ),
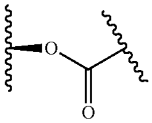
( —O(C=O)— ),
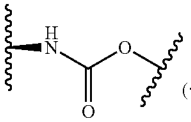
( —NH(C=O)O— ),
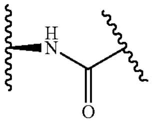
( —NH(C=O)— ),
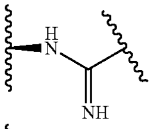
( —NH(C=NH)— ),
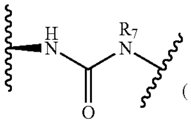
( —NH(C=O)$NR_7$— ),
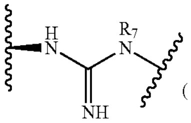
( —NH(C=NH)$NR_7$— ),
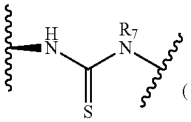
( —NH(C=S)$NR_7$— ),
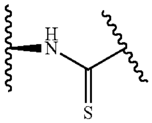
( —NH(C=S)— ),
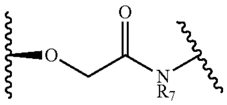
( —$OCH_2$(C=O)$NR_7$— ),
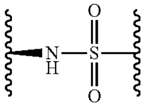
( —NH($SO_2$)— ),
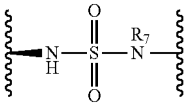
( —NH($SO_2$)$NR_7$— ),
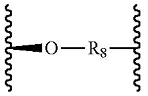
( —$OR_8$— ),
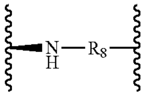
( —$NR_8$— ), and
-continued
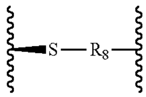
( —$SR_8$— );
$R_6$ is selected from
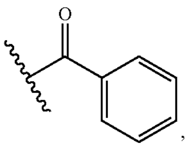
,
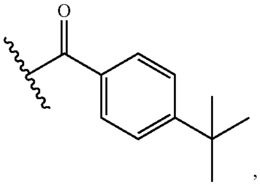
,
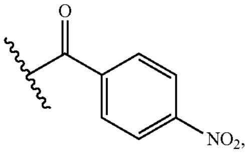
,
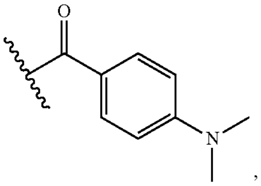
,
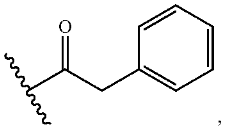
,
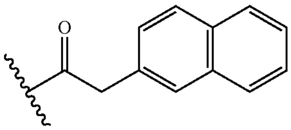
,
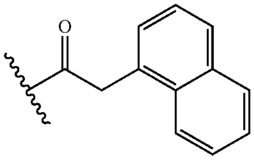
,
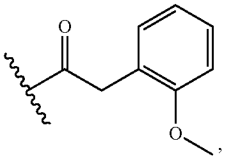
,
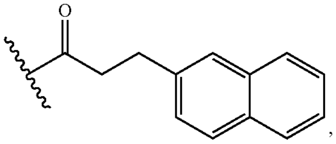
,
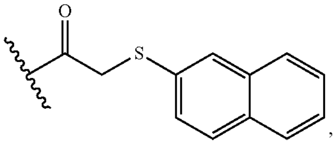
,
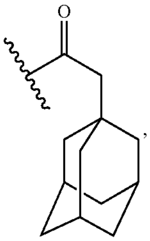
,
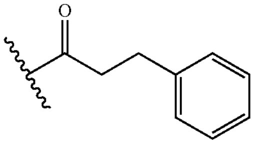
,
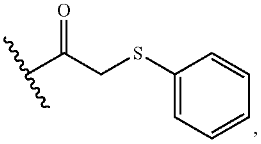
,
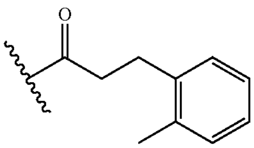
,
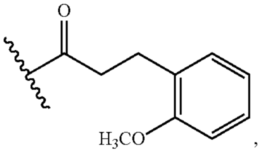
,
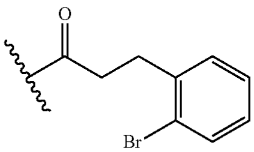
,
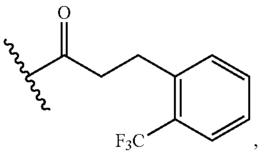
, -continued

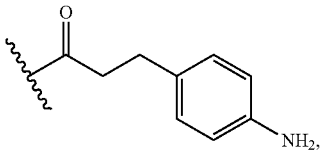

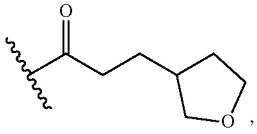
,

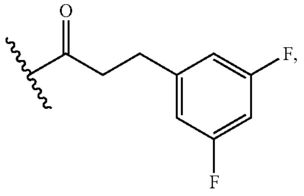

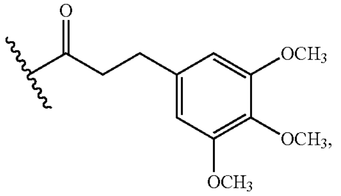

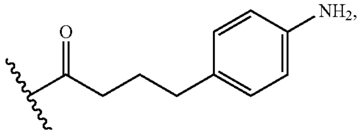

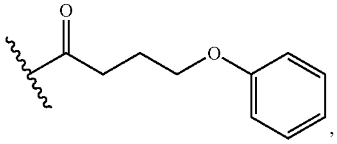
,

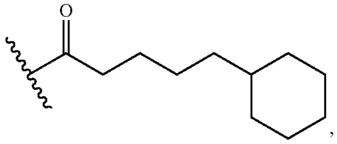
,

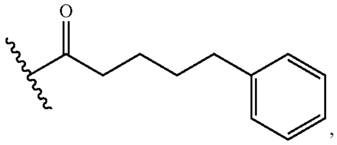
,

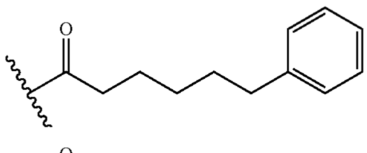
,

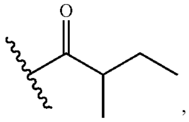
,
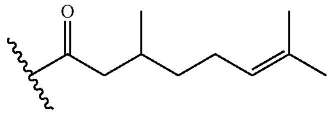
,

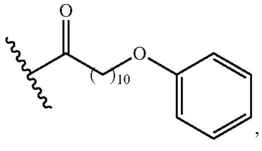
,
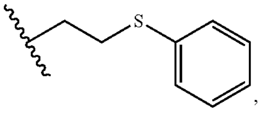
,

-continued

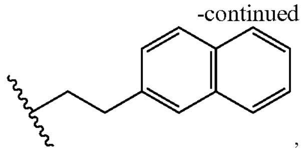
, and
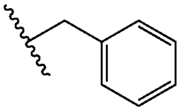
;

$R_7$ is selected from H, C1-C20 alkyl, C3-C20 cycloalkyl, C3-C20 heterocycloalkyl; C5-C15 aryl, and C2-C15 heteroaryl; $R_8$ is selected from C3-C20 heterocycloalkyl, C5-C15 aryl, and C2-C15 heteroaryl; each E comprises an Fc domain monomer (e.g., an Fc domain monomer having the sequence of any one of SEQ ID NOs: 1-68), an albumin protein (e.g., an albumin protein having the sequence of any one of SEQ ID NOs: 69-71), an albumin protein-binding peptide, or an Fc-binding peptide; n is 1 or 2; $T_1$ is an integer from 1 to 10 (e.g., $T_1$ is 1, 2, 3, 4, 5, 6, 7, 8, 9, 10); $L_1$ is a linker covalently conjugated to E and $A_1$; $T_1$ is an integer from 1 to 10 (e.g., $T_1$ is 1, 2, 3, 4, 5, 6, 7, 8, 9, 10); $L_2$ is a linker covalently conjugated to E and $A_2$; $T_2$ is an integer from 1 to 10 (e.g., $T_2$ is 1, 2, 3, 4, 5, 6, 7, 8, 9, 10), or a pharmaceutically acceptable salt thereof.

In some embodiments, each $A_1$-L is conjugated specifically to a lysine residue of E (e.g., the nitrogen atom of a surface exposed lysine residue of E), and each the $A_2$-L is conjugated specifically to a cysteine residue of E (e.g., the sulfur atom of a surface exposed cysteine residue of E). In some embodiments, each $A_1$-L moiety is conjugated specifically a cysteine residue of E (e.g., the sulfur atom of a surface exposed cysteine residue of E), and each $A_2$-L moiety is conjugated specifically to a lysine residue of E (e.g., the nitrogen atom of a surface exposed lysine residue of E).

In another aspect, the invention provides a pharmaceutical composition comprising any of the conjugates described herein (e.g., a conjugate of any one of formulas (1)-(5), (D-I)-(D-X), (D'-I), (M-I)-(M-X), or (M'-I)), or a pharmaceutically acceptable salt thereof, and a pharmaceutically acceptable excipient.

In another aspect, the invention provides a method for the treatment of a subject having a viral infection or presumed to have a viral infection, the method comprising administering to the subject an effective amount of any of the conjugates or compositions described herein (e.g., a conjugate of any one of formulas (1)-(5), (D-I)-(D-X), (D'-I), (M-I)-(M-X), or (M'-I)).

In another aspect, the invention provides a method for the prophylactic treatment of a viral infection in a subject in need thereof, the method comprising administering to the subject an effective amount of any of the conjugates or compositions described herein (e.g., a conjugate of any one of formulas (1)-(5), (D-I)-(D-X), (D'-I), (M-I)-(M-X), or (M'-I)).

In some embodiments, the viral infection is caused by influenza virus or parainfluenza virus. In some embodiments, the viral infection is influenza virus A, B, or C, or parainfluenza virus.

In some embodiments, the subject is immunocompromised.

In some embodiments, the subject has been diagnosed with humoral immune deficiency, T cell deficiency, neutropenia, asplenia, or complement deficiency.

In some embodiments, the subject is being treated or is about to be treated with an immunosuppresive therapy.

In some embodiments, the subject has been diagnosed with a disease which causes immunosuppression. In some embodiments, the disease is cancer or acquired immunodeficiency syndrome. In some embodiments, the cancer is leukemia, lymphoma, or multiple myeloma.

In some embodiments, the subject has undergone or is about to undergo hematopoietic stem cell transplantation.

In some embodiments, wherein the subject has undergone or is about to undergo an organ transplant.

In some embodiments, the conjugate of composition is administered intramuscularly, intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularlly, mucosally, intrapericardially, intraumbilically, intraocularally, orally, locally, by inhalation, by injection, or by infusion.

In some embodiments, the subject is treated with a second therapeutic agent. In some embodiments, the second therapeutic agent is an antiviral agent. In some embodiments, the antiviral agent is selected from oseltamivir, zanamivir, peramivir, laninamivir, amantadine, or rimantadine. In some embodiments, the second therapeutic agent is a viral vaccine. In some embodiments, the viral vaccine elicits an immune response in the subject against influenza virus A, B, or C, or parainfluenza virus.

In some embodiments, an Fc-domain-containing composition may be substituted for an Fc domain and an Fc-domain-monomer-containing composition may be substituted for an Fc domain monomer in any one of formulas (1)-(5), (D-I)-(D-X), (D'-I), (M-I)-(M-X), or (M'-I) (e.g., any one of formulas (1), (2), (3), (4), (5), (D-I), (D-II), (D-II-1), (D-II-2), (D-II-3), (D-II-4), (D-II-5), (D-II-6), (D-II-7), (D-II-8), (D-II-9), (D-II-10), (D-III), (D-III-1), (D-III-2), (D-III-3), (D-III-4), (D-III-5), (D-III-6), (D-III-7), (D-III-8), (D-III-9), (D-IV), (D-IV-1), (D-IV-2), (D-V), (D-V-1), (D-V-2), (D-V-3), (D-V-4), (D-V-5), (D-V-6), (D-V-7), (D-V-8), (D-V-9), (D-V-10), (D-VI), (D-VI-1), (D-VI-2), (D-VI-3), (D-VI-4), (D-VI-5), (D-VI-6), (D-VI-7), (D-VI-8), (D-VI-9), (D-VII), (D-VIII), (D-VIII-1), (D-VIII-2), (D-VIII-3), (D-VIII-4), (D-VIII-5), (D-VIII-6), (D-VIII-7), (D-VIII-8), (D-VIII-9), (D-VIII-10), (D-VIII-11), (D-IX), (D-IX-1), (D-IX-2), (D-IX-3), (D-IX-4), (D-IX-5), (D-X-6), (D-X), (D-X-1), (D-X-2), (D-X-3), (D'-I), (M-I), (M-II), (M-II-1), (M-II-2), (M-II-3), (M-II-4), (M-II-5), (M-II-6), (M-II-7), (M-II-8), (M-II-9), (M-II-10), (M-III), (M-III-1), (M-III-2), (M-III-3), (M-III-4), (M-III-5), (M-III-6), (M-III-7), (M-III-8), (M-III-9), (M-IV), (M-IV-1), (M-IV-2), (M-V), (M-V-1), (M-V-2), (M-V-3), (M-V-4), (M-V-5), (M-V-6), (M-V-7), (M-V-8), (M-V-9), (M-V-10), (M-VI), (M-VI-1), (M-VI-2), (M-VI-3), (M-VI-4), (M-VI-5), (M-VI-6), (M-VI-7), (M-VI-8), (M-VI-9), (M-VIII), (M-VIII), (M-VIII-1), (M-VIII-2), (M-VIII-3), (M-VIII-4), (M-VIII-5), (M-VIII-6), (M-VIII-7), (M-VIII-8), (M-VIII-9), (M-VIII-10), (M-VIII-11), (M-IX), (M-IX-1), (M-IX-2), (M-IX-3), (M-IX-4), (M-IX-5), (M-IX-6), (M-X), (M-X-1), (M-X-2), (M-X-3), or (M'-I)). In any of the formulas described herein (e.g., any one of formulas (1)-(5), (D-I)-(D-X), (D'-I), (M-I)-(M-X), or (M'-I)), when n is 1, E is an Fc-domain-monomer-containing composition. In any of the formulas described herein (e.g., any one of formulas (1)-(5), (D-I)-(D-X), (D'-I), (M-I)-(M-X), or (M'-I)), when n is 2, E is an Fc-domain-containing composition.

In certain embodiments, the Fc-domain-containing composition is an antibody or an antibody fragment. An antibody may include any form of immunoglobulin, heavy chain antibody, light chain antibody, LRR-based antibody, or other protein scaffold with antibody-like properties, as well as any other immunological binding moiety known in the art, including antibody fragments (e.g., a Fab, Fab', Fab'2, F(ab')2, Fd, Fv, Feb, scFv, or SMIP). The subunit structures and three-dimensional configurations of different classes of antibodies are known in the art. An antibody fragment may include a binding moiety that includes a portion derived from or having significant homology to an antibody, such as the antigen-determining region of an antibody. Exemplary antibody fragments include Fab, Fab', Fab'2, F(ab')2, Fd, Fv, Feb, scFv, and SMIP.

In particular embodiments, the antibody or antibody fragment is a human, mouse, camelid (e.g., llama, alpaca, or camel), goat, sheep, rabbit, chicken, guinea pig, hamster, horse, or rat antibody or antibody fragment. In specific embodiments, the antibody is an IgG, IgA, IgD, IgE, IgM, or intrabody. In certain embodiments, the antibody fragment includes an scFv, sdAb, dAb, Fab, Fab', Fab'2, F(ab')2, Fd, Fv, Feb, or SMIP.

In some embodiments, the Fc-domain-containing composition (e.g., an antibody or antibody fragment) confers binding specificity to a one or more targets (e.g., an antigen).

In some embodiments, the one or more targets (e.g., an antigen) bound by the Fc-domain-containing composition (e.g., an antibody or antibody fragment) is a viral (e.g., influenza) protein such as neuraminidase or hemagglutinin. In some embodiments, the antibody or antibody fragment recognizes a viral surface antigen. In some embodiments, the antibody or antibody fragment targets hemagglutinin. Hemagglutinin-targeting antibodies include monoclonal antibodies, such as CR6261, CR8020, MEDI8852, MHAA4549A, and VIS410. In some embodiments, the antibody or antibody fragment is a broadly neutralizing antibody or antibody fragment targeting influenza hemagglutinin (e.g., an antibody or antibody fragment described in Wu et al., J. Mol. Biol. 429:2694-2709 (2017)). In some embodiments the antibody or antibody fragment targets a viral matrix protein (e.g., matrix 2 protein). TCN032 is a matrix 2 protein targeting monoclonal antibody.

In some embodiments, the Fc-domain-containing composition (e.g., an antibody or antibody fragment) includes one or more single-domain antibodies (sdAbs). In some embodiments the Fc-domain-containing composition is an antibody or antibody fragment including a sdAb with influenza A reactivity, such as a sdAb that binds to hemagglutinin of influenza A (e.g., SD36 or SD38, described in Laursen et al. Science. 362:598-602 (2018)). In some embodiments the Fc-domain-containing composition is an antibody or antibody fragment including a sdAb with influenza B reactivity, such as a sdAb that binds to hemagglutinin of influenza B (e.g., SD83 or SD84, described in Laursen et al. Science. 362:598-602 (2018)).

In some embodiments the Fc-domain-containing composition is a multidomain antibody (MDAb) or multidomain antibody fragment including 2 or more (e.g., 2, 3, 4, 5, 6, 7, 8, 9 or 10 or more) sdAbs. In some embodiments, the MDAb or fragment thereof includes one or more sdABs that binds to hemaglutinin of influenza A, and one or more sdAbs that binds to hemagglutinin of influenza B. In some embodiments, the MDAb is JNJ-7445 (also known as MD3606), which is described in Laursen et al. Science. 362:598-602 (2018). In brief, JNJ-7445 is an MDAb that includes two sdAbs that bind to hemagglutinin of influenza A (SD36 and SD38) and two sdAbs that bind to hemagglutinin of influenza B (SD83 and SD84), which are linked to an Fc domain (IgG1). The sdAbs were produced by immunizing llamas with influenza vaccine and H7 and H2 recombinant hemagglutinin.

In another aspect, the invention includes a conjugate described by any one of formulas (1)-(5), (D-I)-(D-X), (D'-I), (M-I)-(M-X), or (M'-I) (e.g., any one of formulas (1), (2), (3), (4), (5), (D-1), (D-II), (D-II-1), (D-II-2), (D-II-3), (D-II-4), (D-II-5), (D-II-6), (D-II-7), (D-II-8), (D-II-9), (D-II-10), (D-III), (D-III-1), (D-III-2), (D-III-3), (D-III-4), (D-III-5), (D-III-6), (D-III-7), (D-III-8), (D-III-9), (D-IV), (D-IV-1), (D-IV-2), (D-V), (D-V-1), (D-V-2), (D-V-3), (D-V-4), (D-V-5), (D-V-6), (D-V-7), (D-V-8), (D-V-9), (D-V-10), (D-VI), (D-VI-1), (D-V I-2), (D-VI-3), (D-VI-4), (D-VI-5), (D-VI-6), (D-VI-7), (D-VI-8), (D-VI-9), (D-VII), (D-VIII), (D-VIII-1), (D-VIII-2), (D-VIII-3), (D-VIII-4), (D-VIII-5), (D-VIII-6), (D-VIII-7), (D-VIII-8), (D-VIII-9), (D-VIII-10), (D-VIII-11), (D-IX), (D-IX-1), (D-IX-2), (D-IX-3), (D-IX-4), (D-IX-5), (D-IX-6), (D-X), (D-X-1), (D-X-2), (D-X-3), (D'-I), (M-I), (M-II), (M-II-1), (M-II-2), (M-II-3), (M-II-4), (M-II-5), (M-II-6), (M-II-7), (M-II-8), (M-II-9), (M-II-10), (M-III), (M-III-1), (M-III-2), (M-III-3), (M-III-4), (M-III-5), (M-III-6), (M-III-7), (M-III-8), (M-III-9), (M-IV), (M-IV-1), (M-IV-2), (M-V), (M-V-1), (M-V-2), (M-V-3), (M-V-4), (M-V-5), (M-V-6), (M-V-7), (M-V-8), (M-V-9), (M-V-10), (M-VI), (M-VI-1), (M-VI-2), (M-VI-3), (M-VI-4), (M-VI-5), (M-VI-6), (M-VI-7), (M-VI-8), (M-VI-9), (M-VII), (M-VIII), (M-VIII-1), (M-VIII-2), (M-VIII-3), (M-VIII-4), (M-VIII-5), (M-VIII-6), (M-VIII-7), (M-VIII-8), (M-VIII-9), (M-VIII-10), (M-VIII-11), (M-IX), (M-IX-1), (M-IX-2), (M-IX-3), (M-IX-4), (M-IX-5), (M-IX-6), (M-X), (M-X-1), (M-X-2), (M-X-3), or (M'-I)), where E is an antibody or antibody fragment. In preferred embodiments, where E is an antibody or antibody fragment, n is 1. In some embodiments, the antibody or antibody fragment includes any antibody or antibody fragment described herein, such as a monoclonal antibody that binds to viral hemagglutinin (e.g., CR6261, CR8020, MEDI8852, MHAA4549A, or VIS410); a broadly neutralizing antibody or antibody fragment targeting viral hemagglutinin (e.g., antibodies or antibody fragments described in Wu et al., J. Mol. Biol. 429:2694-2709 (2017)); a sdAb targeting viral hemagglutinin (e.g., SD36, SD38, SD83, or SD84); or a MDAb or fragment thereof targeting viral hemaglutinin (e.g., JNJ-7445).

In some embodiments of any of the aspects described herein, E (e.g., each E) includes the amino acid sequence of SEQ ID NO: 1. In some embodiments, E includes an amino acid sequence that is at least 70%, 75%, 80%, 85%, 90%, 95%, 96%, 97%, 98%, 99%, or 100% identical to the amino acid sequence of SEQ ID NO: 1.

In some embodiments of any of the aspects described herein, E (e.g., each E) includes the amino acid sequence of SEQ ID NO: 2. In some embodiments, E includes an amino acid sequence that is at least 70%, 75%, 80%, 85%, 90%, 95%, 96%, 97%, 98%, 99%, or 100% identical to the amino acid sequence of SEQ ID NO: 2.

In some embodiments of any of the aspects described herein, E (e.g., each E) includes the amino acid sequence of SEQ ID NO: 3. In some embodiments, E includes an amino acid sequence that is at least 70%, 75%, 80%, 85%, 90%, 95%, 96%, 97%, 98%, 99%, or 100% identical to the amino acid sequence of SEQ ID NO: 3.

In some embodiments of any of the aspects described herein, E (e.g., each E) includes the amino acid sequence of SEQ ID NO: 4. In some embodiments, E includes an amino acid sequence that is at least 70%, 75%, 80%, 85%, 90%, 95%, 96%, 97%, 98%, 99%, or 100% identical to the amino acid sequence of SEQ ID NO: 4.

In some embodiments of any of the aspects described herein, E (e.g., each E) includes the amino acid sequence of SEQ ID NO: 5. In some embodiments, E includes an amino acid sequence that is at least 70%, 75%, 80%, 85%, 90%, 95%, 96%, 97%, 98%, 99%, or 100% identical to the amino acid sequence of SEQ ID NO: 5.

In some embodiments of any of the aspects described herein, E (e.g., each E) includes the amino acid sequence of SEQ ID NO: 6. In some embodiments, E includes an amino acid sequence that is at least 70%, 75%, 80%, 85%, 90%, 95%, 96%, 97%, 98%, 99%, or 100% identical to the amino acid sequence of SEQ ID NO: 6.

In some embodiments of any of the aspects described herein, E (e.g., each E) includes the amino acid sequence of SEQ ID NO: 7. In some embodiments, E includes an amino acid sequence that is at least 70%, 75%, 80%, 85%, 90%, 95%, 96%, 97%, 98%, 99%, or 100% identical to the amino acid sequence of SEQ ID NO: 7.

In some embodiments of any of the aspects described herein, E (e.g., each E) includes the amino acid sequence of SEQ ID NO: 8. In some embodiments, E includes an amino acid sequence that is at least 70%, 75%, 80%, 85%, 90%, 95%, 96%, 97%, 98%, 99%, or 100% identical to the amino acid sequence of SEQ ID NO: 8.

In some embodiments of any of the aspects described herein, E (e.g., each E) includes the amino acid sequence of SEQ ID NO: 9. In some embodiments, E includes an amino acid sequence that is at least 70%, 75%, 80%, 85%, 90%, 95%, 96%, 97%, 98%, 99%, or 100% identical to the amino acid sequence of SEQ ID NO: 9.

In some embodiments of any of the aspects described herein, E (e.g., each E) includes the amino acid sequence of SEQ ID NO: 10. In some embodiments, E includes an amino acid sequence that is at least 70%, 75%, 80%, 85%, 90%, 95%, 96%, 97%, 98%, 99%, or 100% identical to the amino acid sequence of SEQ ID NO: 10.

In some embodiments of any of the aspects described herein, E (e.g., each E) includes the amino acid sequence of SEQ ID NO: 11. In some embodiments, E includes an amino acid sequence that is at least 70%, 75%, 80%, 85%, 90%, 95%, 96%, 97%, 98%, 99%, or 100% identical to the amino acid sequence of SEQ ID NO: 11.

In some embodiments of any of the aspects described herein, E (e.g., each E) includes the amino acid sequence of SEQ ID NO: 12. In some embodiments, E includes an amino acid sequence that is at least 70%, 75%, 80%, 85%, 90%, 95%, 96%, 97%, 98%, 99%, or 100% identical to the amino acid sequence of SEQ ID NO: 12.

In some embodiments of any of the aspects described herein, E (e.g., each E) includes the amino acid sequence of SEQ ID NO: 13. In some embodiments, E includes an amino acid sequence that is at least 70%, 75%, 80%, 85%, 90%, 95%, 96%, 97%, 98%, 99%, or 100% identical to the amino acid sequence of SEQ ID NO: 13.

In some embodiments of any of the aspects described herein, E (e.g., each E) includes the amino acid sequence of SEQ ID NO: 14. In some embodiments, E includes an amino acid sequence that is at least 70%, 75%, 80%, 85%, 90%, 95%, 96%, 97%, 98%, 99%, or 100% identical to the amino acid sequence of SEQ ID NO: 14.

In some embodiments of any of the aspects described herein, E (e.g., each E) includes the amino acid sequence of SEQ ID NO: 15. In some embodiments, E includes an amino acid sequence that is at least 70%, 75%, 80%, 85%, 90%, 95%, 96%, 97%, 98%, 99%, or 100% identical to the amino acid sequence of SEQ ID NO: 15.

In some embodiments of any of the aspects described herein, E (e.g., each E) includes the amino acid sequence of SEQ ID NO: 16. In some embodiments, E includes an amino acid sequence that is at least 70%, 75%, 80%, 85%, 90%, 95%, 96%, 97%, 98%, 99%, or 100% identical to the amino acid sequence of SEQ ID NO: 16.

In some embodiments of any of the aspects described herein, E (e.g., each E) includes the amino acid sequence of SEQ ID NO: 17. In some embodiments, E includes an amino acid sequence that is at least 70%, 75%, 80%, 85%, 90%, 95%, 96%, 97%, 98%, 99%, or 100% identical to the amino acid sequence of SEQ ID NO: 17.

In some embodiments of any of the aspects described herein, E (e.g., each E) includes the amino acid sequence of SEQ ID NO: 18. In some embodiments, E includes an amino acid sequence that is at least 70%, 75%, 80%, 85%, 90%, 95%, 96%, 97%, 98%, 99%, or 100% identical to the amino acid sequence of SEQ ID NO: 18.

In some embodiments of any of the aspects described herein, E (e.g., each E) includes the amino acid sequence of SEQ ID NO: 19. In some embodiments, E includes an amino acid sequence that is at least 70%, 75%, 80%, 85%, 90%, 95%, 96%, 97%, 98%, 99%, or 100% identical to the amino acid sequence of SEQ ID NO: 19.

In some embodiments of any of the aspects described herein, E (e.g., each E) includes the amino acid sequence of SEQ ID NO: 20. In some embodiments, E includes an amino acid sequence that is at least 70%, 75%, 80%, 85%, 90%, 95%, 96%, 97%, 98%, 99%, or 100% identical to the amino acid sequence of SEQ ID NO: 20.

In some embodiments of any of the aspects described herein, E (e.g., each E) includes the amino acid sequence of SEQ ID NO: 21. In some embodiments, E includes an amino acid sequence that is at least 70%, 75%, 80%, 85%, 90%, 95%, 96%, 97%, 98%, 99%, or 100% identical to the amino acid sequence of SEQ ID NO: 21.

In some embodiments of any of the aspects described herein, E (e.g., each E) includes the amino acid sequence of SEQ ID NO: 22. In some embodiments, E includes an amino acid sequence that is at least 70%, 75%, 80%, 85%, 90%, 95%, 96%, 97%, 98%, 99%, or 100% identical to the amino acid sequence of SEQ ID NO: 22.

In some embodiments of any of the aspects described herein, E (e.g., each E) includes the amino acid sequence of SEQ ID NO: 23. In some embodiments, E includes an amino acid sequence that is at least 70%, 75%, 80%, 85%, 90%, 95%, 96%, 97%, 98%, 99%, or 100% identical to the amino acid sequence of SEQ ID NO: 23.

In some embodiments of any of the aspects described herein, E (e.g., each E) includes the amino acid sequence of SEQ ID NO: 24. In some embodiments, E includes an amino acid sequence that is at least 70%, 75%, 80%, 85%, 90%, 95%, 96%, 97%, 98%, 99%, or 100% identical to the amino acid sequence of SEQ ID NO: 24.

In some embodiments of any of the aspects described herein, E (e.g., each E) includes the amino acid sequence of SEQ ID NO: 25. In some embodiments, E includes an amino acid sequence that is at least 70%, 75%, 80%, 85%, 90%, 95%, 96%, 97%, 98%, 99%, or 100% identical to the amino acid sequence of SEQ ID NO: 25.

In some embodiments of any of the aspects described herein, E (e.g., each E) includes the amino acid sequence of SEQ ID NO: 26. In some embodiments, E includes an amino acid sequence that is at least 70%, 75%, 80%, 85%, 90%, 95%, 96%, 97%, 98%, 99%, or 100% identical to the amino acid sequence of SEQ ID NO: 26.

In some embodiments of any of the aspects described herein, E (e.g., each E) includes the amino acid sequence of SEQ ID NO: 27. In some embodiments, E includes an amino acid sequence that is at least 70%, 75%, 80%, 85%, 90%, 95%, 96%, 97%, 98%, 99%, or 100% identical to the amino acid sequence of SEQ ID NO: 27.

In some embodiments of any of the aspects described herein, E (e.g., each E) includes the amino acid sequence of SEQ ID NO: 28. In some embodiments, E includes an amino acid sequence that is at least 70%, 75%, 80%, 85%, 90%, 95%, 96%, 97%, 98%, 99%, or 100% identical to the amino acid sequence of SEQ ID NO: 28.

In some embodiments of any of the aspects described herein, E (e.g., each E) includes the amino acid sequence of SEQ ID NO: 29. In some embodiments, E includes an amino acid sequence that is at least 70%, 75%, 80%, 85%, 90%, 95%, 96%, 97%, 98%, 99%, or 100% identical to the amino acid sequence of SEQ ID NO: 29.

In some embodiments of any of the aspects described herein, E (e.g., each E) includes the amino acid sequence of SEQ ID NO: 30. In some embodiments, E includes an amino acid sequence that is at least 70%, 75%, 80%, 85%, 90%, 95%, 96%, 97%, 98%, 99%, or 100% identical to the amino acid sequence of SEQ ID NO: 30.

In some embodiments of any of the aspects described herein, E (e.g., each E) includes the amino acid sequence of SEQ ID NO: 31. In some embodiments, E includes an amino acid sequence that is at least 70%, 75%, 80%, 85%, 90%, 95%, 96%, 97%, 98%, 99%, or 100% identical to the amino acid sequence of SEQ ID NO: 31.

In some embodiments of any of the aspects described herein, E (e.g., each E) includes the amino acid sequence of SEQ ID NO: 32. In some embodiments, E includes an amino acid sequence that is at least 70%, 75%, 80%, 85%, 90%, 95%, 96%, 97%, 98%, 99%, or 100% identical to the amino acid sequence of SEQ ID NO: 32.

In some embodiments of any of the aspects described herein, E (e.g., each E) includes the amino acid sequence of SEQ ID NO: 33. In some embodiments, E includes an amino acid sequence that is at least 70%, 75%, 80%, 85%, 90%, 95%, 96%, 97%, 98%, 99%, or 100% identical to the amino acid sequence of SEQ ID NO: 33.

In some embodiments of any of the aspects described herein, E (e.g., each E) includes the amino acid sequence of SEQ ID NO: 34. In some embodiments, E includes an amino acid sequence that is at least 70%, 75%, 80%, 85%, 90%, 95%, 96%, 97%, 98%, 99%, or 100% identical to the amino acid sequence of SEQ ID NO: 34.

In some embodiments of any of the aspects described herein, E (e.g., each E) includes the amino acid sequence of SEQ ID NO: 35. In some embodiments, E includes an amino acid sequence that is at least 70%, 75%, 80%, 85%, 90%, 95%, 96%, 97%, 98%, 99%, or 100% identical to the amino acid sequence of SEQ ID NO: 35.

In some embodiments of any of the aspects described herein, E (e.g., each E) includes the amino acid sequence of SEQ ID NO: 36. In some embodiments, E includes an amino acid sequence that is at least 70%, 75%, 80%, 85%, 90%, 95%, 96%, 97%, 98%, 99%, or 100% identical to the amino acid sequence of SEQ ID NO: 36.

In some embodiments of any of the aspects described herein, E (e.g., each E) includes the amino acid sequence of SEQ ID NO: 37. In some embodiments, E includes an amino acid sequence that is at least 70%, 75%, 80%, 85%, 90%, 95%, 96%, 97%, 98%, 99%, or 100% identical to the amino acid sequence of SEQ ID NO: 37.

In some embodiments of any of the aspects described herein, E (e.g., each E) includes the amino acid sequence of SEQ ID NO: 38. In some embodiments, E includes an amino acid sequence that is at least 70%, 75%, 80%, 85%, 90%, 95%, 96%, 97%, 98%, 99%, or 100% identical to the amino acid sequence of SEQ ID NO: 38.

In some embodiments of any of the aspects described herein, E (e.g., each E) includes the amino acid sequence of SEQ ID NO: 39. In some embodiments, E includes an amino acid sequence that is at least 70%, 75%, 80%, 85%, 90%, 95%, 96%, 97%, 98%, 99%, or 100% identical to the amino acid sequence of SEQ ID NO: 39.

In some embodiments of any of the aspects described herein, E (e.g., each E) includes the amino acid sequence of SEQ ID NO: 40. In some embodiments, E includes an amino acid sequence that is at least 70%, 75%, 80%, 85%, 90%, 95%, 96%, 97%, 98%, 99%, or 100% identical to the amino acid sequence of SEQ ID NO: 40.

In some embodiments of any of the aspects described herein, E (e.g., each E) includes the amino acid sequence of SEQ ID NO: 41. In some embodiments, E includes an amino acid sequence that is at least 70%, 75%, 80%, 85%, 90%, 95%, 96%, 97%, 98%, 99%, or 100% identical to the amino acid sequence of SEQ ID NO: 41.

In some embodiments of any of the aspects described herein, E (e.g., each E) includes the amino acid sequence of SEQ ID NO: 42. In some embodiments, E includes an amino acid sequence that is at least 70%, 75%, 80%, 85%, 90%, 95%, 96%, 97%, 98%, 99%, or 100% identical to the amino acid sequence of SEQ ID NO: 42.

In some embodiments of any of the aspects described herein, E (e.g., each E) includes the amino acid sequence of SEQ ID NO: 43. In some embodiments, E includes an amino acid sequence that is at least 70%, 75%, 80%, 85%, 90%, 95%, 96%, 97%, 98%, 99%, or 100% identical to the amino acid sequence of SEQ ID NO: 43.

In some embodiments of any of the aspects described herein, E (e.g., each E) includes the amino acid sequence of SEQ ID NO: 44. In some embodiments, E includes an amino acid sequence that is at least 70%, 75%, 80%, 85%, 90%, 95%, 96%, 97%, 98%, 99%, or 100% identical to the amino acid sequence of SEQ ID NO: 45.

In some embodiments of any of the aspects described herein, E (e.g., each E) includes the amino acid sequence of SEQ ID NO: 46. In some embodiments, E includes an amino acid sequence that is at least 70%, 75%, 80%, 85%, 90%, 95%, 96%, 97%, 98%, 99%, or 100% identical to the amino acid sequence of SEQ ID NO: 46.

In some embodiments of any of the aspects described herein, E (e.g., each E) includes the amino acid sequence of SEQ ID NO: 47. In some embodiments, E includes an amino acid sequence that is at least 70%, 75%, 80%, 85%, 90%, 95%, 96%, 97%, 98%, 99%, or 100% identical to the amino acid sequence of SEQ ID NO: 47.

In some embodiments of any of the aspects described herein, E (e.g., each E) includes the amino acid sequence of SEQ ID NO: 48. In some embodiments, E includes an amino acid sequence that is at least 70%, 75%, 80%, 85%, 90%, 95%, 96%, 97%, 98%, 99%, or 100% identical to the amino acid sequence of SEQ ID NO: 48.

In some embodiments of any of the aspects described herein, E (e.g., each E) includes the amino acid sequence of SEQ ID NO: 49. In some embodiments, E includes an amino acid sequence that is at least 70%, 75%, 80%, 85%, 90%, 95%, 96%, 97%, 98%, 99%, or 100% identical to the amino acid sequence of SEQ ID NO: 49.

In some embodiments of any of the aspects described herein, E (e.g., each E) includes the amino acid sequence of SEQ ID NO: 50. In some embodiments, E includes an amino acid sequence that is at least 70%, 75%, 80%, 85%, 90%, 95%, 96%, 97%, 98%, 99%, or 100% identical to the amino acid sequence of SEQ ID NO: 50.

In some embodiments of any of the aspects described herein, E (e.g., each E) includes the amino acid sequence of SEQ ID NO: 51. In some embodiments, E includes an amino acid sequence that is at least 70%, 75%, 80%, 85%, 90%, 95%, 96%, 97%, 98%, 99%, or 100% identical to the amino acid sequence of SEQ ID NO: 51.

In some embodiments of any of the aspects described herein, E (e.g., each E) includes the amino acid sequence of SEQ ID NO: 52. In some embodiments, E includes an amino acid sequence that is at least 70%, 75%, 80%, 85%, 90%, 95%, 96%, 97%, 98%, 99%, or 100% identical to the amino acid sequence of SEQ ID NO: 52.

In some embodiments of any of the aspects described herein, E (e.g., each E) includes the amino acid sequence of SEQ ID NO: 53. In some embodiments, E includes an amino acid sequence that is at least 70%, 75%, 80%, 85%, 90%, 95%, 96%, 97%, 98%, 99%, or 100% identical to the amino acid sequence of SEQ ID NO: 53.

In some embodiments of any of the aspects described herein, E (e.g., each E) includes the amino acid sequence of SEQ ID NO: 54. In some embodiments, E includes an amino acid sequence that is at least 70%, 75%, 80%, 85%, 90%, 95%, 96%, 97%, 98%, 99%, or 100% identical to the amino acid sequence of SEQ ID NO: 54.

In some embodiments of any of the aspects described herein, E (e.g., each E) includes the amino acid sequence of SEQ ID NO: 55. In some embodiments, E includes an amino acid sequence that is at least 70%, 75%, 80%, 85%, 90%, 95%, 96%, 97%, 98%, 99%, or 100% identical to the amino acid sequence of SEQ ID NO: 55.

In some embodiments of any of the aspects described herein, E (e.g., each E) includes the amino acid sequence of SEQ ID NO: 56. In some embodiments, E includes an amino acid sequence that is at least 70%, 75%, 80%, 85%, 90%, 95%, 96%, 97%, 98%, 99%, or 100% identical to the amino acid sequence of SEQ ID NO: 56.

In some embodiments of any of the aspects described herein, E (e.g., each E) includes the amino acid sequence of SEQ ID NO: 57. In some embodiments, E includes an amino acid sequence that is at least 70%, 75%, 80%, 85%, 90%, 95%, 96%, 97%, 98%, 99%, or 100% identical to the amino acid sequence of SEQ ID NO: 57.

In some embodiments of any of the aspects described herein, E (e.g., each E) includes the amino acid sequence of SEQ ID NO: 58. In some embodiments, E includes an amino acid sequence that is at least 70%, 75%, 80%, 85%, 90%, 95%, 96%, 97%, 98%, 99%, or 100% identical to the amino acid sequence of SEQ ID NO: 58.

In some embodiments of any of the aspects described herein, E (e.g., each E) includes the amino acid sequence of SEQ ID NO: 59. In some embodiments, E includes an amino acid sequence that is at least 70%, 75%, 80%, 85%, 90%, 95%, 96%, 97%, 98%, 99%, or 100% identical to the amino acid sequence of SEQ ID NO: 59.

In some embodiments of any of the aspects described herein, E (e.g., each E) includes the amino acid sequence of SEQ ID NO: 60. In some embodiments, E includes an amino acid sequence that is at least 70%, 75%, 80%, 85%, 90%, 95%, 96%, 97%, 98%, 99%, or 100% identical to the amino acid sequence of SEQ ID NO: 60.

In some embodiments of any of the aspects described herein, E (e.g., each E) includes the amino acid sequence of SEQ ID NO: 61. In some embodiments, E includes an amino acid sequence that is at least 70%, 75%, 80%, 85%, 90%, 95%, 96%, 97%, 98%, 99%, or 100% identical to the amino acid sequence of SEQ ID NO: 61.

In some embodiments of any of the aspects described herein, E (e.g., each E) includes the amino acid sequence of SEQ ID NO: 62. In some embodiments, E includes an amino acid sequence that is at least 70%, 75%, 80%, 85%, 90%, 95%, 96%, 97%, 98%, 99%, or 100% identical to the amino acid sequence of SEQ ID NO: 62.

In some embodiments of any of the aspects described herein, E (e.g., each E) includes the amino acid sequence of SEQ ID NO: 63. In some embodiments, E includes an amino acid sequence that is at least 70%, 75%, 80%, 85%, 90%, 95%, 96%, 97%, 98%, 99%, or 100% identical to the amino acid sequence of SEQ ID NO: 63.

In some embodiments of any of the aspects described herein, E (e.g., each E) includes the amino acid sequence of SEQ ID NO: 64. In some embodiments, E includes an amino acid sequence that is at least 70%, 75%, 80%, 85%, 90%, 95%, 96%, 97%, 98%, 99%, or 100% identical to the amino acid sequence of SEQ ID NO: 64.

In some embodiments of any of the aspects described herein, E (e.g., each E) includes the amino acid sequence of SEQ ID NO: 65. In some embodiments, E includes an amino acid sequence that is at least 70%, 75%, 80%, 85%, 90%, 95%, 96%, 97%, 98%, 99%, or 100% identical to the amino acid sequence of SEQ ID NO: 65.

In some embodiments of any of the aspects described herein, E (e.g., each E) includes the amino acid sequence of SEQ ID NO: 66. In some embodiments, E includes an amino acid sequence that is at least 70%, 75%, 80%, 85%, 90%, 95%, 96%, 97%, 98%, 99%, or 100% identical to the amino acid sequence of SEQ ID NO: 66.

In some embodiments of any of the aspects described herein, E (e.g., each E) includes the amino acid sequence of SEQ ID NO: 67. In some embodiments, E includes an amino acid sequence that is at least 70%, 75%, 80%, 85%, 90%, 95%, 96%, 97%, 98%, 99%, or 100% identical to the amino acid sequence of SEQ ID NO: 67.

In some embodiments of any of the aspects described herein, E (e.g., each E) includes the amino acid sequence of SEQ ID NO: 68. In some embodiments, E includes an amino acid sequence that is at least 70%, 75%, 80%, 85%, 90%, 95%, 96%, 97%, 98%, 99%, or 100% identical to the amino acid sequence of SEQ ID NO: 68.

In some embodiments of any of the aspects described herein, E (e.g., each E) includes the amino acid sequence of SEQ ID NO: 69. In some embodiments, E includes an amino acid sequence that is at least 70%, 75%, 80%, 85%, 90%, 95%, 96%, 97%, 98%, 99%, or 100% identical to the amino acid sequence of SEQ ID NO: 69.

In some embodiments of any of the aspects described herein, E (e.g., each E) includes the amino acid sequence of SEQ ID NO: 70. In some embodiments, E includes an amino acid sequence that is at least 70%, 75%, 80%, 85%, 90%, 95%, 96%, 97%, 98%, 99%, or 100% identical to the amino acid sequence of SEQ ID NO: 70.

In some embodiments of any of the aspects described herein, E (e.g., each E) includes the amino acid sequence of SEQ ID NO: 71. In some embodiments, E includes an amino acid sequence that is at least 70%, 75%, 80%, 85%, 90%, 95%, 96%, 97%, 98%, 99%, or 100% identical to the amino acid sequence of SEQ ID NO: 71.

In some embodiments of any of the aspects described herein, wherein E includes an Fc domain monomer, the Fc domain monomer (e.g., the Fc domain monomer having the sequence of any one of SEQ ID NOs: 1-68) includes a triple mutation corresponding to M252Y/S254T/$T_{256}$E (YTE). As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-68 may be mutated to include a YTE mutation.

In some embodiments of any of the aspects described herein, wherein E includes an Fc domain monomer, the Fc domain monomer (e.g., the Fc domain monomer having the sequence of any one of SEQ ID NOs: 1-68) includes a double mutant corresponding to M428L/N434S (LS). As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-68 may be mutated to include a LS mutation.

In some embodiments of any of the aspects described herein, wherein E includes an Fc domain monomer, the Fc domain monomer (e.g., the Fc domain monomer having the sequence of any one of SEQ ID NOs: 1-68) includes a mutant corresponding to N434H. As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-68 may be mutated to include an N434H mutation.

In some embodiments of any of the aspects described herein, wherein E includes an Fc domain monomer, the Fc domain monomer (e.g., the Fc domain monomer having the sequence of any one of SEQ ID NOs: 1-68) includes a mutant corresponding to C220S. As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-68 may be mutated to include a C220S mutation.

In some embodiments of any of the aspects described herein, wherein E includes an Fc domain monomer, the Fc domain monomer (e.g., the Fc domain monomer having the sequence of any one of SEQ ID NOs: 1-68) is a fragment of the Fc domain monomer (e.g., a fragment of at least 25 (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more), at least 50 (e.g., 51, 52, 53, 54, 55, 56, 57, 58, 59, 60, 61, 62, 63, 64, 65, 66, 67, 68, 69, 70, 71, 72, 73, 74, 75 or more), at least 75 (e.g., 75, 76, 77, 78, 79, 80, 81, 82, 83, 84, 85, 86, 87, 88, 89, 90, 91, 92, 93, 94, 95, 96, 97, 98, 99, 100 or more) consecutive amino acids in length from SEQ ID NOs: 1-68.

In some embodiments of any of the aspects described herein (e.g., a conjugate of any one of formulas (1)-(5), (D-I)-(D-X), (D'-I), (M-I)-(M-X), or (M'-I)), one or more nitrogen atoms of one or more surface exposed lysine residues of E or one or more sulfur atoms of one or more surface exposed cysteines in E is covalently conjugated to a linker (e.g., a $PEG_2$-$PEG_{20}$ linker). The linker conjugated to E may be functionalized such that it may reacts to form a covalent bond with the L of any $A_1$-L or any $A_2$-L-$A_1$ described herein. In preferred embodiments, E is conjugated to a linker functionalized with an azido group and the L of $A_1$-L or any $A_2$-L-$A_1$ is functionalized with an alkyne group. Conjugation (e.g., by click chemistry) of the linker-azido of E and linker-alkyne of $A_1$-L or $A_2$-L-$A_1$ forms a conjugate of the invention, for example a conjugate described by any one of formulas (1)-(5), (D-I)-(D-X), (D'-I), (M-I)-(M-X), or (M'-I). In yet other embodiments, E is conjugated to a linker functionalized with an alkyne group and L of any $A_1$-L or of any $A_2$-L-$A_1$ is functionalized with an azido group. Conjugation (e.g., by click chemistry) of the linker-alkyne of E and linker-azido of $A_1$-L or $A_2$-L-$A_1$ forms a conjugate of the invention, for example a conjugate described by formula (1)-(5), (D-I)-(D-X), (D'-I), (M-I)-(M-X), or (M'-I).

In some embodiments of any of the aspects described herein, the squiggly line of any one of formulas (1)-(5), (D-I)-(D-X), (D'-I), (M-I)-(M-X), or (M'-I) may represent a covalent bond between E and the L of $A_1$-L or $A_2$-L-$A_1$.

In some embodiments of any of the aspects described herein, the squiggly line of any one of formulas (1)-(5), (D-I)-(D-X), (D'-I), (M-I)-(M-X), or (M'-I) may represent that one or more amino acid side chains of E (e.g., one or more nitrogen atoms of one or more surface exposed lysine residues of E or one or more sulfur atoms of one or more surface exposed cysteines in E) have been conjugated to a linker (e.g., a $PEG_2$-$PEG_{20}$ linker) wherein the linker has been functionalized with a reactive moiety, such that the reactive moiety forms a covalent bond with the L of any $A_1$-L or any $A_2$-L-$A_1$ described herein (e.g., by click chemistry between an azido functionalized linker and an alkyne functionalized linker, as described above). In some embodiments of any of the aspects described herein, $A_1$ and/or $A_2$ have the structure described by (A-1):

(A-I)

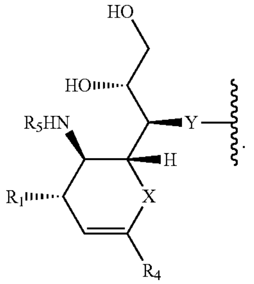

In preferred embodiments, wherein $A_1$ and/or $A_2$ have the structure described by (A-1): $R_1$ is —NHC(=NH)$NH_2$, $R_4$ is —$CO_2H$, Rs is —$COCH_3$, and/or X is —O—. In preferred embodiments, $A_1$ and/or $A_2$ have the structure of zanamivir described by:

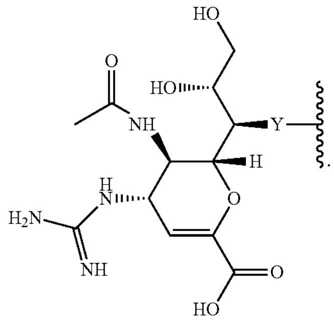

In some embodiments of any of the aspects described herein, $A_1$ and/or $A_2$ have the structure described by (A-II):

(A-II)

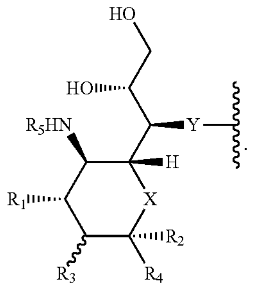

In preferred embodiments, wherein $A_1$ and/or $A_2$ have the structure described by (A-II): $R_1$ is —NHC(=NH)$NH_2$, $R_2$ is H or F, $R_3$ is H or F, $R_4$ is —$CO_2H$, Rs is —$COCH_3$, and/or X is —O—. In preferred embodiments, $A_1$ and/or $A_2$ have the structure described by:

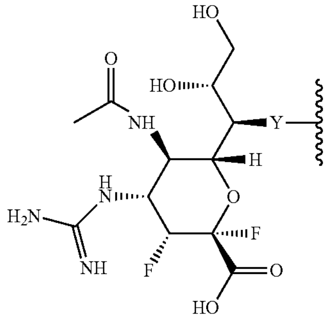

or

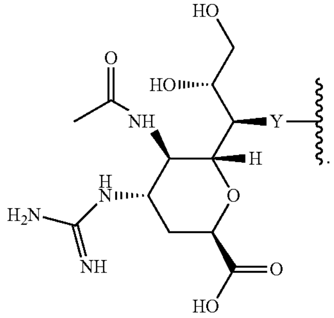

In some embodiments of any of the aspects described herein, $A_1$ and/or $A_2$ have the structure described by (A-III):

(A-III)

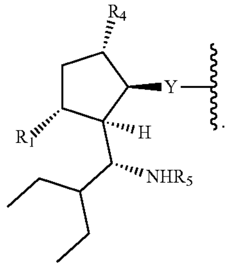

In preferred embodiments, wherein $A_1$ and/or $A_2$ have the structure described by (A-III): $R_1$ is —NHC(=NH)$NH_2$, $R_4$ is —$CO_2H$, and/or Rs is —$COCH_3$. In preferred embodiments, $A_1$ and/or $A_2$ have the structure of peramivir described by:

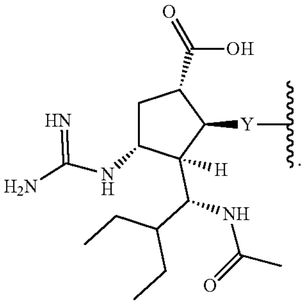

In some embodiments of any of the aspects described herein, $A_1$ and/or $A_2$ have the structure described by (A-IV):

(A-IV)

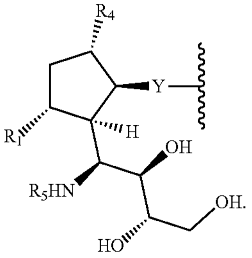

In preferred embodiments, wherein $A_1$ and/or $A_2$ have the structure described by (A-IV): $R_1$ is —NHC(═NH)$NH_2$, $R_4$ is —$CO_2H$, and/or Rs is —$COCH_3$. In preferred embodiments, $A_1$ and/or $A_2$ have the structure described by:

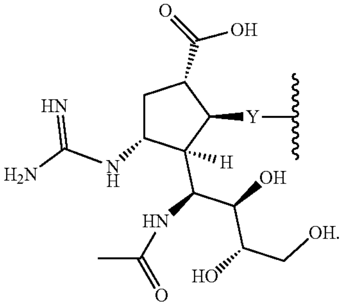

In some embodiments of any of the aspects described herein, $A_1$ and/or $A_2$ have the structure described by (A-V):

(A-V)

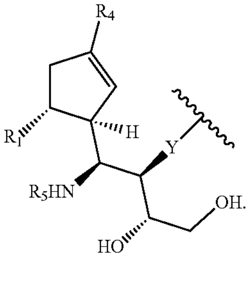

In preferred embodiments, wherein $A_1$ and/or $A_2$ have the structure described by (A-V): $R_1$ is —NHC(═NH)$NH_2$, $R_4$ is —$CO_2H$, and/or Rs is —$COCH_3$. In preferred embodiments, $A_1$ and/or $A_2$ have the structure described by:

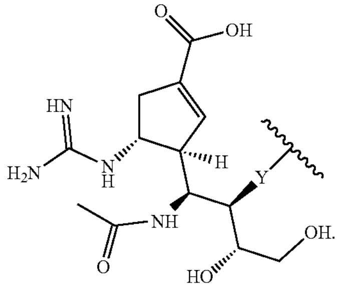

In some embodiments of any of the aspects described herein, $A_1$ and/or $A_2$ have the structure described by (A-VI):

(A-VI)

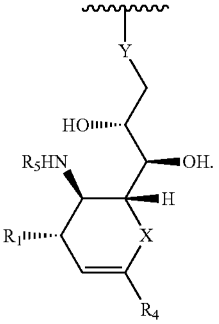

In preferred embodiments, wherein $A_1$ and/or $A_2$ have the structure described by (A-VI): $R_1$ is —NHC(═NH)$NH_2$, $R_4$ is —$CO_2H$, Rs is —$COCH_3$, and/or X is —O—. In preferred embodiments, $A_1$ and/or $A_2$ have the structure of zanamivir described by:

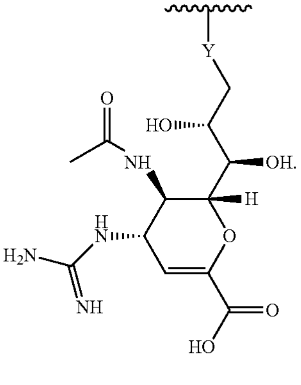

In some embodiments of any of the aspects described herein, $A_1$ and/or $A_2$ have the structure described by (A-VII):

(A-VII)

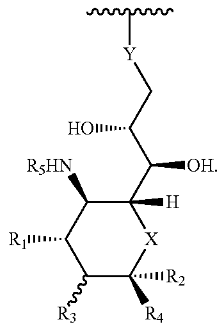

In preferred embodiments, wherein $A_1$ and/or $A_2$ have the structure described by (A-VII): $R_1$ is —NHC(═NH)$NH_2$, $R_2$ is H or F, $R_3$ is H or F, $R_4$ is —$CO_2H$, Rs is —$COCH_3$, and/or X is —O—. In preferred embodiments, $A_1$ and/or $A_2$ have the structure described by:

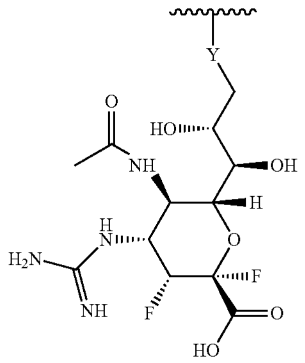

or

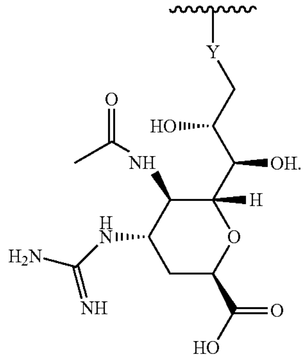

In some embodiments of any of the aspects described herein, $A_1$ and/or $A_2$ have the structure described by (A-VIII):

(A-VIII)

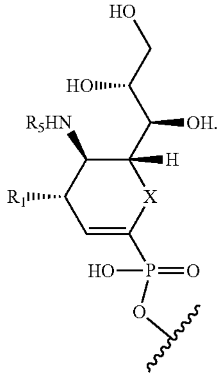

In preferred embodiments, wherein $A_1$ and/or $A_2$ have the structure described by (A-VIII): $R_1$ is —NHC(═NH)$NH_2$, Rs is —$COCH_3$, and/or X is —O—. In preferred embodiments, $A_1$ and/or $A_2$ have the structure described by:

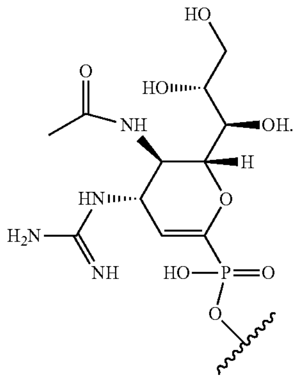 [SMILES: *OP(=O)(O)C1=C[C@H](NC(=N)N)[C@@H](NC(C)=O)[C@H]([C@H](O)[C@H](O)CO)O1]

In some embodiments of any of the aspects described herein, $A_1$ and/or $A_2$ have the structure described by (A-IX):

(A-IX)

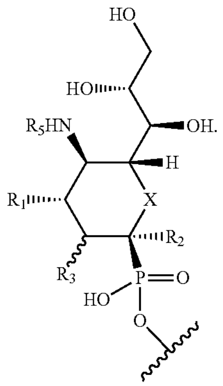

In preferred embodiments, wherein $A_1$ and/or $A_2$ have the structure described by (A-IX): $R_1$ is —NHC(═NH)$NH_2$, $R_2$ is H or F, $R_3$ is H or F, Rs is —$COCH_3$, and/or X is —O—. In preferred embodiments, $A_1$ and/or $A_2$ have the structure described by:

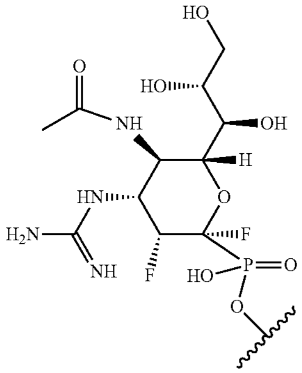

or

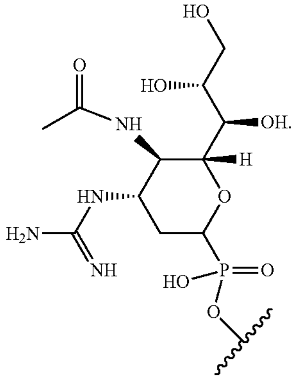

In some embodiments of any of the aspects described herein, $A_1$ and/or $A_2$ have the structure described by (A-X):

(A-X)

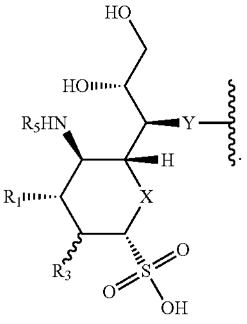

In preferred embodiments, wherein $A_1$ and/or $A_2$ have the structure described by (A-X): $R_1$ is —NHC(=NH)$NH_2$, $R_3$ is H, Rs is —$COCH_3$, and/or X is —O—. In preferred embodiments, $A_1$ and/or $A_2$ have the structure of sulfozanamivir described by:

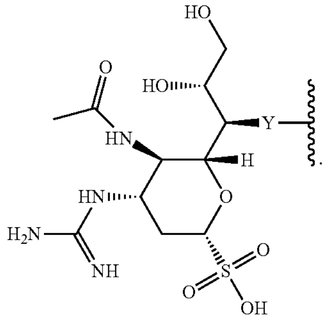

In some embodiments of any of the aspects described herein, $A_1$ and/or $A_2$ have the structure described by (A-XI):

(A-XI)

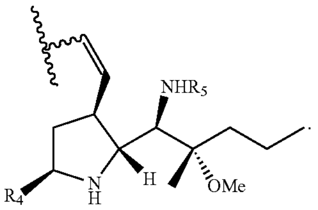

In preferred embodiments, wherein $A_1$ and/or $A_2$ have the structure described by (A-XI): $R_4$ is —$CO_2H$, and/or Rs is —$COCH_3$. In preferred embodiments, the alkene is (E), (Z), or a racemic mixture of (E)/(Z). In preferred embodiments, $A_1$ and/or $A_2$ have the structure of A-315675 (Abbott) described by:

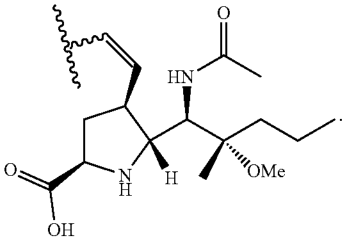

In some embodiments of any of the aspects described herein, $A_1$ and/or $A_2$ have the structure described by (A-XII):

(A-XII)

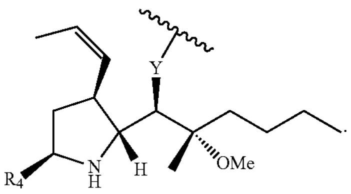

In preferred embodiments, wherein $A_1$ and/or $A_2$ have the structure described by (A-XII): $R_4$ is —$CO_2H$. In preferred embodiments, $A_1$ and/or $A_2$ have the structure of A-315675 (Abbott) described by:

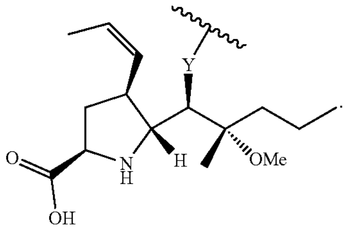

In some embodiments, the conjugate is conjugate 1, or any regioisomer thereof, and the drug-to-antibody ratio (DAR) (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 2, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 3, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 4, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 5, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 6, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 7, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 8, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 9, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 10, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 11, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 12, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 13, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 14, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 15, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 16, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 17, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 18, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 19, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 20, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 21, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 22, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 23, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 24, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 25, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 26, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 27, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 28, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 29, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 30, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 31, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 32, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 33, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 34, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 35, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 36, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 37, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 38, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 39, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 40, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 41, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 42, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

In some embodiments, the conjugate is conjugate 43, or any regioisomer thereof, and the DAR (e.g., T) is between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments the DAR is between 0.5 and 2.0, between 2.0 and 4.0, between 4.0 and 6.0 between 6.0 and 8.0, or between 8.0 and 10.0.

Definitions

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity, but include the general class of which a specific example may be used for illustration. The terminology herein is used to describe specific embodiments of the invention, but their usage does not delimit the invention, except as outlined in the claims.

The term "neuraminidase inhibitor" or ""viral neuraminidase inhibitor," as used herein, refers to compounds that decreases the activity of the enzyme influenza virus neuraminidase (e.g., from influenza virus A, B, or C). A neuraminidase inhibitor may be identified by methods known to those of skill in the art, for example, by reduction of viral replication in an influenza viral plaque reduction assay, e.g., at concentrations less than 20 μM (e.g., less than 10 μM, 5 μM, 2 μM, 1 μM, 500 nM or 100 nM). Viral neuraminidase inhibitors known to those of skill in the art include zanamivir, sulfozanamivir, peramivir, and A-315675 (Abbott) (see, for example, Hadházi et al. A sulfozanamivir analogue has potent anti-influenza virus activity. *ChemMedChem Comm.* 13:785-789 (2018) and In vitro characterization of A-315675, a highly potent inhibitor of A and B strain of influenze virus neuraminidases and influenza virus replication. *Antimicrobial Agents and Chemotherapy* 46(4): 1014-1021 (2002)). Viral neuraminidase inhibitors of the invention include zanamivir, sulfozanamivir, peramavir, A-315675 and analogs thereof, such as the viral neuraminidase inhibitors of formulas (A-I)-(A-XII):

(A-I)

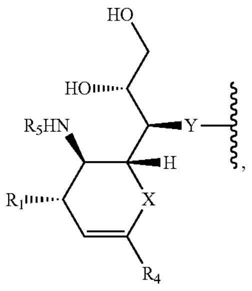

(A-II)

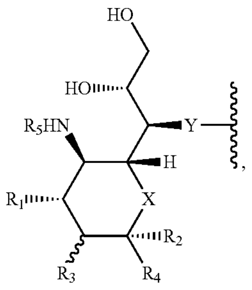

(A-III)

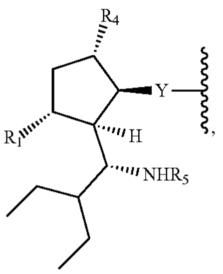

-continued (A-IV)

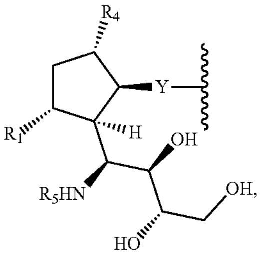

(A-V)

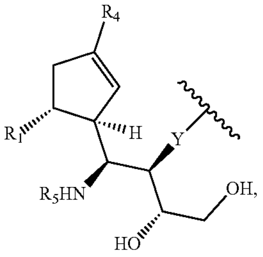

(A-VI)

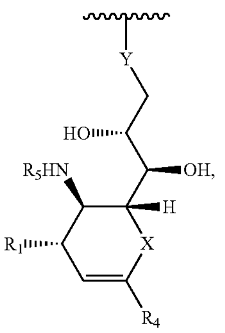

(A-VII)

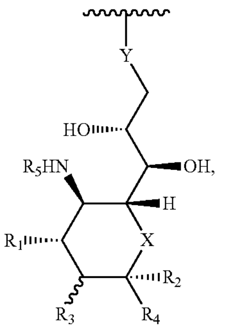

(A-VIII)

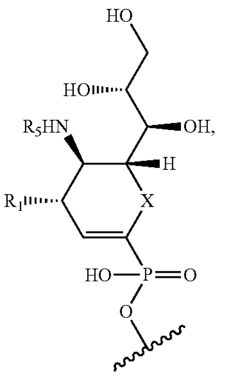

-continued (A-IX)

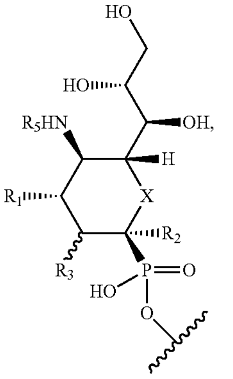

(A-X)

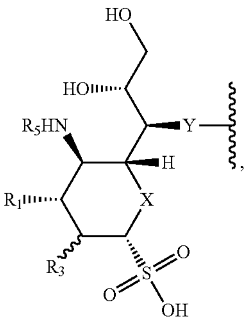

(A-XI)

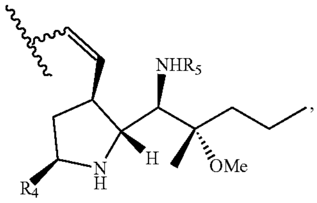

(A-XII)

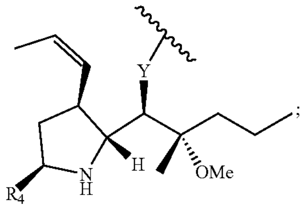

wherein $R_1$ is selected from —OH, —$NH_2$, —NHC(═NH)$NH_2$, and —NHC(═NH)$NHR_6$; $R_2$ and $R_3$ are each independently selected from —H, —OH, —F, —Cl, and —Br; $R_4$ is selected from —$CO_2H$, —P(═O)$(OH)_2$, —$SO_3H$; $R_5$ is selected from —$COCH_3$, —$COCF_3$, —$SO_2CH_3$; X is selected from —O— and —S—; Y is selected from

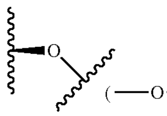
(—O—),

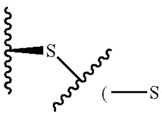
(—S—),

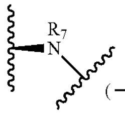
(—$NR_7$—),

-continued

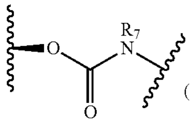
(—O(C═O)$NR_7$—),

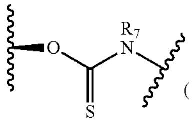
(—O(C═S)$NR_7$—),

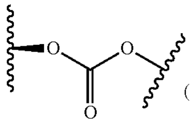
(—O(C═O)O—),

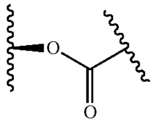
(—O(C═O)—),

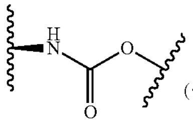
(—NH(C═O)O—),

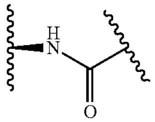
(—NH(C═O)—),

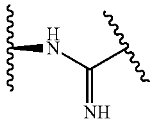
(—NH(C═NH)—),

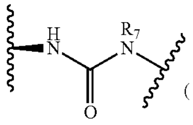
(—NH(C═O)$NR_7$—),

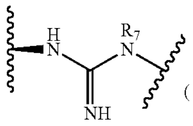
(—NH(C═NH)$NR_7$—),

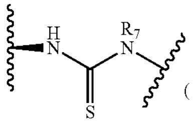
(—NH(C═S)$NR_7$—),

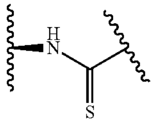
(—NH(C═S)—),

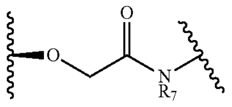
(—$OCH_2$(C═O)$NR_7$—),

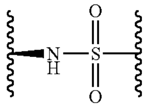
(—$NH(SO_2)$—),

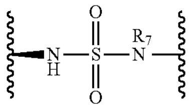
(—$NH(SO_2)NR_7$—),

-continued
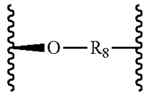
( —OR$_8$— ),
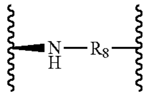
( —NR$_8$— ), and
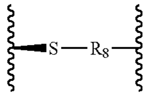
( —SR$_8$— );
$R_6$ is selected from
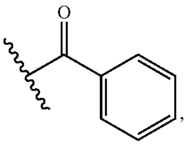,
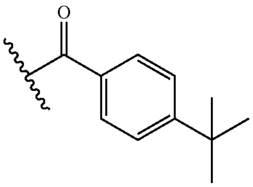,
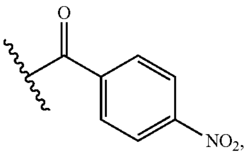
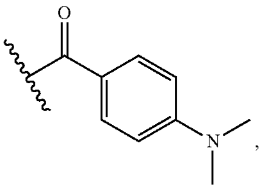,
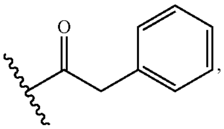,
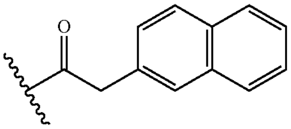,
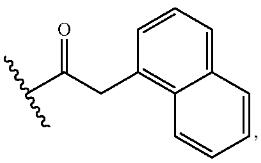,
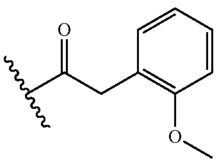,
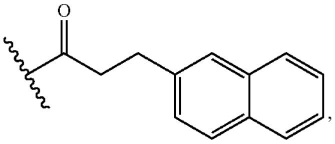,
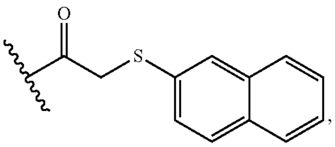,
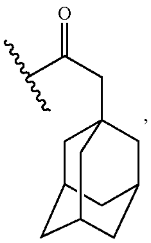,
-continued
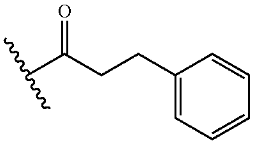,
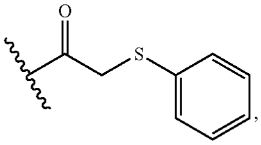,
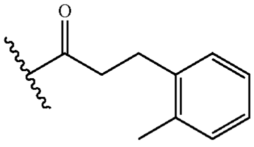,
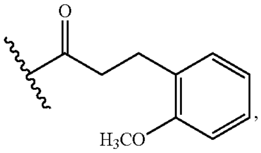,
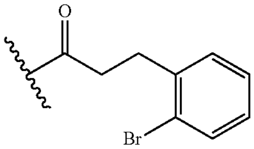,
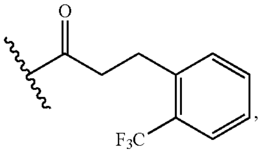,
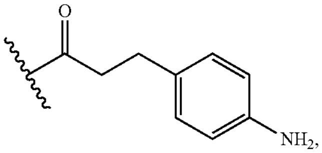
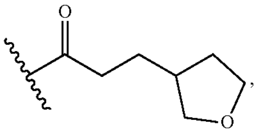,
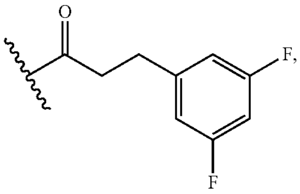
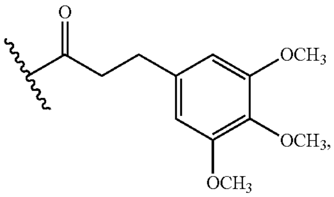
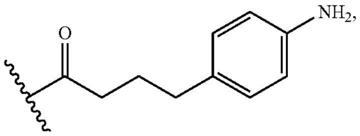
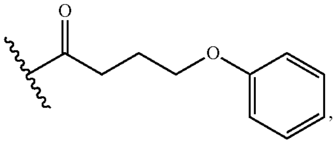,
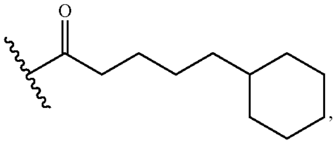,
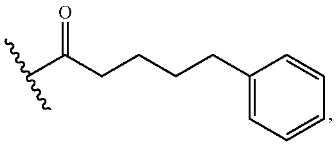, -continued

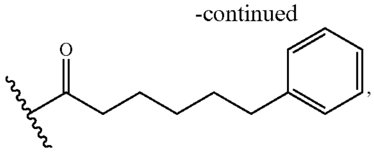

,

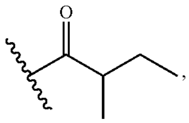

,

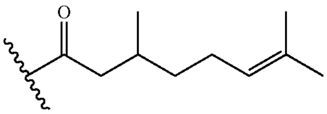

,

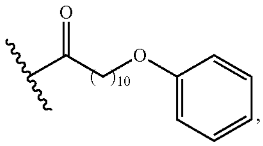

,

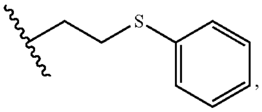

,

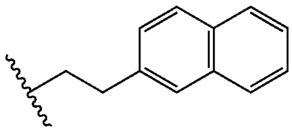

, and

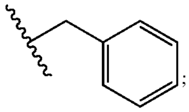

;

$R_7$ is selected from H, C1-C20 alkyl, C3-C20 cycloalkyl, C3-C20 heterocycloalkyl; C5-C15 aryl, and C2-C15 heteroaryl; and Ra is selected from C3-C20 heterocycloalkyl, C5-C15 aryl, and C2-C15 heteroaryl. The term "inhibits neuraminidase activity," as used herein refers to an $IC_{50}$ of less than or equal to 1,000 nM, for example, as measured in accordance with the neuraminidase inhibition assay in Example 2 herein. Specifically, the $IC_{50}$ represents the concentration of the influenza virus neuraminidase inhibitor that is required for 50% inhibition in vitro. In some aspects, an $IC_{50}$ of less than or equal to 100 nM or less than or equal to 10 nM in accordance with neuraminidase inhibition assay is indicative of a compound inhibiting neuraminidase activity.

By "viral infection" is meant the pathogenic growth of a virus (e.g., the influenza virus) in a host organism (e.g., a human subject). A viral infection can be any situation in which the presence of a viral population(s) is damaging to a host body. Thus, a subject is "suffering" from a viral infection when an excessive amount of a viral population is present in or on the subject's body, or when the presence of a viral population(s) is damaging the cells or other tissue of the subject.

As used herein, the term "Fc domain monomer" refers to a polypeptide chain that includes at least a hinge domain and second and third antibody constant domains ($C_H2$ and $C_H3$) or functional fragments thereof (e.g., fragments that that capable of (i) dimerizing with another Fc domain monomer to form an Fc domain, and (ii) binding to an Fc receptor. The Fc domain monomer can be any immunoglobulin antibody isotype, including IgG, IgE, IgM, IgA, or IgD (e.g., IgG). Additionally, the Fc domain monomer can be an IgG subtype (e.g., IgG1, IgG2a, IgG2b, IgG3, or IgG4) (e.g., IgG1). An Fc domain monomer does not include any portion of an immunoglobulin that is capable of acting as an antigen-recognition region, e.g., a variable domain or a complementarity determining region (CDR). Fc domain monomers in the conjugates as described herein can contain one or more changes from a wild-type Fc domain monomer sequence (e.g., 1-10, 1-8, 1-6, 1-4 amino acid substitutions, additions, or deletions) that alter the interaction between an Fc domain and an Fc receptor. Examples of suitable changes are known in the art. In certain embodiments, a human Fc domain monomer (e.g., an IgG heavy chain, such as IgG1) comprises a region that extends from any of Asn208, Glu216, Asp221, Lys222, or Cys226 to the carboxyl-terminus of the heavy chain at Lys447. C-terminal Lys447 of the Fc region may or may not be present, without affecting the structure or stability of the Fc region. Unless otherwise specified herein, numbering of amino acid residues in the IgG or Fc domain monomer is according to the EU numbering system for antibodies, also called the Kabat EU index, as described, for example, in Kabat et al., *Sequences of Proteins of Immunological Interest,* 5th Ed. Public Health Service, National Institutes of Health, Bethesda, M D, 1991.

As used herein, the term "Fc domain" refers to a dimer of two Fc domain monomers that is capable of binding an Fc receptor. In the wild-type Fc domain, the two Fc domain monomers dimerize by the interaction between the two $C_H3$ antibody constant domains, in some embodiments, one or more disulfide bonds form between the hinge domains of the two dimerizing Fc domain monomers. The term "covalently attached" refers to two parts of a conjugate that are linked to each other by a covalent bond formed between two atoms in the two parts of the conjugate.

As used herein, the term "Fc-binding peptide" refers to refers to a polypeptide having an amino acid sequence of 5 to 50 (e.g., 5 to 40, 5 to 30, 5 to 20, 5 to 15, 5 to 10, 10 to 50, 10 to 30, or 10 to 20) amino acid residues that has affinity for and functions to bind an Fc domain, such as any of the Fc domain described herein. An Fc-binding peptide peptide can be of different origins, e.g., synthetic, human, mouse, or rat. Fc-binding peptides of the invention include Fc-binding peptides which have been engineered to include one or more (e.g., two, three, four, or five) solvent-exposed cysteine or lysine residues, which may provide a site for conjugation to a compound of the invention (e.g., conjugation to a neuraminidase inhibitor monomer or dimer, including by way of a linker). Most preferably, the Fc-binding peptide will contain a single solvent-exposed cysteine or lysine, thus enabling site-specific conjugation of a compound of the invention. Fc-binding peptides may include only naturally occurring amino acid residues, or may include one or more non-naturally occurring amino acid residues. Where included, a non-naturally occurring amino acid residue (e.g., the side chain of a non-naturally occurring amino acid residue) may used as the point of attachment for a compound of the invention (e.g., a neuraminidase inhibitor monomer or dimer, including by way of a linker). Fc-binding peptides of the invention may be linear or cyclic. Fc-binding peptides of the invention include any Fc-binding peptides known to one of skill in the art.

As used here, the term "albumin protein" refers to a polypeptide comprising an amino acid sequence corresponding to a naturally-occurring albumin protein (e.g., human serum albumin) or a variant thereof, such as an engineered variant of a naturally-occurring albumin protein. Variants of albumin proteins include polymorphisms, fragments such as domains and sub-domains, and fusion proteins (e.g., an albumin protein having a C-terminal or N-terminal fusion, such as a polypeptide linker). Preferably the albumin protein has the amino acid sequence of human serum albumin (HSA) or a variant or fragment thereof, most preferably a functional variant or fragment thereof. Albumin proteins of the invention include proteins having at least 70%, 75%, 80%, 85%, 90%, 91%, 92%, 93%, 94%, 95%, 96%, 97%, 98%, or 99% identity to any one of SEQ ID NOs: 69-71.

Albumin proteins of the invention include albumin proteins which have been engineered to include one or more (e.g., two, three, four, or five) solvent-exposed cysteine or lysine residues, which may provide a site for conjugation to a compound of the invention (e.g., conjugation to a neuraminidase inhibitor monomer or dimer, including by way of a linker). Most preferably, the albumin protein will contain a single solvent-exposed cysteine or lysine, thus enabling site-specific conjugation of a compound of the invention. Albumin proteins may include only naturally occurring amino acid residues, or may include one or more non-naturally occurring amino acid residues. Where included, a non-naturally occurring amino acid residue (e.g., the side chain of a non-naturally occurring amino acid residue) may used as the point of attachment for a compound of the invention (e.g., a neuraminidase inhibitor monomer or dimer, including by way of a linker).

As used herein, the term "albumin protein-binding peptide" refers to a polypeptide having an amino acid sequence of 5 to 50 (e.g., 5 to 40, 5 to 30, 5 to 20, 5 to 15, 5 to 10, 10 to 50, 10 to 30, or 10 to 20) amino acid residues that has affinity for and functions to bind an albumin protein, such as any of the albumin proteins described herein. Preferably, the albumin protein-binding peptide binds to a naturally-occurring serum albumin, most preferably human serum albumin. An albumin protein-binding peptide can be of different origins, e.g., synthetic, human, mouse, or rat. Albumin protein-binding peptides of the invention include albumin protein-binding peptides which have been engineered to include one or more (e.g., two, three, four, or five) solvent-exposed cysteine or lysine residues, which may provide a site for conjugation to a compound of the invention (e.g., conjugation to a neuraminidase inhibitor monomer or dimer, including by way of a linker). Most preferably, the albumin protein-binding peptide will contain a single solvent-exposed cysteine or lysine, thus enabling site-specific conjugation of a compound of the invention. Albumin protein-binding peptides may include only naturally occurring amino acid residues, or may include one or more non-naturally occurring amino acid residues. Where included, a non-naturally occurring amino acid residue (e.g., the side chain of a non-naturally occurring amino acid residue) may be used as the point of attachment for a compound of the invention (e.g., a neuraminidase inhibitor monomer or dimer, including by way of a linker). Albumin protein-binding peptides of the invention may be linear or cyclic. Albumin protein-binding peptide of the invention include any albumin protein-binding peptides known to one of skill in the art, examples of which, are provided herein. Further exemplary albumin protein-binding peptides are provided in U.S. Patent Application No. 2005/0287153, which is incorporated herein by reference in its entirety.

As used-herein, a "surface exposed amino acid" or "solvent-exposed amino acid," such as a surface exposed cysteine or a surface exposed lysine refers to an amino acid that is accessible to the solvent surrounding the protein. A surface exposed amino acid may be a naturally-occurring or an engineered variant (e.g., a substitution or insertion) of the protein. In some embodiments, a surface exposed amino acid is an amino acid that when substituted does not substantially change the three-dimensional structure of the protein.

The terms "linker," "L," and "L'," as used herein, refer to a covalent linkage or connection between two or more components in a conjugate (e.g., between two neuraminidase inhibitors in a conjugate described herein, between a neuraminidase inhibitor and an Fc domain or albumin protein in a conjugate described herein, and between a dimer of two neuraminidase inhibitors and an Fc domain or an albumin protein in a conjugate described herein). In some embodiments, a conjugate described herein may contain a linker that has a trivalent structure (e.g., a trivalent linker). A trivalent linker has three arms, in which each arm is covalently linked to a component of the conjugate (e.g., a first arm conjugated to a first neuraminidase inhibitor, a second arm conjugated to a second neuraminidase inhibitor, and a third arm conjugated to an Fc domain or an albumin protein).

Molecules that may be used as linkers include at least two functional groups, which may be the same or different, e.g., two carboxylic acid groups, two amine groups, two sulfonic acid groups, a carboxylic acid group and a maleimide group, a carboxylic acid group and an alkyne group, a carboxylic acid group and an amine group, a carboxylic acid group and a sulfonic acid group, an amine group and a maleimide group, an amine group and an alkyne group, or an amine group and a sulfonic acid group. The first functional group may form a covalent linkage with a first component in the conjugate and the second functional group may form a covalent linkage with the second component in the conjugate. In some embodiments of a trivalent linker, two arms of a linker may contain two dicarboxylic acids, in which the first carboxylic acid may form a covalent linkage with the first neuraminidase inhibitor in the conjugate and the second carboxylic acid may form a covalent linkage with the second neuraminidase inhibitor in the conjugate, and the third arm of the linker may for a covalent linkage with an Fc domain or albumin protein in the conjugate. Examples of dicarboxylic acids are described further herein. In some embodiments, a molecule containing one or more maleimide groups may be used as a linker, in which the maleimide group may form a carbon-sulfur linkage with a cysteine in a component (e.g., an Fc domain or an albumin protein) in the conjugate. In some embodiments, a molecule containing one or more alkyne groups may be used as a linker, in which the alkyne group may form a 1,2,3-triazole linkage with an azide in a component (e.g., an Fc domain or an albumin protein) in the conjugate. In some embodiments, a molecule containing one or more azide groups may be used as a linker, in which the azide group may form a 1,2,3-triazole linkage with an alkyne in a component (e.g., an Fc domain or an albumin protein) in the conjugate. In some embodiments, a molecule containing one or more bis-sulfone groups may be used as a linker, in which the bis-sulfone group may form a linkage with an amine group a component (e.g., an Fc domain or an albumin protein) in the conjugate. In some embodiments, a molecule containing one or more sulfonic acid groups may be used as a linker, in which the sulfonic acid group may form a sulfonamide linkage with a component in the conjugate. In some embodiments, a molecule containing one or more isocyanate groups may be used as a linker, in which the isocyanate group may form a urea linkage with a component in the conjugate. In some embodiments, a molecule containing one or more haloalkyl groups may be used as a linker, in which the haloalkyl group may form a covalent linkage, e.g., C—N and C—O linkages, with a component in the conjugate.

In some embodiments, a linker provides space, rigidity, and/or flexibility between the two or more components. In some embodiments, a linker may be a bond, e.g., a covalent bond. The term "bond" refers to a chemical bond, e.g., an amide bond, a disulfide bond, a C—O bond, a C—N bond, a N—N bond, a C—S bond, or any kind of bond created from a chemical reaction, e.g., chemical conjugation. In some embodiments, a linker includes no more than 250 atoms. In some embodiments, a linker includes no more than 250 non-hydrogen atoms. In some embodiments, the backbone of a linker includes no more than 250 atoms. The "backbone" of a linker refers to the atoms in the linker that together form the shortest path from one part of a conjugate to another part of the conjugate (e.g., the shortest path linking a first neuraminidase inhibitor and a second neuraminidase inhibitor). The atoms in the backbone of the linker are directly involved in linking one part of a conjugate to another part of the conjugate (e.g., linking a first neuraminidase inhibitor and a second neuraminidase inhibitor). For examples, hydrogen atoms attached to carbons in the backbone of the linker are not considered as directly involved in linking one part of the conjugate to another part of the conjugate.

In some embodiments, a linker may comprise a synthetic group derived from, e.g., a synthetic polymer (e.g., a polyethylene glycol (PEG) polymer). In some embodiments, a linker may comprise one or more amino acid residues, such as D- or L-amino acid residues. In some embodiments, a linker may be a residue of an amino acid sequence (e.g., a 1-25 amino acid, 1-10 amino acid, 1-9 amino acid, 1-8 amino acid, 1-7 amino acid, 1-6 amino acid, 1-5 amino acid, 1-4 amino acid, 1-3 amino acid, 1-2 amino acid, or 1 amino acid sequence). In some embodiments, a linker may comprise one or more, e.g., 1-100, 1-50, 1-25, 1-10, 1-5, or 1-3, optionally substituted alkylene, optionally substituted heteroalkylene (e.g., a PEG unit), optionally substituted alkenylene, optionally substituted heteroalkenylene, optionally substituted alkynylene, optionally substituted heteroalkynylene, optionally substituted cycloalkylene, optionally substituted heterocycloalkylene, optionally substituted cycloalkenylene, optionally substituted heterocycloalkenylene, optionally substituted cycloalkynylene, optionally substituted heterocycloalkynylene, optionally substituted arylene, optionally substituted heteroarylene (e.g., pyridine), O, S, $NR^i$ ($R^i$ is H, optionally substituted alkyl, optionally substituted heteroalkyl, optionally substituted alkenyl, optionally substituted heteroalkenyl, optionally substituted alkynyl, optionally substituted heteroalkynyl, optionally substituted cycloalkyl, optionally substituted heterocycloalkyl, optionally substituted cycloalkenyl, optionally substituted heterocycloalkenyl, optionally substituted cycloalkynyl, optionally substituted heterocycloalkynyl, optionally substituted aryl, or optionally substituted heteroaryl), P, carbonyl, thiocarbonyl, sulfonyl, phosphate, phosphoryl, or imino. For example, a linker may comprise one or more optionally substituted C1-C20 alkylene, optionally substituted C1-C20 heteroalkylene (e.g., a PEG unit), optionally substituted C2-C20 alkenylene (e.g., C2 alkenylene), optionally substituted C2-C20 heteroalkenylene, optionally substituted C2-C20 alkynylene, optionally substituted C2-C20 heteroalkynylene, optionally substituted C3-C20 cycloalkylene (e.g., cyclopropylene, cyclobutylene), optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene (e.g., C6 arylene), optionally substituted C2-C15 heteroarylene (e.g., imidazole, pyridine), O, S, $NR^i$ ($R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl), P, carbonyl, thiocarbonyl, sulfonyl, phosphate, phosphoryl, or imino.

The terms "alkyl," "alkenyl," and "alkynyl," as used herein, include straight-chain and branched-chain monovalent substituents, as well as combinations of these, containing only C and H when unsubstituted. When the alkyl group includes at least one carbon-carbon double bond or carbon-carbon triple bond, the alkyl group can be referred to as an "alkenyl" or "alkynyl" group respectively. The monovalency of an alkyl, alkenyl, or alkynyl group does not include the optional substituents on the alkyl, alkenyl, or alkynyl group. For example, if an alkyl, alkenyl, or alkynyl group is attached to a compound, monovalency of the alkyl, alkenyl, or alkynyl group refers to its attachment to the compound and does not include any additional substituents that may be present on the alkyl, alkenyl, or alkynyl group. In some embodiments, the alkyl or heteroalkyl group may contain, e.g., 1-20. 1-18, 1-16, 1-14, 1-12, 1-10, 1-8, 1-6, 1-4, or 1-2 carbon atoms (e.g., C1-C20, C1-C18, C1-C16, C1-C14, C1-C12, C1-C10, C1-C8, C1-C6, C1-C4, or C1-C2). In some embodiments, the alkenyl, heteroalkenyl, alkynyl, or heteroalkynyl group may contain, e.g., 2-20, 2-18, 2-16, 2-14, 2-12, 2-10, 2-8, 2-6, or 2-4 carbon atoms (e.g., C2-C20, C2-C18, C2-C16, C2-C14, C2-C12, C2-C10, C2-C8, C2-C6, or C2-C4). Examples include, but are not limited to, methyl, ethyl, isobutyl, sec-butyl, tert-butyl, 2-propenyl, and 3-butynyl.

The term "cycloalkyl," as used herein, represents a monovalent saturated or unsaturated non-aromatic cyclic alkyl group. A cycloalkyl may have, e.g., three to twenty carbons (e.g., a C3-C7, C3-C8, C3-C9, C3-C10, C3-C11, C3-C12, C3-C14, C3-C16, C3-C18, or C3-C20 cycloalkyl). Examples of cycloalkyls include, but are not limited to, cyclopropyl, cyclobutyl, cyclopentyl, cyclohexyl, and cycloheptyl. When the cycloalkyl group includes at least one carbon-carbon double bond, the cycloalkyl group can be referred to as a "cycloalkenyl" group. A cycloalkenyl may have, e.g., four to twenty carbons (e.g., a C4-C7, C4-C8, C4-C9, C4-C10, C4-C11, C4-C12, C4-C14, C4-C16, C4-C18, or C4-C20 cycloalkenyl). Exemplary cycloalkenyl groups include, but are not limited to, cyclopentenyl, cyclohexenyl, and cycloheptenyl. When the cycloalkyl group includes at least one carbon-carbon triple bond, the cycloalkyl group can be referred to as a "cycloalkynyl" group. A cycloalkynyl may have, e.g., eight to twenty carbons (e.g., a C8-C9, C8-C10, C8-C11, C8-C12, C8-C14, C8-C16, C8-C18, or C8-C20 cycloalkynyl). The term "cycloalkyl" also includes a cyclic compound having a bridged multicyclic structure in which one or more carbons bridges two non-adjacent members of a monocyclic ring, e.g., bicyclo [2.2.1.]heptyl and adamantane. The term "cycloalkyl" also includes bicyclic, tricyclic, and tetracyclic fused ring structures, e.g., decalin and spiro cyclic compounds.

The term "aryl," as used herein, refers to any monocyclic or fused ring bicyclic or tricyclic system which has the characteristics of aromaticity in terms of electron distribution throughout the ring system, e.g., phenyl, naphthyl, or phenanthrene. In some embodiments, a ring system contains 5-15 ring member atoms or 5-10 ring member atoms. An aryl group may have, e.g., five to fifteen carbons (e.g., a C5-C6, C5-C7, C5-C8, C5-C9, C5-C10, C5-C11, C5-C12, C5-C13, C5-C14, or C5-C15 aryl). The term "heteroaryl"

also refers to such monocyclic or fused bicyclic ring systems containing one or more, e.g., 1-4, 1-3, 1, 2, 3, or 4, heteroatoms selected from O, S and N. A heteroaryl group may have, e.g., two to fifteen carbons (e.g., a C2-C3, C2-C4, C2-C5, C2-C6, C2-C7, C2-C8, C2-C9. C2-C10, C2-C11, C2-C12, C2-C13, C2-C14, or C2-C15 heteroaryl). The inclusion of a heteroatom permits inclusion of 5-membered rings to be considered aromatic as well as 6-membered rings. Thus, typical heteroaryl systems include, e.g., pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, and imidazolyl. Because tautomers are possible, a group such as phthalimido is also considered heteroaryl. In some embodiments, the aryl or heteroaryl group is a 5- or 6-membered aromatic rings system optionally containing 1-2 nitrogen atoms. In some embodiments, the aryl or heteroaryl group is an optionally substituted phenyl, pyridyl, indolyl, pyrimidyl, pyridazinyl, benzothiazolyl, benzimidazolyl, pyrazolyl, imidazolyl, isoxazolyl, thiazolyl, or imidazopyridinyl. In some embodiments, the aryl group is phenyl. In some embodiments, an aryl group may be optionally substituted with a substituent such an aryl substituent, e.g., biphenyl.

The term "alkaryl," refers to an aryl group that is connected to an alkylene, alkenylene, or alkynylene group. In general, if a compound is attached to an alkaryl group, the alkylene, alkenylene, or alkynylene portion of the alkaryl is attached to the compound. In some embodiments, an alkaryl is C6-C35 alkaryl (e.g., C6-C16, C6-C14, C6-C12, C6-C10, C6-C9, C6-C8, C7, or C6 alkaryl), in which the number of carbons indicates the total number of carbons in both the aryl portion and the alkylene, alkenylene, or alkynylene portion of the alkaryl. Examples of alkaryls include, but are not limited to, (C1-C8)alkylene(C6-C12)aryl, (C2-C8)alkenylene(C6-C12)aryl, or (C2-C8)alkynylene(C6-C12)aryl. In some embodiments, an alkaryl is benzyl or phenethyl. In a heteroalkaryl, one or more heteroatoms selected from N, O, and S may be present in the alkylene, alkenylene, or alkynylene portion of the alkaryl group and/or may be present in the aryl portion of the alkaryl group. In an optionally substituted alkaryl, the substituent may be present on the alkylene, alkenylene, or alkynylene portion of the alkaryl group and/or may be present on the aryl portion of the alkaryl group.

The term "amino," as used herein, represents $—N(R^x)_2$ or $—N^+(R^x)_3$, where each $R^x$ is, independently, H, alkyl, alkenyl, alkynyl, aryl, alkaryl, cycloalkyl, or two $R^x$ combine to form a heterocycloalkyl. In some embodiment, the amino group is $—NH_2$.

The term "alkamino," as used herein, refers to an amino group, described herein, that is attached to an alkylene (e.g., C1-C5 alkylene), alkenylene (e.g., C2-C5 alkenylene), or alkynylene group (e.g., C2-C5 alkenylene). In general, if a compound is attached to an alkamino group, the alkylene, alkenylene, or alkynylene portion of the alkamino is attached to the compound. The amino portion of an alkamino refers to $—N(R^x)_2$ or $—N^+(R^x)_3$, where each $R^x$ is, independently, H, alkyl, alkenyl, alkynyl, aryl, alkaryl, cycloalkyl, or two $R^x$ combine to form a heterocycloalkyl. In some embodiment, the amino portion of an alkamino is $—NH_2$. An example of an alkamino group is C1-C5 alkamino, e.g., C2 alkamino (e.g., $CH_2CH_2NH_2$ or $CH_2CH_2N(CH_3)_2$). In a heteroalkamino group, one or more, e.g., 1-4, 1-3, 1, 2, 3, or 4, heteroatoms selected from N, O, and S may be present in the alkylene, alkenylene, or alkynylene portion of the heteroalkamino group. In some embodiments, an alkamino group may be optionally substituted. In a substituted alkamino group, the substituent may be present on the alkylene, alkenylene, or alkynylene portion of the alkamino group and/or may be present on the amino portion of the alkamino group.

The term "alkamide," as used herein, refers to an amide group that is attached to an alkylene (e.g., C1-C5 alkylene), alkenylene (e.g., C2-C5 alkenylene), or alkynylene (e.g., C2-C5 alkenylene) group. In general, if a compound is attached to an alkamide group, the alkylene, alkenylene, or alkynylene portion of the alkamide is attached to the compound. The amide portion of an alkamide refers to $—C(O)—N(R^x)_2$, where each $R^x$ is, independently, H, alkyl, alkenyl, alkynyl, aryl, alkaryl, cycloalkyl, or two $R^x$ combine to form a heterocycloalkyl. In some embodiment, the amide portion of an alkamide is $—C(O)NH_2$. An alkamide group may be $—(CH_2)_2—C(O)NH_2$ or $—CH_2—C(O)NH_2$. In a heteroalkamide group, one or more, e.g., 1-4, 1-3, 1, 2, 3, or 4, heteroatoms selected from N, O, and S may be present in the alkylene, alkenylene, or alkynylene portion of the heteroalkamide group. In some embodiments, an alkamide group may be optionally substituted. In a substituted alkamide group, the substituent may be present on the alkylene, alkenylene, or alkynylene portion of the alkamide group and/or may be present on the amide portion of the alkamide group.

The terms "alkylene," "alkenylene," and "alkynylene," as used herein, refer to divalent groups having a specified size. In some embodiments, an alkylene may contain, e.g., 1-20, 1-18, 1-16, 1-14, 1-12, 1-10, 1-8, 1-6, 1-4, or 1-2 carbon atoms (e.g., C1-C20, C1-C18, C1-C16, C1-C14, C1-C12, C1-C10, C1-C8, C1-C6, C1-C4, or C1-C2). In some embodiments, an alkenylene or alkynylene may contain, e.g., 2-20, 2-18, 2-16, 2-14, 2-12, 2-10, 2-8, 2-6, or 2-4 carbon atoms (e.g., C2-C20, C2-C18, C2-C16, C2-C14, C2-C12, C2-C10, C2-C8, C2-C6, or C2-C4). Alkylene, alkenylene, and/or alkynylene includes straight-chain and branched-chain forms, as well as combinations of these. The divalency of an alkylene, alkenylene, or alkynylene group does not include the optional substituents on the alkylene, alkenylene, or alkynylene group. For example, two neuraminidase inhibitors may be attached to each other by way of a linker that includes alkylene, alkenylene, and/or alkynylene, or combinations thereof. Each of the alkylene, alkenylene, and/or alkynylene groups in the linker is considered divalent with respect to the two attachments on either end of alkylene, alkenylene, and/or alkynylene group. For example, if a linker includes -(optionally substituted alkylene)-(optionally substituted alkenylene)-(optionally substituted alkylene)-, the alkenylene is considered divalent with respect to its attachments to the two alkylenes at the ends of the linker. The optional substituents on the alkenylene are not included in the divalency of the alkenylene. The divalent nature of an alkylene, alkenylene, or alkynylene group (e.g., an alkylene, alkenylene, or alkynylene group in a linker) refers to both of the ends of the group and does not include optional substituents that may be present in an alkylene, alkenylene, or alkynylene group. Because they are divalent, they can link together multiple (e.g., two) parts of a conjugate, e.g., a first neuraminidase inhibitor and a second neuraminidase inhibitor. Alkylene, alkenylene, and/or alkynylene groups can be substituted by the groups typically suitable as substituents for alkyl, alkenyl and alkynyl groups as set forth herein. For example, C═O is a C1 alkylene that is substituted by an oxo (═O). For example, —HCR—C≡C— may be considered as an optionally substituted alkynylene and is considered a divalent group even though it has an optional substituent, R. Heteroalkylene, heteroalkenylene, and/or heteroalkynylene groups refer to alkylene, alkenylene, and/or alkynylene groups including one or more, e.g., 1-4, 1-3, 1, 2, 3, or 4, heteroatoms, e.g., N, O, and S. For example, a polyethylene glycol (PEG) polymer or a PEG unit —$(CH_2)_2$—O— in a PEG polymer is considered a heteroalkylene containing one or more oxygen atoms.

The term "cycloalkylene," as used herein, refers to a divalent cyclic group linking together two parts of a compound. For example, one carbon within the cycloalkylene group may be linked to one part of the compound, while another carbon within the cycloalkylene group may be linked to another part of the compound. A cycloalkylene group may include saturated or unsaturated non-aromatic cyclic groups. A cycloalkylene may have, e.g., three to twenty carbons in the cyclic portion of the cycloalkylene (e.g., a C3-C7, C3-C8, C3-C9, C3-C10, C3-C11, C3-C12, C3-C14, C3-C16, C3-C18, or C3-C20 cycloalkylene). When the cycloalkylene group includes at least one carbon-carbon double bond, the cycloalkylene group can be referred to as a "cycloalkenylene" group. A cycloalkenylene may have, e.g., four to twenty carbons in the cyclic portion of the cycloalkenylene (e.g., a C4-C7, C4-C8, C4-C9. C4-C10, C4-C11, C4-C12, C4-C14, C4-C16, C4-C18, or C4-C20 cycloalkenylene). When the cycloalkylene group includes at least one carbon-carbon triple bond, the cycloalkylene group can be referred to as a "cycloalkynylene" group. A cycloalkynylene may have, e.g., four to twenty carbons in the cyclic portion of the cycloalkynylene (e.g., a C4-C7, C4-C8, C4-C9. C4-C10, C4-C11, C4-C12, C4-C14, C4-C16, C4-C18, or C8-C20 cycloalkynylene). A cycloalkylene group can be substituted by the groups typically suitable as substituents for alkyl, alkenyl and alkynyl groups as set forth herein. Heterocycloalkylene refers to a cycloalkylene group including one or more, e.g., 1-4, 1-3, 1, 2, 3, or 4, heteroatoms, e.g., N, O, and S. Examples of cycloalkylenes include, but are not limited to, cyclopropylene and cyclobutylene. A tetrahydrofuran may be considered as a heterocycloalkylene.

The term "arylene," as used herein, refers to a multivalent (e.g., divalent or trivalent) aryl group linking together multiple (e.g., two or three) parts of a compound. For example, one carbon within the arylene group may be linked to one part of the compound, while another carbon within the arylene group may be linked to another part of the compound. An arylene may have, e.g., five to fifteen carbons in the aryl portion of the arylene (e.g., a C5-C6, C5-C7, C5-C8, C5-C9. C5-C10, C5-C11, C5-C12, C5-C13, C5-C14, or C5-C15 arylene). An arylene group can be substituted by the groups typically suitable as substituents for alkyl, alkenyl and alkynyl groups as set forth herein. Heteroarylene refers to an aromatic group including one or more, e.g., 1-4, 1-3, 1, 2, 3, or 4, heteroatoms, e.g., N, O, and S. A heteroarylene group may have, e.g., two to fifteen carbons (e.g., a C2-C3, C2-C4, C2-C5, C2-C6, C2-C7, C2-C8, C2-C9. C2-C10, C2-C11, C2-C12, C2-C13, C2-C14, or C2-C15 heteroarylene).

The term "optionally substituted," as used herein, refers to having 0, 1, or more substituents, such as 0-25, 0-20, 0-10 or 0-5 substituents. Substituents include, but are not limited to, alkyl, alkenyl, alkynyl, aryl, alkaryl, acyl, heteroaryl, heteroalkyl, heteroalkenyl, heteroalkynyl, heteroalkaryl, halogen, oxo, cyano, nitro, amino, alkamino, hydroxy, alkoxy, alkanoyl, carbonyl, carbamoyl, guanidinyl, ureido, amidinyl, any of the groups or moieties described above, and hetero versions of any of the groups or moieties described above. Substituents include, but are not limited to, F, Cl, methyl, phenyl, benzyl, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $OCF_3$, $SiR_3$, and $NO_2$, wherein each R is, independently, H, alkyl, alkenyl, aryl, heteroalkyl, heteroalkenyl, or heteroaryl, and wherein two of the optional substituents on the same or adjacent atoms can be joined to form a fused, optionally substituted aromatic or nonaromatic, saturated or unsaturated ring which contains 3-8 members, or two of the optional substituents on the same atom can be joined to form an optionally substituted aromatic or nonaromatic, saturated or unsaturated ring which contains 3-8 members.

An optionally substituted group or moiety refers to a group or moiety (e.g., any one of the groups or moieties described above) in which one of the atoms (e.g., a hydrogen atom) is optionally replaced with another substituent. For example, an optionally substituted alkyl may be an optionally substituted methyl, in which a hydrogen atom of the methyl group is replaced by, e.g., OH. As another example, a substituent on a heteroalkyl or its divalent counterpart, heteroalkylene, may replace a hydrogen on a carbon or a hydrogen on a heteroatom such as N. For example, the hydrogen atom in the group —R—NH—R— may be substituted with an alkamide substituent, e.g., —R—N[$(CH_2C(O)N(CH_3)_2$]—R.

Generally, an optional substituent is a noninterfering substituent. A "noninterfering substituent" refers to a substituent that leaves the ability of the conjugates described herein (e.g., conjugates of any one of formulas (1)-(5), (D-I)-(D-X), (D'-I), (M-I)-(M-X), or (M'-I)) to either bind to viral neuraminidase or to inhibit the proliferation of influenza virus. Thus, in some embodiments, the substituent may alter the degree of such activity. However, as long as the conjugate retains the ability to bind to viral neuraminidase or to inhibitor viral proliferation, the substituent will be classified as "noninterfering." For example, the noninterfering substituent would leave the ability of the compound to provide antiviral efficacy based on an IC50 value of 10 μM or less in a viral plaque reduction assay, such as in Example 2 based on an IC50 value against influenza virus neuraminidase of less than 500 nM. Thus, the substituent may alter the degree of inhibition based on plaque reduction or influenza virus neuraminidase inhibition. However, as long as the compounds herein such as compounds of formulas (A-I), (A-II), (A-III), (A-IV), (A-V), (A-VI), (A-VII), (A-VIII), (A-IX), (A-X), (A-XI), and (A-XII) retain the ability to inhibit influenza virus neuraminidase activity, the substituent will be classified as "noninterfering." A number of assays for determining viral plaque reduction or the ability of any compound to inhibit influenza virus neuraminidase are available in the art, and some are exemplified in the Examples below.

The term "hetero," when used to describe a chemical group or moiety, refers to having at least one heteroatom that is not a carbon or a hydrogen, e.g., N, O, and S. Any one of the groups or moieties described above may be referred to as hetero if it contains at least one heteroatom. For example, a heterocycloalkyl, heterocycloalkenyl, or heterocycloalkynyl group refers to a cycloalkyl, cycloalkenyl, or cycloalkynyl group that has one or more heteroatoms independently selected from, e.g., N, O, and S. An example of a heterocycloalkenyl group is a maleimido. For example, a heteroaryl group refers to an aromatic group that has one or more heteroatoms independently selected from, e.g., N, O, and S. One or more heteroatoms may also be included in a substituent that replaced a hydrogen atom in a group or moiety as described herein. For example, in an optionally substituted heteroaryl group, if one of the hydrogen atoms in the heteroaryl group is replaced with a substituent (e.g., methyl), the substituent may also contain one or more heteroatoms (e.g., methanol).

The term "acyl," as used herein, refers to a group having the structure:

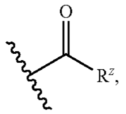

wherein $R_z$ is an optionally substituted alkyl, alkenyl, alkynyl, cycloalkyl, cycloalkenyl, cycloalkynyl, aryl, alkaryl, alkamino, heteroalkyl, heteroalkenyl, heteroalkynyl, heterocycloalkyl, heterocycloalkenyl, heterocycloalkynyl, heteroaryl, heteroalkaryl, or heteroalkamino.

The term "halo" or "halogen," as used herein, refers to any halogen atom, e.g., F, Cl, Br, or I. Any one of the groups or moieties described herein may be referred to as a "halo moiety" if it contains at least one halogen atom, such as haloalkyl.

The term "hydroxyl," as used herein, represents an —OH group.

The term "oxo," as used herein, refers to a substituent having the structure =O, where there is a double bond between an atom and an oxygen atom.

The term "carbonyl," as used herein, refers to a group having the structure:

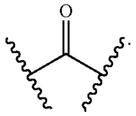

The term "thiocarbonyl," as used herein, refers to a group having the structure:

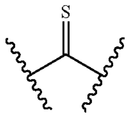 [SMILES: *C(*)=S]

The term "phosphate," as used herein, represents the group having the structure:

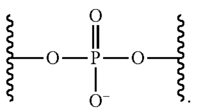 [SMILES: *OP(=O)([O-])O*]

The term "phosphoryl," as used herein, represents the group having the structure:

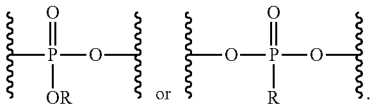

The term "sulfonyl," as used herein, represents the group having the structure:

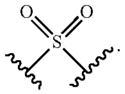 [SMILES: *S(*)(=O)=O]

The term "imino," as used herein, represents the group having the structure:

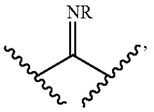

wherein R is an optional substituent.

The term "N-protecting group," as used herein, represents those groups intended to protect an amino group against undesirable reactions during synthetic procedures. Commonly used N-protecting groups are disclosed in Greene, "Protective Groups in Organic Synthesis," 5th Edition (John Wiley & Sons, New York, 2014), which is incorporated herein by reference. N-protecting groups include, e.g., acyl, aryloyl, and carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, carboxybenzyl (CBz), 4-chlorobenzoyl, 4-bromobenzoyl, 4-nitrobenzoyl, and chiral auxiliaries such as protected or unprotected D, L or D, L-amino acid residues such as alanine, leucine, phenylalanine; sulfonyl-containing groups such as benzenesulfonyl and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl (BOC), diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl (Fmoc), cyclopentyloxycarbonyl, adamantyloxycarbonyl, cyclohexyloxycarbonyl, and phenylthiocarbonyl; alkaryl groups such as benzyl, triphenylmethyl, and benzyloxymethyl; and silyl groups such as trimethylsilyl.

The term "amino acid," as used herein, means naturally occurring amino acids and non-naturally occurring amino acids.

The term "naturally occurring amino acids," as used herein, means amino acids including Ala, Arg, Asn, Asp, Cys, Gln, Glu, Gly, His, lie, Leu, Lys, Met, Phe, Pro, Ser, Thr, Trp, Tyr, and Val.

The term "non-naturally occurring amino acid," as used herein, means an alpha amino acid that is not naturally produced or found in a mammal. Examples of non-naturally occurring amino acids include D-amino acids; an amino acid having an acetylaminomethyl group attached to a sulfur atom of a cysteine; a pegylated amino acid; the omega amino acids of the formula $NH_2(CH_2)_nCOOH$ where n is 2-6, neutral nonpolar amino acids, such as sarcosine, t-butyl alanine, t-butyl glycine, N-methyl isoleucine, and norleucine; oxymethionine; phenylglycine; citrulline; methionine sulfoxide; cysteic acid; ornithine; diaminobutyric acid; 3-aminoalanine; 3-hydroxy-D-proline; 2,4-diaminobutyric acid; 2-aminopentanoic acid; 2-aminooctanoic acid, 2-carboxy piperazine; piperazine-2-carboxylic acid, 2-amino-4-phenylbutanoic acid; 3-(2-naphthyl)alanine, and hydroxyproline. Other amino acids are α-aminobutyric acid, α-amino-α-methylbutyrate, aminocyclopropane-carboxylate, aminoisobutyric acid, aminonorbornyl-carboxylate, L-cyclohexylalanine, cyclopentylalanine, L-N-methylleucine, L-N-methylmethionine, L-N-methylnorvaline, L-N-methylphenylalanine, L-N-methylproline, L-N-methylserine, L-N-methyltryptophan, D-ornithine, L-N-methylethylglycine, L-norleucine, α-methyl-aminoisobutyrate, α-methylcyclohexylalanine, D-α-methylalanine, D-α-methylarginine, D-α-methylasparagine, D-α-methylaspartate, D-α-methylcysteine, D-α-methylglutamine, D-α-methylhistidine, D-α-methylisoleucine, D-α-methylleucine, D-α-methyllysine, D-α-methylmethionine, D-α-methylornithine, D-α-methylphenylalanine, D-α-methylproline, D-α-methylserine, D-N-methylserine, D-α-methylthreonine, D-α-methyltryptophan, D-α-methyltyrosine, D-α-methylvaline, D-N-methylalanine, D-N-methylarginine, D-N-methylasparagine, D-N-methylaspartate, D-N-methylcysteine, D-N-methylglutamine, D-N-methylglutamate, D-N-methylhistidine, D-N-methylisoleucine, D-N-methylleucine, D-N-methyllysine, N-methylcyclohexylalanine, D-N-methylornithine, N-methylglycine, N-methylaminoisobutyrate, N-(1-methylpropyl) glycine, N-(2-methylpropyl)glycine, D-N-methyltryptophan, D-N-methyltyrosine, D-N-methylvaline, γ-aminobutyric acid, L-t-butylglycine, L-ethylglycine, L-homophenylalanine, L-α-methylarginine, L-α-methylaspartate, L-α-methylcysteine, L-α-methylglutamine, L-α-methylhistidine, L-α-methylisoleucine, L-α-methylleucine, L-α-methylmethionine, L-α-methylnorvaline, L-α-methylphenylalanine, L-α-methylserine, L-α-methyltryptophan, L-α-methylvaline, N—(N-(2,2-diphenylethyl) carbamylmethylglycine, 1-carboxy-1-(2,2-diphenyl-ethylamino)cyclopropane, 4-hydroxyproline, ornithine, 2-aminobenzoyl (anthraniloyl), D-cyclohexylalanine, 4-phenyl-phenylalanine, L-citrulline, α-cyclohexylglycine, L-1,2,3,4-tetrahydroisoquinoline-3-carboxylic acid, L-thiazolidine-4-carboxylic acid, L-homotyrosine, L-2-furylalanine, L-histidine (3-methyl), N-(3-guanidinopropyl)glycine, O-methyl-L-tyrosine, O-glycan-serine, meta-tyrosine, nor-tyrosine, L-N, N',N"-trimethyllysine, homolysine, norlysine, N-glycan asparagine, 7-hydroxy-1,2,3,4-tetrahydro-4-fluorophenylalanine, 4-methylphenylalanine, bis-(2-picolyl)amine, pentafluorophenylalanine, indoline-2-carboxylic acid, 2-aminobenzoic acid, 3-amino-2-naphthoic acid, asymmetric dimethylarginine, L-tetrahydroisoquinoline-1-carboxylic acid, D-tetrahydroisoquinoline-1-carboxylic acid, 1-aminocyclohexane acetic acid, D/L-allylglycine, 4-aminobenzoic acid, 1-amino-cyclobutane carboxylic acid, 2 or 3 or 4-aminocyclohexane carboxylic acid, 1-amino-1-cyclopentane carboxylic acid, 1-aminoindane-1-carboxylic acid, 4-amino-pyrrolidine-2-carboxylic acid, 2-aminotetraline-2-carboxylic acid, azetidine-3-carboxylic acid, 4-benzyl-pyrolidine-2-carboxylic acid, tert-butylglycine, b-(benzothiazolyl-2-yl)-alanine, b-cyclopropyl alanine, 5,5-dimethyl-1,3-thiazolidine-4-carboxylic acid, (2R,4S)4-hydroxypiperidine-2-carboxylic acid, (2S,4S) and (2S,4R)-4-(2-naphthylmethoxy)-pyrolidine-2-carboxylic acid, (2S,4S) and (2S,4R)4-phenoxy-pyrrolidine-2-carboxylic acid, (2R,5S) and (2S,5R)-5-phenyl-pyrrolidine-2-carboxylic acid, (2S,4S)-4-amino-1-benzoyl-pyrrolidine-2-carboxylic acid, t-butylalanine, (2S,5R)-5-phenyl-pyrrolidine-2-carboxylic acid, 1-aminomethyl-cyclohexane-acetic acid, 3,5-bis-(2-amino)ethoxy-benzoic acid, 3,5-diamino-benzoic acid, 2-methylamino-benzoic acid, N-methylanthranylic acid, L-N-methylalanine, L-N-methylarginine, L-N-methylasparagine, L-N-methylaspartic acid, L-N-methylcysteine, L-N-methylglutamine, L-N-methylglutamic acid, L-N-methylhistidine, L-N-methylisoleucine, L-N-methyllysine, L-N-methylnorleucine, L-N-methylornithine, L-N-methylthreonine, L-N-methyltyrosine, L-N-methylvaline, L-N-methyl-t-butylglycine, L-norvaline, α-methyl-γ-aminobutyrate, 4,4'-biphenylalanine, α-methylcylcopentylalanine, α-methyl-α-napthylalanine, α-methylpenicillamine, N-(4-aminobutyl)glycine, N-(2-aminoethyl)glycine, N-(3-aminopropyl)glycine, N-amino-α-methylbutyrate, α-napthylalanine, N-benzylglycine, N-(2-carbamylethyl)glycine, N-(carbamylmethyl)glycine, N-(2-carboxyethyl)glycine, N-(carboxymethyl)glycine, N-cyclobutylglycine, N-cyclodecylglycine, N-cycloheptylglycine, N-cyclohexylglycine, N-cyclodecylglycine, N-cylcododecylglycine, N-cyclooctylglycine, N-cyclopropylglycine, N-cycloundecylglycine, N-(2,2-diphenylethyl)glycine, N-(3,3-diphenylpropyl)glycine, N-(3-guanidinopropyl)glycine, N-(1-hydroxyethyl) glycine, N-(hydroxyethyl))glycine, N-(imidazolylethyl)) glycine, N-(3-indolylyethyl)glycine, N-methyl-γ-aminobutyrate, D-N-methylmethionine, N-methylcyclopentylalanine, D-N-methylphenylalanine, D-N-methylproline, D-N-methylthreonine, N-(1-methylethyl)glycine, N-methyl-napthylalanine, N-methylpenicillamine, N-(p-hydroxyphenyl)glycine, N-(thiomethyl)glycine, penicillamine, L-α-methylalanine, L-α-methylasparagine, L-α-methyl-t-butylglycine, L-methylethylglycine, L-α-methylglutamate, L-α-methylhomophenylalanine, N-(2-methylthioethyl)glycine, L-α-methyllysine, L-α-methylnorleucine, L-α-methylornithine, L-α-methylproline, L-α-methylthreonine, L-α-methyltyrosine, L-N-methyl-homophenylalanine, N—(N-(3,3-diphenylpropyl) carbamylmethylglycine, L-pyroglutamic acid, D-pyroglutamic acid, O-methyl-L-serine, O-methyl-L-homoserine, 5-hydroxylysine, α-carboxyglutamate, phenylglycine, L-pipecolic acid (homoproline), L-homoleucine, L-lysine (dimethyl), L-2-naphthylalanine, L-dimethyldopa or L-dimethoxy-phenylalanine, L-3-pyridylalanine, L-histidine (benzoyloxymethyl), N-cycloheptylglycine, L-diphenylalanine, O-methyl-L-homotyrosine, L-β-homolysine, O-glycan-threoine, Ortho-tyrosine, L-N,N'-dimethyllysine, L-homoarginine, neotryptophan, 3-benzothienylalanine, isoquinoline-3-carboxylic acid, diaminopropionic acid, homocysteine, 3,4-dimethoxyphenylalanine, 4-chlorophenylalanine, L-1,2,3,4-tetrahydronorharman-3-carboxylic acid, adamantylalanine, symmetrical dimethylarginine, 3-carboxythiomorpholine, D-1,2,3,4-tetrahydronorharman-3-carboxylic acid, 3-aminobenzoic acid, 3-amino-1-carboxymethyl-pyridin-2-one, 1-amino-1-cyclohexane carboxylic acid, 2-aminocyclopentane carboxylic acid, 1-amino-1-cyclopropane carboxylic acid, 2-aminoindane-2-carboxylic acid, 4-amino-tetrahydrothiopyran-4-carboxylic acid, azetidine-2-carboxylic acid, b-(benzothiazol-2-yl)-alanine, neopentylglycine, 2-carboxymethyl piperidine, b-cyclobutyl alanine, allylglycine, diaminopropionic acid, homo-cyclohexyl alanine, (2S,4R)-4-hydroxypiperidine-2-carboxylic acid, octahydroindole-2-carboxylic acid, (2S,4R) and (2S,4R)-4-(2-naphthyl), pyrrolidine-2-carboxylic acid, nipecotic acid, (2S,4R) and (2S,4S)-4-(4-phenylbenzyl) pyrrolidine-2-carboxylic acid, (3S)-1-pyrrolidine-3-carboxylic acid, (2S,4S)-4-tritylmercapto-pyrrolidine-2-carboxylic acid, (2S, 4S)-4-mercaptoproline, t-butylglycine, N,N-bis(3-amino-propyl)glycine, 1-amino-cyclohexane-1-carboxylic acid, N-mercaptoethylglycine, and selenocysteine. In some embodiments, amino acid residues may be charged or polar. Charged amino acids include alanine, lysine, aspartic acid, or glutamic acid, or non-naturally occurring analogs thereof. Polar amino acids include glutamine, asparagine, histidine, serine, threonine, tyrosine, methionine, or tryptophan, or non-naturally occurring analogs thereof. It is specifically contemplated that in some embodiments, a terminal amino group in the amino acid may be an amido group or a carbamate group.

As used herein, the term "percent (%) identity" refers to the percentage of amino acid residues of a candidate sequence, e.g., an Fc-IgG, or fragment thereof, that are identical to the amino acid residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid sequence identity of a given candidate sequence to, with, or against a given reference sequence (which can alternatively be phrased as a given candidate sequence that has or includes a certain percent amino acid sequence identity to, with, or against a given reference sequence) is calculated as follows:

$$100\times(\text{fraction of } A/B)$$

where A is the number of amino acid residues scored as identical in the alignment of the candidate sequence and the reference sequence, and where B is the total number of amino acid residues in the reference sequence. In some embodiments where the length of the candidate sequence does not equal to the length of the reference sequence, the percent amino acid sequence identity of the candidate sequence to the reference sequence would not equal to the percent amino acid sequence identity of the reference sequence to the candidate sequence.

Two polynucleotide or polypeptide sequences are said to be "identical" if the sequence of nucleotides or amino acids in the two sequences is the same when aligned for maximum correspondence as described above. Comparisons between two sequences are typically performed by comparing the sequences over a comparison window to identify and compare local regions of sequence similarity. A "comparison window" as used herein, refers to a segment of at least about 15 contiguous positions, about 20 contiguous positions, about 25 contiguous positions, or more (e.g., about 30 to about 75 contiguous positions, or about 40 to about 50 contiguous positions), in which a sequence may be compared to a reference sequence of the same number of contiguous positions after the two sequences are optimally aligned.

The term "treating" or "to treat," as used herein, refers to a therapeutic treatment of a viral infection (e.g., a viral infection such as and influenza infection) in a subject. In some embodiments, a therapeutic treatment may slow the progression of the viral infection, improve the subject's outcome, and/or eliminate the infection. In some embodiments, a therapeutic treatment of a viral infection in a subject may alleby way ofte or ameliorate of one or more symptoms or conditions associated with the viral infection, diminish the extent of the viral, stabilize (i.e., not worsening) the state of the viral infection, prevent the spread of the viral infection, and/or delay or slow the progress of the viral infection, as compare the state and/or the condition of the viral infection in the absence of the therapeutic treatment.

The term "average value of T," as used herein, refers to the mean number of monomers of neuraminidase inhibitor or dimers of neuramindase inhibitors conjugated to an Fc domain or an albumin protein within a population of conjugates. In some embodiments, within a population of conjugates, the average number of monomers of neuraminidase inhibitor or dimers of neuramindase inhibitors conjugated to an Fc domain monomer may be from 1 to 20 (e.g., the average value of T is 1 to 2, 1 to 3, 1 to 4, 1 to 5, 5 to 10, 10 to 15, or 15 to 20). In some embodiments, the average value of T is 1, 2, 3, 4, 5, 6, 7, 8, 9, 10, 11, 12, 13, 14, 15, 16, 17, 18, 19, or 20.

The term "subject," as used herein, can be a human, non-human primate, or other mammal, such as but not limited to dog, cat, horse, cow, pig, turkey, goat, fish, monkey, chicken, rat, mouse, and sheep.

The term "therapeutically effective amount," as used herein, refers to an amount, e.g., pharmaceutical dose, effective in inducing a desired effect in a subject or in treating a subject having a condition or disorder described herein (e.g., a viral infection, such as an influeza infection). It is also to be understood herein that a "therapeutically effective amount" may be interpreted as an amount giving a desired therapeutic and/or preventative effect, taken in one or more doses or in any dosage or route, and/or taken alone or in combination with other therapeutic agents (e.g., an antiviral agent described herein). For example, in the context of administering a conjugate described herein (e.g., a conjugate of any one of formulas (1)-(5), (D-I)-(D-X), (D'-I), (M-I)-(M-X), or (M'-I)) that is used for the treatment of a viral infection, an effective amount of a conjugate is, for example, an amount sufficient to prevent, slow down, or reverse the progression of the viral infection as compared to the response obtained without administration of the conjugate.

As used herein, the term "pharmaceutical composition" refers to a medicinal or pharmaceutical formulation that contains at least one active ingredient (e.g., a conjugate of any one of formulas (1)-(5), (D-I)-(D-X), (D'-I), (M-I)-(M-X), or (M'-I)) as well as one or more excipients and diluents to enable the active ingredient suitable for the method of administration. The pharmaceutical composition of the present disclosure includes pharmaceutically acceptable components that are compatible with a conjugate described herein (e.g., a conjugate of any one of formulas (1)-(5), (D-I)-(D-X), (D'-I), (M-I)-(M-X), or (M'-I)).

As used herein, the term "pharmaceutically acceptable carrier" refers to an excipient or diluent in a pharmaceutical composition. For example, a pharmaceutically acceptable carrier may be a vehicle capable of suspending or dissolving the active conjugate (e.g., a conjugate of any one of formulas (1)-(5), (D-I)-(D-X), or (M-I)-(M-VI)). The pharmaceutically acceptable carrier must be compatible with the other ingredients of the formulation and not deleterious to the recipient. In the present disclosure, the pharmaceutically acceptable carrier must provide adequate pharmaceutical stability to a conjugate described herein. The nature of the carrier differs with the mode of administration. For example, for oral administration, a solid carrier is preferred; for intravenous administration, an aqueous solution carrier (e.g., WFI, and/or a buffered solution) is generally used.

The term "pharmaceutically acceptable salt," as used herein, represents salts of the conjugates described herein (e.g., conjugates of any one of formulas (1)-(5), (D-I)-(D-X), (D'-I), (M-I)-(M-X), or (M'-I)) that are, within the scope of sound medical judgment, suitable for use in methods described herein without undue toxicity, irritation, and/or allergic response. Pharmaceutically acceptable salts are well known in the art. For example, pharmaceutically acceptable salts are described in: *Pharmaceutical Salts: Properties, Selection, and Use* (Eds. P. H. Stahl and C. G. Wermuth), Wiley-VCH, 2008. The salts can be prepared in situ during the final isolation and purification of the conjugates described herein or separately by reacting the free base group with a suitable organic acid.

The term "drug-to-antibody ratio" or "DAR" refers to the average number of small molecule drug moieties (e.g., the average number of small molecule drug monomers or dimers) conjugated to an antibody, Fc domain, or albumin protein described herein. In some embodiments described herein, the DAR is represented by "T" (e.g., in formulas (1)-(5), (D-I)-(D-X), (D'-I), (M-I)-(M-X), or (M'-I)). As used herein, each monomer moiety (e.g., each zanamivir or peramivir monomer) or each dimer moiety (e.g., each zanamivir dimer or peramivir dimer) conjugated to the Fc domain, antibody, or albumin protein corresponds to a DAR value of 1.0 (e.g., a "T" value of 1.0). For example, an Fc domain conjugated to 4 zanamivir monomers would have a DAR of 4.0 (e.g., a "T" of 4.0). An Fc domain conjugated to 4 zanamivir dimers (e.g., 8 total zanamivir molecules) would also have a DAR of 4.0 (e.g., a "T" of 4.0). DAR may also be computed as the average DAR for a population of molecules, such as a population of Fc domains, antibodies, or albumin proteins. DAR values may affect the efficacy, potency, pharmacokinetics, or toxicity of the drug.

The term "about," as used herein, indicates a deby way oftion of ±5%. For example, about 10% refers to from 9.5% to 10.5%.

Any values provided in a range of values include both the upper and lower bounds, and any values contained within the upper and lower bounds.

The term "(1)-(5), (D-I)-(D-X), (D'-I), (M-I)-(M-X), or (M'-I)", as used herein, represents the formulas of any one of (1), (2), (3), (4), (5), (D-I), (D-II), (D-II-1), (D-II-2), (D-II-3), (D-II-4), (D-II-5), (D-II-6), (D-II-7), (D-II-8), (D-II-9), (D-II-10), (D-III), (D-III-1), (D-III-2), (D-III-3), (D-III-4), (D-III-5), (D-III-6), (D-III-7), (D-III-8), (D-III-9), (D-IV), (D-IV-1), (D-IV-2), (D-V), (D-V-1), (D-V-2), (D-V-3), (D-V-4), (D-V-5), (D-V-6), (D-V-7), (D-V-8), (D-V-9), (D-V-10), (D-VI), (D-VI-1), (D-VI-2), (D-VI-3), (D-VI-4), (D-VI-5), (D-VI-6), (D-VI-7), (D-VI-8), (D-VI-9), (D-VII), (D-VIII), (D-VIII-1), (D-VIII-2), (D-VIII-3), (D-VIII-4), (D-VIII-5), (D-VIII-6), (D-VIII-7), (D-VII-8), (D-VIII-9), (D-VIII-10), (D-VIII-11), (D-IX), (D-IX-1), (D-IX-2), (D-IX-3), (D-IX-4), (D-IX-5), (D-IX-6), (D-X), (D-X-1), (D-X-2), (D-X-3), (D'-I), (M-I), (M-II), (M-II-1), (M-II-2), (M-II-3), (M-II-4), (M-II-5), (M-II-6), (M-II-7), (M-II-8), (M-II-9), (M-II-10), (M-III), (M-III-1), (M-III-2), (M-III-3), (M-III-4), (M-III-5), (M-III-6), (M-III-7), (M-III-8), (M-III-9), (M-IV), (M-IV-1), (M-IV-2), (M-V), (M-V-1), (M-V-2), (M-V-3), (M-V-4), (M-V-5), (M-V-6), (M-V-7), (M-V-8), (M-V-9), (M-V-10), (M-VI), (M-VI-1), (M-VI-2), (M-VI-3), (M-VI-4), (M-VI-5), (M-VI-6), (M-VI-7), (M-VI-8), (M-VI-9), (M-VII), (M-VIII), (M-VIII-1), (M-VIII-2), (M-VIII-3), (M-VIII-4), (M-VIII-5), (M-VIII-6), (M-VIII-7), (M-VIII-8), (M-VIII-9), (M-VIII-10), (M-VIII-11), (M-IX), (M-IX-1), (M-IX-2), (M-IX-3), (M-IX-4), (M-IX-5), (M-IX-6), (M-X), (M-X-1), (M-X-2), (M-X-3), or (M'-I)).

Other features and advantages of the conjugates described herein will be apparent from the following Detailed Description and the claims.

DESCRIPTION OF THE DRAWINGS

FIGS. 32A-32F is a series of graphs showing that Conjugate 6 extends treatment window as compared to Oseltamivir (Tamiflu™) as determined by survival in a lethal mouse influenza model. Mice were treated with either vehicle (PBS), Fc only 10 mpk, or Conjugate 6, 4 hours prior to infection (FIG. 32A); Conjugate 6 or Oseltamivir (Tamiflu™), 8 hours post-infection (FIG. 32B); Conjugate 6 or Oseltamivir (Tamiflu™), 24 hours post-infection (FIG. 32C); Conjugate 6 or Oseltamivir (Tamiflu™) 48 hours post-infection (FIG. 32D); Conjugate 6 or Oseltamivir (Tamiflu™), 72 hours post-infection (FIG. 32E); or Conjugate 6 or Oseltamivir (Tamiflu™), 96 hours post-infection (FIG. 32F). The study was performed as described in Example 34.

DETAILED DESCRIPTION

Figure 1:
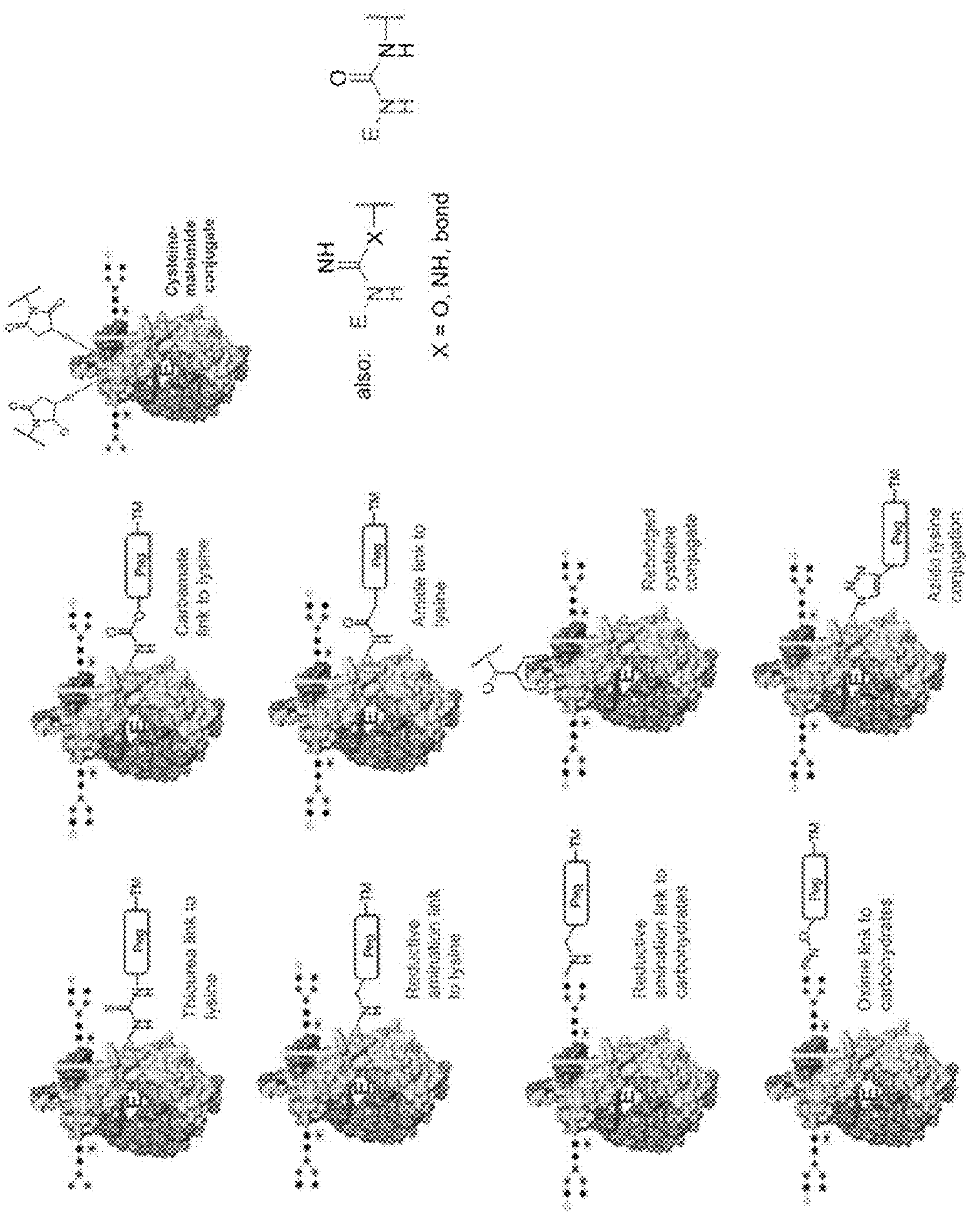
FIG. 1 is an image depicting exemplary methods of conjugating a neuraminidase inhibitor monomer or dimer, e.g., by way of a linker, to an Fc domain monomer, an Fc domain, an Fc-binding peptide, an albumin protein, or an albumin protein-binding peptide.
Figure 2:
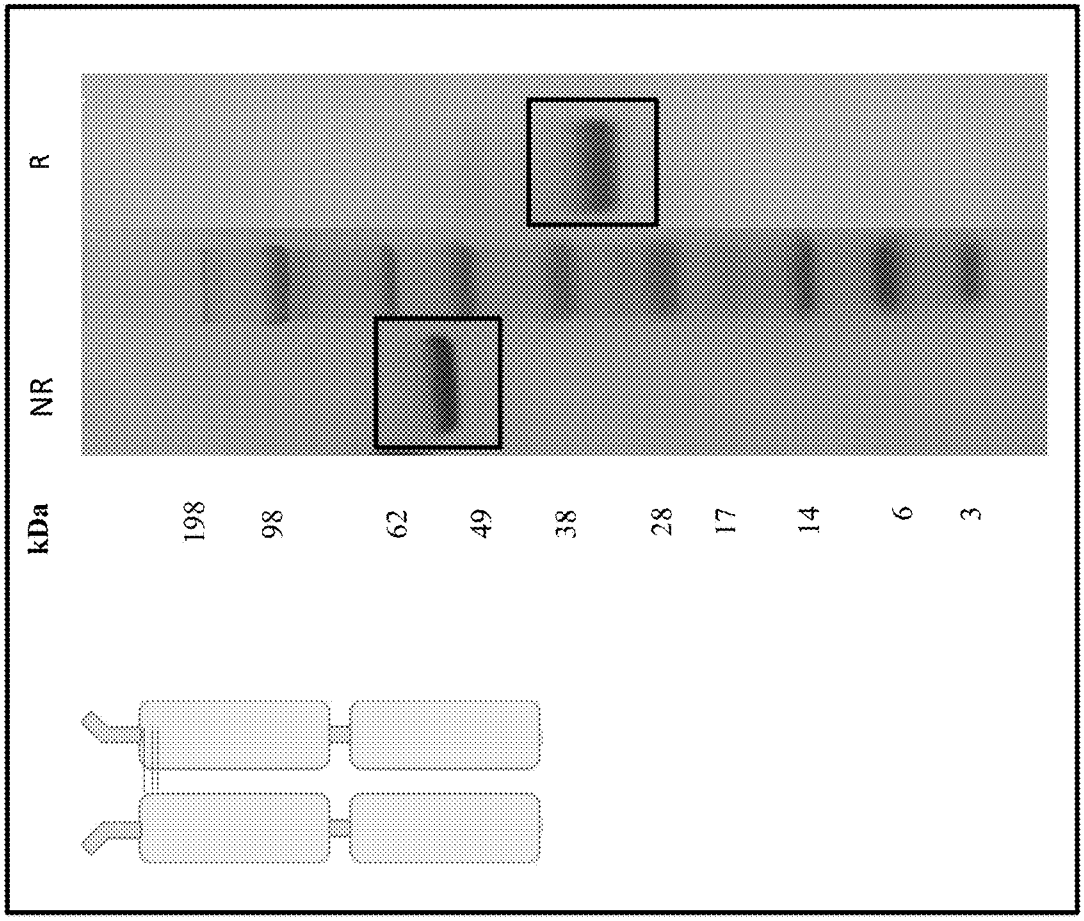
FIG. 2 shows non-reducing and reducing SDS-PAGE and a schematic illustration of an Fc domain formed from Fc domain monomers having the sequence of SEQ ID NO: 1.
Figure 3:
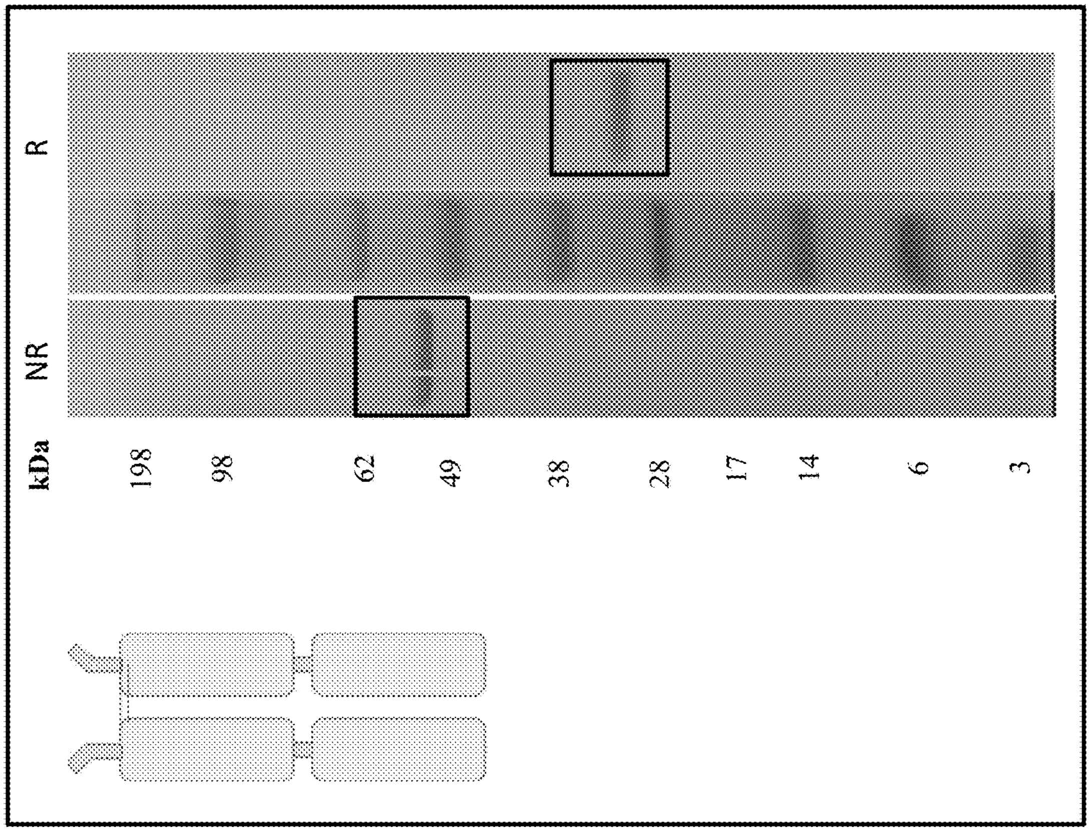
FIG. 3 shows non-reducing and reducing SDS-PAGE and a schematic illustration of an Fc domain formed from Fc domain monomers having the sequence of SEQ ID NO: 3.
Figure 4:
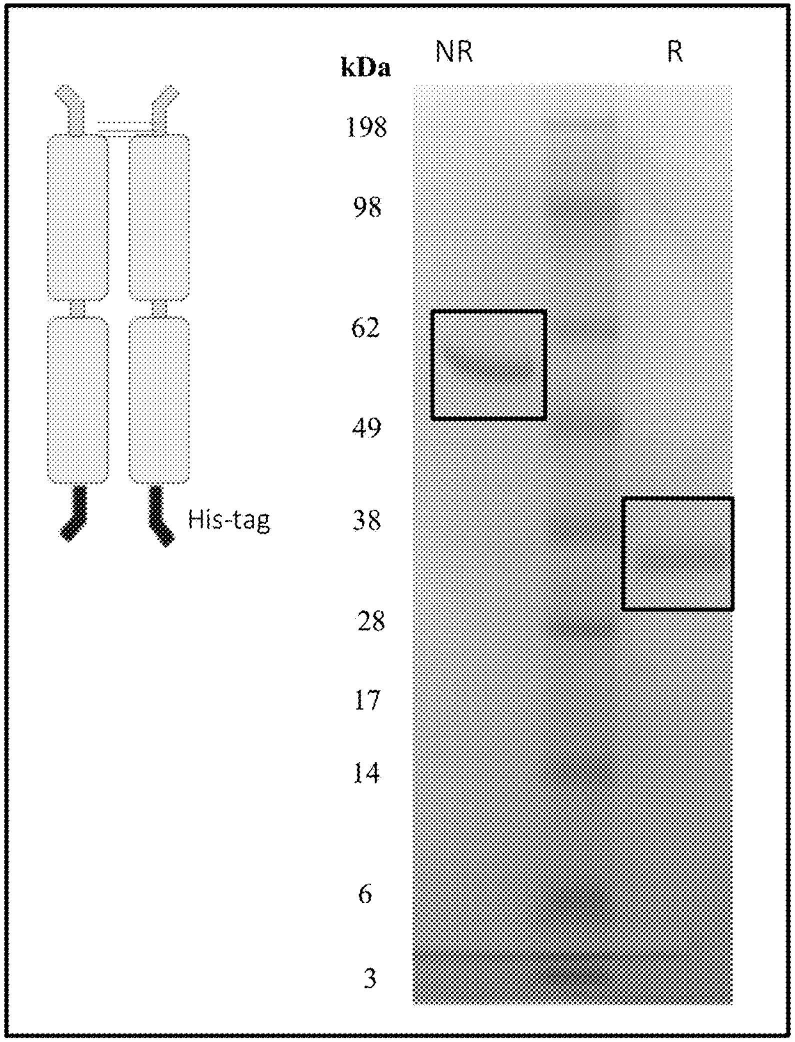
FIG. 4 shows non-reducing and reducing SDS-PAGE and a schematic illustration of an Fc domain formed from Fc domain monomers having the sequence of SEQ ID NO: 5.
Figure 5:
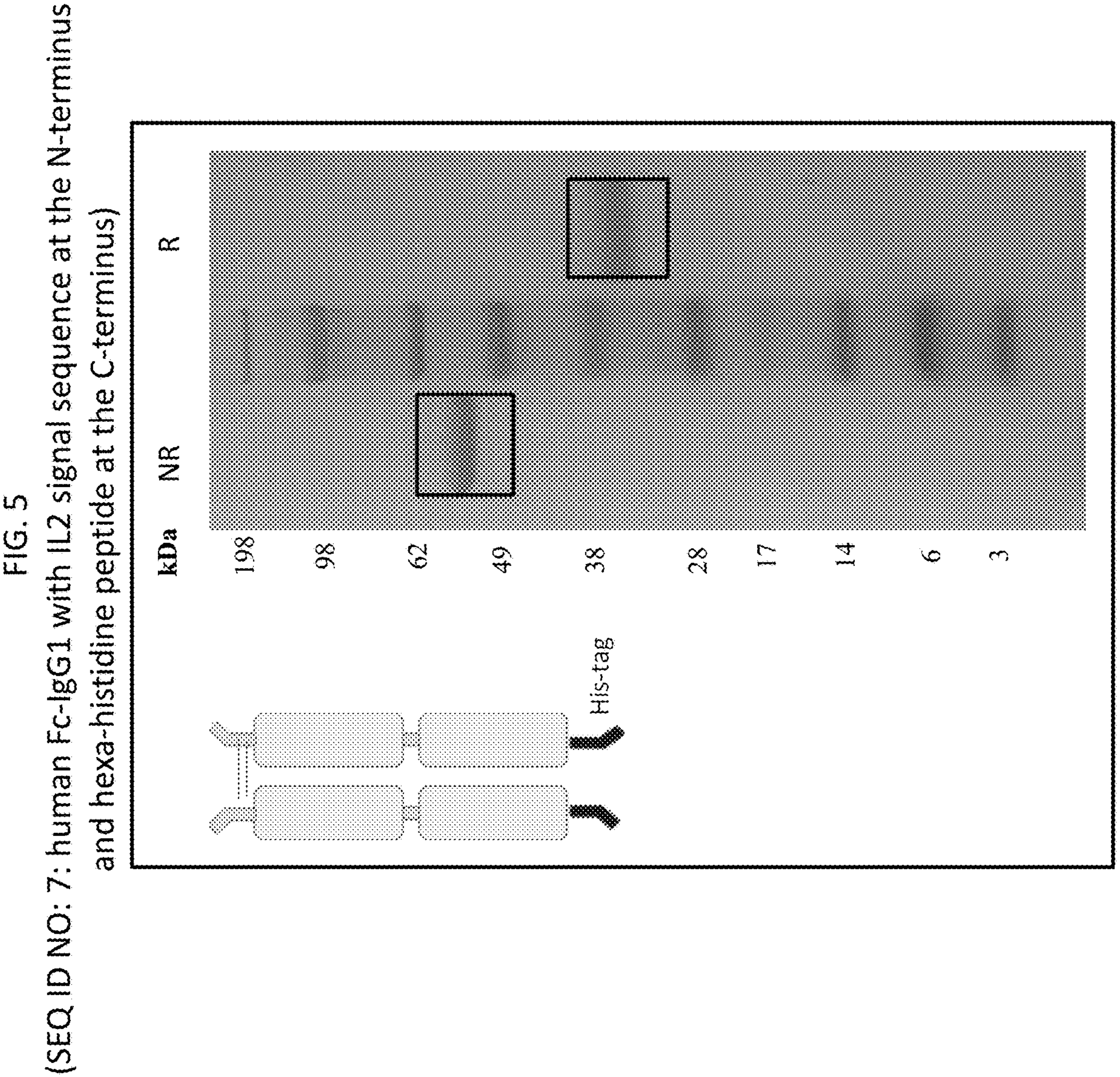
FIG. 5 shows non-reducing and reducing SDS-PAGE and a schematic illustration of an Fc domain formed from Fc domain monomers having the sequence of SEQ ID NO: 7.
Figure 6:
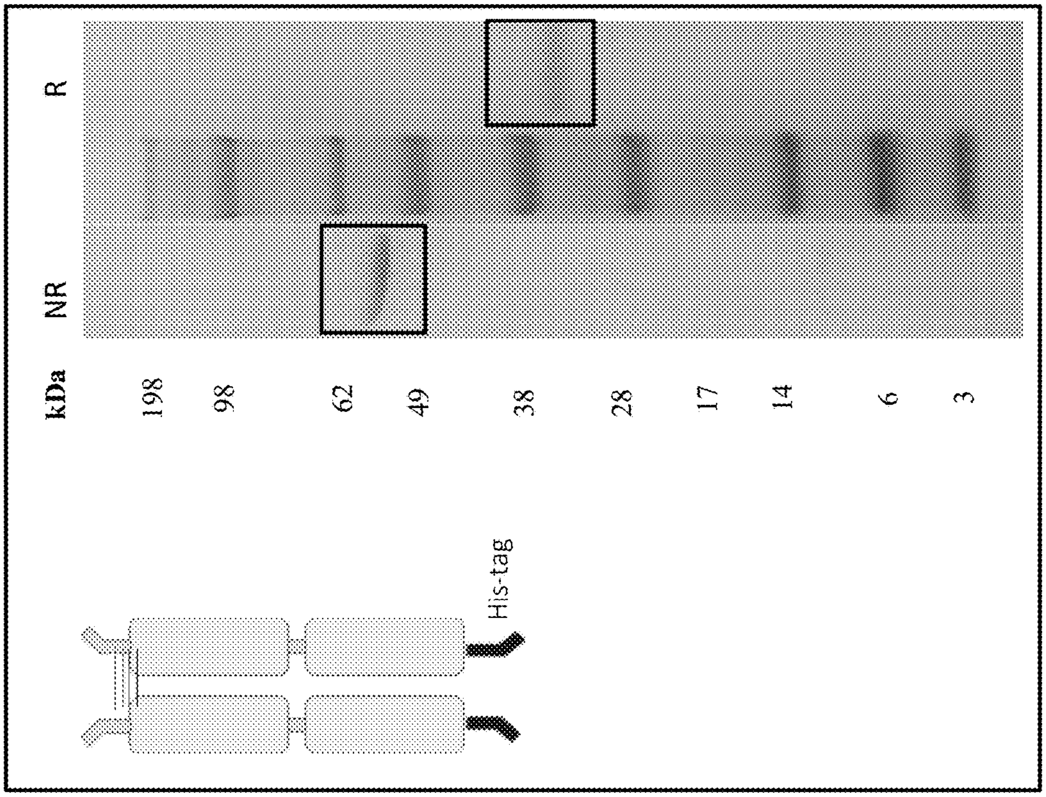
FIG. 6 shows non-reducing and reducing SDS-PAGE and a schematic illustration of an Fc domain formed from Fc domain monomers having the sequence of SEQ ID NO: 9.
Figure 7:
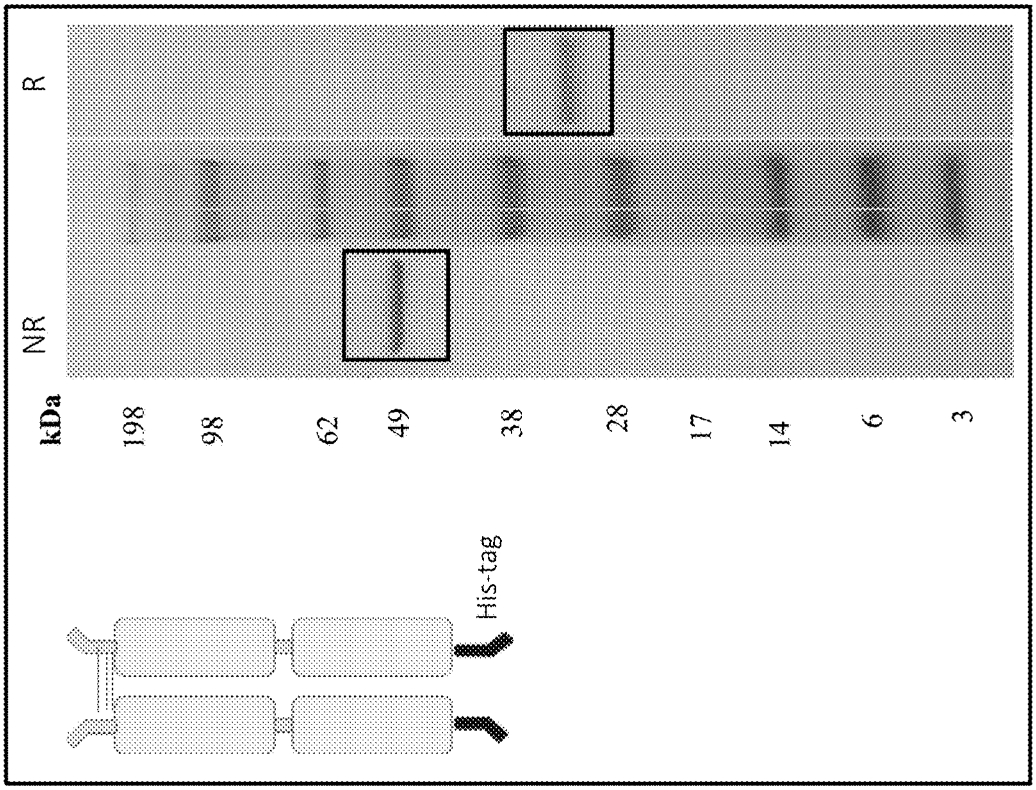
FIG. 7 shows non-reducing and reducing SDS-PAGE and a schematic illustration of an Fc domain formed from Fc domain monomers having the sequence of SEQ ID NO: 12.
Figure 8:
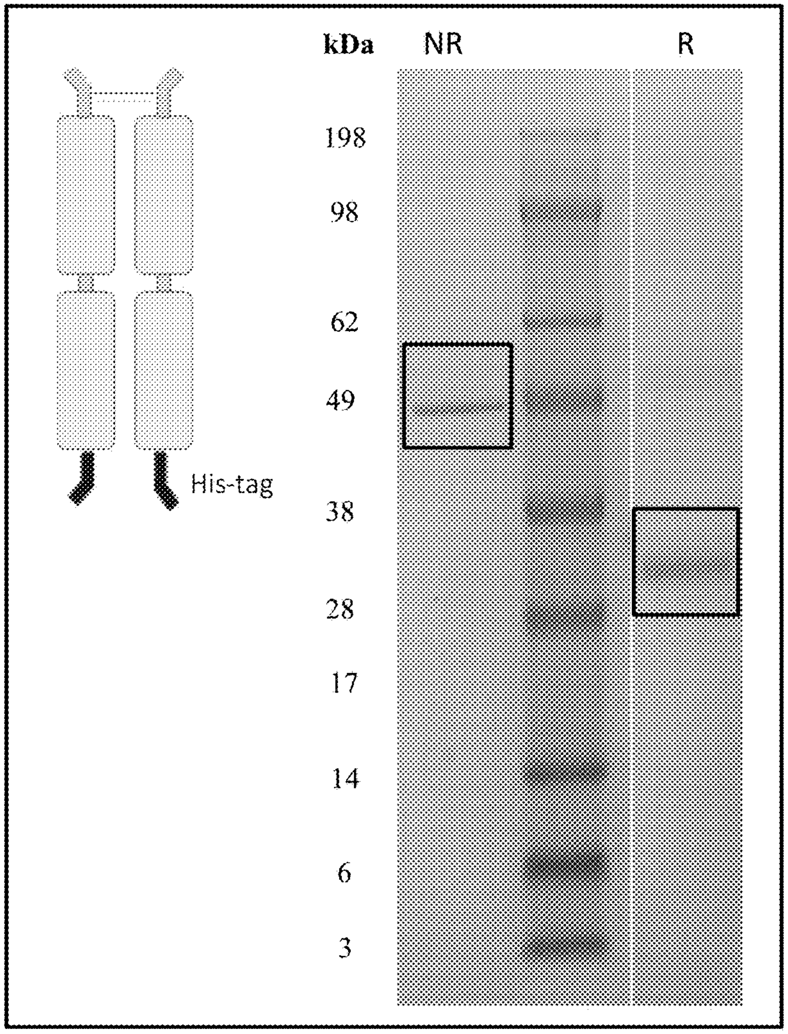
FIG. 8 shows non-reducing and reducing SDS-PAGE and a schematic illustration of an Fc domain formed from Fc domain monomers having the sequence of SEQ ID NO: 14.

The disclosure features conjugates, compositions, and methods for the treatment of viral infections (e.g., influenza viral infections). The conjugates disclosed herein include monomers or dimers of viral neuraminidase inhibitors (e.g., zanamivir, peramivir, or analogs thereof) conjugated to Fc monomers, Fc domains, Fc-binding peptides, albumin proteins, or albumin protein-binding peptides. The neuraminidase inhibitor (e.g., zanamivir, peramivir, or analogs thereof) in the conjugates targets neuraminidase on the surface of the viral particle. The Fc monomers or Fc domains in the conjugates bind to FcγRs (e.g., FcRn, FcγRI, FcγRIIa, FcγRIIc, FcγRIIIa, and FcγRIIIb) on immune cells, e.g., neutrophils, to activate phagocytosis and effector functions, such as antibody-dependent cell-mediated cytotoxicity (ADCC), thus leading to the engulfment and destruction of viral particles by immune cells and further enhancing the antiviral activity of the conjugates. The albumin or albumin-binding peptide may extend the half-life of the conjugate, for example, by binding of albumin to the recycling neonatal Fc receptor. Such compositions are useful in methods for the inhibition of viral growth and in methods for the treatment of viral infections, such as those caused by an influenza virus A, influenza virus B and influenza virus C.

I. Viral Infections

The compounds and pharmaceutical compositions described herein (e.g., a conjugate of any one of formulas (1)-(5), (D-I)-(D-X), (D'-I), (M-I)-(M-X), or (M'-I)) can be used to treat a viral infection (e.g., an influenza viral infection, such as influenza A, B, C, or parainfluenza).

Viral infection refers to the pathogenic growth of a virus (e.g., the influenza virus) in a host organism (e.g., a human subject). A viral infection can be any situation in which the presence of a viral population(s) is damaging to a host body. Thus, a subject is suffering from a viral infection when an excessive amount of a viral population is present in or on the subject's body, or when the presence of a viral population(s) is damaging the cells or other tissue of the subject.

Influenza, commonly known as "the flu", is an infectious disease caused by an influenza virus. Symptoms can be mild to severe. The most common symptoms include: a high fever, runny nose, sore throat, muscle pains, headache, coughing, and feeling tired. These symptoms typically begin two days after exposure to the virus and most last less than a week. The cough, however, may last for more than two weeks. In children, there may be nausea and vomiting, but these are less common in adults. Complications of influenza may include viral pneumonia, secondary bacterial pneumonia, sinus infections, and worsening of previous health problems such as asthma or heart failure. Sever complications may occur in subjects having weakened immune systems, such as the young, the old, those with illnesses that weaken the immune system, and those undergoing therapy treatment resulting in a weakening of the immune system.

Three types of influenza viruses affect human subjects, namely Type A, Type B, and Type C. Usually, the virus is spread through the air from coughs or sneezes. This is believed to occur mostly over relatively short distances. It can also be spread by touching surfaces contaminated by the virus and then touching the mouth or eyes. A person may be infectious to others both before and during the time they are showing symptoms. The infection may be confirmed by testing the throat, sputum, or nose for the virus. A number of rapid tests are available; however, people may still have the infection if the results are negative. A type of polymerase chain reaction that detects the virus's RNA may be used to diagnose influenza infection.

II. Conjugates of the Disclosure

Provided herein are synthetic conjugates useful in the treatment of viral infections (e.g., influenza infections). The conjugates disclosed herein include an Fc domain or an albumin protein conjugated to one or more monomers neuraminidase inhibitors or one or more dimers of two neuraminidase inhibitors (e.g., neuraminidase inhibitors selected from zanamivir, sulfozanamivir, peramivir, A-315675, or analogs thereof). The dimers of two neuraminidase inhibitors include a neuraminidase inhibitor (e.g., a first neuraminidase inhibitor of formula (A-I), (A-II), (A-III), (A-IV), (A-V), (A-VI), (A-VII), (A-VIII), (A-IX), (A-X), (A-XI), or (A-XII)) and a second neuraminidase inhibitor (e.g., a second neuraminidase inhibitor of formula (A-I), (A-II), (A-III), (A-IV), (A-V), (A-VI), (A-VII), (A-VIII), (A-IX), (A-X), (A-XI), or (A-XII)). The first and second neuraminidase inhibitors are linked to each other by way of a linker.

Without being bound by theory, in some aspects, conjugates described herein bind to the surface of a viral particle (e.g., bind to viral neuraminidase enzyme on the surface on an influenza viral particle) through the interactions between the neuraminidase inhibitor moieties in the conjugates and proteins on the surface of the viral particle. The neuraminidase inhibitor disrupts neuraminidase, an envelope glycoprotein that cleaves sialic acids, i.e., terminal neuraminic acid residues, from glycan structures on the surface of infected host cells, releasing progeny viruses and allowing the spread of the virus from the host cell to uninfected surrounding cells.

Conjugates of the invention include neuraminidase inhibitor monomers and dimers conjugated to an Fc domain, Fc monomer, or Fc-binding peptide. The Fc domain in the conjugates described herein binds to the FcγRs (e.g., FcRn, FcγRI, FcγRIIa, FcγRIIc, FcγRIIIa, and FcγRIIIb) on immune cells. The binding of the Fc domain in the conjugates described herein to the FcγRs on immune cells activates phagocytosis and effector functions, such as antibody-dependent cell-mediated cytotoxicity (ADCC), thus leading to the engulfment and destruction of viral particles by immune cells and further enhancing the antiviral activity of the conjugates.

Conjugates of the invention include neuraminidase inhibitor monomers and dimers conjugated to an albumin protein or an albumin protein-binding peptide. The albumin protein or albumin protein-binding peptide may extend the half-life of the conjugate, for example, by binding of albumin to the recycling neonatal Fc receptor.

Conjugates provided herein are described by any one of formulas (1)-(5), (D-I)-(D-X), (D'-I), (M-I)-(M-X), or (M'-I). In some embodiments, the conjugates described herein include one or more monomers of neuraminidase inhibitors conjugated to an Fc domain or an albumin protein. In some embodiments, the conjugates described herein include one or more dimers of neuraminidase inhibitors conjugated to an Fc domain or an albumin protein. In some embodiments, when n is 2, E (an Fc domain monomer)dimerizes to form an Fc domain.

Conjugates described herein may be synthesized using available chemical synthesis techniques in the art. In cases where a functional group is not available for conjugation, a molecule may be derivatized using conventional chemical synthesis techniques that are well known in the art. In some embodiments, the conjugates described herein contain one or more chiral centers. The conjugates include each of the isolated stereoisomeric forms as well as mixtures of stereoisomers in varying degrees of chiral purity, including racemic mixtures. It also encompasses the various diastereomers, enantiomers, and tautomers that can be formed.

Neuraminidase Inhibitors

A component of the conjugates described herein is an influenza virus neuraminidase inhibitor moiety. An influenza virus neuraminidase inhibitor disrupts neuraminidase, an envelope glycoprotein that cleaves sialic acids, i.e., terminal neuraminic acid residues, from glycan structures on the surface of infected host cells, releasing progeny viruses and allowing the spread of the virus from the host cell to uninfected surrounding cells. Examples of an influenza virus neuraminidase inhibitor include zanamivir (Relenza), sulfozanamivir, A-315675 and peramivir. In addition, derivatives of zanamivir, sulfozanamivir, A-315675 and peramivir, such as those found in the literature, have neuraminidase inhibitor activity and are useful as neuraminidase inhibitor moieties of the compounds herein (see, for example, Hadházi et al. A sulfozanamivir analogue has potent anti-influenza virus activity. *ChemMedChem Comm.* 13:785-789 (2018) and In vitro characterization of A-315675, a highly potent inhibitor of A and B strain of influenze virus neuraminidases and influenza virus replication. *Antimicrobial Agents and Chemotherapy* 46(4):1014-1021 (2002)).

Conjugates described herein are separated into two types: (1) one or more dimers of neuraminidase inhibitors conjugated to an Fc domain or an albumin protein and (2) one or more monomers of neuraminidase inhibitors conjugated to an Fc domain or an albumin protein. The dimers of neuraminidase inhibitors are linked to each other by way of a linker, such as the linkers described herein.

Viral neuraminidase inhibitors of the invention include zanamivir, sulfozanamivir, A-315675, peramavir, and analogs thereof, such as the viral neuraminidase inhibitors of formulas (A-I)-(A-XII):

(A-I)
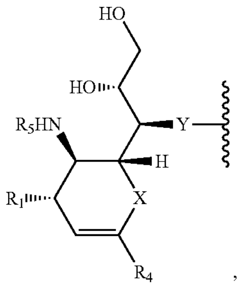
,
(A-II)
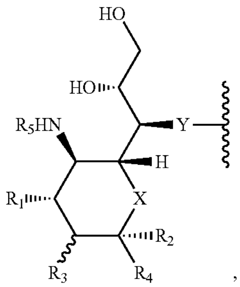
,
(A-III)
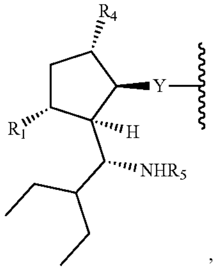
,
(A-IV)
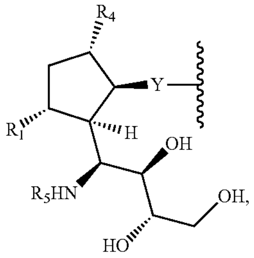
(A-V)
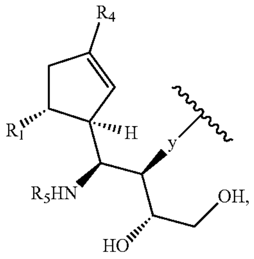
-continued
(A-VI)
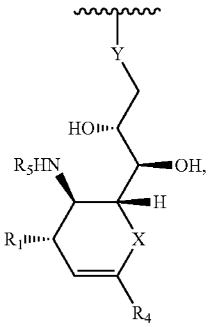
(A-VII)
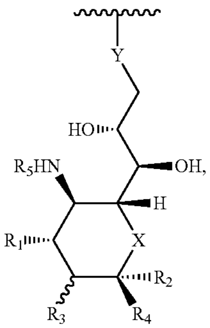
(A-VIII)
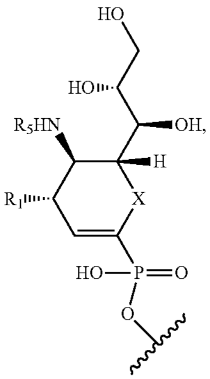
(A-IX)
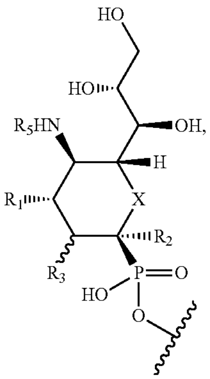

-continued (A-X)

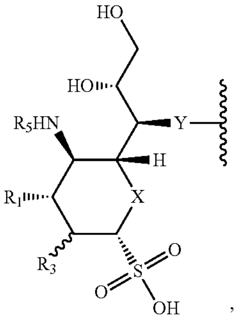

, (A-XI)

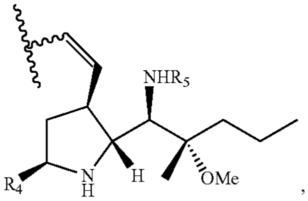

, (A-XII)

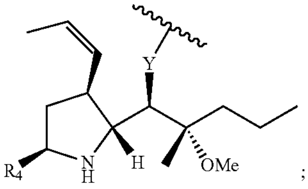

;

wherein $R_1$ is selected from —OH, —$NH_2$, —NHC(=NH)$NH_2$, and —NHC(=NH)$NHR_6$; $R_2$ and $R_3$ are each independently selected from —H, —OH, —F, —Cl, and —Br; $R_4$ is selected from —$CO_2H$, —P(=O)$(OH)_2$, —$SO_3H$; $R_5$ is selected from —$COCH_3$, —$COCF_3$, —$SO_2CH_3$; X is selected from —O— and —S—; Y is selected from

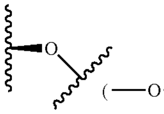

(—O—),

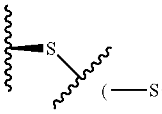

(—S—),

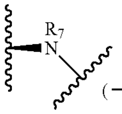

(—$NR_7$—),

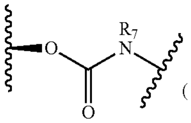

(—O(C=O)$NR_7$—),

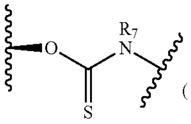

(—O(C=S)$NR_7$—),

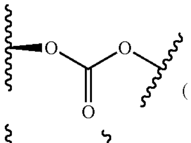

(—O(C=O)O—),

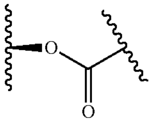

(—O(C=O)—),

-continued

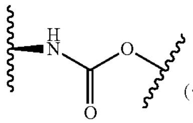

(—NH(C=O)O—),

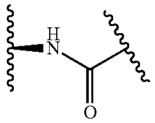

(—NH(C=O)—),

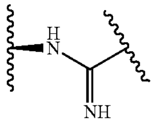

(—NH(C=NH)—),

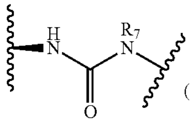

(—NH(C=O)$NR_7$—),

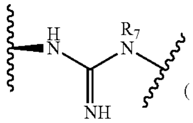

(—NH(C=NH)$NR_7$—),

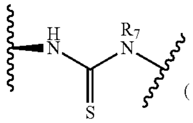

(—NH(C=S)$NR_7$—),

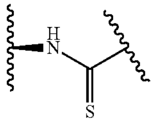

(—NH(C=S)—),

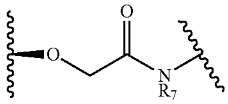

(—$OCH_2$(C=O)$NR_7$—),

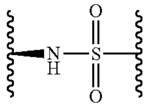

(—NH($SO_2$)—),

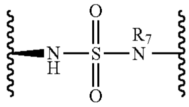

(—NH($SO_2$)$NR_7$—),

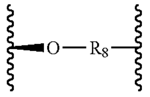

(—$OR_8$—),

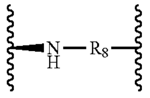

(—$NR_8$—), and

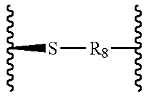

(—$SR_8$—);

$R_6$ is selected from

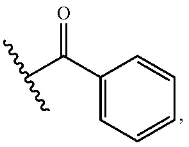, 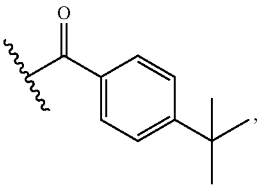,
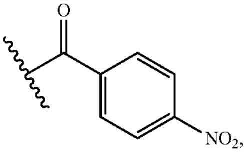, 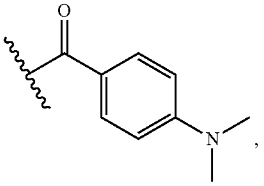,
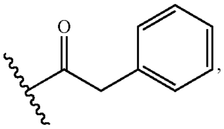,
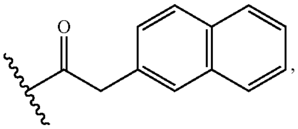,
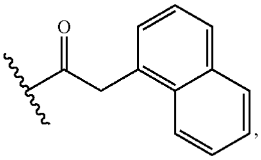, 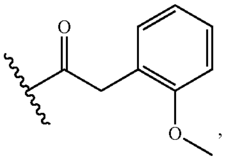,
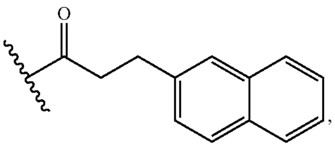,
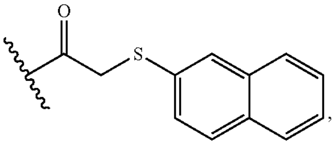, 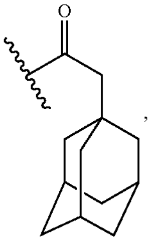,
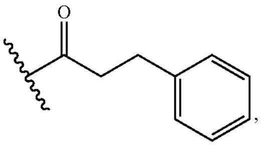, 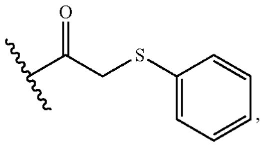,
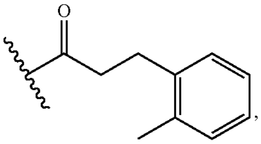, 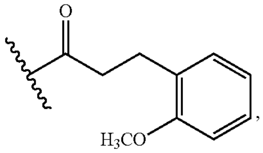,
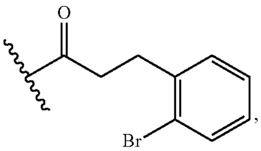, 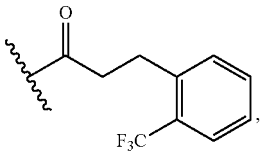,
-continued
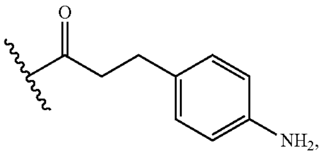,
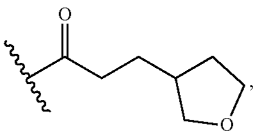,
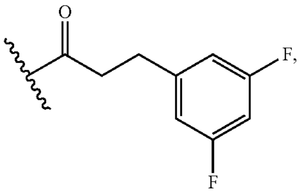,
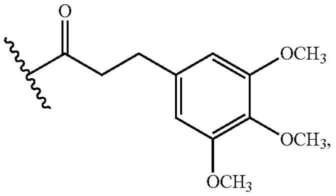,
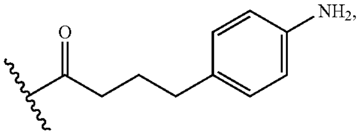,
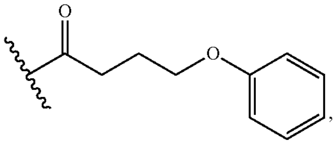,
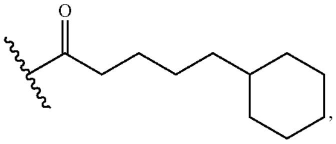,
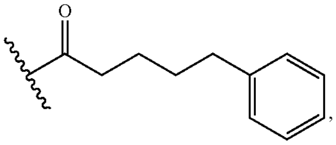,
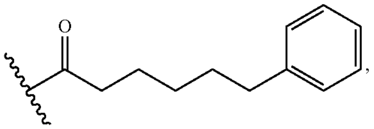,
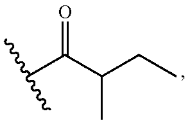, 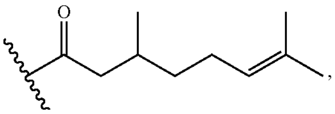,
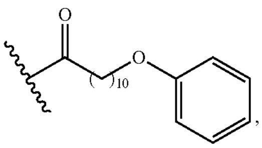, 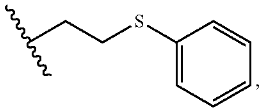, -continued

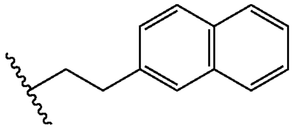

, and

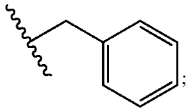

;

$R_7$ is selected from H, C1-C20 alkyl, C3-C20 cycloalkyl, C3-C20 heterocycloalkyl; C5-C15 aryl, and C2-C15 heteroaryl; and Ra is selected from C3-C20 heterocycloalkyl, C5-C15 aryl, and C2-C15 heteroaryl. Most preferably the viral neuraminidase inhibitor of formula (A-I), (A-II), (A-III), (A-IV), (A-V), (A-VI), (A-VII), (A-VIII), (A-IX), (A-X), (A-XI), or (A-XII) is covalently attached to the conjugate through Y.

Preferably the viral neuraminidase inhibitor is selected from zanamivir, sulfozanamivir, peramivir, or A-315675:

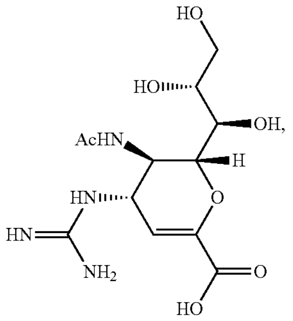

Zanamivir

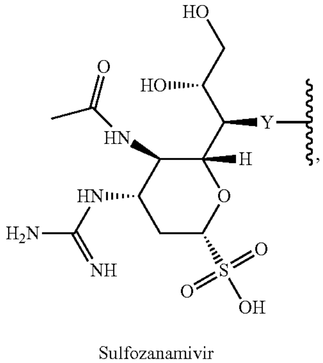

Sulfozanamivir

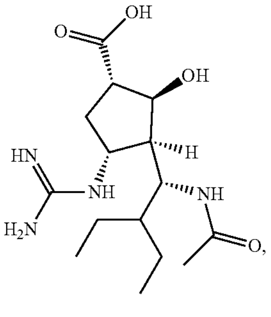

Peramivir

-continued

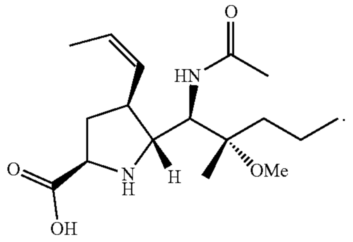

A-315675

Conjugates of Dimers of Neuraminidase Inhibitors Linked to an Fc Domain or an Albumin Protein The conjugates described herein include an Fc domain, and Fc monomer, an Fc-binding peptide, and albumin protein, or an albumin protein-binding peptide covalently linked to one or more dimers of neuraminidase inhibitors. The dimers of two neuraminidase inhibitors include a first neuraminidase inhibitor (e.g., a first viral neuraminidase inhibitor of formulas (A-I)-(A-XII)) and a second neuraminidase inhibitor (e.g., a second viral neuraminidase inhibitor of formulas (A-I)-(A-XII)). The first and second neuraminidase inhibitors are linked to each other by way of a linker, such as a linker described herein. In some embodiments of the dimers of neuraminidase inhibitors, the first and second neuraminidase inhibitors are the same. In some embodiments, the first and second neuraminidase inhibitors are different.

Dimers of neuraminidase inhibitors include homo-dimers of zanamivir or analogs thereof (e.g., (A-I), (A-II), (A-VI), (A-VII), (A-VIII), or (A-IX)). For example, neuraminidase inhibitor dimers of the invention include dimers having the structure $A_1$-L-$A_2$, wherein each $A_1$ and each $A_2$ is selected from (A-I), (A-II), (A-VI), (A-VII), (A-VIII), and (A-IX).

Dimers of neuraminidase inhibitors include homo-dimers of peramivir or analogs thereof (e.g., (A-III), (A-IV), or (A-V)). For example, neuraminidase inhibitor dimers of the invention include dimers having the structure $A_1$-L-$A_2$, wherein each $A_1$ and each $A_2$ is selected from (A-III), (A-IV), and (A-V).

Dimers of neuraminidase inhibitors include hetero-dimers including zanamivir or analogs thereof and peramivir of analogs thereof (e.g., (A-I)-(A-IX)). For example, neuraminidase inhibitor dimers of the invention include dimers having the structure $A_1$-L-$A_2$, wherein each $A_1$ is selected from (A-I), (A-II), (A-VI), (A-VII), (A-VIII), and (A-IX), and each $A_2$ is selected from (A-III), (A-IV), and (A-V).

In some embodiments, when T is greater than 1 (e.g., T is 2, 3, 4, 5, 6, 7, 8, 9, 10, 11, 12, 13, 14, 15, 16, 17, 18, 19, or 20), each $A_1$-L-$A_2$ may be independently selected (e.g., independently selected from any of the $A_1$-L-$A_2$ structures described herein). In some embodiments, E may be conjugated to 2, 3, 4, 5, 6, 7, 8, 9, 10, or more different $A_1$-L-$A_2$ moieties. In some embodiments, E is conjugated to a first $A_1$-L-$A_2$ moiety, and a second $A_1$-L-$A_2$, moiety. In some embodiments, $A_1$ and $A_2$ of the first $A_1$-L-$A_2$ moiety are independently selected from any one of formulas (A-III)-(A-V):

(A-III)

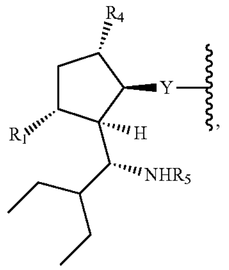

(A-IV)

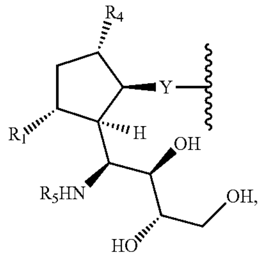

(A-V)

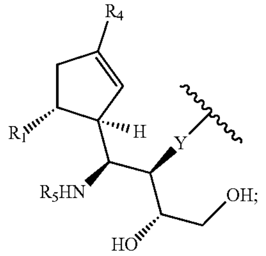

and $A_1$ and $A_2$ of the second $A_1$-L-$A_2$ moiety are independently selected from any one of formulas (A-I), (A-II), (A-VI), (A-VII), (A-VIII), or (A-IX):

(A-I)

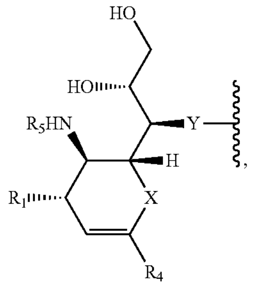

(A-II)

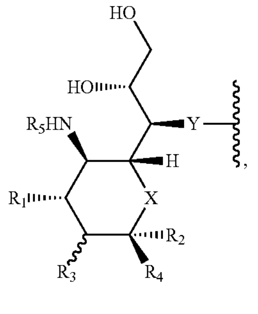

-continued (A-VI)

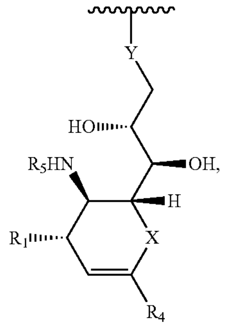

(A-VII)

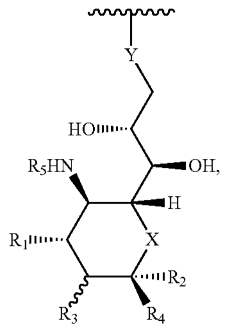

(A-VIII)

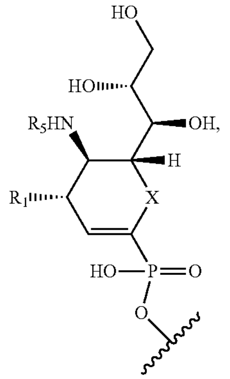

(A-IX)

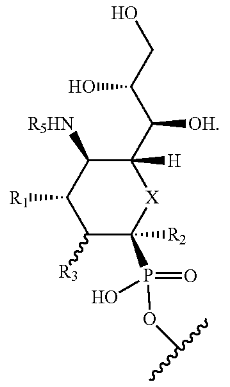

In some embodiments, the first $A_1$-L-$A_2$ moiety is conjugated specifically to lysine residues of E (e.g., the nitrogen atoms of surface exposed lysine residues of E), and the second $A_1$-L-$A_2$ moiety is conjugated specifically to cysteine residues of E (e.g., the sulfur atoms of surface exposed cysteine residues of E). In some embodiments, the first $A_1$-L-$A_2$ moiety is conjugated specifically to cysteine residues of E (e.g., the sulfur atoms of surface exposed cysteine residues of E), and the second $A_1$-L-$A_2$ moiety is conjugated specifically to lysine residues of E (e.g., the nitrogen atoms of surface exposed lysine residues of E).
In some embodiments, the disclosure provides a conjugate, or a pharmaceutically acceptable salt thereof, described by the formulae below:
(1)
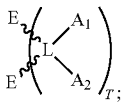
(3)
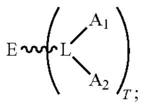
(D-I)
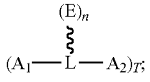
(D-II)
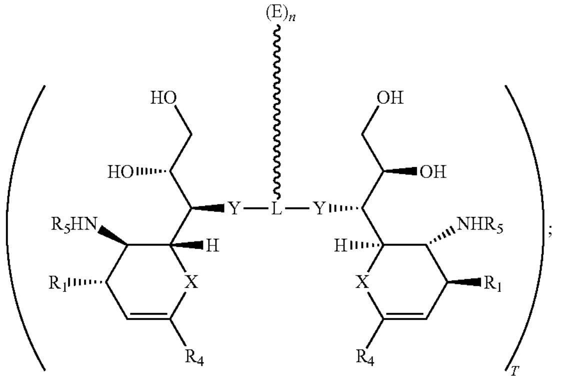
(D-II-1)
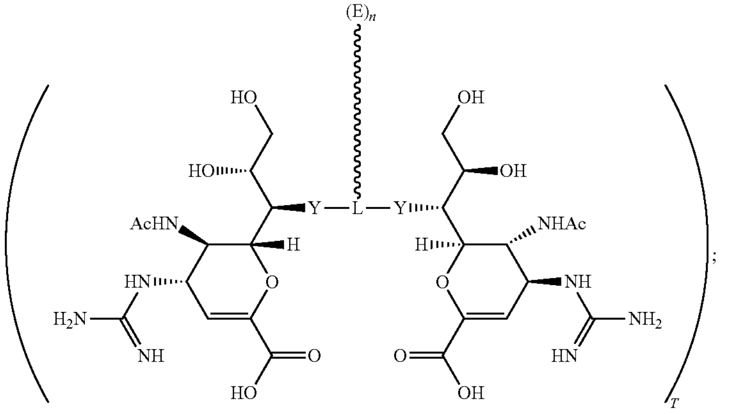
(D-II-2)
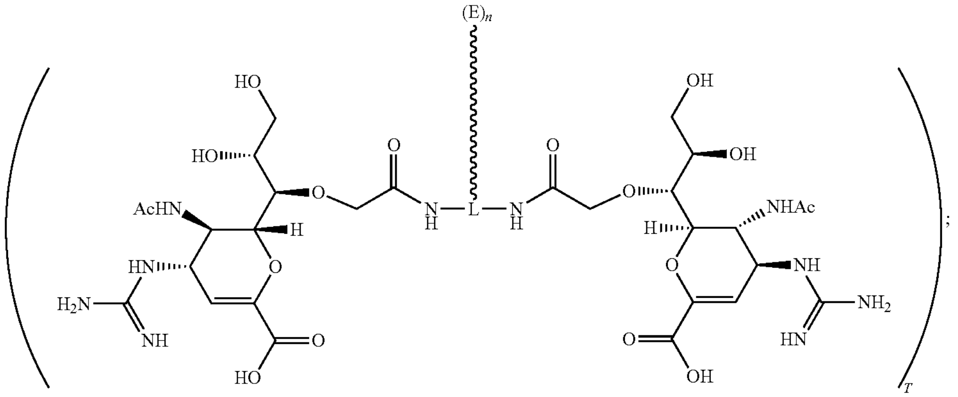

-continued
(D-II-5)
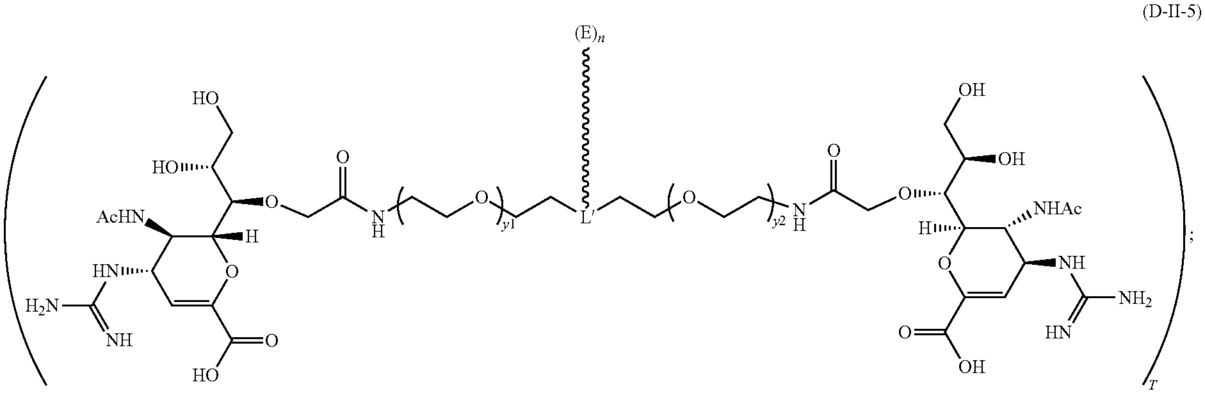
(D-II-6)
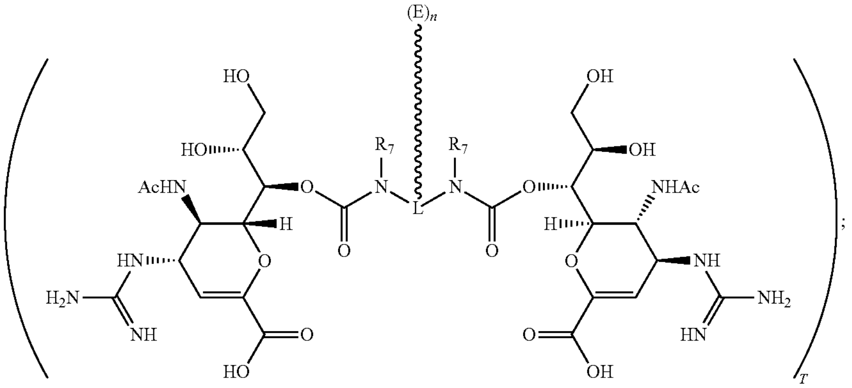
(D-II-7)
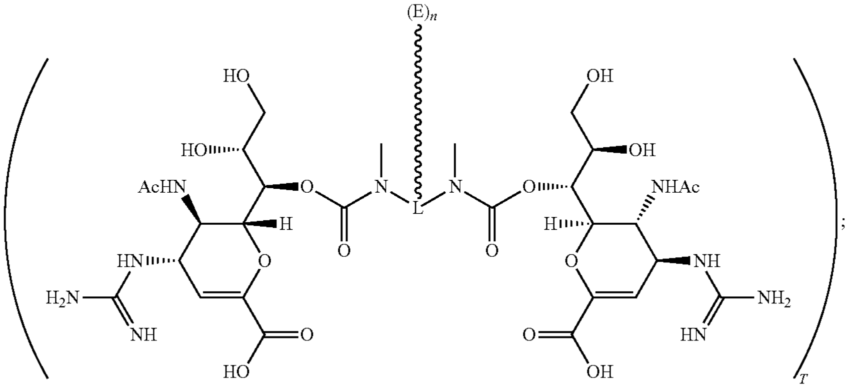
(D-II-8)
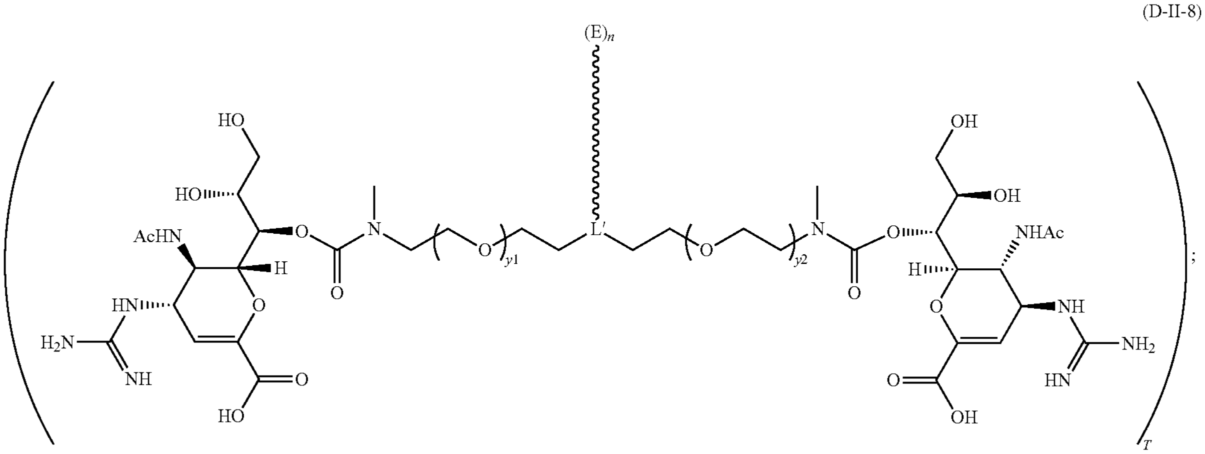

-continued
(D-II-9)
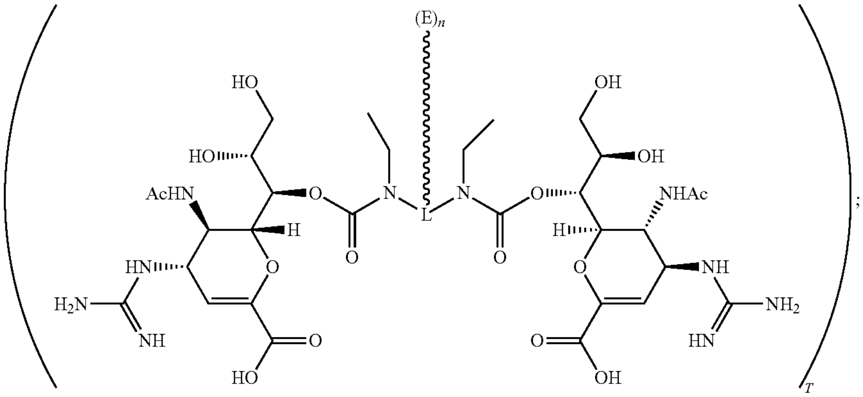
;
(D-II-10)
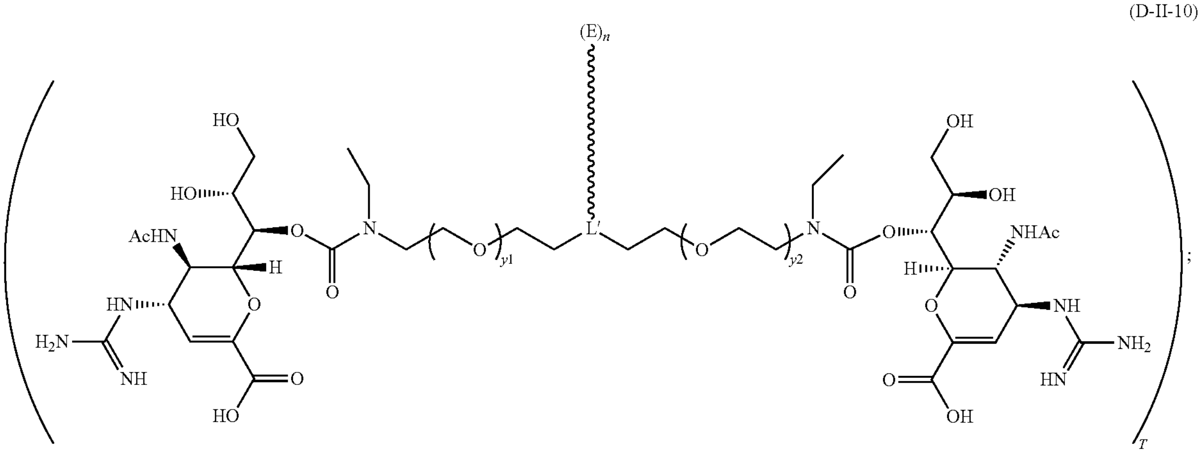
;
(D-III)
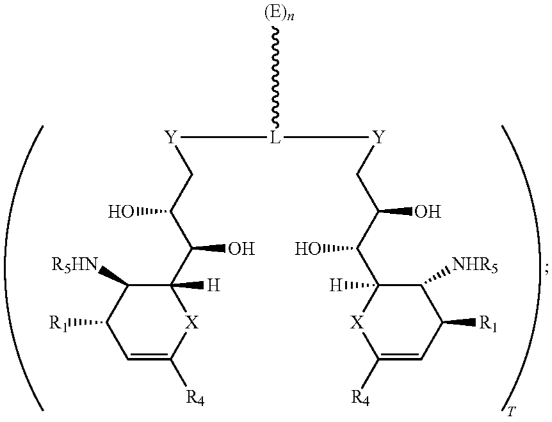
;

-continued
(D-III-1)
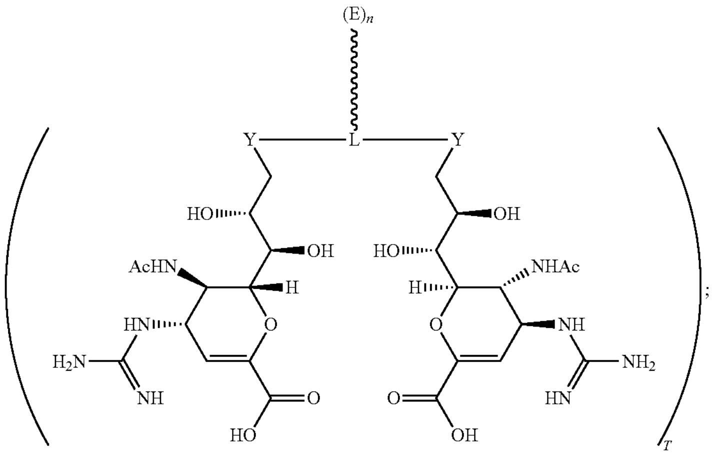
;
(D-III-2)
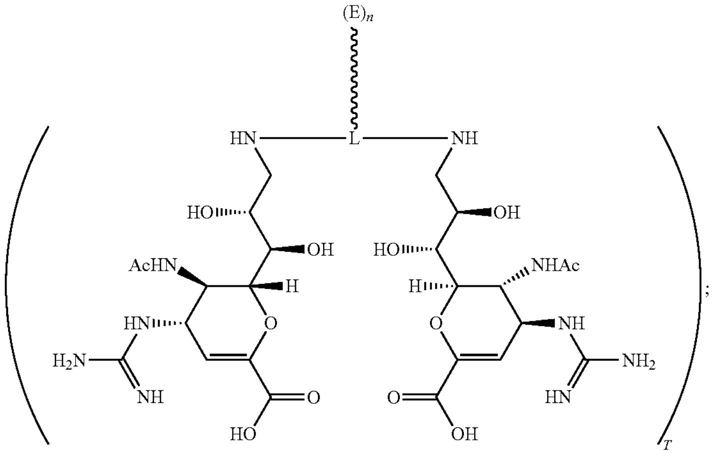
;
(D-III-3)
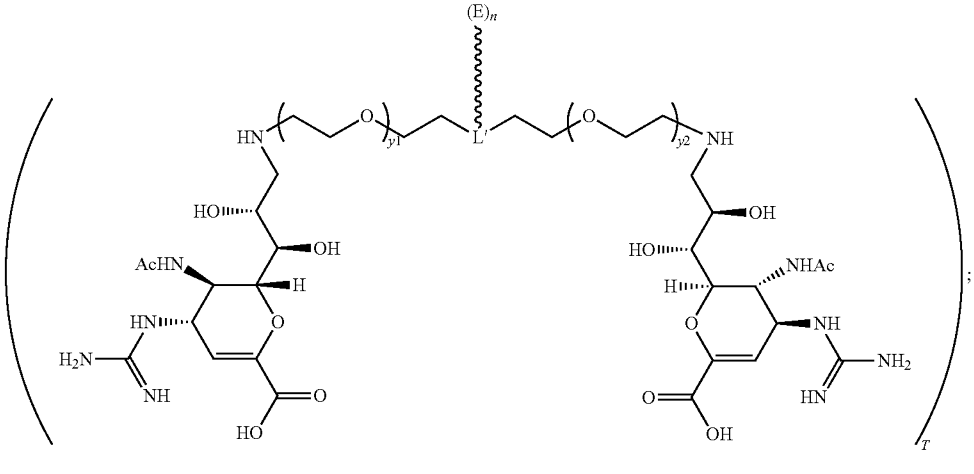
;

-continued
(D-III-4)
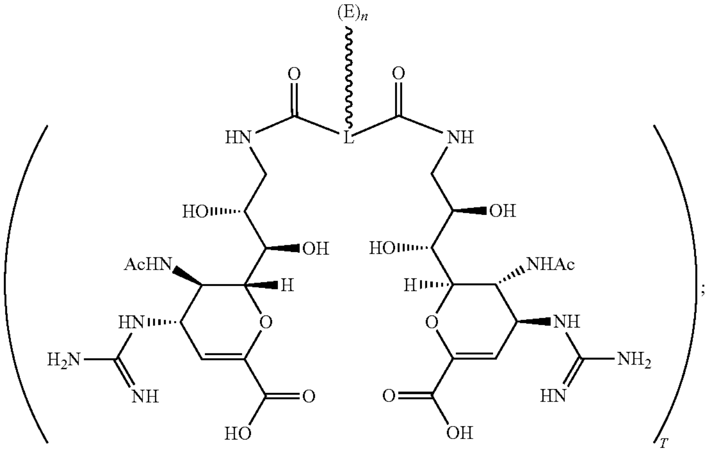
;
(D-III-5)
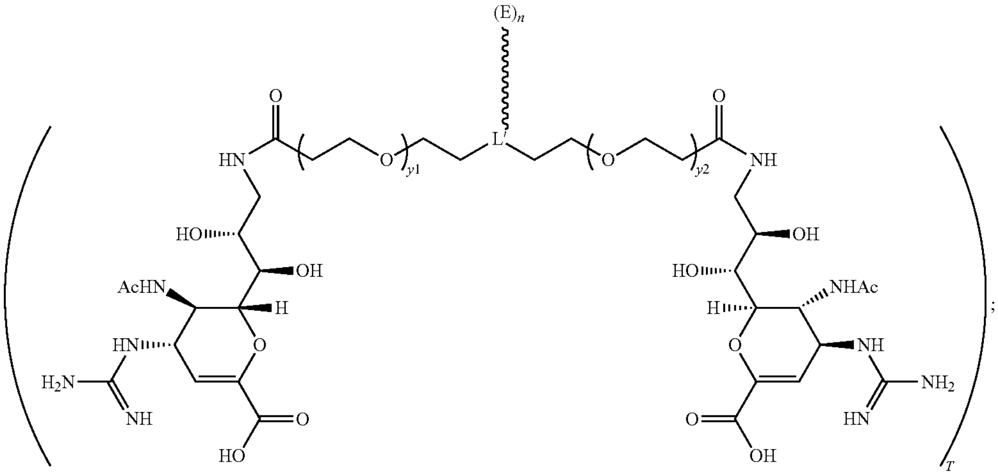
;
(D-III-6)
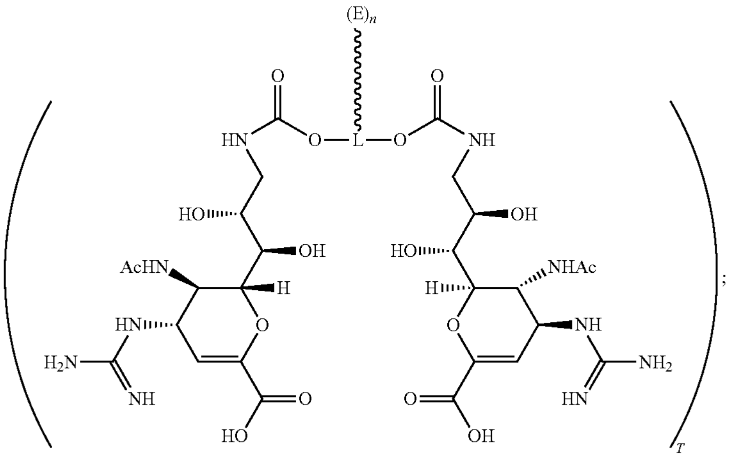
;

-continued
(D-III-7)
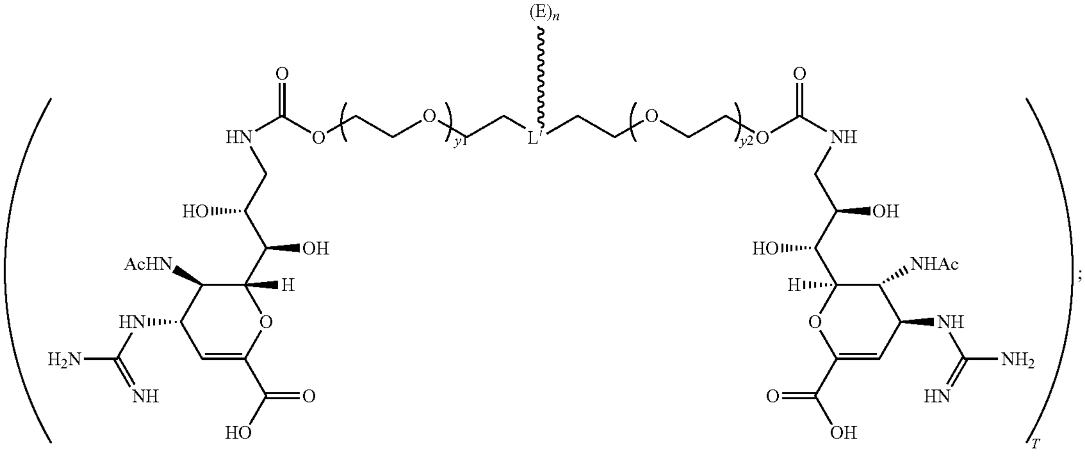
;
(D-III-8)
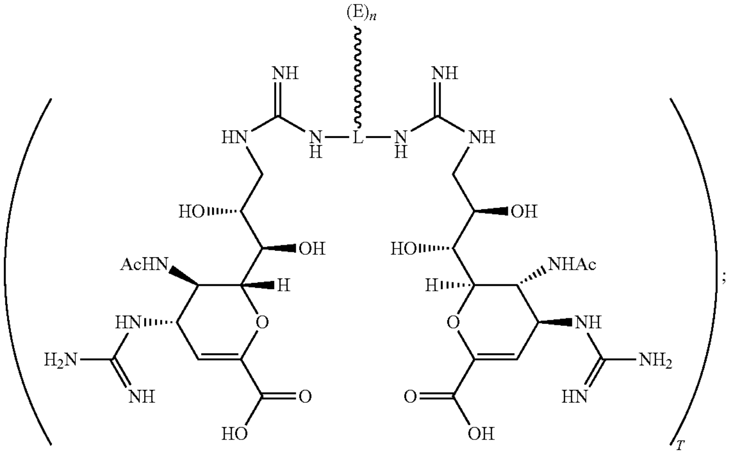
;
(D-III-9)
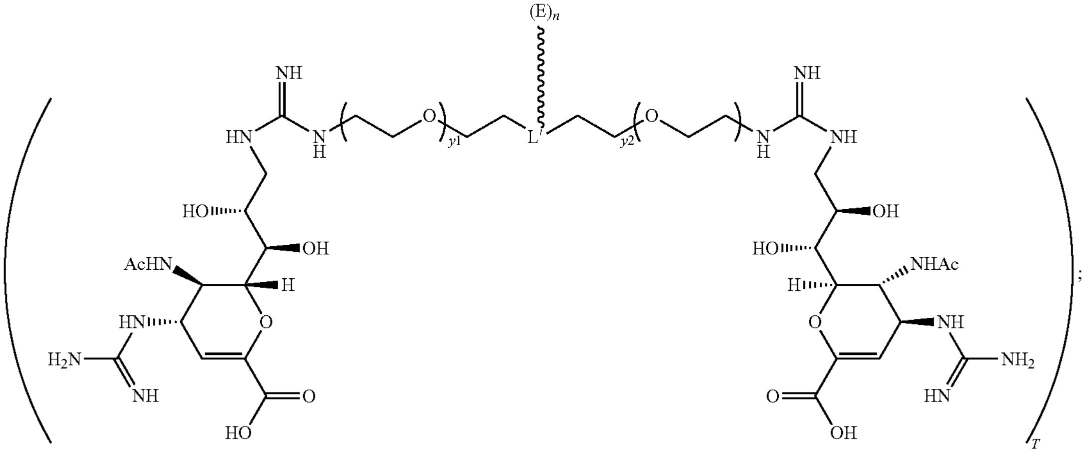
;

-continued
(D-IV)
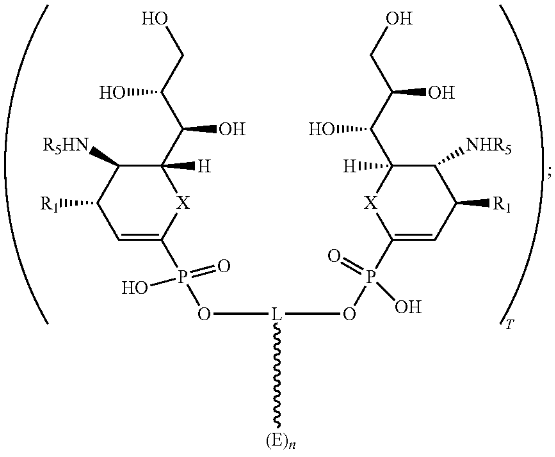
;
(D-IV-1)
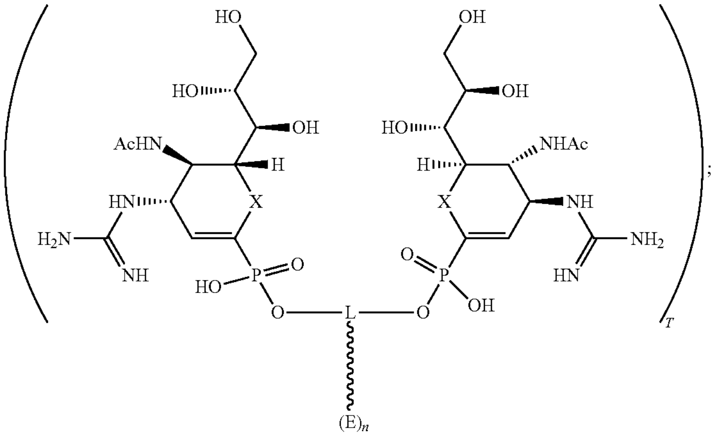
;
(D-IV-2)
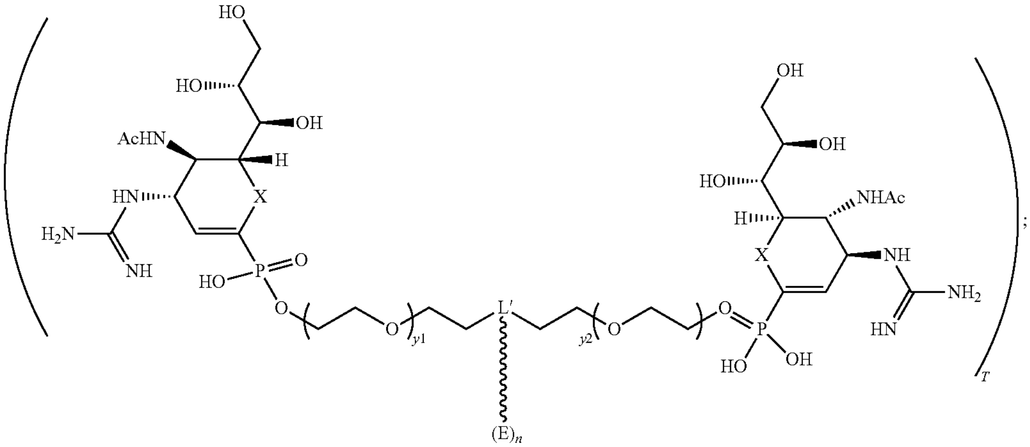
;

-continued
(D-V)
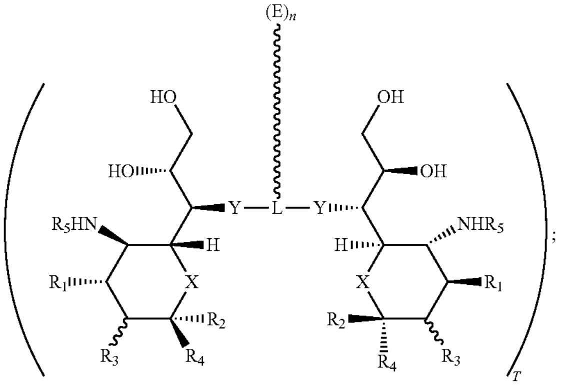
(D-V-1)
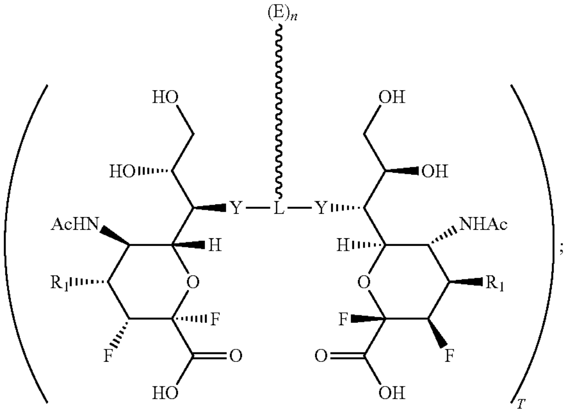
(D-V-2)
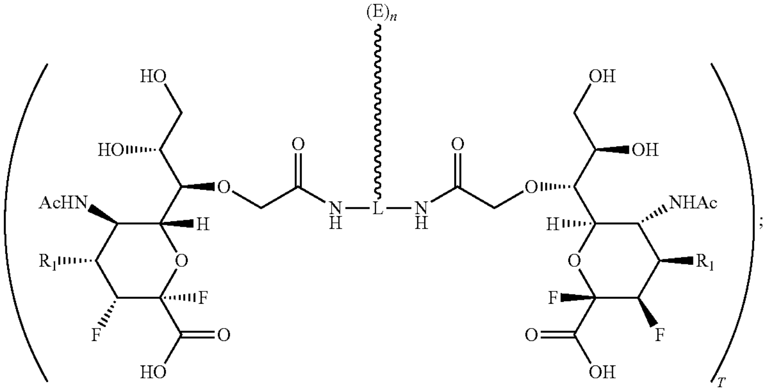
(D-V-3)
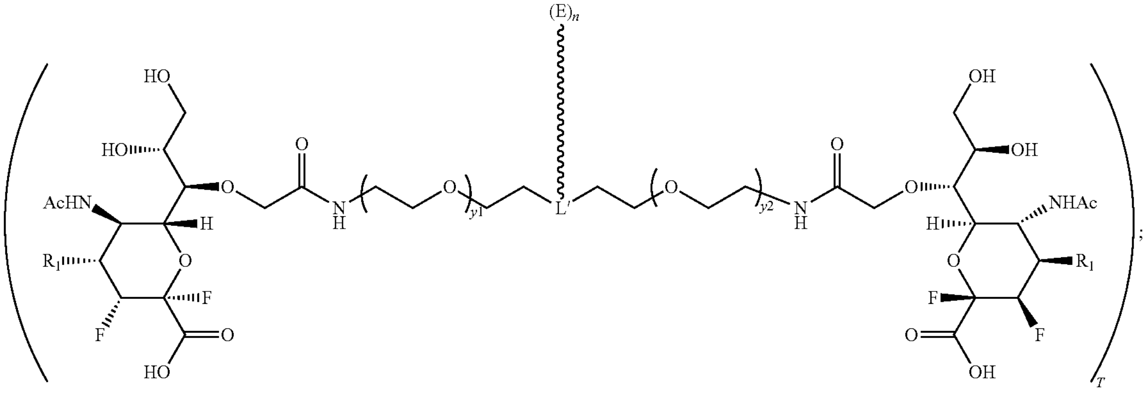

-continued
(D-V-4)
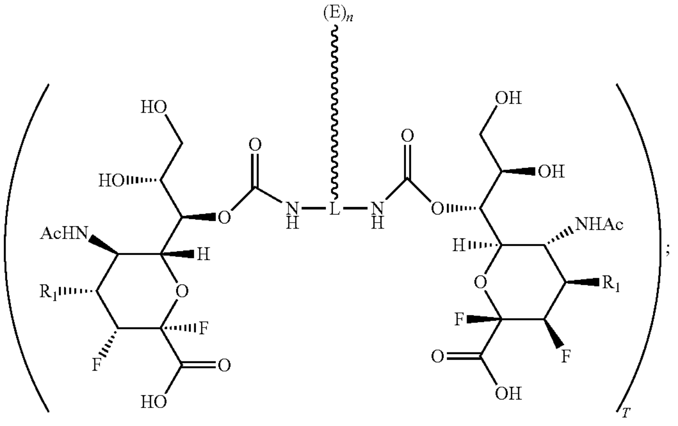
(D-V-5)
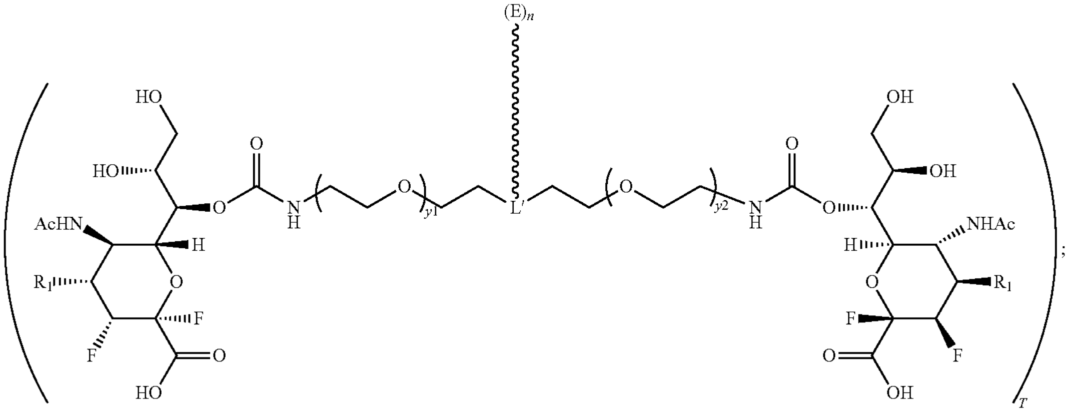
(D-V-6)
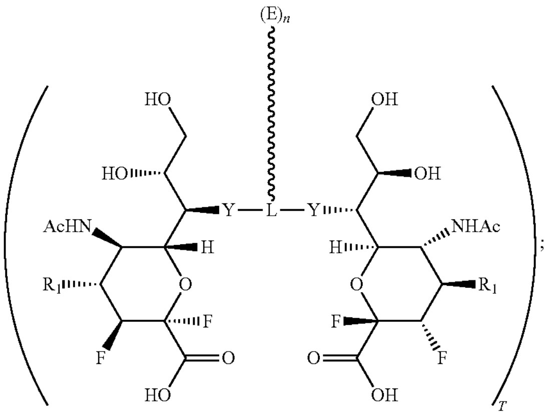
(D-V-7)
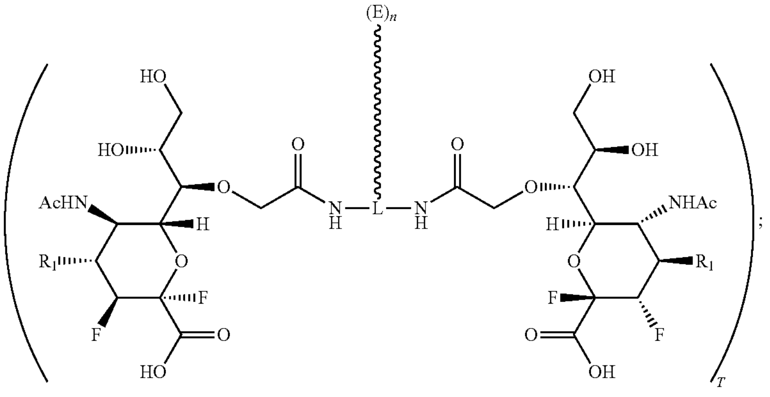

-continued
(D-V-8)
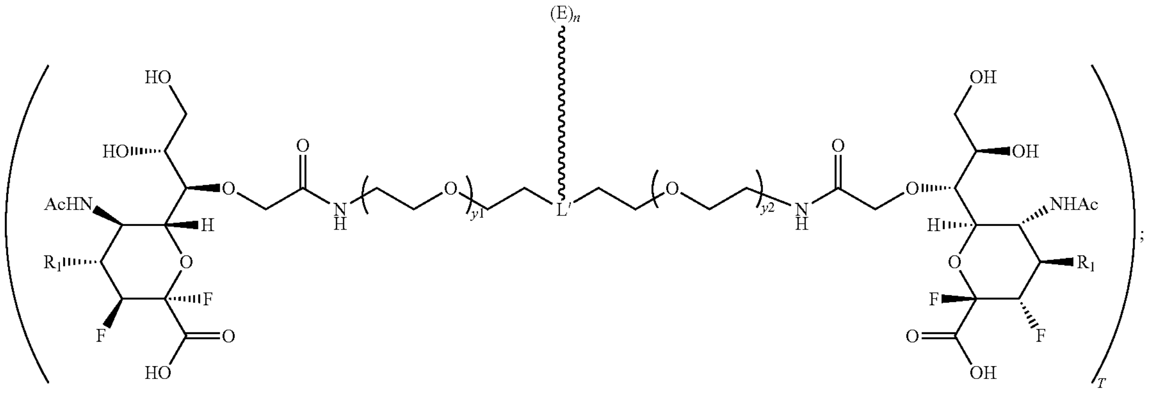
(D-V-9)
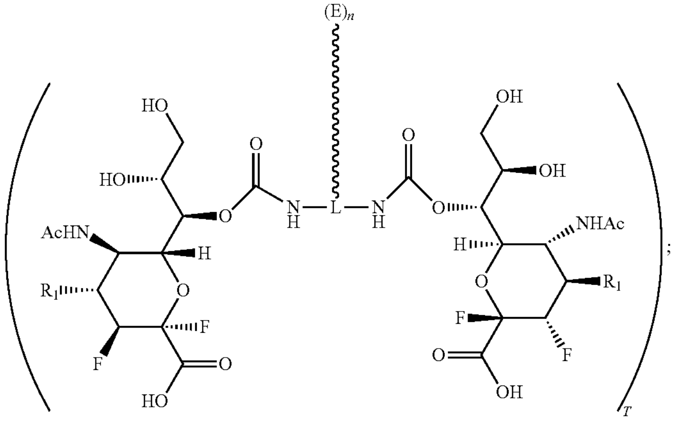
(D-V-10)
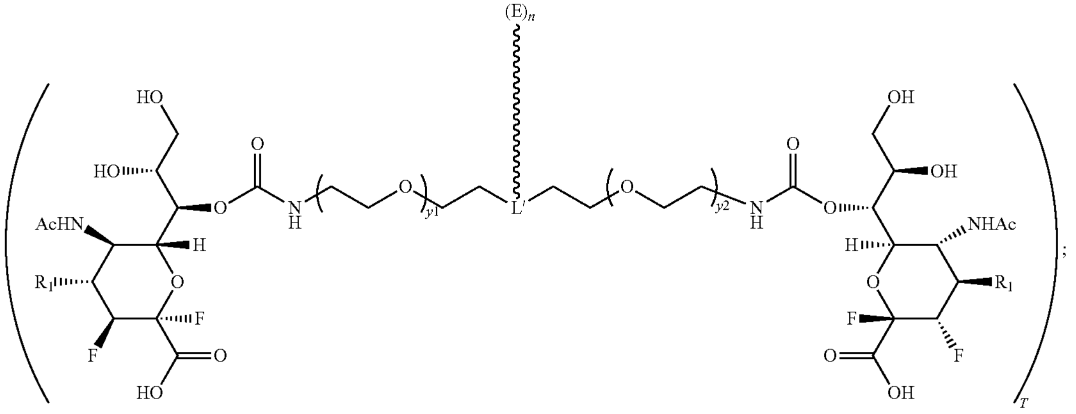

-continued
(D-VI)
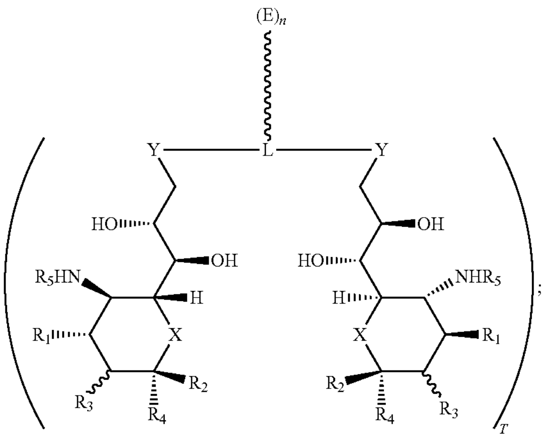
(D-VI-1)
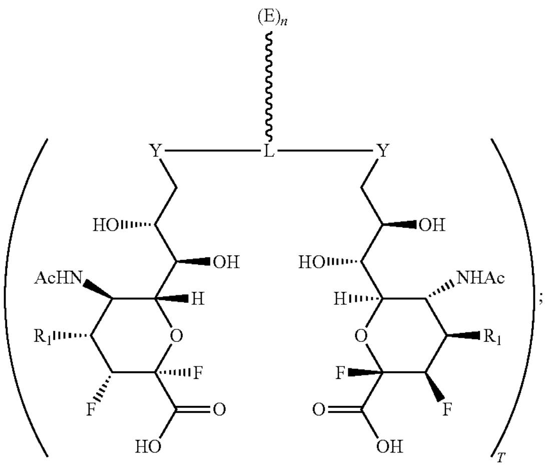
(D-VI-2)
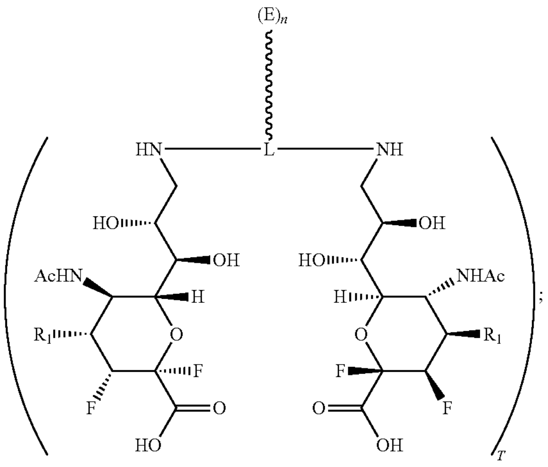

-continued
(D-VI-3)
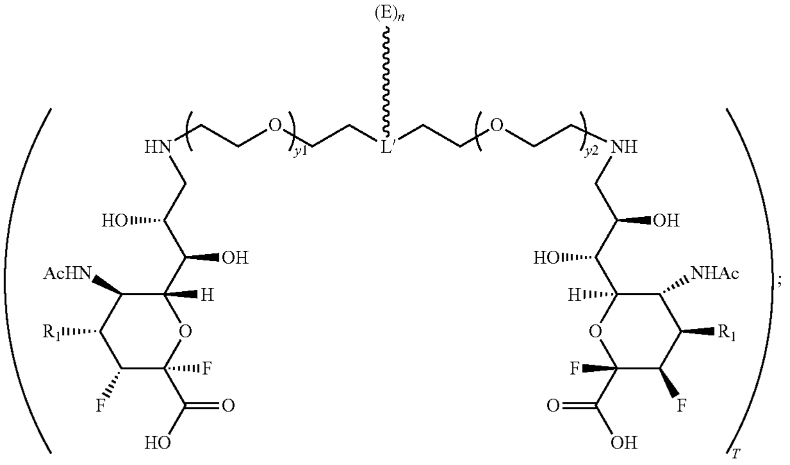
(D-VI-4)
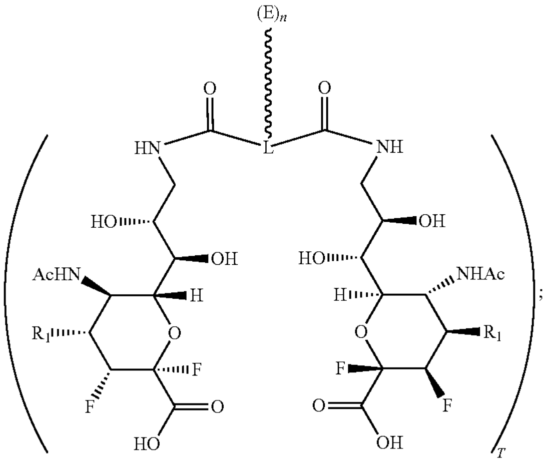
(D-VI-5)
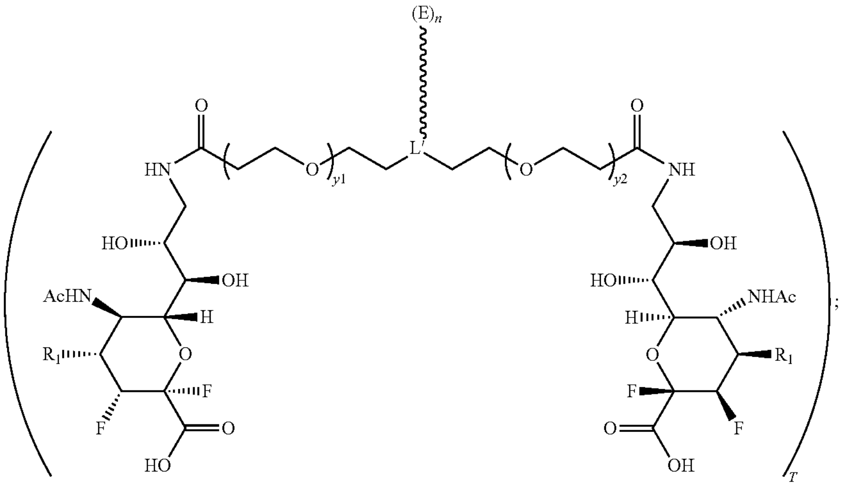

-continued
(D-VI-6)
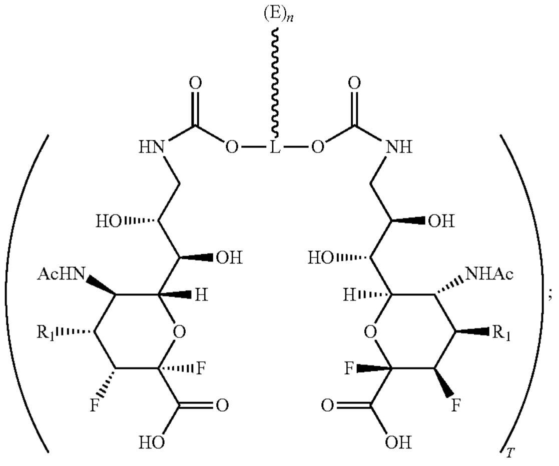
(D-VI-7)
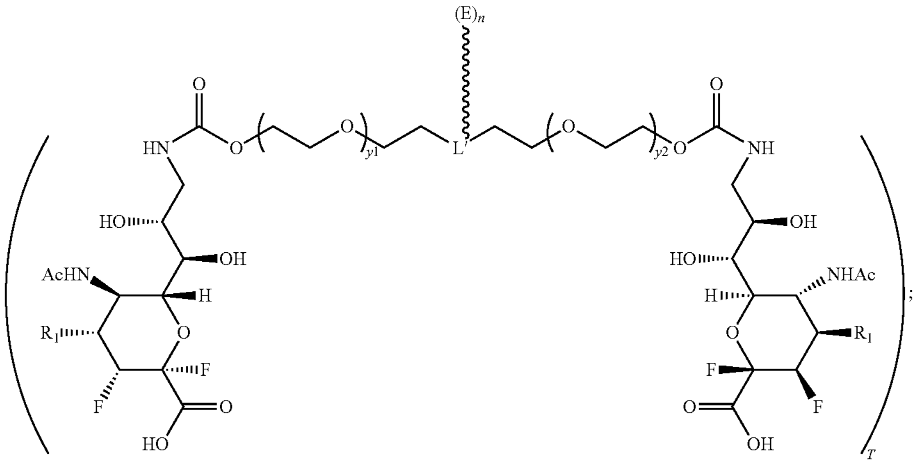
(D-VI-8)
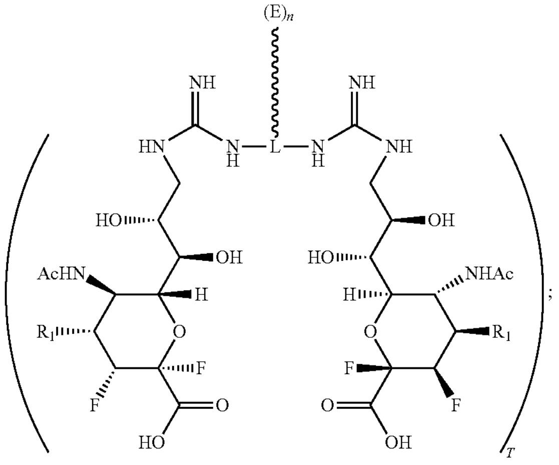

-continued
(D-VI-9)
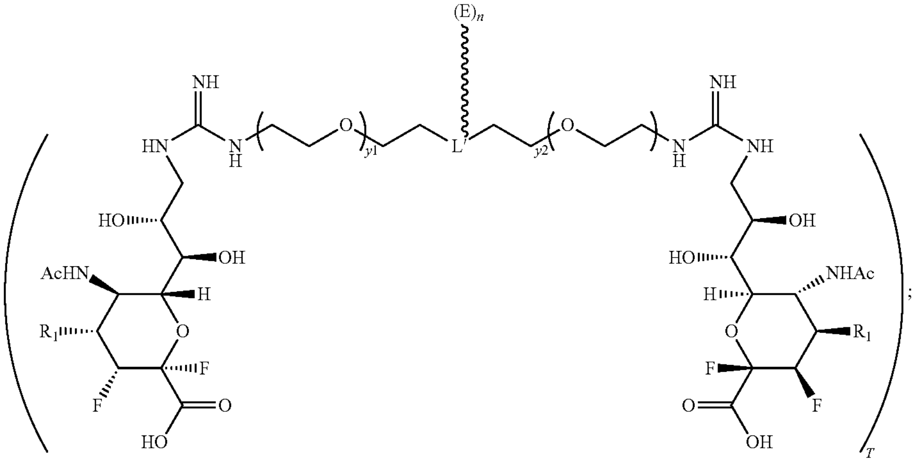
(D-VII)
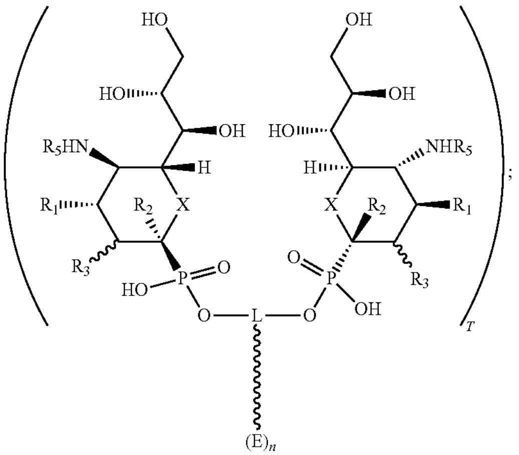
(D-VIII)
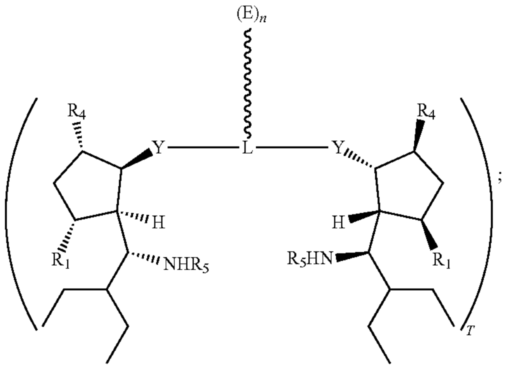
(D-VIII-1)
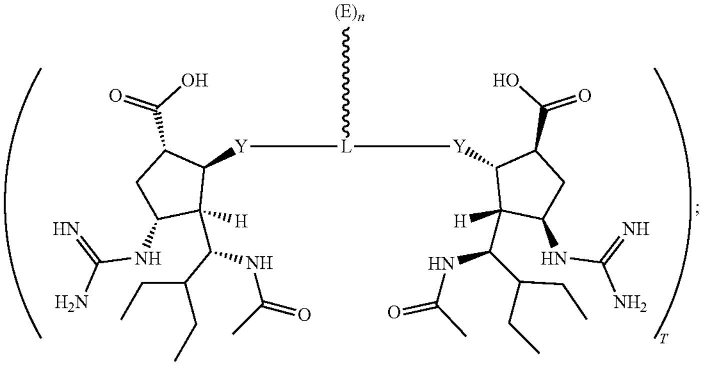

-continued
(D-VIII-2)
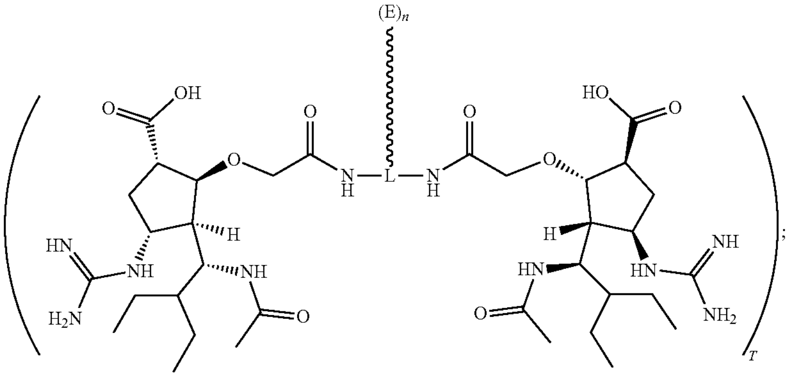
(D-VIII-3)
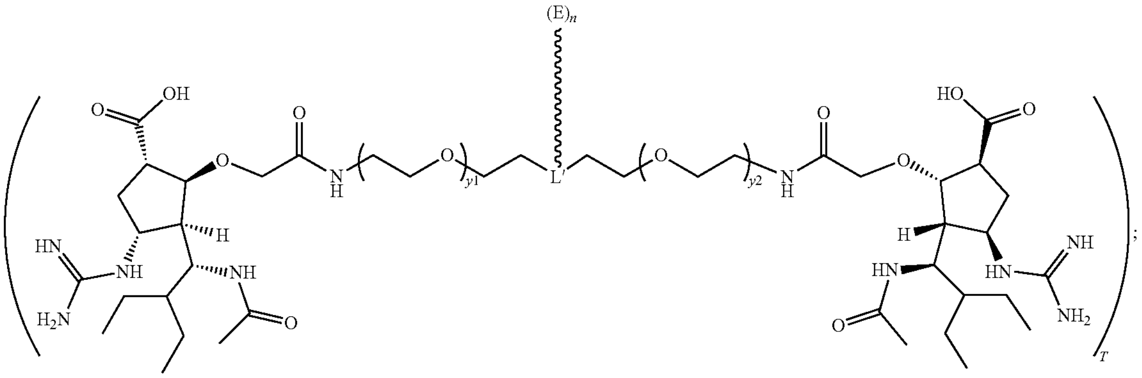
(D-VIII-4)
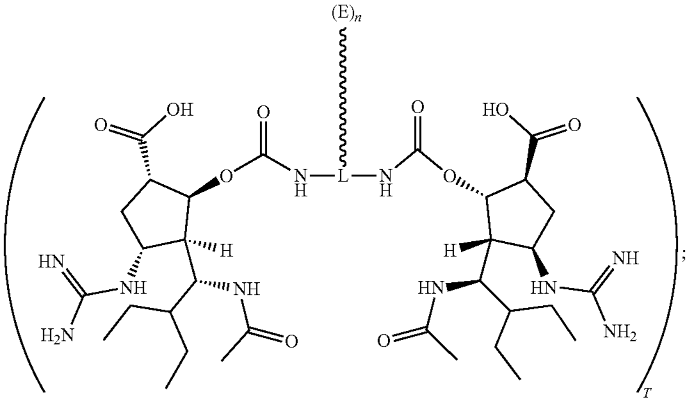
(D-VIII-5)
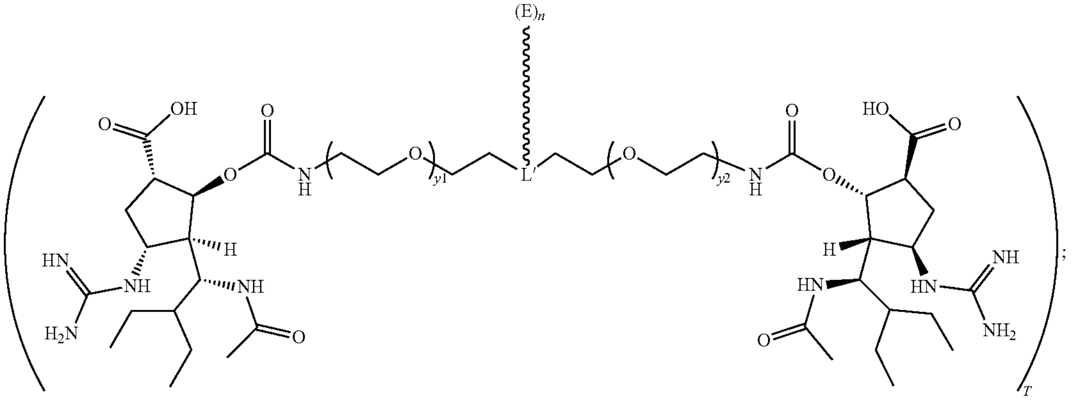

-continued
(D-VIII-6)
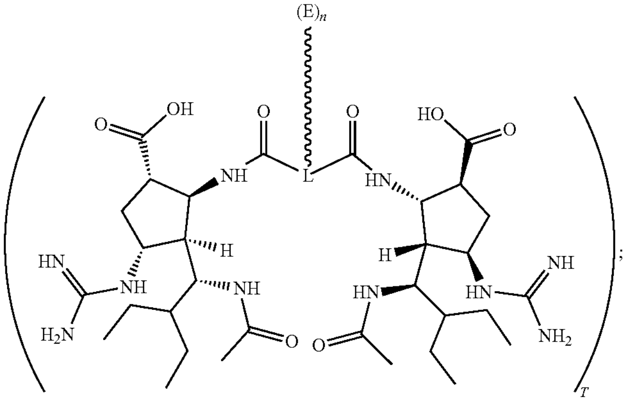
;
(D-VIII-7)
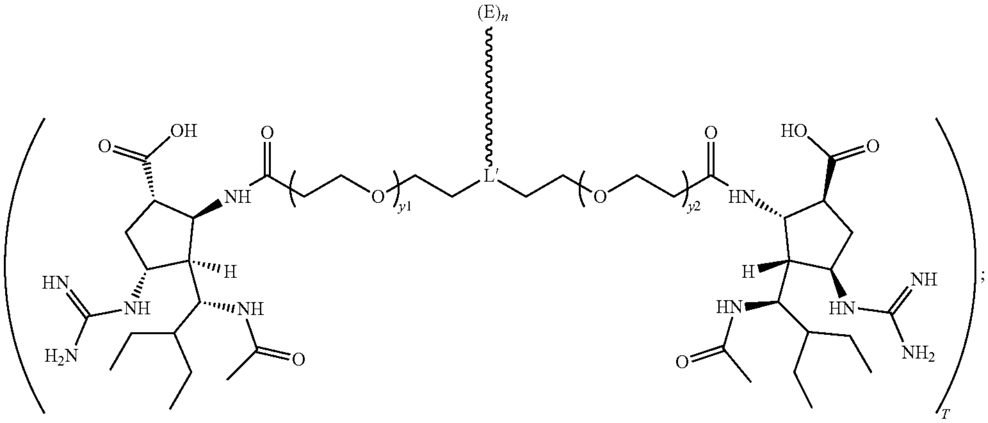
;
(D-VIII-8)
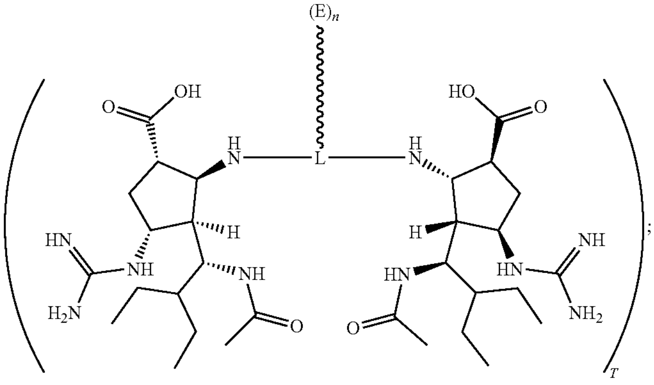
;
(D-VIII-9)
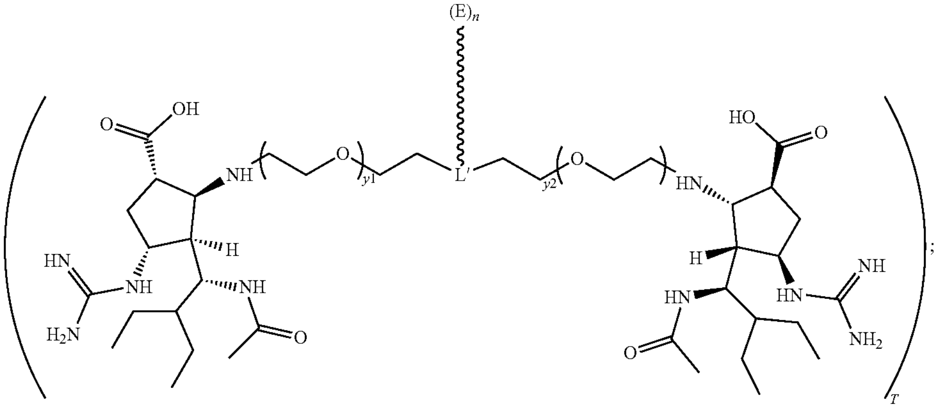
;

-continued
(D-VIII-10)
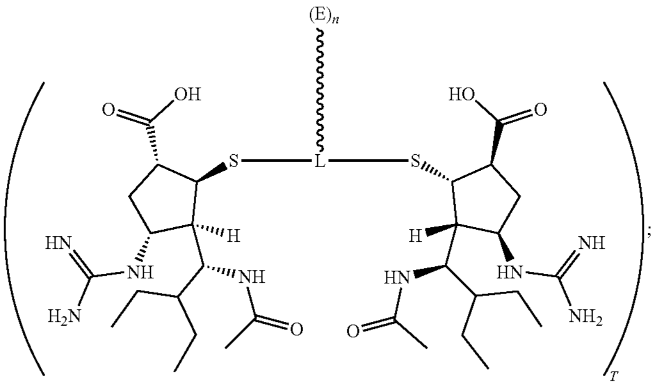
(D-VIII-11)
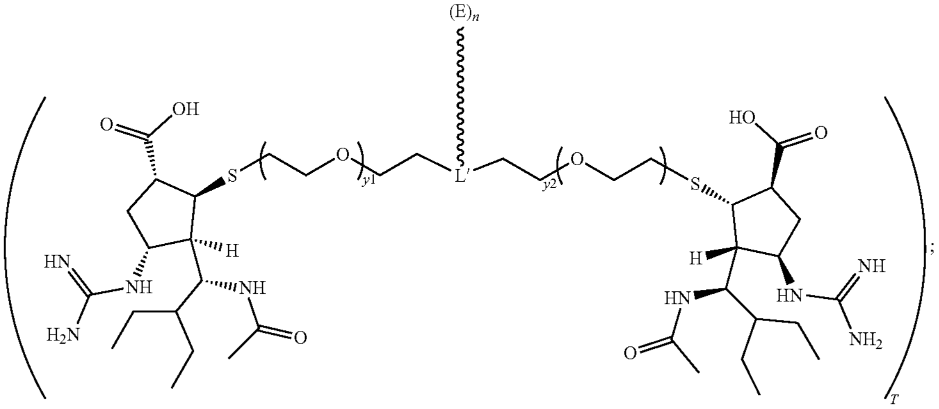
(D-IX)
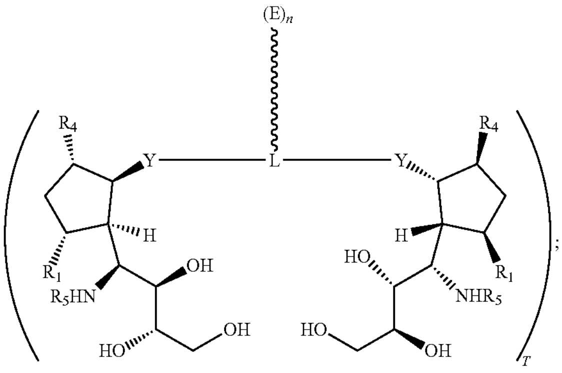
(D-IX-1)
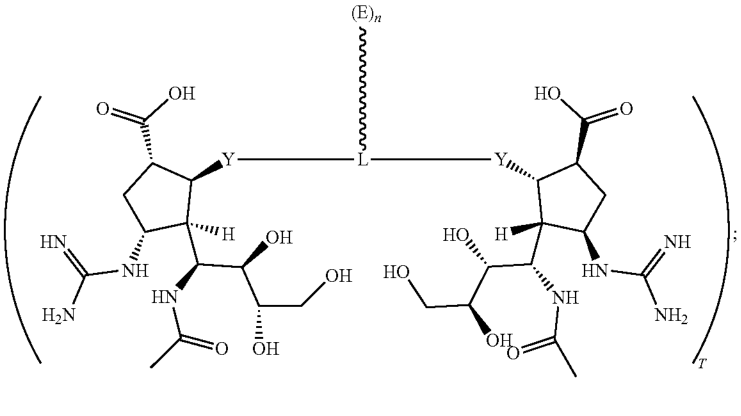

-continued
(D-IX-2)
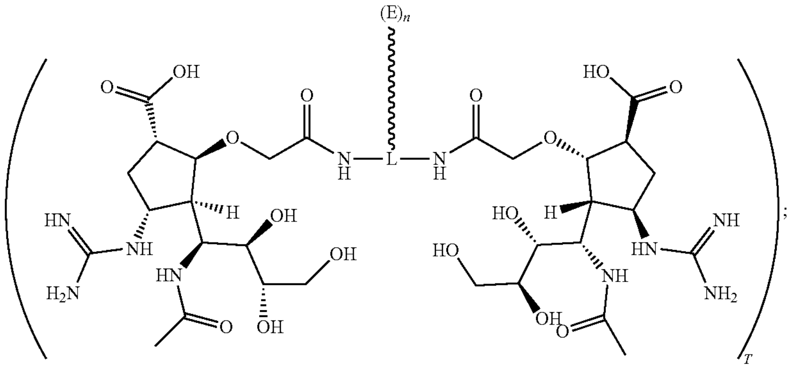
;
(D-IX-3)
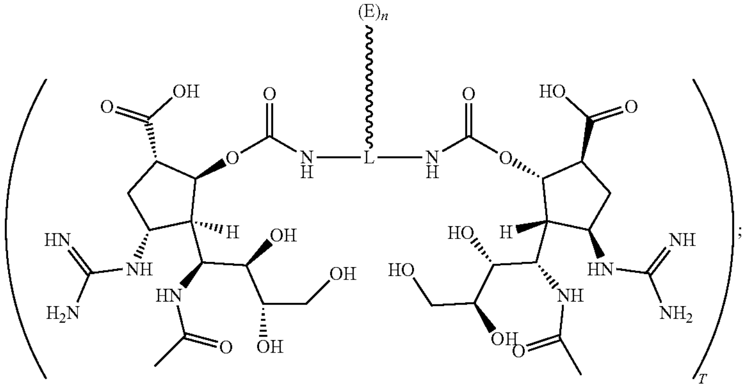
;
(D-IX-4)
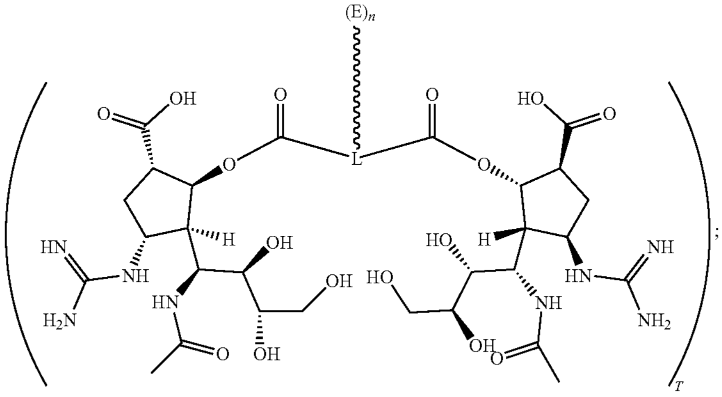
;
(D-IX-5)
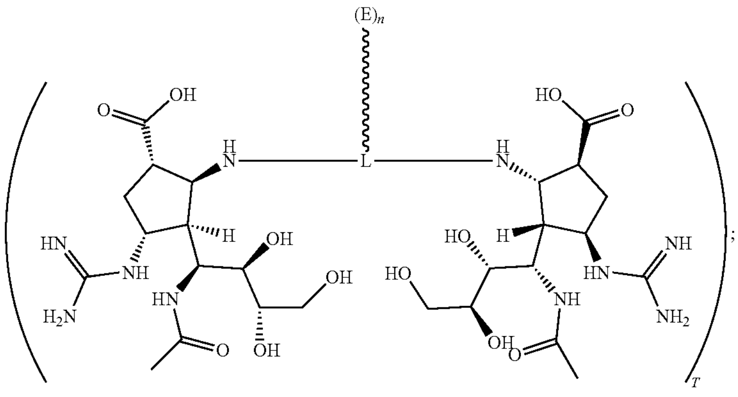
;

-continued
(D-IX-6)
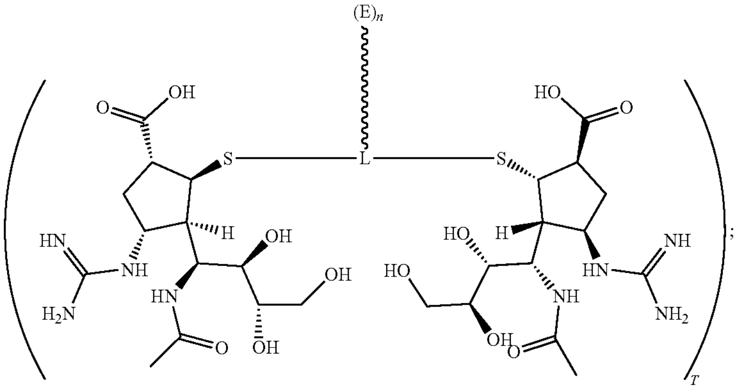
(D-X)
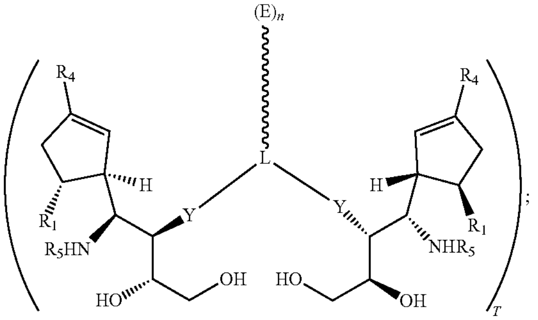
(D-X-1)
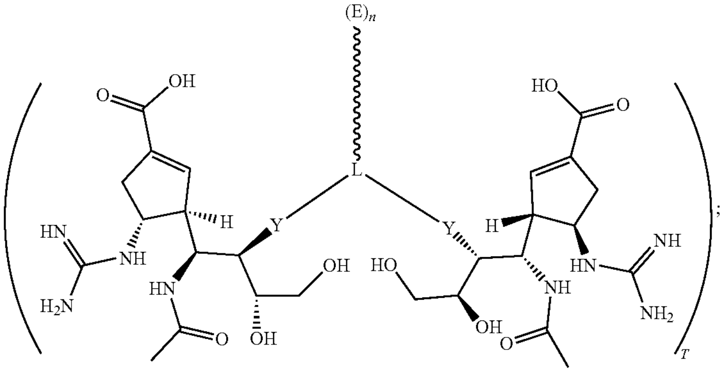
(D-X-2)
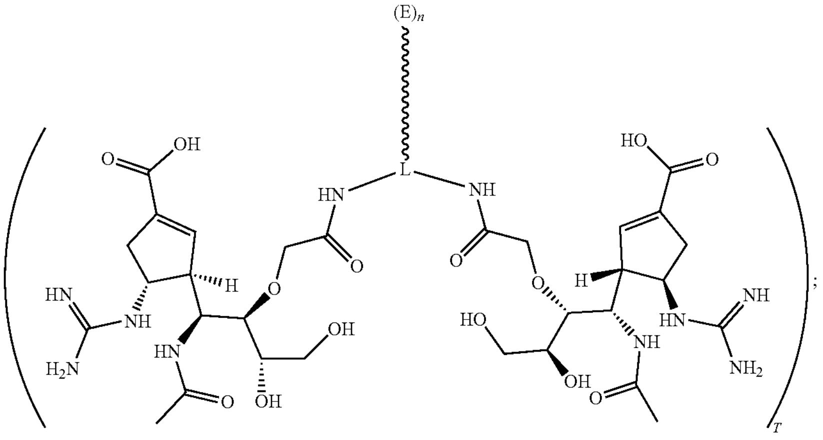

-continued (D-X-3)

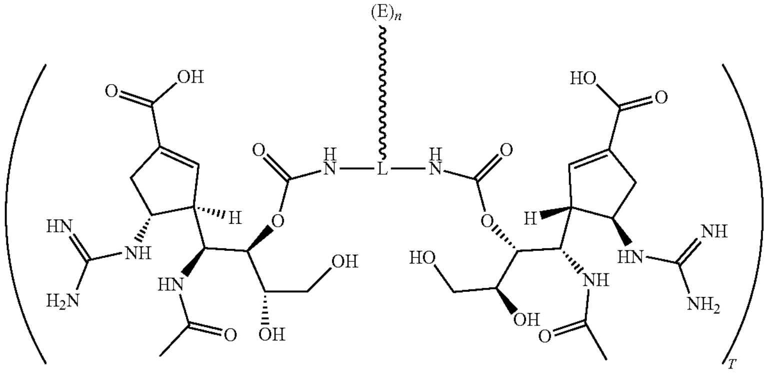

; or (D'-I)

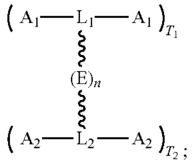

or a pharmaceutically acceptable salt thereof.

In the conjugates described herein, the squiggly line connected to E indicates that one or more (e.g., 1, 2, 3, 4, 5, 6, 7, 8, 9, 10, 11, 12, 13, 14, 15, 16, 17, 18, 19, or 20) dimers of neuraminidase inhibitors may be attached to an Fc domain monomer, Fc domain, Fc-binding peptide, albumin protein, or albumin protein-binding peptide. In some embodiments, when n is 1, one or more (e.g., 1, 2, 3, 4, 5, 6, 7, 8, 9, or 10) dimers of neuraminidase inhibitors may be attached to an Fc domain monomer, Fc domain, Fc-binding peptide, albumin protein, or albumin protein-binding peptide. In some embodiments, when n is 2, one or more (e.g., 1, 2, 3, 4, 5, 6, 7, 8, 9, 10, 11, 12, 13, 14, 15, 16, 17, 18, 19, or 20) dimers of neuraminidase inhibitors may be attached to an Fc domain. The squiggly line in the conjugates described herein is not to be construed as a single bond between one or more dimers of neuraminidase inhibitors and an atom in the Fc domain or albumin protein. In some embodiments, when T is 1, one dimer of neuraminidase inhibitors may be attached to an atom in the Fc domain monomer, Fc domain, Fc-binding peptide, albumin protein, or albumin protein-binding peptide. In some embodiments, when T is 2, two dimers of neuraminidase inhibitors may be attached to an atom in the Fc domain monomer, Fc domain, Fc-binding peptide, albumin protein, or albumin protein-binding peptide.

As described further herein, a linker in a conjugate described herein (e.g., L or L') may be a branched structure. As described further herein, a linker in a conjugate described herein (e.g., L or L') may be a multivalent structure, e.g., a divalent or trivalent structure having two or three arms, respectively. In some embodiments when the linker has three arms, two of the arms may be attached to the first and second neuraminidase inhibitors and the third arm may be attached to the Fc domain monomer, Fc domain, Fc-binding peptide, albumin protein, or albumin protein-binding peptide.

In conjugates having an Fc domain covalently linked to one or more dimers of neuraminidase inhibitors, as represented by the formulae above, when n is 2, two Fc domain monomers (each Fc domain monomer is represented by E) dimerize to form an Fc domain.

Conjugates of Monomers of Neuraminidase Inhibitors Linked to an Fc Domain or an Albumin Protein In some embodiments, the conjugates described herein include an Fc domain monomer, Fc domain, Fc-binding peptide, albumin protein, or albumin protein-binding peptide covalently linked to one or more monomers of neuraminidase inhibitors. Conjugates of an Fc domain monomer or albumin protein and one or more monomers of neuraminidase inhibitors may be formed by linking the Fc domain or albumin protein to each of the monomers of neuraminidase inhibitors through a linker, such as any of the linkers described herein.

In the conjugates having an Fc domain or albumin protein covalently linked to one or more monomers of neuraminidase inhibitors described herein, the squiggly line connected to E indicates that one or more (e.g., 1, 2, 3, 4, 5, 6, 7, 8, 9, 10, 11, 12, 13, 14, 15, 16, 17, 18, 19, or 20) monomers of neuraminidase inhibitors may be attached to an Fc domain monomer, Fc domain, Fc-binding peptide, albumin protein, or albumin protein-binding peptide. In some embodiments, when n is 1, one or more (e.g., 1, 2, 3, 4, 5, 6, 7, 8, 9, or 10) monomers of neuraminidase inhibitors may be attached to an Fc domain monomer or an albumin protein. In some embodiments, when n is 2, one or more (e.g., 1, 2, 3, 4, 5, 6, 7, 8, 9, 10, 11, 12, 13, 14, 15, 16, 17, 18, 19, or 20) monomers of neuraminidase inhibitors may be attached to an Fc domain. The squiggly line in the conjugates described herein is not to be construed as a single bond between one or more monomers of neuraminidase inhibitors and an atom in the Fc domain monomer, Fc domain, Fc-binding peptide, albumin protein, or albumin protein-binding peptide. In some embodiments, when T is 1, one monomer of neuraminidase inhibitor may be attached to an atom in the Fc domain monomer, Fc domain, Fc-binding peptide, albumin protein, or albumin protein-binding peptide. In some embodiments, when T is 2, two monomers of neuraminidase inhibitors may be attached to an atom in the Fc domain monomer, Fc domain, Fc-binding peptide, albumin protein, or albumin protein-binding peptide.

In some embodiments, when T is greater than 1 (e.g., T is 2, 3, 4, 5, 6, 7, 8, 9, 10, 11, 12, 13, 14, 15, 16, 17, 18, 19, or 20), each $A_1$-L may be independently selected (e.g., independently selected from any of the $A_1$-L structures described herein). In some embodiments, E may be conjugated to 2, 3, 4, 5, 6, 7, 8, 9, 10, or more different $A_1$-L moieties. In some embodiments, E is conjugated to a first $A_1$-L moiety, and a second $A_1$-L, moiety. In some embodiments, $A_1$ of the first $A_1$-L moiety is selected from any one of formulas (A-III)-(A-V):

(A-III)

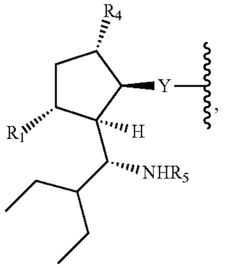

(A-IV)

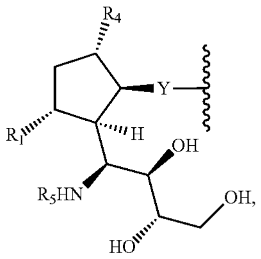

(A-V)

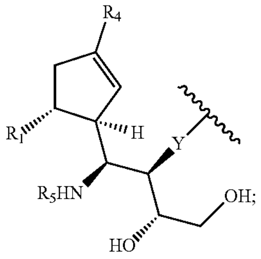

and $A_1$ of the second $A_1$-L moiety is selected from any one of formulas (A-I), (A-II), (A-VI), (A-VII), (A-VIII), or (A-IX):

(A-I)

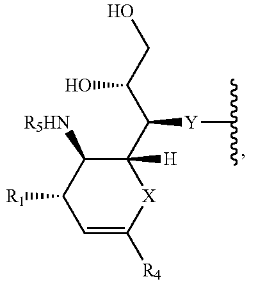

-continued (A-II)

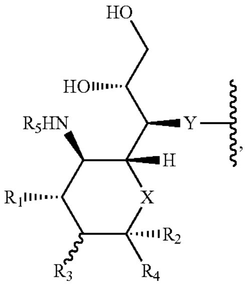

(A-VI)

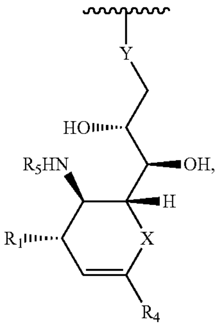

(A-VII)

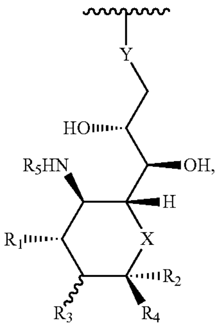

(A-VIII)

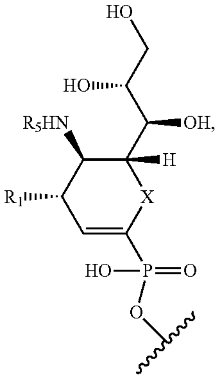

-continued (A-IX)

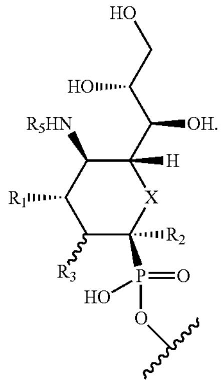

In some embodiments, the first $A_1$-L moiety is conjugated specifically to lysine residues of E (e.g., the nitrogen atoms of surface exposed lysine residues of E), and the second $A_1$-L moiety is conjugated specifically to cysteine residues of E (e.g., the sulfur atoms of surface exposed cysteine residues of E). In some embodiments, the first $A_1$-L moiety is conjugated specifically to cysteine residues of E (e.g., the sulfur atoms of surface exposed cysteine residues of E), and the second $A_1$-L moiety is conjugated specifically to lysine residues of E (e.g., the nitrogen atoms of surface exposed lysine residues of E).

As described further herein, a linker in a conjugate having an Fc domain monomer, Fc domain, Fc-binding peptide, albumin protein, or albumin protein-binding peptide covalently linked to one or more monomers of neuraminidase inhibitors described herein (e.g., L or L') may be a divalent structure having two arms. One arm in a divalent linker may be attached to the monomer of neuraminidase inhibitor and the other arm may be attached to the Fc domain monomer, Fc domain, Fc-binding peptide, albumin protein, or albumin protein-binding peptide.

In some embodiments, a conjugate containing an Fc domain monomer, Fc domain, Fc-binding peptide, albumin protein, or albumin protein-binding peptide covalently linked to one or more monomers of neuraminidase inhibitors provided herein is described by any one of formulae below:

(2)

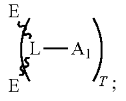

(4)

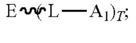

(5)

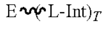

(M-I)

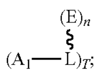

-continued (M-II)

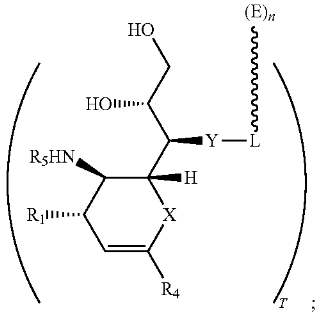

(M-II-1)

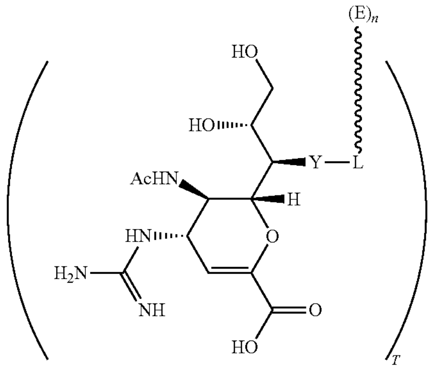

(M-II-2)

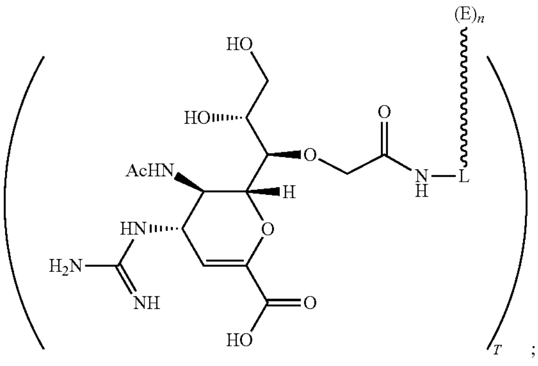

(M-II-3)

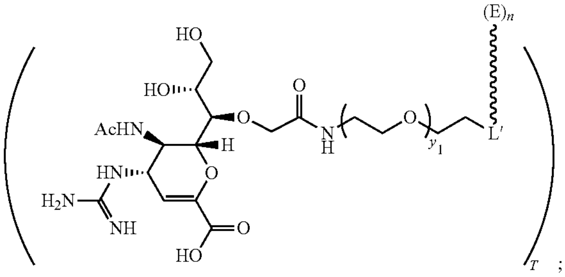

-continued
(M-II-4)
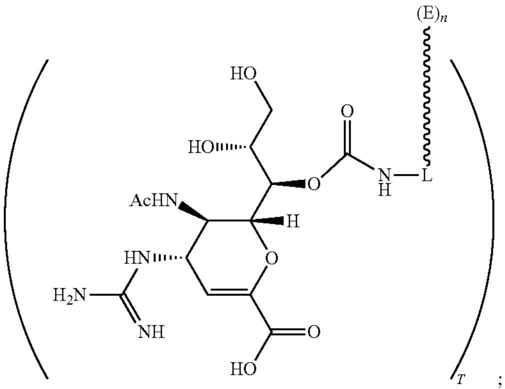
;
(M-II-5)
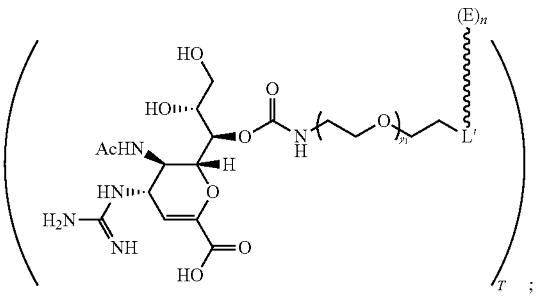
;
(M-II-6)
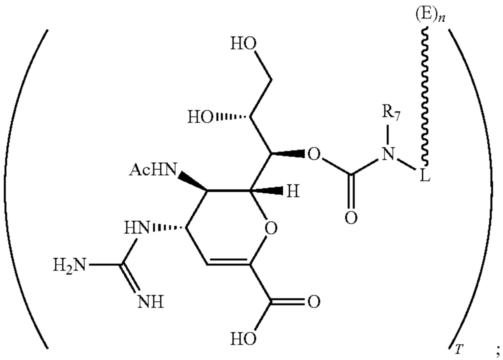
;
(M-II-7)
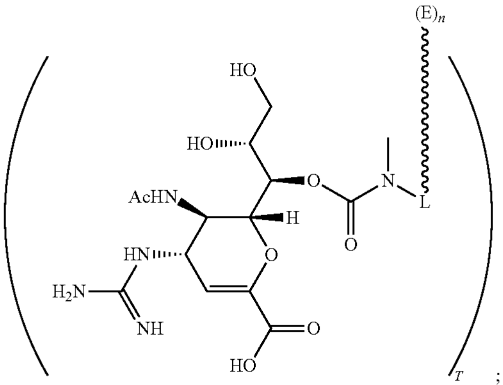
;
-continued
(M-II-8)
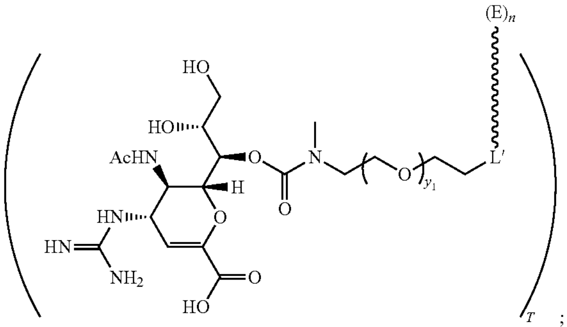
;
(M-II-9)
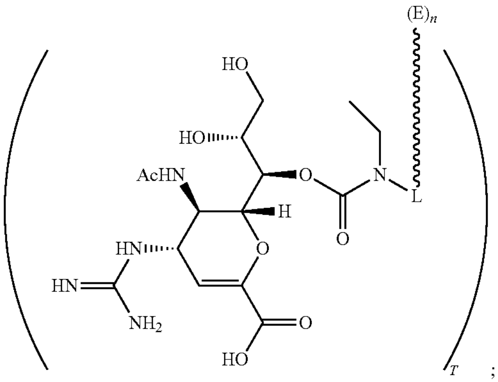
;
(M-II-10)
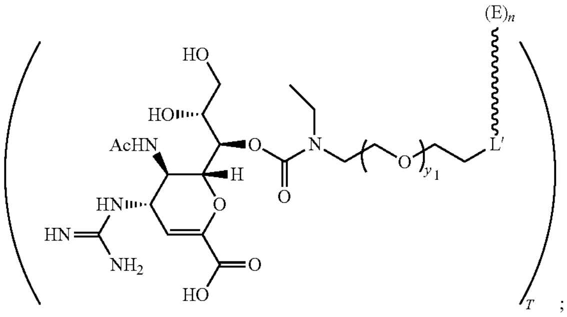
;
(M-III)
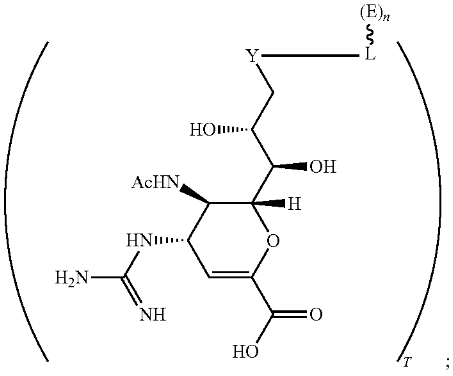
;

-continued
(M-III-1)
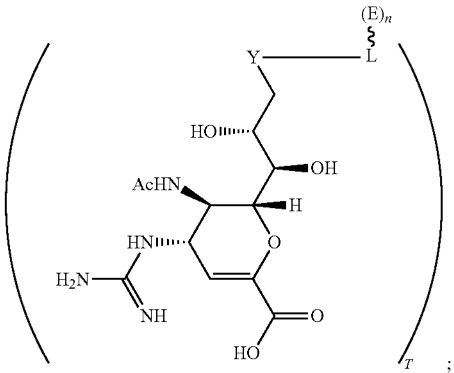
;
(M-III-2)
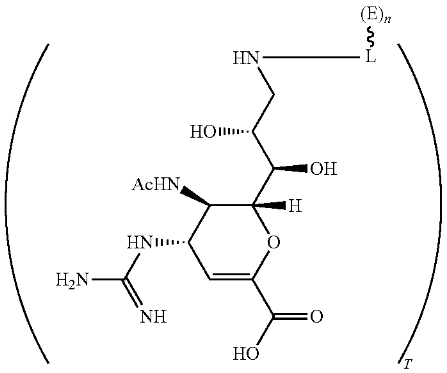
;
(M-III-3)
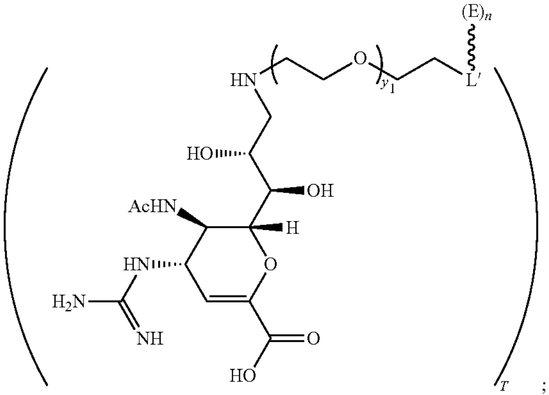
;
-continued
(M-III-4)
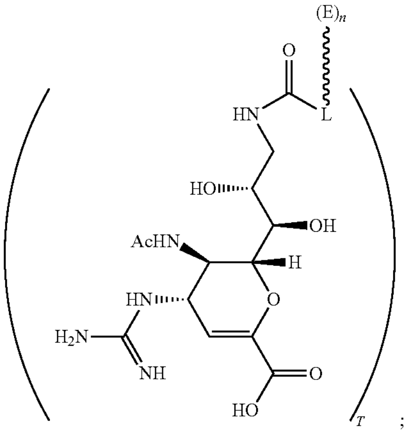
;
(M-III-5)
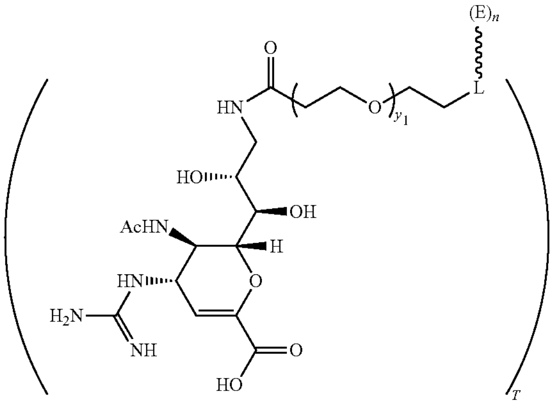
;
(M-III-6)
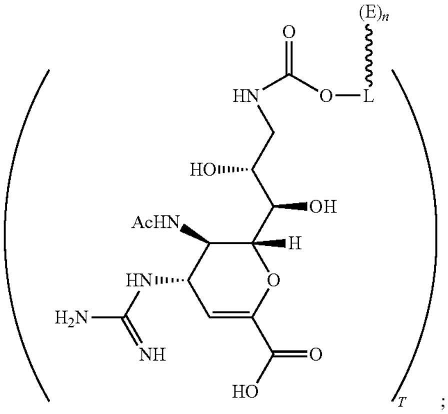
;

-continued
(M-III-7)
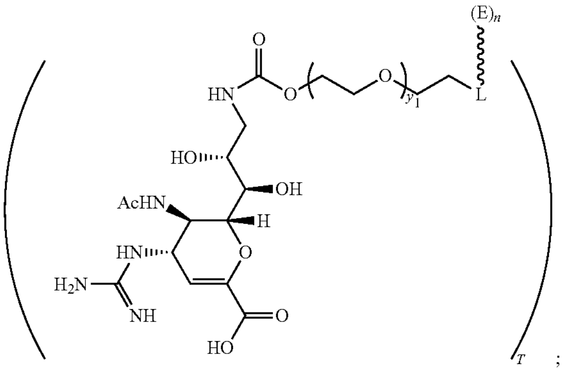
;
(M-III-8)
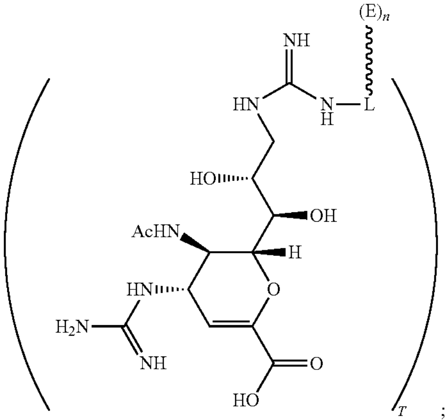
;
(M-III-9)
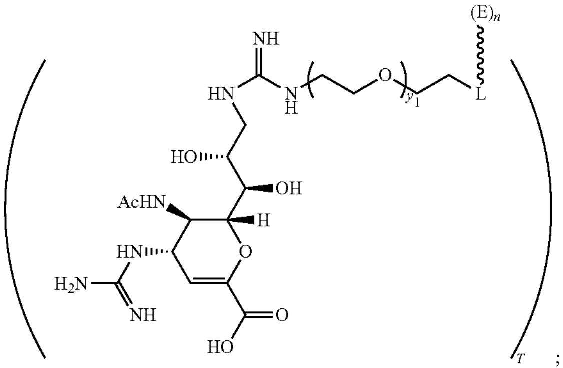
;
(M-IV)
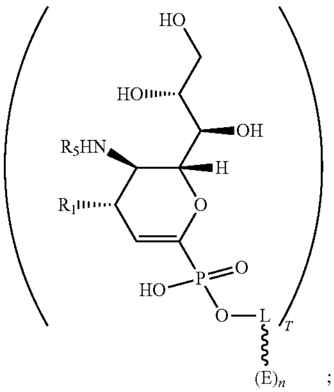
;
-continued
(M-IV-1)
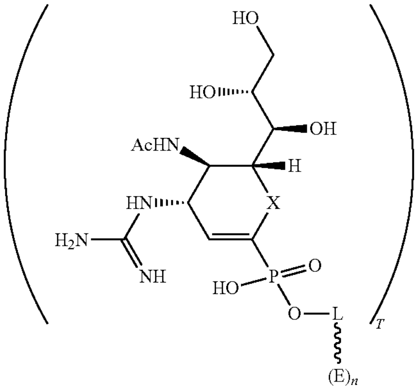
;
(M-IV-2)
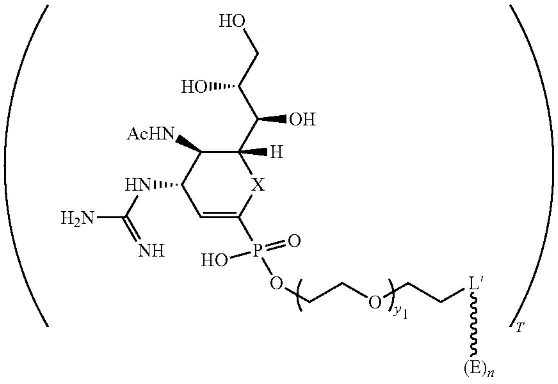
;
(M-V)
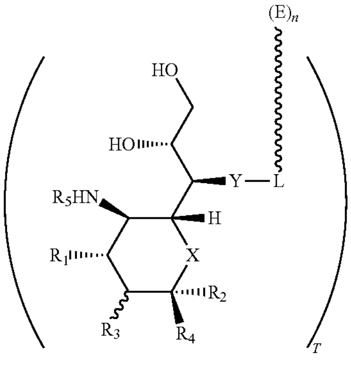
;
(M-V-1)
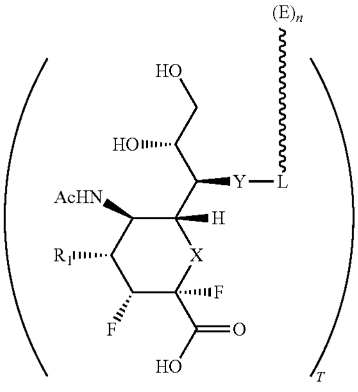
;

-continued
(M-V-2)
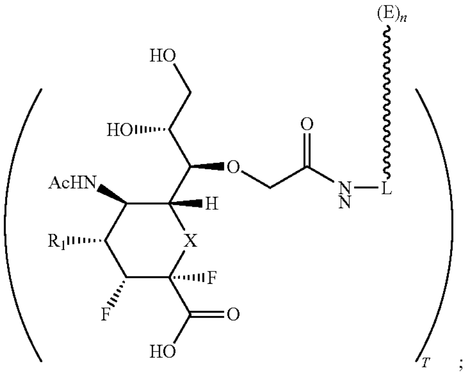
(M-V-3)
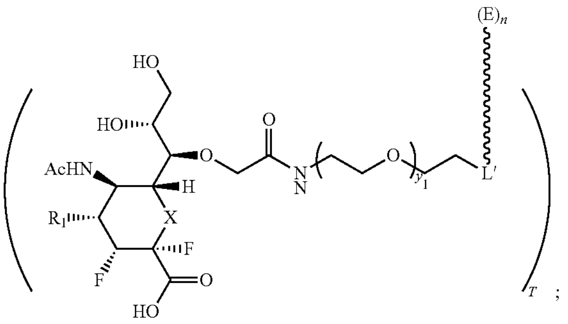
(M-V-4)
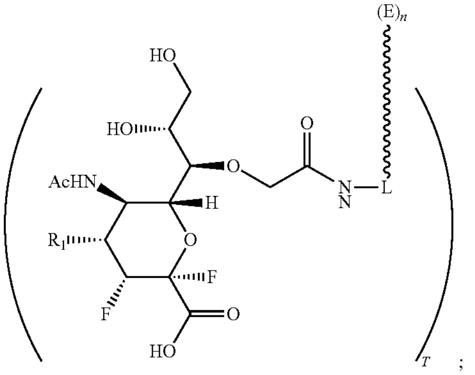
(M-V-5)
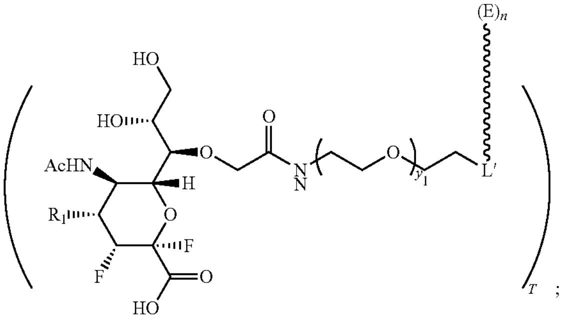
-continued
(M-V-6)
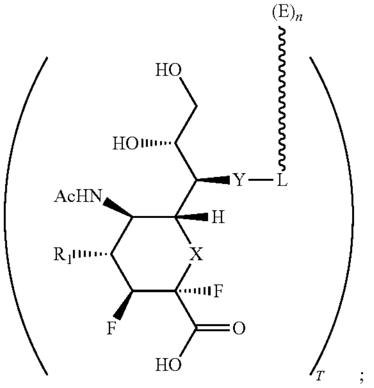
(M-V-7)
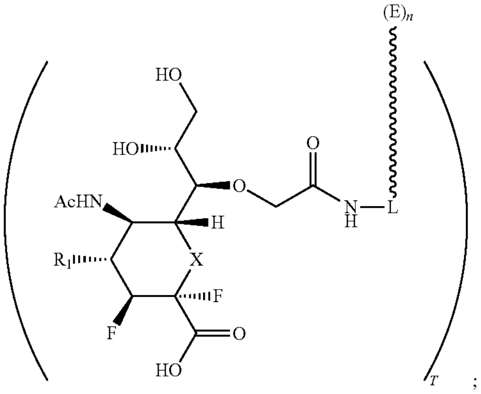
(M-V-8)
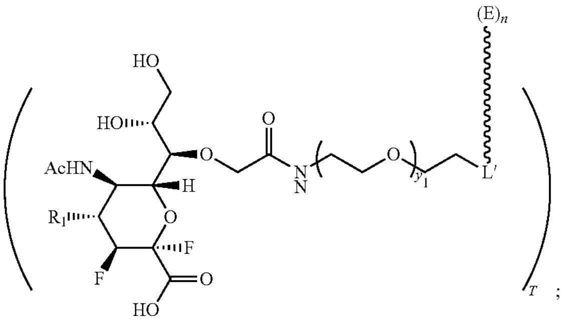
(M-V-9)
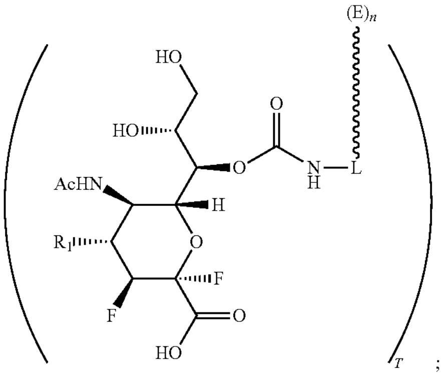

-continued
(M-V-10)
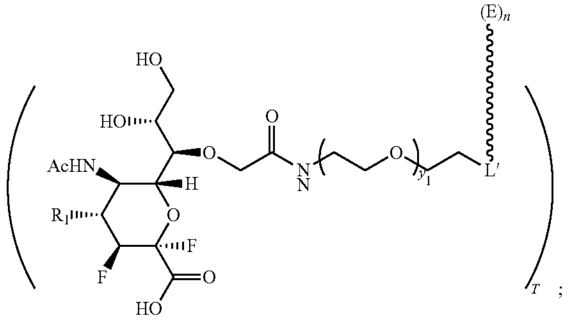
(M-VI)
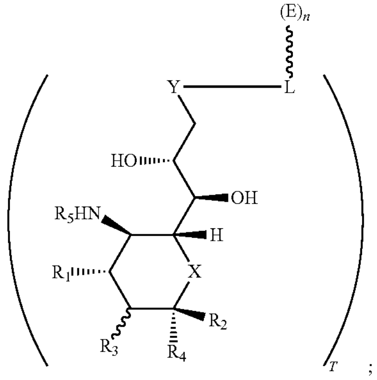
(M-VI-1)
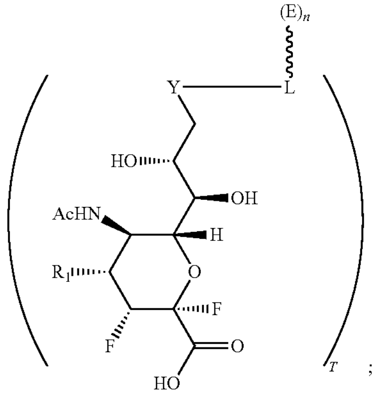
(M-VI-2)
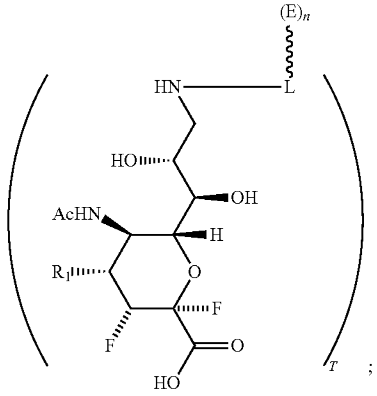
-continued
(M-VI-3)
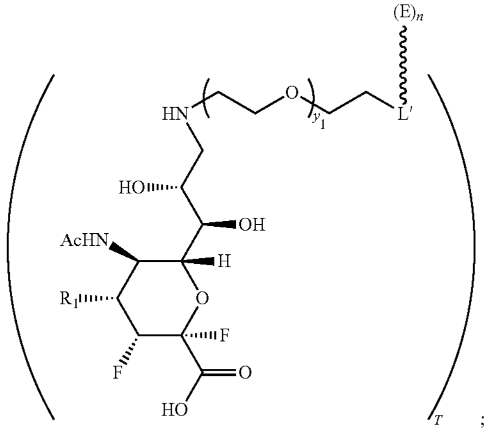
(M-VI-4)
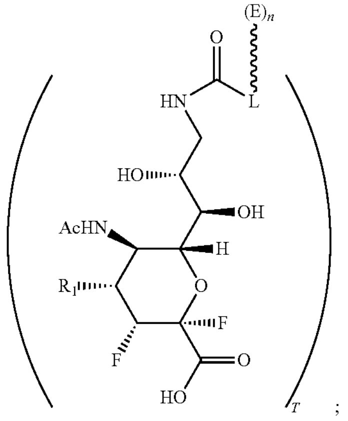
(M-VI-5)
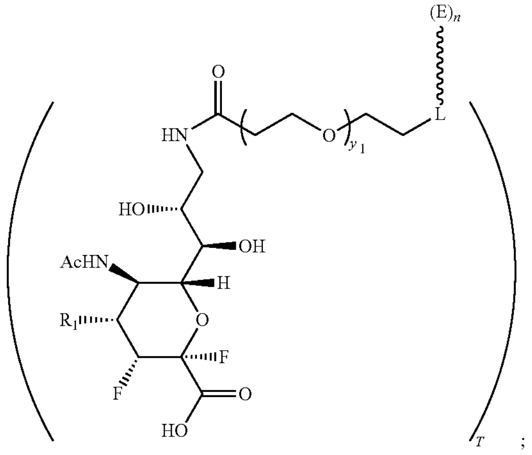

-continued
(M-VI-6)
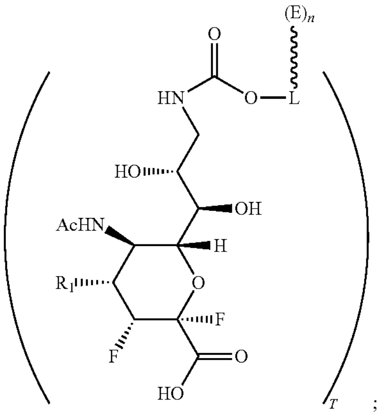
;
(M-VI-7)
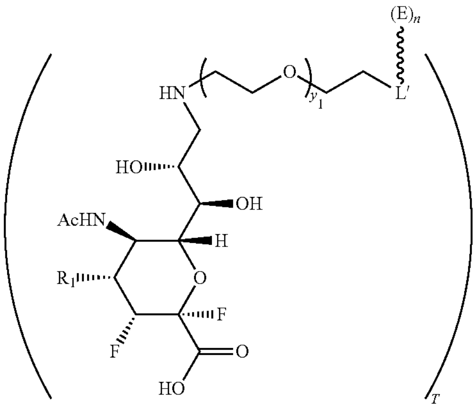
;
(M-VI-8)
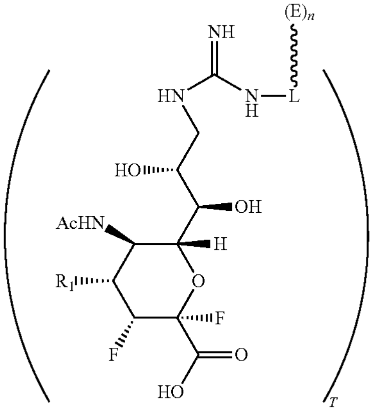
;
-continued
(M-VI-9)
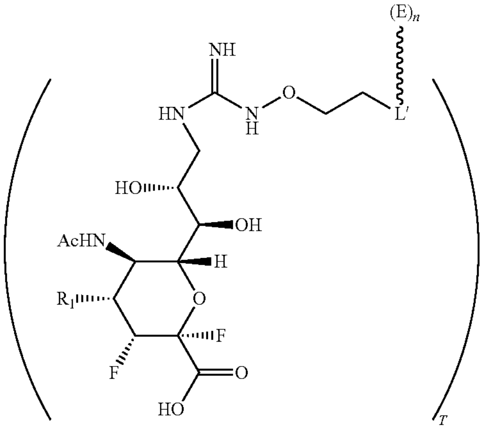
;
(M-VII)
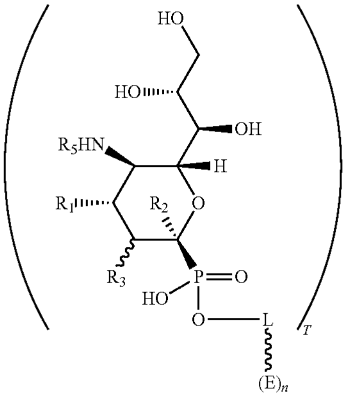
;
(M-VIII)
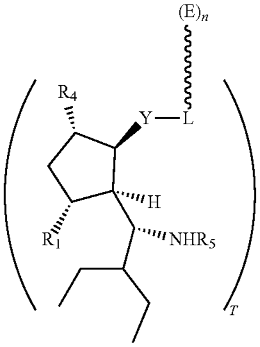
;
(M-VIII-1)
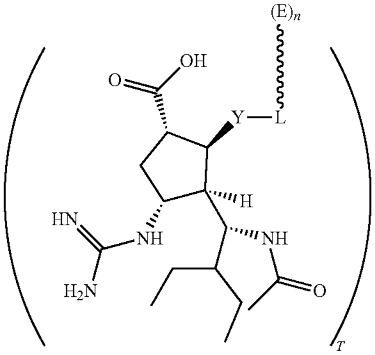
;

-continued
(M-VIII-2)
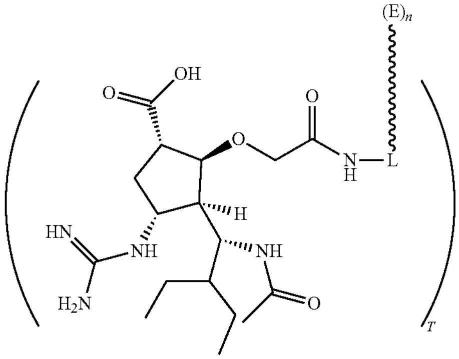
;
(M-VIII-3)
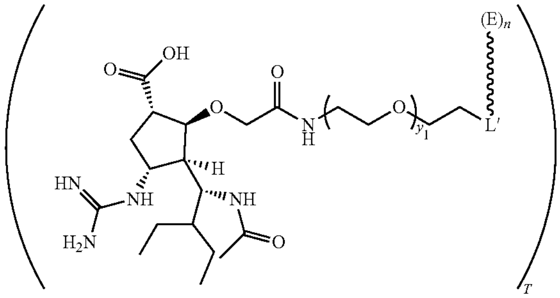
;
(M-VIII-4)
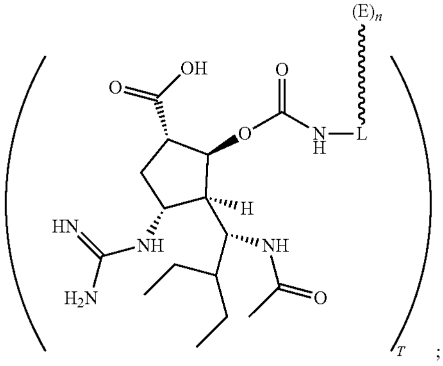
;
(M-VIII-5)
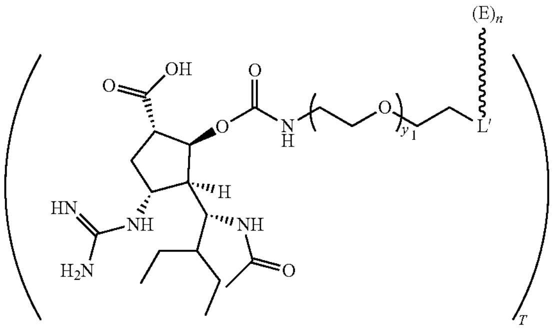
;
-continued
(M-VIII-6)
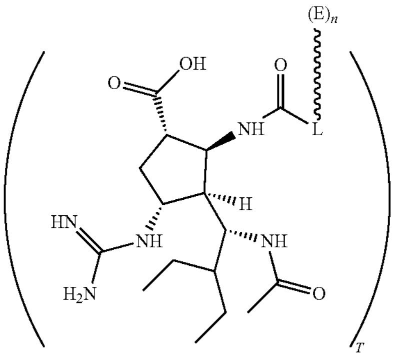
;
(M-VIII-7)
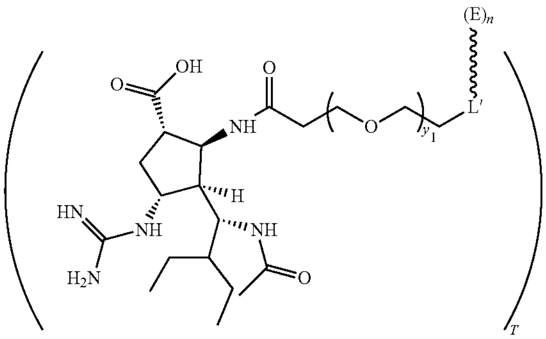
;
(M-VIII-8)
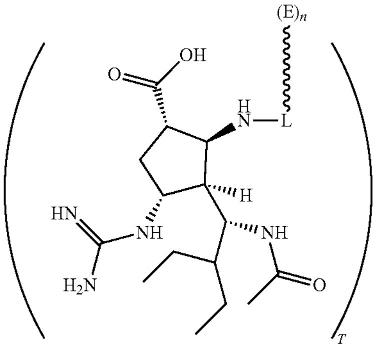
;
(M-VIII-9)
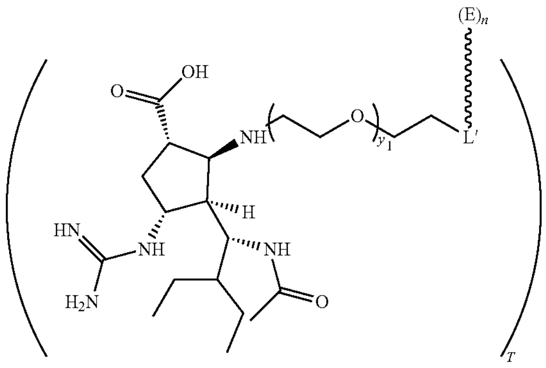
;

-continued
(M-VIII-10)
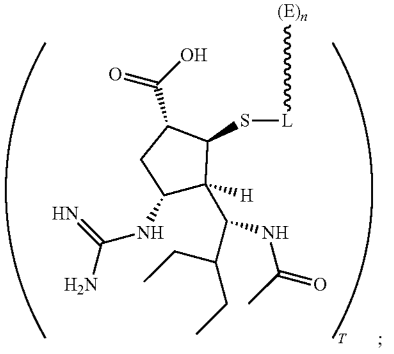
(M-VIII-11)
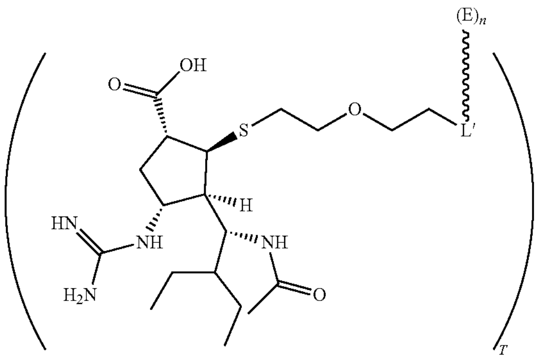
(M-IX)
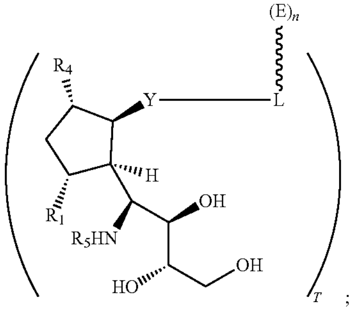
(M-IX-1)
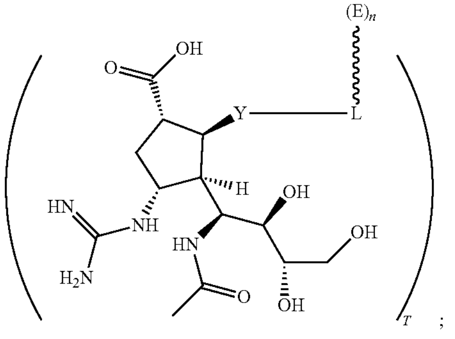
-continued
(M-IX-2)
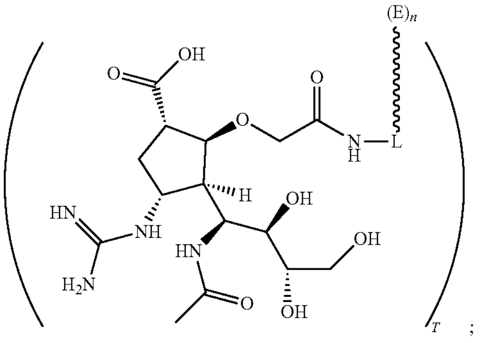
(M-IX-3)
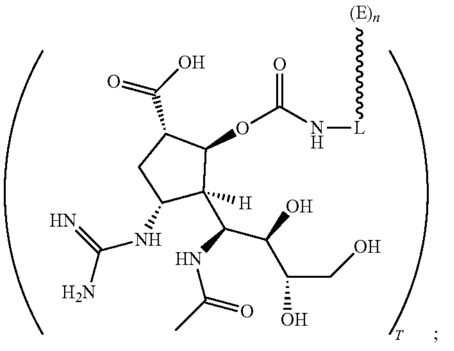
(M-IX-4)
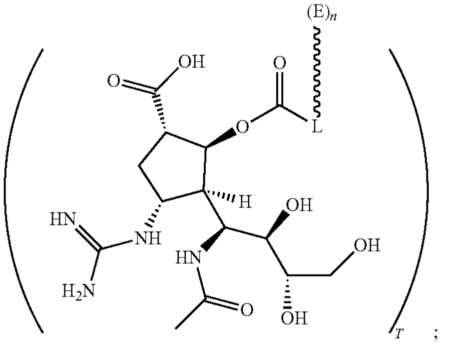
(M-IX-5)
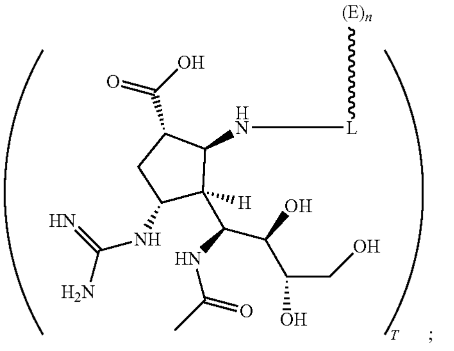

-continued (M-IX-6)

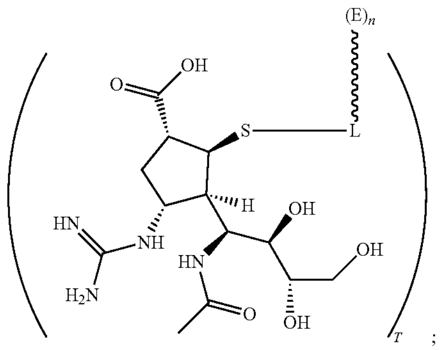

;

(M-X)

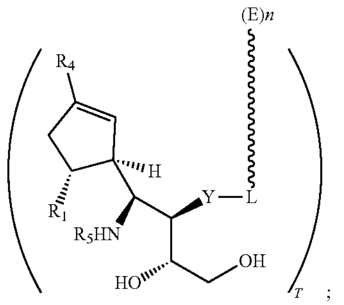

;

(M-X-1)

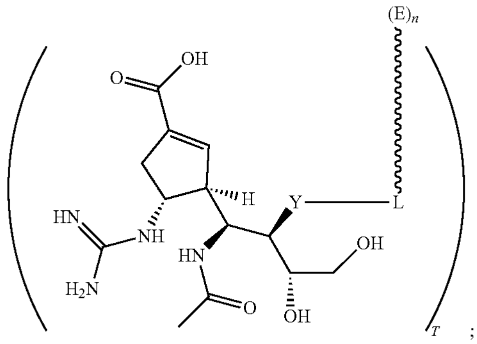

;

(M-X-2)

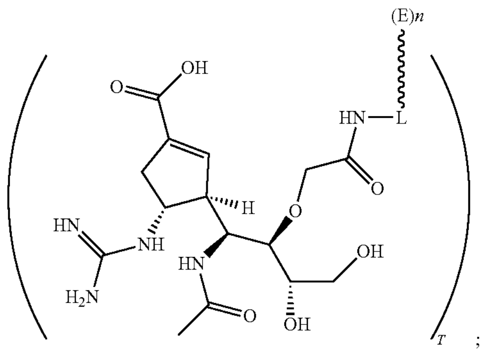

;

-continued (M-X-3)

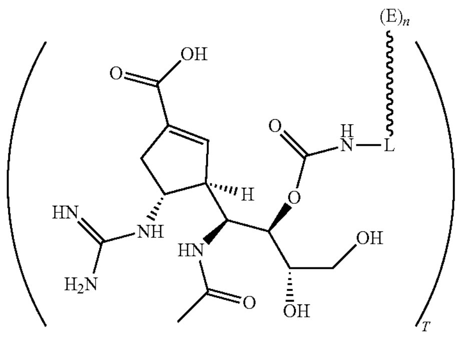

; or (M'-I)

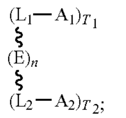

;

or a pharmaceutically acceptable salt thereof.

In conjugates having an Fc domain covalently linked to one or more monomers of neuraminidase inhibitors, as represented by the formulae above, when n is 2, two Fc domain monomers (each Fc domain monomer is represented by E) dimerize to form an Fc domain.

Regioisomers of Conjugates Including Zanamivir or Analogs Thereof

Conjugates (e.g., monomer or dimer conjugates as described in detail herein) may be produced as a mixture or regioisomers. A particular regioisomer or mixture of regioisomers may be preferred for reasons such as ease of synthesis, thermostability, oxidative stability, pharmacokinetics (e.g., metabolic stability or bioavailability), effector binding, or therapeutic efficacy.

In some embodiments, a conjugate of the invention includes zanamivir or an analog thereof (e.g., any of (A-I), (A-II), (A-VI), (A-VII), (A-VIII), (A-IX), or (A-X)). Zanamivir or an analog thereof may be conjugated to an Fc domain or an albumin protein (e.g., by way of a linker) through, for example, the C7 position (see, e.g., (A-I), (A-II), or (A-X)) or through the C9 position (see, e.g., (A-VI) or (A-VII)):

(A-I)

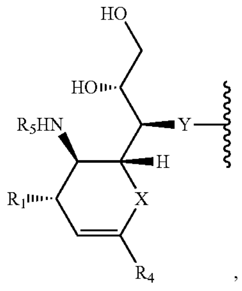

,

C7 conjugation

-continued (A-II)

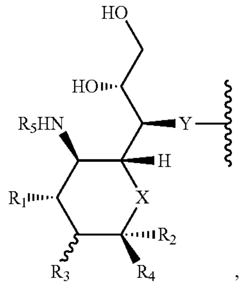

C7 conjugation (A-X)

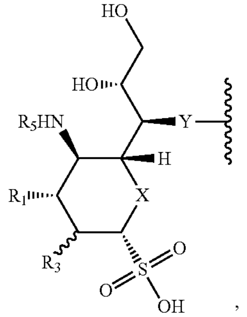

C7 conjugation (A-VI)

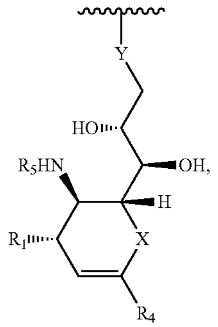

C9 conjugation (A-VII)

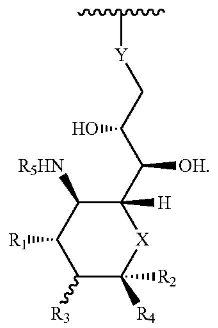

C9 conjugation

The present disclosure includes a population of monomeric conjugates (e.g., a population of conjugates of formula (M-I)) wherein the population of conjugates includes any of the monomeric conjugates described herein and one or more of its corresponding regioisomers. For example, a population of conjugates may include (1) zanamivir or an analog thereof conjugated (e.g., by way of a linker) at the C7 position to an Fc domain or an albumin protein, and (2) zanamivir or an analog thereof conjugated (e.g., by way of a linker) at the C9 position to an Fc domain or an albumin protein.

The population of monomeric conjugates may have a specified ratio of C7-linked conjugate to C9-linked conjugate. For example, the population of conjugates may have substantially 100% C-7 linked conjugate and substantially 0% C-9 linked conjugate. The population of conjugates may have about 95% C-7 linked conjugate and about 5% C-9 linked conjugate. The population of conjugates may have about 90% C-7 linked conjugate and about 10% C-9 linked conjugate. The population of conjugates may have about 85% C-7 linked conjugate and about 15% C-9 linked conjugate. The population of conjugates may have about 80% C-7 linked conjugate and about 20% C-9 linked conjugate. The population of conjugates may have about 75% C-7 linked conjugate and about 25% C-9 linked conjugate. The population of conjugates may have about 70% C-7 linked conjugate and about 30% C-9 linked conjugate. The population of conjugates may have about 65% C-7 linked conjugate and about 35% C-9 linked conjugate.

The population of conjugates may have about 60% C-7 linked conjugate and about 40% C-9 linked conjugate. The population of conjugates may have about 55% C-7 linked conjugate and about 45% C-9 linked conjugate. The population of conjugates may have about 50% C-7 linked conjugate and about 50% C-9 linked conjugate. The population of conjugates may have about 45% C-7 linked conjugate and about 55% C-9 linked conjugate. The population of conjugates may have about 40% C-7 linked conjugate and about 60% C-9 linked conjugate. The population of conjugates may have about 35% C-7 linked conjugate and about 65% C-9 linked conjugate. The population of conjugates may have about 30% C-7 linked conjugate and about 70% C-9 linked conjugate. The population of conjugates may have about 25% C-7 linked conjugate and about 75% C-9 linked conjugate. The population of conjugates may have about 20% C-7 linked conjugate and about 80% C-9 linked conjugate. The population of conjugates may have about 15% C-7 linked conjugate and about 85% C-9 linked conjugate. The population of conjugates may have about 10% C-7 linked conjugate and about 90% C-9 linked conjugate. The population of conjugates may have substantially 0% C-7 linked conjugate and substantially 100% C-9 linked conjugate.

The population of conjugates may have greater than 99%, 98%, 97%, 96%, 95%, 90%, 85%, 80%, 75%, 70%, 60%, 65%, 60%, 55%, or 50% C7-linked conjugate.

The population of conjugates may have less than 50%, 40%, 30%, 25%, 20%, 15%, 10%, 5%, 4%, 3%, 2%, or 1% C9-linked conjugate.

The present disclosure also includes a population of dimeric conjugates (e.g., a population of conjugates of formula (D-1)) wherein the population of conjugates includes any of the dimeric conjugates described herein and one or more of its corresponding regioisomers. For example, a population of conjugates may include a (1) a C7-C7 dimer (e.g., both zanamivir or analog thereof moieties of the dimer are conjugated (e.g., by way of a linker) at their respective C7 positions to an Fc domain or an albumin protein), (2) a C9-C9 dimer (e.g., both zanamivir or analog thereof moieties of the dimer are conjugated (e.g., by way of a linker) at their respective C9 positions to an Fc domain or an albumin protein), and/or (3) a C7-C7 dimer (e.g., one zanamivir or analog thereof moiety is conjugated (e.g., by way of a linker) to and Fc domain or an albumin protein through its C7 position and the other zanamivir or analog thereof moiety is conjugated (e.g., by way of a linker) to an Fc domain or an albumin protein through its C9 position).

The population of dimeric conjugates may have a specified ratio of C7-C7 linked conjugate to C7-C9 linked conjugate to C9-C9 linked conjugate. For example, the population of conjugates may have substantially 100% C7-C7 linked conjugate, and substantially 0% C7-C9 or C9-C9 linked conjugate. The population of conjugates may have substantially 100% C9-C9 linked conjugate, and substantially 0% C7-C7 or C7-C9 linked conjugate. The population of conjugates may have substantially 100% C7-C9 linked conjugate, and substantially 0% C7-C7 or C9-C9 linked conjugate.

The population of conjugates may have greater than 99%, 98%, 97%, 96%, 95%, 90%, 85%, 80%, 75%, 70%, 60%, 65%, 60%, 55%, or 50% C7-C7 linked conjugate.

The population of conjugates may have less than 50%, 40%, 30%, 25%, 20%, 15%, 10%, 5%, 4%, 3%, 2%, or 1% C9-C9 linked conjugate.

The population of conjugates may have less than 50%, 40%, 30%, 25%, 20%, 15%, 10%, 5%, 4%, 3%, 2%, or 1% C7-C9 linked conjugate.

For any of the above-described populations of regioisomers, $A_1$ and/or $A_2$ (e.g., of (M-I) or (D-I)) may be selected from zanamivir or any of the zanamivir analogs described herein (e.g., any of (A-I), (A-II), (A-VI), (A-VII), (A-VIII), (A-IX), or (A-X)). In particular, the C7-linked zanamivir or analogs thereof is described by (A-I), (A-II), and (A-X), and C9-linked zanamivir or analogs thereof is described by (A-VI) or (A-VII). Exemplary methods for preparing regioisomers, e.g., C7, C9, C7-C7, C7-C9, and C9-C9 linked regioisomers, are described in Examples 100-103, 123 and 124. In some instances, it may be prefereable to have 95% or more, 96% or more, 97% or more, 98% or more, 99% or more, or substantially 100% C7 linked monomer conjugates or C7-C7 linked dimer conjugates. In these instances, it may be preferable to prepare the intermediate with a method that forms substantially C7 linked monomer or C7-C7 linked dimer intermediates, such as the methods described, for example, in Examples 103 and 123. The method of Example 103 is exemplary of methods used to achieve primarily the C7 or C7-C7 linked intermediate and may be used to prepare any intermediate described herein.

In preferred embodiments, the conjugate is a conjugate of any one of formulas (D-I)-(D-X), (D'-I), (M-I)-(M-X), or (M'-I), wherein $A_1$ and/or $A_2$ are described by formula (A-I), (A-II), or (A-X) and Y is

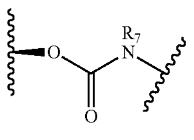

$(-O(C{=}O)NR_7-)$, wherein $R_7$ is selected from H, C1-C20 alkyl, C3-C20 cycloalkyl, C3-C20 heterocycloalkyl; C5-C15 aryl, and C2-C15 heteroaryl. In preferred embodiments, $A_1$ and/or $A_2$ are described by formula (A-I) (e.g., zanamivir). In preferred embodiments, $R_7$ is C1-C20 alkyl (e.g., $-CH_3$, $-CH_2CH_3$, $-CH_2CH_2CH_3$). Such conjugates have been shown to exhibit increased stability of the C7-linkage, resulting in less C7 to C9 migration. The resulting product is therefore expected to be more homogenous and exhibit increased efficacy.

III. Fc Domain Monomers and Fc Domains

An Fc domain monomer includes a hinge domain, a $C_H2$ antibody constant domain, and a $C_H3$ antibody constant domain. The Fc domain monomer can be of immunoglobulin antibody isotype IgG, IgE, IgM, IgA, or IgD. The Fc domain monomer can also be of any immunoglobulin antibody isotype (e.g., IgG1, IgG2a, IgG2b, IgG3, or IgG4). The Fc domain monomer can be of any immunoglobulin antibody allotype (e.g., IGHG1*01 (i.e., G1m(za)), IGHG1*07 (i.e., G1m(zax)), IGHG1*04 (i.e., G1m(zav)), IGHG1*03 (G1m(f)), IGHG1*08 (i.e., G1m(fa)), IGHG2*01, IGHG2*06, IGHG2*02, IGHG3*01, IGHG3*05, IGHG3*10, IGHG3*04, IGHG3*09, IGHG3*11, IGHG3*12, IGHG3*06, IGHG3*07, IGHG3*08, IGHG3*13, IGHG3*03, IGHG3*14, IGHG3*15, IGHG3*16, IGHG3*17, IGHG3*18, IGHG3*19, IGHG2*04, IGHG4*01, IGHG4*03, or IGHG4*02) (as described in, for example, in Vidarsson et al. IgG subclasses and allotypes: from structure to effector function. *Frontiers in Immunology.* 5(520):1-17 (2014)). The Fc domain monomer can also be of any species, e.g., human, murine, or mouse. A dimer of Fc domain monomers is an Fc domain that can bind to an Fc receptor, which is a receptor located on the surface of leukocytes.

In some embodiments, an Fc domain monomer in the conjugates described herein may contain one or more amino acid substitutions, additions, and/or deletion relative to an Fc domain monomer having a sequence of any one of SEQ ID NOs: 1-68. In some embodiments, an Asn in an Fc domain monomer in the conjugates as described herein may be replaced by Ala in order to prevent N-linked glycosylation (see, e.g., SEQ ID NOs: 12-15, where Asn to Ala substitution is labeled with *). In some embodiments, an Fc domain monomer in the conjugates described herein may also containing additional Cys additions (see, e.g., SEQ ID NOs: 9, 10, and 11, where Cys additions are labeled with *).

In some embodiments, an Fc domain monomer in the conjugates as described herein includes an additional moiety, e.g., an albumin-binding peptide, a purification peptide (e.g., a hexa-histidine peptide (HHHHHH (SEQ ID NO: 72)), or a signal sequence (e.g., IL2 signal sequence MYRMQLLSCIALSLALVTNS (SEQ ID NO: 73)) attached to the N- or C-terminus of the Fc domain monomer. In some embodiments, an Fc domain monomer in the conjugate does not contain any type of antibody variable region, e.g., $V_H$, $V_L$, a complementarity determining region (CDR), or a hypervariable region (HVR).

In some embodiments, an Fc domain monomer in the conjugates as described herein may have a sequence that is at least 95% identical (e.g., 97%, 99%, or 99.5% identical) to the sequence of any one of SEQ ID NOs: 1-68 shown below. In some embodiments, an Fc domain monomer in the conjugates as described herein may have a sequence of any one of SEQ ID NOs: 1-68 shown below.

SEQ ID NO: 1: murine Fc-IgG2a with IL2 signal sequence at the N-terminus (bold)
MYRMQLLSCIALSLALVTNSPRGPTIKPCPPCKCPAPNLLGGPSVFIFPPKIKDVLMISLSPIVTCVVVDVS

EDDPDVQISWFVNNVEVHTAQTQTHREDYNSTLRVVSALPIQHQDWMSGKEFKCKVNNKDLPAPIERTIS

-continued

KPKGSVRAPQVYVLPPPEEEMTKKQVTLTCMVTDFMPEDIYVEVVTNNGKTELNYKNTEPVLDSDGSYFM

YSKLRVEKKNWVERNSYSCSVVHEGLHNHHTTKSFSRTPGK

SEQ ID NO: 2: mature murine Fc-IgG2a
PRGPTIKPCPPCKCPAPNLLGGPSVFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERTISKPKGSVRAPQVYVLPPPEEE

MTKKQVTLTCMVTDFMPEDIYVEWTNNGKTELNYKNTEPVLDSDGSYFMYSKLRVEKKNWVERNSYSC

SVVHEGLHNHHTTKSFSRTPGK

SEQ ID NO: 3: human Fc-IgG1 with IL2 signal sequence at the N-terminus (bold) and N-terminal MVRS amino acid residues added (underlined)
MYRMQLLSCIALSLALVTNSMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

SEQ ID NO: 4: mature human Fc-IgG1 with N-terminal MVRS amino acid residues added (underlined)
MVRSDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDKSRWQQGNVFS

CSVMHEALHNHYTQKSLSLSPGK

SEQ ID NO: 5: murine Fc-IgG2a with IL2 signal sequence (bold) at the N-terminus and hexa-histidine peptide (italicized) at the C-terminus
MYRMQLLSCIALSLALVTNSPRGPTIKPCPPCKCPAPNLLGGPSVFIFPPKIKDVLMISLSPIVTCVVVDVS

EDDPDVQISWFVNNVEVHTAQTQTHREDYNSTLRVVSALPIQHQDWMSGKEFKCKVNNKDLPAPIERTIS

KPKGSVRAPQVYVLPPPEEEMTKKQVTLTCMVTDFMPEDIYVEWTNNGKTELNYKNTEPVLDSDGSYFM

YSKLRVEKKNWVERNSYSCSVVHEGLHNHHTTKSFSRTPGK*HHHHHH*

SEQ ID NO: 6: mature murine Fc-IgG2a with hexa-histidine peptide (italicized) at the C-terminus
PRGPTIKPCPPCKCPAPNLLGGPSVFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERTISKPKGSVRAPQVYVLPPPEEE

MTKKQVTLTCMVTDFMPEDIYVEWTNNGKTELNYKNTEPVLDSDGSYFMYSKLRVEKKNWVERNSYSC

SVVHEGLHNHHTTKSFSRTPGK*HHHHHH*

SEQ ID NO: 7: human Fc-IgG1 with IL2 signal sequence (bold) at the N-terminus, N-terminal MVRS amino acid residues added (underlined), and hexa-histidine peptide (italicized) at the C-terminus
MYRMQLLSCIALSLALVTNSMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK*HHHHHH*

SEQ ID NO: 8: mature human Fc-IgG1 with hexa-histidine peptide (italicized) at the C-terminus and N-terminal MVRS amino acid residues added (underlined)
MVRSDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDKSRWQQGNVFS

CSVMHEALHNHYTQKSLSLSPGK*HHHHHH*

SEQ ID NO: 9: human Fc-IgG1 with IL2 signal sequence (bold) at the N-terminus, N-terminal MVRS amino acid residues added (underlined), two additional cysteines in the hinge region (*), and hexa-histidine peptide (italicized) at the C-terminus
MYRMQLLSCIALSLALVTNSMVRSDKTHTCPPCPPC*KC*PAPELLGGPSVFLFPPKPKDTLMISRTPEVT

CVVVDVSHEDPEVKFNWYVDGVEVHNAKTKPREEQYNSTYRVVSVLTVLHQDWLNGKEYKCKVSNKAL

-continued

PAPIEKTISKAKGQPREPQVYTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK*HHHHHH*

SEQ ID NO: 10: mature human Fc-IgG1 with N-terminal MVRS amino acid residues added (underlined), two additional cysteines in the hinge region (*), and hexa-histidine peptide (italicized) at the C-terminus

MVRSDKTHTCPPCPPC*KC*PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK*HHHHHH*

SEQ ID NO: 11: mature human Fc-IgG1 with N-terminal MVRS amino acid residues added (underlined) and two additional cysteines in the hinge region (*)

MVRSDKTHTCPPCPPC*KC*PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO: 12: murine Fc-IgG2a with IL2 signal sequence (bold) at the N-terminus, Asn to Ala substitution (*), and hexa-histidine peptide (italicized) at the C-terminus

MYRMQLLSCIALSLALVTNSPRGPTIKPCPPCKCPAPNLLGGPSVFIFPPKIKDVLMISLSPIVTCVVVDVS

EDDPDVQISWFVNNVEVHTAQTQTHREDYA*STLRVVSALPIQHQDWMSGKEFKCKVNNKDLPAPIERTI

SKPKGSVRAPQVYVLPPPEEEMTKKQVTLTCMVTDFMPEDIYVEWTNNGKTELNYKNTEPVLDSDGSYF

MYSKLRVEKKNWVERNSYSCSVVHEGLHNHHTTKSFSRTPGK*HHHHHH*

SEQ ID NO: 13: mature murine Fc-IgG2a with Asn to Ala substitution (*) and hexa-histidine peptide (italicized) at the C-terminus

PRGPTIKPCPPCKCPAPNLLGGPSVFIFPPKIKDVLMISLSPIVTCVVVDVSEDDPDVQISWFVNNVEVHTA

QTQTHREDYA*STLRVVSALPIQHQDWMSGKEFKCKVNNKDLPAPIERTISKPKGSVRAPQVYVLPPPEE

EMTKKQVTLTCMVTDFMPEDIYVEVVTNNGKTELNYKNTEPVLDSDGSYFMYSKLRVEKKNWVERNSYS

CSVVHEGLHNHHTTKSFSRTPGK*HHHHHH*

SEQ ID NO: 14: human Fc-IgG1 with IL2 signal sequence (bold) at the N-terminus, N-terminal MVRS amino acid residues added (underlined), Asn to Ala substitution (*), and hexa-histidine peptide (italicized) at the C-terminus

MYRMQLLSCIALSLALVTNSMVRSDKTHTCPPCPAPELLGGPSVFLFPPKPKDTLMISRTPEVTCVVVDV

SHEDPEVKFNWYVDGVEVHNAKTKPREEQYA*STYRVVSVLTVLHQDWLNGKEYKCKVSNKALPAPIEK

TISKAKGQPREPQVYTLPPSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGKHHHHHH

SEQ ID NO: 15: mature human Fc-IgG1 with Asn to Ala substitution (*), N-terminal MVRS amino acid residues added (underlined), and hexa-histidine peptide (italicized) at the C-terminus

MVRSDKTHTCPPCPAPELLGGPSVFLFPPKPKDTLMISRTPEVTCVVVDVSHEDPEVKFNWYVDGVEVH

NAKTKPREEQYA*STYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVDKSRWQQGNV

FSCSVMHEALHNHYTQKSLSLSPGK*HHHHHH*

SEQ ID NO: 16: human IgG1 Fc with Human Serum Albumin Signal Sequence (bold) at the N-terminus and N-terminal ISAMVRS amino acid residues added (underlined)

MKWVTFISLLFLFSSAYSISAMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

SEQ ID NO: 17: human IgG1 Fc with Human Serum Albumin Signal Sequence (bold) at the N-terminus, N-terminal ISAMVRS amino acid residues added (underlined), C-terminal G4S linker (italicized), and C-terminal c-Myc tag (underlined, italicized)

-continued

MKWVTFISLLFLFSSAYSISAMVRSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPG*GGGGSEQKLISEEDL*

SEQ ID NO: 18: mature human IgG1 Fc with N-terminal ISAMVRS amino acid residues added (underlined), C-terminal G4S linker (italicized), and C-terminal c-Myc tag (underlined, italicized)
ISAMVRSDKTHTCPPCPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSFFLYSKLTVDKSRWQQGN

VFSCSVMHEALHNHYTQKSLSLSPG*GGGGSEQKLISEEDL*

SEQ ID NO: 19: human IgG1 Fc with Human Serum Albumin Signal Sequence (bold), N-terminal ISAMVRS amino acid residues added (underlined), and lysine to serine modification (*) to prevent lysine conjugation at this site
MKWVTFISLLFLFSSAYSISAMVRSDKTHTCPPCPAPELLGGPSVFLFPPKPS*DTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

SEQ ID NO: 20: mature human IgG1 Fc with N-terminal ISAMVRS amino acid residues added (underlined) and lysine to serine modification (*) to prevent lysine conjugation at this site
ISAMVRSDKTHTCPPCPAPELLGGPSVFLFPPKPS*DTLMISRTPEVTCVVVDVSHEDPEVKFNWYVDGV

EVHNAKTKPREEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLTVDKSRWQQG

NVFSCSVMHEALHNHYTQKSLSLSPGK

SEQ ID NO: 21: human IgG1 Fc with Human Serum Albumin Signal Sequence (bold) at the N-terminus, N-terminal ISAMVRS amino acid residues added (underlined), lysine to serine modification (*) to prevent lysine conjugation at this site, C-terminal G4S linker (italicized), and C-terminal C-Myc tag (underlined, italicized)
MKWVTFISLLFLFSSAYSISAMVRSDKTHTCPPCPAPELLGGPSVFLFPPKPS(*)DTLMISRTPEVTCVVV

DVSHEDPEVKFNWYVDGVEVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG*GGGGSEQKLISEEDL*

SEQ ID NO: 22: mature human IgG1 Fc with N-terminal ISAMVRS amino acid residues added (underlined), lysine to serine modification (*) to prevent lysine conjugation at this site, C-terminal G4S linker (italicized), and C-terminal C-Myc tag (underlined, italicized)
ISAMVRSDKTHTCPPCPAPELLGGPSVFLFPPKPS(*)DTLMISRTPEVTCVVVDVSHEDPEVKFNWYVDG

VEVHNAKTKPREEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLTVDKSRWQQ

GNVFSCSVMHEALHNHYTQKSLSLSPG*GGGGSEQKLISEEDL*

SEQ ID NO: 23: human IgG1 Fc with Human Serum Albumin Signal Sequence (bold) at the N-terminus, N-terminal ISAMVRS amino acid residues added (underlined), Asn to Ala substitution (*), C-terminal G4S linker (italicized), and C-terminal C-myc tag (underlined, italicized)
MKWVTFISLLFLFSSAYSISAMVRSDKTHTCPPCPAPELLGGPSVFLFPPKPKDTLMISRTPEVTCVVVDV

SHEDPEVKFNWYVDGVEVHNAKTKPREEQYA(*)STYRVVSVLTVLHQDWLNGKEYKCKVSNKALPAPIE

KTISKAKGQPREPQVYTLPPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPG*GGGGSEQKLISEEDL*

SEQ ID NO: 24: mature human IgG1 Fc with N-terminal ISAMVRS amino acid residues added (underlined), Asn to Ala substitution (*), C-terminal G45 linker (italicized), and C-terminal C-myc tag (underlined, italicized)
ISAMVRSDKTHTCPPCPAPELLGGPSVFLFPPKPKDTLMISRTPEVTCVVVDVSHEDPEVKFNWYVDGVE

VHNAKTKPREEQYA(*)STYRVVSVLTVLHQDWLNGKEYKCKVSNKALPAPIEKTISKAKGQPREPQVYTL

-continued

PPSREEMTKNQVSLTCLVKGFYPSDIAVEWESNGQPENNYKTTPPVLDSDGSFFLYSKLTVDKSRWQQ

GNVFSCSVMHEALHNHYTQKSLSLSPG*GGGGS*<u>*EQKLISEEDL*</u>

SEQ ID NO: 25: human IgG1 Fc with Human Serum Albumin Signal Sequence (bold) at the N-terminus, N-terminal ISAMVRS amino acid residues added (underlined), H310A (*) and H435A (*) mutations to impede FcRn binding, C-terminal G45 (italicized), and C-terminal C-myc tag (underlined, italicized)
MKWVTFISLLFLFSSAYS<u>ISAMVRS</u>DKTHTCPPCPAPELLGGPSVFLFPPKPKDTLMISRTPEVTCVVVDV

SHEDPEVKFNWYVDGVEVHNAKTKPREEQYNSTYRVVSVLTVLA(*)QDWLNGKEYKCKVSNKALPAPIE

KTISKA(*)KGQPREPQVYTLPPSREEMTKNQVSLTCLVKGFYPSDIAVEWESNGQPENNYKTTPPVLDSD

GSFFLYSKLTVDKSRWQQGNVFSCSVMHEALHNAYTQKSLSLSPG*GGGGS*<u>*EQKLISEEDL*</u>

SEQ ID NO: 26: mature human IgG1 Fc with Human Serum Albumin Signal Sequence (bold) at the N-terminus, N-terminal ISAMVRS amino acid residues added (underlined), with H310A (*) and H435A (*) mutations to impede FcRn binding, C-terminal G45 (italicized), and C-terminal C-myc tag (underlined, italicized)
<u>ISAMVRS</u>DKTHTCPPCPAPELLGGPSVFLFPPKPKDTLMISRTPEVTCVVVDVSHEDPEVKFNWYVDGVE

VHNAKTKPREEQYNSTYRVVSVLTVLA(*)QDWLNGKEYKCKVSNKALPAPIEKTISKA(*)KGQPREPQVY

TLPPSREEMTKNQVSLTCLVKGFYPSDIAVEWESNGQPENNYKTTPPVLDSDGSFFLYSKLTVDKSRWQ

QGNVFSCSVMHEALHNAYTQKSLSLSPG*GGGGS*<u>*EQKLISEEDL*</u>

SEQ ID NO: 27: human IgG1 Fc with Human Serum Albumin Signal Sequence (bold) at the N-terminus, N-terminal ISAMVRS amino acid residues added (underlined), C-terminal G4S linker (italicized), and C-terminal mutated (lysine to phenylalanine, bold) C-myc tag (underlined, italicized)
MKWVTFISLLFLFSSAYS<u>ISAMVRS</u>DKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPG*GGGGS*<u>*EQ*FLISEEDL</u>

SEQ ID NO: 28: mature human IgG1 Fc with N-terminal ISAMVRS amino acid residues added (underlined), C-terminal G4S linker (italicized), and C-terminal mutated (lysine to phenylalanine, bold) C-myc tag (underlined, italicized)
<u>ISAMVRS</u>DKTHTCPPCPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSFFLYSKLTVDKSRWQQGN

VFSCSVMHEALHNHYTQKSLSLSPG*GGGGS*

SEQ ID NO: 29: human IgG1 Fc with Human Serum Albumin Signal Sequence (bold) at the N-terminus, N-terminal ISAMVRS amino acid residues added (underlined), Asn to Ala substitution (*), C-terminal G4S linker (italicized), and C-terminal mutated (lysine to phenylalanine, bold) C-myc tag (underlined, italicized)
MKWVTFISLLFLFSSAYS<u>ISAMVRS</u>DKTHTCPPCPAPELLGGPSVFLFPPKPKDTLMISRTPEVTCVVVDV

SHEDPEVKFNWYVDGVEVHNAKTKPREEQYA(*)STYRVVSVLTVLHQDWLNGKEYKCKVSNKALPAPIE

KTISKAKGQPREPQVYTLPPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGG*GGGS*<u>EQFLISEEDL</u>

SEQ ID NO: 30: mature human IgG1 Fc with N-terminal MVRS amino acid residues added (underlined), Asn to Ala substitution (*), C-terminal G4S linker (italicized), and C-terminal mutated (lysine to phenylalanine, bold) C-myc tag (underlined, italicized)
<u>ISAMVRS</u>DKTHTCPPCPAPELLGGPSVFLFPPKPKDTLMISRTPEVTCVVVDVSHEDPEVKFNWYVDGVE

VHNAKTKPREEQYA(*)STYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLTVDKSRWQQ

GNVFSCSVMHEALHNHYTQKSLSLSPGG*GGGS*<u>*EQ*F*LISEEDL*</u>

SEQ ID NO: 31: human IgG1 Fc with Human Serum Albumin Signal Sequence (bold) at the N-terminus, allotype G1m(fa) (bold italics), C-termainl G4S linker (italicized), and C-terminal mutated (lysine to phenylalanine, bold) C-myc tag (underlined)
MKWVTFISLLFLFSSAYSDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALPAPIEKTISKAKG

-continued

QPREPQVYTLPPSR*DEL*TKNQVSLTCLVKGFYPSDIAVEWESNGQPENNYKTTPPVLDSDGSFFLYSKLT

VDKSRWQQGNVFSCSVMHEALHNHYTQKSLSLSPG*GGGGS*EQFLISEEDL

SEQ ID NO: 32: human IgG1 Fc with Human Serum Albumin Signal Sequence (bold) at the N-terminus, allotype G1m(fa) (bold italics)
MKWVTFISLLFLFSSAYSDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALPAPIEKTISKAKG

QPREPQVYTLPPSR*DEL*TKNQVSLTCLVKGFYPSDIAVEWESNGQPENNYKTTPPVLDSDGSFFLYSKLT

VDKSRWQQGNVFSCSVMHEALHNHYTQKSLSLSPGK

SEQ ID NO: 33: mature human IgG1 Fc with a YTE triple mutation (bold and underlined) with N-terminal MVRS amino acid residues added (underlined)
MVRSDKTHTCPPCPAPELLGGPSVFLFPPKPKDTLYITREPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDKSRWQQGNVFS

CSVMHEALHNHYTQKSLSLSPGK

SEQ ID NO: 34: human IgG1 Fc with Human Serum Albumin Signal Sequence (bold) at the N-terminus, contains residues EPKSS comprising the full hinge region on the N-terminus of mature human IgG1 Fc(underlined), Cys to Ser substitution (#), allotype G1m(fa) (bold italics)
MKWVTFISLLFLFSSAYSEPKSS(#)DKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKT

ISKAKGQPREPQVYTLPPSR*DEL*TKNQVSLTCLVKGFYPSDIAVEWESNGQPENNYKTTPPVLDSDGSFF

LYSKLTVDKSRWQQGNVFSCSVMHEALHNHYTQKSLSLSPGK

SEQ ID NO: 35: human IgG1 Fc with murine IgG signal sequence (bold) at the N-terminus, with removal of EPKSSD hinge residues from the N-terminus of the mature human IgG1 Fc, allotype G1m(fa) (bold italics)
MGWSCIILFLVATATGVHSKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKALPAPIEKTISKAKG

QPREPQVYTLPPSR*DEL*TKNQVSLTCLVKGFYPSDIAVEWESNGQPENNYKTTPPVLDSDGSFFLYSKLT

VDKSRWQQGNVFSCSVMHEALHNHYTQKSLSLSPGK

SEQ ID NO: 36: mature human IgG1 Fc with a YTE triple mutation (bold and underlined), with removal of EPKSSD hinge residues from the N-terminus of the mature human IgG1 Fc, allotype G1m(fa) (bold italics)
KTHTCPPCPAPELLGGPSVFLFPPKPKDTLYITREPEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPSR*DEL*

TKNQVSLTCLVKGFYPSDIAVEWESNGQPENNYKTTPPVLDSDGSFFLYSKLTVDKSRWQQGNVFSCS

VMHEALHNHYTQKSLSLSPGK

SEQ ID NO: 37: mature human IgG1 Fc with an LS double mutation (bold and underlined), with removal of EPKSSD hinge residues from the N-terminus of the mature human IgG1 Fc, allotype G1m(fa) (bold italics)
KTHTCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTLPPSR*DEL*

TKNQVSLTCLVKGFYPSDIAVEWESNGQPENNYKTTPPVLDSDGSFFLYSKLTVDKSRWQQGNVFSCS

VLHEALHSHYTQKSLSLSPGK

SEQ ID NO: 38: mature human IgG1 Fc with Human Serum Albumin Signal Sequence (bold) at the N-terminus, a YTE triple mutation (bold and underlined), allotype G1m(fa) (bold italics), C-terminal G4S linker (italicized), and C-terminal C-myc tag (underlined)
MKWVTFISLLFLFSSAYSDKTHTCPPCPAPELLGGPSVFLFPPKPKDTLYITREPEVTCVVVDVSHEDPEV

KFNWYVDGVEVHNAKTKPREEQYNSTYRVVSVLTVLHQDWLNGKEYKCKVSNKALPAPIEKTISKAKGQ

PREPQVYTLPPSR*DEL*TKNQVSLTCLVKGFYPSDIAVEWESNGQPENNYKTTPPVLDSDGSFFLYSKLTV

DKSRWQQGNVFSCSVMHEALHNHYTQKSLSLSPG*GGGGS*EQKLISEEDL

SEQ ID NO: 39: mature human Fc IgG1, wherein $X_1$ is Met or Trp, $X_2$ is Ser or Thr, $X_3$ is Thr -continued or Glu, $X_4$ is Asp or Glu, and $X_5$ is Leu or Met, $X_6$ is Met or Leu, and $X_7$ is Asn or Ser
DKTHTCPPCPAPELLGGPSVFLFPPKPKDTLX$_1$IX$_2$RX$_3$PEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPSRX$_4$E

X$_5$TKNQVSLTCLVKGFYPSDIAVEWESNGQPENNYKTTPPVLDSDGSFFLYSKLTVDKSRWQQGNVFSC

SVX$_6$HEALHX$_7$HYTQKSLSLSPG

SEQ ID NO: 40: mature human Fc IgG1 wherein $X_4$ is Asp or Glu, and $X_5$ is Leu or Met
DKTHTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLPPSRX$_4$EX$_5$

TKNQVSLTCLVKGFYPSDIAVEWESNGQPENNYKTTPPVLDSDGSFFLYSKLTVDKSRWQQGNVFSCSV

MHEALHNHYTQKSLSLSPG

SEQ ID NO: 41: mature human Fc IgG1 with a YTE triple mutation (bold and underlined), and wherein $X_4$ is Asp or Glu, and $X_5$ is Leu or Met
DKTHTCPPCPAPELLGGPSVFLFPPKPKDTLYITREPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSRX$_4$EX$_5$T

KNQVSLTCLVKGFYPSDIAVEWESNGQPENNYKTTPPVLDSDGSFFLYSKLTVDKSRWQQGNVFSCSV

MHEALHNHYTQKSLSLSPG

SEQ ID NO: 42: mature human Fc IgG1 with a YTE triple mutation (bold and underlined), allotype G1m(fa) (bold italics)
DKTHTCPPCPAPELLGGPSVFLFPPKPKDTLYITREPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSR*D*E*L*TK

NQVSLTCLVKGFYPSDIAVEWESNGQPENNYKTTPPVLDSDGSFFLYSKLTVDKSRWQQGNVFSCSVM

HEALHNHYTQKSLSLSPG

SEQ ID NO: 43: mature human Fc IgG1 with a YTE triple mutation (bold and underlined), allotype G1m(f) (bold italics)
DKTHTCPPCPAPELLGGPSVFLFPPKPKDTLYITREPEVTCVVVDVSHEDPEVKFNWYVDGVEVHNAKTK PREEQYNSTYRVVSVLTVLHQDWLNGKEYKCKVSNKALPAPIEKTISKAKGQPREPQVYTLPPSR*D*E*L*TK

NQVSLTCLVKGFYPSDIAVEWESNGQPENNYKTTPPVLDSDGSFFLYSKLTVDKSRWQQGNVFSCSVM

HEALHNHYTQKSLSLSPG

SEQ ID NO: 44: mature human Fc IgG1 with a LS double mutation (bold and underlined), and wherein $X_4$ is Asp or Glu, and $X_5$ is Leu or Met
DKTHTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLPPSRX$_4$EX$_5$

TKNQVSLTCLVKGFYPSDIAVEWESNGQPENNYKTTPPVLDSDGSFFLYSKLTVDKSRWQQGNVFSCSV

LHEALHSHYTQKSLSLSPG

SEQ ID NO: 45: mature human Fc IgG1 with a LS double mutation (bold and underlined), allotype G1m(fa) (bold italics)
DKTHTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLPPSR*D*E*L*T

KNQVSLTCLVKGFYPSDIAVEWESNGQPENNYKTTPPVLDSDGSFFLYSKLTVDKSRWQQGNVFSCSVL

HEALHSHYTQKSLSLSPG

SEQ ID NO: 46: mature human Fc IgG1 with a LS double mutation (bold and underlined), allotype G1m(f) (bold italics)
DKTHTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLPPSR*E*E*M*T

KNQVSLTCLVKGFYPSDIAVEWESNGQPENNYKTTPPVLDSDGSFFLYSKLTVDKSRWQQGNVFSCSVL

HEALHSHYTQKSLSLSPG

SEQ ID NO: 47: mature human Fc IgG1 with mouse heavy chain MIgG Vh signal sequence (bold), Cys to Ser substitution (#), and wherein $X_1$ is Met or Trp, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser -continued

MGWSCIILFLVATATGVHSNVNHKPSNTKVDKKVEPKSS(#)DKTHTCPPCPAPELLGGPSVFLFPPKPKD

TL$X_1$I$X_2$R$X_3$PEVTCVVVDVSHEDPEVKFNWYVDGVEVHNAKTKPREEQYNSTYRVVSVLTVLHQDWLNG

KEYKCKVSNKALPAPIEKTISKAKGQPREPQVYTLPPSR$X_4$E$X_5$TKNQVSLTCLVKGFYPSDIAVEWESNG

QPENNYKTTPPVLDSDGSFFLYSKLTVDKSRWQQGNVFSCSV$X_6$HEALH$X_7$HYTQKSLSLSPG

SEQ ID NO: 48: mature human IgG1 Fc with mouse heavy chain MIgG Vh signal sequence (bold), Cys to Ser substitution (#), allotype G1m(fa) (bold italics)

MGWSCIILFLVATATGVHSNVNHKPSNTKVDKKVEPKSS(#)DKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*DEL*TKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 49: mature human IgG1 Fc with mouse heavy chain MIgG Vh signal sequence (bold), Cys to Ser substitution (#), allotype G1m(f) (bold italics)

MGWSCIILFLVATATGVHSNVNHKPSNTKVDKKVEPKSS(#)DKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*EEM*TKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 50: mature human IgG1 Fc with mouse heavy chain MIgG Vh signal sequence (bold), Cys to Ser substitution (#), M428L, N4345 mutations (Bold/Underlined), allotype G1m(fa) (bold italics)

MGWSCIILFLVATATGVHSNVNHKPSNTKVDKKVEPKSS(#)DKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*DEL*TKNQVSLTCLVKGFYPSDIAVEWESNGQPE

NNYKTTPPVLDSDGSFFLYSKLTVDKSRWQQGNVFSCSV<u>L</u>HEALH<u>S</u>HYTQKSLSLSPGK

SEQ ID NO: 51: mature human IgG1 Fc with mouse heavy chain MIgG Vh signal sequence (bold), Cys to Ser substitution (#), M428L, N4345 mutations (Bold/Underlined), allotype G1m(f) (bold italics)

MGWSCIILFLVATATGVHSNVNHKPSNTKVDKKVEPKSS(#)DKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*EEM*TKNQVSLTCLVKGFYPSDIAVEWESNGQPE

NNYKTTPPVLDSDGSFFLYSKLTVDKSRWQQGNVFSCSV<u>L</u>HEALH<u>S</u>HYTQKSLSLSPGK

SEQ ID NO: 52: mature human IgG1 Fc with mouse heavy chain MIgG Vh signal sequence (bold), Cys to Ser substitution (#), YTE triple mutation (bold and underlined), allotype G1m(fa) (bold italics)

MGWSCIILFLVATATGVHSNVNHKPSNTKVDKKVEPKSS(#)DKTHTCPPCPAPELLGGPSVFLFPPKPKD

TL<u>Y</u>I<u>T</u>R<u>E</u>PEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*EEM*TKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 53: mature human IgG1 Fc with mouse heavy chain MIgG Vh signal sequence (bold), Cys to Ser substitution (#), YTE triple mutation (bold and underlined), allotype G1m(f) (bold italics)

MGWSCIILFLVATATGVHSNVNHKPSNTKVDKKVEPKSS(#)DKTHTCPPCPAPELLGGPSVFLFPPKPKD

TL<u>Y</u>I<u>T</u>R<u>E</u>PEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSR*EEM*TKNQVSLTCLVKGFYPSDIAVEWESNGQPE

NNYKTTPPVLDSDGSFFLYSKLTVDKSRWQQGNVFSCSVMHEALHNHYTQKSLSLSPGK

SEQ ID NO: 54: mature human IgG1 Fc with mouse heavy chain MIgG Vh signal sequence (bold), N-terminal ISAMVRS amino acid residues added (italicized), M428L, N434S mutations (bold/underlined), G4S linker (italicized), and C-terminal C-myc-tag (underlined), allotype G1m(f) (bold italics)

MGWSCIILFLVATATGVHS*ISAMVRS*DKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR*EEM*TKNQVSLTCLVKGFYPSDIAVEWESNGQPENNYKTTPPVLDSDGS

-continued

FFLYSKLTVDKSRWQQGNVFSCSVLHEALHSHYTQKSLSLSPG*GGGGS*EQKLISEEDL

SEQ ID NO: 55: mature human IgG1 Fc with mouse heavy chain MIgG Vh signal sequence (bold), N-terminal ISAMVRS amino acid residues added (italicized), M428L, N434S mutations (bold/underlined), G4S linker (italicized), C-terminal C-myc-tag (underlined), allotype G1m(fa) (bold italics)
MGWSCIILFLVATATGVHS*ISAMVRS*DKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR*DEL*TKNQVSLTCLVKGFYPSDIAVEWESNGQPENNYKTTPPVLDSDGSF

FLYSKLTVDKSRWQQGNVFSCSVLHEALHSHYTQKSLSLSPG*GGGGS*EQKLISEEDL

SEQ ID NO: 56: mature human IgG1 Fc with mouse heavy chain MIgG Vh signal sequence (bold), N-terminal ISAMVRS amino acid residues added (italicized), YTE triple mutant (bold/underlined), G4S linker (italicized), and C-terminal C-myc-tag (underlined), allotype G1m(f) (bold italics)
MGWSCIILFLVATATGVHS*ISAMVRS*DKTHTCPPCPAPELLGGPSVFLFPPKPKDTLYITREPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR*EEM*TKNQVSLTCLVKGFYPSDIAVEWESNGQPENNYKTTPPVLDSDGS

FFLYSKLTVDKSRWQQGNVFSCSVMHEALHNHYTQKSLSLSPG*GGGGS*EQKLISEEDL

SEQ ID NO: 57: mature human IgG1 Fc with mouse heavy chain MIgG Vh signal sequence (bold), N-terminal ISAMVRS amino acid residues added (italicized), YTE triple mutant (bold/underlined), G4S linker (italicized), C-terminal C-myc-tag (underlined), allotype G1m(fa) (bold italics)
MGWSCIILFLVATATGVHS*ISAMVRS*DKTHTCPPCPAPELLGGPSVFLFPPKPKDTLYITREPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR*DEL*TKNQVSLTCLVKGFYPSDIAVEWESNGQPENNYKTTPPVLDSDGSF

FLYSKLTVDKSRWQQGNVFSCSVMHEALHNHYTQKSLSLSPG*GGGGS*EQKLISEEDL

SEQ ID NO: 58: mature human IgG1 with mouse heavy chain MIgG1 signal sequence (bold), Cys to Ser substitution (#), C-terminal G4S (italics), and C-terminal IgA peptide (underline), allotype G1m(fa) (bold italics)
MGWSCIILFLVATATGVHSEPKSS(#)DKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR*DEL*TKNQVSLTCLVKGFYPSDIAVEWESNGQPENNYKTTPPVLDSDGSF

FLYSKLTVDKSRWQQGNVFSCSVMHEALHNHYTQKSLSLSPG*GGGGS*QRNPRLRLIRRHPTLRIPPI

SEQ ID NO: 59: mature human IgG1 with mouse heavy chain MIgG1 signal sequence (bold), Cys to Ser substitution (#), M428L, N4345 mutations (bold/underlined), C-terminal G4S (italics), and C-terminal IgA peptide (underline), allotype G1m(fa) (bold italics)
MGWSCIILFLVATATGVHSEPKSS(#)DKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEK

TISKAKGQPREPQVYTLPPSR*DEL*TKNQVSLTCLVKGFYPSDIAVEWESNGQPENNYKTTPPVLDSDGSF

FLYSKLTVDKSRWQQGNVFSCSVLHEALHSHYTQKSLSLSPG*GGGGS*QRNPRLRLIRRHPTLRIPPI

SEQ ID NO: 60: mature human Fc IgG1, $Z_1$ is Cys or Ser, and wherein $X_1$ is Met or Trp, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
NVNHKPSNTKVDKKVEPKS$\mathbf{Z}_1$DKTHTCPPCPAPELLGGPSVFLFPPKPKDTL$\mathbf{X}_1$I$\mathbf{X}_2$R$\mathbf{X}_3$PEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR$\mathbf{X}_4$E$\mathbf{X}_5$TKNQVSLTCLVKGFYPSDIAVEWESNGQPENNYKTTPPVLDSDGSFF LYSKLTVDKSRWQQGNVFSCSV$\mathbf{X}_6$HEALH$\mathbf{X}_7$HYTQKSLSLSPGK SEQ ID NO: 61: mature human Fc IgG1, Cys to Ser substitution (#), and wherein $X_1$ is Met or Trp, $X_2$ is Ser or Thr, $X_3$ is Thr or Glu, $X_4$ is Asp or Glu, and $X_5$ is Leu or Met, $X_6$ is Met or Leu, and $X_7$ is Asn or Ser
NVNHKPSNTKVDKKVEPKSS(#)DKTHTCPPCPAPELLGGPSVFLFPPKPKDTL$\mathbf{X}_1$I$\mathbf{X}_2$R$\mathbf{X}_3$PEVTCVVVDVS

HEDPEVKFNWYVDGVEVHNAKTKPREEQYNSTYRVVSVLTVLHQDWLNGKEYKCKVSNKALPAPIEKTI

SKAKGQPREPQVYTLPPSR$\mathbf{X}_4$E$\mathbf{X}_5$TKNQVSLTCLVKGFYPSDIAVEWESNGQPENNYKTTPPVLDSDGSF -continued

FLYSKLTVDKSRWQQGNVFSCSVX$_6$HEALHX$_7$HYTQKSLSLSPGK

SEQ ID NO: 62: mature human IgG1 Fc, Cys to Ser substitution (#), $X_4$ is Asp or Glu, and $X_5$ is Leu or Met

NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSRX$_4$EX$_5$TKNQVSLTCLVKGFYPSDIAVEWESNGQPENNYKTTPPVLDSDGSFF

LYSKLTVDKSRWQQGNVFSCSVMHEALHNHYTQKSLSLSPGK

SEQ ID NO: 63: mature human IgG1 Fc, Cys to Ser substitution (#), allotype G1m(f) (bold italics)

NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 64: mature human IgG1 Fc, Cys to Ser substitution (#), allotype G1m(fa) (bold italics)

NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 65: mature human IgG1 Fc, Cys to Ser substitution (#), M428L, N434S mutations (Bold/Underlined), allotype G1m(fa) (bold italics)

NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVLHEALHSHYTQKSLSLSPGK

SEQ ID NO: 66: mature human IgG1 Fc, Cys to Ser substitution (#), M428L, N434S mutations (Bold/Underlined), allotype G1m(f) (bold italics)

NVNHKPSNTKVDKKVEPKSS(#)DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVLHEALHSHYTQKSLSLSPGK

SEQ ID NO: 67: mature human IgG1 Fc, Cys to Ser substitution (#), YTE triple mutation (bold and underlined), allotype G1m(fa) (bold italics)

NVNHKPSNTKVDKKVEPKSSMDKTHTCPPCPAPELLGGPSVFLFPPKPKDTLYITREPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*DEL*TKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 68: mature human IgG1 Fc, Cys to Ser substitution (#), YTE triple mutation (bold and underlined), allotype G1m(f) (bold italics)

NVNHKPSNTKVDKKVEPKSSMDKTHTCPPCPAPELLGGPSVFLFPPKPKDTLYITREPEVTCVVVDVSH

EDPEVKFNWYVDGVEVHNAKTKPREEQYNSTYRVVSVLTVLHQDWLNGKEYKCKVSNKALPAPIEKTIS

KAKGQPREPQVYTLPPSR*EEM*TKNQVSLTCLVKGFYPSDIAVEWESNGQPENNYKTTPPVLDSDGSFFL

YSKLTVDKSRWQQGNVFSCSVMHEALHNHYTQKSLSLSPGK

As defined herein, an Fc domain includes two Fc domain monomers that are dimerized by the interaction between the $C_H3$ antibody constant domains, as well as one or more disulfide bonds that form between the hinge domains of the two dimerizing Fc domain monomers. An Fc domain forms the minimum structure that binds to an Fc receptor, e.g., Fc-gamma receptors (i.e., Fcγ receptors (FcγR)), Fc-alpha receptors (i.e., Fcα receptors (FcαR)), Fc-epsilon receptors (i.e., Fcε receptors (FcεR)), and/or the neonatal Fc receptor (FcRn). In some embodiments, an Fc domain of the present invention binds to an Fcγ receptor (e.g., FcRn, FcγRI (CD64), FcγRIIa (CD32), FcγRIIb (CD32), FcγRIIIa (CD16a), FcγRIIIb (CD16b)), and/or FcγRIV and/or the neonatal Fc receptor (FcRn).

In some embodiments, the Fc domain monomer or Fc domain of the invention is an aglycosylated Fc domain monomer or Fc domain (e.g., an Fc domain monomer or and Fc domain that maintains engagement to an Fc receptor (e.g., FcRn). For example, the Fc domain is an aglycosylated IgG1 variants that maintains engagement to an Fc receptor (e.g., an IgG1 having an amino acid substitution at N297 and/or $T_{299}$ of the glycosylation motif). Exemplary aglycosylated Fc domains and methods for making aglycosylated Fc domains are known in the art, for example, as described in Sazinsky S. L. et al., Aglycosylated immunoglobulin G1 variants productively engage activating Fc receptors, PNAS, 2008, 105(51):20167-20172, which is incorporated herein in its entirety.

In some embodiments, the Fc domain or Fc domain monomer of the invention is engineered to enhance binding to the neonatal Fc receptor (FcRn). For example, the Fc domain may include the triple mutation corresponding to M252Y/S254T/$T_{256}$E (YTE) (e.g., an IgG1, such as a human or humanized IgG1 having a YTE mutation, for example SEQ ID NO: 33, SEQ ID NO: 36, SEQ ID NO: 38, SEQ ID NO: 39, SEQ ID NO: 41, SEQ ID NO: 42, SEQ ID NO: 43, SEQ ID NO: 52, SEQ ID NO: 53, SEQ ID NO: 56, or SEQ ID NO: 57). The Fc domain may include the double mutant corresponding to M428L/N434S (LS) (e.g., an IgG1, such as a human or humanized IgG1 having an LS mutation, such as SEQ ID NO: 37, SEQ ID NO: 39, SEQ ID NO: 44, SEQ ID NO: 45, SEQ ID NO: 46, SEQ ID NO: 50, SEQ ID NO: 51, SEQ ID NO: 54, SEQ ID NO: 55, or SEQ ID NO: 59). The Fc domain may include the single mutant corresponding to N434H (e.g., an IgG1, such as a human or humanized IgG1 having an N434H mutation). The Fc domain may include the single mutant corresponding to C220S (e.g., an IgG1, such as a human or humanized IgG1 having a C220S mutation, such as SEQ ID NOs: 34, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 58, SEQ ID NO: 59, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68). The Fc domain may include a combination of one or more of the above-described mutations that enhance binding to the FcRn. Enhanced binding to the FcRn may increase the half-life Fc domain-containing conjugate. For example, incorporation of one or more amino acid mutations that increase binding to the FcRn (e.g., a YTE mutation, an LS mutation, or an N434H mutation) may increase the half life of the conjugate by 5%, 10%, 15%, 20%, 30%, 40%, 50%, 60%, 70%, 80%, 90%. 100%, 200%, 300%, 400%, 500% or more relative to a conjugate having an the corresponding Fc domain without the mutation that enhances FcRn binding. Exemplary Fc domains with enhanced binding to the FcRN and methods for making Fc domains having enhanced binding to the FcRN are known in the art, for example, as described in Maeda, A. et al., Identification of human IgG1 variant with enhanced FcRn binding and without increased binding to rheumatoid factor autoantibody, MABS, 2017, 9(5):844-853, which is incorporated herein in its entirety. As used herein, an amino acid "corresponding to" a particular amino acid residue (e.g., of a particular SEQ ID NO.) should be understood to include any amino acid residue that one of skill in the art would understand to align to the particular residue (e.g., of the particular sequence). For example, any one of SEQ ID NOs: 1-68 may be mutated to include a YTE mutation, an LS mutation, and/or an N434H mutation by mutating the "corresponding residues" of the amino acid sequence.

As used herein, a sulfur atom "corresponding to" a particular cysteine residue of a particular SEQ ID NO. should be understood to include the sulfur atom of any cysteine residue that one of skill in the art would understand to align to the particular cysteine of the particular sequence. The protein sequence alignment of human IgG1 (UniProtKB: P01857; SEQ ID NO: 94), human IgG2 (UniProtKB: P01859; SEQ ID NO: 95), human IgG3 (UniProtKB: P01860; SEQ ID NO: 96), and human IgG4 (UniProtKB: P01861; SEQ ID NO: 97) is provided below (aligned with Clustal Omega Multiple Pairwise Alignment). The alignment indicates cysteine residues (e.g., sulfur atoms of cysteine residues) that "correspond to" one another (in boxes and indicated by the • symbol). One of skill in the art would readily be able to perform such an alignment with any IgG variant of the invention to determine the sulfur atom of a cysteine that corresponds to any sulfur atom of a particular cysteine of a particular SEQ ID NO. described herein (e.g., any one of SEQ ID NOs: 1-68). For example, one of skill in the art would readily be able to determine that Cys10 of SEQ ID NO: 10 (the first cysteine of the conserved CPPC motif of the hinge region of the Fc domain) corresponds to, for example, Cys109 of IgG1, Cys106 of IgG2, Cys156 of IgG3, Cys29 of SEQ ID NO: 1, Cys9 of SEQ ID NO: 2, Cys30 of SEQ ID NO: 3, or Cys10 of SEQ ID NO: 10.

In some embodiments, the Fc domain or Fc domain monomer of the invention has the sequence of any one of SEQ ID NOs: 39-68 may further include additional amino acids at the N-terminus (Xaa)x and/or additional amino acids at the C-terminus (Xaa)z, wherein Xaa is any amino acid and x and z are a whole number greater than or equal to zero, generally less than 100, preferably less than 10 and more preferably 0, 1, 2, 3, 4, or 5. In some embodiments, the additional amino acids are least 70% (e.g., 70%, 75%, 80%, 85%, 90%, 95%, 96%, 97%, 98%, 99%, or 100%) identical to one or more consecutive amino acids of SEQ ID NO: 94. For example, the additional amino acids may be a single amino aid on the C-terminus corresponding to Lys330 of IgG1 (SEQ ID NO: 94).

As used herein, a nitrogen atom "corresponding to" a particular lysine residue of a particular SEQ ID NO. should be understood to include the nitrogen atom of any lysine residue that one of skill in the art would understand to align to the particular lysine of the particular sequence. The protein sequence alignment of human IgG1 (UniProtKB: P01857; SEQ ID NO: 94), human IgG2 (UniProtKB: P01859; SEQ ID NO: 95), human IgG3 (UniProtKB: P01860; SEQ ID NO: 96), and human IgG4 (UniProtKB: P01861; SEQ ID NO: 97) is provided below (aligned with Clustal Omega Multiple Pairwise Alignment). The alignment indicates lysine residues (e.g., nitrogen atoms of lysine residues) that "correspond to" one another (in boxes and indicated by the * symbol). One of skill in the art would readily be able to perform such an alignment with any IgG variant of the invention to determine the nitrogen atom of a lysine that corresponds to any nitrogen atom of a particular lysine of a particular SEQ ID NO. described herein (e.g., any one of SEQ ID NOs: 1-68). For example, one of skill in the art would readily be able to determine that Lys35 of SEQ ID NO: 10 corresponds to, for example, Lys129 of IgG1, Lys126 of IgG2, Lys176 of IgG3, Lys51 of SEQ ID NO: 1, Lys31 of SEQ ID NO: 2, Lys50 of SEQ ID NO: 3, or Lys30 of SEQ ID NO: 10.

Protein Sequence Alignment of IgG1 (SEQ ID NO: 94), IgG2 (SEQ ID NO: 95), IgG3 (SEQ ID NO: 96), and IgG4 (SEQ ID NO: 97)

```
human_IgG1    ASTKGPSVFPLAPSSKSTSGGTAALGCLVKDYFPEPVTVSWNSGALTSGVHTFPAVLQSS
human_IgG2    ASTKGPSVFPLAPCSRSTSESTAALGCLVKDYFPEPVTVSWNSGALTSGVHTFPAVLQSS
human_IgG3    ASTKGPSVFPLAPCSRSTSGGTAALGCLVKDYFPEPVTVSWNSGALTSGVHTFPAVLQSS
human_IgG4    ASTKGPSVFPLAPCSRSTSESTAALGCLVKDYFPEPVTVSWNSGALTSGVHTFPAVLQSS
                 *         •            •  *

human_IgG1    GLYSLSSVVTVPSSSLGTQTYICNVNHKPSNIKVIKKVE---------------------
human_IgG2    GLYSLSSVVTVPSSNFGIQTYICNVDHKPSNIKVIKIVERKC------------------
human_IgG3    GLYSLSSVVTVPSSSLGTQTYICNVNHKPSNTKVDKRVELKTPLGDTTHTCPRCPEPKSC
human_IgG4    GLYSLSSVVTVPSSSLGIKTYTCNVDHKPSNTKVDKRVESK-------------------
                                    •    *    *  *

human_IgG1    --------------------------PKSCDKTHTCPPCPAPELLGGPSVFLFPPKPKDT
human_IgG2    -----------------------------C---VECPPCPAPP-VAGPSVFLFPPKPKDT
human_IgG3    DIPPPCPRCPEPKSCDIPPPCPRCPEPKSCDIPPPCPRCPAPELLGGPSVFLFPPKPKDT
human_IgG4    -------------------------------YGPPCPSCPAPEFLGGPSVFLFPPKPKDI
                                         * •     *  *                * *

human_IgG1    LMISRTPEVTCVVVDVSHEDPEVKFNWYVDGVEVHNAKIKPREEQYNSTYRVVSVLTVLH
human_IgG2    LMISRTPEVICVVVDVSHEDPEVQFNWYVDGVEVHNAKIKPREEQFNSTFRVVSVLTVVH
human_IgG3    LMISRTPEVICVVVDVSHEDPEVQFRWYVDGVEVHNAKIKPREEQYNSIFRVVSVLIVLH
human_IgG4    LMISRTPEVTCVVVDVSQEDPEVQFNWYVDGVEVHNAKTKPREEQFNSIYRVVSVLIVLH
                        •                          * *

human_IgG1    QDWLNGKEYKCKVSNKALPAPIEKTISKAKGQPREPQVYTLPPSRDELIKNQVSLTCLVK
human_IgG2    QDWLNGKEYKCKVSNKGLPAPIEKTISKIKGQPREPQVYTLPPSREEMIKNQVSLTCLVK
human_IgG3    QDWLNGKEYKCKVSNKALPAPIEKTISKIKGQPREPQVYTLPPSREEMTKNQVSLTCLVK
human_IgG4    QDWLNGKEYKCKVSNKGLPSSIEKIISKAKGQPREPQVYILPPSQEEMTKNQVSLTCLVK
                    *  *•*   *       *   * *                   *      •  *

human_IgG1    GFYPSDIAVEWESNGQPENNYKIIPPVLDSDGSFFLYSKLTVIKSRWQQGNVFSCSVMHE
human_IgG2    GFYPSDISVEWESNGQPENNYKITPPMLDSDGSFFLYSKLIVDKSRWQQGNVFSCSVMHE
human_IgG3    GFYPSDIAVEWESSGQPENNYNITPPMLDSDGSFFLYSKLIVDKSRWQQGNIFSCSVMHE
human_IgG4    GFYPSDIAVEWESNGQPENNYKIIPPVLDSDGSFFLYSRLTVDKSRWQEGNVFSCSVMHE
                                   *                     *          •

human_IgG1    ALHNHYIQKSLSLSPGK
human_IgG2    ALHNHYIQKSLSLSPGK
human_IgG3    ALHNRFIQKSLSLSPGK
human_IgG4    ALHNHYIQKSLSLSLGK
                      *       *
```

Activation of Immune Cells

Fc-gamma receptors (FcγRs) bind the Fc portion of immunoglobulin G (IgG) and play important roles in immune activation and regulation. For example, the IgG Fc domains in immune complexes (ICs) engage FcγRs with high avidity, thus triggering signaling cascades that regulate immune cell activation. The human FcγR family contains several activating receptors (FcγRI, FcγRIIa, FcγRIIc, FcγRIIIa, and FcγRIIIb) and one inhibitory receptor (FcγRIIb). FcγR signaling is mediated by intracellular domains that contain immune tyrosine activating motifs (ITAMs) for activating FcγRs and immune tyrosine inhibitory motifs (ITIM) for inhibitory receptor FcγRIIb. In some embodiments, FcγR binding by Fc domains results in ITAM phosphorylation by Src family kinases; this activates Syk family kinases and induces downstream signaling networks, which include PI3K and Ras pathways.

In the conjugates described herein, the portion of the conjugates including monomers or dimers of neuraminidase inhibitors bind to and inhibits viral neuraminidase leading to inhibition of viral replication, while the Fc domain portion of the conjugates bind to FcγRs (e.g., FcRn, FcγRI, FcγRIIa, FcγRIIc, FcγRIIIa, and FcγRIIIb) on immune cells and activate phagocytosis and effector functions, such as antibody-dependent cell-mediated cytotoxicity (ADCC), thus leading to the engulfment and destruction of viral particles by immune cells and further enhancing the antiviral activity of the conjugates. Examples of immune cells that may be activated by the conjugates described herein include, but are not limited to, macrophages, neutrophils, eosinophils, basophils, lymphocytes, follicular dendritic cells, natural killer cells, and mast cells.

IV. Albumin Proteins and Albumin Protein-Binding Peptides

Albumin Proteins

An albumin protein of the invention may be a naturally-occurring albumin or a variant thereof, such as an engineered variant of a naturally-occurring albumin protein. Variants include polymorphisms, fragments such as domains and sub-domains, and fusion proteins. An albumin protein may include the sequence of an albumin protein obtained from any source. Preferably the source is mammalian, such as human or bovine. Most preferably, the albumin protein is human serum albumin (HSA), or a variant thereof. Human serum albumins includes any albumin protein having an amino acid sequence naturally occurring in humans, and variants thereof. An albumin protein coding sequence is obtainable by methods know to those of skill in the art for isolating and sequencing cDNA corresponding to human genes. An albumin protein of the invention may include the amino acid sequence of human serum albumin (HSA), provided in SEQ ID NO: 69 or SEQ ID NO: 70, or the amino acid sequence of mouse serum albumin (MSA), provided in SEQ ID NO: 71, or a variant or fragment thereof, preferably a functional variant or fragment thereof. A fragment or variant may or may not be functional, or may retain the function of albumin to some degree. For example, a fragment or variant may retain the ability to bind to an albumin receptor, such as HSA or MSA, by at least 10%, 20%, 30%, 40%, 50%, 60%, 70%, 80%, 90%, 100%, or 105% of the ability of the parent albumin (e.g., the parent albumin from which the fragment or variant is derived). Relative binding ability may be determined by methods known in the art, such as by surface plasmon resonance.

The albumin protein may be a naturally-occurring polymorphic variant of an albumin protein, such as human serum albumin. Generally, variants or fragments of human serum albumin will have at least 5%, 10%, 15%, 20%, 30%, 40%, 50%, 60%, or 70%, and preferably 80%, 90%, 95%, 100%, or 105% or more of human serum albumin or mouse serum albumin's ligand binding activity.

The albumin protein may include the amino acid sequence of bovine serum albumin. Bovine serum albumin proteins include any albumin having an amino acid sequence naturally occurring in cows, for example, as described by Swissprot accession number P02769, and variants thereof as defined herein. Bovine serum albumin proteins also includes fragments of full-length bovine serum albumin or variants thereof, as defined herein.

The albumin protein may comprise the sequence of an albumin derived from one of serum albumin from dog (e.g., Swissprot accession number P49822-1), pig (e.g., Swissprot accession number P08835-1), goat (e.g., Sigma product no. A2514 or A4164), cat (e.g., Swissprot accession number P49064-1), chicken (e.g., Swissprot accession number P19121-1), ovalbumin (e.g., chicken ovalbumin) (e.g., Swissprot accession number P01012-1), turkey ovalbumin (e.g., Swissprot accession number O73860-1), donkey (e.g., Swissprot accession number Q5XLE4-1), guinea pig (e.g., Swissprot accession number Q6WDN9-1), hamster (e.g., as described in DeMarco et al. International Journal for Parasitology 37(11): 1201-1208 (2007)), horse (e.g., Swissprot accession number P35747-1), rhesus monkey (e.g., Swissprot accession number Q28522-1), mouse (e.g., Swissprot accession number P07724-1), pigeon (e.g., as defined by Khan et al. Int. J. Biol. Macromol. 30(3-4), 171-8 (2002)), rabbit (e.g., Swissprot accession number P49065-1), rat (e.g., Swissprot accession number P02770-1) or sheep (e.g., Swissprot accession number P14639-1), and includes variants and fragments thereof as defined herein.

Many naturally-occurring mutant forms of albumin are known to those skilled in the art. Naturally-occurring mutant forms of albumin are described in, for example, Peters, et al. *All About Albumin: Biochemistry, Genetics and Medical Applications*, Academic Press, Inc., San Diego, Calif., p. 170-181 (1996).

Albumin proteins of the invention include variants of naturally-occurring albumin proteins. A variant albumin refers to an albumin protein having at least one amino acid mutation, such as an amino acid mutation generated by an insertion, deletion, or substitution, either conservative or non-conservative, provided that such changes result in an albumin protein for which at least one basic property has not been significantly altered (e.g., has not been altered by more than 5%, 10%, 15%, 20%, 25%, 30%, 35%, or 40%). Exemplary properties which may define the activity of an albumin protein include binding activity (e.g., including binding specificity or affinity to bilirubin, or a fatty acid such as a long-chain fatty acid), osmolarity, or behavior in a certain pH-range.

Typically an albumin protein variant will have at least 40%, at least 50%, at least 60%, and preferably at least 70%, at least 80%, at least 90%, at least 95%, at least 96%, at least 97%, at least 98%, or at least 99% amino acid sequence identity with a naturally-occurring albumin protein, such as the albumin protein of any one of SEQ ID NOs: 69-71.

Methods for the production and purification of recombinant human albumins are well-established (Sleep et al. Biotechnology, 8(1):42-6 (1990)), and include the production of recombinant human albumin for pharmaceutical applications (Bosse et al. J Clin Pharmacol 45(1):57-67 (2005)). The three-dimensional structure of HSA has been elucidated by X-ray crystallography (Carter et al. Science. 244(4909): 1195-8(1998)); Sugio et al. Protein Eng. 12(6): 439-46 (1999)). The HSA polypeptide chain has 35 cysteine residues, which form 17 disulfide bonds, and one unpaired (e.g., free) cysteine at position 34 of the mature protein. Cys-34 of HSA has been used for conjugation of molecules to albumin (Leger et al. Bioorg Med Chem Lett 14(17): 4395-8 (2004); Thibaudeau et al. Bioconjug Chem 16(4): 1000-8 (2005)), and provides a site for site-specific conjugation.

```
(Human serum albumin (HSA), variant 1)
                                          SEQ ID NO: 69
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC
```

-continued

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVAASQAALGL (Human serum albumin (HSA), variant 2)

SEQ ID NO: 70

RGVFRRDAHKSEVAHRFKDLGEENFKALVLIAFAQYLQQCPFEDHVKLV

NEVTEFAKTCVADESAENCDKSLHTLFGDKLCTVATLRETYGEMADCCA

KQEPERNECFLQHKDDNPNLPRLVRPEVDVMCTAFHDNEETFLKKYLYE

IARRHPYFYAPELLFFAKRYKAAFTECCQAADKAACLLPKLDELRDEGK

ASSAKQRLKCASLQKFGERAFKAWAVARLSQRFPKAEFAEVSKLVTDLT

KVHTECCHGDLLECADDRADLAKYICENQDSISSKLKECCEKPLLEKSH

CIAEVENDEMPADLPSLAADFVESKDVCKNYAEAKDVFLGMFLYEYARR

HPDYSVVLLLRLAKTYETTLEKCCAAADPHECYAKVFDEFKPLVEEPQN

LIKQNCELFEQLGEYKFQNALLVRYTKKVPQVSTPTLVEVSRNLGKVGS

KCCKHPEAKRMPCAEDYLSVVLNQLCVLHEKTPVSDRVTKCCTESLVNR

RPCFSALEVDETYVPKEFNAETFTFHADICTLSEKERQIKKQTALVELV

KHKPKATKEQLKAVMDDFAAFVEKCCKADDKETCFAEEGKKLVAASQAA

LGL (Mouse serum albumin (MSA))

SEQ ID NO: 71

RGVFRREAHKSEIAHRYNDLGEQHFKGLVLIAFSQYLQKCSYDEHAKLV

QEVTDFAKTCVADESAANCDKSLHTLFGDKLCAIPNLRENYGELADCCT

KQEPERNECFLQHKDDNPSLPPFERPEAEAMCTSFKENPTTFMGHYLHE

VARRHPYFYAPELLYYAEQYNEILTQCCAEADKESCLTPKLDGVKEKAL

VSSVRQRMKCSSMQKFGERAFKAWAVARLSQTFPNADFAEITKLATDLT

KVNKECCHGDLLECADDRAELAKYMCENQATISSKLQTCCDKPLLKKAH

CLSEVEHDTMPADLPAIAADFVEDQEVCKNYAEAKDVFLGTFLYEYSRR

HPDYSVSLLLRLAKKYEATLEKCCAEANPPACYGTVLAEFQPLVEEPKN

LVKTNCDLYEKLGEYGFQNAILVRYTQKAPQVSTPTLVEAARNLGRVGT

KCCTLPEDQRLPCVEDYLSAILNRVCLLHEKTPVSEHVTKCCSGSLVER

RPCFSALTVDETYVPKEFKAETFTFHSDICTLPEKEKQIKKQTALAELV

KHKPKATAEQLKTVMDDFAQFLDTCCKAADKDTCFSTEGPNLVTRCKDA

LA

Conjugation of Albumin Proteins

An albumin protein of the invention may be conjugated to (e.g., by way of a covalent bond) to any compound of the invention (e.g., by way of the linker portion of a neuraminidase inhibitor monomer or dimer). The albumin protein may be conjugated to any compound of the invention by any method well-known to those of skill in the art for producing small-molecule-protein conjugates. This may include covalent conjugation to a solvent-exposed amino acid, such as a solvent exposed cysteine or lysine. For example, human serum albumin may be conjugated to a compound of the invention by covalent linkage to the sulfur atom corresponding to Cys34 of SEQ ID NO: 69 or Cys40 of SEQ ID NO: 70.

An albumin protein of the invention may be conjugated to any compound of the invention by way of an amino acid located within 10 amino acid residues of the C-terminal or N-terminal end of the albumin protein. An albumin protein may include a C-terminal or N-terminal polypeptide fusion of 1, 2, 3, 4, 5, 6, 7, 8, 9, 10, 15, or 20 or more amino acid. The C-terminal or N-terminal polypeptide fusion may include one or more solvent-exposed cysteine or lysine residues, which may be used for covalent conjugation of a compound of the invention (e.g., conjugation to a neuraminidase inhibitor monomer or dimer, including by way of a linker).

Albumin proteins of the invention include any albumin protein which has been engineered to include one or more solvent-exposed cysteine or lysine residues, which may provide a site for conjugation to a compound of the invention (e.g., conjugation to a neuraminidase inhibitor monomer or dimer, including by way of a linker). Most preferably, the albumin protein will contain a single solvent-exposed cysteine or lysine, thus enabling site-specific conjugation of a compound of the invention.

Exemplary methods for the production of engineered variants of albumin proteins that include one or more conjugation-competent cysteine residues are provided in U.S. Patent Application No. 2017/0081389, which is incorporated herein by reference in its entirety. Briefly, preferred albumin protein variants are those comprising a single, solvent-exposed, unpaired (e.g., free) cysteine residue, thus enabling site-specific conjugation of a linker to the cysteine residue.

Albumin proteins which have been engineered to enable chemical conjugation to a solvent-exposed, unpaired cysteine residue include the following albumin protein variants:

(a) an albumin protein having a substitution of a non-cysteine amino acid residue with a cysteine at an amino acid residue corresponding to any of L585, D1, A2, D562, A364, A504, E505, $T_{79}$, E86, D129, D549, A581, D121, E82, S270, Q397, and A578 of SEQ ID NO: 69;

(b) an albumin protein having an insertion of a cysteine at a position adjacent the N- or C-terminal side of an amino acid residue corresponding to any of L585, D1, A2, D562, A364, A504, E505, $T_{79}$, E86, D129, D549, A581, D121, E82, S270, Q397, and A578 of SEQ ID NO: 69;

(c) an albumin protein engineered to have an unpaired cysteine having a free thiol group at a residue corresponding to any of C369, C361, C91, C177, C567, C316, C75, C169, C124, or C558 of SEQ ID NO: 69, and which may or may not be generated by deletion or substitution of a residue corresponding to C360, C316, C75, C168, C558, C361, C91, C124, C169, or C567 of SEQ ID NO: 69; and/or (d) addition of a cysteine to the N- or C-terminus of an albumin protein.

In some embodiments of the invention, the net result of the substitution, deletion, addition, or insertion events of (a), (b), (c) and/or (d) is that the number of conjugation competent cysteine residues of the polypeptide sequence is increased relative to the parent albumin sequence. In some embodiments of the invention, the net result of the substitution, deletion, addition, or insertion events of (a), (b), (c) and/or (d) is that the number of conjugation competent-cysteine residues of the polypeptide sequence is one, thus enabling site-specific conjugation.

Preferred albumin protein variants also include albumin proteins having a single solvent-exposed lysine residue, thus enabling site-specific conjugation of a linker to the lysine residue. Such variants may be generated by engineering an albumin protein, including any of the methods previously described (e.g., insertion, deletion, substitution, or C-terminal or N-terminal fusion).

Albumin Protein-Binding Peptides

Conjugation of a biologically-active compound to an albumin protein-binding peptide can alter the pharmacodynamics of the biologically-active compound, including the alteration of tissue uptake, penetration, and diffusion. In a preferred embodiment, conjugation of an albumin protein-binding peptide to a compound of the invention (e.g., a neuraminidase inhibitor monomer or dimer, by way of a linker) increases the efficacy or decreases the toxicity of the compound, as compared to the compound alone.

Albumin protein-binding peptides of the invention include any polypeptide having an amino acid sequence of 5 to 50 (e.g., 5 to 40, 5 to 30, 5 to 20, 5 to 15, 5 to 10, 10 to 50, 10 to 30, or 10 to 20) amino acid residues that has affinity for and functions to bind an albumin protein, such as any of the albumin proteins described herein. Preferably, the albumin protein-binding peptide binds to a naturally occurring serum albumin, most preferably human serum albumin. An albumin protein-binding peptide can be of different origins, e.g., synthetic, human, mouse, or rat. Albumin protein-binding peptides of the invention include albumin protein-binding peptides which have been engineered to include one or more (e.g., two, three, four, or five) solvent-exposed cysteine or lysine residues, which may provide a site for conjugation to a compound of the invention (e.g., conjugation to a neuraminidase inhibitor monomer or dimer, including by way of a linker). Most preferably, the albumin protein-binding peptide will contain a single solvent-exposed cysteine or lysine, thus enabling site-specific conjugation of a compound of the invention. Albumin protein-binding peptides may include only naturally occurring amino acid residues, or may include one or more non-naturally occurring amino acid residues. Where included, a non-naturally occurring amino acid residue (e.g., the side chain of a non-naturally occurring amino acid residue) may be used as the point of attachment for a compound of the invention (e.g., a neuraminidase inhibitor monomer or dimer, including by way of a linker). Albumin protein-binding peptides of the invention may be linear or cyclic. Albumin protein-binding peptides of the invention include any albumin protein-binding peptides known to one of skill in the art, examples of which, are provided herein.

Albumin protein-binding peptide, and conjugates including an albumin protein-binding peptide, preferably bind an albumin protein (e.g., human serum albumin) with an affinity characterized by a dissociation constant, Kd, that is less than about 100 μM, preferably less than about 100 nM, and most preferably do not substantially bind other plasma proteins. Specific examples of such compounds are linear or cyclic peptides, preferably between about 10 and 20 amino acid residues in length, optionally modified at the N-terminus or C-terminus or both.

Albumin protein-binding peptides include linear and cyclic peptides comprising the following general formulae, wherein Xaa is any amino acid:

SEQ ID NO: 74
Xaa-Xaa-Cys-Xaa-Xaa-Xaa-Xaa-Xaa-Cys-Xaa-Xaa-Phe-

Cys-Xaa-Asp-Trp-Pro-Xaa-Xaa-Xaa-Ser-Cys

SEQ ID NO: 75
Val-Cys-Tyr-Xaa-Xaa-Xaa-Ile-Cys-Phe

SEQ ID NO: 76
Cys-Tyr-Xaa-Pro-Gly-Xaa-Cys

SEQ ID NO: 77
Asp-Xaa-Cys-Leu-Pro-Xaa-Trp-Gly-Cys-Leu-Trp

SEQ ID NO: 78
Trp-Cys-Asp-Xaa-Xaa-Leu-Xaa-Ala-Xaa-Asp-Leu-Cys

SEQ ID NO: 79
Asp-Leu-Val-Xaa-Leu-Gly-Leu-Glu-Cys-Trp

Albumin protein-binding peptides of the invention further include any of the following peptide sequences, which may be linear or cyclic:

SEQ ID NO: 80
DLCLRDWGCLW

SEQ ID NO: 81
DICLPRWGCLW

SEQ ID NO: 82
MEDICLPRWGCLWGD

SEQ ID NO: 83
QRLMEDICLPRWGCLWEDDE

SEQ ID NO: 84
QGLIGDICLPRWGCLWGRSV

SEQ ID NO: 85
QGLIGDICLPRWGCLWGRSVK

SEQ ID NO: 86
EDICLPRWGCLWEDD

SEQ ID NO: 87
RLMEDICLPRWGCLWEDD

SEQ ID NO: 88
MEDICLPRWGCLWEDD

SEQ ID NO: 89
MEDICLPRWGCLWED

SEQ ID NO: 90
RLMEDICLARWGCLWEDD

SEQ ID NO: 91
EVRSFCTRWPAEKSCKPLRG

SEQ ID NO: 92
RAPESFVCYWETICFERSEQ

SEQ ID NO: 93
EMCYFPGICWM

Albumin protein-binding peptides of SEQ ID NOs: 74-93 may further include additional amino acids at the N-terminus (Xaa)x and/or additional amino acids at the C-terminus (Xaa)z, wherein Xaa is any amino acid and x and z are a whole number greater or equal to zero, generally less than 100, preferably less than 10 and more preferably 0, 1, 2, 3, 4 or 5.

Further exemplary albumin protein-binding peptides are provided in U.S. Patent Application No. 2005/0287153, which is incorporated herein by reference in its entirety.

Conjugation of Albumin Protein-Binding Peptides

An albumin protein-binding peptide of the invention may be conjugated to (e.g., by way of a covalent bond) to any compound of the invention (e.g., by way of the linker portion of a neuraminidase inhibitor monomer or dimer). The albumin protein-binding peptide may be conjugated to any compound of the invention by any method known to those of skill in the art for producing peptide-small molecule conjugates. This may include covalent conjugation to the side chain group of an amino acid residue, such as a cysteine, a lysine, or a non-natural amino acid. Alternately, covalent conjugation may occur at the C-terminus (e.g., to the C-terminal carboxylic acid, or to the side chain group of the C-terminal residue) or at the N-terminus (e.g., to the N-terminal amino group, or to the side chain group of the N-terminal amino acid).

V. Linkers

A linker refers to a linkage or connection between two or more components in a conjugate described herein (e.g., between two neuraminidase inhibitors in a conjugate described herein, between a neuraminidase inhibitor and an Fc domain or an albumin protein in a conjugate described herein, and between a dimer of two neuraminidase inhibitors and an Fc domain or an albumin protein in a conjugate described herein).

Linkers in Conjugates Having an Fc Domain or an Albumin Protein Covalently Linked to Dimers of Neuraminidase Inhibitors In a conjugate containing an Fc domain monomer, an Fc domain, an Fc-binding peptide, an albumin protein, or an albumin protein-binding peptide covalently linked to one or more dimers of neuraminidase inhibitors as described herein, a linker in the conjugate (e.g., L or L') may be a branched structure. As described further herein, a linker in a conjugate described herein (e.g., L or L') may be a multivalent structure, e.g., a divalent or trivalent structure having two or three arms, respectively. In some embodiments when the linker has three arms, two of the arms may be attached to the first and second neuraminidase inhibitors and the third arm may be attached to the Fc domain monomer, and Fc domain, an Fc-binding peptide, an albumin protein, or an albumin protein-binding peptide. In some embodiments when the linker has two arms, one arm may be attached to an Fc domain or an albumin protein and the other arm may be attached to one of the two neuraminidase inhibitors. In other embodiments, a linker with two arms may be used to attach the two neuraminidase inhibitors on a conjugate containing an Fc domain or albumin protein covalently linked to one or more dimers of neuraminidase inhibitors.

In some embodiments, a linker in a conjugate having an Fc domain or an albumin protein covalently linked to one or more dimers of neuraminidase inhibitors is described by formula (D-L-1):

(L-I)

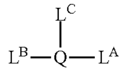

wherein $L^A$ is described by formula $G^{A1}$-$(Z^{A1})_{g1}$—$(Y^{A1})_{h1}$—$(Z^{A2})_{i1}$—$(Y^{A2})_{j1}$—$(Z^{A3})_{k1}$—$(Y^{A3})_{l1}$—$(Z^{A4})_{m1}$—$(Y^{A4})_{n1}$—$(Z^{A5})o_1$-$G^{A2}$; $L^B$ is described by formula $G^{B1}$-$(Z^{B1})_{g2}$—$(Y^{B1})_{h2}$—$(Z^{B2})_{i2}$—$(Y_{B2})_{j2}$—$(Z^{B3})_{k2}$—$(Y^{B3})_{l2}$—$(Z^{B4})_{m2}$—$(Y^{B4})_{n2}$—$(Z^{B5})o_2$-$G^{B2}$; $L^C$ is described by formula $G^{C1}$-$(Z^{C1})_{g3}$—$(Y^{C1})_{h3}$—$(Z^{C2})_{i3}$—$(Y^{C2})_{j3}$—$(Z^{C3})_{k3}$—$(Y^{C3})_{l3}$—$(Z^{C4})_{m3}$—$(Y^{C4})_{n3}$—$(Z^{C5})o_3$-$G^{C2}$; $G^{A1}$ is a bond attached to Q in formula (D-L-1); $G^{A2}$ is a bond attached to the first neuraminidase inhibitor (e.g., $A_1$); $G^{B1}$ is a bond attached to Q in formula (D-L-I); $G^{B2}$ is a bond attached to the second neuraminidase inhibitor (e.g., $A_2$); $G^{C1}$ is a bond attached to Q in formula (D-L-I); $G^{C2}$ is a bond attached to an Fc domain monomer, an Fc domain, an Fc-binding peptide, an albumin protein, or an albumin protein-binding peptide, or a functional group capable of reacting with a functional group conjugated to an Fc domain monomer, an Fc domain, an Fc-binding peptide, an albumin protein, or an albumin protein-binding peptide (e.g., maleimide and cysteine, amine and activated carboxylic acid, thiol and maleimide, activated sulfonic acid and amine, isocyanate and amine, azide and alkyne, and alkene and tetrazine); each of $Z^{A1}$, $Z^{A2}$, $Z^{A3}$, $Z^{A4}$, $Z^{A5}$, $Z^{B1}$, $Z^{B2}$, $Z^{B3}$, $Z^{B4}$, $Z^{B5}$, $Z^{C1}$, $Z^{C2}$, $Z^{C3}$, $Z^{C4}$, and $Z^{C5}$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene; each of $Y^{A1}$, $Y^{A2}$, $Y^{A3}$, $Y^{A4}$, $Y^{B1}$, $Y^{B2}$, $Y^{B3}$, $Y^{B4}$, $Y^{C1}$, $Y^{C2}$, $Y^{C3}$ and $Y^{C4}$ is, independently, O, S, $NR^i$, P, carbonyl, thiocarbonyl, sulfonyl, phosphate, phosphoryl, or imino; $R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; each of g1, h1, i1, j1, k1, l1, m1, n1, o1, g2, h2, i2, j2, k2, l2, m2, n2, o2, g3, h3, i3, j3, k3, l3, m3, n3, and o3 is, independently, 0 or 1; Q is a nitrogen atom, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene.

In some embodiments, $L^C$ may have two points of attachment to the Fc domain (e.g., two $G^{C2}$) In some embodiments, L includes a polyethylene glycol (PEG) linker. A PEG linker includes a linker having the repeating unit structure $(—CH_2CH_2O—)_n$, where n is an integer from 2 to 100. A polyethylene glycol linker may covalently join a neuraminidase inhibitor and E (e.g., in a conjugate of any one of formulas (M-I)-(M-X)). A polyethlylene glycol linker may covalently join a first neuraminidase inhibitor and a second neuraminidase inhibitor (e.g., in a conjugate of any one of formulas (D-I)-(D-X)). A polyethylene glycol linker may covalently join a neuraminidase inhibitor dimer and E (e.g., in a conjugate of any one of formulas (D-I)-(D-X)). A polyethylene glycol linker may selected any one of $PEG_2$ to $PEG_{100}$ (e.g., $PEG_2$, $PEG_3$, $PEG_4$, $PEG_5$, $PEG_5$-$PEG_{10}$, $PEG_{10}$-$PEG_{20}$, $PEG_{20}$-$PEG_{30}$, $PEG_{30}$-$PEG_{40}$, $PEG_{50}$-$PEG_{60}$, $PEG_{60}$-$PEG_{70}$, $PEG_{70}$-$PEG_{80}$, $PEG_{80}$-$PEG_{90}$, $PEG_{90}$-$PEG_{100}$). In some embodiments, $L^c$ includes a PEG linker, where $L^C$ is covalently attached to each of Q and E.

Linkers of formula (D-L-1) that may be used in conjugates described herein include, but are not limited to

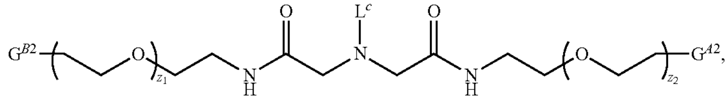,

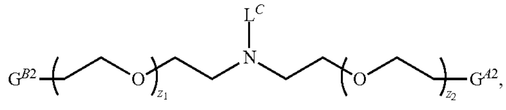,

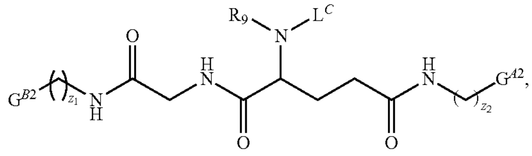,

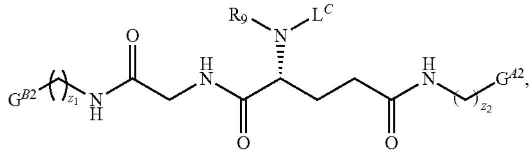,

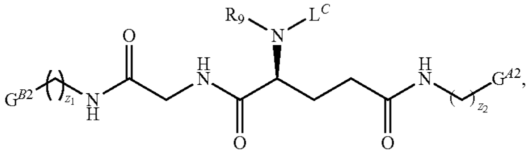,

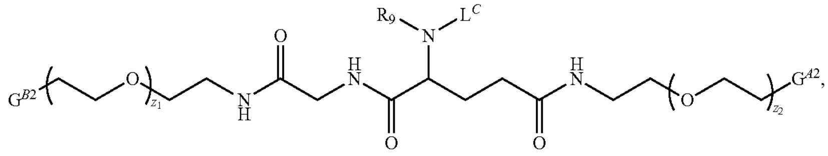,

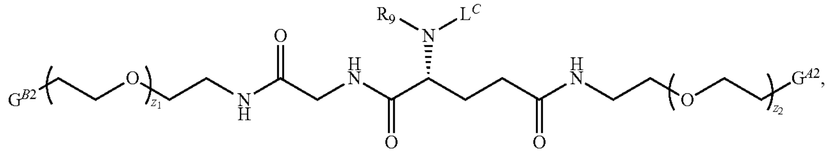,

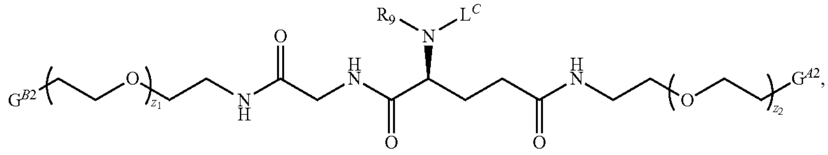,

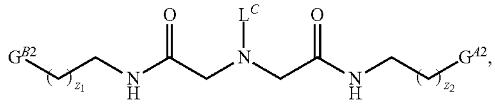,

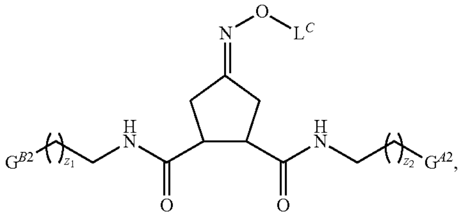,

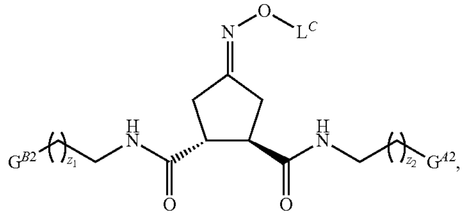,

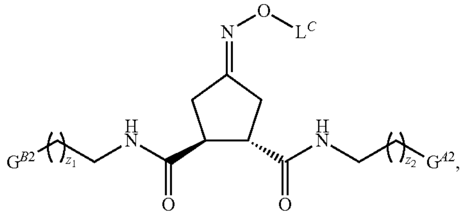,

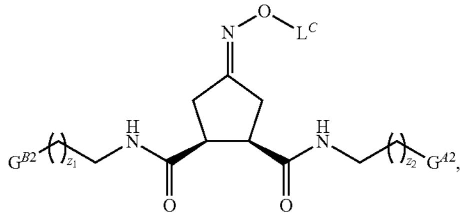,

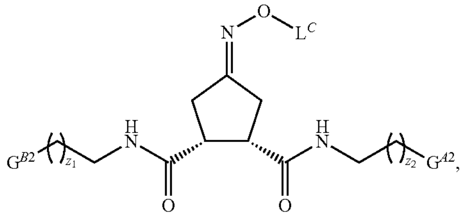,

-continued
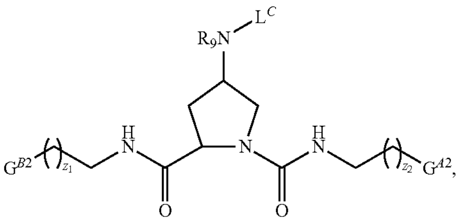
,
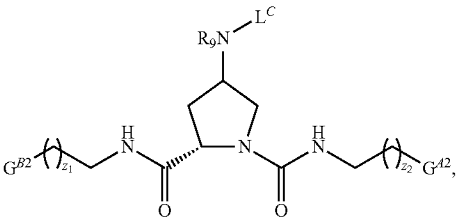
,
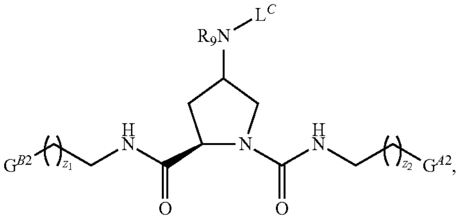
,
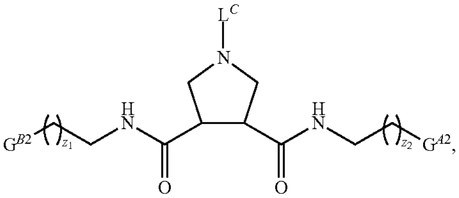
,
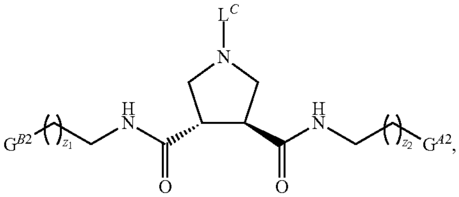
,
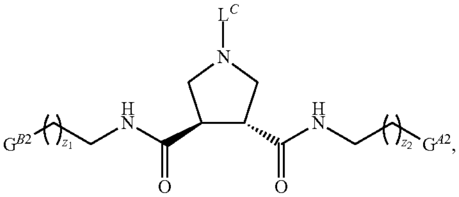
,
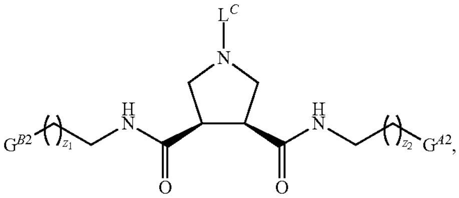
,
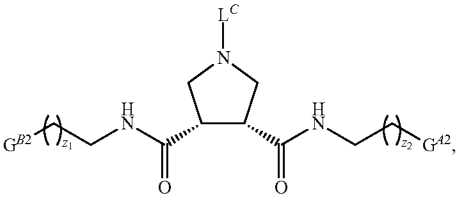
,
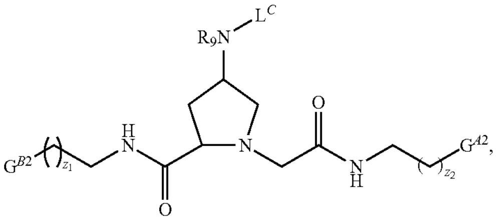
,
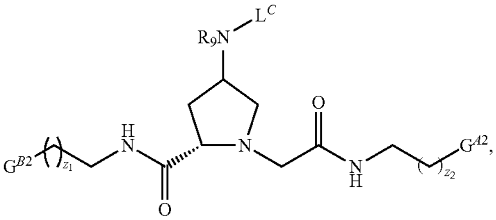
,
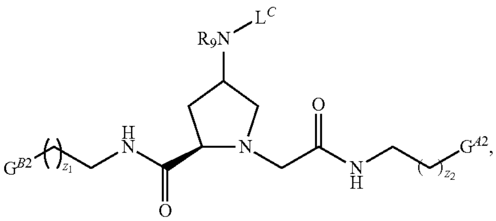
,
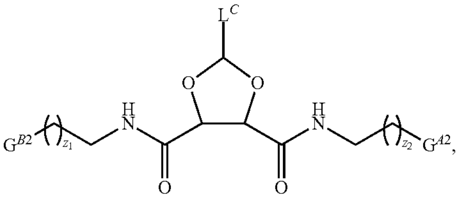
,
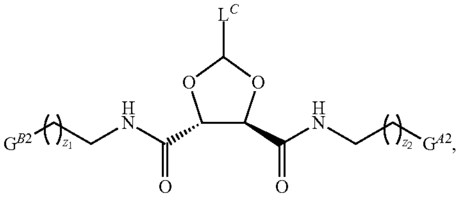
,
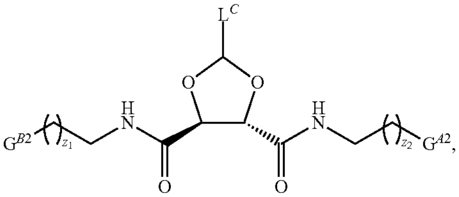
,
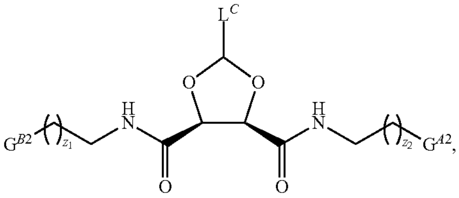
,
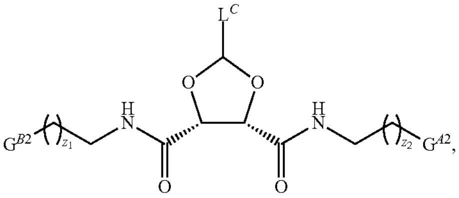
, -continued
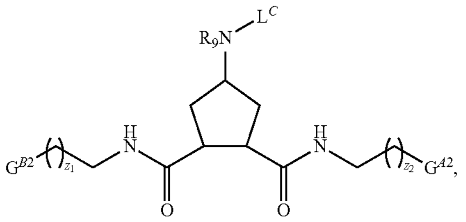,
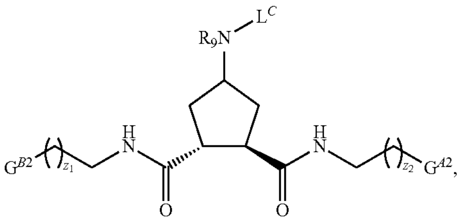,
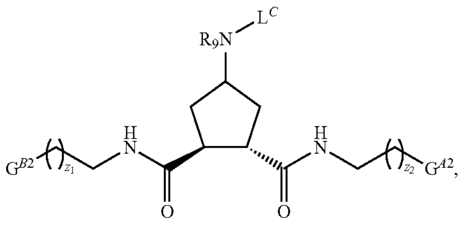,
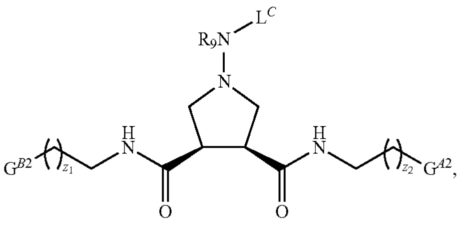,
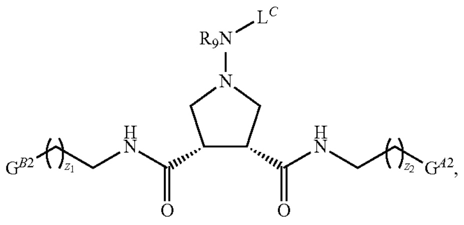,
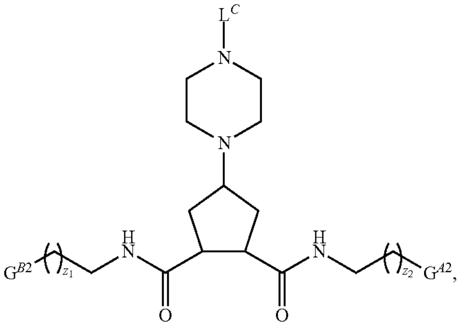,
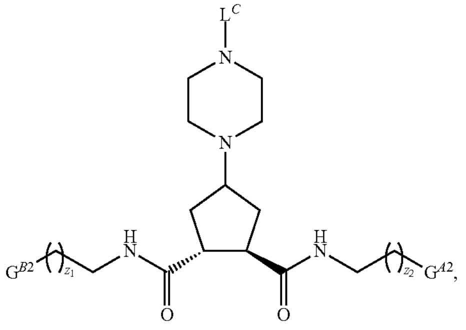,
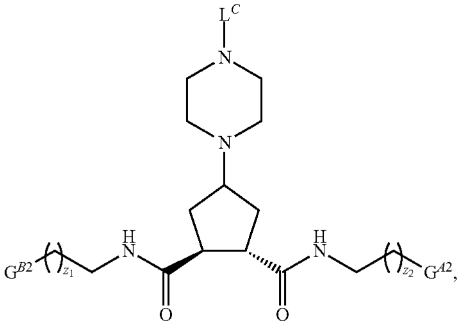,
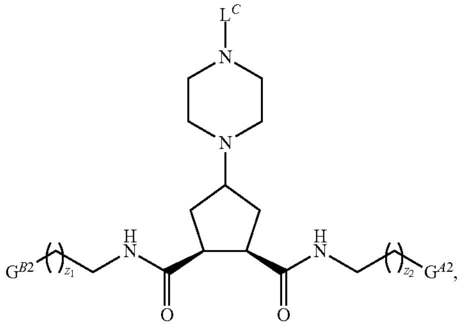,
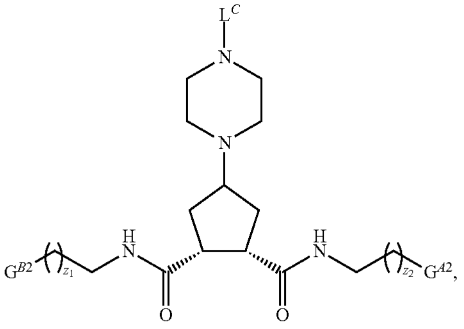,
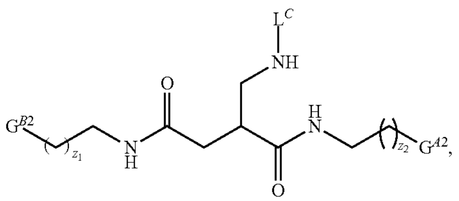,
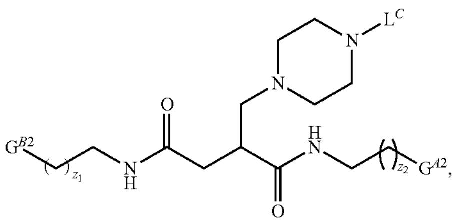, -continued
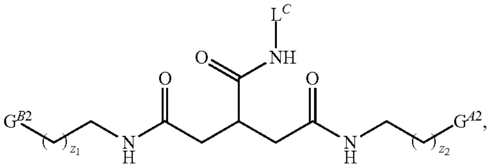
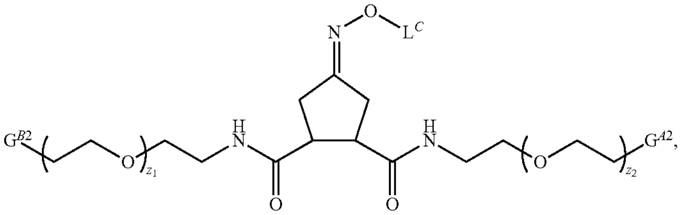
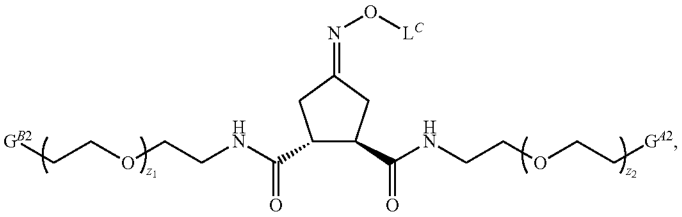
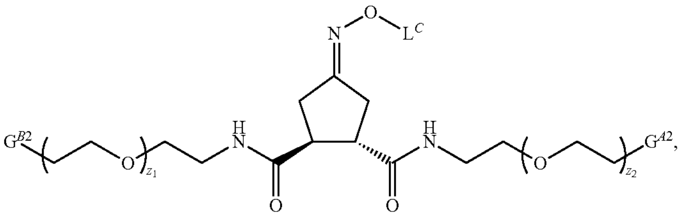
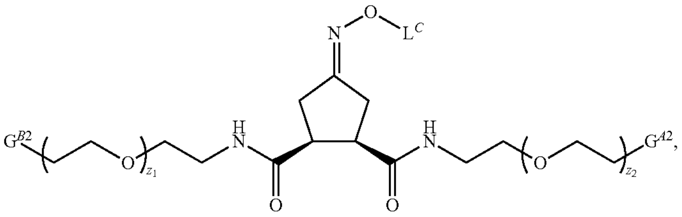
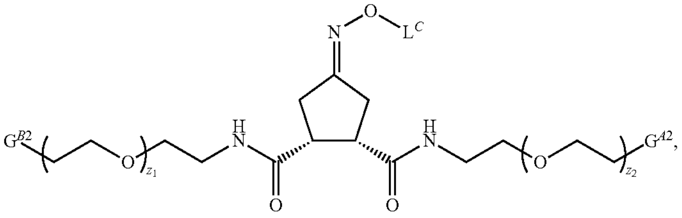
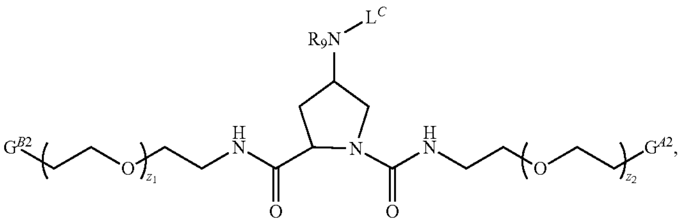
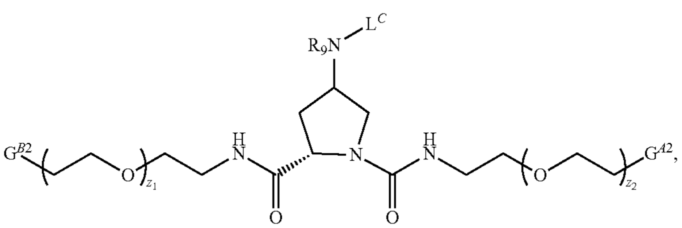

-continued
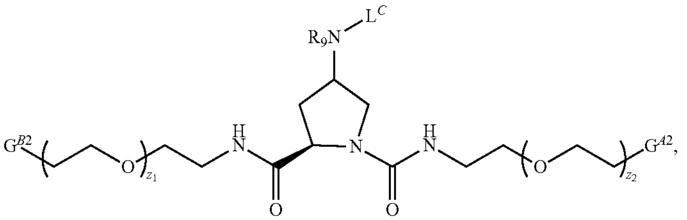
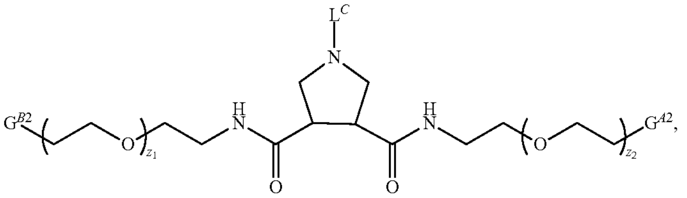
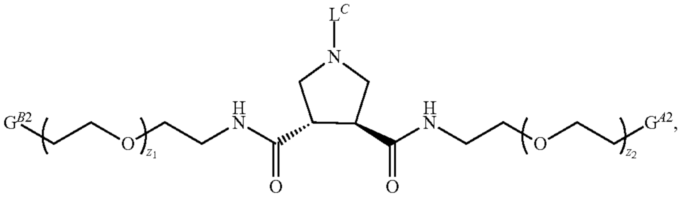
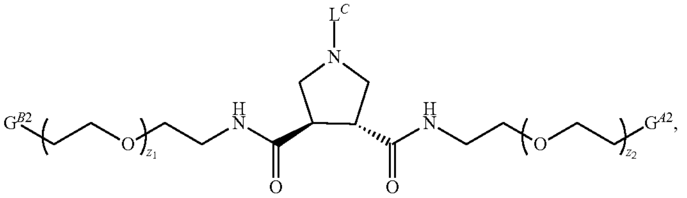
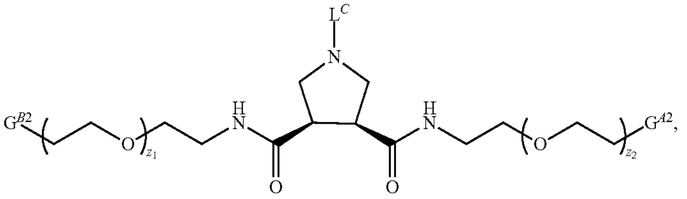
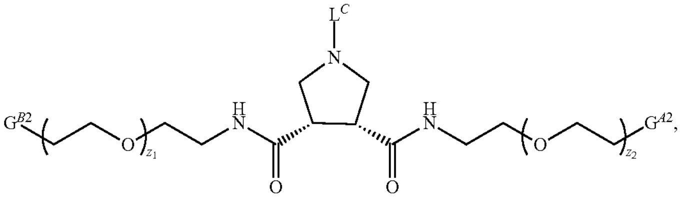
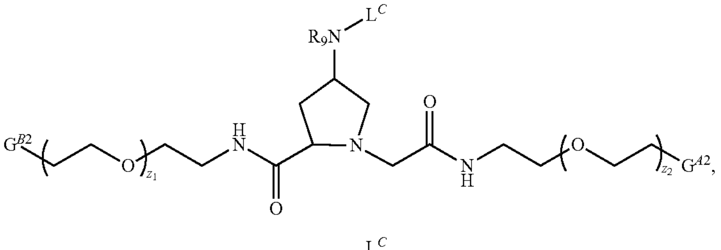
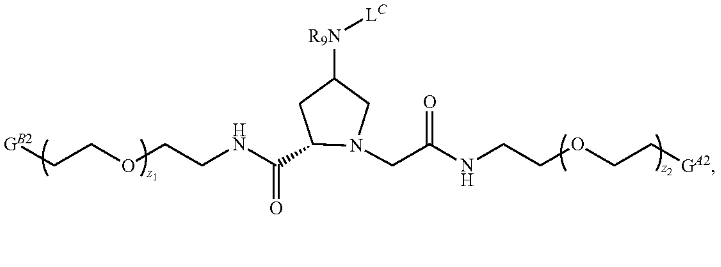

-continued
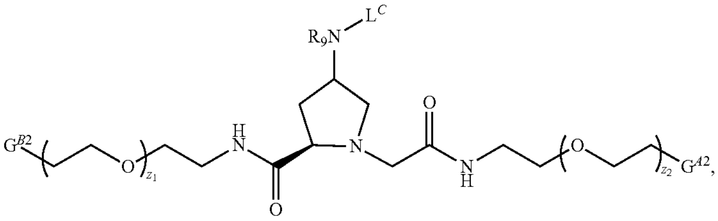
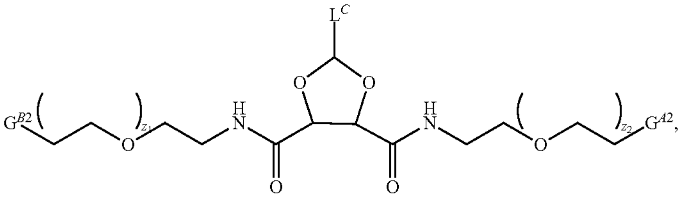
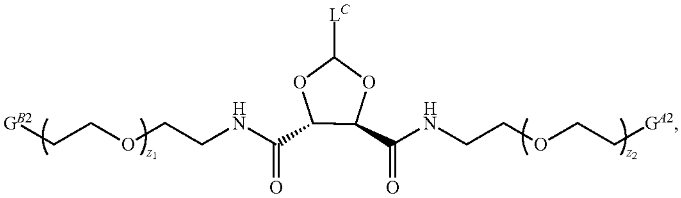
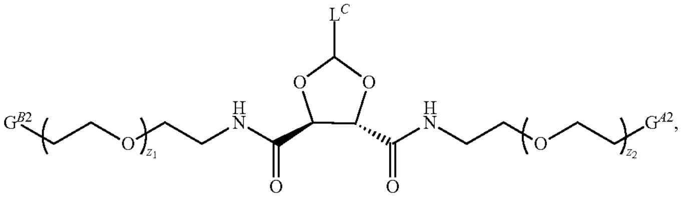
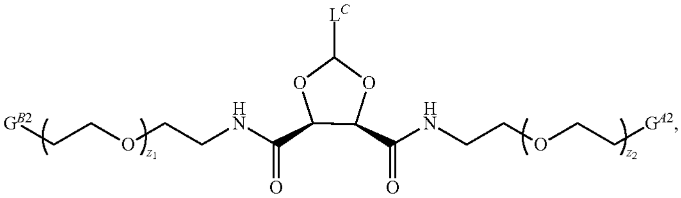
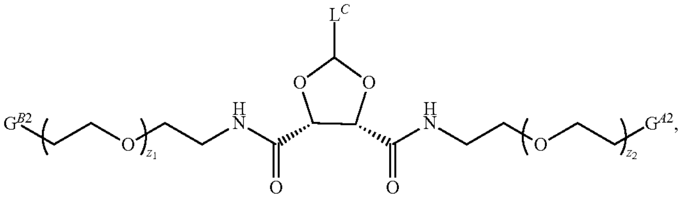
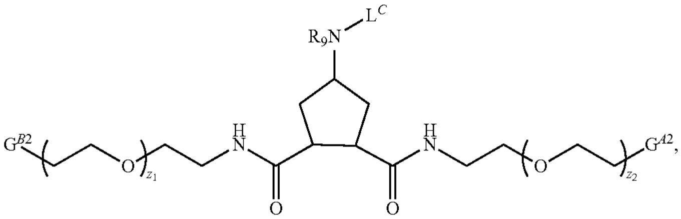
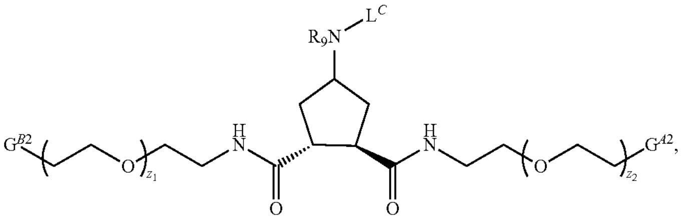

-continued
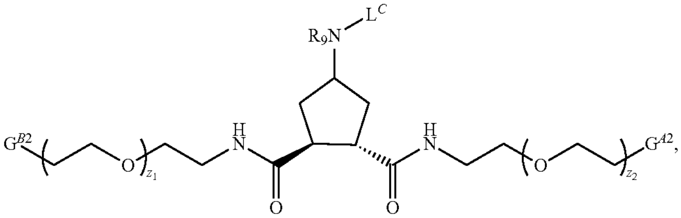,
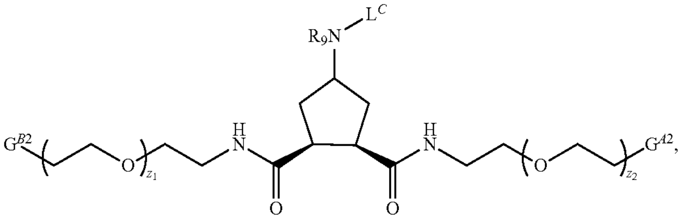,
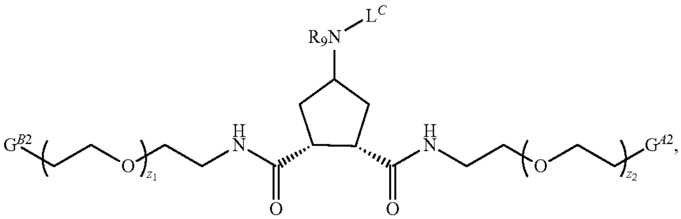,
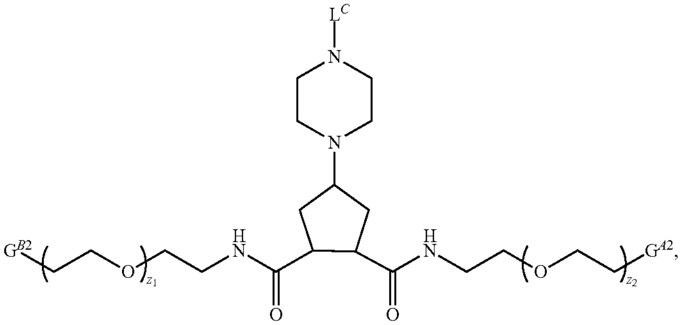,
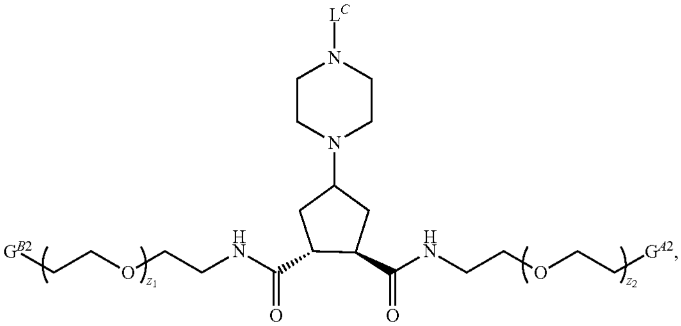,
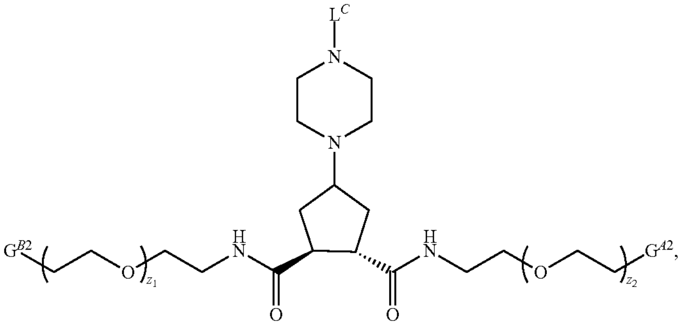, -continued
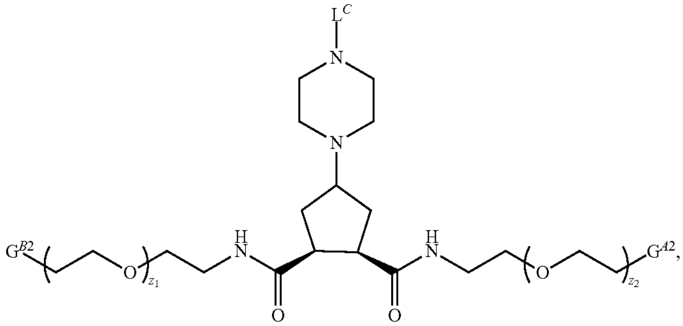
,
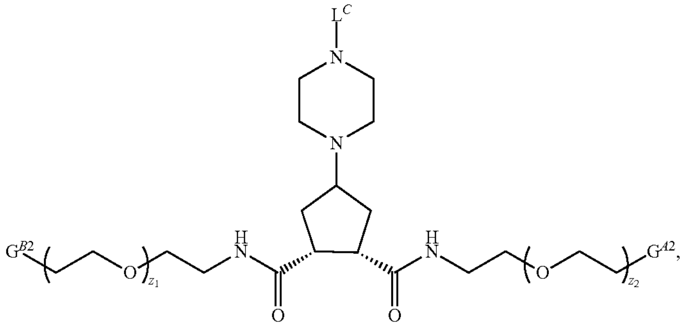
,
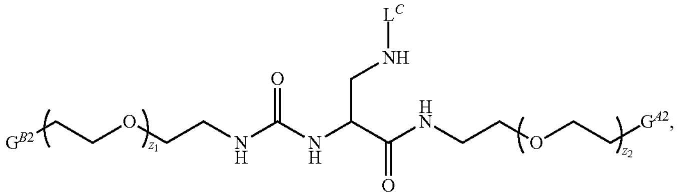
,
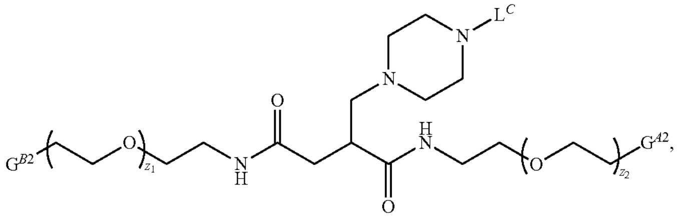
,
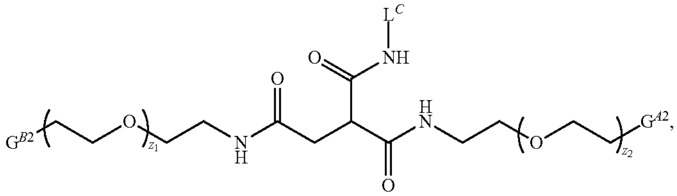
,
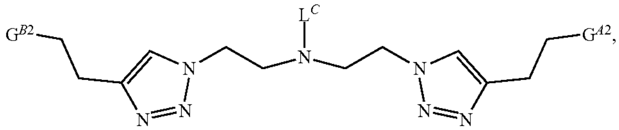
,
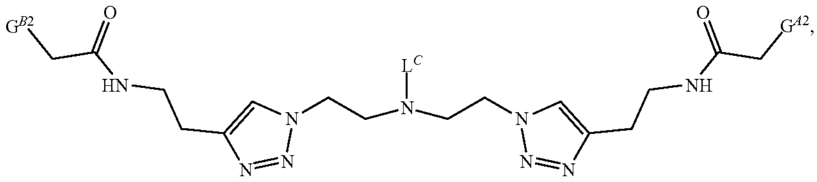
, -continued
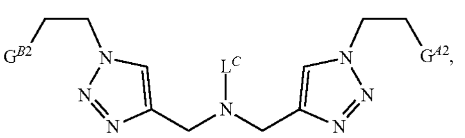
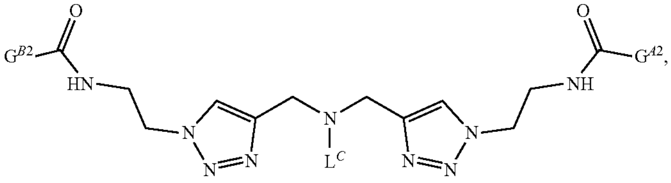
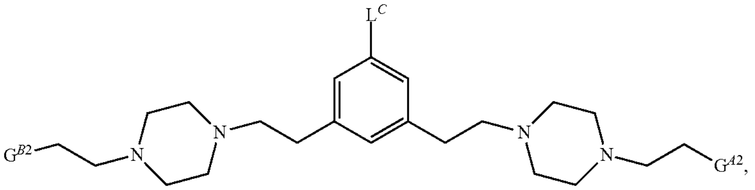
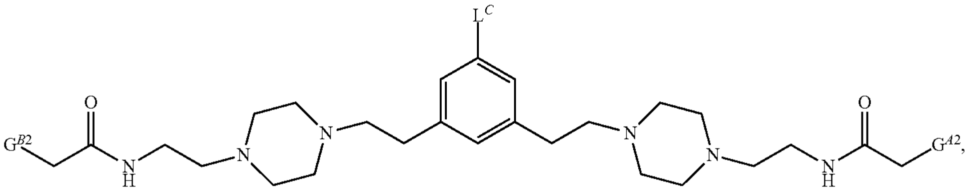
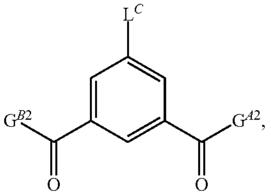
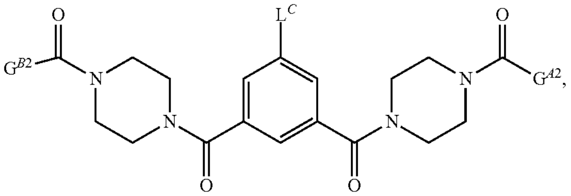
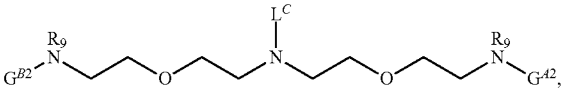
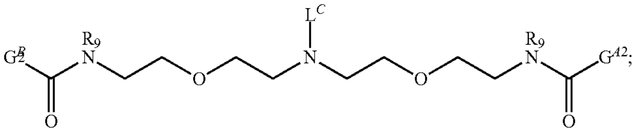
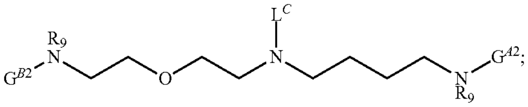
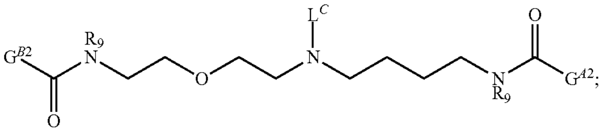
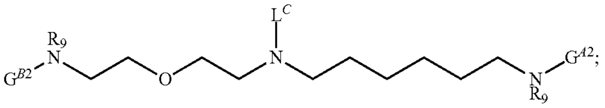
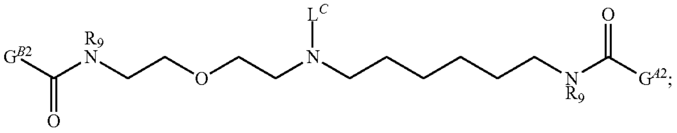
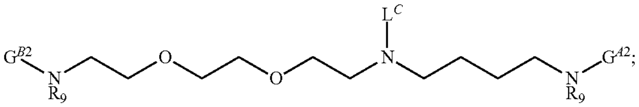
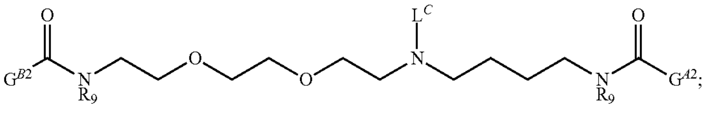

-continued
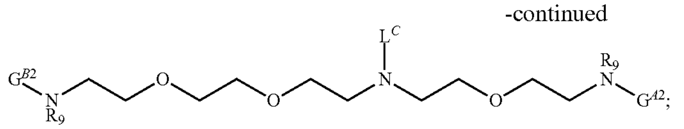
or
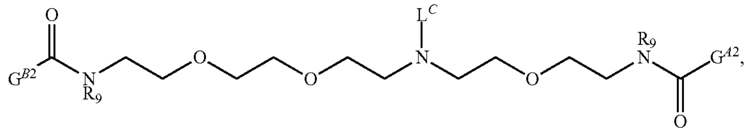
wherein $z_1$ and $z_2$ are each, independently, and integer from 1 to 20; and $R_9$ is selected from H, C1-C20 alkyl, C3-C20 cycloalkyl, C3-C20 heterocycloalkyl; C5-C15 aryl, and C2-C15 heteroaryl.
Linkers of the formula (D-L-1) may also include any of
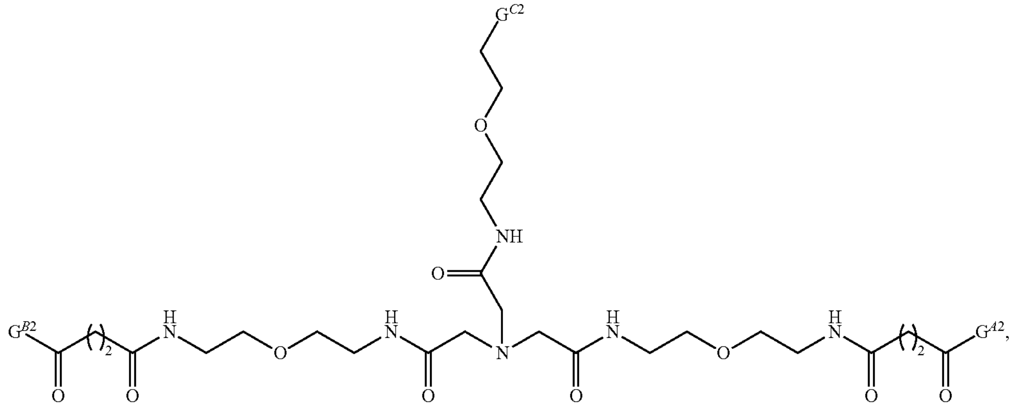
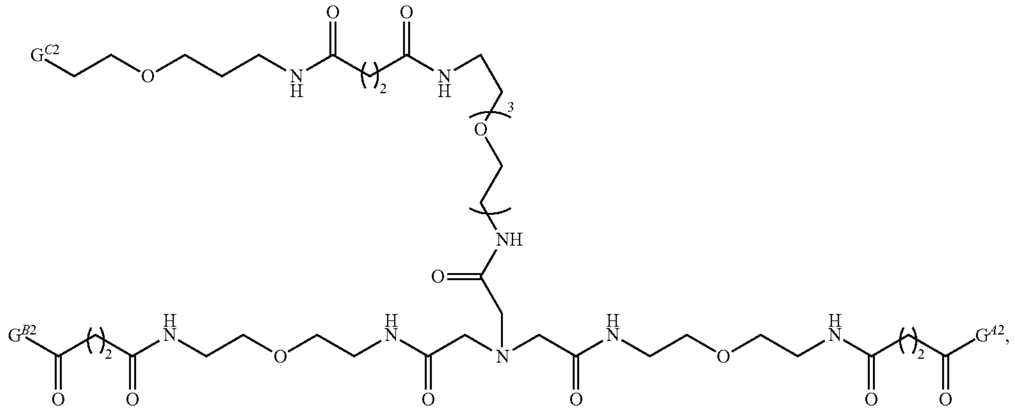
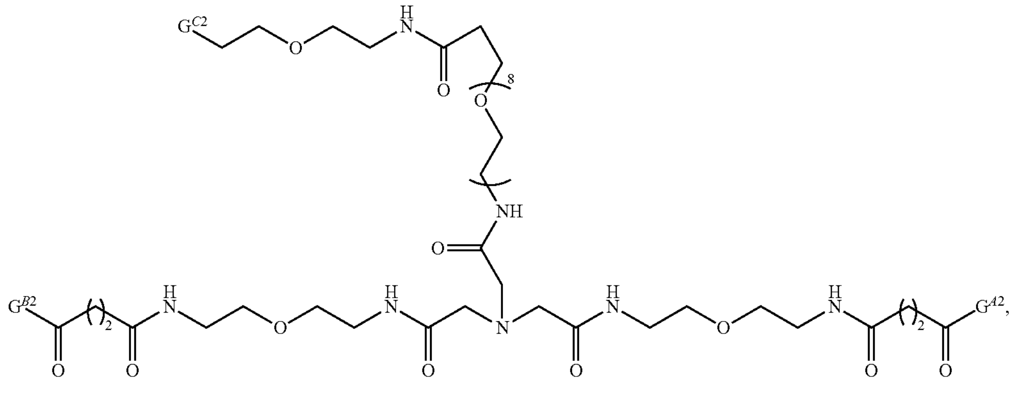

-continued
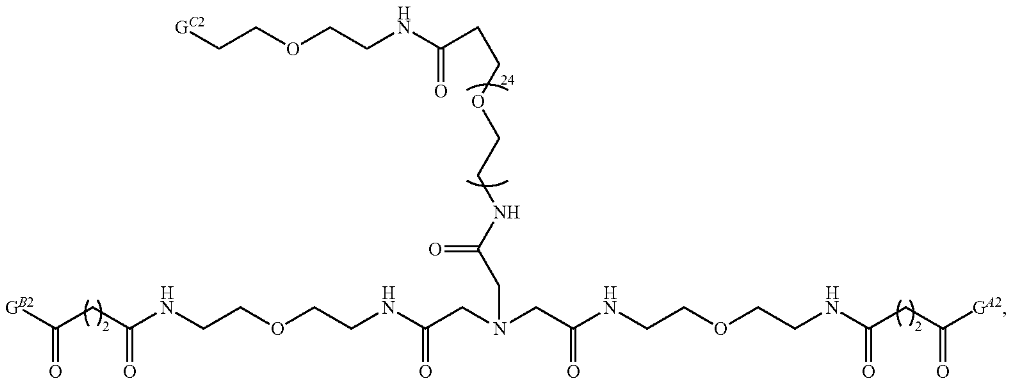
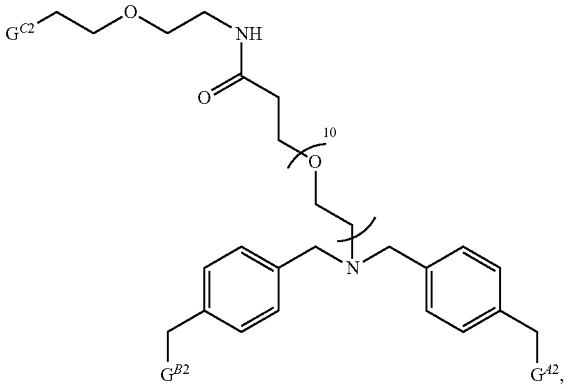
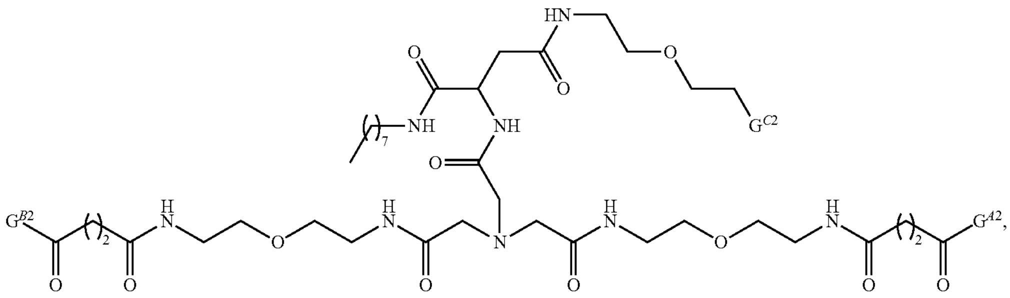
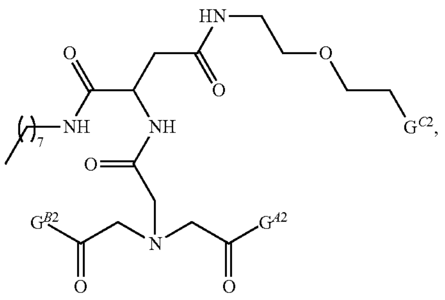
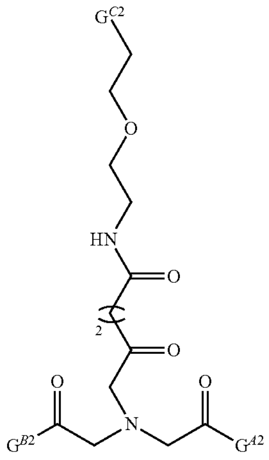
,

-continued
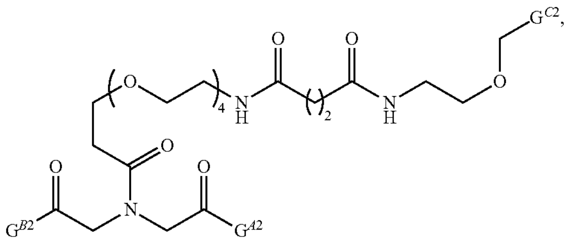
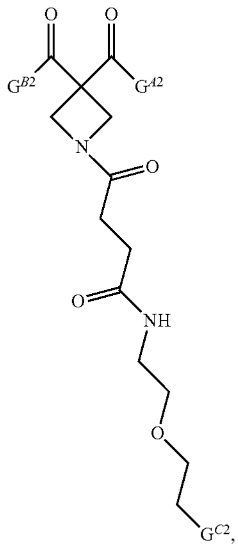
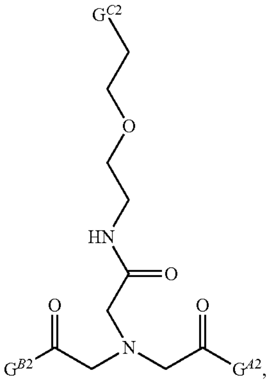
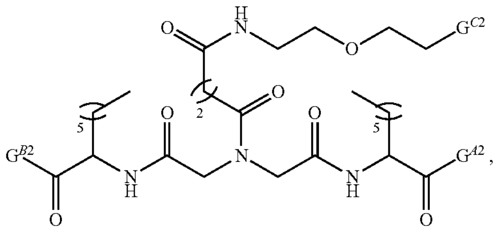
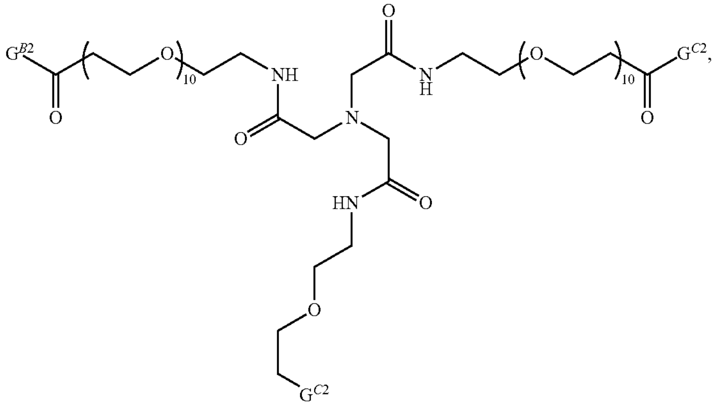
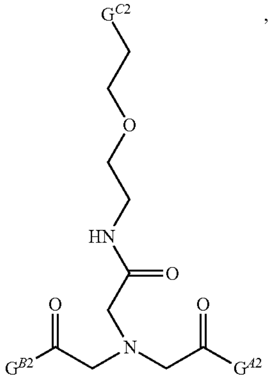
, -continued
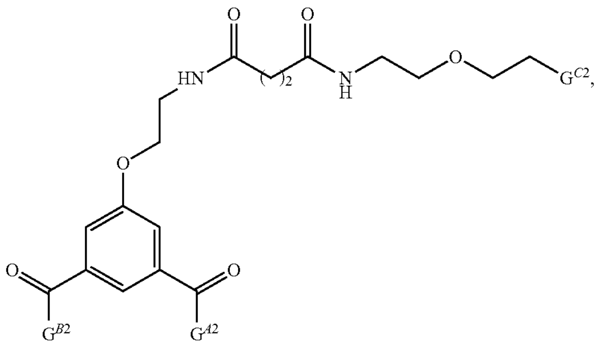
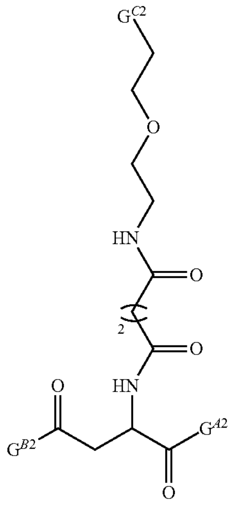
,
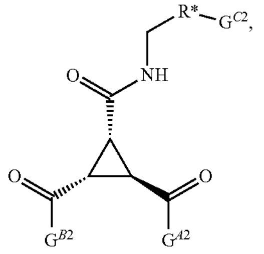
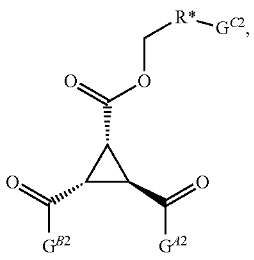
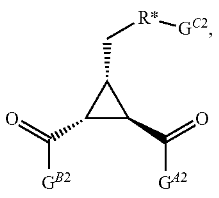
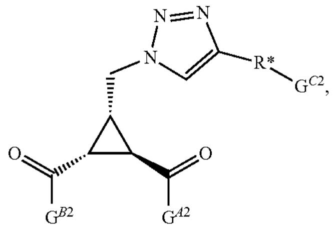
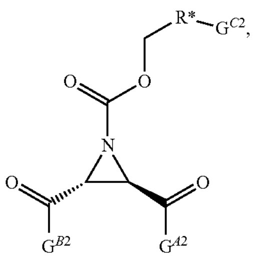
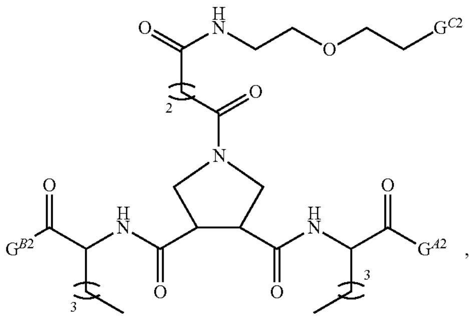
,
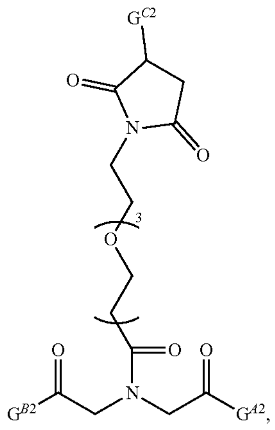

-continued
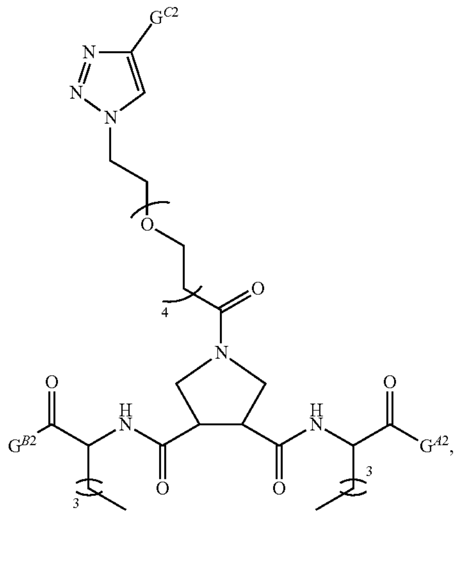
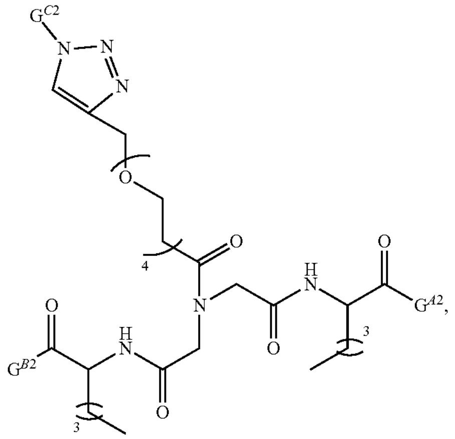
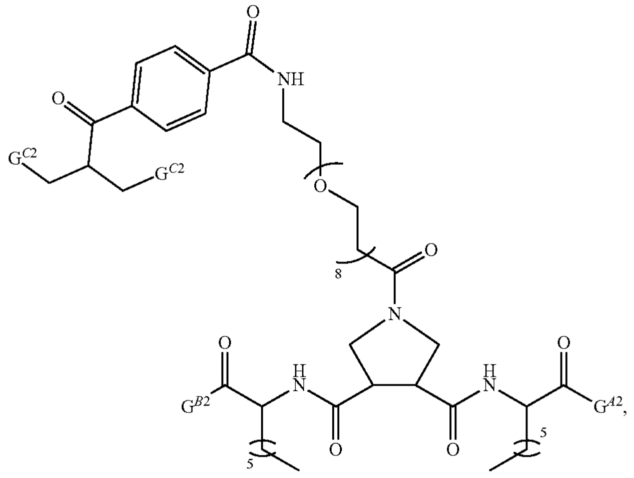
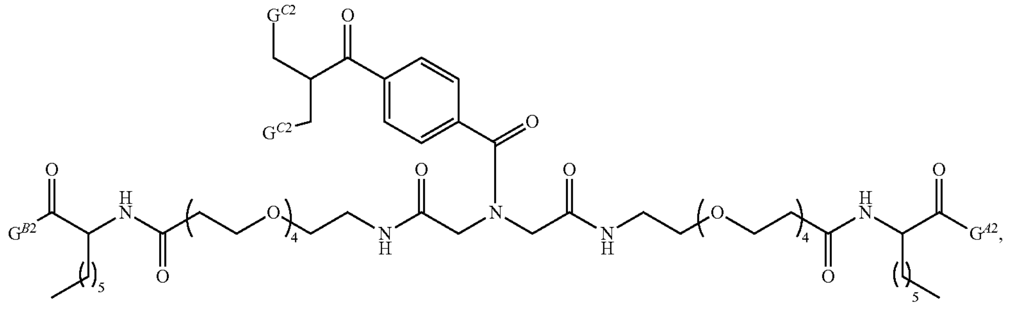
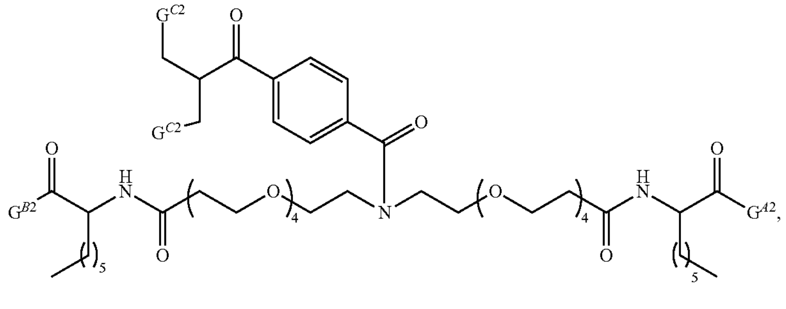

-continued
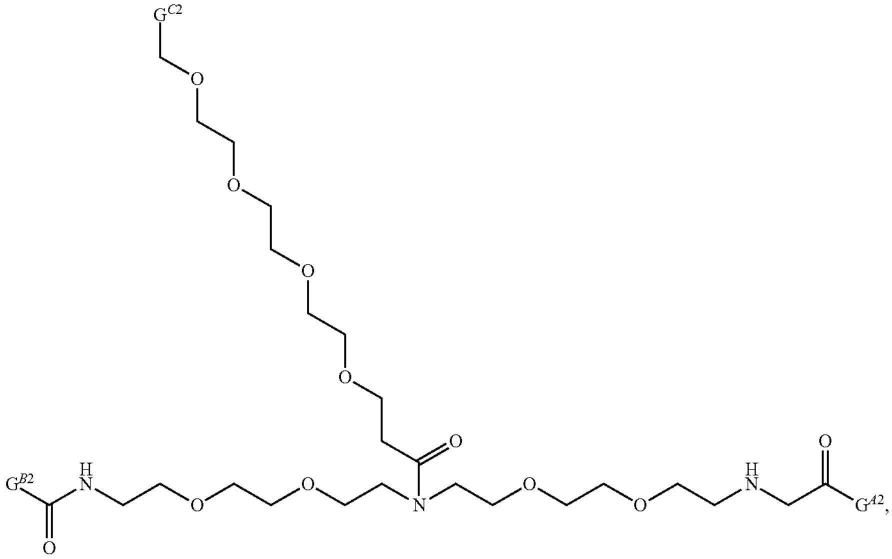
,
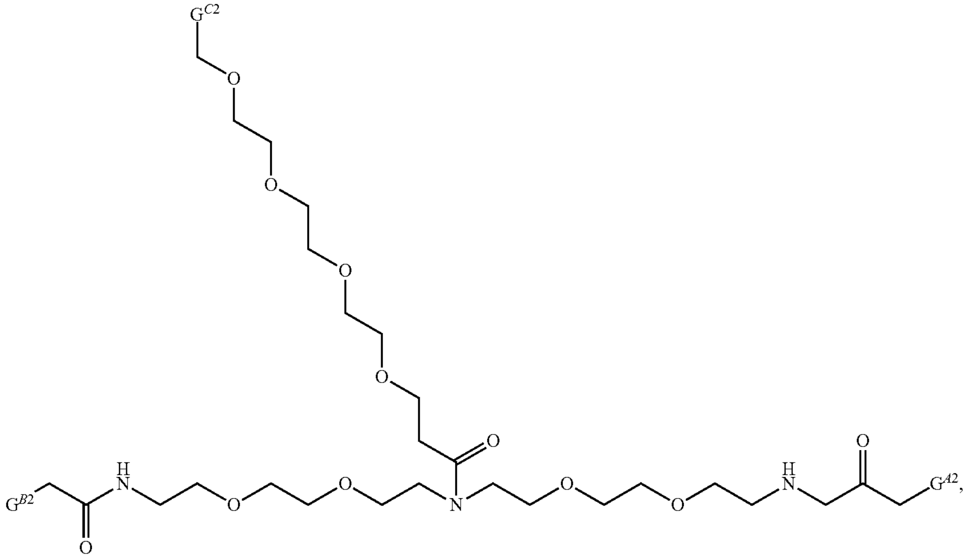
,
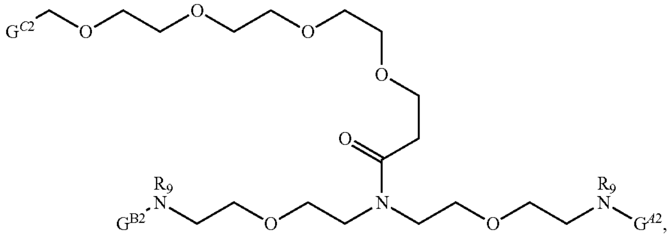
,
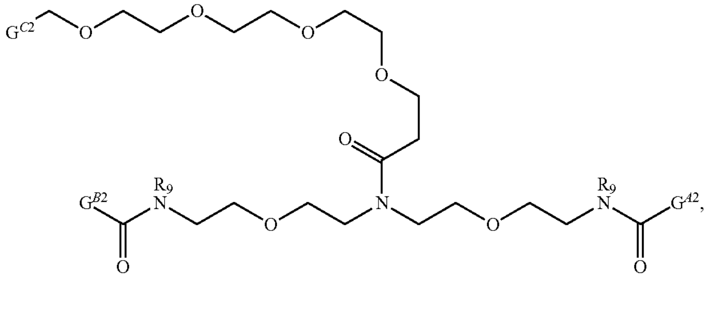
,

-continued
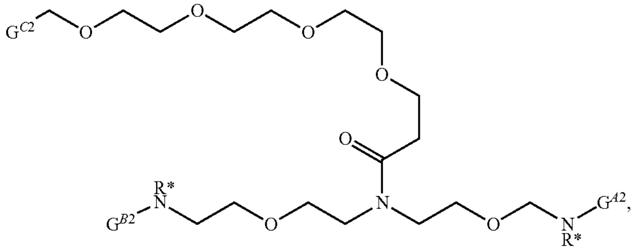
,
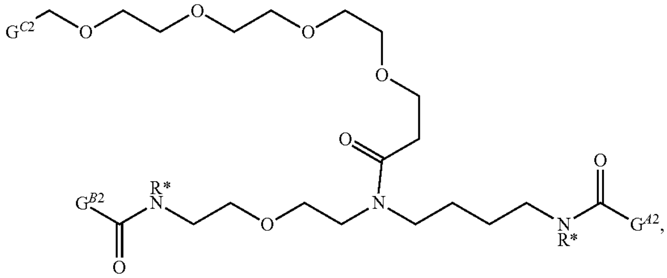
,
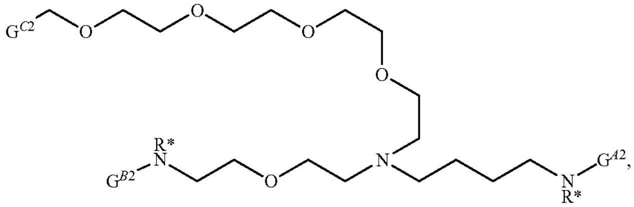
,
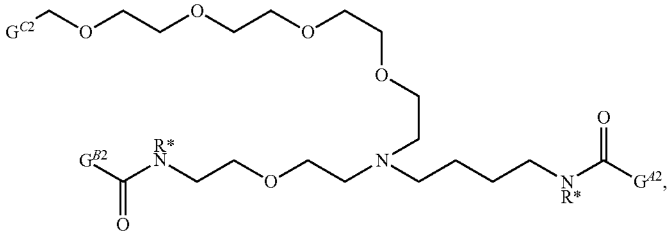
,
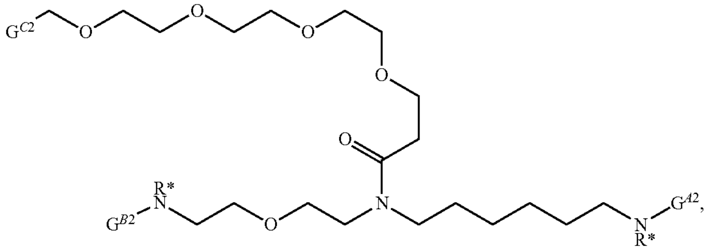
,
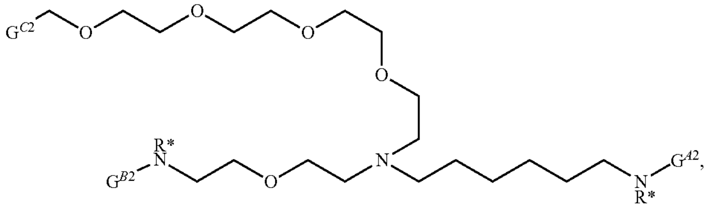
,
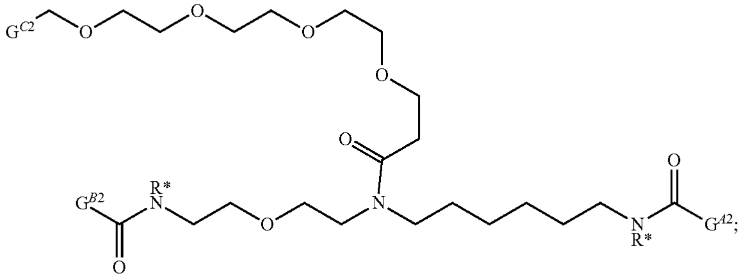
;

-continued
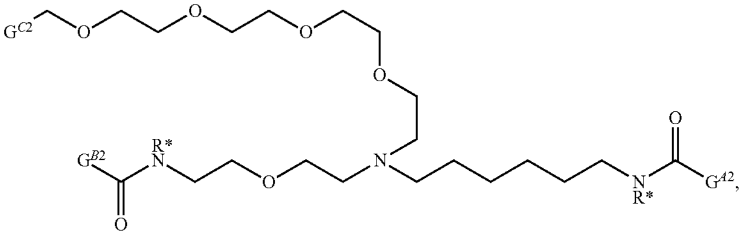
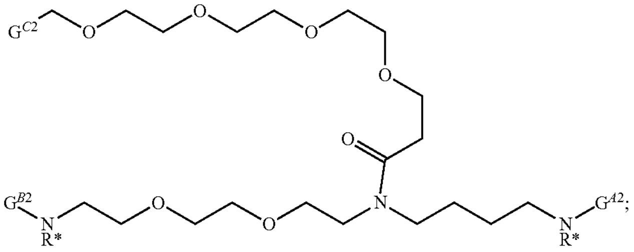
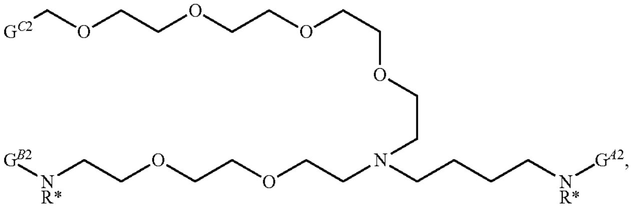
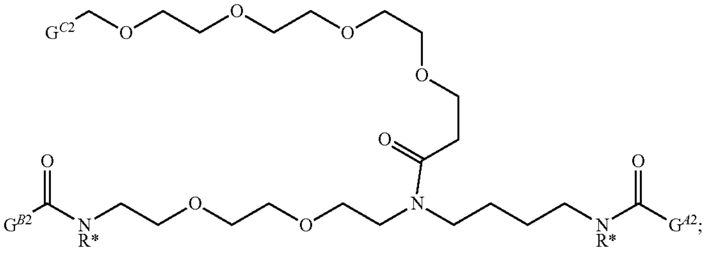
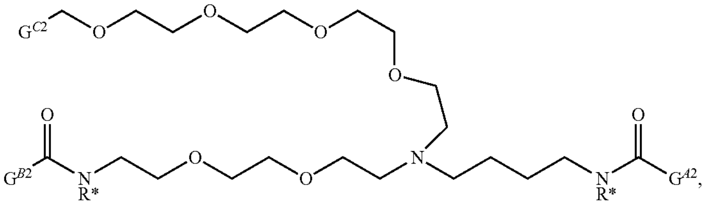
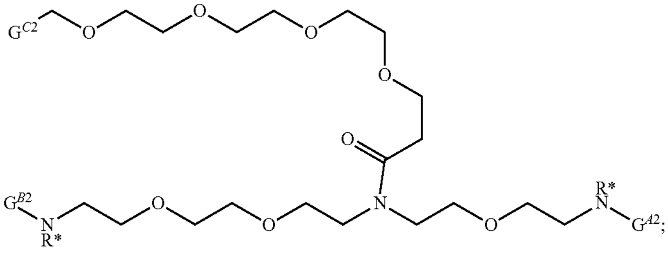
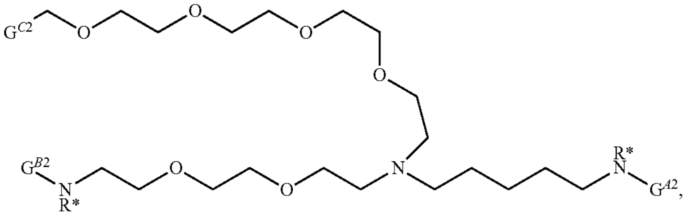

-continued

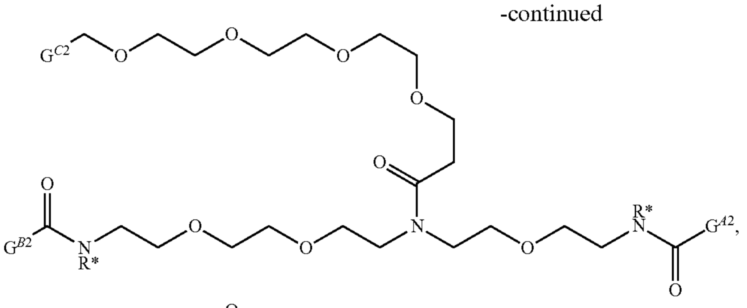

or

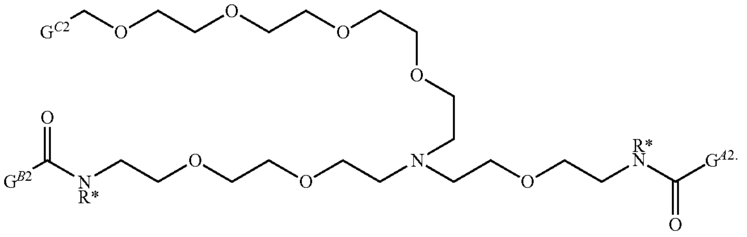

Linkers in Conjugates Having an Fc Domain or an Albumin Protein Covalently Linked to Monomers of Neuraminidase Inhibitors In a conjugate containing an Fc domain monomer, an Fc domain, an Fc-binding peptide, an albumin protein, or an albumin protein-binding peptide covalently linked to one or more monomers of neuraminidase inhibitors as described herein, a linker in the conjugate (e.g., L, or L') may be a divalent structure having two arms. One arm in a divalent linker may be attached to the monomer of neuraminidase inhibitor and the other arm may be attached to the Fc domain monomer, and Fc domain, an Fc-binding peptide, an albumin protein, or an albumin protein-binding peptide. In some embodiments, the one or more monomers of neuraminidase inhibitors in the conjugates described herein may each be, independently, connected to an atom in the Fc domain monomer, and Fc domain, an Fc-binding peptide, an albumin protein, or an albumin protein-binding peptide.

In some embodiments, a linker is described by formula (M-L-1):

$$J^1\text{-}(Q^1)_g\text{-}(T^1)_h\text{-}(Q^2)_i\text{-}(T^2)_j\text{-}(Q^3)_k\text{-}(T^3)_l\text{-}(Q^4)_m\text{-}(T^4)_n\text{-}(Q^5)_o\text{-}J^2$$

wherein $J^1$ is a bond attached to a neuraminidase inhibitor; $J^2$ is a bond attached to an Fc domain monomer, an Fc domain, an Fc-binding peptide, an albumin protein, or an albumin protein-binding peptide, or a functional group capable of reacting with a functional group conjugated to an Fc domain monomer, an Fc domain, an Fc-binding peptide, an albumin protein, or an albumin protein-binding peptide (e.g., maleimide and cysteine, amine and activated carboxylic acid, thiol and maleimide, activated sulfonic acid and amine, isocyanate and amine, azide and alkyne, and alkene and tetrazine); each of $Q^1$, $Q^2$, $Q^3$, $Q^4$ and $Q^5$ is, independently, optionally substituted C1-C20 alkylene, optionally substituted C1-C20 heteroalkylene, optionally substituted C2-C20 alkenylene, optionally substituted C2-C20 heteroalkenylene, optionally substituted C2-C20 alkynylene, optionally substituted C2-C20 heteroalkynylene, optionally substituted C3-C20 cycloalkylene, optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene, or optionally substituted C2-C15 heteroarylene; each of $T^1$, $T^2$, $T^3$, $T^4$ is, independently, O, S, $NR^i$, P, carbonyl, thiocarbonyl, sulfonyl, phosphate, phosphoryl, or imino; $R_i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl; and each of g, h, i, j, k, l, m, n, and o is, independently, 0 or 1.

In some embodiments, J2 may have two points of attachment to the Fc domain monomer, and Fc domain, an Fc-binding peptide, an albumin protein, or an albumin protein-binding peptide (e.g., two $J^2$).

Linkers of formula (M-L-1) that may be used in conjugates described herein include, but are not limited to,

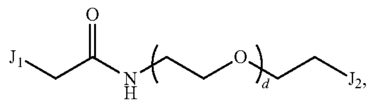

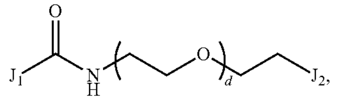

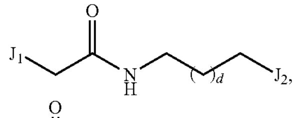

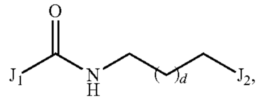

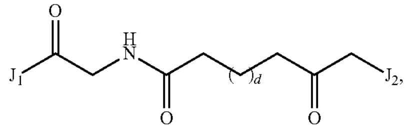

wherein d is an integer from 1 to 20 (e.g., d is 1, 2, 3, 4, 5, 6, 7, 8, 9, 10, 11, 12, 13, 14, 15, 16, 17, 18, 19, or 20).

Linkers of formula (M-L-I) that may be used in conjugates described herein include, but are not limited to,

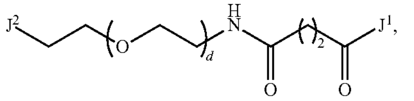

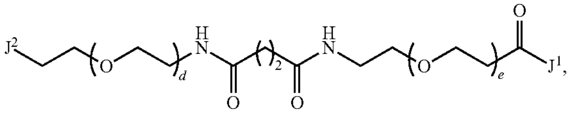

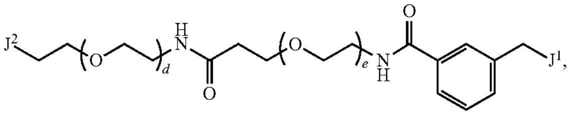

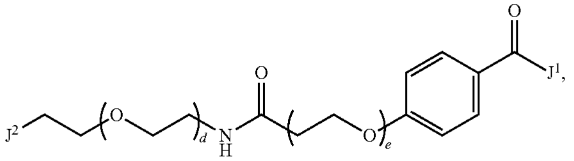

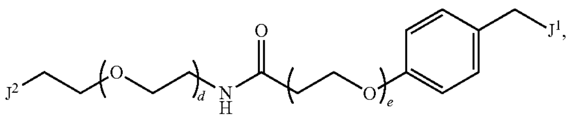

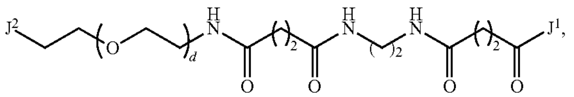

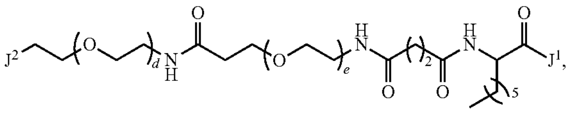

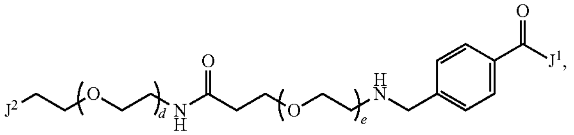

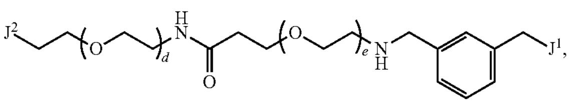

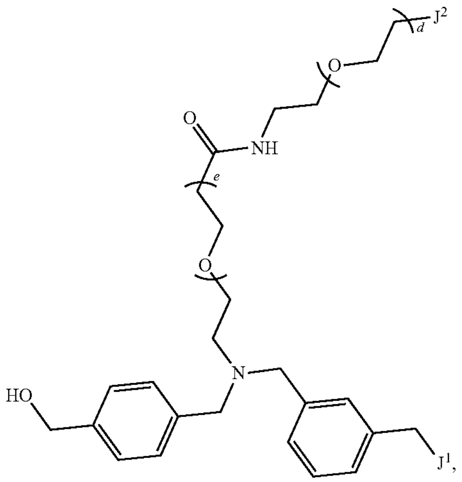

-continued

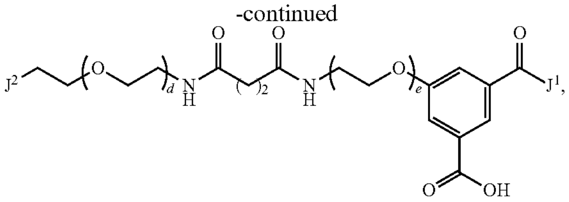

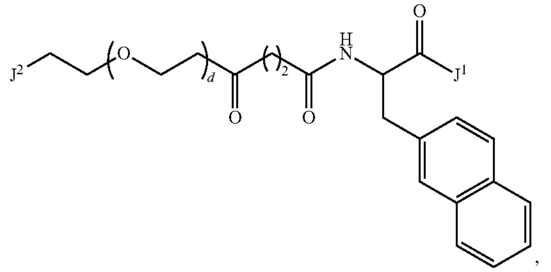

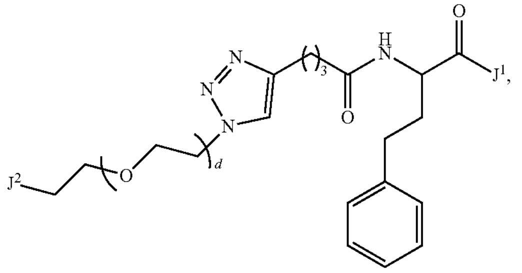

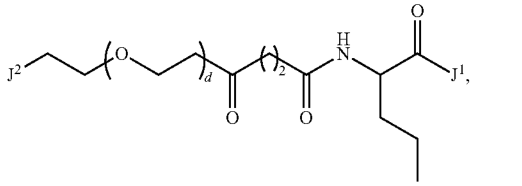

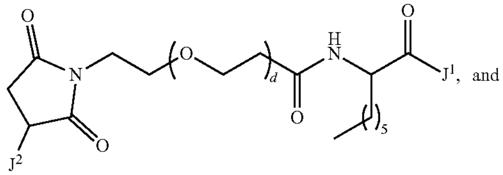

and

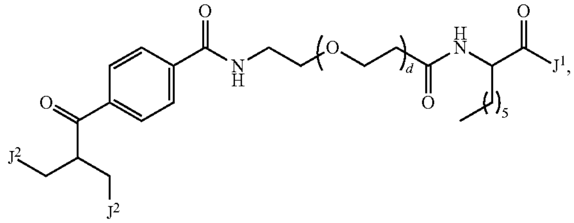

wherein each of d and e is, independently, an integer from 1 to 26.

Linking Groups

In some embodiments, a linker provides space, rigidity, and/or flexibility between the neuraminidase inhibitors and the Fc domain monomer, and Fc domain, an Fc-binding peptide, an albumin protein, or an albumin protein-binding peptide in the conjugates described here or between two neuraminidase inhibitors in the conjugates described herein. In some embodiments, a linker may be a bond, e.g., a covalent bond, e.g., an amide bond, a disulfide bond, a C—O bond, a C—N bond, a N—N bond, a C—S bond, or any kind of bond created from a chemical reaction, e.g., chemical conjugation. In some embodiments, a linker (L or L' as shown in any one of formulas (1)-(5), (D-I)-(D-X), (D'-I), (M-I)-(M-X), or (M'-)) includes no more than 250 atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 atom(s)). In some embodiments, a linker (L or L) includes no more than 250 non-hydrogen atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 non-hydrogen atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 non-hydrogen atom(s)). In some embodiments, the backbone of a linker (L or L) includes no more than 250 atoms (e.g., 1-2, 1-4, 1-6, 1-8, 1-10, 1-12, 1-14, 1-16, 1-18, 1-20, 1-25, 1-30, 1-35, 1-40, 1-45, 1-50, 1-55, 1-60, 1-65, 1-70, 1-75, 1-80, 1-85, 1-90, 1-95, 1-100, 1-110, 1-120, 1-130, 1-140, 1-150, 1-160, 1-170, 1-180, 1-190, 1-200, 1-210, 1-220, 1-230, 1-240, or 1-250 atom(s); 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 28, 26, 24, 22, 20, 18, 16, 14, 12, 10, 9, 8, 7, 6, 5, 4, 3, 2, or 1 atom(s)). The "backbone" of a linker refers to the atoms in the linker that together form the shortest path from one part of the conjugate to another part of the conjugate. The atoms in the backbone of the linker are directly involved in linking one part of the conjugate to another part of the conjugate. For examples, hydrogen atoms attached to carbons in the backbone of the linker are not considered as directly involved in linking one part of the conjugate to another part of the conjugate.

Molecules that may be used to make linkers (L or L') include at least two functional groups, e.g., two carboxylic acid groups. In some embodiments of a trivalent linker, two arms of a linker may contain two dicarboxylic acids, in which the first carboxylic acid may form a covalent linkage with the first neuraminidase inhibitor in the conjugate and the second carboxylic acid may form a covalent linkage with the second neuraminidase inhibitor in the conjugate, and the third arm of the linker may for a covalent linkage (e.g., a C—O bond) with an Fc domain monomer, an Fc domain, an Fc-binding peptide, an albumin protein, or an albumin protein-binding peptide in the conjugate. In some embodiments of a divalent linker, the divalent linker may contain two carboxylic acids, in which the first carboxylic acid may form a covalent linkage with one component (e.g., a neuraminidase inhibitor) in the conjugate and the second carboxylic acid may form a covalent linkage (e.g., a C—S bond or a C—N bond) with another component (e.g., an Fc domain monomer, an Fc domain, an Fc-binding peptide, an albumin protein, or an albumin protein-binding peptide) in the conjugate.

In some embodiments, dicarboxylic acid molecules may be used as linkers (e.g., a dicarboxylic acid linker). For example, in a conjugate containing an Fc domain monomer, an Fc domain, an Fc-binding peptide, an albumin protein, or an albumin protein-binding peptide covalently linked to one or more dimers of neuraminidase inhibitors, the first carboxylic acid in a dicarboxylic acid molecule may form a covalent linkage with a hydroxyl or amine group of the first neuraminidase inhibitor and the second carboxylic acid may form a covalent linkage with a hydroxyl or amine group of the second neuraminidase inhibitor.

Examples of dicarboxylic acids molecules that may be used to form linkers include, but are not limited to,

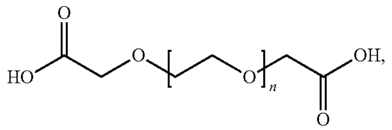

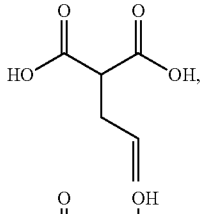
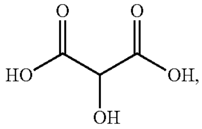

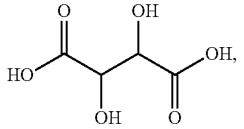

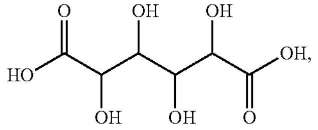

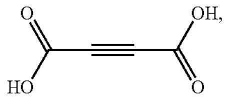
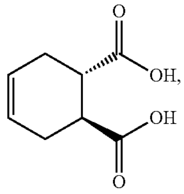

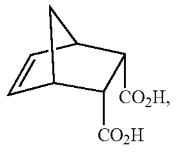
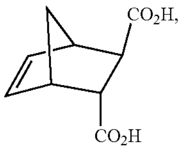

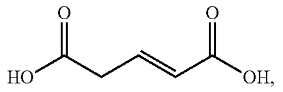

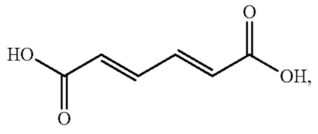

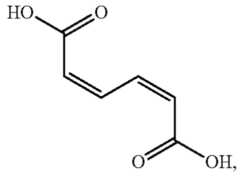
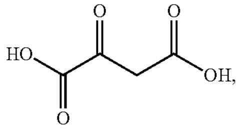

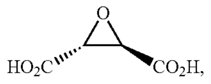
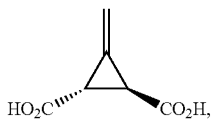

-continued
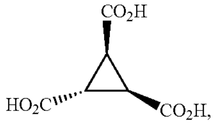
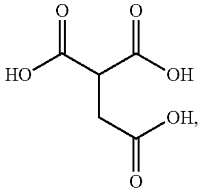
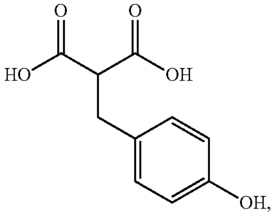
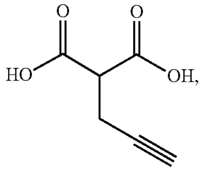
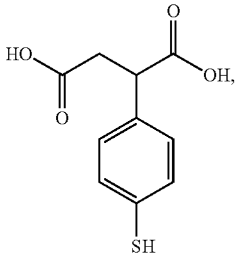
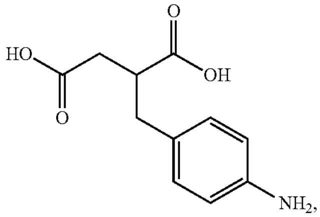
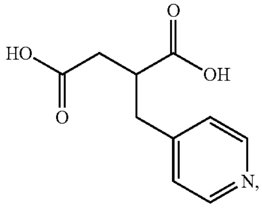
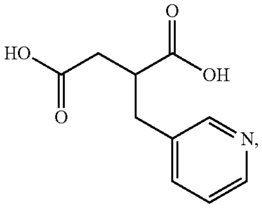
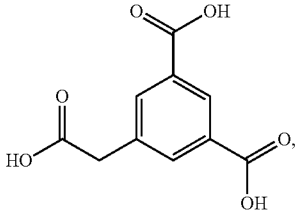
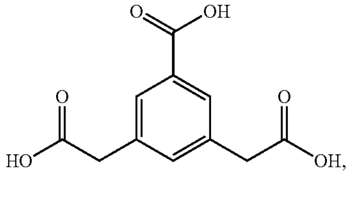
-continued
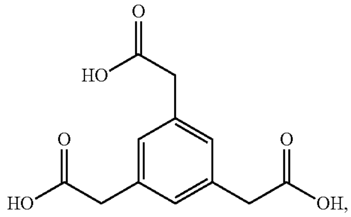
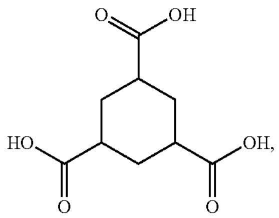
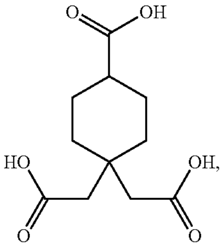
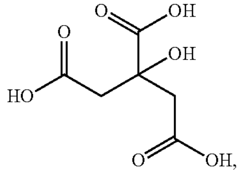
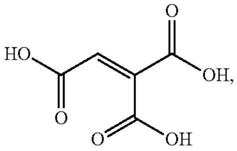
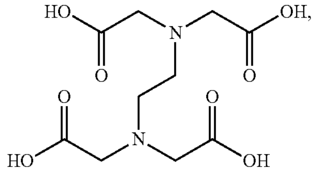
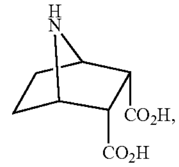
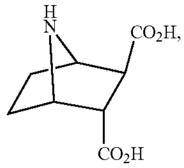
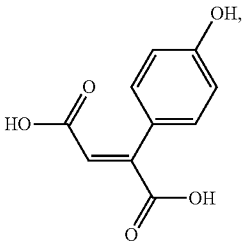
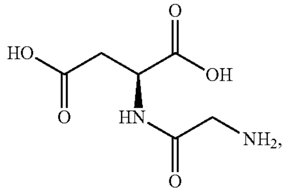
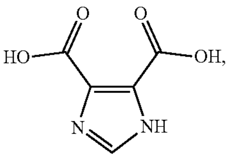
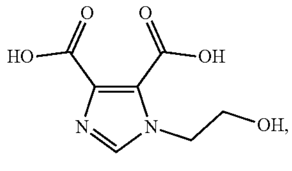

-continued
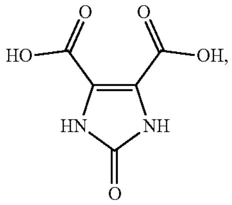
and
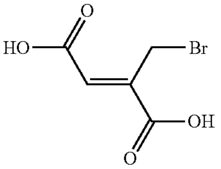
wherein n is an integer from 1 to 20 (e.g., n is 1, 2, 3, 4, 5, 6, 7, 8, 9, 10, 11, 12, 13, 14, 15, 16, 17, 18, 19, or 20).
Other examples of dicarboxylic acids molecules that may be used to form linkers include, but are not limited to,
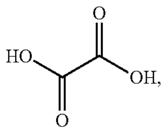
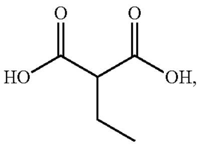
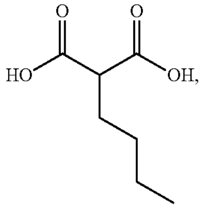
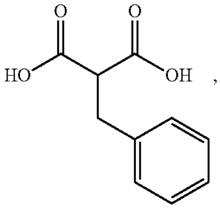
,
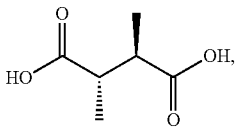
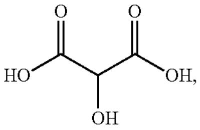
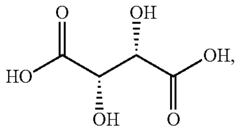
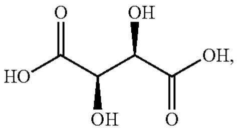
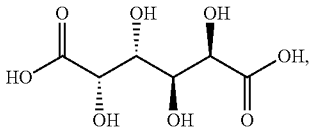
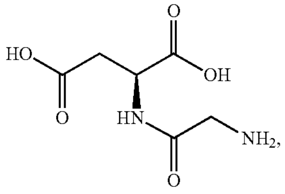
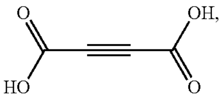
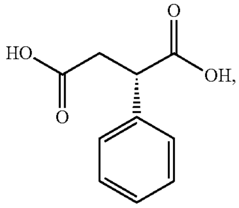
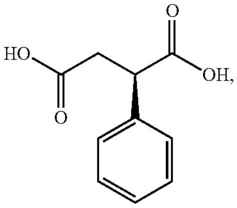
-continued
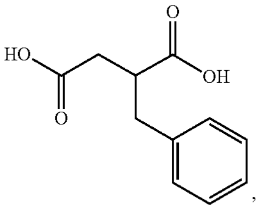
,
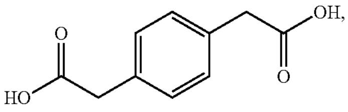
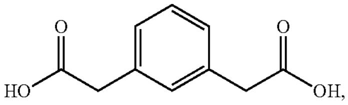
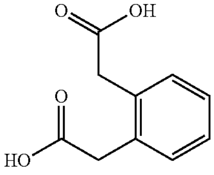
,
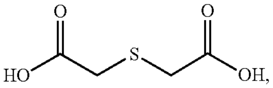
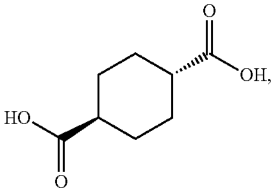
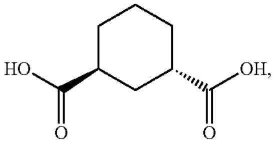
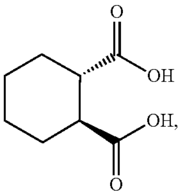
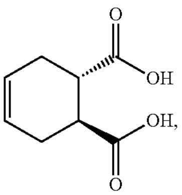
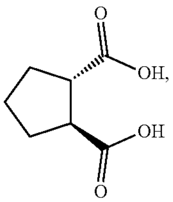
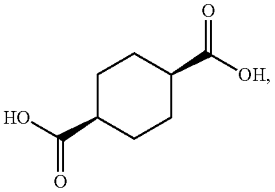
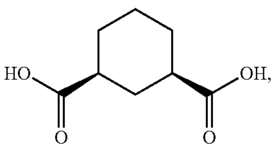
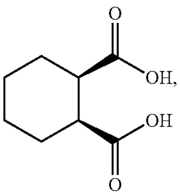

-continued

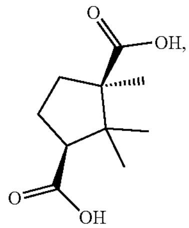 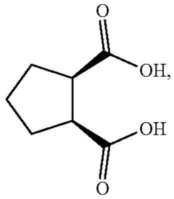

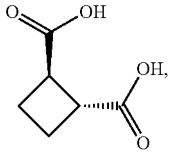 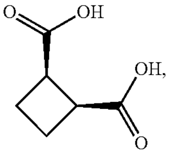

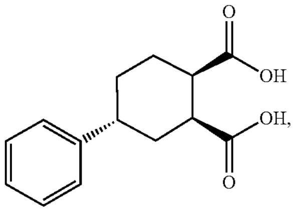

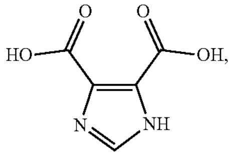 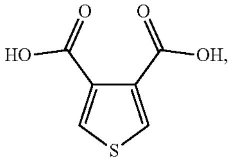

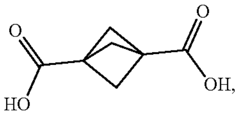 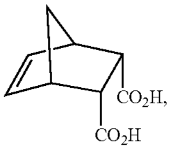

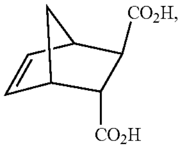 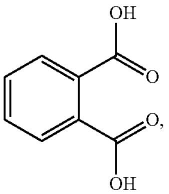

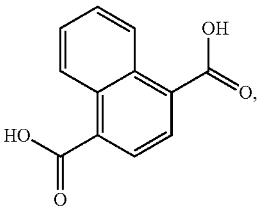

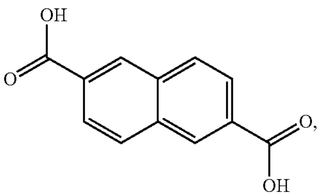

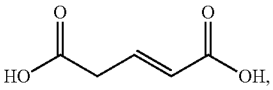

-continued

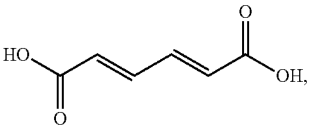

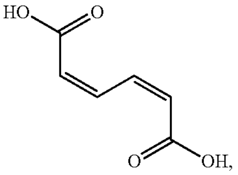 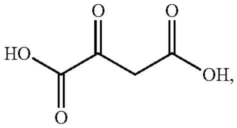

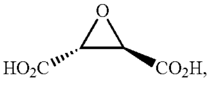 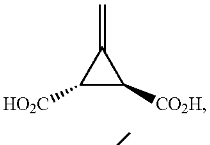

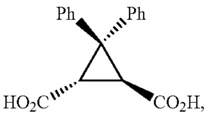 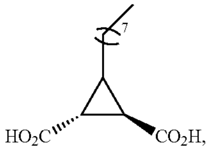

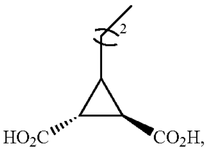 and 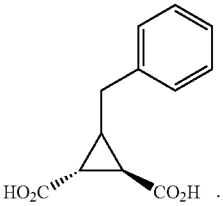

In some embodiments, dicarboxylic acid molecules, such as the ones described herein, may be further functionalized to contain one or more additional functional groups. Dicarboxylic acids may be further functionalized, for example, to provide an attachment point to an Fc domain monomer, an Fc domain, an Fc-binding peptide, an albumin protein, or an albumin protein-binding peptide (e.g., by way of a linker, such as a PEG linker).

In some embodiments, when the neuraminidase inhibitor is attached to Fc domain monomer, an Fc domain, an Fc-binding peptide, an albumin protein, or an albumin protein-binding peptide, the linking group may comprise a moiety comprising a carboxylic acid moiety and an amino moiety that are spaced by from 1 to 25 atoms. Examples of such linking groups include, but are not limited to,

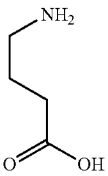 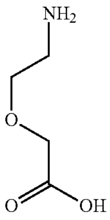 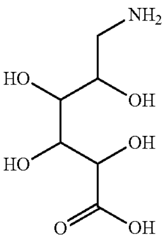

-continued

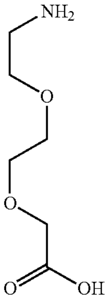
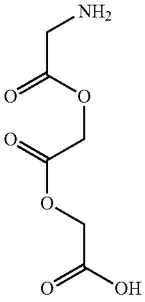
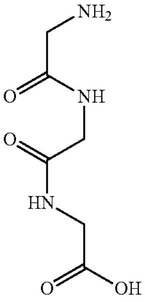
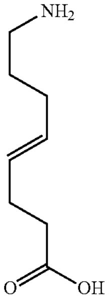
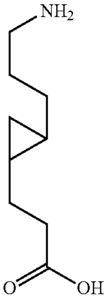
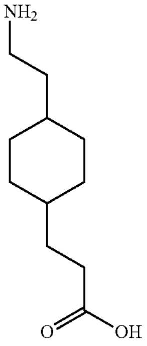
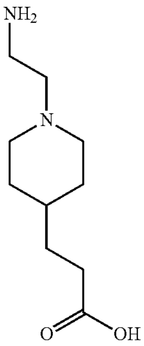
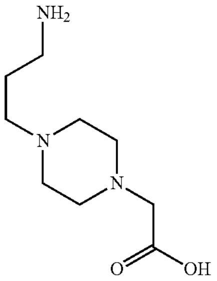
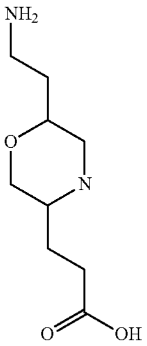
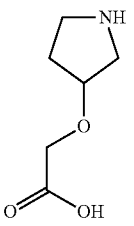
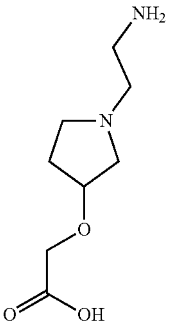
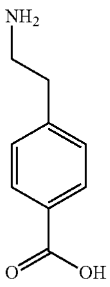
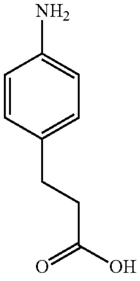
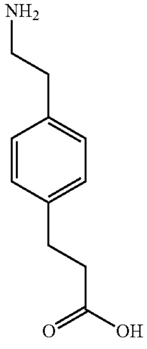
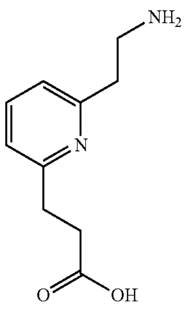

-continued

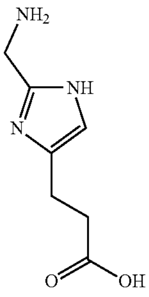
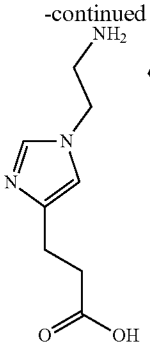
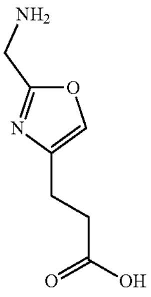
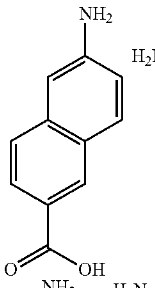
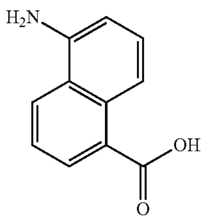
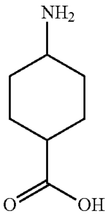
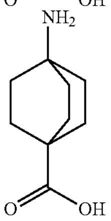
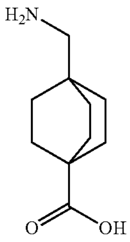
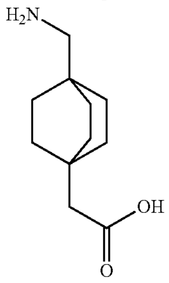
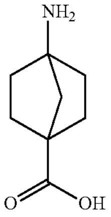
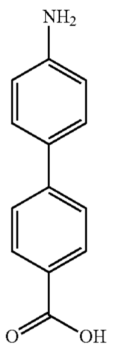
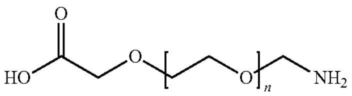

wherein n is an integer from 1 to 20 (e.g., n is 1, 2, 3, 4, 5, 6, 7, 8, 9, 10, 11, 12, 13, 14, 15, 16, 17, 18, 19, or 20).

In some embodiments, a linking group may including a moiety including a carboxylic acid moiety and an amino moiety, such as the ones described herein, may be further functionalized to contain one or more additional functional groups. Such linking groups may be further functionalized, for example, to provide an attachment point to an Fc domain monomer, an Fc domain, an Fc-binding peptide, an albumin protein, or an albumin protein-binding peptide (e.g., by way of a linker, such as a PEG linker). In some embodiments, when the neuraminidase inhibitor is attached to Fc domain monomer, an Fc domain, an Fc-binding peptide, an albumin protein, or an albumin protein-binding peptide, the linking group may comprise a moiety comprising two or amino moieties (e.g., a diamino moiety) that are spaced by from 1 to 25 atoms. Examples of such linking groups include, but are not limited to,

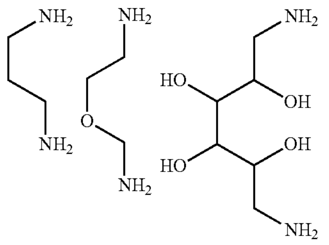

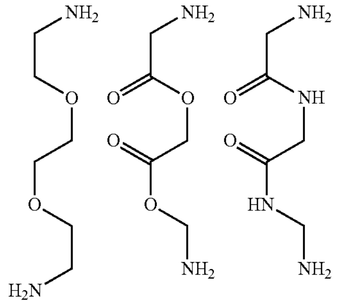

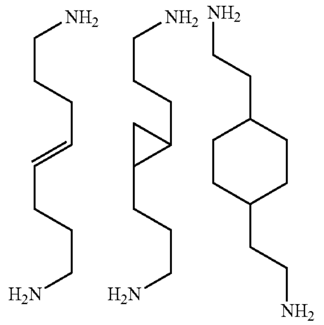

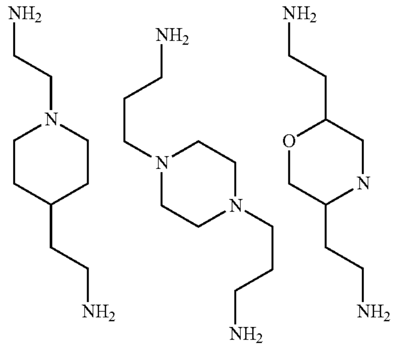

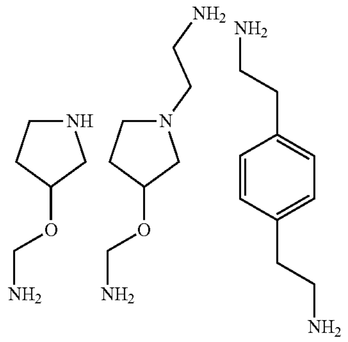

-continued

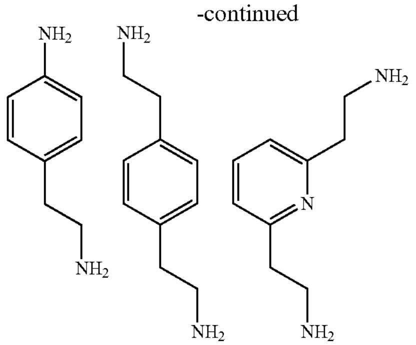

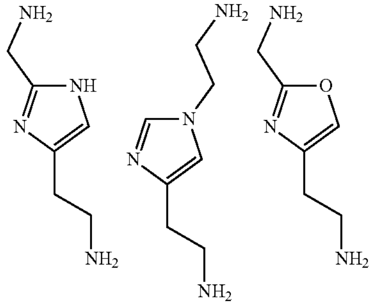

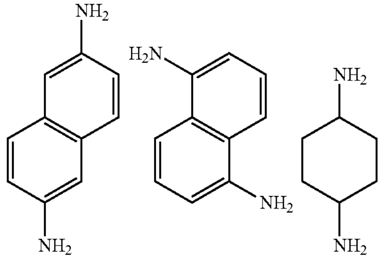

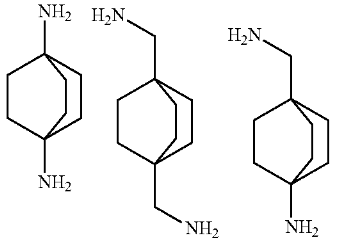

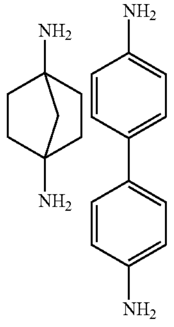

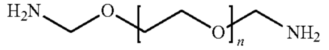

wherein n is an integer from 1 to 20 (e.g., n is 1, 2, 3, 4, 5, 6, 7, 8, 9, 10, 11, 12, 13, 14, 15, 16, 17, 18, 19, or 20).

In some embodiments, a linking group may including a diamino moiety, such as the ones described herein, may be further functionalized to contain one or more additional functional groups. Such diamino linking groups may be further functionalized, for example, to provide an attachment point to an Fc domain monomer, an Fc domain, an Fc-binding peptide, an albumin protein, or an albumin protein-binding peptide (e.g., by way of a linker, such as a PEG linker).

In some embodiments, a molecule containing an azide group may be used to form a linker, in which the azide group may undergo cycloaddition with an alkyne to form a 1,2,3-triazole linkage. In some embodiments, a molecule containing an alkyne group may be used to form a linker, in which the alkyne group may undergo cycloaddition with an azide to form a 1,2,3-triazole linkage. In some embodiments, a molecule containing a maleimide group may be used to form a linker, in which the maleimide group may react with a cysteine to form a C—S linkage. In some embodiments, a molecule containing one or more sulfonic acid groups may be used to form a linker, in which the sulfonic acid group may form a sulfonamide linkage with the linking nitrogen in a neuraminidase inhibitor. In some embodiments, a molecule containing one or more isocyanate groups may be used to form a linker, in which the isocyanate group may form a urea linkage with the linking nitrogen in a neuraminidase inhibitor. In some embodiments, a molecule containing one or more haloalkyl groups may be used to form a linker, in which the haloalkyl group may form a covalent linkage, e.g., C—N and C—O linkages, with a neuraminidase inhibitor.

In some embodiments, a linker (L or L') may comprise a synthetic group derived from, e.g., a synthetic polymer (e.g., a polyethylene glycol (PEG) polymer). In some embodiments, a linker may comprise one or more amino acid residues. In some embodiments, a linker may be an amino acid sequence (e.g., a 1-25 amino acid, 1-10 amino acid, 1-9 amino acid, 1-8 amino acid, 1-7 amino acid, 1-6 amino acid, 1-5 amino acid, 1-4 amino acid, 1-3 amino acid, 1-2 amino acid, or 1 amino acid sequence). In some embodiments, a linker (L or L') may include one or more optionally substituted C1-C20 alkylene, optionally substituted C1-C20 heteroalkylene (e.g., a PEG unit), optionally substituted C2-C20 alkenylene (e.g., C2 alkenylene), optionally substituted C2-C20 heteroalkenylene, optionally substituted C2-C20 alkynylene, optionally substituted C2-C20 heteroalkynylene, optionally substituted C3-C20 cycloalkylene (e.g., cyclopropylene, cyclobutylene), optionally substituted C3-C20 heterocycloalkylene, optionally substituted C4-C20 cycloalkenylene, optionally substituted C4-C20 heterocycloalkenylene, optionally substituted C8-C20 cycloalkynylene, optionally substituted C8-C20 heterocycloalkynylene, optionally substituted C5-C15 arylene (e.g., C6 arylene), optionally substituted C2-C15 heteroarylene (e.g., imidazole, pyridine), O, S, $NR^i$ ($R^i$ is H, optionally substituted C1-C20 alkyl, optionally substituted C1-C20 heteroalkyl, optionally substituted C2-C20 alkenyl, optionally substituted C2-C20 heteroalkenyl, optionally substituted C2-C20 alkynyl, optionally substituted C2-C20 heteroalkynyl, optionally substituted C3-C20 cycloalkyl, optionally substituted C3-C20 heterocycloalkyl, optionally substituted C4-C20 cycloalkenyl, optionally substituted C4-C20 heterocycloalkenyl, optionally substituted C8-C20 cycloalkynyl, optionally substituted C8-C20 heterocycloalkynyl, optionally substituted C5-C15 aryl, or optionally substituted C2-C15 heteroaryl), P, carbonyl, thiocarbonyl, sulfonyl, phosphate, phosphoryl, or imino.

Conjugation Chemistries

Neuraminidase inhibitor monomer or dimers (e.g., in a conjugate of any one of formulas (1)-(5), (D-I)-(D-X), (D'-I), (M-I)-(M-X), or (M'-I)) may be conjugated to an Fc domain monomer, an Fc domain, an Fc-binding peptide, an albumin protein, or an albumin protein-binding peptide, e.g., by way of a linker, by any standard conjugation chemistries known to those of skill in the art. The following conjugation chemistries are specifically contemplated, e.g., for conjugation of a PEG linker (e.g., a functionalized PEG linker) to an Fc domain monomer, an Fc domain, an Fc-binding peptide, an albumin protein, or an albumin protein-binding peptide.

Covalent conjugation of two or more components in a conjugate using a linker may be accomplished using well-known organic chemical synthesis techniques and methods. Complementary functional groups on two components may react with each other to form a covalent bond. Examples of complementary reactive functional groups include, but are not limited to, e.g., maleimide and cysteine, amine and activated carboxylic acid, thiol and maleimide, activated sulfonic acid and amine, isocyanate and amine, azide and alkyne, and alkene and tetrazine. Site-specific conjugation to a polypeptide (e.g., an Fc domain monomer, an Fc domain, an Fc-binding peptide, an albumin protein, or an albumin protein-binding peptide) may be accomplished using techniques known in the art. Exemplary techniques for site-specific conjugation of a small molecule to an Fc domain are provided in Agarwall. P., et al. Bioconjugate Chem. 26:176-192 (2015).

Other examples of functional groups capable of reacting with amino groups include, e.g., alkylating and acylating agents. Representative alkylating agents include: (i) an α-haloacetyl group, e.g., $XCH_2CO$— (where X=Br, Cl, or I); (ii) a N-maleimide group, which may react with amino groups either through a Michael type reaction or through acylation by addition to the ring carbonyl group; (iii) an aryl halide, e.g., a nitrohaloaromatic group; (iv) an alkyl halide; (v) an aldehyde or ketone capable of Schiff's base formation with amino groups; (vi) an epoxide, e.g., an epichlorohydrin and a bisoxirane, which may react with amino, sulfhydryl, or phenolic hydroxyl groups; (vii) a chlorine-containing of s-triazine, which is reactive towards nucleophiles such as amino, sufhydryl, and hydroxyl groups; (viii) an aziridine, which is reactive towards nucleophiles such as amino groups by ring opening; (ix) a squaric acid diethyl ester; and (x) an α-haloalkyl ether.

Examples of amino-reactive acylating groups include, e.g., (i) an isocyanate and an isothiocyanate; (ii) a sulfonyl chloride; (iii) an acid halide; (iv) an active ester, e.g., a nitrophenylester or N-hydroxysuccinimidyl ester, or derivatives thereof (e.g., azido-$PEG_2$-$PEG_{40}$-NHS ester); (v) an acid anhydride, e.g., a mixed, symmetrical, or N-carboxyanhydride; (vi) an acylazide; and (vii) an imidoester. Aldehydes and ketones may be reacted with amines to form Schiff's bases, which may be stabilized through reductive amination.

It will be appreciated that certain functional groups may be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

In some embodiments, a linker of the invention (e.g., L or L', such as $L^C$ of D-L-I), is conjugated (e.g., by any of the methods described herein) to E (e.g., an Fc domain or albumin protein). In preferred embodiments of the invention, the linker is conjugated by way of: (a) a thiourea linkage (i.e., —NH(C═S)NH—) to a lysine of E; (b) a carbamate linkage (i.e., —NH(C═O)—O) to a lysine of E; (c) an amine linkage by reductive amination (i.e., —$NHCH_2$) between a lysine and E; (d) an amide (i.e., —NH—(C═O)$CH_2$) to a lysine of E; (e) a cysteine-maleimide conjugate between a maleimide of the linker to a cysteine of E; (f) an amine linkage by reductive amination (i.e., —$NHCH_2$) between the linker and a carbohydrate of E (e.g., a glycosyl group of an Fc domain monomer or an Fc domain); (g) a rebridged cysteine conjugate, wherein the linker is conjugated to two cysteines of E; (h) an oxime linkage between the linker and a carbohydrate of E (e.g., a glycosyl group of an Fc domain monomer or an Fc domain); (i) an oxime linkage between the linker and an amino acid residue of E; (j) an azido linkage between the linker and E; (k) direct acylation of a linker to E; or (l) a thioether linkage between the linker and E.

In some embodiments, a linker is conjugated to E, wherein the linkage includes the structure —NH(C═NH)X—, wherein X is O, HN, or a bond. In some embodiments, a linker is conjugated to E, wherein the linkage between the remainder of the linker and E includes the structure —NH(C═O)NH—.

Figure 43:
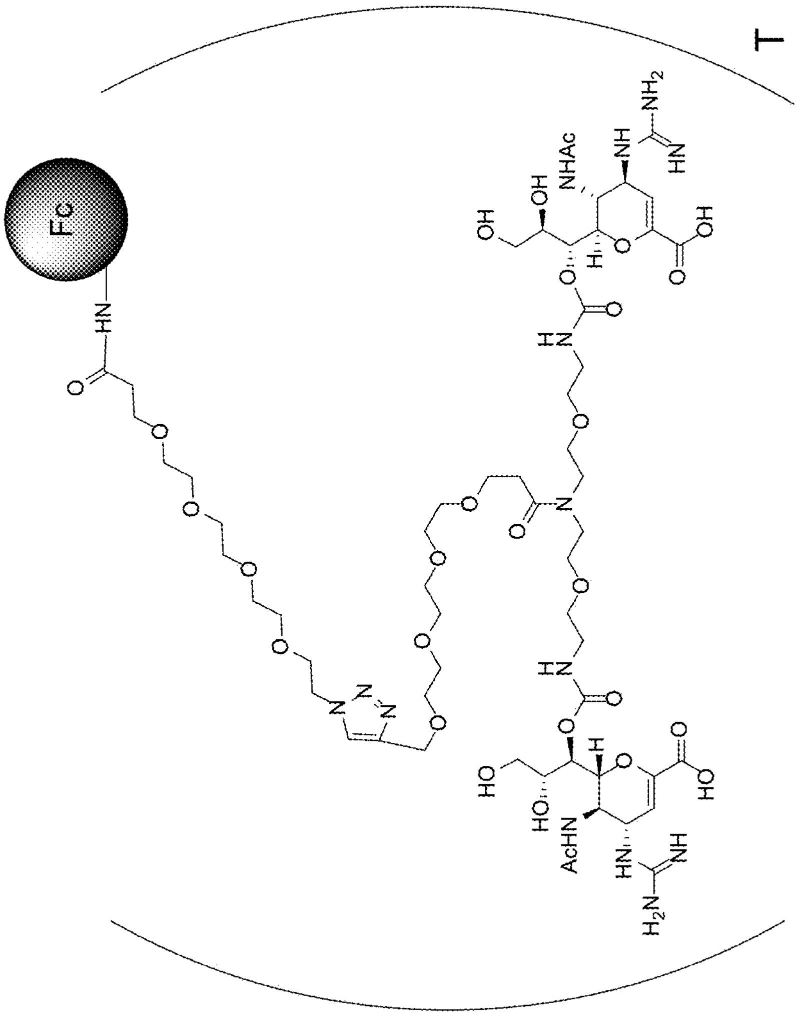
FIG. 43 shows the structure of Conjugate 6.
Figure 61:
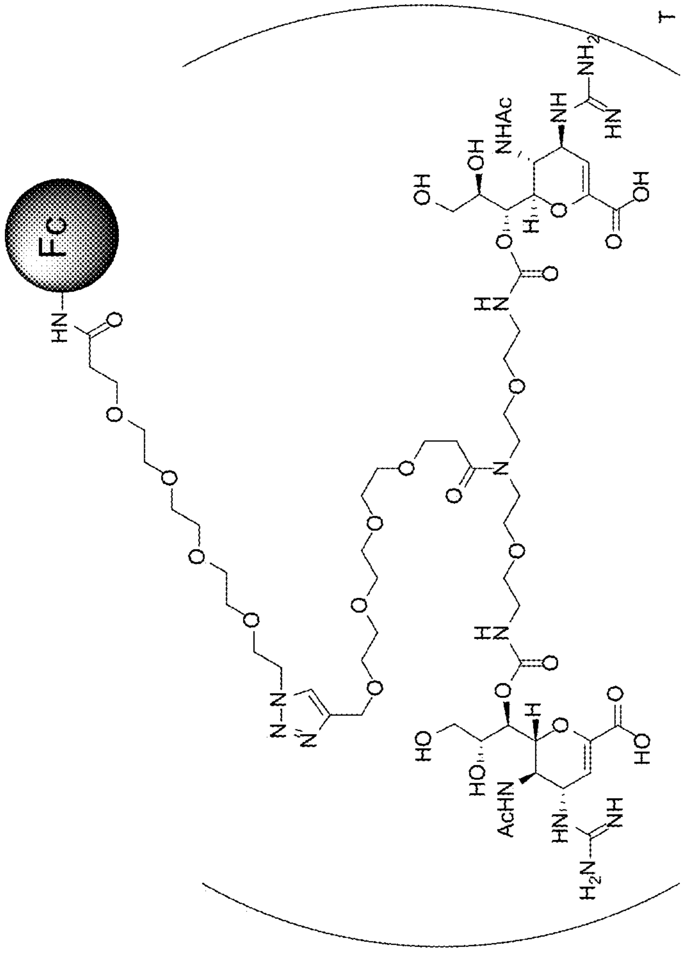
FIG. 61 is an image depicting conjugate 33.

In some embodiments, a linker (e.g., an active ester, e.g., a nitrophenylester or N-hydroxysuccinimidyl ester, or derivatives thereof (e.g., a functionalized PEG linker (e.g., azido-$PEG_2$-$PEG_{40}$-NHS ester), is conjugated to E, with a T of (e.g., DAR) of between 0.5 and 10.0, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8.0, 7.9, 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In these instances, the E-($PEG_2$-$PEG_{40}$)-azide can react with an Int having a terminal alkyne linker (e.g., L, or L', such as $L^C$ of D-L-I) through click conjugation. During click conjugation, the copper-catalyzed reaction of the an azide (e.g., the Fc-($PEG_2$-$PEG_{40}$)-azide) with the alkyne (e.g., the Int having a terminal alkyne linker (e.g., L or L', such as $L^C$ of D-L-I) forming a 5-membered heteroatom ring. In some embodiments, the linker conjugated to E is a terminal alkyne and is conjugated to an Int having a terminal azide. Exemplary preparations of preparations of E-($PEG_2$-$PEG_{40}$)-azide are described in Examples 7, 8, 61, 84, 88, and 124. Exemplary figures of conjugates prepared through click conjugation are depicted in FIGS. 43 and 61. One of skill in the art would readily understand the final product from a click chemistry conjugation.

Exemplary linking strategies (e.g., methods for linking a monomer or a dimer of a neuraminidase inhibitor to E, such as, by way of a linker) are further depicted in FIGS. 1, 28, 29, 30, 43, and 61.

VI. Combination Therapies

Antiviral Agents

In some embodiments, one or more antiviral agents may be administered in combination (e.g., administered substantially simultaneously (e.g., in the same pharmaceutical composition or in separate pharmaceutical compositions) or administered separately at different times) with a conjugate described herein (e.g., a conjugate of any one of formulas (1)-(5), (D-I)-(D-X), (D'-I), (M-I)-(M-X), or (M'-I)).

In some embodiments, the antiviral agent is an antiviral agent for the treatment of influenza virus. For example, the antiviral agent may be an M2 ion channel blocker, a neuraminidase inhibitor (e.g., a long-acting neuraminidase inhibitor), a polymerase inhibitor, a hemagglutinin inhibitor, a fusion protein inhibitor, a COX-2 inhibitor, or a PPAR agonist. The antiviral agent may target either the virus or the host subject. The antiviral agent for the treatment of influenza virus used in combination with a conjugate described herein (e.g., a conjugate of any one of formulas (1)-(5), (D-I)-(D-X), (D'-I), (M-I)-(M-X), or (M'-I)) may be selected from oseltamivir, zanamivir, peramivir, laninamivir, CS-8958, amantadine, rimantadine, cyanovirin-N, a cap-dependent endonuclease inhibitor (e.g., baloxavir marboxil), a polymerase inhibitor (e.g., T-705), a PB2 inhibitor (e.g., JNJ-63623872), a conjugated sialidase (e.g., DAS181), a thiazolide (e.g., nitazoxanide), a COX inhibitor, a PPAR agonist, a hemagglutinin-targeting antibody (e.g., a monoclonal antibody such as CR6261, CR8020, MEDI8852, MHAA4549A, or VIS410), or an siRNA targeting a host or viral gene, or prodrugs thereof, or pharmaceutically acceptable salts thereof.

Antiviral Vaccines

In some embodiments, any one of conjugates described herein (e.g., a conjugate of any one of formulas (1)-(5), (D-I)-(D-X), (D'-I), (M-I)-(M-X), or (M'-I)) is administered in combination with an antiviral vaccine (e.g., a composition that elicits an immune response in a subject directed against a virus). The antiviral vaccine may be administered substantially simultaneously (e.g., in the same pharmaceutical composition or in separate pharmaceutical compositions) as the conjugates, or may be administered prior to or following the conjugates (e.g., within a period of 1 day, 2, days, 5, days, 1 week, 2 weeks, 3 weeks, 1 month, 2 months, 6 months, or 12 months, or more).

In some embodiments the viral vaccine comprises an immunogen that elicits an immune response in the subject against influenza virus A, B, C, or parainfluenza virus. In some embodiments the immunogen is an inactivated virus (e.g., the vaccine is a trivalent influenza vaccine that contains purified and inactivated material influenza virus A, B, C, or parainfluenza virus or any combination thereof). In some embodiments the vaccine is given as an intramuscular injection. In some embodiments, the vaccine is a live virus vaccine that contains live viruses that have been attenuated (weakened). In some embodiments the vaccine is administered as a nasal spray.

VII. Methods

Methods described herein include, e.g., methods of protecting against or treating a viral infection (e.g., an influenza viral infection) in a subject and methods of preventing, stabilizing, or inhibiting the growth of viral particles. A method of treating a viral infection (e.g., an influenza viral infection) in a subject includes administering to the subject a conjugate described herein (e.g., a conjugate of any one of formulas (1)-(5), (D-I)-(D-X), (D'-I), (M-I)-(M-X), or (M'-I)) or a pharmaceutical composition thereof. In some embodiments, the viral infection is cause by the influenza virus (e.g., influenza virus A, B, C, or parainfluenza virus). In some embodiments, the viral infection is caused by a resistant strain of virus. A method of preventing, stabilizing, or inhibiting the growth of viral particles or preventing the replication and spread of the virus includes contacting the virus or a site susceptible to viral growth with a conjugate described herein (e.g., a conjugate of any one of formulas (1)-(5), (D-I)-(D-X), (D'-I), (M-I)-(M-X), or (M'-I)) or a pharmaceutical composition thereof.

Moreover, methods described herein also include methods of protecting against or treating viral infection in a subject by administering to the subject a conjugate described herein (e.g., a conjugate of any one of formulas (1)-(5), (D-I)-(D-X), (D'-I), (M-I)-(M-X), or (M'-I)). In some embodiments, the method further includes administering to the subject an antiviral agent or an antiviral vaccine.

Methods described herein also include methods of protecting against or treating a viral infection in a subject by administering to said subject (1) a conjugate described herein (e.g., a conjugate of any one of formulas (1)-(5), (D-I)-(D-X), (D'-I), (M-I)-(M-X), or (M'-I)) and (2) an antiviral agent or an antiviral vaccine. Methods described herein also include methods of preventing, stabilizing, or inhibiting the growth of viral particles or preventing the replication or spread of a virus, by contacting the virus or a site susceptible to viral growth with (1) a conjugate described herein (e.g., a conjugate of any one of formulas (1)-(5), (D-I)-(D-X), (D'-I), (M-I)-(M-X), or (M'-I)) and (2) an antiviral agent or an antiviral vaccine.

In some embodiments, the conjugate described herein (e.g., a conjugate of any one of formulas (1)-(5), (D-I)-(D-X), (D'-I), (M-I)-(M-X), or (M'-I)) is administered first, followed by administering of the antiviral agent or antiviral vaccine alone. In some embodiments, the antiviral agent or antiviral vaccine is administered first, followed by administering of the conjugate described herein alone. In some embodiments, the conjugate described herein and the antiviral agent or antiviral vaccine are administered substantially simultaneously (e.g., in the same pharmaceutical composition or in separate pharmaceutical compositions). In some embodiments, the conjugate described herein or the antiviral agent or antiviral vaccine is administered first, followed by administering of the conjugate described herein and the antiviral agent or antiviral vaccine substantially simultaneously (e.g., in the same pharmaceutical composition or in separate pharmaceutical compositions). In some embodiments, the conjugate described herein and the antiviral agent or antiviral vaccine are administered first substantially simultaneously (e.g., in the same pharmaceutical composition or in separate pharmaceutical compositions), followed by administering of the conjugate described herein or the antiviral agent or antiviral vaccine alone. In some embodiments, when a conjugate described herein (e.g., a conjugate of any one of formulas (1)-(5), (D-I)-(D-X), (D'-I), (M-I)-(M-X), or (M'-I)) and an antiviral agent or antiviral vaccine are administered together (e.g., substantially simultaneously in the same or separate pharmaceutical compositions, or separately in the same treatment regimen), inhibition of viral replication of each of the conjugate and the antiviral agent or antiviral vaccine may be greater (e.g., occur at a lower concentration) than inhibition of viral replication of each of the conjugate and the antiviral agent or antiviral vaccine when each is used alone in a treatment regimen.

VIII. Pharmaceutical Compositions and Preparations

A conjugate described herein may be formulated in a pharmaceutical composition for use in the methods described herein. In some embodiments, a conjugate described herein may be formulated in a pharmaceutical composition alone. In some embodiments, a conjugate described herein may be formulated in combination with an antiviral agent or antiviral vaccine in a pharmaceutical composition. In some embodiments, the pharmaceutical composition includes a conjugate described herein (e.g., a conjugate described by any one of formulas (1)-(5), (D-I)-(D-X), (D'-I), (M-I)-(M-X), or (M'-I)) and pharmaceutically acceptable carriers and excipients.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acid residues such as glycine, glutamine, histidine, and lysine, and carbohydrates such as glucose, mannose, sucrose, and sorbitol.

Examples of other excipients include, but are not limited to, antiadherents, binders, coatings, compression aids, disintegrants, dyes, emollients, emulsifiers, fillers (diluents), film formers or coatings, flavors, fragrances, glidants (flow enhancers), lubricants, sorbents, suspensing or dispersing agents, or sweeteners. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The conjugates herein may have ionizable groups so as to be capable of preparation as pharmaceutically acceptable salts. These salts may be acid addition salts involving inorganic or organic acids or the salts may, in the case of acidic forms of the conjugates herein be prepared from inorganic or organic bases. Frequently, the conjugates are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include, but are not limited to, acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include, but are not limited to, sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

Depending on the route of administration and the dosage, a conjugate herein or a pharmaceutical composition thereof used in the methods described herein will be formulated into suitable pharmaceutical compositions to permit facile delivery. A conjugate (e.g., a conjugate of any one of formulas (1)-(5), (D-I)-(D-X), (D'-I), (M-I)-(M-X), or (M'-I)) or a pharmaceutical composition thereof may be formulated to be administered intramuscularly, intravenously (e.g., as a sterile solution and in a solvent system suitable for intravenous use), intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularlly, mucosally, intrapericardially, intraumbilically, intraocularally, orally (e.g., a tablet, capsule, caplet, gelcap, or syrup), topically (e.g., as a cream, gel, lotion, or ointment), locally, by inhalation, by injection, or by infusion (e.g., continuous infusion, localized perfusion bathing target cells directly, catheter, lavage, in cremes, or lipid compositions). Depending on the route of administration, a conjugate herein or a pharmaceutical composition thereof may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

A conjugate described herein may be formulated in a variety of ways that are known in the art. For use as treatment of human and animal subjects, a conjugate described herein can be formulated as pharmaceutical or veterinary compositions. Depending on the subject (e.g., a human) to be treated, the mode of administration, and the type of treatment desired, e.g., prophylaxis or therapy, a conjugate described herein is formulated in ways consonant with these parameters. A summary of such techniques is found in Remington: The Science and Practice of Pharmacy, 22nd Edition, Lippincott Williams & Wilkins (2012); and Encyclopedia of Pharmaceutical Technology, 4th Edition, J. Swarbrick and J. C. Boylan, Marcel Dekker, New York (2013), each of which is incorporated herein by reference.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, and preservatives. The conjugates can be administered also in liposomal compositions or as microemulsions. Systemic administration may also include relatively noninvasive methods such as the use of suppositories, transdermal patches, transmucosal delivery and intranasal administration. Oral administration is also suitable for conjugates herein. Suitable forms include syrups, capsules, and tablets, as is understood in the art.

The pharmaceutical compositions can be administered parenterally in the form of an injectable formulation. Pharmaceutical compositions for injection can be formulated using a sterile solution or any pharmaceutically acceptable liquid as a vehicle. Formulations may be prepared as solid forms suitable for solution or suspension in liquid prior to injection or as emulsions. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Such injectable compositions may also contain amounts of nontoxic auxiliary substances such as wetting or emulsifying agents, pH buffering agents, such as sodium acetate and sorbitan monolaurate. Formulation methods are known in the art, see e.g., Pharmaceutical Preformulation and Formulation, 2nd Edition, M. Gibson, Taylor & Francis Group, CRC Press (2009).

The pharmaceutical compositions can be prepared in the form of an oral formulation. Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Other pharmaceutically acceptable excipients for oral formulations include, but are not limited to, colorants, flavoring agents, plasticizers, humectants, and buffering agents. Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release of a conjugate described herein (e.g., a conjugate of any one of formulas (1)-(5), (D-I)-(D-X), (D'-I), (M-I)-(M-X), or (M'-I)) or a pharmaceutical composition thereof can be achieved by appropriate coating of a tablet, capsule, pellet, or granulate formulation of the conjugate, or by incorporating the conjugate into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The pharmaceutical composition may be formed in a unit dose form as needed. The amount of active component, e.g., a conjugate described herein (e.g., a conjugate of any one of formulas (1)-(5), (D-I)-(D-X), (D'-I), (M-I)-(M-X), or (M'-I)), included in the pharmaceutical compositions are such that a suitable dose within the designated range is provided (e.g., a dose within the range of 0.01-100 mg/kg of body weight).

IX. Routes of Administration and Dosages

In any of the methods described herein, conjugates herein may be administered by any appropriate route for treating or protecting against a viral infection (e.g., an influenza infection), or for preventing, stabilizing, or inhibiting the proliferation or spread of a virus (e.g., an influenza virus). Conjugates described herein may be administered to humans, domestic pets, livestock, or other animals with a pharmaceutically acceptable diluent, carrier, or excipient. In some embodiments, administering comprises administration of any of the conjugates described herein (e.g., conjugates of any one of formulas (1)-(5), (D-I)-(D-X), (D'-I), (M-I)-(M-X), or (M'-I)) or compositions intramuscularly, intravenously (e.g., as a sterile solution and in a solvent system suitable for intravenous use), intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctival, intravesicularlly, mucosally, intrapericardially, intraumbilically, intraocularally, orally (e.g., a tablet, capsule, caplet, gelcap, or syrup), topically (e.g., as a cream, gel, lotion, or ointment), locally, by inhalation, by injection, or by infusion (e.g., continuous infusion, localized perfusion bathing target cells directly, catheter, lavage, in cremes, or lipid compositions). In some embodiments, if an antiviral agent is also administered in addition to a conjugate described herein, the antiviral agent or a pharmaceutical composition thereof may also be administered in any of the routes of administration described herein.

The dosage of a conjugate described herein (e.g., a conjugate of any one of formulas (1)-(5), (D-I)-(D-X), (D'-I), (M-I)-(M-X), or (M'-I)) or pharmaceutical compositions thereof depends on factors including the route of administration, the disease to be treated (e.g., the extent and/or condition of the viral infection), and physical characteristics, e.g., age, weight, general health, of the subject. Typically, the amount of the conjugate or the pharmaceutical composition thereof contained within a single dose may be an amount that effectively prevents, delays, or treats the viral infection without inducing significant toxicity. A pharmaceutical composition may include a dosage of a conjugate described herein ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 30 mg/kg and, in a more specific embodiment, about 1 to about 30 mg/kg. In some embodiments, when a conjugate described herein (e.g., a conjugate of any one of formulas (1)-(5), (D-I)-(D-X), (D'-I), (M-I)-(M-X), or (M'-I)) and an antiviral agent or antiviral vaccine are administered in combination (e.g., substantially simultaneously in the same or separate pharmaceutical compositions, or separately in the same treatment regimen), the dosage needed of the conjugate described herein may be lower than the dosage needed of the conjugate if the conjugate was used alone in a treatment regimen.

A conjugate described herein (e.g., a conjugate of any one of formulas (1)-(5), (D-I)-(D-X), (D'-I), (M-I)-(M-X), or (M'-I)) or a pharmaceutical composition thereof may be administered to a subject in need thereof, for example, one or more times (e.g., 1-10 times or more; 1, 2, 3, 4, 5, 6, 7, 8, 9, or 10 times) daily, weekly, monthly, biannually, annually, or as medically necessary. Dosages may be provided in either a single or multiple dosage regimens. The timing between administrations may decrease as the medical condition improves or increase as the health of the patient declines. The dosage and frequency of administration may be adapted by the physician in accordance with conventional factors such as the extent of the infection and different parameters of the subject.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: Preparation of Fc Constructs

Reverse translations of the amino acids comprising the protein constructs (SEQ ID NOs: 1, 3, 5, 7, 9, 12, and 14) were synthesized by solid-phase synthesis. The oligonucleotide templates were cloned into pcDNA3.1 (Life Technologies, Carlsbad, CA, USA) at the cloning sites BamHI and XhoI (New England Biolabs, Ipswich, MA, USA) and included signal sequences derived from the human Interleukin-2 or human albumin. The pcDNA3.1 plasmids were transformed into Top10 *E. coli* cells (LifeTech). DNA was amplified, extracted, and purified using the PURELINK® HiPure Plasmid Filter Maxiprep Kit (LifeTech). The plasmid DNA is delivered, using the ExpiFectamine™ 293 Transfection Kit (LifeTech), into HEK-293 cells per the manufacturer's protocol. Cells were centrifuged, filtered, and the supernatants were purified using MabSelect Sure Resin (GE Healthcare, Chicago, IL, USA). Purified molecules were analyzed using 4-12% Bis Tris SDS PAGE gels by loading 1-2 μg of each molecule into the gel, and staining using instant Blue staining. Each gel included a molecular weight ladder with the indicated molecular weight standards (FIGS. 2-8). Reduced and non-reduced lanes are denoted by "R" and "NR". FIGS. 2-8 show non-reducing and reducing SDS-PAGE of an Fc domain formed from Fc domain monomers having the sequences of SEQ ID NOs: 1, 3, 5, 7, 9, 12, and 14, respectively.

Example 2. Synthesis of Zanamivir Intermediate

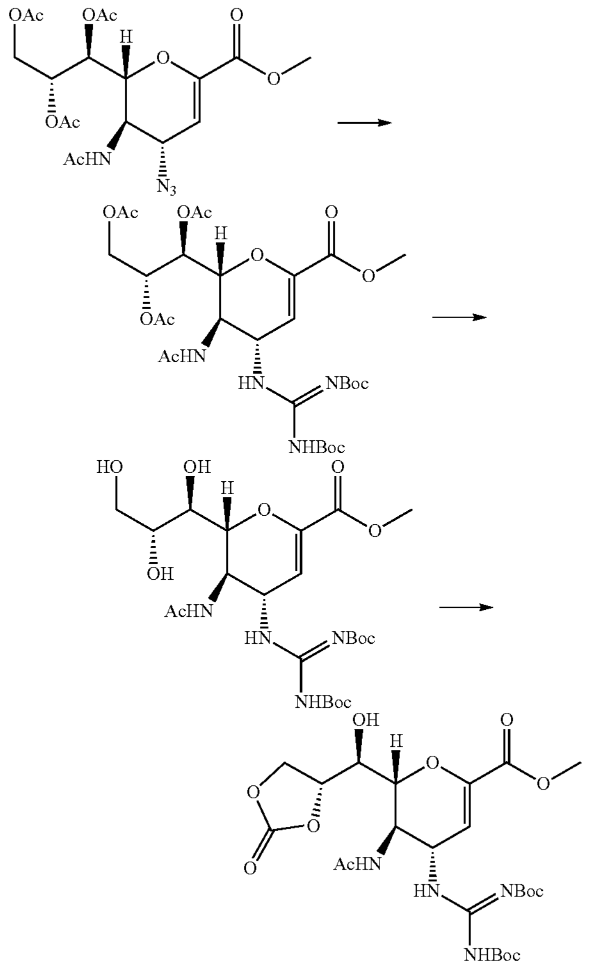

Step a.

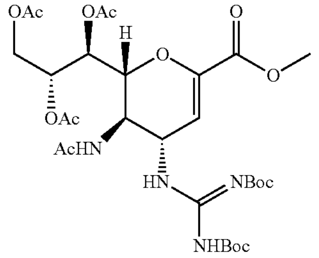

Methyl 5-acetamido-7,8,9-O-triacetyl-2,6-anhydro-4-azido-3,4,5-trideoxy-D-glycero-D-galacto-non-2-enonate (4.56 g, 10.0 mmol) was dissolved in anhydrous THE (15 mL), and the solution was cooled to approximately 13° C. Triphenylphosphine (2.89 g, 11 mmol) was added in portions over 20 minutes. The resulting mixture was stirred at approximately 13° C. to room temperature for 2 hours, then a solution of LiOH (24 mg, 1 mmol) in water (1.5 mL) was added dropwise. After stirring for 28 hours, the reaction mixture was added with N,N'-bis-boc-1-guanylpyrazole (3.26 g, 10.5 mmol) and 4-dimethylaminopyridine (244.4 mg, 2 mmol). The reaction was stirred for 1.5 days. It was then diluted with a 1:1 mixture of ethyl acetate: hexanes (100 mL) and extracted with water (30 mL). The aqueous layer was back-extracted with ethyl acetate (30 mL). The combined organic layers were concentrated by rotary evaporation. The residue was purified through C18 reversed phase column chromatography (150 g, 25 to 70% acetonitrile and water). The collected fractions were concentrated by rotary evaporation at room temperature. A cloudy aqueous solution resulted and the majority of the product deposited on the flask as a gel. The solution was then extracted with ethyl acetate (150 mL). The organic layer was used to re-dissolve the gel material. It was then dried over $Na_2SO_4$, concentrated by rotary evaporation, and further dried under high vacuum to afford the title compound as a white foam. Yield 6.24 g, 92.8%. Ion found by LCMS: $[M+H]^+$=673.2.

Step b.

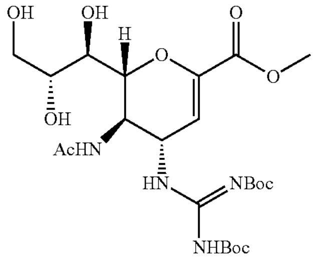

A solution of the product from step-a (6.24 g, 9.28 mmol) in anhydrous MeOH (20 mL) was cooled in an ice-water bath and a 0.5 M solution of sodium methoxide in MeOH (26 mL, 13 mmol) was slowly added. The reaction was stirred for 1 hour, then its pH was carefully adjusted to 7 to 7.5 by dropwise addition of a 4 N solution of HCl in dioxane (3 mL). The solvent was removed by rotary evaporation at a temperature not greater than room temperature. The residue was diluted with a 2:1 mixture of ethyl acetate and hexanes (150 mL), and the resulting solution was extracted with water (20 mL). The aqueous layer was back-extracted with ethyl acetate (30 mL). The combined organic layers were dried over $Na_2SO_4$, concentrated by rotary evaporation, and further dried under high vacuum. The product was carried to the subsequent step without further purification. Yield 5.03 g, 99.2%. Ion found by LCMS: $[M+H]^+$=547.2.

Step c.

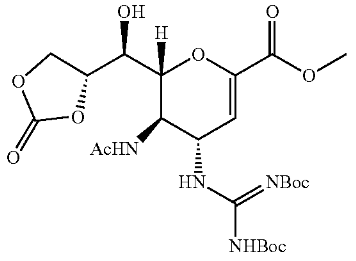

The step-b product (713 mg, 1.3 mmol) in anhydrous DCM (6 mL) was cooled in an ice-water bath and 4-dimethylaminopyridine (159.8 mg, 1.3 mmol) and DIPEA (520 mg, 4 mmol) were added. The mixture was then dropwise added with a solution of 4-nitrophenyl chloroformate (356.6 mg, 2.2 mmol) in anhydrous DCM (2 mL). The ice-water bath was then removed, and the reaction mixture was stirred for 3 hours and monitored by LCMS (additional 4-nitrophenyl chloroformate may be added if needed). After the reaction was complete, it was quenched with water (10 mL), and the organic layer was extracted and concentrated by rotary evaporation. The residue was purified by C18 reversed phase column chromatography (100 g, 20 to 70% acetonitrile and water). Acetonitrile in the collected fractions was removed by rotary evaporation at room temperature. The aqueous layer was then extracted with a 1:1 mixture of ethyl acetate and hexane (120 mL). The aqueous layer was back-extracted with ethyl acetate (30 mL). The combined organic layers were dried over $Na_2SO_4$, concentrated by rotary evaporation, and further dried under high vacuum to afford the title compound as a white solid. Yield 520 mg, 70%. Ion found by LCMS: $[M+H]^+$=573.2.

Example 3. Synthesis of Linker-1

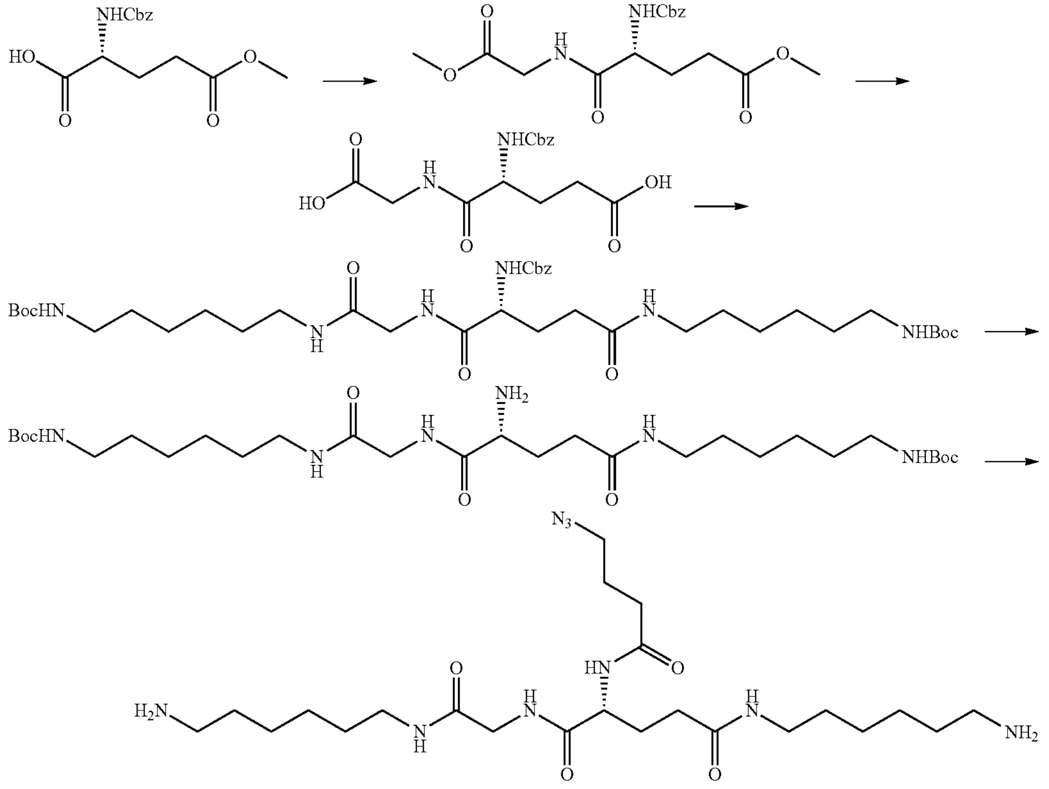

Step a.

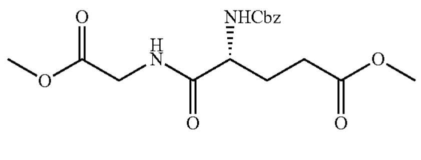

To a mixture of Z-D-glutamic γ-methyl ester (2.0 g, 6.77 mmol) and glycine methyl ester HCl (1.282 g, 10.2 mmol) in anhydrous DMF (7 mL) was added DIPEA (2.02 g, 15.57 mmol) followed by HATU (2.66 g, 7.0 mmol) in portions over 25 minutes. After HATU was dissolved, an additional amount of DIPEA (1.15 g, 8.8 mmol) was added. The reaction mixture was stirred for 1.5 hours, then extracted with 5% aqueous HCl (100 mL) and EtOAc (100 mL×2). The organic layer was concentrated by rotary evaporation. The residue was re-extracted with water (100 mL) and EtOAc/hexanes (2:1, 150 mL). The organic layer was dried over $Na_2SO_4$, concentrated by rotary evaporation and further dried under high vacuum to a white solid. The crude product was carried on to the subsequent step without further purification. Yield 2.3 g, 93%. Ion found by LCMS: $[M+H]^+$=367.

Step b.

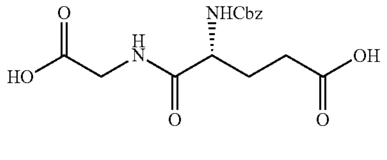 [SMILES: O=C(O)CC[C@@H](NC(=O)OCc1ccccc1)C(=O)NCC(=O)O]

The step-a product (2.3 g, 6.29 mmol) was dissolved in a 1:1 mixture of MeOH and THE (10 mL). After the solution was cooled in an ice-water bath, a LiOH monohydrate (630 mg, 15 mmol) solution in water (9 mL) was added in portions over 1.5 hours. After stirring for 2 additional hours, the reaction mixture was neutralized with 4N HCl in dioxane (3.7 mL). The organic solvent was partially removed by rotary evaporation at room temperature. The remaining material was directly purified by RPLC (150 g, 0 to 39% acetonitrile and water). Yield 2.03 g, 88.7% over two steps. Ion found by LCMS: $[M+H]^+$=339.2.

Step c.

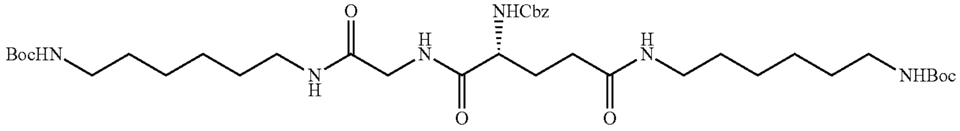 [SMILES: CC(C)(C)OC(=O)NCCCCCCNC(=O)CC[C@@H](NC(=O)OCc1ccccc1)C(=O)NCC(=O)NCCCCCCNC(=O)OC(C)(C)C]

To a mixture of the step-b product (1.41 g, 4.17 mmol) and N-Boc-1,6-diaminohexane (1.99 g, 9.2 mmol) in anhydrous DMF (6 mL) and DIPEA (1.3 g, 10 mmol), a solution of HATU (3.5 g, 9.2 mmol) in DMF (10 mL) was added by way of syringe pump at a rate of 11 mL/hr. Upon complete addition of the HATU, the reaction was stirred for 30 more minutes and directly purified by RPLC (150 g, 10 to 50% acetonitrile and water, using 0.1% TFA as modifier). Yield 1.3 g, 42.4%. Ion found by LCMS: $[M+H]^+$=735, $[M\text{-}Boc+H]^+$=635.4.

Step d.

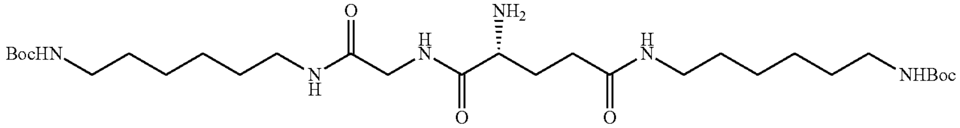 [SMILES: CC(C)(C)OC(=O)NCCCCCCNC(=O)CC[C@@H](N)C(=O)NCC(=O)NCCCCCCNC(=O)OC(C)(C)C]

The step-c product (1.3 g, 1.77 mmol) was dissolved in MeOH (20 mL), and Pd/C was added to the solution. The mixture was stirred under hydrogen for 4 hours. Pd/C was filtered off, and the filtrate was concentrated by rotary evaporation and further dried under high vacuum. Yield 1.03 g, 96.9%. Ion found by LCMS: $[M+H]^+$=601.

Step e.

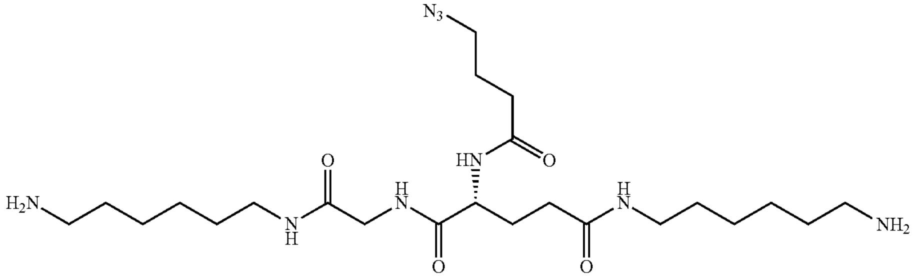 [SMILES: [N-]=[N+]=NCCCC(=O)N[C@H](CCC(=O)NCCCCCCN)C(=O)NCC(=O)NCCCCCCN]

A flamed-dried reaction flask was flushed with nitrogen and charged with 4-azidobutyric acid (77 mg, 0.6 mmol), N-hydroxy succinimide (92 mg, 0.8 mmol) and anhydrous DMF (0.5 mL). The mixture was stirred to dissolve the solids, and then DCC (125.5 mg, 0.608 mmol) was added. After stirring for one hour, the step-d product (300 mg, 0.5 mmol) was added to the reaction mixture. The reaction was stirred for 6 hours and directly purified using RPLC (150 g, 10 to 70% acetonitrile and water, using 01.% TFA as modifier). The collected fractions were lyophilized to a white solid (LCMS: $[M+H]^+$=712, $[M\text{-}Boc+H]^+$=612). The material was re-dissolved in DCM (~2 mL) and TFA (~1 mL) and stirred for 15 minutes. It was then concentrated by rotary evaporation, and the residue was purified by RPLC (50 g, 0 to 40% acetonitrile and water). Yield 255 mg, 68.9%. Ions found by LCMS: $[M+H]^+$=512, $[(M+2H)/2]+$ =256.

Example 4. Synthesis of Int-1

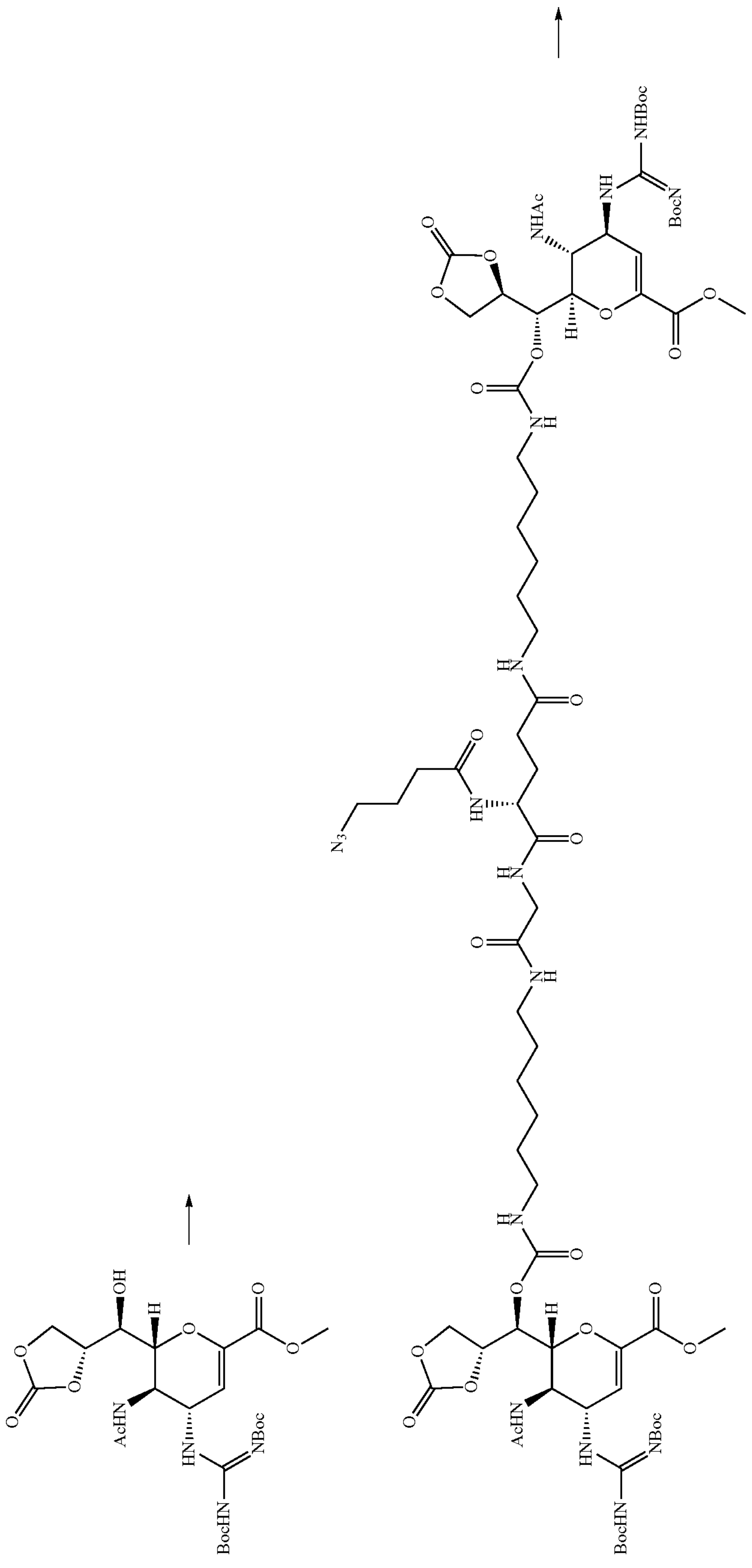

-continued
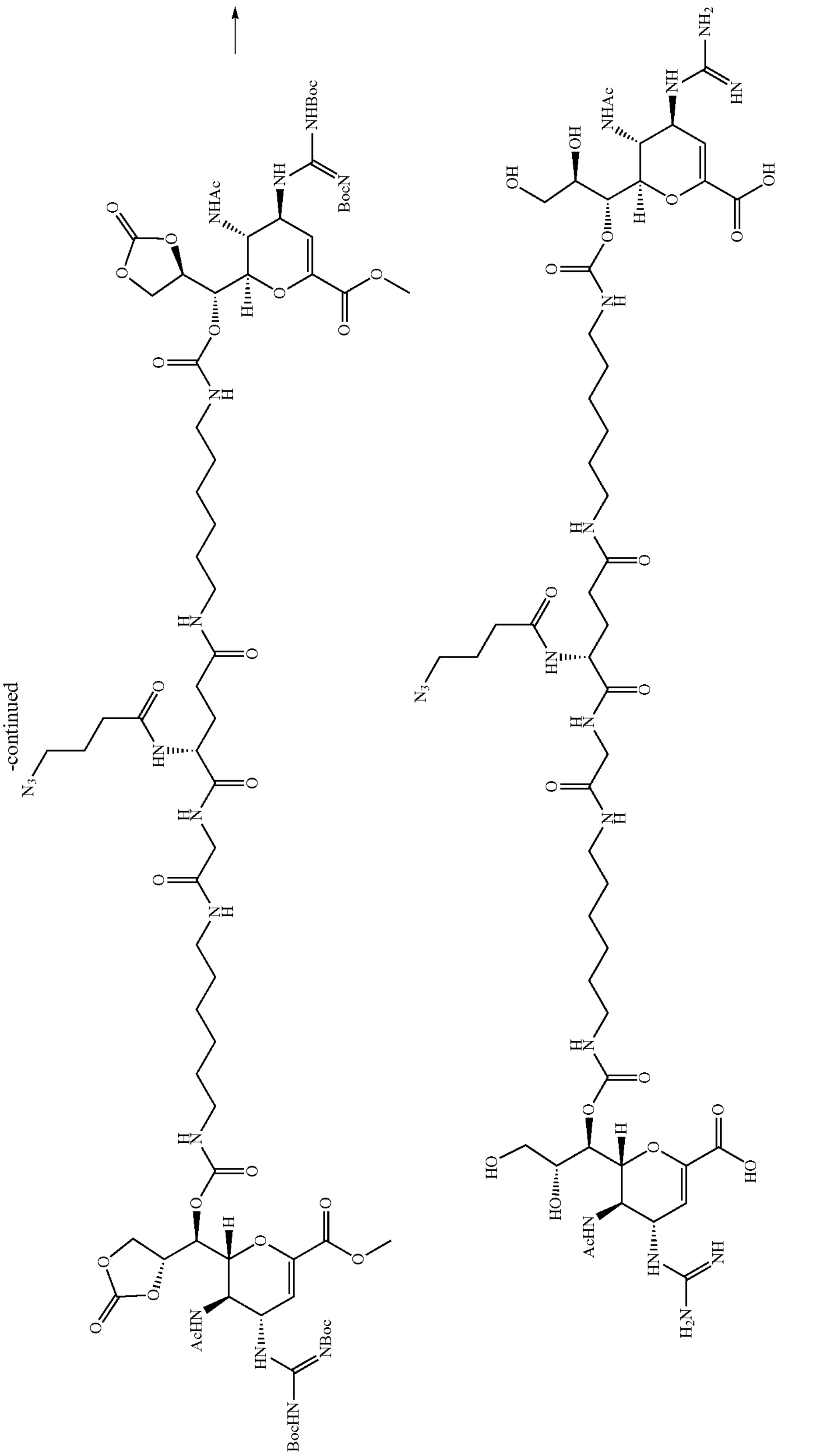

Step a.

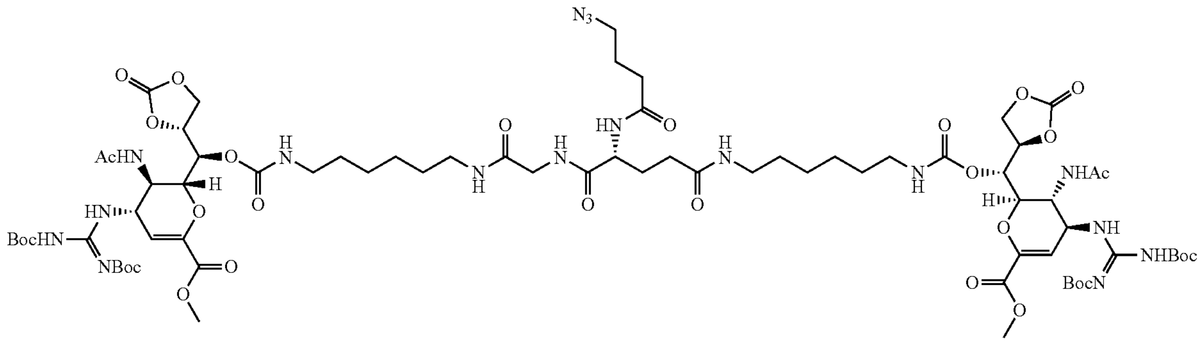

To a solution of the Zanamivir intermediate (Example 2) (532.5 mg, 0.93 mmol) in anhydrous THE (2 mL) was added DMAP (490 mg, 4 mmol), followed by bis(pentafluorophenyl)carbonate (385 mg, 0.911 mmol). After stirring overnight, a solution of Linker-1 (Example 3) (245.6 mg, 0.332 mmol) in anhydrous DMF (1 mL) and DIPEA (91 mg, 0.3 mmol) was added to the reaction mixture. The reaction was continued for 2 hours, then purified by RPLC (100 g, 5 to 67% acetonitrile and water). Yield 135 mg, 23.8%. Ion found by LCMS: $[(M+2H)/2]^+$=845.9.

Step b.

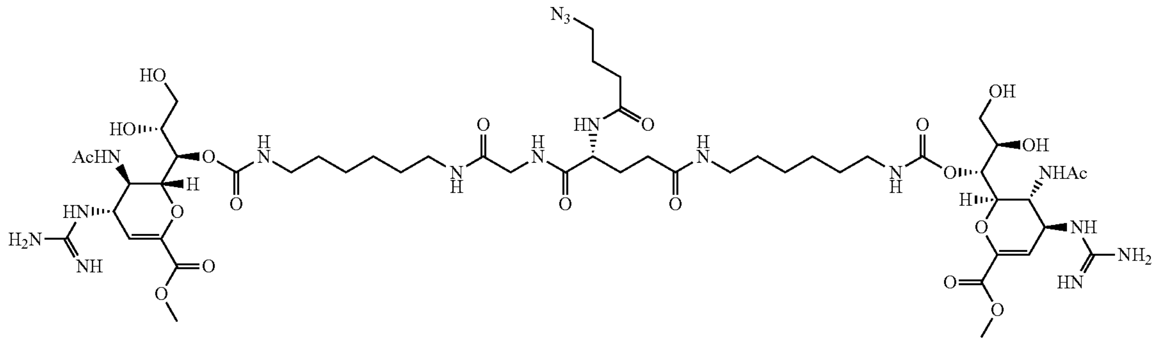 [SMILES: COC(=O)C1=C[C@H](NC(=N)N)[C@@H](NC(C)=O)[C@H]([C@H](OC(=O)NCCCCCCNC(=O)CC[C@@H](NC(=O)CCCN=[N+]=[N-])C(=O)NCC(=O)NCCCCCCNC(=O)O[C@@H]([C@@H]2OC(C(=O)OC)=C[C@H](NC(=N)N)[C@H]2NC(C)=O)[C@H](O)CO)[C@H](O)CO)O1]

The step-a product (135 mg, 0.079 mmol) was dissolved in TFA (0.5 mL), and the solution was stirred at room temperature for 20 minutes. It was then directly purified by RPLC (50 g, 5 to 32% acetonitrile and water). Yield 88 mg, 85.1%. Ion found by LCMS: $[(M+2H)/2]^+$=654.8.

Step c.

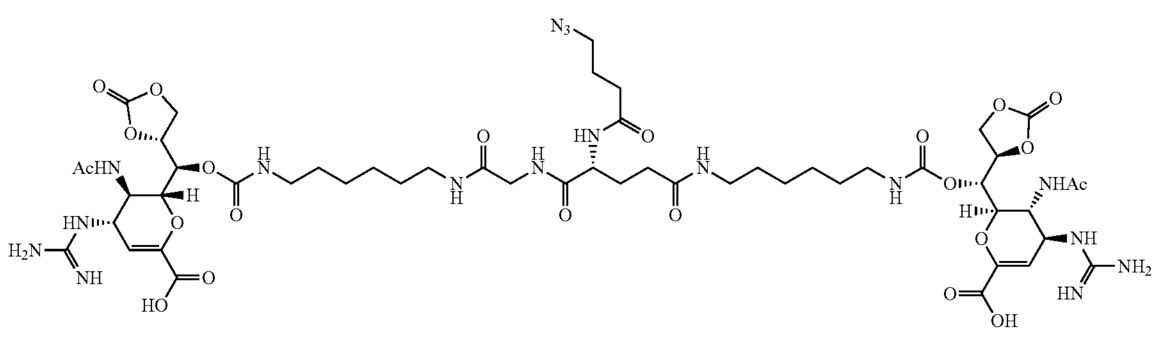 [SMILES: CC(=O)N[C@H]1[C@H]([C@H](OC(=O)NCCCCCCNC(=O)CC[C@@H](NC(=O)CCCN=[N+]=[N-])C(=O)NCC(=O)NCCCCCCNC(=O)O[C@@H]([C@@H]2OC(C(=O)O)=C[C@H](NC(=N)N)[C@H]2NC(C)=O)[C@H]2COC(=O)O2)[C@H]2COC(=O)O2)OC(C(=O)O)=C[C@@H]1NC(=N)N]

A solution of the step-b product (88 mg, 0.0673 mmol) in MeOH (1.5 mL) was cooled in an ice-water bath and LiOH (5 mg, 0.2 mmol) in water (0.5 mL) was added. After the mixture was stirred for 5 hours, it was acidified with 4N HCl solution in dioxane (0.1 mL) and purified by HPLC (5 to 20% acetonitrile and water, using 0.1% TFA as modifier). Yield 76.4 mg, 78%. Ion found by LCM: $[(M+2H)/2]^+$ =614.8.

Example 5. Synthesis of Linker-2

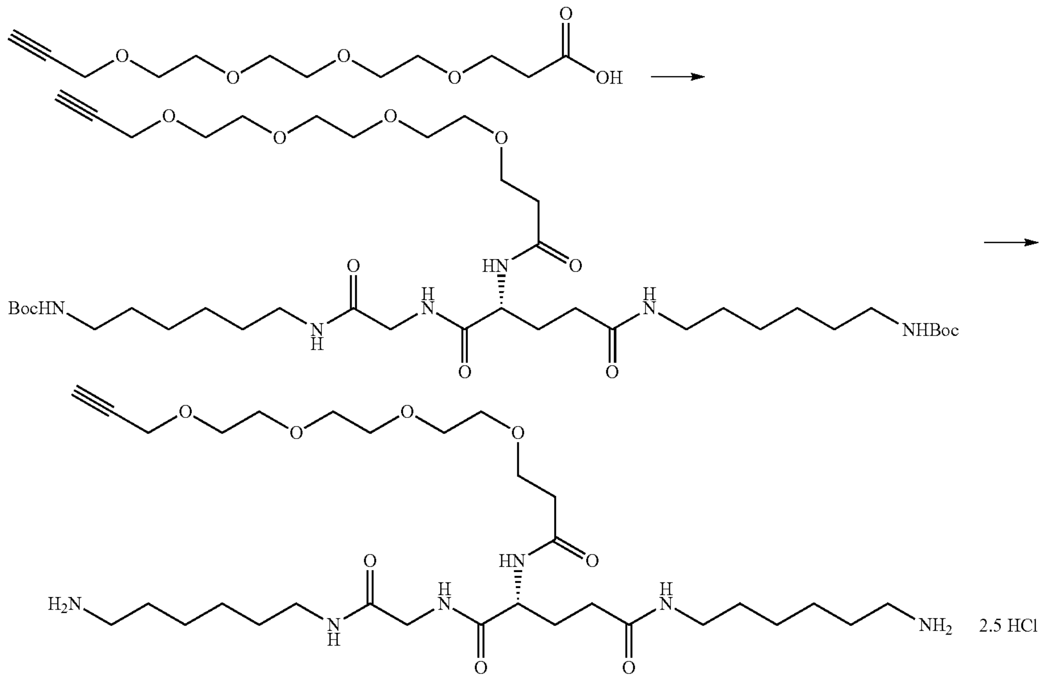

Step a.

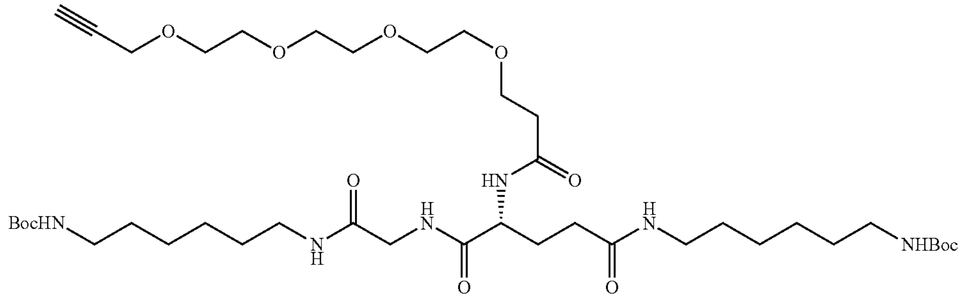 [SMILES: C#CCOCCOCCOCCOCCC(=O)N[C@H](CCC(=O)NCCCCCCNC(=O)OC(C)(C)C)C(=O)NCC(=O)NCCCCCCNC(=O)OC(C)(C)C]

To a solution of propargyl-PEG4-acid (364.4 mg, 1.4 mmol) in anhydrous DMF (2 mL) was added HATU (558.9 mg, 1.47 mmol). After stirring to dissolve all the coupling reagent, DIPEA (390 mg, 3 mmol) was added and stirred for 10 minutes. A solution of the Linker-1 step-d product (Example 3, step d) (701.1 mg, 1.167 mmol) in anhydrous DMF (1 mL) was added. The resulting mixture was stirred for 30 minutes and directly purified by RPLC (100 g, 5 to 60% acetonitrile and water). Yield 830 mg, 84.4%. Ion found by LCMS: $[M+H]^+$=843.

Step b.

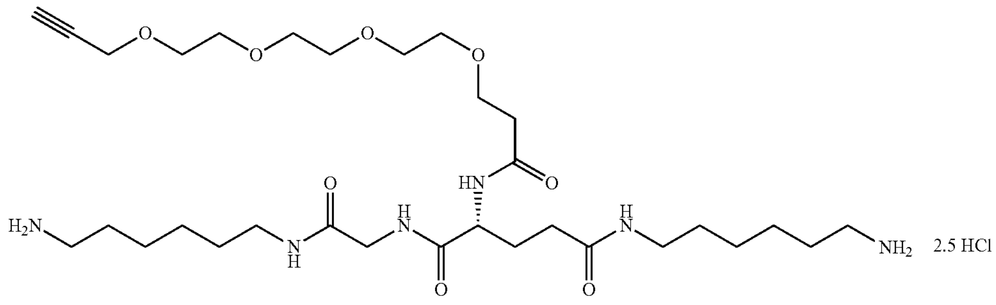 [SMILES: C#CCOCCOCCOCCOCCC(=O)N[C@H](CCC(=O)NCCCCCCN)C(=O)NCC(=O)NCCCCCCN]

The step-a product was dissolved in THE (5 mL) and treated with 4N HCl solution in dioxane (2.5 mL). After stirring at room temperature overnight, the reaction mixture was concentrated by rotary evaporation. The residue was re-dissolved in acetonitrile/water (1:1, 16 mL), and the solution was lyophilized. The crude product was carried on to the subsequent step without further purification. Yield 761.8 mg, 100%. Ion found by LCMS: $[M+H]^+$=643.8.

Example 6. Synthesis of Int-2

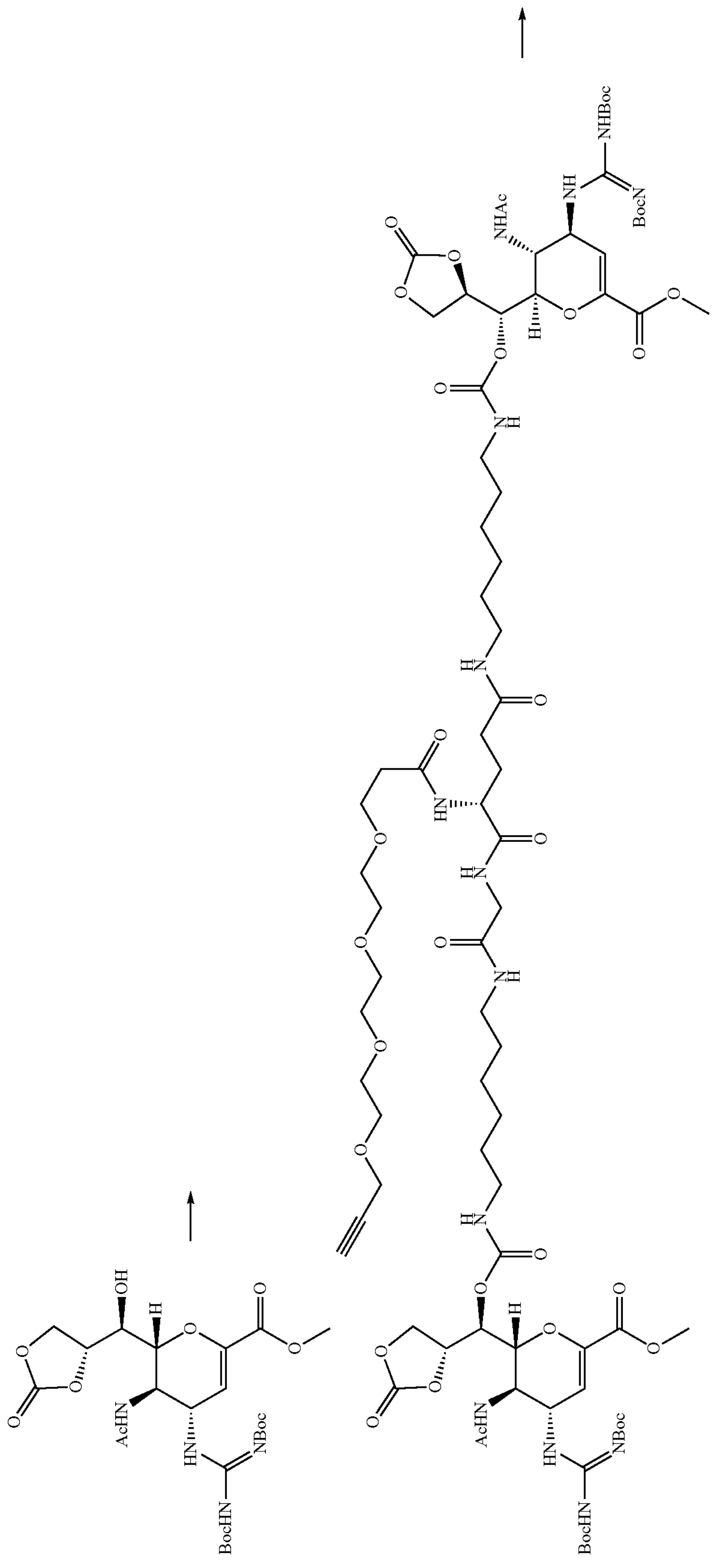

-continued
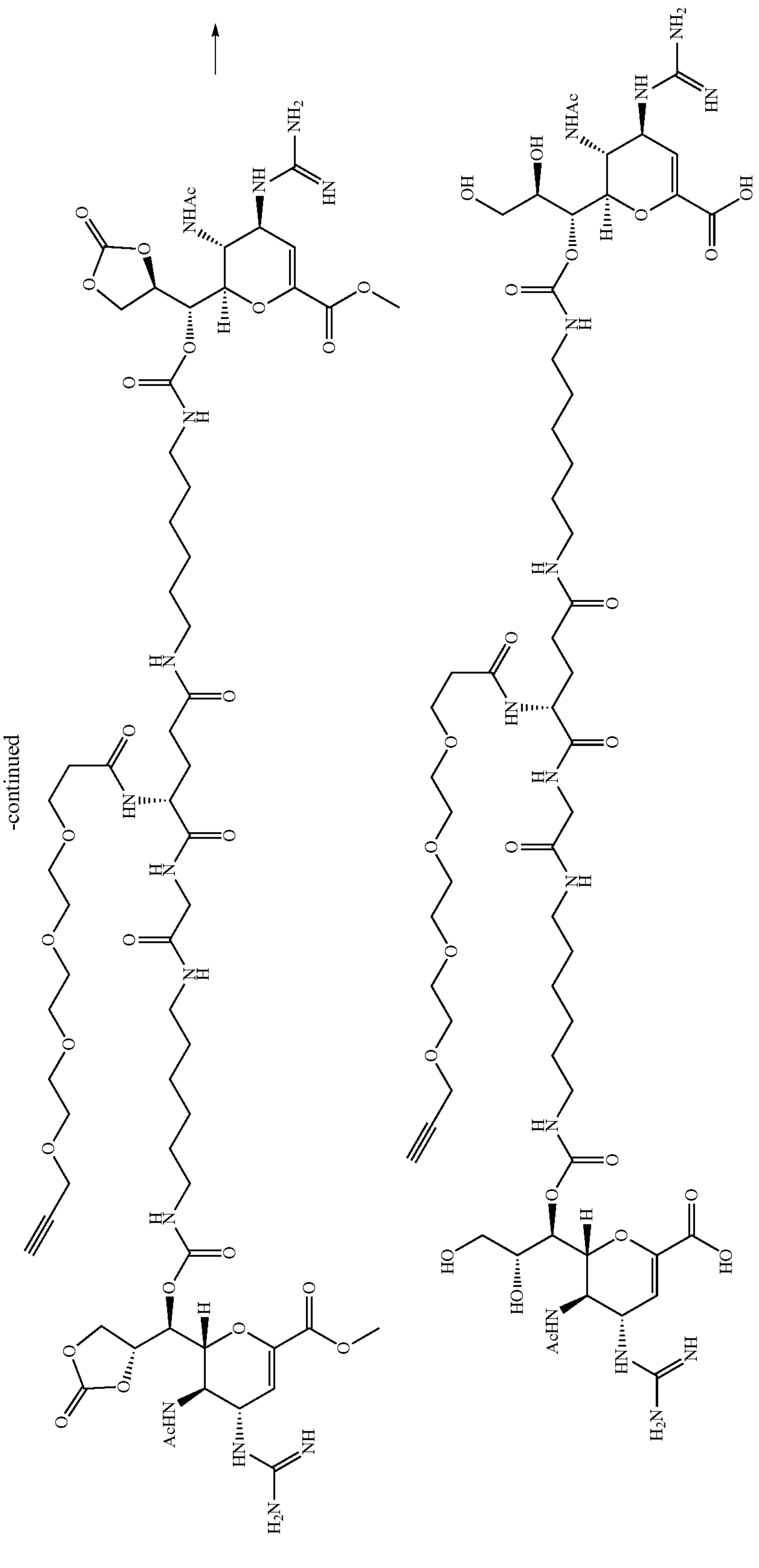

Step a.

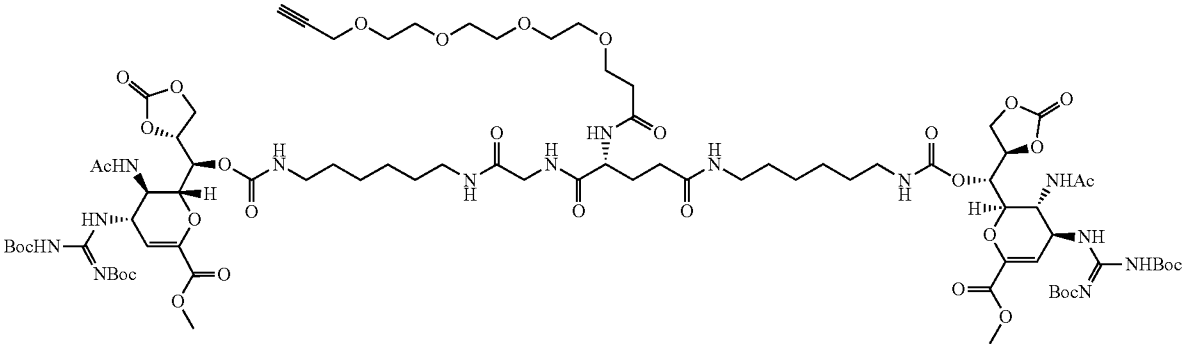

A flame-dried reaction flask was flushed with nitrogen and charged with Zanamivir intermediate (Example 2) (533.6 mg, 0.812 mmol), DMAP (99.8 mg, 0.81 mmol), and anhydrous DCM (1 mL). After stirring to dissolve the starting material, the solution was cooled in an ice-water bath and 4-nitrophenyl chloroformate (242 mg, 1.2 mmol) was added. The resulting mixture was stirred for 5 hours, then added into a solution of the Linker-2 (Example 5) (228.4 mg, 0.319 mmol) in anhydrous DMF (1 mL) and DIPEA (130 mg, 1 mmol). The reaction was stirred overnight and purified by RPLC (150 g, 20 to 65% acetonitrile and water, using 0.1% TFA as modifier). The collected fractions were lyophilized. Yield 178.3 mg, 30.4%. Ion found by LCMS: $[(M+2H)/2]^+=920.5$, $[(M+3H)/3]^+=614.2$.

Step b

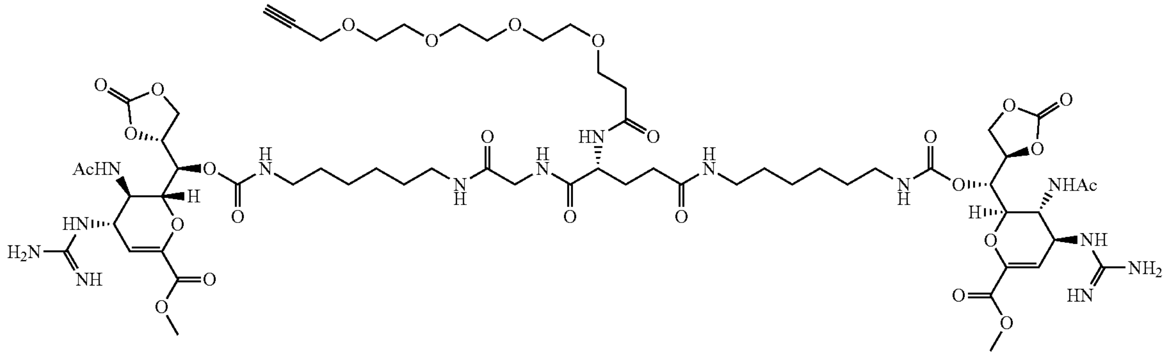 [SMILES: C#CCOCCOCCOCCOCCC(=O)N[C@H](CCC(=O)NCCCCCCNC(=O)O[C@@H]([C@@H]1OC(C(=O)OC)=C[C@H](NC(=N)N)[C@H]1NC(C)=O)[C@H]1COC(=O)O1)C(=O)NCC(=O)NCCCCCCNC(=O)O[C@@H]([C@@H]1OC(C(=O)OC)=C[C@H](NC(=N)N)[C@H]1NC(C)=O)[C@H]1COC(=O)O1]

The step-a product (178.3 mg, 0.0969 mmol) was dissolved in TFA (0.5 mL). The solution was stirred for 20 minutes, then directly purified by HPLC (0 to 25% acetonitrile and water, using 0.1% TFA as modifier). Yield 91.8 mg, 56.8%. Ions found by LCMS: $[(M+2H)/2]^+=720.4$, $[(M+3H)/3]^+=480.6$.

Step c.

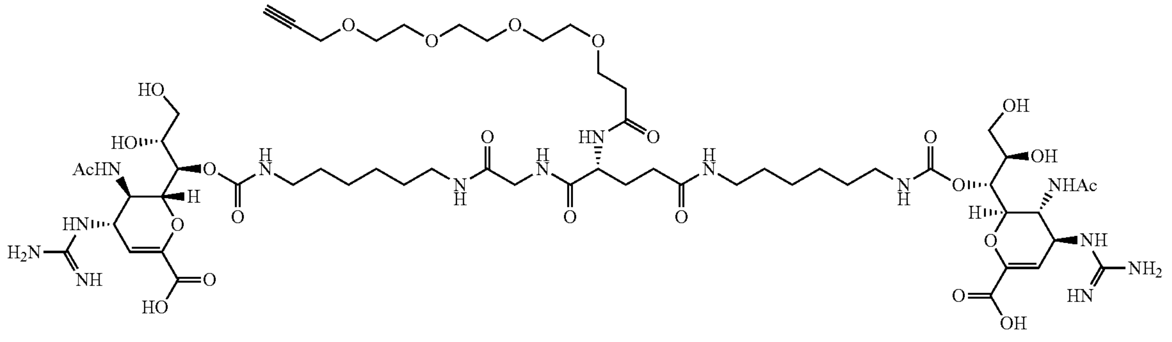 [SMILES: C#CCOCCOCCOCCOCCC(=O)N[C@H](CCC(=O)NCCCCCCNC(=O)O[C@@H]([C@@H]1OC(C(=O)O)=C[C@H](NC(=N)N)[C@H]1NC(C)=O)[C@H](O)CO)C(=O)NCC(=O)NCCCCCCNC(=O)O[C@@H]([C@@H]1OC(C(=O)O)=C[C@H](NC(=N)N)[C@H]1NC(C)=O)[C@H](O)CO]

The step-b product (91.8 mg, 0.055 mmol) was dissolved in MeOH (1 mL), and the solution was cooled in an ice-water bath. LiOH monohydrate (21 mg, 0.5 mmol) in water (1 mL) was added in portions over 1 hour. After stirring for 2 more hours, the reaction mixture was acidified with a 4N HCl solution in dioxane (0.3 mL) and purified by HPLC (0 to 20% acetonitrile and water, using 0.1% TFA as modifier). Yield 36.2 mg, 59.4%.%. Ions found by LCMS: $[(M+2H)/2]^{+}$=680.3, [(M+3H)/3]+=454.0.

Example 7. Synthesis of h-IgG1 Fc-PEG4-azide

PEG4-azidoNHS ester (98%, 180 μmol, 9.5 equivalents, 71.4 mg in 0.5 mL of DMF and diluted to 3.60 mL with pH 7.4 PBS 1× buffer solution) was added to a solution of h-IgG1 Fc (SEQ ID NO: 4) (1103 mg in 70.0 mL of pH 7.4 PBS, MW~58,000 Da, 19.0 μmol) and the mixture was shaken gently for 12 hours at ambient temperature. The solution was concentrated using a centrifugal concentrator (30,000 MWCO) to a volume of ~1.5 mL. The crude mixture was diluted 1:10 in PBS pH 7.4, and concentrated again. This wash procedure was repeated for total of three times. The small molecule reagent was removed with this wash procedure. The concentrated Fc-PEG4-azide was diluted to 70.0 mL with pH 7.4 PBS 1× buffer and ready for Click conjugation. The purified material was quantified using a Nanodrop™ UV visible spectrophotomer (using a calculated extinction coefficient based on the amino acid sequence of h-IgG1). Yield is quantitative after purification. DAR=4.3 determined by MALDI. The DAR value can be adjusted by altering the equivalents of PEG4-azido NHS ester in near linear relation. For example, when 7.0 equivalents of PEG4-azide NHS ester is used the DAR value will be at 3.0.

Example 8. Synthesis of Recombinant Mouse Serum Albumin (MSA)-PEG4-Azide

PEG4-azidoNHS ester (98%, 81.7 μmol, 4.5 equivalents, 32.4 mg in 0.3 mL of DMF and diluted to 1.63 mL with pH 7.4 PBS 1× buffer solution) was added to a solution of recombinant mouse serum albumin (SEQ ID NO: 71) (1200 mg in 75.0 mL of pH 7.4 PBS, MW~66,000 Da, 18.2 μmol) and the mixture was shaken gently for 12 hours at ambient temperature. The solution was concentrated using a centrifugal concentrator (30,000 MWCO) to a volume of ~1.5 mL. The crude mixture was diluted 1:10 in PBS pH 7.4, and concentrated again. This wash procedure was repeated for total of three times. The small molecule reagent was removed with this wash procedure. The concentrated MSA-PEG4-azide was diluted to 75.0 mL with pH 7.4 PBS 1× buffer and ready for Click conjugation. The purified material was quantified using a Nanodrop™ UV visible spectrophotomer (using a calculated extinction coefficient based on the amino acid sequence of h-IgG1). Yield is quantitative after purification. DAR=3.5 determined by MALDI. The DAR value can be adjusted by altering the equivalents of PEG4-azido NHS ester similar to h-IgG1 Fc (Example 7).

Example 9. Synthesis of Conjugate 1

Figure 9:
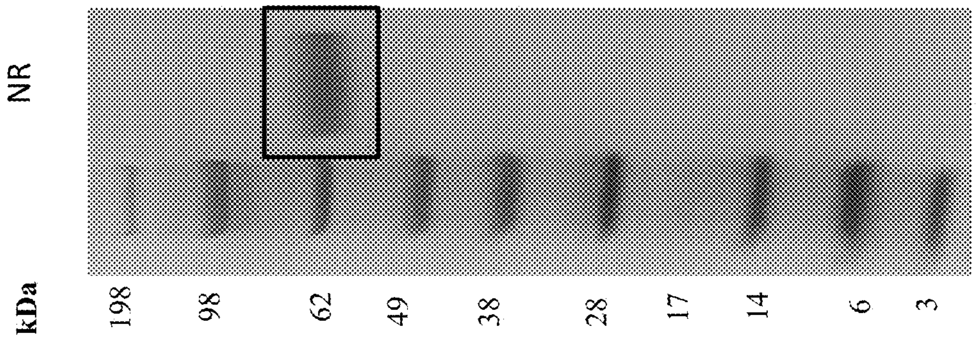
FIG. 9 shows a non-reducing SDS-PAGE of Conjugate 1.

A PBS solution of h-IgG1 Fc-PEG4-azide (Example 7) (50 mg, 2.815 mL, 0.8591 μmol) was added into a 15 mL centrifuge tube containing Int-2 (Example 6) (35.2 mg, 0.02217 mmol). After the mixture was gently shaken to dissolve all Int-2, 344 μl of a solution of L-ascorbic acid sodium (59.4 mg, 0.3 mmol), copper (II) sulfate (10 mg, 0.05 mmol), and THPTA (23 mg, 0.05 mmol) in PBS 7.4 buffer (1 mL) was added. The resulting mixture was gently shaken overnight. It was purified by affinity chromatography over a protein A column, followed by size exclusion chromatography as described in Example 8. Maldi TOF analysis of the purified final product gave an average mass of 63797 Da (DAR=3.4). Yield 27.39 mg, 55% yield. FIG. 9 shows a non-reducing SDS-PAGE of Conjugate 1.

Example 10. Purification of Conjugates

Crude mixture was diluted 1:10 in PBS pH 7.4, and purified using MabSelect Sure Resin (GE Healthcare, Chicago, IL, USA), followed by size exclusion chromatography. (HiLoad 26/600 Superdex200 μg, GE Healthcare, Chicago, IL, USA). Fractions containing purified conjugate were pooled and concentrated to approximately 20 mg/mL using a centrifugal concentrator (30,000 MWCO). Purified material was quantified using a Nanodrop™ UV visible spectrophotomer using a calculated extinction coefficient based on the amino acid sequence of hIgG1 Fc(myc). Purified molecules were analyzed using 4-12% Bis Tris SDS PAGE gels by loading 1 μg of each molecule into the gel, and staining using Instant Blue (Expedeon, San Diego, CA, USA). Each gel included a molecular weight ladder with the indicated molecular weight standards. Yields were calculated and purity determined by Agilent Analytical HPLC. Product peak and MW were found by Maldi MS and a final DAR calculated.

Example 11. Synthesis of Int-3

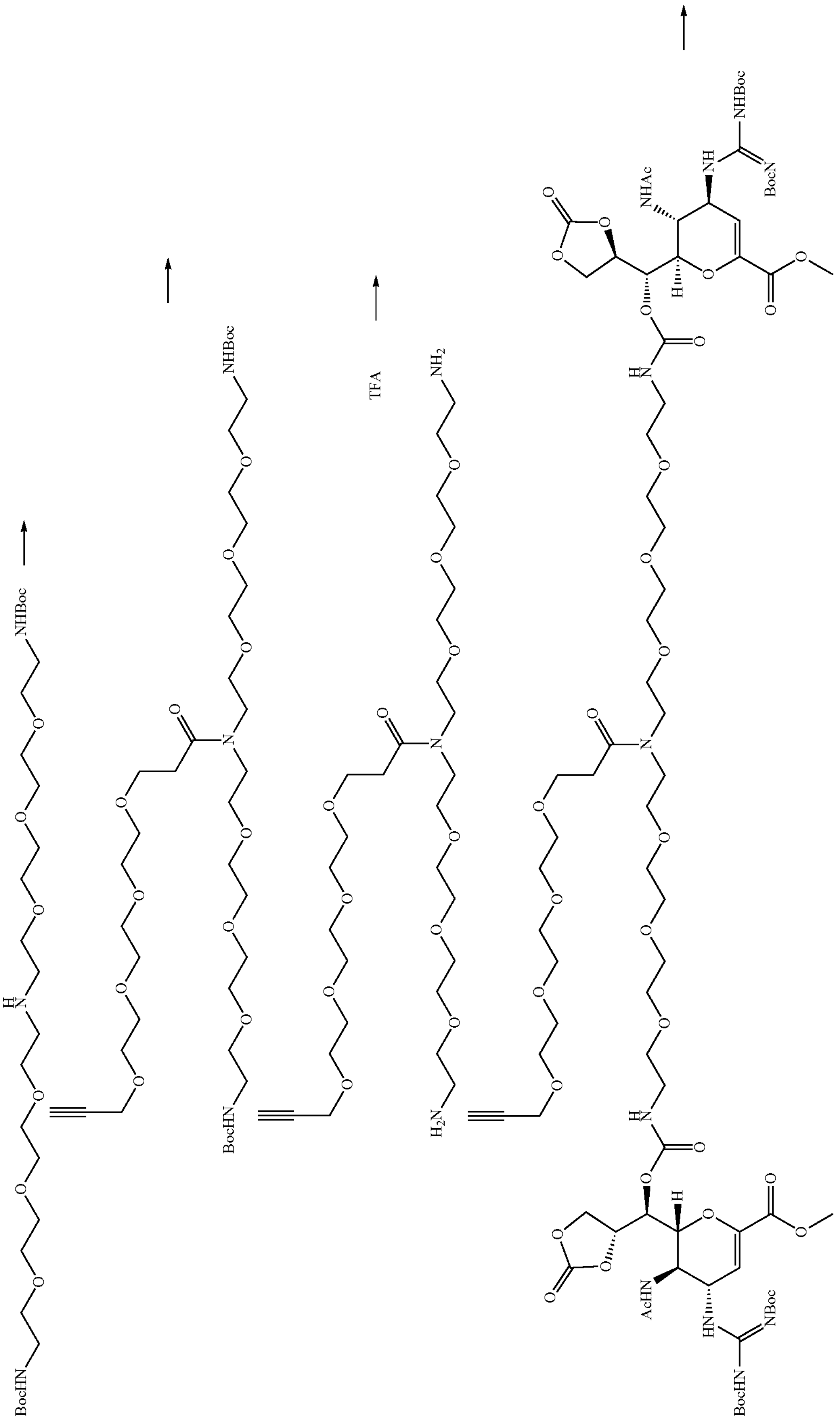
TFA

-continued
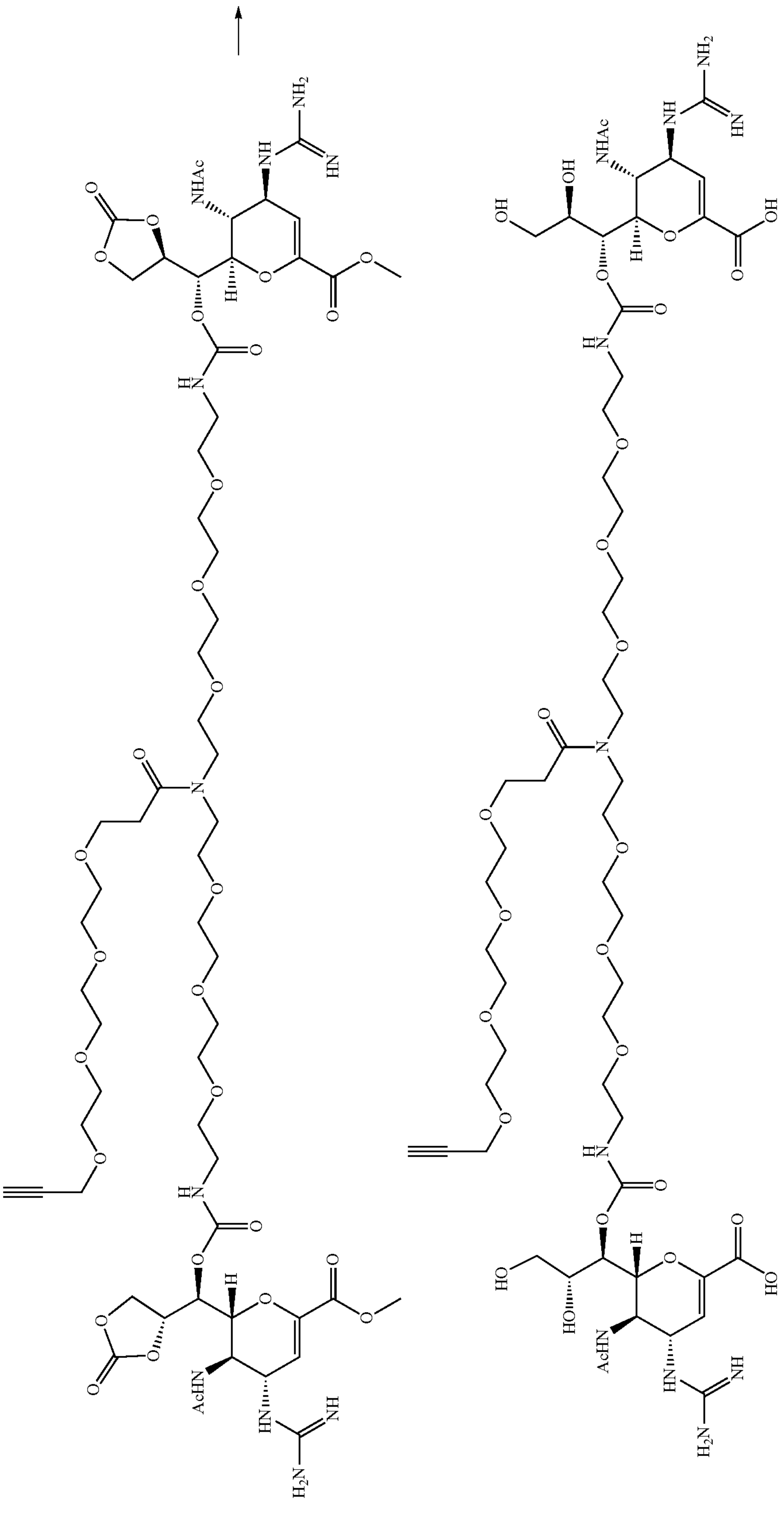

Step a.

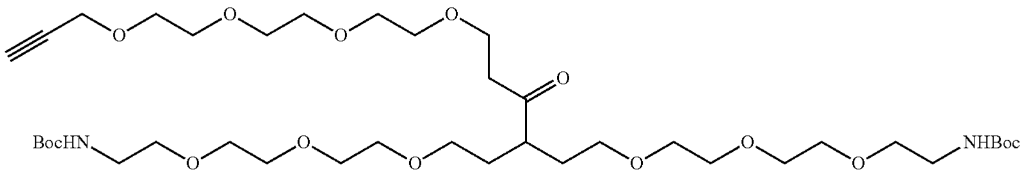 [SMILES: C#CCOCCOCCOCCOCCC(=O)C(CCOCCOCCOCCNC(=O)OC(C)(C)C)CCOCCOCCOCCNC(=O)OC(C)(C)C]

To a solution of propargyl-PEG4-acid (260 mg, 1 mmol) and HATU (380.2 mg, 1 mmol) in anhydrous DMF (1 mL) was added DIPEA (130 mg). After stirring 5 minutes, NH-bis(PEG3-Boc) (500 mg, 0.881 mmol) was added and stirring was continued at room temperature overnight. It was then directly purified by RPLC 9100 g, 5 to 50% acetonitrile and water, using 0.1% TFA as modifier). Yield 683 mg, 95.8%. Ions found by LCMS: $[M+H]^+$=810.4, $[M\text{-}Boc+H]^+$ =710.4, $[(M-2Boc+2H)/2]^+$=305.8.

Step b.

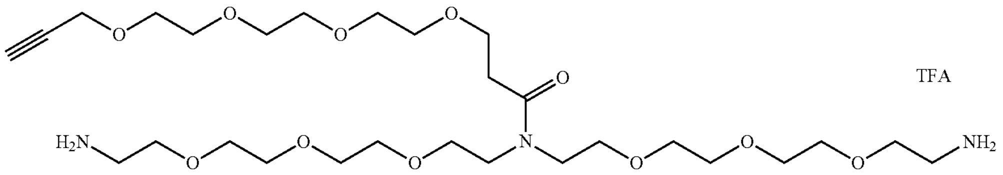 [SMILES: C#CCOCCOCCOCCOCCC(=O)N(CCOCCOCCOCCN)CCOCCOCCOCCN]

The step-a product was dissolved in TFA (1 mL). The solution was stirred for 2 hours and then directly purified through RPLC (100 g, 0 to 30% acetonitrile and water). Yield 589 mg, 98.7%. Ion found by LCMS: $[(M+2H)/2]^+$ =305.8.

Step c.

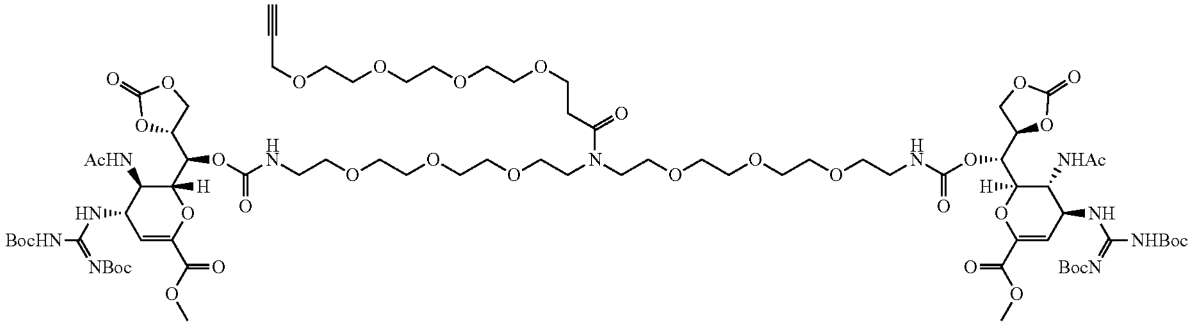

A flame-dried reaction flask was flushed with nitrogen and charged with Zanamivir intermediate (Example 2) (572 mg, 1 mmol) and anhydrous DCM (1 mL). After stirring to dissolve the starting material, the solution was cooled in an ice-water bath and 4-nitrophenyl chloroformate (302.4 mg, 1.5 mmol) was added followed by DMAP (22.4 mg, 0.2 mmol). The resulting mixture was stirred for 5 hours, then quenched water (0.2 mL) was added. After stirring for 10 minutes, the step-b product (256.7 mg, 0.355 mmol) in anhydrous DMF (1 mL) and DIPEA (163.8 mg, 1.26 mmol) was added. Stirring was continued for 2 hours and then the reaction was directly purified by RPLC (150 g, 20 to 65% acetonitrile and water, using 0.1% TFA as modifier). The collected fractions were lyophilized. Yield 422.8 mg of the desired product which was contaminated with some impurities, <69% yield. The material was carried on to the subsequent step without further purification. Ion found by LCMS: $[(M+2H)/2]^+$=903.9, $[(M+3H)/3]^+$=603.2.

Step d.

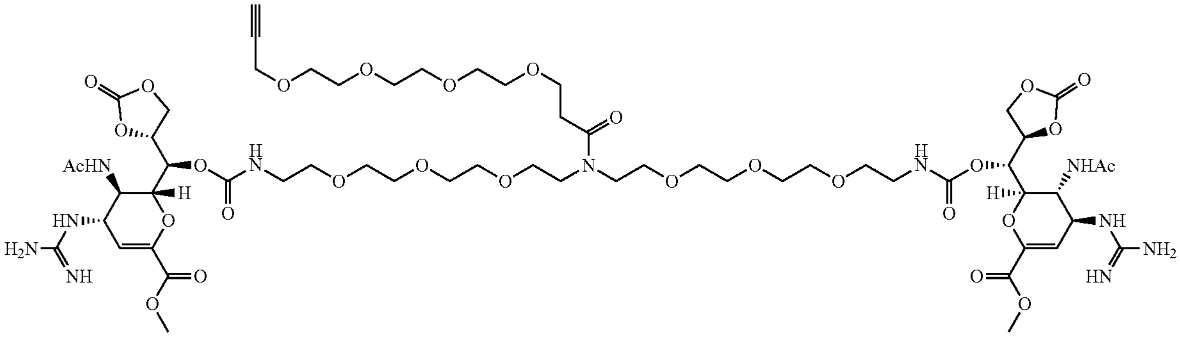 [SMILES: C#CCOCCOCCOCCOCCC(=O)N(CCOCCOCCOCCNC(=O)O[C@@H]([C@@H]1OC(C(=O)OC)=C[C@H](NC(=N)N)[C@H]1NC(C)=O)[C@H]1COC(=O)O1)CCOCCOCCOCCNC(=O)O[C@@H]([C@@H]1OC(C(=O)OC)=C[C@H](NC(=N)N)[C@H]1NC(C)=O)[C@H]1COC(=O)O1]

The step-c product (422.8 mg, <0.245 mmol) was dissolved in TFA (1 mL). The solution was stirred for 20 minutes, then directly purified by HPLC (5 to 25% acetonitrile and water, using 0.1% TFA as modifier). Yield 169.7 mg, 29.2% over two steps. Ions found by LCMS: $[(M+2H)/2]^{+}$=704.0, $[(M+3H)/3]^{+}$=469.6.

Step e.

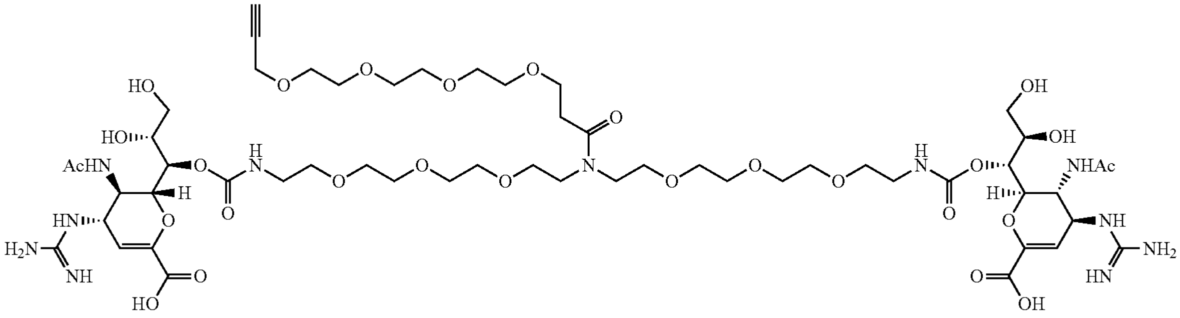 [SMILES: C#CCOCCOCCOCCOCCC(=O)N(CCOCCOCCOCCNC(=O)O[C@@H]([C@@H]1OC(C(=O)O)=C[C@H](NC(=N)N)[C@H]1NC(C)=O)[C@H](O)CO)CCOCCOCCOCCNC(=O)O[C@@H]([C@@H]1OC(C(=O)O)=C[C@H](NC(=N)N)[C@H]1NC(C)=O)[C@H](O)CO]

The step-d product (169.7 mg, 0.0923 mmol) was dissolved in MeOH (1.5 mL), and the solution was cooled in an ice-water bath. LiOH monohydrate (21 mg, 0.5 mmol) in water (1 mL) was added in portions over 1 hour. After stirring overnight, the reaction mixture was acidified with Dowex 50Wx8 hydrogen form and purified through RPLC (0 to 30% acetonitrile and water, using 0.1% TFA as modifier). Yield 107.9 mg, 66.9%. Ions found by LCMS: $[(M+2H)/2]^{+}$=663.8, $[(M+3H)/3]^{+}$=442.9.

Example 12. Synthesis of Conjugate 2

Figure 10:
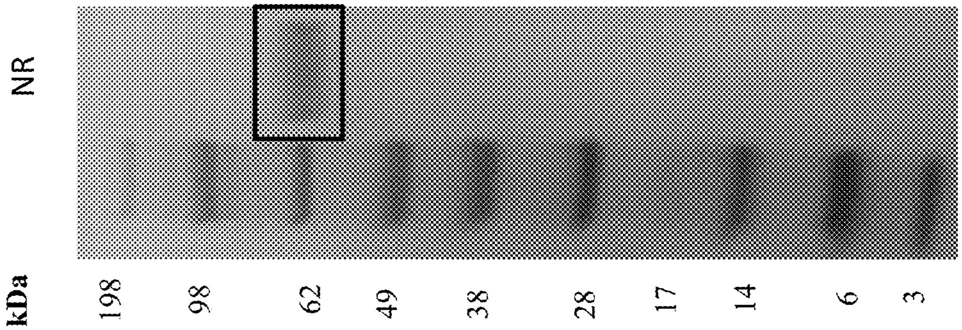
FIG. 10 shows a non-reducing SDS-PAGE of Conjugate 2.

The title conjugate was prepared analogously to Conjugate 1 (Example 9) using Int-3 (Example 11). Maldi TOF analysis of the purified final product gave an average mass of 63561 Da (DAR=3.3). Yield 43.4 mg, 43% yield. FIG. 10 shows a non-reducing SDS-PAGE of Conjugate 2.

Example 13. Synthesis of Int-4

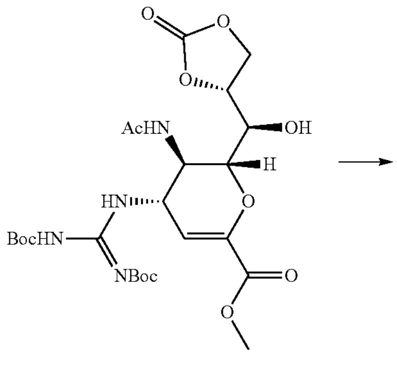

-continued

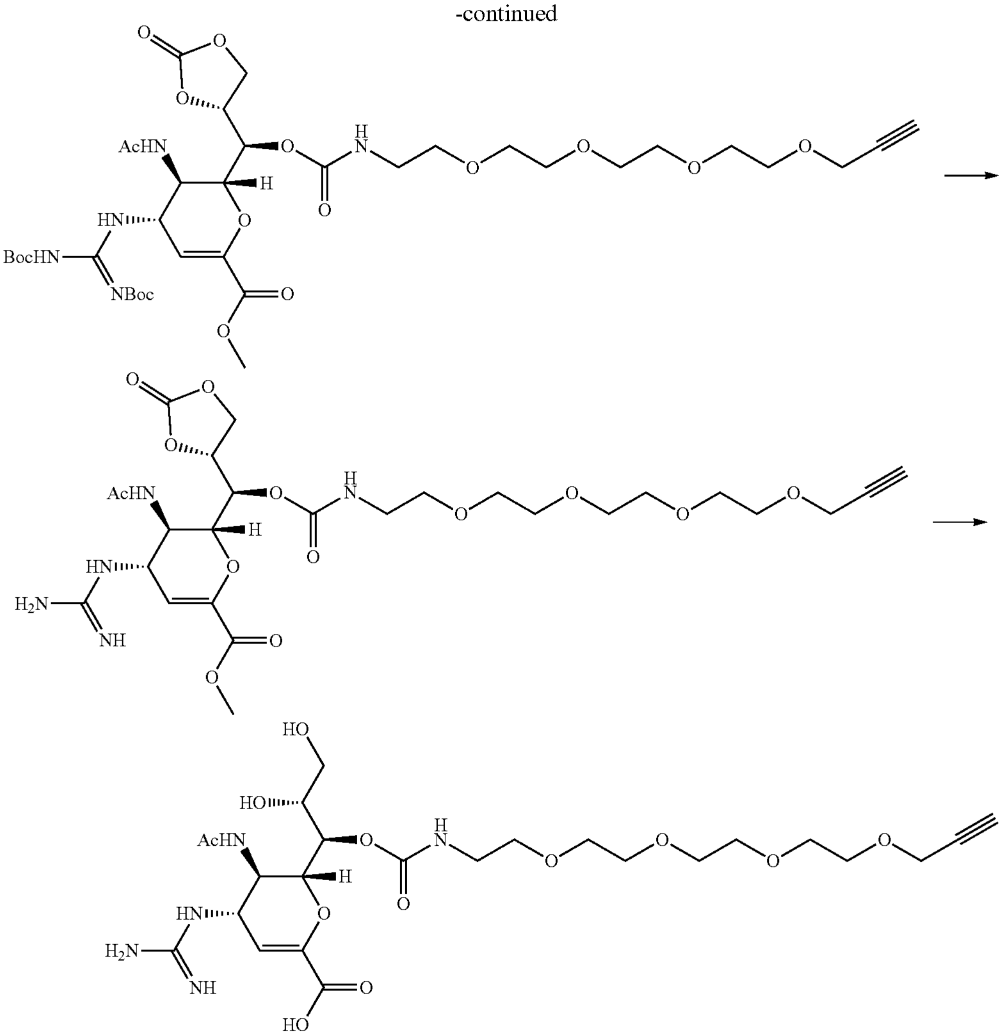

Step a.

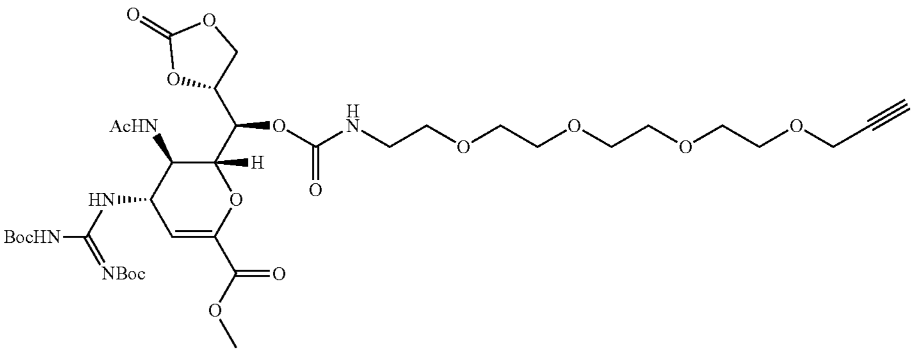

A flame-dried reaction flask was flushed with nitrogen and charged with Zanamivir Intermediate (Example 2) (343.2 mg, 0.6 mmol) and anhydrous DCM (1.5 mL). The solution was cooled in an ice-water bath and added with DIPEA (234 mg, 1.8 mmol) followed by 4-nitrophenyl chloroformate (121 mg, 0.6 mmol) and DMAP (67.4 mg, 0.6 mmol). The resulting mixture was stirred for 15 minutes, then added with an additional amount of 4-nitrophenyl chloroformate (121 mg, 0.6 mmol). After stirring for 2 hours, water (0.2 mL) was added to quench unreacted chloroformate. After stirred for 10 minutes, the reaction mixture was added with a solution of propargyl-PEG4-amine (185 mg, 0.8 mmol) in anhydrous DMF (0.5 mL). The reaction was continued for 1 hour and then directly purified through RPLC (100 g, 5 to 60% acetonitrile and water, using 0.1% TFA as modifier).

The collected fractions were lyophilized. Yield 355 mg, 71.3%. Ion found by LCMS: $[M+H]^+$=830.2.

Step b.

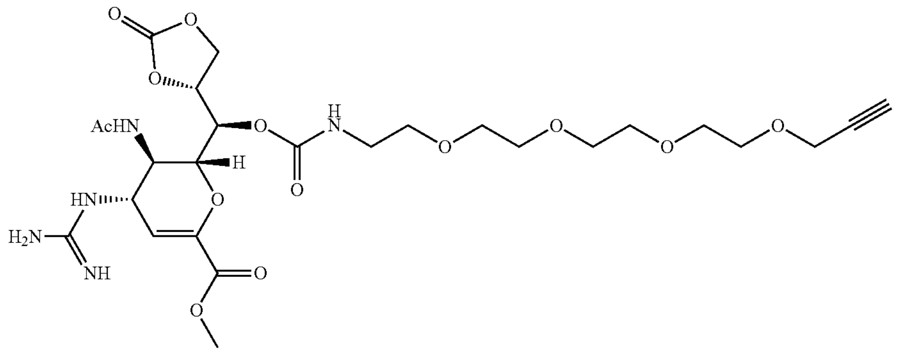 [SMILES: C#CCOCCOCCOCCOCCNC(=O)O[C@@H]([C@@H]1OC(C(=O)OC)=C[C@H](NC(=N)N)[C@H]1NC(C)=O)[C@H]1COC(=O)O1]

The step-a product (355 mg, 0.428 mmol) was dissolved in TFA (1 mL). The solution was stirred overnight, then directly purified by RPLC (5 to 25% acetonitrile and water, using 0.1% TFA as modifier). Yield 260.2 mg, 70.9% over two steps. Ion found by LCMS: $[M+H]^+$=630.2.

Step c.

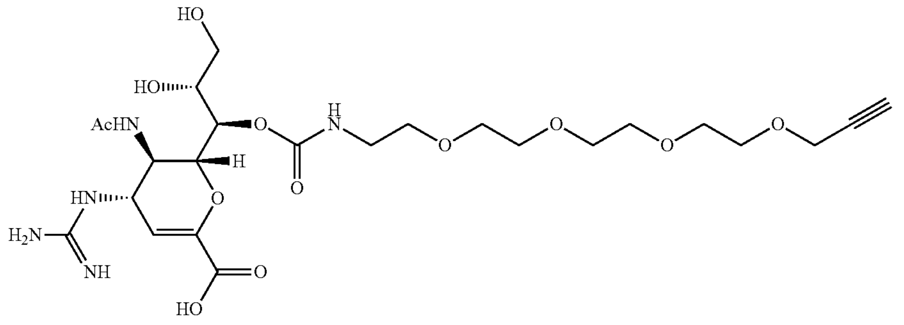 [SMILES: C#CCOCCOCCOCCOCCNC(=O)O[C@@H]([C@@H]1OC(C(=O)O)=C[C@H](NC(=N)N)[C@H]1NC(C)=O)[C@H](O)CO]

The step-b product (260.2 mg, 0.303 mmol) was dissolved in MeOH (1.5 mL). After the solution was cooled in an ice-water bath, a solution of LiOH monohydrate (42 mg, 1 mmol) in water (1 mL) was added in portions over 1 hour. The reaction was stirred overnight, then acidified with Dowex 50W×8 hydrogen form and purified by RPLC (0 to 50% acetonitrile and water, using 0.1% TFA as modifier). Yield 78.1 mg, 99%. Ions found by LCMS: $[M+H]^+$=590.2.

Example 14. Synthesis of Conjugate 3

Figure 11:
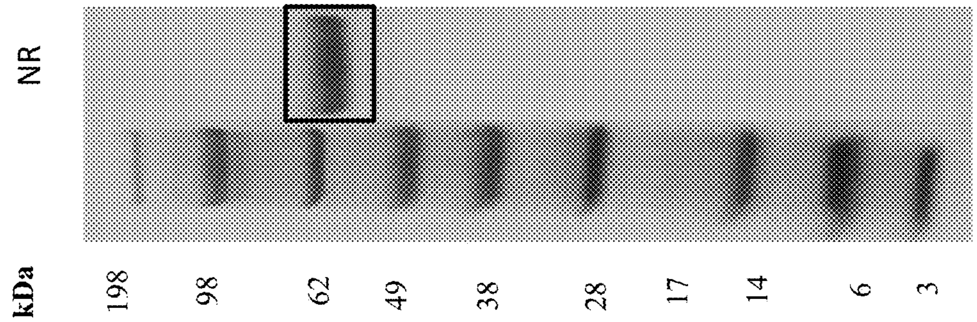
FIG. 11 shows a non-reducing SDS-PAGE of Conjugate 3.

The title conjugate was prepared analogously to Conjugate 1 (Example 9) using Int-4 (Example 13). Maldi TOF analysis of the purified final product gave an average mass of 61182 Da (DAR=3.4). Yield 50.89 mg, 51% yield. FIG. 11 shows a non-reducing SDS-PAGE of Conjugate 3.

Example 15. Synthesis of Int-5

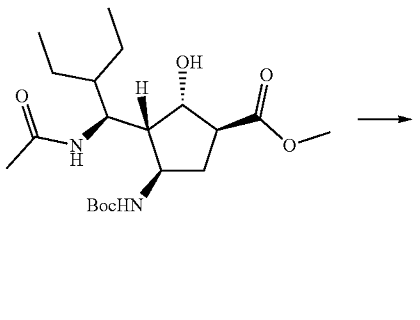

-continued
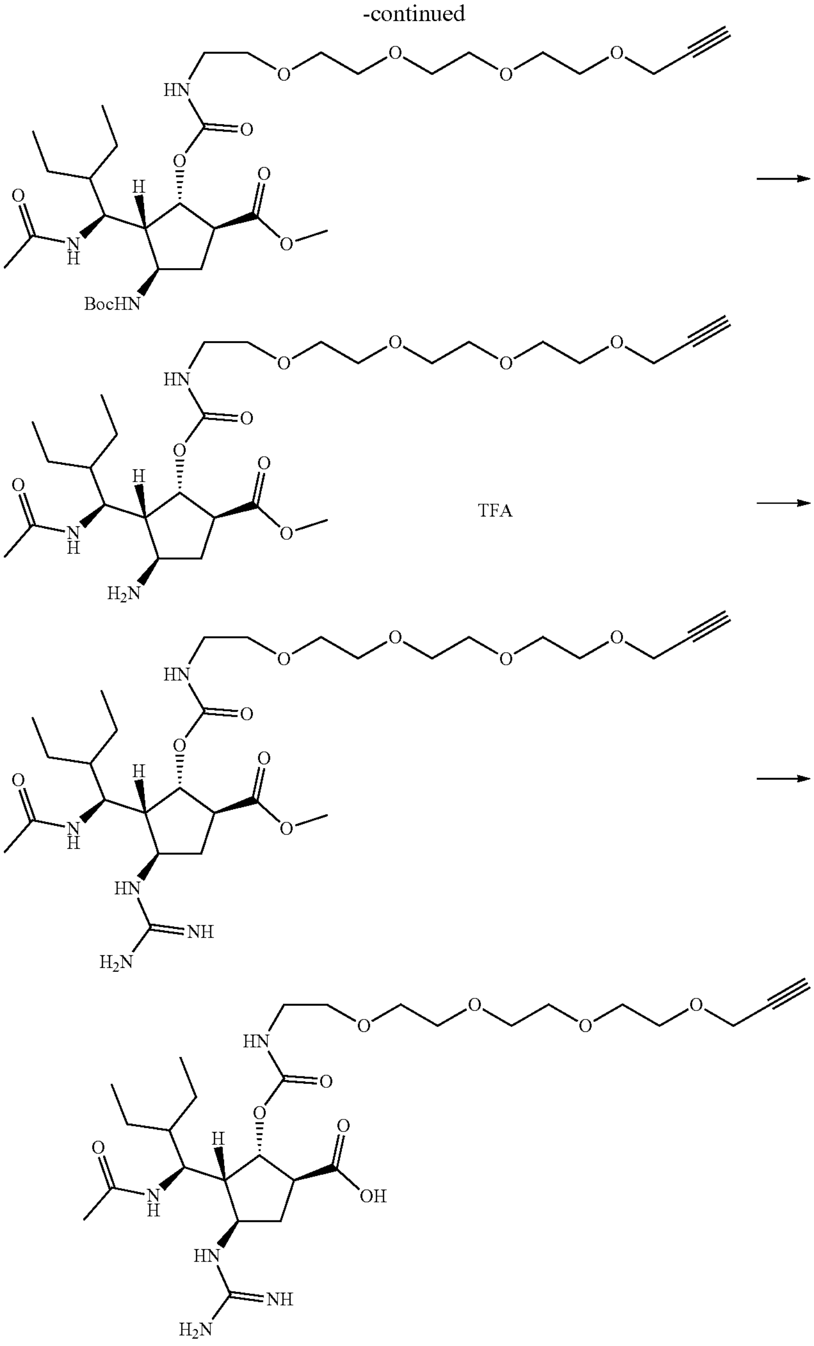
Step a.

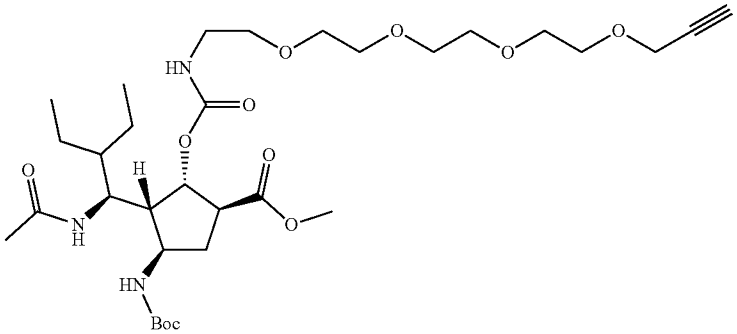 [SMILES: C#CCOCCOCCOCCOCCNC(=O)O[C@H]1[C@@H]([C@@H](NC(C)=O)C(CC)CC)[C@H](NC(=O)OC(C)(C)C)C[C@@H]1C(=O)OC]

A flame-dried reaction flask was flushed with nitrogen and charged with (1S, 2S, 3R, 4R)-methyl 3-((S)-1-acetamido-2-ethylbutyl)-4-(tert-butoxycarbonylamino)-2-hydroxycyclopentanecarboxylate (320.4 mg, 0.8 mmol) and anhydrous DCM (2 mL). The solution was cooled in an ice-water bath and DIPEA (312 mg, 2.4 mmol) was added followed by 4-nitrophenyl chloroformate (161.3 mg, 0.8 mmol) and DMAP (98 mg, 0.8 mmol). The resulting mixture was stirred for 15 minutes, then an additional amount of 4-nitrophenyl chloroformate (161.3 mg, 0.8 mmol) was added. The reaction was stirred for 2 hours, then water (0.2 mL) was added to quench unreacted chloroformate. After stirring for 10 minutes, a solution of propargyl-PEG4-amine (259 mg, 1.12 mmol) in anhydrous DMF (0.5 mL) was added. The reaction was stirred for 1 hour and then purified directly by RPLC (100 g, 5 to 60% acetonitrile and water, using 0.1% TFA as modifier). The collected fractions were lyophilized. Yield 391.2 mg, 74.4%. Ion found by LCMS: $[M+H]^+$=658.3, $[M\text{-}Boc+H]^+$=558.3.

Step b.

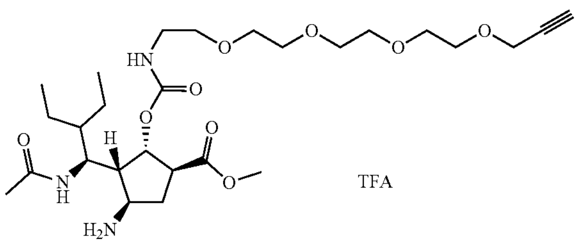 [SMILES: C#CCOCCOCCOCCOCCNC(=O)O[C@H]1[C@@H]([C@@H](NC(C)=O)C(CC)CC)[C@H](N)C[C@@H]1C(=O)OC ; "TFA"]

TFA

The step-a product (391.2 mg, 0.595 mmol) was dissolved in TFA (0.8 mL), and the solution was stirred at room temperature for 20 minutes. It was then directly purified by RPLC (100 g, 5 to 60% acetonitrile and water). Yield 323.2 mg, 81%. Ion found by LCMS: $[M+H]^+$=558.3.

Step c.

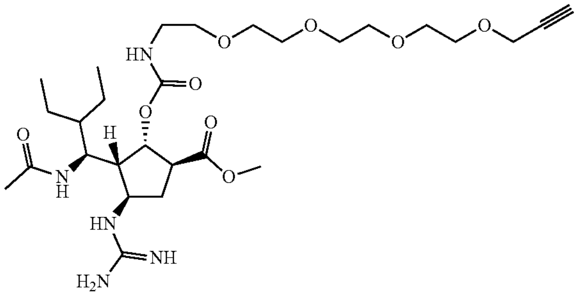 [SMILES: C#CCOCCOCCOCCOCCNC(=O)O[C@H]1[C@@H]([C@@H](NC(C)=O)C(CC)CC)[C@H](NC(=N)N)C[C@@H]1C(=O)OC]

To a solution of the step-b product (323.2 mg, 0.482 mmol) in THE (2 mL) was added N,N'-Bis-Boc-1-guanylpyrazole (224.4 mg, 0.723 mmol) and PIPEA (260 mg, 2 mmol). The reaction mixture was stirred for 1 day and then extracted with water (3 mL) and EtOAc/hexanes (1:1, 8 mL). The organic layer was dried over $Na_2SO_4$ and concentrated by rotary evaporation. The residue was re-dissolved in TFA (~1 mL), and the solution was stirred overnight. It was then directly purified by RPLC (100 g, 0 to 30% acetonitrile and water, using 0.1% TFA as modifier). The collected fractions were lyophilized. Yield 254.2 mg, 83.2%. Ions found by LCMS: $[M+H]^+$=600.3, $[M\text{-}Boc+H]^+$=300.6.

Step d.

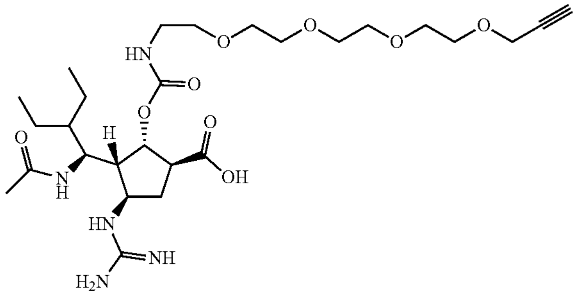 [SMILES: C#CCOCCOCCOCCOCCNC(=O)O[C@H]1[C@@H]([C@@H](NC(C)=O)C(CC)CC)[C@H](NC(=N)N)C[C@@H]1C(=O)O]

The step-c product (254.2 mg, 0.356 mmol) was dissolved in THE (1.5 mL), and the solution was cooled in an ice-water bath. $CaCl_2$ dihydrate (419 mg, 2.85 mmol) was added, then 1.8 mL of KOH (112 mg, 2 mmol) in water (2 mL) was added in portions over 1 hour. After stirred for 3 more hours, the reaction mixture was acidified by Dowex 50W×8 hydrogen form and purified by RPLC (0 to 30% acetonitrile and water, using 0.1% TFA as modifier). Yield 102 mg, 49.8%. Ions found by LCMS: $[M+H]^+$=586.4, $[(M+2H)/2]^+$=293.8.

Example 16. Synthesis of Conjugate 4

Figure 12:
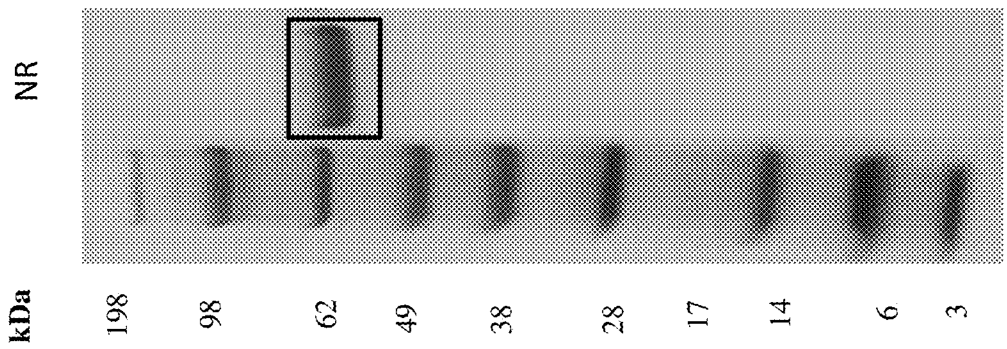
FIG. 12 shows a non-reducing SDS-PAGE of Conjugate 4.

The title conjugate was prepared analogously to Conjugate 1 (Example 9) using Int-5 (Example 15). Maldi TOF analysis of the purified final product gave an average mass of 63002 Da (DAR=3.4). Yield 49.315 mg, 49% yield. FIG. 12 shows a non-reducing SDS-PAGE of Conjugate 4.

Example 17. Synthesis of Int-6

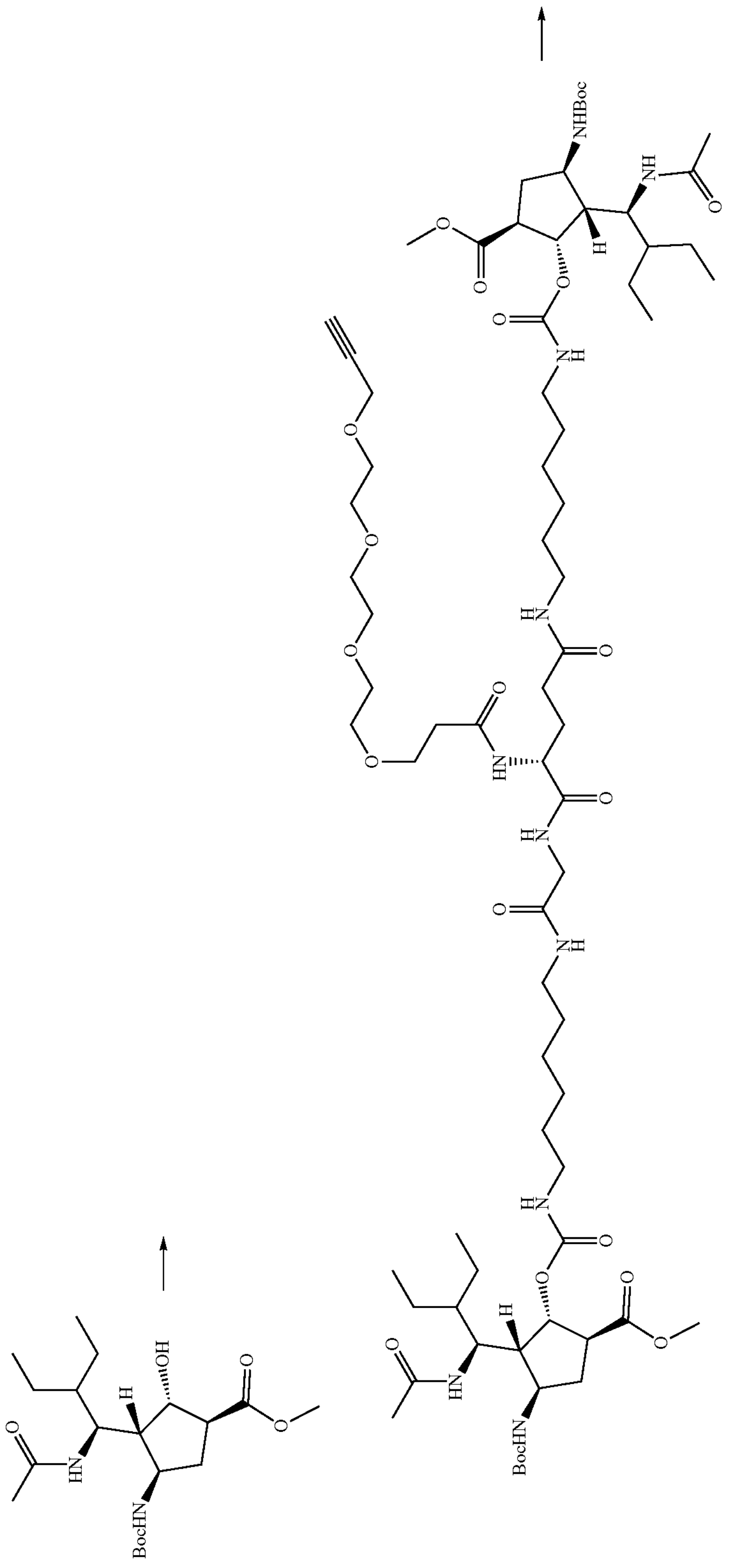

-continued
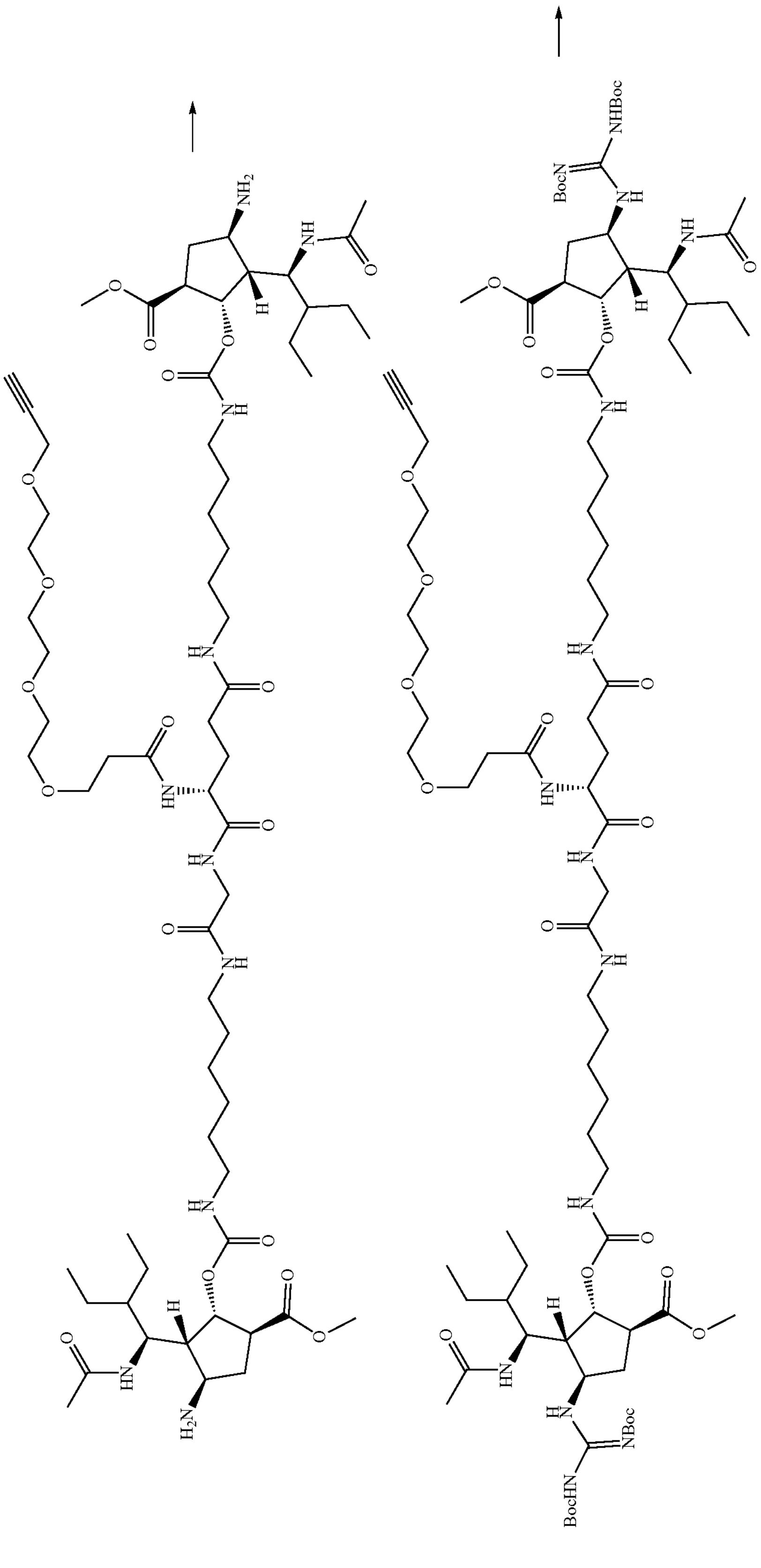

-continued
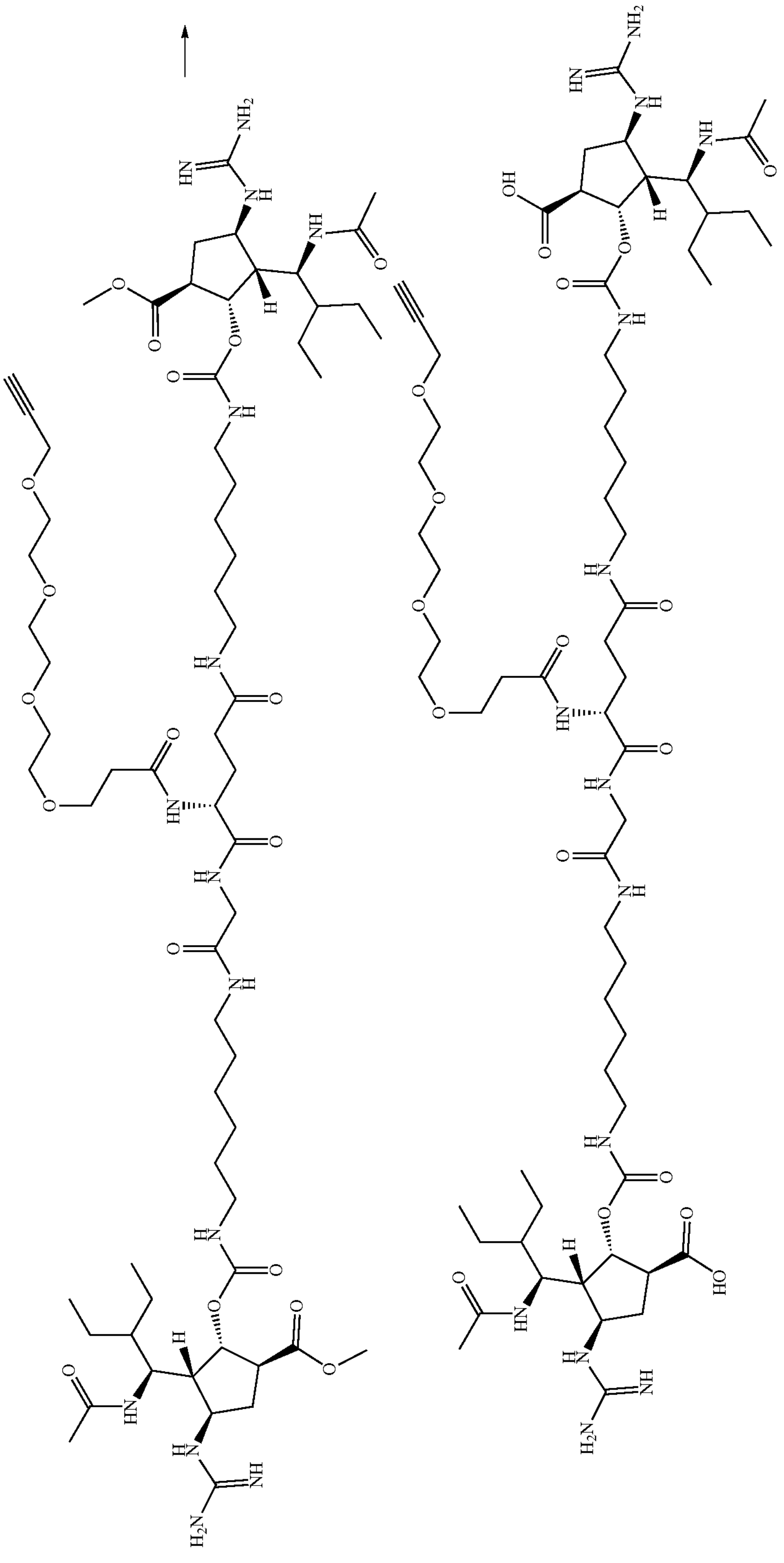

Step a.

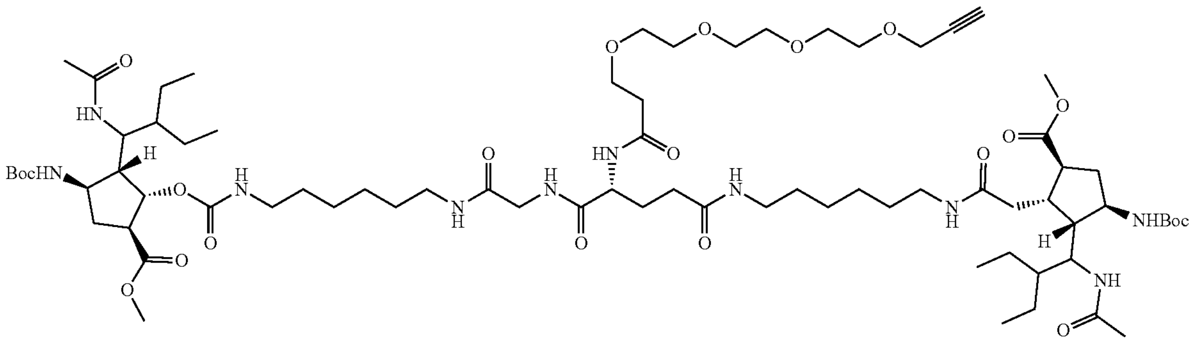 [SMILES: C#CCOCCOCCOCCOCCC(=O)N[C@H](CCC(=O)NCCCCCCNC(=O)C[C@H]1[C@@H](C(NC(C)=O)C(CC)CC)[C@H](NC(=O)OC(C)(C)C)C[C@@H]1C(=O)OC)C(=O)NCC(=O)NCCCCCCNC(=O)O[C@H]1[C@@H](C(NC(C)=O)C(CC)CC)[C@H](NC(=O)OC(C)(C)C)C[C@@H]1C(=O)OC]

A flame-dried reaction flask was flushed with nitrogen and charged with (1S, 2S, 3R, 4R)-methyl 3-((S)-1-acetamido-2-ethylbutyl)-4-(tert-butoxycarbonylamino)-2-hydroxy cyclopentanecarboxylate (280.4 mg, 0.7 mmol) and anhydrous DCM (1 mL). After stirring to dissolve the starting material, DMAP (85.7 mg, 0.7 mmol) was added to the solution, followed by bis(pentafluorophenyl)carbonate (295.6 mg, 0.75 mmol). The resulting mixture was stirred for 1 hour, then added into a solution of Linker-2 (Example 5) (157.5 mg, 0.22 mmol) in anhydrous DMF (1 mL) and DIPEA (130 mg, 1 mmol). The reaction was stirred overnight and purified by RPLC (50 g, 5 to 90% acetonitrile and water). The collected fractions were lyophilized. Yield 134.1 mg, 40.7%. Ion found by LCMS: $[(M+2H)/2]^+$=748.6.

Step b.

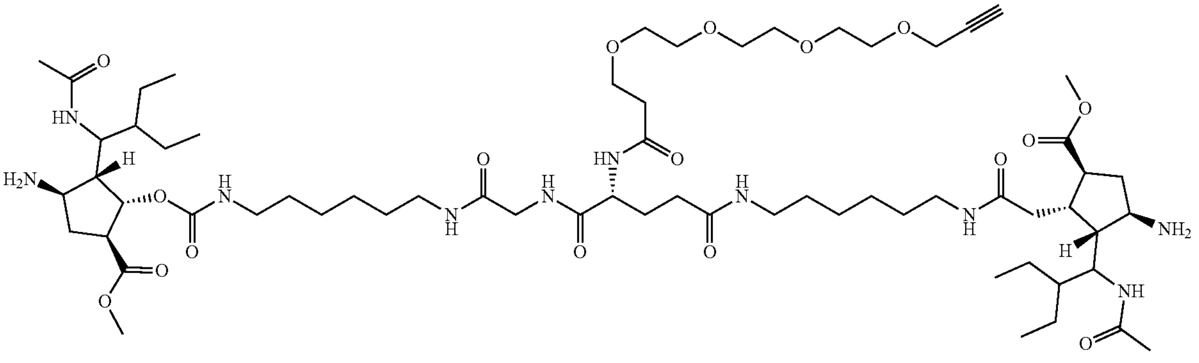 [SMILES: C#CCOCCOCCOCCOCCC(=O)N[C@H](CCC(=O)NCCCCCCNC(=O)C[C@H]1[C@@H](C(NC(C)=O)C(CC)CC)[C@H](N)C[C@@H]1C(=O)OC)C(=O)NCC(=O)NCCCCCCNC(=O)O[C@H]1[C@@H](C(NC(C)=O)C(CC)CC)[C@H](N)C[C@@H]1C(=O)OC]

The step-a product (134.1 mg, 0.0896 mmol) was dissolved in TFA (0.5 mL). The solution was stirred for 20 minutes, then directly purified by RPLC (50 g, 5 to 60% acetonitrile and water). Yield 108.4 mg, 93.4%. Ions found by LCMS: $[(M+2H)/2]^+$=648.3, $[(M+3H)/3]^+$=432.8.

Step c.

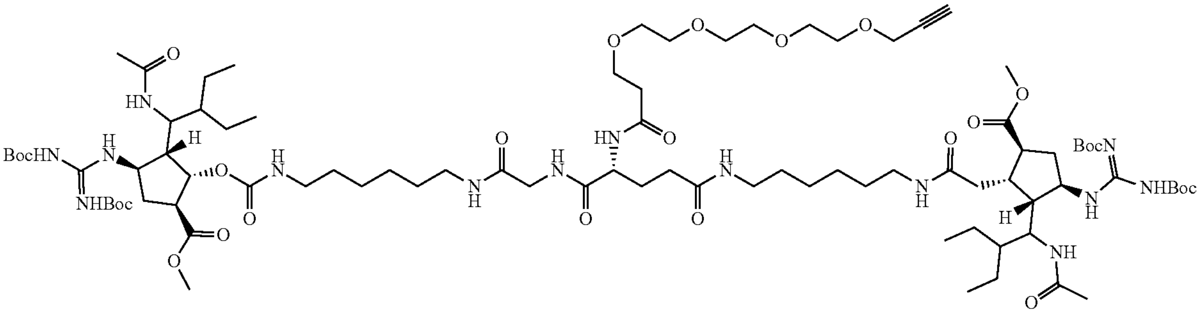

To a solution of the step-b product (108.4 mg, 0.0837 mmol) in anhydrous THE (1 mL) was added N,N'-bis-boc-1-guanylpyrazole (81.3 mg, 0.285 mmol) and DIPEA (65 mg, 0.5 mmol). The reaction was stirred at room temperature for 2.5 days, then directly purified by RPLC (100 g, 40 to 75% acetonitrile and water). Yield 73.6 mg, 49.4%. Ion found by LCMS: $[(M+3H)/3]^+=594.2$.

Step d.

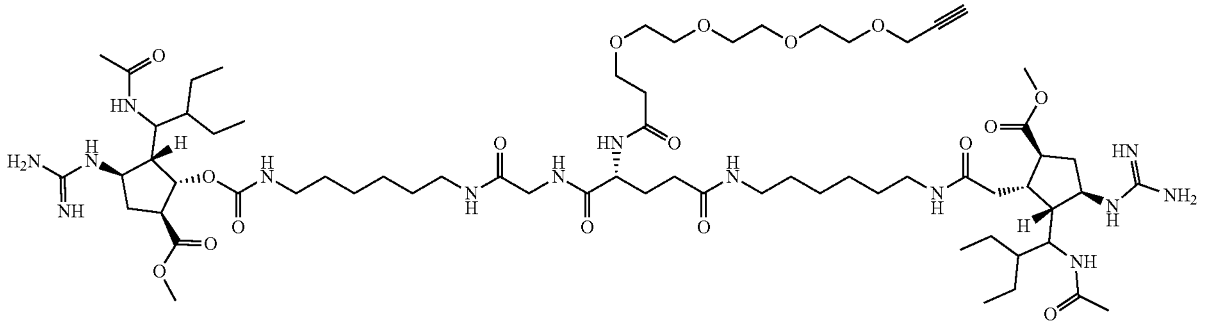 [SMILES: C#CCOCCOCCOCCOCCC(=O)N[C@H](CCC(=O)NCCCCCCNC(=O)C[C@H]1[C@@H](C(NC(C)=O)C(CC)CC)[C@H](NC(=N)N)C[C@@H]1C(=O)OC)C(=O)NCC(=O)NCCCCCCNC(=O)O[C@H]1[C@@H](C(NC(C)=O)C(CC)CC)[C@H](NC(=N)N)C[C@@H]1C(=O)OC]

The step-c product (73.6 mg, 0.041 mmol) was dissolved in TFA (0.5 mL). The solution was stirred for 20 minutes, then directly purified by RPLC (50 g, 5 to 60% acetonitrile and water). Yield 62.1 mg, 94.1%. Ions found by LCMS: $[(M+2H)/2]^+=690.4$, $[(M+3H)/3]^+=460.8$.

Step e.

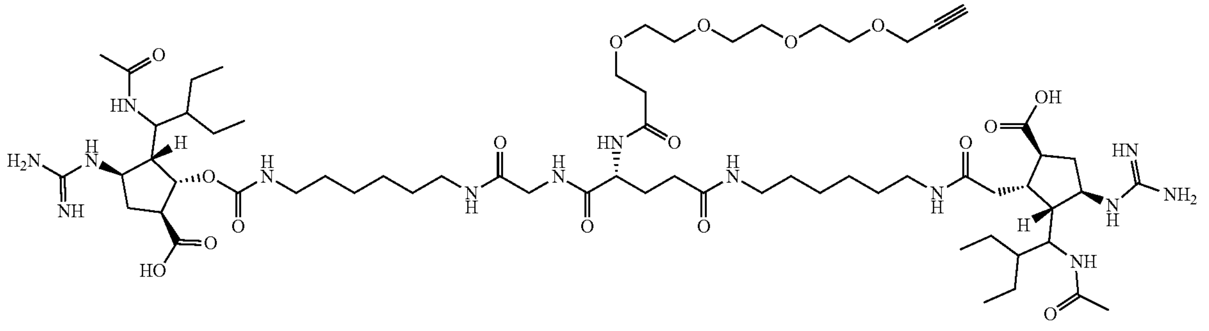 [SMILES: C#CCOCCOCCOCCOCCC(=O)N[C@H](CCC(=O)NCCCCCCNC(=O)C[C@H]1[C@@H](C(NC(C)=O)C(CC)CC)[C@H](NC(=N)N)C[C@@H]1C(=O)O)C(=O)NCC(=O)NCCCCCCNC(=O)O[C@H]1[C@@H](C(NC(C)=O)C(CC)CC)[C@H](NC(=N)N)C[C@@H]1C(=O)O]

The step-d product (62.1 mg, 0.0386 mmol) in THE (3 mL) was cooled in an ice-water bath and a 45% w/w solution of KOH (0.2 mL) was added in portions over 1 hour. The reaction was stirred for 2 more hours, then acidified with 4N HCl solution in dioxane (0.8 mL) and extracted with hexanes (10 mL) and water (1.5 mL). The aqueous layer was purified by HPLC (0 to 20% acetonitrile and water, using 0.1% TFA as modifier). Yield 36.2 mg, 59.4%. Ions found by LCMS: $[(M+2H)/2]^+=676.5$, $[(M+3H)/3]^+=451.4$.

Example 18. Synthesis of Conjugate 5

Figure 13:
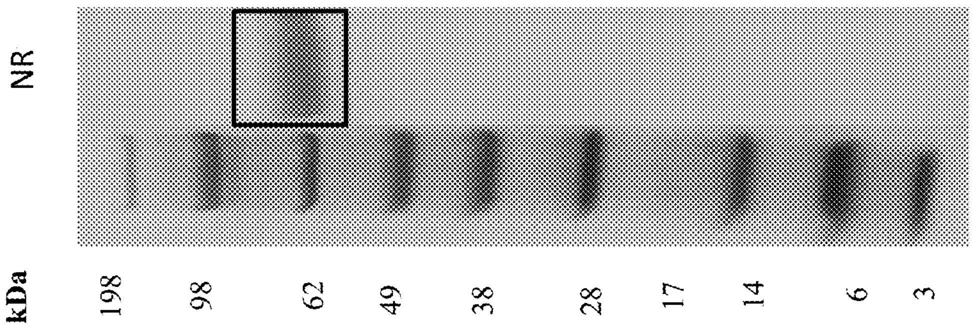
FIG. 13 shows a non-reducing SDS-PAGE of Conjugate 5.

The title conjugate was prepared analogously to Conjugate 1 (Example 9) using Int-6 (Example 17). Maldi TOF analysis of the purified final product gave an average mass of 63561 Da (DAR=3.3). Yield 43.4 mg, 43% yield. FIG. 13 shows a non-reducing SDS-PAGE of Conjugate 5.

Example 19. Synthesis of Int-7

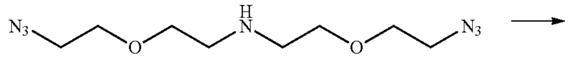

-continued
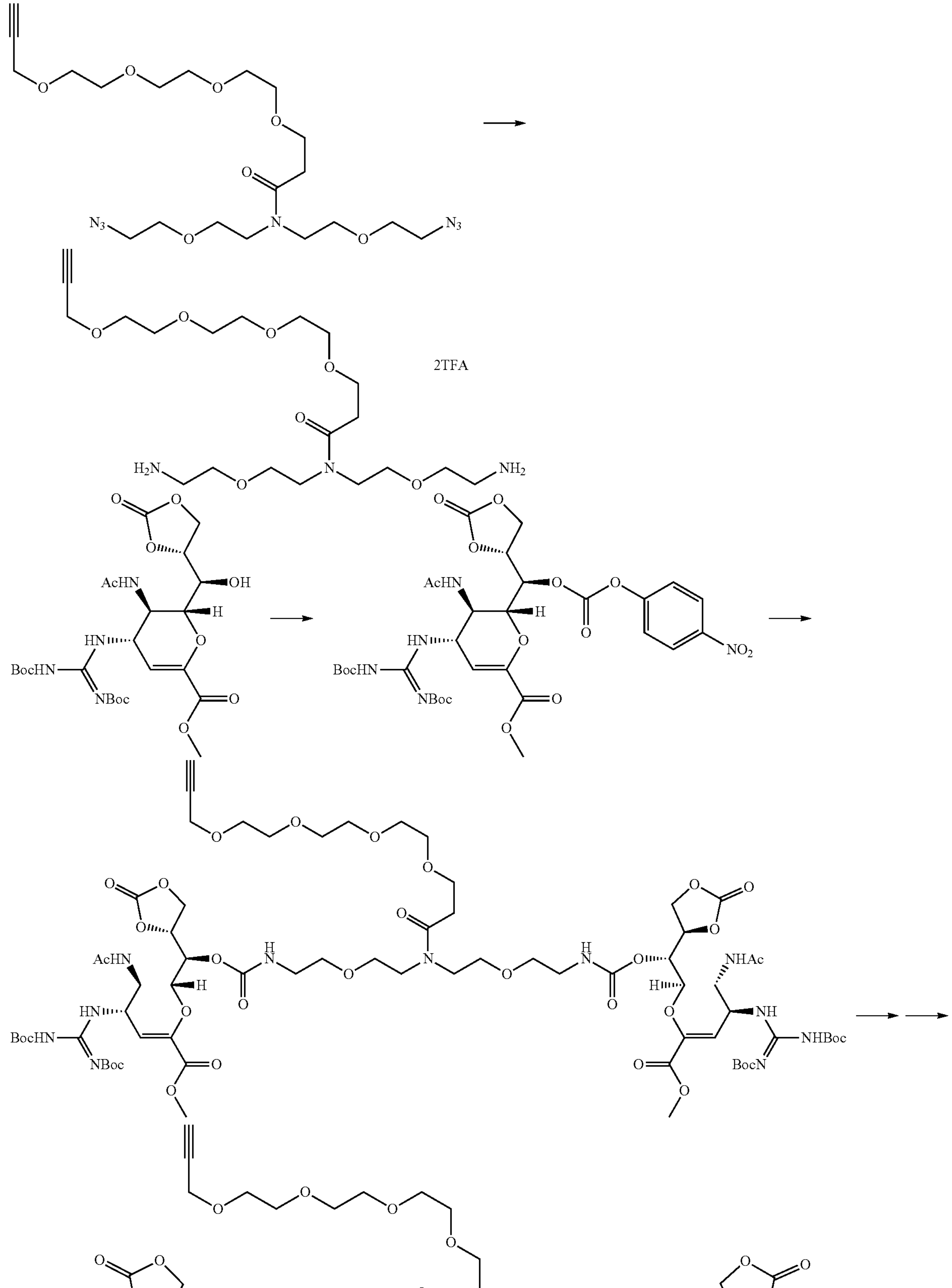

Step a.

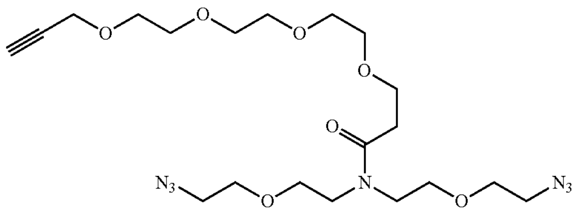 [SMILES: C#CCOCCOCCOCCOCCC(=O)N(CCOCCN=[N+]=[N-])CCOCCN=[N+]=[N-]]

To a solution of propargyl-PEG4-acid (609 mg, 2.34 mmol) and NH-bis(PEG1-azide) (500 mg, 2.055 mmol) in anhydrous DMF (2 mL) was added HATU (889.7 mg, 2.34 mmol) in portions over 5 minutes. After stirring to dissolve all the coupling reagent, DIPEA (390 mg, 3 mmol) was added and stirring continued for 1 hour. It was then purified directly by RPLC (100 g, 5 to 40% acetonitrile and water). Yield 918 mg, 92%. Ion found by LCMS: $[M+H]^+$=486.2.

Step b.

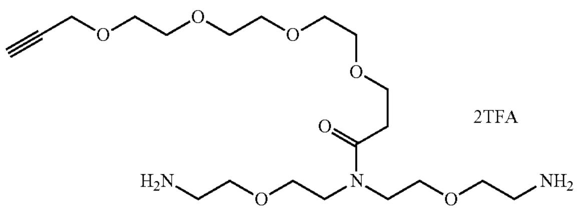 [SMILES: C#CCOCCOCCOCCOCCC(=O)N(CCOCCN)CCOCCN]

2TFA

The step-a product (918 mg, 1.89 mmol) was dissolved in THF, and the solution was cooled to 13° C. Triphenylphosphine (1.141 g, 4.35 mmol) was added in portions over 10 minutes. The resulting mixture was stirred at ~13° C. to room temperature for 2 hours. A solution of LiOH monohydrate (42 mg, 1 mmol) in water (2 mL) and MeOH (1 mL) was added. After stirring was continued for 20 hours, the reaction was purified by RPLC (100 g, 0 to 30% acetonitrile and water, using 0.1% TFA as modifier). Yield 825 mg, 65.9%. Ion found by LCMS: $[M+H]^+$=434.4.

Step c.

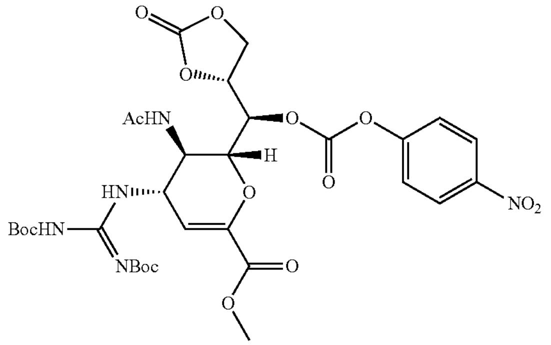

A flame-dried reaction flask was flushed with nitrogen and charged with Zanamivir intermediate (Example 2) (865 mg, 1.51 mmol) and anhydrous DCM (5 mL). After stirring to dissolve the starting material, the solution was cooled in an ice-water bath and 4-nitrophenyl chloroformate (365.3 mg, 1.81 mmol) was added followed by DMAP (152.2 mg, 0.755 mmol). The ice-water bath was removed, and the mixture was stirred for 3 hours. An additional amount of 4-nitrophenyl chloroformate (304.4 mg, 1.51 mmol) was added, and stirring was continued for 1 hour. The reaction was then quenched with water (1 mL). After vigorously stirred for 1 hour, the reaction mixture was extracted with water (20 mL×2) and DCM (20 mL). The organic layer was stirred overnight, dried over $Na_2SO_4$, and concentrated by rotary evaporation. The material was carried on to the subsequent step without further purification. Ion found by LCMS: $[M+H]^+$=738.2.

Step d.

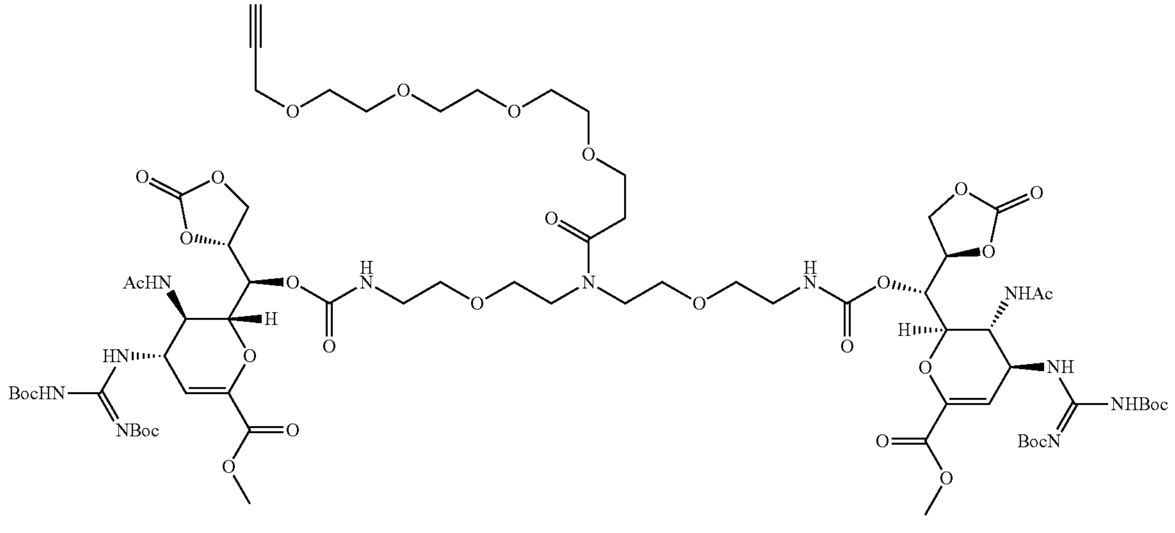

A solution of a mixture of the step-b product (429.7 mg, 0.65 mmol) and DIPEA (260 mg, 2 mmol) in anhydrous THE (1 mL) was added dropwise to the step-c product. The resulting mixture was stirred for 2 hours, then directly purified by RPLC (100 g, 10 to 65% acetonitrile and water). Acetonitrile in the collected fractions was removed by rotary evaporation at room temperature. The heterogeneous aqueous layer was extracted with EtOAc (200 mL), then back-extracted with EtOAc (50 mL). The combined organic layers were dried over $Na_2SO_4$ and concentrated by rotary evaporation to dryness. Yield 442 mg, 41.7%. Ions found by LCMS: $[(M+2H)/2]^+$=815.8, $[(M\text{-}Boc+2H)/2]^+$=765.8, $[(M-2Boc+2H)/2]^+$=716.

Step e.

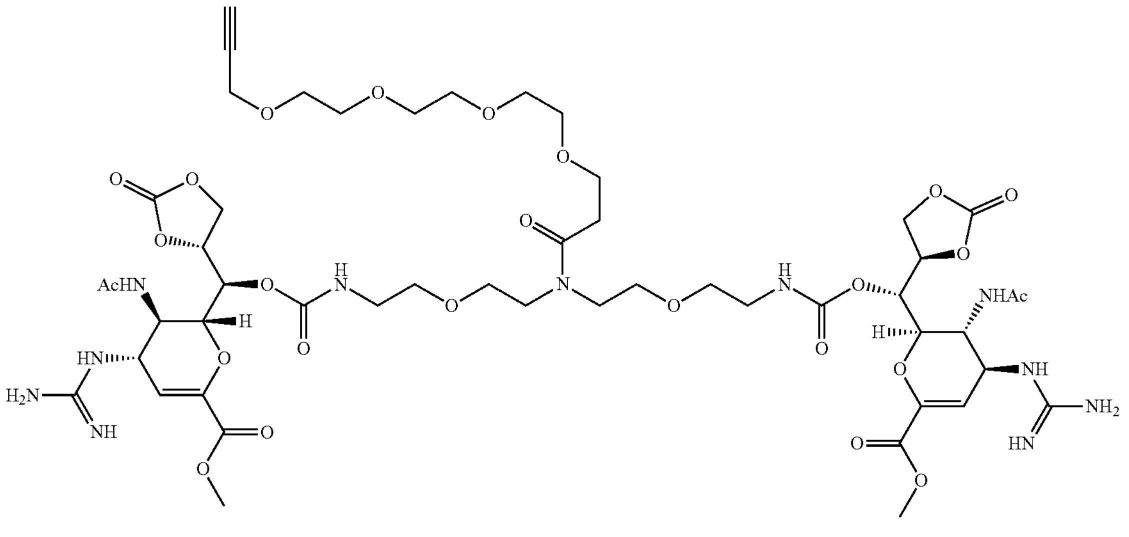 [SMILES: C#CCOCCOCCOCCOCCC(=O)N(CCOCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

The step-d product (441 mg, 0.271 mmol) was dissolved in TFA (1 mL). The solution was stirred for 20 minutes, then directly purified by HPLC (5 to 20% acetonitrile and water, using 0.1% TFA as modifier). Yield 308 mg, 77.9%. Ions found by LCMS: $[(M+2H)/2]^+$=615.8, $[(M+3H)/3]^+$=411.

Step f.

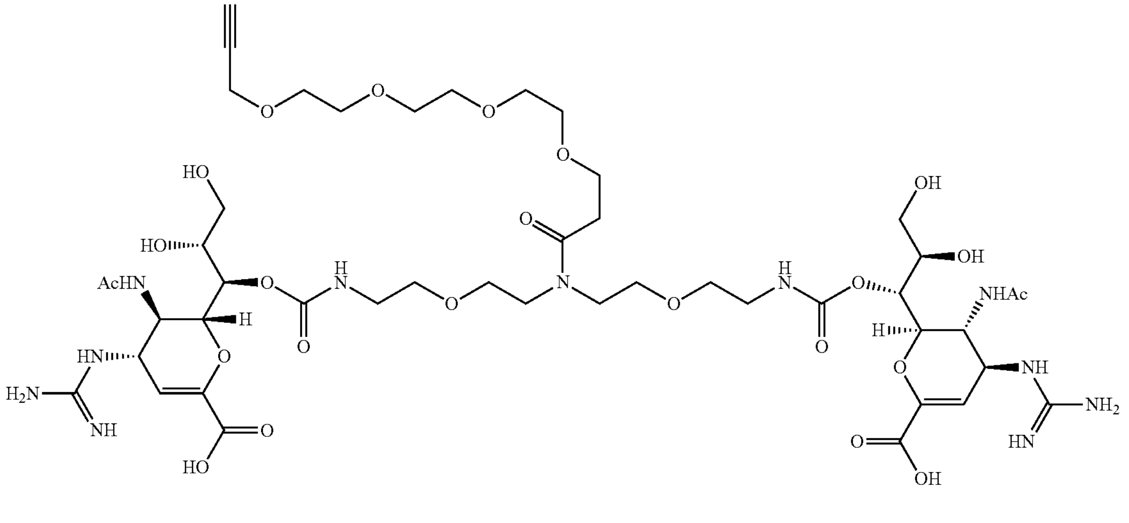 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

The step-e product (308 mg, 0.211 mmol) was dissolved in MeOH (1 mL) and water (0.5 mL), and the solution was cooled in an ice-water bath. A solution of LiOH monohydrate (42 mg, 1 mmol) in water (1 mL) was added in portions over 1 hour. The reaction was stirred overnight, acidified by 4 N HCl solution in dioxane (0.25 mL), and purified by RPLC (0 to 20% acetonitrile and water, using 0.1% TFA as modifier). Yield 198 mg, 64%. Ions found by LCMS: $[(M+2H)/2]^+$=575.8, $[(M+3H)/3]^+$=384.2.

Example 20. Synthesis of Conjugate 6

Figure 14:
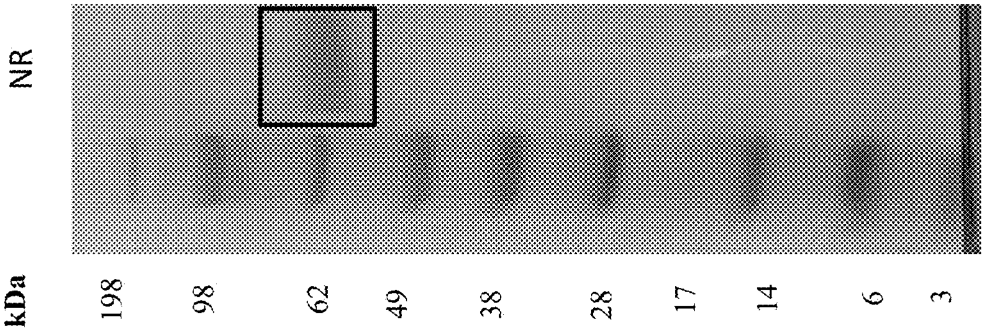
FIG. 14 shows a non-reducing SDS-PAGE of Conjugate 6.

The title conjugate is prepared analogously to Conjugate 1 (Example 9) using Int-7 (Example 19). Maldi TOF analysis of the purified final product gave an average mass of 62854. Da (DAR=3.1). Yield 175.4 mg, 50% yield. FIG. 14 shows a non-reducing SDS-PAGE of Conjugate 6.

Example 21. Synthesis of Int-8

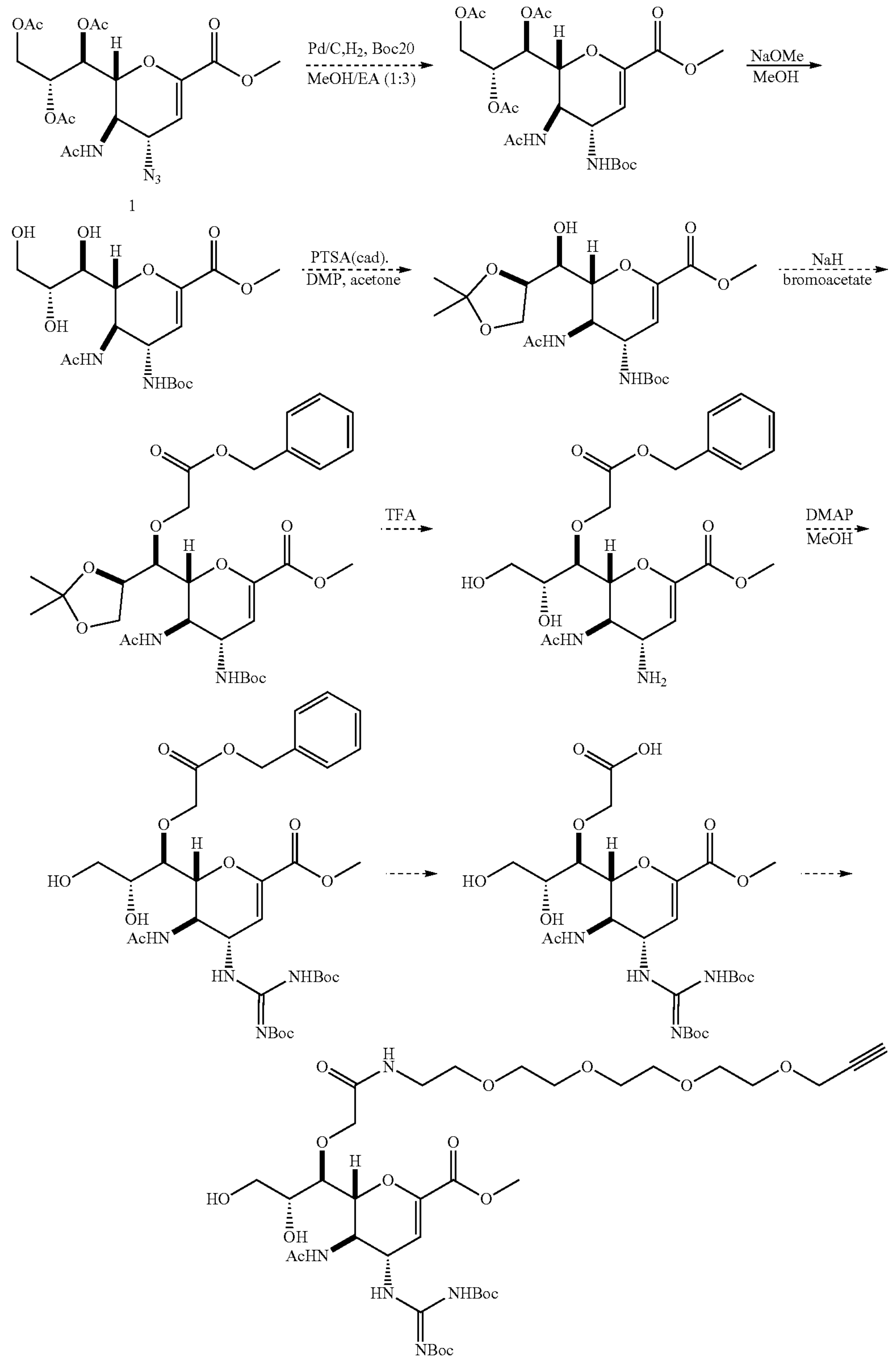
Int-8
65
Step a.

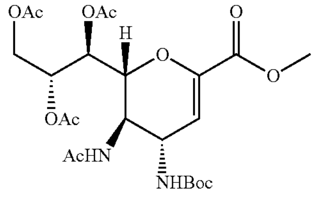 [SMILES: COC(=O)C1=C[C@H](NC(=O)OC(C)(C)C)[C@@H](NC(C)=O)[C@H]([C@H](OC(C)=O)[C@@H](COC(C)=O)OC(C)=O)O1]

Methyl 5-acetoamido-7,8,9-O-triacetyl-2,6-anhydro-4-azido-3,4,5-trideoxy-D-glycero-D-galacto-non-2-enonate (1.8 g, 4.0 mmol) was dissolved into 40 mL methanol and then treated with 400 mg of 5% Pd/C and 10.1 g Boc anhydride (5.0 mmol), then the reaction mixture was stirred at room temperature under a hydrogen atmosphere for 1 hour. The palladium-charcoal was removed by filtration. The filtrate was concentrated and used in next step without purification.

Step b.

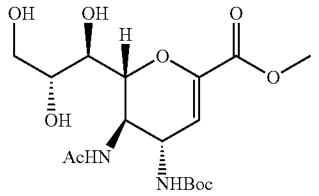 [SMILES: COC(=O)C1=C[C@H](NC(=O)OC(C)(C)C)[C@@H](NC(C)=O)[C@H]([C@H](O)[C@H](O)CO)O1]

The product from the previous step was dissolved into 20 mL dry methanol and then treated with 2 mL sodium methoxide in methanol (0.5 M) dropwise with cooling in an ice-water bath. After 2 hours, the progress of reaction was determined by LCMS. The reaction was quenched with 1 N HCl to pH 5-6. The resulting solution was concentrated and purified by reversed phase liquid chromatography (RPLC) using an Isco COMBIFLASH® liquid chromatograph eluted with 5% to 100% acetonitrile and water, using 0.1% TFA as the modifier. Ion(s) found by LCMS: $(M+H)^+=405$ Step c.

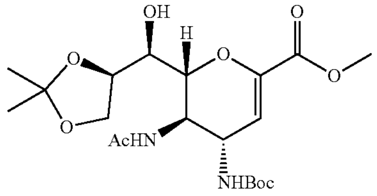

Methyl 5-acetamido-2,6-anhydro-4-[(tert-butoxycarbonyl)amino]-3,4,5-trideoxy-D-erythro-non-2-enonate (0.4 g, 1 mmol) was dissolved in 10 mL of acetone, 4 mL of 2,2-dimethoxypropane and 20 mg of p-toluenesulfonic acid hydrate (0.1 mmol). The resulting solution was stirred at room temperature overnight, then quenched with 1 mL saturated $NaHCO_3$. The mixture was concentrated and purified by reversed phase liquid chromatography (RPLC) using an Isco COMBIFLASH® liquid chromatograph eluted with 5% to 100% acetonitrile and water without modifier. Ion(s) found by LCMS: $(M+H)^+=445$.

Step d.

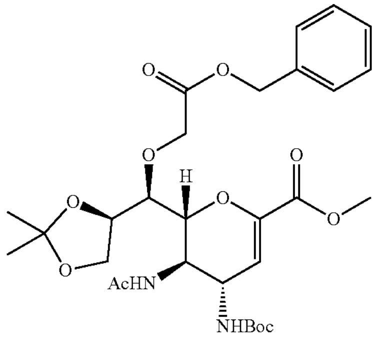

Sodium hydride (40 mg, 60% in oil, 1.0 mmol) was added into methyl 5-acetamido-2,6-anhydro-4-[(tert-butoxycarbonyl)amino]-3,4,5-trideoxy-8,9-O-(1-methylethylidene)-D-erythro-non-2-enonate (0.25 g, 0.50 mmol) in 5 mL dry THF with cooling from an ice-water bath. The resulting solution was stirred for 0.5 hour, then benzyl bromoacetate (0.23 g, 1.0 mmol) was added. The resulting solution was stirred for 2 hours and quenched with 5 mL 10% ammonium chloride in water. Then the solution was diluted with 50 mL ethyl acetate. The organic layer was separated and dried with sodium sulfate. The dried organic solution was concentrated and purified by reversed phase liquid chromatography (RPLC) using an Isco COMBIFLASH® liquid chromatograph eluted with 5% to 100% acetonitrile and water without modifier. Ion(s) found by LCMS: $(M+H)^+=593$.

Example 22. Synthesis of Int-9

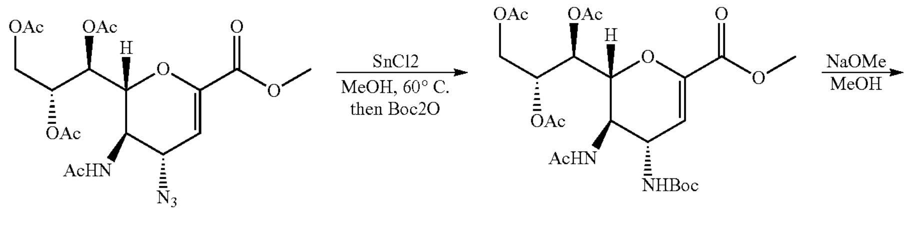

-continued
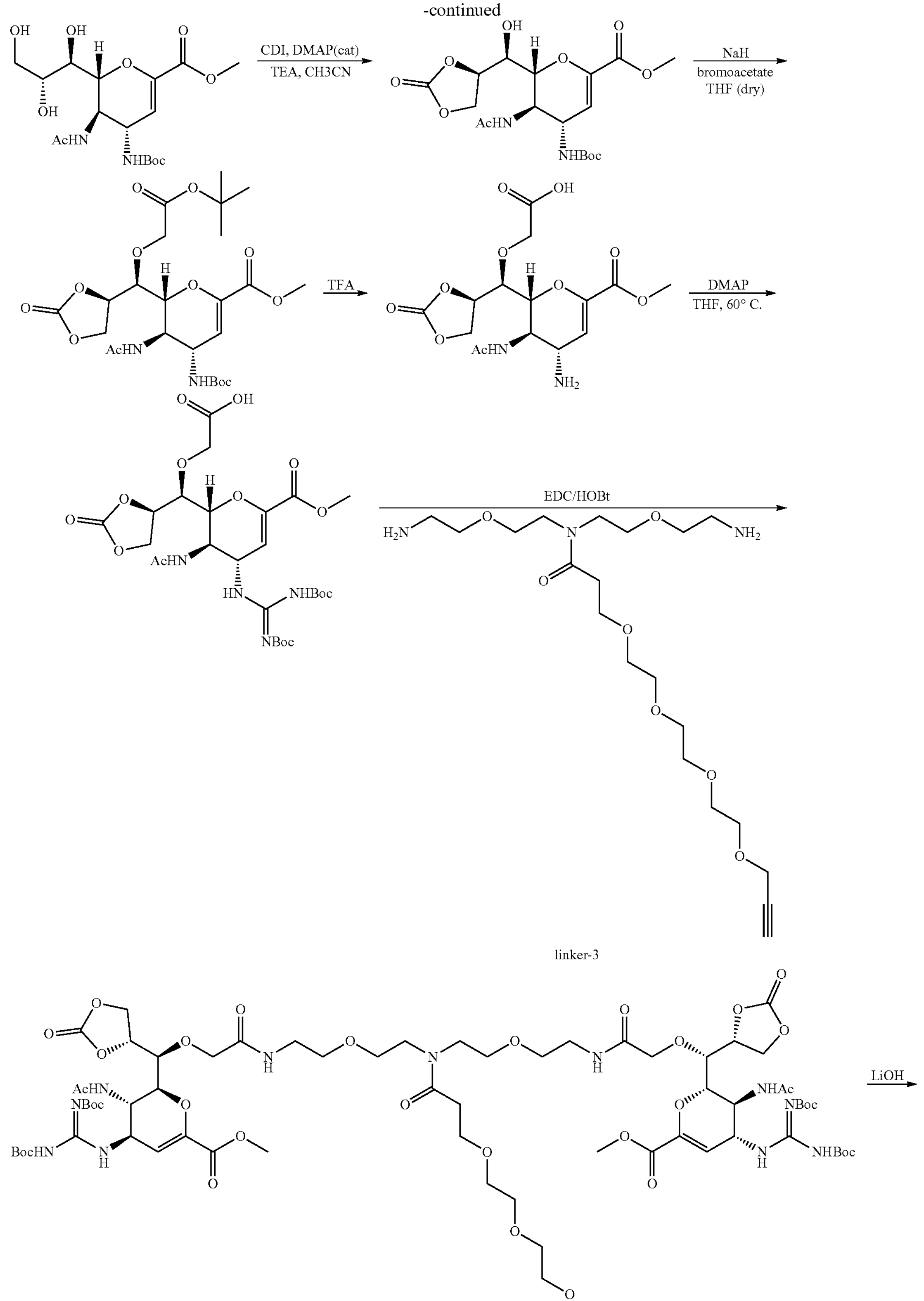

Step a.

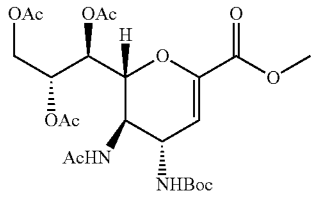 [SMILES: COC(=O)C1=C[C@H](NC(=O)OC(C)(C)C)[C@@H](NC(C)=O)[C@H]([C@H](OC(C)=O)[C@@H](COC(C)=O)OC(C)=O)O1]

Methyl 5-acetoamido-7,8,9-O-triacetyl-2,6-anhydro-4-azido-3,4,5-trideoxy-D-glycero-D-galacto-non-2-enonate (10 g, 22 mmol) was dissolved into 100 ml methanol and then heated to 60° C. with an oil bath, the $SnCl_2$ (5.7 g, 20 mmol) was added to the solution in 3 portions (caution, gas evolves). The reaction mixture was stirred for 10 min, at which time the reaction was complete by HPLC. The reaction solution was slowly added to a solution of 50 ml Sat $NaHCO_3$ and 50 g celite with vigorous stirring. The resulting slurry was filtered. The filtrate was treated with $Boc_2O$ (6.6 g, 30 mmol, 1.5 equiv). After 2 hour at room temperature, the solution was concentrated to remove most of the methanol, dissolved in 200 ml DCM, and extracted twice with 100 ml DCM. The combined extracts were dried with sodium sulfate, filtered and used for next step without further purification. Crude yield 12 g, 100%. Ion(s) found by LCMS: M+H=531.

Step b.

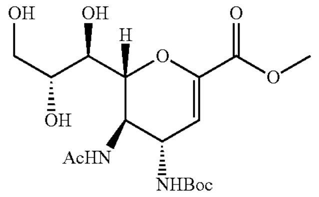 [SMILES: COC(=O)C1=C[C@H](NC(=O)OC(C)(C)C)[C@@H](NC(C)=O)[C@H]([C@H](O)[C@H](O)CO)O1]

The material from the previous step was dissolved into 60 ml dry methanol, then treated with 10 ml sodium methoxide in methanol (0.5M) while cooling with an ice-water bath. Progress of reaction was monitored by LCMS which was complete after 2h. The reaction was quenched with 1 N HCl to a pH of 5-6. The resulting solution was concentrated and purified by reverse phase liquid chromatography (RPLC) using an Isco COMBIFLASH® liquid chromatograph eluted with 0% to 30% acetonitrile and water, using 0.1% TFA as the modifier. Yield of the products 7.2 g, 80%. Ion(s) found by LCMS: M+H=405.

Step c.

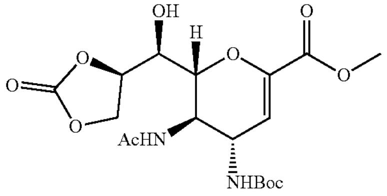 [SMILES: COC(=O)C1=C[C@H](NC(=O)OC(C)(C)C)[C@@H](NC(C)=O)[C@H]([C@H](O)[C@H]2COC(=O)O2)O1]

A solution of the product from the previous step (3.5 g, 8.5 mmol), CDI (2.8 g, 2 equiv), trimethylamine (4.2 ml, 30 mmol) and DMAP (240 mg, 2 mmol) were heated in acetonitrile (50 ml) overnight, then concentrated and purified by reverse phase liquid chromatography (RPLC) using an Isco COMBIFLASH® liquid chromatograph eluted with 0% to 30% acetonitrile and water without modifier. Yield of desired product 2.3 g, 60%. Ion(s) found by LCMS: M+H=431.

Step d.

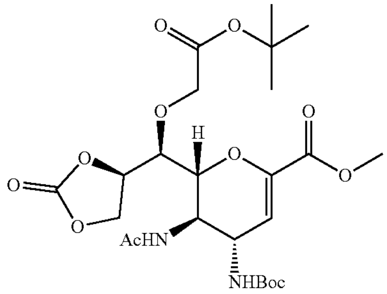 [SMILES: COC(=O)C1=C[C@H](NC(=O)OC(C)(C)C)[C@@H](NC(C)=O)[C@H]([C@H](OCC(=O)OC(C)(C)C)[C@H]2COC(=O)O2)O1]

Sodium hydride (400 mg, 60% in oil, 10 mmol) was added to the product from the previous step (1.45 g, 3.3 mmol) in 50 ml dry THE (moisture-sensitive reaction) under the ice-water bath. The resulted solution was stirred for 0.5 hour, then tertbutyl bromo-acetate (2 g, 10 mmol) was added to the above solution, the resulted solution was heated up to 60° C. for overnight and quenched with acetic acid. The resulting solution was concentrated and purified by reverse phase liquid chromatography (RPLC) using an Isco COMBIFLASH® liquid chromatograph eluted with 0% to 50% acetonitrile and water with TFA as modifier. Yield of 1 g, 57%. Ion(s) found by LCMS: M+H=593.

Step e.

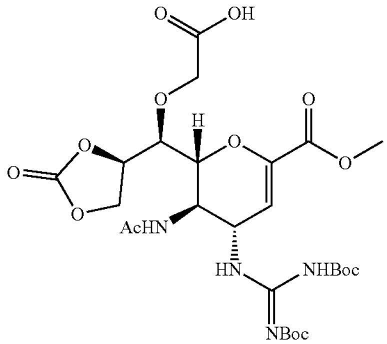

The product from the previous step (1.2 g, 2.2 mmol) was stirred with 10 ml TFA at room temperature for overnight, and the progress of deprotection was monitored by LCMS. The resulted solution was concentrated and used for next step without purification. The residue was re-dissolved into 20 ml THF, then N,N'-bis-boc-1-guanylpyrazole (1 g, 3.3 mmol), 4-dimethylaminopyridine (120 mg, 1 mmol) and triethylamine (0.7 ml, 5 mmol) were added to the solution, and the resulting solution was heated to 60° C. for 2 hours. The resulting solution was concentrated and purified by reverse phase liquid chromatography (RPLC) using an Isco COMBIFLASH® liquid chromatograph eluted with 0% to 50% acetonitrile and water with no modifier. Yield of 700 mg, 84%. Ion(s) found by LCMS: M+H=631.

Step f.

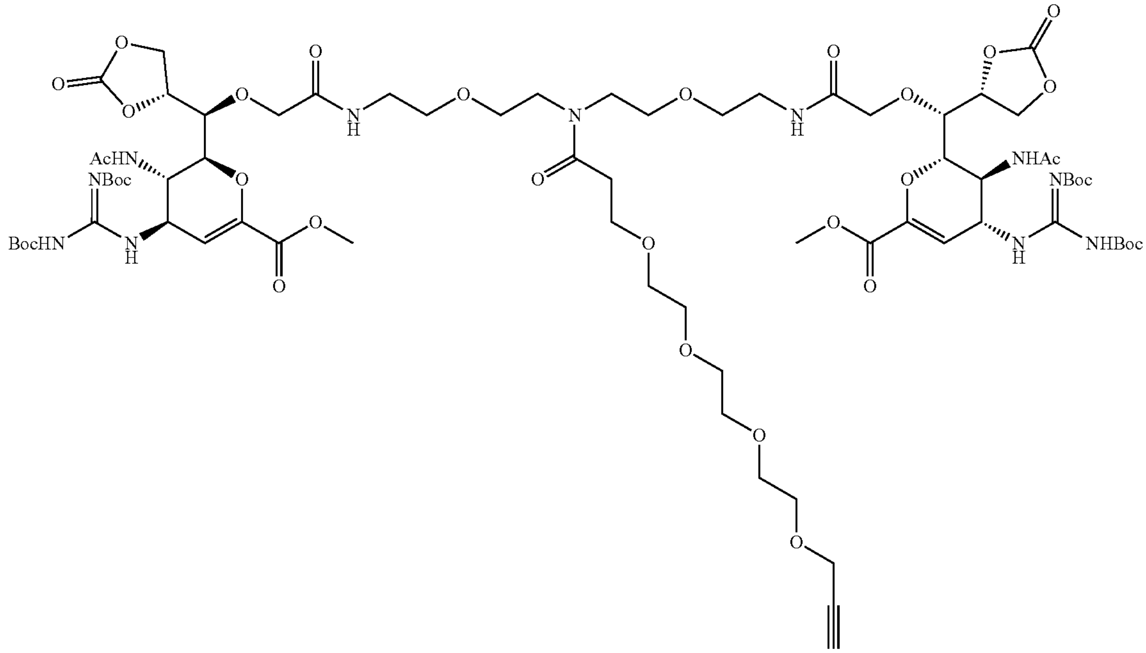

To a solution of linker-3 (prepared as described in Example 19) (73 mgg, 0.14 mmol) and the product of the previous step (200 mg, 0.32 mmol, 2.2 equi) in DMF (30 ml) was added EDC (100 mg, 0.5 mmol), HOAt (65 mg, 3 mmol), and DIEA (0.14 ml, 1 mmol) at room temperature. The solution was stirred overnight. The resulting solution was concentrated and purified by and purified by reverse phase liquid chromatography (RPLC) using an Isco COMBIFLASH® liquid chromatograph eluted with 0% to 50% acetonitrile and water with no modifier. Yield of 120 mg, 52%. Ion(s) found by LCMS: M/2+H=830.

Step g.

Lithium hydroxide (24 mg, 1 mmol) in 2 ml $H_2O$ was added into the solution of the product from the previous step (120 mg, 0.07 mmol) in 2 ml THF and 1 ml MeOH, LCMS monitored the progress of the reaction. After the completion, the solution was added AMBERLITE® IRN-77, ion exchange resin to adjust to pH1, then the resulting solution was filtered and the filtrate was concentrated and used for next step without purification. The resulting compound was treated with 2 ml TFA at room temperature, the solution was stirred for overnight at 40° C., then concentrated and purified by HPLC eluted with 0% to 20% acetonitrile and water,

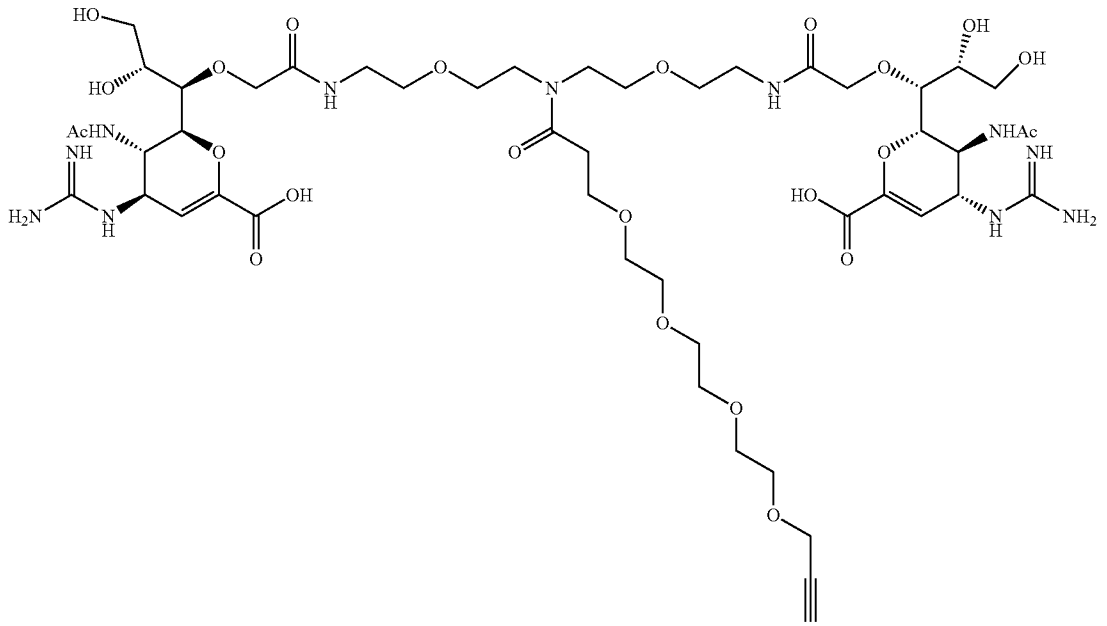 [SMILES: C#CCOCCOCCOCCOCCC(=O)N(CCOCCNC(=O)CO[C@@H]([C@H]1OC(C(=O)O)=C[C@@H](NC(=N)N)[C@@H]1NC(C)=O)[C@H](O)CO)CCOCCNC(=O)CO[C@@H]([C@H]1OC(C(=O)O)=C[C@@H](NC(=N)N)[C@@H]1NC(C)=O)[C@H](O)CO]

using TFA as the modifier. Yield 60 mg, 74% yield. Ion(s) found by LCMS: [M/2]+1=589.8.

Example 23. Neuraminidase Inhibition Assay

Figure 15:
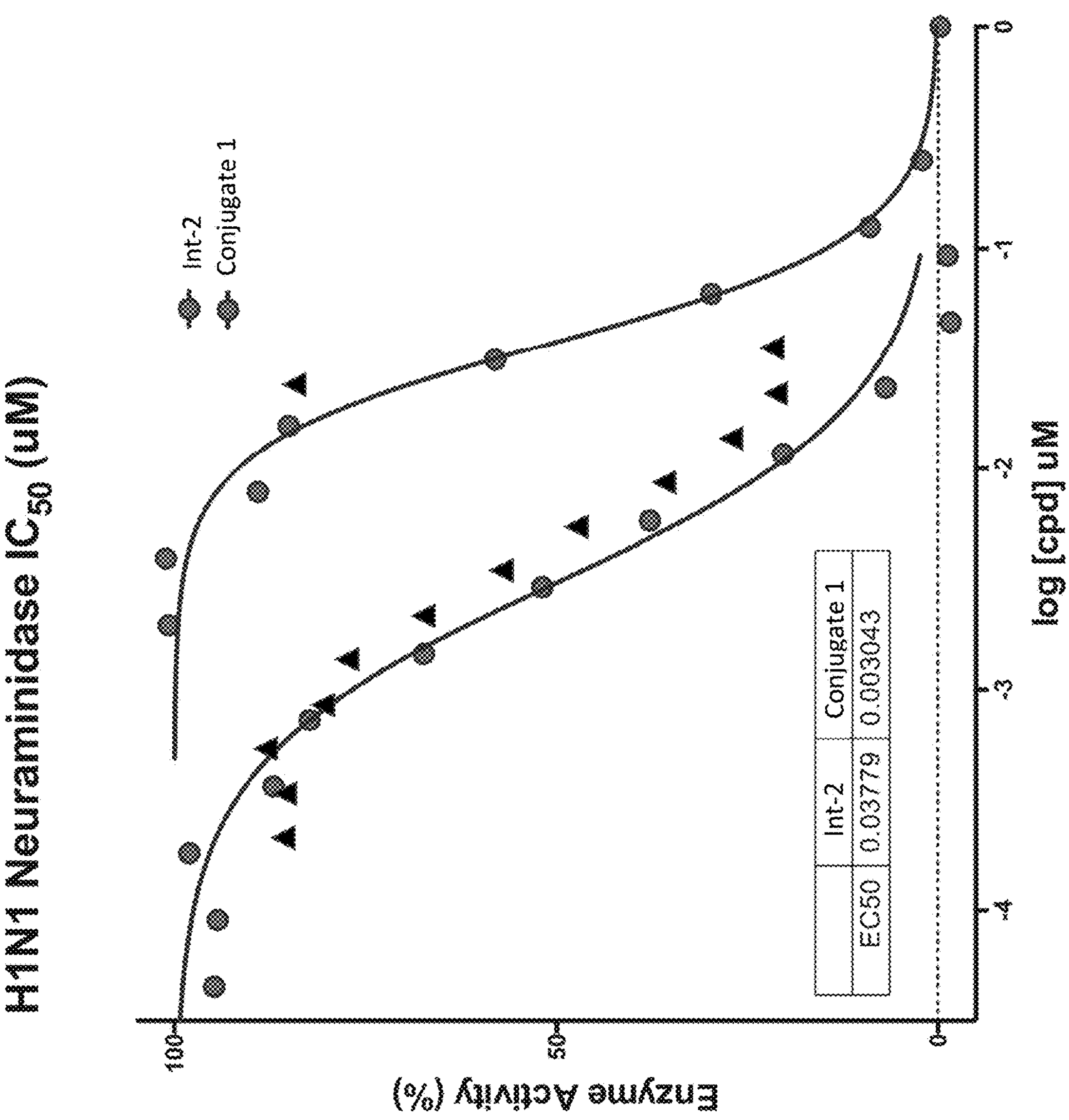
FIG. 15 is a graph showing the IC50 values from an H1N1 neuraminidase inhibition assay for Int-2 and Conjugate 1.
Figure 16:
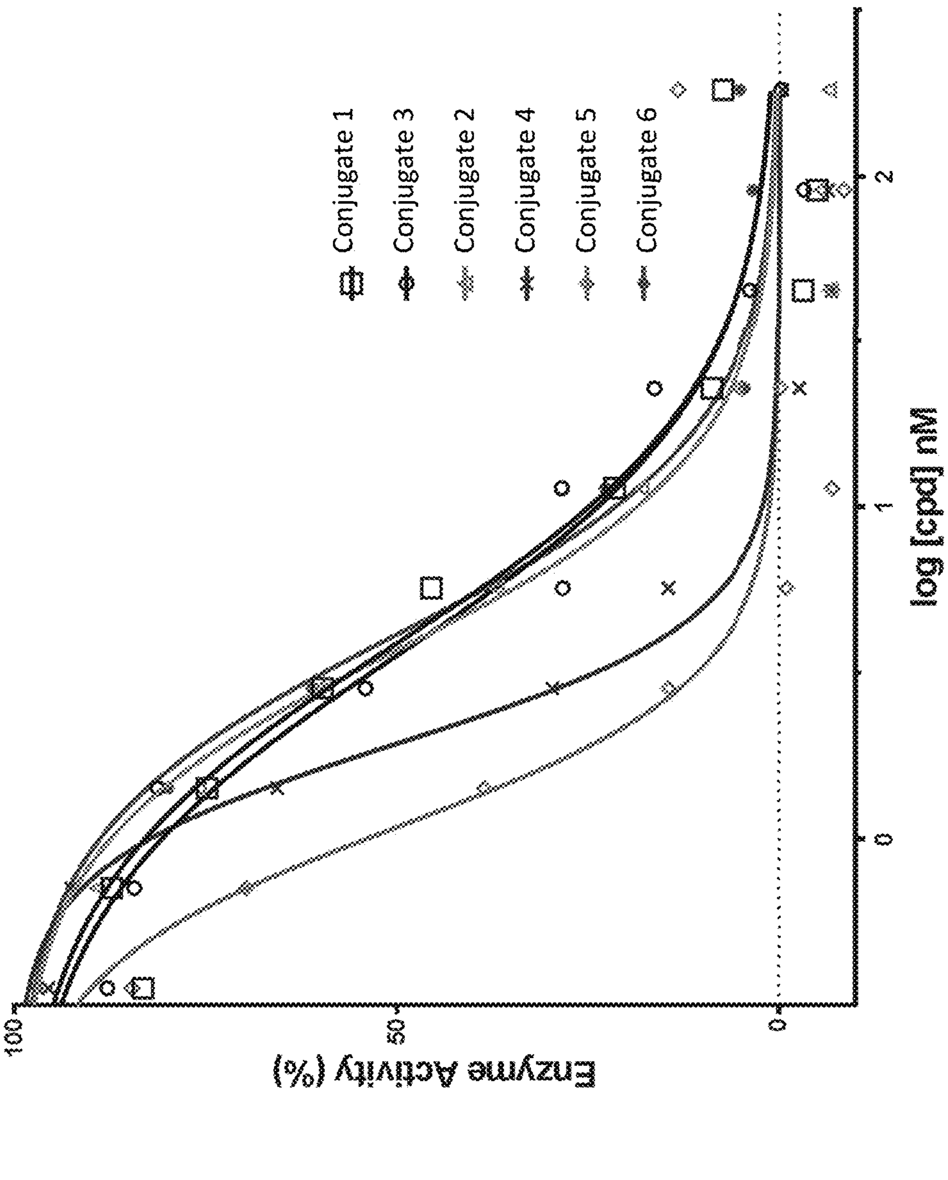
FIG. 16 is a graph showing the IC50 values from an H1N1 neuraminidase inhibition assay for Conjugates 1-6.
Figure 17:
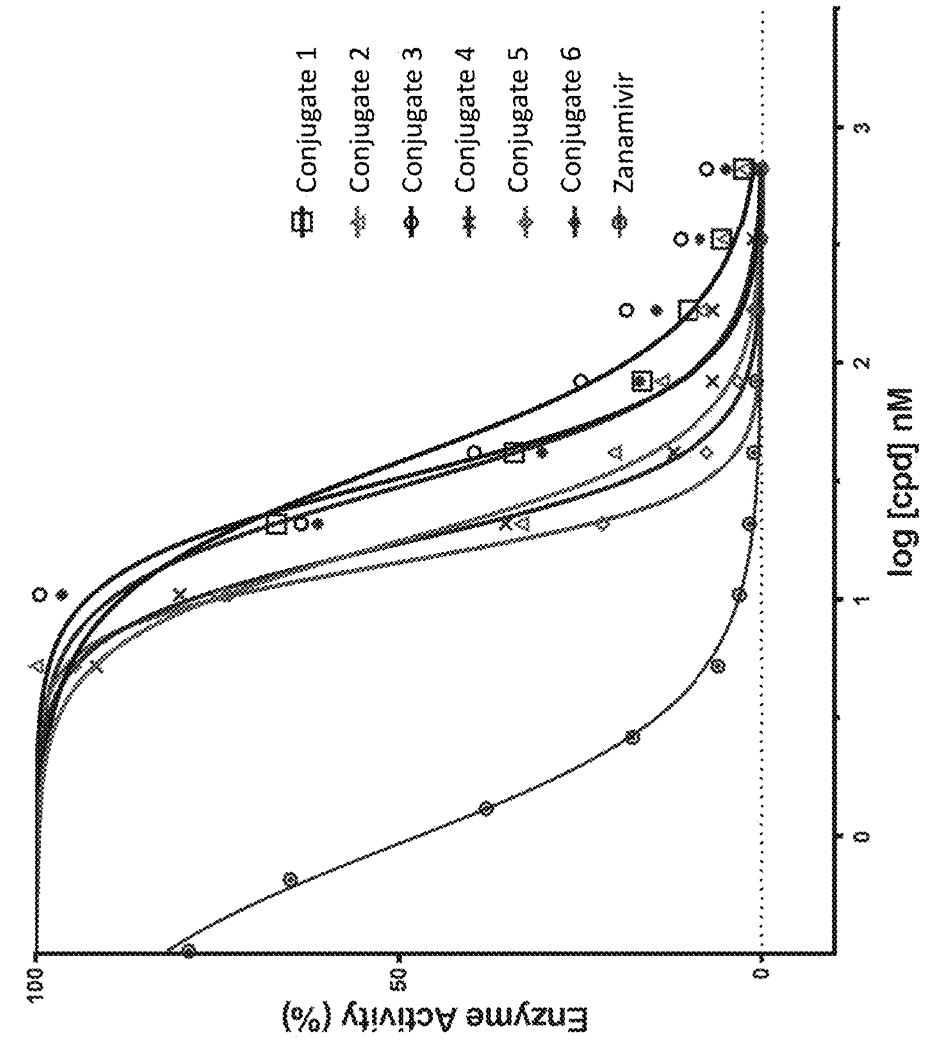
FIG. 17 is a graph showing the IC50 values from an H3N2 neuraminidase inhibition assay for Conjugates 1-6.

A neuraminidase inhibition assay using 2'-(4-Methylumbelliferyl)-alpha-D-N-aceylneuraminic acid (MUNANA) substrate was performed as described below. Briefly, 50 μL of purified, recombinant influenza virus neuraminidase (0.1 ng/μL, 50 mM Tris, 5 mM $CaCl_2$), 200 mM NaCl, pH 7.5) was mixed with 50 μL of inhibitor and incubated for 30 min at room temperature. At least 5 concentrations of each inhibitor at an appropriate range were used for each repeat. Following incubation, 50 μL of 400 μM MUNANA in 50 mM Tris, 5 mM $CaCl_2$), 200 mM NaCl, (pH 7.5) was added to the solution to start the reaction using a 12-tip pipette (Eppendorf). A positive and a negative control were included in each 12-well lane. After starting the reaction for each lane on the plate, the reaction mixture was immediately loaded on a SpectraMax M5 (Molecular Devices) where fluorescence was quantified over the course of 25 min at an excitation wavelength of 365 nm and an emission wavelength of 445 nm. Single time points were chosen where the positive control produced a fluorescence signal of approximately 1,000. All assays were done in triplicates and IC50 values for each inhibitor were calculated with sigmoidal fitting of the log[inhibitor] vs. inhibition percentage using GraphPad Prism. FIG. 15 shows the plot of the kinetic data as RFU/min over a linear range for Conjugate 1 and Int-2 showing the greater efficacy of Conjugate 1 as a neuraminidase inhibitor. FIG. 16 and FIG. 17 show the assay results for Conjugates 1-6 against rH1N1 Neuraminidase and rH3N2 Neuraminidase, respectively (Table 2).

TABLE 2

IC50 values for conjugates against H1N1 and H3N2 Neuraminidase

| Conjugate Number | H1N1 IC50 (nM) | H3N2 IC50 (nM) |
|---|---|---|
| Conjugate 1 | 3.9 | 32.5 |
| Conjugate 2 | 3.7 | 17.6 |
| Conjugate 3 | 3.6 | 38 |
| Conjugate 4 | 1.9 | 17.2 |
| Conjugate 5 | 1.1 | 14.3 |
| Conjugate 6 | 4.1 | 29.8 |

Example 24: Cytotoxicity Assay

Conjugates 1, 2, 3, and 6 were tested for cytotoxicity. Ten two-fold serial dilutions of each conjugate starting at 10 μM were prepared in triplicate for inoculation with MDCK cells in 96-well culture plates. The cell by way of bility was determined four days post treatment using CellTiter-GLO kit. 50% of cytotoxicity concentration ($CC_{50}$) was calculated using XLfit dose response model (Table 3). For all compounds tested, cytotoxicity was not observed up to the 10 μM, with the exception of conjugate 3. In the case of Conjugate 3, The $EC_{50}$ in the cytopathic effect (CPE) assay (see Example 23) is 725-fold below the $CC_{50}$ in this assay.

TABLE 3

Cytotoxicity test

| Conjugate Number | CC50 (μM) |
|---|---|
| Conjugate 1 | >10 |

TABLE 3-continued

Cytotoxicity test

| Conjugate Number | CC50 (μM) |
|---|---|
| Conjugate 2 | >10 |
| Conjugate 3 | 7.98 |
| Conjugate 6 | >10 |
| PBS | >10 |
| Zanamavir | >10 |

Example 25. Cytopathic Effect Assay

CPE-Based Microneutralization Assay #1

To measure the ability of neuraminidase conjugates to protect mammalian cells from infection and destruction by influenza virus, cytopathic effect (CPE)-based microneutralization assays were conducted. Briefly, twenty two-fold serial dilutions of each conjugate starting at 0.25 μM were prepared in duplicate for one-hour inoculation with MDCK cells seeded in 96-well plates. INFV CA/09 virus was added to cells at a multiplicity of infection (MOI) 0.001 for one-hour incubation. On day four post incubation, cells were stained with crystal violet and optical density was read for calculation of 50 percent effective concentration (EC50) of each TA using XLfit dose response model. Zanamivir was used as a comparator and positive control. human Fc was included as a negative control. Conjugates 1, 2, 3, and 6 all demonstrated superior performance to the zanamivir control, demonstrating EC50s 42- to 227-fold lower than zanamivir (Table 4).

TABLE 4

CPE-based microneutralization assay #1

| Conjugate Number | EC50 (nM) |
|---|---|
| 1 | 2.0574 |
| 2 | 4.1487 |
| 3 | 11.007 |
| 6 | 5.2167 |
| PBS | N/C |
| Human Fc | N/C |
| Zanamavir† | 468.7 |

N/C: Not calculatable

†Starting concentration 10000 nM

CPE-Based Microneutralization Assay #2

An additional CPE-based microneutralization assay was run to further evaluate the in vitro activity of Conjugate 6 and Conjugate 7. Briefly, test articles were prepared at a starting concentration of 160 nM, and a total of ten, 2-fold dilutions were made. The test article dilutions were then pre-mixed with Influenza A virus (INFV CA/09) at a multiplicity of infection of 0.001 relative to the monolayer. After one hour the test article+viral mix was added to Madin-Darby Canine Kidney (MDCK) cells grown to 70-80% confluence under standard conditions in a 96-well plate. The zanamivir control was treated the same, except the starting concentration was 9600 nM since it was expected to be less potent than the Conjugates being tested. After four days of incubation the monolayer was stained with crystal violet and optical density (reflective of monolayer health) was determined to calculate the 50% effective concentration (EC50) using the XLfit dose response model (idbs; https://www.idbs.com).

As shown in Table 5, zanamivir at a concentration of 496 nM reduced the virus mediated cytopathic effects by half. In contrast, Conjugate 6 was approximately 100× more active with an EC50 of only 4.64 nM. Conjugate 7, further improved activity by approximately 15-fold, reducing the EC50 to the sub-nM level.

TABLE 5

| CPE-based microneutralization assay #2 | |
|---|---|
| Conjugate Number | EC50 (nM) |
| 6 | 4.64 |
| 7 | 0.31 |
| Zanamivir | 496 |

Example 26. Cell by Way of Bility Assay

Figure 18A:
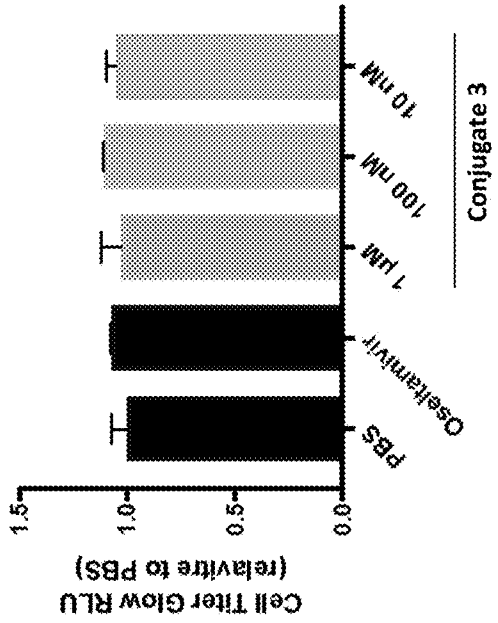
FIGS. 18A-18C are a series of graphs showing the cell by way of bility of A549 cells treated with Conjugate 3 (FIG. 18A), Conjugate 4 (FIG. 18B), or Conjugate 6 (FIG. 18C).
Figure 18B:
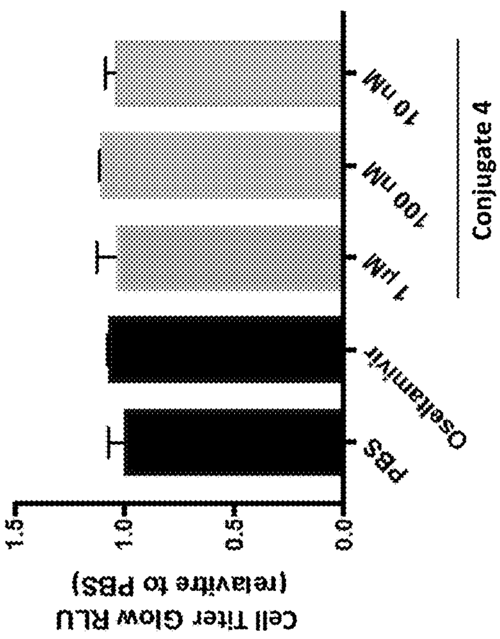
Figure 18C:
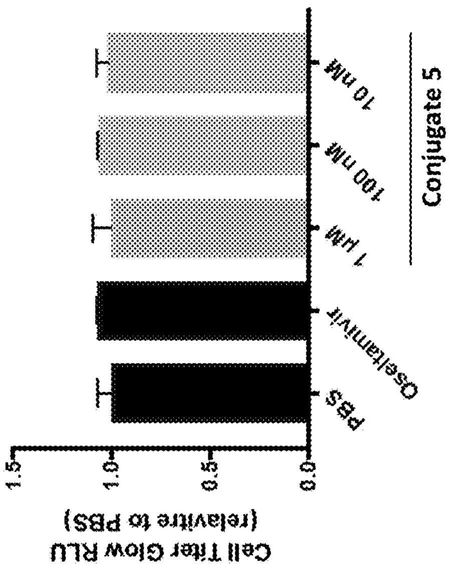
Figure 19B:
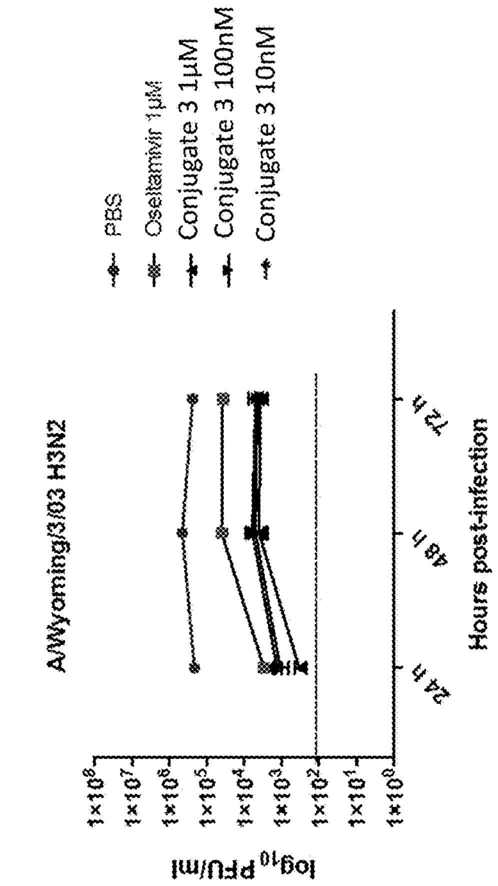
FIGS. 19A-19E are a series of graphs showing the ability of Conjugate 3 to inhibit the growth of pathogenic influenza viral strains A/WSN/33 H1N1 (FIG. 19A), A/Wyoming/3/03 H3N2 (FIG. 19B), A/California/04/09 H1N1 pdm (FIG. 19C), A/Vietnam/1203/04 H5N1 HALo (FIG. 19D), or B/Lee/40 Victoria (FIG. 19E) in human epithelial cells.
Figure 19A:
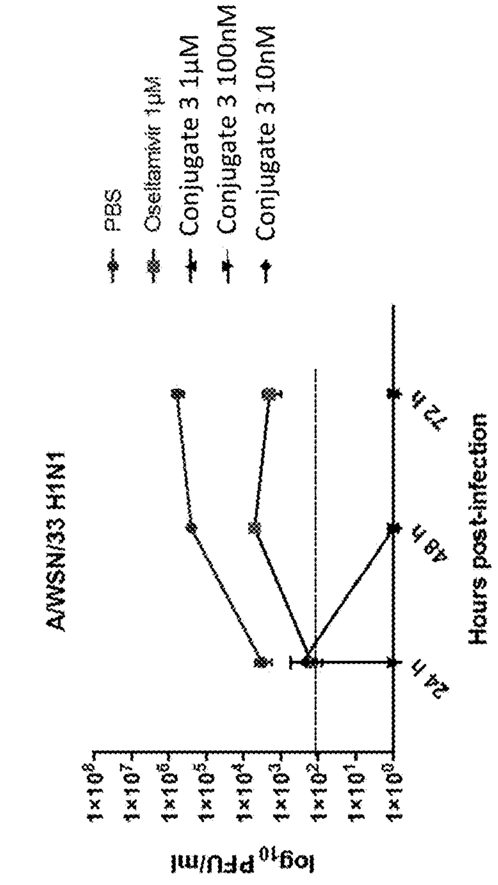
Figure 19C:
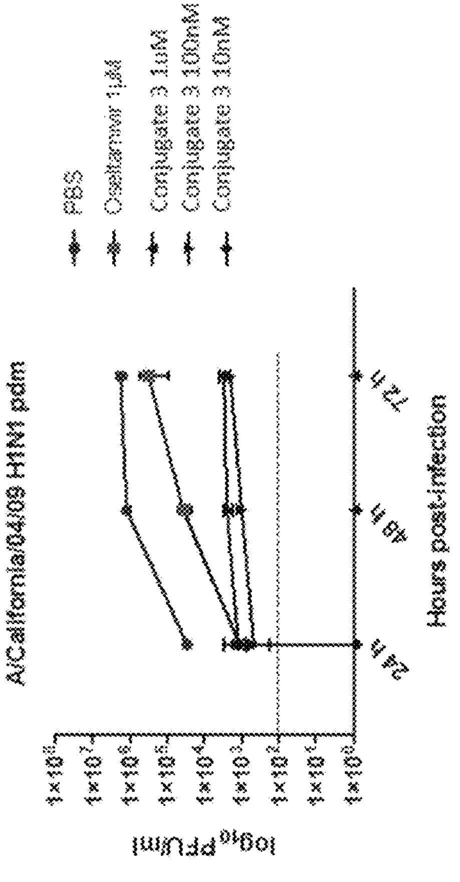
Figure 19D:
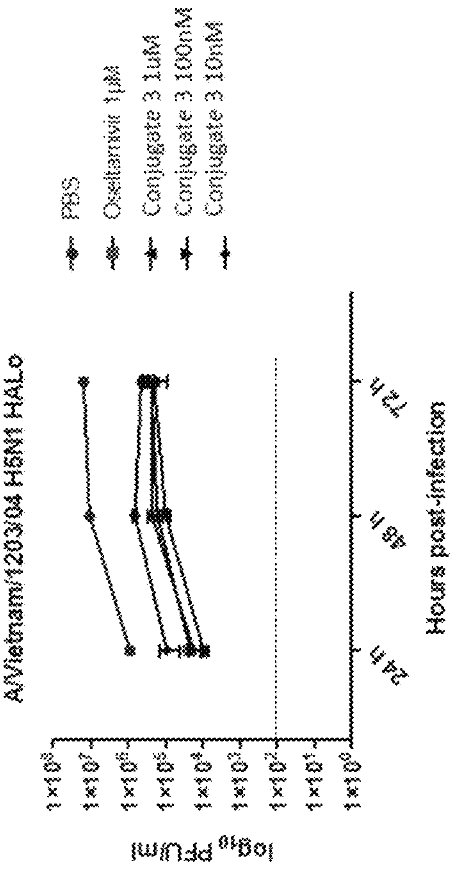
Figure 19E:
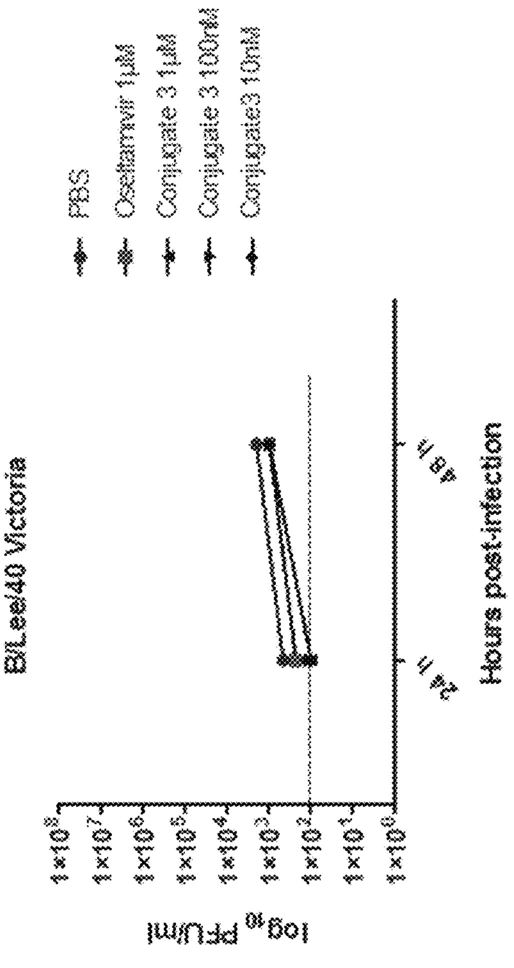
Figure 20B:
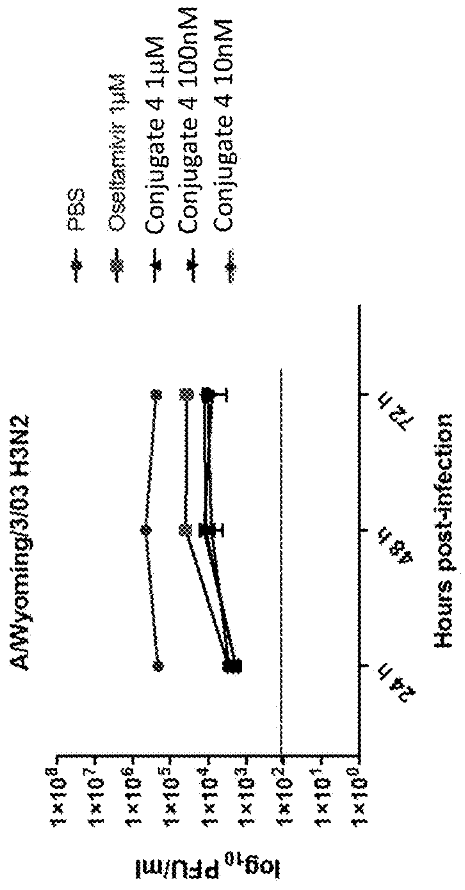
FIGS. 20A-20E are a series of graphs showing the ability of Conjugate 4 to inhibit the growth of pathogenic influenza viral strains A/WSN/33 H1N1 (FIG. 20A), A/Wyoming/3/03 H3N2 (FIG. 20B), A/California/04/09 H1N1 pdm (FIG. 20C), A/Vietnam/1203/04 H5N1 HALo (FIG. 20D), or B/Lee/40 Victoria (FIG. 20E) in human epithelial cells.
Figure 20A:
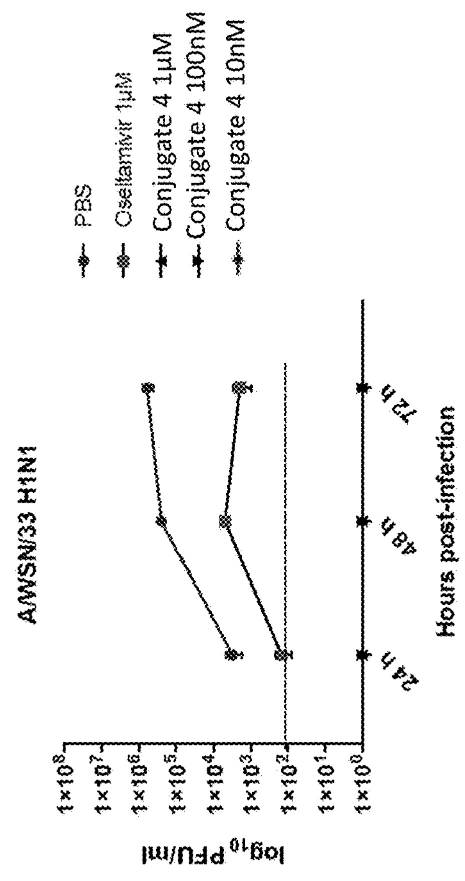
Figure 20C:
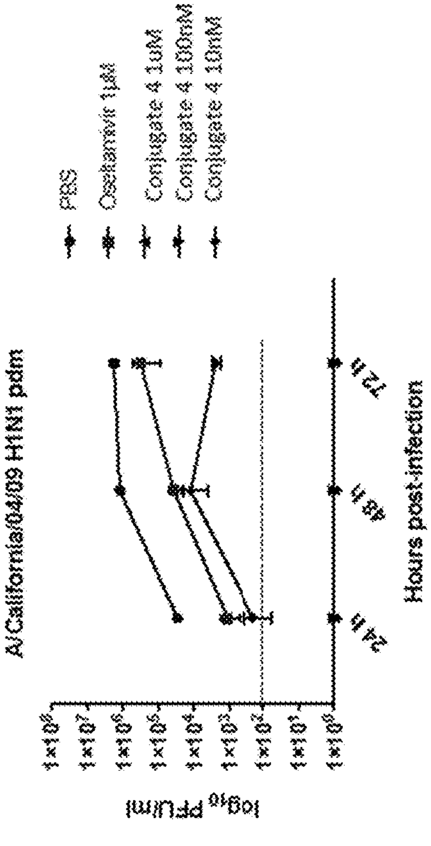
Figure 20D:
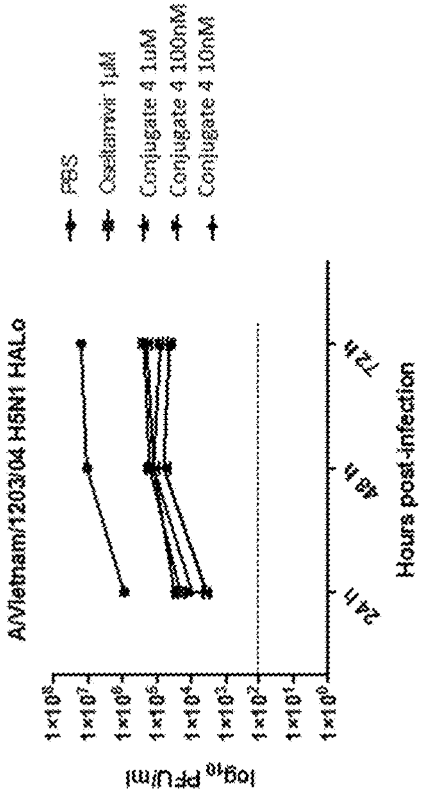
Figure 20E:
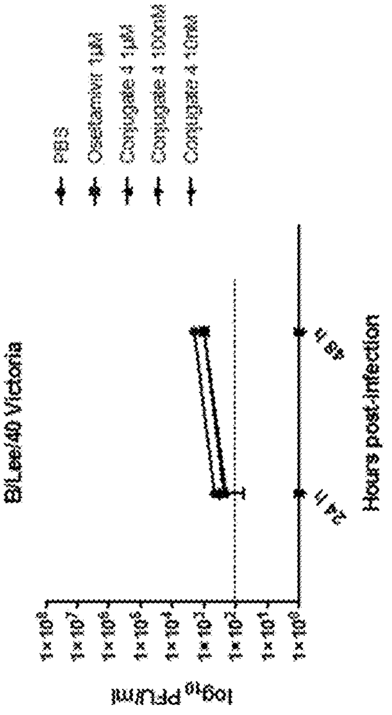
Figure 21B:
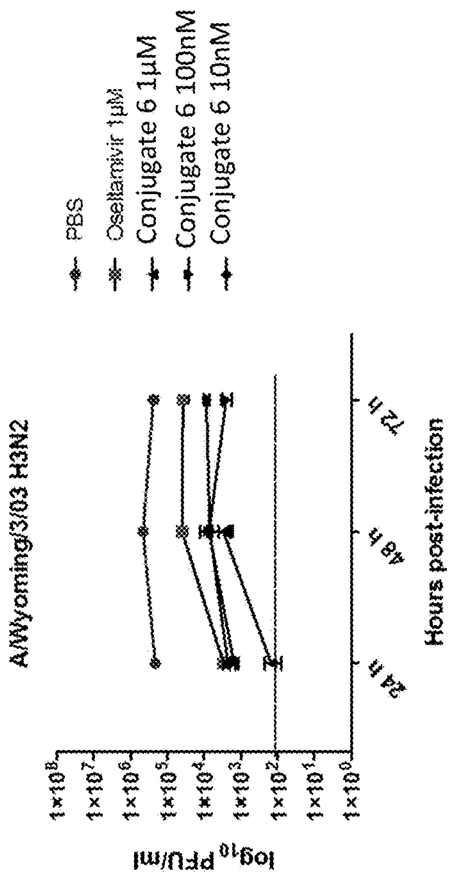
FIGS. 21A-21E are a series of graphs showing the ability of Conjugate 6 to inhibit the growth of pathogenic influenza viral strains A/WSN/33 H1N1 (FIG. 21A), A/Wyoming/3/03 H3N2 (FIG. 21B), A/California/04/09 H1N1 pdm (FIG. 21C), A/Vietnam/1203/04 H5N1 HALo (FIG. 21D), or B/Lee/40 Victoria (FIG. 21E) in human epithelial cells.
Figure 21A:
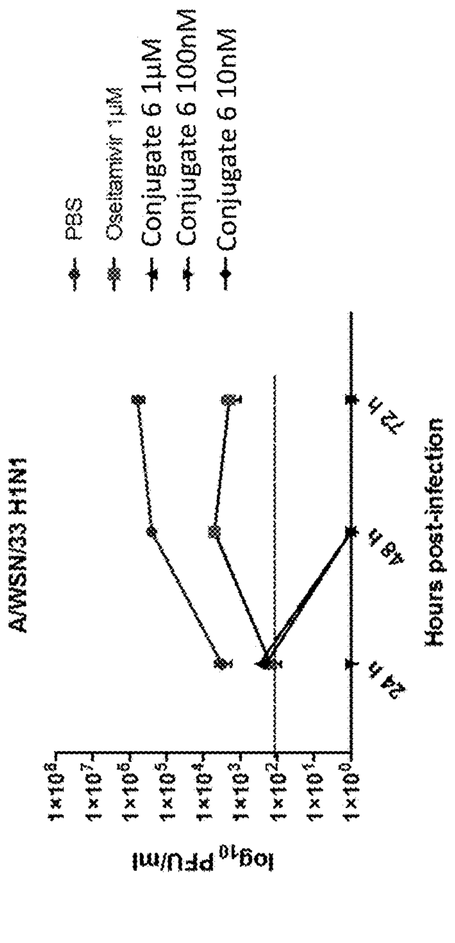
Figure 21D:
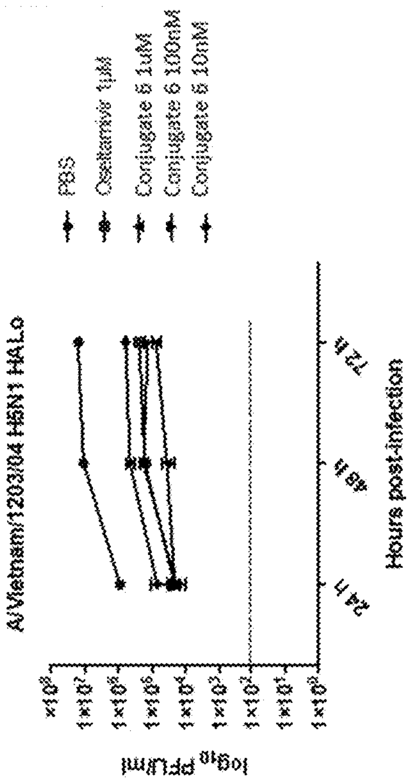
Figure 21C:
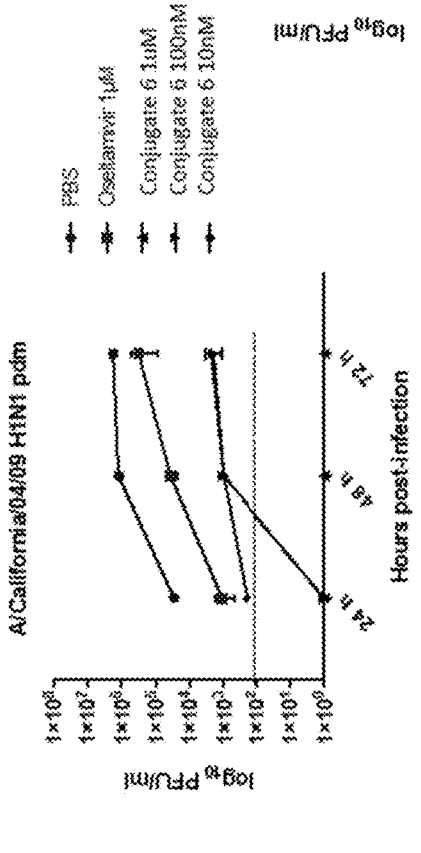
Figure 21E:
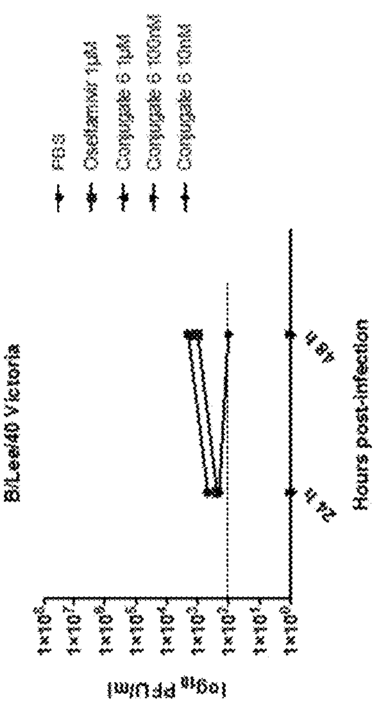
Figure 22A:
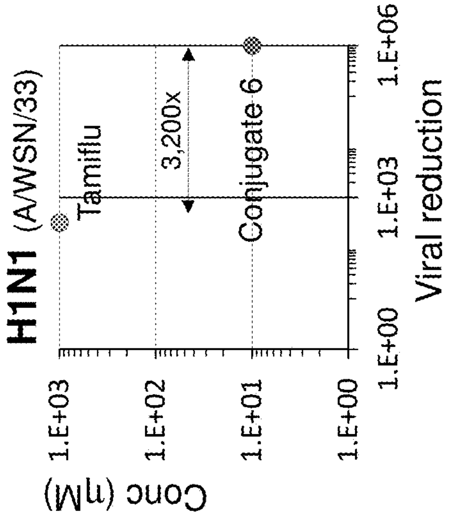
FIGS. 22A-22E are a series of graphs showing the ability of Conjugate 6 to inhibit the growth of pathogenic influenza viral strains A/WSN/33 H1N1 (FIG. 22A), A/Wyoming/3/03 H3N2 (FIG. 22B), A/California/04/09 H1N1 pdm (FIG. 22C), B/Lee/40 Victoria (FIG. 22D), or A/Vietnam/1203/04 (FIG. 22E) in human epithelial cells, compared to Oseltamivir.
Figure 22B:
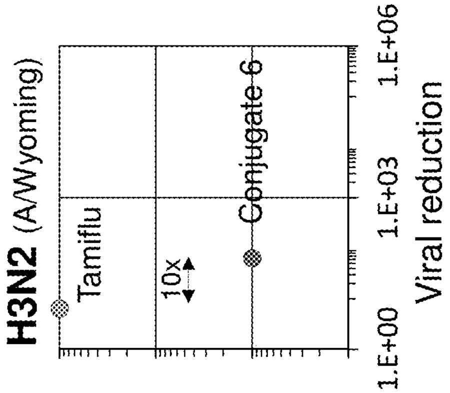
Figure 22C:
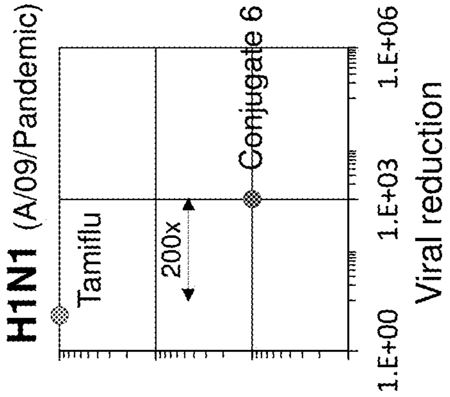
Figure 22D:
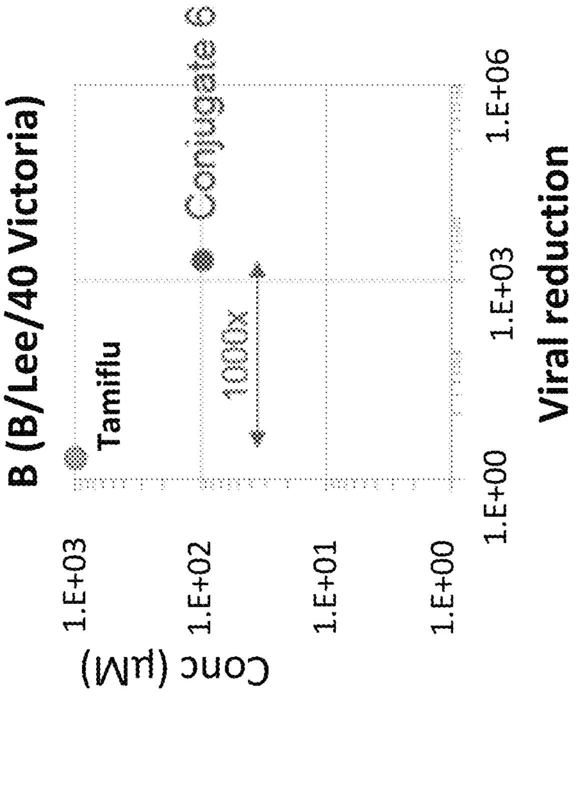
Figure 22E:
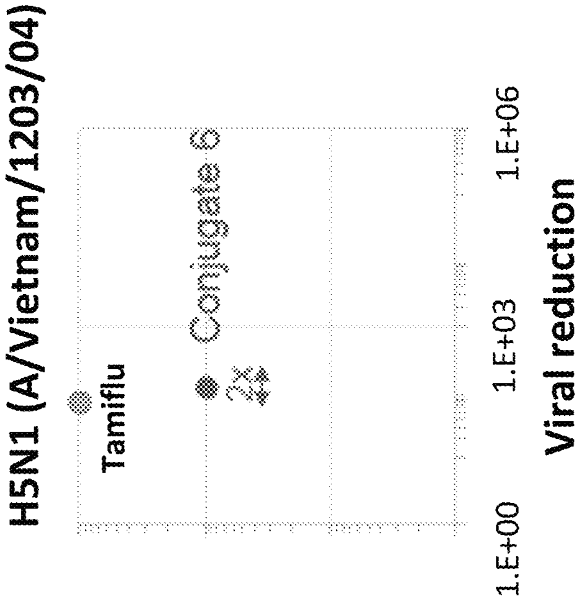

A549 cells were seeded in 96-well plates one day prior to compound treatment. Cells were treated with either Conjugate 3 (FIG. 18A), Conjugate 4 (FIG. 18B), or Conjugate 6 (FIG. 18C) at concentrations 1 μM-10 nM for 24 hours. Cell by way of bility was then measured using Cell Titer Glow (Promega). Results represent average and SD of three biological replicates. No effects were observed on cell by way of bility for any of the conjugates at any concentrations at any of the concentrations used in the viral growth assay (Example 27).

Example 27. Viral Growth Assay

To measure the ability of neuraminidase conjugates to inhibit the growth of pathogenic influenza viral strains of interest in human epithelial cells, viral plaque reduction assays were conducted. Briefly, A549 cells were seeded in 24-well plates one day prior to compound treatment. Cells were treated with compounds at concentrations 1 μM-10 nM for 2 hours and infected with indicated viral strains at MOI 0.01 for one-hour incubation. Virus was removed, cells were washed and compounds were re-applied at concentrations 1 μM-10 nM. Supernatants were collected at indicated time points and titrated using plaque assay method in MDCK cells. Results represent average and SD of three biological replicates. Oseltamivir was used as a comparator and a positive control. Conjugate 3 (FIGS. 19A-19E), Conjugate 4 (FIGS. 20A-E), or Conjugate 6 (FIGS. 21A-21E and FIGS. 22A-22E) all demonstrated superior performance to the oseltamivir control, showing similar or (usually) superior plaque reduction to oseltamivir at 100-fold lower concentrations. The effects of the compounds (to evaluate test articles for potential cytotoxicity) on the $A_{549}$ cells was evaluated for each test article using a cell by way of bility assay (Example 26). Briefly, $A_{549}$ cells were seeded in 96-well plates one day prior to compound treatment. Cells were treated with compounds at concentrations 1 μM-10 nM for 24 hours. Cell by way of bility was then measured using Cell Titer Glow (Promega). Results represent average and SD of three biological replicates.

Example 28. Mouse Serum Half-Life

Pharmacokinetic (PK) studies used female CD-1 mice (Charles River Laboratories) between 20 and 22 grams. Mice were injected IV by way of the tail vein, with 50 mg/kg of test article (10 ml/kg dose volume). Animals were housed under standard IACUC approved housing conditions. At appropriate times animals were non-terminally bled (retro-orbital, cheek, or by tail vein) with blood collected in EDTA tubes to prevent coagulation. Collected blood was centrifuged (2,000×g, for 10 minutes) and plasma withdrawn for analysis of test article concentrations over time.

The plasma concentrations for Conjugate 6 or hIgG1 Fc at each time point were measured by sandwich ELISA as follows: Conjugate 6 molecules were captured either on Neuraminidase coated plates or anti-hIgG1 antibody coated plates and then detected using an HRP-conjugated anti-human IgG-Fc antibody. hIgG1 was captured using anti-hIgG1 Fc antibody. Protein concentration was calculated in GraphPad Prism using 4PL non-linear regression of Conjugate 6 (or hIgG1 Fc) standard curves. A more detailed method description is provided below.

Qiagen Ni-NTA HisSorb plates (Cat No. 35061, Qiagen) were coated with either Neuraminidase from A/California/04/2009 (H1N1) (11058-VNAHC, Sino Bio) or anti-IgG1 Fc antibody in 1×KPL coating buffer (5150-0041, SeraCare). In the cases where the anti-IgG1 Fc antibody was used to capture test article, capture and detection anti-IgG1 Fc antibodies were selected that bind different epitopes. Plates were incubated at room temperature for 1 hour. Serial dilutions of the plasma samples were plated and incubated at room temperature for 2 hrs (sample diluent: 0.5% nonfat dry milk+3% Goat serum in PBS 0.05% Tween20; naïve mouse plasma final concentration of 1:900). Conjugate 6 or hIgG1 Fc standard curves ranging from 500-0.230 ng/mL, in duplicate were run on each plate.

Following the 2 hr incubation, plates were washed 5× in 300 uL PBS with 0.05% Tween20. Conjugate 6 bound to neuraminidase on the plates (or anti-hIgG1 Fc antibody) was then probed with an HRP conjugated anti-human IgG Fc F(ab')2 (Jackson 709-036-098) diluted 1:2000 in sample diluent for 1 hour at room temp. Plates were then washed 8× in 300 uL PBS with 0.05% Tween20 and developed with TMB substrate for 7 minutes. The reaction was stopped with 1 N H2SO4. Absorbance was read at 450 nm. A similar protocol was used for hIgG1 Fc, where only anti-hIgG1 Fc antibody was used for capture. The quantities of Conjugate 6 measured at different timepoints using either neuraminidase or anti-hIgG1 Fc antibody capture were similar within experimental error, suggesting that the intact conjugate is stable in vivo.

Figure 23:
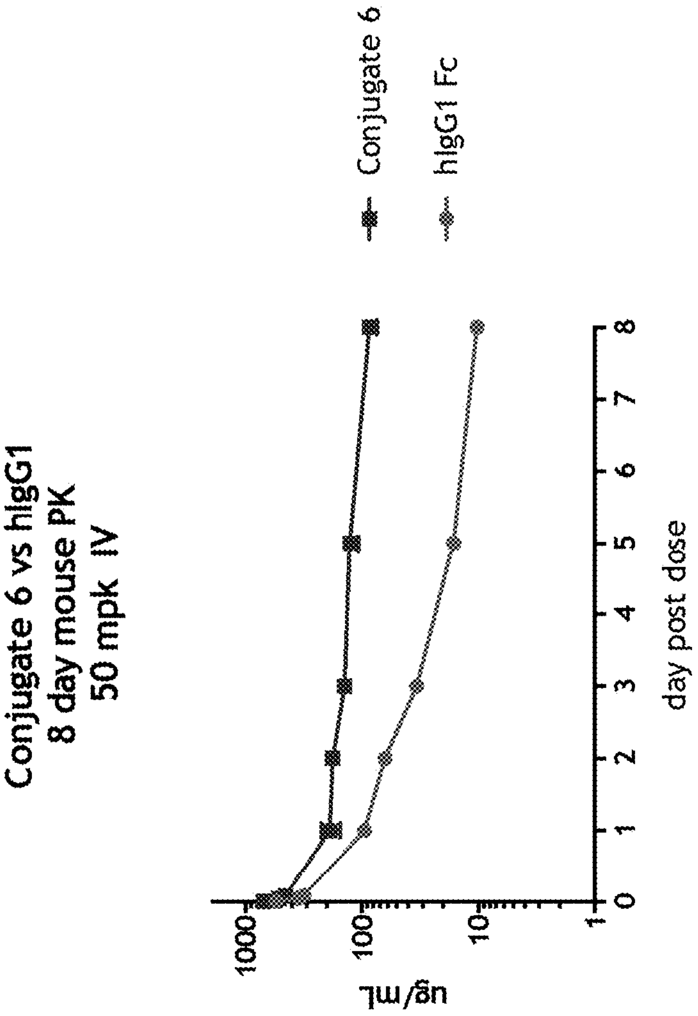
FIG. 23 is a graph showing the relative mouse serum concentration of Conjugate 6 compared to Fc (hIgG1) alone.

Total Conjugate 6 (or hIgG1 Fc) in test samples was interpolated using in Graphpad Prism Version 6 following nonlinear regression analysis (Sigmoidal, 4PL analysis) of the Conjugate 6 (or hIgG1 Fc) standard curves. PK parameters were calculated using WinNonlin software. The curves comparing Conjugate 6 and hIgG1 Fc are shown in FIG. 23 and a summary of key PK parameters is provided in Table 6. Unexpectedly, plasma exposures and terminal half-life are significantly better for Conjugate 6 than for wild-type hIgG1 Fc. The AUCs over 8-days are 3× higher for Conjugate 6 than for hIgG1 Fc, and the terminal half-life for Conjugate 6 is 214 hours, versus 52 hours for human IgG1 Fc.

TABLE 6

| Mouse PK of Conjugate 6 compared to hIgG1 Fc | | |
|---|---|---|
| | Half-life (hrs) | AUClast (hr * mg/mL) |
| Conjugate 6 | 214 | 33100 |
| hIgG1 | 51.8 | 10600 |

Example 29. Efficacy of Conjugate 6 in a Lethal Mouse Influenza Model: Study #1

Figure 24:
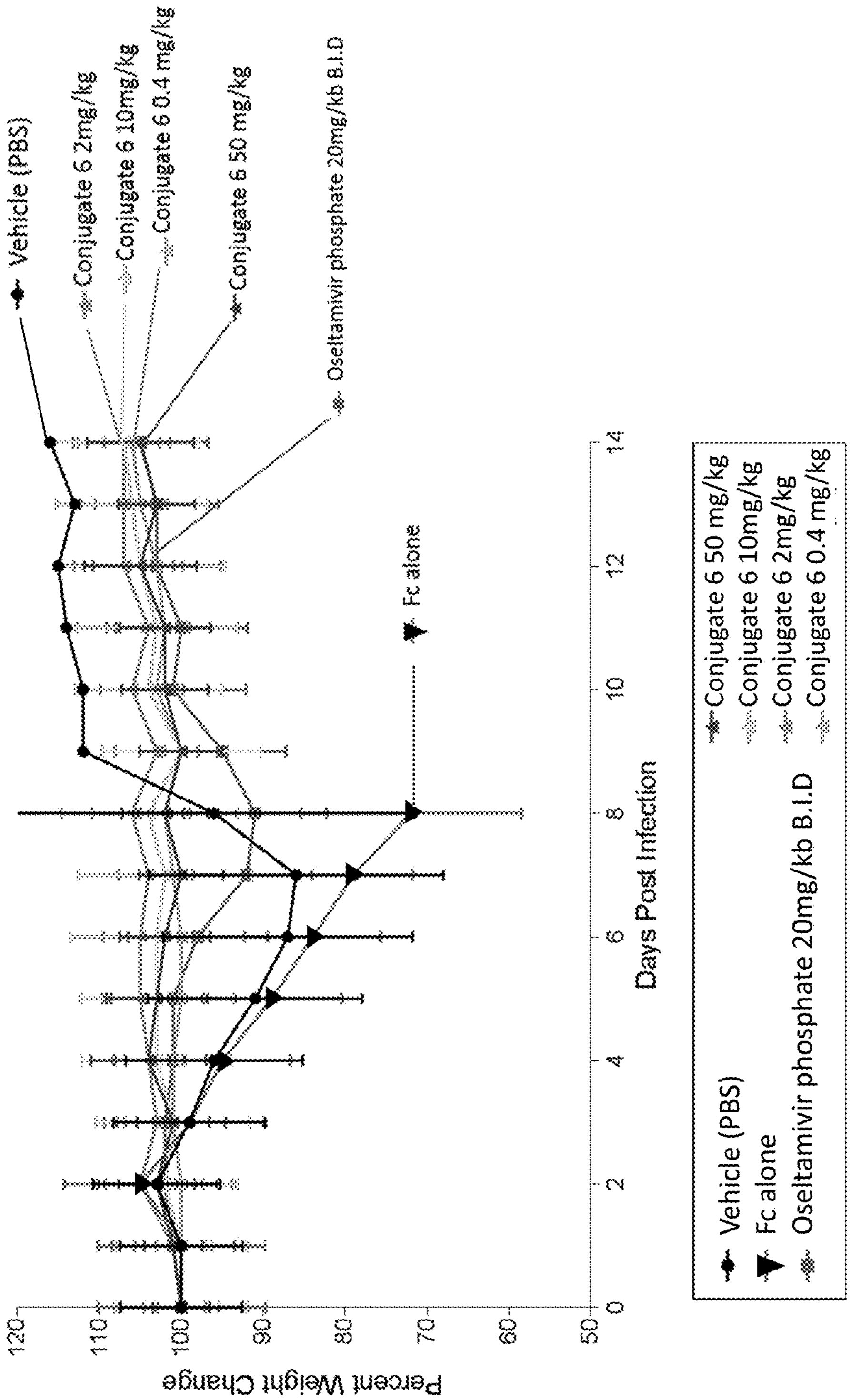
FIG. 24 is a graph showing the effect of Conjugate 6 on mouse weight in a lethal mouse influenza model. The study was performed as described in Example 29.
Figure 25:
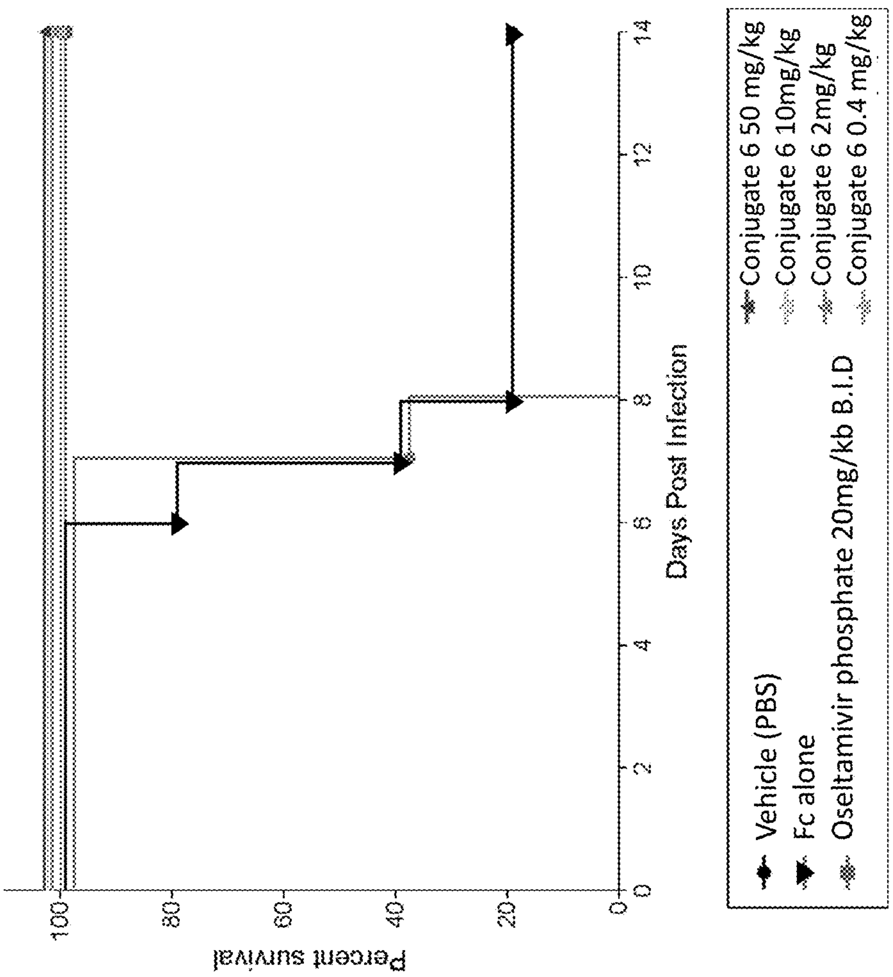
FIG. 25 is a graph showing the effect of Conjugate 6 on survival in a lethal mouse influenza model. The study was performed as described in Example 29.

Conjugate 6 was evaluated against a lethal INFV A H1N1 influenza infection in female BALB/c mice. The experiment comprised 7 groups of 5 mice. At day 0, all mice were challenged with 1×LD90 H1N1 A/Texas/36/91. Groups 1-6 received treatment IV, 4 hours before challenge (Table 7). Human IgG1 (Fc alone) was included as an additional negative control. Group 7 received Oseltamivir phosphate by way of oral delivery, starting 8 hours post infection twice daily for 5 days. All mice were monitored for weight loss (FIG. 24, Table 8) and survival (FIG. 25, Table 9) for 15 days after challenge.

Mice treated with Conjugate 6 showed 100% survival with single doses in all the concentrations tested, compared with 20% and 0% survival in the vehicle control and hIgG1 control groups, respectively. The results were statistically significant when compared to the vehicle group (p=0.0135) despite the small group size (n=5). When compared to the Oseltamivir phosphate group, Conjugate 6 demonstrated similar efficacy at a 500× lower cumulative dose (in mg/kg). Mice at all Conjugate 6 doses maintained their weight through the entire course of the experiment, superior to the Oseltamivir control group.

TABLE 7

Study design

| Group n = 5 | Challenge Day 0 | Compound | Dose (mg/kg) | Treatment Route/Schedule |
|---|---|---|---|---|
| 1 | Influenza A virus, | Vehicle (PBS) | N/A | IV, q.d. 4 hours pre-challenge |
| 2 | H1N1 strain | Fc alone | 50 | |
| 3 | A/Texas/36/91 by way | Conjugate 6 | 50 | |
| 4 | of IN route. | Conjugate 6 | 10 | |
| 5 | | Conjugate 6 | 2 | |
| 6 | | Conjugate 6 | 0.4 | |
| 7 | | Oseltamivir (Tamiflu ™) | 20 | PO, b.i.d. 8 hours after challenge for 5 days |

TABLE 8

Daily Weight Average

| Days post in- fection | Daily average weight (The mice number is added only for Group 1 & 2) | | | | | | |
|---|---|---|---|---|---|---|---|
| | Vehicle (PBS) | Fc alone 50 mg/kg | Conjugate 6 50 mg/kg | Conjugate 6 10 mg/kg | Conjugate 6 2 mg/kg | Conjugate 6 0.4 mg/kg | Oseltamivir phosphate 20 mg/kg |
| 0 | 17.9 (5) | 17.9 (5) | 18.7 | 19.3 | 18.5 | 18.8 | 18.8 |
| 1 | 18.0 (5) | 18.0 (5) | 18.8 | 19.36 | 18.6 | 18.8 | 18.9 |
| 2 | 18.5 (5) | 18.8 (5) | 19.2 | 19.6 | 19.4 | 18.8 | 19.2 |
| 3 | 17.7 (5) | 17.7 (5) | 18.9 | 19.5 | 19.1 | 18.9 | 19.1 |
| 4 | 17.2 (5) | 17.0 (5) | 19.5 | 19.9 | 19.3 | 18.9 | 18.9 |
| 5 | 16.3 (5) | 15.8 (5) | 19.2 | 19.8 | 19.5 | 18.7 | 18.8 |
| 6 | 15.6 (4) | 15.0 (5) | 19.1 | 19.9 | 19.5 | 18.7 | 18.4 |
| 7 | 15.5 (2) | 14.0 (2) | 18.8 | 19.6 | 19.2 | 18.9 | 17.3 |
| 8 | 17.2 (1) | | 19.1 | 20.0 | 19.7 | 19.2 | 17.1 |
| 9 | 20.1 (1) | | 18.7 | 19.3 | 19.1 | 18.8 | 17.8 |
| 10 | 20.0 (1) | | 19.1 | 20.1 | 19.5 | 19.3 | 18.9 |
| 11 | 20.4 (1) | | 19.0 | 19.8 | 19.2 | 19.2 | 18.7 |
| 12 | 20.6 (1) | | 19.6 | 20.3 | 19.8 | 19.3 | 19.2 |
| 13 | 20.3 (1) | | 19.2 | 20.4 | 19.7 | 19.7 | 19.3 |
| 14 | 20.7 (1) | | 19.5 | 20.6 | 19.9 | 19.8 | 19.6 |

TABLE 9

Mouse survival

| Compound | Dosage | Mean Survival | % Survival | Significance to vehicle (p) |
|---|---|---|---|---|
| Vehicle (PBS) | N/A | 7 | 20 | N/A |
| Fc alone | 50 mg/kg | 7 | 0 | 0.8335 |
| Conjugate 6 | 50 mg/kg | 15 | 100 | 0.0135 |
| Conjugate 6 | 10 mg/kg | 15 | 100 | 0.0135 |
| Conjugate 6 | 2 mg/kg | 15 | 100 | 0.0135 |
| Conjugate 6 | 0.4 mg/kg | 15 | 100 | 0.0135 |
| Oseltamivir phosphate | 20 mg/kg B.I.D | 15 | 100 | 0.0135 |

Example 30. Efficacy of Conjugate 6 in a Lethal Mouse Influenza Model: Study #2

Figure 26:
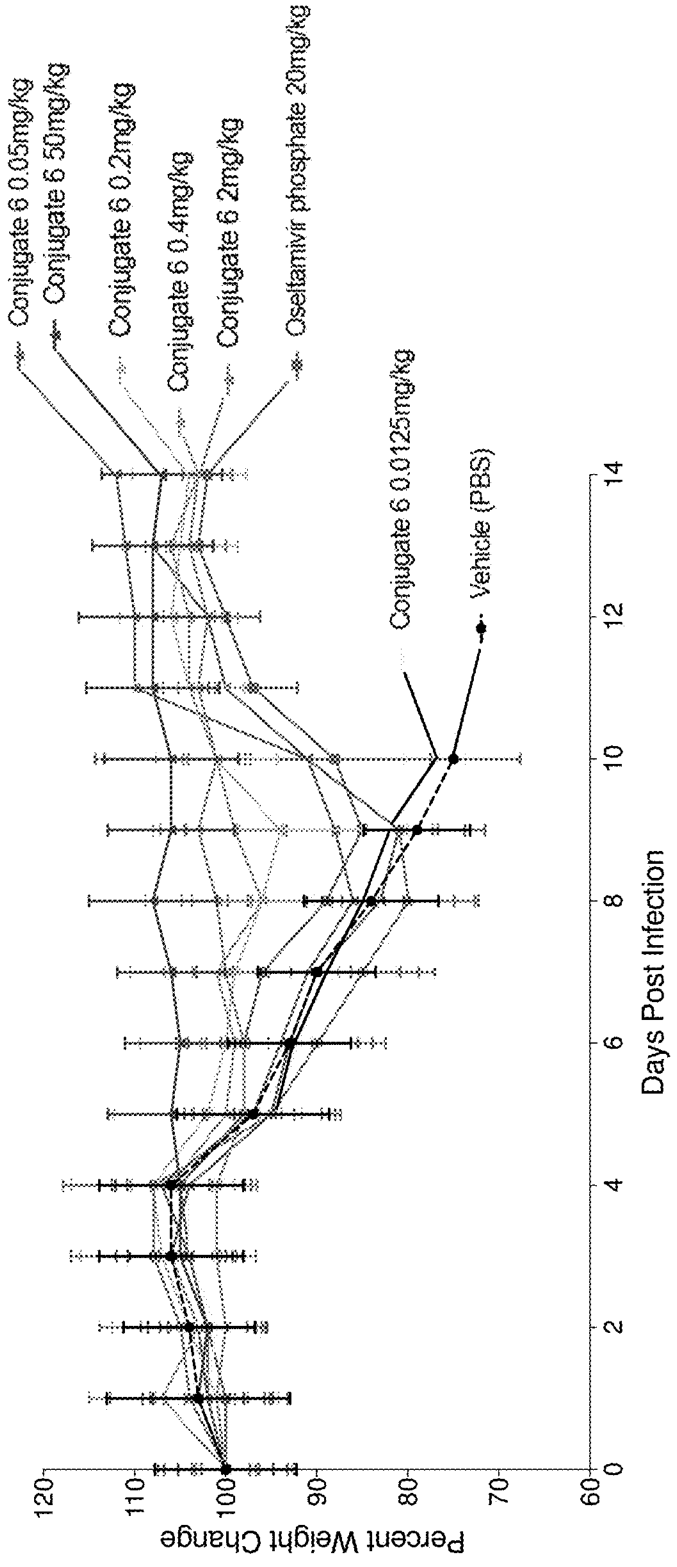
FIG. 26 is a graph showing the effect of Conjugate 6 on mouse weight in a lethal mouse influenza model. The study was performed as described in Example 30.
Figure 27:
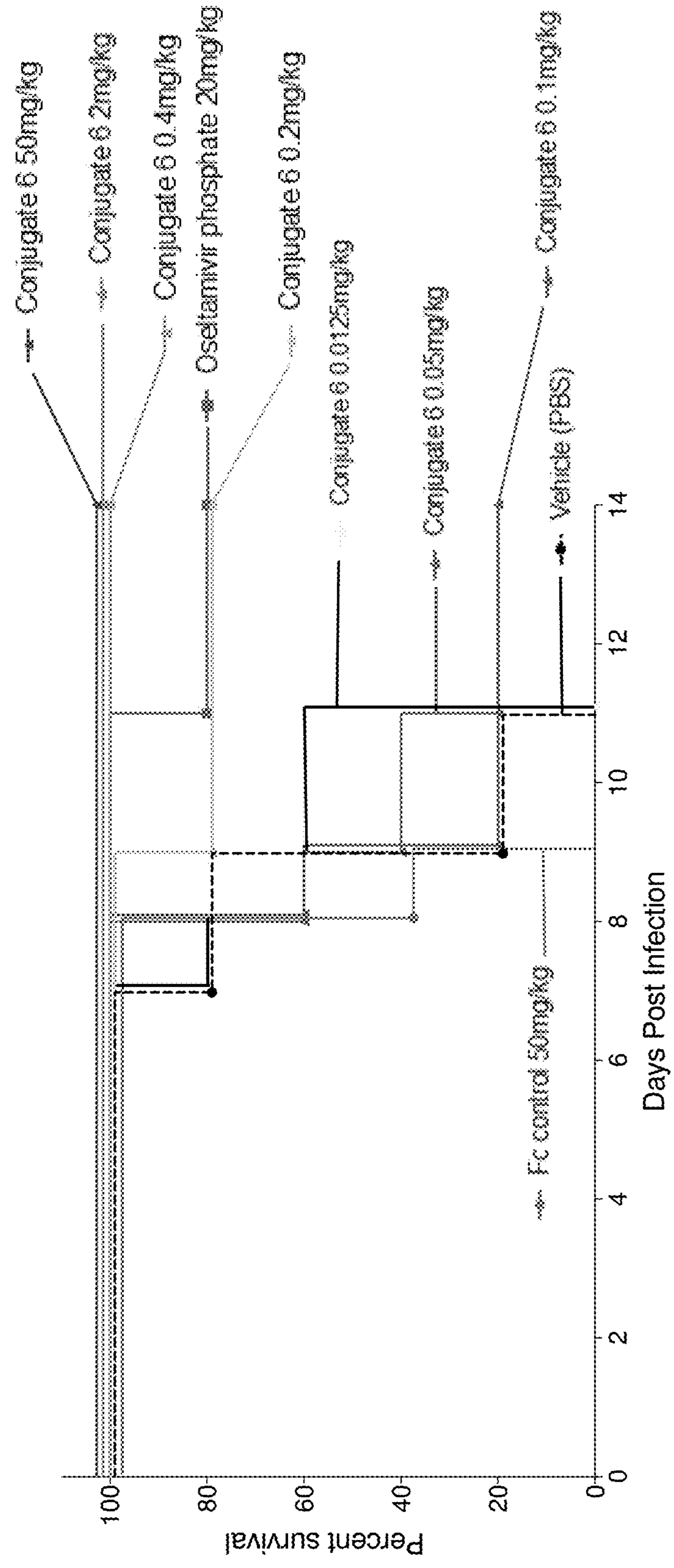
FIG. 27 is a graph showing the effect of Conjugate 6 on survival in a lethal mouse influenza model. The study was performed as described in Example 30.
Figure 28:
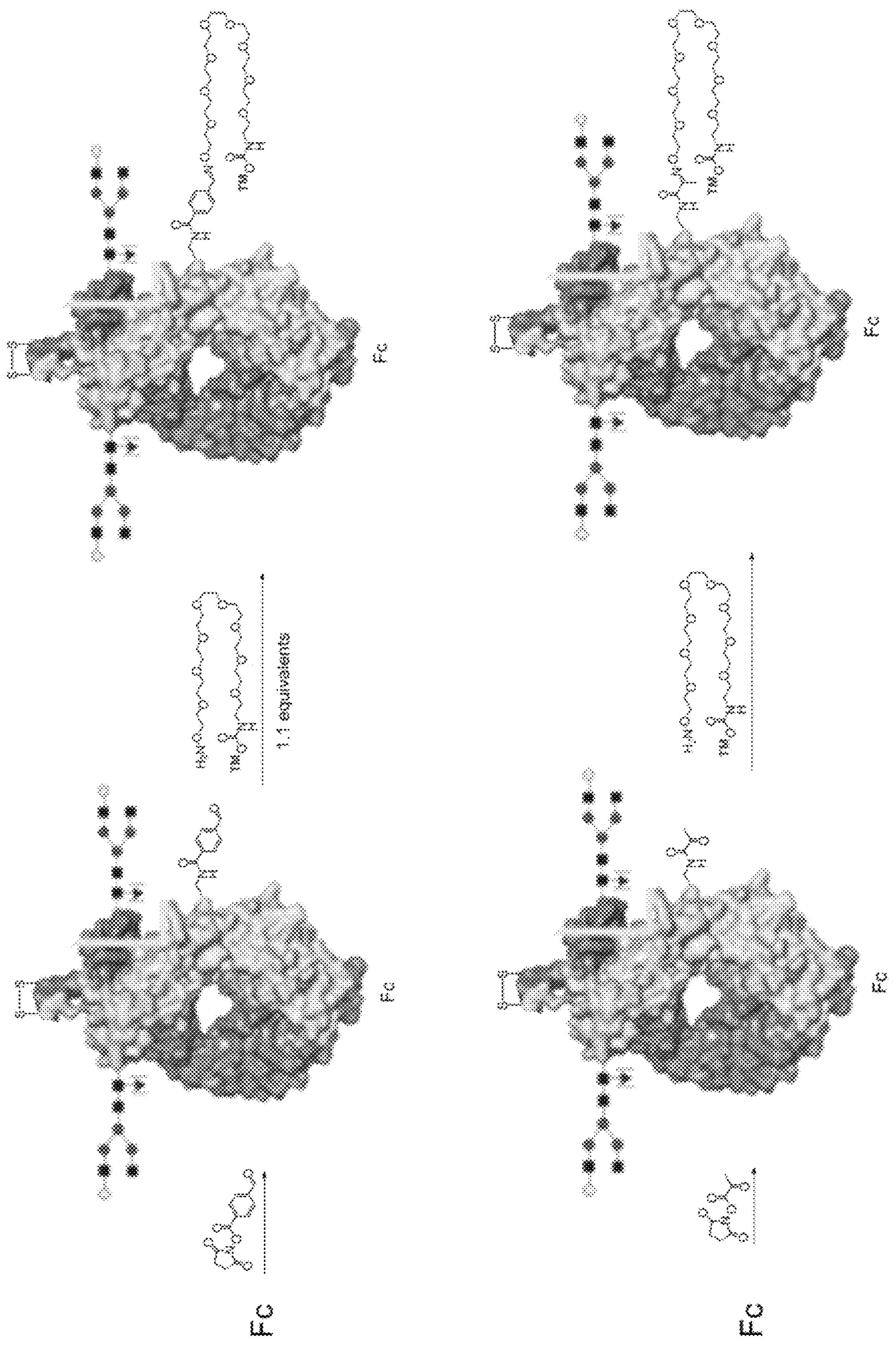
FIG. 28 is an image depicting a method of conjugating a neuraminidase inhibitor monomer or dimer, e.g., by way of a linker, to an Fc domain monomer, an Fc domain, an Fc-binding peptide, an albumin protein, or an albumin protein-binding peptide by oxime conjugation to an amino acid residue, e.g., a nitrogen atom of a surface exposed lysine.
Figure 29:
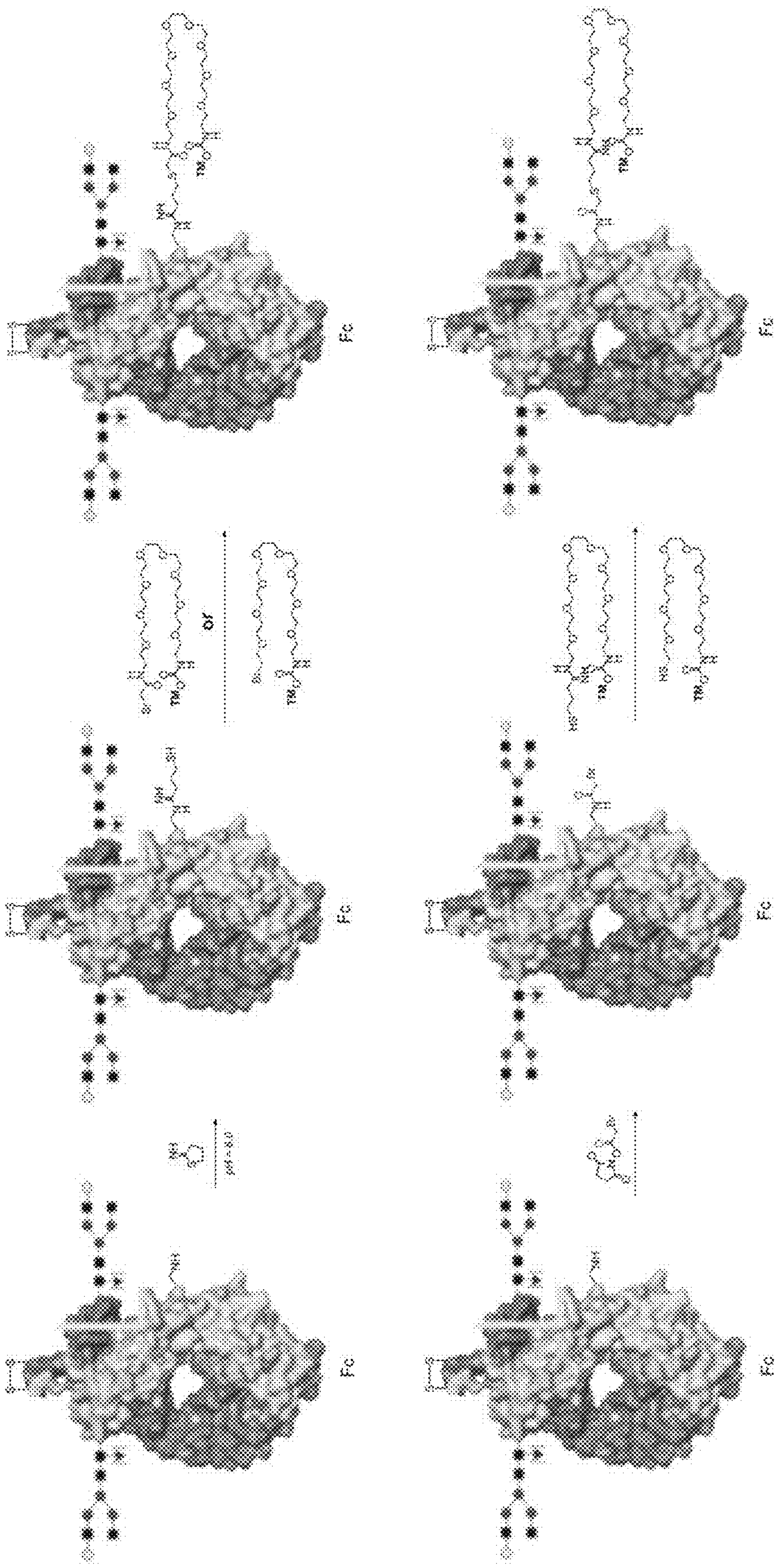
FIG. 29 is an image depicting a method of conjugating a neuraminidase inhibitor monomer or dimer, e.g., by way of a linker, to an Fc domain monomer, an Fc domain, an Fc-binding peptide, an albumin protein, or an albumin protein-binding peptide by thioether conjugation to an amino acid residue, e.g., a nitrogen atom of a surface exposed lysine.
Figure 30:
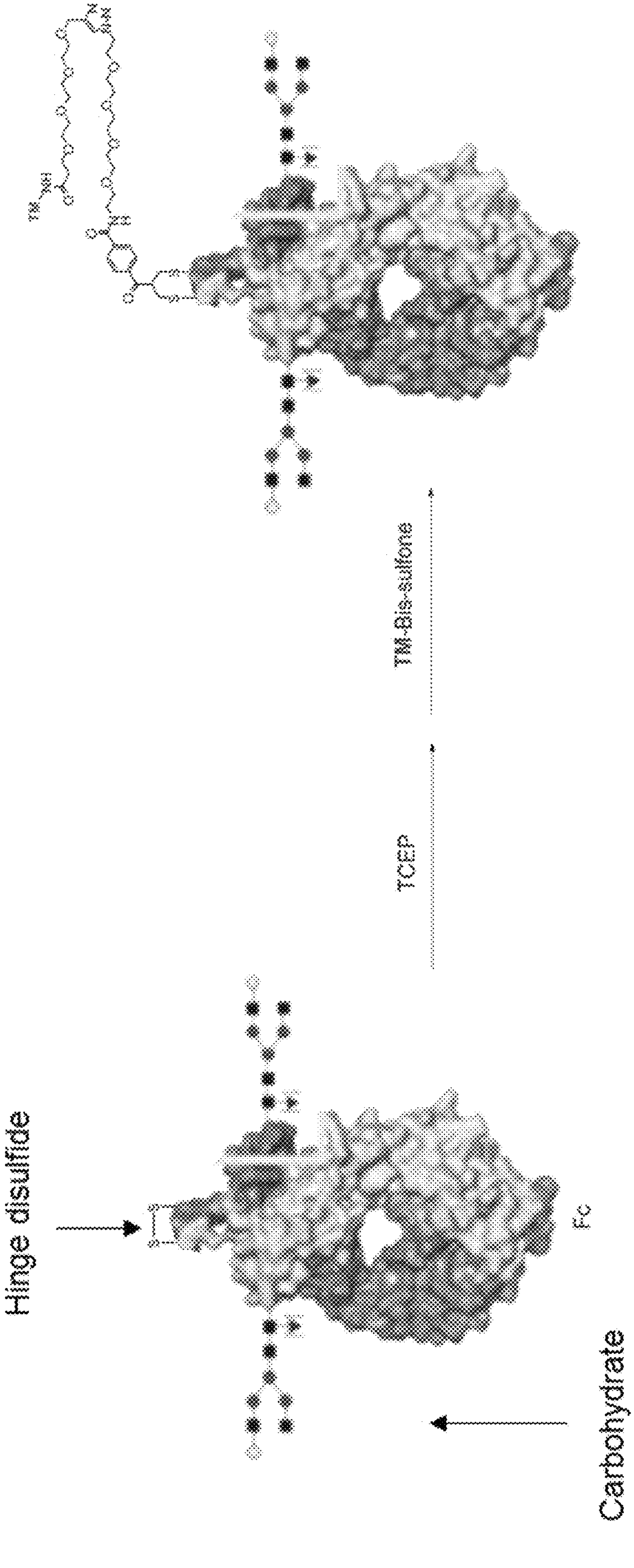
FIG. 30 is an image depicting a method of conjugating a neuraminidase inhibitor monomer or dimer, e.g., by way of a linker, to an Fc domain monomer, an Fc domain, an Fc-binding peptide, an albumin protein, or an albumin protein-binding peptide by rebridged cysteine conjugation, e.g., rebridged cysteine conjugation to a pair of sulfur atoms of two hinge cysteines in an Fc domain monomer or Fc domain.
Figure 31A:
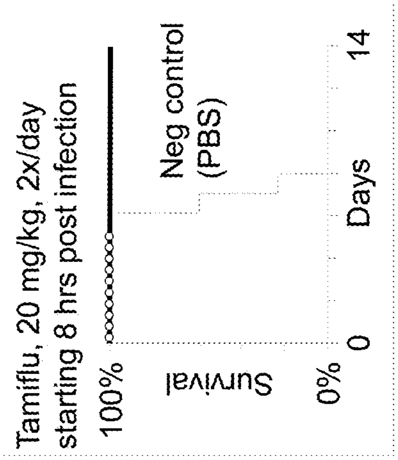
FIGS. 31A-31F are a series of graphs showing the survival of mice treated with Conjugate 6 in a lethal mouse influenza model. Mice were treated with either Oseltamivir (Tamiflu™) control, 20 mg/kg, 2× daily, starting 8 hours post-infection (FIG. 31A); Conjugate 6, 50 mg/kg, 1 dose 28 days prior to infection (FIG. 31B); Conjugate 6, 10 mg/kg, 1 dose 28 days prior to infection (FIG. 31C); Conjugate 6, 5 mg/kg, 1 dose 28 days prior to infection (FIG. 31D); Conjugate 6, 2.5 mg/kg, 1 dose 28 days prior to infection (FIG. 31E); or Conjugate 6, 1.25 mg/kg, 1 dose 28 days prior to infection (FIG. 31F). This study was performed as described in Example 33.
Figure 31B:
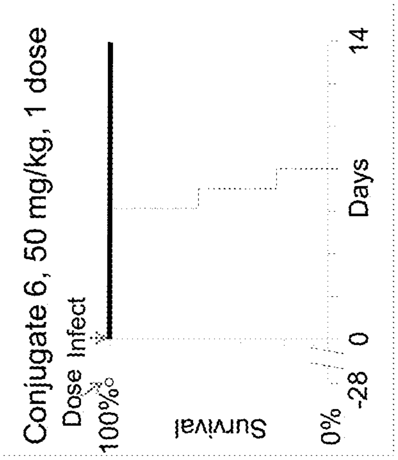
Figure 31C:
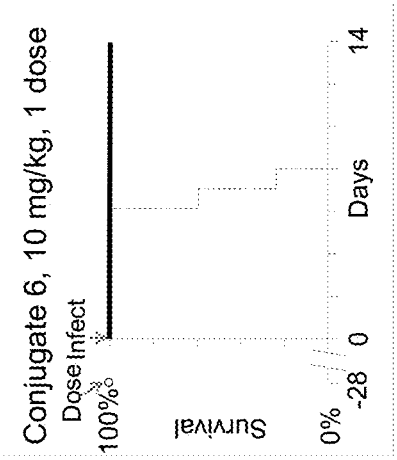
Figure 31D:
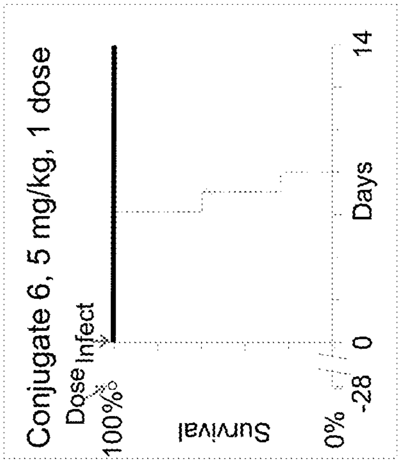
Figure 31E:
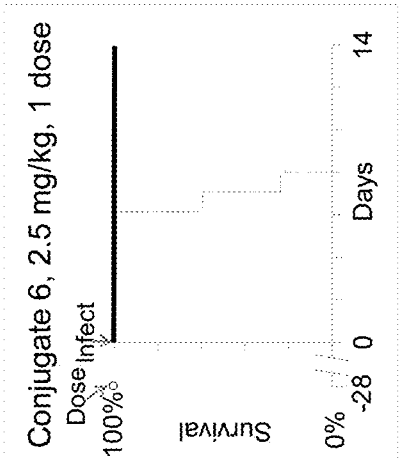
Figure 31F:
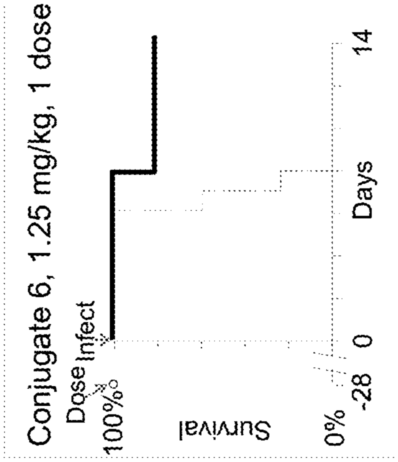

Conjugate 6 was evaluated against a lethal INFV A H3N2 influenza infection in female BALB/c mice. The experiment comprised 11 groups of 5 mice. At day 0, all mice were challenged with 1×LD90 H3N2 A/Hong Kong/1/68. Groups 1-10 received treatment IV, 4 hours before challenge (Table 10). Human IgG1 (Fc alone) was included as an additional negative control. Group 11 received Oseltamivir phosphate by way of oral delivery, starting 8 hours post infection twice daily for 5 days. All mice were monitored for weight loss (FIG. 26) and survival (FIG. 27, Table 11) for 15 days after challenge.

Mice treated with Conjugate 6 showed 100% survival with single doses in down to 0.4 mg/kg, and 80% survival with a single dose of 0.2 mg/kg compared with 0% survival in the vehicle control and hIgG1 control groups, respectively. 80% of the mice survived in the oseltamivir control group. The results were statistically significant when compared to the vehicle group (p=0.0128) despite the small group size (n=5). When compared to the Oseltamivir phosphate group, Conjugate 6 demonstrated similar efficacy at a 1000× lower cumulative dose (in mg/kg). Mice at all Conjugate 6 doses maintained down to 0.4 mg/kg their weight within 5%, superior to the Oseltamivir control group.

TABLE 10

Study design

| Group n = 5 | Challenge Day 0 | Test Article | Dose (mg/kg) | Treatment Route/Schedule | Readout/Endpoint |
|---|---|---|---|---|---|
| 1 | H3N2 A/HongKong/ | Vehicle (PBS) | N/A | IV, q.d. 4 hours pre-challenge | Daily weight and health score monitoring for 15 |
| 2 | 1/68 | Fc alone | 50 | | days after challenge |
| 3 | by way of | Conjugate 6 | 50 | | % Survival |
| 4 | IN route | | 2 | | |
| 5 | | | 0.4 | | |
| 6 | | | 0.2 | | |
| 7 | | | 0.1 | | |
| 8 | | | 0.05 | | |
| 9 | | | 0.025 | | |
| 10 | | | 0.0125 | | |
| 11 | | Oseltamivir (Tamiflu ™) | 20 | PO, b.i.d. 8 hours after challenge for 5 days | |

TABLE 11

Mouse survival

| Compound | Dosage | Mean Survival (days) | % Survival | Significance to vehicle (p-value) |
|---|---|---|---|---|
| Vehicle (PBS) | N/A | 9 | 0 | N/A |
| Fc control | 50 mg/kg | 8 | 0 | 0.2498 |
| Conjugate 6 | 50 mg/kg | 15 | 100 | 0.002 |
| | 2 mg/kg | 15 | 100 | 0.002 |
| | 0.4 mg/kg | 15 | 100 | 0.002 |
| | 0.2 mg/kg | 15 | 80 | 0.0128 |
| | 0.1 mg/kg | 9 | 20 | 0.8264 |
| | 0.05 mg/kg | 9 | 20 | 0.5769 |
| | 0.025 mg/kg | 8 | 20 | >0.9999 |
| | 0.0125 mg/kg | 11 | 0 | 0.4703 |
| Oseltamivir phosphate | 20 mg/kg | 15 | 80 | 0.0052 |

TABLE 11-continued

Mouse survival

| Compound | Dosage | Mean Survival (days) | % Survival | Significance to vehicle (p-value) |
|---|---|---|---|---|
| (B.I.D for 5 days) | | | | |

Example 31. Synthesis of Int-10

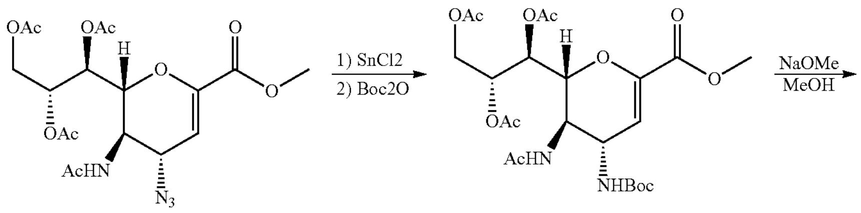

-continued
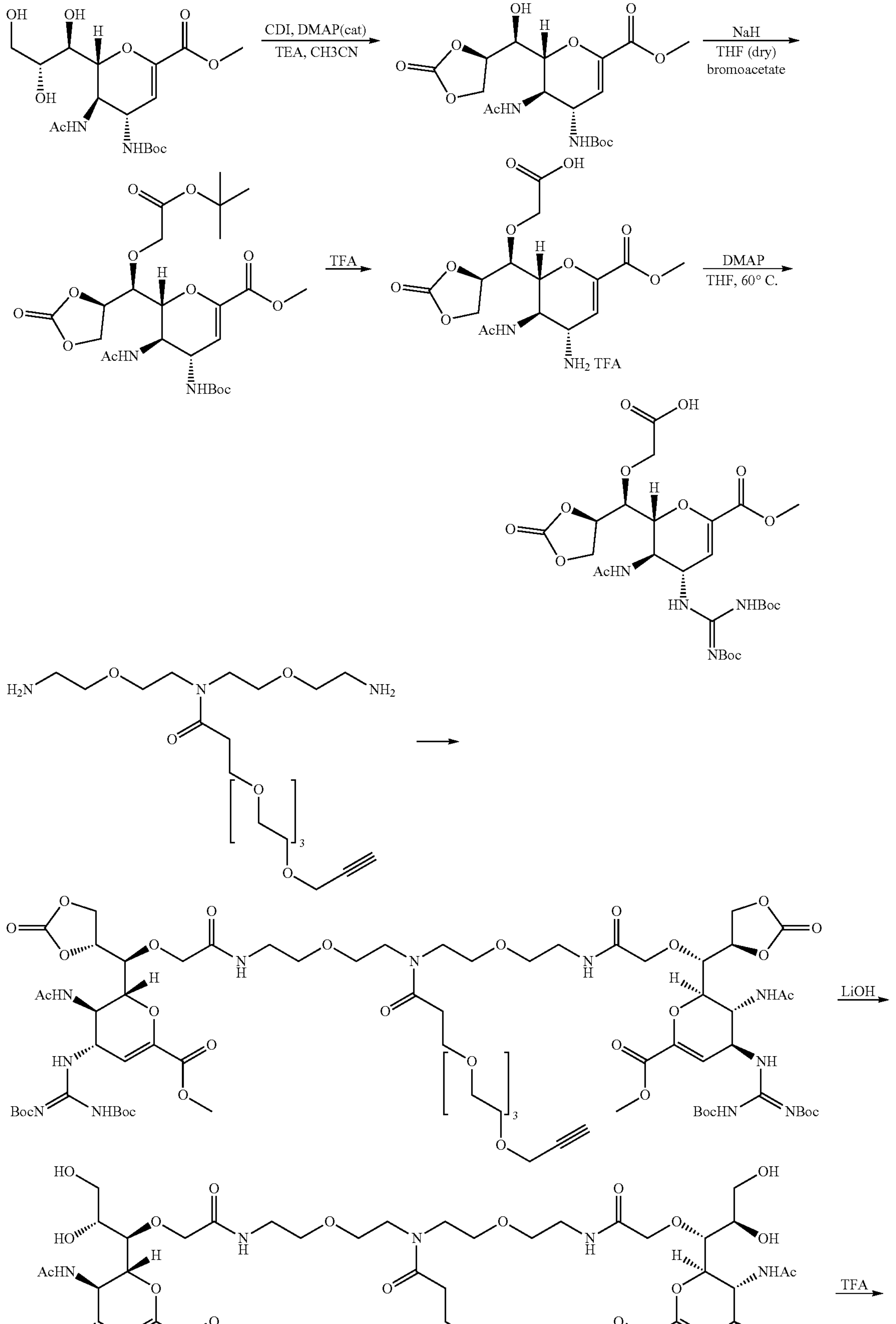

Step a.

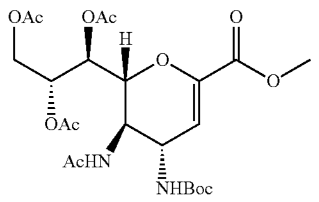 [SMILES: COC(=O)C1=C[C@H](NC(=O)OC(C)(C)C)[C@@H](NC(C)=O)[C@H]([C@H](OC(C)=O)[C@@H](COC(C)=O)OC(C)=O)O1]

Methy I 5-acetamido-7,8,9-O-triacetyl-2,6-anhydro-4-azido-3,4,5-trideoxy-D-glycero-D-galacto-non-2-enonate (SM-1, 10 g, 22 mmol) was dissolved into 100 ml methanol and then heated to 60° C. with an oil bath, the $SnCl_2$ (5.7 g, 20 mmol) was added to the solution in 3 portions (caution, gas evolves). The reaction mixture was stirred for 10 min, at which time the reaction was complete by HPLC. The reaction solution was slowly added to a solution of 50 ml Sat $NaHCO_3$ and 50 g celite with vigorous stirring. The resulting slurry was filtered. The filtrate was treated with $Boc_2O$ (6.6 g, 30 mmol, 1.5 equiv). After 2 hour at room temperature, the solution was concentrated to remove most of the methanol, dissolved in 200 ml DCM, and extracted twice with 100 ml DCM. The combined extracts were dried with sodium sulfate, filtered and used for next step without further purification. Crude yield 12 g, 100%. Ion(s) found by LCMS: M+H=531.

Step b.

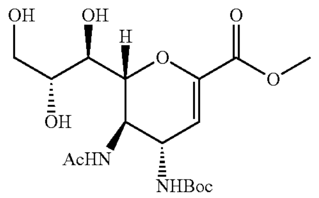 [SMILES: COC(=O)C1=C[C@H](NC(=O)OC(C)(C)C)[C@@H](NC(C)=O)[C@H]([C@H](O)[C@H](O)CO)O1]

The material from the previous step was dissolved into 60 ml dry methanol, then treated with 10 ml sodium methoxide in methanol (0.5M) while cooling with an ice-water bath. Progress of reaction was monitored by LCMS which was complete after 2h. The reaction was quenched with 1 N HCl to a pH of 5-6. The resulting solution was concentrated and purified by reverse phase liquid chromatography (RPLC) using an Isco COMBIFLASH® liquid chromatograph eluted with 0% to 30% acetonitrile and water, using 0.1% TFA as the modifier. Yield of the products 7.2 g, 80%. Ion(s) found by LCMS: M+H=405.

Step c.

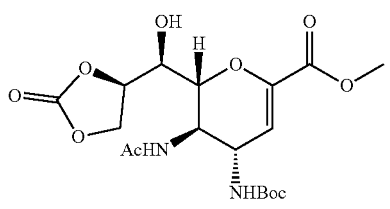 [SMILES: COC(=O)C1=C[C@H](NC(=O)OC(C)(C)C)[C@@H](NC(C)=O)[C@H]([C@H](O)[C@H]2COC(=O)O2)O1]

A solution of intermediate from the previous step (3.5 g, 8.5 mmol), CDI (2.8 g, 2 equiv), trimethylamine (4.2 ml, 30 mmol) and DMAP (240 mg, 2 mmol) were heated at 60° C. in DMF (50 ml) overnight, then concentrated and purified by reverse phase liquid chromatography (RPLC) using an Isco COMBIFLASH® liquid chromatograph eluted with 0% to 30% acetonitrile and resulting without modifier. Yield of desired product 2.3 g, 60%. Ion(s) found by LCMS: M+H=431.

Step d.

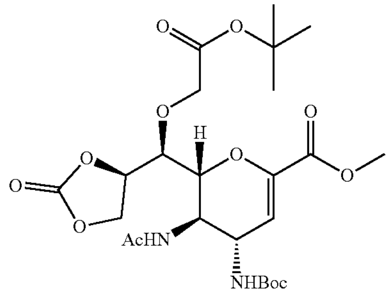 [SMILES: COC(=O)C1=C[C@H](NC(=O)OC(C)(C)C)[C@@H](NC(C)=O)[C@H]([C@H](OCC(=O)OC(C)(C)C)[C@H]2COC(=O)O2)O1]

Sodium hydride (400 mg, 60% in oil, 10 mmol) was added to Int-4 (1.45 g, 3.3 mmol) in 50 ml dry THE (moisture-sensitive reaction) under the ice-water bath. The resulting solution was stirred for 0.5 hour, then tert-butyl bromo acetate (2 g, 10 mmol) was added to the above solution. The resulting solution was heated to 60° C. overnight and quenched with acetic acid, concentrated and purified by reverse phase liquid chromatography (RPLC) using an Isco COMBIFLASH® liquid chromatograph eluted with 0% to 50% acetonitrile and water with TFA as modifier. Yield of 1 g, 57%. Ion(s) found by LCMS: M+H=593. (The reaction is pretty clean by HPLC, but low isolated yield)

Step f.

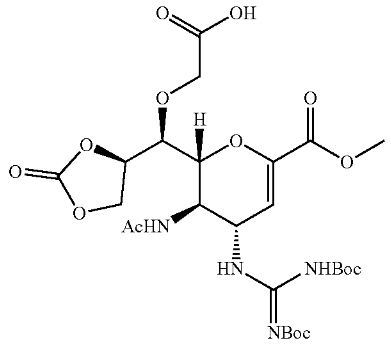

Intermediate from the previous step (1.2 g, 2.2 mmol) was stirred with 10 ml TFA at room temperature overnight. The progress of deprotection was monitored by LCMS. The resulting solution was concentrated and used in the next step without purification. The residue from the previous reaction was dissolved into 20 ml THF, then N,N'-bis-boc-1-guanylpyrazole (1 g, 3.3 mmol), 4-dimethylaminopyridine (120 mg, 1 mmol) and triethyl amine (0.7 ml, 5 mmol) were added to the solution, and the resulting solution was heated to 60° C. for 2 hours. The resulting solution was concentrated and purified by reverse phase liquid chromatography (RPLC) using an Isco COMBIFLASH® liquid chromatograph eluted with 0% to 50% acetonitrile and water with no modifier. Yield of 700 mg, 84%. Ion(s) found by LCMS: M+H=631.

Step g.

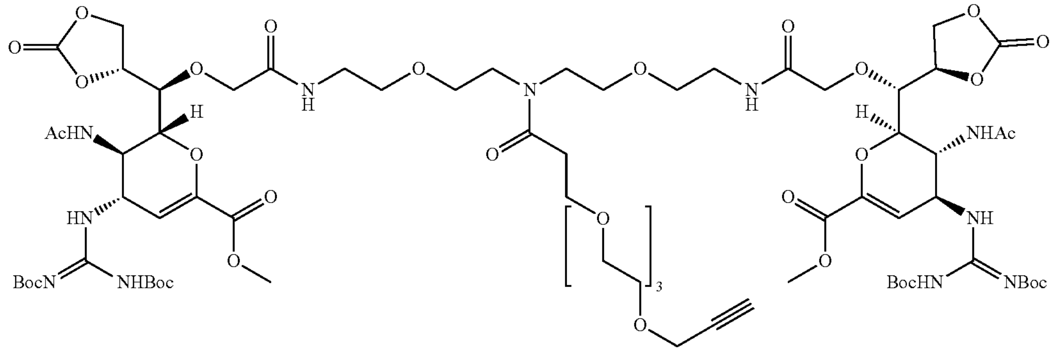

To a solution of linker-3 (prepared as described in Example 19) (73 mgg, 0.14 mmol) and intermediate from the previous step. (200 mg, 0.32 mmol, 2.2 equi) in DMF (30 ml) was added EDC (100 mg, 0.5 mmol), HOAt (65 mg, 3 mmol), and DIEA (0.14 ml, 1 mmol) at room temperature. The solution was stirred overnight. The resulting solution was concentrated and purified by and purified by reverse phase liquid chromatography (RPLC) using an Isco COMBIFLASH® liquid chromatograph eluted with 0% to 50% acetonitrile and water with no modifier. Yield of 120 mg, 52%. Ion(s) found by LCMS: M/2+H=830.

Step h.

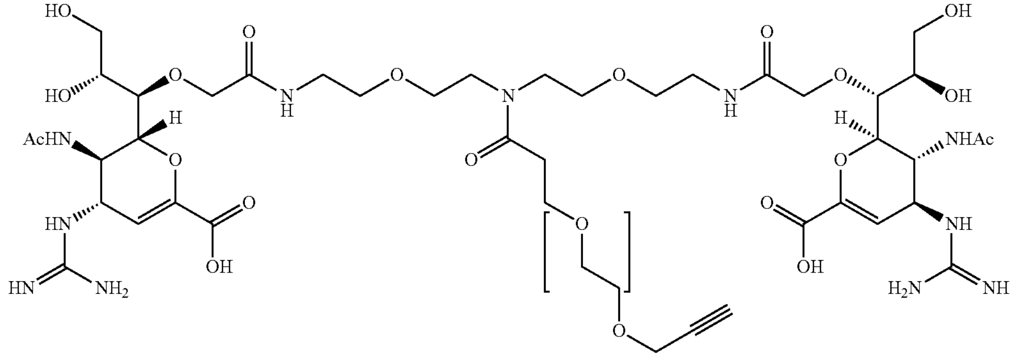

Lithium hydroxide (24 mg, 1 mmol) in 2 ml water was added to a solution of intermediate from the previous step (120 mg, 0.07 mmol) in 2 ml THE and 1 ml MeOH. After the reaction is complete by LCMS, the solution was quenched with AMBERLITE® IRN-77, ion exchange resin to adjust to pH=1, then the solution was filtered and the filtrate was concentrated and in the next step without further purification. Intermediate from the previous step was treated in 2 ml TFA at room temperature overnight at 40° C. The crude reaction was concentrated and purified by HPLC with 0% to 20% acetonitrile and water, using TFA as the modifier. Yield 60 mg, 74% yield. Ion(s) found by LCMS: [M/2]+1=589.8.

Example 32. Synthesis of Conjugate 7

A solution of Fc-PEG4-azide (each Fc domain monomer having the sequence of SEQ ID NO: 38) in PBS×1 buffer solution (100 mg, 1.28 μmol, 6.1 mL, MW=57260 Da, DAR=3.6) were added to Int-10 (prepared as described in Example 31) (TFA salt, 44 mg, 0.031 mmol) and freshly prepared pH 7.4 PBS solutions of $CuSO_4$ (0.7 mL of 50.0 mM, 20 eq), tris(3-hydroxypropyltriazolylmethyl)-amine (THPTA, 0.7 mL of 50.0 mM, 20 eq), and sodium ascorbate (1.05 mL of 50.0 mM, 30 eq). The resulting homogeneous solution was agitated by rocker table for 12h. The crude solutions were diluted with pH 7.4 PBS to a final concentration of 1 mg/mL, and ultrafiltered (10,000 MWCO) to a volume of 1 mL, two times. The crude mixtures were then diluted 1:10 in PBS pH 7.4, and purified using MabSelect Sure Resin (GE Healthcare, Chicago, IL, USA), followed by size exclusion chromatography. Purified material was quantified using a Nanodrop™ UV visible spectrophotomer (using a calculated extinction coefficient based on the amino acid sequence of the Fc used in the conjugation, and concentrated to approximately 10 mg/mL using a centrifugal concentrator (10,000 MWCO). Purified molecules were analyzed using 4-12% Bis Tris SDS PAGE gels by loading 1-2 μg of each molecule into the gel, and staining using instant Blue staining. Each gel included a molecular weight ladder with the indicated molecular weight standards. Yields are typically 40-60%. MALDI MS analysis showed a range of masses (60000-90000) with an average of mass of 63633. Average DAR=4.5.

Example 33. Efficacy of Conjugate 6 in a Lethal Mouse Influenza Model: Study #3

Conjugate 6 was evaluated against a lethal INFV A H1N1 influenza infection in female BALB/c mice. The experiment comprised 7 groups of 5 mice. At day 0, all mice were challenged with 1×LD90 H1N1 A/Texas/36/91. Groups 1-6 received treatment IV, 28 days before challenge (Table 12). Vehicle (PBS) was included as an additional negative control. Group 7 received Oseltamivir phosphate by way of oral delivery, starting 8 hours post infection twice daily for 5 days. All mice were monitored for survival (FIGS. 31A-31F) for 15 days after challenge.

Mice treated with Conjugate 6 showed 100% survival with single doses in all the concentrations down to 2.5 mg/kg, and 80% survival at 1.25 mg/kg, compared with 0% survival in the vehicle control group. All mice in the Oseltamivir phosphate control group survived. When compared to the Oseltamivir phosphate group, Conjugate 6 demonstrated similar efficacy to Oseltamivir at a 20× lower cumulative dose (in mg/kg), despite the fact that all Conjugate 6 groups were dosed once, 28 days prior to infection.

TABLE 12

| Study design | | | | |
|---|---|---|---|---|
| Group n = 5 | Challenge Day 0 | Compound | Dose (mg/kg) | Treatment Route/Schedule |
| 1 | Influenza A | Vehicle (PBS) | N/A | IV, q.d. 28 days |
| 2 | virus, | Conjugate 6 | 50 | pre-challenge |
| 3 | H1N1 strain | Conjugate 6 | 10 | |
| 4 | A/Texas/36/91 | Conjugate 6 | 5 | |
| 5 | by way | Conjugate 6 | 2.5 | |
| 6 | of IN route. | Conjugate 6 | 1.25 | |
| 7 | | Oseltamivir (Tamiflu ™) | 20 | PO, b.i.d. 8 hours after challenge for 5 days |

Example 34. Efficacy of Conjugate 6 in a Lethal Mouse Influenza Model: Study #4

Conjugate 6 was evaluated against a lethal INFV A H1N1 influenza infection in female BALB/c mice. The experiment comprised 13 groups of 5 mice. At day 0, all mice were challenged with 1xLD90 H1N1 A/Texas/36/91. All Conjugate 6 groups (8-13) received single 10 mg/kg IV doses at different times, pre- and post-infection, as outlined in Table 13. Vehicle (PBS) and Fc only were included as negative controls. Groups 3-7 received Oseltamivir phosphate (20 mg/kg) by way of oral delivery, starting at different time points post-infection twice daily for 5 days, as outlined in Table 13. All mice were monitored for survival (FIGS. 32A-32F) for 15 days after challenge.

Mice treated with Conjugate 6 showed 100% survival with single 10 mg/kg doses when treated out to 24 hrs post-infection, and 60 and 80% survival at 48 and 72 hrs post-infection, respectively. In the Oseltamivir phosphate group, survival dropped sharply to 0% and 20%, respectively, in the groups where treatment was initiated at 48 and 72 hrs post-infection. These results suggest that Conjugate 6 potentially possesses a superior treatment window versus Oseltamivir for treating influenza A infections.

TABLE 13

| Study design | | | | | |
|---|---|---|---|---|---|
| Group (N = 5) | Influenza A strain | Test Article | Route, Schedule | Dose (mg/kg) | Dose timing (hours) |
| 1 | A/Texas/36/91 | Vehicle (PBS) | IV, single | — | T − 4 |
| 2 | (H1N1) by | Fc only | IV, single | 10 | T − 4 |
| 3 | way of IN | Oseltamivir | PO, bid × 5 days | 20 | T + 8 |
| 4 | | Oseltamivir | PO, bid × 5 days | 20 | T + 24 |
| 5 | | Oseltamivir | PO, bid × 5 days | 20 | T + 48 |
| 6 | | Oseltamivir | PO, bid × 5 days | 20 | T + 72 |
| 7 | | Oseltamivir | PO, bid × 5 days | 20 | T + 96 |
| 8 | | Conjugate 6 | IV, single | 10 | T − 4 |
| 9 | | Conjugate 6 | IV, single | 10 | T + 8 |
| 10 | | Conjugate 6 | IV, single | 10 | T + 24 |
| 11 | | Conjugate 6 | IV, single | 10 | T + 48 |
| 12 | | Conjugate 6 | IV, single | 10 | T + 72 |
| 13 | | Conjugate 6 | IV, single | 10 | T + 96 |

Example 35. Conjugate 6 Toxicity Study

Figure 33:
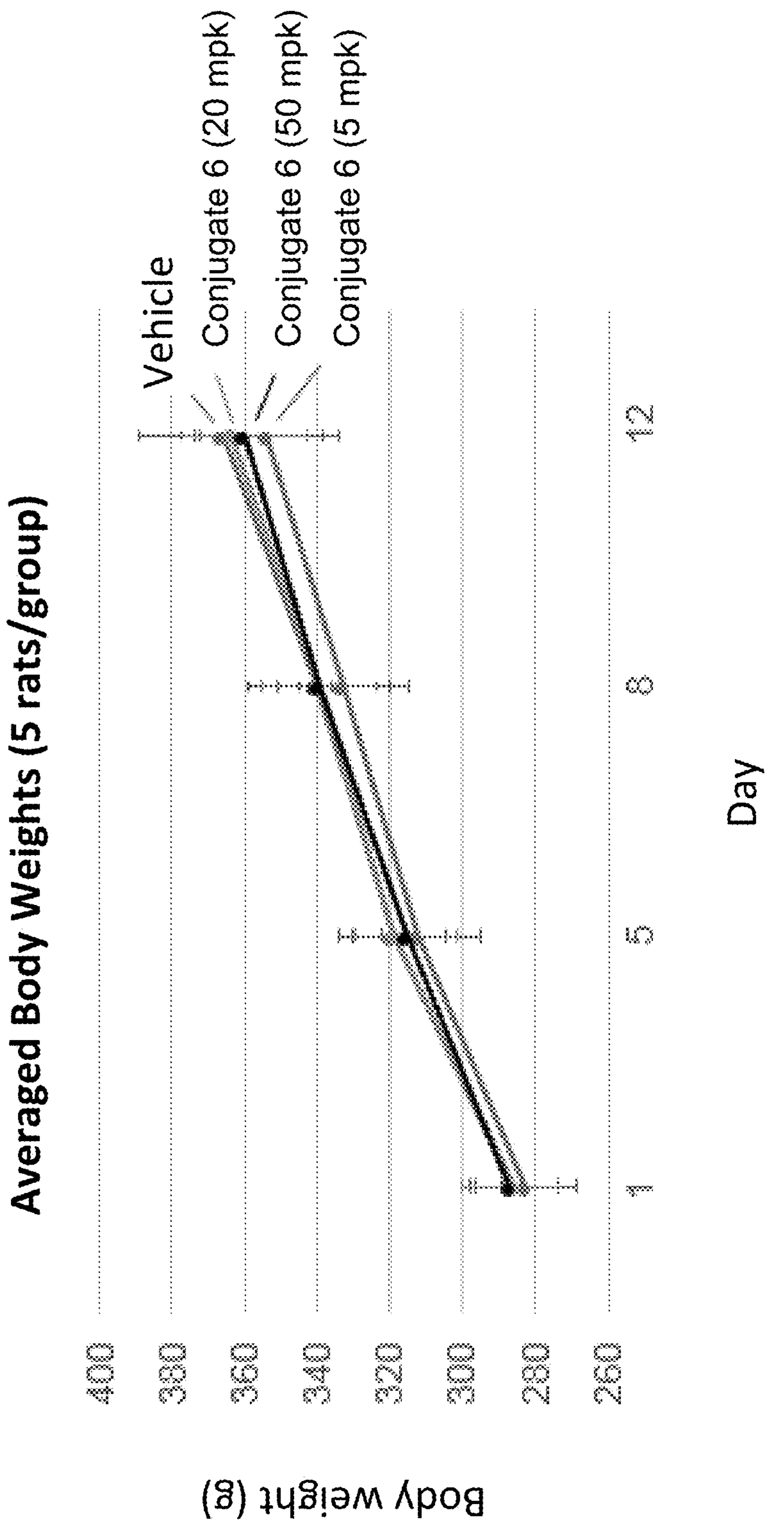
FIG. 33 is a graph showing no significant effect of body weight gain were observed following administration of Conjugate 6 in a 14 day rat dose-range finder toxicity study. The study was performed as described in Example 35.
Figure 34A:
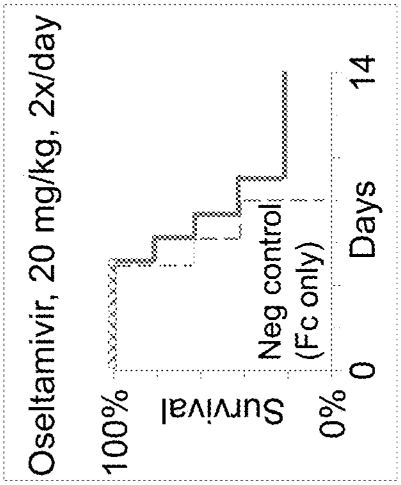
FIGS. 34A-34D is a series of graphs showing that Conjugate 6 extends treatment window as compared to Oseltamivir (Tamiflu™) as determined by survival in a lethal mouse influenza model. Mice were treated with either Oseltamivir (Tamiflu™) control, 20 mg/kg, 2× daily, starting 8 hours post-infection (FIG. 34A); Conjugate 6, 10 mg/kg, 1 dose 4 hours prior to infection (FIG. 34B); Conjugate 6, 2 mg/kg, 1 dose 4 hours prior to infection (FIG. 34C); or Conjugate 6, 0.4 mg/kg, 1 dose 4 days prior to infection (FIG. 34D). The study was performed as described in Example 37.
Figure 34B:
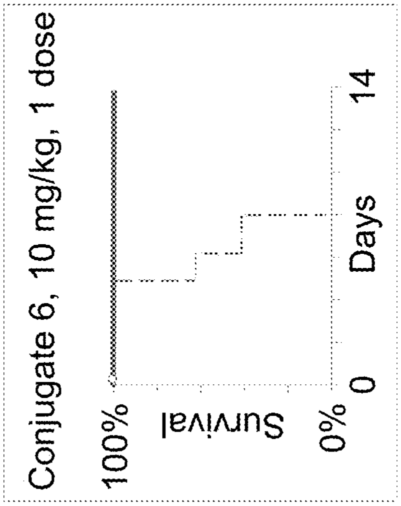
Figure 34C:
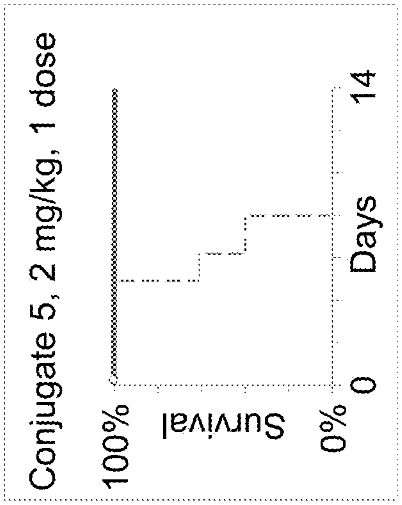
Figure 34D:
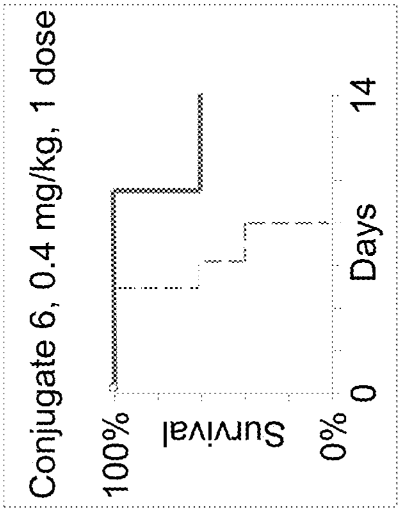

The safety of Conjugate 6 was evaluated in a 14 day rat dose-range finder toxicity study. Rats were administered either 5 mpk, 20 mpk, or 50 mpk of Conjugate 6 by intravenous administration on days 0 and 7 of the study. Compared with vehicle controls, no significant effects on body weight gain (FIG. 33), organ weights, food consumption were observed at any dose tested. Plasma exposures (measured by AUC) increased proportionally with dose. These preclinical safety results are consistent with a high therapeutic index. A summary of observations is provided in Table 14.

TABLE 14

| Summary of 14 day rat dose-range finder toxicity study | |
|---|---|
| Parameter | Findings at highest dose (50 mpk), compared to vehicle |
| Clinical observations | No findings |
| Hematology | No change from vehicle |
| Clinical Chemistry | No change from vehicle |
| Coagulation | No change from vehicle |
| Urinalysis | No change from vehicle |
| Histopathology | No observations |

Example 36. Efficacy of Conjugate 6 Against in a Lethal Mouse Influenza Model Dose by Three Different Routes: Study #5

Conjugate 6 was evaluated against a lethal IAV H1N1 influenza infection in female BALB/c mice (Charles River Laboratories, 6-8 weeks). The challenge virus (A/Texas/36/91) is a mouse-adapted isolate capable of causing lethal infections in mice. The experiment comprised 15 groups of 5 mice. At day 0, all mice were challenged with virus at 1× the LD90 by intranasal inoculation in a volume of 50 μl, after being lightly anesthetized with isoflurane. Groups 1-14 received a single treatment, 4 hours before challenge (Table 15). In order to determine the potency of Conjugate 6 by different dose routes matching concentrations of Conjugate (10, 2, 0.4, and 0.1 mg/kg) were dosed either IV, IM, or SC. In addition to the vehicle (PBS) only group, Human IgG1 (Fc alone) was included as an additional negative control (group 2). Group 15 received Oseltamivir phosphate by way of oral delivery, starting 8 hours post infection twice daily for 5 days. All mice were monitored for survival (Table 15) for 14 days.

Mice treated with Conjugate 6 showed 100% survival at day 14 against challenge by influenza (H1N1) with single doses of 10, 2, or 0.4 mg/kg, regardless of dose route. Only at the lowest test article concentration were single mouse differences seen between IV, IM, and SC dosing (Table 16; 60, 80, and 100% survival, respectively). These results strongly suggest that protective lung concentrations of Conjugate 6 is achievable by multiple dose routes.

TABLE 15

Study design

| Group n = 5 | Challenge Day 0 | Compound | Dose (mg/kg) | Dose route | Treatment Route/Schedule |
|---|---|---|---|---|---|
| 1 | Influenza A | Vehicle (PBS) | N/A | | Single dose, |
| 2 | virus (H1N1) | Fc alone | 50 | IV | 4 hours |
| 3 | A/Texas/36/91 | Conjugate 6 | 10 | IV | before viral |
| 4 | by way of IN | Conjugate 6 | 2 | | challenge |
| 5 | | Conjugate 6 | 0.4 | | |
| 6 | | Conjugate 6 | 0.1 | | |
| 7 | | Conjugate 6 | 10 | IM | |
| 8 | | Conjugate 6 | 2 | | |
| 9 | | Conjugate 6 | 0.4 | | |
| 10 | | Conjugate 6 | 0.1 | | |
| 11 | | Conjugate 6 | 10 | SC | |
| 12 | | Conjugate 6 | 2 | | |
| 13 | | Conjugate 6 | 0.4 | | |
| 14 | | Conjugate 6 | 0.1 | | |
| 15 | | Oseltamivir (Tamiflu ™) | 20 | PO | b.i.d. 8 hours after challenge for 5 days |

TABLE 16

Mouse survival

| Test article | mg/kg | Dose route | % Survival (Day 14) |
|---|---|---|---|
| Vehicle (PBS) | na | IV | 0 |
| hIgG1 (Fc only) | 10 | IV | 0 |
| Conjugate 6 | 10 | IV | 100 |
| | 2 | | 100 |
| | 0.4 | | 100 |
| | 0.1 | | 60 |
| Conjugate 6 | 10 | | 100 |
| | 2 | | 100 |
| | 0.4 | | 100 |
| | 0.1 | | 80 |
| Conjugate 6 | 10 | SC | 100 |
| | 2 | | 100 |
| | 0.4 | | 100 |
| | 0.1 | | 100 |
| oseltamivir | 20 | PO | 100 |

Example 37. Efficacy of Conjugate 6 Against an Oseltamivir-Resistant Isolate in a Lethal Mouse Influenza Model: Study #6

Conjugate 6 was evaluated against a lethal IAV H1N1 influenza infection in female BALB/c mice (Charles River Laboratories, 6-8 weeks). The challenge virus (A/Perth/261/2009) is a mouse-adapted isolate that carries the H275Y mutation resulting in resistance to the neuraminidase inhibitor oseltamivir. The experiment comprised 10 groups of 5 mice. At day 0, all mice were challenged with A/Perth/261/2009 (H1N1) at 1× the LD90 by intranasal inoculation in a volume of 50 μl, to mice lightly anesthetized with isoflurane. Groups 1-9 received a single treatment by IV, 4 hours before challenge (Table 17). In addition to the vehicle (PBS) only group, Human IgG1 (Fc alone) was included as an additional negative control. Group 10 received Oseltamivir phosphate by way of oral delivery, starting 8 hours post infection twice daily for 5 days. All mice were monitored for survival (FIGS. 34A-34D, Table 18) and weight loss (FIG. 35, Table 19) for 15 days after challenge.

Mice treated with Conjugate 6 showed 100% survival against challenge by influenza (A/Perth/261/2009) with single doses at 50, 10, and 2 mg/kg. Furthermore, despite the small group size (n=5) these results were statistically significant relative to the vehicle control (Table 18). At Conjugate 6 concentrations of 0.4, 0.2, or 0.1 mg/kg survival was 60%, while no mice survived to the end of the study if dosed with vehicle (PBS) or hIgG1 (Fc only) only. The oseltamivir group only had a single animal surviving (20% efficacy) despite treatment with a dose shown to be protective against oseltamivir sensitive isolates previously (20 mg/kg, bid×5 days). These results confirm that the challenge virus is resistant to oseltamivir, and sensitive to Conjugate 6.

Figure 35:
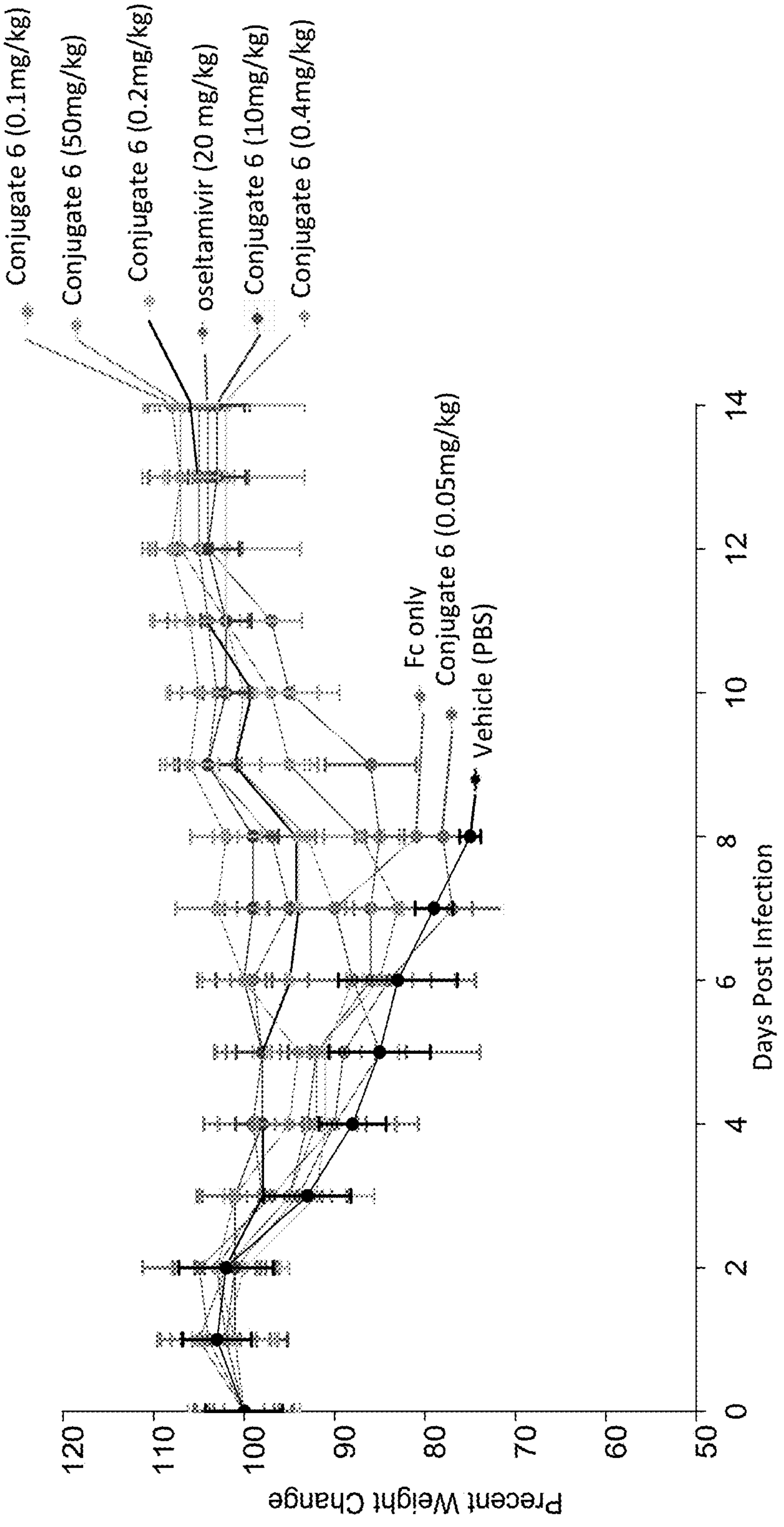
FIG. 35 is a graph showing the effect of Conjugate 6 on mouse weight in a lethal mouse influenza model. The study was performed as described in Example 37.

The potency of Conjugate 6 against mutants containing the H275Y mutation was further supported by body weight data (FIG. 35, Table 19). Groups receiving a single dose of Conjugate 6 at concentrations of 2 mg/kg or more demonstrated 5%, or less, transient weight loss.

TABLE 17

Study design

| Group n = 5 | Challenge Day 0 | Compound | Dose (mg/kg) | Treatment Route/Schedule |
|---|---|---|---|---|
| 1 | Influenza A virus | Vehicle (PBS) | N/A | IV, q.d. 4 hours |
| 2 | (H1N1) | Fc alone | 50 | pre-challenge |
| 3 | A/Perth/261/2009 | Conjugate 6 | 50 | |
| 4 | by way of IN | Conjugate 6 | 10 | |
| 5 | route. | Conjugate 6 | 2 | |
| 6 | | Conjugate 6 | 0.4 | |
| 7 | | Conjugate 6 | 0.2 | |
| 8 | | Conjugate 6 | 0.1 | |
| 9 | | Conjugate 6 | 0.05 | |
| 10 | | Oseltamivir (Tamiflu ™) | 20 | PO, b.i.d. 8 hours after challenge for 5 days |

TABLE 18

Mouse survival

| Compound | Dosage | Median Survival | % Survival | Significance to vehicle (p) |
|---|---|---|---|---|
| Vehicle (PBS) | N/A | 7 | 0 | N/A |
| Fc alone | 50 mg/kg | 6 | 0 | ns |
| Conjugate 6 | 50 mg/kg | Undef | 100 | 0.0027 |
| Conjugate 6 | 10 mg/kg | Undef | 100 | 0.0027 |
| Conjugate 6 | 2 mg/kg | Undef | 100 | 0.0027 |
| Conjugate 6 | 0.4 mg/kg | Undef | 60 | 0.1167 |
| Conjugate 6 | 0.2 mg/kg | Undef | 60 | 0.0185 |
| Conjugate 6 | 0.1 mg/kg | Undef | 60 | 0.1047 |
| Conjugate 6 | 0.05 mg/kg | 7 | 0 | 0.9241 |
| Oseltamivir phosphate | 20 mg/kg B.I.D | 7 | 20 | 0.3470 |

TABLE 19

| Daily Weight Average | | | | | | | | | | |
|---|---|---|---|---|---|---|---|---|---|---|
| | Daily average weight (# of mice shown in parenthesis if less than 5) | | | | | | | | | |
| Days post | Vehicle | Fc alone | Conjugate 6 | | | | | | | Oseltamivir phosphate |
| infection | (PBS) | 50 mg/kg | 50 mg/kg | 10 mg/kg | 2 mg/kg | 0.4 mg/kg | 0.2 mg/kg | 0.1 mg/kg | 0.05 mg/kg | 20 mg/kg |
| 0 | 100 (5) | 100 (5) | 100 | 100 | 100 | 100 | 100 | 100 | 100 | 100 |
| 1 | 103 (5) | 104 (5) | 101 | 101 | 102 | 102 | 103 | 105 | 102 | 105 |
| 2 | 102 (5) | 105 (5) | 103 | 101 | 103 | 100 | 102 | 102 | 101 | 102 |
| 3 | 93 (5) | 97 (5) | 101 | 101 | 98 | 92 | 98 | 95 | 94 | 95 |
| 4 | 88 (5) | 90 (5) | 95 | 98 | 99 | 91 | 98 | 92 | 90 | 93 |
| 5 | 85 (5) | 85 (5) | 94 | 98 | 98 | 91 | 98 | 92 | 89 | 92 |
| 6 | 83 (4) | 88 (3) | 100 | 100 | 99 | 88 | 95 | 85 | 84 (4) | 86 |
| 7 | 79 (3) | 90 (2) | 103 | 99 | 95 | 90 (3) | 94 | 83 (4) | 77 (1) | 86 (3) |
| 8 | 75 (2) | 81 (1) | 102 | 99 | 97 | 93 (3) | 94 (4) | 87 (3) | 78 (1) | 85 (2) |
| 9 | | | 106 | 104 | 104 | 101 (3) | 101 (4) | 95 (3) | | 86 (2) |
| 10 | | | 105 | 102 | 103 | 100 (3) | 99 (4) | 97 (3) | | 95 (1) |
| 11 | | | 106 | 102 | 104 | 102 (3) | 104 (4) | 102 (3) | | 97 (1) |
| 12 | | | 108 | 104 | 105 | 102 (3) | 105 (3) | 107 (3) | | 104 (1) |
| 13 | | | 107 | 103 | 105 | 102 (3) | 105 (3) | 107 (3) | | 104 (1) |
| 14 | | | 107 | 103 | 105 | 102 (3) | 106 (3) | 108 (3) | | 104 (1) |
| 15 | | | 100 | 100 | 100 | 100 (3) | 100 (3) | 100 (3) | | 100 (1) |

Example 38. 7-Day Rat PK Study Following IV Administration of Test Article

Rat pharmacokinetic (PK) studies were performed by Seventh Wave Laboratories (Maryland Heights, MO) using male Sprague Dawley Rats 46-49 days of age. Rats were injected IV by way of the tail vein with 75 mg/kg of test article (5 ml/kg dose volume). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations over time.

The plasma concentrations for Conjugate 6 or hIgG1 Fc at each time point were measured by sandwich ELISA as follows: Conjugate 6 molecules were captured either on neuraminidase coated plates or anti-hIgG1 antibody coated plates and then detected using an HRP-conjugated anti-human IgG-Fc antibody. hIgG1 was captured using anti-hIgG1 Fc antibody. Protein concentration was calculated in GraphPad Prism using 4PL non-linear regression of Conjugate 6 (or hIgG1 Fc) standard curves. A more detailed method description is provided below.

Nunc Maxisorp 96-well plates (Cat No. 12-565-136, ThermoFisher) were coated with either neuraminidase from A/California/04/2009 (H1N1) (11058-VNAHC, Sino Biological) or anti-IgG1 Fc antibody in 1×KPL coating buffer (5150-0041, SeraCare). In the cases where the anti-IgG1 Fc antibody was used to capture test article, capture and detection anti-IgG1 Fc antibodies were selected that bind different epitopes. Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve rat plasma final concentration of 1:900). Conjugate 6 or hIgG1 Fc standard curves ranging from 500-0.230 ng/mL, in duplicate were run on each plate.

Following the 2 hr incubation, plates were washed 5× in 300 uL PBS with 0.05% Tween 20. Conjugate 6 bound to neuraminidase on the plates (or anti-hIgG1 Fc antibody) was then probed with an HRP conjugated anti-human IgG Fc F(ab')2 (709-036-098, Jackson) diluted 1:1,000 in sample diluent for 1 hr at room temp. Plates were then washed 8× in 300 uL PBS with 0.05% Tween 20 and developed with TMB substrate for 7-8 minutes. The reaction was stopped with 1 N $H_2SO_4$. Absorbance was read at 450 nm. A similar protocol was used for hIgG1 Fc, where only anti-hIgG1 Fc antibody was used for capture. The quantities of Conjugate 6 measured at different time points using either neuraminidase or anti-hIgG1 Fc antibody capture were similar within experimental error, suggesting that the intact conjugate is stable in vivo.

Figure 36:
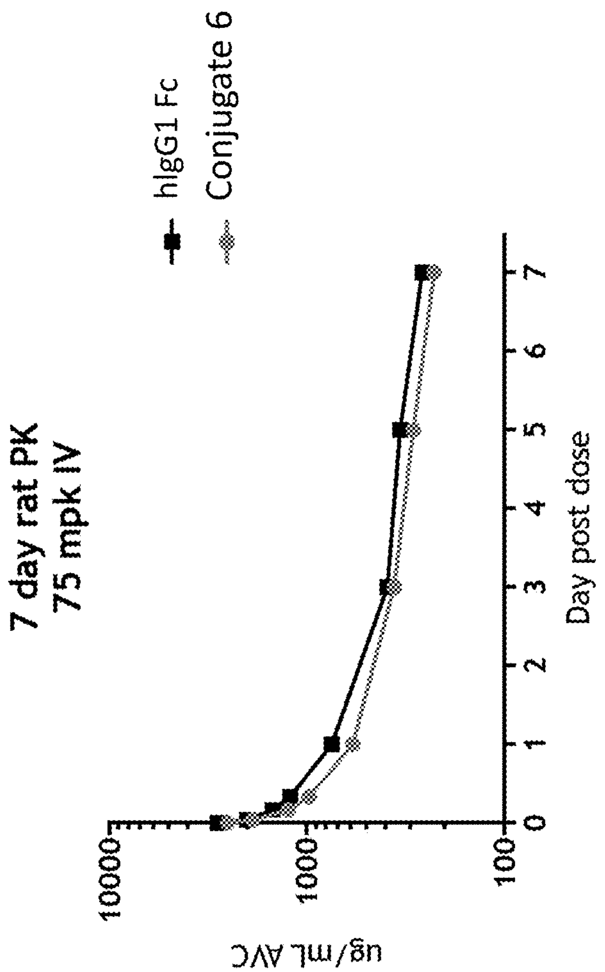
FIG. 36 is a graph showing a 7-day rat pharmacokinetic study following IV administration of Conjugate 6. The study was performed as described in Example 38.

Total Conjugate 6 (or hIgG1 Fc) in test samples was interpolated using in Graphpad Prism Version 6 following nonlinear regression analysis (Sigmoidal, 4PL analysis) of the Conjugate 6 (or hIgG1 Fc) standard curves. The curves comparing Conjugate 6 and hIgG1 Fc are shown in FIG. 36. The quantities of Conjugate 6 measured at different time points using either neuraminidase or anti-hIgG1 Fc antibody capture were similar within experimental error, suggesting that the intact conjugate is stable in vivo.

Example 39. 14-Day Rat PK Study Following IV Administration of Test Article

Rat PK studies were performed by Seventh Wave Laboratories (Maryland Heights, MO) using male Sprague Dawley Rats 46-49 days of age. Rats were injected IV by way of the tail vein with 5, 20, or 50 mg/kg of test article (5 ml/kg dose volume) at days 1 and 8. Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations over time.

The plasma concentrations for Conjugate 6 at each time point were measured by sandwich ELISA as follows: Conjugate 6 molecules were captured either on neuraminidase coated plates and then detected using an HRP-conjugated anti-human IgG-Fc antibody. hIgG1 was captured using anti-hIgG1 Fc antibody. Protein concentration was calculated in GraphPad Prism using 4PL non-linear regression of Conjugate 6 standard curves. A more detailed method description is provided below. Nunc Maxisorp 96-well plates (Cat No. 12-565-136, ThermoFisher) were coated with either neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve rat plasma final concentration of 1:900). Conjugate 6 standard curves ranging from 500-0.230 ng/mL, in duplicate were run on each plate.

Following the 2 hr incubation, plates were washed 5× in 300 uL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 uL PBS with 0.05% Tween 20 and developed with TMB substrate for 7-8 minutes. The reaction was stopped with 1 N $H_2SO_4$. Absorbance was read at 450 nm.

Figure 37:
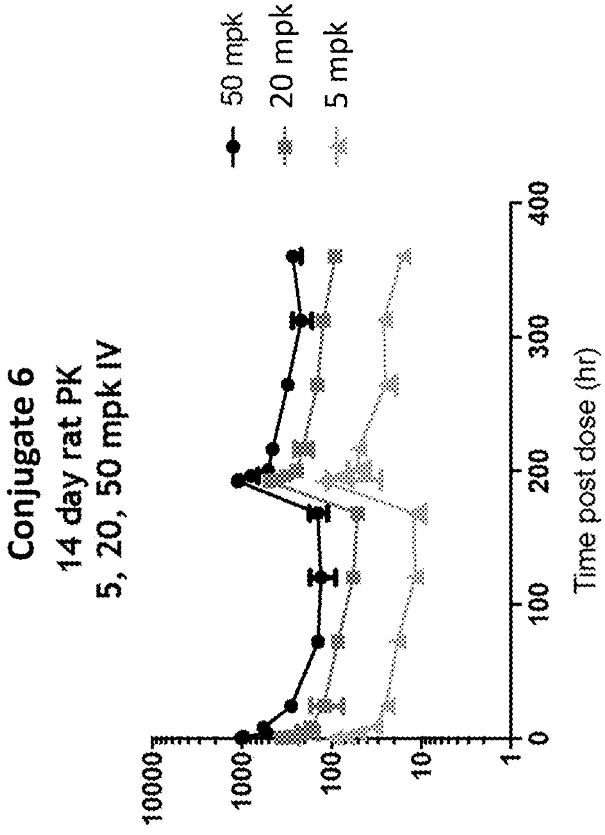
FIG. 37 is a graph showing a 14-day rat pharmacokinetic study following IV administration of Conjugate 6. The study was performed as described in Example 39.

Total Conjugate 6 (or hIgG1 Fc) in test samples was interpolated using in Graphpad Prism Version 6 following nonlinear regression analysis (Sigmoidal, 4PL analysis) of the Conjugate 6 standard curves. The curves comparing Conjugate 6 shown in FIG. 37 demonstrate linear dose proportionality.

Example 40. 28-Day Rat PK Study Comparing IV and SC Administration of Test Article Rat PK studies were performed by Seventh Wave Laboratories (Maryland Heights, MO) using male Sprague Dawley Rats 46-49 days of age. Rats were injected IV or SC with 5 mg/kg of test article (5 m1/kg dose volume). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations overtime.

The plasma concentrations for Conjugate 6 or hIgG1 Fc at each time point were measured by sandwich ELISA as follows: Conjugate 6 molecules were captured on neuraminidase coated plates and then detected using an HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with either neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve rat plasma final concentration of 1:900). Conjugate 6 standard curves ranging from 500-0.230 ng/mL, in duplicate were run on each plate.

Following the 2 hr incubation, plates were washed 5× in 300 uL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 uL PBS with 0.05% Tween 20 and developed with TMB substrate for 7-8 minutes. The reaction was stopped with 1 N $H_2SO_4$. Absorbance was read at 450 nm.

Figure 38:
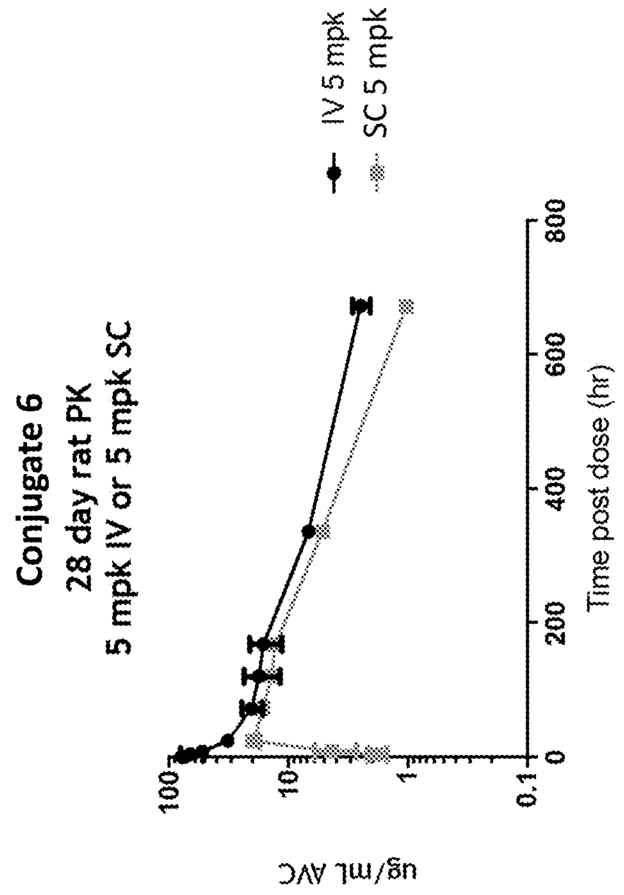
FIG. 38 is a graph showing a 28-day rat pharmacokinetic study comparing IV and SC administration of Conjugate 6. The study was performed as described in Example 40.

Total Conjugate 6 (or hIgG1 Fc) in test samples was interpolated using in Graphpad Prism Version 6 following nonlinear regression analysis (Sigmoidal, 4PL analysis) of the Conjugate 6 standard curves. The curves comparing Conjugate 6 in FIG. 38 show that SC and IV plasma levels converged at 24 h and were similar within experimental error out to 336 h.

Example 41. 28-Day Non-Human Primate PK Study Following IV Administration of Test Article Non-human primate (NHP) PK studies were performed by BTS Research (San Diego, CA) using male and female Cynomolgus monkeys 4.5-8 years old with body weights ranging from 2.5-6.5 kg. NHPs were injected IV by way of the saphenous or cephalic vein with 5 or 20 mg/kg of test article (5 ml/kg dose volume). Animals were housed under standard IACUC approved housing conditions. At appropriate times animals were non-terminally bled (by way of femoral or cephalic veins) with blood collected in K2EDTA tubes to prevent coagulation. Collected blood was centrifuged (2,000×g, for 10 minutes) and plasma withdrawn for analysis of test article concentrations over time.

The plasma concentrations for Conjugate 6 at each time point were measured by sandwich ELISA as follows: Conjugate 6 molecules were captured on neuraminidase coated plates and then detected using an HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve cynomolgus monkey plasma final concentration of 1:2,500). Conjugate 6 standard curves ranging from 500-0.230 ng/mL, in duplicate were run on each plate.

Following the 2 hr incubation, plates were washed 5× in 300 uL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 uL PBS with 0.05% Tween 20 and developed with TMB substrate for 7-8 minutes. The reaction was stopped with 1 N $H_2SO_4$. Absorbance was read at 450 nm.

Figure 39:
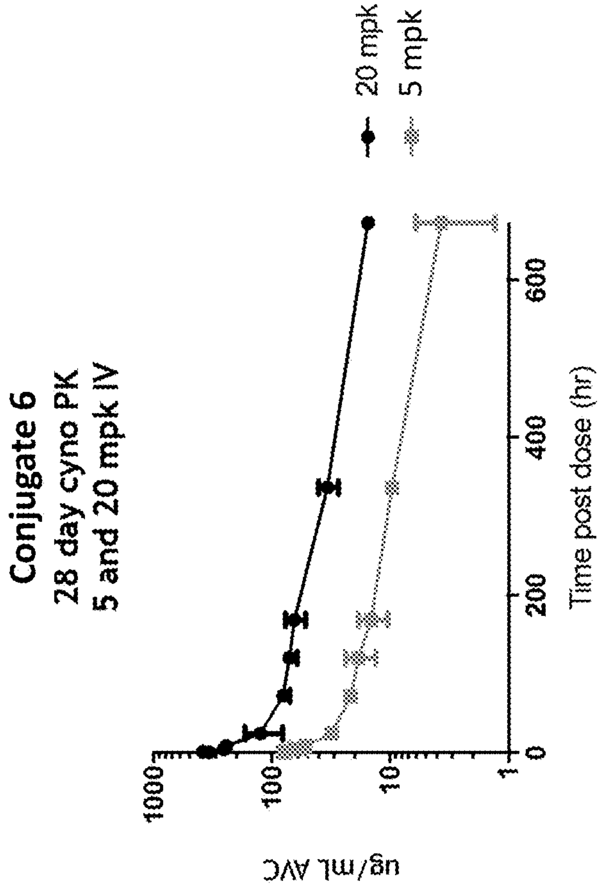
FIG. 39 is a graph showing a 28-day non-human primate pharmacokinetic study following IV administration of Conjugate 6. The study was performed as described in Example 41.

Total Conjugate 6 in test samples was interpolated using in Graphpad Prism Version 6 following nonlinear regression analysis (Sigmoidal, 4PL analysis) of the Conjugate 6 (or hIgG1 Fc) standard curves. PK parameters were calculated using WinNonlin software. The curves comparing Conjugate 6 are shown in FIG. 39 and a summary of key PK parameters is provided in Table 20. The dose response is linear between 5 and 20 mg/kg IV, resulting in a half-life of approximately 9 days across both doses (comparable to mouse/rat).

TABLE 20

| Cynomolgus monkey PK of Conjugate 6 | | |
|---|---|---|
| Conjugate 6 | Half-life (hrs) | AUClast (hr * mg/mL) |
| 5 mg/kg IV | 230 | 6240 |
| 20 mg/kg IV | 197 | 25400 |

Example 42. Mouse Lung Distribution PK Study Following IV Administration of Test Article Mouse PK studies were performed using male CD-1 mice 6 weeks of age. Mice were injected IV by way of the tail vein with 10 mg/kg of test article (5 ml/kg dose volume). Animals were housed under standard IACUC approved housing conditions. At the indicated time points, the animals were euthanized to harvest blood (by way of cardiac puncture) in $K_2$EDTA tubes and lungs. Blood was centrifuged (2,000×g, for 10 minutes) to obtain plasma. The lungs were weighed and homogenized in 1.5 ml tubes with a sterile disposable pestle (Z359947, Sigma) in 100 uL of homogenization buffer comprised of 11.64 mL tissue protein extraction reagent (78510, Thermo Scientific), 0.24 ml of protease inhibitor cocktail (78410, Thermo Scientific), and 0.12 ml of EDTA. After 1-2 min homogenization, the volume was adjusted to 1 mL with homogenization buffer and the samples incubated on ice for 20 min with periodic mixing by gentle vortexing. The homogenates were centrifuged at 8,000×g for 10 min and the supernatant retained for analysis of test article concentrations overtime.

The plasma and lung concentrations for Conjugate 6 at each time point were measured by sandwich ELISA as follows: Conjugate 6 molecules were captured on neuraminidase coated plates and detected using an HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve mouse plasma final concentration of 1:100). Conjugate 6 standard curves ranging from 500-0.230 ng/mL, in duplicate were run on each plate.

Following the 2 hr incubation, plates were washed 5× in 300 uL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 uL PBS with 0.05% Tween 20 and developed with TMB substrate for 7-8 minutes. The reaction was stopped with 1 N $H_2SO_4$. Absorbance was read at 450 nm.

Figure 40:
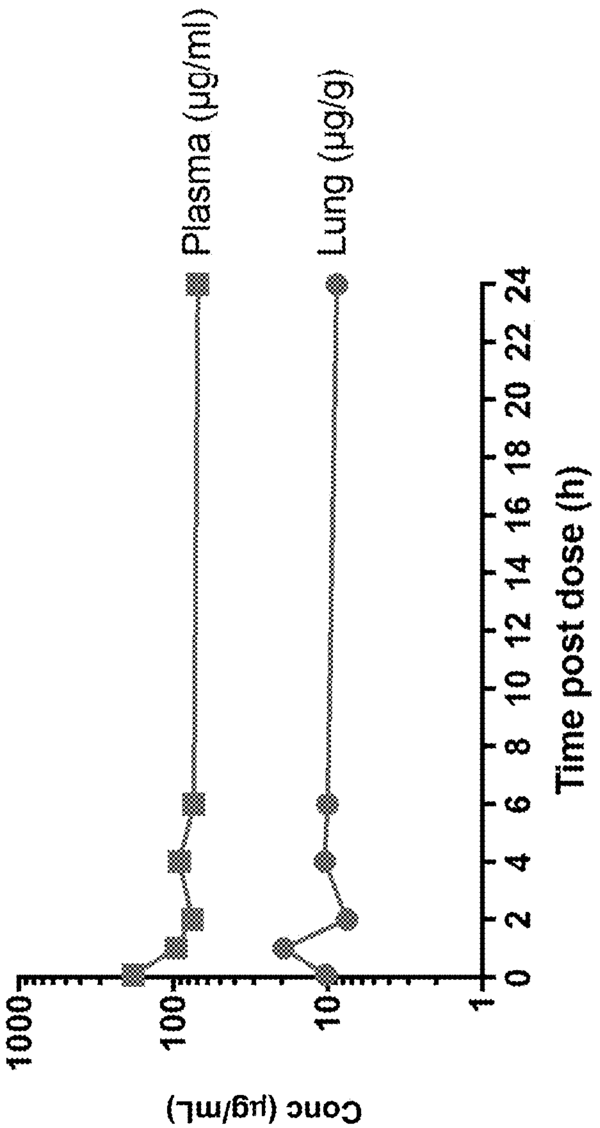
FIG. 40 is a graph showing a mouse lung distribution pharmacokinetic study following IV administration of Conjugate 6. The study was performed as described in Example 42.

Total Conjugate 6 in test samples was interpolated using in Graphpad Prism Version 6 following nonlinear regression analysis (Sigmoidal, 4PL analysis) of the Conjugate 6 standard curves. The curves comparing Conjugate 6 plasma and lung concentrations are shown in FIG. 40. Unexpectedly, lung $C_{max}$ was reached at t=1 h (19.5 µg/g lung tissue, ~310 nM). There was approximately 10% lung exposure of Conjugate 6, relative to plasma Example 43. 5-Day Mouse PK Study Comparing IV, SC and IM Administration of Test Article Mouse PK studies were performed using male CD-1 mice 6 weeks of age. Mice were injected IV by way of the tail vein with 5 mg/kg of test article (5 ml/kg dose volume). Animals were housed under standard IACUC approved housing conditions. At appropriate times animals were non-terminally bled (retro-orbital, cheek, or by tail vein) with blood collected in K2EDTA tubes to prevent coagulation. Collected blood was centrifuged (2,000×g, for 10 minutes) and plasma withdrawn for analysis of test article concentrations overtime.

The plasma concentrations for Conjugate 6 at each time point were measured by sandwich ELISA as follows: Conjugate 6 molecules were captured on neuraminidase coated plates and then detected using an HRP-conjugated anti-human IgG-Fc antibody. Protein concentration was calculated in GraphPad Prism using 4PL non-linear regression of Conjugate 6 (or hIgG1 Fc) standard curves. A more detailed method description is provided below.

Nunc Maxisorp 96-well plates (Cat No. 12-565-136, ThermoFisher) were coated with neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hrs (sample diluent: 1% BSA in PBS 0.05% Tween 20+naïve mouse plasma final concentration of 1:100). Conjugate 6 standard curves ranging from 500-0.230 ng/mL, in duplicate were run on each plate.

Following the 2 hr incubation, plates were washed 5× in 300 uL PBS with 0.05% Tween 20. Conjugate 6 bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 uL PBS with 0.05% Tween 20 and developed with TMB substrate for 7-8 minutes. The reaction was stopped with 1 N $H_2SO_4$. Absorbance was read at 450 nm.

Figure 41:
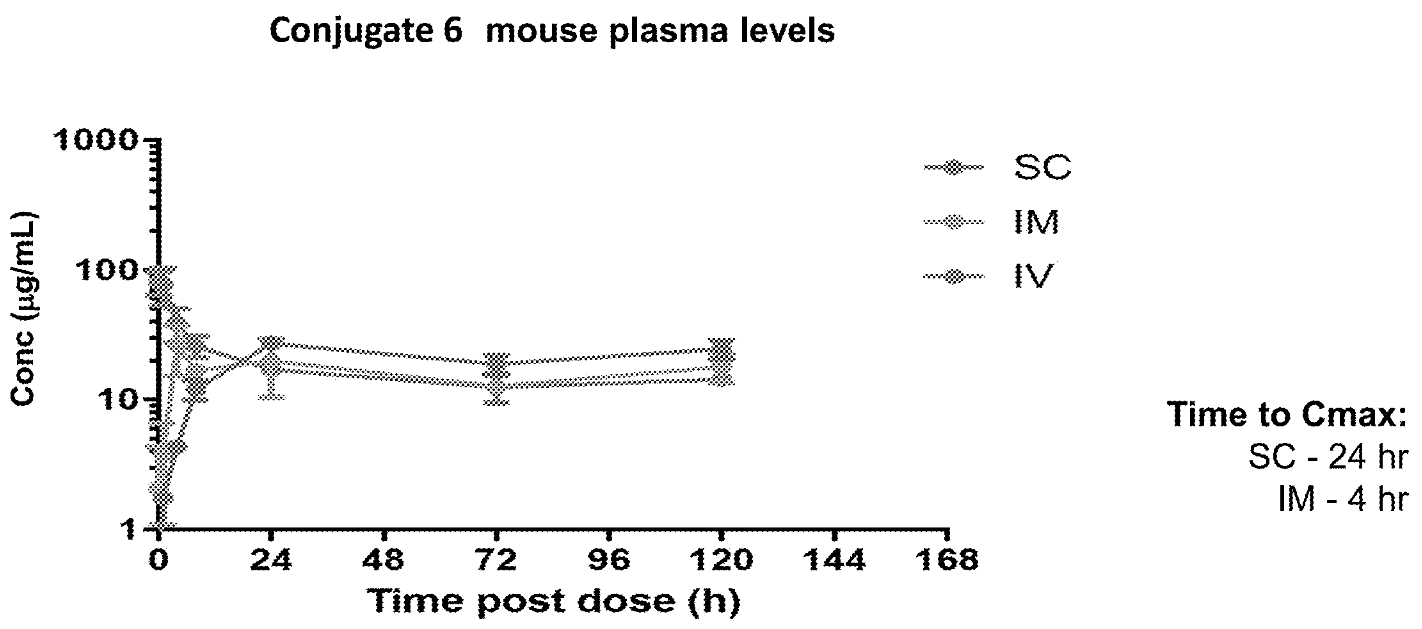
FIG. 41 is a graph showing a 5-day mouse pharmacokinetic study comparing IV, SC and IM administration of Conjugate 6. The study was performed as described in Example 43.

Total Conjugate 6 in test samples was interpolated using in Graphpad Prism Version 6 following nonlinear regression analysis (Sigmoidal, 4PL analysis) of the Conjugate 6 standard curves. The curves comparing Conjugate 6 are shown in FIG. 41. The exposure levels for IV, IM and SC were similar with AUCs of 2082, 1944 and 2500, respectively.

Example 44. Mouse Efficacy and Multi-Species PK Supports Infrequent Prophylactic Dosing in Human Subjects Allometric scaling of mouse efficacy dosing based on mouse, rat, and primate PK studies was used to predict dosing and PK parameters in human subjects. Allometric scaling was based on the Area Under the Curve (AUC) at a 2.5 mg/kg efficacious dose in a 28-day mouse prevention study (see Example 33).

For cynomolgus monkey-only allometric scaling, human clearance (CL) was calculated based on cynomolgus monkey PK data (Example 41) only using a simple allometric equation: CL(human)=CL(monkey)·[BW(human)/BW (monkey)]$^w$, where BW=bodyweight and w is the scaling exponent fixed at 0.85. The results of cynomolgus monkey-only scaling are provided in Table 21.

For Mouse-rat-cynomolgus allometric scaling, human clearance (CL) from animal species was plotted against the animal body weight (BW) on a log-log scale according to the following allometric equation: $CL=a\cdot BW^x$, where a is the coefficient and x is the exponent of the allometric equation. The coefficient a and exponent x were calculated from the intercept and slope of the linear regression line, respectively. The results of mouse-rat-cyno scaling are provided in Table 22.

Human clearance values calculated by respective algorithms above were then used to calculate the corresponding human dose needed to achieve the Efficacy AUC target of 3700 ug-hr/mL (from mouse 2.5 mg/kg dose, Example 33) using the following equation: $Dose=CL\cdot AUC$.

TABLE 21

| Cynomolgus monkey-only allometric scaling (β = 0.85) | |
|---|---|
| Efficacy Area Under the Curve (AUC) | 3700 μg-hr/mL |
| Human Clearance (CL) | 0.43 mL/min |
| Human Dose | 95.46 mg, 1.4 mg/kg |

TABLE 22

| Mouse-rat-cyno allometric scaling (β = 0.97) | |
|---|---|
| Efficacy Area Under the Curve (AUC) | 3700 μg-hr/mL |
| Human Clearance (CL) | 0.59 mL/min |
| Human Dose | 130.98 mg, 1.9 mg/kg |

Example 45. Synthesis of Int-11

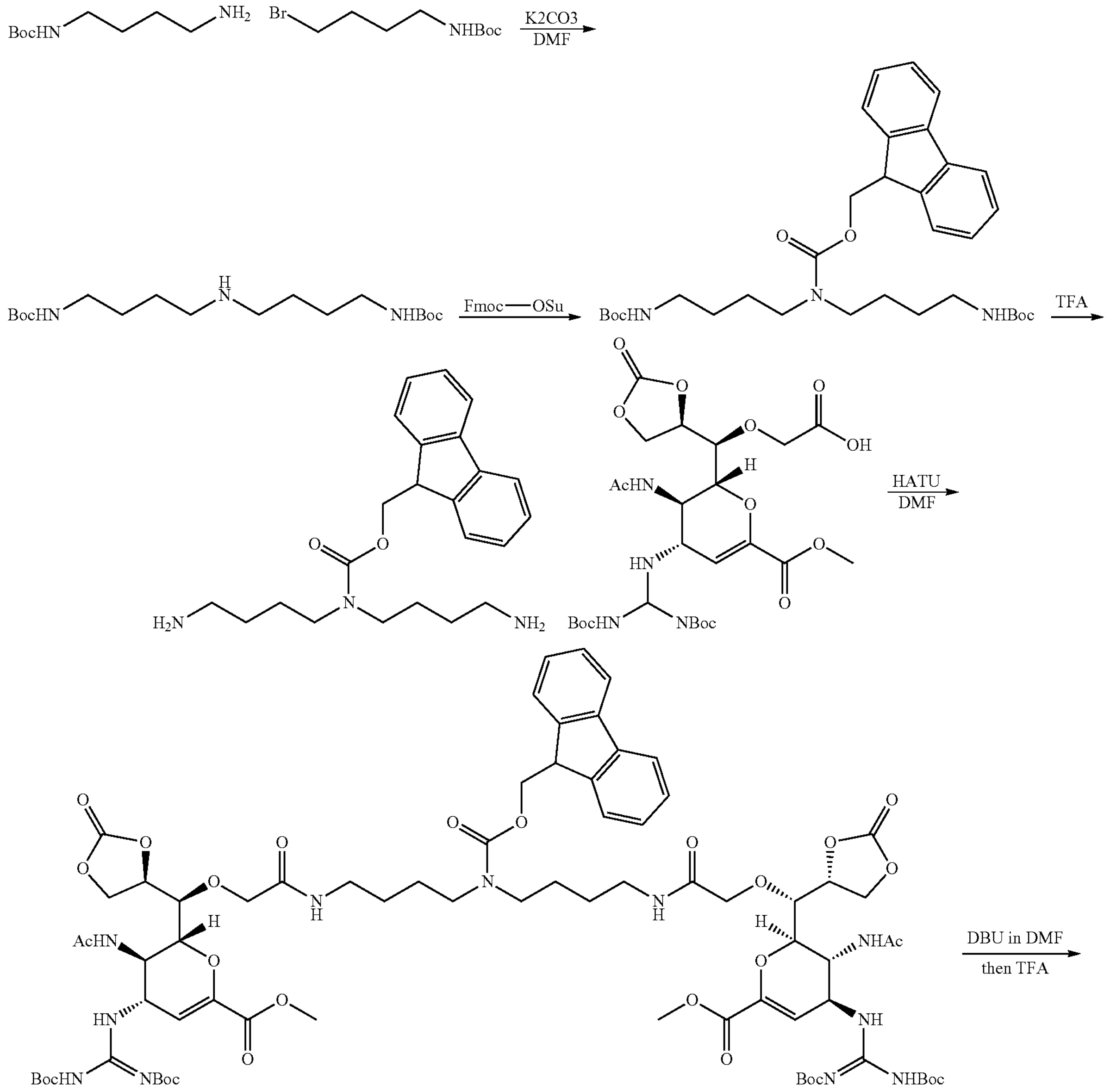

-continued

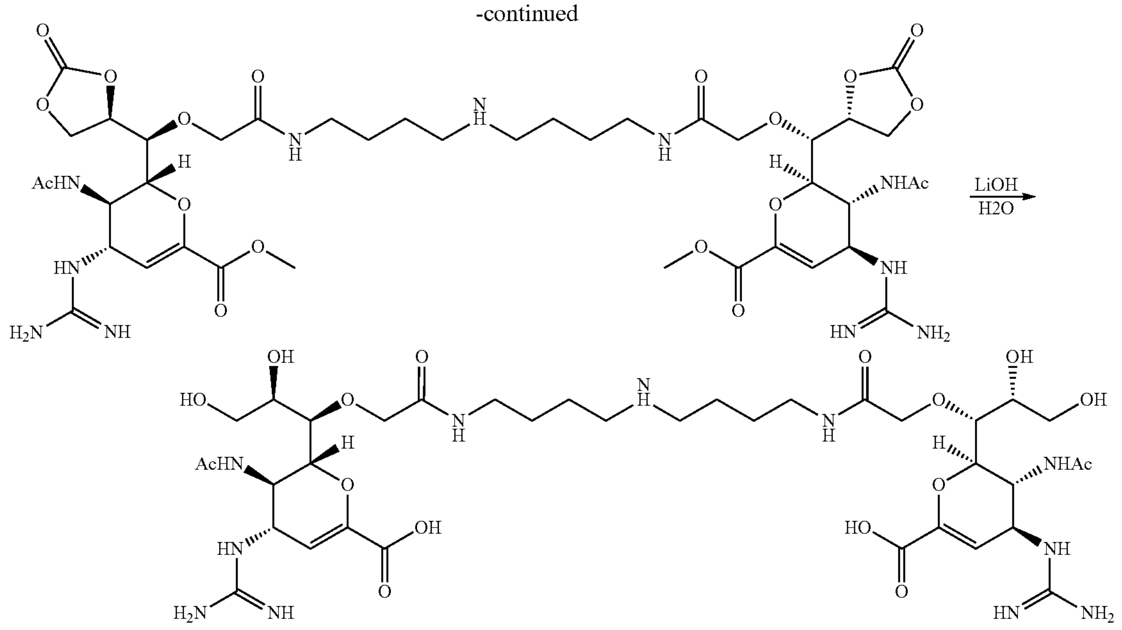

Step a.

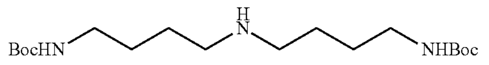 [SMILES: CC(C)(C)OC(=O)NCCCCNCCCCNC(=O)OC(C)(C)C]

A solution of the tert-butyl (4-bromobutyl)carbamate (11.2 g, 60 mmol) and tert-butyl (4-aminobutyl)carbamate (10 g, 40 mmol) dissolved in DMF (150 mL) was treated with potassium carbonate (16.4 g, 120 mmol), then stirred at 80° C. for 6 hrs. The reaction mixture was partitioned between DCM (500 ml) and brine (100 ml). The organic layer was separated and washed with brine then dried with sodium sulfate. The solution was filtered, concentrated, and purified by reverse phase liquid chromatography (RPLC) using an Isco COMBIFLASH® liquid chromatograph eluted with 10% to 100% acetonitrile and water with 0.1% TFA as modifier. Yield of the product 11.0 g, 77%. Ion(s) found by LCMS: M+H=360.4

Step b.

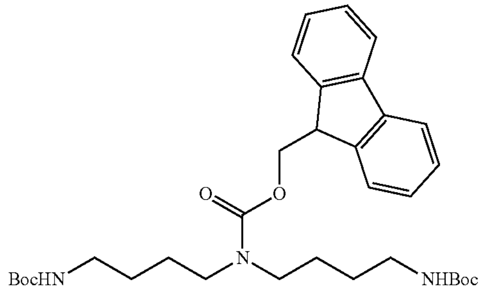 [SMILES: CC(C)(C)OC(=O)NCCCCN(CCCCNC(=O)OC(C)(C)C)C(=O)OCC1c2ccccc2-c2ccccc21]

Product from the previous step (0.4 g, 1.11 mmol) and Fmoc-OSu (0.45 mg, 1.3 mmol) were dissolved in DCM (10 mL), then treated with N-methylmorpholine (0.22 ml, 2 mmol), and stirred for 1 hr at room temperature. The reaction was concentrated and purified by and purified by reverse phase liquid chromatography (RPLC) using an Isco COMBIFLASH® liquid chromatograph eluted with 10% to 100% acetonitrile and water with no 0.1% TFA as modifier. Yield of the products 450 mg, 69%. Ion(s) found by LCMS: M/2+H=582.4.

Step c.

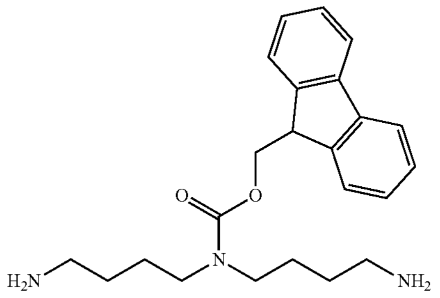 [SMILES: NCCCCN(CCCCN)C(=O)OCC1c2ccccc2-c2ccccc21]

Product from the previous step (0.4 g, 0.7 mmol) was treated with TFA (5 mL) at room temperature for 0.5 hour, then concentrated to dryness and used for next step without further purification. Yield was quantitative for this step. Ion(s) found by LCMS: M/2+H=382.3.

Step d.

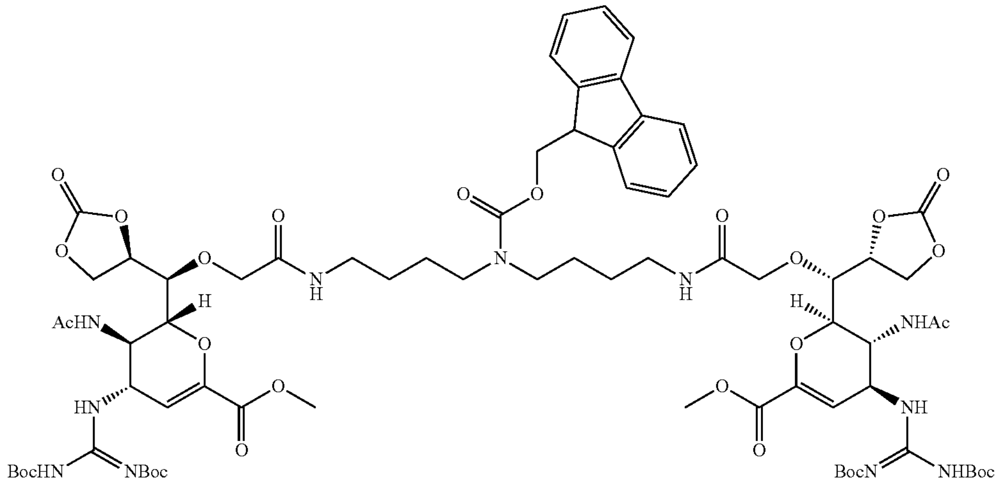

Fmoc diamine (24 mg, 0.063 mmol) from the previous step was added to a solution of carboxylic acid (80 mg, 0.126 mmol, described in the synthesis Int-10, step f) in DMF (5 mL), then treated with HATU (50 mg, 0.13 mmol), followed N-methylmorpholine (0.06 ml, 0.50 mmol). After stirring for 1 h the resulting solution was concentrated and purified by reverse phase liquid chromatography (RPLC) using an Isco COMBIFLASH® liquid chromatograph eluted with 10% to 100% acetonitrile and water without TFA as a modifier. Yield of the products 80 mg, 79%. Ion(s) found by LCMS: M/2+H=803.9.

Step e.

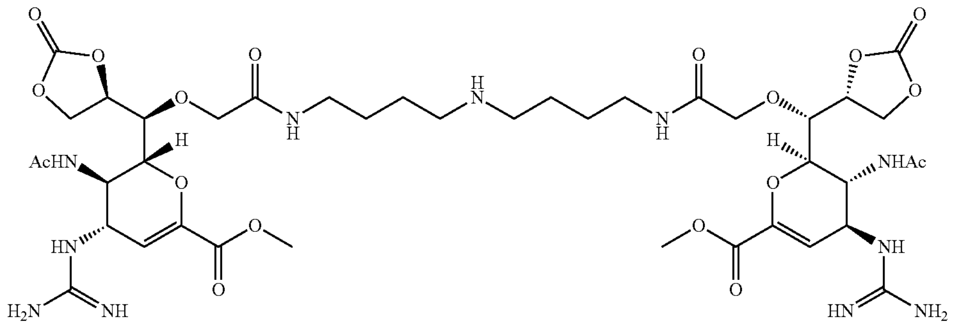 [SMILES: COC(=O)C1=C[C@H](NC(=N)N)[C@@H](NC(C)=O)[C@H]([C@H](OCC(=O)NCCCCNCCCCNC(=O)CO[C@@H]([C@@H]2OC(C(=O)OC)=C[C@H](NC(=N)N)[C@H]2NC(C)=O)[C@H]2COC(=O)O2)[C@H]2COC(=O)O2)O1]

Product from the previous step (80 mg, 0.050 mmol) was treated with 1% DBU (1,8-diazabicyclo[5.4.0]undec-7-ene) in DMF (2 mL) and stirred at room temperature. When the reaction was complete by LCMS (15 min), it was concentrated, then treated with TFA (2 mL) and stirred for 30 min at room temperature. The reaction solution was concentrated and purified by reverse phase liquid chromatography (RPLC) using an Isco COMBIFLASH® liquid chromatograph eluted with 10% to 100% acetonitrile and water, using 0.1% TFA as the modifier. Yield of product was 52 mg as TFA salt. Ion(s) found by LCMS: M/2+H=492.7.

Step f.

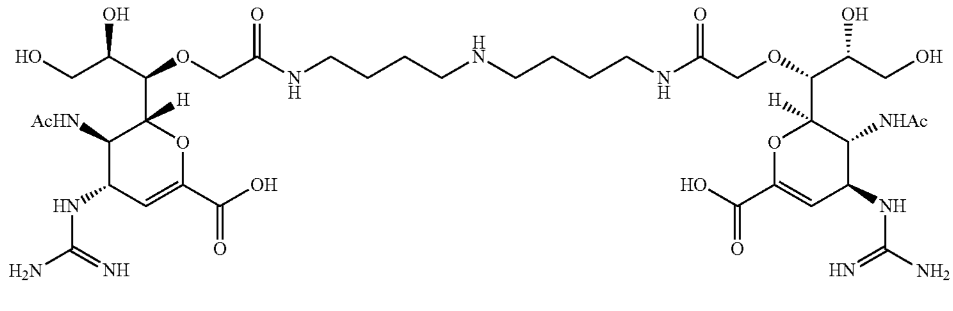 [SMILES: CC(=O)N[C@H]1[C@H]([C@H](OCC(=O)NCCCCNCCCCNC(=O)CO[C@@H]([C@@H]2OC(C(=O)O)=C[C@H](NC(=N)N)[C@H]2NC(C)=O)[C@H](O)CO)[C@H](O)CO)OC(C(=O)O)=C[C@@H]1NC(=N)N]

Product from the previous step was dissolved into water (2 mL), then treated with a lithium hydroxide (12 mg, 0.50 mmol, in 1 mL water) solution. The resulting reaction was monitored by LCMS. After stirring for 10 min the reaction was quenched with 0.1 ml acetic acid. The resulting solution was concentrated and purified by reverse phase liquid chromatography (RPLC) using an Isco COMBIFLASH® liquid chromatograph eluted with 0% to 30% acetonitrile and water, using 0.1% TFA as the modifier. Yield of the product: 30 mg as TFA salt, 66%. Ion(s) found by LCMS: M/2+H=452.7. M/3+H=302.1.

Example 46. Synthesis of Int-12

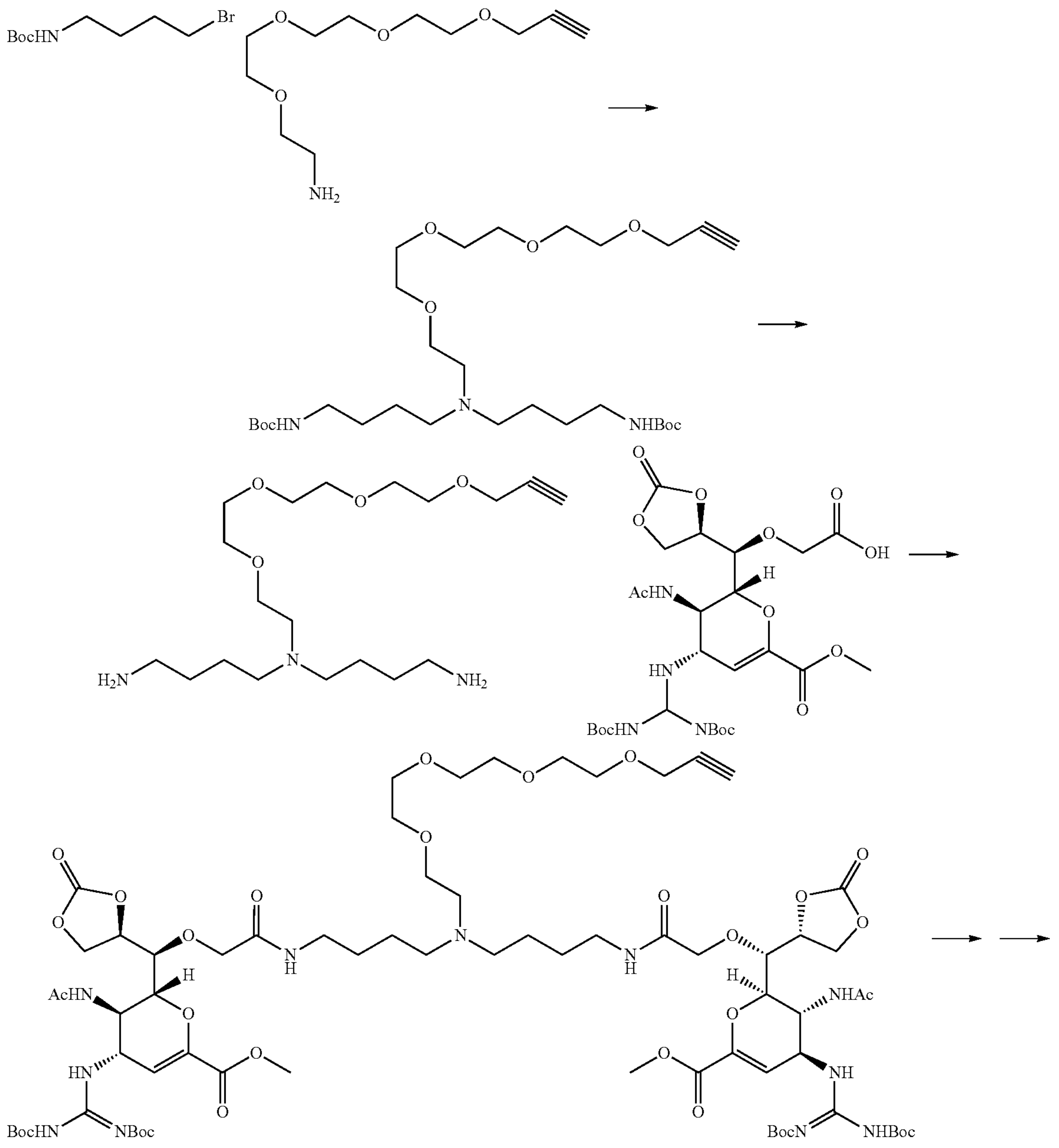

-continued

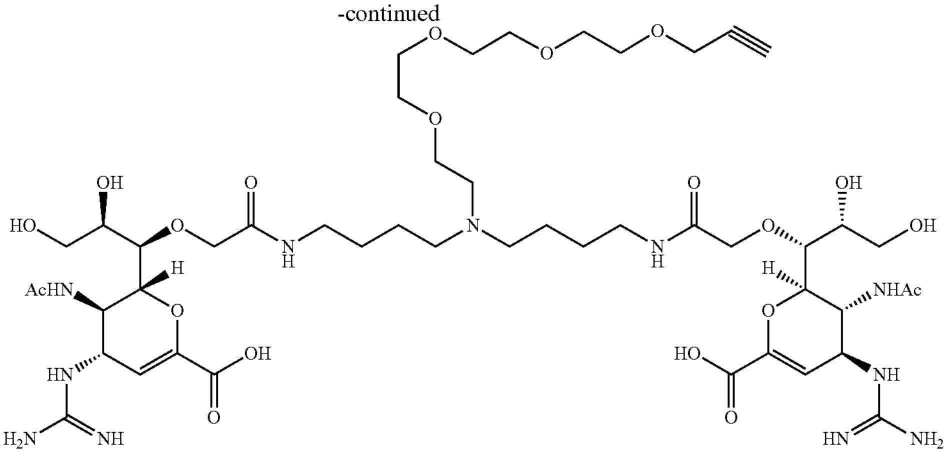

Step a.

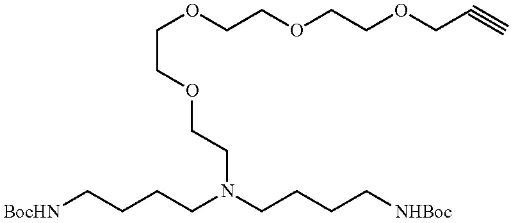 [SMILES: C#CCOCCOCCOCCOCCN(CCCCNC(=O)OC(C)(C)C)CCCCNC(=O)OC(C)(C)C]

To a solution of tert-butyl (4-bromobutyl)carbamate (4.8 g, 19 mmol) and propargyl-PEG4 amine (2 g, 8.6 mmol) in DMF (50 mL) was added potassium carbonate (3.6 g, 26 mmol). The solution was stirred at 80° C. for 6 hrs, then partitioned between DCM (200 ml) and brine (50 ml). The organic layer was separated, washed with brine, dried with sodium sulfate, filtered, and concentrated, then purified by reverse phase liquid chromatography (RPLC) using an Isco COMBIFLASH® liquid chromatograph eluted with 10% to 100% acetonitrile and water with 0.1% TFA as modifier. Yield of product 3.5 g, 70%. Ion(s) found by LCMS: M/2+H=574.4.

Step b.

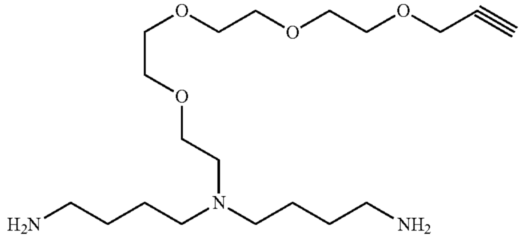 [SMILES: C#CCOCCOCCOCCOCCN(CCCCN)CCCCN]

Product from the previous step (3.5 g, 8.6 mmol) was treated with TFA (20 ml) at room temperature for 0.5 hour, then concentrated to dryness, dissolved in water, frozen, lyophilized, and used in the next step without further purification. The yield was quantitative for this step. Ion(s) found by LCMS: M/2+H=374.3.

Step c.

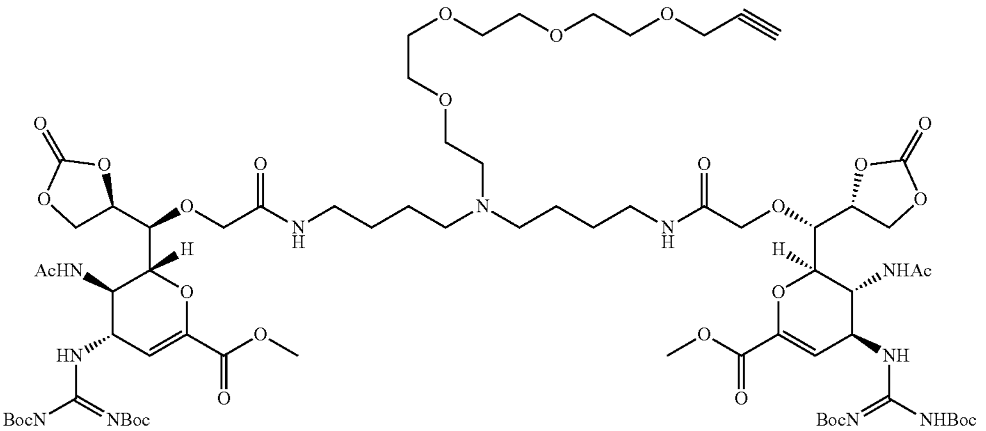

Diamine TFA salt from the previous step (37 mg, 0.1 mmol) was added to a solution of the carboxylic acid (130 mg, 0.2 mmol, described in the synthesis Int-10, step f) in 10 ml DMF, then treated with HATU (80 mg, 0.2 mmol), and N-methylmorpholine (0.25 ml, 2 mmol). The resulting solution was stirred for 1 hr, then concentrated and purified by reverse phase liquid chromatography (RPLC) using an Isco COMBIFLASH® liquid chromatograph eluted with 10% to 100% acetonitrile and water with no 0.1% TFA as modifier. Yield of the product 120 mg, 75%. Ion(s) found by LCMS: M/2+H=799.9.

Step d.

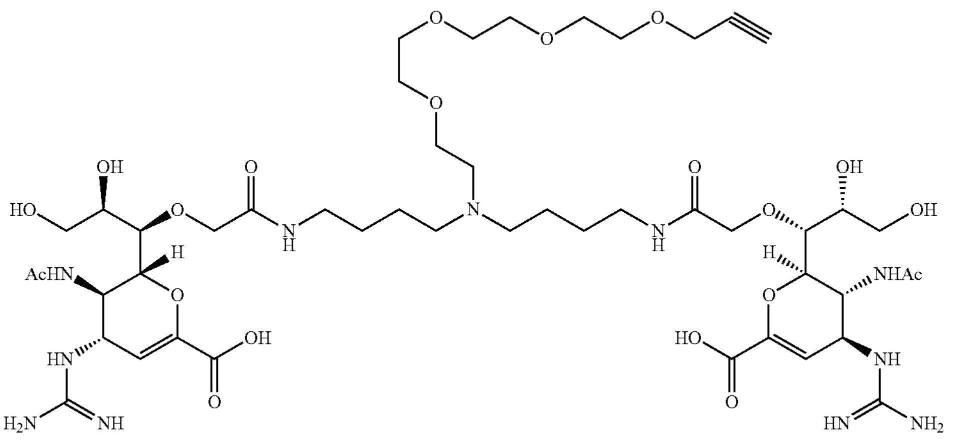 [SMILES: C#CCOCCOCCOCCOCCN(CCCCNC(=O)CO[C@@H]([C@@H]1OC(C(=O)O)=C[C@H](NC(=N)N)[C@H]1NC(C)=O)[C@H](O)CO)CCCCNC(=O)CO[C@@H]([C@@H]1OC(C(=O)O)=C[C@H](NC(=N)N)[C@H]1NC(C)=O)[C@H](O)CO]

Product from the previous step (120 mg, 0.075 mmol) was treated with 2 ml trifluoroacetic acid and stirred for 30 min at room temperature. The resulting solution was concentrated, dissolved into water (2 mL), then treated with a solution of lithium hydroxide (12 mg, 0.5 mmol) dissolved in water (1 mL). The resulting solution was stirred 10 min, then made slightly acidic with 0.1 ml acetic acid, concentrated and purified by reverse phase liquid chromatography (RPLC) using an Isco COMBIFLASH® liquid chromatograph eluted with 0% to 30% acetonitrile and water, using 0.1% TFA as the modifier. Yield of the products 48 mg as TFA salt, 57%. Ion(s) found by LCMS: M/2+H=559.757. M/3+H=373.5.

Example 47. Synthesis of Conjugate 8

Figure 42:
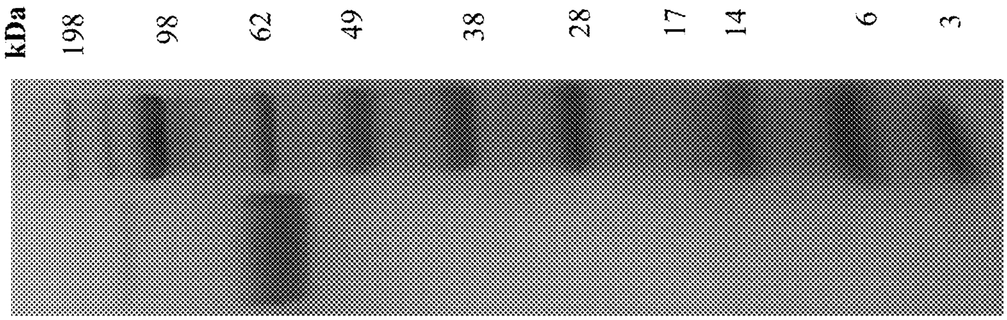
FIG. 42 shows a non-reducing SDS-PAGE of Conjugate 8.

A solution of h-IgG1 Fc-PEG4-azide in PBS×1 buffer solution (100 mg, 1.71 μmol, 7.011 mL, MW=58200 Da, DAR=3.7) were added alkyne derivatized small molecule (Int-12 TFA salt, 45 mg, 0.031 mmol) and freshly prepared pH 7.4 PBS solutions of CuSO4 (0.7 mL of 50.0 mM, 20 eq), tris(3-hydroxypropyltriazolylmethyl)-amine (THPTA, 0.7 mL of 50.0 mM, 20 eq), and sodium ascorbate (1.05 mL of 50.0 mM, 30 eq). The resulting homogeneous solution was agitated by rocker table for 12h. The crude solutions were diluted with pH 7.4 PBS to a final concentration of 1 mg/mL, and ultrafiltered (10,000 MWCO) to a volume of 1 mL, two times. The crude mixtures were then diluted 1:10 in PBS pH 7.4, and purified using MabSelect Sure Resin (GE Healthcare, Chicago, IL, USA), followed by size exclusion chromatography. Purified material was quantified using a Nanodrop™ UV visible spectrophotomer (using a calculated extinction coefficient based on the amino acid sequence of the Fc used in the conjugation, and concentrated to approximately 10 mg/mL using a centrifugal concentrator (10,000 MWCO). Purified molecules were analyzed using 4-12% Bis Tris SDS PAGE gels by loading 1-2 μg of each molecule into the gel, and staining using instant Blue staining. Each gel included a molecular weight ladder with the indicated molecular weight standards (FIG. 42). Yields are typically 40-60%. MALDI MS analysis showed a range of masses (60000-90000) with an average of mass of 62358. Average DAR=3.

Example 48. Comparison of In Vitro and In Vivo Potency of Selected Inhibitors with their Fc-Conjugates in CPE Assays and in a Lethal Mouse Influenza Model To demonstrate that conjugation of neuraminidase inhibitors described herein to Fc enhances their activities in viral replication assays and in in vivo efficacy models, we compared the activities of selected unconjugated inhibitors to their Fc conjugates in Cytopathic Effect (CPE) assays, and in a lethal mouse influenza infection model. For the CPE microneutralization assay, ten two-fold serial dilutions of each test article (TA), starting at 160 nM or 400 nM (9600 nM for zanamivir and oseltamivir controls), were prepared in duplicate for one-hour inoculation with INFV A (A/CA/09 H1N1) at a multiplicity of infection (MOI) 0.001 and INFV B at a MOI of 0.01 for one-hour incubation. The TA-virus mix was then added to MDCK cells seeded in 96-well plates, and incubated for one hour. On day 3 post infection for INFV A and 5 for INFV B (B/Brisbane), Cells were fixed and stained with crystal violet and optical density was read for calculation of 50 percent effective concentration ($EC_{50}$) of each TA using XLfit dose response model. The intrinsic cytotoxicity of each TA was also evaluated using ten two-fold serial dilutions of each TA starting at 160 nM or 400 nM were prepared in duplicate for inoculation with MDCK cells in 96-well culture plates. The cell by way of bility was determined 3 and 5 days post treatment using CellTiter-Glo kit. 50% of cytotoxicity concentration ($CC_{50}$) was calculated using XLfit dose response model. No cytotoxicity was observed for any of the TAs to the highest concentrations tested. A summary of the CPE-based microneutralization assay is shown in Table 23.

TABLE 23

CPE-based microneutralization assay

| | $EC_{50}$ vs INFV A (nM) | $EC_{50}$ vs INFV B (nM) |
|---|---|---|
| Oseltamivir | 390.0 | 1065.0 |

TABLE 23-continued

| CPE-based microneutralization assay | | |
|---|---|---|
| | $EC_{50}$ vs INFV A (nM) | $EC_{50}$ vs INFV B (nM) |
| Zanamivir | 264.8 | 382.6 |
| Int-7 (Targeting Moiety corresponding to Conugate 6) | 665.7 | 106.6 |
| Int-12 (Targeting Moiety corresponding to Conjugate 8) | 15.4 | 0.6 |
| Conjugate 6 | 4.0 | 52.1 |
| Conjugate 8 | 0.6 | 0.3 |

The data summarized in Table 23 demonstrate that the Fc-conjugated forms of the neuraminidase dimers possess superior activity in CPE microneutralization assay to their unconjugated counterpart. Enhancements of 166-fold and 2-fold, versus INFV A and INFV B, respectively, were observed when comparing Conjugate 6 to Int-7. Enhancements of 26-fold and 2-fold, versus INFV A and INFV B, respectively, were observed when comparing Conjugate 8 to Int-12.

Conjugate 6 was compared to a the most potent neuraminidase inhibitor dimer from the study summarized in Table 23 (Int-11, dimer-only corresponding to Int-12 without the trimeric linker allowing for conjugation to an Fc) in a lethal IAV H1N1 influenza infection model using female BALB/c mice (Charles River Laboratories, 6-8 weeks). The challenge virus (A/Puerto Rico/08/1934, aka PR8) is a mouse-adapted isolate with a $LD_{90}$ of approximately 30 plaque-forming units (pfu) per mouse.

The experiment comprised 8 groups of 5 mice. At day 0, all mice were challenged with PR8 at 10× the $LD_{90}$ by intranasal inoculation in a volume of 50 μl, to mice anesthetized with a mixture of ketamine/xylazine (150 and 10 mg/kg respectively). Groups received a single treatment of vehicle, hIgG1 Fc only, conjugate 6, or Int-11 by IV, 2 hours after challenge (Table 24; groups 1-6). Group 7 received Int-11 (15 mg/kg) twice daily (bid) for 5 days, also by IV. Group 8 received oseltamivir (15 mg/kg) orally (PO), bid, for 5 days. All mice were monitored for survival (Table 25) and weight loss (data not shown) for 10 days after viral challenge.

As expected, mice treated with vehicle or hIgG1 Fc only succumbed to the infection by day 7 (Table 25). Mice treated with 10 doses (150 mg/mouse in total) of oseltamivir demonstrated a statistically significant delay in death but only a single animal survived until day 10. All mice receiving a single dose of conjugate 6 at 0.3 or 3 mg/kg survived to the end of the study and showed a net weight gain over the course of the experiment. Importantly, all mice receiving the Int-11 at 0.3 or 3 mg/kg died over the course of the study, with only a minimal (2 days or less) delay in death relative to the vehicle and hIgG1 Fc only controls. As the hIgG1 Fc has no inherent antiviral activity (group 2) this suggests the greatly improved activity of conjugate 6 is the result of the improved avidity resulting from the multivalent display on an Fc, as suggested by the results summarized in Table 23, as well as improved pharmacokinetics and contribution from Fc mediated immune engagement. The difference in activity between the inhibitor dimer alone and conjugate 6 was statistically significant at both dose concentrations (compare groups 3 and 6, and groups 4 and 5; Table 25). On a mass basis, a 500× greater cumulative dose of Int-11 was required to observe equivalent efficacy to conjugate 6.

TABLE 24

| Study design | | | | |
|---|---|---|---|---|
| Group n = 5 | Challenge Day 0 | Compound | Dose (mg/kg) | Treatment Route/Schedule |
| 1 | Influenza A virus (H1N1) A/Puerto Rico/08/1934 by way of IN route. | Vehicle (PBS) | N/A | IV, Singe dose starting 2 hours post infection |
| 2 | | hIgG1 Fc only | 3 | |
| 3 | | Conjugate 6 | 3 | |
| 4 | | Conjugate 6 | 0.3 | |
| 5 | | Int-11 | 0.3 | |
| 6 | | Int-11 | 3 | |
| 7 | | Int-11 | 15 | IV, bid for 5 days starting 2 hours post infection |
| 8 | | Oseltamivir (Tamiflu ™) | 20 | PO, bid for 5 days starting 2 hours post infection |

TABLE 25

| Mouse survival | | | | | | |
|---|---|---|---|---|---|---|
| Group | Test article | Dose (mg/kg) | Dosing schedule | % Survival | Signficance to vehicle | Significance to Int-11 0.3 mg/kg* or 3 mg/kg^ |
| 1 | Vehicle (PBS) | | IV, Single | 0 | | |
| 2 | hIgG1 Fc only | 3 | IV, Single | 0 | NS | |
| 3 | Conjugate 6 | 3 | IV, Single | 100 | 0.0027 | 0.0035^ |
| 4 | Conjugate 6 | 0.3 | IV, Single | 100 | 0.0027 | 0.0027* |
| 5 | Int-11 | 0.3 | IV, Single | 0 | 0.0027 | |
| 6 | Int-11 | 3 | IV, Single | 0 | 0.0027 | |
| 7 | Int-11 | 15 | IV, bid × 5 days | 100 | 0.0027 | |
| 8 | Oseltamivir | 15 | PO, bid × | 20 | 0.0027 | |

TABLE 25-continued
| Mouse survival | | | | | |
|---|---|---|---|---|---|
| Group Test article | Dose (mg/kg) | Dosing schedule | % Survival | Signficance to vehicle | Significance to Int-11 0.3 mg/kg* or 3 mg/kg^ |
| | | 5 days | | | |
Example 49. Synthesis of Int-13 ((5R)-((1R)-Acetylamino-(2S)-methoxy-(2S)-methylpentyl)-(4S)-E/Z-[3-(propargyl-PEG4)-propenyl]-pyrrolidine-(2R)-carboxylic acid)
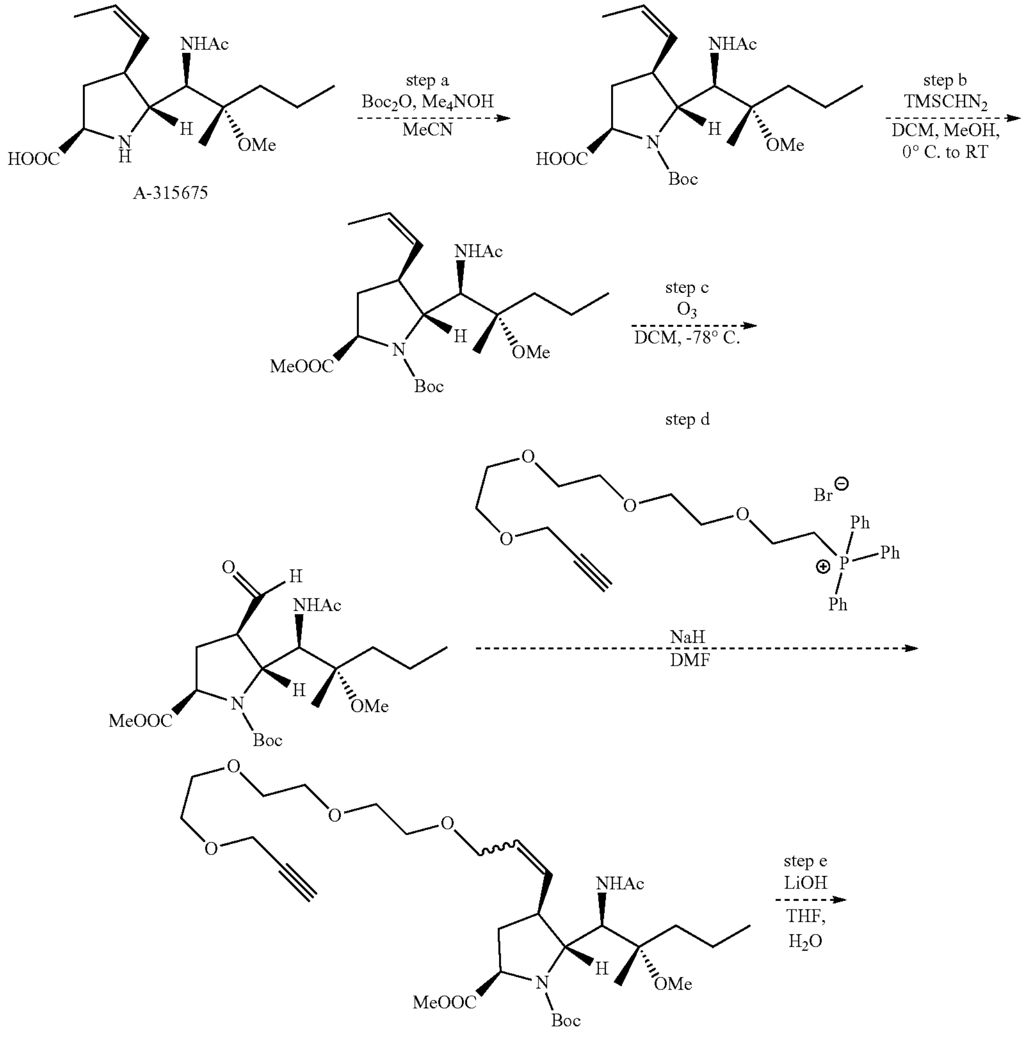
A-315675

-continued

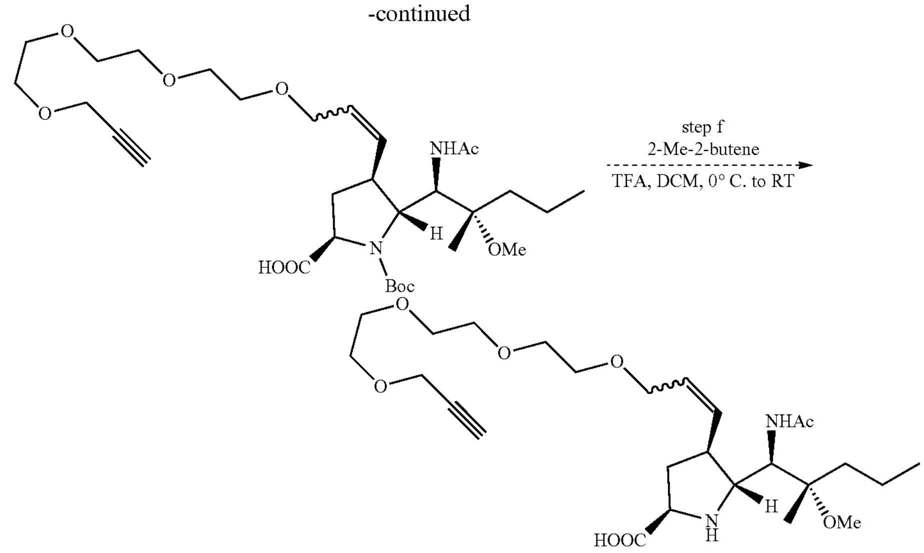

Step a. (2R)-((1R)-Acetylamino-(2S)-methoxy-(2S)-methylpentyl)-(5R)-carboxy-(3S)—Z-propenylpyrrolidine-1-carboxylic acid tert-butyl ester To a stirring mixture of (5R)-((1R)-acetylamino-(2S)-methoxy-(2S)-methylpentyl)-(4S)—Z-propenylpyrrolidine-(2R)-carboxylic acid, HCl salt (prepared accordingly to reference JACS, 2002, 124, 4716-4721; 1.0 mmol) in acetonitrile (10 mL) it is added trimethylammonium hydroxide (1.5 mmol). After stirring for 3 h at room temperature the di-tert-butyldicarbonate (4 eqmol) is added. Upon reaction completion, all the volatiles are evaporated per vacuum techniques. The residue is diluted with water (10 ml). Ethyl acetate (10 ml) is added, and 1 M sulfuric acid aqueous solution is added until the water layer reaches pH ~ 3. The water layer is washed with two additional aliquots of ethyl acetate (10 mL). The combined organics are dried over sodium sulfate, filtered and concentrated. The residue is purified by chromatographic techniques to afford the desired product.

Step b. (2R)-((1R)-Acetylamino-(2S)-methoxy-(2S)-methylpentyl)-(5R)-carboxymethyl-(3S)—Z-propenylpyrrolidine-1-carboxylic acid tert-butyl ester To a 0° C. stirring mixture of (2R)-((1R)-acetylamino-(2S)-methoxy-(2S)-methylpentyl)-(5R)-carboxy-(3S)—Z-propenylpyrrolidine-1-carboxylic acid tert-butyl ester (1.0 mmol) in dichloromethane (5.0 mL) and methanol (1.0 mL) it is slowly added (trimethylsilyl)diazomethane (1.1 mmol). The mixture is stirred until completion, while temperature is gently allowed to reach ambient. All the volatiles are evaporated per vacuum techniques. If necessary, the residue is purified by chromatographic techniques to afford the desired product.

Step c. (2R)-((1R)-Acetylamino-(2S)-methoxy-(2S)-methylpentyl)-(5R)-carboxymethyl-(3S)-formylpyrrolidine-1-carboxylic acid tert-butyl ester A room temperature mixture of (2R)-((1R)-acetylamino-(2S)-methoxy-(2S)-methylpentyl)-(5R)-carboxymethyl-(3S)—Z-propenylpyrrolidine-1-carboxylic acid tert-butyl ester (1 mmol) in dichloromethane (15 mL) is cooled to −78° C. Ozone is bubbled through the solution until a faint blue color of dissolved ozone persists. Nitrogen is bubbled through the solution until blue color disappears, then dimethyl sulfide (4.0 mmol) is added, the flask transferred into a freezer (−20° C.) and let sit for 1 hour. The solution is concentrated and the residue is purified by chromatographic techniques to afford the desired product.

Step d. (2R)-((1R)-Acetylamino-(2S)-methoxy-(2S)-methylpentyl)-(5R)-carboxymethyl-(3S)-E/Z-[3-(propargyl-PEG4)-propenyl]pyrrolidine-1-carboxylic acid tert-butyl ester To a 0° C. stirring mixture of propargyl-PEG4-phosphonium bromide (1.0 mmol) in DMF (5.0 mL) it is added sodium hydride (1.1 mmol), and after 10 minutes temperature is raised to ambient. Stirring is continued for 1 h, then (2R)-((1R)-Acetylamino-(2S)-methoxy-(2S)-methylpentyl)-(5R)-carboxymethyl-(3S)-formylpyrrolidine-1-carboxylic acid tert-butyl ester (1.0 mmol) is added in DMF (1.0 mL). Upon completion, the reaction is quenched by saturated ammonium chloride solution. The aqueous solution is extracted several times with ethyl acetate, and the combined organic phases are washed with brine, dried, and evaporated. The residue is purified by chromatographic techniques to afford the desired product.

Step e. (2R)-((1R)-Acetylamino-(2S)-methoxy-(2S)-methylpentyl)-(5R)-carboxy-(3S) E/Z-[3-(propargyl-PEG4)-propenyl]pyrrolidine-1-carboxylic acid tert-butyl ester To a 0° C. stirring mixture of (2R)-((1R)-Acetylamino-(2S)-methoxy-(2S)-methylpentyl)-(5R)-carboxymethyl-(3S)-E/Z-[3-(propargyl-PEG4)-propenyl]pyrrolidine-1-carboxylic acid tert-butyl ester (1.0 mmol) in tetrahydrofuran (12.0 mL) and water (3.0 mL) it is added lithium hydroxide (1.1 mmol). Stirring is continued and the temperature is raised to ambient after 15 minutes. Upon completion, the solution is brought to acidic pH by the means of the excess addition of AMBERLITE® IRN-77 resin. The mixture is filtered and the filtrate is concentrated per vacuum techniques, yielding to the title compound. If necessary, the residue is purified by chromatographic techniques to afford the desired product.

Step f. (5R)-((1R)-Acetylamino-(2S)-methoxy-(2S)-methylpentyl)-(4S)-E/Z-[3-(propargyl-PEG4)-propenyl]-pyrrolidine-(2R)-carboxylic acid To a 0° C. stirring mixture of (2R)-((1R)-Acetylamino-(2S)-methoxy-(2S)-methylpentyl)-(5R)-carboxy-(3S) E/Z-[3-(propargyl-PEG4)-propenyl]pyrrolidine-1-carboxylic acid tert-butyl ester (1.0 mmol) and 2-methyl-2-butene (0.5 mL) in dichloromethane (8.0 mL), it is added trifluoroacetic acid (4.0 mL). After 10 minutes, the temperature is raised to ambient. Upon completion, all the volatiles are evaporated per vacuum techniques. The residue is purified by chromatographic techniques to afford the desired product.

Example 50. Synthesis of Conjugate 9

A solution of hIgG1 Fc-PEG4-azide in pH 7.4 PBS×1 buffer solution (100 mg, 1.71 umol, 7.011 mL, MW=58,200 Da, DAR=3.7) is added to a pH 7.4 PBS×1 buffer solution (2.45 mL) of Int-13 ((5R)-((1R)-Acetylamino-(2S)-methoxy-(2S)-methylpentyl)-(4S)-E/Z-[3-(propargyl-PEG4)-propenyl]-pyrrolidine-(2R)-carboxylic acid) (0.031 mmol), cupric sulfate (0.62 mmol), tris(3-hydroxypropyltriazolylmethyl)-amine (0.62 mmol), and sodium ascorbate (0.93 mmol). The resulting homogeneous solution is gently shaken with a rocker table for 12h. The crude solution is diluted with pH 7.4 PBS to a final concentration of 1 mg/mL, and ultrafiltered (10,000 MWCO) to a volume of 1 mL, for two times. The crude mixture is then diluted 1:10 in PBS pH 7.4, and purified using MabSelect Sure Resin (GE Healthcare, Chicago, IL, USA), followed by size exclusion chromatography. Purified material is quantified using a Nanodrop™ UV visible spectrophotomer (using a calculated extinction coefficient based on the amino acid sequence of the Fc used in the conjugation, and concentrated to approximately 10 mg/mL using a centrifugal concentrator (10,000 MWCO). Purified molecules are analyzed using 4-12% Bis Tris SDS PAGE gels by loading 1-2 ug of each molecule into the gel, and staining using instant Blue staining. Each gel includes a molecular weight ladder with the indicated molecular weight standards. MALDI MS analysis is used to determine the average DAR.

Example 51. Synthesis of Propargyl-PEG4-Phosphonium Bromide

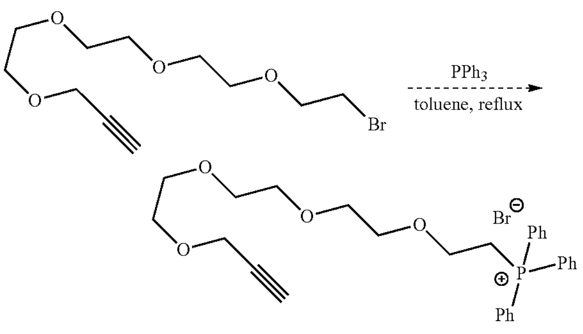

A mixture of propargyl-PEG4-bromide (1.0 mmol) and triphenylphosphine (1.2 mmol) in toluene (10 mL) are refluxed. Upon completion, the mixture is cooled to ambient. The solids are filtered and used in the next step without any additional purification.

Example 52. Synthesis of Int-14 ((5R)-[(1R)-(propargyl-PEG4-carboxyamide)-(2S)-methoxy-(2S)-methylpentyl]-(4S)—Z-propenylpyrrolidine-(2R)-carboxylic acid, HCl salt)

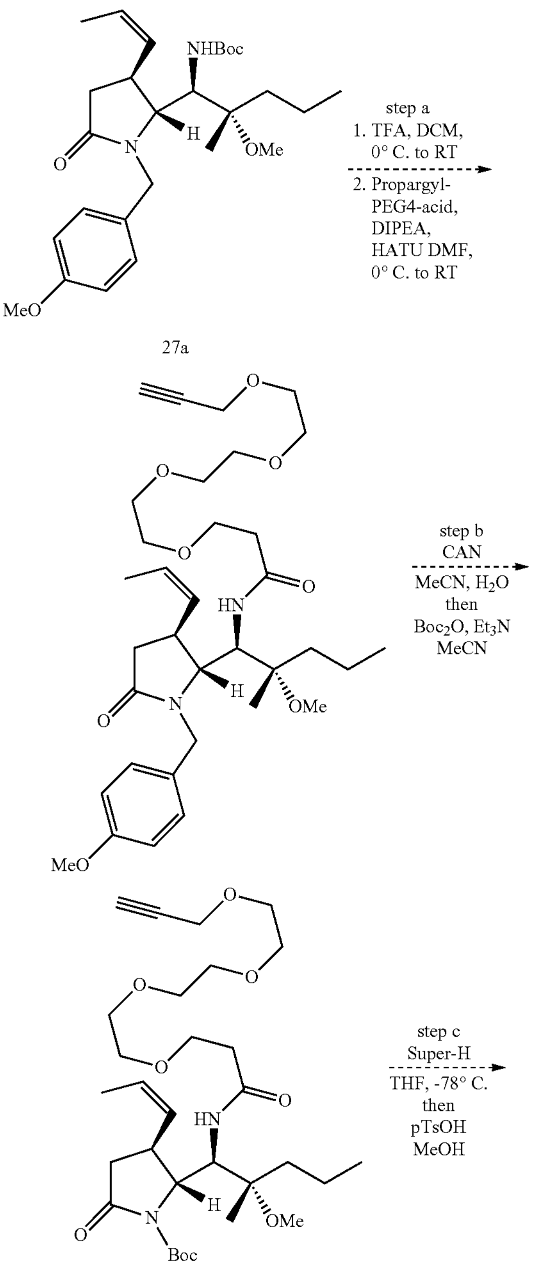

-continued

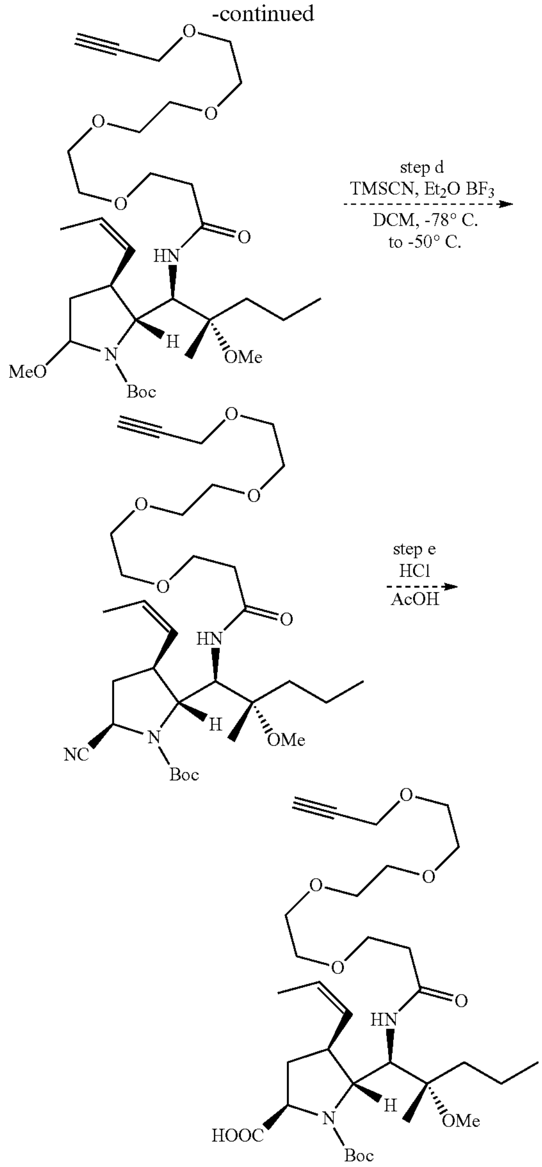

Step a. N-{(2.S)-methoxy-((1R)-[1-(4-methoxybenzyl)-5-oxo-(3S)—Z-propenylpyrrolidin-(2R)-yl]-(2S)-methylpentyl}-(propargyl-PEG4)-carboxyamide To 0° C. a stirring mixture of {(2S)-Methoxy-(1R)-[1-(4-methoxybenzyl)-5-oxo-(3S)—Z-propenylpyrrolidin-(2R)-yl]-(2S)-methylpentyl}-carbamic acid tert-butyl ester (it is prepared accordingly to reference JACS, 2002, 124, 4716-4721; 1.0 mmol) in dry dichloromethane (5 mL) is added trifluoroacetic acid (10 mmol), and the temperature is raised to ambient. Upon completion, the solvent is removed under reduced pressure. The resulting residue is dissolved in dichloromethane (20 mL) and extracted with a saturated aqueous solution of sodium bicarbonate. The organic layer is separated, dried (sodium sulfate), filtered and evaporated. The crude amine is dissolved in DMF (5 mL) and treated at 0° C. under stirring with propargyl-PEG4-acid (1.1 mmol), diisopropylethylamine (3.0 mmol) and HATU (1.1 mmol). Upon reaction completion, all the volatiles are evaporated per vacuum techniques. The residue is taken up in ethyl acetate (15 ml), and washed with saturated aqueous solution of sodium bicarbonate (10 mL), then 1 M sulfuric acid aqueous solution (10 mL). The combined organics are dried over sodium sulfate, filtered and concentrated. The residue is purified by chromatographic techniques to afford the desired product.

Step b. (2R)-((1R)-(propargyl-PEG4-carboxyamide)-(2S)-methoxy-(2S)-methylpentyl)-(5R)-oxo-(3S)—Z-propenylpyrrolidine-1-carboxylic acid tert-butyl ester To a stirring solution of N-{(2.S)-methoxy-(1R)-[1-(4-methoxybenzyl)-5-oxo-(3S)—Z-propenylpyrrolidin-(2R)-yl]-(2S)-methylpentyl}-(propargyl-PEG4)-carboxyamide (1.0 mmol) in a mixture of acetonitrile and water (10:1, 5 mL) is added ceric ammonium nitrate (2.0 mmol) in small portions at 45° C. during 1 h, and stirring is continued until completion. The reaction is quenched with a saturated aqueous solution of sodium bicarbonate (5 mL). The aqueous layer is extracted with EtOAc (3×10 mL), the combined organic layers are dried (sodium sulfate) and evaporated to give a crude which is used for the next step without further purification. The material is dissolved in acetonitrile (5 mL), di-tert-butylcarbonate is added (1.5 mmol) followed by triethylamine (2.0 mmol) and DMAP (catalytic). Upon completion, the reaction is quenched with a saturated solution of ammonium chloride (5 mL). The aqueous layer is extracted with EtOAc (3×10 mL), and the combined organic layers are dried (sodium sulfate). All the volatiles are removed per vacuum techniques. If necessary, the residue is purified by chromatographic techniques to afford the desired product.

Step c. (2R)-((1R)-(propargyl-PEG4-carboxyamide)-(2S)-methoxy-(2S)-methylpentyl)-(5R/S)-methoxy-(3S)—Z-propenylpyrrolidine-1-carboxylic acid tert-butyl ester To a −78° C. stirring solution of (2R)-((1R)-(propargyl-PEG4-carboxyamide)-(2S)-methoxy-(2S)-methylpentyl)-(5R)-oxo-(3S)—Z-propenylpyrrolidine-1-carboxylic acid tert-butyl ester (1.0 mmol) in THE (8 mL) is added SUPER-HYDRIDE® (1 M in THF, 2.2 mmol). After 30 min the reaction mixture is quenched with a saturated aqueous solution of sodium bicarbonate (4 mL) and 30% hydrogen peroxyde (5 drops). The mixture is warmed up to rt and stirred for another 30 min and the aqueous layer is extracted with EtOAc (3×10 mL). The combined organic layers are dried (sodium sulfate) and the solvent is evaporated to give the hemiaminal, which is used without further purification. To a solution of the above product in methanol (16 mL) is added p-toluenesulfonic acid hydrate (0.1 mmol) at rt. The reaction mixture is stirred overnight and is quenched with a saturated aqueous solution of sodium bicarbonate (10 mL). Methanol is removed under reduced pressure, water (10 mL) is added to the resulting residue and extracted with EtOAc (3×10 mL). The organics are separated and dried with brine and sodium sulfate, filtered and concentrated. If necessary, the residue is purified by chromatographic techniques to afford the desired product.

Step d. (2R)-((1R)-(propargyl-PEG4-carboxyamide)-(2S)-methoxy-(2S)-methylpentyl)-(5R)-cyano-(3S)—Z-propenylpyrrolidine-1-carboxylic acid tert-butyl ester To a −78° C. stirring solution of (2R)-((1R)-(propargyl-PEG4-carboxyamide)-(2S)-methoxy-(2S)-methylpentyl)-

(5R/S)-methoxy-(3S)—Z-propenylpyrrolidine-1-carboxylic acid tert-butyl ester (1.0 mmol) in dichloromethane (20 mL) it is added trimethylsilyl cyanide (2.0 mmol) followed by boron trifluoride diethyl etherate (1.2 mmol). The reaction mixture is stirred from −78° C. to −50° C. over a period of 3 h. A saturated aqueous solution of sodium bicarbonate (40 mL) is added and the aqueous layer is extracted with EtOAc (3×15 mL). The combined organic layers are dried (sodium sulfate), filtered and concentrated under reduced pressure. The resulting residue consisting of a mixture of epimeric cyano derivatives is purified by chromatographic techniques to afford the desired product.

Step e. (5R)-[(1R)-(propargyl-PEG4-carboxy-amide)-(2S)-methoxy-(2S)-methylpentyl]-(4S)—Z-propenylpyrrolidine-(2R)-carboxylic acid, HCl salt To a solution of (2R)-((1R)-(propargyl-PEG4-carboxy-amide)-(2S)-methoxy-(2S)-methylpentyl)-(5R)-cyano-(3S)—Z-propenylpyrrolidine-1-carboxylic acid tert-butyl ester (1.0 mmol) in AcOH (10 mL), 12N HCl (10 mL) is added at rt. The solution is stirred at rt until completion, the solvent is evaporated under reduced pressure. If necessary, the residue is purified by chromatographic techniques to afford the desired product.

Example 53. Synthesis of Conjugate 10

A solution of hIgG1 Fc-PEG4-azide in pH 7.4 PBS×1 buffer solution (100 mg, 1.71 umol, 7.011 mL, MW=58,200 Da, DAR=3.7) is added to a pH 7.4 PBS×1 buffer solution (2.45 mL) of Int-14 ((5R)-[(1R)-(propargyl-PEG4-carboxy-amide)-(2S)-methoxy-(2S)-methylpentyl]-(4S)—Z-propenylpyrrolidine-(2R)-carboxylic acid, HCl salt) (0.031 mmol), cupric sulfate (0.62 mmol), tris(3-hydroxypropyltri-azolylmethyl)-amine (0.62 mmol), and sodium ascorbate (0.93 mmol). The resulting homogeneous solution is gently shaken with a rocker table for 12h. The crude solution is diluted with pH 7.4 PBS to a final concentration of 1 mg/mL, and ultrafiltered (10,000 MWCO) to a volume of 1 mL, for two times. The crude mixture is then diluted 1:10 in PBS pH 7.4, and purified using MabSelect Sure Resin (GE Healthcare, Chicago, IL, USA), followed by size exclusion chromatography. Purified material is quantified using a Nanodrop™ UV visible spectrophotomer (using a calculated extinction coefficient based on the amino acid sequence of the Fc used in the conjugation, and concentrated to approximately 10 mg/mL using a centrifugal concentrator (10,000 MWCO). Purified molecules are analyzed using 4-12% Bis Tris SDS PAGE gels by loading 1-2 ug of each molecule into the gel, and staining using instant Blue staining. Each gel includes a molecular weight ladder with the indicated molecular weight standards. MALDI MS analysis is used to determine the average DAR.

Example 54. Synthesis of Int-15, HCl Salt

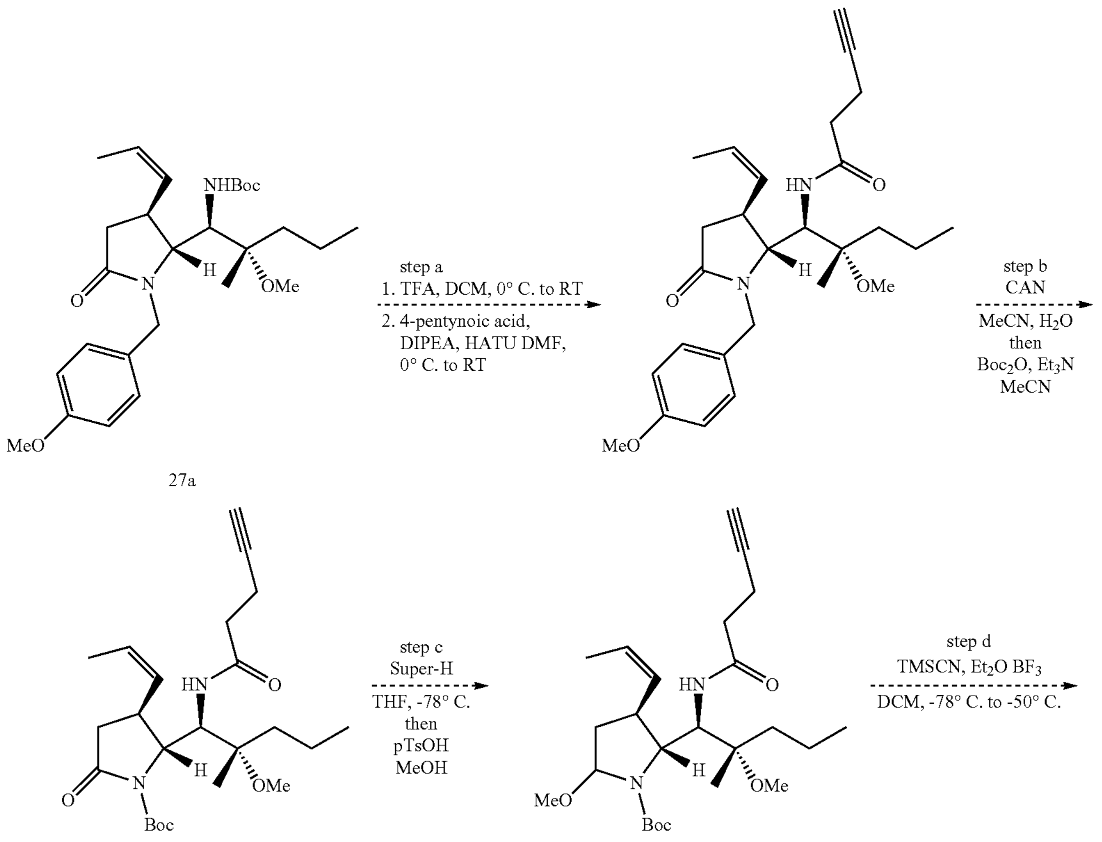

-continued
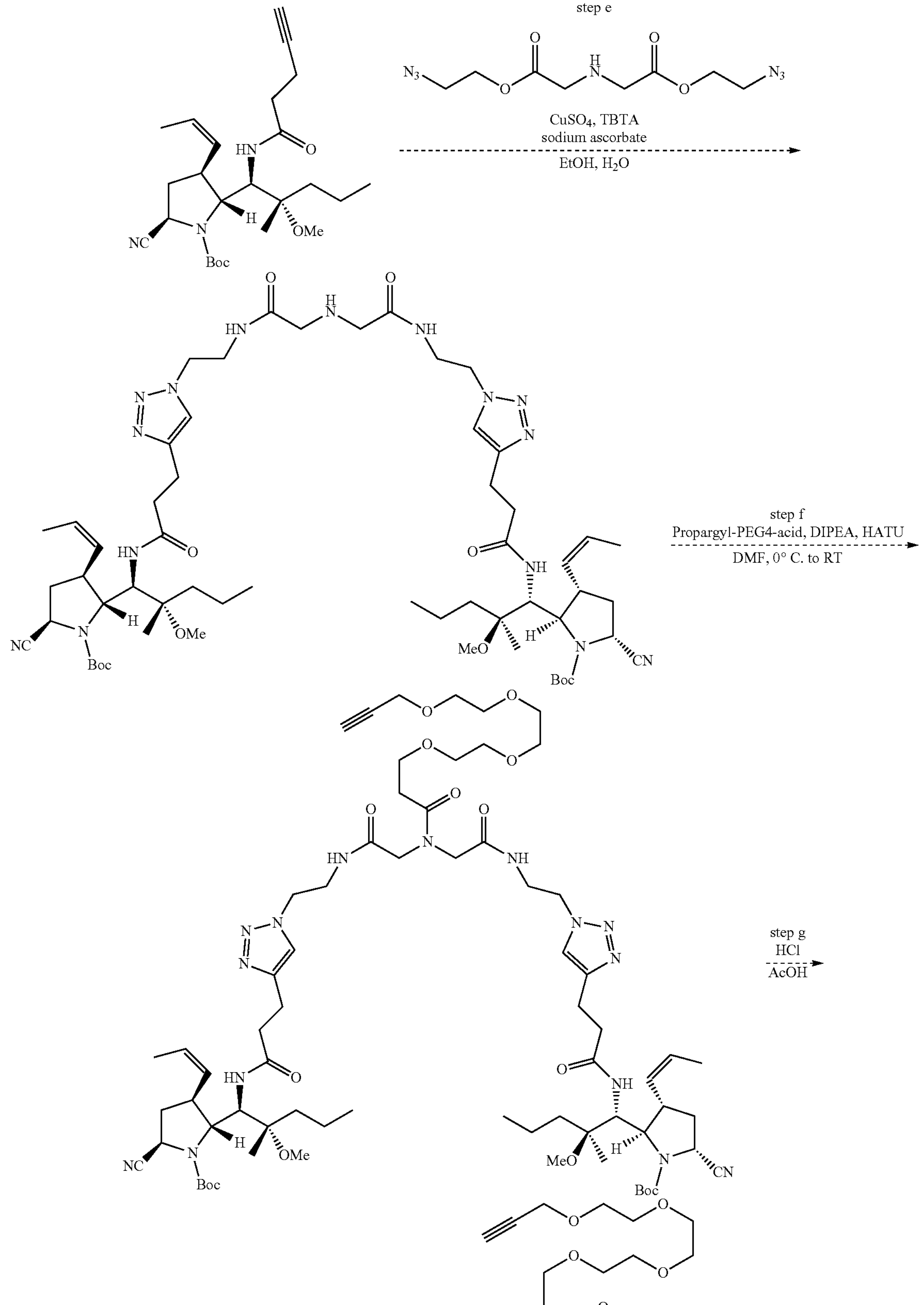

Step a. N-{(2.S)-methoxy-((1R)-[1-(4-methoxybenzyl)-5-oxo-(3S)—Z-propenylpyrrolidin-(2R)-yl]-(2S)-methylpentyl}-(3-butynyl)-carboxyamide To 0° C. a stirring mixture of {(2S)-Methoxy-(1R)-[1-(4-methoxybenzyl)-5-oxo-(3S)—Z-propenylpyrrolidin-(2R)-yl]-(2S)-methylpentyl}-carbamic acid tert-butyl ester (it is prepared accordingly to reference JACS, 2002, 124, 4716-4721; 1.0 mmol) in dry dichloromethane (5 mL) is added trifluoroacetic acid (10 mmol), and the temperature is raised to ambient. Upon completion, the solvent is removed under reduced pressure. The resulting residue is dissolved in dichloromethane (20 mL) and extracted with a saturated aqueous solution of sodium bicarbonate. The organic layer is separated, dried (sodium sulfate), filtered and evaporated. The crude amine is dissolved in DMF (5 mL) and treated at 0° C. under stirring with 4-pentynoic acid (1.1 mmol), diisopropylethylamine (3.0 mmol) and HATU (1.1 mmol). Upon reaction completion, all the volatiles are evaporated per vacuum techniques. The residue is taken up in ethyl acetate (15 ml), and washed with saturated aqueous solution of sodium bicarbonate (10 mL), then 1 M sulfuric acid aqueous solution (10 mL). The combined organics are dried over sodium sulfate, filtered and concentrated. The residue is purified by chromatographic techniques to afford the desired product.

Step b. (2R)-((1R)-(4-pentynoyl)-(2S)-methoxy-(2S)-methylpentyl)-(5R)-oxo-(3S)—Z-propenylpyrrolidine-1-carboxylic acid tert-butyl ester To a stirring solution of N-{(2.S)-methoxy-((1R)-[1-(4-methoxybenzyl)-5-oxo-(3S)—Z-propenylpyrrolidin-(2R)-yl]-(2S)-methylpentyl}-(3-butynyl)-carboxyamide (1.0 mmol) in a mixture of acetonitrile and water (10:1, 5 mL) is added ceric ammonium nitrate (2.0 mmol) in small portions at 45° C. during 1 h, and stirring is continued until completion. The reaction is quenched with a saturated aqueous solution of sodium bicarbonate (5 mL). The aqueous layer is extracted with EtOAc (3×10 mL), the combined organic layers are dried (sodium sulfate) and evaporated to give a crude which is used for the next step without further purification. The material is dissolved in acetonitrile (5 mL), di-tert-butylcarbonate is added (1.5 mmol) followed by triethylamine (2.0 mmol) and DMAP (catalytic). Upon completion, the reaction is quenched with a saturated solution of ammonium chloride (5 mL). The aqueous layer is extracted with EtOAc (3×10 mL), and the combined organic layers are dried (sodium sulfate). All the volatiles are removed per vacuum techniques. If necessary, the residue is purified by chromatographic techniques to afford the desired product.

Step c. (2R)-((1R)-(4-pentynoyl)-(2S)-methoxy-(2S)-methylpentyl)-(5R/S)-methoxy-(3S)—Z-propenylpyrrolidine-1-carboxylic acid tert-butyl ester To a −78° C. stirring solution of (2R)-((1R)— (2R)-((1R)-(4-pentynoyl)-(2S)-methoxy-(2S)-methylpentyl)-(5R)-oxo-(3S)—Z-propenylpyrrolidine-1-carboxylic acid tert-butyl ester (1.0 mmol) in THE (8 mL) is added SUPER-HYDRIDE® (1 M in THF, 2.2 mmol). After 30 min the reaction mixture is quenched with a saturated aqueous solution of sodium bicarbonate (4 mL) and 30% hydrogen peroxyde (5 drops). The mixture is warmed up to rt and stirred for another 30 min and the aqueous layer is extracted with EtOAc (3×10 mL). The combined organic layers are dried (sodium sulfate) and the solvent is evaporated to give the hemiaminal, which is used without further purification. To a solution of the above product in methanol (16 mL) is added p-toluenesulfonic acid hydrate (0.1 mmol) at rt. The reaction mixture is stirred overnight and is quenched with a saturated aqueous solution of sodium bicarbonate (10 mL). Methanol is removed under reduced pressure, water (10 mL) is added to the resulting residue and extracted with EtOAc (3×10 mL). The organics are separated and dried with brine and sodium sulfate, filtered and concentrated. If necessary, the residue is purified by chromatographic techniques to afford the desired product.

Step d. (2R)-((1R)-(4-pentynoyl)-(2S)-methoxy-(2S)-methylpentyl)-(5R)-cyano-(3S)—Z-propenylpyrrolidine-1-carboxylic acid tert-butyl ester To a −78° C. stirring solution of (2R)-((1R)-(4-pentynoyl)-(2S)-methoxy-(2S)-methylpentyl)-(5R/S)-methoxy-(3S)—Z-propenylpyrrolidine-1-carboxylic acid tert-butyl ester (1.0 mmol) in dichloromethane (20 mL) it is added trimethylsilyl cyanide (2.0 mmol) followed by boron trifluoride diethyl etherate (1.2 mmol). The reaction mixture is stirred from −78° C. to −50° C. over a period of 3 h. A saturated aqueous solution of sodium bicarbonate (40 mL) is added and the aqueous layer is extracted with EtOAc (3×15 mL). The combined organic layers are dried (sodium sulfate), filtered and concentrated under reduced pressure. The resulting residue consisting of a mixture of epimeric cyano derivatives is purified by chromatographic techniques to afford the desired product.

Step e

To a stirring mixture of N-{(2.S)-methoxy-((1R)-[1-(4-methoxybenzyl)-5-oxo-(3S)—Z-propenylpyrrolidin-(2R)-yl]-(2S)-methylpentyl}-(3-butynyl)-carboxyamide (1.0 mmol), bis-[N'-(2-azidoethyl)]-iminodiacetic amide (0.5 mmol), 1 H-1,2,3-Triazole-4-methanamine, 1-(phenylmethyl)-N,N-bis[1-(phenylmethyl)-1H-1,2,3-triazol-4-yl] methyl]- (0.1 mmol) and sodium ascorbate (1.0 mmol) in ethanol (5 mL) and water (5 mL), it is added copper sulfate (0.1 mmol). Upon completion, the reaction is treated with SiliaMetS TAAcONa (0.3 mmol) for 30 minutes. The reaction is filtered and all the volatiles are evaporated per vacuum techniques. The residue is purified by chromatographic techniques to afford the desired product.

Step f

To 0° C. a stirring solution of the intermediate from step e. (1.0 mmol), propargyl-PEG4-acid (1.05 mmol), and DIPEA (3.0 mmol) in DMF (10 mL) it is added HATU (2.0 mmol). All the volatiles are evaporated per vacuum techniques and the residue is purified by chromatographic techniques to afford the desired product.

Step g. Int-15, HCl Salt

To a solution of the intermediate from step f. (1.0 mmol) in AcOH (10 mL), 12N HCl (10 mL) is added at rt. The solution is stirred at rt until completion, the solvent is evaporated under reduced pressure. If necessary, the residue is purified by chromatographic techniques to afford the desired product.

Example 55. Synthesis of Conjugate 11

A solution of hIgG1 Fc-PEG4-azide in pH 7.4 PBS×1 buffer solution (100 mg, 1.71 umol, 7.011 mL, MW=58,200

Da, DAR=3.7) is added to a pH 7.4 PBS×1 buffer solution (2.45 mL) of Int-15 HCl salt (0.031 mmol), cupric sulfate (0.62 mmol), tris(3-hydroxypropyltriazolylmethyl)-amine (0.62 mmol), and sodium ascorbate (0.93 mmol). The resulting homogeneous solution is gently shaken with a rocker table for 12h. The crude solution is diluted with pH 7.4 PBS to a final concentration of 1 mg/mL, and ultrafiltered (10,000 MWCO) to a volume of 1 mL, for two times. The crude mixture is then diluted 1:10 in PBS pH 7.4, and purified using MabSelect Sure Resin (GE Healthcare, Chicago, IL, USA), followed by size exclusion chromatography. Purified material is quantified using a Nanodrop™ UV visible spectrophotomer (using a calculated extinction coefficient based on the amino acid sequence of the Fc used in the conjugation, and concentrated to approximately 10 mg/mL using a centrifugal concentrator (10,000 MWCO). Purified molecules are analyzed using 4-12% Bis Tris SDS PAGE gels by loading 1-2 ug of each molecule into the gel, and staining using instant Blue staining. Each gel includes a molecular weight ladder with the indicated molecular weight standards. MALDI MS analysis is used to determine the average DAR.

Example 56. Synthesis of bis-[N'-(2-azidoethyl)]-iminodiacetic amide

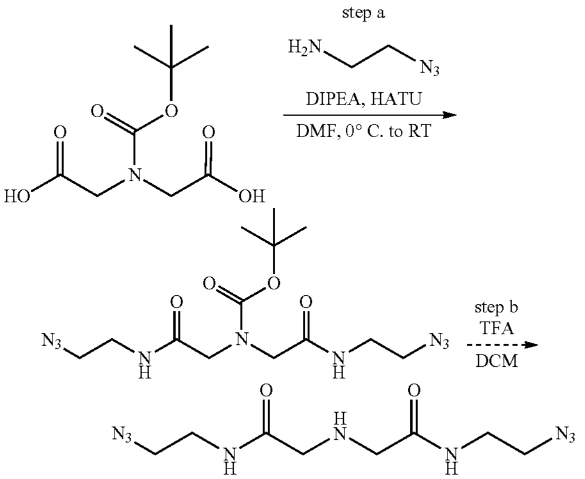

Step a. Bis-[N'-(2-azidoethyl)]-N-Boc-iminodiacetic amide

To 0° C. a stirring solution of N-Boc-iminodiacetic acid (1.0 mmol), 2-azidoethan-1-amine hydrochloride (2.0 mmol), and DIPEA (6.0 mmol) in DMF (10 mL) it is added HATU (2.0 mmol). All the volatiles are evaporated per vacuum techniques and the residue is purified by chromatographic techniques to afford the desired product.

Step b. Bis-[N'-(2-azidoethyl)]-iminodiacetic amide

To a 0° C. stirring mixture of Bis-[N'-(2-azidoethyl)]-N-Boc-iminodiacetic amide (1.0 mmol) and 2-methyl-2-butene (0.5 mL) in dichloromethane (8.0 mL), it is added trifluoroacetic acid (4.0 mL). After 10 minutes, the temperature is raised to ambient. Upon completion, all the volatiles are evaporated per vacuum techniques. The residue is purified by chromatographic techniques to afford the desired product.

Example 57. Synthesis of Int-16

A monomer of sulfozanamivir conjugated to a PEG4-alkyne linker and which may be further conjugated to an Fc domain or an albumin protein is produced according to the following synthetic scheme. Sulfozanamivir starting material is produced according to Hadházi et al. A sulfozanamivir analogue has potent anti-influenza virus activity. *ChemMedChem Comm.* 13:785-789 (2018).

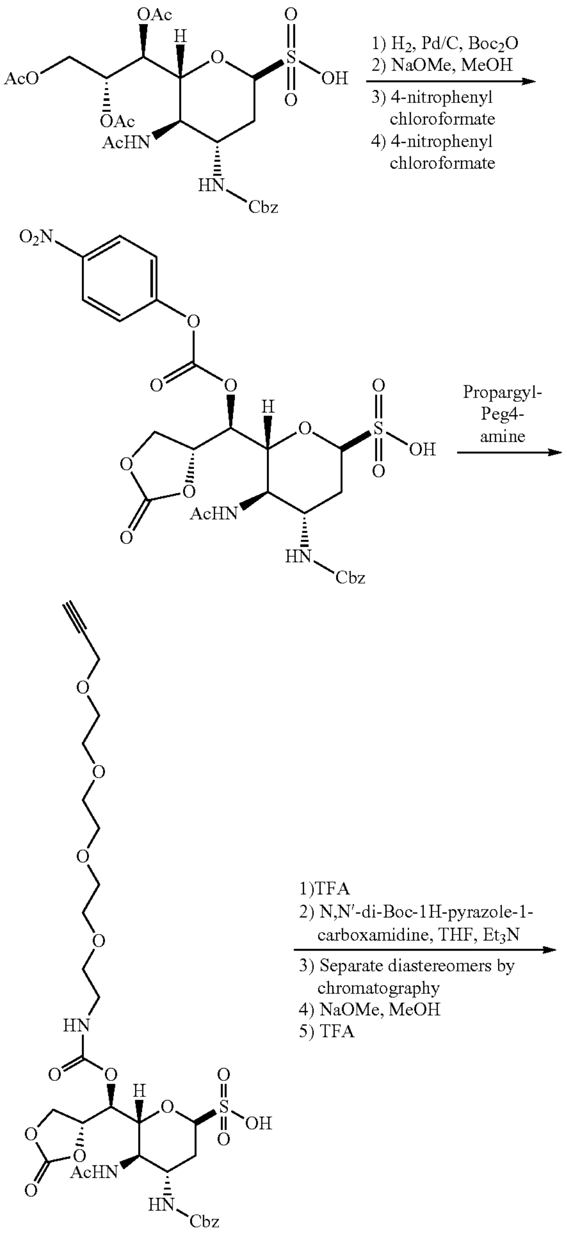

-continued

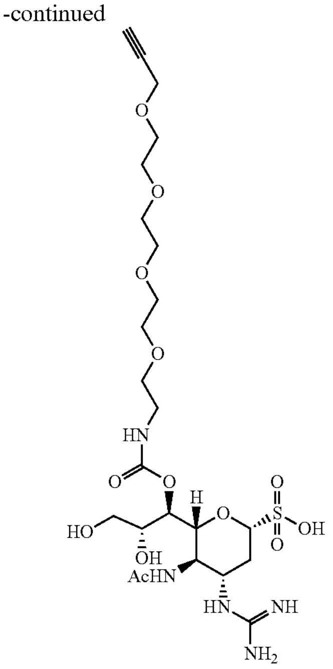

Example 58. Synthesis of Int-17

A dimer of sulfozanamivir conjugated to a PEG4-alkyne linker and which may be further conjugated to an Fc domain or an albumin protein is produced according to the following synthetic scheme. Sulfozanamivir starting material is produced according to Hadházi et al. A sulfozanamivir analogue has potent anti-influenza virus activity. *ChemMedChem Comm.* 13:785-789 (2018).

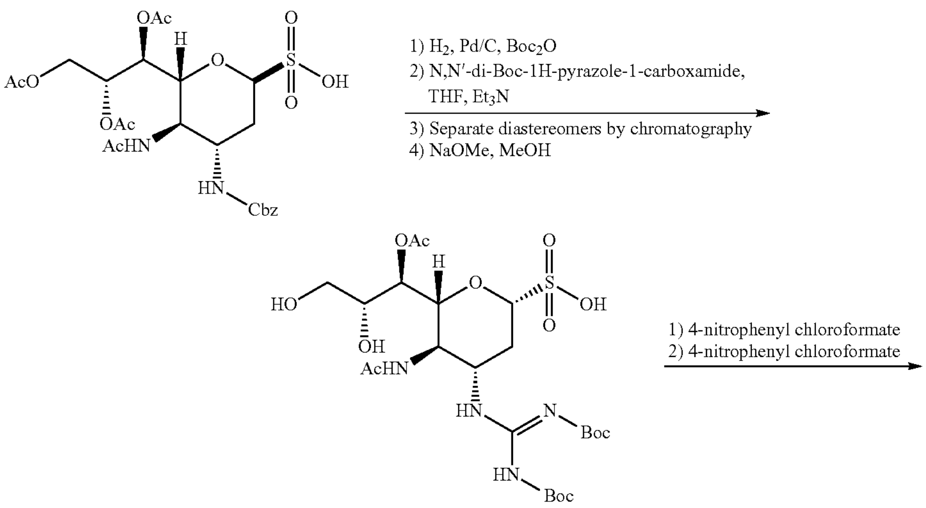

-continued

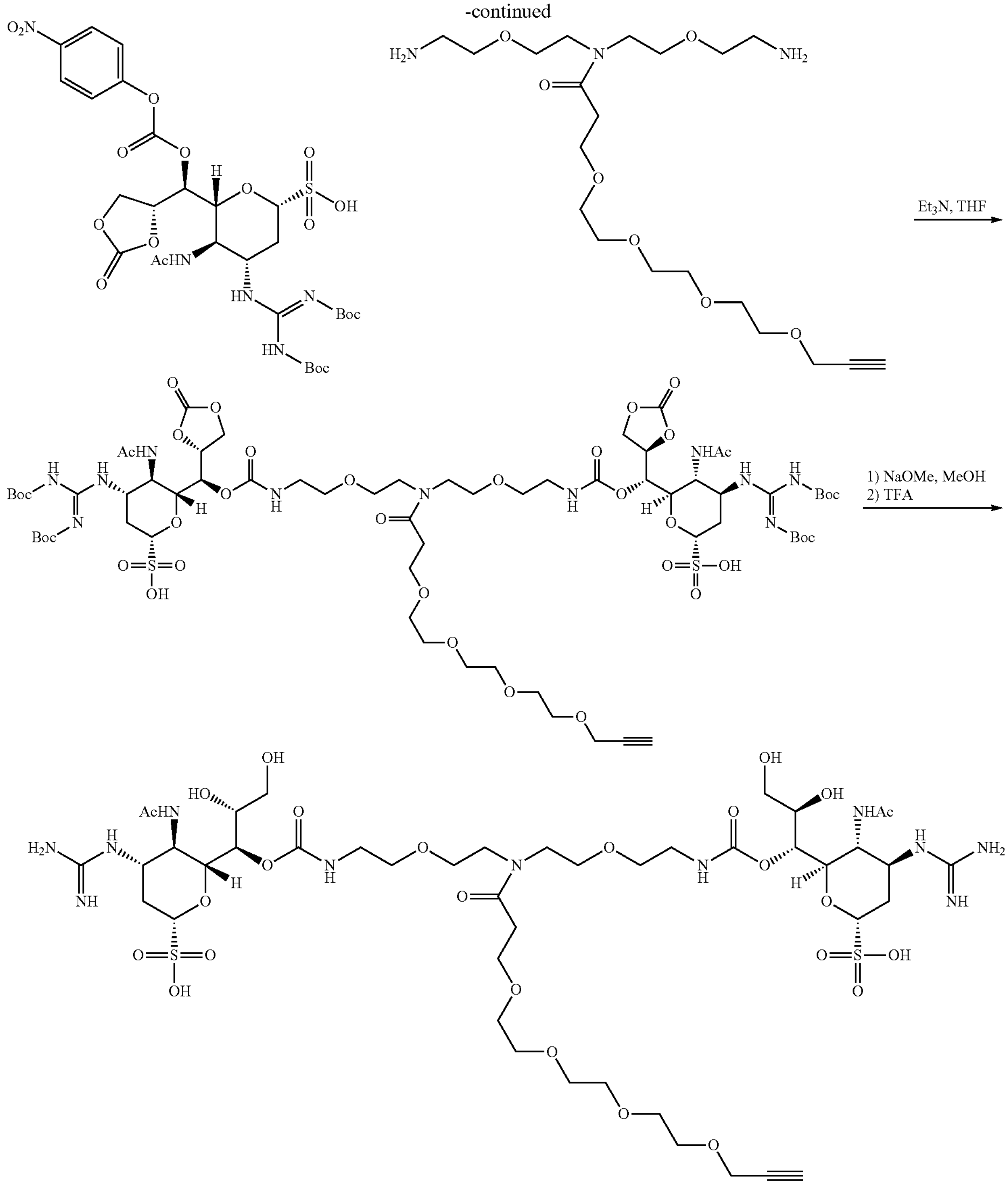

Example 59. Synthesis of Conjugate 12

Figure 54:
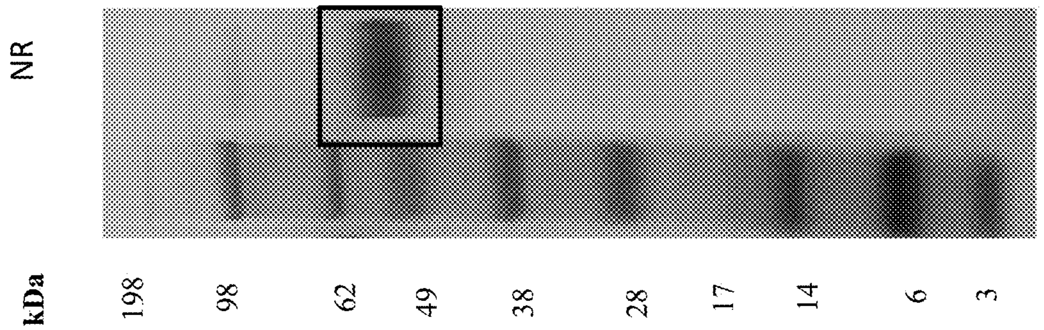
FIG. 54 shows a non-reducing SDS-PAGE of Conjugate 12.

A solution of azido functionalized aglycosylated Fc (70 mg, 4.7 mL, 1.3709 μmol) was added to a 15 mL centrifuge tube containing alkyne derivatized small molecule (29.8 mg, 0.0216 mmol, Int-7). After gently shaking to dissolve all solids, the mixture was added with 206 μl of a mixture solution of L-ascorbic acid sodium (59.4 mg, 0.3 mmol), copper (II) sulfate (15.9 mg, 0.1 mmol), and THPTA (43.5 mg, 0.1 mmol) in PBS 7.4 buffer (1 ml). The resulting mixture was gently shaken overnight. It was purified by affinity chromatogragphy over a protein A column, followed by size exclusion chromatography as described in Example 8. Maldi TOF analysis of the purified final product gave an average mass of 56,177 Da (DAR=3.6). Yield 10.1 mg, 14% yield. A non-reducing SDS-PAGE of Conjugate 12 is provided in FIG. 54.

Example 60. Synthesis of Int-18

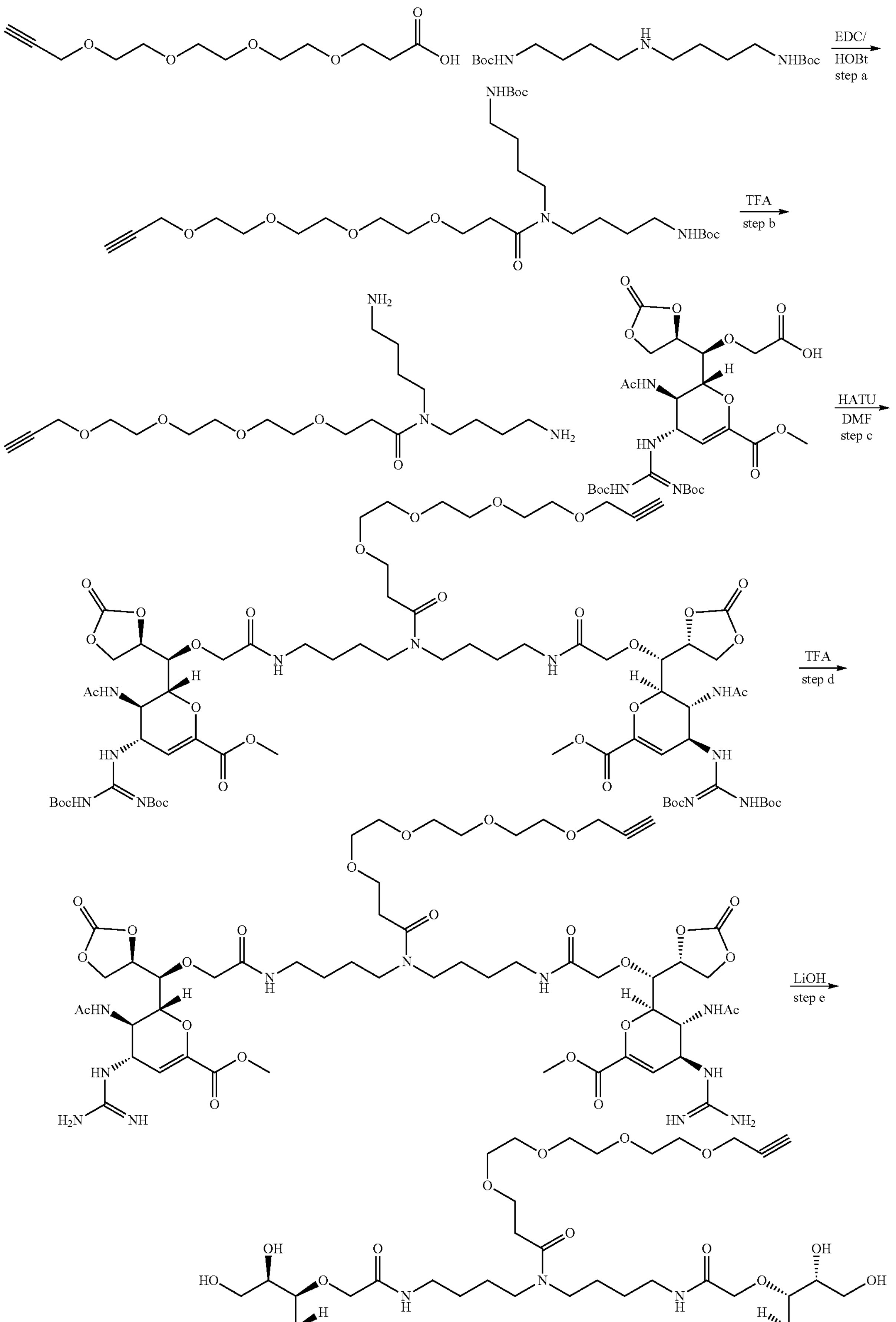
EDC/
HOBt
step a
TFA
step b
HATU
DMF
step c
TFA
step d
LiOH
step e

Step a. Synthesis of tert-butyl (17-{4-[(tert-butoxy-carbonyl)amino]butyl}-16-oxo-4,7,10,13-tetraoxa-17-azahenicos-1-yn-21-yl)carbamate

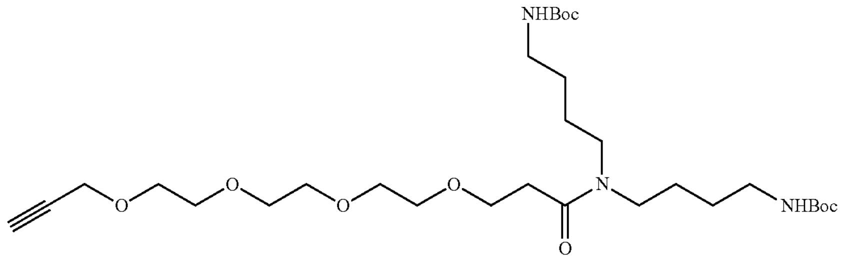 [SMILES: C#CCOCCOCCOCCOCCC(=O)N(CCCCNC(=O)OC(C)(C)C)CCCCNC(=O)OC(C)(C)C]

To the solution of di-tert-butyl [azanediyldi(butane-4,1-diyl)]biscarbamate (1.5 g, 4.17 mmol from Example 45, step a) and propargyl-PEG4-acid (1.08 g, 4.17 mmol) in DCM (40 mL) was added EDC (1.0 g, 5 mmol), HOBt (650 mg, 5 mmol), and DIEA (1.4 ml, 10 mmol) at room temperature, then stirred overnight at room temperature. The resulting solution was concentrated and purified by and purified by reverse phase liquid chromatography (RPLC) using an Isco COMBIFLASH® liquid chromatograph eluted with 10% to 100% acetonitrile and water with no modifier. Yield of 1.9 g, 76%. Ion(s) found by LCMS: M+H=602.4.

Step b. Synthesis of N,N-bis(4-aminobutyl)-4,7,10,13-tetraoxahexadec-15-yn-1-amide

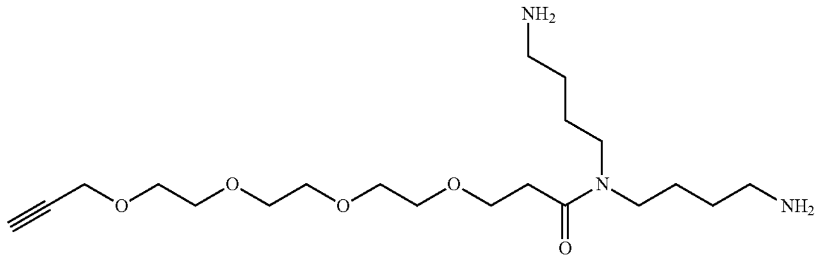 [SMILES: C#CCOCCOCCOCCOCCC(=O)N(CCCCN)CCCCN]

Tert-butyl (17-{4-[(tert-butoxycarbonyl)amino]butyl}-16-oxo-4,7,10,13-tetraoxa-17-azahenicos-1-yn-21-yl)carbamate (1.90, 3.1 mmol) was treated with 20 ml TFA at room temperature for 0.5 hour, then concentrated to dryness and used in the next step without further purification. Yield is quantitative for this step. Ion(s) found by LCMS: M/2+H=402.3.

Step c. Synthesis of Full Protected Int-18

N,N-bis(4-aminobutyl)-4,7,10,13-tetraoxahexadec-15-yn-1-amide (0.150 g, 0.32 mmol) was added to a solution of the ether linked of zanamivir acid (0.400 g, 0.63 mmol, described in Example 31, step f) in DCM (10 mL), then treated with EDC (0.200 g, 1.0 mmol), HOBt (0.135 g, 1.00 mmol), and DIEA (0.14 ml, 1.00 mmol) at room temperature for overnight. The resulting solution was concentrated and purified by and purified by reverse phase liquid chromatography (RPLC) using an Isco COMBIFLASH® liquid chromatograph eluted with 10% to 100% acetonitrile and water with no 0.1% TFA as modifier. Yield of the products 310 mg, 60.3%. Ion(s) found by LCMS: M/2+H=813.9.

Step d. Synthesis Int-18

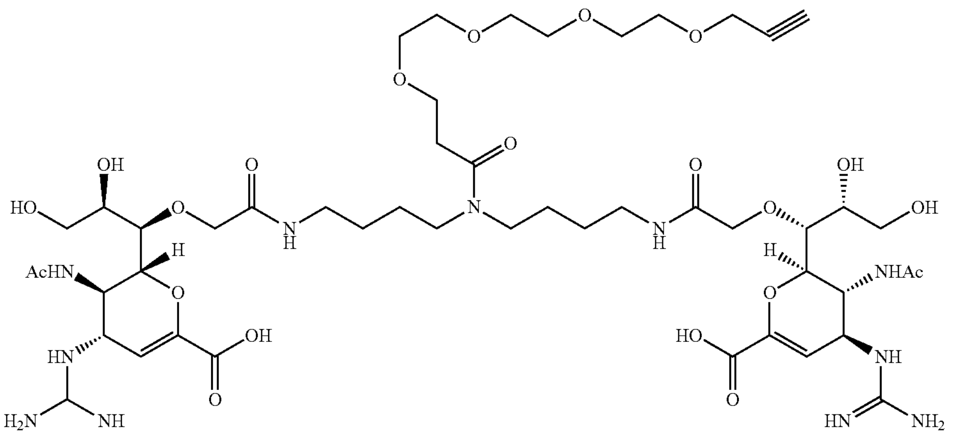 [SMILES: C#CCOCCOCCOCCOCCC(=O)N(CCCCNC(=O)CO[C@@H]([C@@H]1OC(C(=O)O)=C[C@H](NC(=N)N)[C@H]1NC(C)=O)[C@H](O)CO)CCCCNC(=O)CO[C@@H]([C@@H]1OC(C(=O)O)=C[C@H](NC(N)N)[C@H]1NC(C)=O)[C@H](O)CO]

Product from the previous step (300 mg, 0.18 mmol) was treated with trifluoroacetic acid (2 mL) acid and stirred for 30 min at room temperature. The resulting solution was concentrated, re-dissolved in water (2 mL), then treated with a solution of lithium hydroxide (24 mg, 1 mmol) dissolved in water (1 mL). The reaction was stirred 10 min then quenched with 0.1 ml acetic acid, concentrated and purified by reverse phase liquid chromatography (RPLC) using an Isco COMBIFLASH® liquid chromatograph eluted with 0% to 50% acetonitrile and water, using 0.1% TFA as the modifier. Yield of the products 140 mg, 52%. Ion(s) found by LCMS: M/2+H=573.8, M/3+H=382.9.

Example 61. Synthesis of PEG4-azido Fc for Conjugate 13a c-Preparation of 0.05M PEG4-azidoNHS Ester Solution in DMF/PBS PEG4-azido NHS ester (80.5 mg) was dissolved in DMF (0.50 mL) at 0° C. and diluted to 4.063 mL by adding 3.50 mL of PBS 1× buffer at 0° C. This solution was used for preparing other PEG4-azido Fc with variety of drug-antibody ratio (DAR) values by adjusting the equivalents of this PEG4-azido NHS ester PBS×1 solution.

Preparation of PEG4-Azido Fc 0.05M PEG4-azidoNHS ester PBS×1 buffer solution (0.0984 mL, 4.92 μmol, 2.5 equivalents) was added to a solution of h-IgG1 Fc (105 mg in 5.031 mL of pH 7.4 PBS, MW~53,360 Da, 1.968 μmol) and the mixture was shaken gently for 12 hours at ambient temperature. The solution was concentrated using a centrifugal concentrator (30,000 MWCO) to a volume of ~1.5 mL. The crude mixture was diluted 1:10 in PBS pH 7.4, and concentrated again. This wash procedure was repeated for total of three times. The unreacted azido reagent was removed with this procedure. The concentrated Fc-PEG4-azide was diluted to 5.03 mL with pH 7.4 PBS 1× buffer and ready for click conjugation. The purified material was quantified using a Nanodrop™ UV visible spectrophotomer (using a calculated extinction coefficient based on the amino acid sequence of h-IgG1). The yield was quantitative after buffer exchange/purification.

Example 62. Synthesis of Conjugate 13a

Preparation of click reagent solution: 0.0050M $CuSO_4$ in PBS buffer solution: 20.0 mg $CuSO_4$ was dissolved in 25.0 mL PBS×1, than took 22.0 mL above $CuSO_4$ solution and added 189.4 mg BTTAA and 1090 mg Na Ascorbate to give a clear solution (0.0050M CuSO4, 0.020M BTTAA and 0.25M Sodium Ascorbate).

A solution of azido functionalized Fc (100 mg, 4.79 mL, 1.87 μmol, CTP-161-4A-Linker-1-Azide) was added to a 15 mL centrifuge tube containing alkyne derivatized small molecule, Int-18 (11.2 mg, 0.00750 mmol, prepared in Example 60). After gently shaking to dissolve all solids, the solution was treated with 3.00 mL of above click reagent solution. The resulting colorless homogeneous solution was gently shaken overnight. It was purified by affinity chromatography over a protein A column, followed by size exclusion chromatography (see general conjugate purification protocol in Example 10). Maldi TOF analysis of the purified final product gave an average mass of 55,913 Da (DAR=1.7). Yield 54.0 mg, 54% yield.

Figure 55:
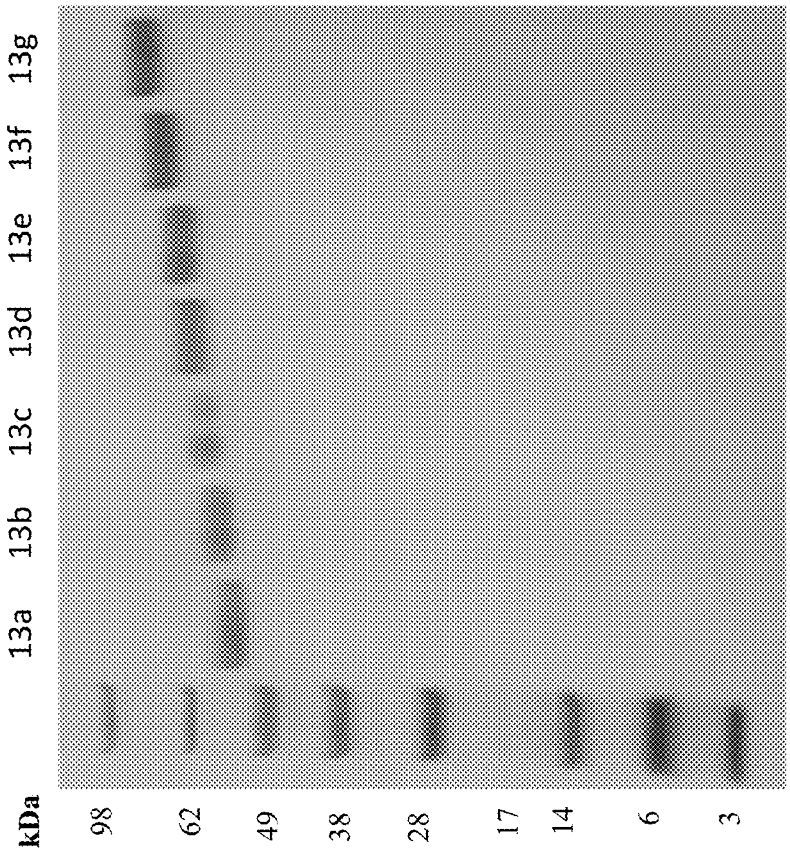
FIG. 55 shows a non-reducing SDS-PAGE of Conjugate 13 having different drug-to-antibody (DAR) ratio values (Conjugate 13a, Conjugate 13b, Conjugate 13c, Conjugate 13d, Conjugate 13e, Conjugate 13f, and Conjugate 13g).

Example 63. Syntheses of Conjugate 13b, Conjugate 13c, Conjugate 13d, Conjugate 13e, Conjugate 13f, and Conjugate 13g The PEG4-azido Fcs for Conjugate 13b, Conjugate 13c, Conjugate 13d, Conjugate 13e, Conjugate 13f, and Conjugate 13g were prepared analogously to the PEG4-azido Fc of Conjugate 13a (Example 61) adjusting the number of equivalents of PEG4-azido NHS ester as described in the table below. Conjugate 13b, Conjugate 13c, Conjugate 13d, Conjugate 13e, Conjugate 13f, and Conjugate 13g were prepared analogously to Conjugate 13a in Example 62 where the number of equivalents of targeting moiety (Int-18) was adjusted based on the desired DAR value (Table 26), and the volume of click reagent solution used was the same volume as employed in the procedure for Example 62. The DAR values, molecular weights and yields are listed in the table below. Product conjugates were purified by affinity chromatography over a protein A column, followed by size exclusion chromatography as described in Example 8. A non-reducing SDS-PAGE of Conjugates 13a-13g is provided in FIG. 55.

TABLE 26

Yields of Conjugates 13a-13g

| Sample Name | Equivalents of PEG4-azido NHS ester | DAR (Average) | MALDI mass Da (Average) | Targeting moiety (TM) | Equivalents of TM | Protein Type | Yield (%) |
|---|---|---|---|---|---|---|---|
| Conjugate 13a | 2.5 | 1.7 | 55913 | Int-18 | 4 | hIgG1 Fc | 54% |
| Conjugate 13b | 4.5 | 2.7 | 57278 | Int-18 | 6 | hIgG1 Fc | 50% |
| Conjugate 13c | 6.5 | 3.8 | 58908 | Int-18 | 8 | hIgG1 Fc | 60% |
| Conjugate 13d | 8.5 | 4.7 | 60149 | Int-18 | 10 | hIgG1 Fc | 54% |
| Conjugate 13e | 11 | 5.8 | 61726 | Int-18 | 12 | hIgG1 Fc | 55% |
| Conjugate 13f | 18 | 8.2 | 65146 | Int-18 | 16 | hIgG1 Fc | 53% |
| Conjugate 13g | 25 | 10.3 | 68153 | Int-18 | 20 | hIgG1 Fc | 45% |

Example 64. In Vitro Stability of Conjugate 6

To demonstrate the in vitro stability of Conjugate 6 using both mouse and human fresh K2EDTA treated plasma and liver microsomes. The in vitro mouse and human plasma stability was determined by comparing the Drug to Antibody Ratio (DAR) envelope after a 24 hr incubation in plasma at 37° C. by MALDI-TOF mass spectrometric detection. Liver microsomal stability using mouse and human microsomes was also performed after incubation for 24 hr at 37° C. with MALDI-TOF mass spectrometric detection. This was to identify potential metabolically labile sites on the Fc protein, linker, or target moiety.

64.1 Plasma Stability Sample Preparation

First, 60 μL of Conjugate 6 at 3 mg/ml was mixed with 120 μL plasma. Each plasma type was aliquoted into 2 tubes. One aliquot was immediately frozen from each plasma type. The remaining aliqoute was placed in a water bath (37° C.) for 24 hours. MAGNE® Protein A beads (Promega) were equilibrated by gently vortexing the beads into suspension. In duplicate for both plasma types, 50 μL of bead slutty was added to a 1.5 mL microcentrifuge tube and placed on the magnetic stand for 10 seconds. After 10 seconds, the storage buffer was removed and discarded. 500 μL of bind/wash buffer (0.1% BSA in 1×PBS pH 7.4) was added to the 1.5 mL microcentrifuge tube containing the beads. The beads were mixed (vortexing) and placed on a magnetic stand for 10 seconds. After 10 seconds, the bind/wash buffer was removed and discarded. 50 μL of buffer (1×PBS, pH 7.4) was added to the microcentrifuge tube containing the beads. 50 μL of the plasma mixture was added to the beads and gently vortexed to mix. Using a tube shaker, the sample was mixed at room temperature for 60 minutes, ensuring the beads remained in suspension. After mixing, the tube was placed on a magnetic stand for 10 seconds and the supernatant was removed. 500 μL of buffer (1×PBS, pH 7.4) was added and gently vortexed to mix. After mixing, the tube was placed on a magnetic stand for 10 seconds, followed by removal and discarding of wash buffer. The wash step was repeated for a total of 2 washed. Following 2 washes with 500 μL of buffer (1×PBS, pH 7.4), 3 washes with 500 μL, 200 μL, and 100 μL, respectively, of water were performed. The appropriate volume of water was added to the tube and gently vortexed to mix well and then placed on a magnetic stand for 10 seconds prior to removal and discarding of the water. After the third wash with water, 30 μL of elution buffer (90:10:0.4 Water:Acetonitrile:TFA) was added to the beads. Using a tube shaker, the elution buffer and sample were mixed for 30 minutes at room temperature. After mixing, the tube was placed on a magnetic stand for 10 seconds, the elution buffer, containing the sample, was removed and kept. 2 μL of sample were mixed with 2 μL of MALDI matrix (20 mg/mL Sinapic Acid in 70:30:0.1 water: acetonitrile:TFA) and spotted onto a MALDI target plate using a dual layer technique. The sample was then analyzed by MALDI-TOF mass spectrometry.

64.2 Liver Microsomal Sample Preparation

A 10× buffer was made with 500 mM Tris-HCl at pH 7.5 and 50 mM magnesium chloride hexahydrate. ACV-006 was diluted to 50 μM in 1×PBS, pH 7.4. Liver microsomes were thawed and vortexed. An aliquot of each species of liver microsomes (human and mouse) were heat killed at 70° C. for 15 minutes for use as a control. Reaction mixtures were prepared for both species according to Table 27. Tubes were incubated in a water bath (37° C.) for 24 hours. Samples were extracted for analysis using MAGNE® Protein A beads (Promega) following the protocol from 59.1.

TABLE 27

0.5 mg/mL final microsomes concentration with 5 μM Conjugate 6

| | Heat Killed | Live |
|---|---|---|
| Total | 400 μL | 400 μL |
| Water | 286 μL | 286 μL |
| 10x Buffer | 40 μL | 40 μL |
| Microsomes (20 mg/mL) | 10 μL | 10 μL |
| Compound (50 μM) | 40 μL | 40 μL |
| NADPH Regenerating Solution A | 20 μL | 20 μL |
| NADPH Regenerating Solution B | 4 μL | 4 μL |

64.3 Sample and Data Analysis

Samples were acquired using Bruker Compass Flex Control version 3.4 to obtain full scan MALDI-TOE mass spectra (Table 28). BSA was used as an internal calibrant for the acquisition mass range. Data was further analyzed with Bruker Compass Flex Analysis version 3.4 software. In addition, the DAR pattern of the control is compared to the DAR pattern of the test sample.

TABLE 28

| Mass Spectrometer (MS) Parameters | |
|---|---|
| Mass Spectrometer | Bruker Microflex LT |
| Detection | |
| Mass Range | 17-141 kDa |
| Sample Rate and Digitizer Settings | 0.5 |
| Detector Gain | 2.05x |
| Baseline Offset Adjustment | 0% |
| Analog Offset | 0.5 mV |
| Laser Frequency | 60 Hz |
| Spectrometer | |
| Ion Source 1 (IS1) | 20.03 kV |
| Ion Source 2 (IS2) | 18.12 kV (90.5% IS1) |
| Lens | 7.17 kV (35.8% IS1) |
| Pulsed Ion Extraction | 1010 ns |
| Sample Carrier | |
| Random Walk | Partial Sample |
| Laser Shots | 100/section |
| Total Laser Shots | 500 |
| Shots at Raster | 20 |
| Raster Shot Diameter Limit | 2000 um |
| Setup | |
| Laser Global Attenuator Offset | 0% |
| Laser Attenuator Offset | 20% |
| Laser Attenuator Range | 30% |
| Digitizer Sensitivity (Full Scale) | 100 mV |
| Digitizer Analog Offset Linear | 0.5 mV |
| Digitizer Digital Offset Linear | 0 cnt |
| Detector Gain Voltage - Linear Base | 2500 V |
| Detector Gain Voltage - Linear Boost | 0 V |
| Calibration | |
| Bovine Serum Albumin | [M + 2H], [M + H], [2M + H] |

64.4 Results

The test compound, Conjugate 6 (FIG. 43), was tested for in vitro stability in both mouse and human fresh K2EDTA treated plasma and liver microsomes.

Figure 44:
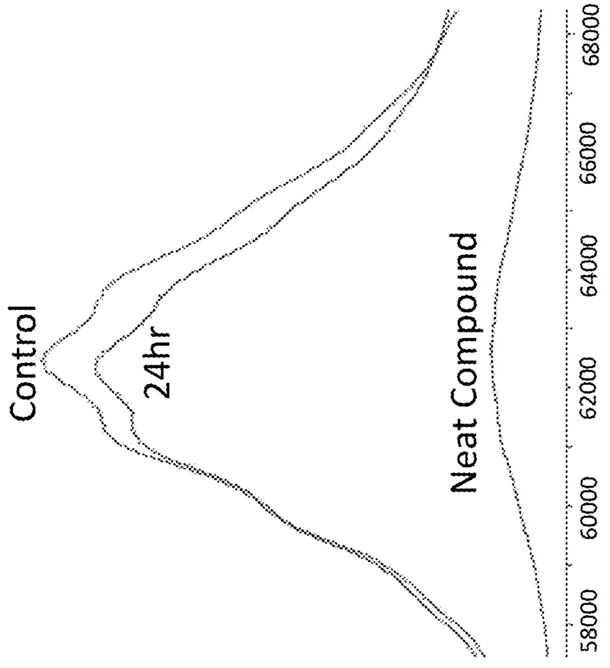
FIG. 44 is a graph showing a 24 hour in vitro mouse plasma stability study comparing Conjugate 6 incubated at 37° C. for 24 hr compared to a control and neat compound.
Figure 45:
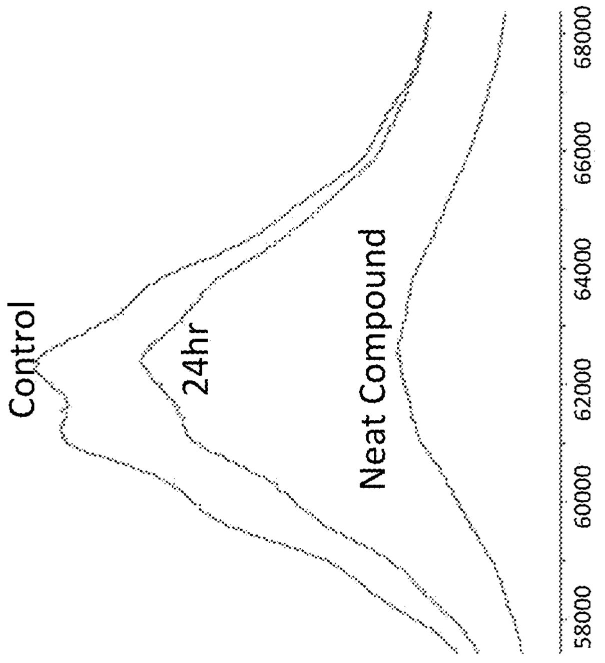
FIG. 45 is a graph showing a 24 hour in vitro human plasma stability study comparing Conjugate 6 incubated at 37° C. for 24 hr compared to a control and neat compound.

Conjugate 6 was spiked into fresh K2EDTA mouse and human plasma at a final concentration of 1 mg/mL. The plasma was split into 2 aliquots, one being frozen immediately, and the other incubated in a water bath at 37° C. for 24 hours. At the end of the incubation, samples were extracted from the plasma matrix by MAGNE® Protein A magnetic beads. Following plasma incubations, samples were analyzed by MALDI-TOF mass spectrometry for changes in DAR. Conjugate 6 in either mouse (FIG. 44) or human (FIG. 45) plasma incubations were not found to generate any changes in DAR.

Figure 46:
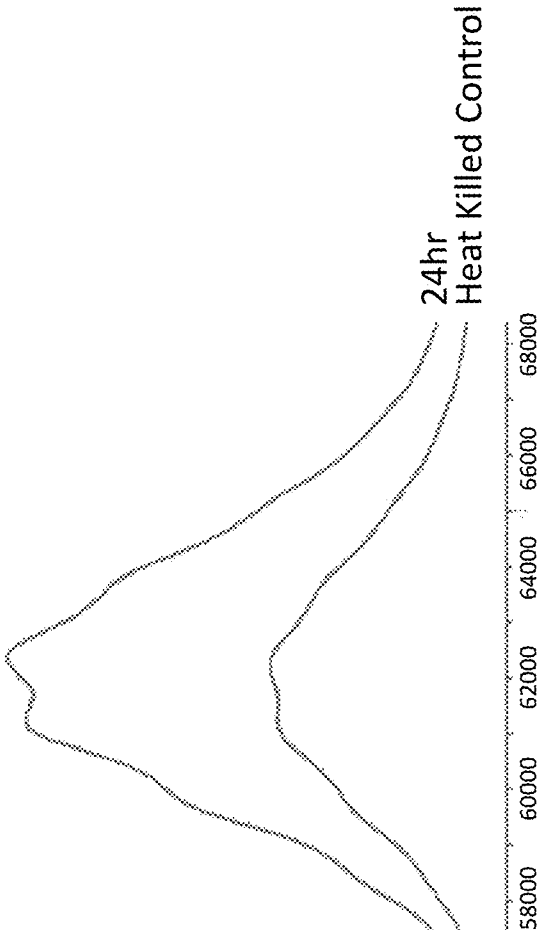
FIG. 46 is a graph showing a 24 hour mouse liver microsomal stability study comparing Conjugate 6 incubated at 37° C. for 24 hr in mouse liver microsomal cells and heat killed mouse liver microsomal cells as a control.
Figure 47:
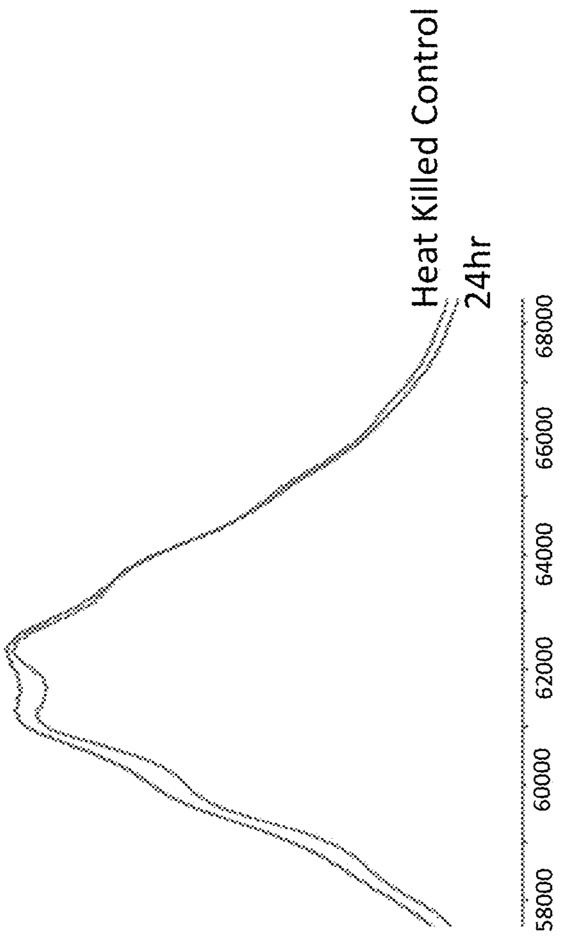
FIG. 47 is a graph showing a 24 hour human liver microsomal stability study comparing Conjugate 6 incubated at 37° C. for 24 hr in human liver microsomal cells and heat killed mouse liver microsomal cells as a control.

Conjugate 6 liver microsomal stability was tested at a final concentration of 5 μM into a 50 mM, pH 7.5 Tris-HCl buffer solution that contained either active or heat killed liver microsomes at a final concentration of 0.5 mg/mL and $MgCl_2$ at a final concentration of 5 mM. All samples were incubated at a constant temperature of 37° C., and nicotinamide adenine dinucleotide phosphate (NADPH) regenerating solution was utilized to provide continuous cofactor availability during the incubation. Incubations were carried out for 24 hours. At the end of the incubation, samples were extracted from the microsomal matrix by Protein A magnetic beads. Following liver microsomal incubations, samples were analyzed by MALDI-TOF mass spectrometry for changes in DAR. Conjugate 6 in either mouse (FIG. 46) or human (FIG. 47) liver microsomal incubations were not found to generate any changes in DAR.

The in vitro plasma stability after incubation at 37° C. for 24 hr, suggests a lack of degradation of the Conjugate 6 Fc, linker, or targeting moiety in either mouse or human. Similarly a lack of degradation was observed after incubation in both mouse and human liver microsomes, suggesting the absence of metabolites. The results of these in vitro stability studies support that this is a stable compound with degradants that could have biological liabilities.

Example 65. Efficacy of Conjugate 13 at Different Drug-to-Antibody Ratios (DARs) Against Influenza A (H1N1) in a Lethal Mouse Model Conjugate 13 was evaluated against a lethal IAV H1N1 influenza infection in female BALB/c mice (Charles River Laboratories, 6-8 weeks). The challenge virus (A/Puerto Rico/8/1934) is a mouse-adapted isolate capable of causing lethal infections in mice. The experiment comprised 13 groups of 5 mice. At day 0, all mice were challenged with virus at 3× the LD95 by intranasal inoculation in a volume of 30 μl, after being anesthetized with a mixture of ketamine/xylazine (150 and 10 mg/kg respectively).

Groups 1-13 received a single IV treatment, 2 hours post viral challenge of test article or vehicle (PBS). The study evaluated 4 different OAR constructs of Conjugate 13 corresponding to Conjugate 13a, Conjugate 13c, Conjugate 13d, and Conjugate 13g (DARs of 1.7, 3.8, 5.8, and 10.3, respectively). The synthesis of Conjugate 13a, Conjugate 13c, Conjugate 13d, and Conjugate 13g is described in Example 61-Example 63. Each construct was evaluated at 0.03, 0.1, and 0.3 mg/kg. The general study design for each conjugate is summarized in Table 29.

TABLE 29

General study design of DAR scan

| Group | Conjugate | DAR | Route/Schedule | Dose (mg/kg) | Dose volume (ml/kg) |
|---|---|---|---|---|---|
| 1 | Conjugate 13a | 1.7 | IV, T + 2 hours | 0.3 | 5 |
| 2 | Conjugate 13a | 1.7 | IV, T + 2 hours | 0.1 | 5 |
| 3 | Conjugate 13a | 1.7 | IV, T + 2 hours | 0.03 | 5 |
| 4 | Conjugate 13c | 3.8 | IV, T + 2 hours | 0.3 | 5 |
| 5 | Conjugate 13c | 3.8 | IV, T + 2 hours | 0.1 | 5 |
| 6 | Conjugate 13c | 3.8 | IV, T + 2 hours | 0.03 | 5 |
| 7 | Conjugate 13d | 5.8 | IV, T + 2 hours | 0.3 | 5 |
| 8 | Conjugate 13d | 5.8 | IV, T + 2 hours | 0.1 | 5 |
| 9 | Conjugate 13d | 5.8 | IV, T + 2 hours | 0.03 | 5 |
| 10 | Conjugate 13g | 10.3 | IV, T + 2 hours | 0.3 | 5 |
| 11 | Conjugate 13g | 10.3 | IV, T + 2 hours | 0.1 | 5 |
| 12 | Conjugate 13g | 10.3 | IV, T + 2 hours | 0.03 | 5 |
| 13 | Vehicle (PBS) | Na | IV, T + 2 hours | na | 5 |

All constructs were fully protective at 0.3 mg/kg, in contrast, no construct was active at 0.03 mg/kg (0% survival for all groups) indicating the low dose was below the threshold efficacious dose. However, groups receiving 0.1 mg/kg of conjugates could be discriminated (Table 30). At this dose level conjugates with DARs of 1.7, 3.8, and 5.8 were significantly more protective than vehicle only treated mice (p=0.0027). The high OAR construct (10.3) however was not significantly more protective than vehicle only treated mice (p=0.091). The underlying mechanism by which the high OAR construct loses activity is currently unknown but could be caused by several factors, including interference with antibody recycling, resulting in shorter half-life.

TABLE 30

| DAR Range Study (0.1 mg/kg dose groups) | | | |
|---|---|---|---|
| Conjugate | DAR | % Survival | Significance* |
| Conjugate 13a | 1.7 | 60 | p = 0.0027 |
| Conjugate 13c | 3.8 | 40 | p = 0.0027 |
| Conjugate 13d | 5.8 | 80 | p = 0.0027 |
| Conjugate 13g | 10.3 | 0 | p = 0.091** |

*= Significance relative to vehicle (PBS) only treated mice by the Log-rank (Mantel-Cox) test.
**= Not significant

Example 66. In Vivo Efficacy of Conjugate 6 and Conjugate 12

Figure 48:
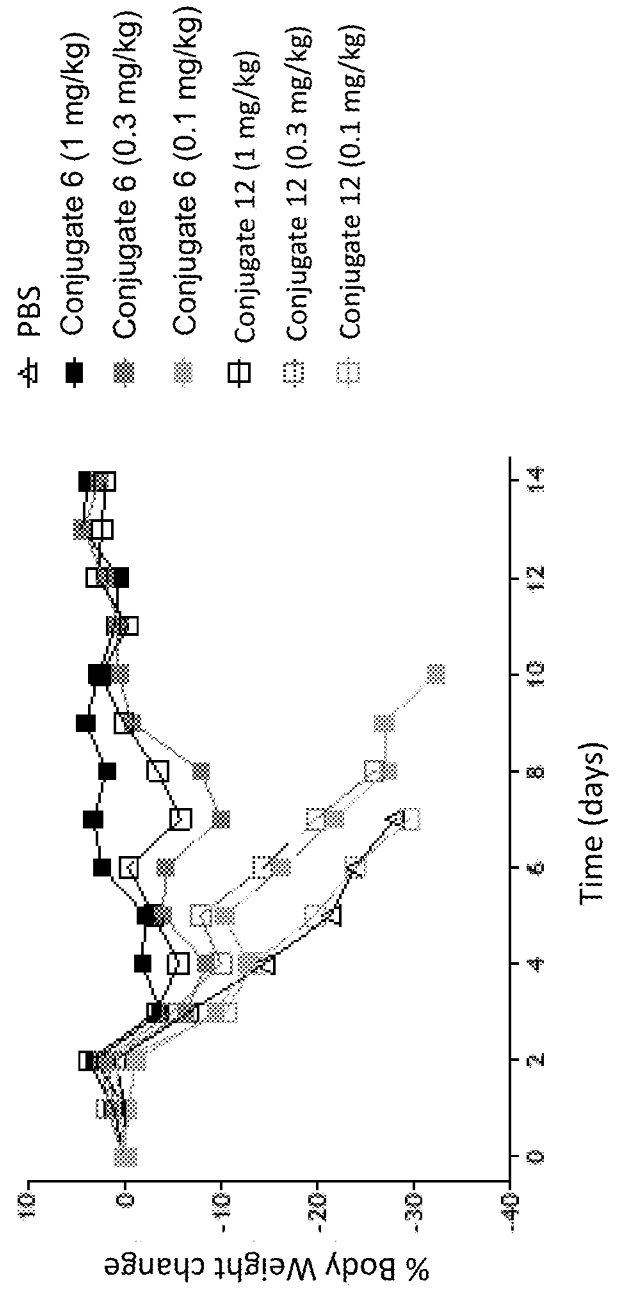
FIG. 48 is a graph showing the % body weight change in mice over 15 days post viral challenge. The study was performed as described in Example 66.
Figure 49:
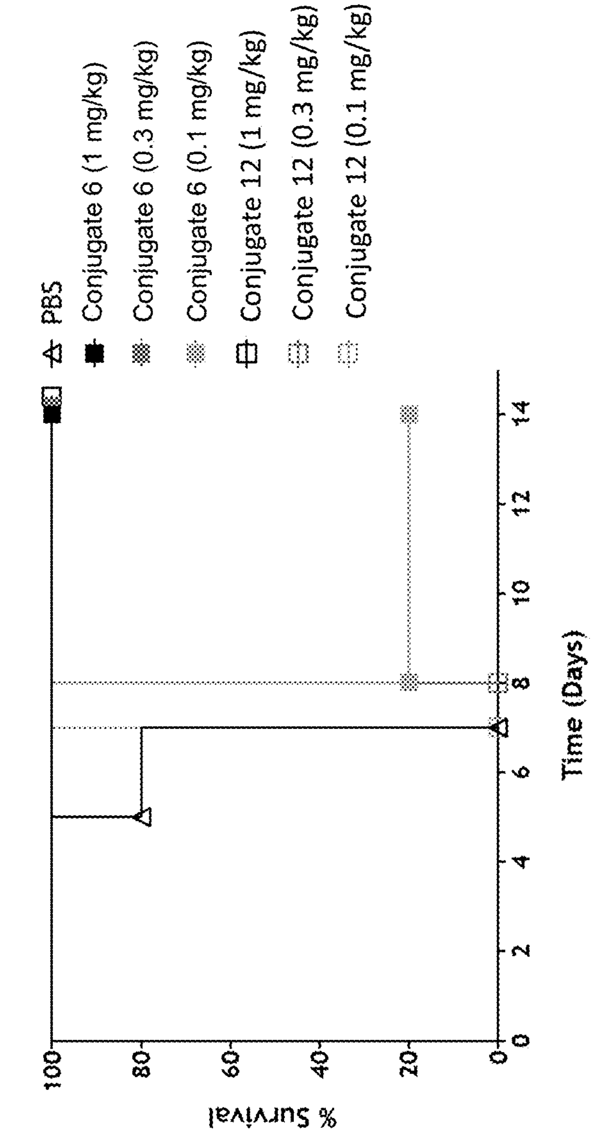
FIG. 49 is a graph showing the % survival in mice over 15 days post viral challenge. The study was performed as described in Example 66.

Conjugate 6 and Conjugate 12, analog with Fc mutation at N297A, was evaluated against a lethal IAV H1N1 influenza infection in female BALB/c mice (Charles River Laboratories, 6-8 weeks). The challenge virus (A/Puerto Rico/8/34) is a mouse-adapted isolate. The experiment comprised 5 mice per group. Mice were anesthetized with ketamine/Xylazine (150/10 mg/kg) and were challenged with influenza virus at 3-5× the LDs by intranasal inoculation in a volume of 30 μL. A single 1 dose of treatment was administered by IV, 2 h post-infection. PBS was given as negative control. All mice were monitored for % body weight loss (FIG. 48) and for survival (FIG. 49) for 15 days after challenge.

Example 67. In Vitro Fcγ Receptor IIIA Binding of Conjugate 6 and Conjugate 12

Binding of Conjugate 6 and Conjugate 12, analog with Fc mutation at N297A, was evaluated against FcγRIIIA by ELISA. The plate was coated with 1 μg/mL recombinant human FcγRIIIA overnight. The next day, the plate was blocked with 1% BSA solution for 1 h. Conjugates were added to plate in dose-response ranging from 0.01-1000 nM and incubated for 2 h. Binding was detected by incubation with peroxidase-conjugated anti-human Fc for 1 h and subsequent incubation with TMB substrate reagent for 10-15 min.

Figure 50:
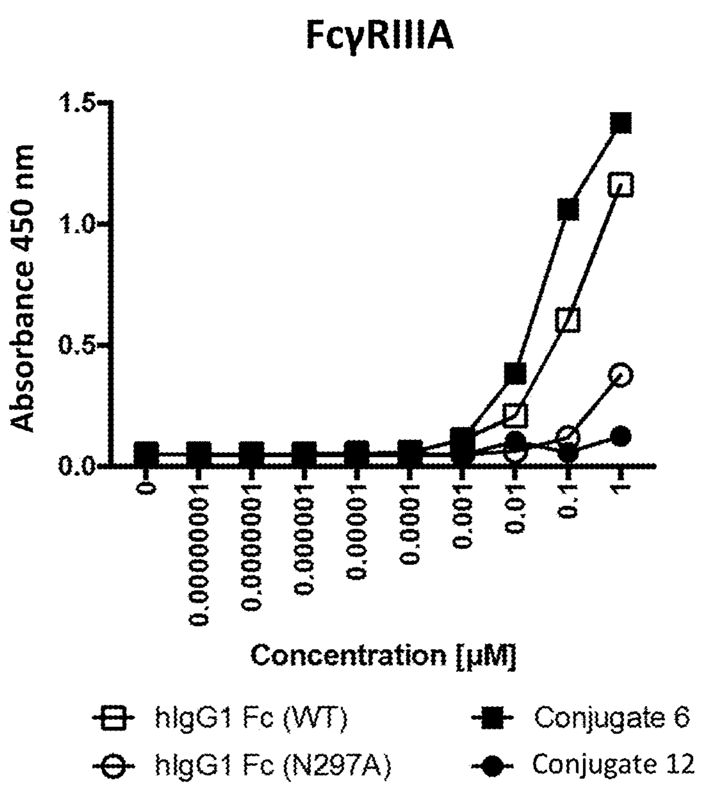
FIG. 50 is a graph showing the binding of Conjugate 6 and Conjugate 12 compared to hIgG1 Fc (WT) and hIgG1 Fc (N297A) to Fcγ receptor IIIA. The study was performed as described in Example 67.
Figure 51:
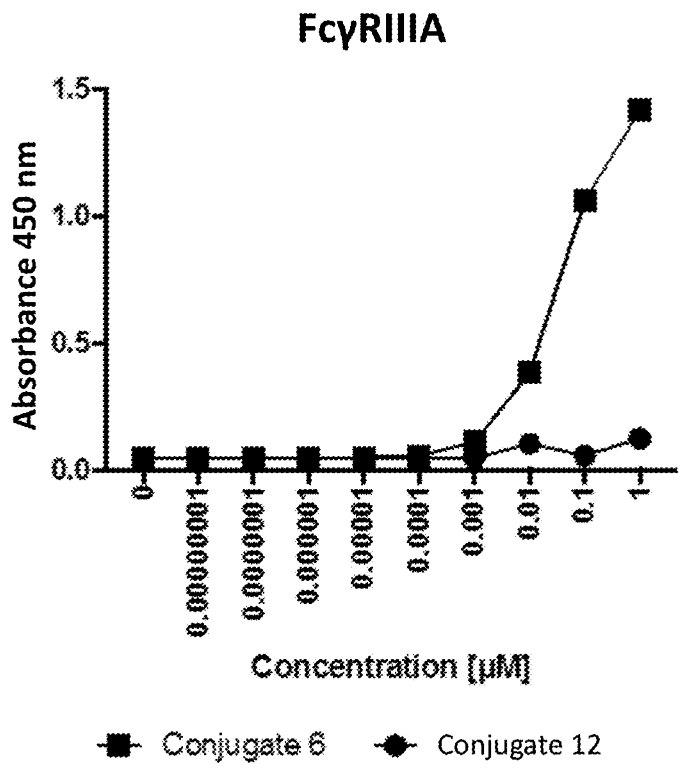
FIG. 51 is a graph showing the binding of Conjugate 6 and Conjugate to Fcγ receptor IIIA. The study was performed as described in Example 67.

Binding was determined by reading absorbance at 450 nm (FIG. 50 and FIG. 51).

Example 68. In Vivo Conjugate 6 Plasma Sample Analysis

Conjugate 6 in plasma samples were quantified by a neuraminidase capture detection ELISA. Briefly, molecules were captured on neuraminidase coated plates and then detected using a HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with 0.1 U/well neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hours (sample diluent: 0.5% BSA in PBS 0.025% Tween 20+naïve cynomolgus monkey plasma final concentration of 1:2,500). Conjugate 6 standard curves ranging from 0.230 to 500 ng/mL, in duplicate were run on each plate. Following the 2 hr incubation, plates were washed 5× in 300 μL PBS with 0.05% Tween 20. Conjugate bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 uL PBS with 0.05% Tween 20 and developed with TMB substrate for 7-8 minutes. The reaction was stopped with 1 N $H_2SO_4$. Absorbance was read at 450 nm. Conjugate 6 in plasma samples was interpolated using GraphPad Prism Version 6 following nonlinear regression analysis (Sigmoidal, 4PL analysis) of the standard curves.

The resulting mean plasma concentrations were then used to calculate pharmacokinetic parameters by non-compartmental analysis using Phoenix WinNonlin 7.0.

Toxicokinetics (TK), Groups 2 (IV, 5 mg/kg) and 3 (IV, 20 mg/kg)

Figure 52:
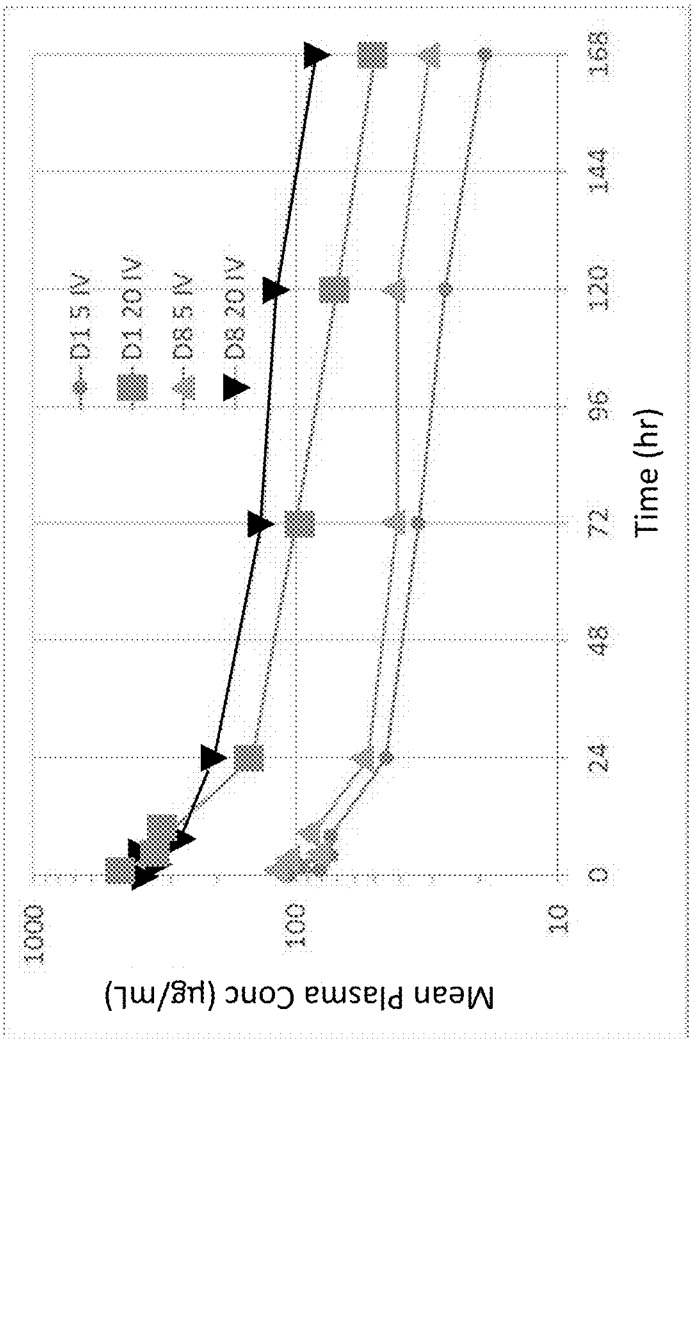
FIG. 52 is a graph showing a 7-day non-human primate toxicokinetic study following IV administration of Conjugate 6. The study was performed as described in Example 68.

Concentrations were comparable between male and female animals within the same dose group on day 1 (Table 31) and day 8 (Table 32) after administration. Mean plasma exposures appeared to increase approximately dose-proportionally across both days. After the 2nd dose administration, a slight accumulation of about 30% was noted across the different dose groups. A plot of days 1 and 8 mean plasma concentrations across the different dose groups is shown in FIG. 52.

TABLE 31

| Toxicokinetics Day 1 | | | | | | | | | | | | | | |
|---|---|---|---|---|---|---|---|---|---|---|---|---|---|---|
| Dose | | | Conc (μg/mL) at Time (hr) | | | | | | | | | Tmax | Cmax | AUC0-t |
| (mg/kg) | Route | Sex | 0.083 | 1 | 2 | 4 | 8 | 24 | 72 | 120 | 168 | (hr) | (μg/mL) | (μg · hr/mL) |
| 5 | IV | F | 112 | 78.8 | 85.8 | 71.0 | 75.1 | 52.5 | 38.6 | 18.5 | 22.3 | 0.083 | 112 | 6190 |
| | IV | M | 101 | 84.6 | 107 | 75.3 | 72.5 | 38.1 | 29.8 | 35.3 | 15.8 | 2 | 107 | 5970 |
| | | Mean | 107 | 81.7 | 96.5 | 73.2 | 73.8 | 45.3 | 34.2 | 26.9 | 19.0 | 1.04 | 110 | 6080 |
| 20 | IV | F | 449 | 510 | 353 | 331 | 303 | 134 | 105 | 63.6 | 46.6 | 1 | 510 | 18800 |
| | IV | M | 448 | 422 | 485 | 373 | 329 | 160 | 96.0 | 76.2 | 53.4 | 2 | 485 | 20500 |
| | | Mean | 449 | 466 | 419 | 352 | 316 | 147 | 100 | 69.9 | 50.0 | 1.50 | 497 | 19600 |

TABLE 32

| Toxicokinetics Day 8 | | | | | | | | | | | | | | | |
|---|---|---|---|---|---|---|---|---|---|---|---|---|---|---|---|
| Dose | | | Conc (μg/mL) at Time (hr) | | | | | | | | | | Tmax | Cmax | AUC0-t |
| (mg/kg) | Route | Sex | 0.083 | 1 | 2 | 4 | 8 | 24 | 72 | 120 | 168 | | (hr) | (μg/mL) | (μg · hr/mL) |
| 5 | IV | F | 111 | 111 | 99.3 | 82.3 | 100 | 52.2 | 46.7 | 35.0 | 33.9 | | 1 | 111 | 7970 |
| | IV | M | 113 | 114 | 113 | 78.4 | 74.4 | 54.7 | 35.2 | 47.1 | 28.2 | | 1 | 114 | 7700 |
| | | Mean | 112 | 112 | 106 | 80.4 | 87.3 | 53.5 | 41.0 | 41.1 | 31.0 | | 1 | 112 | 7830 |
| 20 | IV | F | 398 | 359 | 319 | 315 | 298 | 190 | 126 | 99.3 | 85.5 | | 0.083 | 398 | 23900 |
| | IV | M | 391 | 443 | 354 | 435 | 263 | 219 | 143 | 142 | 83.8 | | 1 | 443 | 27800 |
| | | Mean | 394 | 401 | 337 | 375 | 280 | 205 | 134 | 120 | 84.7 | | 0.542 | 420 | 25800 |

Pharmacokinetics (PK), Groups 4 (IV, 10 mg/kg) and 5 (SC, 10 mg/kg)

Following IV administration, plasma concentrations form the male and female animals were comparable. Very low clearance, resulting in a long terminal half-life was observed following IV administration (Table 33A and Table 33B).

TABLE 33A

| Plasma concentrations for male and female animals | | | | | | | | | | | | | | |
|---|---|---|---|---|---|---|---|---|---|---|---|---|---|---|
| Dose | | | Conc (μg/mL) at Time (hr) | | | | | | | | | | | |
| (mg/kg) | Route | Sex | 0.083 | 1 | 2 | 4 | 8 | 24 | 72 | 120 | 168 | 336 | 504 | 672 |
| 5 | IV | F | 166 | 174 | 220 | 153 | 144 | 58.6 | 40.6 | 21.2 | 20.7 | 14.7 | n/a | 2.7 |
| 5 | IV | M | 191 | 135 | 258 | 161 | 154 | 71 | 43.7 | 47.6 | 32 | 22.9 | n/a | 5.3 |

TABLE 33B

| PK parameters for male and female animals | | | | | | | | |
|---|---|---|---|---|---|---|---|---|
| $T_{max}$ (hr) | C0 (μg/mL) | $C_{max}$ (μg/mL) | AUClast (hr * μg/mL) | AUCINF_obs (hr * μg/mL) | Half-life (hr) | Cl_obs (mL/min/kg) | Vss_obs (mL/kg) | Vz_obs (mL/kg) |
| 1 | 166 | 220 | 13700 | 14400 | 170 | 0.00579 | 68.9 | 85.1 |
| 1 | 204 | 258 | 19400 | 20800 | 183 | 0.004 | 56.6 | 63.2 |

Figure 53:
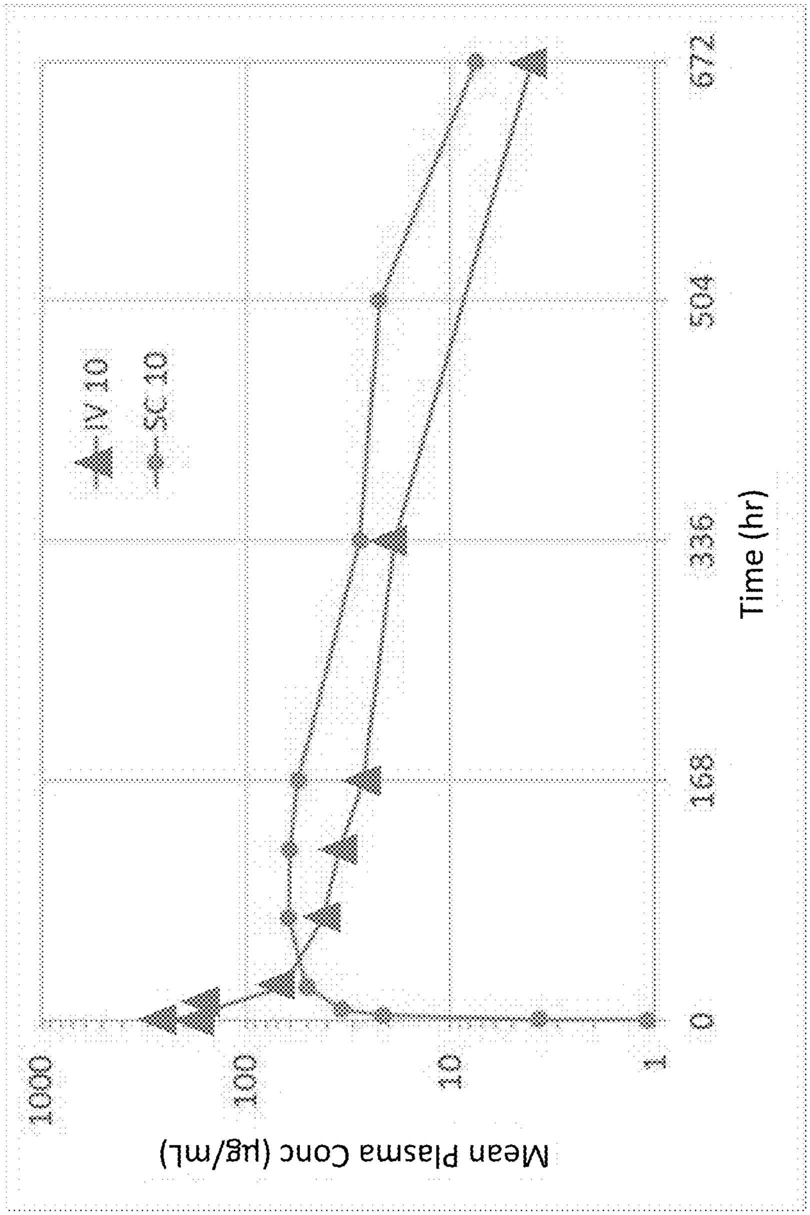
FIG. 53 is a graph showing a 28-day non-human primate pharmacokinetic study comparing IV and SC administration of Conjugate 6. The study was performed as described in Example 68.

Following SC administration, the time to reach maximum concentrations was reached 72 hours after dosing but concentrations were measurable through 672 hours post-dose (Table 34A and Table 34B). Bioavailability after SC dosing was high at approximately 139%. A comparison of the plasma concentration over time between 10 mg/kg IV and SC administration is shown in FIG. 53.

TABLE 34A

| Plasma concentrations for male and female animals | | | | | | | | | | | | | | |
|---|---|---|---|---|---|---|---|---|---|---|---|---|---|---|
| | Dose | | Conc (μg/mL) at Time (hr) | | | | | | | | | | | |
| Route | (mg/kg) | Sex | 0.083 | 0.5 | 1 | 4 | 8 | 24 | 72 | 120 | 168 | 336 | 504 | 672 |
| SC | 10 | F | n/a | 1.9 | 5.3 | 23.1 | 39.5 | 54 | 58.6 | 66.9 | 54 | 28.4 | 18.9 | 6.4 |
| SC | 10 | M | n/a | 0.3 | 2.1 | 19.9 | 28.1 | 46.8 | 64.9 | 54.7 | 57.2 | 26.8 | 25.5 | 8.6 |

TABLE 34B

| PK parameters for male and female animals | | | |
|---|---|---|---|
| $T_{max}$ (hr) | $C_{max}$ (μg/mL) | $AUC_{0-t}$ (μg × hr/mL) | F (%) |
| 120 | 66.9 | 22600 | 137% |
| 72 | 64.9 | 23300 | 141% |

Example 69. Efficacy of Conjugate 6 Against Influenza A/Puerto Rico/8/1934 (H1N1) in a Lethal Mouse Model Conjugate 6 was evaluated against a lethal IAV H1N1 influenza infection in female BALB/c mice (Charles River Laboratories, 6-8 weeks). The challenge virus (A/Puerto Rico/8/1934) is a mouse-adapted isolate capable of causing lethal infections in mice. The experiment comprised 7 groups of 5 mice. At day 0, all mice were challenged with virus at 3× the LD95 by intranasal inoculation in a volume of 30 μl, after being anesthetized with a mixture of ketamine/xylazine (150 and 10 mg/kg respectively). Mortality and body weights were recorded daily and any animal with a 20% loss of body weight was scored as a death. Test groups received a single IV treatment, 2 hours post viral challenge of conjugate 6, hIgG1 Fc control, or vehicle (PBS). Animals receiving oseltamivir were dosed orally, twice daily, for 5 days, starting 2 hours after viral challenge. The study design is summarized in Table 35.

TABLE 35

| Study design for Influenza A/PR/8/34 (h1N1) study | | | | | |
|---|---|---|---|---|---|
| Group | Test article | Route/Schedule | Dose (mq/kq) | Dose volume (ml/kq) | # of mice |
| 1 | Vehicle | IV, T + 2 hrs. | na | 5 | 5 |
| 2 | hIgG1 Fc | IV, T + 2 hrs. | 10 | 5 | 5 |
| 3 | Oseltamivir | PO, bid x5, T + 2 hrs. | 20 | 5 | 5 |
| 4 | Oseltamivir | PO, bid x5, T + 2 hrs. | 5 | 5 | 5 |
| 5 | Conjugate 6 | IV, T + 2 hrs. | 10 | 5 | 5 |
| 6 | Conjugate 6 | IV, T + 2 hrs. | 2 | 5 | 5 |
| 7 | Conjugate 6 | IV, T + 2 hrs. | 0.4 | 5 | 5 |

As expected, mice receiving vehicle or the hIgG1 Fc only succumbed to the infection by day 6. Similarly, mice treated with oseltamivir at the low dose (5 mg/kg; bid for 5 days) reached mortality by day 8 (Table 36). However, mice receiving 20 mg/kg of oseltamivir with the same dosing schedule were fully protected (p=0.0027). In contrast to that seen with oseltamivir, mice treated with conjugate 6 were fully protected at all dose levels (10, 2, and 0.4 mg/kg) from a single IV dose (p=0.0027).

TABLE 36

| Survival for Influenza A/PR/8/34 (H1N1) study (Day 14) | | | |
|---|---|---|---|
| Test article | Dose | % Survival | Significance* |
| hIgG1 Fc | 10 | 0 | p = 0.85** |
| Oseltamivir | 20 | 100 | p = 0.0027 |
| Oseltamivir | 5 | 0 | p = 0.091** |
| Conjugate 6 | 10 | 100 | p = 0.0027 |
| Conjugate 6 | 2 | 100 | p = 0.0027 |
| Conjugate 6 | 0.4 | 100 | p = 0.0027 |

*= Significance relative to vehicle (PBS) only treated mice by the Log-rank (Mantel-Cox) test.

TABLE 36-continued

| Survival for Influenza A/PR/8/34 (H1N1) study (Day 14) | | | |
|---|---|---|---|
| Test article | Dose | % Survival | Significance* |

**= Not significant

The potency of conjugate 6 was further supported by daily body weight measurements. As expected, mice treated with vehicle or hIgG1 Fc demonstrated a steady drop in body weight until it exceeded 20%, at which time they were scored as a death (Table 37). The group treated with oseltamivir at 5 mg/kg also displayed a consistent loss of weight until reaching mortality at day 8. Mice treated with oseltamivir at the high dose (20 mg/kg) showed a steady, but reduced loss of body weight, which reached i4% at day 8, before recovering.

In contrast to control and oseltamivir treated mice, those groups receiving conjugate 6 maintained healthy body weights throughout the study even at the lowest dose concentration (0.4 mg/kg) (Table 37). The largest transient loss of weight among conjugate 6 treated mice was only 2% at day 14 in the 2 mg/kg dose group. By both survival and body weight measurements conjugate 6 demonstrated robust protection from Influenza A/Puerto Rico/8/i1934 with a single IV dose as low as 0.4 mg/kg.

TABLE 37

| Mouse body weight data (% BW relative to day 0). Average of 5 mice; | | | | | | | |
|---|---|---|---|---|---|---|---|
| Day post | Vehicle | hIgG1 Fc (mg/kg) | Oseltamivir (mg/kg) | | Conjugate 6 (mg/kg) | | |
| challenge | (PBS) | 10 | 20 | 5 | 10 | 2 | 0.4 |
| 0 | 100 | 100 | 100 | 100 | 100 | 100 | 100 |
| 1 | 99 | 99 | 102 | 99 | 103 | 102 | 101 |
| 2 | 102 | 102 | 103 | 96 | 104 | 102 | 103 |
| 3 | 96 | 96 | 102 | 95 | 102 | 102 | 100 |
| 4 | 89 | 88 | 100 | 90 | 103 | 100 | 100 |
| 5 | 82 | 81 | 95 | 89 | 102 | 99 | 99 |
| 6 | 77 | 77 | 98 | 90 | 102 | 100 | 101 |
| 7 | | | 90 | 84 | 103 | 101 | 102 |
| 8 | | | 86 | 78 | 105 | 101 | 102 |
| 9 | | | 91 | | 101 | 102 | 102 |
| 10 | | | 95 | | 102 | 101 | 103 |
| 11 | | | 97 | | 102 | 101 | 102 |
| 12 | | | 97 | | 101 | 99 | 102 |
| 13 | | | 97 | | 103 | 100 | 102 |
| 14 | | | 96 | | 104 | 98 | 101 |

*data not included once the first animal reaches mortality within a group

Example 70. Synthesis of Conjugate 14

The title conjugate was prepared analogously to Conjugate 13a (Example 61) using PEG-azido-Fc (SEQ ID NO:35) and Int-7 (Example 19). Maldi TOF analysis of the purified final product gave an average mass of 56,502. Da (DAR=2.1). Yield 43.4 mg, 43.4%.

Example 71. Synthesis of Conjugate 15

This conjugate was prepared analogously to Example 62 (Conjugate 13a) by PEG4-azido-Fc (SEQ ID NO: 35, Example 61) and Int-12 (Example 46). Maldi TOF analysis of the purified final product gave an average mass of 56,528. Da (DAR=2.2). Yield 40.0 mg, 40.0%.

Example 72. Synthesis of Conjugate 16

This conjugate was prepared analogously to Example 62 (Conjugate 13a) by PEG4-azido-Fc (SEQ ID NO: 35, Example 61) and Int-10 (Example 31). Maldi TOF analysis of the purified final product gave an average mass of 56,507. Da (DAR=2.1). Yield 41.7 mg, 42%.
Example 73. Synthesis of Int-19
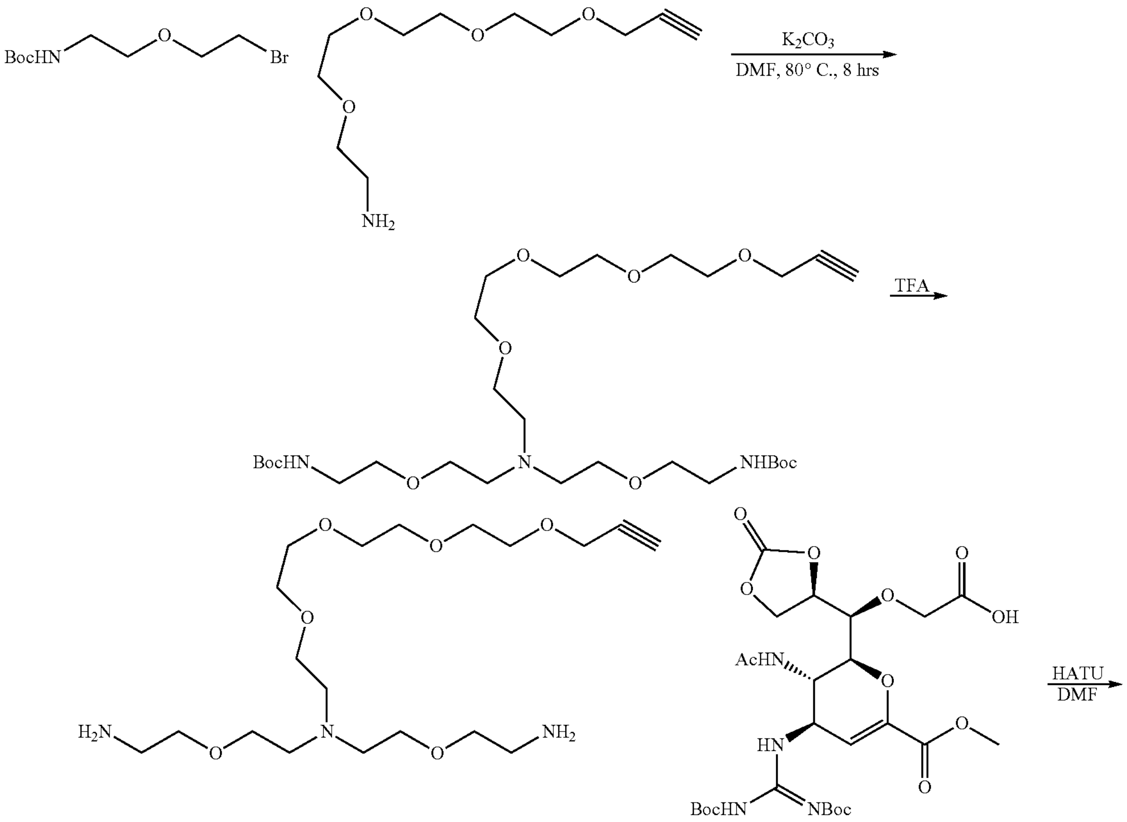

-continued

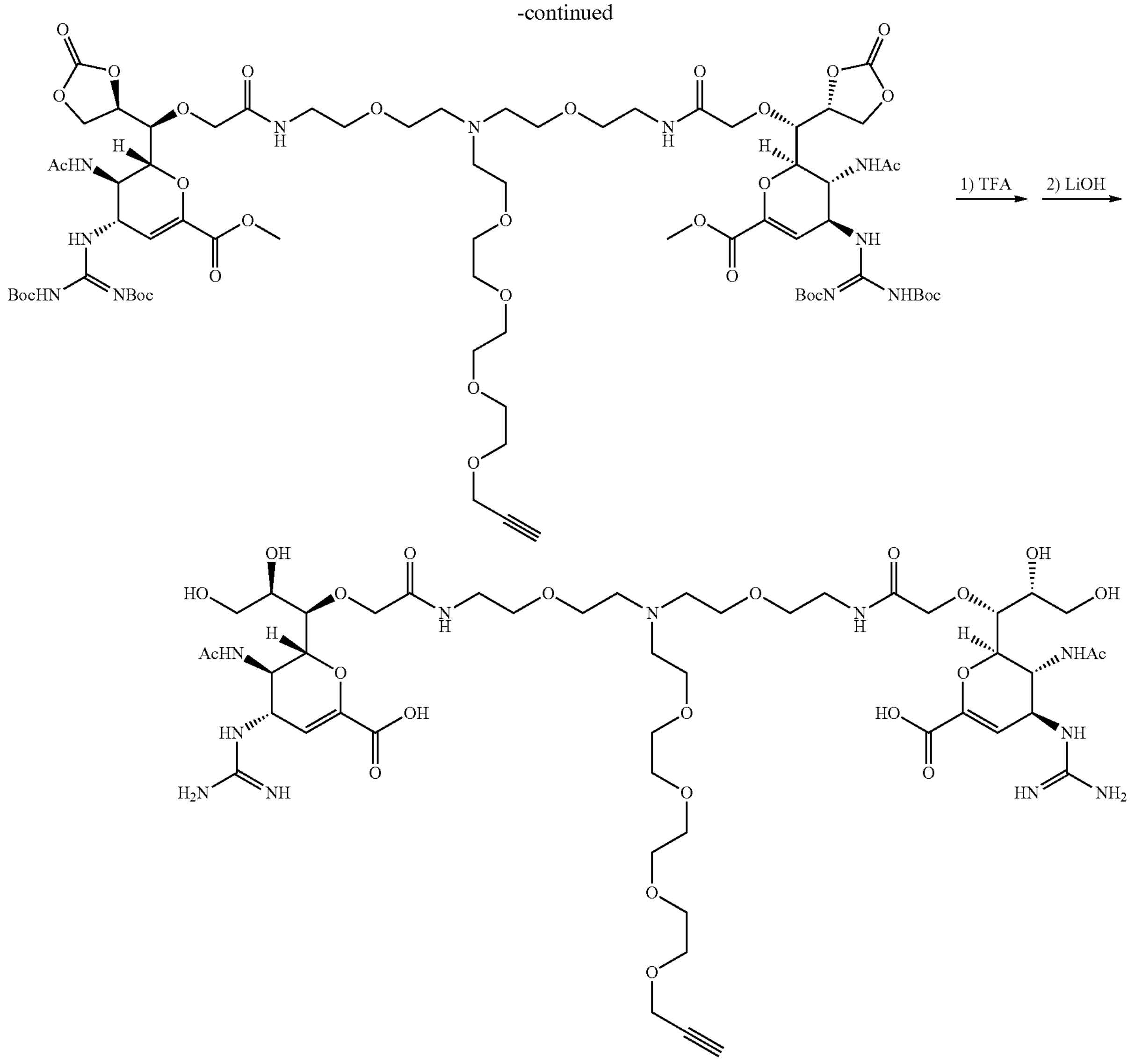

Step a.

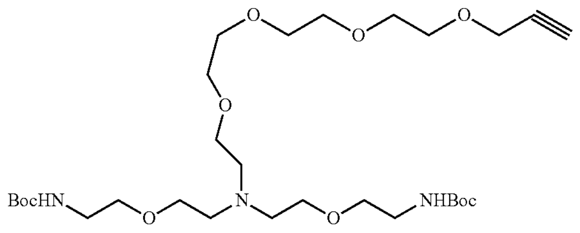 [SMILES: C#CCOCCOCCOCCOCCN(CCOCCNC(=O)OC(C)(C)C)CCOCCNC(=O)OC(C)(C)C]

To a solution of tert-butyl [2-(2-bromoethoxy)ethyl]carbamate (1.8 g, 6.6 mmol) and propargyl-PEG4 amine (0.7 g, 3.0 mmol) in 30 ml DMF was added potassium carbonate (1.2 g, 9 mmol). The reaction was stirred at 80° C. for 6 hrs, and then partitioned between DCM (200 mL) and brine (50 mL). The organic layer was separated and washed with brine and dried with anhydrous sodium sulfate. Upon filtration, the resulting filtrate was concentrated and purified by reverse phase liquid chromatography (RPLC) using an Isco COMBIFLASH® liquid chromatograph eluted with 10% to 100% acetonitrile and water with 0.1% TFA as modifier. Yield of the products 1.0 g, 65%. Ion(s) found by LCMS: M/2+H=606.4.

Step b.

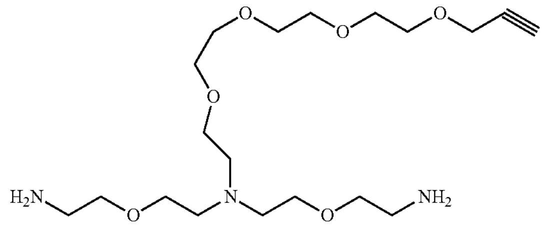 [SMILES: C#CCOCCOCCOCCOCCN(CCOCCN)CCOCCN]

Product from the previous step (1.0 g, 1.6 mmol) was treated with TFA (10 mL) at room temperature for 0.5 hour, then concentrated to dryness and used in next step without further purification. Yield was quantitative for this step. Ion(s) found by LCMS: M/2+H=406.3.

Step c.

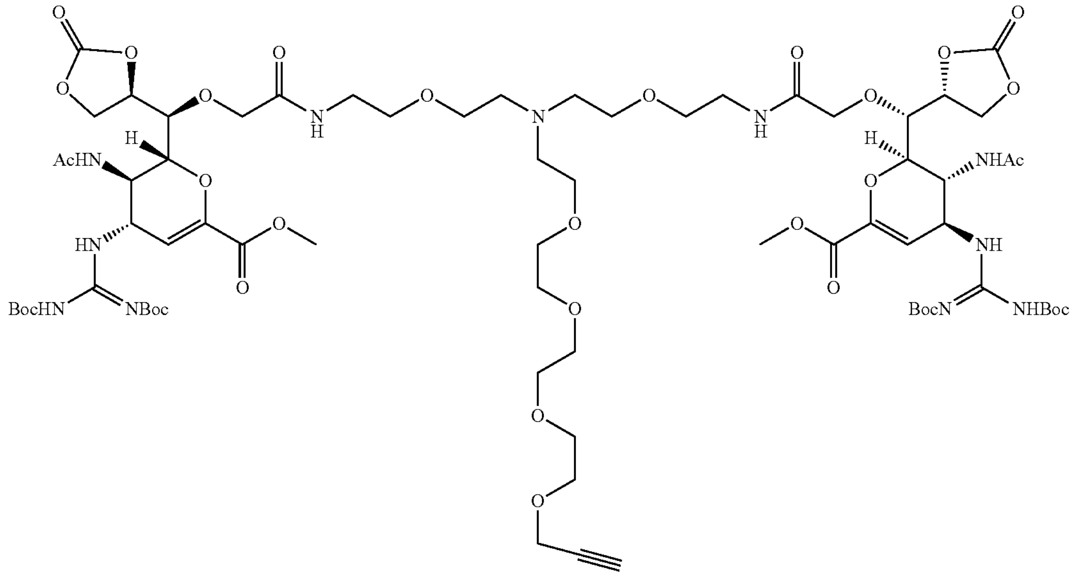

Product from the previous step (120 mg, 0.17 mmol) was treated with a solution of ether zanamivir acid (230 mg, 0.38 mmol, Example 31) in 10 ml DMF. To this solution was added EDC (100 mg, 0.5 mmol), HOBt (65 mg, 0.5 mmol), and DIEA (0.14 ml, 1 mmol). The resulting solution was stirred at room temperature overnight, then purified by and purified by reverse phase liquid chromatography (RPLC) using an Isco COMBIFLASH® liquid chromatograph eluted with 10% to 100% acetonitrile and water with no TFA as modifier. Yield of the products 180 mg, 60.2%. Ion(s) found by LCMS: M/2+H=816.9.

Step d.

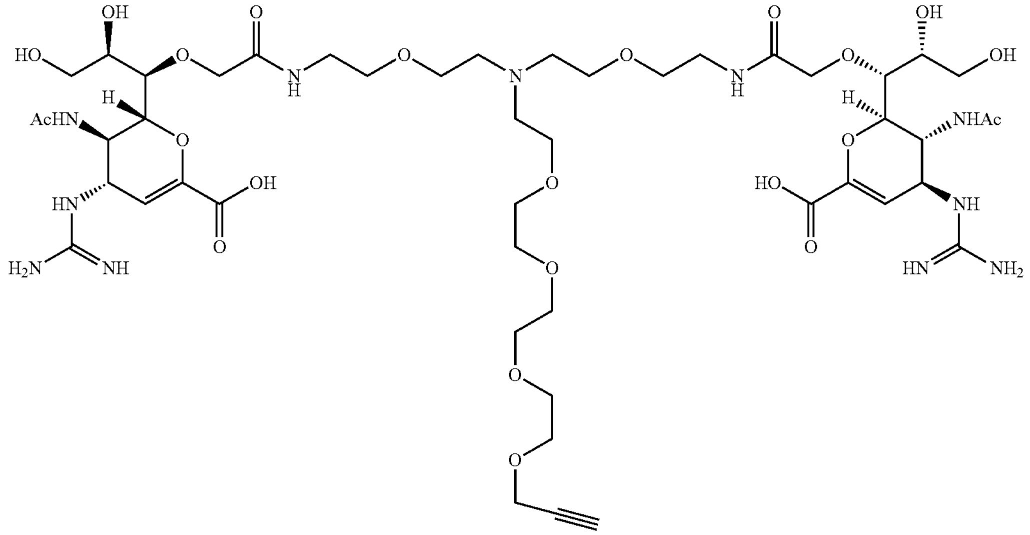 [SMILES: C#CCOCCOCCOCCOCCN(CCOCCNC(=O)CO[C@@H]([C@@H]1OC(C(=O)O)=C[C@H](NC(=N)N)[C@H]1NC(C)=O)[C@H](O)CO)CCOCCNC(=O)CO[C@@H]([C@@H]1OC(C(=O)O)=C[C@H](NC(=N)N)[C@H]1NC(C)=O)[C@H](O)CO]

Product from the previous step (180 mg, 0.11 mmol) was treated with trifluoroacetic acid (2 mL) for 30 min at room temperature. The resulting solution was concentrated and was dissolved into water (2 mL), then treated with a solution of lithium hydroxide (24 mg, 1 mmol) dissolved in H2O (1 mL). The resulting reaction was stirred 10 min then quenched with 0.1 ml acetic acid. The solution was concentrated and purified by reverse phase liquid chromatography (RPLC) using an Isco COMBIFLASH® liquid chromatograph eluted with 0% to 50% acetonitrile and water, using 0.1% TFA as the modifier. Yield of product 140 mg, 52%. Ion(s) found by LCMS: M/2+H=575.8, M/3+H=384.2.

Example 74. Synthesis of Conjugate 17

This conjugate was prepared analogously to Example 62 (Conjugate 13a) by PEG4-azido-Fc (SEQ ID NO: 35, Example 61) and Int-19 (Example 73). Maldi TOF analysis of the purified final product gave an average mass of 56,672. Da (DAR=2.2). Yield 36.7 mg, 36.7%.

Example 75. Synthesis of Int-20
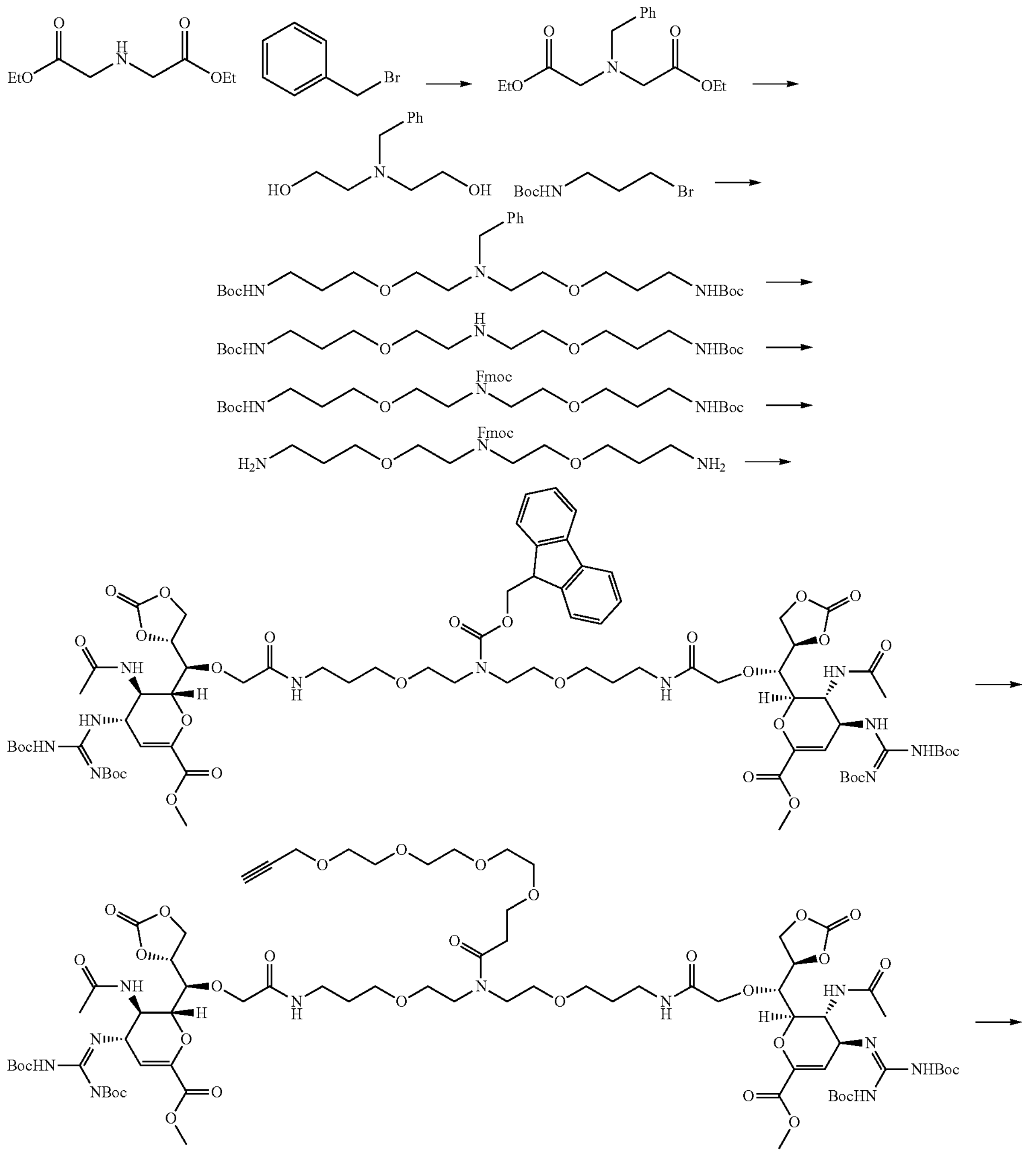

-continued

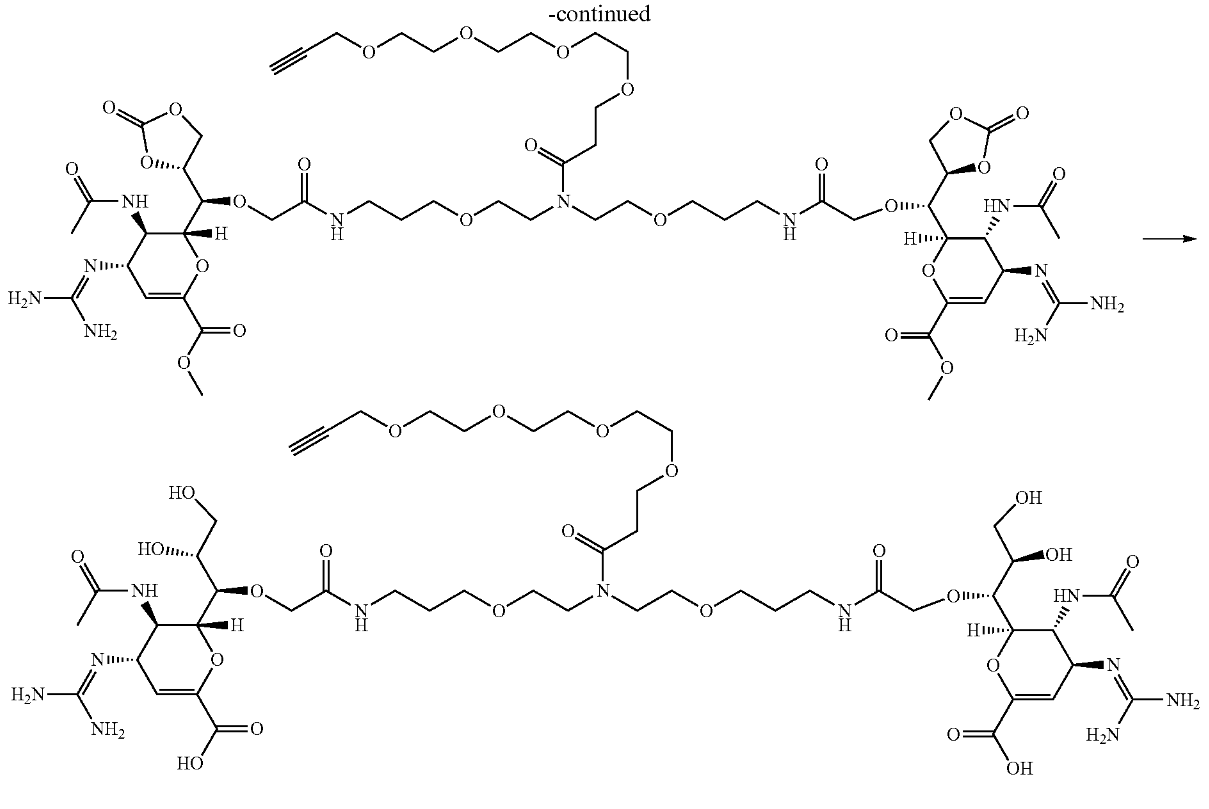

Step a.

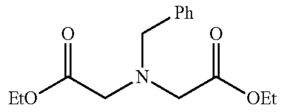

To a solution of diethyl iminodiacetate (3.1 g, 16.06 mmol) in anhydrous DMF (36 mL) was added benzyl bromide (2.38 mL, 19.64 mmol) and potassium carbonate (6.44 g, 46.46 mmol). The resulting mixture was heated at 70° C. for 16 hours. After cooling to room temperature, the reaction mixture was diluted water and extracted with tertiarybutylmethylether (3×100 mL). The organic layers were washed with brine, dried over $Na_2SO_4$ and filtered then concentrated. The residue was purified by normal phase silica gel chromatography (Isco, 0 to 10% ethyl acetate and hexane). Yield 3.13 g, 69.8%. Ion found by LCMS: $[M+H]^+$ =280.2.

Step b.

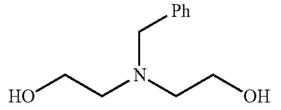 [SMILES: OCCN(CCO)Cc1ccccc1]

A solution of di-ethyl ester from step-a (3.2 g, 11.2 mmol) in anhydrous THE (5 mL) was added slowly to a round bottom flask containing $LiALH_4$ (425 mg, 14.2 mmol) in THE (2 mL) under nitrogen gas at 0° C. The syringe was rinsed with THE (2×5 mL). The resulting mixture was slowly warmed up to room temperature overnight. Methanol (2 mL) was added slowly to quench the reaction following by addition of NaOH aqueous (1 mL). The resulting mixture was stirred for 1 hour then filtered under vacuum. The filtrate was concentrated and used in the next step without purification. Yield 2.4 g, 109%. Ion found by LCMS: $[M+H]^+$ =196.2.

Step c.

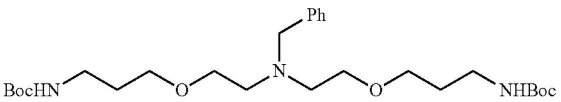 [SMILES: CC(C)(C)OC(=O)NCCCOCCN(CCOCCCNC(=O)OC(C)(C)C)Cc1ccccc1]

Product from the previous step (1.02 g, 5.24 mmol) in anhydrous THE (4 mL) was added slowly into a flask containing NaH (60% purity, 2.09 g, 52.4 mmol) and THE (5 mL) at 0° C. under nitrogen gas. The resulting mixture was stirred for 1 hour followed by dropwise addition of 3-(Boc-amino)propylbromide (3.8 g, 15.7 mmol) in THE (20 mL). The reaction mixture was slowly warmed to room temperature and stirred for 3 days. The reaction was cooled down to 0° C. then quenched with water (6 mL) and stirred for 1 hour. It was extracted with ethyl acetate (2×100 mL). The combined organic layers were washed with 1 N HCl aqueous and brine. It was dried over $Na_2SO_4$, filtered and concentrated. The residue was purified by normal phase chromatography (Isco, 0 to 5% methanol and dichloromethane). Yield 984 mg, 37%. Ion found by LCMS $[M+H]^+$ =510.0.

Step d.

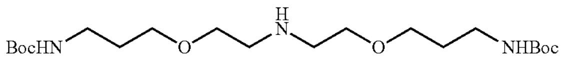 [SMILES: CC(C)(C)OC(=O)NCCCOCCNCCOCCCNC(=O)OC(C)(C)C]

Palladium hydroxide (543 mg, 0.77 mmol) was added into a flask containing the step-c product (985.3 mg, 1.93 mmol) in anhydrous methanol (19.5 mL), under an H2 atmosphere. The resulting mixture was stirred at room temperature for 16 hours. It was then filtered through a pad of celite and washed with methanol, and concentrated. The residue was carried on to the next step without purification. Yield 828.6 mg, 102%. Ion found by LCMS $[M+H]^+=420.0$.

Step e.

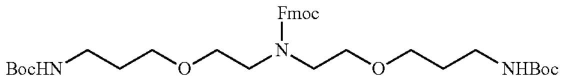

The step-d product (829 mg, 1.97 mmol) in $H_2O$:THF (1:1, 16 mL) was cooled down to 0° C. To this solution was added $Na_2CO_3$ (314 mg, 2.96 mmol) following by addition of Fmoc N-hydroxysuccinimide ester (826 mg, 2.37 mmol). The resulting mixture was warmed up to room temperature and stirred until complete by LCMS, then extracted with ethyl acetate. The organic layer was washed with brine and dried over $Na_2SO_4$, filtered and concentrated. The residue was purified by normal phase chromatography (Isco, 0 to 60% ethyl acetate and hexane). Yield 784 mg, 62%. Ion found by LCMS $[M+H-Boc]^+=542.0$.

Step f.

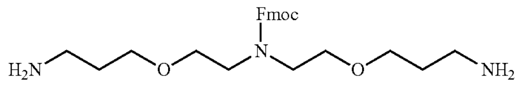

The step-e product (1.01 g, 1.57 mmol) was stirred in TFA (5 mL) and $CH_2Cl_2$ (9 mL) at room temperature for 1 hour then concentrated under reduced pressure. The residue was purified by RPLP (Isco, 5 to 100% methanol and water without modifier). Yield 903 mg, 86%. Ion found by LCMS $[M+H]^+=442.2$.

Step g.

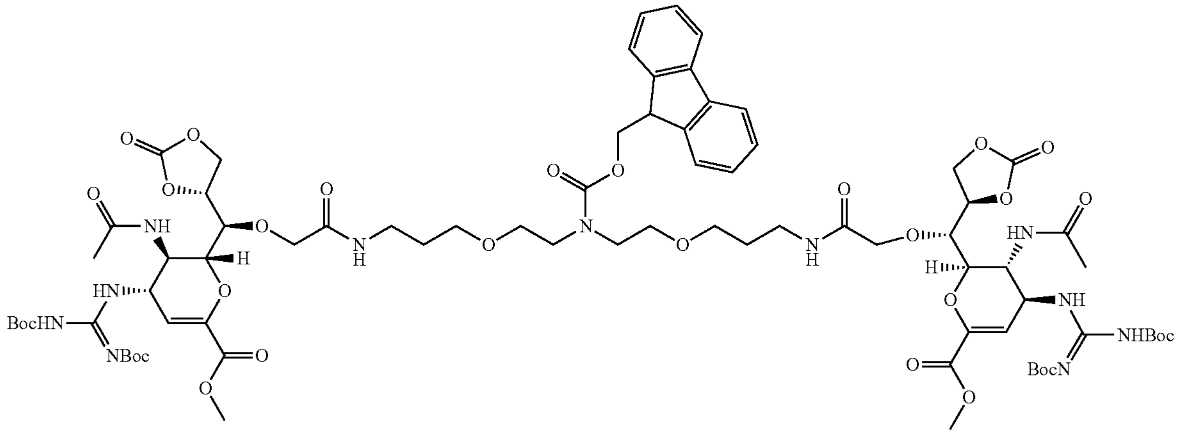

To a mixture of ether zanamivir acid (340 mg, 0.49 mmol), step-f product (111 mg, 0.25 mmol, Example 31) and HATU (206 mg, 0.53 mmol) in anhydrous DMF (3 mL) was added DIEA (162 mg, 1.23 mmol). The resulting mixture was stirred at room temperature for 1 hour, then directly purified by RPLC (Isco, 30 to 100% methanol and water without modifier). Yield 249 mg, 61%. Ion found by LCMS $[(M+2H)/2]^+=833.8$.

Step h.

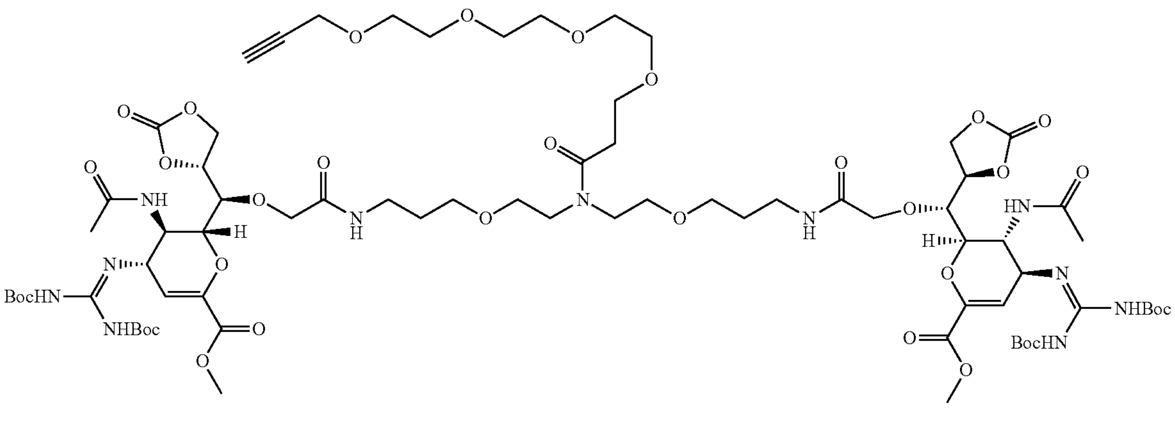 [SMILES: C#CCOCCOCCOCCOCCC(=O)N(CCOCCCNC(=O)CO[C@@H]([C@@H]1OC(C(=O)OC)=C[C@H](N=C(NC(=O)OC(C)(C)C)NC(=O)OC(C)(C)C)[C@H]1NC(C)=O)[C@H]1COC(=O)O1)CCOCCCNC(=O)CO[C@@H]([C@@H]1OC(C(=O)OC)=C[C@H](N=C(NC(=O)OC(C)(C)C)NC(=O)OC(C)(C)C)[C@H]1NC(C)=O)[C@H]1COC(=O)O1]

To a solution of the step-g product (249 mg, 0.15 mmol) in anhydrous DMF (0.5 mL) was added SilaMetS Thiol (1.2 g, 1.47 mmol) and 1,8-diazabicyclo[5.4.0]undec-7-ene (12 mg, 0.07 mmol). The resulting mixture was stirred for 1.5 hours, then filtered directly into a by way of containing HATU (69 mg, 0.18 mmol), propargyl PEG-4 acid (43 mg, 0.16 mmol) and DIEA (43 mg, 0.33 mmol). The reaction mixture was stirred for 1 hour, then directly purified by RPLC (Isco, 30 to 100% methanol and water without modifier). Yield 298 mg, 118%. Ion found by LCMS [(M+2H-Boc)/2]+=843.9.

Step i.

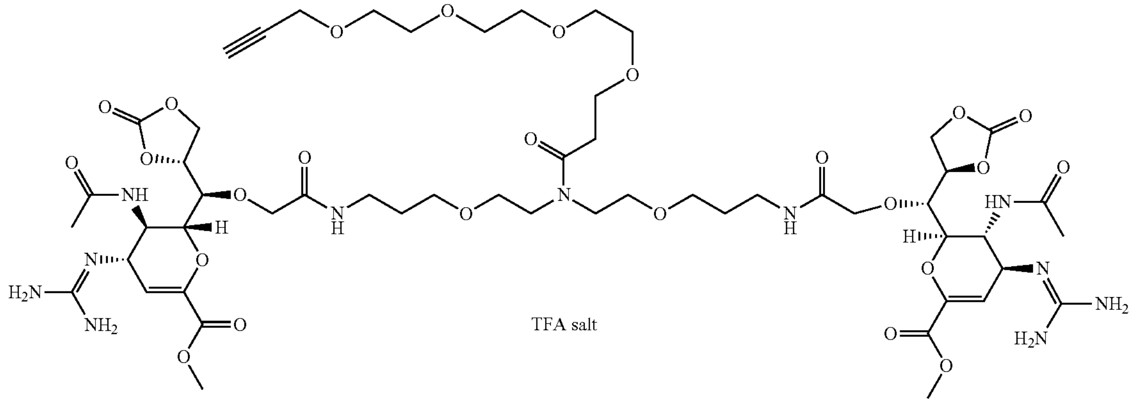 [SMILES: C#CCOCCOCCOCCOCCC(=O)N(CCOCCCNC(=O)CO[C@@H]([C@@H]1OC(C(=O)OC)=C[C@H](N=C(N)N)[C@H]1NC(C)=O)[C@H]1COC(=O)O1)CCOCCCNC(=O)CO[C@@H]([C@@H]1OC(C(=O)OC)=C[C@H](N=C(N)N)[C@H]1NC(C)=O)[C@H]1COC(=O)O1]

TFA salt

The step-h product (298 mg, 0.18 mmol) was dissolved in TFA (3 mL) and $CH_2Cl_2$ (3 mL), and the solution was stirred at room temperature for 16 hours. It was then concentrated under reduced pressure and purified by HPLC (ACCQ Isco, 0 to 25% acetonitrile and water, using 0.1% TFA as a modifier). Yield 112 mg, 44%. Ions found by LCMS $[(M+2H)/2]^+$=643.8 and [(M+3H)/3]+=429.6.

Step j.

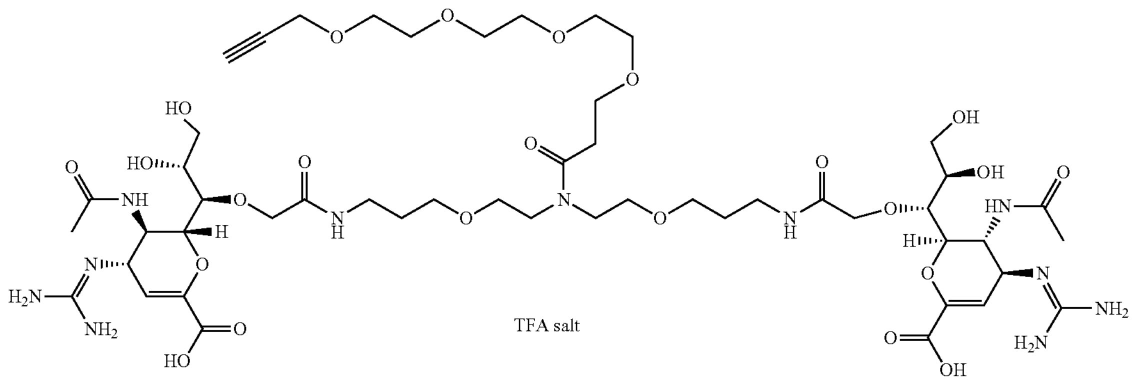 [SMILES: C#CCOCCOCCOCCOCCC(=O)N(CCOCCCNC(=O)CO[C@@H]([C@@H]1OC(C(=O)O)=C[C@H](N=C(N)N)[C@H]1NC(C)=O)[C@H](O)CO)CCOCCCNC(=O)CO[C@@H]([C@@H]1OC(C(=O)O)=C[C@H](N=C(N)N)[C@H]1NC(C)=O)[C@H](O)CO]

TFA salt

To a solution of the step-i product (112 mg, 0.072 mmol) in MeOH (4 mL) and water (2 mL) was added LiOH (10.6 mg, 0.43 mmol). The resulting solution was stirred at room temperature for 1 hour, then acidified with TFA and concentrated under reduced pressure. The residue was purified by HPLC (ACCQ Isco, 0 to 25% acetonitrile and water, using 0.1% TFA as modifier). Yield 37 mg, 36%. Ions found by LCMS $[(M+2H)/2]^+=603.8$, $[(M+3H)/3]+=402.9$.

Example 76. Synthesis of Conjugate 18

A solution of azido functionalized aglycosylated Fc (100 mg, 5.4 mL, 1.87 μmol, SEQ ID NO: 35) was added to a 15 mL centrifuge tube containing alkyne derivatized small molecule (16.1 mg, 0.011 mmol, Int-20). After gently shaking to dissolve all solids, the mixture was added to 3 mL premixed solution of L-ascorbic acid sodium (149 mg, 0.75 mmol, 0.25 M), copper (II) sulfate (2.4 mg, 0.015 mmol, 0.005 M) and BTTAA (25.8 mg, 0.6 mmol, 0.02 M) in PBS 7.4 buffer. The resulting solution was gently shaken overnight. It was purified by affinity chromatography over a protein A column, followed by size exclusion chromatography (see general conjugate purification protocol in Example 10). Maldi TOF analysis of the purified final product gave an average mass of 56826 Da (DAR 2.2). Yield 36.64 mg, 37%.

Example 77. Synthesis of Int-21

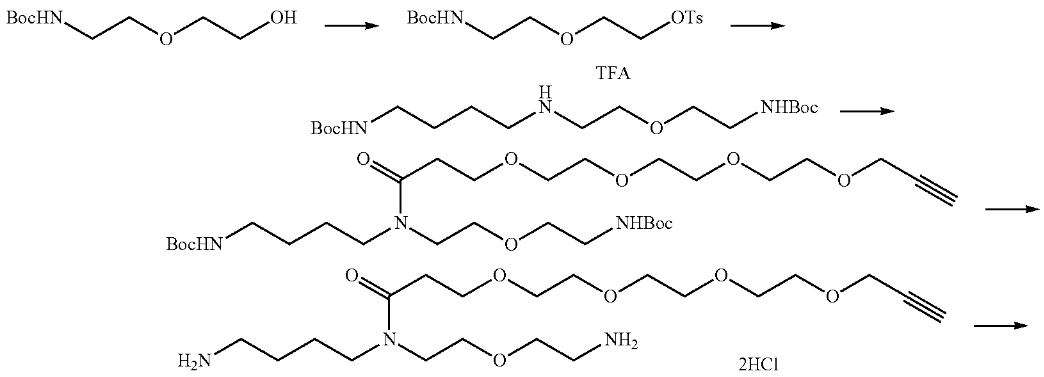

-continued
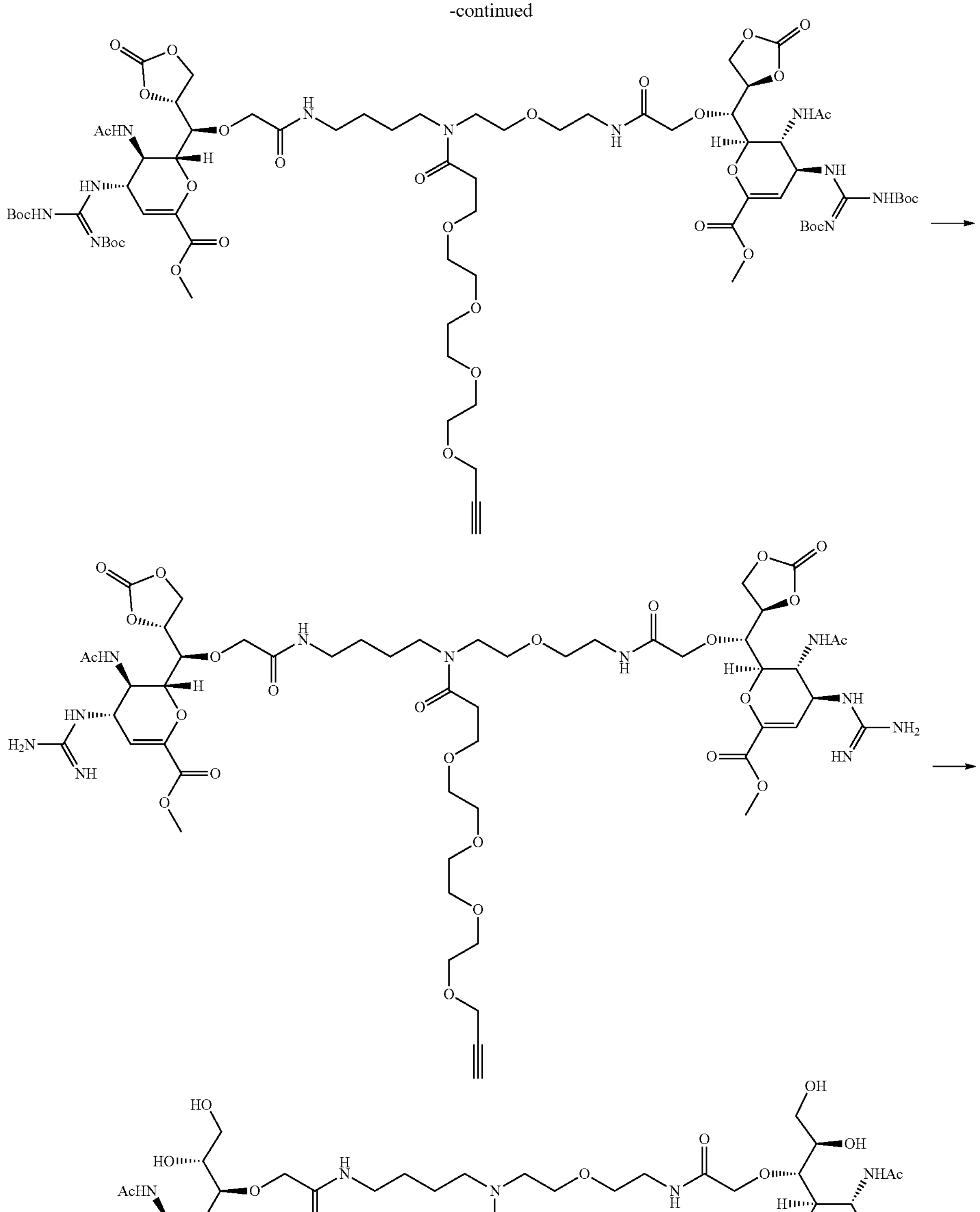

Step a.

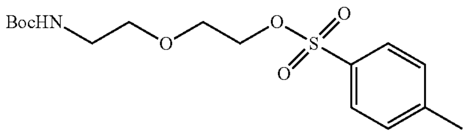 [SMILES: Cc1ccc(S(=O)(=O)OCCOCCNC(=O)OC(C)(C)C)cc1]

To a solution of 2-(2-Boc-aminoethoxy) ethanol (6.15 g, 30 mmol) in anhydrous DCM (60 ml) was added DIPEA (7.8 g, 60 mmol) and DMAP (366.6 mg, 3 mmol). P-toluenesulfonyl chloride (6.86 g, 36 mmol) was then added in portions over 30 minutes. After the resulting mixture was stirred for 3 days, it was concentrated by rotary evaporation and purified by RPLC (20% to 70% acetonitrile/water with no modifier). Yield 3.71 g, 34.4%. Ion found by LCMS: [M-Boc+H]+=260.

Step b.

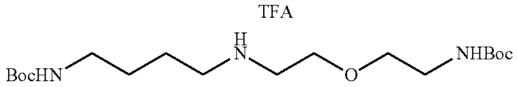 [SMILES: CC(C)(C)OC(=O)NCCCCNCCOCCNC(=O)OC(C)(C)C]

To a solution of the step-a product (2.1 g, 5.83 mmol) in anhydrous THE (10 ml) was added sodium carbonate (1.24 g, 11.7 mmol) and mono-N-Boc-1,4-diaminobutane (1.32 g, 7 mmol). The resulting mixture was heated at 60° C. for 1 day. The salt was then filtered off, and the filtrate was concentrated by rotary evaporation. The residue was purified through RPLC (100 g, 5 to 50% acetonitrile and water, using 0.1% TFA as modifier). Yield 1.94 g, 88.6%. Ion found by LCMS: $[M+H]^+$=376.0.

Step c.

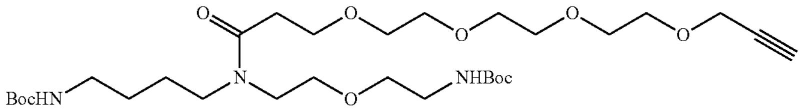 [SMILES: C#CCOCCOCCOCCOCCC(=O)N(CCCCNC(=O)OC(C)(C)C)CCOCCNC(=O)OC(C)(C)C]

To a solution of propargyl PEG-4 acid (781 mg, 3 mmol) and HATU (1.14 g, 3 mmol) in anhydrous DMF (3 ml) was added DIPEA (390 mg, 3 mmol), followed by the addition of the solution step-b product (940 mg, 2.5 mmol) and DIPEA (390 mg, 3 mmol) in anhydrous DMF (3 ml). The reaction mixture was stirred for 30 minutes, then directly purified through RPLC (100 g, 5 to 80% acetonitrile and water, using 0.1% TFA as modifier). Yield 960.2 mg, 65.3%. Ion found by LCMS: $[M+H]^+$=618.3, [M−Boc+H]+=518.3.

Step d.

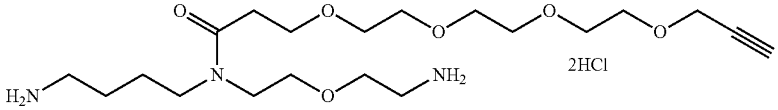 [SMILES: C#CCOCCOCCOCCOCCC(=O)N(CCCCN)CCOCCN]

The step-c product (960.2 mg, 1.63 mmol) was dissolved in anhydrous THE (6 ml). 4N HCl solution in dioxane (4 ml) was added, and the reaction mixture was stirred overnight. It was then concentrated by rotary evaporation. The residue was extracted with water (3 ml×3) and ethyl acetate (10 ml). The combined aqueous layers were lyophilized. Yield 760 mg, 95.1%. Ion found by LCMS: $[M+H]^+$=418.0.

Step e.

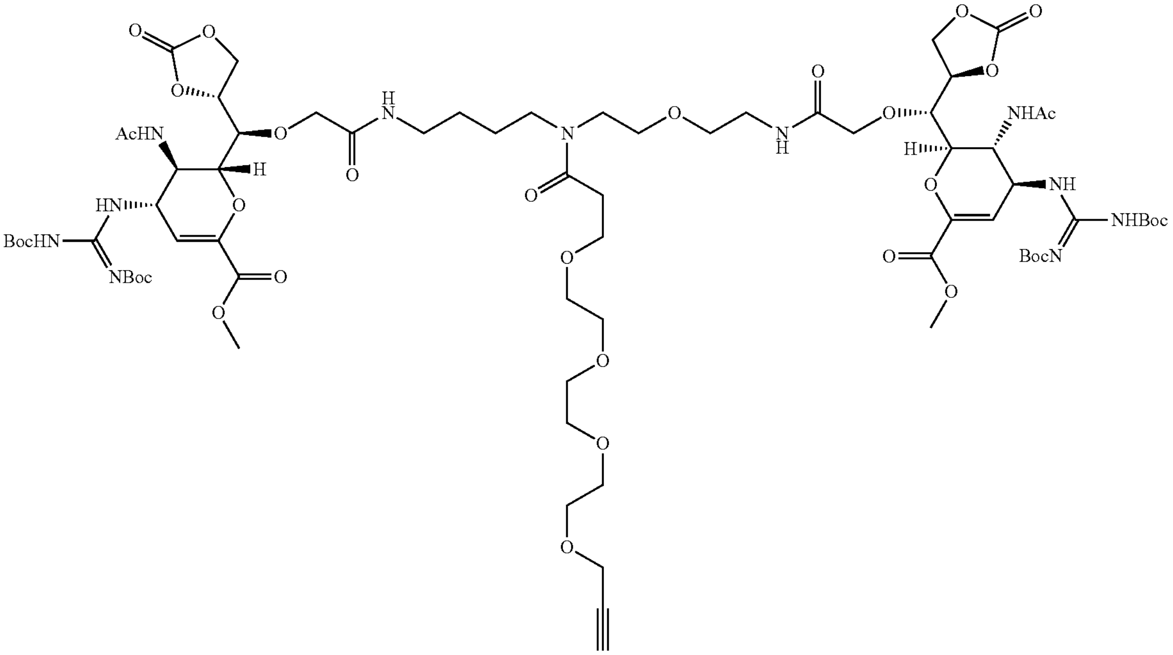

To a mixture of ether zanamivir acid (315 mg, 0.5 mmol) and HATU (190 mg, 0.5 mmol) in anhydrous DME (1 ml) was added in portions a solution of the step-d diamine product (148 mg, 0.3 mmol) and DIPEA (165 mg, 1.5 mmol) in anhydrous DMF (1 ml) over 20 minutes. After the addition, the reaction was stirred for 30 more minutes and directly purified by RPLC (50 g, 30 to 90% acetonitrile and water, using 0.1% TFA as modifier). Yield 233 mg, 56.7%. Ion found by LCMS: $[(M+2H)/2]^+$=821.3.

Step f.

The step-e product (233 mg, 0.142 mmol) was dissolved in TFA (1.5 ml), and the solution was heated at 30° C. for 30 minutes. It was then concentrated and directly purified by RPLC (0% to 30% acetonitrile and water, using 0.1% TFA as modifier). Yield 120 mg, 57.4%. Ions found by LCMS: $[(M+2H)/2]^+$=621.4, [(M+3H)/3]+=414.7.

Step g.

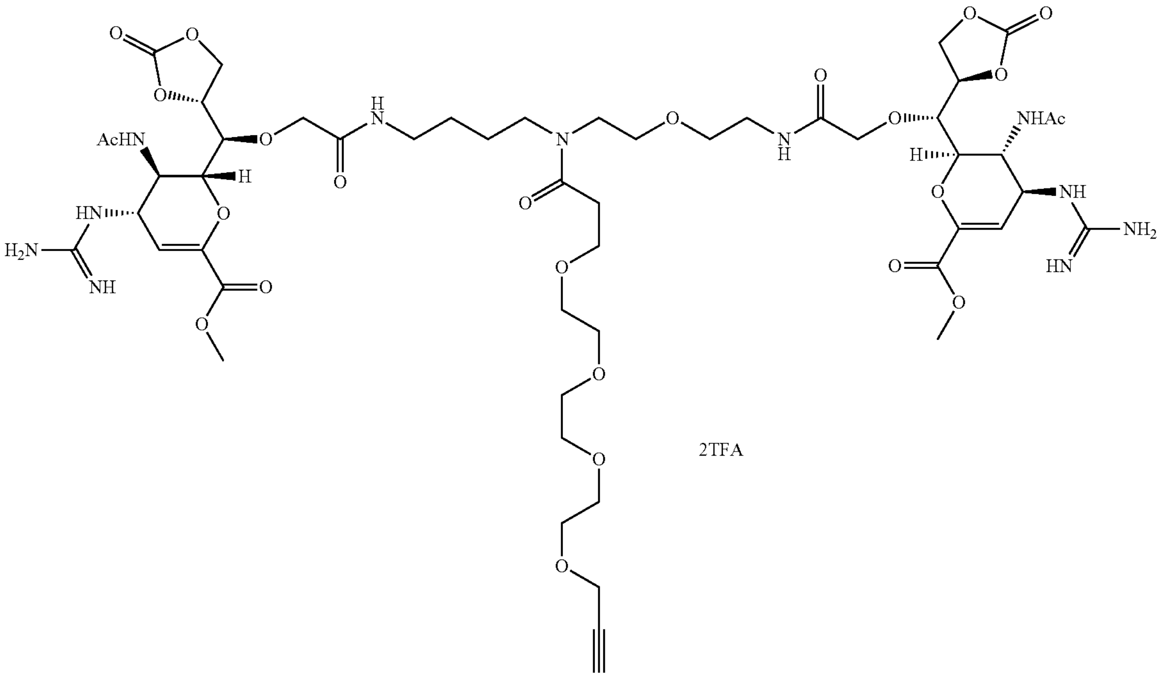 [SMILES: C#CCOCCOCCOCCOCCC(=O)N(CCCCNC(=O)CO[C@@H]([C@@H]1OC(C(=O)OC)=C[C@H](NC(=N)N)[C@H]1NC(C)=O)[C@H]1COC(=O)O1)CCOCCNC(=O)CO[C@@H]([C@@H]1OC(C(=O)OC)=C[C@H](NC(=N)N)[C@H]1NC(C)=O)[C@H]1COC(=O)O1]

2TFA

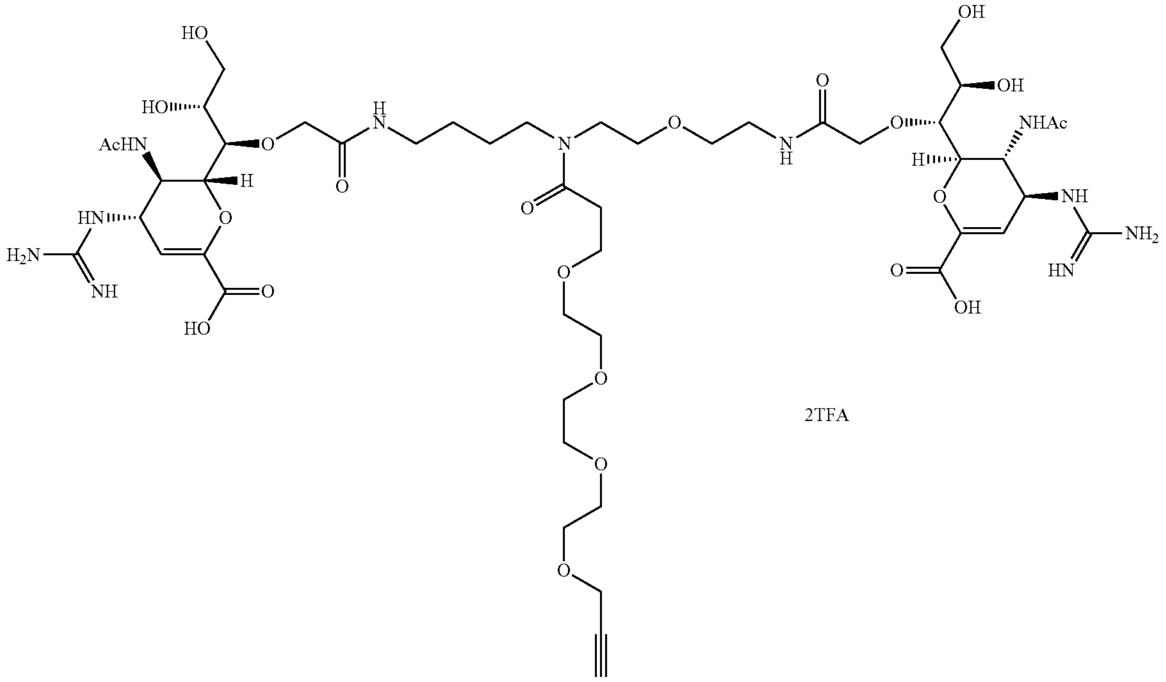 [SMILES: C#CCOCCOCCOCCOCCC(=O)N(CCCCNC(=O)CO[C@@H]([C@@H]1OC(C(=O)O)=C[C@H](NC(=N)N)[C@H]1NC(C)=O)[C@H](O)CO)CCOCCNC(=O)CO[C@@H]([C@@H]1OC(C(=O)O)=C[C@H](NC(=N)N)[C@H]1NC(C)=O)[C@H](O)CO]

2TFA

To a solution of the step-f product (120 mg, 0.0816 mmol) in MeOH (2 ml) was added LiOH monohydrate (63 mg, 1.5 mmol) solution in water (2 ml). The resulting mixture was stirred for 1.5 hours and then concentrated by rotary evaporation. The residue was acidified by 4N HCl solution in dioxane (0.5 ml) and was purified by HPLC (0 to 15% acetonitrile and water, using 0.1% TFA as modifier). Yield 98.2 mg, 86.6%. Ions found by LCMS: $[(M+2H)/2]^+=581.8$, $[(M+3H)/3]+=388.2$.

Example 78. Synthesis of Conjugate 19

This conjugate was prepared analogously to Example 62 (Conjugate 13a) by PEG4-azido-Fc (SEQ ID NO: 35, Example 61) and Int-21 (Example 78). Maldi TOF analysis of the purified final product gave an average mass of 56,548. Da (DAR=2.1). Yield 39.7 mg, 39.7%.

Example 79. Synthesis of Int-22

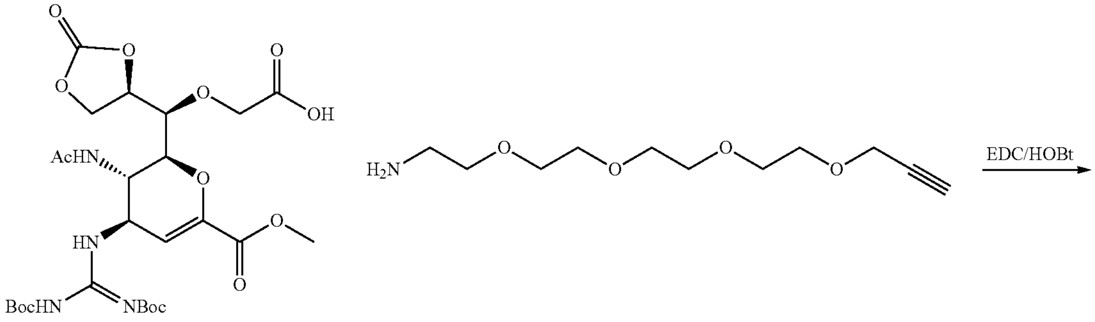

-continued

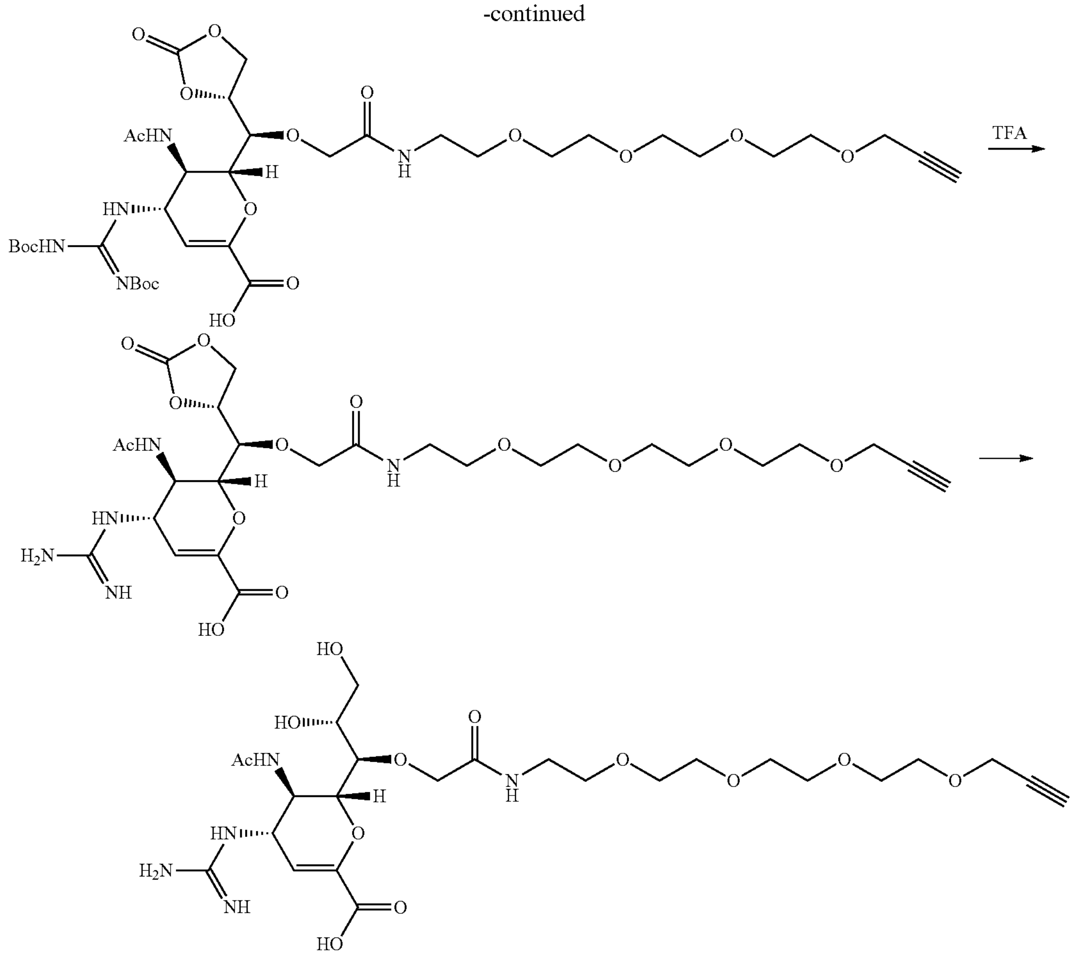

Step a.

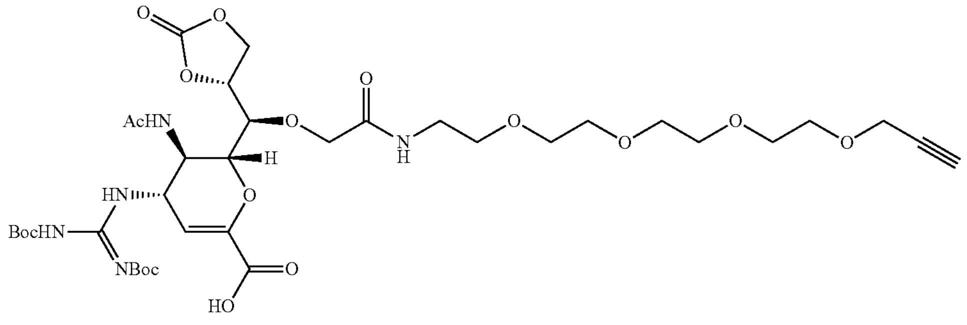

To a mixture of ether zanamivir acid (1.8 g, 2.8 mmol Example 31) and propargyl-PEG4-amine (0.82 g, 3.5 mmol. 1.2 eq.) in dichloromethane (50 mL), was added EDC (1.0 g, 5 mmol), HOBt (0. 65 g, 5 mmol), and DIEA (1.4 ml, 10 mmol). The resulting solution was stirred at room temperature overnight, concentrated, and purified by reverse phase liquid chromatography (RPLC) using an Isco COMBI-FLASH® liquid chromatograph eluted with 10% to 100% acetonitrile and water with no 0.1% TFA as modifier. Yield of products 1.35 g, 50.2%. Ion(s) found by LCMS: M+H=830.4.

Step b.

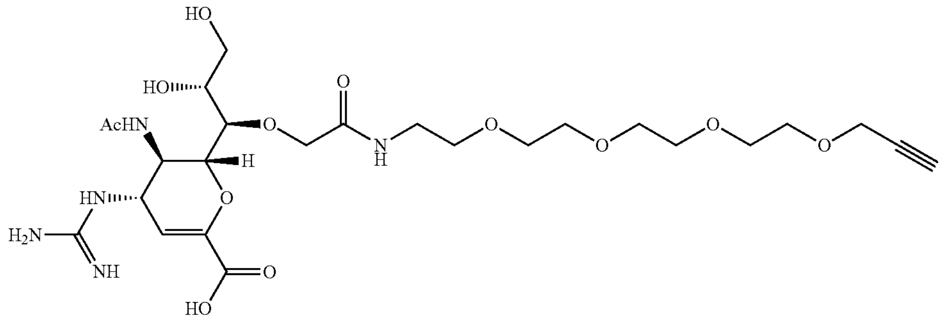 [SMILES: C#CCOCCOCCOCCOCCNC(=O)CO[C@@H]([C@@H]1OC(C(=O)O)=C[C@H](NC(=N)N)[C@H]1NC(C)=O)[C@H](O)CO]

Product from the previous step (1.35 g, 1.6 mmol) was treated with trifluoacetic acid (20 mL) for 30 min at room temperature. The resulting solution was concentrated, dissolved in water (10 mL) and MeOH (10 mL), then treated with a lithium hydroxide (120 mg, 5 mmol) solution in water (10 mL). The reaction was stirred 10 min then quenched with 0.5 ml acetic acid. The reaction was concentrated and purified by reverse phase liquid chromatography (RPLC) using an Isco COMBIFLASH® liquid chromatograph eluted with 0% to 50% acetonitrile and water, using 0.1% TFA as the modifier. Yield of the products 510 mg, 52.8%. Ion(s) found by LCMS: M+H=604.3.

Example 80. Synthesis of Conjugate 20

This conjugate was prepared analogously to Example 62 (Conjugate 13a) by PEG4-azido-Fc (SEQ ID NO: 35, Example 61) and Int-22 (Example 79). Maldi TOF analysis of the purified final product gave an average mass of 55,508. Da (DAR=2.3). Yield 37.0 mg, 37.0%.

Example 81. Synthesis of Int-23

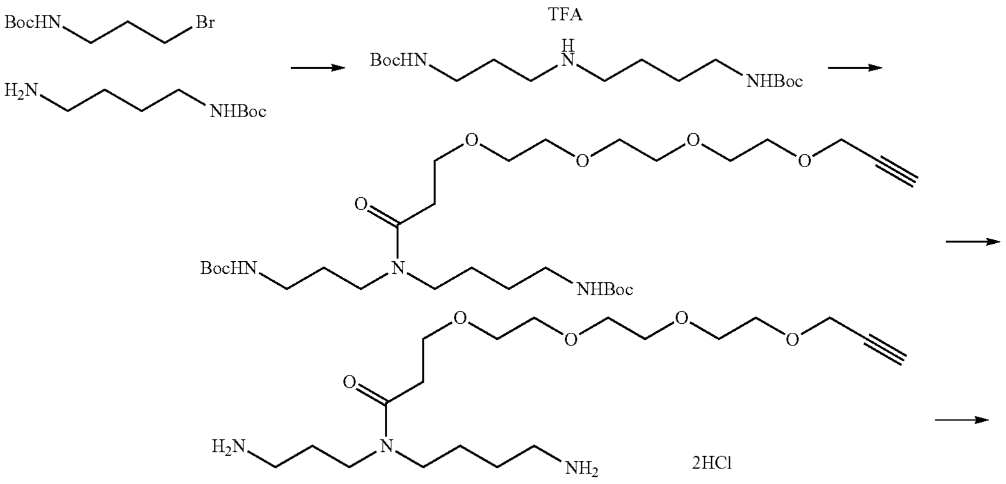

-continued

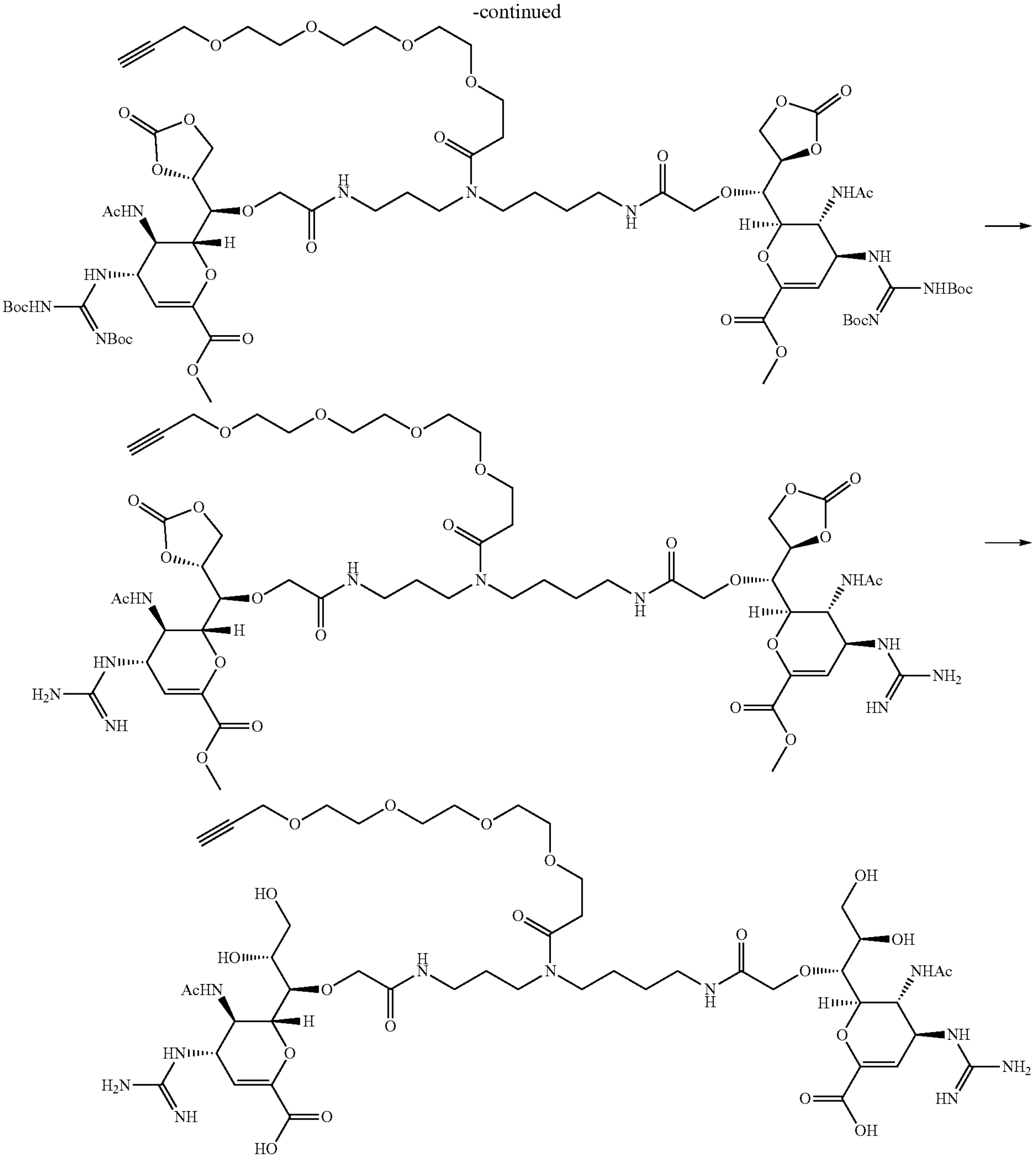

Step a.

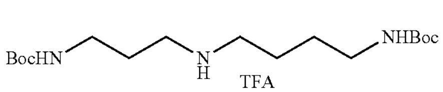 [SMILES: CC(C)(C)OC(=O)NCCCCNCCCNC(=O)OC(C)(C)C]

To a solution of N-Boc-1.4-diaminobutane (941.5 mg, 5 mmol) in anhydrous THE (10 ml) was added sodium carbonate (1.06 g, 10 mmol) and 3-(Boc-amino)propylbromide (1.43 g, 6 mmol). The resulting mixture was heated at 50° C. for 1 day. The salt was then filtered, and concentrated by rotary evaporation. The residue was purified by RPLC (100 g, 5 to 50% acetonitrile and water, using 0.1% TFA as modifier). Yield 1.35 g, 58.8%. Ion found by LCMS: $[M+H]^+=346.0$.

Step b.

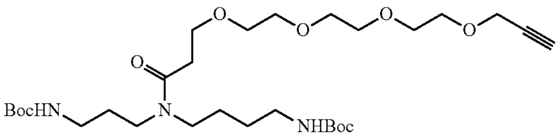 [SMILES: C#CCOCCOCCOCCOCCC(=O)N(CCCCNC(=O)OC(C)(C)C)CCCNC(=O)OC(C)(C)C]

To a solution of propargyl PEG-4 acid (781 mg, 3 mmol) and HATU (1.14 g, 3 mmol) in anhydrous DMF (3 ml) was added DIPEA (390 mg, 3 mmol), followed by the addition of the solution step-a product (863.8 mg, 2.5 mmol) and DIPEA (390 mg, 3 mmol) in anhydrous DMF (3 ml). The reaction mixture was stirred for 30 minutes, then directly purified by RPLC (100 g, 5 to 80% acetonitrile and water, using 0.1% TFA as modifier). Yield 1.19 g, 81%. Ion found by LCMS: $[M+H]^+$=588.3.

Step c.

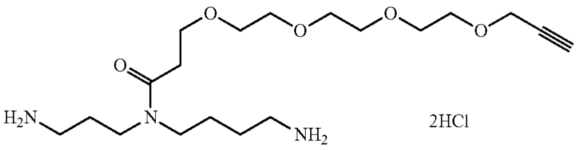 [SMILES: C#CCOCCOCCOCCOCCC(=O)N(CCCN)CCCCN]

2HCl

The step-b product (1.19 g, 2.02 mmol) was dissolved in anhydrous THF (6 ml). 4N HCl solution in dioxane (4.5 ml) was added, and the reaction mixture was stirred for 1 day. It was then concentrated by rotary evaporation. The residue was extracted with water (3 ml×3) and ethyl acetate (15 ml). The combined aqueous layers were lyophilized. Yield 940 mg, quantitative yield. Ion found by LCMS: $[M+H]^+$=388.3.

Step d.

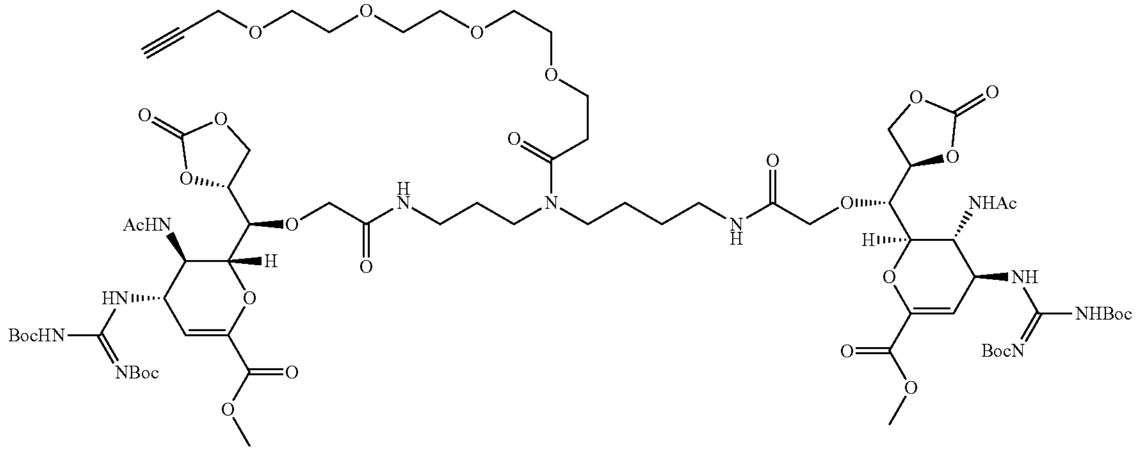

To a mixture of ether zanamivir acid (315 mg, 0.5 mmol, Example 31) and HATU (209.1 mg, 0.55 mmol) in anhydrous DMF (1 ml) was added DIPEA (65 mg, 0.5 mmol). After 5 minutes, a solution of the step-c product (170 mg, 0.439 mmol) and DIPEA (130 mg, 1 mmol) in anhydrous DMF (1 ml) was added in portions over 20 minutes. The reaction was stirred for an additional 30 minutes, then directly purified by RPLC (50 g, 30 to 90% acetonitrile and water, using 0.1% TFA as modifier). Yield 208 mg, 51.6%. Ion found by LCMS: $[(M+2H)/2]^+$=806.7.

Step e.

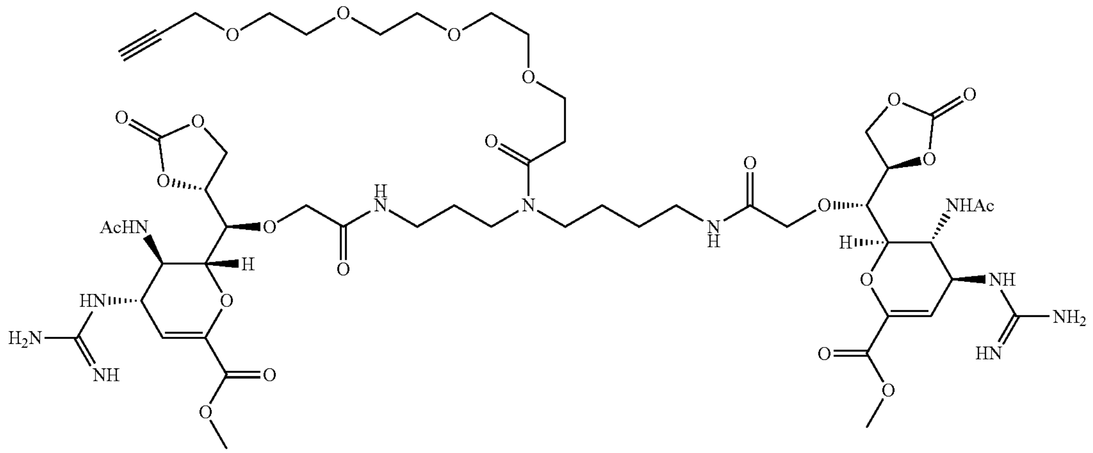 [SMILES: C#CCOCCOCCOCCOCCC(=O)N(CCCCNC(=O)CO[C@@H]([C@@H]1OC(C(=O)OC)=C[C@H](NC(=N)N)[C@H]1NC(C)=O)[C@H]1COC(=O)O1)CCCNC(=O)CO[C@@H]([C@@H]1OC(C(=O)OC)=C[C@H](NC(=N)N)[C@H]1NC(C)=O)[C@H]1COC(=O)O1]

The step-d product (208 mg, 0.129 mmol) was dissolved in TFA (1.5 ml), and the solution was heated at 30° C. for 30 minutes. It was then directly purified by RPLC (100 g, 0 to 30% acetonitrile and water, using 0.1% TFA as modifier). Yield 134 mg, 72%. Ions found by LCMS: $[(M+2H)/2]^+$ =606.8, [(M+3H)/3]+=405.0.

Step f.

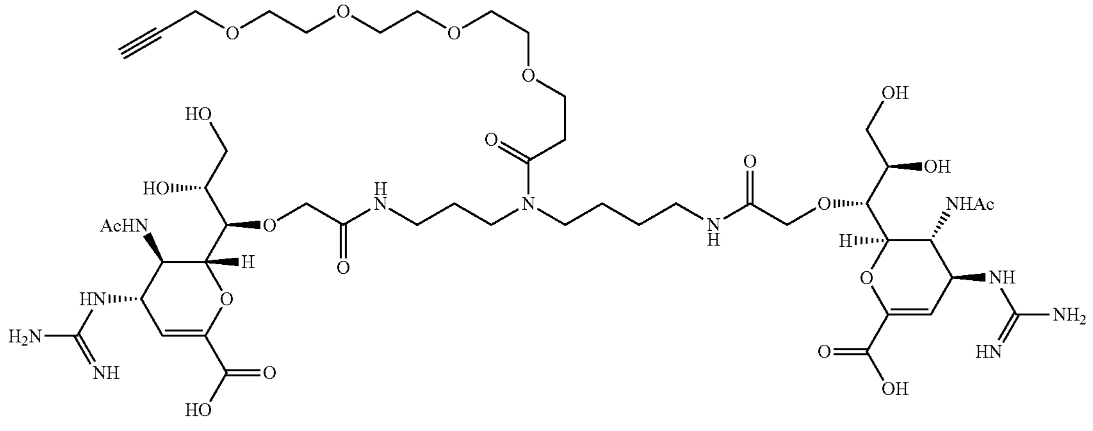 [SMILES: C#CCOCCOCCOCCOCCC(=O)N(CCCCNC(=O)CO[C@@H]([C@@H]1OC(C(=O)O)=C[C@H](NC(=N)N)[C@H]1NC(C)=O)[C@H](O)CO)CCCNC(=O)CO[C@@H]([C@@H]1OC(C(=O)O)=C[C@H](NC(=N)N)[C@H]1NC(C)=O)[C@H](O)CO]

To a solution of the step-e product (134 mg, 0.093 mmol) in MeOH (2 ml) was added a solution of LiOH monohydrate (63 mg, 1.5 mmol) in water (2 ml). The resulting mixture was stirred for 1.5 hours and then concentrated by rotary evaporation. The residue was acidified by 4N HCl solution in dioxane (0.5 ml) and was purified by HPLC (0 to 15% acetonitrile and water, using 0.1% TFA as modifier). Yield 78.4 mg, 62%. Ions found by LCMS: $[(M+2H)/2]^+$=566.4, [(M+3H)/3]+=378.4.

Example 82. Synthesis of Conjugate 21

This conjugate was prepared analogously to Example 62 (Conjugate 13a) by PEG4-azido-Fc (SEQ ID NO: 35, Example 61) and Int-23 (Example 81). Maldi TOF analysis of the purified final product gave an average mass of 56,503. Da (DAR=2.2). Yield 34.4 mg, 34%.

Example 83. Activity of Conjugates 13 to 21 Against High Path H7N9 Influenza A, and Two Influenza B Isolates in a Cytopathic Effects (CPE) Assay A total of 9 conjugates (Table 38) were run at concentrations of 100, 10, 1, and 0.1 nM and compared to ribavirin in a CPE assay. The CPE assay followed standard methodology, but briefly, utilized 80-100% confluent monolayers of MOCK cells in a 96-well plate. To these, test articles were added in triplicate and allowed to incubate at 37° C. (+5% $CO_2$) until CPE effects were visually apparent. Once CPE was noted, cell layers were stained with 0.011% neutral red for approximately 2 hours. Afterwards, a 50:50 mix of Sorensen citrate buffer/ethanol was added and allowed to incubate for 30 min, then the $A_{540}$ was read on a spectrophotometer and EC50/CC50 values calculated by regression analysis.

All conjugates had significant activity against the Influenza B/Florida/4/2006 isolate, with an $EC_{50}$ values ranging from 3.05 to 33.5 nm (Table 39). On average, conjugates demonstrated a 275-fold potency advantage over ribavirin (EC50 of 3,250 nM). Activity of conjugates against Influenza B/Brisbane/60/2008 was very similar to that seen against B/Florida with the exception of conjugate 14, which had an $EC_{50}$ of greater than 100 nM Importantly, all conjugates were highly active against the high path Influenza A/Anhui/1/2013 (H-7N9) isolate as well.

The average EC50 for all conjugates was 21.2 nM against this isolate (ranging from 12 to 28.5 nM), compared to 14,000 nM for ribavirin. Lastly, no direct cytotoxic effects of the conjugates on MOCK monolayers were detected at the concentrations tested.

TABLE 38

| Conjugates and properties | | | | | |
|---|---|---|---|---|---|
| Conjugate | Int | Fc domain | DAR | Linker | Notes |
| 13 | 18 | SEQ ID NO: 35 | 2.2 | 15 atom | ether, dimer |
| 14 | 7 | SEQ ID NO: 35 | 2.1 | 15 atom | carbamate, dimer |
| 15 | 12 | SEQ ID NO: 35 | 2.2 | 15 atom | ether, dimer |
| 16 | 9 | SEQ ID NO: 35 | 2.1 | 17 atom | ether, dimer |
| 17 | 19 | SEQ ID NO: 35 | 2.2 | 17 atom | ether, dimer |
| 18 | 20 | SEQ ID NO: 35 | 2.2 | 19 atom | ether, dimer |
| 19 | 21 | SEQ ID NO: 35 | 2.1 | 16 atom | ether, dimer |
| 20 | 22 | SEQ ID NO: 35 | 2.3 | na | ether, monomer |
| 21 | 23 | SEQ ID NO: 35 | 2.2 | 14 atom | ether, dimer |

TABLE 39

| Activity of conjugates in a CPE assay against Influenza subtypes | | | |
|---|---|---|---|
| | EC50 (nM)* | | |
| Conjugate | A/Anhui/1/2013 (H7N9) (zoonotic aby way ofn) | B/Brisbane/60/2008 (Victoria lineage) | B/Florida/4/2006 (Yamagata lineage) |
| Ribavirin | 14000 | 3300 | 3250 |
| 13 | 24 | 21 | 33.5 |
| 14 | 12 | >100 | 18.5 |
| 15 | 21.5 | 5.95 | 4.6 |
| 16 | 28.5 | 14.5 | 11 |
| 17 | 28** | 11 | 13 |
| 18 | 31 | 4.35 | 3.05 |
| 19 | 14.5 | 6.8 | 4.55 |
| 20 | 20.5 | 12.5 | 14.5 |
| 21 | 17.5 | 4.05 | 3.05 |

*Average of 2 values (VIS + NR)

**EC50 of 28 by VIS, >100 by NR

Example 84. Syntheses of Conjugate 22

Step a. Synthesis of PEG4-Azido IVIG

Preparation of 0.05M PEG4-azidoNHS ester solution in DMF/PBS: 6.05 mg of PEG4-azido NHS ester was dissolved in 0.050 mL of DMF at 0° C. and diluted to 0.305 mL by adding 0.250 mL of PBS 1× buffer at 0° C. This solution was used for preparing other PEG4-azido IVIG with variety of DAR values by adjusting the equivalents of this PEG4-azido NHS ester PBS solution.

Preparation of PEG4-azido IVIG: 0.05M PEG4-azidoNHS ester PBS buffer solution (0.301 mL, 15.0 μmol, 5.5 equivalents) was added to a solution of IVIG (Intravenous Immune Globulin, Baxter)) (407 mg in 9.25 mL of pH 7.4 PBS, MW~148863 Da, 1.968 μmol) and the mixture was shaken gently for 12 hours at ambient temperature. The solution was concentrated using a centrifugal concentrator (100,000 MWCO) to a volume of ~1.5 mL. The crude mixture was diluted 1:10 in PBS pH 7.4, and concentrated again. This wash procedure was repeated for total of three times. The small molecule reagent was removed with this wash procedure. The concentrated IVIG-PEG4-azide was diluted to 9.25 mL with pH 7.4 PBS 1× buffer and ready for Click conjugation. The purified material was quantified using a NANODROP™ UV visible spectrophotomer (using a calculated extinction coefficient based on the amino acid sequence of IVIG). Yield is quantitative after purification.

Step b. Synthesis of Conjugates

Prepared the Click reagent solution: 0.0050M $CuSO_4$ in PBS buffer solution: 10.0 mg $CuSO_4$ was dissolved in 12.53 mL PBS×1, than took 6.00 mL 0.0050M $CuSO_4$ solution and added 57.7 mg BTTAA (CAS number 1334179-85-9) and 297.6 mg Na Ascorbate to give the Click reagent solution (0.0050M CuSO4, 0.020M BTTAA and 0.25M Sodium Ascorbate).

A solution of azido functionalized IVIG (140 mg, 3.17 mL, 0.936 μmol, IVIG-Linker-1-Azide) was added to a 15 mL centrifuge tube containing alkyne derivatized small molecule (8.4 mg, 0.00618 mmol, 6.6 eq, described in Example 60). After gently shaking to dissolve all solids, 1.50 mL of above click reagent solution of (L-ascorbic acid sodium, 0.25 M, 74.2 mg, 0.374 mmol, copper (II) sulfate 0.0050M, 1.2 mg, 0.0075 mmol, and BTTAA 0.020M, 12.9 mg, 0.0300 mmol). The resulting mixture was gently shaken overnight. It was purified by affinity chromatography over a Protein A column, followed by size exclusion chromatography (see conjugate purification protocol in Example 10). Maldi TOF analysis of the purified final product gave an average mass of 151873 Da (DAR=2.7). Yield 51.0 mg, 36% yield.

Example 85. Syntheses of Conjugate 23

Conjugate 23 was prepared analogously to Conjugate 22, substituting the appropriate alkyne functionalized small molecule (Int-23 described in Example 81) in the click conjugation step.

Example 86. Syntheses of Conjugate 24

Conjugate 24 was prepared analogously to Conjugate 22, substituting the appropriate alkyne functionalized small molecule (described in Example 19) in the click conjugation step.

Example 87. Efficacy of Conjugates 13, 14, and 21 Against Influenza B in a Lethal Mouse Model Conjugates were evaluated against a lethal Influenza B influenza infection in female BALB/c mice (Charles River Laboratories, 6-8 weeks). The challenge virus (B/Malaysia/2506/04) is a mouse-adapted isolate capable of causing lethal infections in mice. The experiment comprised 11 groups of 5 mice. At day 0, all mice were challenged with virus at 3× the LD95 by intranasal inoculation in a volume of 30 μl (approx. 1E4 per mouse), after being anesthetized with a mixture of ketamine/xylazine (150 and 10 mg/kg respectively).

All groups received a single IV treatment, 2 hours post viral challenge of test article, vehicle (PBS), or Fc only control (hIgG1 Fc). The study evaluated Int-18, Int-7, and Int-23 conjugated to identical Fc monomers (conjugates 13, 14, and 21, respectively), tested at 3.0, 1.0, and 0.3 mg/kg. Mice were monitored for 2 weeks and animals exceeding 20% body weight loss, or were found moribund, were scored as a mortality.

All mice treated with vehicle or the Fc only control, reached mortality by day 7. In contrast, mice receiving conjugates 13, 14, and 21 were fully protected after receiving a single IV dose at 0.3 mg/kg (Table 40). As expected, groups receiving the conjugates at 1.0 or 3.0 mg/kg were fully protected as well. The potency of all conjugates against Influenza B was further supported by the daily body measurements (Table 41), which show a less than 5% transient drop across the entire study for any conjugate treated group. The activity of conjugates 13, 14, and 21 is comparable by dose to the activity of conjugate 6 against Influenza A H1N1 and H3N2 subtypes. Since conjugates, 6 and 14 have identical targeting moieties (corresponding to Int-7), a single conjugate may be active against the dominant seasonal influenza types (Influenza A (H1N1), Influenza A (H3N2), and Influenza B).

TABLE 40

Mortality data at study end (day 14). Average of 5 mice; p-values calculated by Log-rank (Mantel-Cox) test

| Compound | Dosage (mg/kg) | % Survival | Significance to vehicle (p-value) |
|---|---|---|---|
| Vehicle (PBS) | na | 0 | na |
| Fc alone | 3.0 | 0 | p = 1 |
| Conjugate 13 | 0.3 | 100 | (0.0027) |
| | 1.0 | 100 | (0.0027) |
| | 3.0 | 100 | (0.0027) |
| Conjugate 14 | 0.3 | 100 | p = 0.0027 |
| | 1.0 | 100 | p = 0.0027 |
| | 3.0 | 100 | p = 0.0027 |
| Conjugate 21 | 0.3 | 100 | (0.0027) |
| | 1.0 | 100 | (0.0027) |
| | 3.0 | 100 | (0.0027) |

TABLE 41

Mouse body weight data (% BW relative to day 0). Average of 5 mice; *data not included once the first animal reaches mortality within a group

| Day post | Vehicle | Fc alone | Conjugate 14 (mg/kg) | | |
|---|---|---|---|---|---|
| challenge | (PBS) | 3.0 | 0.3 | 1.0 | 3.0 |
| 0 | 100.0 | 100.0 | 100.0 | 100.0 | 100.0 |
| 1 | 98.1 | 98.1 | 99.3 | 99.1 | 96.5 |
| 2 | 99.6 | 96.7 | 98.6 | 98.6 | 98.3 |
| 3 | 96.4 | 94.9 | 96.8 | 97.0 | 98.7 |
| 4 | 89.8 | 87.8 | 98.4 | 97.5 | 97.8 |
| 5 | 83.6 | 80.8 | 97.4 | 97.8 | 98.0 |
| 6 | 79.0 | 76.1 | 96.9 | 98.3 | 99.7 |
| 7 | * | * | 99.2 | 100.5 | 100.6 |
| 8 | * | * | 100.3 | 101.9 | 101.1 |
| 9 | * | * | 102.5 | 100.4 | 100.6 |
| 10 | * | * | 100.6 | 102.0 | 101.2 |
| 11 | * | * | 100.9 | 100.9 | 100.9 |
| 12 | * | * | 101.8 | 101.7 | 101.8 |
| 13 | * | * | 101.4 | 101.7 | 101.4 |
| 14 | * | * | 102.2 | 102.6 | 102.2 |

Example 88. Synthesis of PEG4-azido Fc for Conjugate 25, Conjugate 26, Conjugate 27, and Conjugate 28

Preparation of 0.05M PEG4-azidoNHS ester solution in DMF/PBS×1: 27.40 mg of PEG4-azido NHS ester was dissolved in 0.155 mL of DMF at 0° C. and diluted to by adding 1.200 mL of PBS 1× buffer at 0° C. This solution was used for preparing other PEG4-azido Fc with variety of DAR values by adjusting the equivalents of this PEG4-azido NHS ester PBS×1 solution.

Preparation of PEG4-azido Fc(SEQ ID NO: 48): 0.05M PEG4-azidoNHS ester PBS×1 buffer solution (0.0984 mL, 4.92 μmol, 2.5 equivalents) was added to a solution of h-IgG1 Fc (SEQ ID NO: 48) (234 mg in 13.605 mL of pH 7.4 PBS, MW~57,976 Da, 4.036 μmol) and the mixture was shaken gently for 2 hours at ambient temperature. The solution was concentrated using a centrifugal concentrator (30,000 MWCO) to a volume of ~2 mL. The crude mixture was diluted 1:7 in PBS pH 7.4, and concentrated again. This wash procedure was repeated for total of three times. The small molecule reagent was removed with this wash procedure. The concentrated Fc(SEQ ID NO: 48)-PEG4-azide was diluted to 13.60 mL with pH 7.4 PBS 1× buffer and ready for Click conjugation. The purified material was quantified using a Nanodrop™ UV visible spectrophotomer (using a calculated extinction coefficient based on the amino acid sequence of h-IgG1).

Preparation of PEG4-azido Fc(SEQ ID NO: 50) was analogous to above PEG4-azido Fc (SEQ ID NO: 48).

Example 89. Synthesis of Conjugate 25

Preparation of the Click reagent solution: 0.0050M $CuSO_4$ in PBS×1 buffer solution: 10.0 mg $CuSO_4$ was dissolved in 12.53 mL PBS×1, than took 10.00 mL this $CuSO_4$ solution and added 86.1 mg BTTAA and 495.3 mg Na Ascorbate to give the Click reagent solution (0.0050M CuSO4, 0.020M BTTAA and 0.25M Sodium Ascorbate). This Click reagent solution will be used for Conjugate 25 and Conjugate 26.

A solution of azido functionalized Fc (78.0 mg, 4.535 mL, 1.35 μmol, SEQ ID NO: 48-PEG4-Azide) was added to a 15 mL centrifuge tube containing alkyne derivatized small molecule (13.2 mg, 8.88 μmol, Int-23). After gently shaking to dissolve all solids, the mixture was added with 2.153 mL of above Click reagent solution of (L-ascorbic acid sodium, 0.25 M, 106.6 mg, 0.538 mmol, copper (II) sulfate 0.0050M, 1.72 mg, 0.0107 mmol, and BTTAA 0.020M, 18.5 mg, 0.0431 mmol). The resulting mixture was gently shaken for 6 hours at ambient temperature. It was purified by affinity chromatography over a protein A column, followed by size exclusion chromatography (see conjugate purification protocol in Example 10). Maldi TOF analysis of the purified final product gave an average mass of 60973 Da (DAR=2.1). Yield 50.3 mg, 64% yield.

Example 90. Synthesis of Conjugate 26

Preparation of Conjugate 26 was analogous to Conjugate 25 by using the same batch of PEG4-azido Fc(SEQ ID NO: 48) and an alkyne-derivatized small molecule (Int-7). Maldi TOF analysis of the purified final product gave an average mass of 61068 Da (DAR=2.2). Yield 49.5 mg, 63% yield.

Example 91. Synthesis of Conjugate 27

Preparation of the Click reagent solution: 0.0050M $CuSO_4$ in PBS×1 buffer solution: 10.0 mg $CuSO_4$ was dissolved in 12.53 mL PBS×1, than took 12.00 mL this $CuSO_4$ solution and added 103.3 mg BTTAA and 594.3 mg Na Ascorbate to give the Click reagent solution (0.0050M CuSO4, 0.020M BTTAA and 0.25M Sodium Ascorbate). This Click reagent solution will be used for Conjugate 28.

A solution of azido functionalized Fc (80.0 mg, 4.535 mL, 1.38 μmol, SEQ ID NO: 50-PEG4-Azide) was added to a 15 mL centrifuge tube containing alkyne derivatized small molecule (13.5 mg, 9.10 μmol, Int-23). After gently shaking to dissolve all solids, the mixture was added with 2.21 mL of above Click reagent solution of (L-ascorbic acid sodium, 0.25 M, 109.3. mg, 0.552 mmol, copper (II) sulfate 0.0050M, 1.76 mg, 0.0110 mmol, and BTTAA 0.020M, 19.0 mg, 0.0441 mmol). The resulting mixture was gently shaken for 6 hours at ambient temperature. It was purified by affinity chromatography over a protein A column, followed by size exclusion chromatography (see conjugate purification protocol in Example 10). Maldi TOF analysis of the purified final product gave an average mass of 61447 Da (DAR=2.5). Yield 37.1 mg, 46% yield.

Example 92. Synthesis of Conjugate 28

Preparation of Conjugate 28 was analogous to Conjugate 27 by using the same batch of PEG4-azido Fc(SEQ ID NO: 50) and an alkyne-derivatized small molecule (Int-7). Maldi TOF analysis of the purified final product gave an average mass of 61388 Da (DAR=2.4). Yield 44.6 mg, 56% yield.

Example 93. Activity of Conjugate 6 and Conjugate 21 Against High Path Influenza a (H5N1, H7N9) in a Cytopathic Effects (CPE) Assay An in vitro assay to determine the potency of conjugates of the invention was conducted against BSL-3 (high path) influenza A, and generally followed standard procedures. Briefly, different concentrations of conjugates were mixed with virus (approximately 250 $TC_{ID50}$) and allowed to incubate @35° C. for one hour. After incubation, the mixture was added to an 80-90% confluent monolayer of MDCK cells. After a 90 minute incubation cells were washed and conjugates re-applied. The monolayer was subsequently overlayed with carboxymethylcellulose to minimize viral spreading and allowed to incubate for two days. After two days of culture cells were washed with PBS and fixed with 10% formalin. After fixation the MDCK monolayer was permeabilized with Triton X-100 and immunostained with a mouse mAb against influenza nucleoprotein. Monolayers were read, and the stained area per well was calculated to determine $EC_{50/100}$ values.

The results of the study are summarized in Table 42 and demonstrate the potency of Conjugate 6 and Conjugate 21 against highly pathogenic strains with pandemic potential. Importantly, both conjugates generated $EC_{100}$ values at, or below, 15 nM against four H5N1 and one H7N9 isolate. In contrast, oseltamivir had an $EC_{100}$ of approximately 15 nM only against one isolate (A/Vietnam/1194/2004) and values ranging from 125 to >1000 nM against the other high path strains. These results suggest that the potential of Conjugate 6 and Conjugate 21 to treat pandemics caused by highly-virulent influenza to be superior to that of oseltamivir.

TABLE 42

*In vitro* activity of Conjugate 6 and Conjugate 12 against high path influenza isolates

| | EC100 (nM) (CPE in MDCK cells) | | | |
|---|---|---|---|---|
| High Path Influenza | Vehicle | Conjugate 6 | Conjugate 21 | Oseltamivir |
| H5N1 | | | | |
| A/Indonesia/5/2005 (clade 2.1) | N/A | ~15 | <15 | ~200-500 |
| A/Vietnam/1194/2004 (clade 1) | N/A | ~15 | <15 | ~15 |
| A/turkey/Turkey/1/2005 (clade 2.2) | N/A | <15 | <15 | ~125-250 |
| A/Hong Kong/156/1997 (clade 0) | N/A | ~15 | <15 | >1000 |
| H7N9 | | | | |
| A/Anhui/01/2013 | N/A | <15 | <15 | ~500-1000 |
| H1N1 (positive control) | | | | |
| A/Netherlands/602/2009 | N/A | <15 | <15 | ~1000 |

Example 94. Activity of Conjugate 6 and Conjugate 21 Against Influenza a (H1N1) at Different Multiplicities of Infection (MOI) in a Cytopathic Effects (CPE) Assay MOCK cells were seeded at $4\times10^4$ cells/well in MEM media in 96 well plate (TC-treated) and incubated at 37° C., 5% C02 for 18-24 h. Test articles (Zanamivir, Oseltamivir, Baloxavir, Conjugate 6, and Conjugate 21) at dose-range between 1.93-10000 nM were incubated with influenza A/WSN/1933 at an multiplicity of infection (MOI) of virus: cell between 0.001-1 for 1 h at room temperature (RT). After 1 h, pre-incubated virus and test article were added to 90-100% confluent monolayer of MOCK cells and incubated for 1 h at RT.

After 1 h, MEM media supplemented with L-glutamine and penicillin/streptomycin was added to wells. Infected cells were incubated at 37 C, 5% C02 for 72 h. CPE was determined after fixing and staining cells with crystal violet. EC50 was calculated with non-linear regression analysis using Graphpad Prism 6 software. The results of the CPE assay provided in Table 43 indicate that Conjugate 6 and Conjugate 21 outperform standard of care agents in vitro, particularly at high MOIs.

TABLE 43

*In vitro* activity of Conjugate 6 and Conjugate 12 against influenza A (H1N1) at different multiplicities of infection

| | $EC_{50}$(nM) H1N1 A/WSN/1933 (CPE in MDCK cells) | | | |
|---|---|---|---|---|
| | MOI 0.001 | MOI 0.01 | MOI 0.1 | MOI 1 |
| Zanamivir | 137 | 938 | >10000 | >10000 |
| Oseltamivir | 525 | 1896 | >10000 | >10000 |
| Baloxavir | 5 | 4 | 79 | >100 |
| Conjugate 6 | 9 | 15 | >100 | >100 |
| Conjugate 12 | 0.6 | 2 | 7 | 10 |

Example 95. Efficacy of Conjugate 6 Against Influenza A (H1N1) in a Lethal Severe Combined Immunodeficiency Mouse Model Conjugates were evaluated against a lethal Influenza A infection in male BALB/c Severe Combined Immunodeficiency (SCID) mice (Stock #001803; Jackson Laboratories, 6-8 weeks old). The challenge virus (A/Puerto Rico/08/1934) is a mouse-adapted isolate capable of causing lethal infections in mice. The experiment comprised 5 groups of 5 mice each. At day 0, all mice were challenged with virus at 3× the LD95 by intranasal inoculation in a volume of 30 μl (approx. 1E3 per mouse), after being anesthetized with a mixture of ketamine and xylazine (150 and 10 mg/kg, respectively).

All groups received a single IV treatment of conjugate 6, 2 hours post viral challenge of test article, vehicle (PBS), or Fc only control (hIgG1 Fc). The study evaluated 3 different dose concentrations of conjugate 6 (0.3, 1.0, or 3.0 mg/kg). Mice were monitored for 5 weeks and animals exceeding 20% body weight loss, or who were found moribund, were scored as a mortality. Body weights were also recorded to monitor the general health of the animals.

Figure 56:
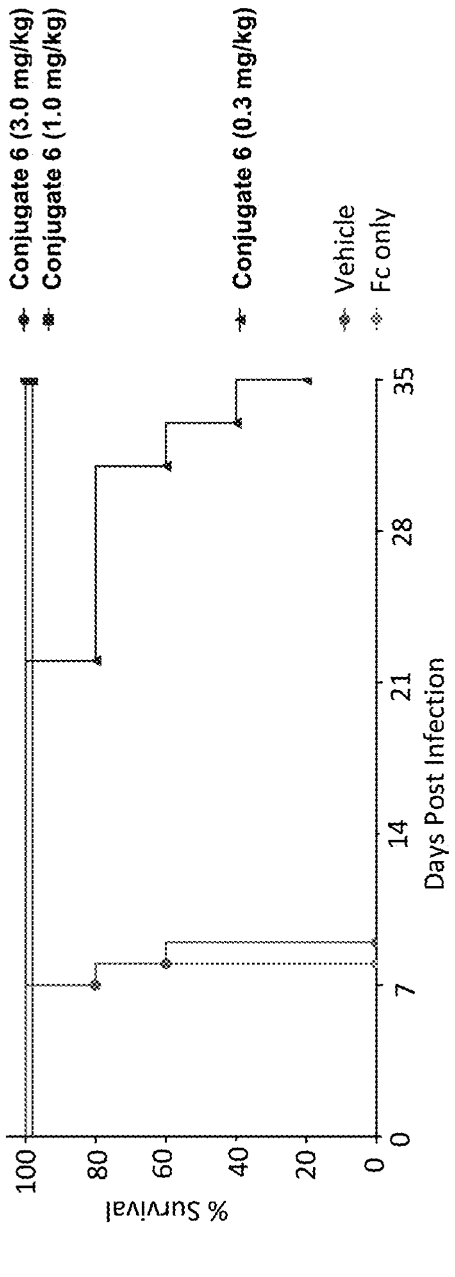
FIG. 56 is a graph showing the % survival in immune compromised mice over 35 days post viral challenge. The 0.3 mg/kg conjugate 6 treatment group remained at 100% survival but is slightly offset in the graph for clarity. The study was performed as described in Example 95
Figure 57:
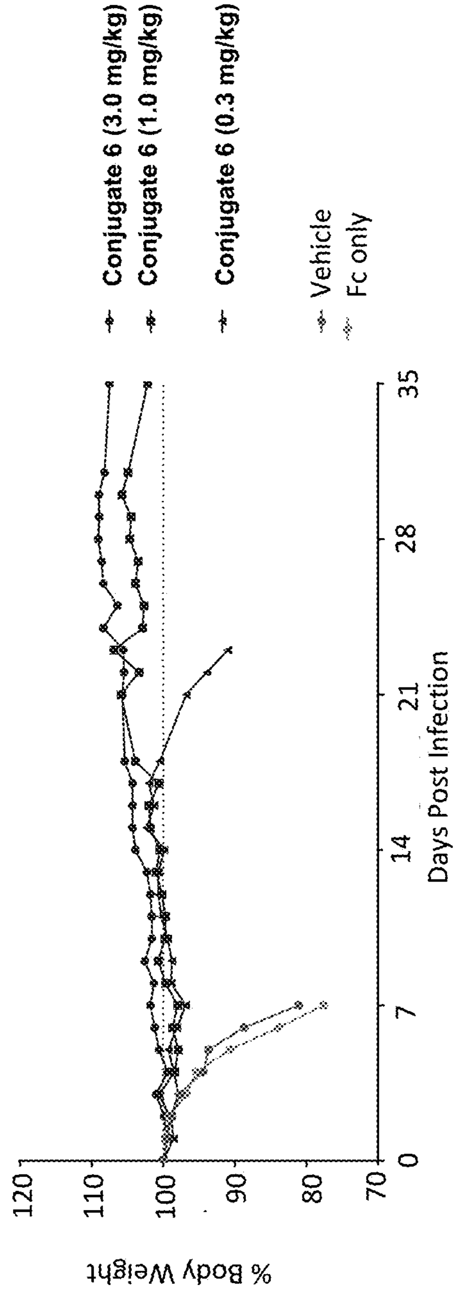
FIG. 57 is a graph showing the % body weight change in immune compromised mice over 35 days post viral challenge. The study was performed as described in Example 95.

All mice treated with vehicle, or the Fc only control, reached mortality by week 2. In contrast, mice receiving conjugate 6 were fully protected after receiving single IV doses of 1 or 3 mg/kg for the duration of the study (FIG. 56, Table 44). When dose of conjugate 6 was lowered to 0.3 mg/kg survival dropped to 20% by study end. The 0.3 mg/kg dose was fully protected for 3 weeks. The potency of conjugate 6 in this model of severe immunodeficiency was further supported by body weight data (FIG. 57, Table 45). Groups receiving conjugate 6 at the 1 or 3 mg/kg dose concentrations demonstrated no more than a transient body weight loss of less than 3% over the entire course of the study. Furthermore, at study end both dose groups showed a net gain in weight (7.5 and 2.2%, respectively). The group dosed with the lowest concentration of conjugate 6 (0.3 mg/kg) had less than a 4% transient loss of body weight over the first 3 weeks of the study before showing signs of infection in week 4, which ultimately resulted in death for four of five animals.

Collectively these data demonstrate the potency of conjugate 6 by protecting lethally challenged mice with single IV doses of conjugate as low as 1 mg/kg. Additionally, this protection was long lasting, extending over the 5 week duration of the study. This was accomplished in an extreme model of immunodeficiency in mice completely lacking T & B immune cells, which are essential in clearing influenza infections. This data supports the use of conjugate 6 to treat both immune competent and deficient patient populations.

TABLE 44

Mortality of study dose groups per week

| | % Survival (Day post viral challenge) | | | | |
|---|---|---|---|---|---|
| Test article | 7 | 14 | 21 | 28 | 35 |
| Vehicle | 80 | 0 | 0 | 0 | 0 |
| Fc only | 80 | 0 | 0 | 0 | 0 |
| Conjugate 6 (3 mg/kg) | 100 | 100 | 100 | 100 | 100 |
| Conjugate 6 (1 mg/kg) | 100 | 100 | 100 | 100 | 100 |
| Conjugate 6 (0.3 mg/kg) | 100 | 100 | 100 | 80 | 20 |

TABLE 45

Average group body weight for study animals over 35 days or until first death within a group

| | | | Conjugate 6 dose | | |
|---|---|---|---|---|---|
| Day | Vehicle | Fc only | 3 mg/kg | 1 mg/kg | 0.3 mg/kg |
| 0 | 100 | 100 | 100 | 100 | 100 |
| 1 | 99.5 | 99.8 | 99.6 | 99.4 | 98.6 |
| 2 | 98.8 | 99.2 | 99.9 | 99.1 | 98.9 |
| 3 | 97.7 | 96.8 | 101 | 100.6 | 97.9 |
| 4 | 94.4 | 95.4 | 99.4 | 98.4 | 98.5 |
| 5 | 93.7 | 90.7 | 100.6 | 97.9 | 99.3 |
| 6 | 88.7 | 83.9 | 101.2 | 98.7 | 98.1 |
| 7 | 81.1 | 77.6 | 101.8 | 98 | 96.9 |
| 8 | | | 101.3 | 99.7 | 98.9 |
| 9 | | | 102.6 | 100.7 | 98.8 |
| 10 | | | 101.6 | 99.8 | 99.4 |
| 11 | | | 101.6 | 99.7 | 100.3 |
| 12 | | | 101.8 | 100.2 | 100.7 |
| 13 | | | 102.3 | 101 | 100.7 |
| 14 | | | 103.9 | 100.5 | 99.9 |
| 15 | | | 104.3 | 101.8 | 102.3 |
| 16 | | | 104.3 | 102 | 101.3 |
| 17 | | | 104.3 | 100.6 | 102 |
| 18 | | | 105.4 | 103.9 | 100.5 |
| 21 | | | 105.7 | 105.9 | 96.8 |
| 22 | | | 105.5 | 103.4 | 93.9 |
| 23 | | | 105.6 | 106.9 | 91 |
| 24 | | | 108.4 | 102.9 | |
| 25 | | | 106.4 | 102.7 | |
| 26 | | | 108.4 | 103.9 | |
| 27 | | | 108.6 | 103.5 | |
| 28 | | | 109.1 | 104.7 | |
| 29 | | | 108.96 | 104.5 | |
| 30 | | | 109 | 105.8 | |
| 31 | | | 108.2 | 104.9 | |
| 35 | | | 107.5 | 102.2 | |

Example 96. Conjugate 6 Dose-Dependent Viral Clearance in Lungs

Efficacy studies were conducted in 6-8 weeks female BALB/c mice (Charles River) challenged intranasally with $3\times10^2$ PFU/mouse (3× the $LD_{95}$) of mouse-adapted influenza A/Puerto Rico/8/1934 (H1N1). Conjugate 6 or human IgG1 Fc control was administered as a single intravenous (IV) dose 2 h post-challenge at 0.1-3 mg/kg. Oseltamivir was dosed orally, twice daily for 4 days starting 2 h post-infection at 5 or 15 mg/kg. Body weights (BW) were recorded for 4 days. At 4 days post-infection, mice were sacrificed by $CO_2$ and both lung lobes were harvested. Lungs were homogenized with 1 mm silica beads in 1 mL PBS using a MagNA Lyser (Roche). Homogenization was carried out at 6,000 rpm for 60 s and chilled on ice for 5 min in-between runs. After lung homogenization tubes were centrifuged for 10 min at 600×g and supernatant was transferred into new tube.

To determine the viral burden in lungs (measured as Plaque Forming Units (PFUs)), supernatants of lung homogenate were diluted in infection buffer ranging from 10-1 to 10-6. 100 μL of virus dilutions were added to confluent monolayer of MDCK cells in 24 well plates and incubated for 1 h at room temperature with rocking every 15 min. After removing the virus, liquid overlay media containing Avicel was added to MDCK cells. Cells were incubation at 37° C., 5% $CO_2$ for 40 h. After incubation, the media was removed and cells were stained with crystal violet to enumerate plaques. PFUs were calculated relative to weight of the lung (PFU/g lung).

Figure 58:
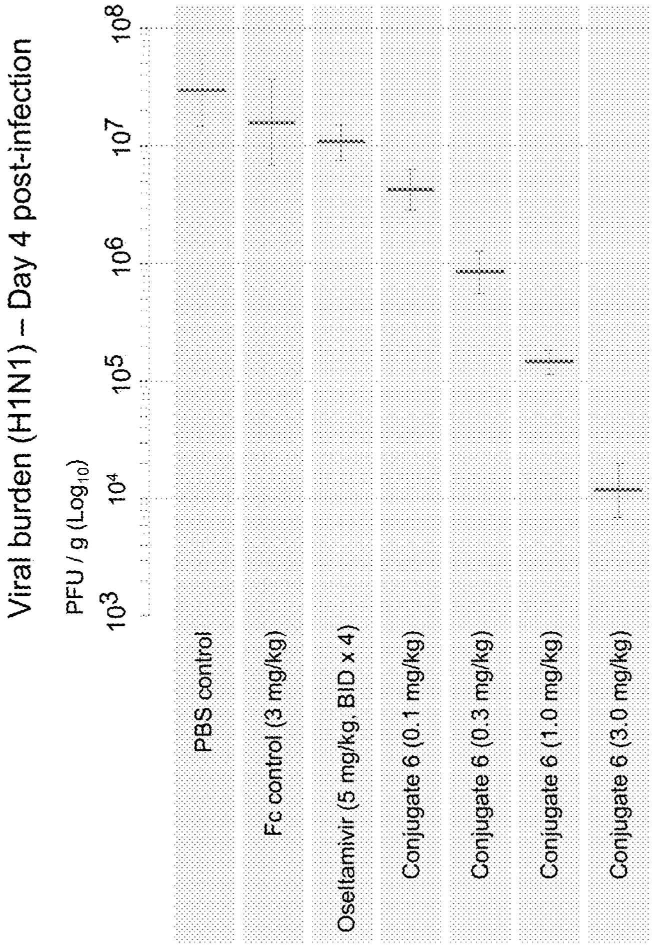
FIG. 58 is a graph showing administration of conjugate 6 results in dose-dependent viral clearance in the lungs of a mouse model infected with Influenza A (H1N1) and that this viral clearance is greater than PBS control, Fc-only control, or Oseltamivir control. This study was performed as described in Example 96.

The results of this study demonstrate that low doses of conjugate 6 rapidly lower the viral burden orders of magnitude better than Oseltamivir (TAMIFLU®) (FIG. 58, Table 46). This observation has clinical significance since severe influenza infections are caused by the virus moving from an initial upper respiratory tract infection to the lungs.

TABLE 46

Viral burden on day 4 post-infection

| Test article [mg/kg] | Log reduction (PFU/mL) | Log reduction (PFU/g) |
|---|---|---|
| PBS [0] | 0.00 | 0.00 |
| hlgG1 Fc [3] | −0.04 | 0.26 |
| Oseltamivir [5] | 0.24 | 0.43 |
| Oseltamivir [15] | 0.52 | 0.75 |
| Conjugate 6 [0.1] | 0.60 | 0.79 |
| Conjugate 6 [0.3] | 1.33 | 1.55 |
| Conjugate 6 [1] | 2.25 | 2.34 |
| Conjugate 6 [3] | 3.20 | 3.40 |

Example 97. Conjugate 6 Dose-Dependent Reduction in Inflammatory Cytokines in Lungs Efficacy studies were conducted in 6-8 weeks female BALB/c mice (Charles River) challenged intranasally with $3\times10^2$ PFU/mouse (3× the LDs) of mouse-adapted influenza A/Puerto Rico/8/1934 (H1N1). Conjugate 6 or human IgG1 Fc control was administered as a single intravenous (IV) dose 2 h post-challenge at 0.1-3 mg/kg. Oseltamivir was dosed orally, twice daily for 4 days starting 2 h post-infection at 5 or 15 mg/kg. Body weights (BW) were recorded for 4 days. At 4 days post-infection, mice were sacrificed by $CO_2$ and both lung lobes were harvested. Lungs were homogenized with 1 mm silica beads in 1 mL PBS using a MagNA Lyser (Roche). Homogenization was carried out at 6,000 rpm for 60 s and chilled on ice for 5 min in-between runs. After lung homogenization tubes were centrifuged for 10 min at 600× g and supernatant was transferred into new tube.

For cytokine analysis, supernatants of lung homogenate were serially diluted 2-fold in 96 well plate. Cytokine levels for INF-γ, TNF-α, IL-6, MIP-1a and MCP-1 were determined by ELISA according to manufacturer's instructions (R&D Systems).

Figure 59:
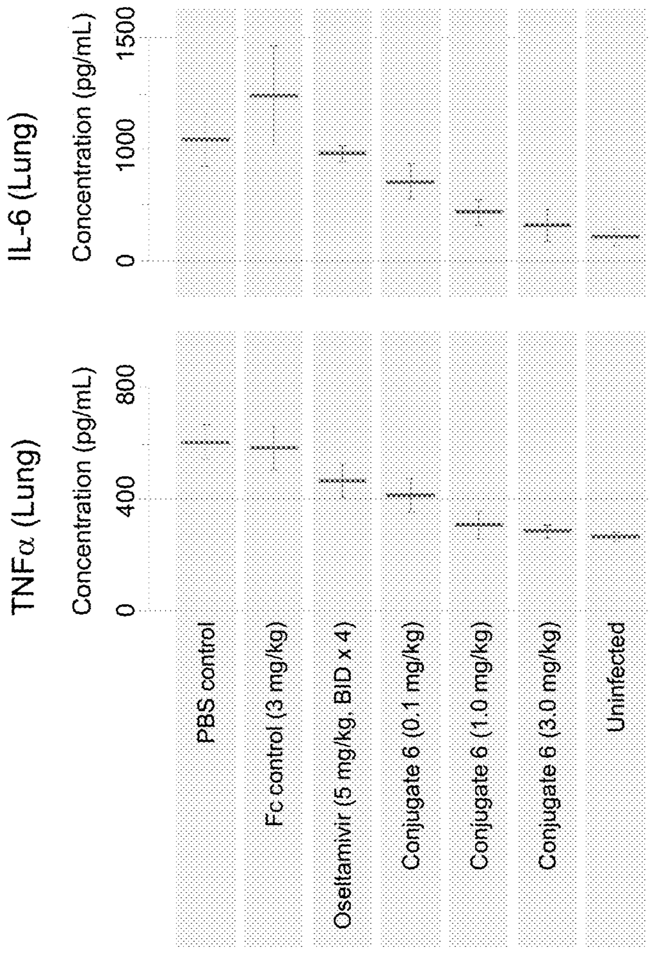
FIG. 59 is a graph showing that administration of conjugate 6 results in a dose-dependent reduction in inflammatory cytokines in the lungs in a mouse model infected with Influenza A (H1N1). This study was performed as described in Example 97.

Morbidity and mortality from severe influenza is ultimately caused by virally induced influx of pro-inflammatory cytokines in the lungs. One potential concern of using an Fc-conjugate to treat influenza is whether the Fc fragment would exacerbate cytokine induced inflammation. The results of the H1N1 lethal infection model show just the opposite: a conjugate 6 dose-dependent decrease in pro-inflammatory cytokines (e.g., TNFα and IL-6) in infected lung tissues (FIG. 59, Table 47).

TABLE 47

Cytokine response on day 4 post-infection

| Test article | Fold-shift compared to unifected control | | | | |
|---|---|---|---|---|---|
| [mg/kg] | INFy | TNFa | IL-6 | MCP-1 | MIP-1a |
| PBS [0] | 0.4 | 2.2 | 4.6 | 16.3 | 16.4 |
| hlgG1 Fc [3] | 0.5 | 2.2 | 6.2 | 20.2 | 16.8 |
| Oseltamivir [5] | 0.2 | 1.7 | 4.0 | 11.7 | 7.5 |
| Oseltamivir [15] | 0.2 | 1.8 | 3.5 | 10.5 | 6.1 |
| Conjugate 6 [0.1] | 0.3 | 1.5 | 3.0 | 10.8 | 7.9 |
| Conjugate 6 [0.3] | 0.2 | 1.2 | 1.9 | 6.7 | 7.4 |
| Conjugate 6 [1] | 0.2 | 1.1 | 1.9 | 6.1 | 3.6 |
| Conjugate 6 [3] | 0.8 | 1.1 | 1.4 | 2.8 | 2.6 |
| Uninfected | 1.0 | 1.0 | 1.0 | 1.0 | 1.0 |

Example 98. In Vivo Conjugate 6 Plasma Sample Analysis. Comparison of PK in CD-1 and BALB/c Severe Combined Immune Deficient Mice Conjugate 6 in plasma samples were quantified by a neuraminidase capture detection ELISA. Briefly, molecules were captured on neuraminidase coated plates and then detected using a HRP-conjugated anti-human IgG-Fc antibody. Protein concentration was calculated in GraphPad Prism using 4PL non-linear regression of Conjugate 6 standard curves. A more detailed method description is provided below.

Nunc Maxisorp 96-well plates (Cat No. 12-565-136, ThermoFisher) were coated with 0.1 U/well neuraminidase from A/California/04/2009 (H1N1) (11058-VNAHC, Sino Biological) in 1×KPL coating buffer (5150-0041, SeraCare). Plates were incubated at room temperature for 1 hr on an orbital plate shaker (500 rpm). Serial dilutions of the plasma samples were plated and incubated at room temperature for 2 hours (sample diluent: 0.5% BSA in PBS 0.025% Tween 20+naïve mouse plasma final concentration of 1:2,500). Conjugate 6 standard curves ranging from 0.230 to 500 ng/mL, in duplicate were run on each plate. Following the 2 hr incubation, plates were washed 5× in 300 μL PBS with 0.05% Tween 20. Conjugate bound to neuraminidase on the plates was then probed with an HRP conjugated anti-human IgG Fc F(ab')2 (709-036-098, Jackson) diluted 1:1,000 in sample diluent for 1 hr at room temp. Plates were then washed 8× in 300 uL PBS with 0.05% Tween 20 and developed with TMB substrate for 7-8 minutes. The reaction was stopped with 1 N $H_2SO_4$. Absorbance was read at 450 nm. Conjugate 6 in plasma samples was interpolated using GraphPad Prism Version 6 following nonlinear regression analysis (Sigmoidal, 4PL analysis) of the standard curves.

PK Profiles, CD-1 vs BALB/c SCID Mouse

Figure 60:
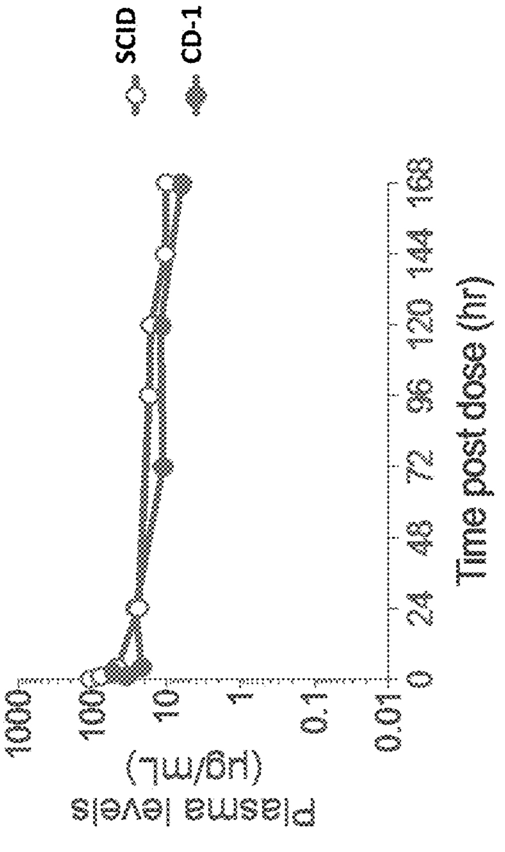
FIG. 60 is a graph showing the pharmacokinetics of conjugate 6 in BALB/c SCID (immunocompromised) mice and CD-1 mice (immunocompetent). This study was performed as described in Example 98.

Conjugate 6 administered intravenously to SCID and CD-1 (immune competent) mice at 5 mg/kg demonstrated similar PK profiles (FIG. 60). Concentrations were comparable at the sampled time points. The two-phase PK profiles comprise 24-hour distribution phases followed by a shallow elimination phase. Conjugate 6 plasma levels remained high (~10 μg/ml) relative to $C_{max}$ levels over the one-week course of the study.

Example 99. Synthesis of the Propargyl Diamine Central Linker

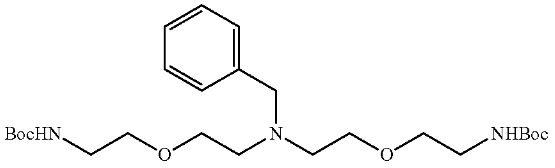 [SMILES: CC(C)(C)OC(=O)NCCOCCN(CCOCCNC(=O)OC(C)(C)C)Cc1ccccc1]

A solution of the step-a product (10 g, 37.3 mmol), benzylamine (1.60 g, 14.9 mmol), and $K_2CO_3$ (6.19 g, 44.8 mmol) in DMF (20 mL) were heated in an oil bath at 75° C.

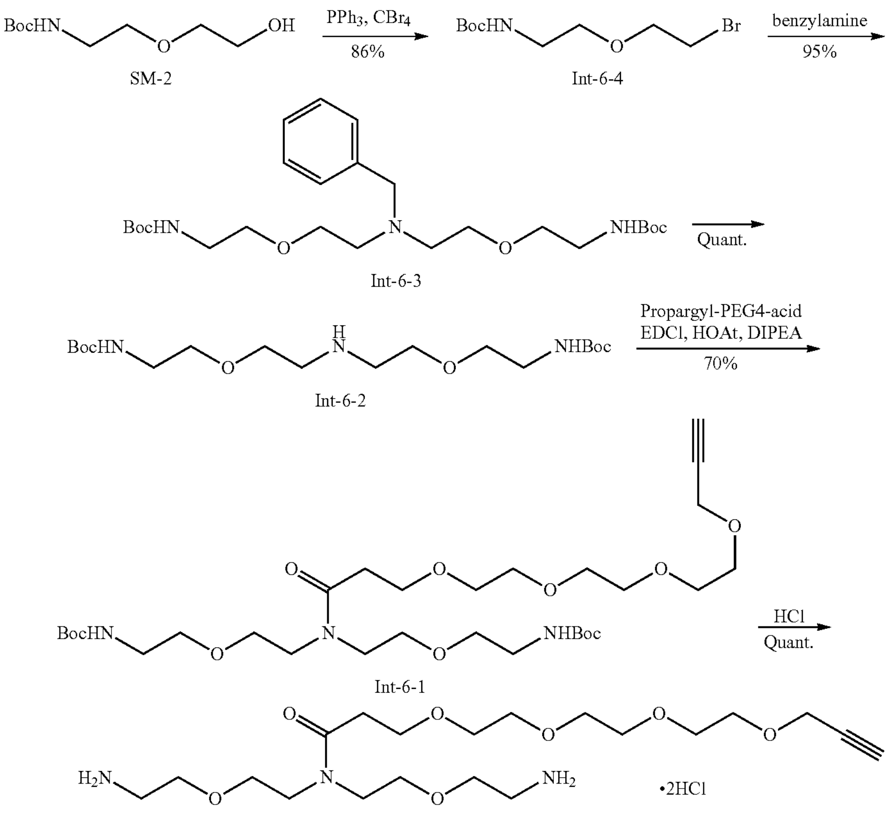

Step a.

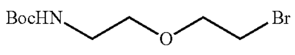

A solution of 2-(2-Boc-Aminoethoxy)ethanol (16.0 g, 78.0 mmol) and $CBr_4$ (31.0 g, 93.5 mmol) in DCM (100 mL) at 0° C. was treated with $PPh_3$ (24.5 g, 93.5 mmol) slowly over 15 minutes (exothermic). During the course of the addition the internal temperature was kept below 30° C. After addition of $PPh_3$ the reaction was stirred overnight at room temperature. The crude reaction was concentrated to an oil then purified by normal phase chromatography, eluting with 10% ethyl acetate/hexanes to 80% ethyl acetate/hexanes. Fractions containing oil droplets on the inside of the collection tubes were combined and concentrated to a colorless oil. Yield 18.1 g, 86%.

Step b.

for 8h. The mixture was filtered, concentrated and purified by RPLC (5% ACN/water to 100% ACN). Yield 6.8 g, 95%.

Step c.

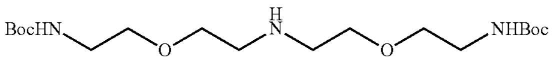 [SMILES: CC(C)(C)OC(=O)NCCOCCNCCOCCNC(=O)OC(C)(C)C]

To a solution of the step-b product (5.35 g, 8.98 mmol) in $CHCl_3$/EtOH (1:20, 100 mL) was added 20% $Pd(OH)_2$/C (1.26 g, 1/80 mmol). The reaction was stirred overnight under hydrogen balloon at ambient temperature. The reaction mixture was filtered through a Celite pad. The solvents were removed and carried to the subsequent step without purification.

Step d.

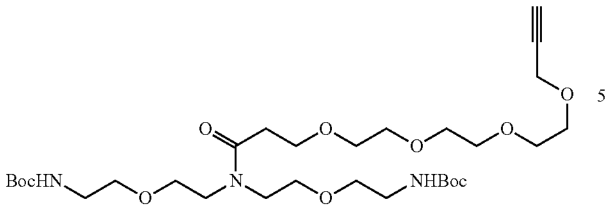

The step-c product was re-dissolved in 20 mL of DMF/dichloromethane (1:5). To this free amine solution propargyl PEG4 acid (2.36 g, 8.98 mmol), EDCI (2.57 g, 13.5 mmol), HOAt (1.83 g, 13.5 mmol) and Hunig's base (3.13 mL, 18.0 mmol) were added. The reaction mixture was stirred for four hours, then concentrated and purified by RPLC (10% ACN/water to 60% ACN/water. Yield 4.00 g, 70% over two steps. Ions found by LCMS: [M-Boc+H]+=534.2, $[M+H]^+$=634.2.

Step e.

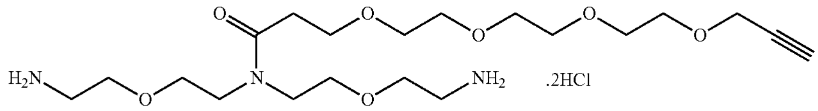 [SMILES: C#CCOCCOCCOCCOCCC(=O)N(CCOCCN)CCOCCN]

.2HCl

The step-d product (4.00 g, 6.31 mmol) was treated with 4N HCl in dioxane (30 mL) for 2 hours. Extra HCl and dioxane were removed by rotary evaporation, and the remaining was further dried under high vacuum to give Int-10 as 2HCl salt. Yield 3.15 g, 99%. Ion found by LCMS: $[M+H]^+$=434.2.

Example 100. Synthesis of Int-7a (C7-C7 Isomer)

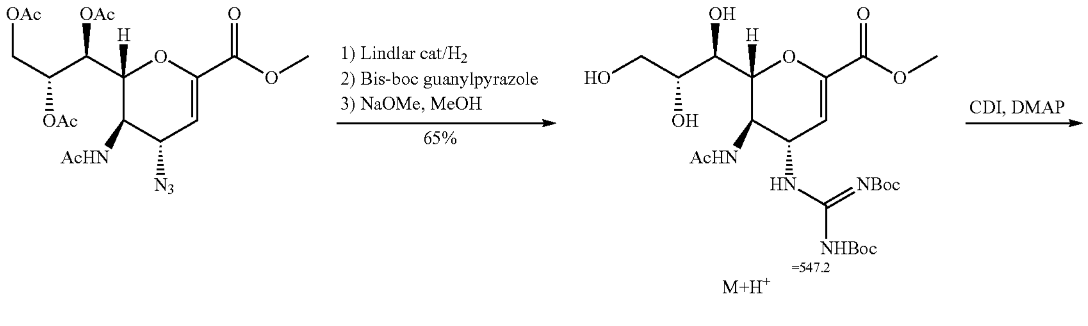

-continued
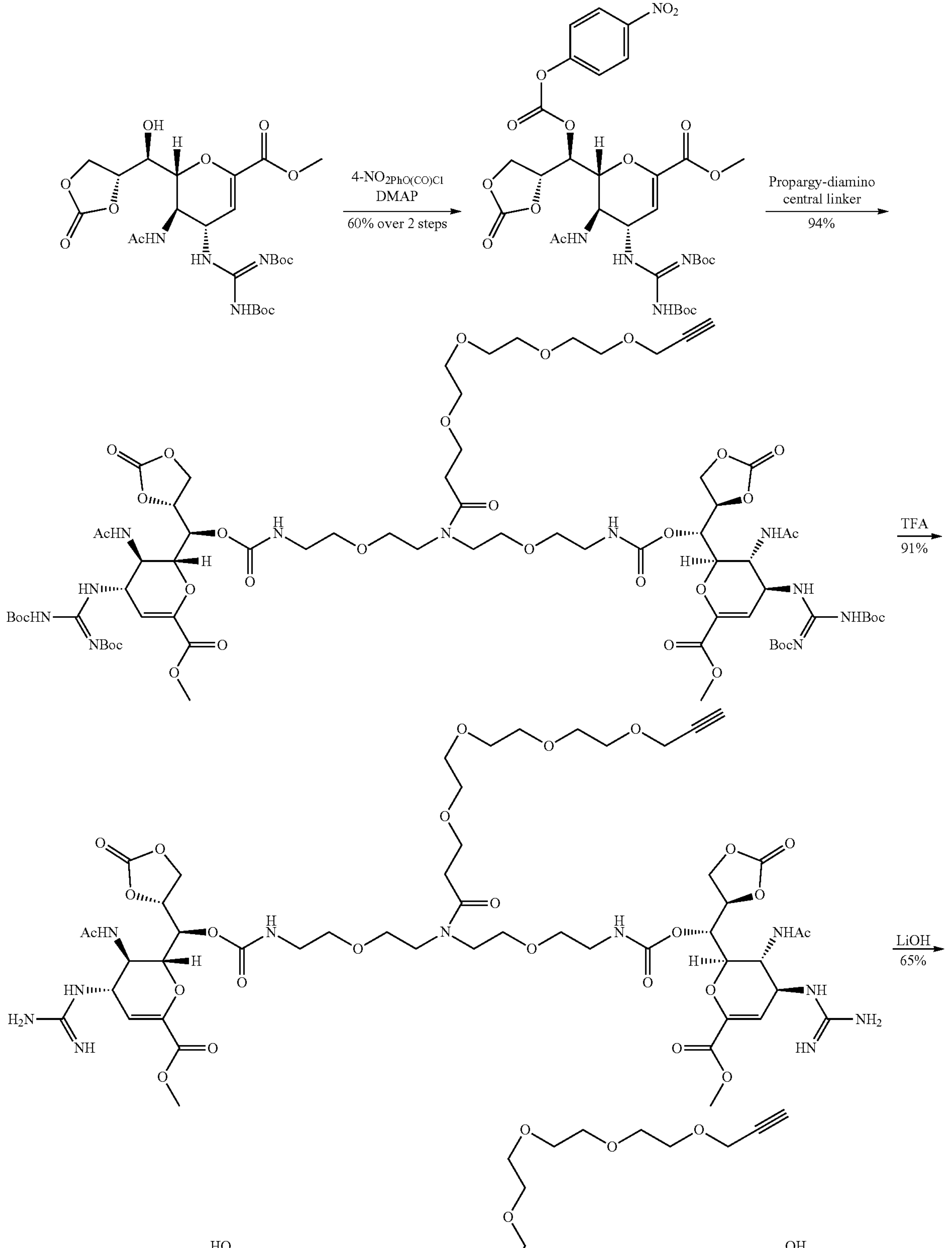

Step a.

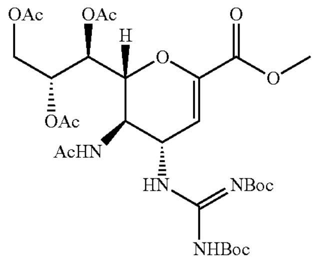

Methyl 5-acetamido-7,8,9-O-triacetyl-2,6-anhydro-4-azido-3,4,5-trideoxy-D-glycero-D-galacto-non-2-enonate (30 g, 65.7 mmol) was dissolved into methanol (100 mL) and combined with Lindlar catalyst (15 g). The resulting mixture was flushed with hydrogen and stirred for 5 hours, flushing hydrogen through the headspace with hydrogen every 30 minutes. After complete reaction as determined by HPLC, the catalyst is filtered through celite. The filtrate was used in the next step.

Crude amine from the previous step (18.9 g, 43.8 mmol) was treated with N,N'-bis-boc-1-guanylpyrazole (14.3 g, 46.0 mmol), and DIEA (9.9 ml, 57.0 mmol) in methanol (100 mL). The resulting solution was stirred at room temperature until all starting material was consumed as determined by LCMS (~30 min). The solution was concentrated to a foam and stored under high vacuum overnight then used without further purification in the next step.

Crude tri-acetate from the previous step (43.8 mmol) was dissolved in 100 ml dry methanol, then treated with sodium methoxide in methanol (1.9 mL, 25% solution in methanol, 8.76 mmol) at room temperature. Progress of reaction was monitored by LCMS which was complete after 10 minutes. The reaction was quenched with 1 N HCl to a pH of ~7. The resulting solution was concentrated and purified by reverse phase liquid chromatography (RPLC) using an Isco COMBIFLASH® liquid chromatograph eluted with 10% to 100% acetonitrile and water. No TFA modifier was used for this purification. Yield of product 15.6 g, 65%.

Step b.

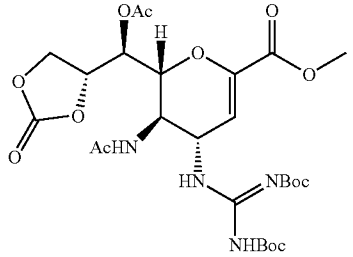

A mixture of the step-a product (5.47 g, 10 mmol) and DMAP (1.222 g, 10 mmol) was dissolved in anhydrous THE (30 ml). After cooling in an ice-water bath, the solution was slowly treated with 1,1'-carbonyldiimidazole (2.6 g, 16 mmol), then stirred for 30 minutes at 0° C., followed by heating at 60° C. for 2 hours. It was then cooled to room temperature and extracted with water (50 ml) and EtOAc/hexane (1:1, 100 ml). The organic layer was washed with water (50 ml×3), dried over $Na_2SO_4$ and concentrated by rotary evaporation. The white foam product was further dried under high vacuum and carried to the subsequent step without further purification. Ion found by LCMS: $[M+H]^+$ =573.2.

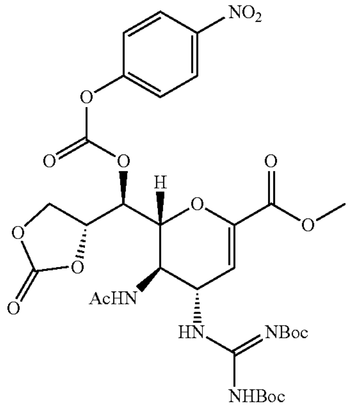

A reaction flask containing the step-b product was vacuum flushed with nitrogen and dissolved in anhydrous DCM (50 ml), then cooled in an ice-water bath. To the cooled solution was added DMAP (4.89 g, 40 mmol), followed by 4-nitrophenylchloroformate (6.05 g, 30 mmol) was added in portions over 20 minutes. The solution was stirred at 0° C. then warmed to room temperature for 1 hour. LCMS shows starting material 1 hr so additional DMAP (1.22 g, 10 mmol) and 4-nitrophenylchloroformate (1 g, 5 mmol) were added. The reaction was continued for 4 hours, then purified with two silica gel columns (220 g, pre-wet by 20% EtOAc and hexane) and eluted with 20% to 80% EtOAc and hexane. Yield 4.42 g, 59.9% for two steps. Ion found by LCMS: $[M+H]^+$=738.2

Step d.

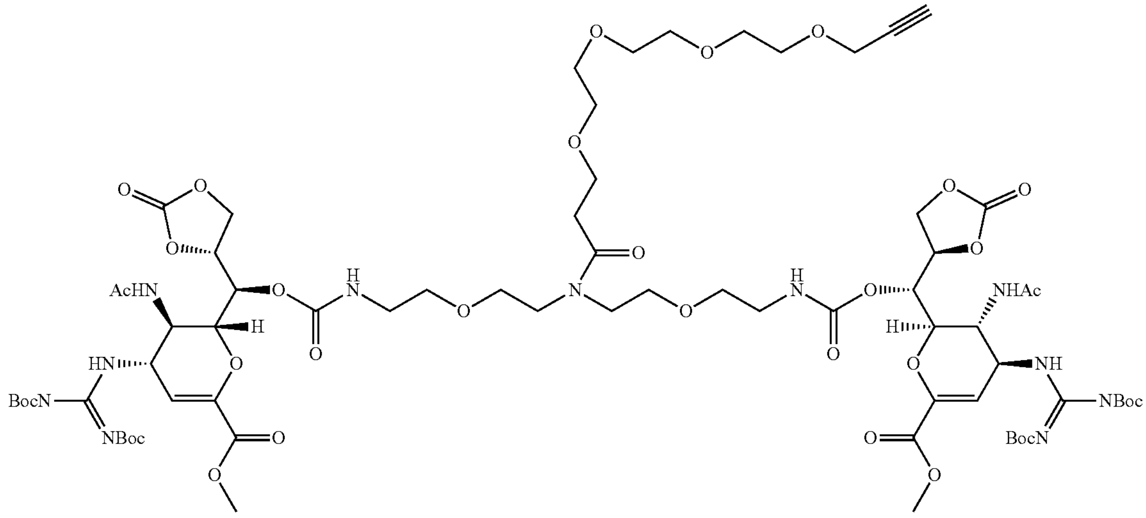

To a solution of the step-c product (3.2 g. 4.34 mmol) in anhydrous DCM (3 ml) was added in-portions over 30 minutes a mixture of propargyl diamine central linker (1.26 g, 2.5 mmol, described in Example 99) and DIPEA (1.68 g, 13 mmol) in anhydrous DMF (5 ml). The reaction was stirred at room temperature for 2 hours. It was then concentrated and purified by RPLC (30% to 90% acetonitrile and water, no TFA modifier). Ions found by LCMS: $[(M+2H)/2]^+$=815.8, $[(M-Boc+2H)/2]^+$=765.8, $[(M-2Boc+2H)/2]^+$ =716. Yield 3.33 g, 94.2%.

Step e.

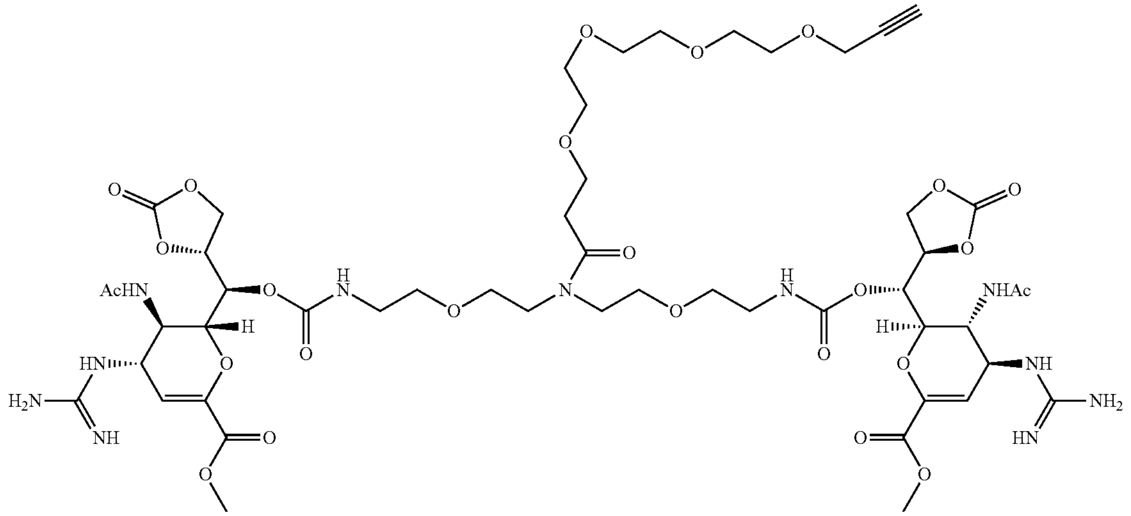 [SMILES: C#CCOCCOCCOCCOCCC(=O)N(CCOCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

The step-d product (3.33 g, 2.04 mmol) was dissolved in DCM (5 ml) and TFA (5 ml) then stirred at 35° C. for ~6 hours. The reaction was monitored by LCMS. When complete the solution was concentrated and purified by RPLC (5 to 30% acetonitrile and water, no TFA). Ions found by LCMS: $[(M+2H)/2]^+$=615.8, [(M+3H)/3]+=411. Yield 2.29 g, 91.3%.

Step f.

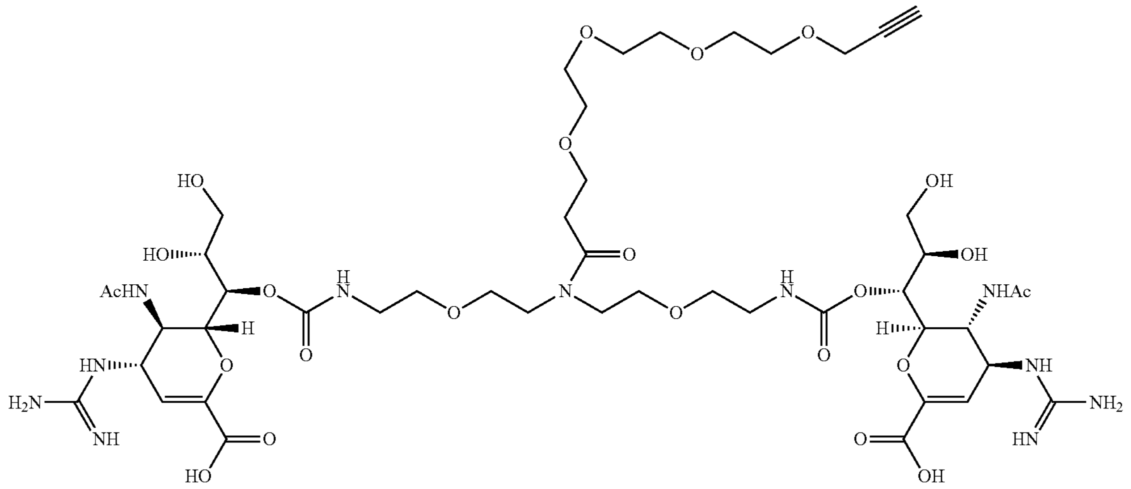 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

The step-e product (61.5 mg, 0.05 mmol) was dissolved in MeOH/water (1:1, 0.6 ml). After the solution was cooled to −6° C. (salt/ice bath), 1.0 M LiOH (0.3 ml, 0.3 mmol) was added drop-wise and the reaction was stirred for 30 minutes. It was then quenched to pH ~7.0 with 4N HCl in dioxane solution (75 μl) and directly purified by prep HPLC (Isco ACCQ prep, Luna 5 μm C18(2) 100 Å LC column 100 mm×30 mm; Gradient: 0% acetonitrile/water for 2 min, then 0% to 15% acetonitrile/water over 12 min, then isocratic at 15% acetonitrile for 10 min, using 0.1% TFA). Yield 45 mg, 65.3%. Ions found by LCMS: $[(M+2H)/2]^{+}$=575.8, [(M+3H)/3]+=384.2. Analytical retention time: 6.013 min. Conditions: Phenomemex Gemini HPLC column, 3 μm WX-C18 110 Å, 100 mm×3 mm, eluted over 25 minutes with 5-95% acetonitrile and water gradient, using 0.1% TFA.

Example 101. Synthesis of Int-7b (C7-C9 Isomer)

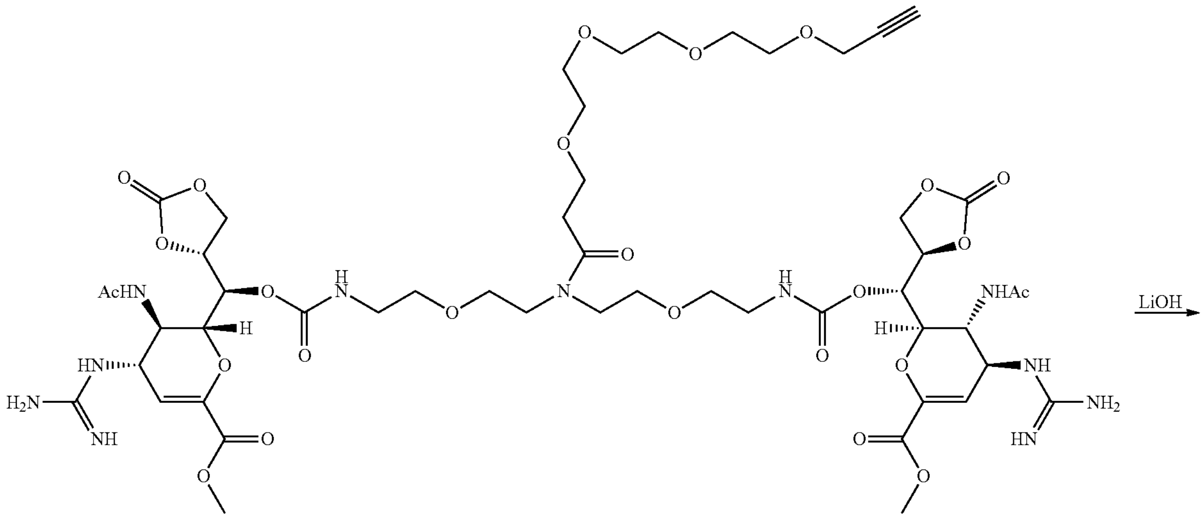

-continued

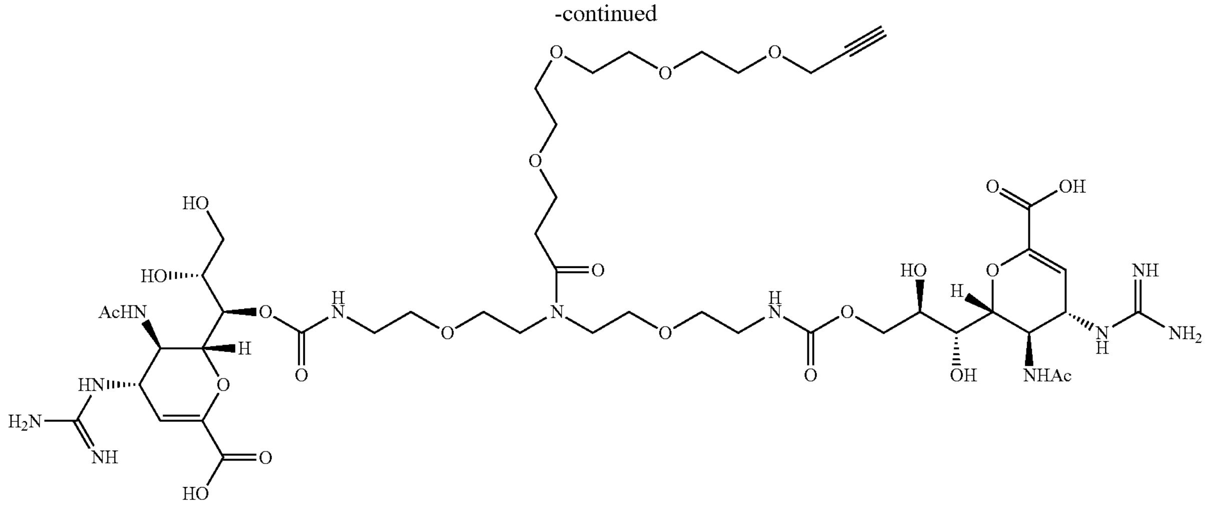

The C7-C9 heterodimer (Int-7b) was prepared analogously to Int-7a (C7-C7 isomer, Example 100), with the exception that the reaction is conducted at 0° C. and is monitored by HPLC (retention time: 6.112 min. Conditions: see Example 100, synthesis of Int-7a and stopped when the C7-C9 isomer predominates (~3h). This isomer is isolated using the same conditions that were used to isolate Int-7a. Ions found by LCMS: $[(M+2H)/2]^{+}$=575.8, [(M+3H)/3]+ =384.2.

Example 102. Synthesis of Int-7c (C9-C9 Isomer)

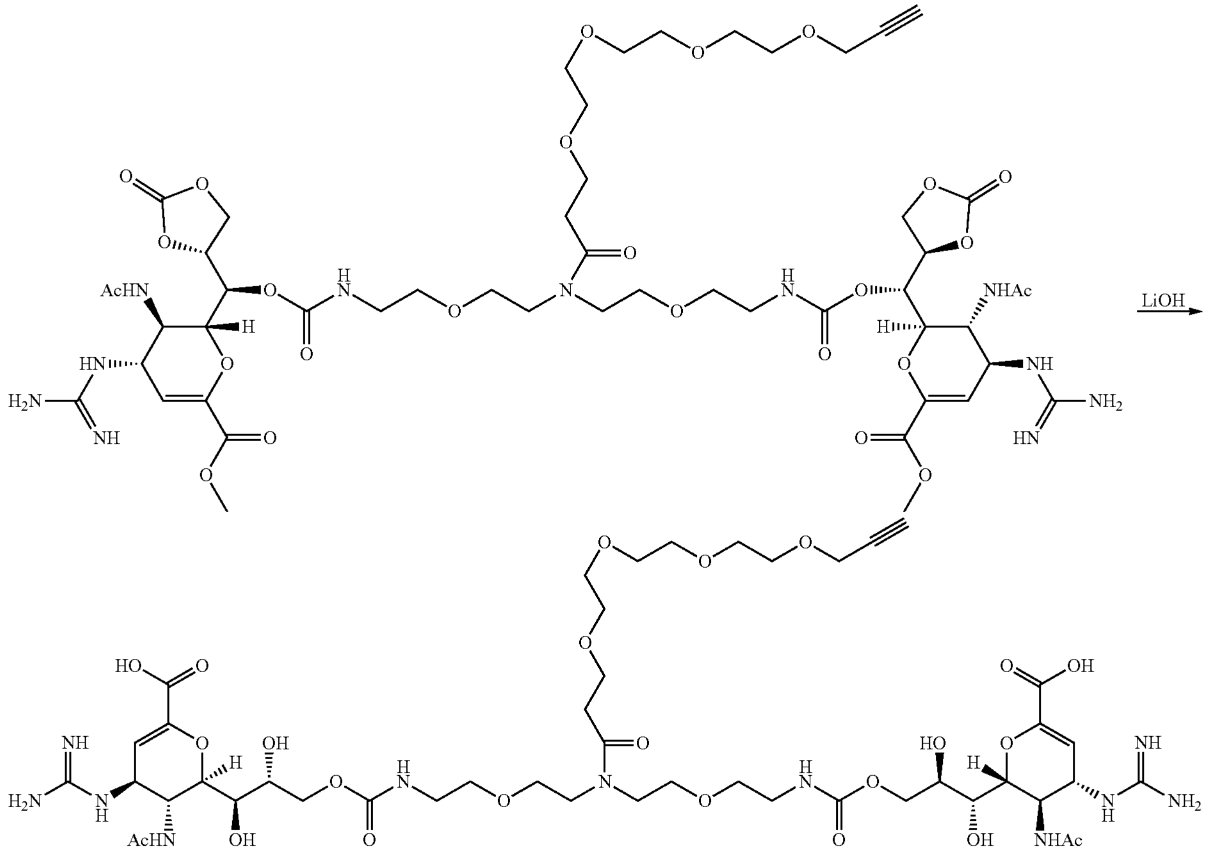

Int-7c (C9-C9 isomer) was prepared analogously to Int-7a (C7-C7 isomer, Example 100), with the exception that the reaction conducted at 0° C. and is monitored by HPLC (retention time: 6.232 min. Conditions: see Example 100, synthesis of Int-7a and stopped when the C9-C9 isomer predominates (~6h). This isomer is isolated using the same conditions that were used to isolate Int-7a. Ions found by LCMS: $[(M+2H)/2]^+=575.8$, $[(M+3H)/3]^+=384.2$.

Example 103. Synthesis of Int-7 (Acetonide Route)

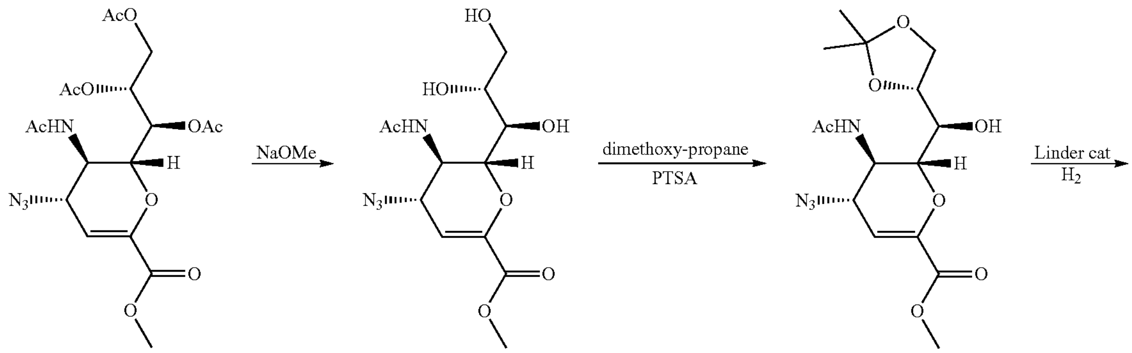

-continued
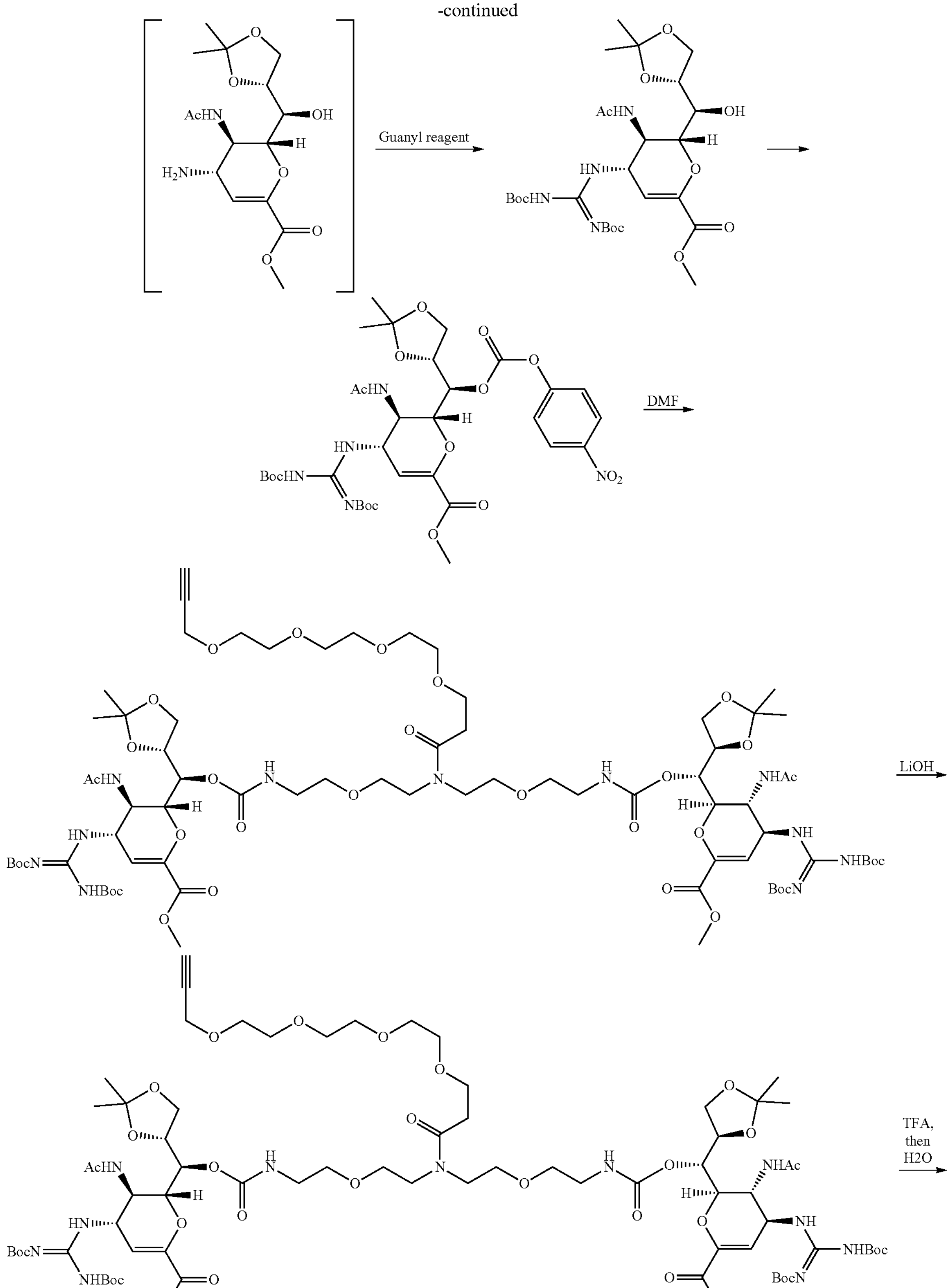

Step a.

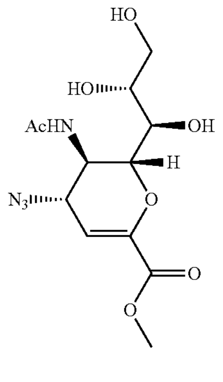 [SMILES: COC(=O)C1=C[C@H](N=[N+]=[N-])[C@@H](NC(C)=O)[C@H]([C@H](O)[C@H](O)CO)O1]

Methyl 5-acetamido-7,8,9-O-triacetyl-2,6-anhydro-4-azido-3,4,5-trideoxy-D-glycero-D-galacto-non-2-enonate (10.0 g, 22 mmol) was dissolved in 60 ml dry methanol, then treated with 20 ml sodium methoxide in methanol (0.5 M in methanol, 10 mmol) while cooling in an ice-water bath. Progress of the reaction was monitored by LCMS, which was complete after 2 hours. The pH of the reaction solution was then adjusted to a value of 5 to 6 by using Amberlite IRN-77 ion exchange resin. The mixture was filtered to remove the resin and evaporated to dryness under vacuum. The resulting oil was used for next step without further purification. Ion(s) found by LCMS: M+H=331.1.

Step b.

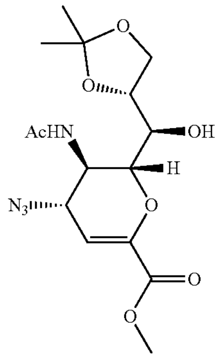 [SMILES: COC(=O)C1=C[C@H](N=[N+]=[N-])[C@@H](NC(C)=O)[C@H]([C@H](O)[C@H]2COC(C)(C)O2)O1]

To a solution of the products from the previous step in 70 ml of acetone were added 30 ml of 2,2-dimethoxypropane and p-toluenesulfonic acid 1 hydrate (400 mg, 2.0 mmol), the resulting solution was stirred at room temperature overnight. At the end of this time, sodium bicarbonate (170 mg, 2.0 mmol) was added, and the mixture was concentrated to dryness. The resulting residue was used in next step without purification. Ion(s) found by LCMS: M+H=371.2.

Step c.

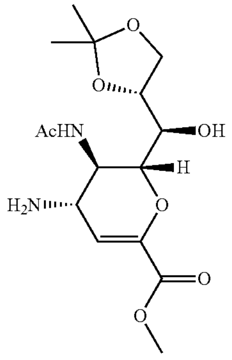 [SMILES: COC(=O)C1=C[C@H](N)[C@@H](NC(C)=O)[C@H]([C@H](O)[C@H]2COC(C)(C)O2)O1]

To a solution of material from the previous step in 60 ml of methanol was added 5.0 g of a Lindlar catalyst. The resulting mixture was flushed with hydrogen every 30 minutes and stirred for 5 hours. After complete reaction as determined by HPLC, the catalyst was filtered off through celite. The filtrate was concentrated and used in the next step without purification.

Crude product from the previous step in 60 ml THE was treated with N,N'-bis-boc-1-guanylpyrazole (9.3 g, 30.0 mmol), and DIEA (9.9 ml, 57.0 mmol). The resulting solution was stirred at room temperature until all starting material was consumed as determined by LCMS (4h). The solution was concentrated and purified by flash chromatography eluted with 20% to 80% ethyl acetate/dichloromethane. Yield 8.8 g, 59.0% for four steps. Ion(s) found by LCMS: M+H 587.3.

Step d.

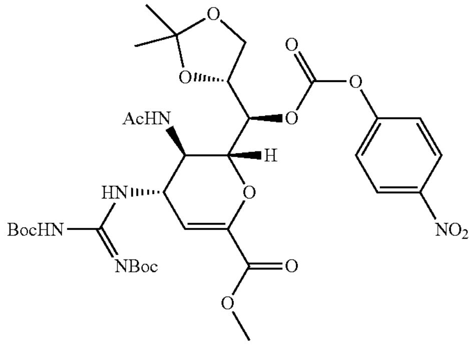

A reaction flask containing product from the previous step (6.5 g, 11 mmol) was vacuum flushed with nitrogen and dissolved in anhydrous dichloromethane (100 ml). After the solution was cooled in an ice-water bath, DMAP (4.89 g, 40 mmol) was added and stirred to dissolve, then 4-nitrophenylchloroformate (5.58 g, 28 mmol) was added in portions, while stirring at 0° C. to room temperature for 1 hour. LCMS shows starting material 1 hr so additional DMAP (1.22 g, 10 mmol) and 4-nitrophenylchloroformate (1.0 g, 5 mmol) were added. The reaction was continued for 4 more hours, then concentrated and purified by flash chromatography eluting with 20% to 80% ethyl acetate/dichloromethane. Yield 5.1 g, 59.9%. Ion found by LCMS: $[M+H]^+$=752.2

Step e.

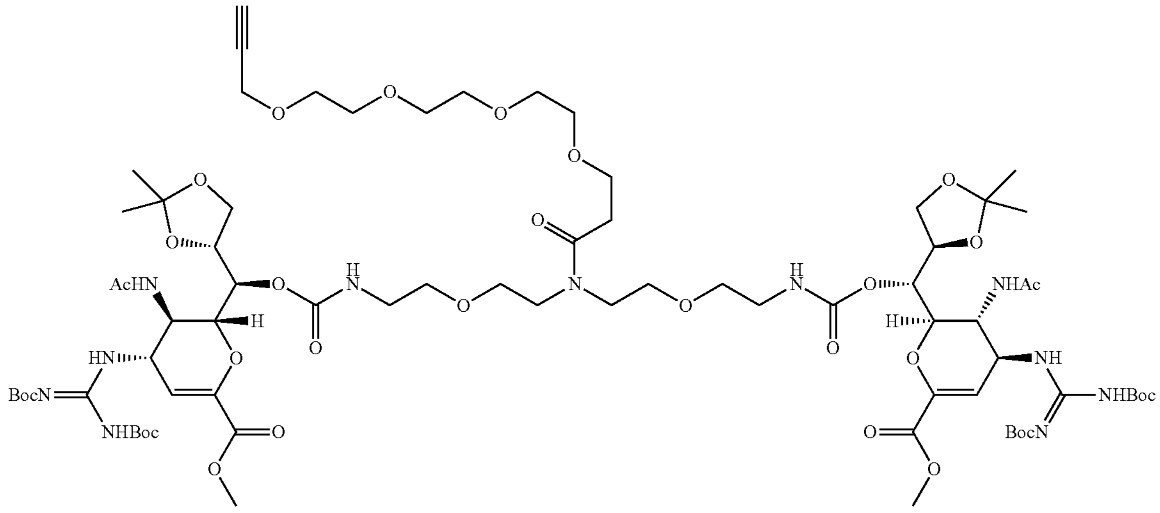

To a solution of the nitrophenyl carbonate from the previous step (1.8 g. 2.3 mmol) in anhydrous dichloromethane (20 ml) was added a mixture of central linker (0.51 g, 1.0 mmol, added in portions over 30 minutes) and DIPEA (1.4 ml, 10 mmol) in anhydrous DMF (20 ml). The reaction was stirred at room temperature overnight, then concentrated and purified by flash chromatography eluting with 0% to 10% methanol/dichloromethane. Yield 1.35 g, 80%. Ions found by LCMS: $[(M+2H)/2]^+$=830.4, $[(M\text{-}Boc+2H)/2]^+$=780.4, $[(M-2Boc+2H)/2]^+$=730.4.

Step f.

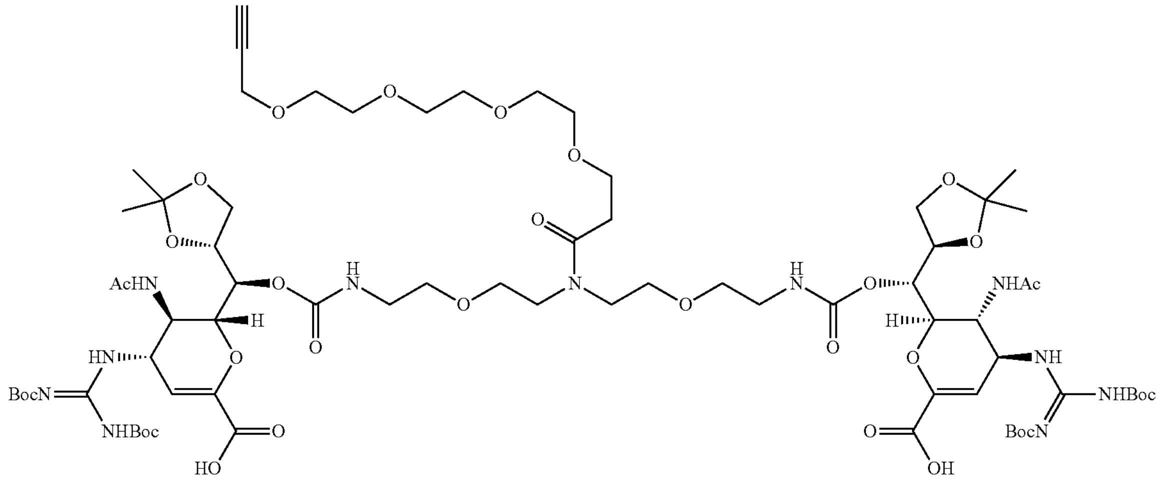

Product from the previous step (200 mg, 0.2 mmol) was dissolved into 2 ml MeOH and 2 ml THF, then treated with a solution of lithium hydroxide (24 mg, 1 mmol) dissolved in 2 ml water. The reaction was stirred for 10 min at room temperature at which time HPLC showed the reaction was complete. The pH of the reaction solution was adjusted to the value of 5 to 6 by using Amberlite IRN-77 ion exchange resin the filtered to remove the resin. The crude product was evaporated to dryness under a vacuum and used in the next step with purification. Ion(s) found by LCMS: $[(M+2H)/2]^+$=815.4, $[(M\text{-}Boc+2H)/2]^+$=765.4, $[(M-2Boc+2H)/2]^+$=715.4.

Step g.

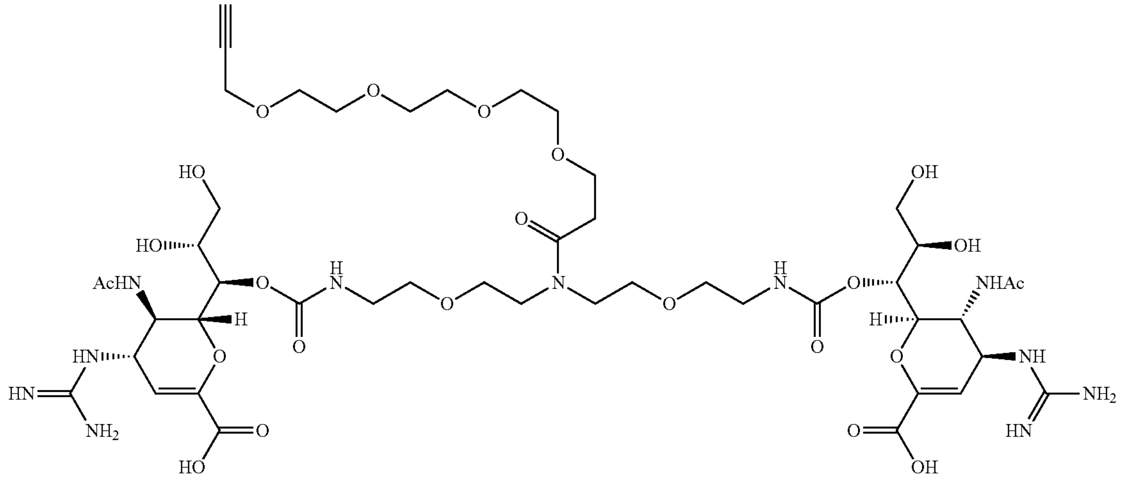 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

The product from step g (400 mg, 0.25 mmol) was dissolved into 5 ml dichloromethane and 5 ml TFA, and the resulting reaction solution was stirred at room temperature. The progress of the reaction was monitored by LCMS. After the completion of the reaction (6h), the solution was stripped to dryness and then dissolved in 4 ml water and 4 ml acetonitrile. The resulting solution was stirred for another 2 hour at room temperature at which LCMS show complete deprotection of the acetonide protecting groups. This mixture was concentrated and purified by reverse phase liquid chromatography (RPLC) using an Isco COMBIFLASH® liquid chromatograph eluted with 5% to 40% acetonitrile/water with 0.1% TFA as the modifier. Yield 270 mg, 68.0%. Ion(s) found by LCMS: $[(M+2H)/2]^{+}$=575.8, [(M+3H)/3]+ =384.2.

Example 104. NMR Results for Int-7a, Int-7b, and Int-7c

NMR of Int-7a

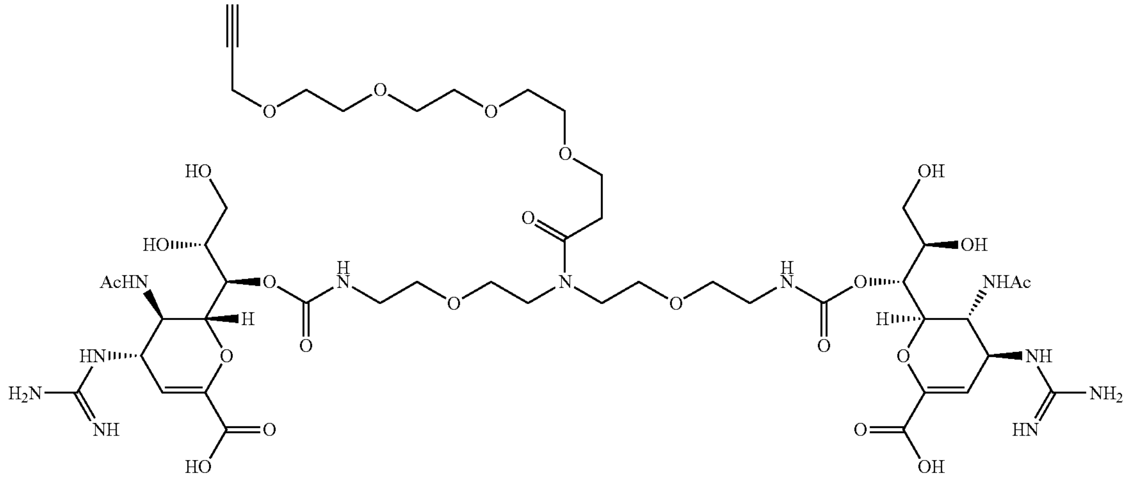 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

$^{1}H$ NMR (500 MHz, Methanol-$d_4$) δ 5.91-5.89 (m, 2H), 5.00-4.96 (m, 2H), 4.58-4.53 (m, 2H), 4.42-4.37 (m, 2H), 4.20-4.17 (m, 6H), 4.02-3.97 (m, 2H), 3.78-3.49 (m, 28H), 3.29-3.18 (m, 4H), 2.86 (t, J=2.6 Hz, 1H), 2.85-2.72 (m, 2H), 1.96 (s, 3H), 1.95 (s, 3H).

$^{13}C$ NMR (125 MHz, MeOD) δ 171.73, 170.80, 170.29, 161.95, 156.06, 155.08, 154.99, 144.07, 143.93, 116.41, 114.10, 106.03, 105.86, 77.71, 74.46, 73.22, 68.62, 68.54, 68.50, 68.38, 68.12, 68.00, 67.94, 67.67, 67.64, 67.53, 67.20, 66.96, 65.44, 61.53, 56.17, 49.74, 49.64, 47.37, 45.17, 39.16, 39.06, 31.73, 19.96, 19.92.

NMR of Int-7b

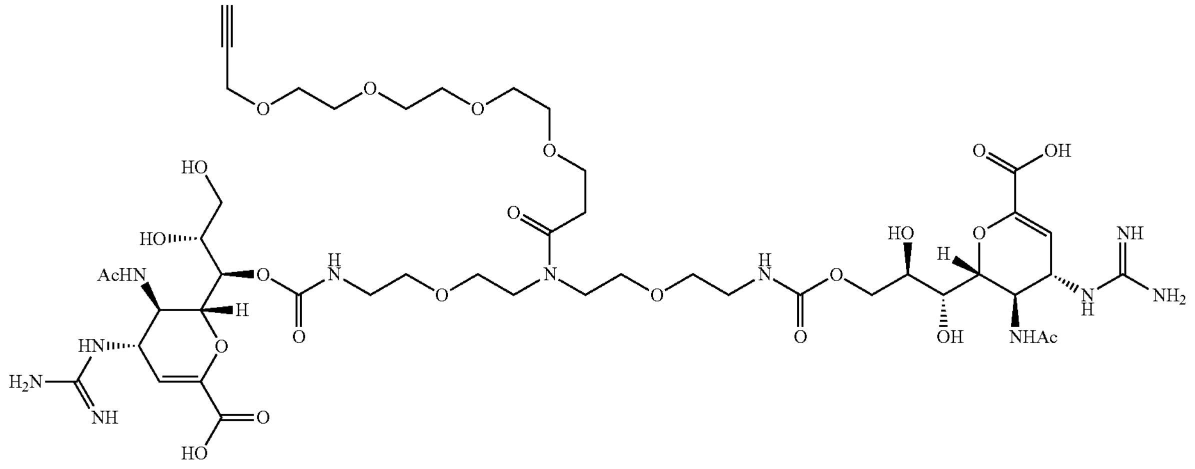 [SMILES: C#CCOCCOCCOCCOCCC(=O)N(CCOCCNC(=O)OC[C@@H](O)[C@@H](O)[C@@H]1OC(C(=O)O)=C[C@H](NC(=N)N)[C@H]1NC(C)=O)CCOCCNC(=O)O[C@@H]([C@@H]1OC(C(=O)O)=C[C@H](NC(=N)N)[C@H]1NC(C)=O)[C@H](O)CO]

$^1$H NMR (500 MHz, Methanol-$d_4$) δ 5.91-5.87 (m, 2H), 5.04-4.95 (m, 1H), 4.58-4.48 (m, 2H), 4.45-4.37 (m, 3H), 4.20-4.10 (m, 5H), 4.08-3.98 (m, 2H), 3.79-3.44 (m, 29H), 3.29-3.18 (m, 4H), 2.88-2.70 (m, 3H), 2.02 (s, 3H), 1.96-1.94 (m, 3H).

$^1$H NMR (500 MHz, DMSO-$d_6$) δ: 8.28 (d, J=8.4 Hz, 2H, —NH), 7.98 (d, J=11.5 Hz, 2H, —NH), 7.78 (d, J=8.7 Hz, 2H, —NH), 7.60 (t, J=8.5 Hz, 2H, —NH), 7.20 (bs, 2H, —NH), 7.06 (bs, 2H, —NH), 5.69 (bs, 1H), 5.67 (d, J=2.4 Hz, 1H), 4.83 (dd, J=9.2, 2.2 Hz, 1H), 4.45 (dt, J=9, 2.5 Hz, 1H), 4.37 (d, J=2.2 Hz, 1H), 4.33-4.24 (m, 2H), 4.13 (d, J=2.5 Hz, 2H), 4.05-4.32 (m, 41H), 3.23 (m, 1H), 3.15-3.09 (m, 2H), 3.06-3.02 (m, 2H), 2.59 (t, J=6.7 Hz, 2H), 1.91 (s, 3H), 1.78 (s, 3H).

$^{13}$C NMR (125 MHz, MeOD) δ:173.19, 172.98, 172.25, 171.75, 164.26, 163.82, 157.88, 157.55, 156.51, 146.09, 107.21, 106.93, 106.59, 79.22, 76.19, 75.92, 74.72, 74.68, 70.12, 70.08, 70.03, 69.99, 69.92, 69.88, 69.66, 69.48, 69.12, 69.01, 68.94, 68.73, 68.69, 68.50, 68.19, 67.08, 66.93, 66.79, 63.04, 57.68, 51.24, 51.15, 50.13, 48.87, 48.72, 46.72, 46.58, 46.23, 40.64, 40.41, 33.21, 21.49, 21.45, 21.40.

NMR of Int-7c

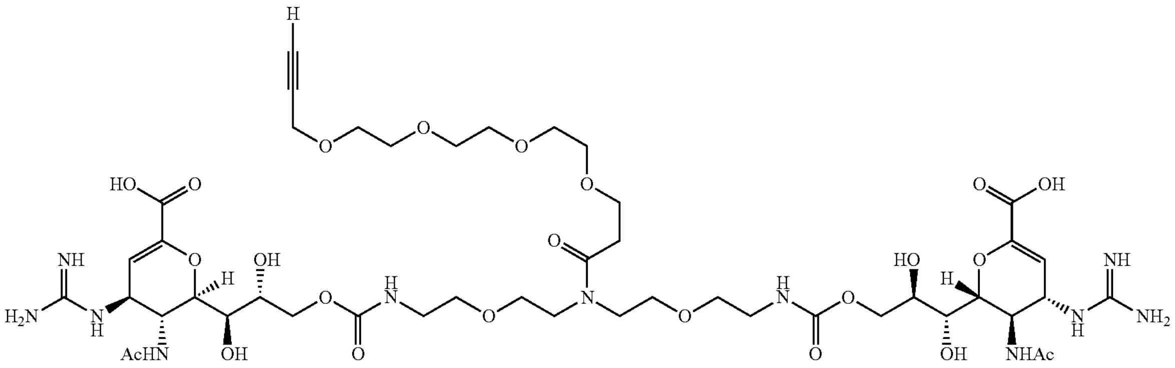 [SMILES: C#CCOCCOCCOCCOCCC(=O)N(CCOCCNC(=O)OC[C@@H](O)[C@@H](O)[C@@H]1OC(C(=O)O)=C[C@H](NC(=N)N)[C@H]1NC(C)=O)CCOCCNC(=O)OC[C@@H](O)[C@@H](O)[C@@H]1OC(C(=O)O)=C[C@H](NC(=N)N)[C@H]1NC(C)=O]

$^1$H NMR (500 MHz, Methanol-$d_4$) δ: 5.88 (d, J=2.6 Hz, 2H), 4.50 (dt, J=8.5, 2.7 Hz, 2H), 4.43 (ddd, J=9.7, 3.9, 1.5 Hz, 2H), 4.39 (dd, J=11.5, 2.4 Hz, 2H), 4.25-4.16 (m, 2H), 4.19 (d, J=2.4 Hz, 2H), 4.13 (dt, J=11.5, 5.9 Hz, 2H), 4.05 (m, 2H), 3.77 (t, J=6.2 Hz, 2H), 3.72-3.55 (m, 22H), 3.51 (m, 4H), 3.35-3.23 (m, 4H), 2.86 (t, J=2.4 Hz, 1H), 2.74 (t, J=6.2 Hz, 2H), 2.02 (s, 6H).

$^{13}$C NMR (125 MHz, MeOD) δ:173.03, 163.76, 157.89, 157.54, 145.60, 107.21, 79.28, 76.29, 74.70, 70.11, 70.07, 70.03, 69.92, 69.70, 69.47, 68.96, 68.89, 68.72, 68.54, 68.19, 67.05, 66.75, 57.69, 50.09, 48.69, 48.08, 46.10, 40.44, 40.38, 33.23, 21.42.

Example 105. Synthesis of Int-60

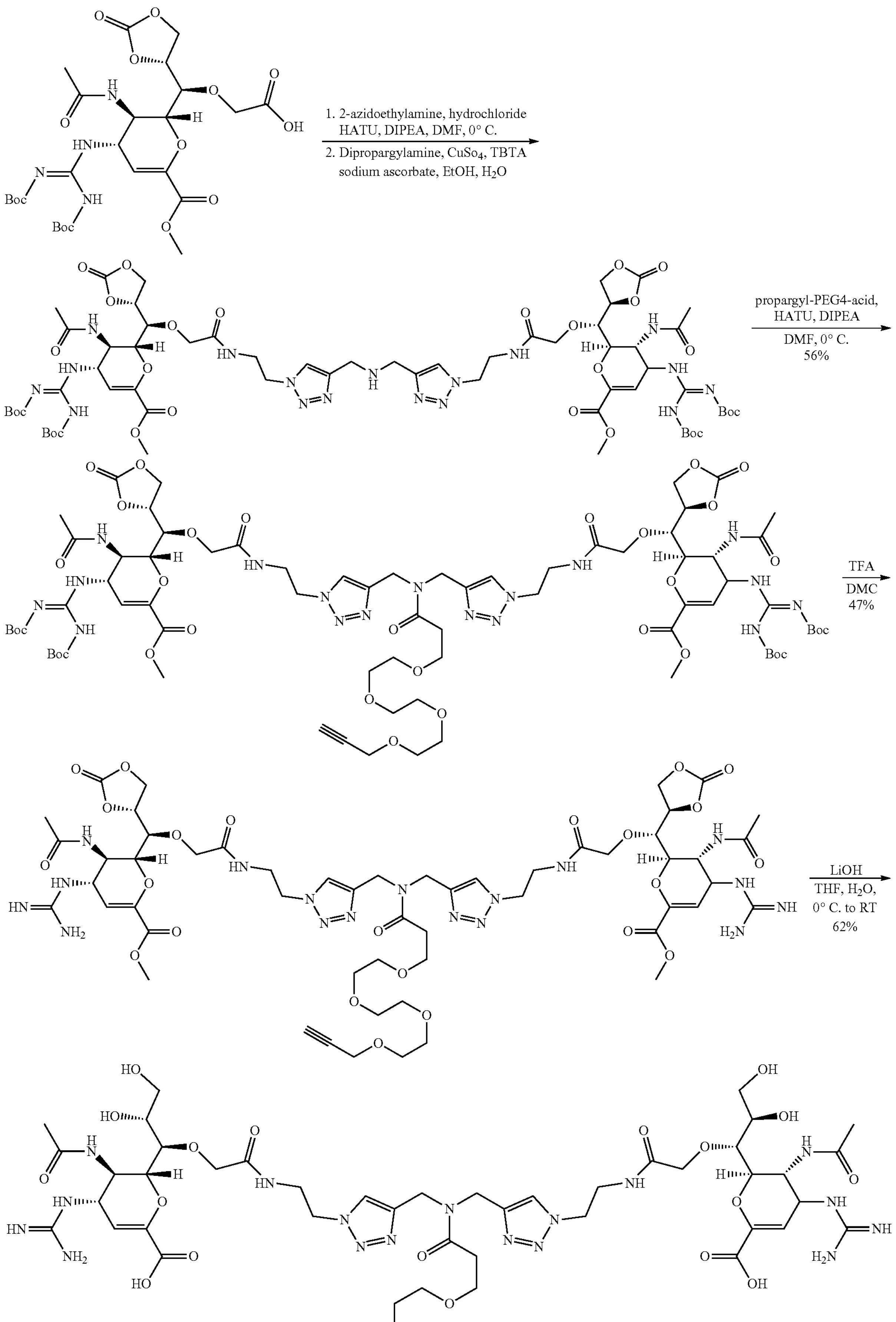
1. 2-azidoethylamine, hydrochloride HATU, DIPEA, DMF, 0° C.
2. Dipropargylamine, CuSo4, TBTA sodium ascorbate, EtOH, H2O
propargyl-PEG4-acid, HATU, DIPEA
DMF, 0° C.
56%
TFA
DMC
47%
LiOH
THF, H2O,
0° C. to RT
62%

Step a.

To a 0° C. stirring solution of previously prepared Ether-zanamivir acid (1.00 g, 1.586 mmol, Example 31), 2-azido-ethylamine hydrochloride (213 mg, 1.744 mmol) and DIPEA (1.105 mL, 6.343 mmol) in DMF (8.0 mL), it was added HATU (615 mg, 1.618 mmol). The temperature was raised to ambient and stirring was continued until completion. All the volatiles were removed per vacuum techniques. The residue was taken up in ethyl acetate, washed with a 1 M aqueous solution of sulfuric acid (1×50 mL), then a saturated aqueous solution of sodium bicarbonate (3×20 mL), and brine (1×50 mL). The resulting organic layers was dried with magnesium sulfate, filtered, and all the volatiles were removed per vacuum techniques. In this way, 816 mg of the desired intermediate azide was obtained in high purity and used in the next step without any further purification. (Ion found by LCMS: $[M+H]^+$=699.2). To a stirring solution of the described crude material (816 mg, 1.168 mmol), dipropargylamine (54 mg, 0.584 mmol), tris((1-benzyl-4-triazolyl)methyl)amine (31 mg, 0.058 mmol), and sodium ascorbate (58 mg, 0.292 mmol) in ethanol (10 mL) and water (5 mL), it was added cupric sulfate (10 mg, 0.061 mmol). Upon completion, copper scavenger SiliaMetS TAAcONa (300 mg, loading 0.45 mmol/g) was added and stirring was continued for 1 h. The mixture was filtered with the aid of dichloromethane. The filtrate was washed with a saturated solution of sodium bicarbonate. The aqueous layer was additionally washed with dichloromethane (3 times). The combined organics were dried with magnesium sulfate, filtered and concentrated. The residue was purified by silica column using an Isco COMBIFLASH® liquid chromatography eluted with 0% to 100% hexanes and ethyl acetate, followed by 0% to 30% dichloromethane and. Yield 817 mg, 94% yield. Ions found by LCMS: $[(M+2H)/2]^+$=745.8, $[(M+3H)/3]^+$=497.5.

Step b.

To a 0° C. stirring solution of step a product (817 mg, 0.548 mmol), propargyl-PEG4-acid (185 mg, 0.712 mmol) and DIPEA (286 uL, 1.644 mmol) in DMF (7.0 mL), it was added HATU (212 mg, 0.544 mmol). The temperature was raised to ambient and stirring was continued until completion. All the volatiles were removed per vacuum techniques. The residue was purified by HPLC (0 to 90% methanol and water). Yield 520 mg, 56%. Ions found by LCMS: $[(M+2H)/2]^+$=866.8, $[(M+3H)/3]^+$=578.4.

Step c.

A stirring solution of step b compound (520 mg, 0.300 mmol) in 2-methyl-2-butene (0.25 mL), dichloromethane (4.0 mL) and TFA (2.0 mL) was stirred until gas evolution ceased. All the volatiles were removed per vacuum techniques. The residue was purified by HPLC (0 to 30% methanol and water, using 0.1% TFA as modifier). Yield 221 mg, 47%. Ions found by LCMS: $[(M+2H)/2]^+$=666.8, $[(M+3H)/3]^+$=444.8.

Step d.

To a 0° C. stirring solution of step c product (221 mg, 0.142 mmol) in water (3.0 mL) it was added lithium hydroxide (20 mg, 0.850 mmol). The reaction was quenched with acetic acid (120 uL), and all the volatiles were removed per vacuum techniques. The residue was purified by HPLC (0 to 20% methanol and water, using 0.1% TFA as modifier). Yield 130 mg, 62%. Ions found by LCMS: $[(M+2H)/2]^+$=626.8, $[(M+3H)/3]^+$=418.2.

Example 106. Synthesis of Conjugate 29

A solution of azido functionalized aglycosylated Fc (SEQ ID NO: 35) in pH 7.4 PBS×1 buffer solution (100 mg, 10 mL, 1.874 μmol) is added to a centrifuge tube containing a pH 7.4 PBS×1 buffer solution (10.50 mL) of alkyne derivatized small molecule (17 mg, 0.0112 mmol; Example 105, Int-60), cupric sulfate (4 mg, 0.0225 mmol), tris(3-hydroxypropyltriazolylmethyl)-amine (39 mg, 0.0900 mmol), and sodium ascorbate (7.4 mg, 0.375 mmol). The resulting mixture was gently shaken overnight. It was purified by affinity chromatography over a protein A column, followed by size exclusion chromatography (see Example 10). Maldi TOF analysis of the purified final product gave an average mass of 56938 Da (DAR=2.3). Yield 49.9 mg, 49% yield.

Example 107. Synthesis of Int-65

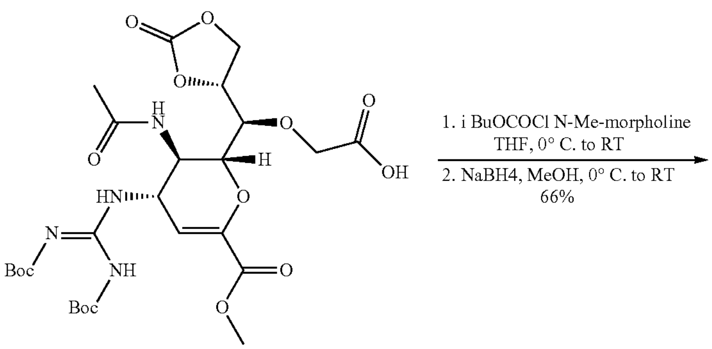

-continued
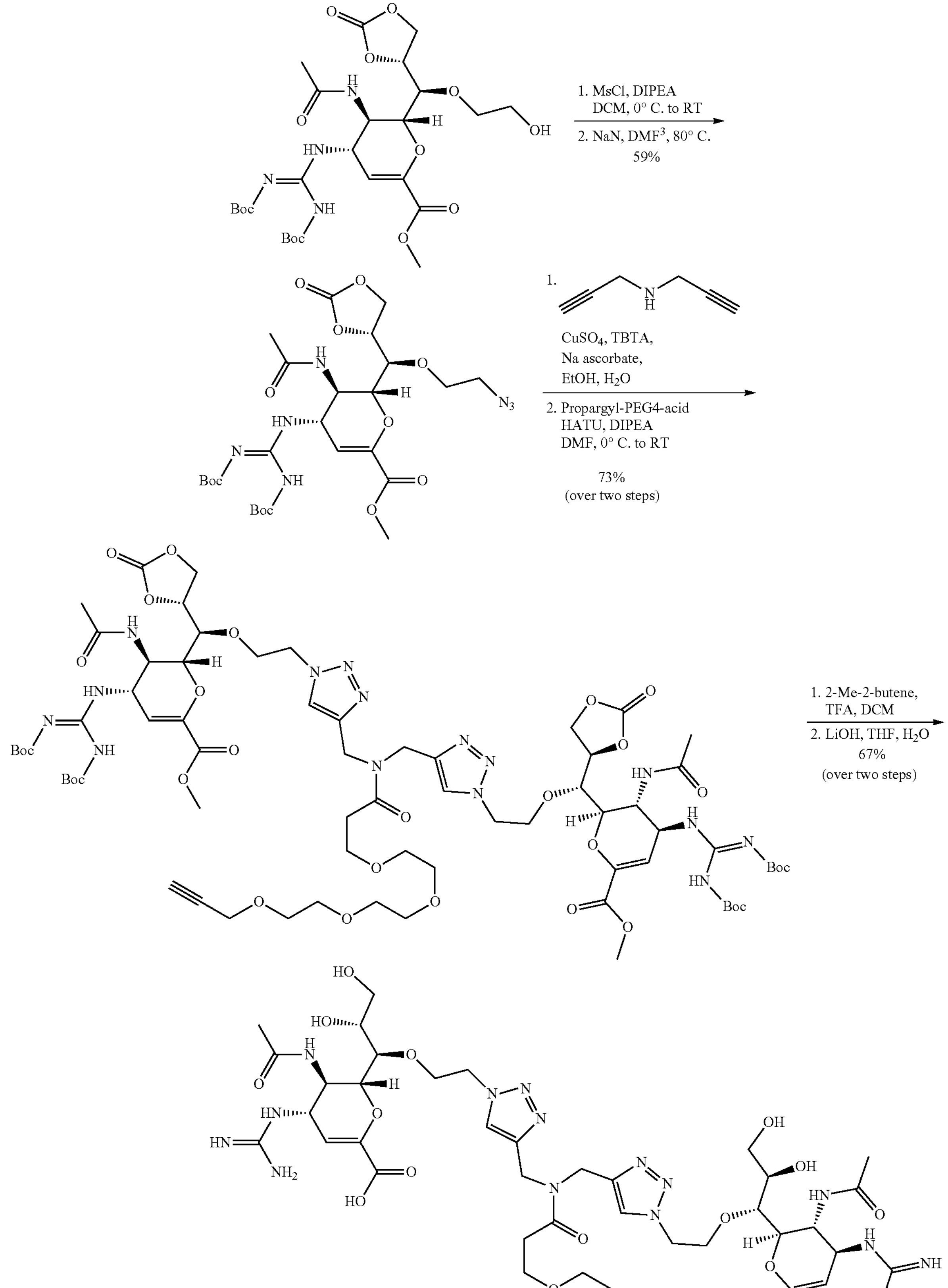

Step a.

To a 0° C. stirring solution of previously prepared ether-zanamivir acid (2.00 g, 3.172 mmol, Example 31) and 4-methylmorpholine (0.628 mL, 5.709 mmol) in tetrahydrofuran (30 mL) it was added isobutyl chloroformate (0.617 mL, 4.7574 mmol). After 10 minutes, the temperature was increased to ambient and stirring continued for 20 minutes. The temperature was decreased back to 0° C., and sodium borohydride (360 mg, 9.515 mmol) was added in one portion, followed by dropwise addition of (10 mL) over 5 minutes. Upon completion, the reaction was quenched with acetic acid (2.860 mL, 50 mmol), and after 5 minutes the temperature was raised to ambient, while stirring was continued until gas evolution ceased. All the volatiles were evaporated and the residue was suspended in dichloromethane and filtered. The filtrate was concentrated and the residue was purified by silica column using an Isco COMBIFLASH® liquid chromatography eluted with 20% to 100% hexanes and ethyl acetate, using 3% methanol as a modifier. Yield 1.302 g, 66% yield. Ions found by LCMS: $[(M+H)]^+$=617.2.

Step b.

To a 0° C. stirring solution of step a product (1.25 g, 2.027 mmol) and DIPEA (1.095 mL, 6.284 mmol) in dichloromethane (15 mL), it was added methanesulfonyl chloride (0.314 mmol, 4.054 mmol). Upon completion, the reaction was treated with water (15 mL). The layers were separated, and the dichloromethane layer was dried with brine, then magnesium sulfate, and filtered. The solution was concentrated and the residue was dissolved in DMF (10 mL), and sodium azide (264 mg, 4.054 mmol) was added, while temperature was raised to 50° C. Completion was observed after 18 h, and all the volatiles were evaporated per vacuum techniques. The residue was purified by silica column using an Isco COMBIFLASH® liquid chromatography eluted with 20% to 100% hexanes and ethyl acetate, using 3% methanol as a modifier. Yield 767 mg, 59% yield. Ions found by LCMS: $[(M+H)]^+$=642.2.

Step c.

To a stirring solution of step b product (496 mg, 0.773 mmol), dipropargylamine (36 mg, 0.386 mmol), tris((1-benzyl-4-triazolyl)methyl)amine (41 mg, 0.077 mmol), and sodium ascorbate (115 mg, 0.580 mmol) in ethanol (16 mL) and water (8 mL), it was added cupric sulfate (13 mg, 0.081 mmol). Upon completion, copper scavenger SiliaMetS TAAcONa (600 mg, loading 0.45 mmol/g) was added and stirring was continued for 1 h. The mixture was filtered with the aid of dichloromethane. The filtrate was washed with a saturated solution of sodium bicarbonate. The aqueous layer was additionally washed with dichloromethane (3 times). The combined organics were dried with magnesium sulfate, filtered and all the volatiles were evaporated per vacuum techniques. To a 0° C. stirring solution of the residue, propargyl-PEG4-acid (151 mg, 0.580 mmol)) and DIPEA (337 uL, 1.933 mmol) in DMF (10.0 mL), it was added HATU (220 mg, 0.580 mmol). The temperature was raised to ambient and stirring was continued until completion. All the volatiles were removed per vacuum techniques. The residue was purified by HPLC (0 to 90% methanol and water). Yield 457 mg, 73%. Ions found by LCMS: [(M+2H)/2]+=809.8, [(M+2H−Boc)/2]+=759.8.

Step d.

A stirring solution of step c compound (451 mg, 0.279 mmol) in 2-methyl-2-butene (0.25 mL), dichloromethane (4.0 mL) and TFA (2.0 mL) was stirred until gas evolution ceased. All the volatiles were removed per vacuum techniques. Ions found by LCMS: $[(M+2H)/2]^+$=609.8, [(M+3H)/3]+=407.0. To a 0° C. stirring solution of the residue in tetrahydrofuran (6 mL) and water (6 mL), it was added lithium hydroxide (240 mg, 10.03 mmol). Upon completion, the reaction was quenched with acetic acid (0.638 mL, 11.14 mmol), and all the volatiles were removed per vacuum techniques. The residue was purified by HPLC (0 to 90% methanol and water, using 0.1% TFA as modifier). Yield 209 mg, 67%. Ions found by LCMS: [(M+2H)/2]+=569.8, [(M+2H−Boc)/2]+=380.3.

Example 108. Synthesis of Conjugate 30

A solution of azido functionalized aglycosylated Fc (Example 7, SEQ ID NO: 35) in pH 7.4 PBS×1 buffer solution (50 mg, 5 mL, 1.874 μmol) is added to a centrifuge tube containing a pH 7.4 PBS×1 buffer solution (9.50 mL) of alkyne derivatized small molecule (8.7 mg, 0.0064 mmol, Int-65), cupric sulfate (2 mg, 0.013 mmol), tris(3-hydroxypropyltriazolylmethyl)-amine (22 mg, 0.0508 mmol), and sodium ascorbate (25 mg, 0.127 mmol). The resulting mixture was gently shaken overnight. It was purified by affinity chromatography over a protein A column, followed by size exclusion chromatography (see Example 10). Maldi TOF analysis of the purified final product gave an average mass of 61548 Da (DAR=2.4). Yield 32.33 mg, 67% yield.

Example 109: Synthesis of p-Nitrophenyl Carbonate Zanamivir Intermediate

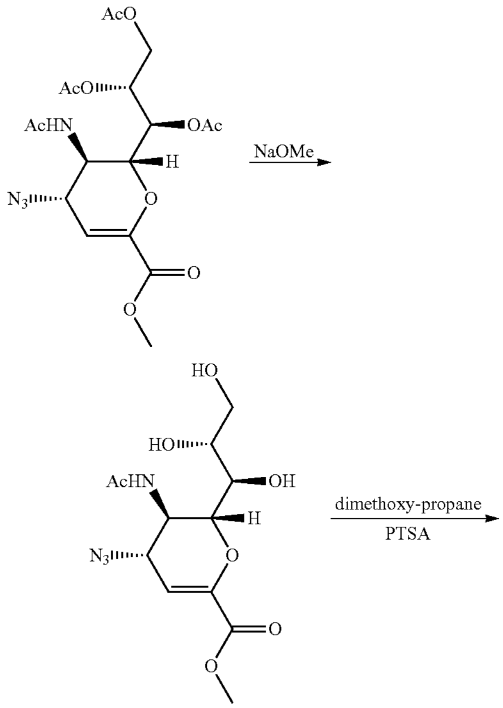

-continued

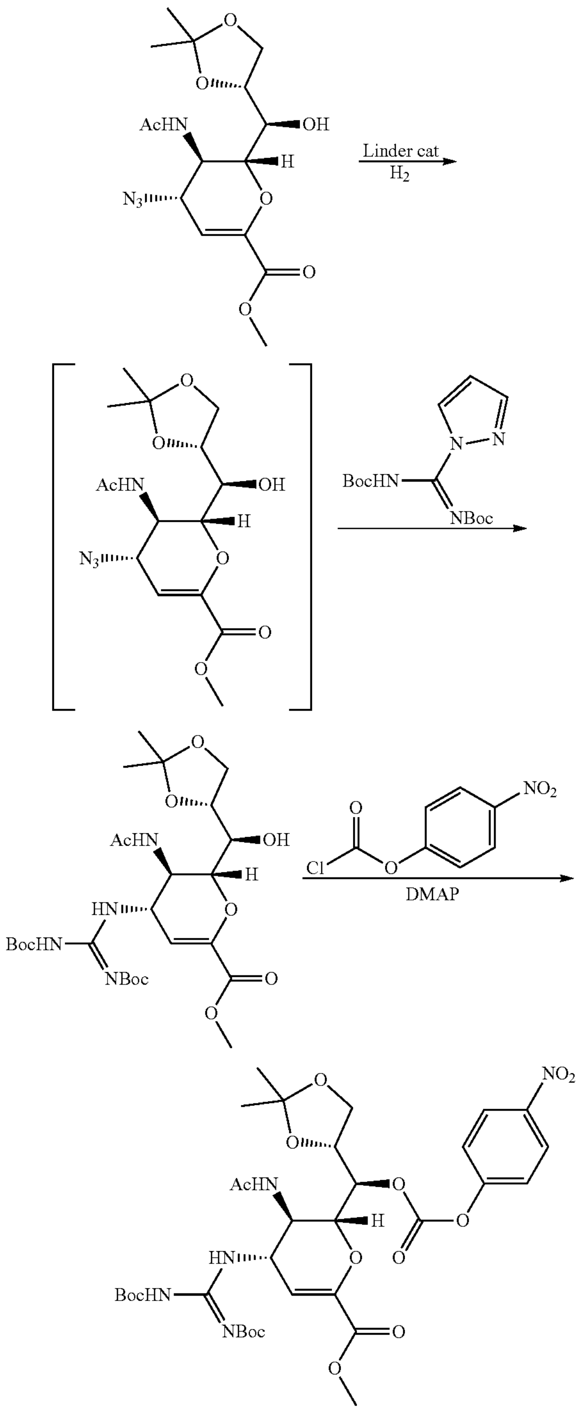

Step a.

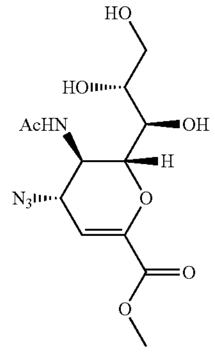 [SMILES: COC(=O)C1=C[C@H](N=[N+]=[N-])[C@@H](NC(C)=O)[C@H]([C@H](O)[C@H](O)CO)O1]

Triacetoxy-azido Zanamivir intermediate (10.0 g, 22 mmol) was dissolved in 60 ml dry methanol, then treated with 20 ml sodium methoxide in methanol (0.5 M in methanol, 10 mmol) while cooling in an ice-water bath. Progress of the reaction was monitored by LCMS, which was complete after 2 hours. The pH of the reaction solution was then adjusted to a value of 5 to 6 by using Amberlite IRN-77 ion exchange resin. The mixture was filtered to remove the resin and evaporated to dryness under vacuum. The resulting oil was used for next step without further purification. Ion(s) found by LCMS: M+H=331.1.

Step b.

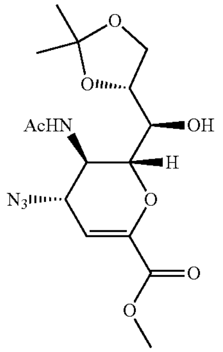 [SMILES: COC(=O)C1=C[C@H](N=[N+]=[N-])[C@@H](NC(C)=O)[C@H]([C@H](O)[C@H]2COC(C)(C)O2)O1]

To a solution of the products from the previous step in 70 ml of acetone were added 30 ml of 2,2-dimethoxypropane and p-toluenesulfonic acid 1 hydrate (400 mg, 2.0 mmol), the resulting solution was stirred at room temperature overnight. At the end of this time, sodium bicarbonate (170 mg, 2.0 mmol) was added, and the mixture was concentrated to dryness. The resulting residue was used in next step without purification. Ion(s) found by LCMS: M+H=371.2.

Steps c & d.

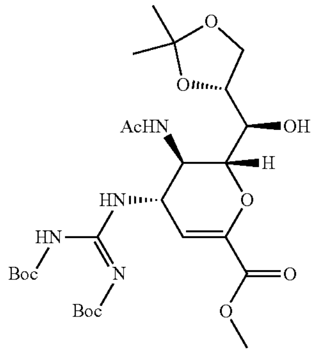 [SMILES: COC(=O)C1=C[C@H](N/C(=N/C(=O)OC(C)(C)C)NC(=O)OC(C)(C)C)[C@@H](NC(C)=O)[C@H]([C@H](O)[C@H]2COC(C)(C)O2)O1]

To a solution of material from the previous step in 60 ml of methanol was added 5.0 g of a Lindlar catalyst. The resulting mixture was flushed with hydrogen every 30 minutes and stirred for 5 hours. After complete reaction as determined by HPLC, the catalyst was filtered off through celite. The filtrate was concentrated and used in the next step without purification.

Crude product from the previous step in 60 ml THE was treated with N,N'-bis-boc-1-guanylpyrazole (9.3 g, 30.0 mmol), and DIEA (9.9 ml, 57.0 mmol). The resulting solution was stirred at room temperature until all starting material was consumed as determined by LCMS (4h). The solution was concentrated and purified by flash chromatography eluted with 20% to 80% ethyl acetate/dichloromethane. Yield 8.8 g, 59.0% for four steps. Ion(s) found by LCMS: M+H 587.3.

Step e.

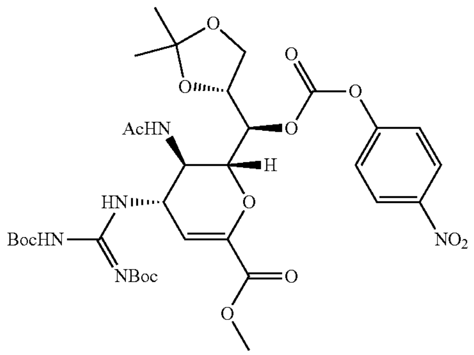

A reaction flask containing product from the previous step (6.5 g, 11 mmol) was vacuum flushed with nitrogen and dissolved in anhydrous dichloromethane (100 ml). After the solution was cooled in an ice-water bath, DMAP (4.89 g, 40 mmol) was added and stirred to dissolve, then 4-nitrophenylchloroformate (5.58 g, 28 mmol) was added in portions, while stirring at 0° C. to room temperature for 1 hour. LCMS shows starting material 1 hr so additional DMAP (1.22 g, 10 mmol) and 4-nitrophenylchloroformate (1.0 g, 5 mmol) were added. The reaction was continued for 4 more hours, then concentrated and purified by flash chromatography eluting with 20% to 80% ethyl acetate/dichloromethane. Yield 5.1 g, 59.9%. Ion found by LCMS: $[M+H]^+=752.2$.

Example 110. Synthesis of Int-71

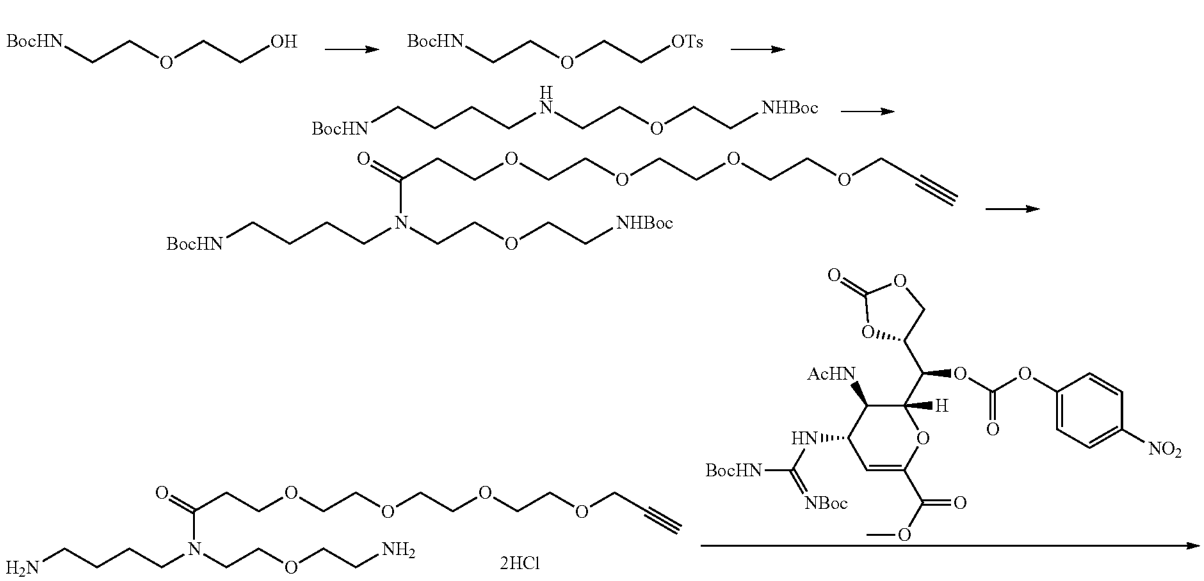

-continued
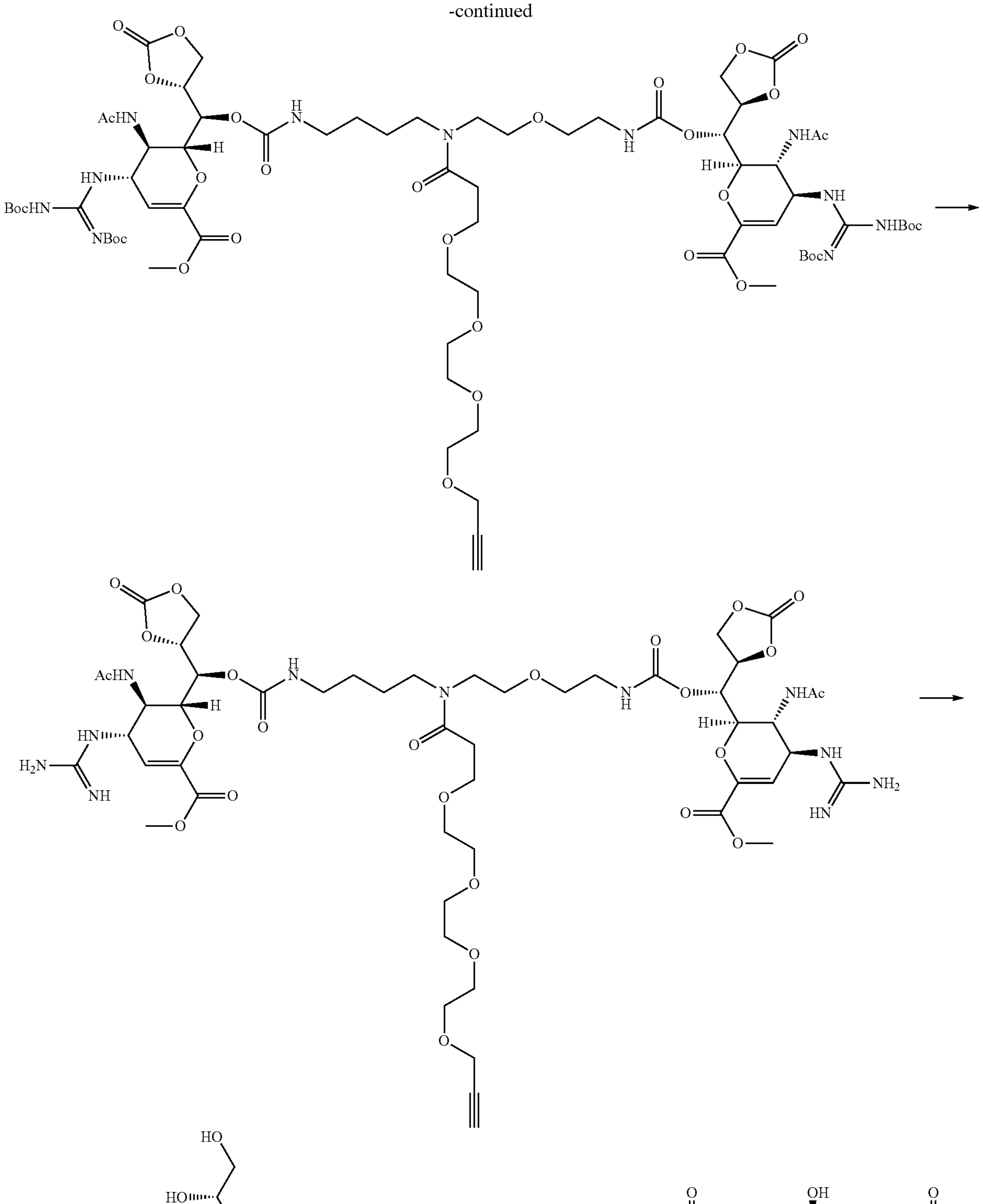

Step a.

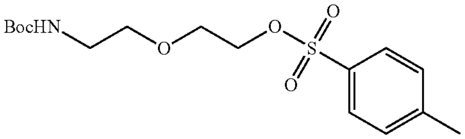 [SMILES: Cc1ccc(S(=O)(=O)OCCOCCNC(=O)OC(C)(C)C)cc1]

To a solution of 2-(2-Boc-aminoethoxy) ethanol (6.15 g, 30 mmol) in anhydrous DCM (60 ml) was added DIPEA (7.8 g, 60 mmol) and DMAP (366.6 mg, 3 mmol). P-toluenesulfonyl chloride (6.86 g, 36 mmol) was then added in portions over 30 minutes. After the resulting mixture was stirred for 3 days, it was concentrated by rotary evaporation and purified by RPLC (20% to 70% acetonitrile/water). Yield 3.71 g, 34.4%. Ion found by LCMS: $[M\text{-}Boc+H]^+$ =260.

Step b.

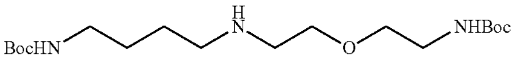 [SMILES: CC(C)(C)OC(=O)NCCCCNCCOCCNC(=O)OC(C)(C)C]

To a solution of the step-a product (2.1 g, 5.83 mmol) in anhydrous THE (10 ml) was added sodium carbonate (1.24 g, 11.7 mmol) and N-Boc-1,4-diaminobutane (1.32 g, 7 mmol). The resulting mixture was heated at 60° C. for 1 day. The salt was then filtered off, and the filtrate was concentrated by rotary evaporation. The residue was purified by RPLC (100 g, 5 to 50% acetonitrile and water). Yield 1.94 g, 88.6%. Ion found by LCMS: $[M+H]^+$=376.0.

Step c.

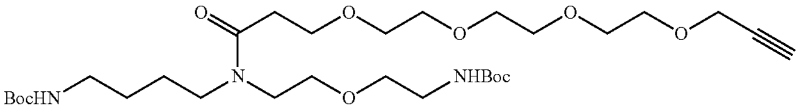 [SMILES: C#CCOCCOCCOCCOCCC(=O)N(CCCCNC(=O)OC(C)(C)C)CCOCCNC(=O)OC(C)(C)C]

To a solution of propargyl PEG-4 acid (781 mg, 3 mmol) and HATU (1.14 g, 3 mmol) in anhydrous DMF (3 ml) was added DIPEA (390 mg, 3 mmol), followed by the addition of the solution step-b product (940 mg, 2.5 mmol) and DIPEA (390 mg, 3 mmol) in anhydrous DMF (3 ml). The reaction mixture was stirred for 30 minutes, then directly purified by RPLC (5% to 80% acetonitrile and water, using 0.1% TFA as modifier). Yield 960.2 mg, 65.3%. Ion found by LCMS: $[M+H]^+$=618.3, $[M\text{-}Boc+H]^+$=518.3.

Step d.

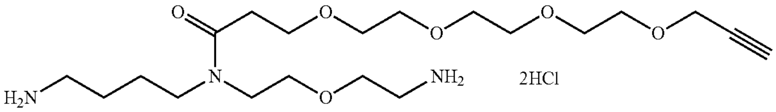 [SMILES: C#CCOCCOCCOCCOCCC(=O)N(CCCCN)CCOCCN]

The step-c product (960.2 mg, 1.63 mmol) was dissolved in anhydrous THE (6 ml). 4N HCl solution in dioxane (4 ml) was added, and the reaction mixture was stirred overnight. It was then concentrated by rotary evaporation. The residue was extracted with water (3×3 ml) and ethyl acetate (10 ml). The combined aqueous layers were lyophilized. Yield 760 mg, 95.1%. Ion found by LCMS: $[M+H]^+$=418.0.

Step e.

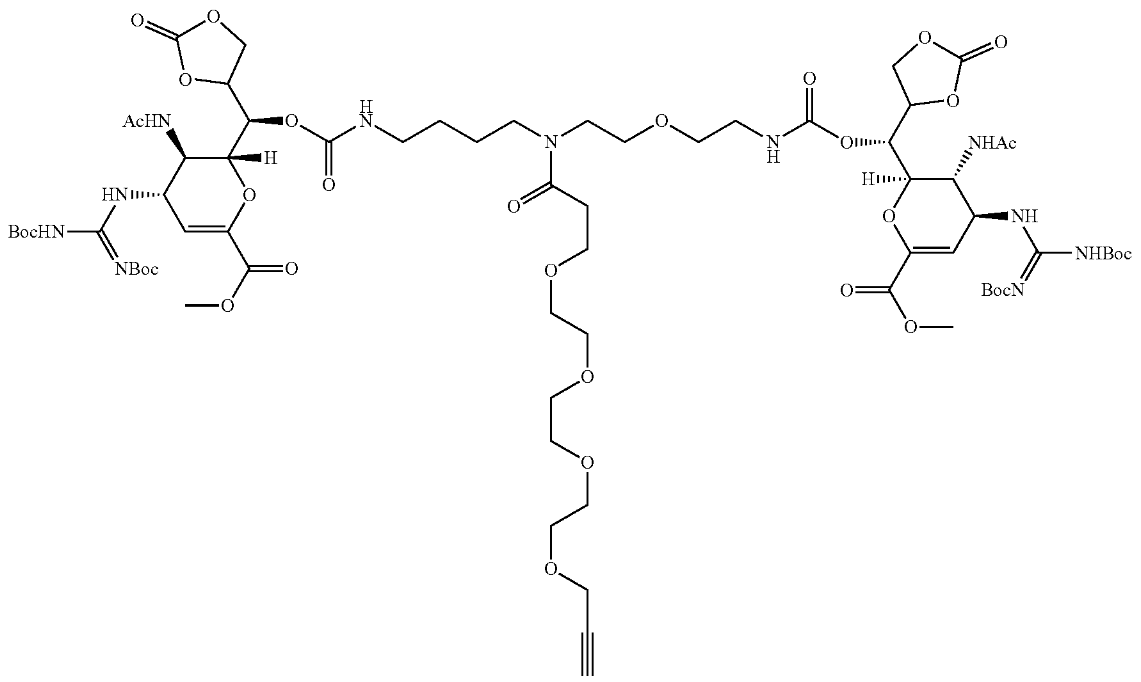

To a mixture of the step-d product (556.2 mg, 1.13 mmol) and DIPEA (741 mg, 5.7 mmol) in anhydrous DMF (3 ml) was added in portions p-nitrophenyl carbonate of zanamivir (1.67 g, 2.26 mmol, described in Example 109) over 20 minutes. The reaction was stirred for 1 hour, then directly purified by RPLC (30% to 90% acetonitrile/water, using 0.1% TFA as modifier). Yield 1.35 g, 74%. Ion found by LCMS: $[(M+2H)/2]^{+}$=807.9.

Step f.

The step-e product (1.35 g, 0.836 mmol) was dissolved in TFA (5 ml). The reaction was heated at 30° C. for 1 hour, it was directly purified by RPLC (0% to 35% acetonitrile/water, using 0.1% TFA as modifier). Yield 1.00 g, 82.9%. Ions found by LCMS: $[(M+2H)/2]^{+}$=607.8.

Step g.

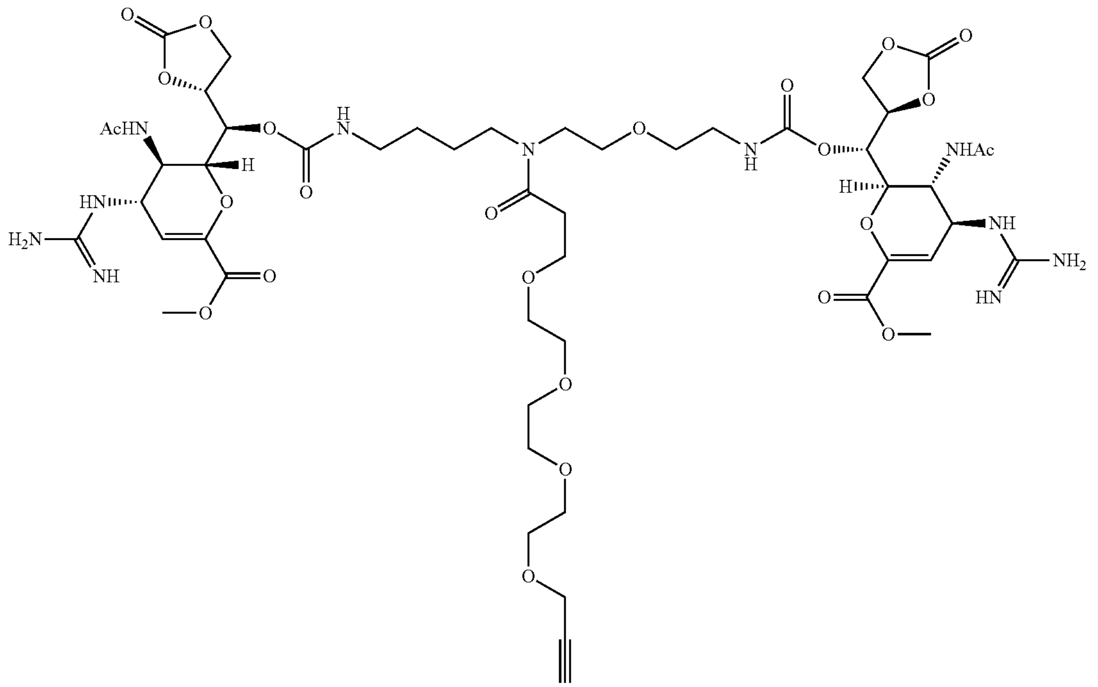 [SMILES: C#CCOCCOCCOCCOCCC(=O)N(CCCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

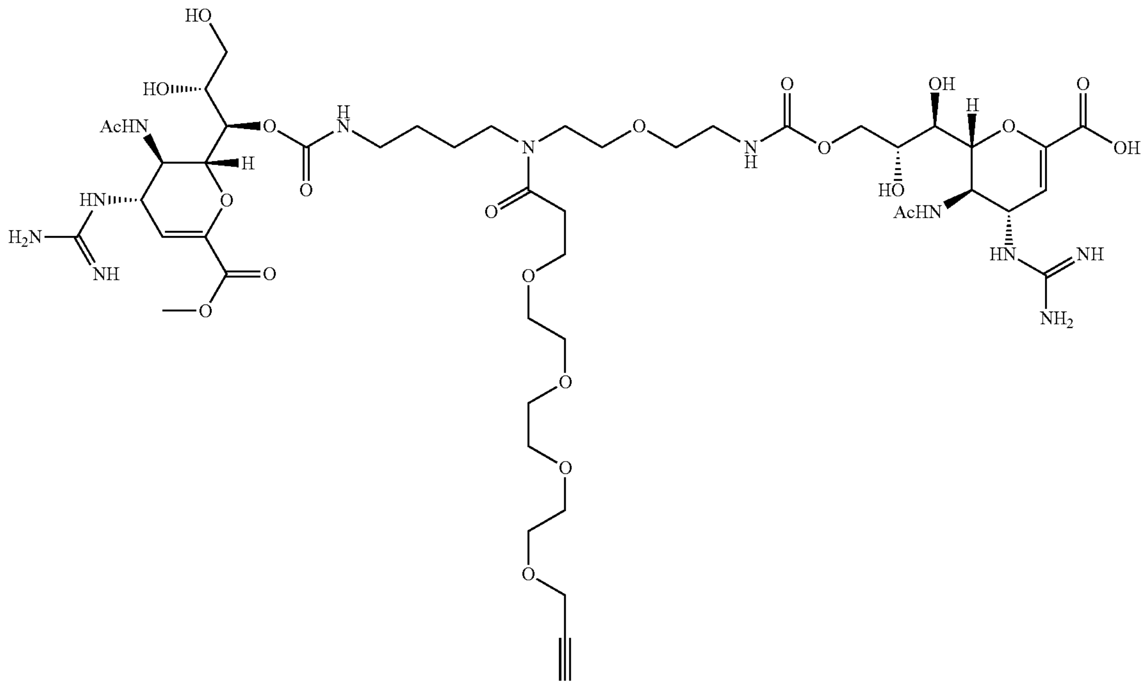 [SMILES: C#CCOCCOCCOCCOCCC(=O)N(CCCCNC(=O)O[C@@H]([C@@H]1OC(C(=O)OC)=C[C@H](NC(=N)N)[C@H]1NC(C)=O)[C@H](O)CO)CCOCCNC(=O)OC[C@@H](O)[C@@H](O)[C@@H]1OC(C(=O)O)=C[C@H](NC(=N)N)[C@H]1NC(C)=O]

The step-f product (1.00 g, 0.693 mmol) was dissolved in MeOH (12 ml), then cooled in an ice-water bath. It was then treated with a solution of LiOH monohydrate (286 mg, 6.6 mmol) in water (9 ml). The resulting mixture was stirred overnight and then acidified by 4N HCl solution in dioxane (2 ml). After organic solvents were removed by rotary evaporation, the residue was purified by preparative HPLC (Isco ACCQ prep, Luna 5 μm C18(2) 100 Å LC column 100 mm×30 mm; Gradient: 0% acetonitrile/water for 2 min, then 0% to 15% acetonitrile/water over 12 min, then isocratic at 15% acetonitrile for 10 min, using 0.1% TFA). Yield 275.9 mg, 29.2%. Ions found by LCMS: $[(M+2H)/2]^{+}$=567.8, [(M+3H)/3]+=378.9.

Example 111. Synthesis of Conjugate 31

A 15-ml sterile centrifuge tube was charged with sodium ascorbate (68.1 mg, 0.344 mmol), THPTA (14.9 mg, 0.0344 mmol), alkyne derivatized small molecule (17.5 mg, 0.00953 mmol, described in Example 110) and buffer PBS 7.4 (1 ml). After stirred by vortex to dissolve everything, Peg 4 azido Fc (50 mg, 0.0008588 mmol, described in Example 7 SEQ ID No. 18) was added followed by a solution of CuSO4 (2.05 mg, 0.0129 mmol) in PBS (0.5 ml). The mixture was gently rotated for 20 hours then purified by affinity chromatography over a protein-A column, followed size exclusion chromatography. Maldi TOF analysis of the purified final product gave an average mass of 63586 Da (DAR=3.8). Yield 32.8 mg, 66% yield.

Example 112. Synthesis of Int-72

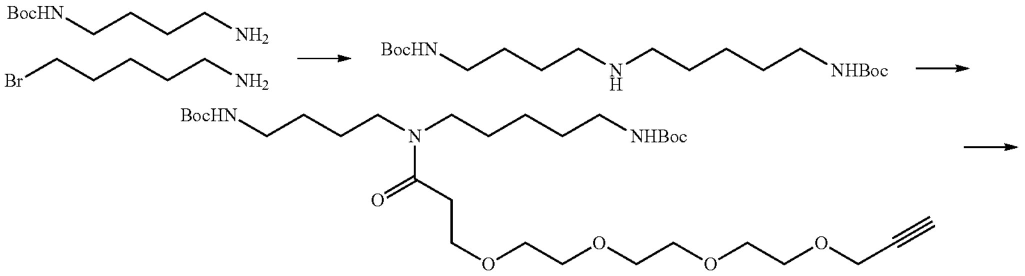

-continued

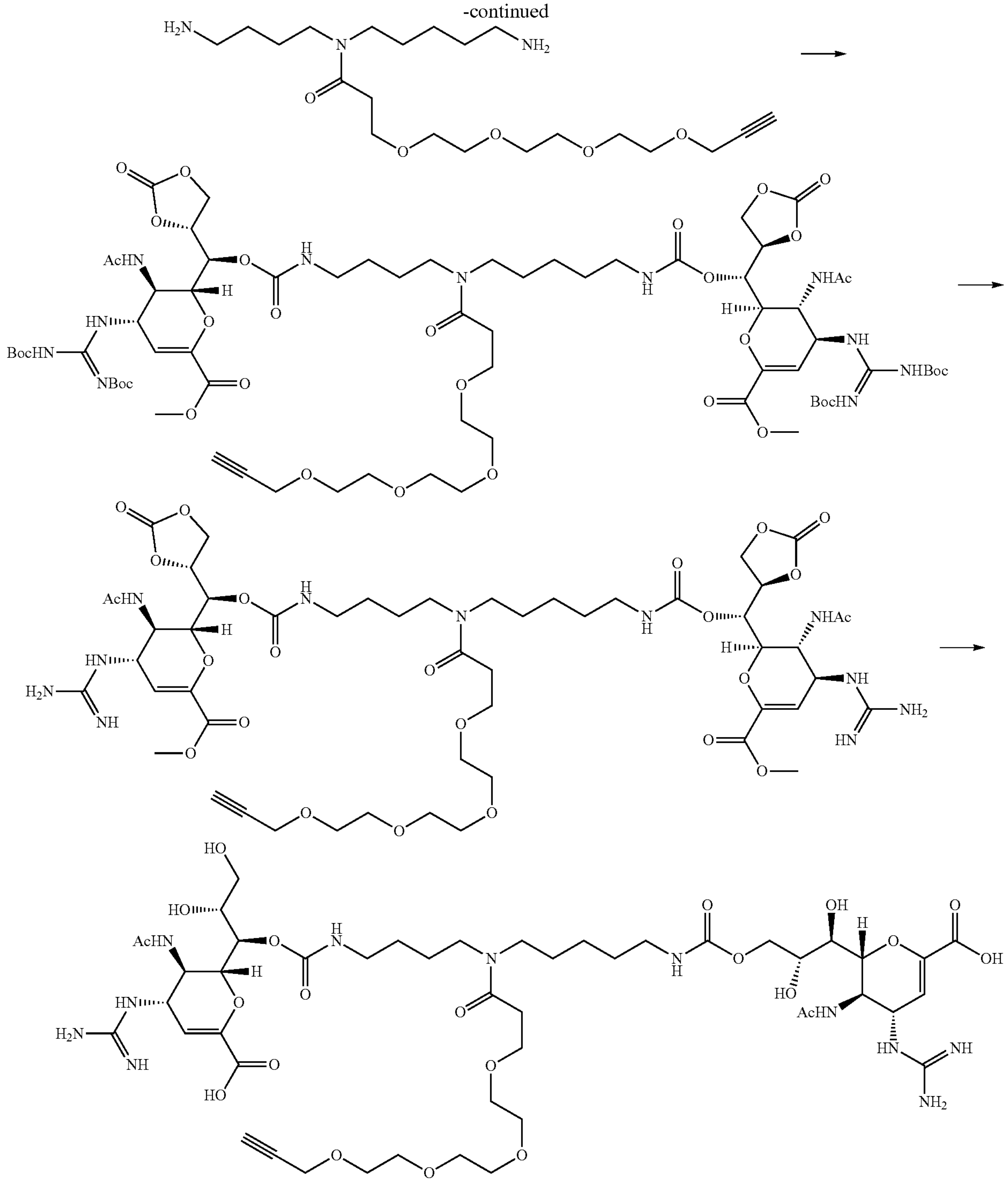

Step a.

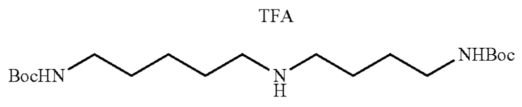 [SMILES: CC(C)(C)OC(=O)NCCCCCNCCCCNC(=O)OC(C)(C)C]

To a solution of N-Boc-1,4-diaminobutane (1.56 g, 8.28 mmol) in anhydrous DMF (7 ml) was added sodium carbonate (742 mg, 7 mmol) and 5-(Boc-amino)-1-pentylbromide (1.73 g, 6.5 mmol). The resulting mixture was heated at 50° C. for 24 hours. The salt was then filtered off, and the filtrate was concentrated by rotary evaporation. The residue was purified by RPLC (5% to 50% acetonitrile/water, using 0.1% TFA as modifier). Yield 2 g, 63.2%. Ion found by LCMS: $[M+H]^+$=374.4.

Step b.

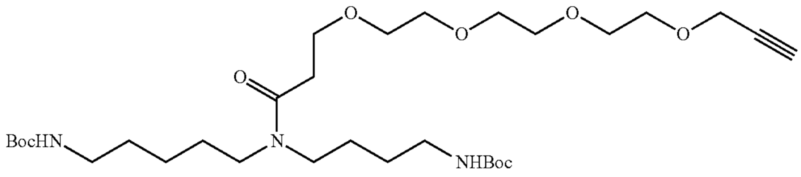 [SMILES: C#CCOCCOCCOCCOCCC(=O)N(CCCCCNC(=O)OC(C)(C)C)CCCCNC(=O)OC(C)(C)C]

To a solution of propargyl PEG-4 acid (1.3 g, 5 mmol) and HATU (2.1 g, 5.5 mmol) in anhydrous DMF (6 ml) was added DIPEA (1.3 g, 10 mmol). After 5 minutes, the reaction mixture was added to the step-a product (2 g, 4.1 mmol) and stirred for 1 hour. It was then directly purified by RPLC (5% to 80% acetonitrile/water, using 0.1% TFA as modifier). Yield 2.34 g, 95%. Ion found by LCMS: $[M+H]^+=616.4$, $[M-Boc+H]^+=516.4$.

Step c.

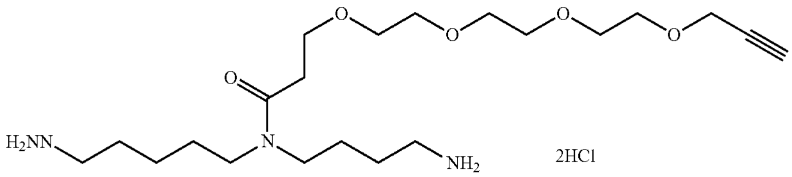

2HCl

The step-b product (2.34 g, 3.8 mmol) was dissolved in anhydrous THE (12 ml). 4N HCl solution in dioxane (10 ml) was added, and the reaction mixture was stirred overnight. It was then concentrated by rotary evaporation. The residue was re-dissolved in acetonitrile/water (1:1, ~16 ml), and the solution was lyophilized. The crude product was carried to the subsequent step without further purification. Yield 1.91 g, quantitative yield. Ion found by LCMS: $[M+H]^+=416.4$.

Step d.

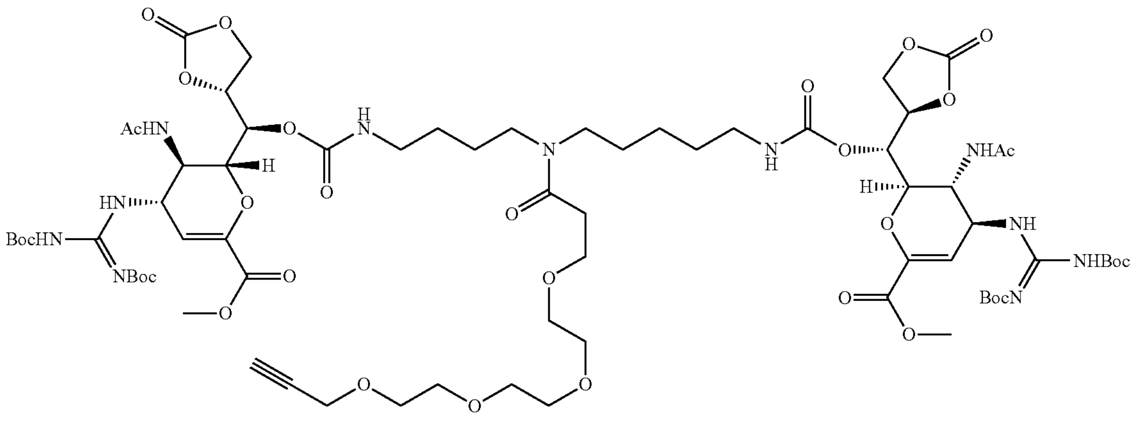

To a solution of p-nitropenyl carbonate of zanamivir (2.25 g, 3.05 mmol, described in Example 109) in anhydrous DCM (3 ml) was added in-portions a mixture of the step-c product (610 mg, 1.249 mmol) and DIPEA (1.05 g, 8.1 mmol) in anhydrous DMF (4 ml) over 20 minutes. After stirring for 1 hour, the reaction mixture was concentrated and purified by RPLC (30% to 80% acetonitrile/water, using 0.1% TFA as modifier). Yield 1.73 g, 85.9%. Ion found by LCMS: $[(M+2H)/2]^+=806.8$, $[(M-Boc+2H)/2]^+=756.8$.

Step e.

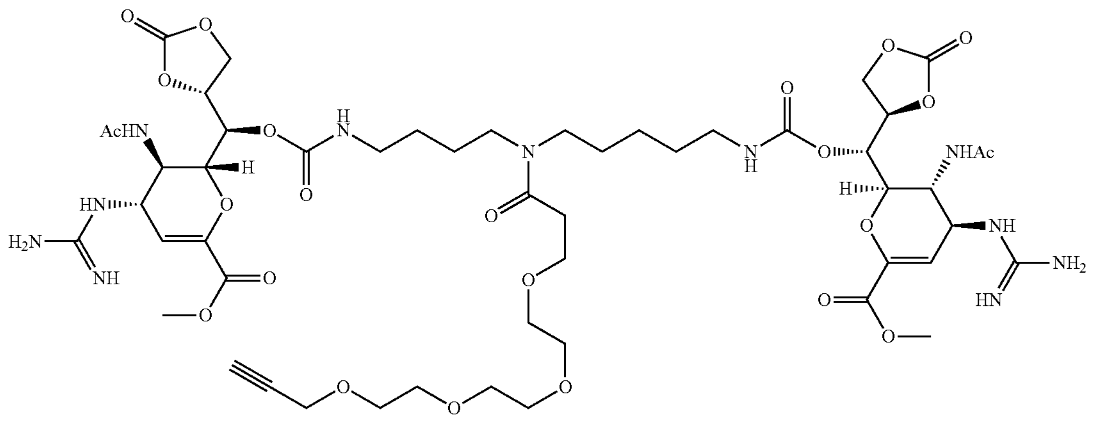 [SMILES: C#CCOCCOCCOCCOCCC(=O)N(CCCCCNC(=O)O[C@@H]([C@@H]1OC(C(=O)OC)=C[C@H](NC(=N)N)[C@H]1NC(C)=O)[C@H]1COC(=O)O1)CCCCNC(=O)O[C@@H]([C@@H]1OC(C(=O)OC)=C[C@H](NC(=N)N)[C@H]1NC(C)=O)[C@H]1COC(=O)O1]

The step-d product (1.73 g, 1.073 mmol) was dissolved in TFA (5 ml). After the solution was heated at 30° C. for 3 hours, it was directly purified by RPLC (0% to 35% acetonitrile/water, using 0.1% TFA as modifier). Yield 1.176 g, 76.1%. Ions found by LCMS: $[(M+2H)/2]^+$=606.8, $[(M+3H)/3]^+$=405.

Step f.

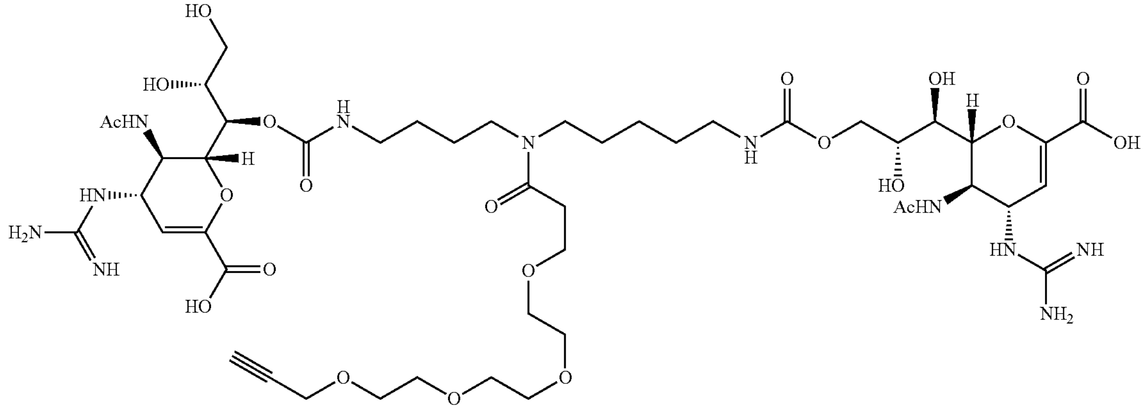 [SMILES: C#CCOCCOCCOCCOCCC(=O)N(CCCCCNC(=O)OC[C@@H](O)[C@@H](O)[C@@H]1OC(C(=O)O)=C[C@H](NC(=N)N)[C@H]1NC(C)=O)CCCCNC(=O)O[C@@H]([C@@H]1OC(C(=O)O)=C[C@H](NC(=N)N)[C@H]1NC(C)=O)[C@H](O)CO]

The step-e product (1.176 g, 0.817 mmol) was dissolved in MeOH (12 ml), and the solution was cooled in an ice-water bath. It was treated dropwise with a solution of LiOH monohydrate (344.4 mg, 8.2 mmol) in water (9 ml). The resulting mixture was stirred overnight and then acidified by 4N HCl solution in dioxane (2 ml). After organic solvents were removed by rotary evaporation, the residue was purified by preparative HPLC (Isco ACCQ prep, Luna 5 μm C18(2) 100 Å LC column 100 mm×30 mm; Gradient: 0% acetonitrile/water for 2 min, then 0% to 15% acetonitrile/water over 12 min, then isocratic at 15% acetonitrile for 10 min, using 0.1% TFA). Yield 108 mg, 9.7%. Ions found by LCMS: $[(M+2H)/2]^+$=566.8, $[(M+3H)/3]^+$=378.2.

Example 113. Synthesis of Conjugate 32

A 15-ml sterile centrifuge tube was charged with sodium ascorbate (68.1 mg, 0.344 mmol), THPTA (14.9 mg, 0.0344 mmol), product from Example 112, Int-72 (17.5 mg, 0.00953 mmol) and PBS 7.4 (1 ml). After stirring by vortex to dissolve everything, azido Fc (50 mg, 0.0008588 mmol, described in Example 7 with SEQ ID NO: 4) was added followed by a solution of CuSO4 (2.05 mg, 0.0129 mmol) in PBS (0.5 ml). The mixture was rotated for 20 hours. It was purified by affinity chromatography over a protein A column, followed size exclusion chromatography. Maldi TOF analysis of the purified final product gave an average mass of 63588. Da (DAR=3.8). Yield 30.9 mg, 62% yield.

Example 114. Synthesis of Int-73

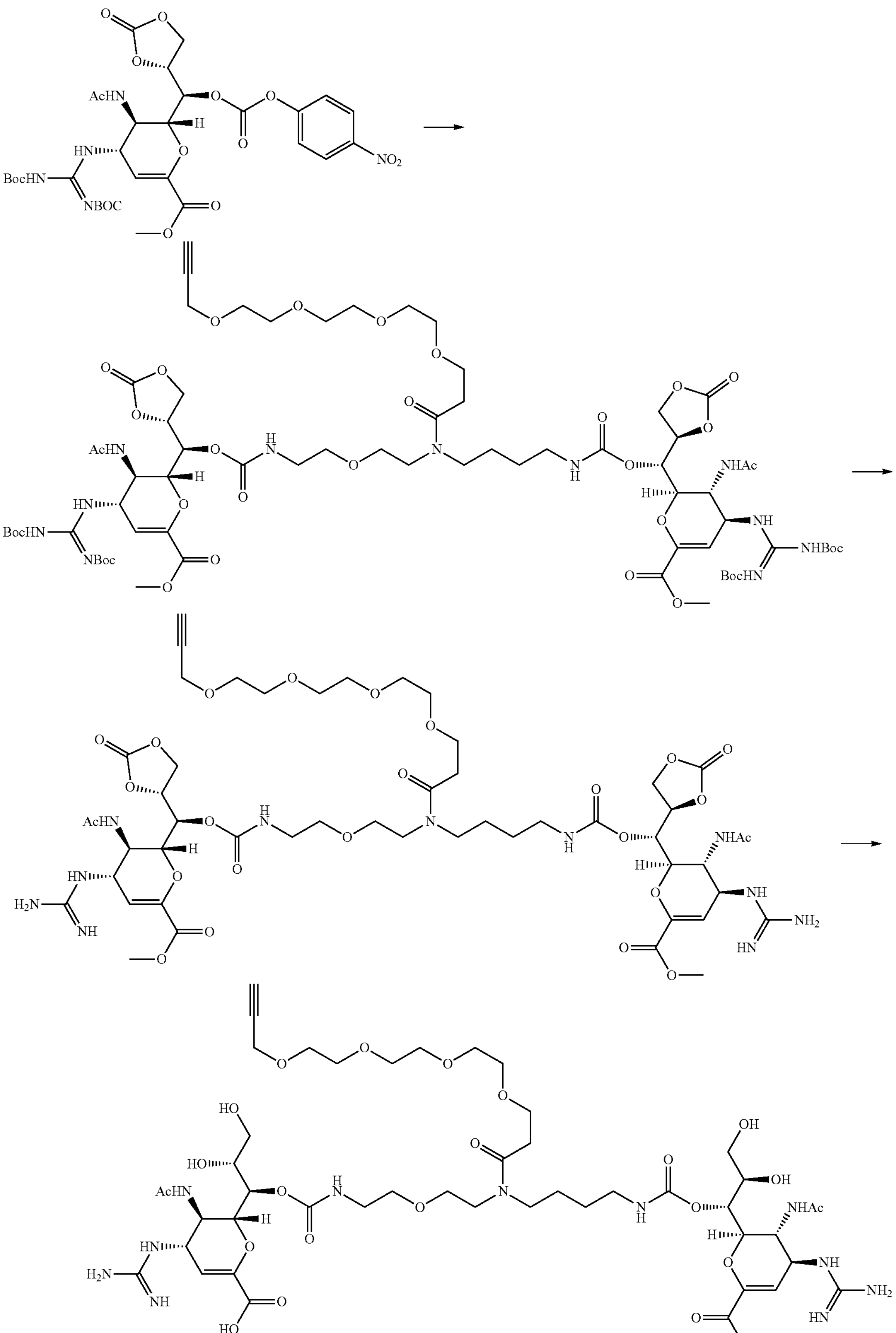

Step a.

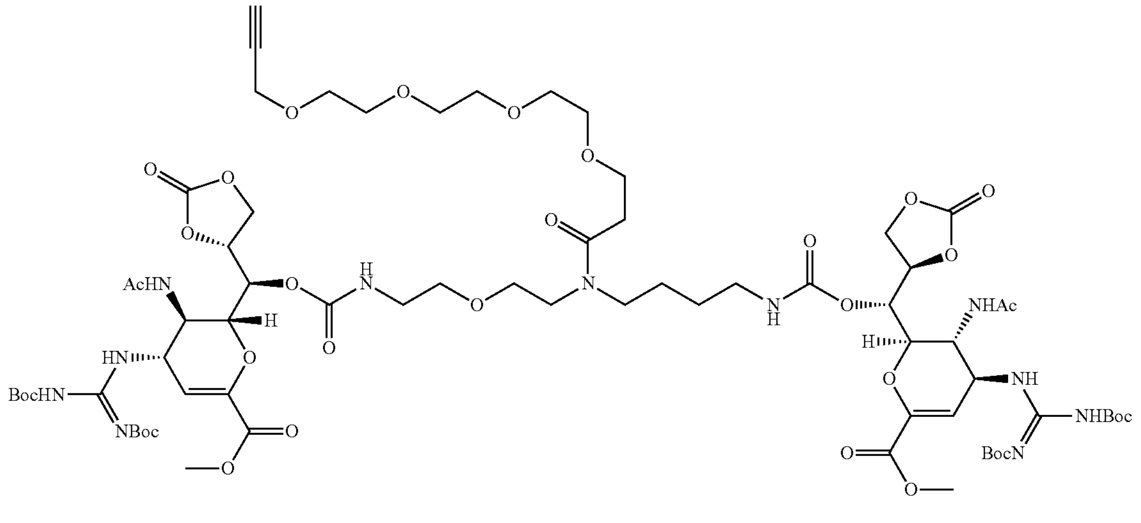

To a solution of the p-nitrophenyl carbonate of zanamivir (698.4 mg, 0.95 mmol, described in Example 109) in anhydrous DCM (2 ml) was added in-portions over 10 minutes a mixture of propargyl diamine central linker (209 mg, 0.426 mmol, described in Example 110) and DIPEA (330.8 mg, 2.56 mmol) in anhydrous DMF (2 ml). The reaction was stirred at room temperature for 1 hour. It was then concentrated and purified by RPLC (30% to 85% acetonitrile/water, no TFA modifier). Yield 531 mg, 69.2%. Ions found by LCMS: $[(M+2H)/2]^{+}$=807.8, $[(M\text{-}Boc+2H)/2]^{+}$=757.8.

Step b.

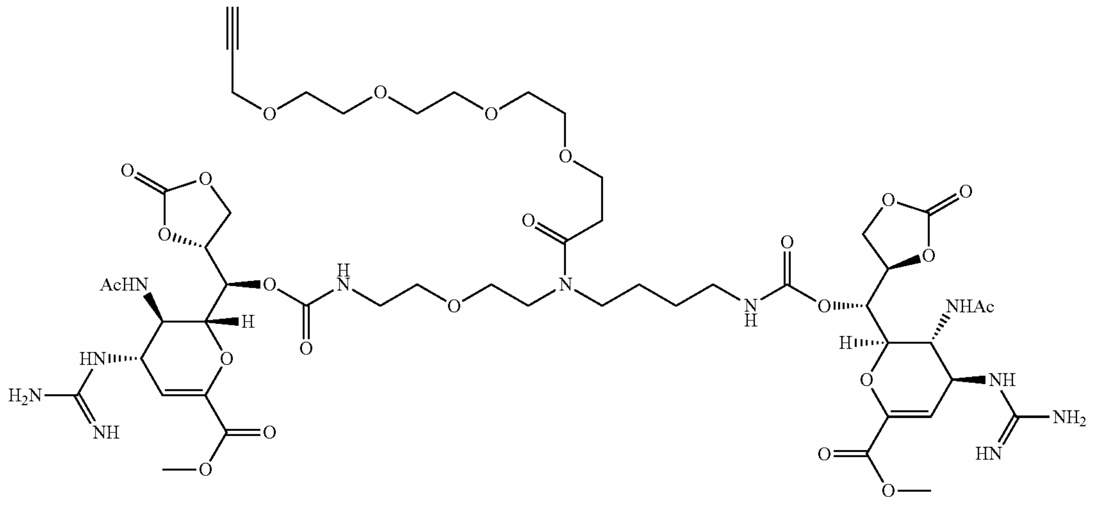 [SMILES: C#CCOCCOCCOCCOCCC(=O)N(CCCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

The step-b product (531 mg, 0.329 mmol) was dissolved in DCM (1.5 ml) and TFA (1.5 ml), then stirred at 35° C. for 3 hours. It was concentrated and purified by RPLC (5% to 30% acetonitrile/water, no TFA modifier). Yield 387 mg, 97.1%. Ions found by LCMS: $[(M+2H)/2]^{+}$=607.6, $[(M+3H)/3]^{+}$=405.4.

Step c.

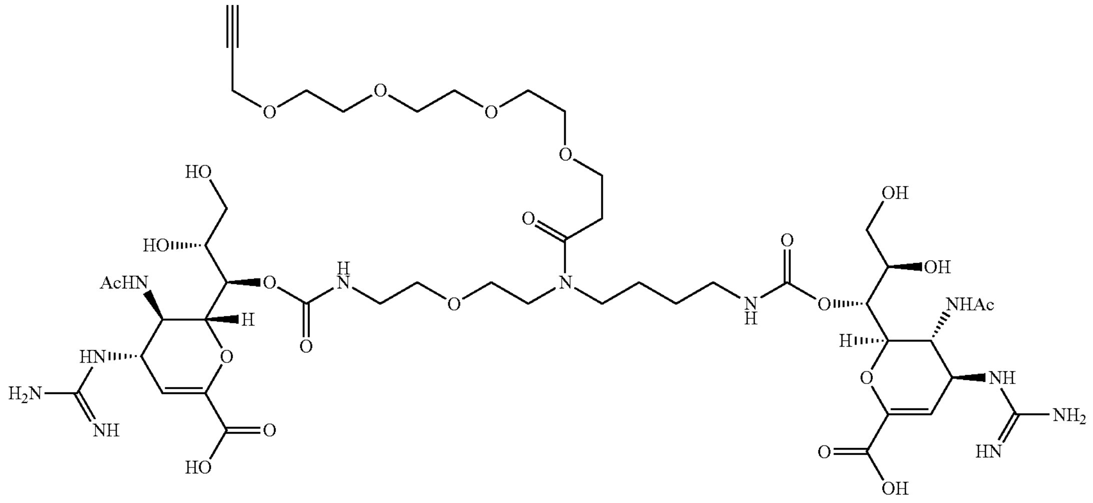 [SMILES: C#CCOCCOCCOCCOCCC(=O)N(CCCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

The step-b product (121.4 mg, 0.1 mmol) was dissolved in 1.0 M NaCl solution (3 ml) and acetonitrile (1 ml). After the solution was cooled to −8° C. (salt/ice bath), 1.0 M NaOH (0.4 ml, 0.4 mmol) was added dropwise and the reaction was stirred at −14° C. to −8° C. for 6 hours. It was then nuetralized with 4N HCl in dioxane solution (100 μl) and directly purified by preparative HPLC (Isco ACCQ prep, Luna 5 μm C18(2) 100 Å LC column 100 mm×30 mm; Gradient: 0% acetonitrile/water for 2 min, then 0% to 17.8% acetonitrile/water over 12 min, then isocratic at 17.8% acetonitrile for 10 min, using 0.1% TFA). Yield 85.5 mg, 62.8%. Ions found by LCMS: $[(M+2H)/2]^+=567.8$, $[(M+3H)/3]^+=378.9$.

Example 115. Synthesis of Int-74

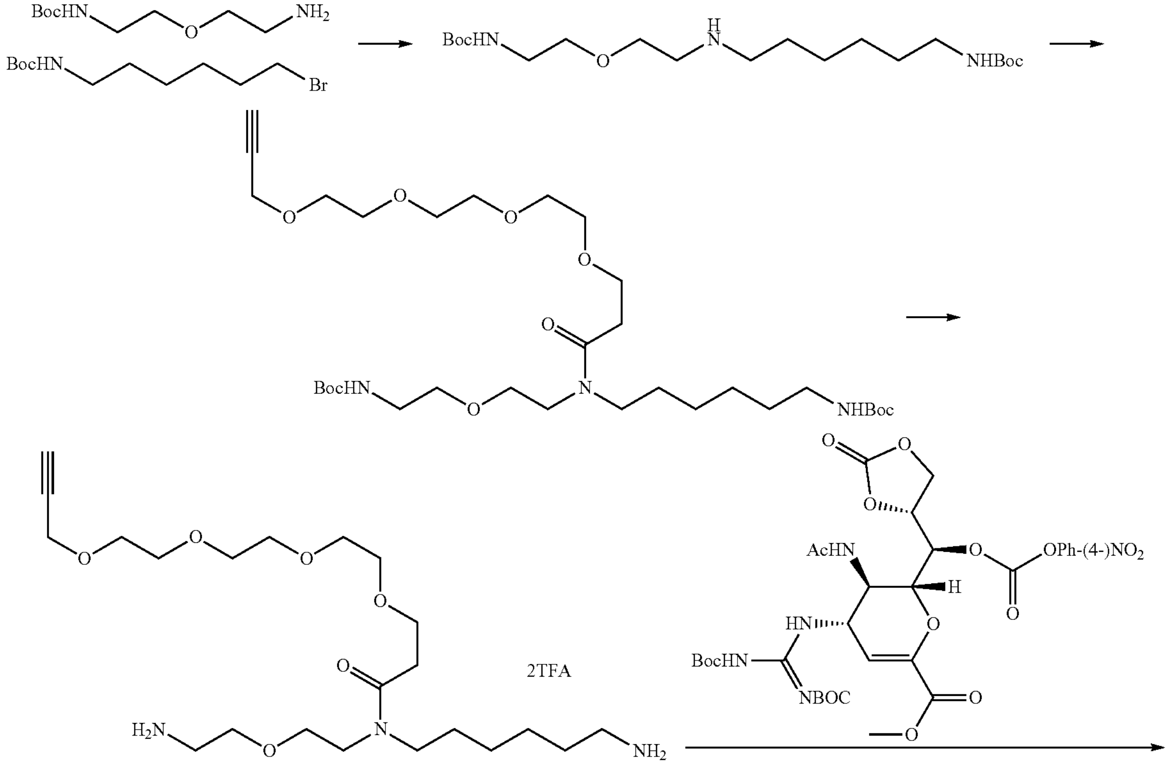

-continued

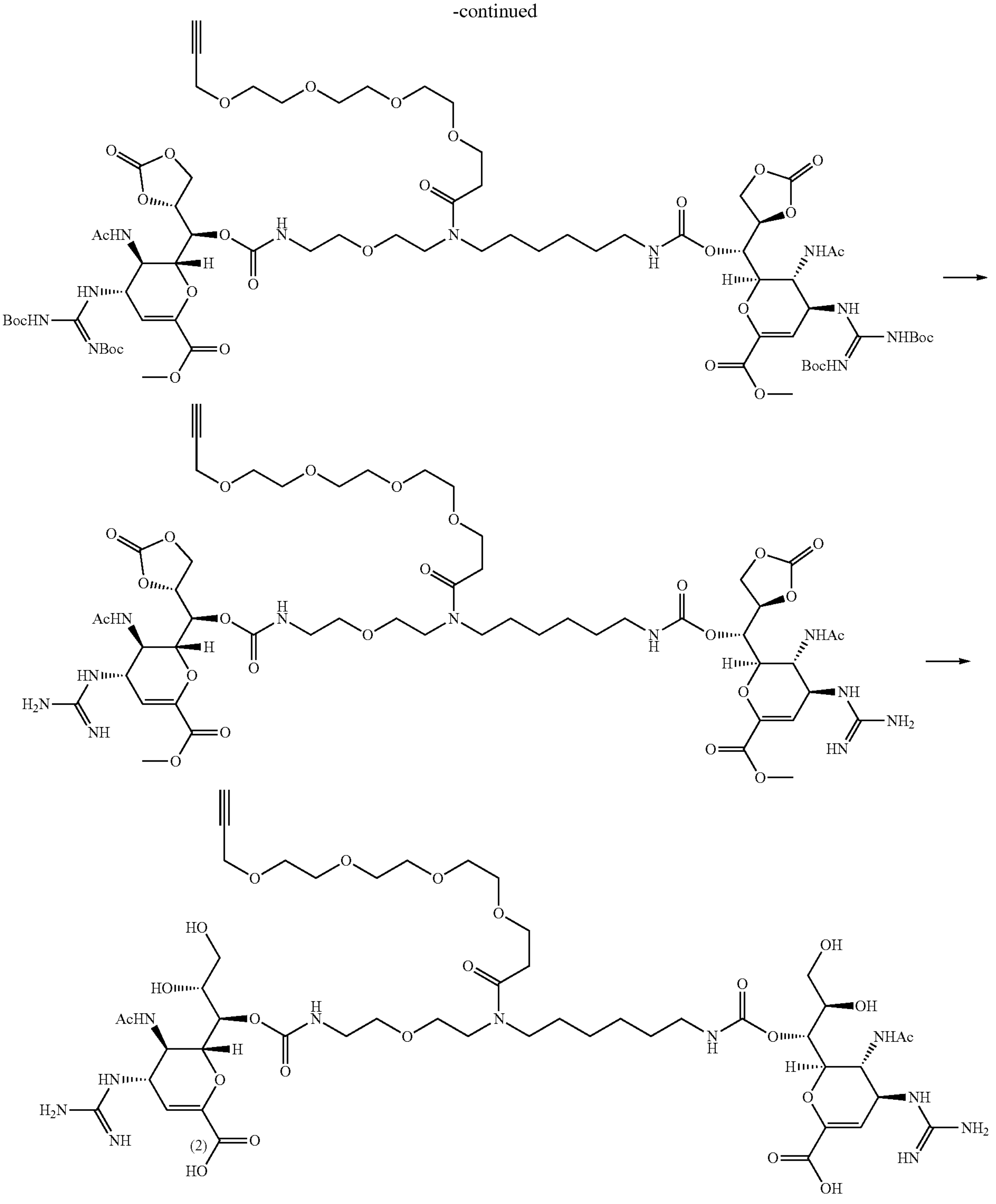

(2)

Step a.

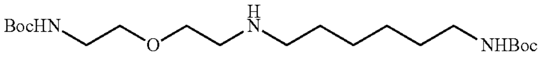 [SMILES: CC(C)(C)OC(=O)NCCCCCCNCCOCCNC(=O)OC(C)(C)C]

To a solution of N-Boc-2-(2-amino-ethoxy)ethylamine (1.2 g, 5 mmol) in anhydrous DMF (5 ml) was added sodium carbonate (691 mg, 5 mmol) and N-Boc-6-bromo-hexylamine (1.4 g, 5 mmol). The resulting mixture was heated at 70° C. for 24 hours. The salt was then filtered off, and the filtrate was concentrated by rotary evaporation. The residue was purified by RPLC (5% to 50% acetonitrile/water, using 0.1% TFA as modifier). Yield 444 mg, 22%. Ion found by LCMS: $[M+H]^+$=404.3.

Step b.

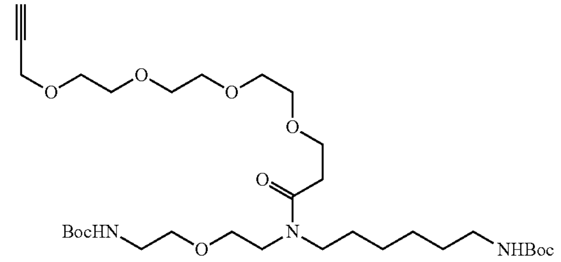 [SMILES: C#CCOCCOCCOCCOCCC(=O)N(CCCCCCNC(=O)OC(C)(C)C)CCOCCNC(=O)OC(C)(C)C]

To a solution of propargyl PEG-4 acid (342.6 mg, 1.32 mmol) and HATU (601.5 mg, 1.58 mmol) in anhydrous DMF (2 ml) was added DIPEA (258 mg, 2 mmol). After 5 minutes, the reaction mixture was added into the step-a product (444.3 mg, 0.858 mmol) and stirred for 1 hour. It was then directly purified by RPLC (5% to 80% acetonitrile/water, using 0.1% TFA as modifier). Yield 297.1 mg, 53.6%. Ion found by LCMS: $[M+H]^+=646.2$, $[M-Boc+H]^+=546.2$.

Step c.

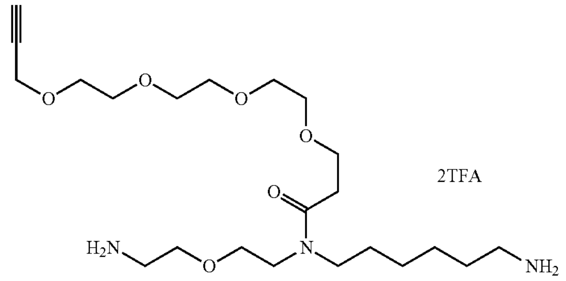 [SMILES: C#CCOCCOCCOCCOCCC(=O)N(CCCCCCN)CCOCCN]

The step-b product (297.1 mg, 0.46 mmol) was dissolved in anhydrous THE (2 ml). 4N HCl solution in dioxane (4 ml) was added, and the reaction mixture was stirred overnight. It was then concentrated by rotary evaporation and purified by preparative HPLC (5% to 50% acetonitrile/water, using 0.1% TFA as modifier). Yield 239.6 mg, 77.3%. Ion found by LCMS: $[M+H]^+=446.2$.

Step d.

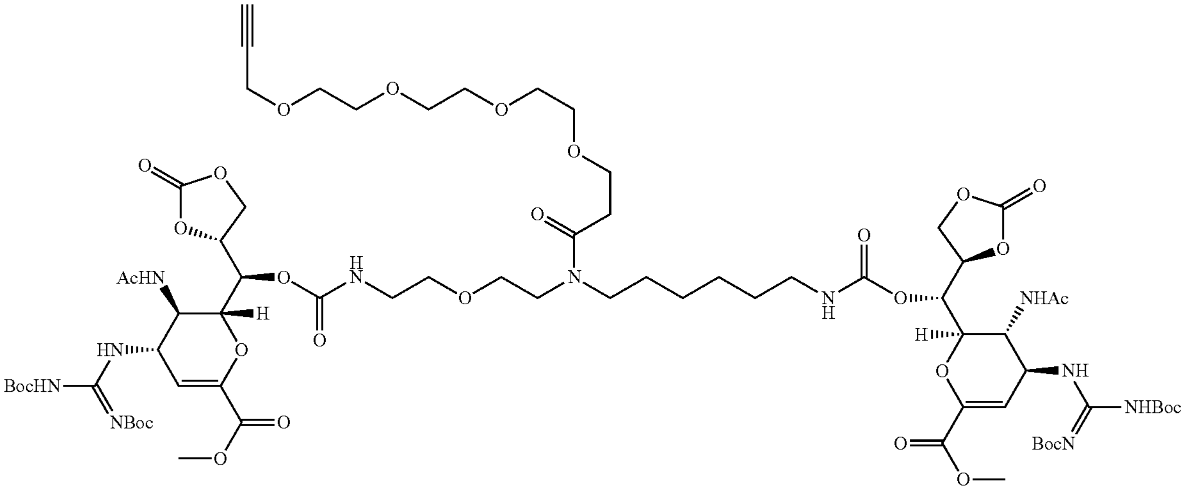

To a solution of the p-nitrophenyl carbonate of zanamivir (523.8 mg, 0.71 mmol, described in Example 2) in anhydrous DCM (2 ml) was added in portions over 10 minutes a mixture of the step-c product (239.6 mg, 0.356 mmol) and DIPEA (245.5 mg, 1.9 mmol) in anhydrous DMF (2 ml). The reaction was stirred at room temperature for 1 hour. It was then concentrated and purified by RPLC (30% to 85% acetonitrile/water, no TFA modifier). Yield 553 mg, 96.5%. Ions found by LCMS: $[(M+2H)/2]^+=821.8$, $[(M-Boc+2H)/2]^+=771.8$.

Step e.

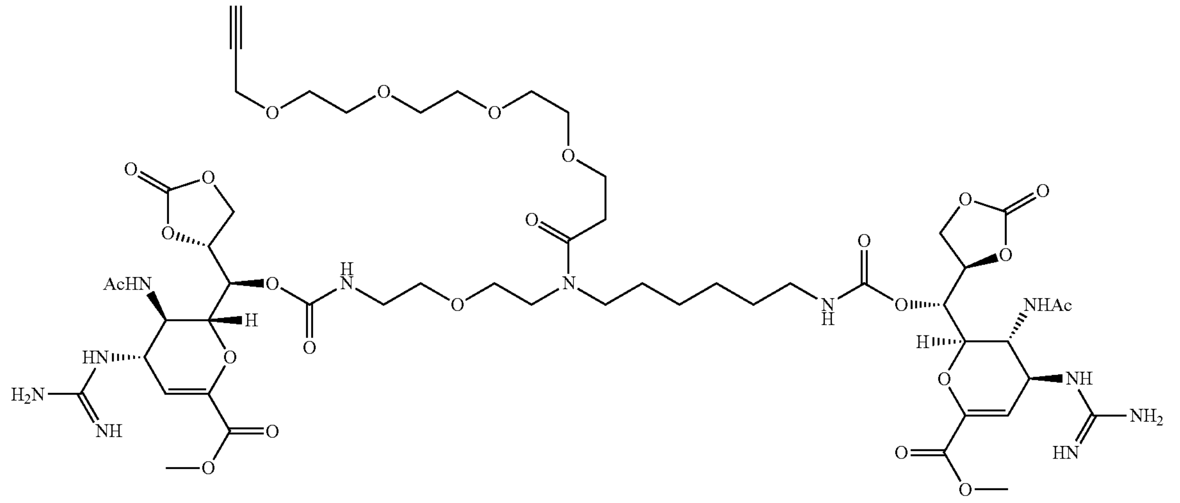 [SMILES: C#CCOCCOCCOCCOCCC(=O)N(CCCCCCNC(=O)O[C@@H]([C@@H]1OC(C(=O)OC)=C[C@H](NC(=N)N)[C@H]1NC(C)=O)[C@H]1COC(=O)O1)CCOCCNC(=O)O[C@@H]([C@@H]1OC(C(=O)OC)=C[C@H](NC(=N)N)[C@H]1NC(C)=O)[C@H]1COC(=O)O1]

The step-d product (553 mg, 0.343 mmol) was dissolved in DCM (1.5 ml) and TFA (1.5 ml), then stirred at 35° C. for 3 hours. It was concentrated and purified by RPLC (5% to 30% acetonitrile/water, no TFA modifier). Yield 424.6 mg, 99.6%. Ions found by LCMS: $[(M+2H)/2]^+$=621.6, $[(M+3H)/3]^+$=415.0.

Step f.

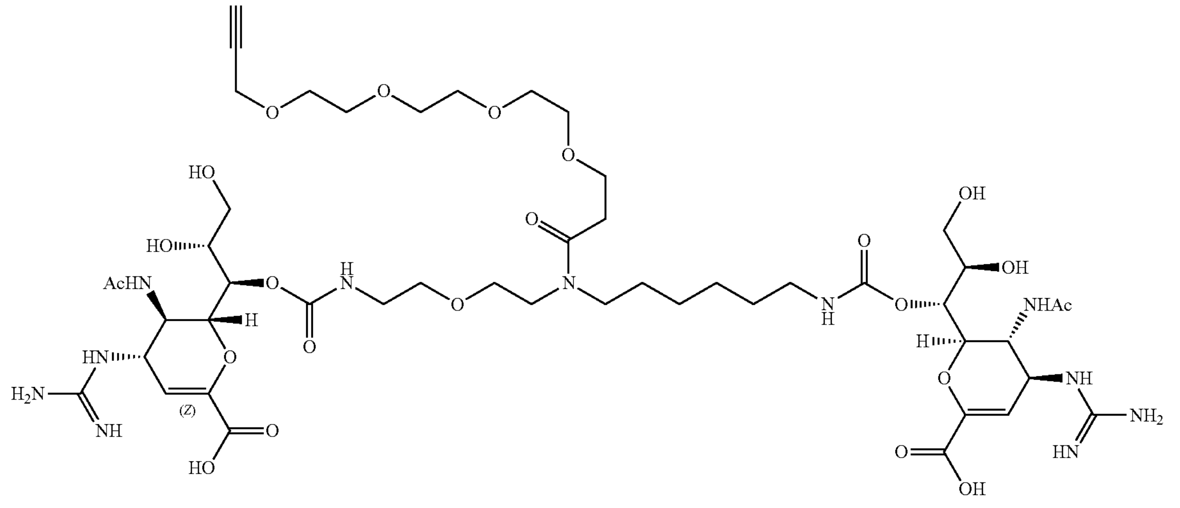 [SMILES: C#CCOCCOCCOCCOCCC(=O)N(CCCCCCNC(=O)O[C@@H]([C@@H]1OC(C(=O)O)=C[C@H](NC(=N)N)[C@H]1NC(C)=O)[C@H](O)CO)CCOCCNC(=O)O[C@@H]([C@@H]1OC(C(=O)O)=C[C@H](NC(=N)N)[C@H]1NC(C)=O)[C@H](O)CO]

The step-e product (424.6 mg, 0342 mmol) was dissolved in 1.0 M NaCl solution (4 ml) and acetonitrile (4 ml). After the solution was cooled to −11° C. (salt/ice bath), 1.0 M NaOH (1.53 ml, 1.53 mmol) was added dropwise and the reaction was stirred at −14° C. to −8° C. for 6 hours. It was then quenched with 4N HCl in dioxane solution (375 μl) and directly purified by preparative HPLC (Isco ACCQ prep, Luna 5 μm C18(2) 100 Å LC column 100 mm×30 mm; Gradient: 0% acetonitrile/water for 2 min, then 0% to 20.9% acetonitrile/water over 13.6 min, then isocratic at 20.9% acetonitrile for 10 min, using 0.1% TFA). Yield 439 mg, 92.3%. Ions found by LCMS: $[(M+2H)/2]^+$=581.8, $[(M+3H)/3]^+$=388.2.

Example 116. Synthesis of Int-75

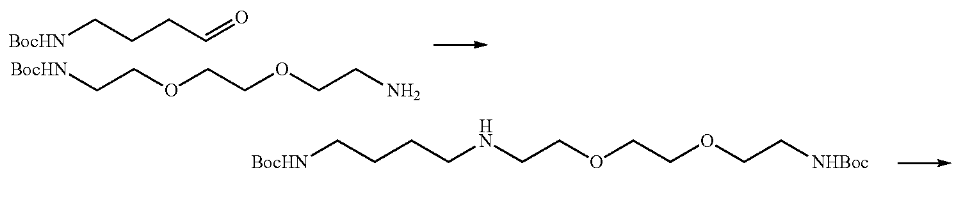

-continued

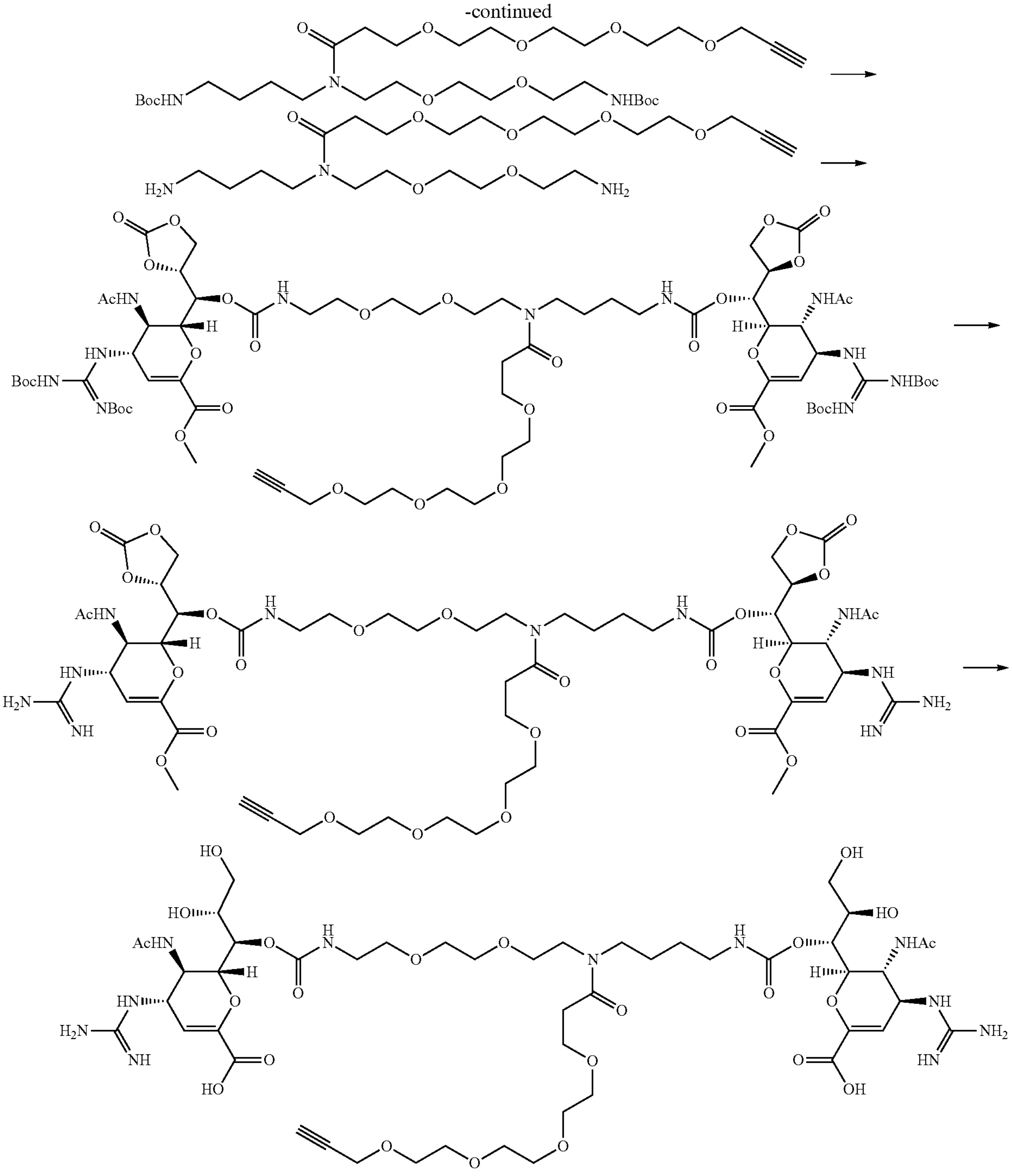

Step a.

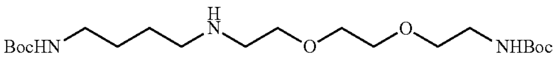 [SMILES: CC(C)(C)OC(=O)NCCCCNCCOCCOCCNC(=O)OC(C)(C)C]

A mixture of tert-butyl (4-oxobutyl) carbamate (850 mg, 4.54 mg) and tert-butyl N-{2-[2-(2-aminoethoxy) ethoxy] ethyl}carbamate (1.99 g, 8 mmol) was dissolved in DCM (30 ml) and dried over $Na_2SO_4$. After filtering and concentrating, the residue was redissolved in anhydrous DCM (20 ml). Acetic acid (641 mg, 11 mmol) was added, followed by sodium triacetoxyborohydride (3.4 g, 16 mmol) in portions over 1 hour. The reaction mixture was stirred overnight, then quenched with AcOH (3 ml) and MeOH (10 ml). The mixture was filtered, and the filtrate was concentrated by rotary evaporation and purified by RPLC (5% to 45% acetonitrile and water). Yield 618 mg, 32.5%. Ion found by LCMS: $[M+H]^+$=420.4.

Step b.

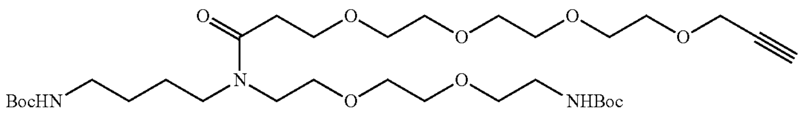 [SMILES: C#CCOCCOCCOCCOCCC(=O)N(CCCCNC(=O)OC(C)(C)C)CCOCCOCCNC(=O)OC(C)(C)C]

This compound was prepared analogously to the step-b product of Example 115. Ions found by LCMS: $[M+H]^+$ =662.4, $[M\text{-}Boc+H]^+$=562.4.

Step c.

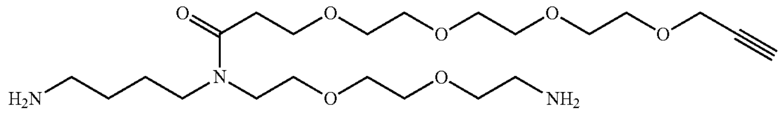 [SMILES: C#CCOCCOCCOCCOCCC(=O)N(CCCCN)CCOCCOCCN]

This compound was prepared analogously to the step-c product of Example 115. Ion found by LCMS: $[M+H]^+$ =462.4.

Step d.

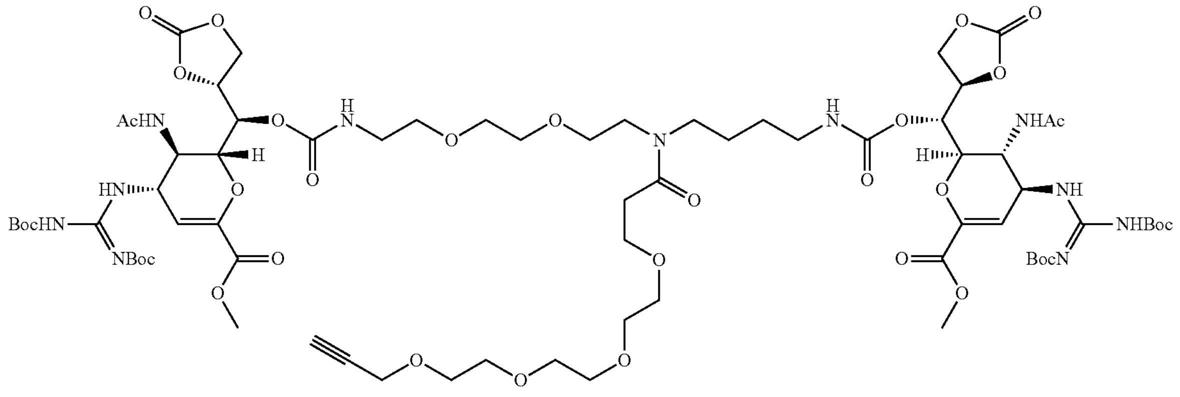

This compound was prepared analogously to the step-d product of Example 115. Ions found by LCMS: $[(M+2H)/2]^+$=829.8, $[(M\text{-}Boc+2H)/2]^+$=779.8.

Step e.

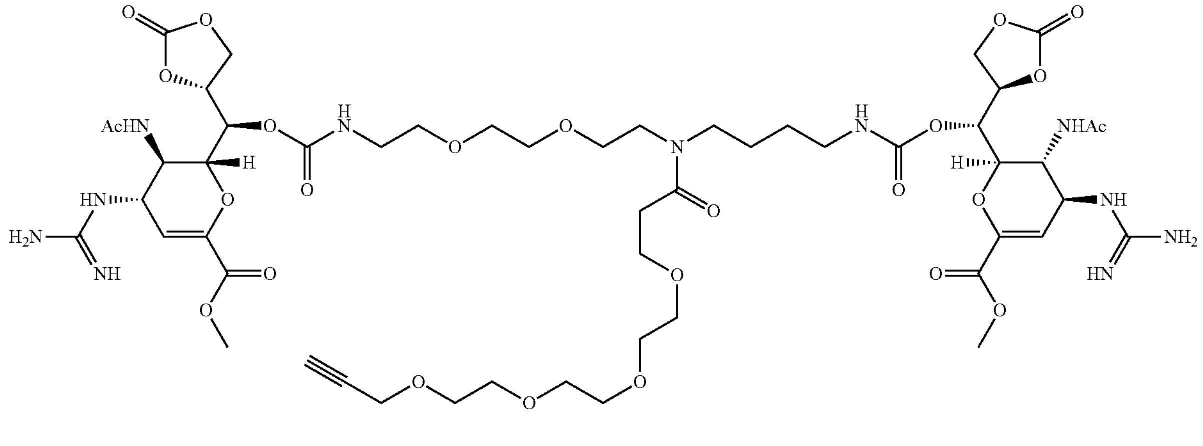 [SMILES: C#CCOCCOCCOCCOCCC(=O)N(CCCCNC(=O)O[C@@H]([C@@H]1OC(C(=O)OC)=C[C@H](NC(=N)N)[C@H]1NC(C)=O)[C@H]1COC(=O)O1)CCOCCOCCNC(=O)O[C@@H]([C@@H]1OC(C(=O)OC)=C[C@H](NC(=N)N)[C@H]1NC(C)=O)[C@H]1COC(=O)O1]

This compound was prepared analogously to the step-e product of Example 115. Ions found by LCMS: $[(M+2H)/2]^+$=629.8, $[(M+3H)/3]^+$=420.2.

Step f.

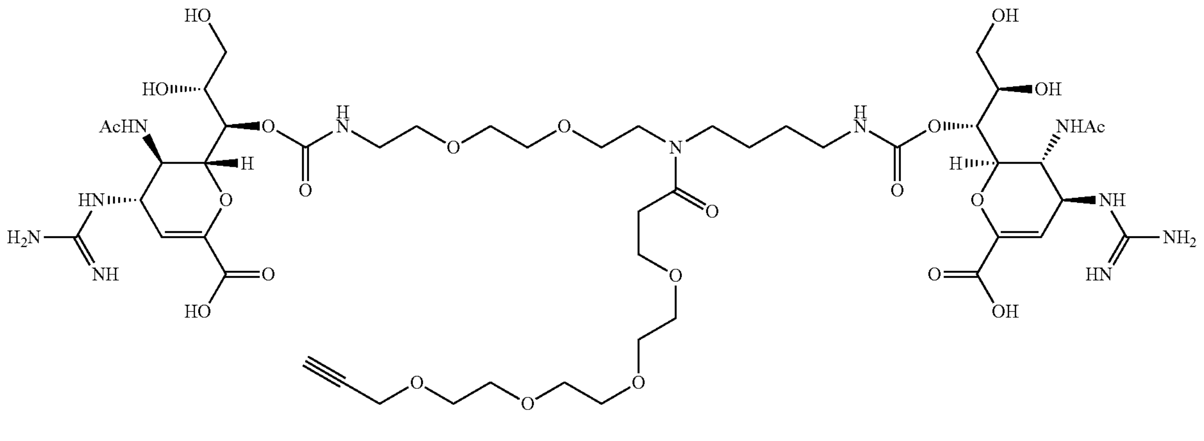 [SMILES: C#CCOCCOCCOCCOCCC(=O)N(CCCCNC(=O)O[C@@H]([C@@H]1OC(C(=O)O)=C[C@H](NC(=N)N)[C@H]1NC(C)=O)[C@H](O)CO)CCOCCOCCNC(=O)O[C@@H]([C@@H]1OC(C(=O)O)=C[C@H](NC(=N)N)[C@H]1NC(C)=O)[C@H](O)CO]
This compound was prepared analogously to the step-f product of Example 115. Ions found by LCMS: [(M+2H)/2]$^+$=598.8, [(M+3H)/3]$^+$=393.6.
Example 117. Synthesis of Int-76
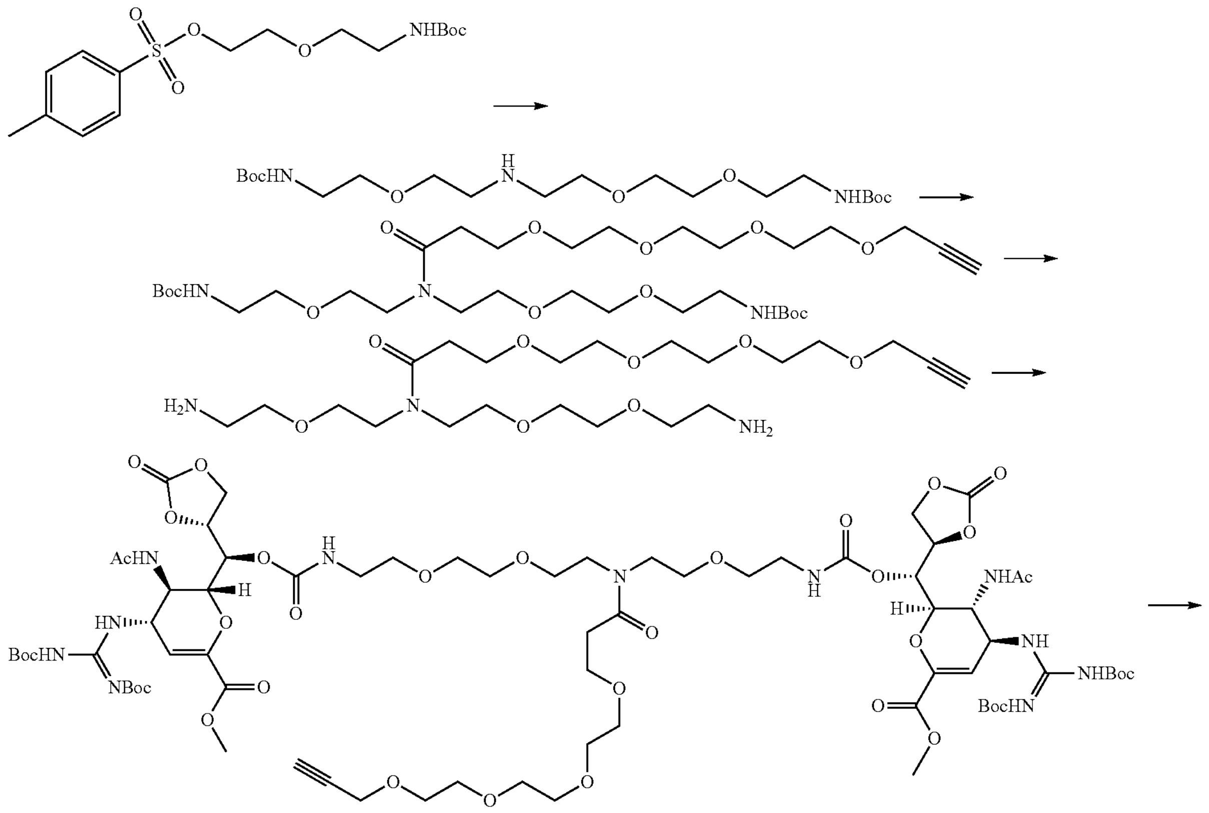

-continued

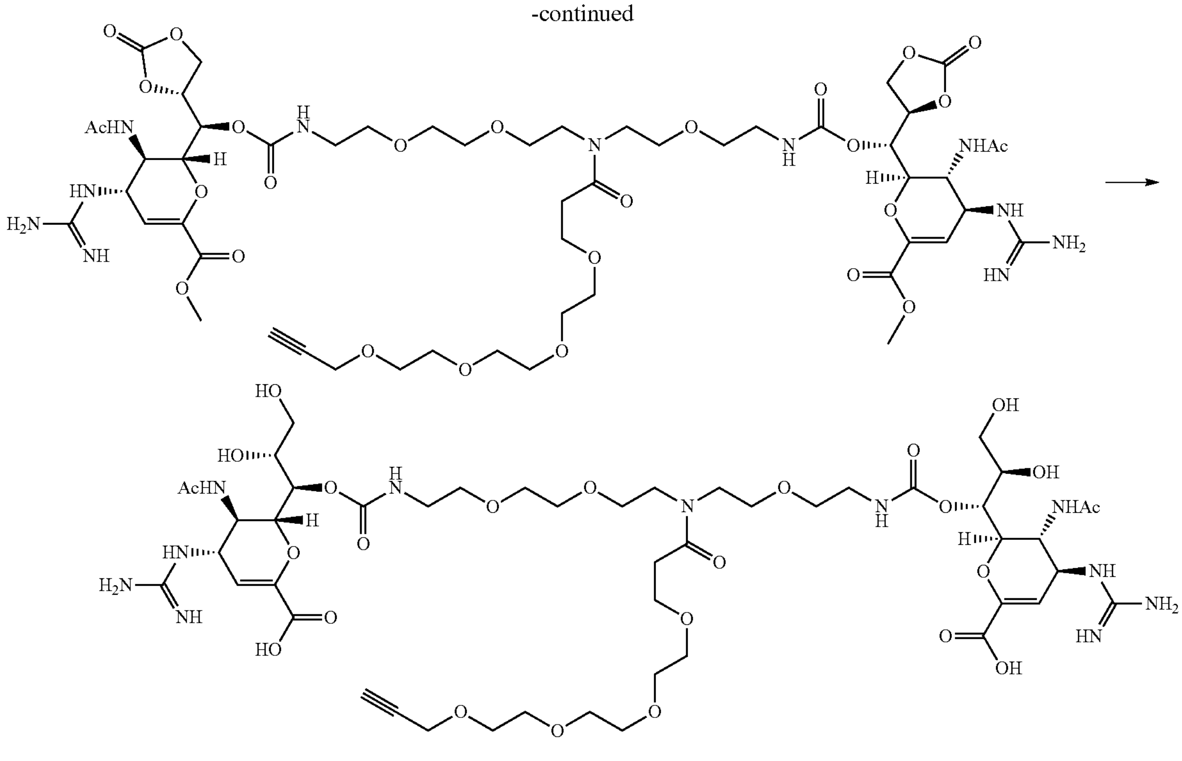

Step a.

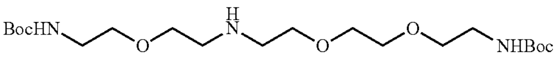 [SMILES: CC(C)(C)OC(=O)NCCOCCNCCOCCOCCNC(=O)OC(C)(C)C]

To a solution of the N-Boc-peg-1 tosylate (1.54 g, 4.28 mmol, described in Example 110) in anhydrous THE (8 ml) was added tert-butyl N-2{2-[2-(2-aminoethoxy) ethoxy] ethyl}carbamate (1.59 g, 6.42 mmol) and sodium carbonate (453.7 mg, 4.28 mmol). The resulting mixture was heated at 50° C. for 24 hours. The solid was filtered and washed with acetonitrile. The filtrate was concentrated and purified by RPLC (100 g, 5 to 90% acetonitrile and water). Yield 1.15 g, 61.7%. Ion found by LCMS: $[M+H]^+=436.4$.

Step b.

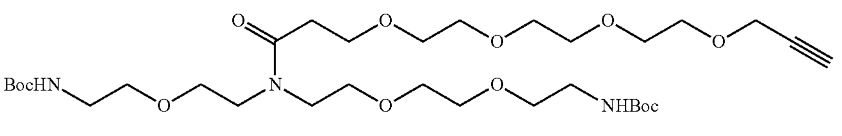 [SMILES: C#CCOCCOCCOCCOCCC(=O)N(CCOCCNC(=O)OC(C)(C)C)CCOCCOCCNC(=O)OC(C)(C)C]

This compound was prepared analogously to the product from step-b of Example 115. Ions found by LCMS: $[M+H]^+=678.2$, $[M-Boc+H]^+=578.2$.

Step c.

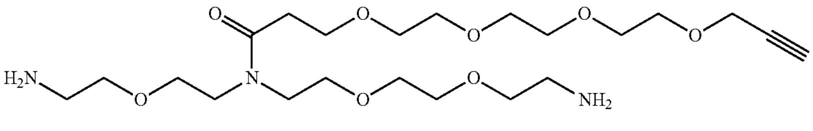 [SMILES: C#CCOCCOCCOCCOCCC(=O)N(CCOCCN)CCOCCOCCN]

This compound was prepared analogously to the product of step-c of Example 115. Ion found by LCMS: $[M+H]^+=478.2$.

Step d.

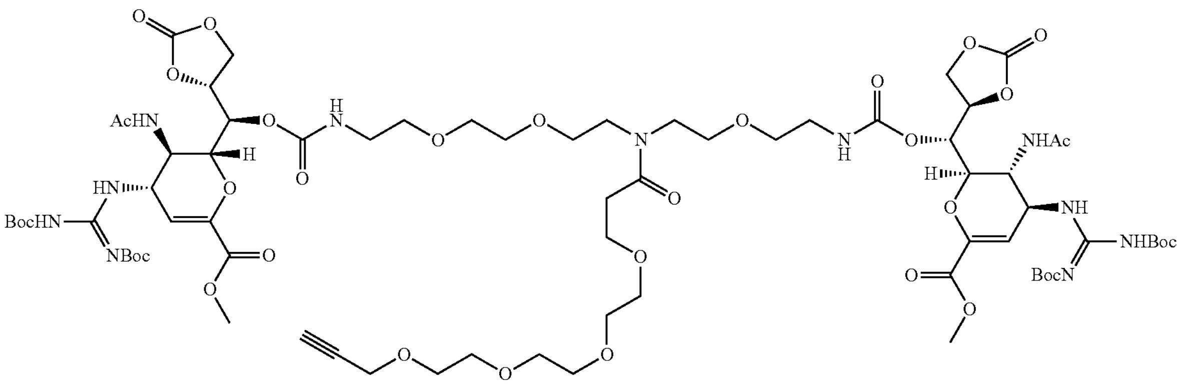

This compound was prepared analogously to the product from step-d of Example 115. Ions found by LCMS: $[(M+2H)/2]^+=837.6$, $[(M\text{-}Boc+2H)/2]^+=767.8$.

Step e.

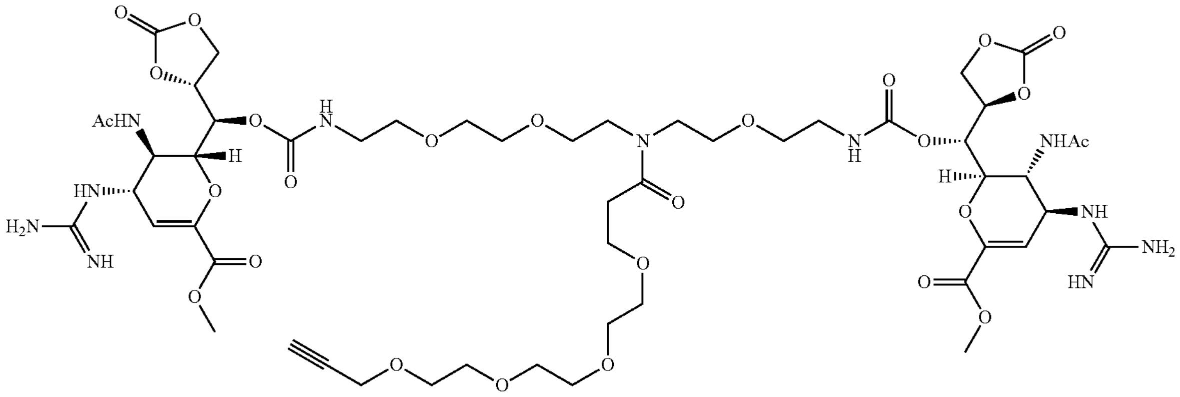 [SMILES: C#CCOCCOCCOCCOCCC(=O)N(CCOCCNC(=O)O[C@@H]([C@@H]1OC(C(=O)OC)=C[C@H](NC(=N)N)[C@H]1NC(C)=O)[C@H]1COC(=O)O1)CCOCCOCCNC(=O)O[C@@H]([C@@H]1OC(C(=O)OC)=C[C@H](NC(=N)N)[C@H]1NC(C)=O)[C@H]1COC(=O)O1]

This compound was prepared analogously to the product from step-e of Example 115. Ions found by LCMS: $[(M+2H)/2]^+=637.5$, $[(M+3H)/3]^+=425.6$.

Step f.

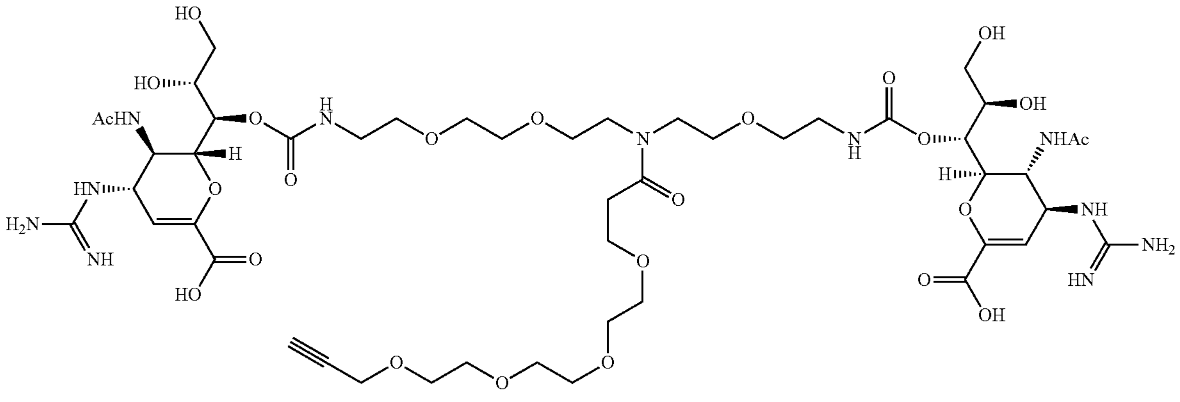 [SMILES: C#CCOCCOCCOCCOCCC(=O)N(CCOCCNC(=O)O[C@@H]([C@@H]1OC(C(=O)O)=C[C@H](NC(=N)N)[C@H]1NC(C)=O)[C@H](O)CO)CCOCCOCCNC(=O)O[C@@H]([C@@H]1OC(C(=O)O)=C[C@H](NC(=N)N)[C@H]1NC(C)=O)[C@H](O)CO]

This compound was prepared analogously to the product from step-f of Example 115. Ions found by LCMS: $[(M+2H)/2]^+=597.8$, $[(M+3H)/3]^+=399.0$.

Example 118 Synthesis of Int-67

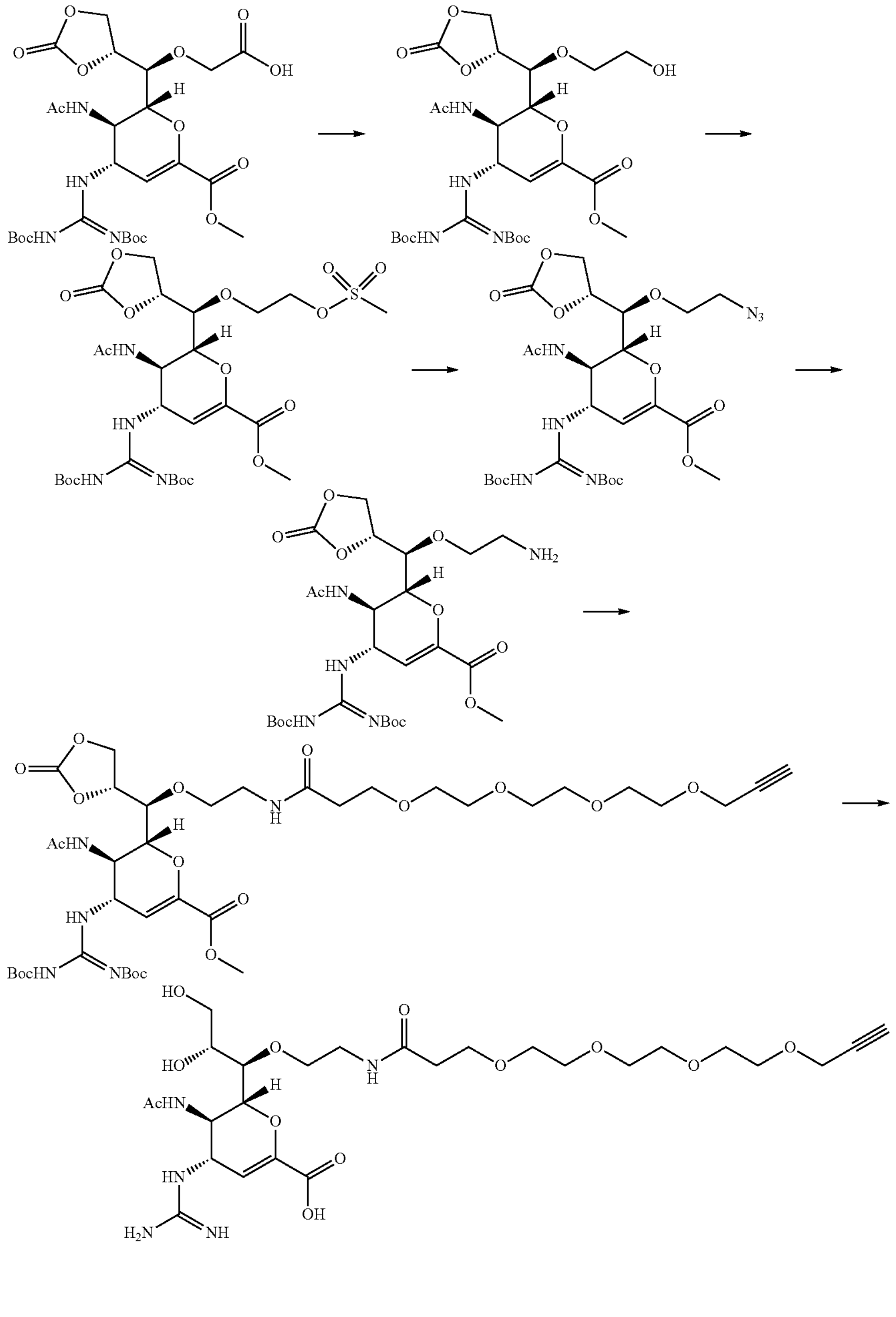
Step a.

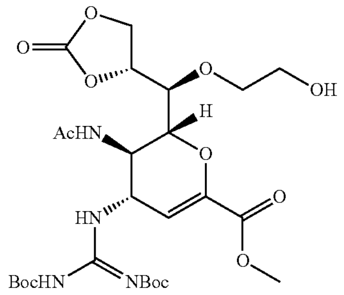

Previously prepared ether zanamivir acid starting material (0.90 g, 1.43 mmol, described in Example 22) and N-methyl morpholine (0.23 mL, 2.14 mmol) were dissolved in THF (35 mL) and cooled to 0° C. (ice water bath) under an atmosphere of nitrogen. Isobutyl chloroformate (0.24 mL, 1.85 mmol, in 2 mL DCM) was added dropwise, by way of syringe over a 5 minute period. The mixture was stirred at 0° C. for 30 minutes then 15 min at ambient temperature, and then cooled to 0° C., where sodium borohydride (540 mg, 14.3 mmol, dissolved in 5 mL of methanol) was added, dropwise over 5 minutes. The reaction was stirred for 15 minutes at which point all starting material had been consumed (by LC/MS). A few drops (~1 mL) of glacial acetic acid was added to acidify the mixture (pH5). The mixture was diluted with ethyl acetate and water and extracted into ethyl acetate (3×). The organic layer was washed was and the organic extracts were dried over sodium sulfate, and concentrated on a rotary evaporator. The crude material was purified by silica gel chromatography, dried onto celite first, and then eluted with 0%-10% methanol in DCM over 30 min. Yield 0.66 g, 75%. Ion found by LCMS: $[M+H]^+$ =617.2.

Step b.

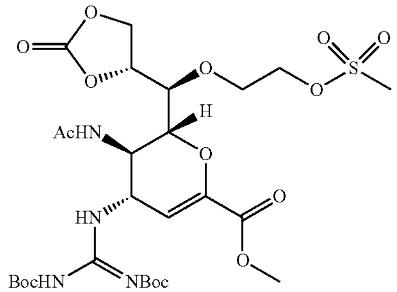

To a stirring mixture of product from the previous step (0.66 g, 1.10 mmol), in 20 mL DCM, was added triethylamine (0.30 mL, 1.3 mmol). The mixture was cooled to 0° C. (ice-water bath) under an atmosphere of nitrogen then treated with mesyl chloride (0.15 g, 1.3 mmol), dropwise over 5 minutes by way of syringe. The ice bath was removed and the reaction was stirred for 45 minutes. The reaction was quenched with saturated aqueous sodium bicarbonate, then extracted into DCM (3×). The combined organic extracts were washed with brine, dried over sodium sulfate and concentrated on the rotary evaporator. Yield 0.74 g, 99%. Ion found by LCMS: $[M+H]^+$=695.2. The intermediate was taken to the next step without purification.

Step c.

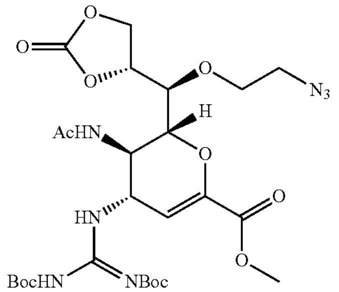

Mesylate from the previous step (0.74 g, 1.1 mmol) was stirred in DMF (5 mL) at 80° C. with 3 eq of sodium azide (0.21 g, 3.3 mmol; for 5 hours. The mixture was diluted with water, extracted into DCM (3×). The combined organic extracts were washed with brine, dried over sodium sulfate and concentrated. Yield 0.67 g, 95%. Ion found by LCMS: $[M+H]^+$=642.4. The azide was taken to the next step without purification.

Step d.

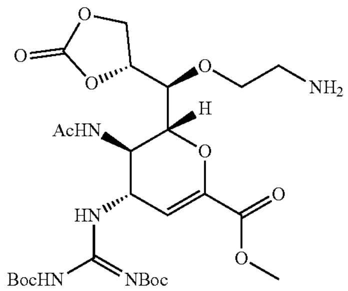

Azide from the previous step (0.67 g, 1.04 mmol) was stirred in methanol (20 mL) in the presence of Lindlar catalyst (300 mg) under 1 atmosphere of hydrogen gas for 12 hours. The mixture was filtered through celite and concentrated to afford the title compound as a clear oil. The amine was taken to the next step without purification. Yield 0.37 g, 54%, 3 steps. Ion found by LCMS: $[M+H]^+$=616.2.

Step e.

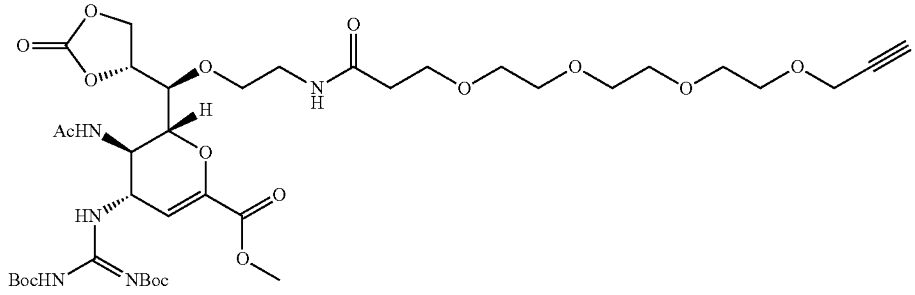

EDC (150 mg, 0.78 mmol) was added to a stirring solution of amine from the previous step (370 mg, 0.60 mmol), propargyl-peg4-carboxylic acid (188 mg, 0.72 mmol) and triethylamine (0.100 mL, 0.72 mmoL), dissolved in DMF (4 mL). The reaction was stirred for 2 hours at ambient temperature then purified directly RPLC (10%-95% acetonitrile/water, no modifier, 30 minute gradient). The pure fractions were pooled and lyophilized and taken directly to the next step. Yield 490 mg, 80%. Ion found by LC/MS: $[M+H]^+$=858.2

Step f.

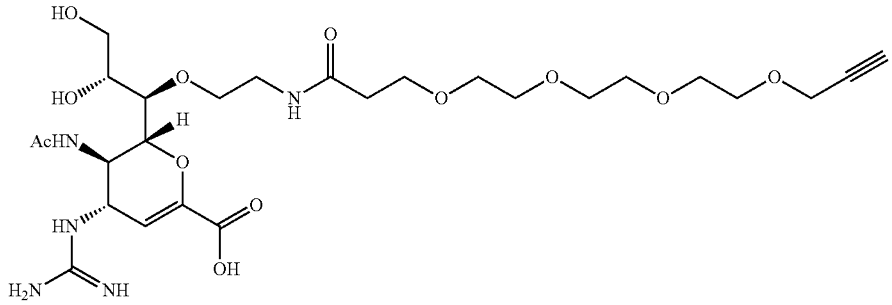 [SMILES: C#CCOCCOCCOCCOCCC(=O)NCCO[C@@H]([C@@H]1OC(C(=O)O)=C[C@H](NC(=N)N)[C@H]1NC(C)=O)[C@H](O)CO]

Product from the previous step (490 mg, 0.57 mmol) was stirred in TFA (4 mL) for 45 minutes then concentrated and azeotroped with methanol (3×) on the rotary evaporator. Ion found by LC/MS: $[M+H]^+$=658.2. The residue was stirred in 1/1 methanol/water containing LiOH (43 mg, 1.8 mmol) for 30 minutes. The reaction was neutralized with a few drops of glacial acetic acid and the volume was reduced by half on the rotary evaporator. The crude product was purified by semi-preparative HPLC (0%-75% acetonitrile/water, 0.1% TFA, 30 minute gradient). The pure fractions were pooled and lyophilized to afford the title compound. Yield 105 mg, 29%, 3 steps. Ion found by LC/MS: $[M+H]^+$=618.2.

Example 119. Synthesis of Int-68

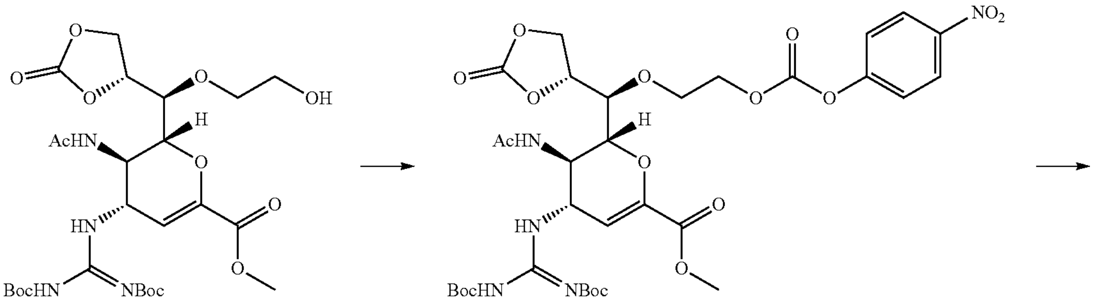

-continued

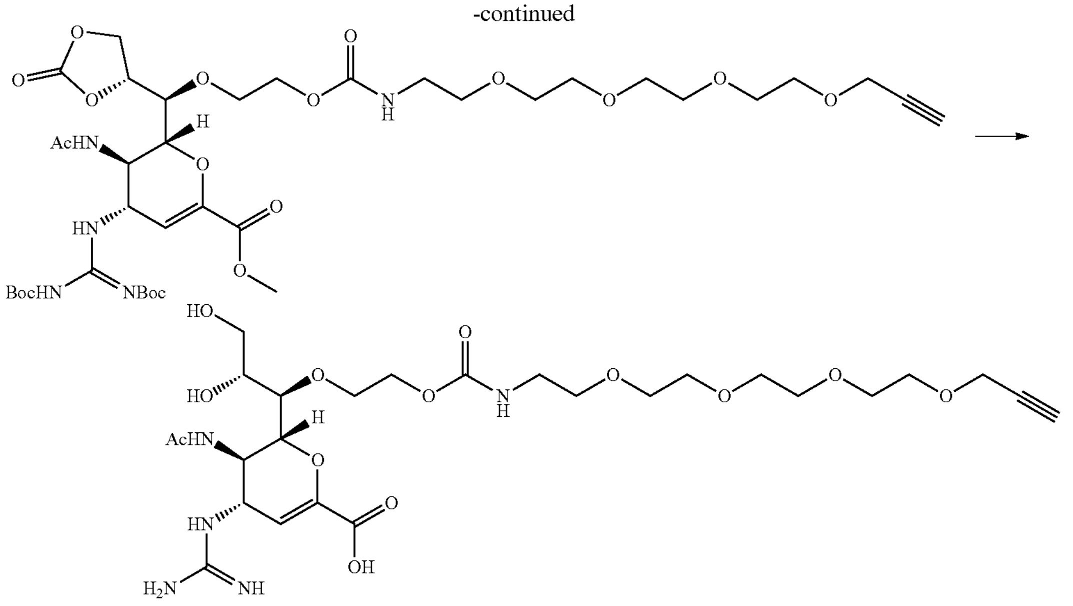

Step a.

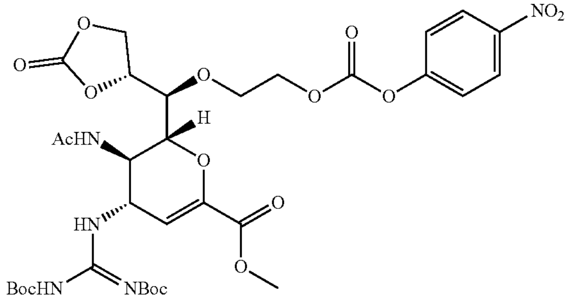

p-Nitrophenyl chloroformate (0.23 g, 1.14 mmol) was added to a stirring mixture of the primary alcohol (0.47 g, 0.76 mmol described in Example 118) and triethylamine (0.21 mL, 1.52 mmol) dissolved in DCM (15 mL, anhydrous). The reaction was stirred for 1 hour then additional trimethylamine (0.21 mL) and p-nitrophenyl chloroformate (230 mg) were added, and stirring was continued another hour, at which time the mixture was diluted with water, and extracted into DCM (3×). The combined organic extracts were washed with brine and dried over sodium sulfate. The solvent was removed by rotary evaporation. The crude residue was dissolved in DCM (3 mL), loaded onto celite and purified by silica gel chromatography (0% to 70% ethyl acetate/hexanes, 30 minute gradient). The pure fractions were pooled and concentrated to afford the title compound as a white solid. Yield 525 mg, 88%. Ion found by LCMS: $[M+H]^+$=782.2.

Step b.

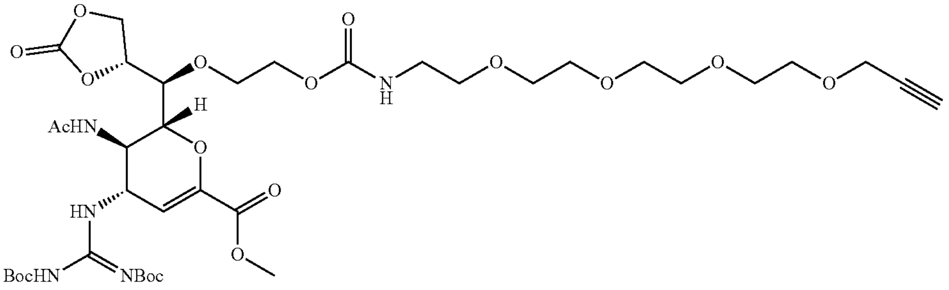

Triethylamine (0.14 mL, 0.97 mmol) was added to a stirring solution of propargyl-peg4-amine (181 mg, 0.78 mmol) in 1 mL of acetonitrile. The triethylamine/propargyl-peg4-amine mixture was added to the product from the previous step (510 mg, 0.65 mmol, in 2 mL acetonitrile) and stirred for 1 hour at which point all starting materials had been consumed. The solvent was removed on a rotary evaporator. The crude residue was purified RPLC (20-95% acetonitrile/water, 30 min gradient, no modifier). Yield 475 mg, 83%. Ion found by LC/MS: $[M+H]^+$=874.2.

Step c.

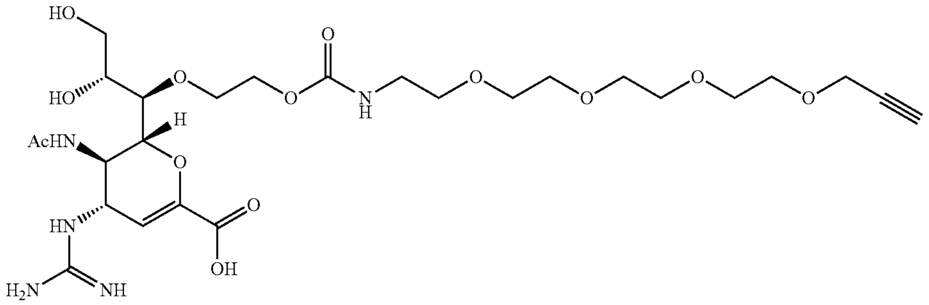 [SMILES: C#CCOCCOCCOCCOCCNC(=O)OCCO[C@@H]([C@@H]1OC(C(=O)O)=C[C@H](NC(=N)N)[C@H]1NC(C)=O)[C@H](O)CO]

The product from the previous step (475 mg, 0.54 mmol), was stirred in TFA (5 mL) for 2 hours and then concentrated and azeotroped with methanol (3×) on a rotary evaporator. Ion found by LC/MS: $[M+H]^+$=674.2. The residue was stirred in 1:1 mixture of methanol/water containing LiOH (49 mg, 1.6 mmol) for 30 minutes. The reaction was neutralized with glacial acetic acid and then concentrated by rotary evaporation. The product was purified by semi-preparative HPLC (0%-75% acetonitrile/water, 0.1% TFA, 30 minute gradient). The pure fractions were pooled and lyophilized. Yield 204 mg, 59%. Ion found by LCMS: $[M+H]^+$=634.2.

Example 120 Synthesis of Int-77

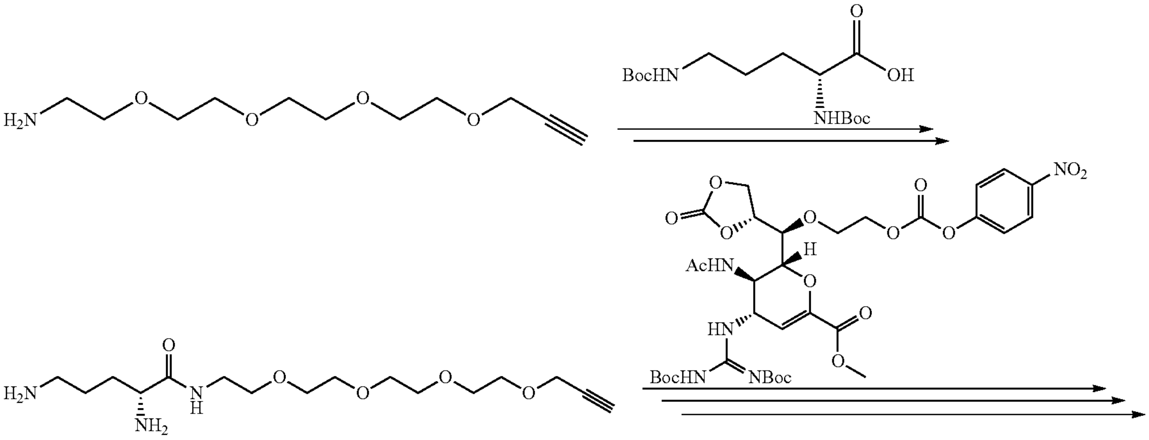

-continued

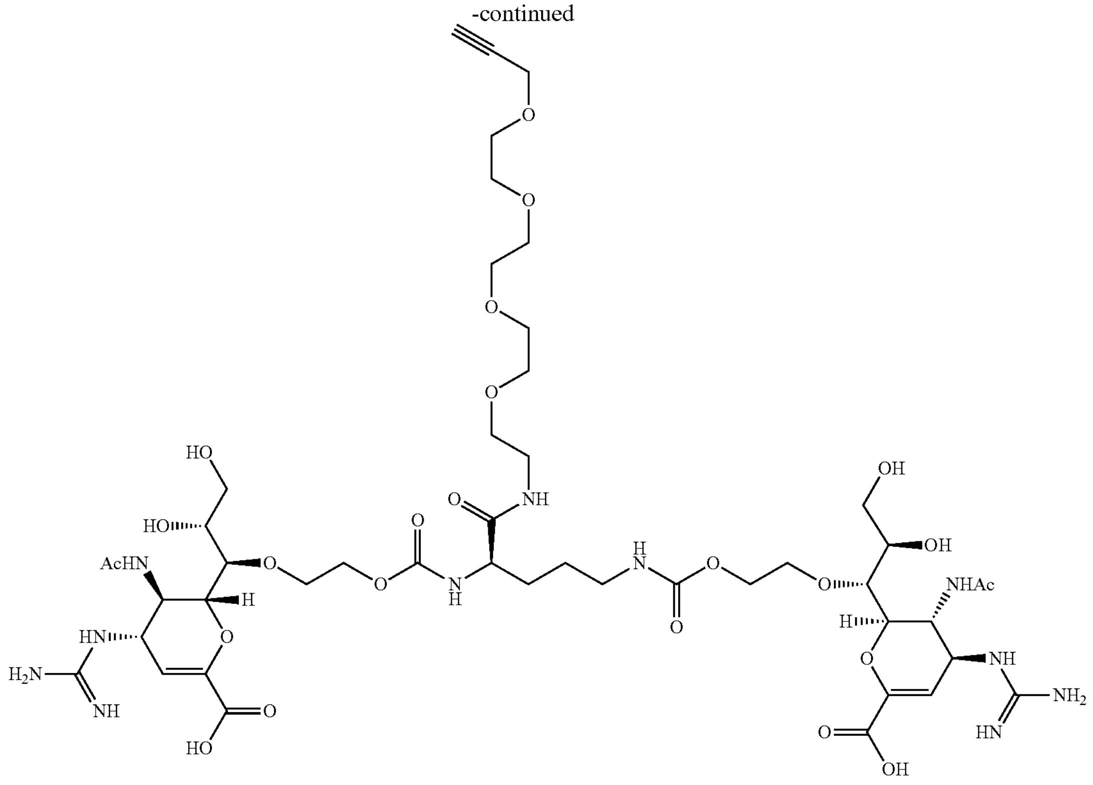

Step a.

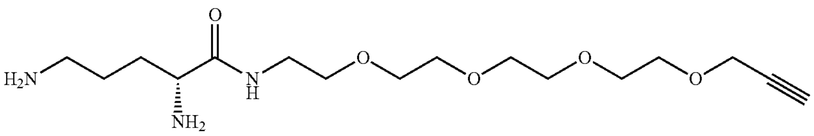 [SMILES: C#CCOCCOCCOCCOCCNC(=O)[C@H](N)CCCN]

HATU (0.44 g, 1.16 mmol, in 1.5 mL of DMF) was added dropwise to a stirring solution of propargyl-peg4-amine (0.24 g, 1.05 mmol), bis-Boc-D-ornithine (0.35 g, 1.05 mmol), and triethylamine (0.59 mL, 4.21 mmol) in DMF (2 mL). The reaction was stirred for 1 hour at ambient temperature, then purified directly by RPLC (5%-90% acetonitrile/water, 0.1% TFA, 35 minute gradient). The pure fractions were pooled and lyophilized to afford the product as a viscous clear oil. Ion found by LC/MS: $[M+H]^+=546.2$ The Boc-protected intermediate was stirred in 4N HCL in dioxane (10 mL) for 45 minutes at ambient temperature. The solvent was removed by rotary evaporation, then the resulting residue was dissolved in DI water (20 mL), frozen, and lyophilized to afford the product as a clear oil. Yield 310 mg, 70%, 2 steps. Ion found by LCMS: $[M+H]^+=346.2$ Step b.

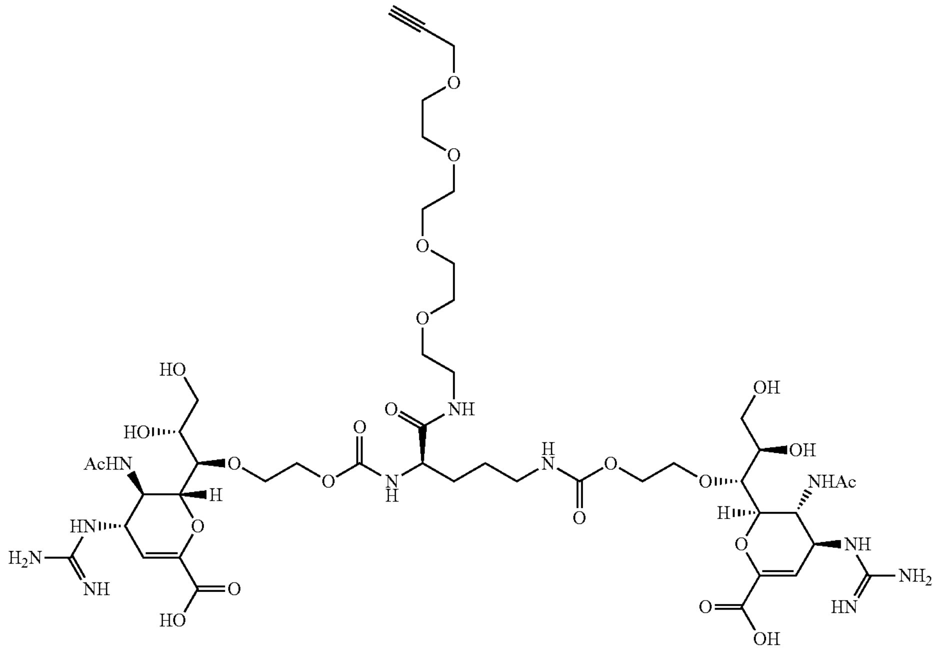 [SMILES: C#CCOCCOCCOCCOCCNC(=O)[C@@H](CCCNC(=O)OCCO[C@@H]([C@@H]1OC(C(=O)O)=C[C@H](NC(=N)N)[C@H]1NC(C)=O)[C@H](O)CO)NC(=O)OCCO[C@@H]([C@@H]1OC(C(=O)O)=C[C@H](NC(=N)N)[C@H]1NC(C)=O)[C@H](O)CO]

The product from the previous step (96 mg, 0.28 mmol) and triethylamine (0.15 mL, 1.11 mmol) in acetonitrile (2 mL) were added to a stirring solution of p-nitrophenyl carbonate of zanamivir (435 mg, 0.56 mmol, described in Example 118, in 6 mL of acetonitrile), and stirred for 12 hours at ambient temperature, then 2 hours at 80° C. The solvent was removed and the crude residue was purified by RPLC (10-95% acetonitrile/water, no modifier, 35 minute gradient). The pure fractions were pooled and concentrated on a rotary evaporator. Ion found by LC/MS: $[(M+2H)/2]^+$ =815.8

This intermediate was stirred in TFA (5 mL) for 45 minutes then concentrated and dried under high vacuum. Ion found by LC/MS$[(M+2H)/2]^+$=615.8.

This TFA salt was stirred in (1/1) MeOH/DI water (5 mL) containing LiOH (27 mg, 1.11 mmol) for 30 minutes at 0° C. The mixture was acidified (~pH~5) with glacial acetic acid. The methanol was removed by rotary evaporation and the resulting residue was purified by semi-preparative HPLC (5%-70% acetonitrile/water, 0.1% TFA, 35 minute gradient). The pure fractions were pooled and lyophilized. Yield 35 mg, 11%, 3 steps. Ion found by LC/MS: $[(M+2H)/2]^+$ =575.8.

Example 121. Synthesis of Int-78

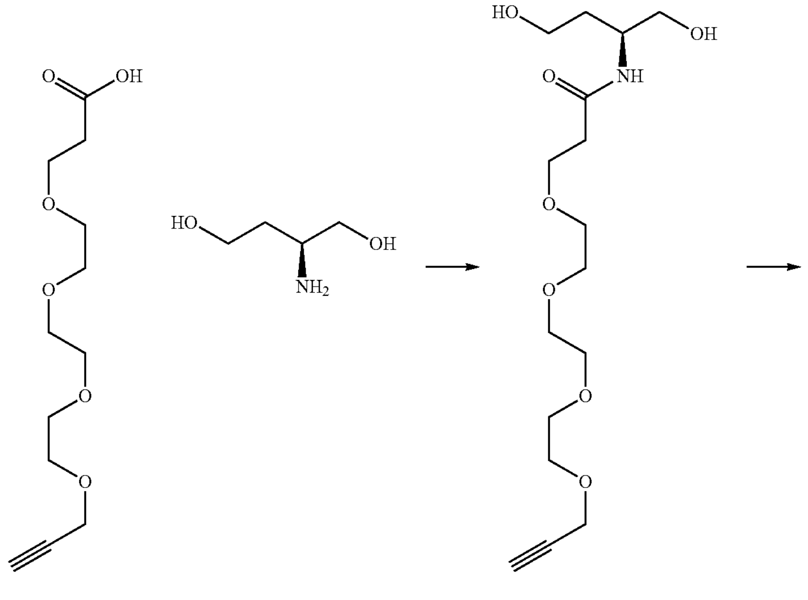

-continued
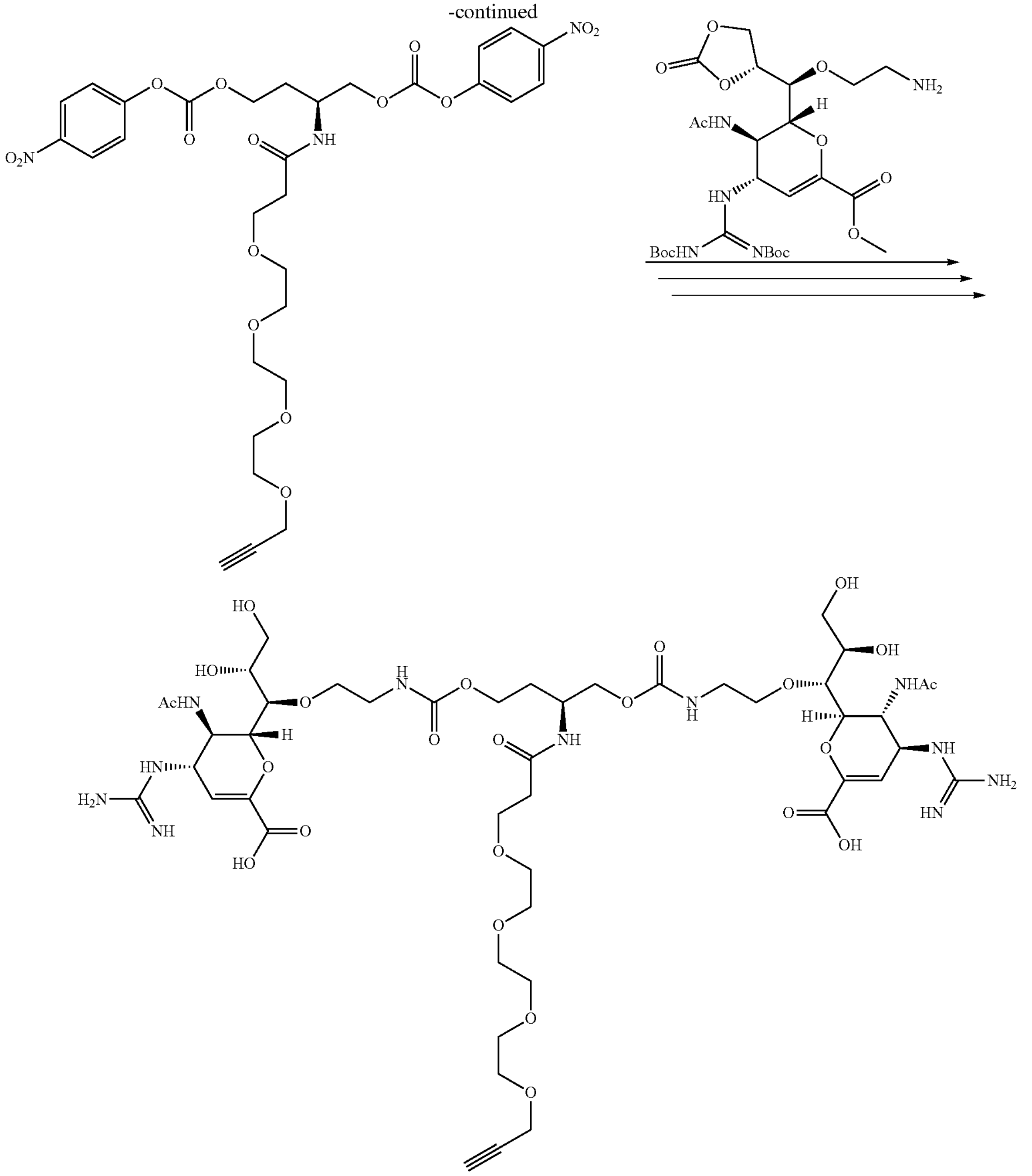
Step a.

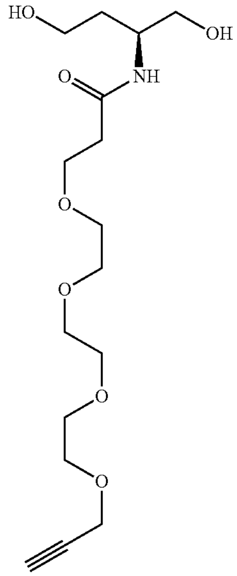 [SMILES: C#CCOCCOCCOCCOCCC(=O)N[C@H](CO)CCO]

Propargyl-Peg4-acid (640 mg, 2.46 mmol), diol-HCl salt (350 mg, 2.46 mmol), EDC (471 mg, 2.46 mmol), HOBt (377 mg, 2.46 mmol), and triethylamine (249 mg, 2.46 mmol) were stirred in DMF (3 mL) at ambient temperature for 4 hours. The mixture purified directly by RPLC (0%-80% acetonitrile/water, no modifier, 35 minute gradient). The pure fractions were pooled and concentrated to afford the product as a clear oil. Yield 580 mg, 68%. Ion found by LCMS: $[M+H]^+$=348.4.

Step b.

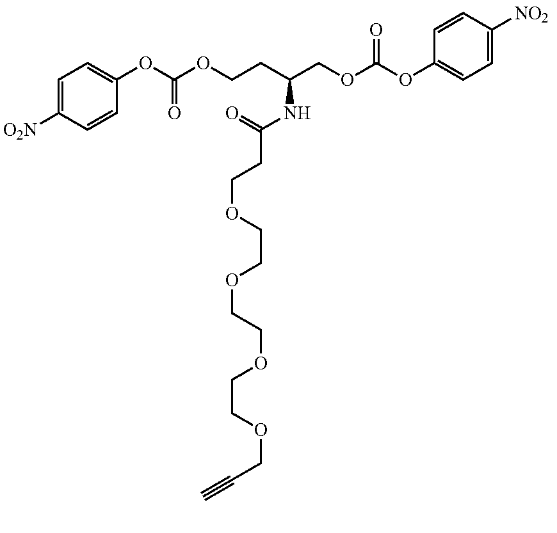 [SMILES: C#CCOCCOCCOCCOCCC(=O)N[C@@H](CCOC(=O)Oc1ccc([N+](=O)[O-])cc1)COC(=O)Oc1ccc([N+](=O)[O-])cc1]

p-Nitro-phenyl chloroformate (1.23 g, 1.25 mmol) was added to a stirring solution of product from the previous step (530 mg, 6.10 mmol) and triethylamine (925 mg, 9.15 mmol) in DCM (25 mL), then cooled to 0° C. under a nitrogen atmosphere. The mixture was stirred for 15 minutes at 0° C. and then at room temperature for 2 hours. The reaction was diluted with DI water and extracted into DCM (3×20 mL). The combined organic extracts were washed with brine and dried over sodium sulfate. The crude residue was purified by silica gel chromatography (10%-100% ethyl acetate/hexanes, 25 minute gradient) to afford the product as a white solid. Yield, 250 mg, 24%. Ion found by LCMS: $[M+H]^+$=678.2.

Step c.

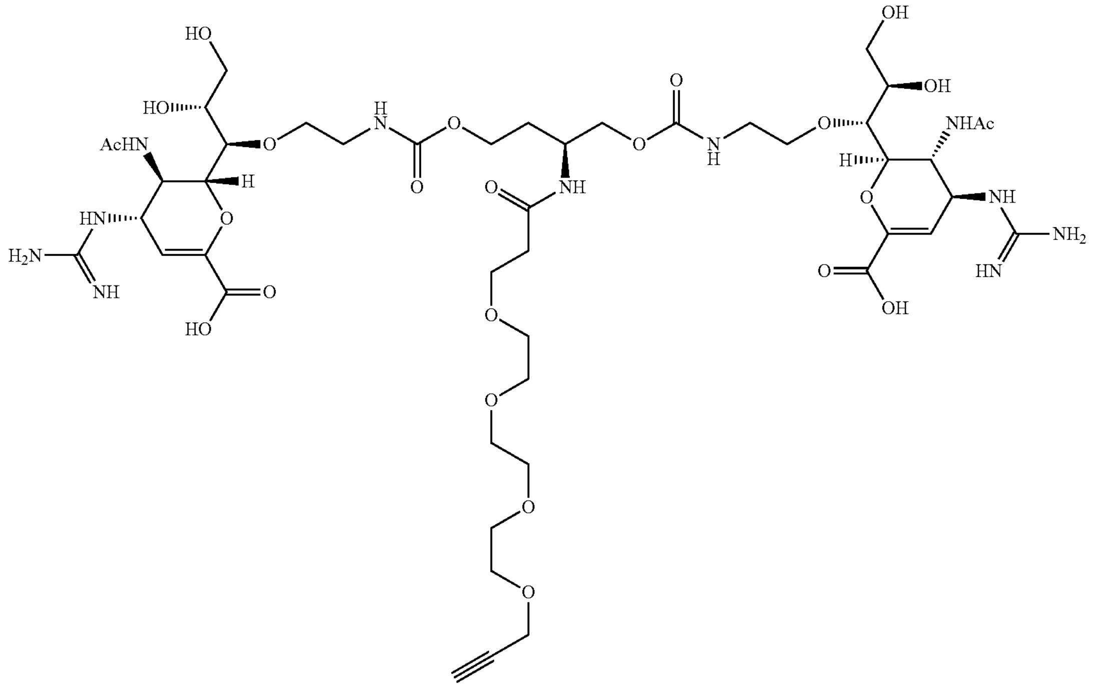 [SMILES: C#CCOCCOCCOCCOCCC(=O)N[C@@H](CCOC(=O)NCCO[C@@H]([C@@H]1OC(C(=O)O)=C[C@H](NC(=N)N)[C@H]1NC(C)=O)[C@H](O)CO)COC(=O)NCCO[C@@H]([C@@H]1OC(C(=O)O)=C[C@H](NC(=N)N)[C@H]1NC(C)=O)[C@H](O)CO]

Amine functionalized zanamivir (505 mg, 0.82 mmol, described in Example 118) and triethylamine (0.15 mL, 1.11 mmol) in acetonitrile (2 mL) were added to a stirring solution of the product of the previous step (220 mg, 0.37 mmol) in acetonitrile (10 mL), and stirred for 4 hours at ambient temperature. The reaction was concentrated on the rotary evaporator. The resulting residue was purified by RPLC (15%-95% acetonitrile/water, no modifier, 35 minute gradient). The pure fractions were pooled and concentrated on a rotary evaporator. Ion found by LC/MS: $[(M+2H)/2]^+$ =815.2.

This intermediate was stirred in TFA (5 mL) for 45 minutes then concentrated and dried under high vac. Ion found by LC/MS: $[(M+2H)/2]^+$=615.2.

The resulting TFA salt was stirred in (1/1) MeOH/DI water (5 mL) containing LiOH (71 mg, 2.98 mmol) for 30 minutes at 0° C. The mixture was acidified (~pH-5) with glacial acetic acid. The methanol was removed by rotary evaporator and purified by semi-preparative HPLC (5%-70% acetonitrile/water, 0.1% TFA, 35 minute gradient). The pure fractions were pooled and lyophilized. Yield 125 mg, 29% for 3 steps. Ion found by LC/MS: $[(M+2H)/2]^+$=575.8.

Example 122. Synthesis of Int-4a

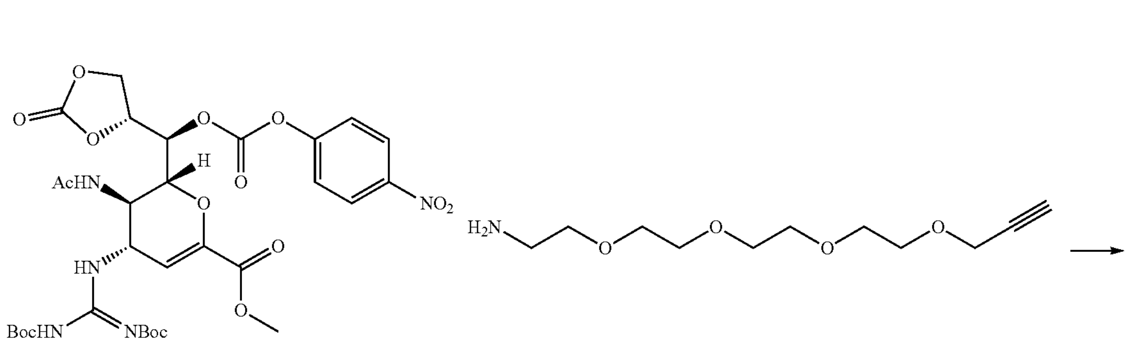

-continued

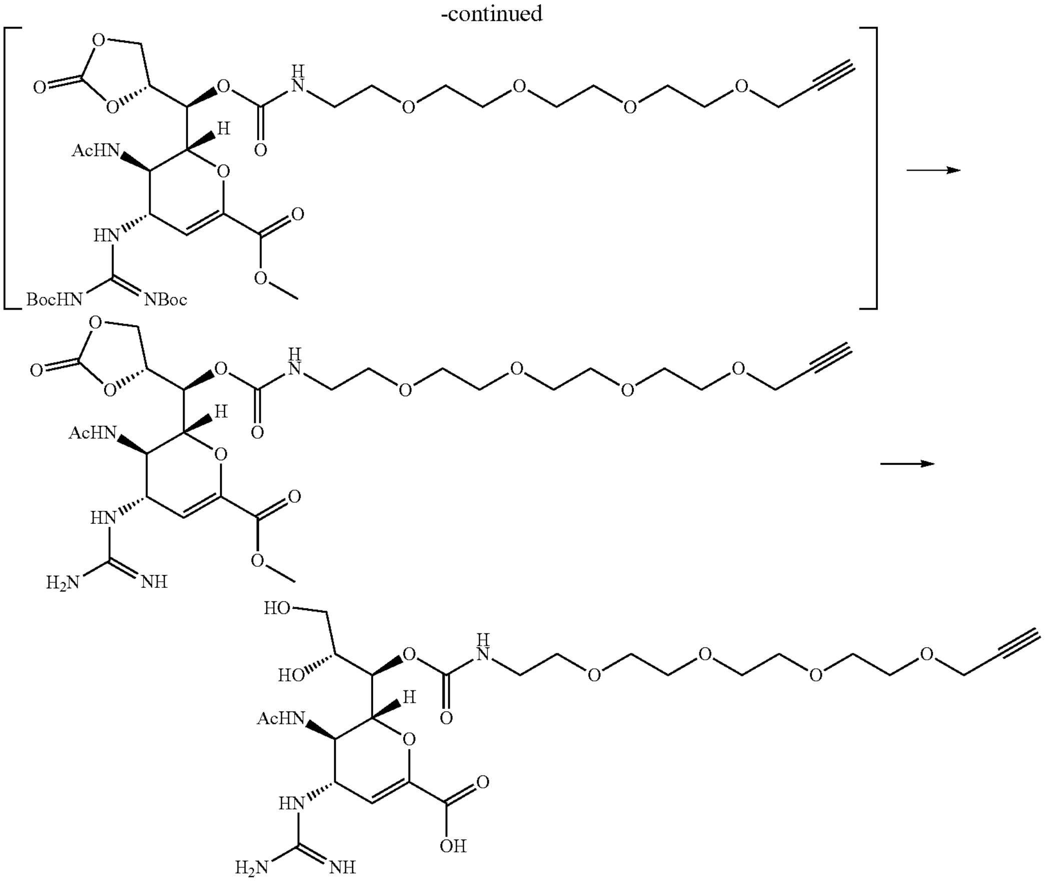

Step a.

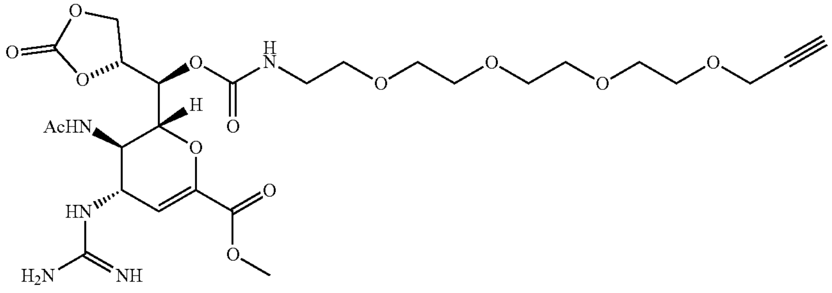

Propargyl-Peg 4-amine (165 mg, 0.71 mmol) was added to a stirring solution of p-nitrophenyl carbonate of zanamivir (350 mg, 0.47 mmol, described in Example 109) in acetonitrile (20 mL). The reaction was stirred for 1 hour at ambient temperature, then solvent was removed by rotary evaporator. The residue was purified by RPLC (10%-95% acetonitrile/water, no modifier, 30 minute gradient). The pure fractions were pooled and lyophilized to afford the boc protected intermediate as a white solid. Ion found by LCMS: $[M+H]^+$ =830.2.

This intermediate was stirred in TFA (5 mL) at ambient temperature for 30 minutes. The solvent was removed by rotary evaporator and the residue was purified by RPLC (10%-95% acetonitrile/water, 0.1% TFA, 30 minute gradient). The pure fractions were pooled and lyophilized to afford the product as a white solid. Yield 155 mg, 52%, 2 steps. Ion found by LCMS: $[M+H]^+$=630.2.

Step b.

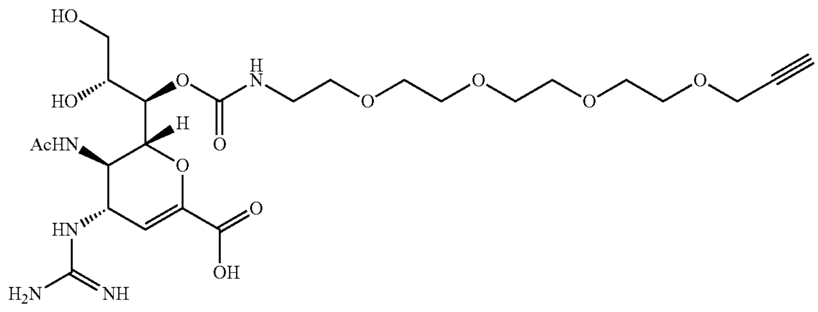 [SMILES: C#CCOCCOCCOCCOCCNC(=O)O[C@@H]([C@@H]1OC(C(=O)O)=C[C@H](NC(=N)N)[C@H]1NC(C)=O)[C@H](O)CO]

The product from the previous step (140 mg, 0.22 mmol) was stirred in a 1:3 mixture of methanol:water (8 mL)

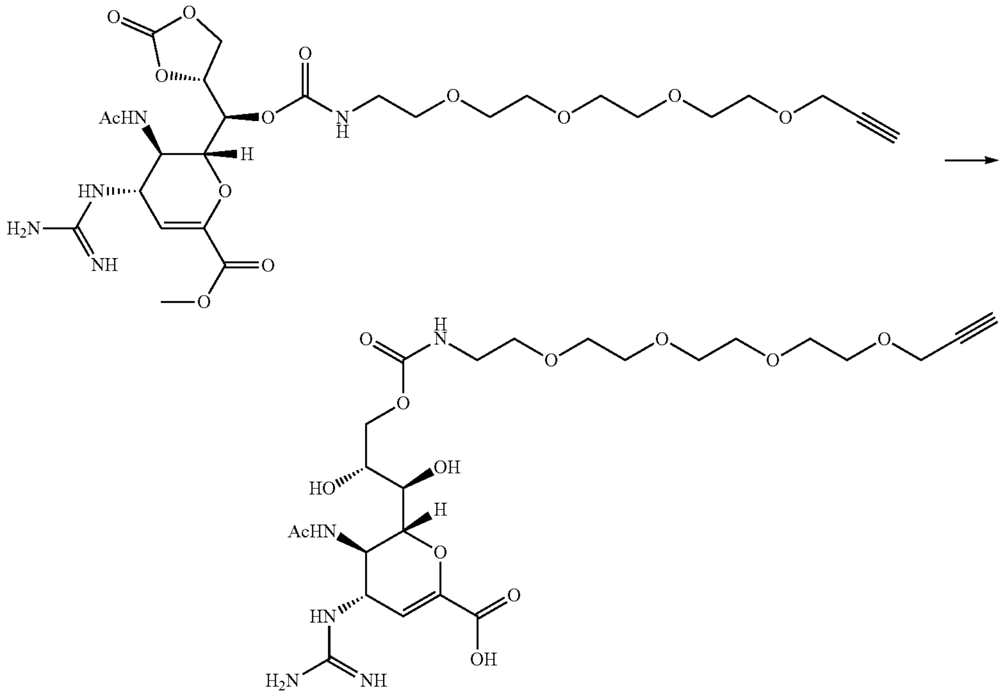

containing LiOH (21 mg, 0.89 mmol) at 0° C. for 20 minutes. The mixture was acidified with a few drops of glacial acetic acid and concentrated on a rotary evaporator. The crude material was purified by semi-preparative HPLC (5%-95% acetonitrile/water, 0.1% TFA, 30 minute gradient). The pure fractions were pooled and lyophilized to afford the product as a white solid. Yield 60 mg, 45%. Ion found by LCMS: $[M+H]^+$=590.2.

$^1$H NMR (500 MHz, Methanol-$d_4$) δ 5.86 (d, J=2.6 Hz, 1H), 4.99 (dd, J=9.0, 2.7 Hz, 1H), 4.55 (dd, J=9.7, 2.7 Hz, 1H), 4.38 (dd, J=8.6, 2.6 Hz, 1H), 4.24-4.14 (m, 1H), 4.19 (d, J=2.6 Hz, 2H), 4.02-3.98 (m, 1H), 3.74-3.59 (m, 13H), 3.54 (t, J=5.6 Hz, 2H), 3.52-3.48 (m, 1H), 3.29-3.22 (m, 2H), 2.84 (t, J=2.4 Hz, 1H), 1.96 (s, 3H).

$^{13}$C NMR (126 MHz, MeOD) δ 172.33, 163.68, 157.54, 156.58, 106.80, 79.23, 75.91, 74.56, 70.18, 70.13, 69.96, 69.87, 69.59, 69.51, 69.14, 68.74, 62.98, 57.67, 51.11, 40.54, 21.37.

Example 123. Synthesis of Int-4b

Peg functionalized intermediate (100 mg, 0.13 mmol, described in Example 122) was stirred in a 1:3 mixture of methanol:water (5 mL) containing LiOH (12 mg, 0.52 mmol) at ambient temperature for 2 hours. The mixture was acidified with glacial acetic acid and concentrated by rotary evaporator. The crude material was purified by RPLC (5-95% acetonitrile in DI water, 0.1% TFA, 30 minute gradient). The pure fractions were pooled and lyophilized to afford the product as a white solid. Yield 21 mg, 31%. Ion found by LCMS: $[M+H]^+$=590.2.

$^1$H NMR (Methanol-$d_4$) δ: 5.86 (d, J=2.6 Hz, 1H), 4.48 (dd, J=8.6, 2.7 Hz, 1H), 4.42 (dd, J=9.6, 1.4 Hz, 1H), 4.38 (d, J=12 Hz, 1H), 4.22-4.19 (m, 1H), 4.19 (d, J=2.4 Hz, 2H), 4.16-4.12 (dd, J=11.5, 6 Hz, 1H), 4.09-4.02 (m, 1H), 3.75-3.58 (m, 13H), 3.55 (t, J=5.5 Hz, 2H), 3.33-3.29 (m, 2H), 2.84 (t, J=2.4 Hz, 1H), 2.02 (s, 3H).

$^{13}C$ NMR (126 MHz, MeOD) δ 172.94, 163.82, 157.90, 157.53, 106.80, 79.23, 76.18, 74.55, 70.19, 70.13, 69.96, 69.90, 69.61, 68.96, 68.74, 68.17, 66.69, 57.67, 50.11, 40.43, 21.33.

Example 124. General Procedure for Synthesis of Azido Fc

Preparation of PEG4-azido NHS ester solution (0.050 M) in DMF/PBS: 16.75 mg of PEG4-azido NHS ester was dissolved in 0.100 mL of DMF at 0° C. and diluted to 0.837 mL by adding PBS 1× buffer at 0° C. This solution was used for preparing other PEG4-azido Fc with a variety of DAR values by adjusting the equivalents of this PEG4-azido NHS ester PBS solution.

Pretreatment of h-IgG1 Fc, SEQ ID NO: 48 (107.2 mg in 8.800 mL of pH 7.4 PBS, MW~57891 Da, 1.852 μmol): The Fc solution was transferred into four centrifugal concentrators (30,000 MWCO, 15 mL) and diluted to 15 mL with PBS×1 buffer and concentrated to a volume of ~1.5 mL. The residue was diluted 1:10 in PBS pH 7.4, and concentrated again. This wash procedure was repeated for total of four times followed by dilution to 8.80 mL.

Preparation of PEG4-azido Fc: 0.050M PEG4-azidoNHS ester PBS buffer solution (0.593 mL, 29.6 μmol, 16 equivalents) was added to above solution of h-IgG1 Fc (SEQ ID NO: 48) and the mixture was shaken rotated for 2 hours at ambient temperature. The solution was concentrated by using four centrifugal concentrators (30,000 MWCO, 15 mL) to a volume of ~1.5 mL. The crude mixture was diluted 1:10 in PBS pH 7.4, and concentrated again. This wash procedure was repeated for total of three times. The concentrated Fc-PEG4-azide was diluted to 8.80 mL with pH 7.4 PBS buffer and ready for Click conjugation. The purified material was quantified using a NANODROP™ UV visible spectrophotomer (using a calculated extinction coefficient based on the amino acid sequence of h-IgG1). Yield was quantitative after purification.

Example 125. Synthesis of Conjugate 34

A solution of azido functionalized Fc (40 mg, 2.5 mL, 0.69 μmol, described in the general preparation of azido Fc, Example 124, SEQ ID No. 18) was added to a 15 mL centrifuge tube containing alkyne derivatized small molecule (6.0 mg, 8.23 μmol, Int-67 Example 118). After gently agitating to dissolve all solids, the mixture was added to a solution of L-ascorbic acid sodium salt (54 mg, 0.27 mmol), copper (II) sulfate (0.88 mg, 5.5 μmol), and BTTA (9.4 mg, 22 μmol) in PBS 7.4 buffer (1.09 mL). The resulting mixture was gently rotated overnight. It was then purified by affinity chromatography over a protein A column, followed size exclusion chromatography (See general conjugate purification protocol). Maldi TOF analysis of the purified final product gave an average mass of 64,678 Da (DAR=7.2). Yield 24 mg, 54% yield.

Example 126. Synthesis of Conjugate 35

A solution of azido functionalized Fc (40 mg, 2.5 mL, 0.69 μmol, described in the general preparation of azido Fc, Example 124, SEQ ID No. 18) was added to a 15 mL centrifuge tube containing alkyne derivatized small molecule (6.1 mg, 8.23 μmol, Int-68 Example 119). After gently agitating to dissolve all solids, the mixture was added to solution of L-ascorbic acid sodium salt (54 mg, 0.27 mmol), copper (II) sulfate (0.88 mg, 5.5 μmol), and BTTA (9.4 mg, 22 μmol) in PBS 7.4 buffer (1.09 mL). The resulting solution was gently rotated overnight. It was then purified by affinity chromatography over a protein A column, followed size exclusion chromatography (See general conjugate purification protocol). Maldi TOF analysis of the purified final product gave an average mass of 64,830 Da (DAR=7.3). Yield 23 mg, 52% yield.

Example 127. Synthesis of Conjugate 36

A solution of azido functionalized Fc (50 mg, 2.5 mL, 0.86 μmol, described in the general preparation of azido Fc, Example 124, SEQ ID No. 18) was added to a 15 mL centrifuge tube containing alkyne derivatized small molecule (7.1 mg, 5.2 μmol, Int-77, Example 120). After gently agitating to dissolve all solids, the mixture was added to a solution of L-ascorbic acid sodium salt (68 mg, 0.34 mmol), copper (II) sulfate (1.1 mg, 6.9 μmol), and BTTA (12 mg, 27 μmol) in PBS 7.4 buffer (1.37 mL). The resulting mixture was gently rotated overnight. It was then purified by affinity chromatography over a protein A column, followed size exclusion chromatography (See general conjugate purification protocol). Maldi TOF analysis of the purified final product gave an average mass of 63,300 Da (DAR=3.6). Yield 37 mg, 73% yield.

Example 128. Synthesis of Conjugate 37

A solution of azido functionalized Fc (70 mg, 2.5 mL, 1.2 μmol, described in the general preparation of azido Fc, Example 124, SEQ ID No. 18) was added to a 15 mL centrifuge tube containing alkyne derivatized small molecule (13.3 mg, 9.6 μmol, Int 78, Example 121). After gently agitating to dissolve all solids, the mixture was added to a solution of L-ascorbic acid sodium salt (96 mg, 0.48 mmol), copper (II) sulfate (1.6 mg, 10 μmol), and BTTA (17 mg, 38 μmol) in PBS 7.4 buffer (1.92 mL). The resulting mixture was gently shaken overnight. It was then purified by affinity chromatography over a protein A column, followed size exclusion chromatography (See general conjugate purification protocol). Maldi TOF analysis of the purified final product gave an average mass of 63,574 Da (DAR=3.6). Yield 42 mg, 61% yield.

Example 129. Synthesis of Conjugate 33

Preparation of the Click reagent solution: 0.0050M $CuSO_4$ in PBS buffer solution: 10.0 mg $CuSO_4$ was dissolved in 12.53 mL PBS, then took 5.00 mL this $CuSO_4$ solution and added 43.1 mg BTTAA (CAS #1334179-85-9) and 247.5 mg sodium ascorbate to give the Click reagent solution (0.0050M CuSO4, 0.020M BTTAA and 0.25M sodium ascorbate).

To a solution of azido functionalized Fc (104.9 mg, 8.60 mL, 18.1 μmol; Example 124, SEQ ID NO: 64) in a 15 mL centrifuge tube was added to alkyne derivatized small molecule (29.7 mg, 19.9 μmol, described in Example 100, 2.5 equivalents for each azido on the Fc). After gently agitating to dissolve all solids, the mixture was treated with the Click reagent solution (4.34 mL) of (L-ascorbic acid sodium, 0.25 M, 1086 μmol, copper (II) sulfate 0.0050M, 21.7 μmol, and BTTAA 0.020M, 86.9 μmol). The resulting mixture was gently rotated for 6 hours at ambient temperature. It was purified by affinity chromatography over a protein A column, followed size exclusion chromatography (see general conjugate purification protocol). Maldi TOF analysis of the purified final product gave an average mass of 64550 Da (DAR=4.6). Yield 90.7 mg with 98% purity.

Example 130. Efficacy of Conjugate 33 Against Influenza B/Brisbane/60/2008 in a Lethal Mouse Model Test articles were evaluated against a lethal Influenza B influenza infection in female BALB/c mice (Jackson Laboratories, 6-8 weeks old). The challenge virus (B/Brisbane/60/2008) is a mouse-adapted isolate capable of causing lethal infections in mice. The experiment comprised 10 groups of 5 mice each. At day 0, all mice were challenged with virus at 3× the LD95 by intranasal inoculation in a volume of 50 μl (approx. 1E5 virus per mouse), after being anesthetized with isoflurane.

All groups received a single IV treatment of conjugate 33 (Example 129), vehicle (PBS), or Fc only control (hIgG1 Fc) two hours post viral challenge. An additional group was treated orally with oseltamivir (20 mg/kg, bid, for 5 days) starting 8 hours after viral challenge.

The study evaluated 7 different dose concentrations of conjugate 33 (10, 3, 1, 0.3, 0.1, 0.03, and 0.01 mg/kg). Mice were monitored for 2 weeks and animals exceeding 20% body weight loss, or were found moribund, were scored as a mortality. Body weights were also recorded to monitor the general health of the animals.

All mice treated with vehicle, or the Fc only control, reached mortality by Day 8 as expected. In contrast, all mice receiving conjugate 33 were fully protected after receiving single IV doses from 10 down to 0.3 mg/kg for the duration of the study (Table 48). In contrast, the oseltamivir treated group only resulted in 40% survival although the cumulative dose these mice received was 200 mg/kg over the course of the experiment. The potency of conjugate 33 was further supported by daily body weight measurements (Table 49; data only shown until the first death within a group). Mice treated with conjugate 33 at 0.3 mg/kg only demonstrated a transient loss of body weight reaching a maximum of 7%, for a single day. Collectively this study demonstrates the potency of conjugate 33 as measured by two parameters indicative of Influenza B infection (survival and body weight) against an influenza strain of the Yamagata lineage.

TABLE 48

| % survival | | | | | | | |
|---|---|---|---|---|---|---|---|
| | | | Conjugate 33 | | | | |
| Day post-infection | PBS | Fc (10 mg/kg) | (10 to 0.3 mg/kg) | (0.1 mg/kg) | (0.03 mg/kg) | (0.01 mg/kg) | Oseltamivir |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 60 | 100 | 100 | 100 | 100 | 100 | 100 |
| 5 | 40 | 40 | 100 | 100 | 60 | 80 | 40 |
| 6 | 0 | 0 | 100 | 60 | 60 | 40 | 0 |
| 7 | 0 | 0 | 100 | 60 | 60 | 0 | 0 |
| 8 | 0 | 0 | 100 | 60 | 60 | 0 | 0 |
| 9 | 0 | 0 | 100 | 60 | 60 | 0 | 0 |
| 10 | 0 | 0 | 100 | 60 | 60 | 0 | 0 |
| 11 | 0 | 0 | 100 | 60 | 60 | 0 | 0 |
| 12 | 0 | 0 | 100 | 60 | 60 | 0 | 0 |
| 13 | 0 | 0 | 100 | 60 | 60 | 0 | 0 |
| 14 | 0 | 0 | 100 | 60 | 60 | 0 | 0 |

TABLE 49

| Body weights (gm) | | | | | | | | | | |
|---|---|---|---|---|---|---|---|---|---|---|
| Day | | Fc | Conjugate 33 | | | | | | | |
| post-infection | PBS | (10 mg/kg) | (10 mg/kg) | (3 mg/kg) | (1 mg/kg) | (0.3 mg/kg) | (0.1 mg/kg) | (0.03 mg/kg) | (0.01 mg/kg) | Oseltamivir |
| 0 | 100 | 100 | 100 | 100 | 100 | 100 | 100 | 100 | 100 | 100 |
| 1 | 99 | 101 | 103 | 98 | 98 | 98 | 98 | 99 | 98 | 98 |
| 2 | 95 | 97 | 100 | 99 | 97 | 101 | 97 | 97 | 97 | 97 |
| 3 | 87 | 90 | 101 | 98 | 96 | 97 | 93 | 95 | 92 | 89 |
| 4 | 82 | 84 | 104 | 99 | 99 | 97 | 93 | 93 | 88 | 85 |
| 5 | 78 | 79 | 102 | 99 | 99 | 97 | 92 | | 84 | 79 |
| 6 | | | 98 | 96 | 98 | 93 | | | 79 | |
| 7 | | | 102 | 98 | 100 | 96 | | | | |
| 8 | | | 101 | 98 | 98 | 97 | | | | |
| 9 | | | 104 | 101 | 102 | 101 | | | | |
| 10 | | | 103 | 100 | 101 | 101 | | | | |
| 11 | | | 104 | 102 | 101 | 101 | | | | |
| 12 | | | 104 | 101 | 102 | 102 | | | | |
| 13 | | | 103 | 102 | 102 | 102 | | | | |
| 14 | | | 103 | 102 | 102 | 101 | | | | |

Example 131. Characterization of Regioisomers

Monomer and dimer intermediates may be produced as a particular regioisomer or a mixture of regioisomers. Examples 100-102 showed how to prepare Int-7 regioisomers (C7-C7, Example 100; C7-C9, Example 101; C9-C9, Example 102; C7-C7 optimized, Example 103). The methods described therein can be used to separate mixtures of regioisomers of any intermediate described herein. Table 50 provides the characterization of the relative percent (%) amounts of C7 and C9 linked monomers and C7-C7, C7-C9, and C9-C9 linked dimers in the previously described syntheses of the pre-conjugation intermediate.

TABLE 50

| Regiosomer Analysis | | | | | |
|---|---|---|---|---|---|
| Int | Example | Monomer (M) or Dimer (D) | % C7 | % C7-C9 | % C9 |
| Int-2 | Example 6 | D | 95 | 5 | |
| Int-3 | Example 11 | D | 70 | 30 | |
| Int-4 | Example 13 | M | 58 | | 42 |
| Int-4a | Example 122 | M | | | 97 |
| Int-7 | Example 19 | D | 3 | 2 | 95 |
| Int-7a | Example 100 | D | 100 | | |
| Int-7b | Example 101 | D | 5 | 95 | |
| Int-7c | Example 102 | D | | | 100 |
| Int-25 | N/A | D | | 5 | 95 |
| Int-26 | N/A | D | 25 | 50 | 25 |
| Int-27 | N/A | D | 29 | 35 | 36 |
| Int-28 | N/A | D | 5 | 28 | 67 |
| Int-31 | N/A | D | 90 | | |
| Int-34 | N/A | D | 12 | 6 | 82 |
| Int-37 | N/A | M | | | 95 |
| Int-71 | Example 110 | D | 3 | 97 | |
| Int-72 | Example 112 | D | | 100 | |

Example 132. Efficacy of Conjugate 33 Subcutaneously Dosed Against Influenza A/Puerto Rico/8/34 (H1N1) in a Lethal Mouse Model Conjugate 33 was evaluated against a lethal IAV H1N1 influenza infection in female BALB/c mice (Charles River Laboratories, 6-8 weeks). The challenge virus (A/Puerto Rico/8/1934) is a mouse-adapted isolate capable of causing lethal infections in mice. The experiment comprised 6 groups of 5 mice. At day 0, all mice were challenged with virus at 3× the $LD_{95}$ by intranasal inoculation in a volume of 30 μl, after being anesthetized with a mixture of ketamine/xylazine (150 and 10 mg/kg respectively). Mortality and body weights were recorded daily and any animal with a 20% loss of body weight was scored as a death. Test groups received a single subcutaneous (SC) treatment of conjugate 33, hIgG1 Fc control, or vehicle (PBS) 2 hours post viral challenge. The study design is summarized in Table 51.

TABLE 51

| Study design for Influenza A/PR/8/34 (H1N1) study | | | | | |
|---|---|---|---|---|---|
| Group | Test article | Route/ Schedule | Dose (mg/kg) | Dose volume (ml/kg) | # of mice |
| 1 | Vehicle | SC, T + 2 hrs. | na | 10 | 5 |
| 2 | hIgG1 Fc | SC, T + 2 hrs. | 1 | 10 | 5 |
| 3 | Conjugate 33 | SC, T + 2 hrs. | 1 | 10 | 5 |
| 4 | Conjugate 33 | SC, T + 2 hrs. | 0.3 | 10 | 5 |
| 5 | Conjugate 33 | SC, T + 2 hrs. | 0.1 | 10 | 5 |
| 6 | Conjugate 33 | SC, T + 2 hrs. | 0.03 | 10 | 5 |

As expected, mice receiving vehicle or the hIgG1 Fc control succumbed to infection on Days 6-7 (Table 52). However, mice treated with conjugate 33 were fully protected at 1, 0.3, and 0.1 mg/kg dose levels. Mortality with conjugate 33 was only seen at the lowest dose concentration of 0.03 mg/kg.

TABLE 52

| Percent survival by study day (n = 5) | | | | | | |
|---|---|---|---|---|---|---|
| | | hIgG1 Fc | Conjugate 33 | | | |
| Day Post Infection | Vehicle | (1.0 mg/kg) | (1.0 mg/kg) | (0.3 mg/kg) | (0.1 mg/kg) | (0.03 mg/kg) |
| 0 | 100 | 100 | 100 | 100 | 100 | 100 |
| 1 | 100 | 100 | 100 | 100 | 100 | 100 |
| 2 | 100 | 100 | 100 | 100 | 100 | 100 |
| 3 | 100 | 100 | 100 | 100 | 100 | 100 |
| 4 | 100 | 100 | 100 | 100 | 100 | 100 |
| 5 | 100 | 100 | 100 | 100 | 100 | 100 |
| 6 | 40 | 60 | 100 | 100 | 100 | 100 |
| 7 | 0 | 0 | 100 | 100 | 100 | 60 |
| 8 | 0 | 0 | 100 | 100 | 100 | 0 |

TABLE 52-continued

| Percent survival by study day (n = 5) | | | | | | |
|---|---|---|---|---|---|---|
| | | hIgG1 Fc | Conjugate 33 | | | |
| Day Post Infection | Vehicle | (1.0 mg/kg) | (1.0 mg/kg) | (0.3 mg/kg) | (0.1 mg/kg) | (0.03 mg/kg) |
| 9 | 0 | 0 | 100 | 100 | 100 | 0 |
| 10 | 0 | 0 | 100 | 100 | 100 | 0 |
| 11 | 0 | 0 | 100 | 100 | 100 | 0 |
| 12 | 0 | 0 | 100 | 100 | 100 | 0 |
| 13 | 0 | 0 | 100 | 100 | 100 | 0 |
| 14 | 0 | 0 | 100 | 100 | 100 | 0 |

The potency of conjugate 33 was further supported by daily body weight measurements. As expected, mice treated with vehicle or hIgG1 Fc demonstrated a steady drop in body weight until it exceeded 20%, at which time they were scored as a mortality (Table 53).

In contrast to control mice, those groups receiving conjugate 33 at 1, 0.3, and 0.1 mg/kg maintained healthy body weights throughout the study and never demonstrated more than a transient body weight drop of less than 8% (0.1 ink/kg dose group, Day 8; Table 53). By both survival and body weight measurements conjugate 33 demonstrated robust protection from a lethal challenge of Influenza A/Puerto Rico/8/1934 with a single SC dose as low as 0.1 mg/kg.

TABLE 53

| Body weight data (gm) | | | | | | |
|---|---|---|---|---|---|---|
| | | hIgG1 Fc | Conjugate 33 | | | |
| Day Post Infection | Vehicle | (1.0 mg/kg) | (1.0 mg/kg) | (0.3 mg/kg) | (0.1 mg/kg) | (0.03 mg/kg) |
| 0 | 100 | 100 | 100 | 100 | 100 | 100 |
| 1 | 98.1 | 97.6 | 98 | 98.6 | 98.7 | 98.5 |
| 2 | 100.9 | 99 | 100.3 | 101.3 | 101.6 | 99.9 |
| 3 | 94.1 | 92.6 | 98.4 | 100.5 | 96.5 | 93.9 |
| 4 | 86 | 85.7 | 102.6 | 99.2 | 93.5 | 88.6 |
| 5 | 79.8 | 79.1 | 98.2 | 97.7 | 94.9 | 86.5 |
| 6 | 75.3 | 75.2 | 102.2 | 102.3 | 99.4 | 84.6 |
| 7 | | | 103.5 | 102.9 | 95.2 | 78.4 |
| 8 | | | 101.8 | 103.2 | 92.4 | |
| 9 | | | 101.2 | 102.9 | 95.4 | |
| 10 | | | 101.3 | 102.5 | 98.8 | |
| 11 | | | 102.8 | 102.6 | 98.7 | |
| 12 | | | 102.4 | 100.7 | 98.6 | |
| 13 | | | 102.2 | 101.1 | 98.3 | |
| 14 | | | 100.2 | 102 | 99.6 | |

Figure 62A:
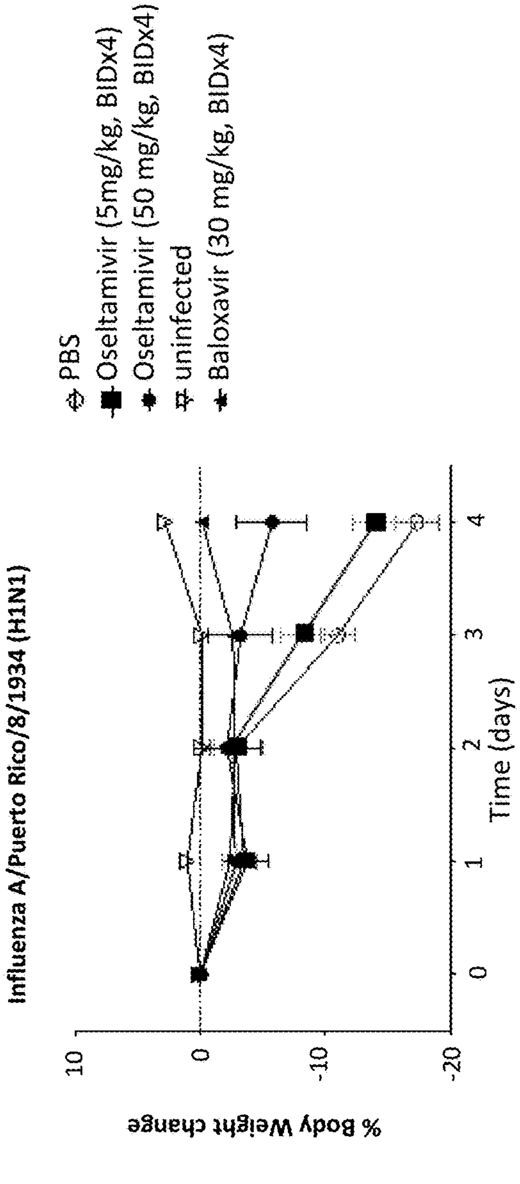
FIGS. 62A-62B are graphs showing the body weight change (%) in BALB/c mice challenged intranasally with 3× the $LD_{95}$ of mouse adapted influenza A.PR/8/1934 (H1N1). This study was performed as described in Example 133.
Figure 62B:
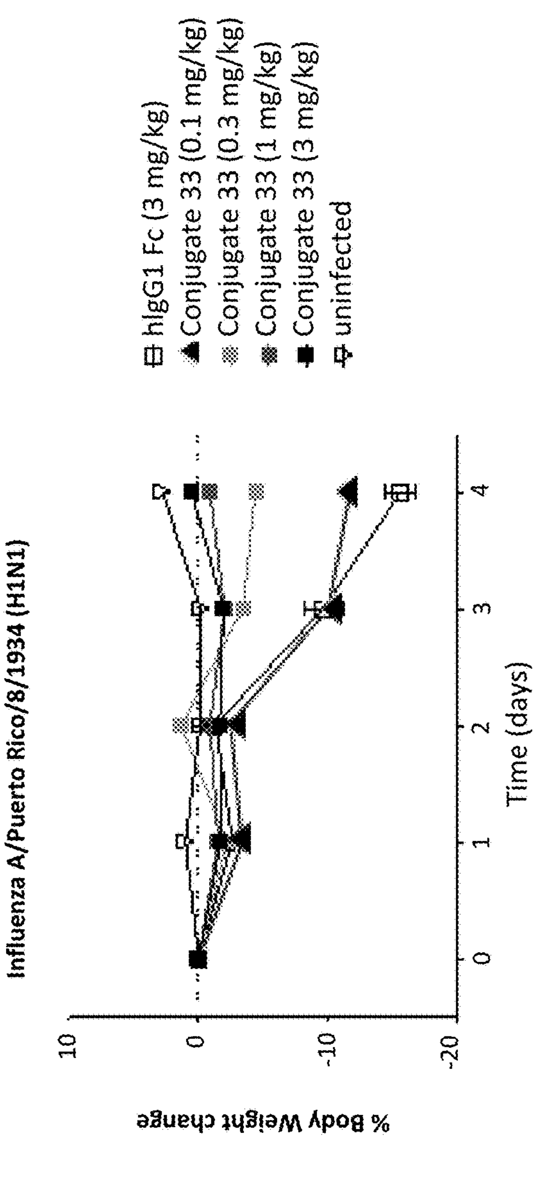

Example 133. Efficacy of Conjugate 33 Against A/PR/8/1934 (H1 N1), Lung PFU Burden and Cytokine Levels Efficacy studies for conjugate 33 were conducted in 6-8 weeks female BALB/c mice (Charles River) challenged intranasally with 3E2 PFU/mouse (3× the $LD_{95}$) of mouse-adapted influenza A/PR/8/1934 (H1N1). Conjugate 33 or human IgG1 Fc controls was administered as a single subcutaneously (SC) dose 2 h post-challenge at 0.1-3 mg/kg. Oseltamivir was dosed orally, twice daily for 4 days starting 2 h post-infection at 5 or 50 mg/kg. Baloxavir was resuspended in 0.5% methylcellulose and dosed orally, twice daily for 4 days starting 2 h post-infection at 30 mg/kg (Table 54). Body weights (BW)O were recorded for 4 days (FIGS. 62A-62B. At 4 days post-infection, mice were sacrificed by C02 and both lung lobes were harvested. Lungs were homogenized with 1 mm silica beads in 1 mL PBS using a MagNA Lyser (Roche). Homogenization was carried out at 6,000 rpm for 60 s and chilled on ice for 5 min in-between runs. After lung homogenization tubes were centrifuged for 10 min at 600×g and supernatant was transferred into new tube.

TABLE 54

| Study Design | | |
|---|---|---|
| Test Article (DAR) | Route/Sechdule | Dose [mg/kg] |
| hIgG1 Fc | IV, T + 2 h | 3 |
| Oseltamivir | PO, BID × 4 | 5 |
| Oseltamivir | PO, BID × 4 | 50 |
| Baloxavir | SC, BID × 4 | 30 |
| Conjugate 33 (4.7) | SC, T + 2 h | 0.1 |
| Conjugate 33 (4.7) | SC, T + 2 h | 0.3 |
| Conjugate 33 (4.7) | SC, T + 2 h | 1 |
| Conjugate 33 (4.7) | SC, T + 2 h | 3 |
| uninfected | N/A | N/A |

For PFU determination, supernatants of lung homogenate were diluted in infection buffer ranging from $10^{-1}$ to $10^{-6}$. 100 μL of virus dilutions were added to confluent monolayer of MDCK cells in 24 well plates and incubated for 1 h at room temperature with rocking every 15 min. After removing the virus, liquid overlay media containing Avicel was added to MDCK cells. Cells were incubation at 37° C., 5% $CO_2$ for 40 h. After incubation, the media was removed and cells were stained with crystal violet to enumerate plaques and Plaque forming units (PFU) were calculated relative to weight of the lung (PFU/g lung).

Figure 63A:
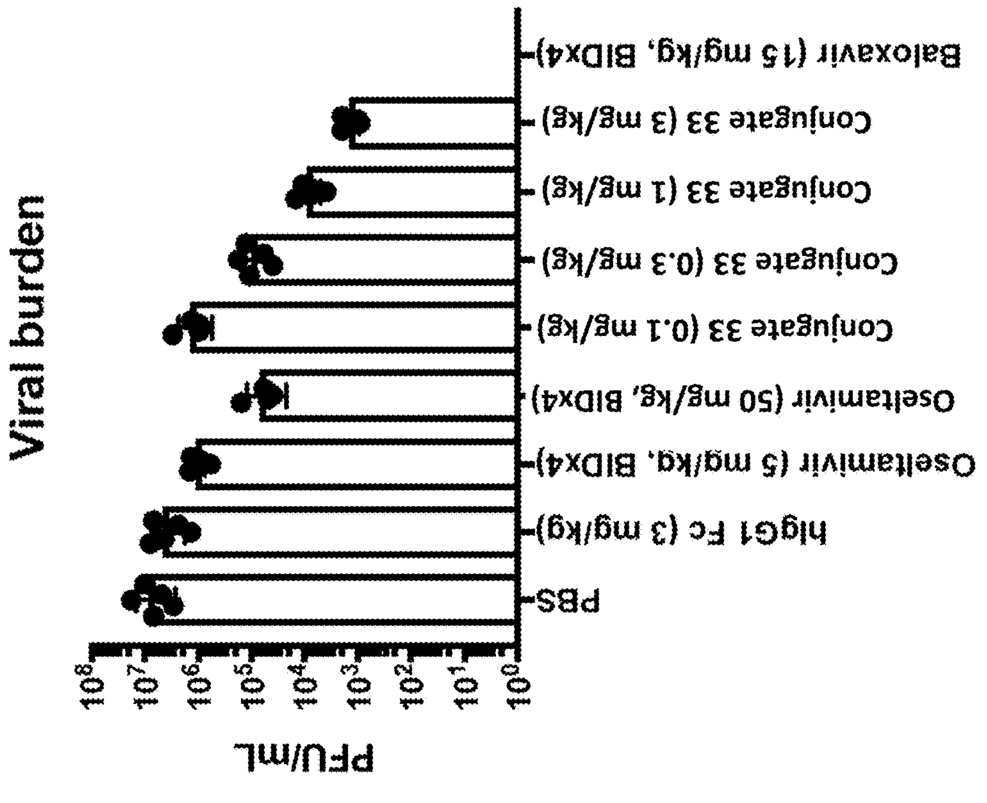
FIG. 63A is a graph showing the viral burden on day 4 post infection. This study was performed as described in Example 133.
Figure 63B:
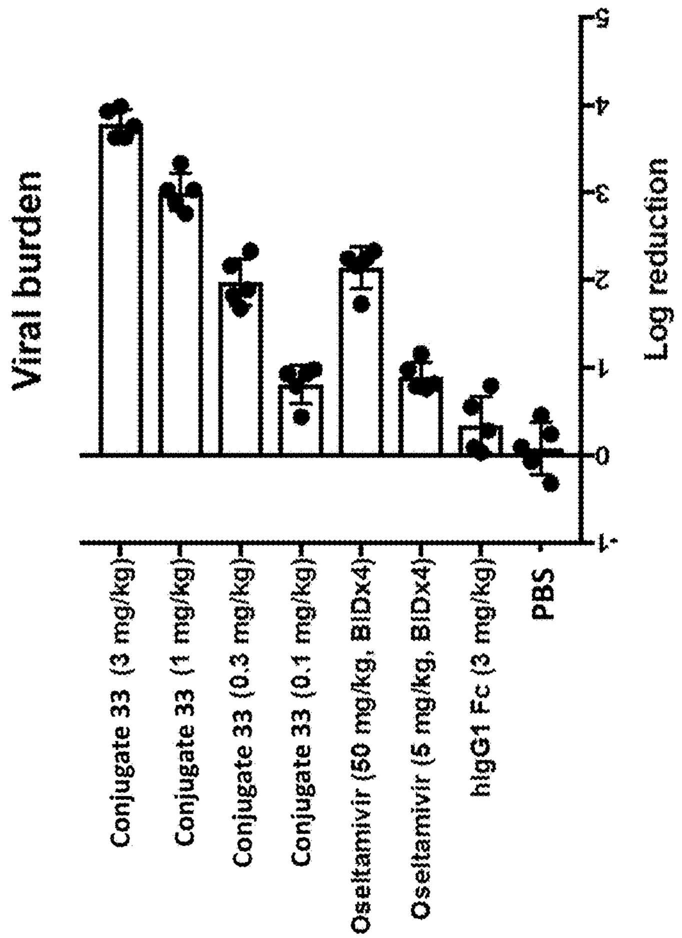
FIG. 63B is a graph showing the log reduction in viral burden on day 4 post infection. This study was performed as described in Example 133.

For cytokine analysis, supernatants of lung homogenate were serially diluted 2-fold in 96 well plate. Cytokine levels for INF-γ, TNF-α, IL-6, MIP-1α and MCP-1 were determined by ELISA according to manufacturer's instructions (R&D Systems). After a lethal challenge with influenza in a mouse model, lung PFU burden (FIGS. 63A-63B) and lung cytokine levels were determined on day 4 post-infection (Table 55, and Table 56, respectively). Conjugate 33 demonstrated a dose-dependent log reduction in viral burden resulting in 0.7 at 0.1 mg/kg, 1.88 at 0.3 mg/kg, 3 at 1 mg/kg and 3.8 at 3 mg/kg. Oseltamivir at 5 mg/kg and 50 mg/kg had modest effects on viral burden resulting in 0.86 and 2 log reduction, respectively. Baloxavir reduced the viral burden below the limit of detection, 1e2 PFU/mL, thereby reducing the viral burden by >5.99 logs as compared to PBS control.

No biological relevant difference was observed between negative controls, PBS and hIgG1 Fc as expected.

Figure 64A:
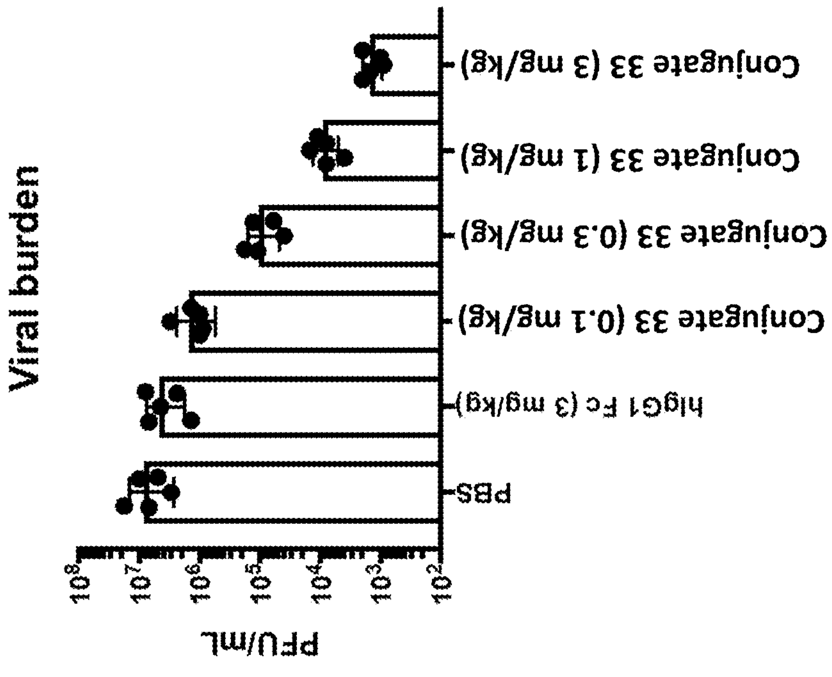
FIG. 64A is a graph showing administration of conjugate 33 results in dose-dependent reduction of viral burden in a mouse model infected with Influenza A (H1N1) compared with PBS control or Fc-only control. This study was performed as described in Example 133.
Figure 64B:
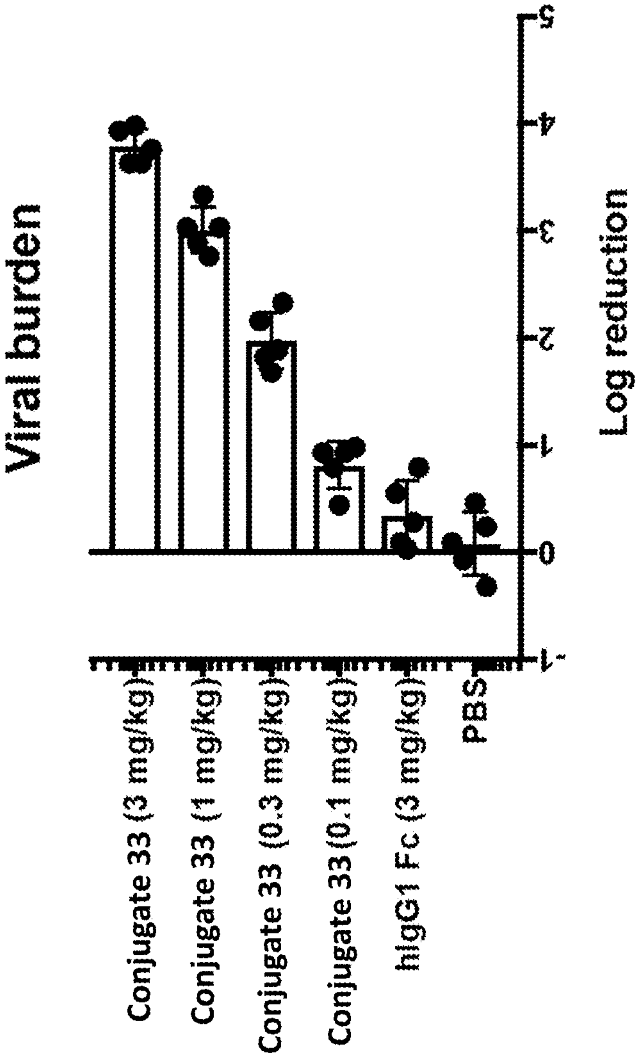
FIG. 64B is a graph showing the log reduction in viral burden on day 4 post infection. This study was performed as described in Example 133.
Figures 65A, 65B, 65C, 65D, 65E:
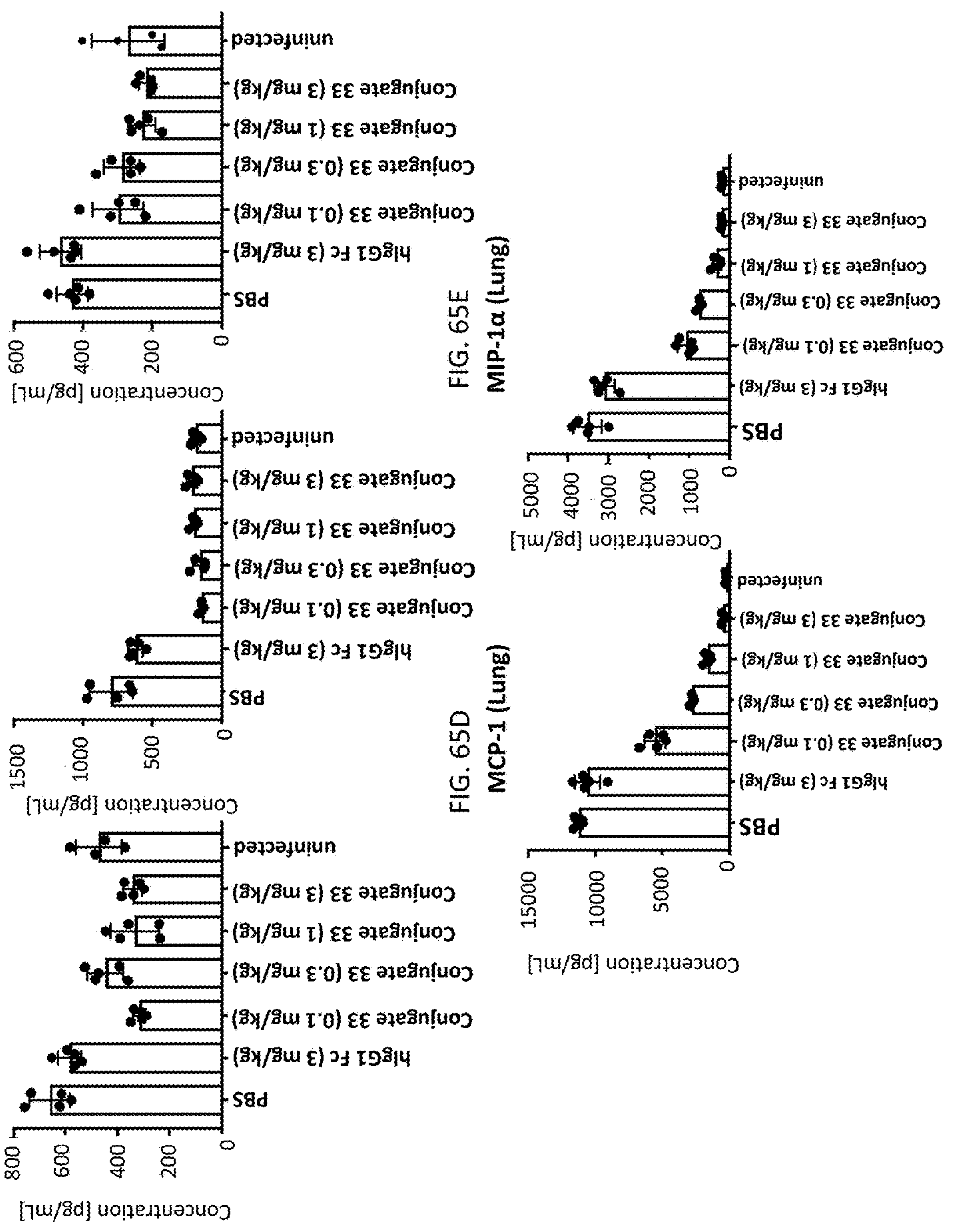
FIGS. 65A-65E are a series bar graphs showing administration of conjugate 33 results in dose-dependent fold-reduction in cytokine levels for TNF-α (FIG. 65A), IL-6 (FIG. 65B), INF-γ (FIG. 65C), MCP-1 (FIG. 65D), and MIP-1α (FIG. 65E). This study was performed as described in Example 133.

Conjugate 33 reduces viral burden in dose dependency on day 4 post-infection challenged with influenza A in a mouse model (Table 55, FIGS. 64A-64B). Similarly, conjugate 33 demonstrated a dose-dependent fold-reduction in cytokine levels for TNF-α, IL-6, INF-γ, MCP-1, and MIP-1α (FIGS. 65A-65E, respectively) compared to uninfected control on day 4 post-infection challenged with influenza A in a mouse model (Table 56).

TABLE 55

| PFU burden | | |
|---|---|---|
| Test article [mg/kg] | PFU/g | Log reduction |
| PBS [0]PBS | 3.26E+07 | 0.0 |
| hIgG1 Fc [3] | 1.74E+07 | 0.364 |
| Oseltamivir [5] | 4.78E+06 | 0.86 |
| Oseltamivir [50] | 3.81E+05 | 2 |

TABLE 55-continued

| PFU burden | | |
|---|---|---|
| Test article [mg/kg] | PFU/g | Log reduction |
| Baloxavir [30] | <1.00E+02* | >5.99* |
| AVC-076-5B [0.1] | 6.85E+06 | 0.715 |
| AVC-076-5B [0.3] | 5.31E+05 | 1.88 |
| AVC-076-5B [1] | 3.69E+04 | 2.99 |
| AVC-076-5B [3] | 5.84E+03 | 3.77 |

*Baloxavir reduced the viral burden below the limit of detection.

TABLE 56

| Lung cytokine levels | | | | | |
|---|---|---|---|---|---|
| Test article [mg/kg] | INF-γ | TNF-α | IL-6 | MCP-1 | MIP-1α |
| PBS [0] | 1.6 | 1.4 | 4.2 | 38.6 | 18.1 |
| hIgG1 Fc [3] | 1.7 | 1.2 | 3.3 | 36.3 | 15.9 |
| Oseltamivir [5] | 1.0 | 0.8 | 1.8 | 24.0 | 6.3 |
| Oseltamivir [50] | 0.8 | 0.8 | 1.4 | 16.2 | 4.0 |
| Baloxavir [30] | 1.2 | 1.0 | 1.0 | 1.0 | 0.8 |
| conjugate 33 [0.1] | 1.1 | 0.7 | 0.8 | 19.1 | 5.6 |
| conjugate 33 [0.3] | 1.1 | 0.9 | 0.8 | 9.6 | 3.9 |
| conjugate 33 [1] | 0.9 | 0.7 | 1.1 | 5.7 | 1.7 |
| conjugate 33 [3] | 0.8 | 0.7 | 1.1 | 1.8 | 1.0 |
| Uninfected | 1 | 1 | 1 | 1 | 1 |

The highest concentration tested of conjugate 33 at 3 mg/kg demonstrated no weight loss throughout the course of infection similar to uninfected control mice (Table 57).

TABLE 57

| Body weigh data (% reduction) | | | | | |
|---|---|---|---|---|---|
| Test article [mg/kg] | Day 0 | Day 1 | Day 2 | Day 3 | Day 4 |
| PBS [0] | 0 | −3.5 | −2.86 | −10.96 | −17.32 |
| hIgG1 Fc [3] | 0 | −2.6 | −1.3 | −9.58 | −15.6 |
| Oseltamivir [5] | 0 | −2.86 | −2.42 | −8.16 | −13.88 |
| Oseltamivir [50] | 0 | −3.78 | −2.12 | −3.22 | −5.74 |
| Baloxavir [30] | 0 | −2.38 | −2.82 | −2.6 | −0.18 |
| conjugate 33 [0.1] | 0 | −3.24 | −2.32 | −10.12 | −11.46 |
| conjugate 33 [0.3] | 0 | −2.16 | 1.34 | −3.4 | −4.36 |
| conjugate 33 [1] | 0 | −1.5 | −0.9 | −1.98 | −0.9 |
| conjugate 33 [3] | 0 | −1.7 | −1.6 | −1.9 | 0.52 |
| Uninfected | 0 | 1.02 | −0.14 | −0.16 | 2.8 |

Example 134. Efficacy of Conjugate 33 Against Influenza A (H1N1) in a Lethal Severe Combined Immunodeficiency (SCID) Mouse Model Test articles were evaluated against a lethal Influenza A influenza infection in female BALB/c scid mice (Jackson Laboratories, 6-8 weeks old). The challenge virus (A/Puerto Rico/8/1934) is a mouse-adapted isolate capable of causing lethal infections in mice. The experiment comprised 11 groups of 5 mice each. At day 0, all mice were challenged with virus at 3× the LD95 by intranasal inoculation in a volume of 30 μl (approx. 1E3 virus per mouse), after being anesthetized with a mixture of ketamine/xylazine (150 and 10 mg/kg respectively).

Groups received a single SC treatment of vehicle (PBS), hIgG1 Fc control, or conjugate 33 (3, 1, 0.3, 0.1, 0.03 mg/kg) two hours post viral challenge. A separate arm of the study consisted of 3 groups of mice treated with baloxavir marboxil (DC Chemicals, Shanghai, China) orally, twice daily, for 1 day; also starting 2 hours post viral challenge. Mice were monitored for 2 weeks and animals exceeding 20% body weight loss, or were found moribund, were scored as a mortality.

At study end (Day 14) mice receiving conjugate 33 were fully protected at all dose concentrations between 3 and 0.1 mg/kg (Table 58). Conjugate 33 only failed to protect against lethal viral challenge at the lowest tested concentration of 0.03 mg/kg. As expected, groups receiving vehicle or hIgG1 Fc were not protected. Mice treated with baloxavir were also protected, but at the significantly higher cumulative doses of 60 and 20 mg/kg, at a total dose of 6 mg/kg only 40% of mice survived to Day 14.

TABLE 58

| % Survival on Day 14. | | | | | | | | | |
|---|---|---|---|---|---|---|---|---|---|
| | hIgG1 Fc | Baloxavir | | | Conjugate 33 | | | | |
| Vehicle (PBS) | (3.0 mg/kg) | (30 mg/kg) | (10 mg/kg) | (3.0 mg/kg) | (3.0 mg/kg) | (1.0 mg/kg) | (0.3 mg/kg) | (0.1 mg/kg) | (0.03 mg/kg) |
| 0 | 0 | 100 | 100 | 40 | 100 | 100 | 100 | 100 | 0 |

The potency of conjugate 33 in this model of severe immunodeficiency was also evident based on body weights (Table 59). The lowest concentration of conjugate providing full protection based on a mortality readout was 0.1 mg/kg. At this dose level, the greatest average weight loss for the group was transient, and resulted in less than a 5% reduction (occurring on Day 2). Furthermore the difference in body weight for groups at the 1 and 3 mg/kg dose levels showed less than a 2% difference on Day 14 compared to uninfected mice.

Collectively this data demonstrates the potency of conjugate 33 by protecting lethally challenged mice with single SC doses of conjugate as low as 0.1 mg/kg. This was accomplished in a severe model of immunodeficiency with mice completely lacking T & B immune cells, which are essential in clearing influenza infections. This data supports the use of conjugate 33 to treat immune deficient patient populations.

TABLE 59

% Average body weight by day. (mg/kg).
Data only shown until the first mortality within a group.

| Day post infection | Vehicle (PBS) | hIgG1 Fc (3 mg/kg) | Baloxavir (30 mg/kg) | Baloxavir (10 mg/kg) | Baloxavir (3 mg/kg) | Conjugate 33 (3 mg/kg) | Conjugate 33 (1 mg/kg) | Conjugate 33 (0.3 mg/kg) | Conjugate 33 (0.1 mg/kg) | Conjugate 33 (0.03 mg/kg) | Uninfected |
|---|---|---|---|---|---|---|---|---|---|---|---|
| 0 | 100.0 | 100.0 | 100.0 | 100.0 | 100.0 | 100.0 | 100.0 | 100.0 | 100.0 | 100.0 | 100.0 |
| 1 | 100.0 | 99.0 | 98.9 | 91.5 | 97.3 | 99.0 | 99.6 | 98.8 | 97.6 | 99.7 | 99.5 |
| 2 | 99.0 | 100.8 | 99.1 | 97.3 | 100.1 | 100.1 | 99.9 | 100.7 | 95.8 | 98.6 | 99.8 |
| 3 | 94.0 | 93.0 | 97.0 | 96.4 | 97.4 | 100.0 | 98.9 | 97.6 | 97.0 | 96.7 | 98.8 |
| 4 | 93.0 | 89.7 | 99.1 | 95.9 | 99.0 | 101.0 | 99.8 | 99.2 | 97.8 | 94.4 | 99.9 |
| 5 | 87.0 | 84.4 | 99.1 | 97.5 | 96.6 | 99.0 | 98.6 | 96.3 | 97.4 | 93.0 | 100.9 |
| 6 | 82.0 | 80.1 | 97.9 | 97.9 | 97.0 | 100.6 | 99.7 | 99.9 | 98.7 | 91.6 | 100.2 |
| 7 | 78.0 | | 98.6 | 97.0 | 97.2 | 101.9 | 99.6 | 99.6 | 98.1 | 87.0 | 101.0 |
| 8 | | | 98.6 | 96.4 | 95.4 | 100.9 | 98.2 | 99.2 | 98.3 | 82.2 | 100.4 |
| 9 | | | 99.6 | 95.1 | 93.1 | 100.6 | 98.4 | 100.0 | 97.0 | | 100.7 |
| 10 | | | 96.0 | 95.9 | 90.5 | 98.8 | 98.8 | 98.5 | 95.8 | | 100.2 |
| 11 | | | 97.3 | 97.3 | | 99.0 | 99.3 | 98.3 | 96.0 | | 99.7 |
| 12 | | | 98.7 | 95.8 | | 99.1 | 99.4 | 98.1 | 96.3 | | 100.4 |
| 13 | | | 98.6 | 96.8 | | 98.4 | 99.0 | 97.9 | 97.3 | | 99.7 |
| 14 | | | 97.9 | 95.9 | | 99.3 | 99.3 | 98.1 | 97.8 | | 100.5 |

Example 135. Efficacy of Conjugate 33 Subcutaneously Dosed Against Influenza A/California/07/2009 (H1N1) Pdm in a Lethal Mouse Model Conjugate 33 was evaluated against a lethal IAV H1N1 influenza infection in female BALB/c mice (Charles River Laboratories, 6-8 weeks). The challenge virus (A/California/07/2009 (H1N1) pdm) is a pandemic isolate capable of causing lethal infections in mice. The experiment comprised 6 groups of 5 mice. At day 0, all mice were challenged with virus at 3× the LD95 by intranasal inoculation in a volume of 30 μl, after being anesthetized with a mixture of ketamine/xylazine (150 and 10 mg/kg respectively). Mortality and body weights were recorded daily and any animal with a 20% loss of body weight was scored as a death.

Test groups received a single subcutaneous (SC) treatment of conjugate 33, hIgG1 Fc control, or vehicle (PBS) 2 hours post viral challenge. The study design and dose levels is summarized in Table 60.

TABLE 60

Study design for Influenza A/California/07/2009 (H1N1) pdm study

| Group | Test article | Route/Schedule | Dose (mg/kg) | Dose volume (ml/kg) | # of mice |
|---|---|---|---|---|---|
| 1 | Vehicle | SC, T + 2 hrs. | na | 10 | 5 |
| 2 | hIgG1 Fc | SC, T + 2 hrs. | 1 | 10 | 5 |
| 3 | conjugate 33 | SC, T + 2 hrs. | 1 | 10 | 5 |
| 4 | conjugate 33 | SC, T + 2 hrs. | 0.3 | 10 | 5 |
| 5 | conjugate 33 | SC, T + 2 hrs. | 0.1 | 10 | 5 |
| 6 | conjugate 33 | SC, T + 2 hrs. | 0.03 | 10 | 5 |

As expected, mice receiving vehicle or the hIgG1 Fc control succumbed to infection on Days 6-7 (Table 61). However, mice treated with conjugate 33 were fully protected at 1 mg/kg, and nearly so at 0.3 (80% survival). Significant mortality with conjugate 33 was only seen at the lower dose concentrations of 0.1 and 0.03 mg/kg.

TABLE 61

Percent survival by day. (mg/kg)

| Day | Vehicle | hIgG1 Fc (1.0 mg/kg) | conjugate 33 (1.0 mg/kg) | conjugate 33 (0.3 mg/kg) | conjugate 33 (0.1 mg/kg) | conjugate 33 (0.03 mg/kg) |
|---|---|---|---|---|---|---|
| 0 | 100 | 100 | 100 | 100 | 100 | 100 |
| 1 | 100 | 100 | 100 | 100 | 100 | 100 |
| 2 | 100 | 100 | 100 | 100 | 100 | 100 |
| 3 | 100 | 100 | 100 | 100 | 100 | 100 |
| 4 | 100 | 100 | 100 | 100 | 100 | 100 |
| 5 | 40 | 20 | 100 | 100 | 60 | 80 |
| 6 | 0 | 20 | 100 | 80 | 20 | 20 |
| 7 | 0 | 0 | 100 | 80 | 0 | 0 |
| 8 | 0 | 0 | 100 | 80 | 0 | 0 |
| 9 | 0 | 0 | 100 | 80 | 0 | 0 |
| 10 | 0 | 0 | 100 | 80 | 0 | 0 |
| 11 | 0 | 0 | 100 | 80 | 0 | 0 |
| 12 | 0 | 0 | 100 | 80 | 0 | 0 |
| 13 | 0 | 0 | 100 | 80 | 0 | 0 |
| 14 | 0 | 0 | 100 | 80 | 0 | 0 |

The potency of conjugate 33 was further supported by daily body weight measurements. As expected, mice treated with vehicle or hIgG1 Fc demonstrated a steady drop in body weight until it exceeded 20%, at which time they were scored as a mortality (Table 62).

In contrast to control mice, mice receiving conjugate 33 at 1 mg/kg only demonstrated a transient drop in bodyweight of approximately 10%, peaking on Day 3 (Table 62). By both survival and body weight measurements conjugate 33 demonstrated robust protection from a lethal challenge of Influenza A/California/07/2009 (H1N1) pdm with a single 1 mg/kg dose administered SC. Activity against the clinically relevant pandemic strain used in this study supports the utility of conjugate 33 in treating serious influenza infections.

TABLE 62

| % Average body weight by day. (mg/kg). Data only shown until the first mortality within a group. | | | | | | |
|---|---|---|---|---|---|---|
| | | hIgG1 Fc | Conjugate 33 | | | |
| Day post infection | Vehicle | (1.0 mg/kg) | (1.0 mg/kg) | (0.3 mg/kg) | (0.1 mg/kg) | (0.03 mg/kg) |
| 0 | 100 | 100 | 100 | 100 | 100 | 100 |
| 1 | 99.5 | 97.9 | 96.8 | 96.7 | 98 | 98.7 |
| 2 | 97.1 | 97.2 | 99.5 | 99.2 | 98 | 98.4 |
| 3 | 86.5 | 86.0 | 89.7 | 89.6 | 87.6 | 88.8 |
| 4 | 80.3 | 80.3 | 91.6 | 88.5 | 81.3 | 81.9 |
| 5 | 76.2 | 76.6 | 92.9 | 91.0 | 76.8 | 77.9 |
| 6 | | | 94.7 | 90.5 | | |
| 7 | | | 94.2 | | | |
| 8 | | | 95.4 | | | |
| 9 | | | 98.0 | | | |
| 10 | | | 96.8 | | | |
| 11 | | | 98.8 | | | |
| 12 | | | 97.7 | | | |
| 13 | | | 100.1 | | | |
| 14 | | | 100.5 | | | |

Example 136. Efficacy of Conjugate 33 Intravenously (IV) Dosed Against Influenza A/Puerto Rico/8/1934 (H1N1) in a Lethal Mouse Model of Delayed Treatment Conjugate 33 was evaluated against a lethal influenza A (H1N1) infection in female BALB/c mice (Charles River Laboratories, 6-8 weeks). The challenge virus (A/Puerto Rico/8/1934) is a mouse-adapted isolate capable of causing lethal infections in mice. At day 0, all mice were challenged with virus at 3× the LD95 by intranasal inoculation in a volume of 30 μl, after being anesthetized with a mixture of ketamine/xylazine (150 and 10 mg/kg respectively). Mortality and body weights were recorded daily and any animal with a 20% loss of body weight was scored as a death.

The study design is detailed in Table 63, and consists of multiple arms. The control arm comprises vehicle (PBS) and hIgG1 Fc only groups, dosed 24 hours after viral challenge (an uninfected group was also part of this arm). The second arm consisted of oseltamivir dosed at 4× its humanized dose, with initiation of treatment delayed for 24, 48, or 72 hours. The final 3 arms consisted of conjugate 33 administered as single IV doses of 10, 3, or 1 mg/kg; each being dosed on the same schedule as the oseltamivir arm above.

As expected, vehicle and hIgG1 Fc were not protective when dosed 24 hours after viral challenge and resulted in complete mortality by Day 7. In our hands, oseltamivir, even at 4× the humanized dose (200 mg/kg cumulative dose) was only partially efficacious when dosing was delayed 24 hours (Table 64; 40% survival). However, conjugate 33 was fully protective at all concentrations (10, 3, & 1 mg/kg) at the same 24 hour dose schedule.

When dosing was delayed a full 48 hours after viral challenge oseltamivir was no longer efficacious (0% survival) while conjugate 33 was 80% protective at doses of 10 and 3 mg/kg. When dosing was delayed until 72 hours, only the 10 mg/kg dose of conjugate 33 demonstrated partial protection (40%). The efficacy of conjugate 33 was also evident based on daily body weight measurements (Table 65). This was especially significant in the T+24 hours groups where less than a 3% reduction was observed for any conjugate 33 group, which was transient and occurred on Day 1. In this study, conjugate 33 is more efficacious than oseltamivir, an approved treatment for influenza.

TABLE 63

| Study design | | | | | | | |
|---|---|---|---|---|---|---|---|
| Group | Influenza A strain | Test Article | Route, Schedule | First dose (hours) | Dose (mg/kg) | Dose volume (ml/kg) | N (balb/c) |
| 1 | A/PR/8/34 | PBS | IV, single | T + 24 | — | 5 | 5 |
| 2 | (H1N1) | hIgG1 Fc | IV, single | T + 24 | 10 | 5 | 5 |
| 3 | 3E2 | Oseltamivir | PO, bid × | T + 24 | 20 | 10 | 5 |
| 4 | PFU/mouse | | 5 days | T + 48 | | | |
| 5 | | | | T + 72 | | | |
| 6 | | AVC-076 | IV, single | T + 24 | 10 | 5 | 5 |
| 7 | | | | T + 48 | | | |
| 8 | | | | T + 72 | | | |
| 9 | | AVC-076 | IV, single | T + 24 | 3 | 5 | 5 |
| 10 | | | | T + 48 | | | |
| 11 | | | | T + 72 | | | |
| 12 | | AVC-076 | IV, single | T + 24 | 1 | 5 | 5 |
| 13 | | | | T + 48 | | | |
| 14 | | | | T + 72 | | | |
| 15 | | | Uninfected BW control | | | | |

TABLE 64

| % Survival by day. Test article/Dose/Time of treatment initiation | | | | | | | | |
|---|---|---|---|---|---|---|---|---|
| | | | Oseltamivir | | | Conjugate 33 | | |
| Day post infection | Vehicle na T + 24 hrs. | hIgG1 Fc 10 mpk T + 24 hrs. | 20 mpk, bid × 5 T + 24 hrs. | 20 mpk, bid × 5 T + 48 hrs. | 20 mpk, bid × 5 T + 72 hrs. | 10 mpk, single T + 24 hrs. | 10 mpk, single T + 48 hrs. | 10 mpk, single T + 72 hrs. |

TABLE 64-continued

% Survival by day. Test article/Dose/Time of treatment initiation

| | | | | | | | | |
|---|---|---|---|---|---|---|---|---|
| 0 | 100 | 100 | 100 | 100 | 100 | 100 | 100 | 100 |
| 1 | 100 | 100 | 100 | 100 | 100 | 100 | 100 | 100 |
| 2 | 100 | 100 | 100 | 100 | 100 | 100 | 100 | 100 |
| 3 | 100 | 100 | 100 | 100 | 100 | 100 | 100 | 100 |
| 4 | 100 | 100 | 100 | 100 | 100 | 100 | 100 | 100 |
| 5 | 100 | 100 | 100 | 100 | 100 | 100 | 100 | 100 |
| 6 | 60 | 100 | 100 | 100 | 100 | 100 | 100 | 60 |
| 7 | 0 | 0 | 100 | 100 | 20 | 100 | 100 | 40 |
| 8 | 0 | 0 | 100 | 100 | 0 | 100 | 80 | 40 |
| 9 | 0 | 0 | 60 | 60 | 0 | 100 | 80 | 40 |
| 10 | 0 | 0 | 40 | 0 | 0 | 100 | 80 | 40 |
| 11 | 0 | 0 | 40 | 0 | 0 | 100 | 80 | 40 |
| 12 | 0 | 0 | 40 | 0 | 0 | 100 | 80 | 40 |
| 13 | 0 | 0 | 40 | 0 | 0 | 100 | 80 | 40 |
| 14 | 0 | 0 | 40 | 0 | 0 | 100 | 80 | 40 |

| | Conjugate 33 | | | Conjugate 33 | | | |
|---|---|---|---|---|---|---|---|
| Day post infection | 3 mpk, single T + 24 hrs. | 3 mpk, single T + 48 hrs. | 3 mpk, single T + 72 hrs. | 1 mpk, single T + 24 hrs. | 1 mpk, single T + 48 hrs. | 1 mpk, single T + 72 hrs. | Un-infected na na |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 100 |
| 5 | 100 | 100 | 100 | 100 | 80 | 100 | 100 |
| 6 | 100 | 100 | 80 | 100 | 80 | 80 | 100 |
| 7 | 100 | 80 | 0 | 100 | 60 | 40 | 100 |
| 8 | 100 | 80 | 0 | 100 | 40 | 0 | 100 |
| 9 | 100 | 80 | 0 | 100 | 40 | 0 | 100 |
| 10 | 100 | 80 | 0 | 100 | 40 | 0 | 100 |
| 11 | 100 | 80 | 0 | 100 | 40 | 0 | 100 |
| 12 | 100 | 80 | 0 | 100 | 40 | 0 | 100 |
| 13 | 100 | 80 | 0 | 100 | 40 | 0 | 100 |
| 14 | 100 | 80 | 0 | 100 | 40 | 0 | 100 |

TABLE 65

Body Weight Data (gm). mpk = mg/kg. Data only shown until the first death within a group. Test article/Dose/Time of treatment initiation

| | | | Oseltamivir | | | Conjugate 33 | | |
|---|---|---|---|---|---|---|---|---|
| Day post infection | Vehicle na T + 24 hrs. | hIgG1 Fc 10 mpk T + 24 hrs. | 20 mpk, bid × 5 T + 24 hrs. | 20 mpk, bid × 5 T + 48 hrs. | 20 mpk, bid × 5 T + 72 hrs. | 10 mpk, single T + 24 hrs. | 10 mpk, single T + 48 hrs. | 10 mpk, single T + 72 hrs. |
| 0 | 100 | 100 | 100 | 100 | 100 | 100 | 100 | 100 |
| 1 | 99.3 | 98.8 | 96.4 | 97.5 | 98.2 | 97.6 | 97.7 | 98.5 |
| 2 | 103.9 | 101 | 100.7 | 101.2 | 102.6 | 102.1 | 101.7 | 100.1 |
| 3 | 96.9 | 97.4 | 95.5 | 97.5 | 95.6 | 102.3 | 96.2 | 95.1 |
| 4 | 88.7 | 90.1 | 92.6 | 89.7 | 87.7 | 102.3 | 88.4 | 88.8 |
| 5 | 81.7 | 83.9 | 92.2 | 88.6 | 81.6 | 101.5 | 88.1 | 82.7 |
| 6 | 77.3 | 79.3 | 91.8 | 86 | 78.6 | 102.6 | 91.1 | 80.4 |
| 7 | | | 87.8 | 81 | | 101.9 | 91.1 | |
| 8 | | | 83.5 | 75.8 | | 101.5 | 91.3 | |
| 9 | | | 81.1 | | | 102.2 | | |
| 10 | | | | | | 102.5 | | |
| 11 | | | | | | 102.4 | | |
| 12 | | | | | | 100.9 | | |
| 13 | | | | | | 101 | | |
| 14 | | | | | | 102.2 | | |

| | Conjugate 33 | | | Conjugate 33 | | | |
|---|---|---|---|---|---|---|---|
| | 3 mpk, | 3 mpk, | 3 mpk, | 1 mpk, | 1 mpk, | 1 mpk, | Un- |

TABLE 65-continued

Body Weight Data (gm). mpk = mg/kg. Data only shown until the first death within a group. Test article/Dose/Time of treatment initiation

| Day post infection | single T + 24 hrs. | single T + 48 hrs. | single T + 72 hrs. | single T + 24 hrs. | single T + 48 hrs. | single T + 72 hrs. | infected na na |
|---|---|---|---|---|---|---|---|
| 0 | 100 | 100 | 100 | 100 | 100 | 100 | 100 |
| 1 | 97.1 | 98.3 | 98.7 | 98.3 | 99.4 | 99.4 | 99.5 |
| 2 | 102 | 102.5 | 99.4 | 104.2 | 102 | 101.4 | 101.7 |
| 3 | 100.6 | 95.9 | 97.6 | 102.3 | 96.9 | 98.6 | 105.8 |
| 4 | 100 | 87.8 | 88.6 | 100 | 89.2 | 89.7 | 105 |
| 5 | 99 | 85.3 | 81.7 | 101.2 | 83.7 | 83.2 | 105.5 |
| 6 | 101.4 | 87.1 | 77.5 | 103.3 | | 78.7 | 104.9 |
| 7 | 102.3 | 86.1 | | 102.1 | | | 103.5 |
| 8 | 101.1 | | | 103.2 | | | 102.9 |
| 9 | 102.1 | | | 104.1 | | | 102.9 |
| 10 | 101.6 | | | 105 | | | 103.3 |
| 11 | 102.1 | | | 103.9 | | | 104.3 |
| 12 | 101.6 | | | 103.4 | | | 102.5 |
| 13 | 101.8 | | | 103.5 | | | 102.5 |
| 14 | 103.6 | | | 104 | | | 103.1 |

Example 137. Synthesis of Conjugate 38 (Int-73), Conjugate 39 (Int-74), Conjugate 40 (Int-75), and Conjugate 41 (Int-76)

A 15-ml sterile centrifuge tube is charged with sodium ascorbate (68.3 mg, 0.345 mmol), BTTAA (11.9 mg, 0.0276 mmol), product from Examples 114 (Int-73), 115 (Int-74), 116 (Int-75), or 117 (Int-76) (0.00953 mmol) and PBS 7.4 (1 ml). The reagents were vortexed until homogeneous then mixed with azido Fc (50 mg, 0.0008624 mmol, described in Example 124, SEQ ID NO: 64) followed by a solution of CuSO4 (1.1 mg, 0.0069 mmol) in water (0.5 ml). The mixture is rotated for 12 hours then purified by affinity chromatography over a protein A column, followed size exclusion chromatography. Conjugates are characterized by Maldi TOF analysis (DAR typically=4.5). Yields are typically 50%.

Example 138. Synthesis of Int-79

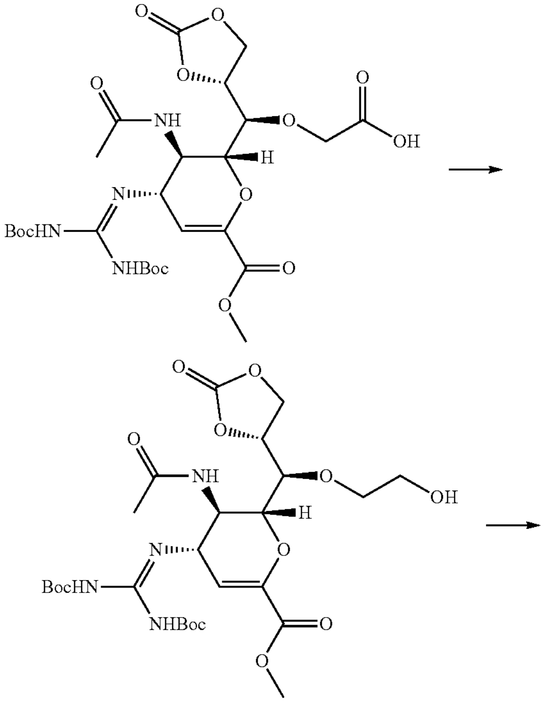

-continued
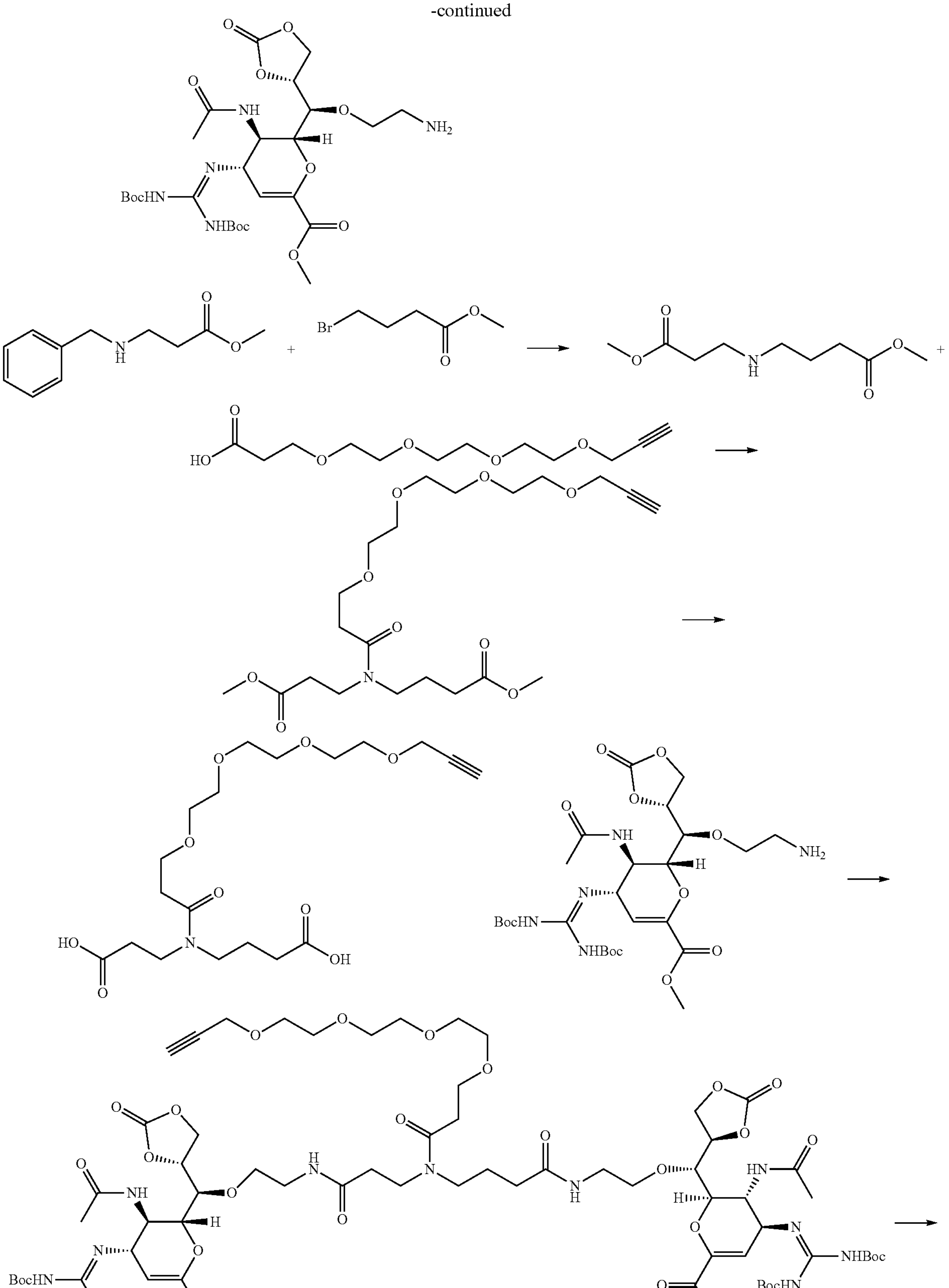

Step a.

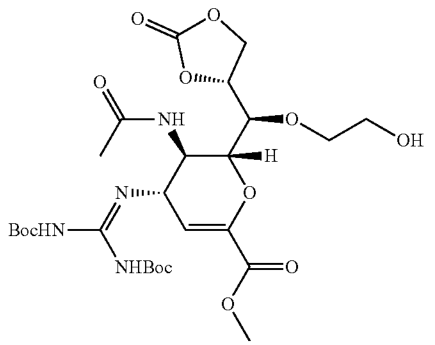 [SMILES: COC(=O)C1=C[C@H](N=C(NC(=O)OC(C)(C)C)NC(=O)OC(C)(C)C)[C@@H](NC(C)=O)[C@H]([C@H](OCCO)[C@H]2COC(=O)O2)O1]

Zanamavir-ether-acid (0.90 g, 1.43 mmol, Example 31) and N-methyl morpholine (0.23 mL, 2.14 mmol) were dissolved in THE (35 mL) and cooled to 0° C. (ice water bath) under an atmosphere of nitrogen. Isobutyl chloroformate (0.24 mL, 1.85 mmol, in 2 mL DCM) was added dropwise, by way of syringe over a 5 minute period. The mixture was stirred at 0° C. for 30 minutes then 15 min at ambient temperature, and then cooled to 0° C. Sodium borohydride (540 mg, 14.3 mmol, dissolved in 5 mL of methanol) was added, dropwise over 5 minutes. The reaction was stirred for 15 minutes at which point all starting material had been consumed (by LC/MS). A few drops (~1 mL) of glacial acetic acid was added to acidify the mixture (pH-5). Dilute with ethyl acetate and water and extract into ethyl acetate (3×). The organic layer was washed with brine, and the organic extracts were dried over sodium sulfate, and concentrated on the rotary evaporator. The crude material was purified by silica gel chromatography (loaded on celite first) (0-10% methanol in DCM, 30 min). Yield 0.66 g, 75%. Ion found by LCMS: $[M+H]^+$=617.2.

Step b.

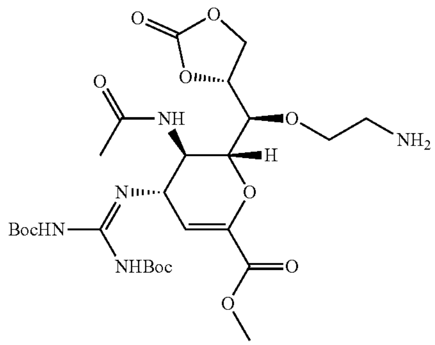 [SMILES: COC(=O)C1=C[C@H](N=C(NC(=O)OC(C)(C)C)NC(=O)OC(C)(C)C)[C@@H](NC(C)=O)[C@H]([C@H](OCCN)[C@H]2COC(=O)O2)O1]

To a stirring mixture of alcohol (0.66, 1.1 mol, in 20 mL $CH_2Cl_2$), was added triethylamine (0.30 mL, 1.3 mmol). The mixture was cooled to 0° C. (ice-water bath) under 1 atmosphere of nitrogen and mesyl chloride (150 mg, 1.3 mmol) was added, dropwise over 5 minutes by way of syringe. The ice bath was removed and the reaction was stirred for 45 minutes. The mixture was diluted with saturated, aqueous sodium bicarbonate, extracted into DCM (3×). The combined organic extracts were washed with brine, dried over sodium sulfate and concentrated on the rotary evaporator. Ion found by LCMS: [M+H]+=695.2. The intermediate was taken to the next step without purification.

The zanamvir mesylate was stirred in DMF at 80° C. with 3 eq of sodium azide for 5 hours. The mixture was diluted with water, extracted into DCM (3×). The combined organic extracts were washed with brine, dried over sodium sulfate and concentrated. Ion found by LCMS: $[M+H]^+$=695.2. The azide was taken to the next step without purification.

The zanamavir azide (670 mg, 1.04 mmol) was stirred in methanol (20 mL) in the presence of Lindlar catalyst (300 mg) under 1 atmosphere of hydrogen gas for 12 hours. The mixture was filtered through celite and concentrated to afford the title compound as a clear oil. The amine was taken to the next step without purification. Yield 0.37 g, 54%, 3 steps. Ion found by LCMS: $[M+H]^+$=616.2.

Step c.

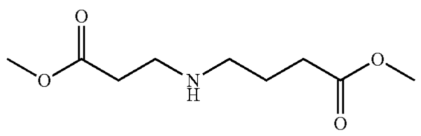

Methyl 3-(benzylamino)propanoate (1 g, 5.2 mmol), methyl 4-bromobutanoate (1.2 g, 6.2 mmol), and diisopropylethylamine (1.34 mL, 7.8 mmol) were stirred in DMF (5 mL) at 65° C. for 4 hours. Most of the solvent was removed by rotary evaporator and the crude material was purified by silica gel chromatography (Isco, 0 to 9% methanol in DCM, 30 minute gradient) to afford the benzyl protected intermediate as a clear oil. The benzyl protected intermediate was stirred in methanol (20 mL) under 1 atmosphere of hydrogen gas in the presence of 20% palladium hydroxide on carbon (300 mg) for 12 hours. The mixture was filtered through celite and concentrated to afford the title compound as a clear oil. Yield 0.72 g, 69%. Ion found by LCMS: $[M+H]^+$=204.2.

Step d.

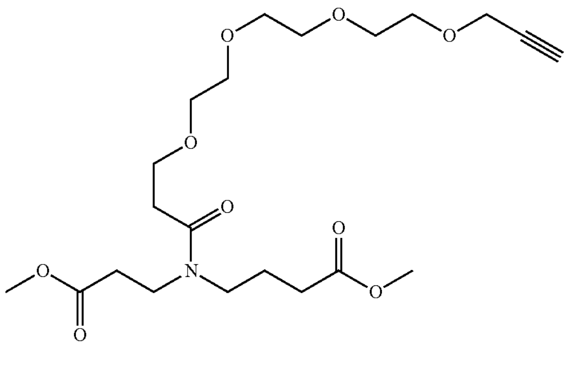 [SMILES: C#CCOCCOCCOCCOCCC(=O)N(CCCC(=O)OC)CCC(=O)OC]

The step-c product (0.70 g, 2.16 mmol), propargyl PEG-4 acid (0.63 mg, 2.38 mmol) HATU (1.26 g, 3.24 mmol) in DMF (2 mL) were stirred at room temperature following by addition of DIEA (1.15 mL, 6.49 mmol). The reaction mixture was stirred for 2 hours then purified by reverse phase liquid chromatography (Isco, 5 to 50% acetonitrile and water with 0.1% TFA as modifier). Yield 840 mg, 87%. Ion found by LCMS $[M+H]^+$=446.2.

Step e.

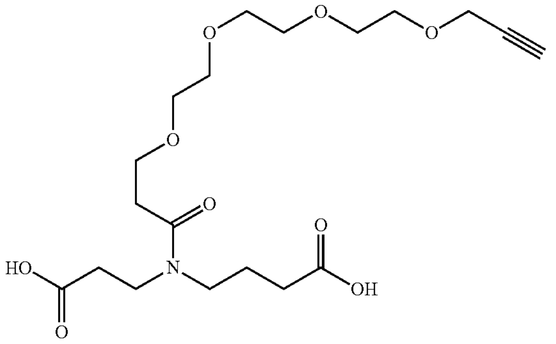 [SMILES: C#CCOCCOCCOCCOCCC(=O)N(CCCC(=O)O)CCC(=O)O]

A solution of step-d product (840 mg, 1.85 mmol) and LiOH (113.1 mg, 4.72 mmol) in $H_2O$:MeOH (1:2, 9 mL) was stirred at room temperature for 2 hours. Then the reaction was acidified with TFA. The resulted solution was concentrated then purified by reverse phase liquid chromatography (Isco, 0% to 20% acetonitrile and water). Yield 454.5 mg, 59%. Ion found by LCMS $[M+H]^+$=418.2.

Step f.

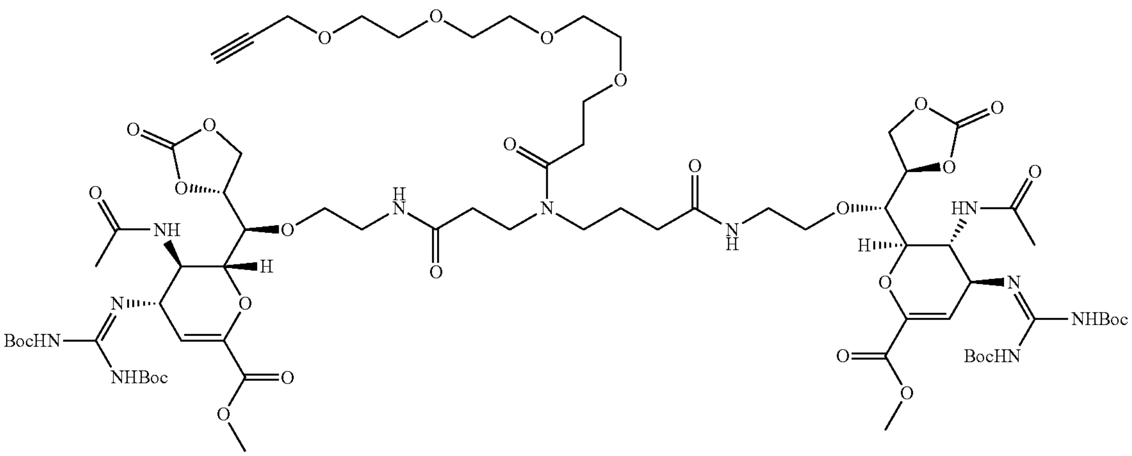 [SMILES: C#CCOCCOCCOCCOCCC(=O)N(CCCC(=O)NCCO[C@@H]([C@@H]1OC(C(=O)OC)=C[C@H](N=C(NC(=O)OC(C)(C)C)NC(=O)OC(C)(C)C)[C@H]1NC(C)=O)[C@H]1COC(=O)O1)CCC(=O)NCCO[C@@H]([C@@H]1OC(C(=O)OC)=C[C@H](N=C(NC(=O)OC(C)(C)C)NC(=O)OC(C)(C)C)[C@H]1NC(C)=O)[C@H]1COC(=O)O1]

To a solution of step-b product (334.7 mg, 0.52 mmol), step-e product (102 mg, 0.24 mmol) and HATU (273.25 mg, 0.704 mmol) in anhydrous DMF (3 mL) at room temperature was added DIEA (217 mg, 16.4 mmol). The resulting mixture was stirred for 1 hour then was purified by RPLC (20% to 100% methanol and water without modifier). Yield 206.5 mg, 55%. Ion found by LCMS [(M+2H)/2]+=806.8.

Step g.

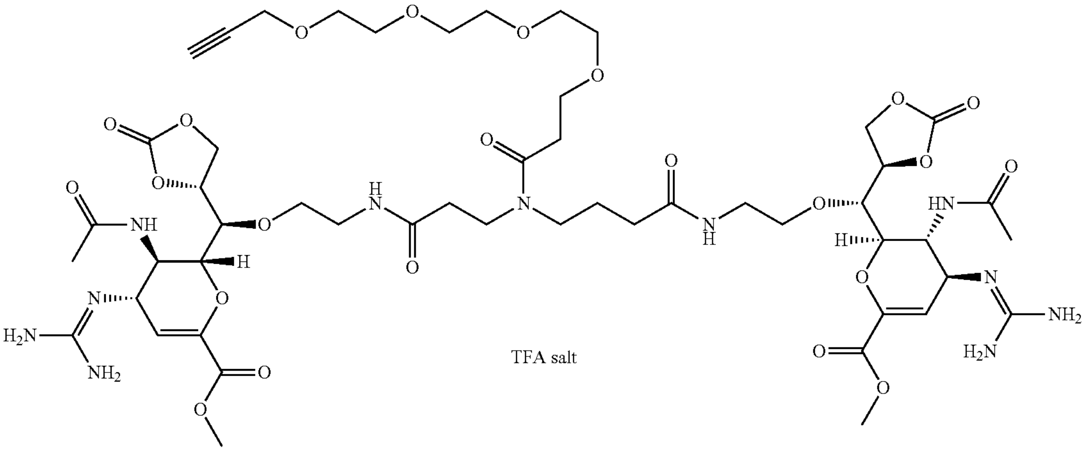 [SMILES: C#CCOCCOCCOCCOCCC(=O)N(CCCC(=O)NCCO[C@@H]([C@@H]1OC(C(=O)OC)=C[C@H](N=C(N)N)[C@H]1NC(C)=O)[C@H]1COC(=O)O1)CCC(=O)NCCO[C@@H]([C@@H]1OC(C(=O)OC)=C[C@H](N=C(N)N)[C@H]1NC(C)=O)[C@H]1COC(=O)O1]

TFA salt

The step-f product (206.5 mg, 0.128 mmol) and TFA (3 mL) in $CH_2Cl_2$ (5 mL) was stirred at room temperature overnight, then concentrated under reduced pressure. The resulting residue was purified by semi-preparative HPLC (0% to 30% acetonitrile and water with 0.1% TFA as modifier). Yield 144.5 mg, 69%. Ion found by LCMS [(M+2H)/2]+=606.8.

Step h.

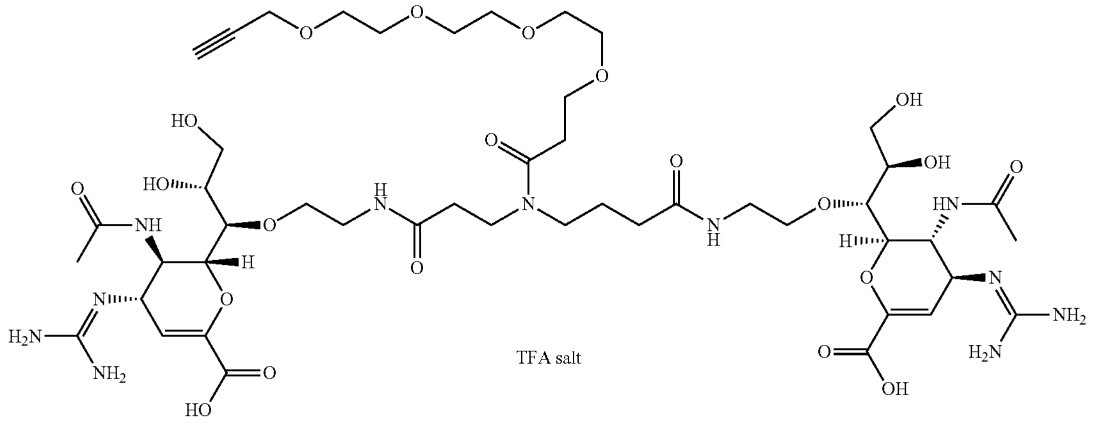 [SMILES: C#CCOCCOCCOCCOCCC(=O)N(CCCC(=O)NCCO[C@@H]([C@@H]1OC(C(=O)O)=C[C@H](N=C(N)N)[C@H]1NC(C)=O)[C@H](O)CO)CCC(=O)NCCO[C@@H]([C@@H]1OC(C(=O)O)=C[C@H](N=C(N)N)[C@H]1NC(C)=O)[C@H](O)CO]

To a solution of the step-g product (144.5 mg, 0.119 mmol) in MeOH (9 mL) and water (3 mL) was added LiOH (18 mg, 0.75 mmol). The resulting solution was stirred at room temperature for 1 hour, then acidified with TFA and concentrated under reduced pressure. The residue was purified by semi-preparative HPLC (0% to 25% acetonitrile and water, using 0.1% TFA as modifier). Yield 45 mg, 28%. Ions found by LCMS [(M+2H)/2]+=566.8.

Example 139. Synthesis of Conjugate 42

A solution of azido functionalized Fc (50 mg, 5.4 mL, 0.859 μmol, Example 124, SEQ ID NO: 18) was added to a 10 mL centrifuge tube containing alkyne derivatized small molecule (7.87 mg, 0.057 mmol, Example 138). After gently shaking to dissolve all solids, the mixture was added to 3 mL premixed solution of L-ascorbic acid sodium (0.68 mg, 0.34 mmol, 0.25 M), copper (II) sulfate (1.1 mg, 0.0069 mmol, 0.005 M) and BTTAA (11.8 mg, 0.027 mmol, 0.02 M) in PBS 7.4 buffer. The resulting solution was gently rotated overnight. It was purified by affinity chromatography over a protein A column, followed by size exclusion chromatography (See general conjugate purification protocol). Maldi TOF analysis of the purified final product gave an average mass of 63623 Da (DAR 3.8). Yield 36.01 mg, 72%.

Example 140. Synthesis of Int-80

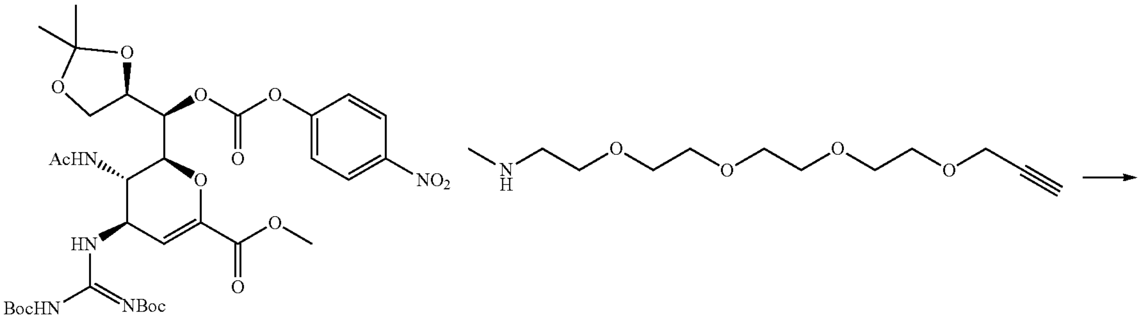

-continued

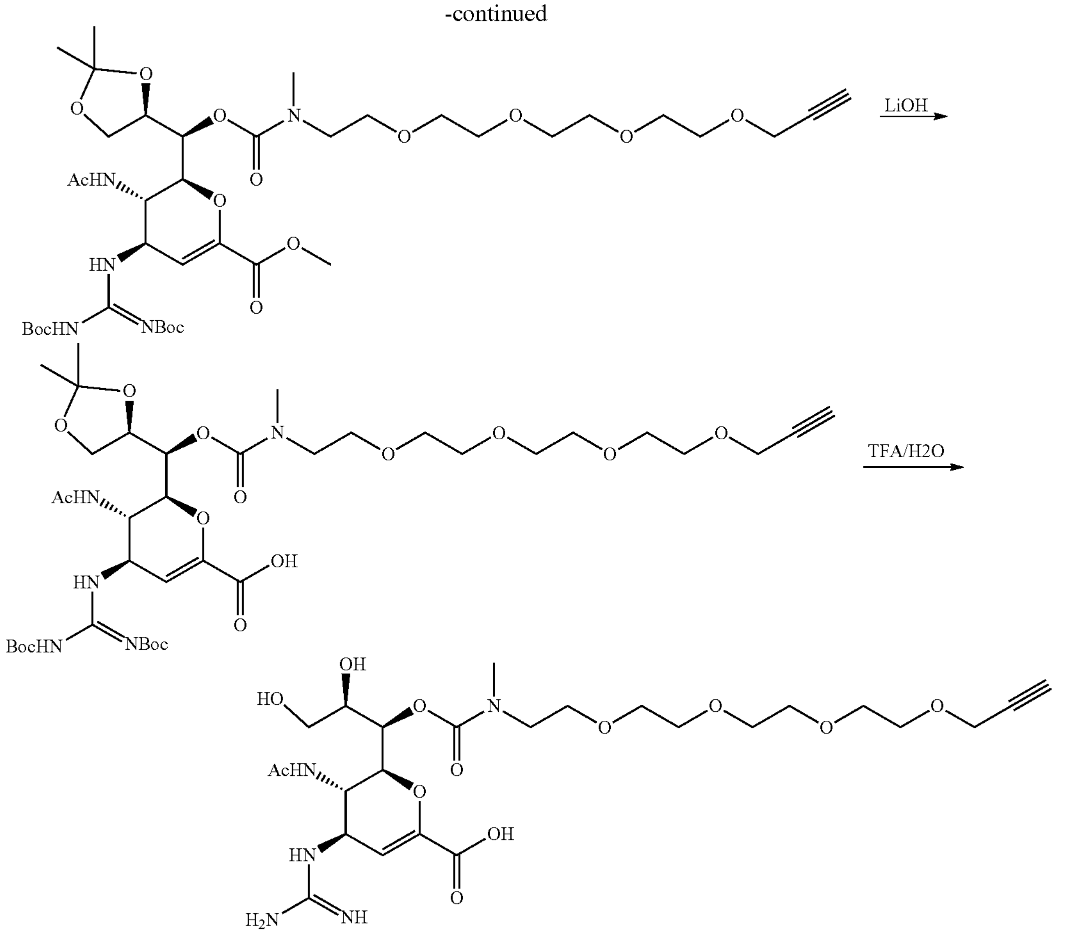

Step a.

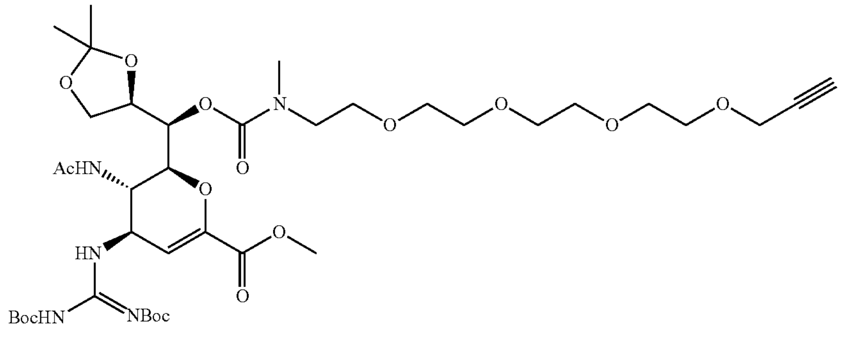

To a solution of the p-nitrophenyl carbonate of Zanamivir (0.3 g. 0.4 mmol, Example 103) in anhydrous dichloromethane (5 ml) was added a propargyl-PEG4-methylamine (0.11 g, 0.44 mmol) and DIPEA (0.14 ml, 1.0 mmol) in anhydrous DMF (5 ml). The reaction was stirred at room temperature overnight, then concentrated and purified by flash chromatography eluting with 0% to 10% methanol/dichloromethane. Yield 0.28 g, 81%. Ions found by LCMS: $(M+H)^+$ =858.4, $(M-Boc)+H^+$=758.4.

Step b.

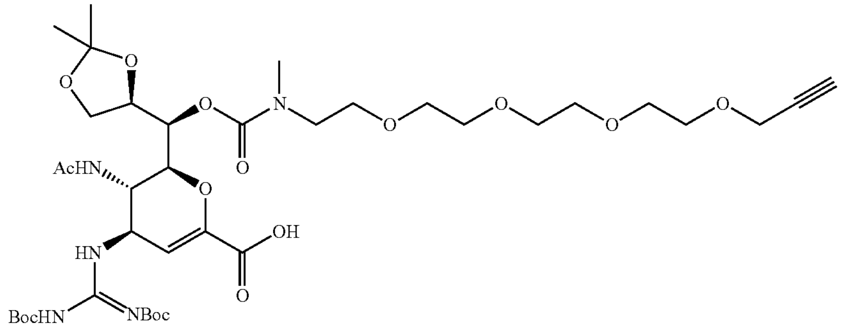

Product from the previous step (280 mg, 0.2 mmol) was dissolved into 2 ml MeOH and 2 ml THF, then treated with a solution of lithium hydroxide (24 mg, 1 mmol) dissolved in 2 ml water. The reaction was stirred for 10 min at room temperature at which time HPLC showed the reaction was complete. The pH of the reaction was adjusted to the value of 5 to 6 by using Amberlite IRN-77 ion exchange resin, then filtered to remove the resin. The crude filtrate was evaporated to dryness under a vacuum and used in the next step with purification, and the yield was quantitative. Ion(s) found by LCMS: $(M+H)^+=844.4$, $(M\text{-}Boc+H)^+=744.4$.

Step c.

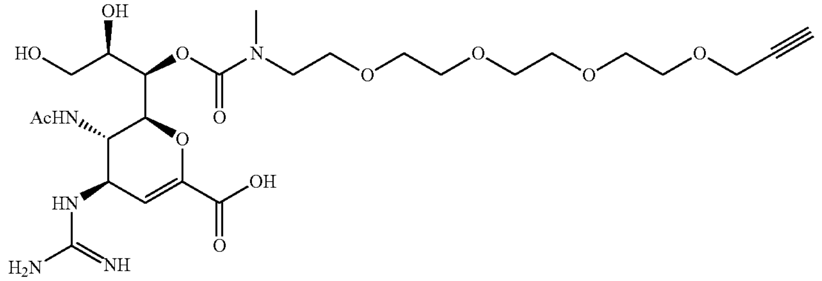 [SMILES: C#CCOCCOCCOCCOCCN(C)C(=O)O[C@@H]([C@H]1OC(C(=O)O)=C[C@@H](NC(=N)N)[C@@H]1NC(C)=O)[C@H](O)CO]

The step-b product was dissolved into 2 ml dichloromethane and 2 ml TFA, and stirred at room temperature. The progress of the reaction was monitored by LCMS. After the completion of the reaction (6h), the solution was stripped to dryness and then dissolved in 2 ml water and 2 ml acetonitrile. The resulting solution was stirred for another 2 hour at room temperature at which time LCMS show complete deprotection of the acetonide protecting groups. This mixture was concentrated and purified by reverse phase liquid chromatography (RPLC) using an Isco CombiFlash liquid chromatograph eluted with 5% to 40% acetonitrile/water with 0.1% TFA as the modifier. Yield 180 mg, 78.0%. Ion(s) found by LCMS: $(M+H)^+=604.2$.

Example 141. Stability Data for Int-80 Compared to Int-4

Figure 66:
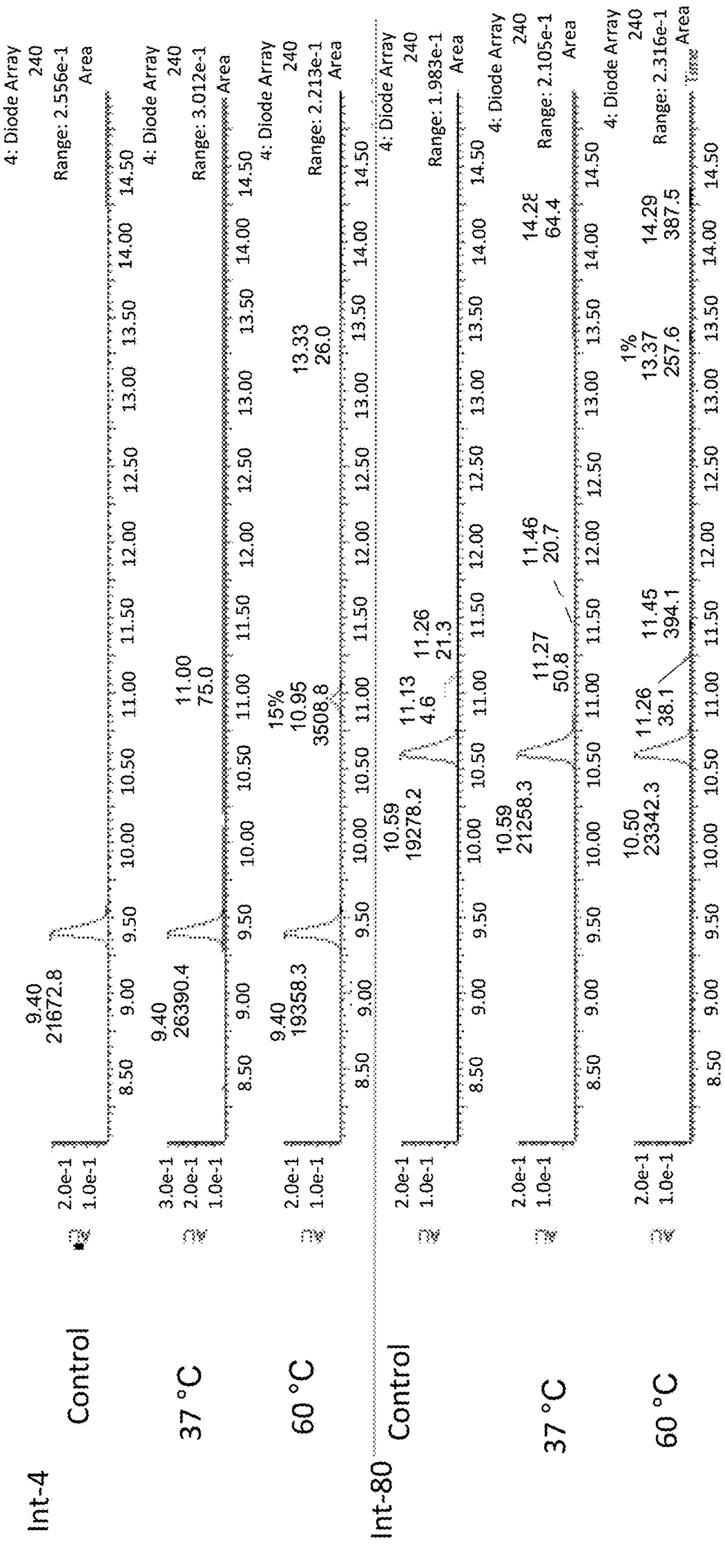
FIG. 66 is a chromatograph showing the stability of Int-80 compared to Int-4 on day 7 of incubating at 37° C. and 60° C. This study was performed as describe in Example 142.

Int-80 (Example 140) and Int-4 (Example 13) were solubilized to 10 mg/mL in deionized water and then diluted 1:10 into 1×PBS to a final concentration of 1 mg/mL. Samples were incubated at 37° C. or 60° C. for 1 week. A 25 uL aliquot was diluted into 75 uL of water for HPLC analysis. Using a Waters Acquity H-Class UPLC with a Phenomenex Biozen PS-C18 column (150×2.1 mm, 1.6 um) a gradient of 0.1% formic acid in water to 0.1% formic acid in acetonitrile was run as follows: 5% B for 0-1 min, 5-20% B from 1-20 min. Detection was at 240 nm using a diode array detector. Int-80 had less than 1% degredation over a week at 60° C., while Int-4 showed 15% degredation over the same time period (FIG. 66)

Example 142. Synthesis of Conjugate 43

Preparation of the Click reagent solution: 0.0050M CuSO4 in PBS×1 buffer solution: 10.0 mg CuSO4 was dissolved in 12.53 mL PBS×1, than took 10.00 mL this CuSO4 solution and added 86.1 mg BTTAA and 495.3 mg Na Ascorbate to give the Click reagent solution (0.0050M CuSO4, 0.020M BTTAA and 0.25M Sodium Ascorbate).

A solution of azido functionalized Fc (78.0 mg, 4.535 mL, 1.35 μmol, Example 124, SEQ ID NO: 64) was added to a 15 mL centrifuge tube containing alkyne derivatized small molecule (13.2 mg, 8.88 umol, Int-80, Example 140). After gently shaking to dissolve all solids, the mixture was added with 2.153 mL of above Click reagent solution of (L-ascorbic acid sodium, 0.25 M, 106.6 mg, 0.538 mmol, copper (II) sulfate 0.0050M, 1.72 mg, 0.0107 mmol, and BTTAA 0.020M, 18.5 mg, 0.0431 mmol). The resulting mixture was gently rotated for 6 hours at ambient temperature. It was purified by affinity chromatography over a protein A column, followed size exclusion chromatography (See conjugate purification protocol). Maldi TOF analysis of the purified final product gave an average mass of 64,012 Da (DAR=7.0). Yield 50.3 mg, 62% yield.

Example 143. Synthesis of Int-81

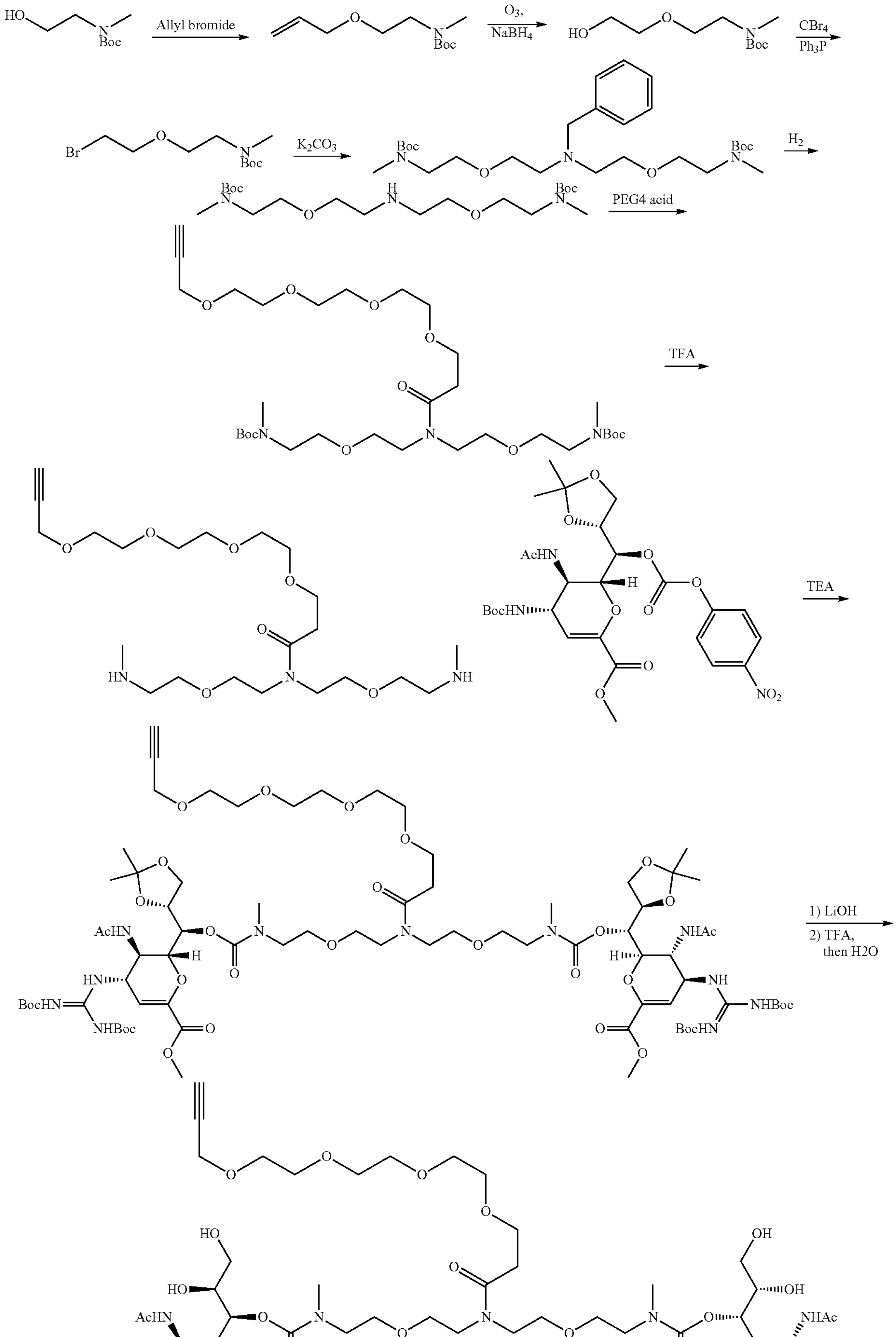
Allyl bromide
O3,
NaBH4
CBr4
Ph3P
K2CO3
H2
PEG4 acid
TFA
TEA
1) LiOH
2) TFA,
then H2O Step a.

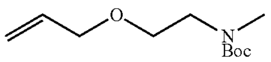

To a well-stirred solution of N-Boc-N-Me-glycinol (3.5 g, 20 mmol) in DMSO (20 mL) cooled with an ice-water bath was add allyl bromide (3.6 g, 30.0 mmol), followed by finely ground KOH powder (3.5 g, 30.0 mmol) over 15 minutes. The resulting solution was stirred for overnight at room temperature. The resulting mixture was partitioned between 5% aq. HOAc (50 mL) and ethyl acetate (200 ml). The organic layer was separated, washed with brine, dried with sodium sulfate, filtered, and concentrated, then purified by flash chromatography eluting with 10% to 80% ethyl acetate/hexane. Yield of product 4.1 g, 95%. Ion(s) found by LCMS: M+H=216.3.

Step b.

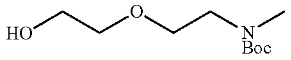

Ozone was bubbled through a solution of the compound from step a (8.0 g, 37 mmol) in MeOH (50 mL) and DCM (50 ml) at −78° C. until the appearance of a light blue color. Unreacted ozone was removed by bubbling with oxygen for 10 minutes before the addition of $NaBH_4$ (1.6 g, 40 mmol) in small portion over 10 minutes. After all $NaBH_4$ was added the mixture was gradually warmed to room temperature. The resulting solution was partitioned between ethyl acetate (100 ml) and brine (50 ml). The organic layer was separated, washed with brine, dried with sodium sulfate, filtered, concentrated to an oil, and then purified by flash chromatography eluting with 10% to 80% ethyl acetate/dichloromethane. Yield of product 5.0 g, 62%. Ion(s) found by LCMS: M+H=220.2.

Step c.

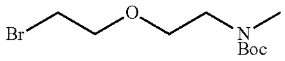

To a solution of the product (4.4 g, 20 mmol) from the previous step and $CBr_4$ (10.0 g, 30.0 mmol) in DCM (50 mL) at 0° C. was added $PPh_3$ (8.0 g, 30 mmol) slowly over 15 minutes (exothermic). During the course of the addition the internal temperature was kept below 30° C. After addition of $PPh_3$ the reaction was stirred overnight at room temperature. The crude reaction was concentrated to an oil then purified by normal phase chromatography, eluting with 10% ethyl acetate/hexanes to 80% ethyl acetate/hexanes. Fractions containing oil droplets on the inside of the collection tubes were combined and concentrated to a colorless oil. 4.0 g, 70.5%. Ion(s) found by LCMS: M+H=282.1.

Step d.

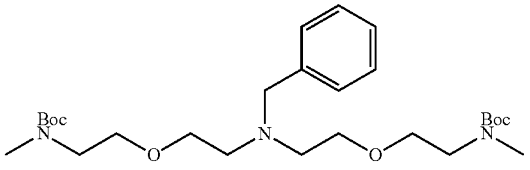

A solution of the step c product (4 g, 14 mmol), benzylamine (0.60 g, 5.7 mmol), and $K_2CO_3$ (2.35 g, 17 mmol) in DMF (20 mL) were heated in an oil bath at 75° C. for 8h. The mixture was filtered, concentrated, and purified by RPLC (5% ACN/water to 100% ACN). Yield 2.1 g, 72.7%.

Step e.

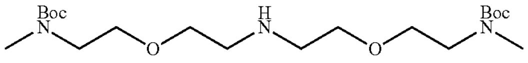

To a solution of the step-d product (1.3 g, 2.0 mmol) dissolved in $CHCl_3$/EtOH (1:20, 20 mL) was added 20% $Pd(OH)_2$/C (0.50 g). The reaction was stirred overnight under hydrogen from a balloon at ambient temperature. The reaction mixture was filtered through a Celite pad, then concentrated by way of rotary evaporator and carried to the subsequent step without further purification.

Step f.

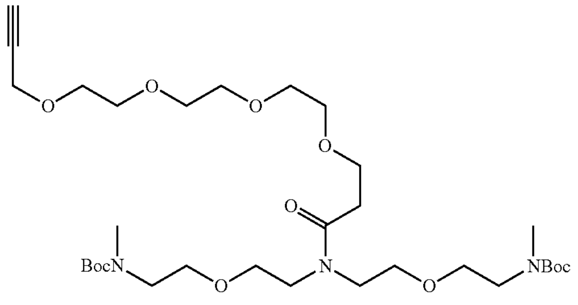 [SMILES: C#CCOCCOCCOCCOCCC(=O)N(CCOCCN(C)C(=O)OC(C)(C)C)CCOCCN(C)C(=O)OC(C)(C)C]

The step-e product was dissolved in 10 mL of DMF, then treated with propargyl PEG4 acid (0.52 g, 2.0 mmol), EDCI (0.6 g, 3.0 mmol), HOAt (0.45 g, 3 mol) and Hunig's base (0.7 mL, 5.0 mmol) at room temperature. The reaction mixture was stirred for four hours, then concentrated and purified by RPLC (10% ACN/water to 60% ACN/water). Yield 0.43 g, 65% for two steps. Ions found by LCMS: $[M\text{-}Boc+H]^+$=562.4, $[M+H]^+$=662.4.

Step g.

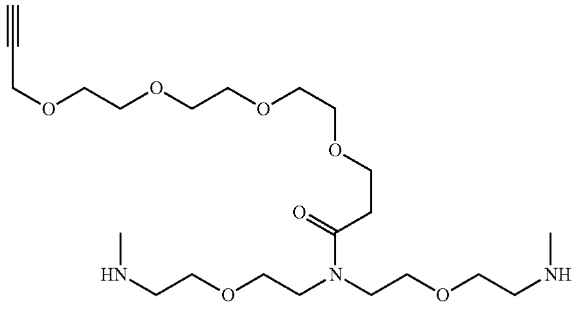 [SMILES: C#CCOCCOCCOCCOCCC(=O)N(CCOCCNC)CCOCCNC]

The step-d product (70 mg, 0.1 mmol) was treated with TFA (2 mL) for 2 hours at room temperature. TFA was removed by rotary evaporation, and the remaining oil was further dried under high vacuum for 12h to give the desired product as bis-TFA salt. Yield was quantative. Ion found by LCMS: $[M+H]^+$=462.4.

Step h.

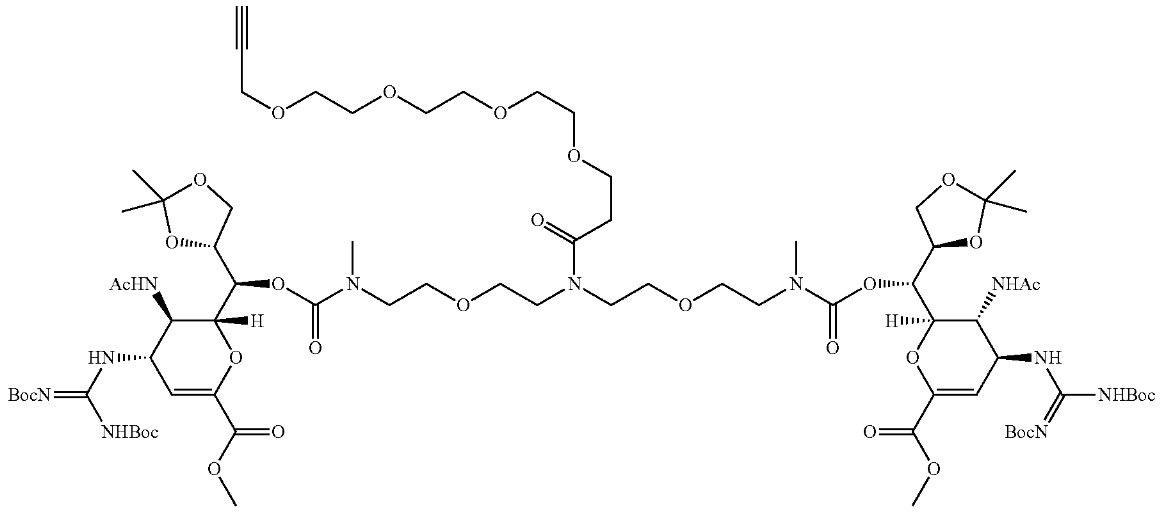

To a solution of the nitrophenyl carbonate described in the Example 109 (0.72 g. 0.95 mmol) in anhydrous DMF (5 ml) was added a mixture of the step g diamine (0.3 g, 0.43 mmol, added in portions over 30 minutes) and DIPEA (0.28 ml, 2 mmol) in anhydrous DMF (20 ml). The reaction was stirred at room temperature overnight, then concentrated and purified by flash chromatography eluting with 0% to 10% methanol/dichloromethane. Yield 0.63 g, 86%. Ions found by LCMS: $[(M+2H)/2]^+$=844.4, $[(M\text{-}Boc+2H)/2]^+$=794.4, $[(M-2Boc+2H)/2]^+$=744.4.

Step i.

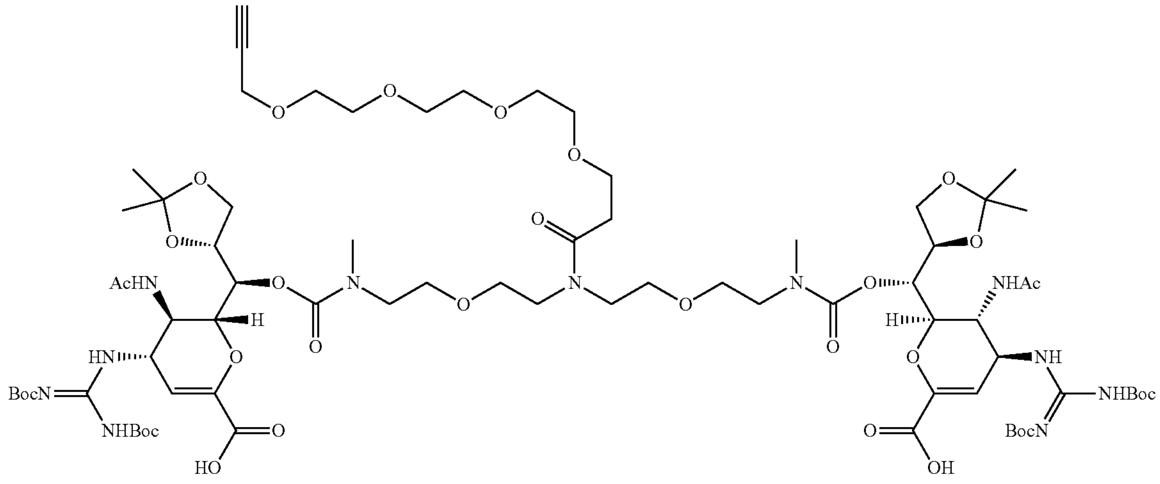

Product from the previous step (600 mg, 0.35 mmol) was dissolved into 5 ml MeOH and 5 ml THF, then treated with a solution of lithium hydroxide (48 mg, 2 mmol) dissolved in 2 ml water. The reaction was stirred for 10 min at room temperature at which time HPLC showed the reaction was complete. The pH of the reaction solution was adjusted to a value of 5 to 6 by using Amberlite IRN-77 ion exchange resin, then filtered to remove the resin. The crude product was evaporated to dryness by rotary evaporation and used in the next step with purification. Ion(s) found by LCMS: $[(M+2H)/2]^+$=829.9, $[(M\text{-}Boc+2H)/2]^+$=779.4, $[(M-2Boc+2H)/2]^+$=729.4.

Step j.

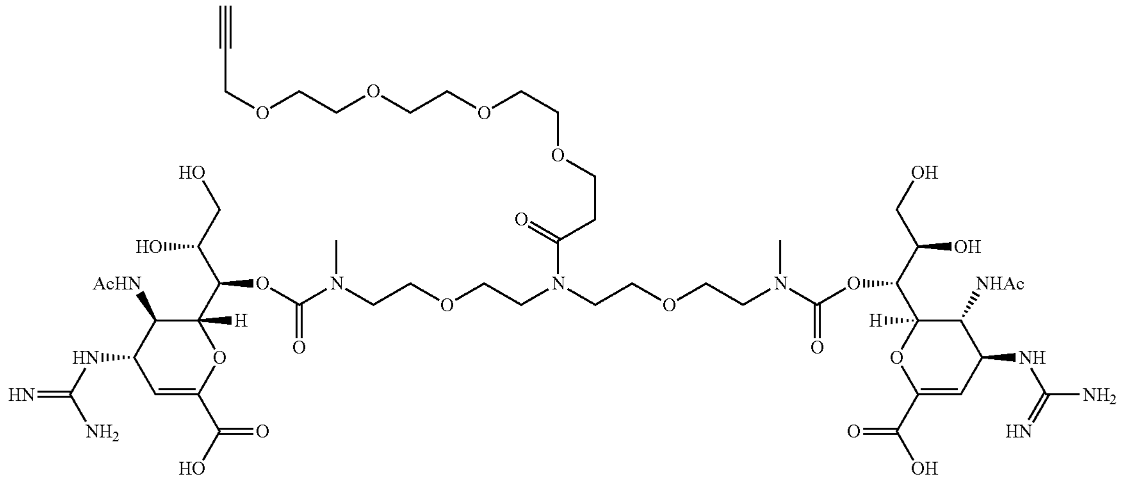 [SMILES: C#CCOCCOCCOCCOCCC(=O)N(CCOCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO]

The product from step-i was dissolved into 5 ml dichloromethane and 5 ml TFA, and stirred at room temperature. The progress of the reaction was monitored by LCMS. After the completion of the reaction (6h), the solution was stripped to dryness and then dissolved in 4 ml water and 4 ml methanol. The resulting solution was stirred for another 2 hour at room temperature at which LCMS show complete deprotection of the acetonide protecting groups. This mixture was concentrated and purified by reverse phase liquid chromatography (RPLC) using an Isco CombiFlash liquid chromatograph eluted with 5% to 40% acetonitrile/water with 0.1% TFA as the modifier. Yield 380 mg, 71.0%. Ion(s) found by LCMS: $[(M+2H)/2]^+=589.8$, $[(M+3H)/3]^+=392.5$.

Example 144. Synthesis of Int-82

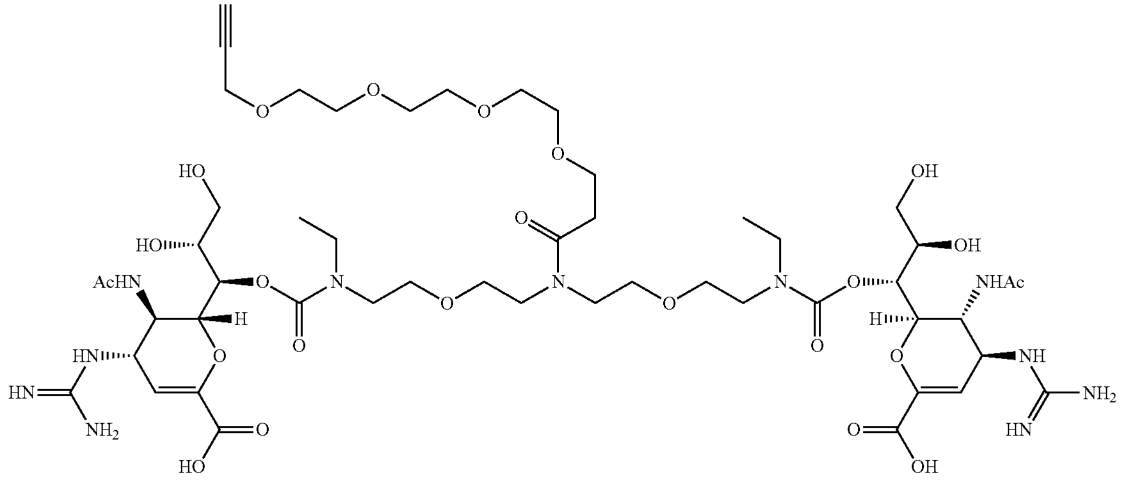 [SMILES: C#CCOCCOCCOCCOCCC(=O)N(CCOCCN(CC)C(=O)O[C@@H]([C@@H]1OC(C(=O)O)=C[C@H](NC(=N)N)[C@H]1NC(C)=O)[C@H](O)CO)CCOCCN(CC)C(=O)O[C@@H]([C@@H]1OC(C(=O)O)=C[C@H](NC(=N)N)[C@H]1NC(C)=O)[C@H](O)CO]

The title compound was prepared analogously to Example 143, Int-81, where the N-Boc-N-Me-glycinol was substituted with N-Boc-N-ethyl-glycinol in the step a. Ion(s) found by LCMS: [M/2]+1=603.8, [M/3]+1=402.9.

Example 145. Synthesis of Int-83

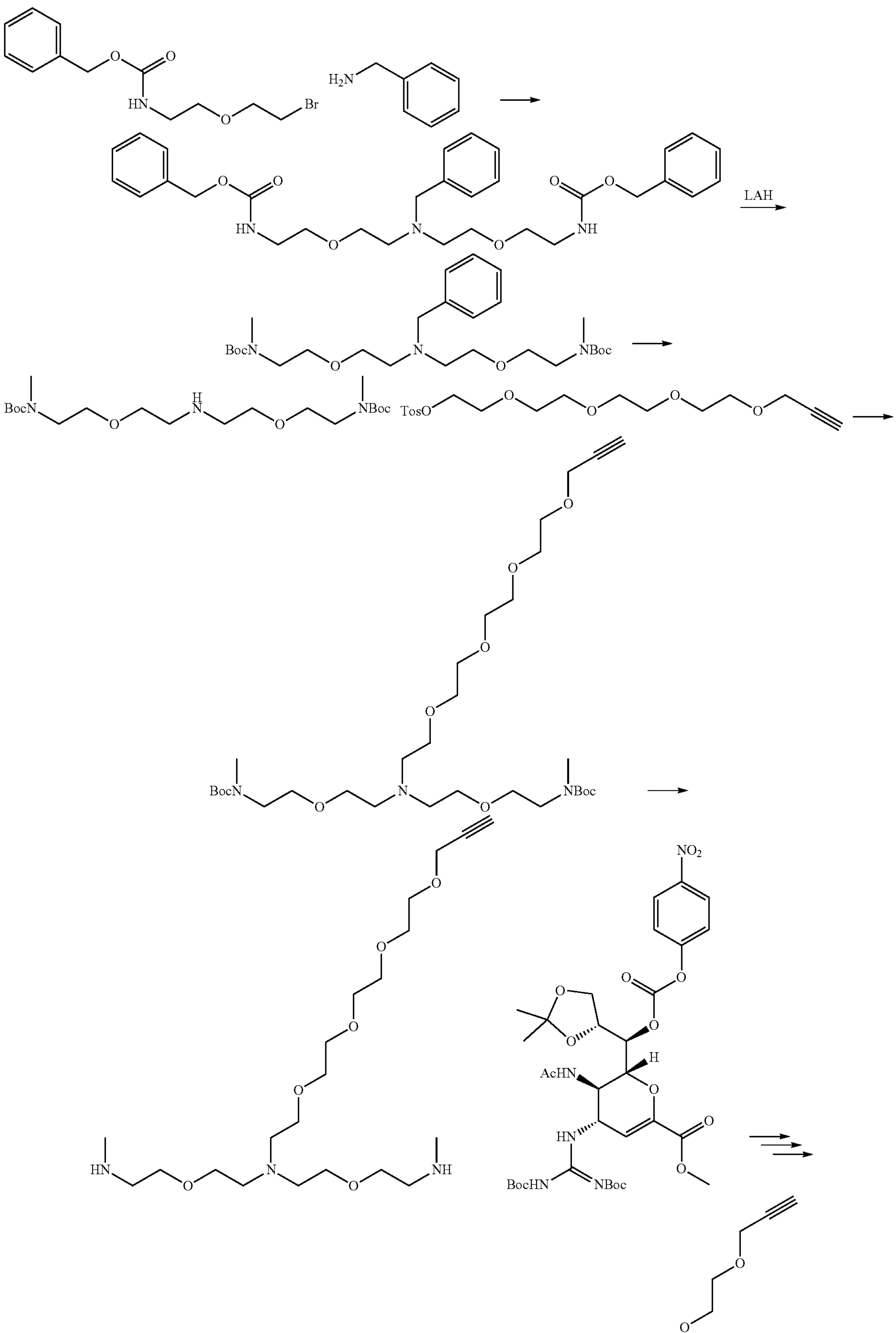
LAH

Step a.

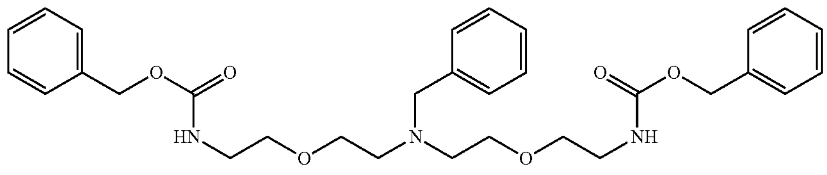 [SMILES: O=C(NCCOCCN(CCOCCNC(=O)OCc1ccccc1)Cc1ccccc1)OCc1ccccc1]

The CBZ-protected-amino-peg 1-bromide (7.6 g, 25.2 mmol), benzylamine (1.1 g, 10.1 mmol), and potassium carbonate (2.8 g, 2.8 mmol) were stirred in DMF (10 mL) at 60° C. for 12 hours. The solution was concentrated on the rotary evaporator and purified by silica gel chromatography (0-10% methanol in DCM, 30 minute gradient) to afford the product as a clear viscous oil. Yield 3.2 grams, 57%. Ion found by LC/MS $[M+H]^+$=550.2.

Step b.

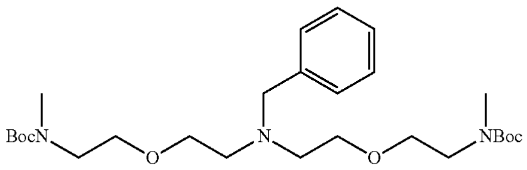 [SMILES: CN(CCOCCN(CCOCCN(C)C(=O)OC(C)(C)C)Cc1ccccc1)C(=O)OC(C)(C)C]

The product of step a (1.9 g, 3.5 mmol) was dissolved in THF (20 mL) and cooled to 0° C. by way of an ice/water bath under an atmosphere of nitrogen. LAH (6.9 ml, 13.8 mmol, 2M in THF) was added dropwise by way of syringe over a period of 10 minutes. The mixture was stirred at reflux for 2 hours then cooled to 0° C. by way of an ice/water bath. 1 mL of water was added, dropwise followed by the dropwise addition of 1 mL of aqueous (15% by weight) NaOH solution. 3 mL of water was added and the mixture was stirred for 15 minutes at which time 2 g of magnesium sulfate was added. The mixture was stirred for 10 minutes then filtered through celite, washed with 2 additional 10 ml portions of THE and the combined filtrates were concentrated by the rotary evaporator. The residue was taken up in acetonitrile (20 mL), triethylamine (1.4 g, 13.8 mmol) and boc anhydride (3.0 g, 13.8 mmol) were added. The mixture was stirred for 45 minutes, concentrated and purified by reversed phase HPLC (5-95% acetonitrile/di water, 0.1% TFA modifier, 30 minute gradient). Yield 1.4 g, 79%. Ion dound by LC/MS $[M+H]^+$=510.2.

Step c.

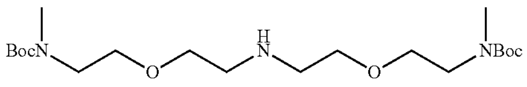 [SMILES: CN(CCOCCNCCOCCN(C)C(=O)OC(C)(C)C)C(=O)OC(C)(C)C]

The product from step b. (1 g, 1.9 mmol) of this example was stirred in methanol (25 mL) in the presence of palladium hydroxide (200 mg) under an atmosphere of hydrogen for 2 hours. The mixture was filtered through celite and concentrated to afford the product as a clear oil which was used with no further purification. Yield 0.73 g, 89%. Ion found by LC/MS $[M+H]^+$=420.4.

Step d.

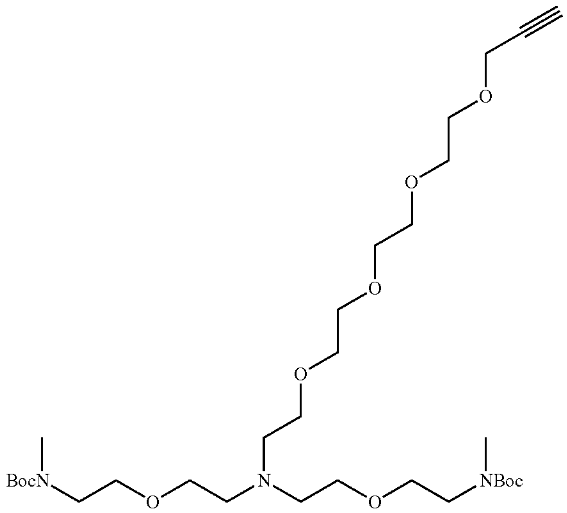 [SMILES: C#CCOCCOCCOCCOCCN(CCOCCN(C)C(=O)OC(C)(C)C)CCOCCN(C)C(=O)OC(C)(C)C]

The product from step c (0.73 g, 1.7 mmol), propargyl-peg4-tosylate (0.91 g, 2.4 mmol), and diisopropylethylamine (0.76 g, 5.9 mmol) were stirred in DMF (5 mL) at 85° C. for 4 hours. The mixture was concentrated on the rotary evaporator, then purified by reversed phase HPLC (5-95% acetonitrile/DI water, 0.1% TFA modifier, 30 minute gradient) to afford the product as a clear viscous oil. Yield 0.89 g, 82%. Ion fond by LC/MS $[M+H]^+$=634.4.

Step e.

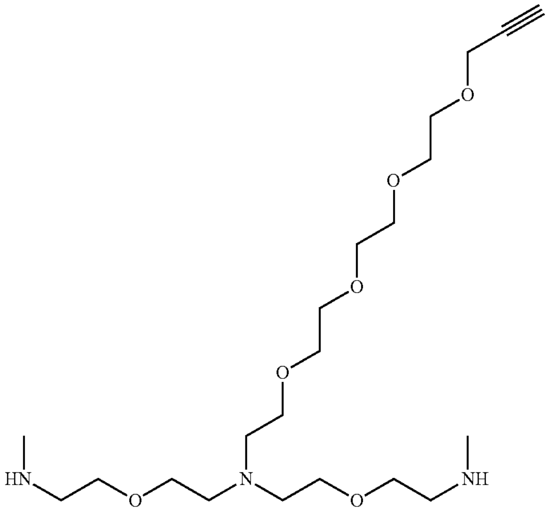 [SMILES: C#CCOCCOCCOCCOCCN(CCOCCNC)CCOCCNC]

The product from step d. (0.89 g, 1.4 mml) was stirred in 4N HCl (in dioxane) for 45 minutes at ambient temperature. The mixture was concentrated on the rotary evaporator and azeotroped (3×) with benzene. The resulting residue was taken up in DI water (15 mL) frozen and lyophilized to afford the product as a clear oil, bis-HCl salt. Yield 0.65 g, 91%. Ion found by LC/MS [M+H}+=434.4.

Step f.

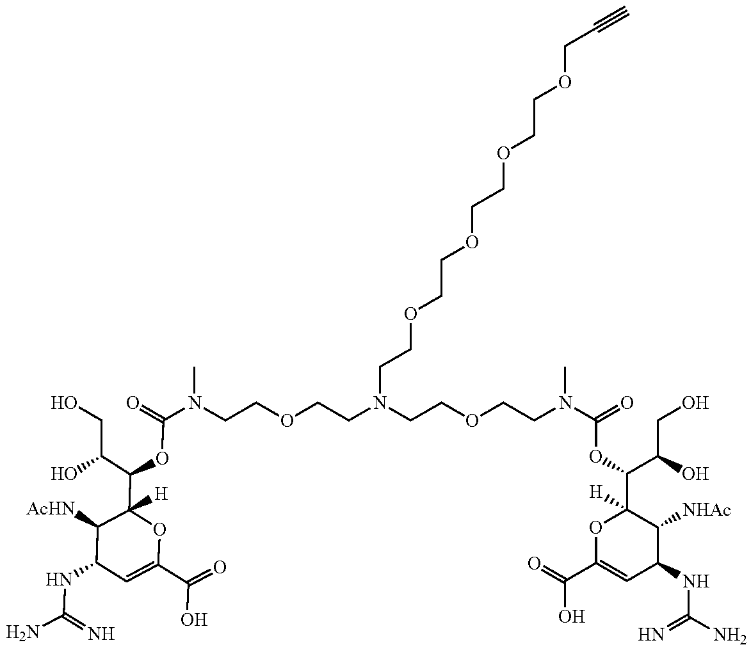 [SMILES: C#CCOCCOCCOCCOCCN(CCOCCN(C)C(=O)O[C@@H]([C@@H]1OC(C(=O)O)=C[C@H](NC(=N)N)[C@H]1NC(C)=O)[C@H](O)CO)CCOCCN(C)C(=O)O[C@@H]([C@@H]1OC(C(=O)O)=C[C@H](NC(=N)N)[C@H]1NC(C)=O)[C@H](O)CO]

The remaining four steps in the synthesis of this compound were analogous to those used in the synthesis of Example 143, Int-81. Ion(s) found by LCMS: (M+2H)/2=575.8

Example 146. Alternate Synthesis of Int-83

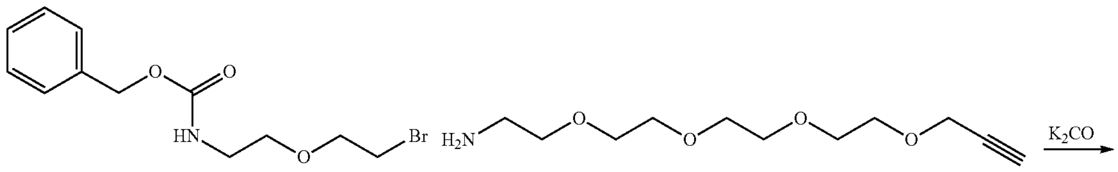

-continued
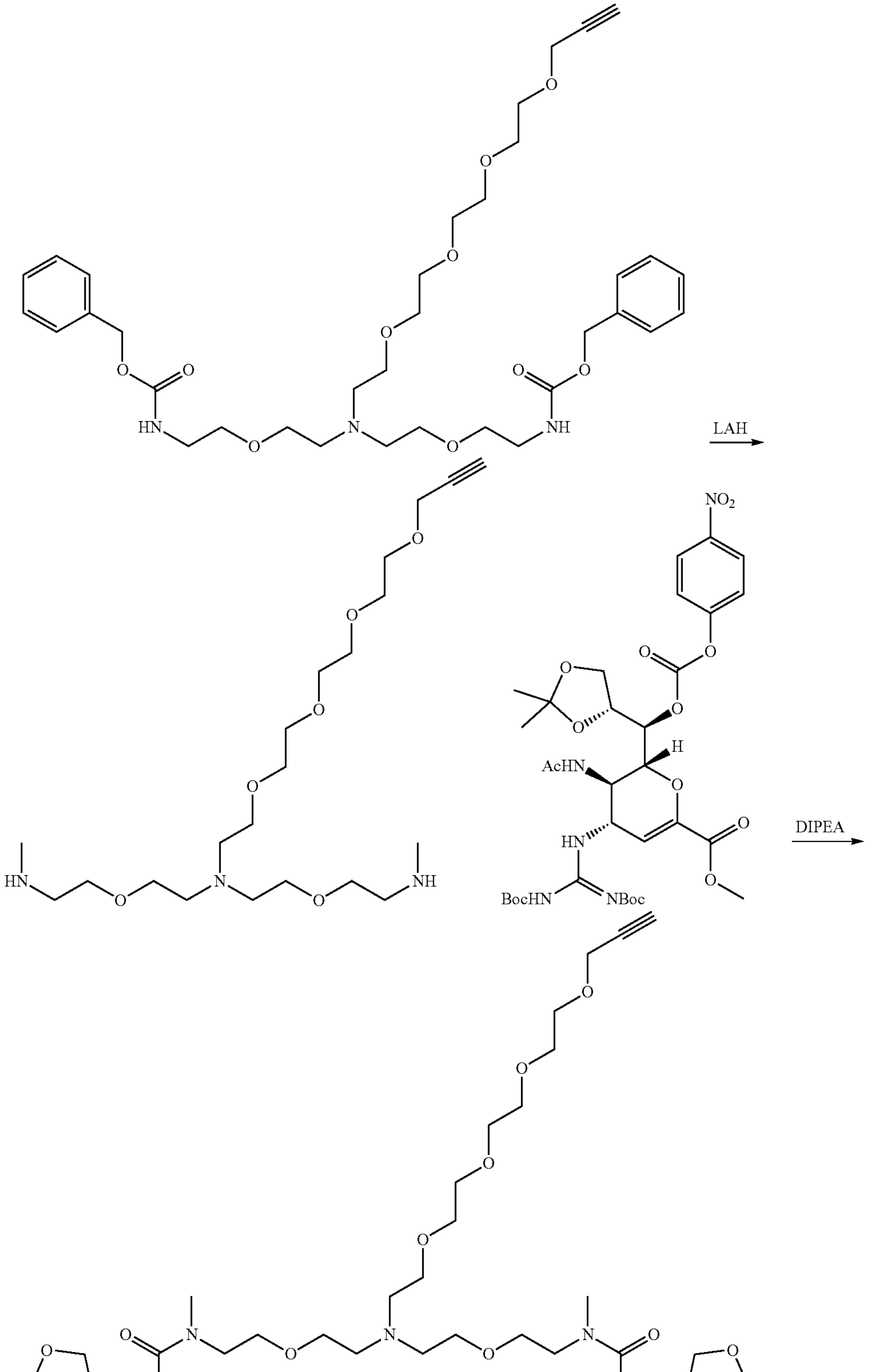

The product described in Example 145, Int-83, can be prepared alternatively using the above reaction scheme by a person skilled in the art using methods described in this patent.

Figure 67:
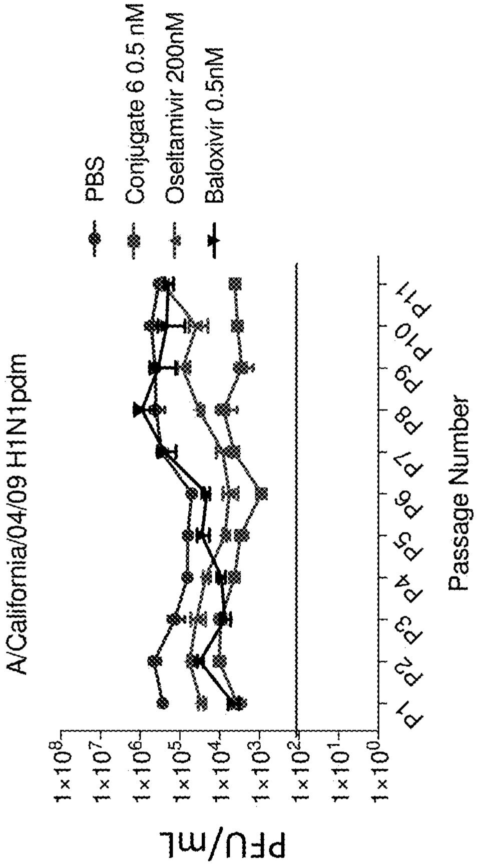
FIG. 67 is a graph showing serial passage of A/CA/09 pdm in the presence of Conjugate 6, oseltamivir, baloxavir or PBS control in A549 cells to evaluate the potential for development of drug resistant mutant viral strains under selective pressure with viral inhibitors. This study was performed as described in Example 147.
Figure 68:
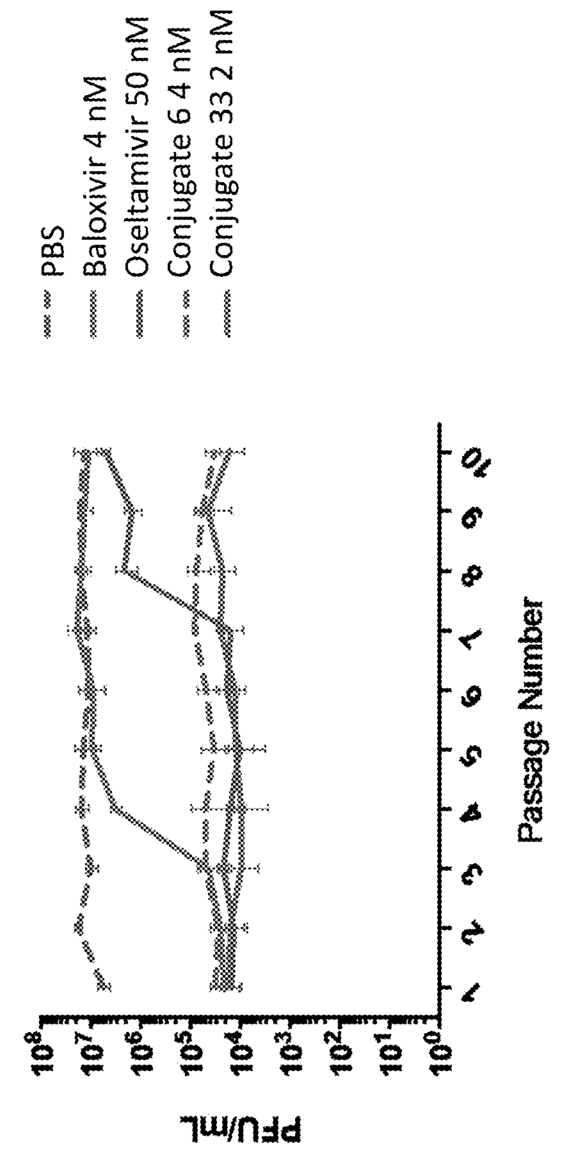
FIG. 68 is a graph showing serial passage of A/WSN/1933 in the presence of Conjugate 6, Conjugate 33, oseltamivir, baloxavir or PBS control in MDCK cells to evaluate the potential for development of drug resistant mutant viral strains under selective pressure with viral inhibitors. This study was performed as described in Example 147.

Example 147. Serial Passage Experiments for Selection of Resistant Influenza Viruses To evaluate the potential for development of drug resistant mutant viral strains under selective pressure with viral inhibitors, serial passage studies were conducted with Conjugates 6 and 33, versus oseltamivir and baloxavir comparators. Serial passage studies were conducted using either A549 or MDCK cells. Passages were conducted as follows: 150,000 A549 or MDCK cells were seeded per well (12-well) in 500 µl DMEM 10% FBS, 1% PS, 1% NaPyr and 1% HEPES and incubated for approximately 24 hours. Once cells reached approximately 80% confluency, they were washed once with PBS and incubated for 2 hours in the presence of compounds or PBS alone under normal culture conditions. Test article concentrations were optimized as required for maximum virus inhibition, while maintaining enough virus production for subsequent passages. Concentrations of test articles used in the serial passage experiments are shown in FIGS. 67 and 68. Cells were then infected at an MOI of 0.01 or 0.05 (MDCK and A549 cells, respectively; 150 ul diluted in infection buffer) for 1 hour at room temperature in a buffer containing PBS, Bovine Albumin 35% and $Ca^{2+}/Mg^{2+}$, followed by removal of inoculum and washing of cells once with DMEM 1% PS, 1% NaPyr and 1% HEPES (No FBS). Cells were then Incubated for 24 hours in the presence of test articles diluted in DMEM 1% PS, 1% NaPyr, 1% HEPES and 1 µg/ml TPCK-treated trypsin. After incubation, viral supernatants were collected, and cells and debris were removed by centrifugation (5 min, 4° C., 1,400×g). Supernatants were then used to:

i Quantify viral titer by plaque assay
ii Conduct a hemagglutination assay to determine if the virus escaped compound inhibition
iii Re-infect freshly seeded A549 or MDCK cells in presence of compounds.

The process was repeated for 10 passages, or until resistance was observed for the oseltamivir and baloxavir controls. Once increased titers in the presence of drugs is detected for two consecutive passages, the viruses may be plaque purified. Following plaque purification, all 8 genome segments may be sequenced and compared to PBS treated control virus to detect escape mutations. Summaries of two different serial passage experiments are shown in FIGS. 67 and 68. In the experiment summarized in FIG. 67, Conjugate 6 was compared to oseltamivir and baloxavir using A549 cells infected with A/California/04/09/H1N1 pdm. Conjugate 6, baloxavir and oseltamivir were used at 0.5 nM, 0.5 nM and 200 nM, respectively. No increases in viral titer were observed for Conjugate 6 through the course of 11 passages (suggesting no emergence of resistant mutants), while baloxavir and oseltamivir titers increased to levels similar to those observed in the PBS control after passages 5 and 11, respectively. In the experiment summarized in FIG. 68, Conjugates 6 and 33 were compared to oseltamivir and baloxavir using MDCK cells infected with A/WSN/1933 H1N1. Conjugate 6, Conjugate 33, baloxavir and oseltamivir were used at 4 nM, 2 nM, 4 nM and 50 nM, respectively. No increases in viral titer were observed for Conjugates 6 or 33 through the course of 10 passages (suggesting no emergence of resistant mutants), while baloxavir and oseltamivir titers increased to levels similar to those observed in the PBS control after passages 5 and 10, respectively.

The invention claimed is:

1. A method for the treatment of a subject having an influenza infection or presumed to have an influenza infection, the method comprising administering to the subject an effective amount of a conjugate described by formula (D-I):

(D-I)

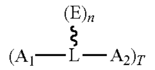

wherein each of $A_1$ and $A_2$ is zanamivir;

E comprises an Fc domain monomer comprising an amino acid sequence of SEQ ID NO: 63, 64, 67, or 68, wherein each Fc domain optionally lacks C-terminal Lys447;

L is a linker covalently attached to each of $A_1$, $A_2$, and E, wherein L is covalently attached to each of $A_1$ and $A_2$ independently at position C7 or position C9 of zanamivir;

n is 1 or 2; and

T is the number of $A_1$-L-$A_2$ moieties conjugated to each E and each T is, independently, an integer from 1 to 20;

or a pharmaceutically acceptable salt thereof.

2. The method of claim 1, wherein each L is covalently attached to the nitrogen atom of a surface exposed lysine of E.

3. The method of claim 1, wherein each L is covalently attached to the sulfur atom of a surface exposed cysteine of E.

4. The method of claim 1, wherein n is 2, and the two Es dimerize with each other to form an Fc domain.

5. The method of claim 1, wherein each T is, independently an integer from 1 to 10.

6. The method of claim 5, wherein the average value of each T is, independently, from 1 to 5.

7. The method of claim 1, wherein the conjugate is administered subcutaneously or intramuscularly.

8. A method for the prophylactic treatment of a subject against an influenza viral infection, the method comprising administering to the subject an effective amount of a conjugate described by formula (D-I):

(D-I)

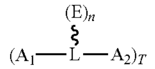

wherein each of $A_1$ and $A_2$ is zanamivir;

E comprises an Fc domain monomer comprising an amino acid sequence of SEQ ID NO: 63, 64, 67, or 68, wherein each Fc domain optionally lacks C-terminal Lys447;

L is a linker covalently attached to each of $A_1$, $A_2$, and E, wherein L is covalently attached to each of $A_1$ and $A_2$ independently at position C7 or position C9 of zanamivir;

n is 1 or 2; and

T is the number of $A_1$-L-$A_2$ moieties conjugated to each E and each T is, independently, an integer from 1 to 20;

or a pharmaceutically acceptable salt thereof.

9. The method of claim 8, wherein each L is covalently attached to the nitrogen atom of a surface exposed lysine of E.

10. The method of claim 8, wherein each L is covalently attached to the sulfur atom of a surface exposed cysteine of E.

11. The method of claim 8, wherein n is 2, and the two Es dimerize with each other to form an Fc domain.

12. The method of claim 8, wherein each T is, independently, an integer from 1 to 10.

13. The method of claim 12, wherein the average value of each T is, independently, from 1 to 5.

14. The method of claim 8, wherein the conjugate is administered subcutaneously or intramuscularly.

* * * * *

SEQUENCE LISTING

```
Sequence total quantity: 97
SEQ ID NO: 1            moltype = AA  length = 252
FEATURE                 Location/Qualifiers
source                  1..252
                        mol_type = protein
                        organism = synthetic construct
SEQUENCE: 1
MYRMQLLSCI ALSLALVTNS PRGPTIKPCP PCKCPAPNLL GGPSVFIFPP KIKDVLMISL  60
SPIVTCVVVD VSEDDPDVQI SWFVNNVEVH TAQTQTHRED YNSTLRVVSA LPIQHQDWMS  120
GKEFKCKVNN KDLPAPIERT ISKPKGSVRA PQVYVLPPPE EEMTKKQVTL TCMVTDFMPE  180
DIYVEWTNNG KTELNYKNTE PVLDSDGSYF MYSKLRVEKK NWVERNSYSC SVVHEGLHNH  240
HTTKSFSRTP GK                                                    252

SEQ ID NO: 2            moltype = AA  length = 232
FEATURE                 Location/Qualifiers
source                  1..232
                        mol_type = protein
                        organism = Mus musculus
SEQUENCE: 2
PRGPTIKPCP PCKCPAPNLL GGPSVFIFPP KIKDVLMISL SPIVTCVVVD VSEDDPDVQI  60
SWFVNNVEVH TAQTQTHRED YNSTLRVVSA LPIQHQDWMS GKEFKCKVNN KDLPAPIERT  120
ISKPKGSVRA PQVYVLPPPE EEMTKKQVTL TCMVTDFMPE DIYVEWTNNG KTELNYKNTE  180
PVLDSDGSYF MYSKLRVEKK NWVERNSYSC SVVHEGLHNH HTTKSFSRTP GK        232

SEQ ID NO: 3            moltype = AA  length = 251
FEATURE                 Location/Qualifiers
source                  1..251
                        mol_type = protein
                        organism = synthetic construct
SEQUENCE: 3
MYRMQLLSCI ALSLALVTNS MVRSDKTHTC PPCPAPELLG GPSVFLFPPK PKDTLMISRT  60
PEVTCVVVDV SHEDPEVKFN WYVDGVEVHN AKTKPREEQY NSTYRVVSVL TVLHQDWLNG  120
KEYKCKVSNK ALPAPIEKTI SKAKGQPREP QVYTLPPSRE EMTKNQVSLT CLVKGFYPSD  180
IAVEWESNGQ PENNYKTTPP VLDSDGSFFL YSKLTVDKSR WQQGNVFSCS VMHEALHNHY  240
```

-continued

```
TQKSLSLSPG K                                                    251

SEQ ID NO: 4            moltype = AA  length = 231
FEATURE                 Location/Qualifiers
source                  1..231
                        mol_type = protein
                        organism = synthetic construct
SEQUENCE: 4
MVRSDKTHTC PPCPAPELLG GPSVFLFPPK PKDTLMISRT PEVTCVVVDV SHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE EMTKNQVSLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 5            moltype = AA  length = 258
FEATURE                 Location/Qualifiers
source                  1..258
                        mol_type = protein
                        organism = synthetic construct
SEQUENCE: 5
MYRMQLLSCI ALSLALVTNS PRGPTIKPCP PCKCPAPNLL GGPSVFIFPP KIKDVLMISL  60
SPIVTCVVVD VSEDDPDVQI SWFVNNVEVH TAQTQTHRED YNSTLRVVSA LPIQHQDWMS  120
GKEFKCKVNN KDLPAPIERT ISKPKGSVRA PQVYVLPPPE EEMTKKQVTL TCMVTDFMPE  180
DIYVEWTNNG KTELNYKNTE PVLDSDGSYF MYSKLRVEKK NWVERNSYSC SVVHEGLHNH  240
HTTKSFSRTP GKHHHHHH                                             258

SEQ ID NO: 6            moltype = AA  length = 238
FEATURE                 Location/Qualifiers
source                  1..238
                        mol_type = protein
                        organism = synthetic construct
SEQUENCE: 6
PRGPTIKPCP PCKCPAPNLL GGPSVFIFPP KIKDVLMISL SPIVTCVVVD VSEDDPDVQI  60
SWFVNNVEVH TAQTQTHRED YNSTLRVVSA LPIQHQDWMS GKEFKCKVNN KDLPAPIERT  120
ISKPKGSVRA PQVYVLPPPE EEMTKKQVTL TCMVTDFMPE DIYVEWTNNG KTELNYKNTE  180
PVLDSDGSYF MYSKLRVEKK NWVERNSYSC SVVHEGLHNH HTTKSFSRTP GKHHHHHH    238

SEQ ID NO: 7            moltype = AA  length = 257
FEATURE                 Location/Qualifiers
source                  1..257
                        mol_type = protein
                        organism = synthetic construct
SEQUENCE: 7
MYRMQLLSCI ALSLALVTNS MVRSDKTHTC PPCPAPELLG GPSVFLFPPK PKDTLMISRT  60
PEVTCVVVDV SHEDPEVKFN WYVDGVEVHN AKTKPREEQY NSTYRVVSVL TVLHQDWLNG  120
KEYKCKVSNK ALPAPIEKTI SKAKGQPREP QVYTLPPSRE EMTKNQVSLT CLVKGFYPSD  180
IAVEWESNGQ PENNYKTTPP VLDSDGSFFL YSKLTVDKSR WQQGNVFSCS VMHEALHNHY  240
TQKSLSLSPG KHHHHHH                                              257

SEQ ID NO: 8            moltype = AA  length = 237
FEATURE                 Location/Qualifiers
source                  1..237
                        mol_type = protein
                        organism = synthetic construct
SEQUENCE: 8
MVRSDKTHTC PPCPAPELLG GPSVFLFPPK PKDTLMISRT PEVTCVVVDV SHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE EMTKNQVSLT CLVKGFYPSD IAVEWESNGQ PENNYKTTPP  180
VLDSDGSFFL YSKLTVDKSR WQQGNVFSCS VMHEALHNHY TQKSLSLSPG KHHHHHH     237

SEQ ID NO: 9            moltype = AA  length = 262
FEATURE                 Location/Qualifiers
source                  1..262
                        mol_type = protein
                        organism = synthetic construct
SEQUENCE: 9
MYRMQLLSCI ALSLALVTNS MVRSDKTHTC PPCPPCKCPA PELLGGPSVF LFPPKPKDTL  60
MISRTPEVTC VVVDVSHEDP EVKFNWYVDG VEVHNAKTKP REEQYNSTYR VVSVLTVLHQ  120
DWLNGKEYKC KVSNKALPAP IEKTISKAKG QPREPQVYTL PPSREEMTKN QVSLTCLVKG  180
FYPSDIAVEW ESNGQPENNY KTTPPVLDSD GSFFLYSKLT VDKSRWQQGN VFSCSVMHEA  240
LHNHYTQKSL SLSPGKHHHH HH                                         262

SEQ ID NO: 10           moltype = AA  length = 242
FEATURE                 Location/Qualifiers
source                  1..242
                        mol_type = protein
                        organism = synthetic construct
SEQUENCE: 10
MVRSDKTHTC PPCPPCKCPA PELLGGPSVF LFPPKPKDTL MISRTPEVTC VVVDVSHEDP  60
EVKFNWYVDG VEVHNAKTKP REEQYNSTYR VVSVLTVLHQ DWLNGKEYKC KVSNKALPAP  120
```

-continued

```
IEKTISKAKG QPREPQVYTL PPSREEMTKN QVSLTCLVKG FYPSDIAVEW ESNGQPENNY  180
KTTPPVLDSD GSFFLYSKLT VDKSRWQQGN VFSCSVMHEA LHNHYTQKSL SLSPGKHHHH  240
HH                                                                242

SEQ ID NO: 11          moltype = AA  length = 236
FEATURE                Location/Qualifiers
source                 1..236
                       mol_type = protein
                       organism = synthetic construct
SEQUENCE: 11
MVRSDKTHTC PPCPPCKCPA PELLGGPSVF LFPPKPKDTL MISRTPEVTC VVVDVSHEDP  60
EVKFNWYVDG VEVHNAKTKP REEQYNSTYR VVSVLTVLHQ DWLNGKEYKC KVSNKALPAP  120
IEKTISKAKG QPREPQVYTL PPSREEMTKN QVSLTCLVKG FYPSDIAVEW ESNGQPENNY  180
KTTPPVLDSD GSFFLYSKLT VDKSRWQQGN VFSCSVMHEA LHNHYTQKSL SLSPGK      236

SEQ ID NO: 12          moltype = AA  length = 258
FEATURE                Location/Qualifiers
source                 1..258
                       mol_type = protein
                       organism = synthetic construct
SEQUENCE: 12
MYRMQLLSCI ALSLALVTNS PRGPTIKPCP PCKCPAPNLL GGPSVFIFPP KIKDVLMISL  60
SPIVTCVVVD VSEDDPDVQI SWFVNNVEVH TAQTQTHRED YASTLRVVSA LPIQHQDWMS  120
GKEFKCKVNN KDLPAPIERT ISKPKGSVRA PQVYVLPPPE EEMTKKQVTL TCMVTDFMPE  180
DIYVEWTNNG KTELNYKNTE PVLDSDGSYF MYSKLRVEKK NWVERNSYSC SVVHEGLHNH  240
HTTKSFSRTP GKHHHHHH                                               258

SEQ ID NO: 13          moltype = AA  length = 238
FEATURE                Location/Qualifiers
source                 1..238
                       mol_type = protein
                       organism = synthetic construct
SEQUENCE: 13
PRGPTIKPCP PCKCPAPNLL GGPSVFIFPP KIKDVLMISL SPIVTCVVVD VSEDDPDVQI  60
SWFVNNVEVH TAQTQTHRED YASTLRVVSA LPIQHQDWMS GKEFKCKVNN KDLPAPIERT  120
ISKPKGSVRA PQVYVLPPPE EEMTKKQVTL TCMVTDFMPE DIYVEWTNNG KTELNYKNTE  180
PVLDSDGSYF MYSKLRVEKK NWVERNSYSC SVVHEGLHNH HTTKSFSRTP GKHHHHHH    238

SEQ ID NO: 14          moltype = AA  length = 257
FEATURE                Location/Qualifiers
source                 1..257
                       mol_type = protein
                       organism = synthetic construct
SEQUENCE: 14
MYRMQLLSCI ALSLALVTNS MVRSDKTHTC PPCPAPELLG GPSVFLFPPK PKDTLMISRT  60
PEVTCVVVDV SHEDPEVKFN WYVDGVEVHN AKTKPREEQY ASTYRVVSVL TVLHQDWLNG  120
KEYKCKVSNK ALPAPIEKTI SKAKGQPREP QVYTLPPSRE EMTKNQVSLT CLVKGFYPSD  180
IAVEWESNGQ PENNYKTTPP VLDSDGSFFL YSKLTVDKSR WQQGNVFSCS VMHEALHNHY  240
TQKSLSLSPG KHHHHHH                                                257

SEQ ID NO: 15          moltype = AA  length = 237
FEATURE                Location/Qualifiers
source                 1..237
                       mol_type = protein
                       organism = synthetic construct
SEQUENCE: 15
MVRSDKTHTC PPCPAPELLG GPSVFLFPPK PKDTLMISRT PEVTCVVVDV SHEDPEVKFN  60
WYVDGVEVHN AKTKPREEQY ASTYRVVSVL TVLHQDWLNG KEYKCKVSNK ALPAPIEKTI  120
SKAKGQPREP QVYTLPPSRE EMTKNQVSLT CLVKGFYPSD IAVEWESNGQ PENNYKTTPP  180
VLDSDGSFFL YSKLTVDKSR WQQGNVFSCS VMHEALHNHY TQKSLSLSPG KHHHHHH     237

SEQ ID NO: 16          moltype = AA  length = 252
FEATURE                Location/Qualifiers
source                 1..252
                       mol_type = protein
                       organism = synthetic construct
SEQUENCE: 16
MKWVTFISLL FLFSSAYSIS AMVRSDKTHT CPPCPAPELL GGPSVFLFPP KPKDTLMISR  60
TPEVTCVVVD VSHEDPEVKF NWYVDGVEVH NAKTKPREEQ YNSTYRVVSV LTVLHQDWLN  120
GKEYKCKVSN KALPAPIEKT ISKAKGQPRE PQVYTLPPSR EEMTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GK                                                     252

SEQ ID NO: 17          moltype = AA  length = 266
FEATURE                Location/Qualifiers
source                 1..266
                       mol_type = protein
                       organism = synthetic construct
SEQUENCE: 17
```

-continued

```
MKWVTFISLL FLFSSAYSIS AMVRSDKTHT CPPCPAPELL GGPSVFLFPP KPKDTLMISR  60
TPEVTCVVVD VSHEDPEVKF NWYVDGVEVH NAKTKPREEQ YNSTYRVVSV LTVLHQDWLN  120
GKEYKCKVSN KALPAPIEKT ISKAKGQPRE PQVYTLPPSR EEMTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GGGGGSEQKL ISEEDL                                      266

SEQ ID NO: 18          moltype = AA  length = 248
FEATURE                Location/Qualifiers
source                 1..248
                       mol_type = protein
                       organism = synthetic construct
SEQUENCE: 18
ISAMVRSDKT HTCPPCPAPE LLGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALPAPIE  120
KTISKAKGQP REPQVYTLPP SREEMTKNQV SLTCLVKGFY PSDIAVEWES NGQPENNYKT  180
TPPVLDSDGS FFLYSKLTVD KSRWQQGNVF SCSVMHEALH NHYTQKSLSL SPGGGGGSEQ  240
KLISEEDL                                                          248

SEQ ID NO: 19          moltype = AA  length = 252
FEATURE                Location/Qualifiers
source                 1..252
                       mol_type = protein
                       organism = synthetic construct
SEQUENCE: 19
MKWVTFISLL FLFSSAYSIS AMVRSDKTHT CPPCPAPELL GGPSVFLFPP KPSDTLMISR  60
TPEVTCVVVD VSHEDPEVKF NWYVDGVEVH NAKTKPREEQ YNSTYRVVSV LTVLHQDWLN  120
GKEYKCKVSN KALPAPIEKT ISKAKGQPRE PQVYTLPPSR EEMTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GK                                                     252

SEQ ID NO: 20          moltype = AA  length = 234
FEATURE                Location/Qualifiers
source                 1..234
                       mol_type = protein
                       organism = synthetic construct
SEQUENCE: 20
ISAMVRSDKT HTCPPCPAPE LLGGPSVFLF PPKPSDTLMI SRTPEVTCVV VDVSHEDPEV  60
KFNWYVDGVE VHNAKTKPRE EQYNSTYRVV SVLTVLHQDW LNGKEYKCKV SNKALPAPIE  120
KTISKAKGQP REPQVYTLPP SREEMTKNQV SLTCLVKGFY PSDIAVEWES NGQPENNYKT  180
TPPVLDSDGS FFLYSKLTVD KSRWQQGNVF SCSVMHEALH NHYTQKSLSL SPGK        234

SEQ ID NO: 21          moltype = AA  length = 266
FEATURE                Location/Qualifiers
source                 1..266
                       mol_type = protein
                       organism = synthetic construct
SEQUENCE: 21
MKWVTFISLL FLFSSAYSIS AMVRSDKTHT CPPCPAPELL GGPSVFLFPP KPSDTLMISR  60
TPEVTCVVVD VSHEDPEVKF NWYVDGVEVH NAKTKPREEQ YNSTYRVVSV LTVLHQDWLN  120
GKEYKCKVSN KALPAPIEKT ISKAKGQPRE PQVYTLPPSR EEMTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GGGGGSEQKL ISEEDL                                      266

SEQ ID NO: 22          moltype = AA  length = 248
FEATURE                Location/Qualifiers
source                 1..248
                       mol_type = protein
                       organism = synthetic construct
SEQUENCE: 22
ISAMVRSDKT HTCPPCPAPE LLGGPSVFLF PPKPSDTLMI SRTPEVTCVV VDVSHEDPEV  60
KFNWYVDGVE VHNAKTKPRE EQYNSTYRVV SVLTVLHQDW LNGKEYKCKV SNKALPAPIE  120
KTISKAKGQP REPQVYTLPP SREEMTKNQV SLTCLVKGFY PSDIAVEWES NGQPENNYKT  180
TPPVLDSDGS FFLYSKLTVD KSRWQQGNVF SCSVMHEALH NHYTQKSLSL SPGGGGGSEQ  240
KLISEEDL                                                          248

SEQ ID NO: 23          moltype = AA  length = 266
FEATURE                Location/Qualifiers
source                 1..266
                       mol_type = protein
                       organism = synthetic construct
SEQUENCE: 23
MKWVTFISLL FLFSSAYSIS AMVRSDKTHT CPPCPAPELL GGPSVFLFPP KPKDTLMISR  60
TPEVTCVVVD VSHEDPEVKF NWYVDGVEVH NAKTKPREEQ YASTYRVVSV LTVLHQDWLN  120
GKEYKCKVSN KALPAPIEKT ISKAKGQPRE PQVYTLPPSR EEMTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GGGGGSEQKL ISEEDL                                      266

SEQ ID NO: 24          moltype = AA  length = 248
FEATURE                Location/Qualifiers
```

-continued

```
source                  1..248
                        mol_type = protein
                        organism = synthetic construct
SEQUENCE: 24
ISAMVRSDKT HTCPPCPAPE LLGGPSVFLF PPKPKDTLMI SRTPEVTCVV VDVSHEDPEV  60
KFNWYVDGVE VHNAKTKPRE EQYASTYRVV SVLTVLHQDW LNGKEYKCKV SNKALPAPIE  120
KTISKAKGQP REPQVYTLPP SREEMTKNQV SLTCLVKGFY PSDIAVEWES NGQPENNYKT  180
TPPVLDSDGS FFLYSKLTVD KSRWQQGNVF SCSVMHEALH NHYTQKSLSL SPGGGGGSEQ  240
KLISEEDL                                                          248

SEQ ID NO: 25           moltype = AA  length = 266
FEATURE                 Location/Qualifiers
source                  1..266
                        mol_type = protein
                        organism = synthetic construct
SEQUENCE: 25
MKWVTFISLL FLFSSAYSIS AMVRSDKTHT CPPCPAPELL GGPSVFLFPP KPKDTLMISR  60
TPEVTCVVVD VSHEDPEVKF NWYVDGVEVH NAKTKPREEQ YNSTYRVVSV LTVLAQDWLN  120
GKEYKCKVSN KALPAPIEKT ISKAKGQPRE PQVYTLPPSR EEMTKNQVSL TCLVKGFYPS  180
DIAVEWESNG QPENNYKTTP PVLDSDGSFF LYSKLTVDKS RWQQGNVFSC SVMHEALHNA  240
YTQKSLSLSP GGGGGSEQKL ISEEDL                                      266

SEQ ID NO: 26           moltype = AA  length = 248
FEATURE                 Location/Qualifiers
source                  1..248
                        mol_type = protein
                        organism = synthetic construct
SEQUENCE: 26
ISAMVRSDKT HTCPPCPAPE LLGGPSVFLF PPKPKDTLMI SRTPEVTCVV VDVSHEDPEV  60
KFNWYVDGVE VHNAKTKPRE EQYNSTYRVV SVLTVLAQDW LNGKEYKCKV SNKALPAPIE  120
KTISKAKGQP REPQVYTLPP SREEMTKNQV SLTCLVKGFY PSDIAVEWES NGQPENNYKT  180
TPPVLDSDGS FFLYSKLTVD KSRWQQGNVF SCSVMHEALH NAYTQKSLSL SPGGGGGSEQ  240
KLISEEDL                                                          248

SEQ ID NO: 27           moltype = AA  length = 266
FEATURE                 Location/Qualifiers
source                  1..266
                        mol_type = protein
                        organism = synthetic construct
SEQUENCE: 27
MKWVTFISLL FLFSSAYSIS AMVRSDKTHT CPPCPAPELL GGPSVFLFPP KPKDTLMISR  60
TPEVTCVVVD VSHEDPEVKF NWYVDGVEVH NAKTKPREEQ YNSTYRVVSV LTVLHQDWLN  120
GKEYKCKVSN KALPAPIEKT ISKAKGQPRE PQVYTLPPSR EEMTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GGGGGSEQFL ISEEDL                                      266

SEQ ID NO: 28           moltype = AA  length = 248
FEATURE                 Location/Qualifiers
source                  1..248
                        mol_type = protein
                        organism = synthetic construct
SEQUENCE: 28
ISAMVRSDKT HTCPPCPAPE LLGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALPAPIE  120
KTISKAKGQP REPQVYTLPP SREEMTKNQV SLTCLVKGFY PSDIAVEWES NGQPENNYKT  180
TPPVLDSDGS FFLYSKLTVD KSRWQQGNVF SCSVMHEALH NHYTQKSLSL SPGGGGGSEQ  240
FLISEEDL                                                          248

SEQ ID NO: 29           moltype = AA  length = 266
FEATURE                 Location/Qualifiers
source                  1..266
                        mol_type = protein
                        organism = synthetic construct
SEQUENCE: 29
MKWVTFISLL FLFSSAYSIS AMVRSDKTHT CPPCPAPELL GGPSVFLFPP KPKDTLMISR  60
TPEVTCVVVD VSHEDPEVKF NWYVDGVEVH NAKTKPREEQ YASTYRVVSV LTVLHQDWLN  120
GKEYKCKVSN KALPAPIEKT ISKAKGQPRE PQVYTLPPSR EEMTKNQVSL TCLVKGFYPS  180
DIAVEWESNG QPENNYKTTP PVLDSDGSFF LYSKLTVDKS RWQQGNVFSC SVMHEALHNH  240
YTQKSLSLSP GGGGGSEQFL ISEEDL                                      266

SEQ ID NO: 30           moltype = AA  length = 248
FEATURE                 Location/Qualifiers
source                  1..248
                        mol_type = protein
                        organism = synthetic construct
SEQUENCE: 30
ISAMVRSDKT HTCPPCPAPE LLGGPSVFLF PPKPKDTLMI SRTPEVTCVV VDVSHEDPEV  60
KFNWYVDGVE VHNAKTKPRE EQYASTYRVV SVLTVLHQDW LNGKEYKCKV SNKALPAPIE  120
KTISKAKGQP REPQVYTLPP SREEMTKNQV SLTCLVKGFY PSDIAVEWES NGQPENNYKT  180
```

-continued

```
TPPVLDSDGS FFLYSKLTVD KSRWQQGNVF SCSVMHEALH NHYTQKSLSL SPGGGGGSEQ  240
FLISEEDL                                                           248

SEQ ID NO: 31          moltype = AA  length = 259
FEATURE                Location/Qualifiers
source                 1..259
                       mol_type = protein
                       organism = synthetic construct
SEQUENCE: 31
MKWVTFISLL FLFSSAYSDK THTCPPCPAP ELLGGPSVFL FPPKPKDTLM ISRTPEVTCV  60
VVDVSHEDPE VKFNWYVDGV EVHNAKTKPR EEQYNSTYRV VSVLTVLHQD WLNGKEYKCK  120
VSNKALPAPI EKTISKAKGQ PREPQVYTLP PSRDELTKNQ VSLTCLVKGF YPSDIAVEWE  180
SNGQPENNYK TTPPVLDSDG SFFLYSKLTV DKSRWQQGNV FSCSVMHEAL HNHYTQKSLS  240
LSPGGGGGSE QFLISEEDL                                               259

SEQ ID NO: 32          moltype = AA  length = 245
FEATURE                Location/Qualifiers
source                 1..245
                       mol_type = protein
                       organism = synthetic construct
SEQUENCE: 32
MKWVTFISLL FLFSSAYSDK THTCPPCPAP ELLGGPSVFL FPPKPKDTLM ISRTPEVTCV  60
VVDVSHEDPE VKFNWYVDGV EVHNAKTKPR EEQYNSTYRV VSVLTVLHQD WLNGKEYKCK  120
VSNKALPAPI EKTISKAKGQ PREPQVYTLP PSRDELTKNQ VSLTCLVKGF YPSDIAVEWE  180
SNGQPENNYK TTPPVLDSDG SFFLYSKLTV DKSRWQQGNV FSCSVMHEAL HNHYTQKSLS  240
LSPGK                                                              245

SEQ ID NO: 33          moltype = AA  length = 231
FEATURE                Location/Qualifiers
source                 1..231
                       mol_type = protein
                       organism = synthetic construct
SEQUENCE: 33
MVRSDKTHTC PPCPAPELLG GPSVFLFPPK PKDTLYITRE PEVTCVVVDV SHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE EMTKNQVSLT CLVKGFYPSD IAVEWESNGQ PENNYKTTPP  180
VLDSDGSFFL YSKLTVDKSR WQQGNVFSCS VMHEALHNHY TQKSLSLSPG K            231

SEQ ID NO: 34          moltype = AA  length = 250
FEATURE                Location/Qualifiers
source                 1..250
                       mol_type = protein
                       organism = synthetic construct
SEQUENCE: 34
MKWVTFISLL FLFSSAYSEP KSSDKTHTCP PCPAPELLGG PSVFLFPPKP KDTLMISRTP  60
EVTCVVVDVS HEDPEVKFNW YVDGVEVHNA KTKPREEQYN STYRVVSVLT VLHQDWLNGK  120
EYKCKVSNKA LPAPIEKTIS KAKGQPREPQ VYTLPPSRDE LTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK                                                         250

SEQ ID NO: 35          moltype = AA  length = 245
FEATURE                Location/Qualifiers
source                 1..245
                       mol_type = protein
                       organism = synthetic construct
SEQUENCE: 35
MGWSCIILFL VATATGVHSK THTCPPCPAP ELLGGPSVFL FPPKPKDTLM ISRTPEVTCV  60
VVDVSHEDPE VKFNWYVDGV EVHNAKTKPR EEQYNSTYRV VSVLTVLHQD WLNGKEYKCK  120
VSNKALPAPI EKTISKAKGQ PREPQVYTLP PSRDELTKNQ VSLTCLVKGF YPSDIAVEWE  180
SNGQPENNYK TTPPVLDSDG SFFLYSKLTV DKSRWQQGNV FSCSVMHEAL HNHYTQKSLS  240
LSPGK                                                              245

SEQ ID NO: 36          moltype = AA  length = 226
FEATURE                Location/Qualifiers
source                 1..226
                       mol_type = protein
                       organism = synthetic construct
SEQUENCE: 36
KTHTCPPCPA PELLGGPSVF LFPPKPKDTL YITREPEVTC VVVDVSHEDP EVKFNWYVDG  60
VEVHNAKTKP REEQYNSTYR VVSVLTVLHQ DWLNGKEYKC KVSNKALPAP IEKTISKAKG  120
QPREPQVYTL PPSRDELTKN QVSLTCLVKG FYPSDIAVEW ESNGQPENNY KTTPPVLDSD  180
GSFFLYSKLT VDKSRWQQGN VFSCSVMHEA LHNHYTQKSL SLSPGK                 226

SEQ ID NO: 37          moltype = AA  length = 226
FEATURE                Location/Qualifiers
source                 1..226
                       mol_type = protein
                       organism = synthetic construct
SEQUENCE: 37
```

-continued

```
KTHTCPPCPA PELLGGPSVF LFPPKPKDTL MISRTPEVTC VVVDVSHEDP EVKFNWYVDG  60
VEVHNAKTKP REEQYNSTYR VVSVLTVLHQ DWLNGKEYKC KVSNKALPAP IEKTISKAKG  120
QPREPQVYTL PPSRDELTKN QVSLTCLVKG FYPSDIAVEW ESNGQPENNY KTTPPVLDSD  180
GSFFLYSKLT VDKSRWQQGN VFSCSVLHEA LHSHYTQKSL SLSPGK                 226

SEQ ID NO: 38           moltype = AA  length = 259
FEATURE                 Location/Qualifiers
source                  1..259
                        mol_type = protein
                        organism = synthetic construct
SEQUENCE: 38
MKWVTFISLL FLFSSAYSDK THTCPPCPAP ELLGGPSVFL FPPKPKDTLY ITREPEVTCV  60
VVDVSHEDPE VKFNWYVDGV EVHNAKTKPR EEQYNSTYRV VSVLTVLHQD WLNGKEYKCK  120
VSNKALPAPI EKTISKAKGQ PREPQVYTLP PSRDELTKNQ VSLTCLVKGF YPSDIAVEWE  180
SNGQPENNYK TTPPVLDSDG SFFLYSKLTV DKSRWQQGNV FSCSVMHEAL HNHYTQKSLS  240
LSPGGGGGSE QKLISEEDL                                               259

SEQ ID NO: 39           moltype = AA  length = 226
FEATURE                 Location/Qualifiers
VARIANT                 32
                        note = MISC_FEATURE - Xaa is Met or Trp
VARIANT                 34
                        note = MISC_FEATURE - Xaa is Ser or Thr
VARIANT                 36
                        note = MISC_FEATURE - Xaa is Thr or Glu
VARIANT                 136
                        note = MISC_FEATURE - Xaa is Asp or Glu
VARIANT                 138
                        note = MISC_FEATURE - Xaa is Leu or Met
VARIANT                 208
                        note = MISC_FEATURE - Xaa is Met or Leu
VARIANT                 214
                        note = MISC_FEATURE - Xaa is Asn or Ser
source                  1..226
                        mol_type = protein
                        organism = synthetic construct
SEQUENCE: 39
DKTHTCPPCP APELLGGPSV FLFPPKPKDT LXIXRXPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRXEXTK NQVSLTCLVK GFYPSDIAVE WESNGQPENN YKTTPPVLDS  180
DGSFFLYSKL TVDKSRWQQG NVFSCSVXHE ALHXHYTQKS LSLSPG                 226

SEQ ID NO: 40           moltype = AA  length = 226
FEATURE                 Location/Qualifiers
VARIANT                 136
                        note = MISC_FEATURE - Xaa is Asp or Glu
VARIANT                 138
                        note = MISC_FEATURE - Xaa is Leu or Met
source                  1..226
                        mol_type = protein
                        organism = synthetic construct
SEQUENCE: 40
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRXEXTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 41           moltype = AA  length = 226
FEATURE                 Location/Qualifiers
VARIANT                 136
                        note = MISC_FEATURE - Xaa is Asp or Glu
VARIANT                 138
                        note = MISC_FEATURE - Xaa is Leu or Met
source                  1..226
                        mol_type = protein
                        organism = synthetic construct
SEQUENCE: 41
DKTHTCPPCP APELLGGPSV FLFPPKPKDT LYITREPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRXEXTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 42           moltype = AA  length = 226
FEATURE                 Location/Qualifiers
source                  1..226
                        mol_type = protein
                        organism = synthetic construct
SEQUENCE: 42
DKTHTCPPCP APELLGGPSV FLFPPKPKDT LYITREPEVT CVVVDVSHED PEVKFNWYVD  60
```

-continued

```
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 43          moltype = AA  length = 226
FEATURE                Location/Qualifiers
source                 1..226
                       mol_type = protein
                       organism = synthetic construct
SEQUENCE: 43
DKTHTCPPCP APELLGGPSV FLFPPKPKDT LYITREPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 44          moltype = AA  length = 226
FEATURE                Location/Qualifiers
VARIANT                136
                       note = MISC_FEATURE - Xaa is Asp or Glu
VARIANT                138
                       note = MISC_FEATURE - Xaa is Leu or Met
source                 1..226
                       mol_type = protein
                       organism = synthetic construct
SEQUENCE: 44
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRXEXTK NQVSLTCLVK GFYPSDIAVE WESNGQPENN YKTTPPVLDS  180
DGSFFLYSKL TVDKSRWQQG NVFSCSVLHE ALHSHYTQKS LSLSPG                 226

SEQ ID NO: 45          moltype = AA  length = 226
FEATURE                Location/Qualifiers
source                 1..226
                       mol_type = protein
                       organism = synthetic construct
SEQUENCE: 45
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPG                 226

SEQ ID NO: 46          moltype = AA  length = 226
FEATURE                Location/Qualifiers
source                 1..226
                       mol_type = protein
                       organism = synthetic construct
SEQUENCE: 46
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVLHE ALHSHYTQKS LSLSPG                 226

SEQ ID NO: 47          moltype = AA  length = 265
FEATURE                Location/Qualifiers
VARIANT                71
                       note = MISC_FEATURE - Xaa is Met or Trp
VARIANT                73
                       note = MISC_FEATURE - Xaa is Ser or Thr
VARIANT                75
                       note = MISC_FEATURE - Xaa is Thr or Glu
VARIANT                175
                       note = MISC_FEATURE - Xaa is Asp or Glu
VARIANT                177
                       note = MISC_FEATURE - Xaa is Leu or Met
VARIANT                247
                       note = MISC_FEATURE - Xaa is Met or Leu
VARIANT                253
                       note = MISC_FEATURE - Xaa is Asn or Ser
source                 1..265
                       mol_type = protein
                       organism = synthetic construct
SEQUENCE: 47
MGWSCIILFL VATATGVHSN VNHKPSNTKV DKKVEPKSSD KTHTCPPCPA PELLGGPSVF  60
LFPPKPKDTL XIXRXPEVTC VVVDVSHEDP EVKFNWYVDG VEVHNAKTKP REEQYNSTYR  120
VVSVLTVLHQ DWLNGKEYKC KVSNKALPAP IEKTISKAKG QPREPQVYTL PPSRXEXTKN  180
QVSLTCLVKG FYPSDIAVEW ESNGQPENNY KTTPPVLDSD GSFFLYSKLT VDKSRWQQGN  240
VFSCSVXHEA LHXHYTQKSL SLSPG                                        265

SEQ ID NO: 48          moltype = AA  length = 266
```

```
FEATURE                Location/Qualifiers
source                 1..266
                       mol_type = protein
                       organism = synthetic construct
SEQUENCE: 48
MGWSCIILFL VATATGVHSN VNHKPSNTKV DKKVEPKSSD KTHTCPPCPA PELLGGPSVF  60
LFPPKPKDTL MISRTPEVTC VVVDVSHEDP EVKFNWYVDG VEVHNAKTKP REEQYNSTYR  120
VVSVLTVLHQ DWLNGKEYKC KVSNKALPAP IEKTISKAKG QPREPQVYTL PPSRDELTKN  180
QVSLTCLVKG FYPSDIAVEW ESNGQPENNY KTTPPVLDSD GSFFLYSKLT VDKSRWQQGN  240
VFSCSVMHEA LHNHYTQKSL SLSPGK                                     266

SEQ ID NO: 49          moltype = AA  length = 266
FEATURE                Location/Qualifiers
source                 1..266
                       mol_type = protein
                       organism = synthetic construct
SEQUENCE: 49
MGWSCIILFL VATATGVHSN VNHKPSNTKV DKKVEPKSSD KTHTCPPCPA PELLGGPSVF  60
LFPPKPKDTL MISRTPEVTC VVVDVSHEDP EVKFNWYVDG VEVHNAKTKP REEQYNSTYR  120
VVSVLTVLHQ DWLNGKEYKC KVSNKALPAP IEKTISKAKG QPREPQVYTL PPSREEMTKN  180
QVSLTCLVKG FYPSDIAVEW ESNGQPENNY KTTPPVLDSD GSFFLYSKLT VDKSRWQQGN  240
VFSCSVMHEA LHNHYTQKSL SLSPGK                                     266

SEQ ID NO: 50          moltype = AA  length = 266
FEATURE                Location/Qualifiers
source                 1..266
                       mol_type = protein
                       organism = synthetic construct
SEQUENCE: 50
MGWSCIILFL VATATGVHSN VNHKPSNTKV DKKVEPKSSD KTHTCPPCPA PELLGGPSVF  60
LFPPKPKDTL MISRTPEVTC VVVDVSHEDP EVKFNWYVDG VEVHNAKTKP REEQYNSTYR  120
VVSVLTVLHQ DWLNGKEYKC KVSNKALPAP IEKTISKAKG QPREPQVYTL PPSRDELTKN  180
QVSLTCLVKG FYPSDIAVEW ESNGQPENNY KTTPPVLDSD GSFFLYSKLT VDKSRWQQGN  240
VFSCSVLHEA LHSHYTQKSL SLSPGK                                     266

SEQ ID NO: 51          moltype = AA  length = 266
FEATURE                Location/Qualifiers
source                 1..266
                       mol_type = protein
                       organism = synthetic construct
SEQUENCE: 51
MGWSCIILFL VATATGVHSN VNHKPSNTKV DKKVEPKSSD KTHTCPPCPA PELLGGPSVF  60
LFPPKPKDTL MISRTPEVTC VVVDVSHEDP EVKFNWYVDG VEVHNAKTKP REEQYNSTYR  120
VVSVLTVLHQ DWLNGKEYKC KVSNKALPAP IEKTISKAKG QPREPQVYTL PPSREEMTKN  180
QVSLTCLVKG FYPSDIAVEW ESNGQPENNY KTTPPVLDSD GSFFLYSKLT VDKSRWQQGN  240
VFSCSVLHEA LHSHYTQKSL SLSPGK                                     266

SEQ ID NO: 52          moltype = AA  length = 266
FEATURE                Location/Qualifiers
source                 1..266
                       mol_type = protein
                       organism = synthetic construct
SEQUENCE: 52
MGWSCIILFL VATATGVHSN VNHKPSNTKV DKKVEPKSSD KTHTCPPCPA PELLGGPSVF  60
LFPPKPKDTL YITREPEVTC VVVDVSHEDP EVKFNWYVDG VEVHNAKTKP REEQYNSTYR  120
VVSVLTVLHQ DWLNGKEYKC KVSNKALPAP IEKTISKAKG QPREPQVYTL PPSRDELTKN  180
QVSLTCLVKG FYPSDIAVEW ESNGQPENNY KTTPPVLDSD GSFFLYSKLT VDKSRWQQGN  240
VFSCSVMHEA LHNHYTQKSL SLSPGK                                     266

SEQ ID NO: 53          moltype = AA  length = 266
FEATURE                Location/Qualifiers
source                 1..266
                       mol_type = protein
                       organism = synthetic construct
SEQUENCE: 53
MGWSCIILFL VATATGVHSN VNHKPSNTKV DKKVEPKSSD KTHTCPPCPA PELLGGPSVF  60
LFPPKPKDTL YITREPEVTC VVVDVSHEDP EVKFNWYVDG VEVHNAKTKP REEQYNSTYR  120
VVSVLTVLHQ DWLNGKEYKC KVSNKALPAP IEKTISKAKG QPREPQVYTL PPSREEMTKN  180
QVSLTCLVKG FYPSDIAVEW ESNGQPENNY KTTPPVLDSD GSFFLYSKLT VDKSRWQQGN  240
VFSCSVMHEA LHNHYTQKSL SLSPGK                                     266

SEQ ID NO: 54          moltype = AA  length = 267
FEATURE                Location/Qualifiers
source                 1..267
                       mol_type = protein
                       organism = synthetic construct
SEQUENCE: 54
MGWSCIILFL VATATGVHSI SAMVRSDKTH TCPPCPAPEL LGGPSVFLFP PKPKDTLMIS  60
RTPEVTCVVV DVSHEDPEVK FNWYVDGVEV HNAKTKPREE QYNSTYRVVS VLTVLHQDWL  120
```

-continued

```
NGKEYKCKVS NKALPAPIEK TISKAKGQPR EPQVYTLPPS REEMTKNQVS LTCLVKGFYP  180
SDIAVEWESN GQPENNYKTT PPVLDSDGSF FLYSKLTVDK SRWQQGNVFS CSVLHEALHS  240
HYTQKSLSLS PGGGGGSEQK LISEEDL                                      267

SEQ ID NO: 55          moltype = AA  length = 267
FEATURE                Location/Qualifiers
source                 1..267
                       mol_type = protein
                       organism = synthetic construct
SEQUENCE: 55
MGWSCIILFL VATATGVHSI SAMVRSDKTH TCPPCPAPEL LGGPSVFLFP PKPKDTLMIS  60
RTPEVTCVVV DVSHEDPEVK FNWYVDGVEV HNAKTKPREE QYNSTYRVVS VLTVLHQDWL  120
NGKEYKCKVS NKALPAPIEK TISKAKGQPR EPQVYTLPPS RDELTKNQVS LTCLVKGFYP  180
SDIAVEWESN GQPENNYKTT PPVLDSDGSF FLYSKLTVDK SRWQQGNVFS CSVLHEALHS  240
HYTQKSLSLS PGGGGGSEQK LISEEDL                                      267

SEQ ID NO: 56          moltype = AA  length = 267
FEATURE                Location/Qualifiers
source                 1..267
                       mol_type = protein
                       organism = synthetic construct
SEQUENCE: 56
MGWSCIILFL VATATGVHSI SAMVRSDKTH TCPPCPAPEL LGGPSVFLFP PKPKDTLYIT  60
REPEVTCVVV DVSHEDPEVK FNWYVDGVEV HNAKTKPREE QYNSTYRVVS VLTVLHQDWL  120
NGKEYKCKVS NKALPAPIEK TISKAKGQPR EPQVYTLPPS REEMTKNQVS LTCLVKGFYP  180
SDIAVEWESN GQPENNYKTT PPVLDSDGSF FLYSKLTVDK SRWQQGNVFS CSVMHEALHN  240
HYTQKSLSLS PGGGGGSEQK LISEEDL                                      267

SEQ ID NO: 57          moltype = AA  length = 267
FEATURE                Location/Qualifiers
source                 1..267
                       mol_type = protein
                       organism = synthetic construct
SEQUENCE: 57
MGWSCIILFL VATATGVHSI SAMVRSDKTH TCPPCPAPEL LGGPSVFLFP PKPKDTLYIT  60
REPEVTCVVV DVSHEDPEVK FNWYVDGVEV HNAKTKPREE QYNSTYRVVS VLTVLHQDWL  120
NGKEYKCKVS NKALPAPIEK TISKAKGQPR EPQVYTLPPS RDELTKNQVS LTCLVKGFYP  180
SDIAVEWESN GQPENNYKTT PPVLDSDGSF FLYSKLTVDK SRWQQGNVFS CSVMHEALHN  240
HYTQKSLSLS PGGGGGSEQK LISEEDL                                      267

SEQ ID NO: 58          moltype = AA  length = 275
FEATURE                Location/Qualifiers
source                 1..275
                       mol_type = protein
                       organism = synthetic construct
SEQUENCE: 58
MGWSCIILFL VATATGVHSE PKSSDKTHTC PPCPAPELLG GPSVFLFPPK PKDTLMISRT  60
PEVTCVVVDV SHEDPEVKFN WYVDGVEVHN AKTKPREEQY NSTYRVVSVL TVLHQDWLNG  120
KEYKCKVSNK ALPAPIEKTI SKAKGQPREP QVYTLPPSRD ELTKNQVSLT CLVKGFYPSD  180
IAVEWESNGQ PENNYKTTPP VLDSDGSFFL YSKLTVDKSR WQQGNVFSCS VMHEALHNHY  240
TQKSLSLSPG GGGGSQRNPR LRLIRRHPTL RIPPI                             275

SEQ ID NO: 59          moltype = AA  length = 275
FEATURE                Location/Qualifiers
source                 1..275
                       mol_type = protein
                       organism = synthetic construct
SEQUENCE: 59
MGWSCIILFL VATATGVHSE PKSSDKTHTC PPCPAPELLG GPSVFLFPPK PKDTLMISRT  60
PEVTCVVVDV SHEDPEVKFN WYVDGVEVHN AKTKPREEQY NSTYRVVSVL TVLHQDWLNG  120
KEYKCKVSNK ALPAPIEKTI SKAKGQPREP QVYTLPPSRD ELTKNQVSLT CLVKGFYPSD  180
IAVEWESNGQ PENNYKTTPP VLDSDGSFFL YSKLTVDKSR WQQGNVFSCS VLHEALHSHY  240
TQKSLSLSPG GGGGSQRNPR LRLIRRHPTL RIPPI                             275

SEQ ID NO: 60          moltype = AA  length = 247
FEATURE                Location/Qualifiers
VARIANT                20
                       note = MISC_FEATURE - Xaa is Cys or Ser
VARIANT                52
                       note = MISC_FEATURE - Xaa is Met or Trp
VARIANT                54
                       note = MISC_FEATURE - Xaa is Ser or Thr
VARIANT                56
                       note = MISC_FEATURE - Xaa is Thr or Glu
VARIANT                156
                       note = MISC_FEATURE - Xaa is Asp or Glu
VARIANT                158
                       note = MISC_FEATURE - Xaa is Leu or Met
VARIANT                228
```

```
                      note = MISC_FEATURE - Xaa is Met or Leu
VARIANT               234
                      note = MISC_FEATURE - Xaa is Asn or Ser
source                1..247
                      mol_type = protein
                      organism = synthetic construct
SEQUENCE: 60
NVNHKPSNTK VDKKVEPKSX DKTHTCPPCP APELLGGPSV FLFPPKPKDT LXIXRXPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRXEXTK NQVSLTCLVK GFYPSDIAVE  180
WESNGQPENN YKTTPPVLDS DGSFFLYSKL TVDKSRWQQG NVFSCSVXHE ALHXHYTQKS  240
LSLSPGK                                                            247

SEQ ID NO: 61         moltype = AA  length = 247
FEATURE               Location/Qualifiers
VARIANT               52
                      note = MISC_FEATURE - Xaa is Met or Trp
VARIANT               54
                      note = MISC_FEATURE - Xaa is Ser or Thr
VARIANT               56
                      note = MISC_FEATURE - Xaa is Thr or Glu
VARIANT               156
                      note = MISC_FEATURE - Xaa is Asp or Glu
VARIANT               158
                      note = MISC_FEATURE - Xaa is Leu or Met
VARIANT               228
                      note = MISC_FEATURE - Xaa is Met or Leu
VARIANT               234
                      note = MISC_FEATURE - Xaa is Asn or Ser
source                1..247
                      mol_type = protein
                      organism = synthetic construct
SEQUENCE: 61
NVNHKPSNTK VDKKVEPKSS DKTHTCPPCP APELLGGPSV FLFPPKPKDT LXIXRXPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRXEXTK NQVSLTCLVK GFYPSDIAVE  180
WESNGQPENN YKTTPPVLDS DGSFFLYSKL TVDKSRWQQG NVFSCSVXHE ALHXHYTQKS  240
LSLSPGK                                                            247

SEQ ID NO: 62         moltype = AA  length = 247
FEATURE               Location/Qualifiers
VARIANT               156
                      note = MISC_FEATURE - Xaa is Asp or Glu
VARIANT               158
                      note = MISC_FEATURE - Xaa is Leu or Met
source                1..247
                      mol_type = protein
                      organism = synthetic construct
SEQUENCE: 62
NVNHKPSNTK VDKKVEPKSS DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRXEXTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGK                                                            247

SEQ ID NO: 63         moltype = AA  length = 247
FEATURE               Location/Qualifiers
source                1..247
                      mol_type = protein
                      organism = synthetic construct
SEQUENCE: 63
NVNHKPSNTK VDKKVEPKSS DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSREEMTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGK                                                            247

SEQ ID NO: 64         moltype = AA  length = 247
FEATURE               Location/Qualifiers
source                1..247
                      mol_type = protein
                      organism = synthetic construct
SEQUENCE: 64
NVNHKPSNTK VDKKVEPKSS DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGK                                                            247
```

-continued

```
SEQ ID NO: 65           moltype = AA  length = 247
FEATURE                 Location/Qualifiers
source                  1..247
                        mol_type = protein
                        organism = synthetic construct
SEQUENCE: 65
NVNHKPSNTK VDKKVEPKSS DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGK                                                            247

SEQ ID NO: 66           moltype = AA  length = 247
FEATURE                 Location/Qualifiers
source                  1..247
                        mol_type = protein
                        organism = synthetic construct
SEQUENCE: 66
NVNHKPSNTK VDKKVEPKSS DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSREEMTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGK                                                            247

SEQ ID NO: 67           moltype = AA  length = 247
FEATURE                 Location/Qualifiers
source                  1..247
                        mol_type = protein
                        organism = synthetic construct
SEQUENCE: 67
NVNHKPSNTK VDKKVEPKSS DKTHTCPPCP APELLGGPSV FLFPPKPKDT LYITREPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGK                                                            247

SEQ ID NO: 68           moltype = AA  length = 247
FEATURE                 Location/Qualifiers
source                  1..247
                        mol_type = protein
                        organism = synthetic construct
SEQUENCE: 68
NVNHKPSNTK VDKKVEPKSS DKTHTCPPCP APELLGGPSV FLFPPKPKDT LYITREPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSREEMTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGK                                                            247

SEQ ID NO: 69           moltype = AA  length = 585
FEATURE                 Location/Qualifiers
source                  1..585
                        mol_type = protein
                        organism = Homo sapiens
SEQUENCE: 69
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                  585

SEQ ID NO: 70           moltype = AA  length = 591
FEATURE                 Location/Qualifiers
source                  1..591
                        mol_type = protein
                        organism = Homo sapiens
SEQUENCE: 70
RGVFRRDAHK SEVAHRFKDL GEENFKALVL IAFAQYLQQC PFEDHVKLVN EVTEFAKTCV  60
ADESAENCDK SLHTLFGDKL CTVATLRETY GEMADCCAKQ EPERNECFLQ HKDDNPNLPR  120
LVRPEVDVMC TAFHDNEETF LKKYLYEIAR RHPYFYAPEL LFFAKRYKAA FTECCQAADK  180
AACLLPKLDE LRDEGKASSA KQRLKCASLQ KFGERAFKAW AVARLSQRFP KAEFAEVSKL  240
VTDLTKVHTE CCHGDLLECA DDRADLAKYI CENQDSISSK LKECCEKPLL EKSHCIAEVE  300
NDEMPADLPS LAADFVESKD VCKNYAEAKD VFLGMFLYEY ARRHPDYSVV LLLRLAKTYE  360
TTLEKCCAAA DPHECYAKVF DEFKPLVEEP QNLIKQNCEL FEQLGEYKFQ NALLVRYTKK  420
VPQVSTPTLV EVSRNLGKVG SKCCKHPEAK RMPCAEDYLS VVLNQLCVLH EKTPVSDRVT  480
```

```
KCCTESLVNR RPCFSALEVD ETYVPKEFNA ETFTFHADIC TLSEKERQIK KQTALVELVK  540
HKPKATKEQL KAVMDDFAAF VEKCCKADDK ETCFAEEGKK LVAASQAALG L           591

SEQ ID NO: 71          moltype = AA  length = 590
FEATURE                Location/Qualifiers
source                 1..590
                       mol_type = protein
                       organism = Mus musculus
SEQUENCE: 71
RGVFRREAHK SEIAHRYNDL GEQHFKGLVL IAFSQYLQKC SYDEHAKLVQ EVTDFAKTCV  60
ADESAANCDK SLHTLFGDKL CAIPNLRENY GELADCCTKQ EPERNECFLQ HKDDNPSLPP  120
FERPEAEAMC TSFKENPTTF MGHYLHEVAR RHPYFYAPEL LYYAEQYNEI LTQCCAEADK  180
ESCLTPKLDG VKEKALVSSV RQRMKCSSMQ KFGERAFKAW AVARLSQTFP NADFAEITKL  240
ATDLTKVNKE CCHGDLLECA DDRAELAKYM CENQATISSK LQTCCDKPLL KKAHCLSEVE  300
HDTMPADLPA IAADFVEDQE VCKNYAEAKD VFLGTFLYEY SRRHPDYSVS LLLRLAKKYE  360
ATLEKCCAEA NPPACYGTVL AEFQPLVEEP KNLVKTNCDL YEKLGEYGFQ NAILVRYTQK  420
APQVSTPTLV EAARNLGRVG TKCCTLPEDQ RLPCVEDYLS AILNRVCLLH EKTPVSEHVT  480
KCCSGSLVER RPCFSALTVD ETYVPKEFKA ETFTFHSDIC TLPEKEKQIK KQTALAELVK  540
HKPKATAEQL KTVMDDFAQF LDTCCKAADK DTCFSTEGPN LVTRCKDALA             590

SEQ ID NO: 72          moltype = AA  length = 6
FEATURE                Location/Qualifiers
source                 1..6
                       mol_type = protein
                       organism = synthetic construct
SEQUENCE: 72
HHHHHH                                                             6

SEQ ID NO: 73          moltype = AA  length = 20
FEATURE                Location/Qualifiers
source                 1..20
                       mol_type = protein
                       organism = synthetic construct
SEQUENCE: 73
MYRMQLLSCI ALSLALVTNS                                              20

SEQ ID NO: 74          moltype = AA  length = 22
FEATURE                Location/Qualifiers
VARIANT                1..2
                       note = MISC_FEATURE - Xaa is any amino acid
VARIANT                4..8
                       note = MISC_FEATURE - Xaa is any amino acid
VARIANT                10..11
                       note = MISC_FEATURE - Xaa is any amino acid
VARIANT                14
                       note = MISC_FEATURE - Xaa is any amino acid
VARIANT                18..20
                       note = MISC_FEATURE - Xaa is any amino acid
source                 1..22
                       mol_type = protein
                       organism = synthetic construct
SEQUENCE: 74
XXCXXXXXCX XFCXDWPXXX SC                                           22

SEQ ID NO: 75          moltype = AA  length = 9
FEATURE                Location/Qualifiers
VARIANT                4..6
                       note = MISC_FEATURE - Xaa is any amino acid
source                 1..9
                       mol_type = protein
                       organism = synthetic construct
SEQUENCE: 75
VCYXXXICF                                                          9

SEQ ID NO: 76          moltype = AA  length = 7
FEATURE                Location/Qualifiers
VARIANT                3
                       note = MISC_FEATURE - Xaa is any amino acid
VARIANT                6
                       note = MISC_FEATURE - Xaa is any amino acid
source                 1..7
                       mol_type = protein
                       organism = synthetic construct
SEQUENCE: 76
CYXPGXC                                                            7

SEQ ID NO: 77          moltype = AA  length = 11
FEATURE                Location/Qualifiers
VARIANT                2
```

-continued

```
                        note = MISC_FEATURE - Xaa is any amino acid
VARIANT                 6
                        note = MISC_FEATURE - Xaa is any amino acid
source                  1..11
                        mol_type = protein
                        organism = synthetic construct
SEQUENCE: 77
DXCLPXWGCL W                                                       11

SEQ ID NO: 78           moltype = AA  length = 12
FEATURE                 Location/Qualifiers
VARIANT                 4..5
                        note = MISC_FEATURE - Xaa is any amino acid
VARIANT                 7
                        note = MISC_FEATURE - Xaa is any amino acid
VARIANT                 9
                        note = MISC_FEATURE - Xaa is any amino acid
source                  1..12
                        mol_type = protein
                        organism = synthetic construct
SEQUENCE: 78
WCDXXLXAXD LC                                                      12

SEQ ID NO: 79           moltype = AA  length = 10
FEATURE                 Location/Qualifiers
VARIANT                 4
                        note = MISC_FEATURE - Xaa is any amino acid
source                  1..10
                        mol_type = protein
                        organism = synthetic construct
SEQUENCE: 79
DLVXLGLECW                                                         10

SEQ ID NO: 80           moltype = AA  length = 11
FEATURE                 Location/Qualifiers
source                  1..11
                        mol_type = protein
                        organism = synthetic construct
SEQUENCE: 80
DLCLRDWGCL W                                                       11

SEQ ID NO: 81           moltype = AA  length = 11
FEATURE                 Location/Qualifiers
source                  1..11
                        mol_type = protein
                        organism = synthetic construct
SEQUENCE: 81
DICLPRWGCL W                                                       11

SEQ ID NO: 82           moltype = AA  length = 15
FEATURE                 Location/Qualifiers
source                  1..15
                        mol_type = protein
                        organism = synthetic construct
SEQUENCE: 82
MEDICLPRWG CLWGD                                                   15

SEQ ID NO: 83           moltype = AA  length = 20
FEATURE                 Location/Qualifiers
source                  1..20
                        mol_type = protein
                        organism = synthetic construct
SEQUENCE: 83
QRLMEDICLP RWGCLWEDDE                                              20

SEQ ID NO: 84           moltype = AA  length = 20
FEATURE                 Location/Qualifiers
source                  1..20
                        mol_type = protein
                        organism = synthetic construct
SEQUENCE: 84
QGLIGDICLP RWGCLWGRSV                                              20

SEQ ID NO: 85           moltype = AA  length = 21
FEATURE                 Location/Qualifiers
source                  1..21
                        mol_type = protein
                        organism = synthetic construct
SEQUENCE: 85
```

```
QGLIGDICLP RWGCLWGRSV K                                          21

SEQ ID NO: 86          moltype = AA  length = 15
FEATURE                Location/Qualifiers
source                 1..15
                       mol_type = protein
                       organism = synthetic construct
SEQUENCE: 86
EDICLPRWGC LWEDD                                                 15

SEQ ID NO: 87          moltype = AA  length = 18
FEATURE                Location/Qualifiers
source                 1..18
                       mol_type = protein
                       organism = synthetic construct
SEQUENCE: 87
RLMEDICLPR WGCLWEDD                                              18

SEQ ID NO: 88          moltype = AA  length = 16
FEATURE                Location/Qualifiers
source                 1..16
                       mol_type = protein
                       organism = synthetic construct
SEQUENCE: 88
MEDICLPRWG CLWEDD                                                16

SEQ ID NO: 89          moltype = AA  length = 15
FEATURE                Location/Qualifiers
source                 1..15
                       mol_type = protein
                       organism = synthetic construct
SEQUENCE: 89
MEDICLPRWG CLWED                                                 15

SEQ ID NO: 90          moltype = AA  length = 18
FEATURE                Location/Qualifiers
source                 1..18
                       mol_type = protein
                       organism = synthetic construct
SEQUENCE: 90
RLMEDICLAR WGCLWEDD                                              18

SEQ ID NO: 91          moltype = AA  length = 20
FEATURE                Location/Qualifiers
source                 1..20
                       mol_type = protein
                       organism = synthetic construct
SEQUENCE: 91
EVRSFCTRWP AEKSCKPLRG                                            20

SEQ ID NO: 92          moltype = AA  length = 20
FEATURE                Location/Qualifiers
source                 1..20
                       mol_type = protein
                       organism = synthetic construct
SEQUENCE: 92
RAPESFVCYW ETICFERSEQ                                            20

SEQ ID NO: 93          moltype = AA  length = 11
FEATURE                Location/Qualifiers
source                 1..11
                       mol_type = protein
                       organism = synthetic construct
SEQUENCE: 93
EMCYFPGICW M                                                     11

SEQ ID NO: 94          moltype = AA  length = 330
FEATURE                Location/Qualifiers
source                 1..330
                       mol_type = protein
                       organism = Homo sapiens
SEQUENCE: 94
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330
```

-continued

```
SEQ ID NO: 95          moltype = AA  length = 326
FEATURE                Location/Qualifiers
source                 1..326
                       mol_type = protein
                       organism = Homo sapiens
SEQUENCE: 95
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDISVEW ESNGQPENNY KTTPPMLDSD GSFFLYSKLT VDKSRWQQGN  300
VFSCSVMHEA LHNHYTQKSL SLSPGK                                      326

SEQ ID NO: 96          moltype = AA  length = 377
FEATURE                Location/Qualifiers
source                 1..377
                       mol_type = protein
                       organism = Homo sapiens
SEQUENCE: 96
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                377

SEQ ID NO: 97          moltype = AA  length = 327
FEATURE                Location/Qualifiers
source                 1..327
                       mol_type = protein
                       organism = Homo sapiens
SEQUENCE: 97
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327
```